United States Patent
Enquist et al.

(10) Patent No.: US 11,535,660 B1
(45) Date of Patent: Dec. 27, 2022

(54) MODULATORS OF G-PROTEIN COUPLED RECEPTORS

(71) Applicant: Carmot Therapeutics, Inc., Berkeley, CA (US)

(72) Inventors: Johan Enquist, San Francisco, CA (US); Shyam Krishnan, Novato, CA (US); Suman Atwal, San Jose, CA (US); Daniel Erlanson, San Francisco, CA (US); Raymond V. Fucini, San Bruno, CA (US); Stig Hansen, Kensington, CA (US); Andrew Sawayama, San Francisco, CA (US); Steven Sethofer, Emeryville, CA (US)

(73) Assignee: Cannot Therapeutics, Inc., Berkeley, CA (US)

( * ) Notice: Subject to any disclaimer, the term of this patent is extended or adjusted under 35 U.S.C. 154(b) by 0 days.

(21) Appl. No.: 17/040,653

(22) PCT Filed: Mar. 22, 2019

(86) PCT No.: PCT/US2019/023726
§ 371 (c)(1),
(2) Date: Sep. 23, 2020

(87) PCT Pub. No.: WO2019/183577
PCT Pub. Date: Sep. 26, 2019

Related U.S. Application Data

(60) Provisional application No. 62/647,604, filed on Mar. 23, 2018.

(51) Int. Cl.
*C07K 14/605* (2006.01)
*A61K 38/00* (2006.01)
*A61K 47/54* (2017.01)

(52) U.S. Cl.
CPC .......... *C07K 14/605* (2013.01); *A61K 47/545* (2017.08); *A61K 38/00* (2013.01)

(58) Field of Classification Search
None
See application file for complete search history.

(56) References Cited

U.S. PATENT DOCUMENTS

| | | |
|---|---|---|
| 2006/0275288 A1 | 12/2006 | Grihalde et al. |
| 2012/0021979 A1 | 1/2012 | Davis et al. |
| 2012/0148586 A1 | 6/2012 | Chou et al. |
| 2013/0040884 A1 | 2/2013 | Lan et al. |
| 2015/0352219 A1 | 12/2015 | Anderson et al. |
| 2017/0095554 A1 | 4/2017 | Brimble et al. |
| 2017/0326233 A1 | 11/2017 | Demeule et al. |

FOREIGN PATENT DOCUMENTS

| | | |
|---|---|---|
| EP | 1883419 | 11/2006 |
| GB | 2551945 | 1/2018 |
| WO | WO 1997/10224 | 3/1997 |
| WO | WO 1999/43707 | 9/1999 |
| WO | WO 00/34331 | 6/2000 |
| WO | WO 01/17568 | 3/2001 |
| WO | WO 2001/14371 | 3/2001 |
| WO | WO 2001/62765 | 8/2001 |
| WO | WO 2002/06234 | 1/2002 |
| WO | WO 2004/039365 | 5/2004 |
| WO | WO 2004/041266 | 5/2004 |
| WO | WO 2004/048363 | 6/2004 |
| WO | WO 2004/067548 | 8/2004 |
| WO | WO 2004/106276 | 12/2004 |
| WO | WO 2005/030740 | 4/2005 |
| WO | WO 2005/058823 | 6/2005 |
| WO | WO 2005/063725 | 7/2005 |
| WO | WO 2005/063729 | 7/2005 |
| WO | WO 2005/087710 | 9/2005 |
| WO | WO 2005/095338 | 10/2005 |
| WO | WO 2005/113504 | 12/2005 |
| WO | WO 2006/112549 | 10/2006 |

(Continued)

OTHER PUBLICATIONS

Angulo et al., "Non-alcoholic fatty liver disease," J Gastroenterol Hepatol., 2002, 17 suppl: S186-90.
Chitturi et al., "NASH and insulin resistance: Insulin hypersecretion and specific association with the insulin resistance syndrome," Hepatology, 2002, 35(2):373-9.
Choi et al., "Highly efficient and fast pre-activation cyclization of the long peptide: Succinimidyl ester-amine reaction revisited," Bioorg & Med. Chem. Lett., 2015, 5335-8.
Chopra et al., "Versatile cyclic templates for assembly of axially oriented ligands," Bioconjugate Chemistry, 2009, 20:2: 231-240.
Deacon et al., "Degradation of glucagon-like peptide-1 by human plasma in vitro yields an N-terminally truncated peptide that is a major endogenous metabolite in vivo," Journal of Clinical Endocrinology & Metabolism, 1995, 80:952-957.

(Continued)

*Primary Examiner* — Thomas S Heard
(74) *Attorney, Agent, or Firm* — Fish & Richardson P.C.

(57) ABSTRACT

This disclosure features chemical entities (e.g., a compound or a pharmaceutically acceptable salt and/or hydrate and/or prodrug of the compound) that modulate (e.g., agonize or partially agonize or antagonize) glucagon‑like peptide‑1 receptor ("GLP‑1R") and/or the gastric inhibitory polypeptide receptor ("GIPR"). The chemical entities are useful, e.g., for treating a subject (e.g., a human) having a disease, disorder, or condition in which modulation (e.g., agonism, partial agonism or antagonism) of GLP‑1R and/or GIPR activities is beneficial for the treatment or prevention of the underlying pathology and/or symptoms and/or progression of the disease, disorder, or condition. In some embodiments, the modulation results in an enhancement of (e.g., an increase in) existing levels (e.g., normal or below normal levels) of GLP‑1R and/or GIPR activity (e.g., signaling). In some embodiments, the chemical entities described herein further modulate (e.g., attenuate, uncouple)-arrestin signaling relative to what is observed with the native ligand. This disclosure also features compositions as well as other methods of using and making the said chemical entities.

34 Claims, 251 Drawing Sheets
Specification includes a Sequence Listing.

(56) References Cited

FOREIGN PATENT DOCUMENTS

| WO | WO 2007/013689 | 2/2007 |
| --- | --- | --- |
| WO | WO 2007/013694 | 2/2007 |
| WO | WO 2007/018314 | 2/2007 |
| WO | WO 2007/028135 | 3/2007 |
| WO | WO 2008/001931 | 1/2008 |
| WO | WO 2008/047821 | 4/2008 |
| WO | WO 2008/050821 | 5/2008 |
| WO | WO 2008/093639 | 8/2008 |
| WO | WO 2008/099794 | 8/2008 |
| WO | WO 2008/136428 | 11/2008 |
| WO | WO 2008/156757 | 12/2008 |
| WO | WO 2011/044212 | 4/2011 |
| WO | WO 2011/094337 | 8/2011 |
| WO | WO 2013/148579 | 10/2013 |
| WO | WO 2014/074218 | 5/2014 |
| WO | WO 2014/165240 | 10/2014 |
| WO | WO 2015/031268 | 3/2015 |
| WO | WO 2016/131893 | 8/2016 |
| WO | WO 2010/011439 | 1/2021 |

OTHER PUBLICATIONS

Elduque et al., "Straightforward synthesis of cyclic and bicyclic peptides," Organic Lett., Mar. 2013, 2038-2041.

Fanil et al., "Revised primary structures of rat pituitary y-lipotrophin and B-endorphin," Neuropeptides, 1999, 32:4:339-349.

Gupta et al., "Whole-Virus Screening to Develop Synbodies for the Influenza Virus," Bioconjugate Chem., Oct. 2019, 27:10:2505-2512.

Guy et al., "De novo helical peptides as target sequences for a specific, fluorogenic protein labelling strategy," Molecular Biosystems, 2010, 6:976-987.

Lisse et al., "Monofunctional Stealth Nanoparticle for Unbiased Single Molecule Tracking Inside Living Cells," NanoLett., 2014, 14:2189-2195.

Lisse et al., "Supplementary information and resilts: Monofunctional Stealth Nanoparticle for Unbiased Single Molecule Tracking Inside Living Cells," NanoLett., 2014, 14:2189-2195.

Moshitzky et al., "Determination of locust akh-I by radioimmunoassay an the identification of an akh-like factor in the locust brain," Insect Biochem., 1987, 17:5:765-769.

Nacheva et al., "Fluorescent properties and resonance energy transfer of3,4-bis(2,4-difluorophenyl)-maleimide," Organic & Biomolecular Chemistiy, 2012, 10:38:7840-7846.

PCT International Preliminary Report on Patentability in International Appln. No. PCT/US2019/023726, dated Sep. 29, 2020, 12 pages.

PCT International Search Report and Written Opinion in International Applne. No. PCT/US2019/023726, dated May 31, 2019, 20 pages.

Sakai et al., "Formation of Functionalized Nanowires by Control of Self-Assembly Using Multiple Modifi ed Amyloid Peptides," Apr. 2013, 23:39:4881-4887.

Sieno et al., "Glucose-dependent insulinotropic polypeptide and glucagon-like peptide-1: Incretin actions beyond the pancreas," J. of Diabetes Investigation Mar. 2013, 4:2:108-130.

Skelly et al., "Finding on liver biopsy to investigate abnormal liver function tests in the absence of diagnostic serology," 2001, J. Hepatol 2001, 35: 195-199.

Bonet et al, "Luminescent lanthanide-binding peptides: sensitising the excited states of Eu (III) and Tb (III) with a 1,8-naphthalimide-based antenna", Organic & Biomolecular Chemistry, 2012, 10(1): 126-133.

Bonnet et al, "Structural studies in aqueous solution of new binuclear lanthanide luminescent peptide conjugates", Chemical Communications, Sep. 12, 2008, 3 pp. 4552-4554 according to the EPSR.

Chopra et al, "Versatile Cyclic Templates for Assembly of Axially Oriented Ligands", Bioeonjugate Chemistry, 2009, 20(2): 231-240.

Extended Search Report in European Application No. 19772275.4, dated Apr. 7, 2022, 12 pages.

Finan et al, "Unimolecular Dual Incretins Maximize MetabolicBenefits Rodents,Monkeys, and Humans", Science Translational Medicine, 5(209): 1-17 according to the EP SR.

Written Opinion and Search Report hi Singaporean Application No. 11202009338S, dated Mar. 15, 2022, 9 pages.

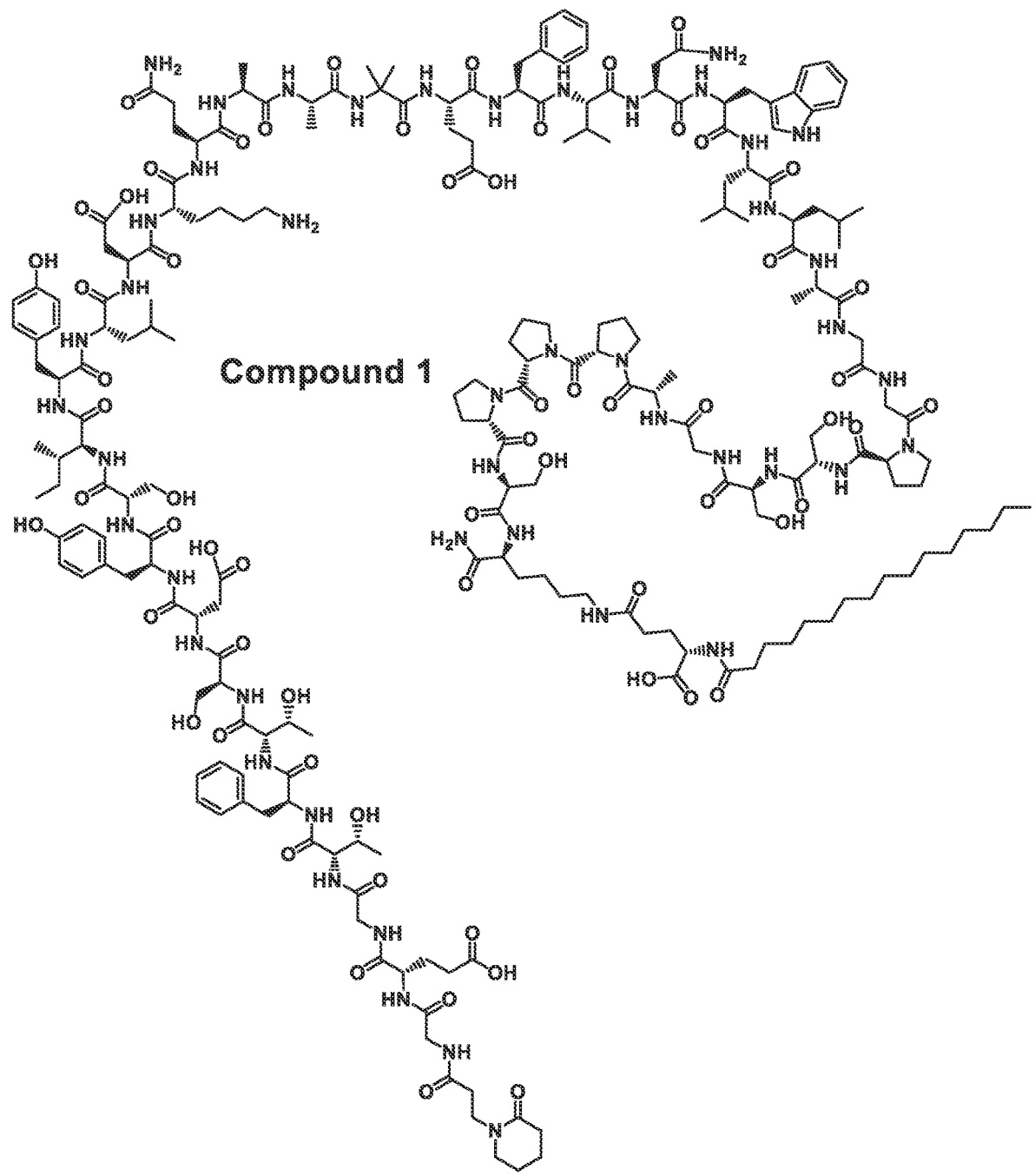
Compound 1

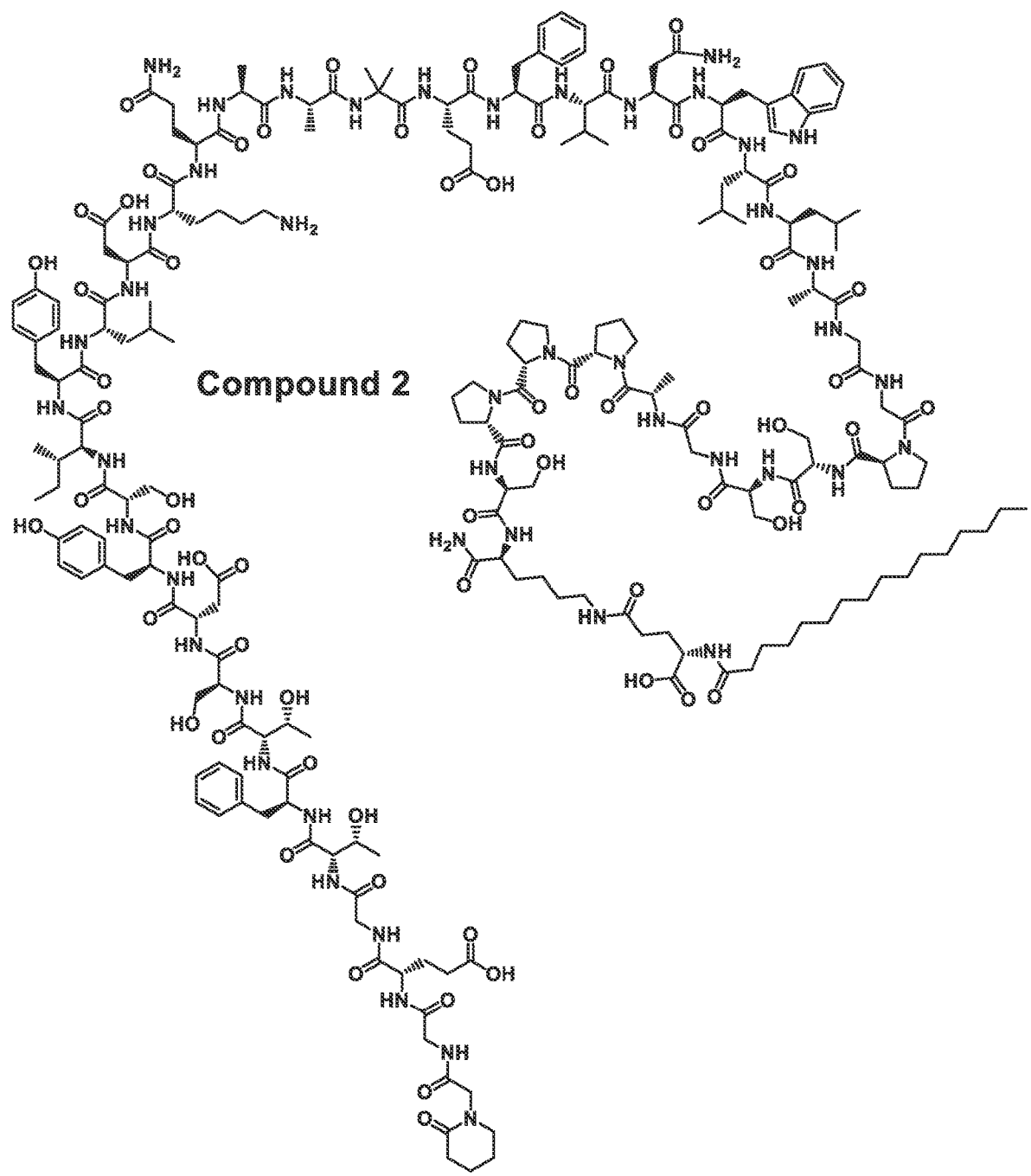
Compound 2
cont'd

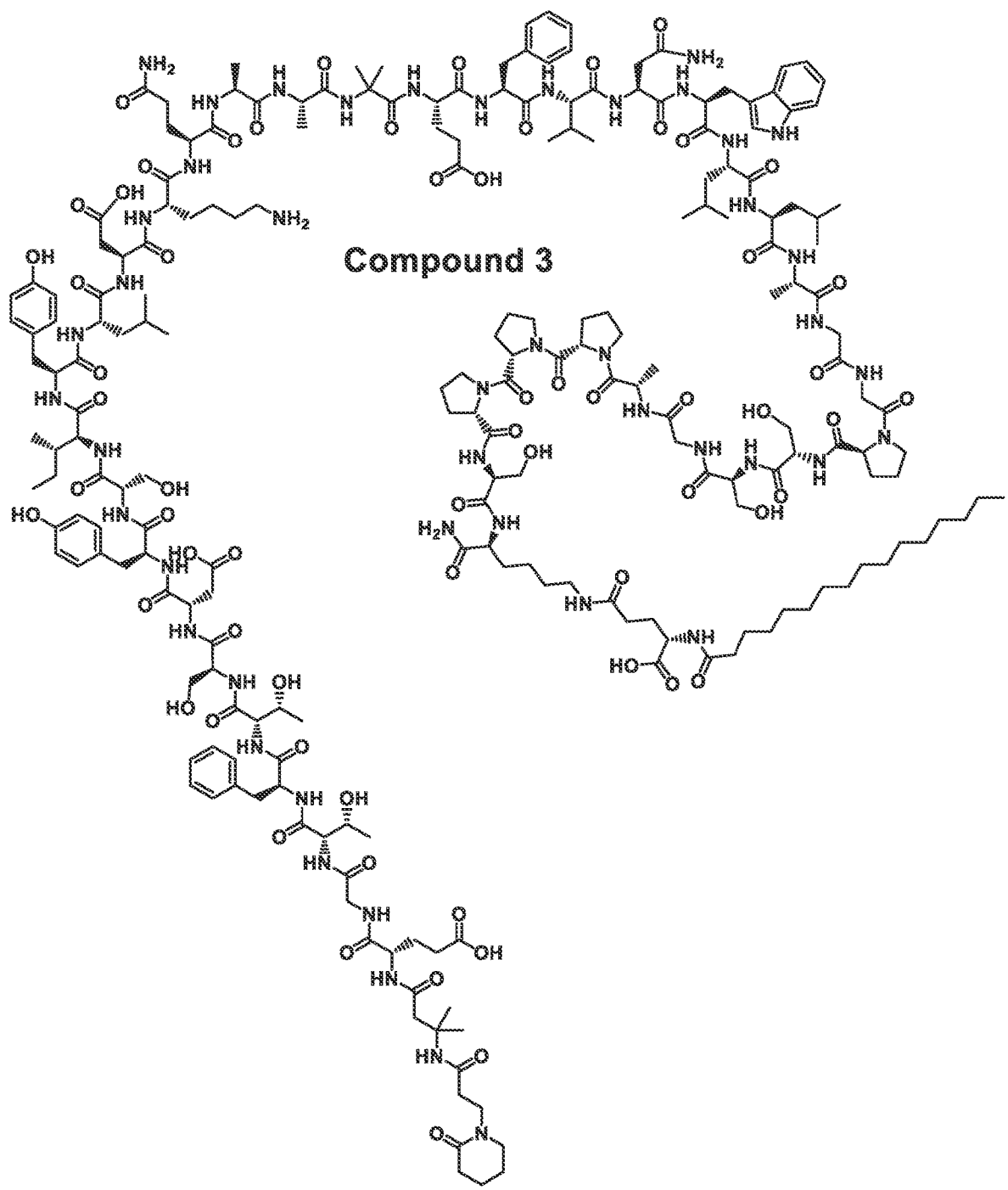
Compound 3
Cont'd

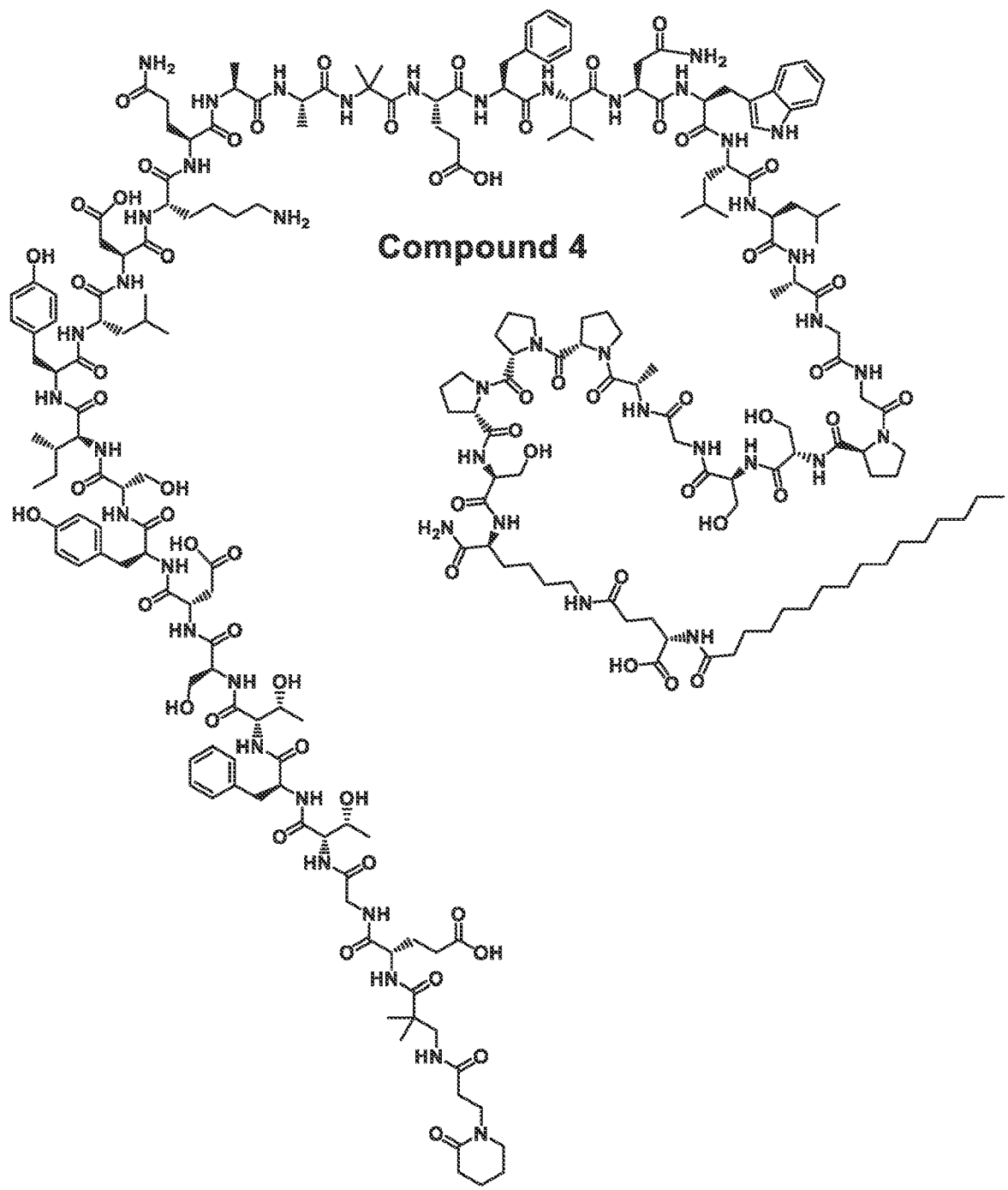
Compound 4
Cont'd

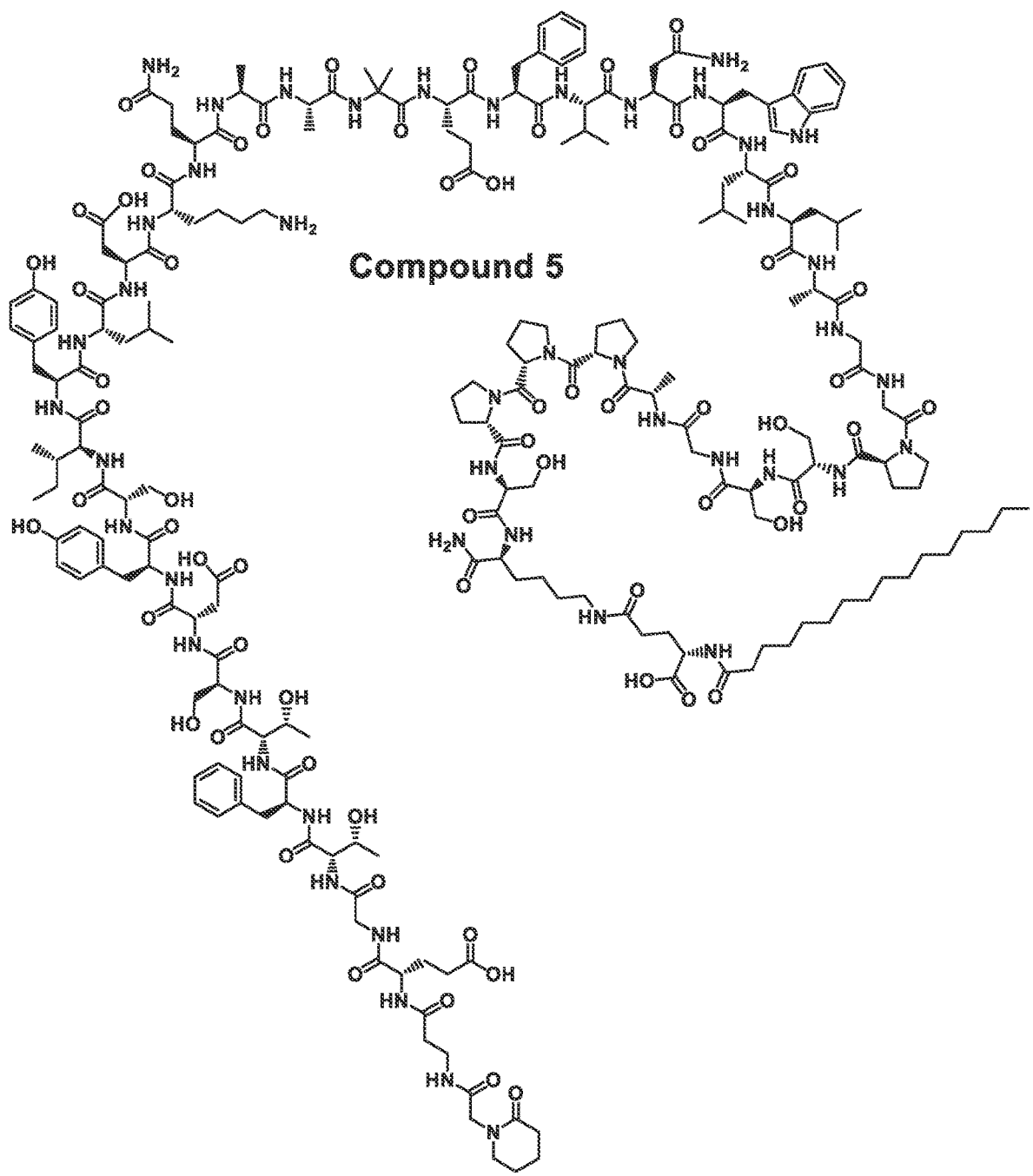
Compound 5
Cont'd

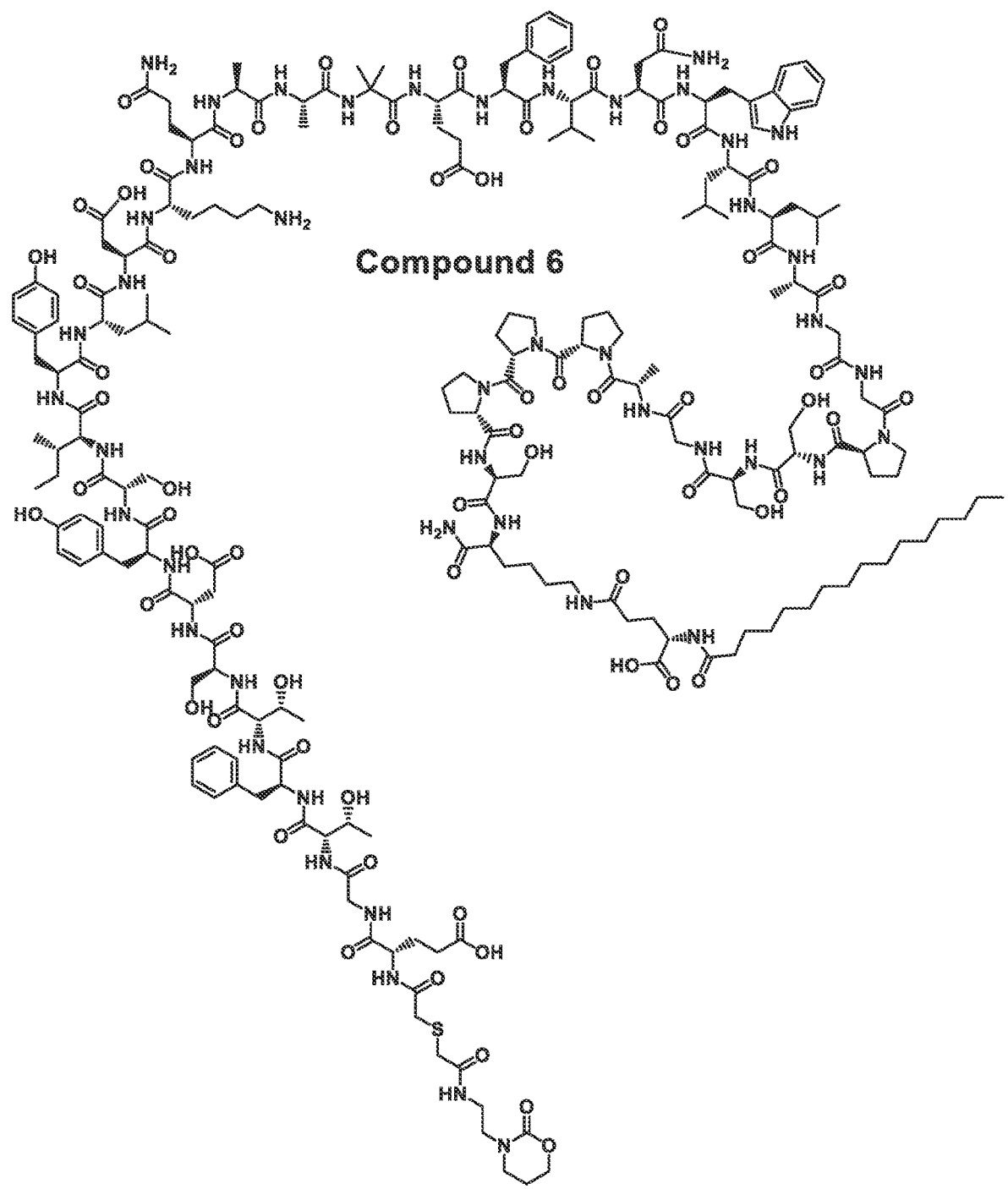
Compound 6
Cont'd

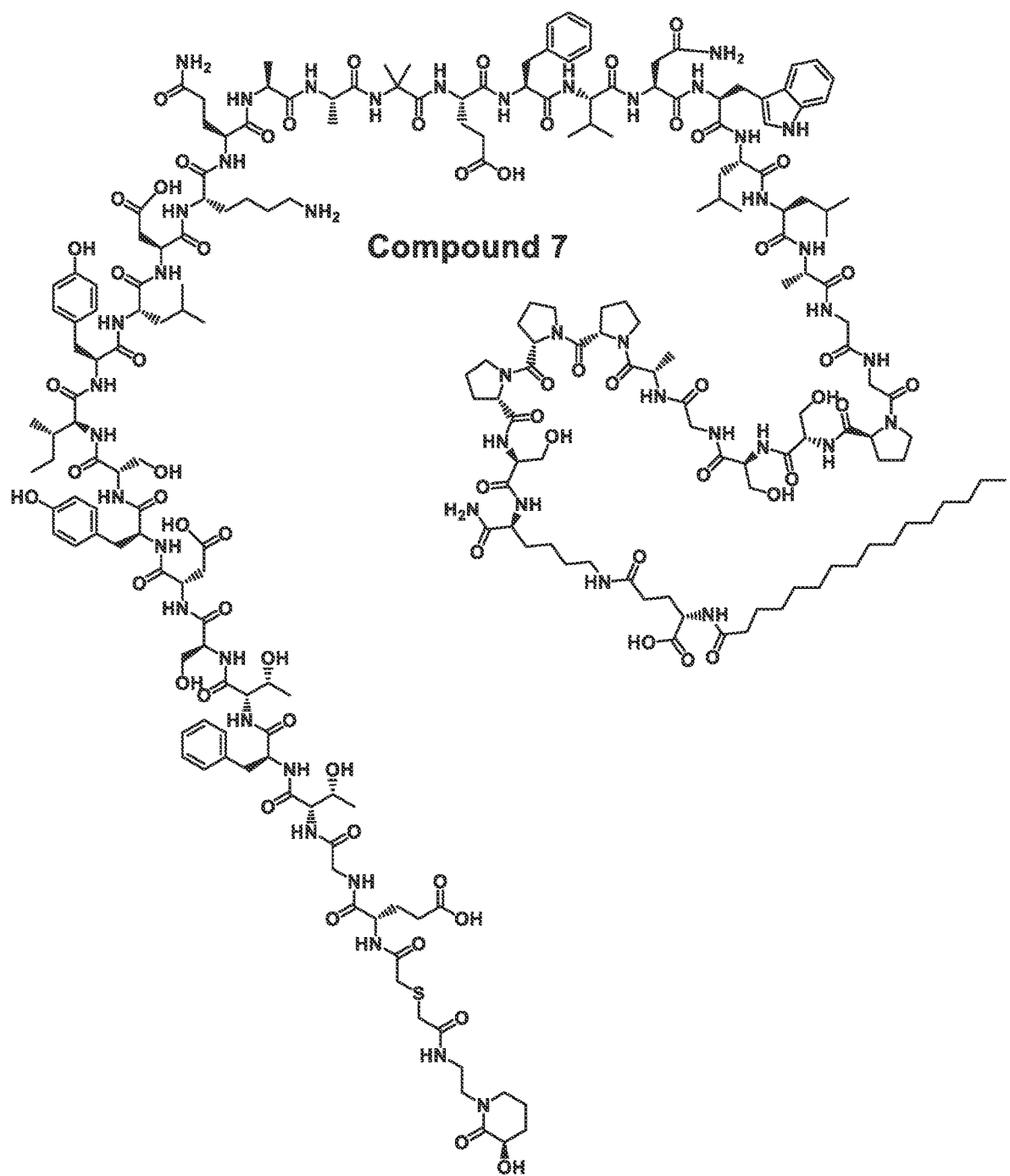
Compound 7
Cont'd

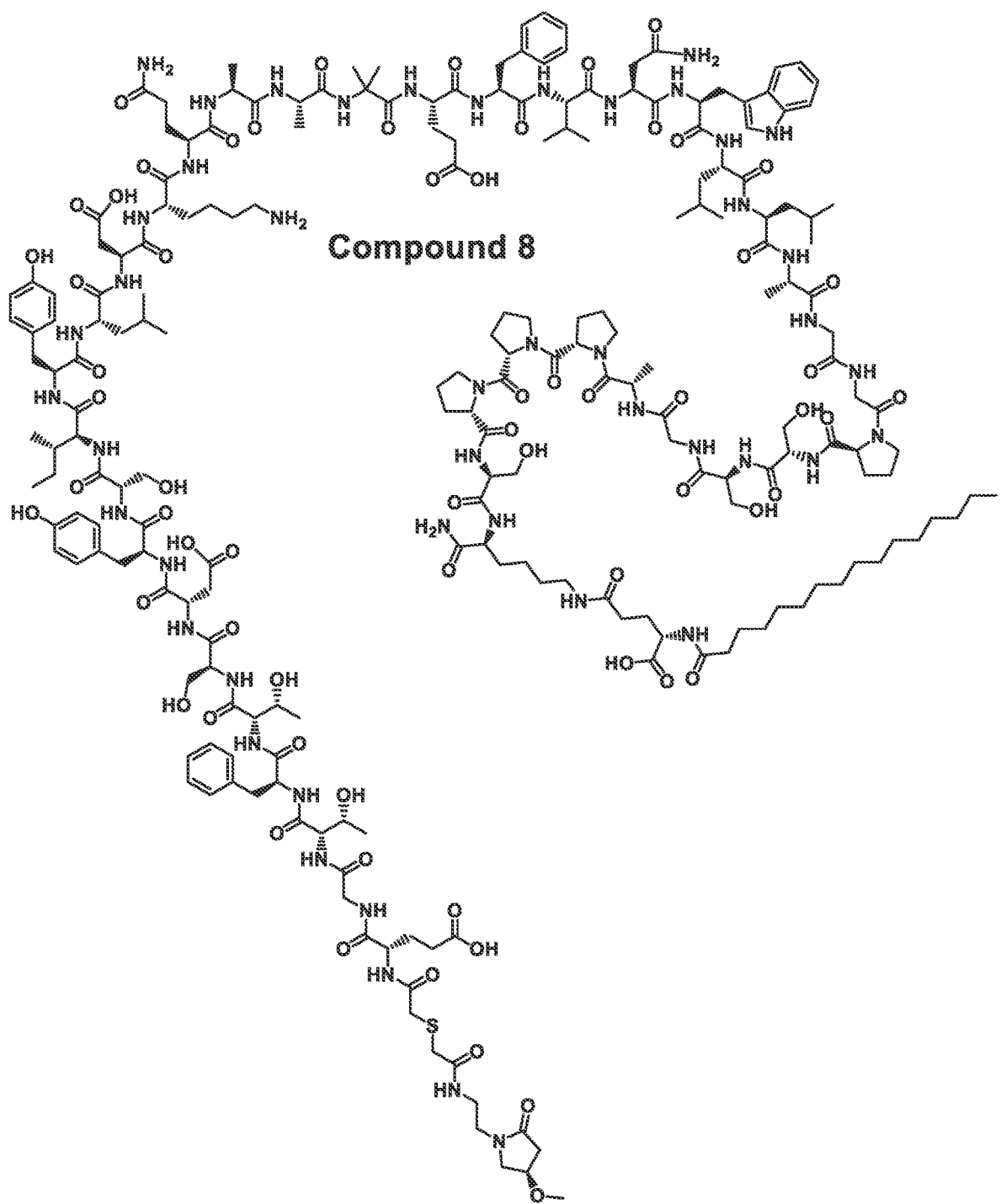
Compound 8
Cont'd

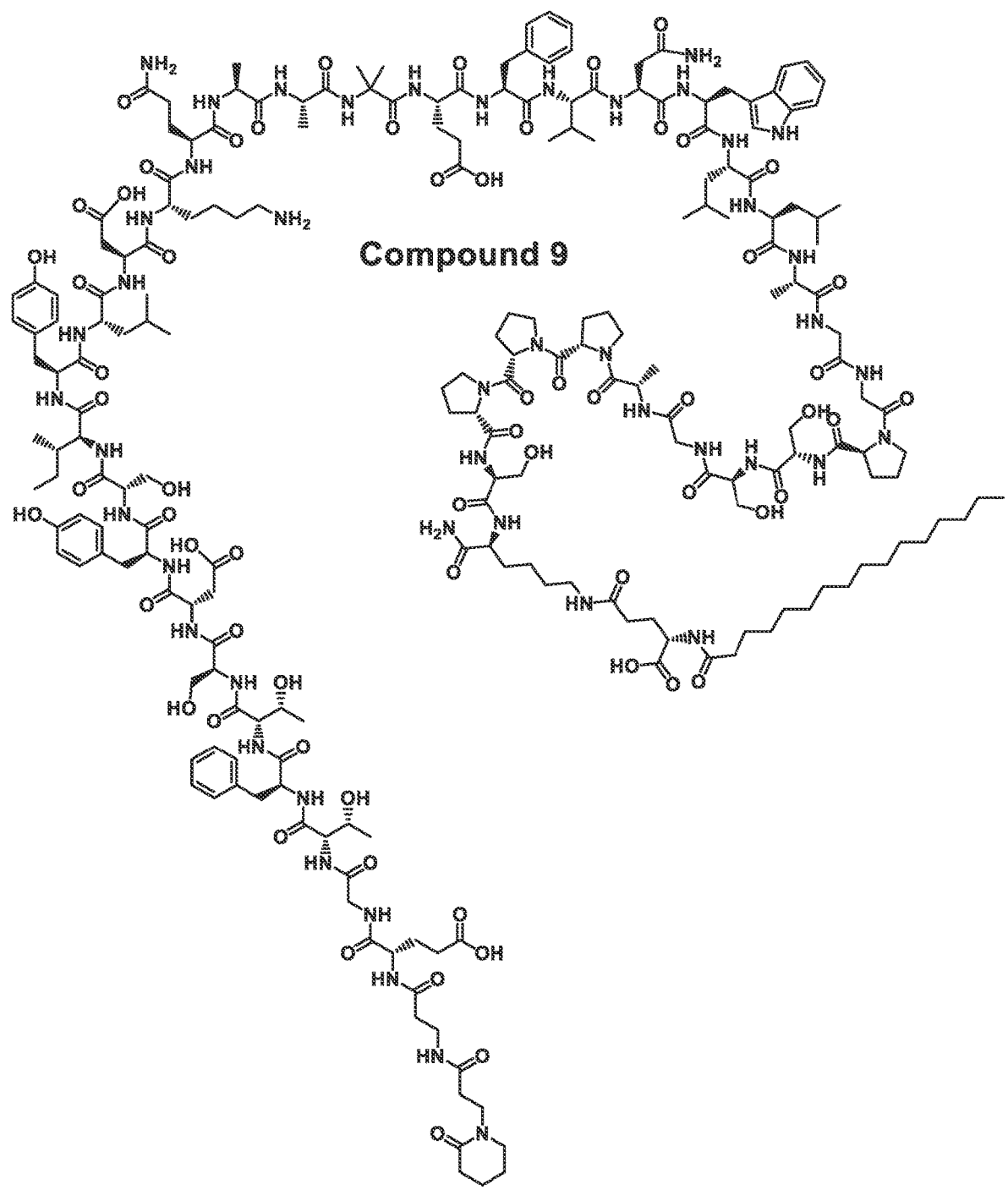
Compound 9
Cont'd

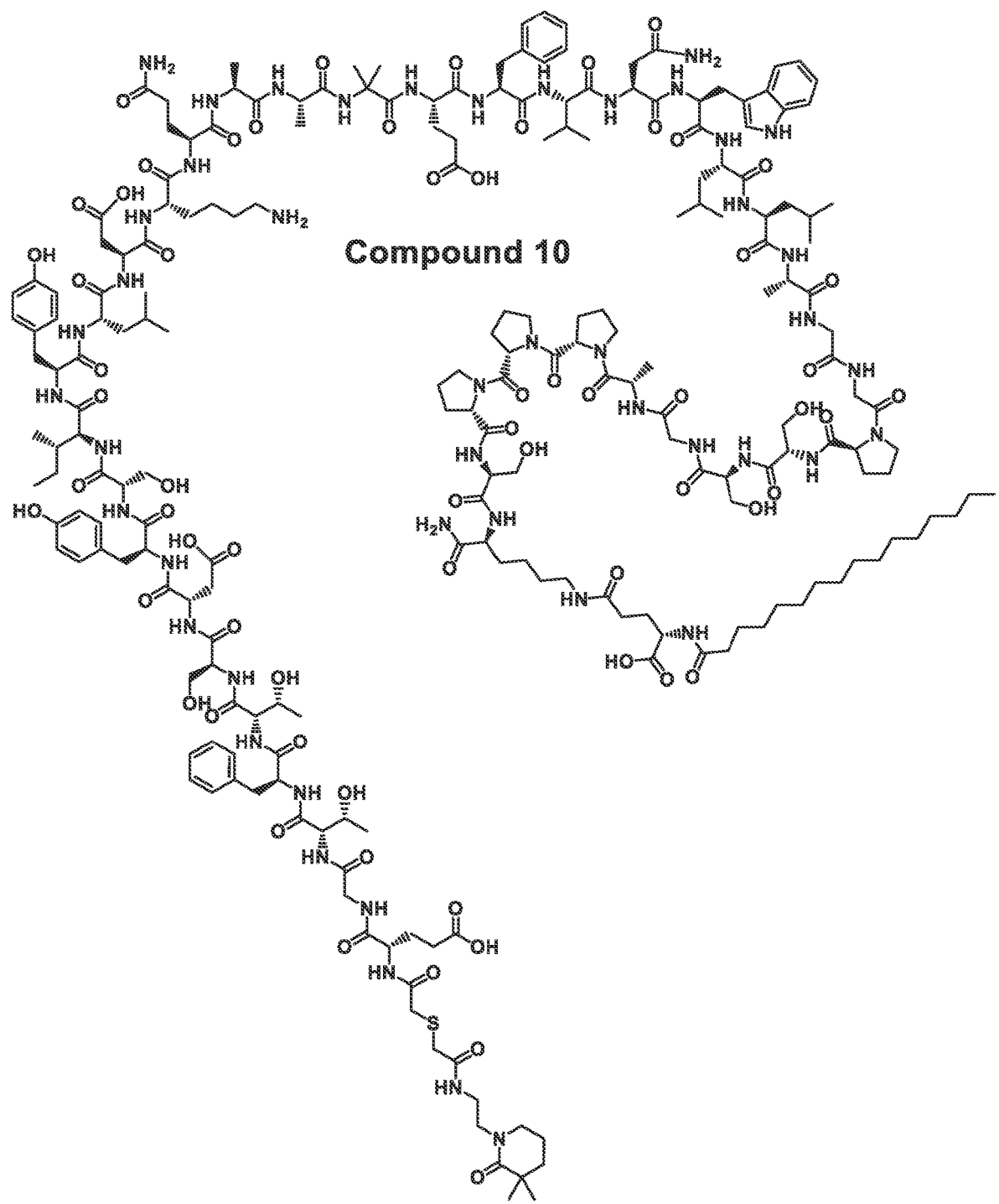
Compound 10
Cont'd

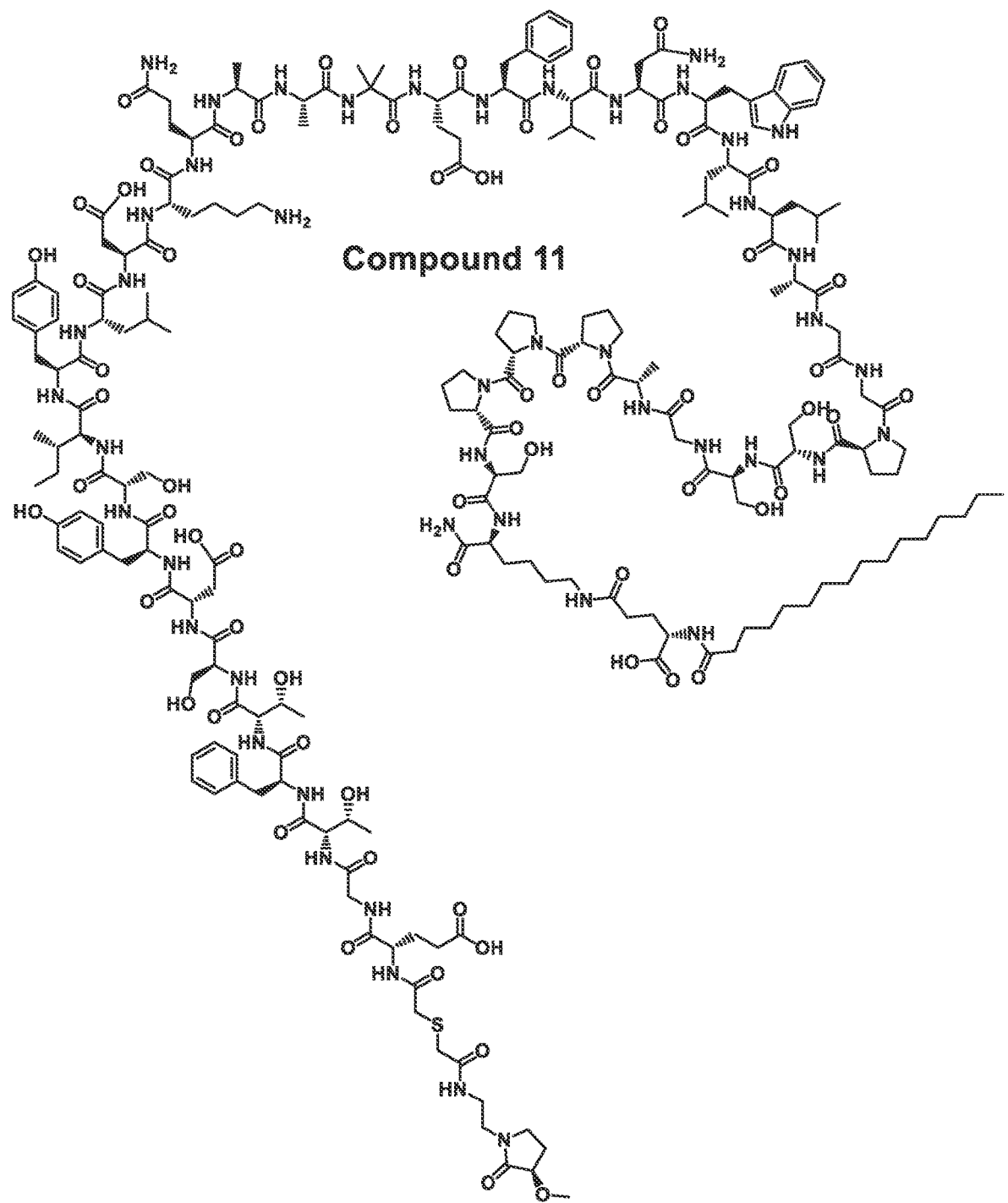
Compound 11
Cont'd

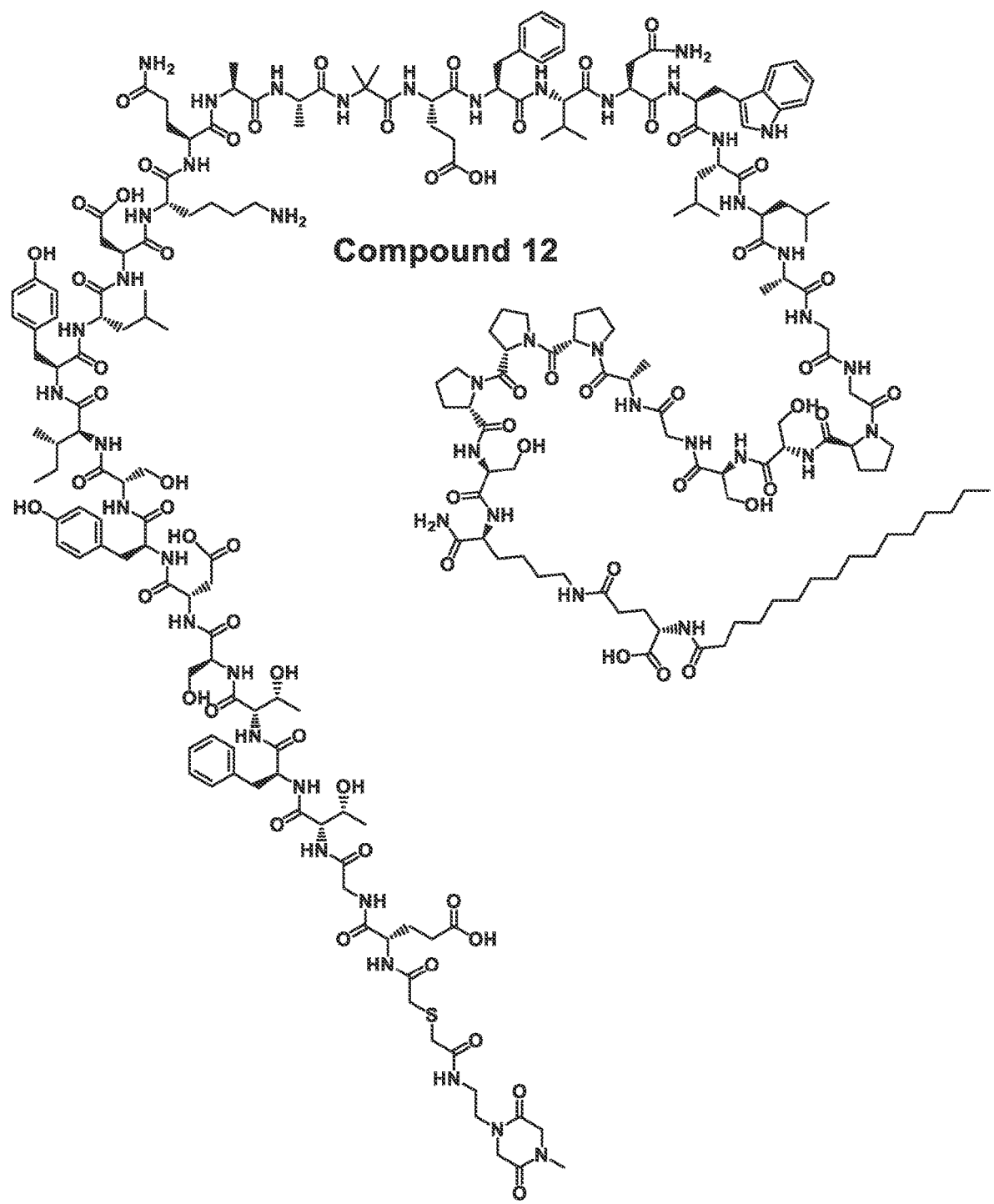
Compound 12
Cont'd

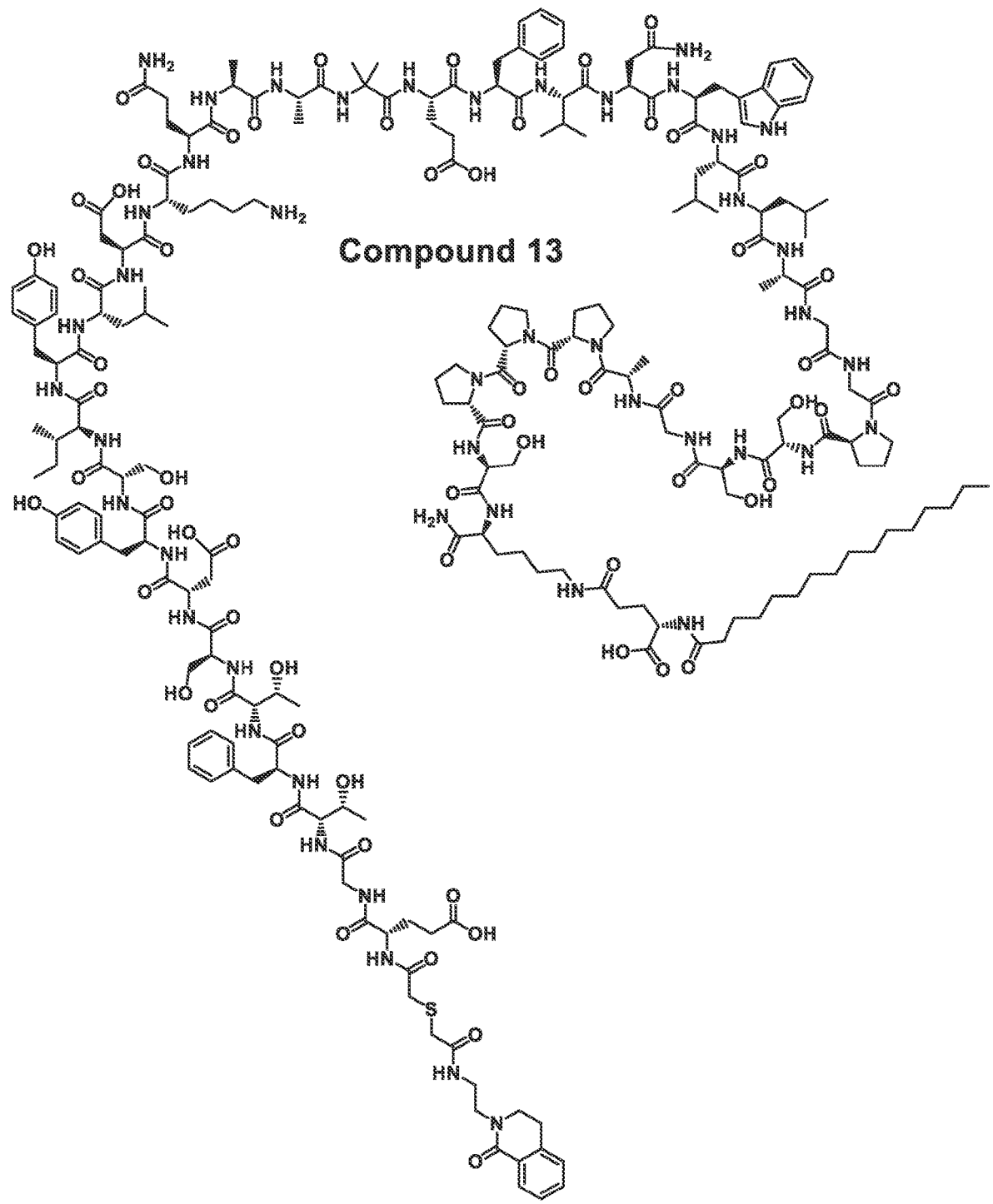
Compound 13
Cont'd

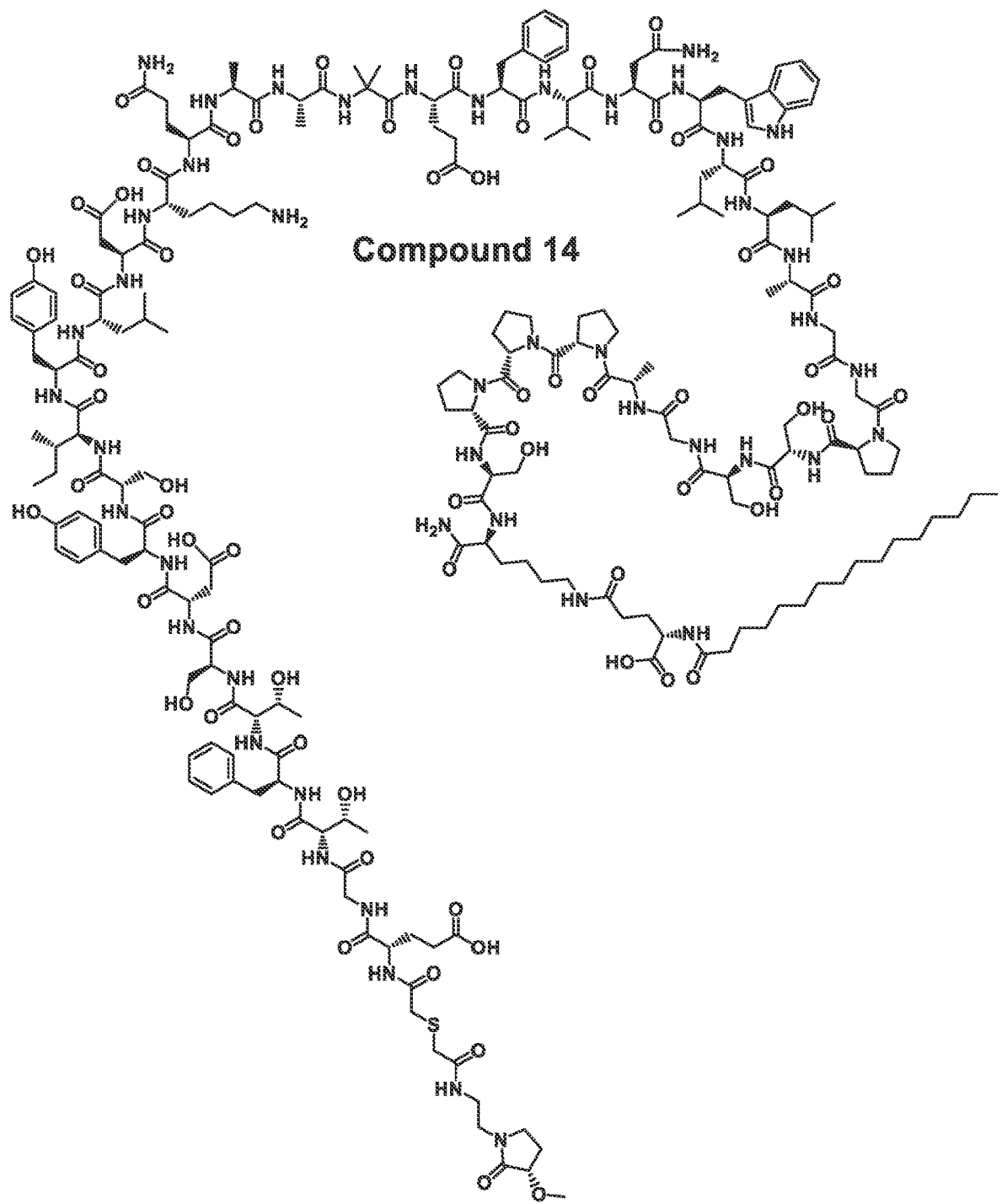
Compound 14
Cont'd

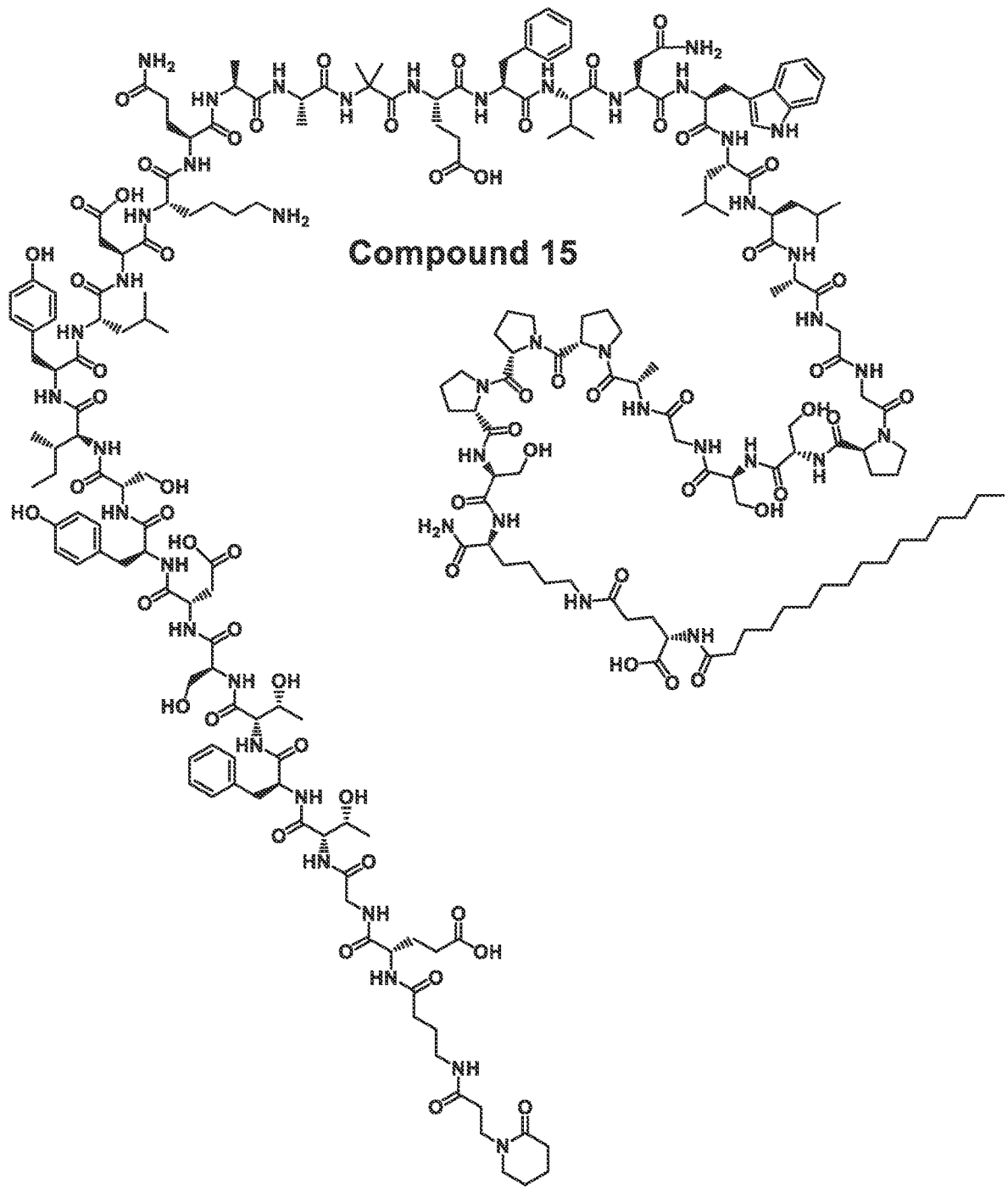
Compound 15
Cont'd

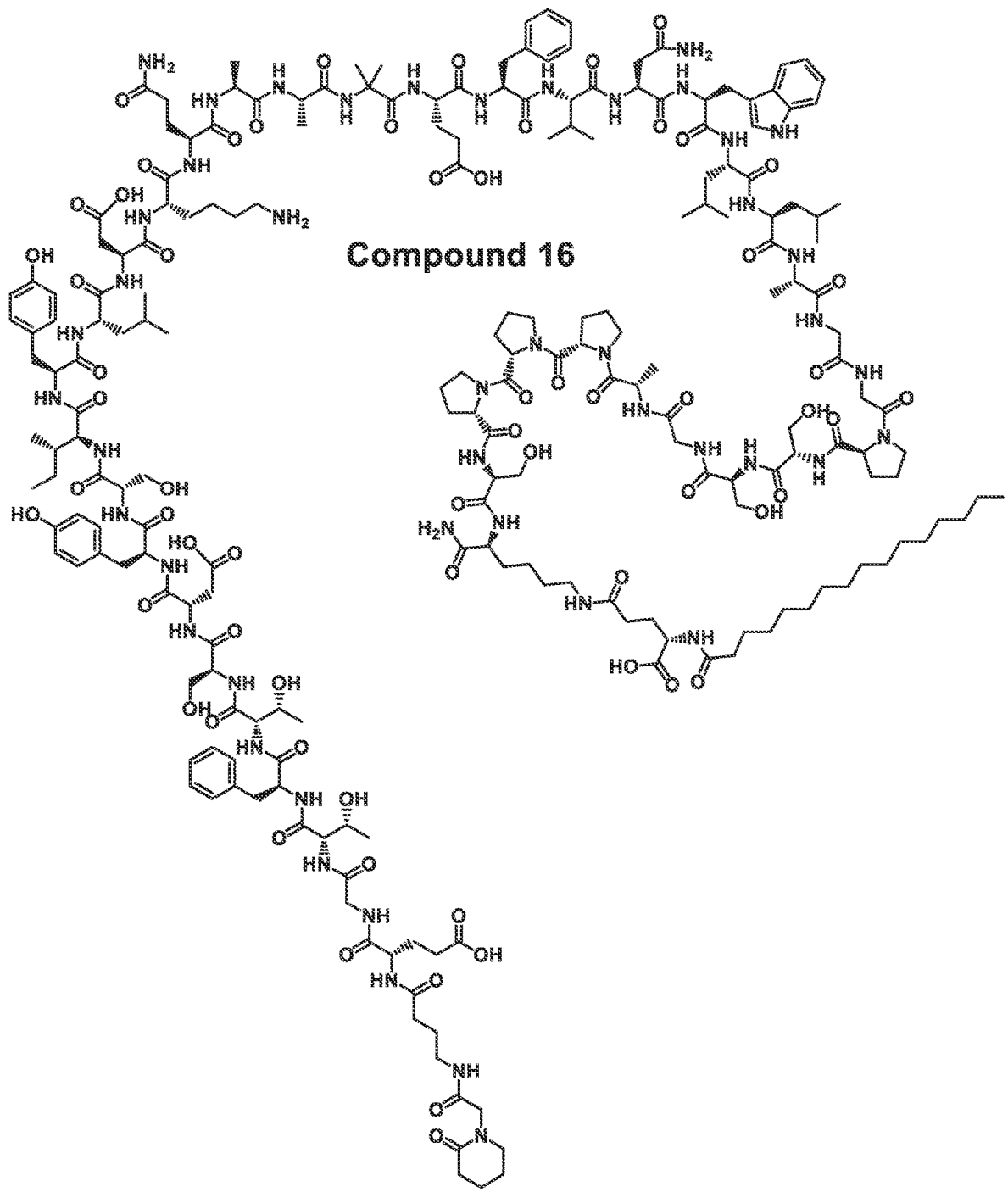
Compound 16
Cont'd

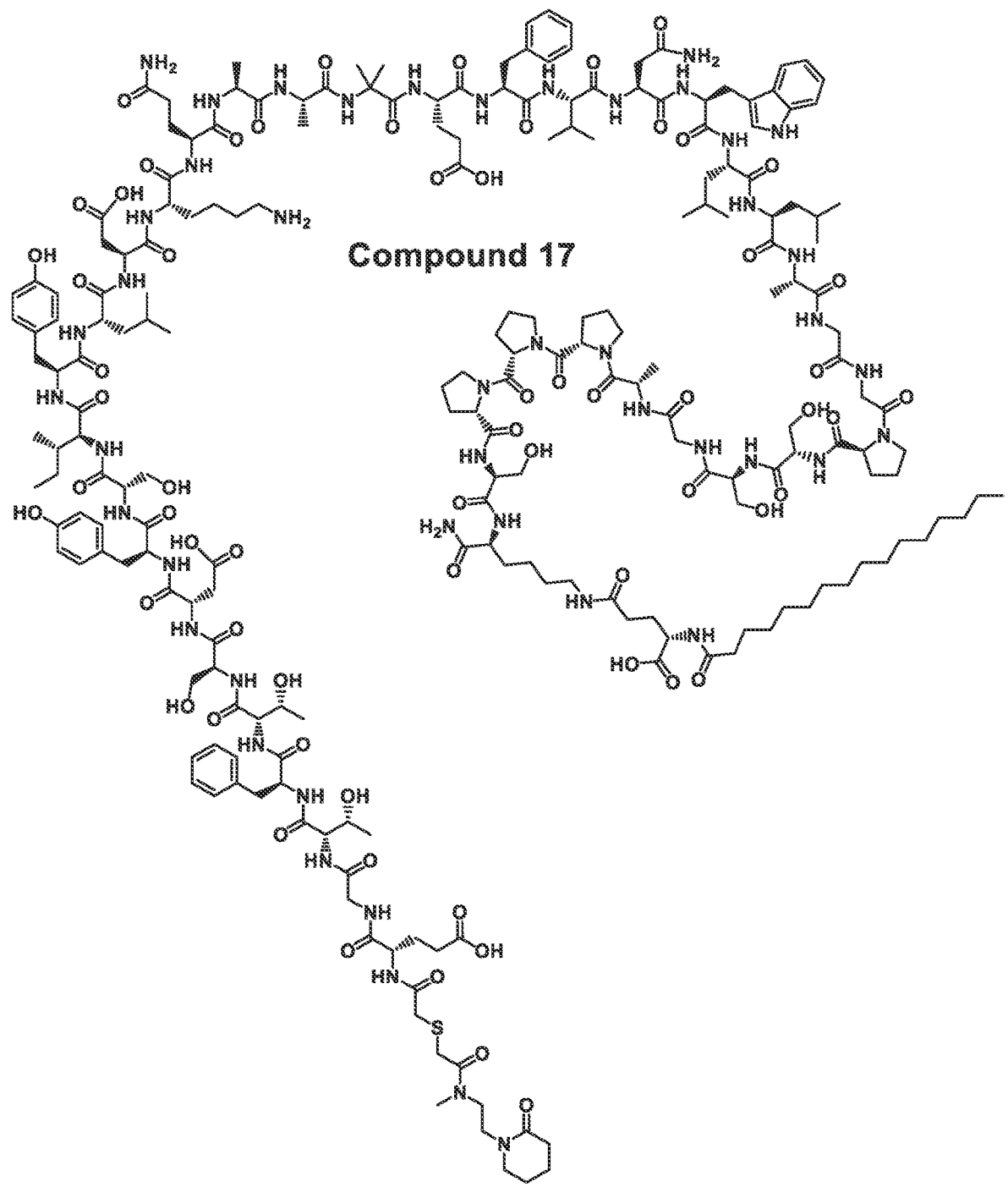
Compound 17
Cont'd

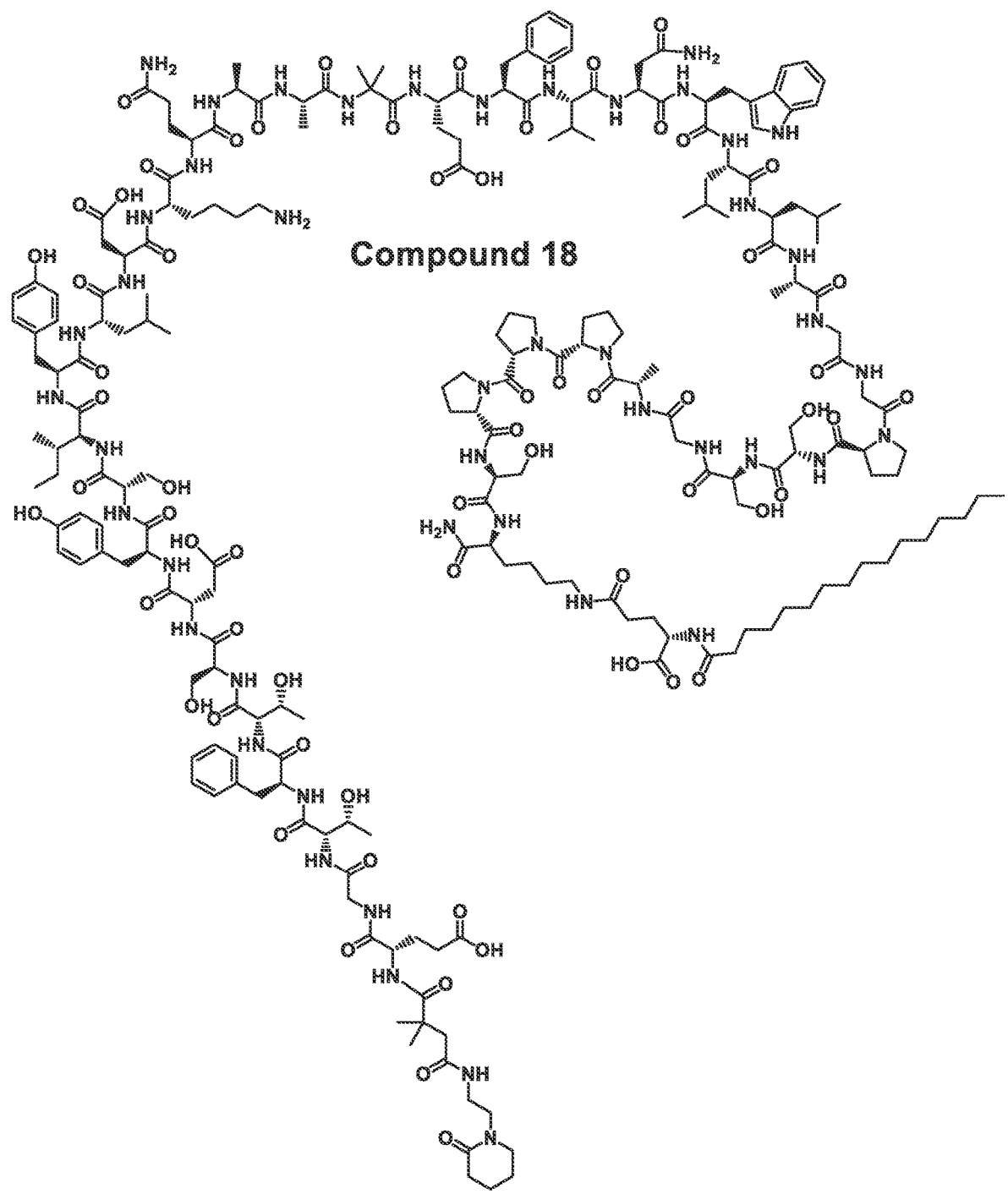
Compound 18
Cont'd

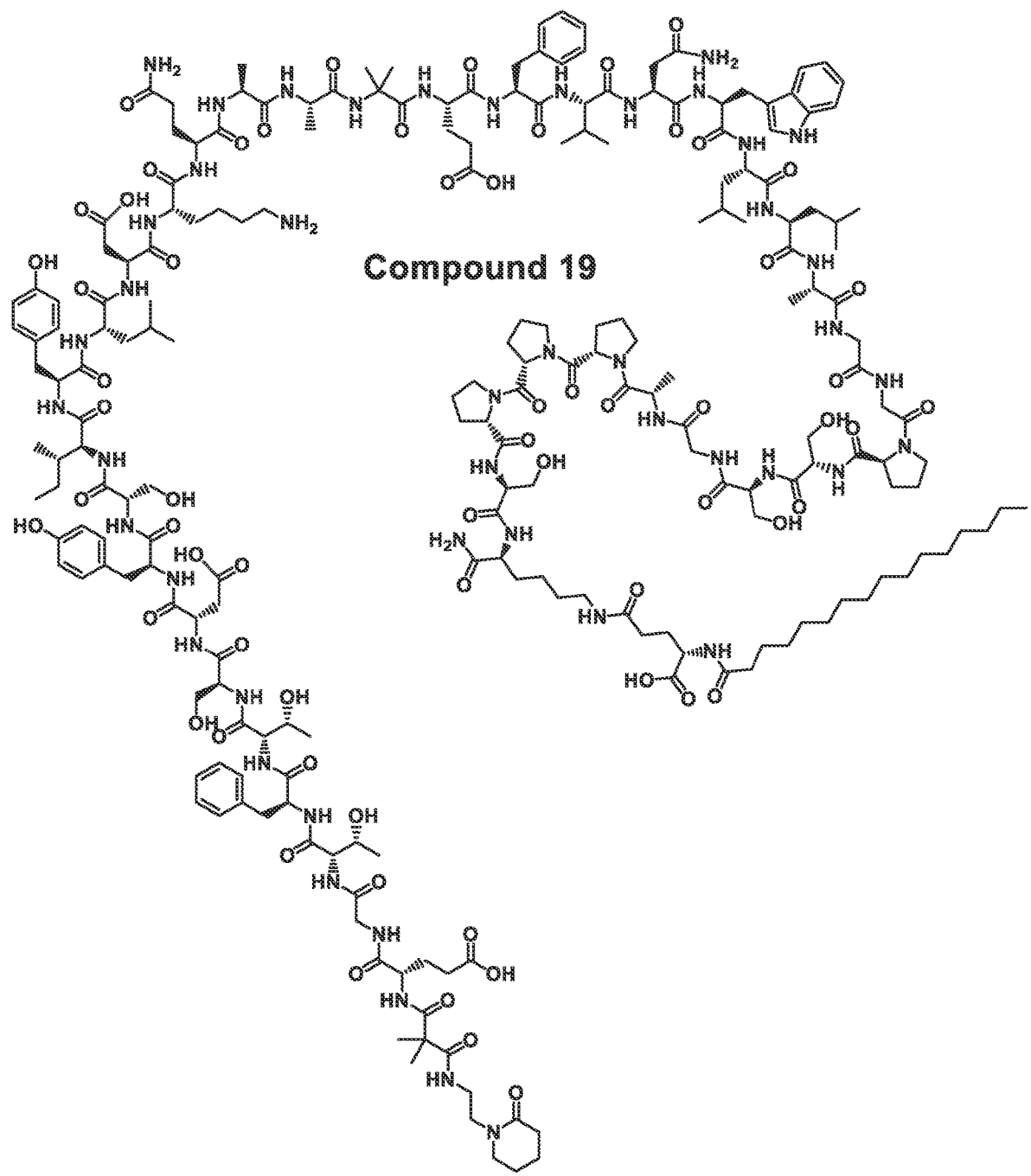
Compound 19
Cont'd

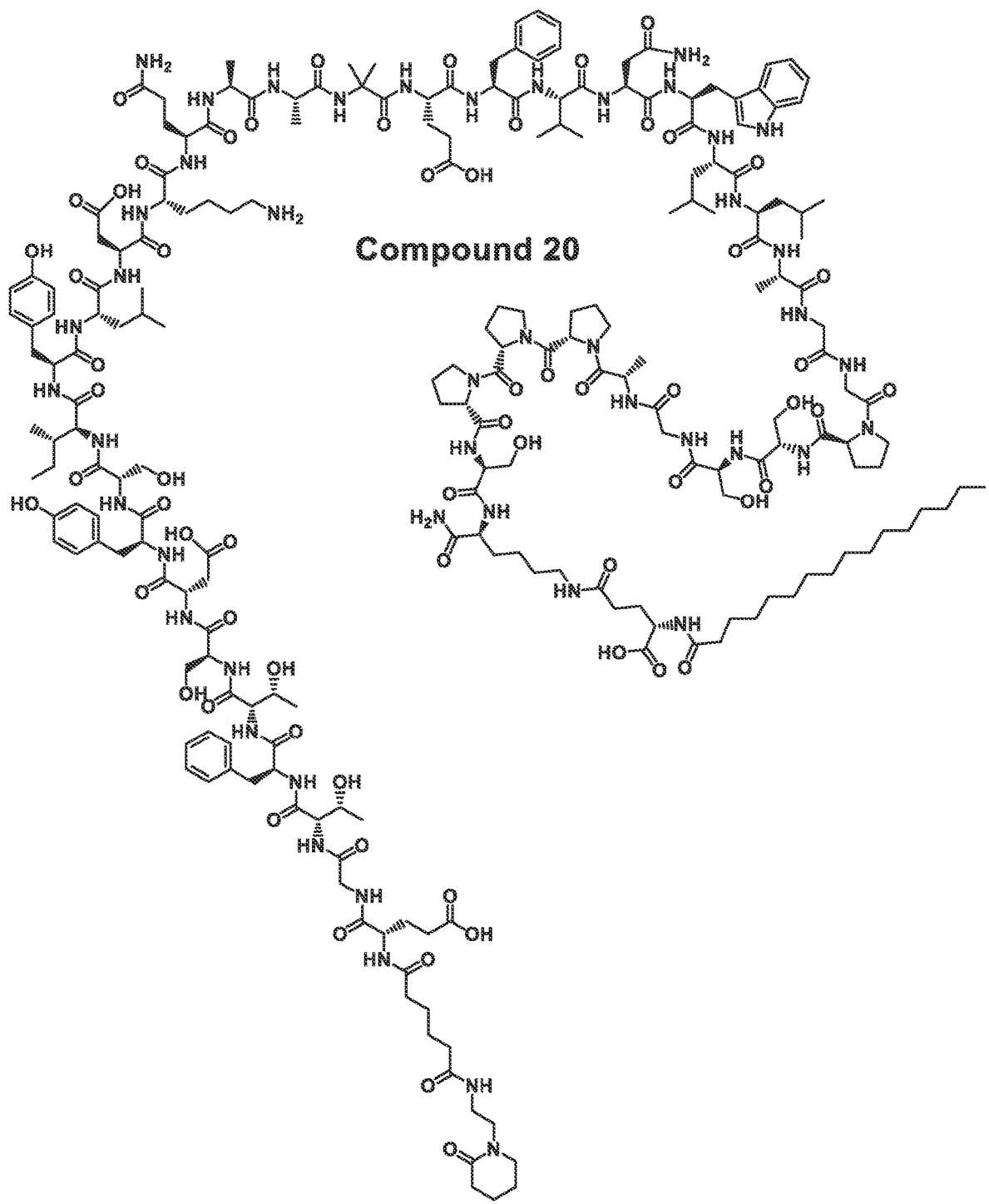
Compound 20
Cont'd

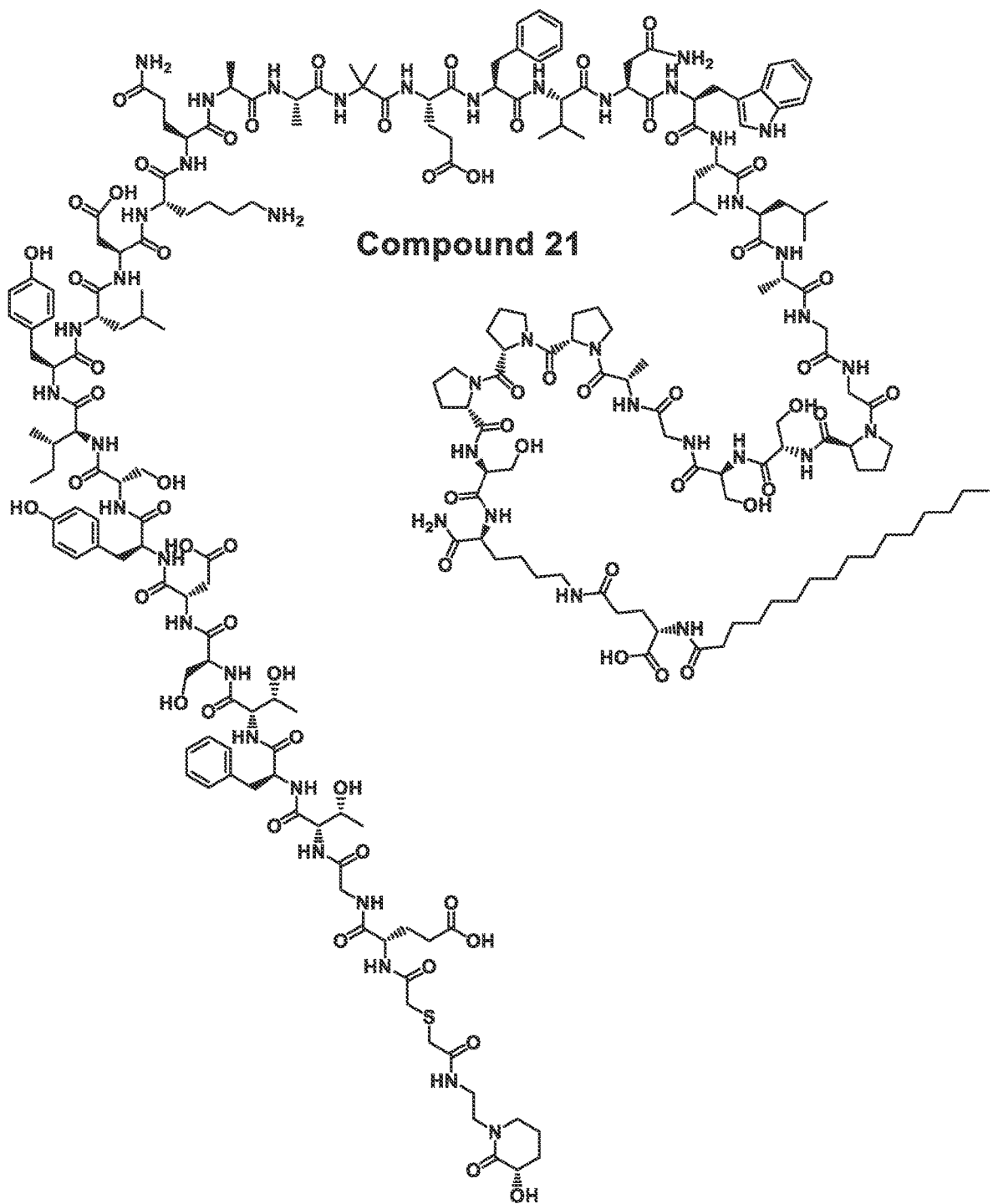
Compound 21
Cont'd

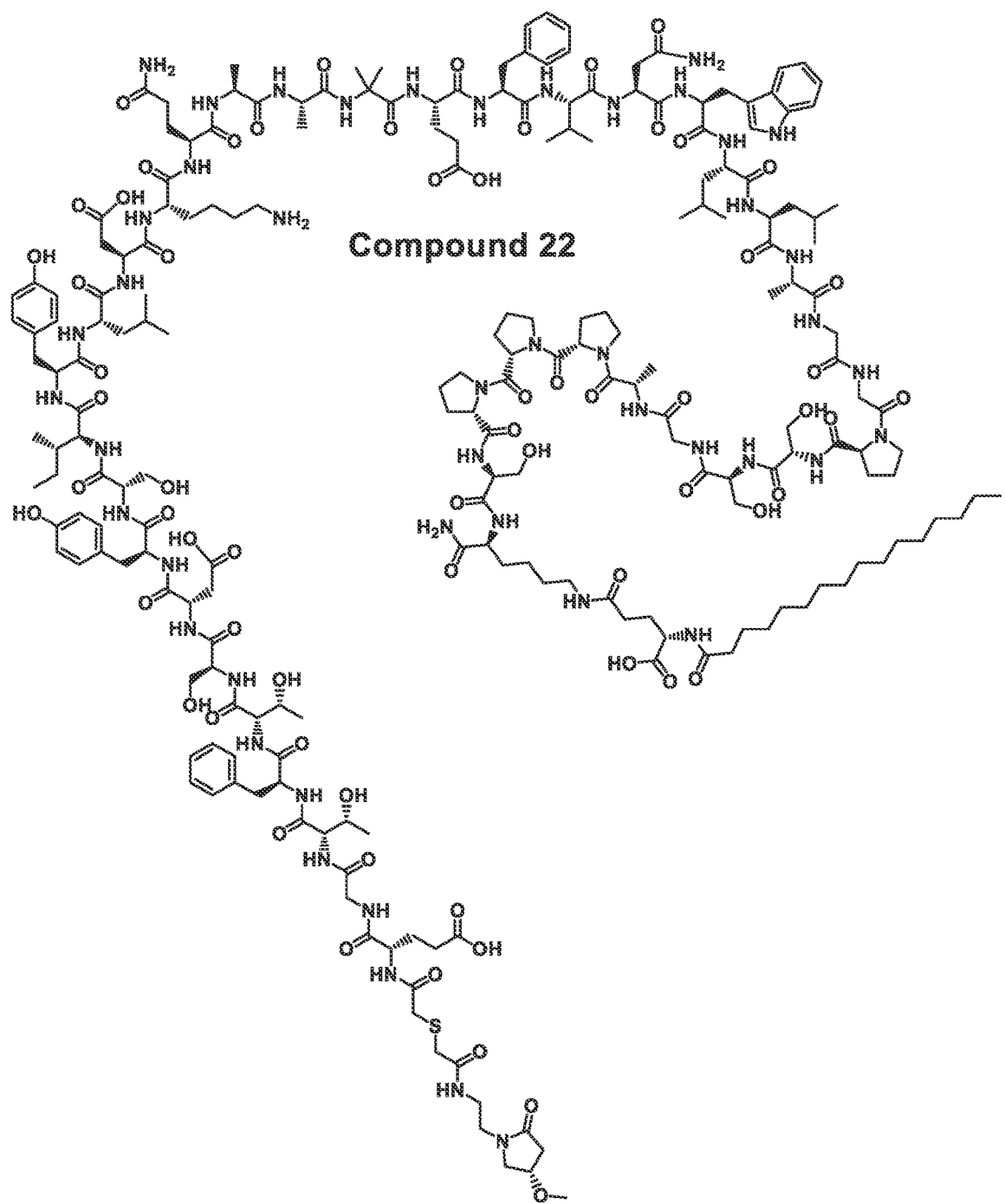
Compound 22
Cont'd

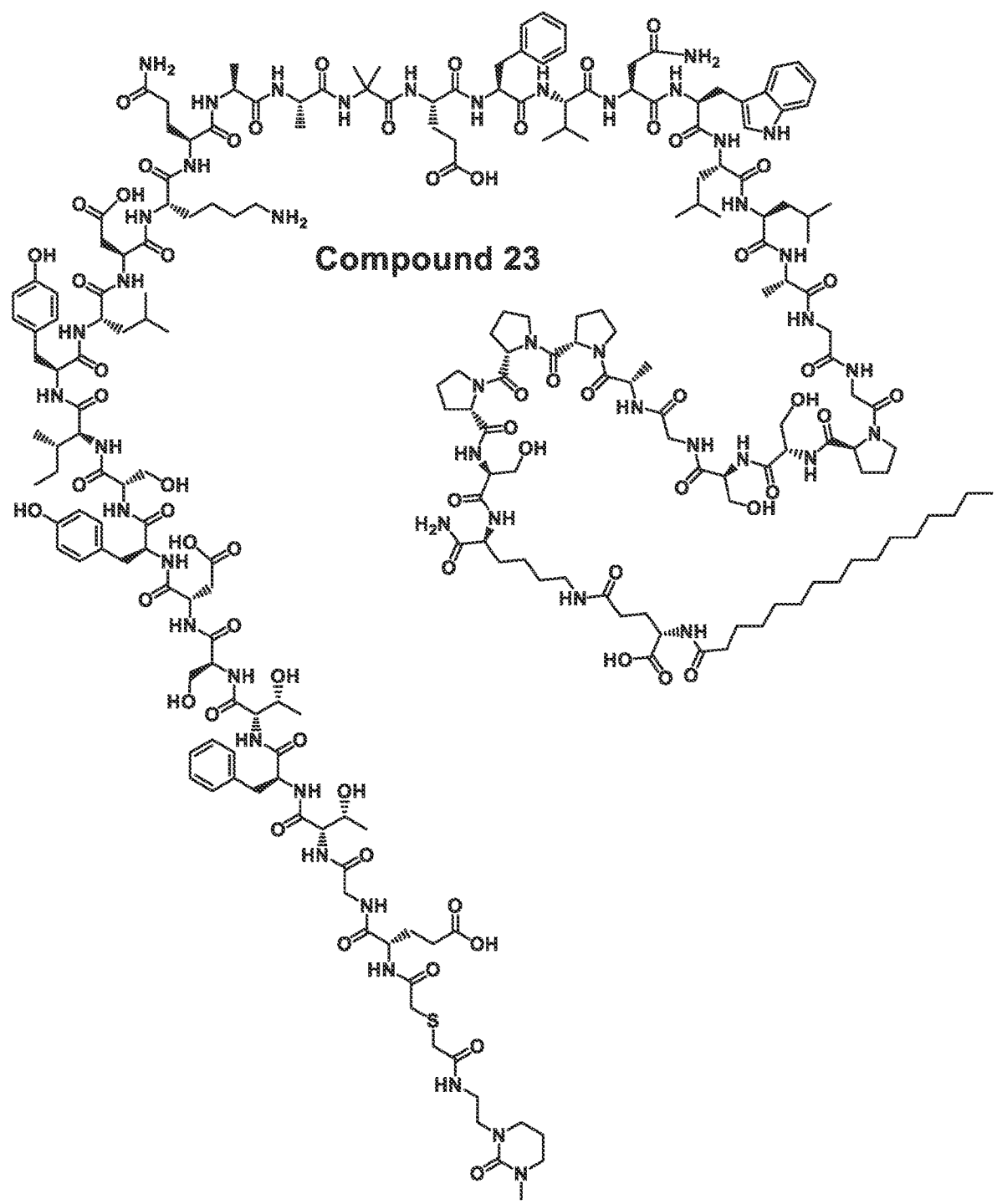
Cont'd

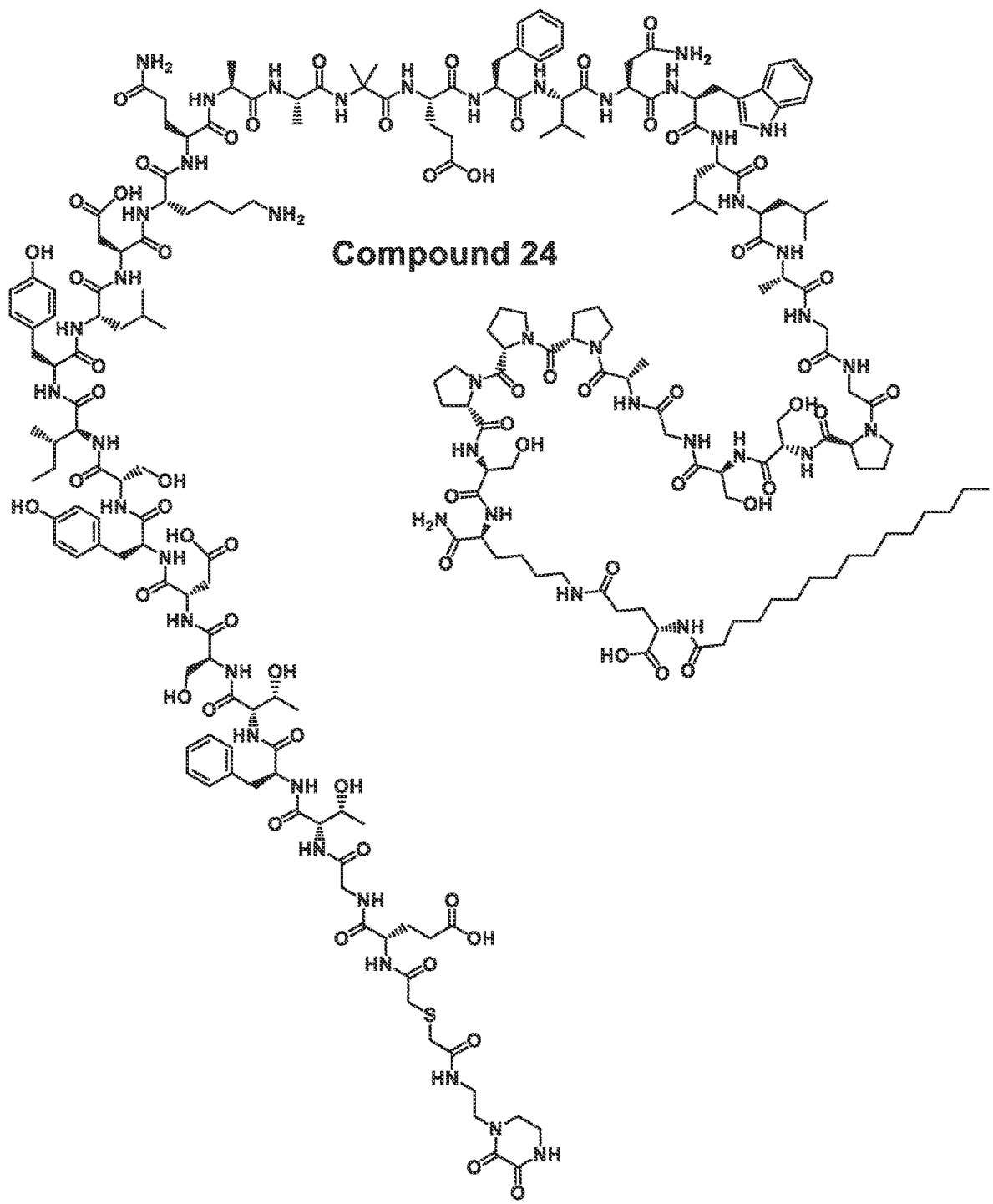
Compound 24
Cont'd

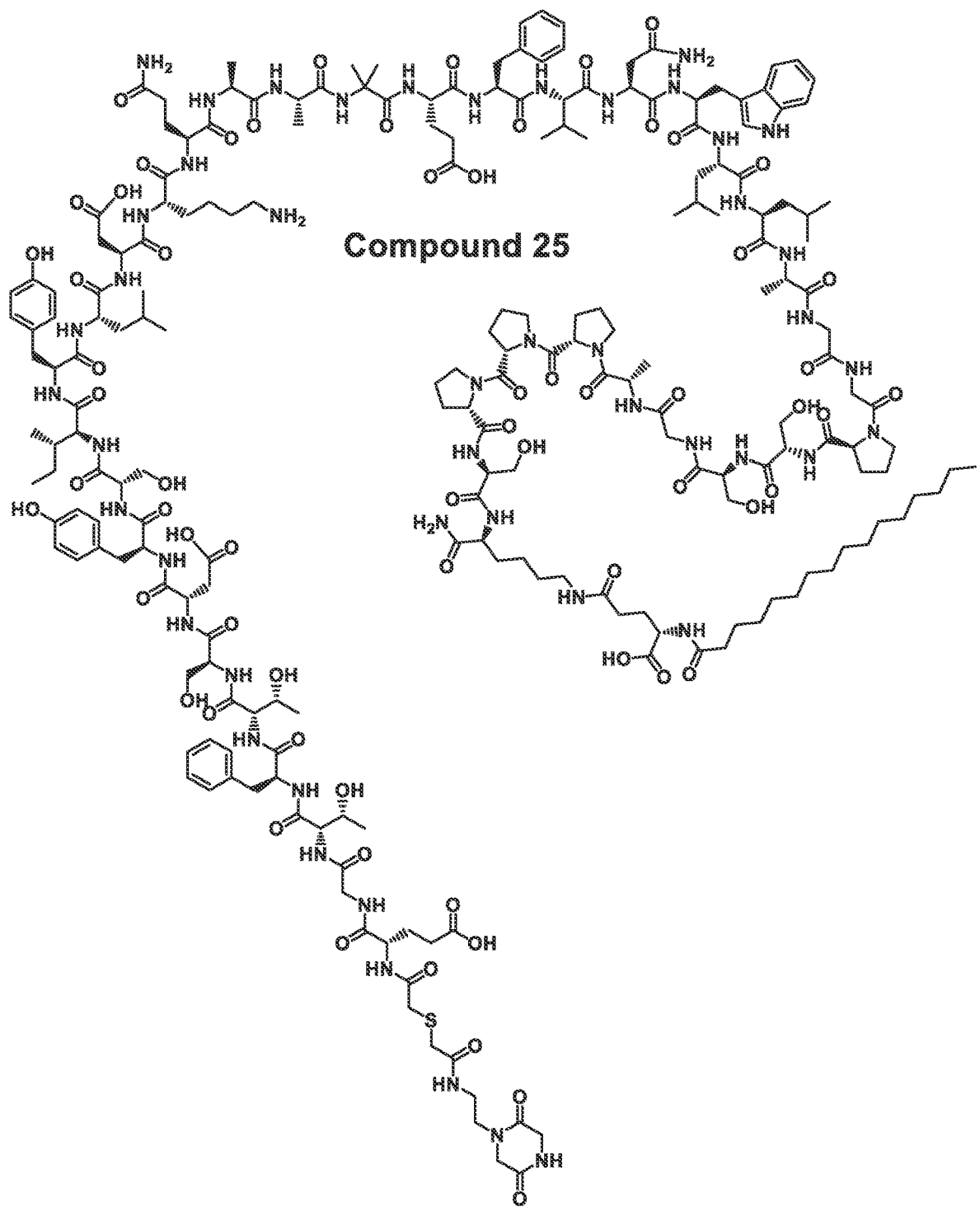
Compound 25
Cont'd

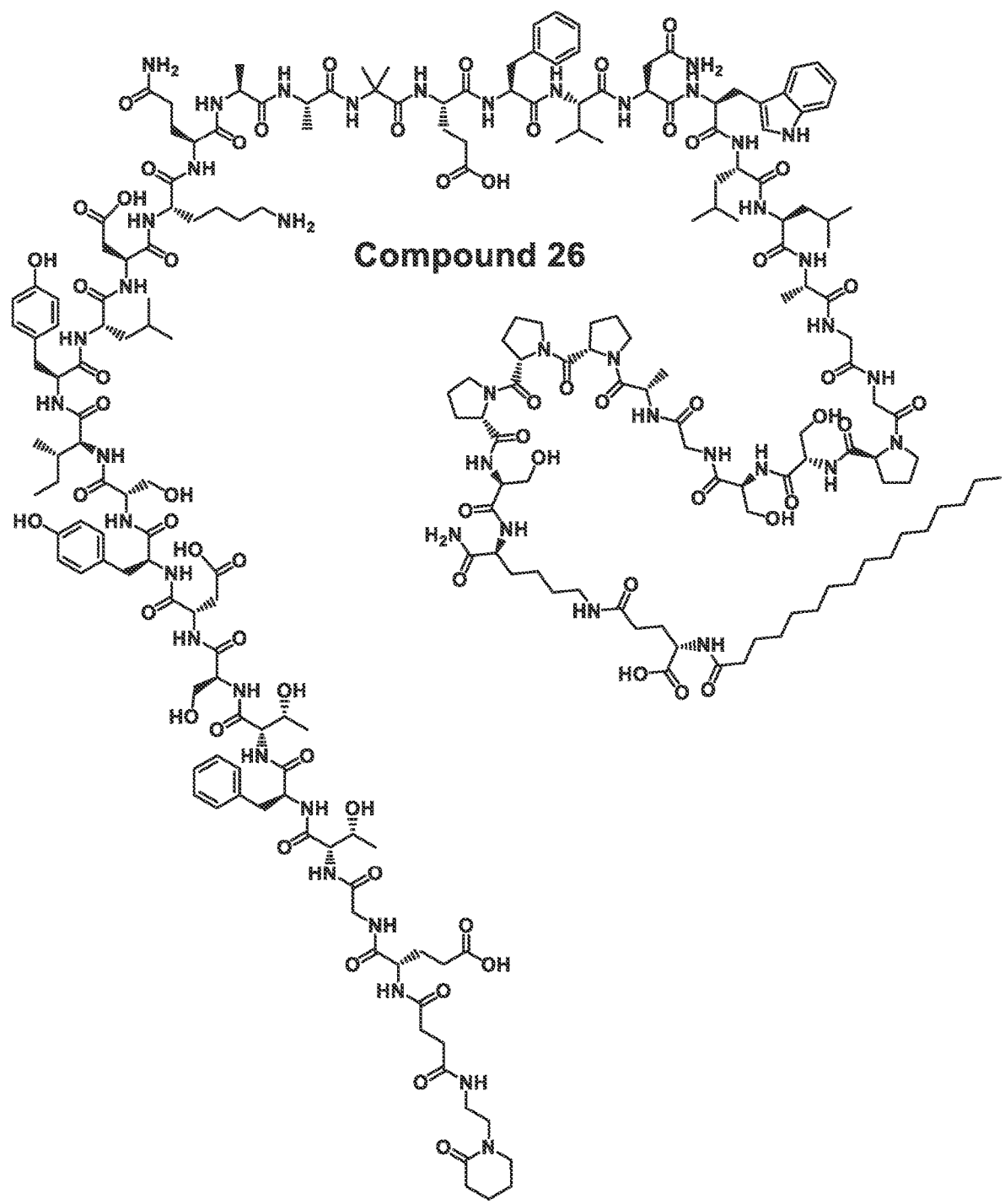
Compound 26
Cont'd

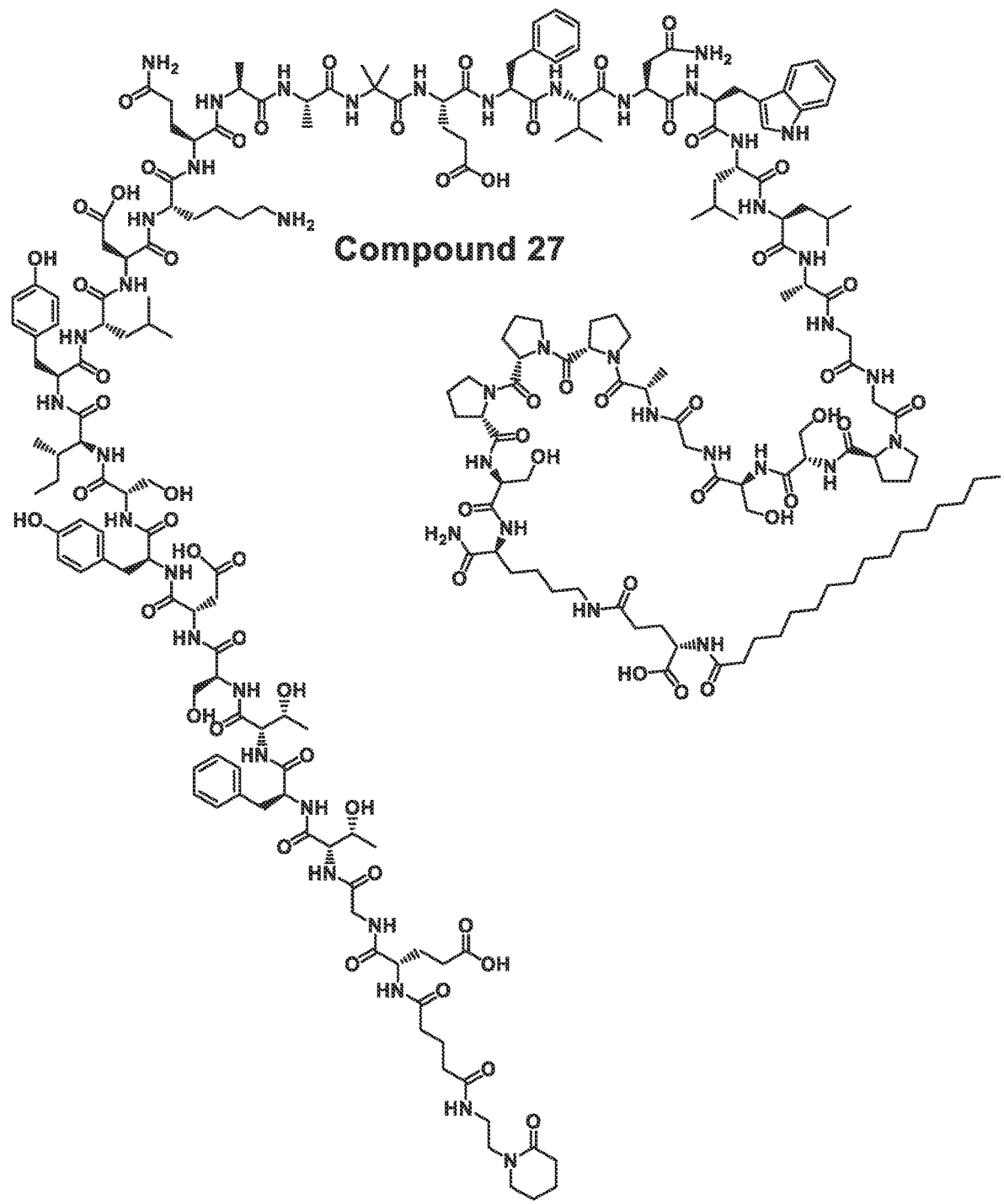
Compound 27
Cont'd

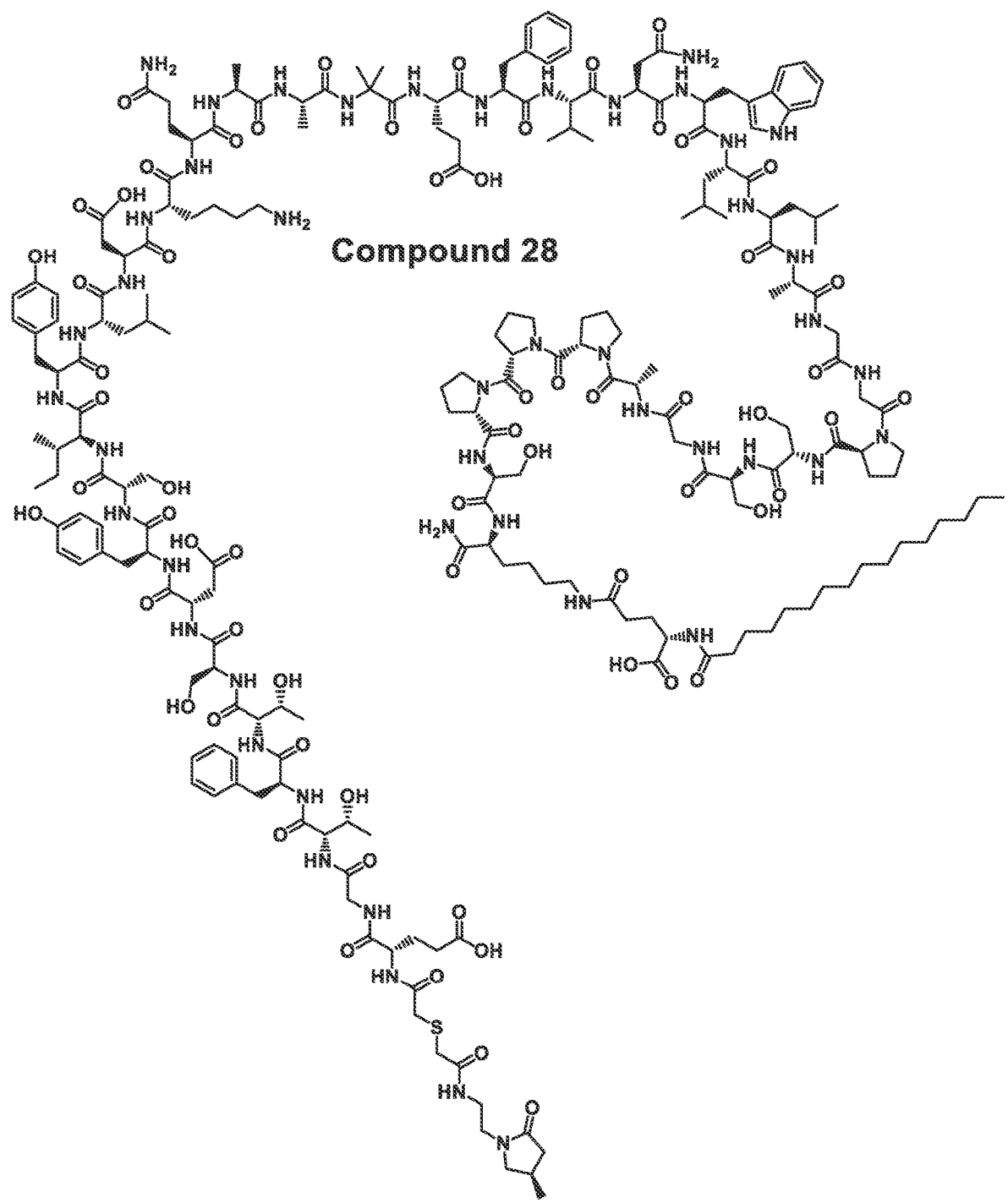
Compound 28
Cont'd

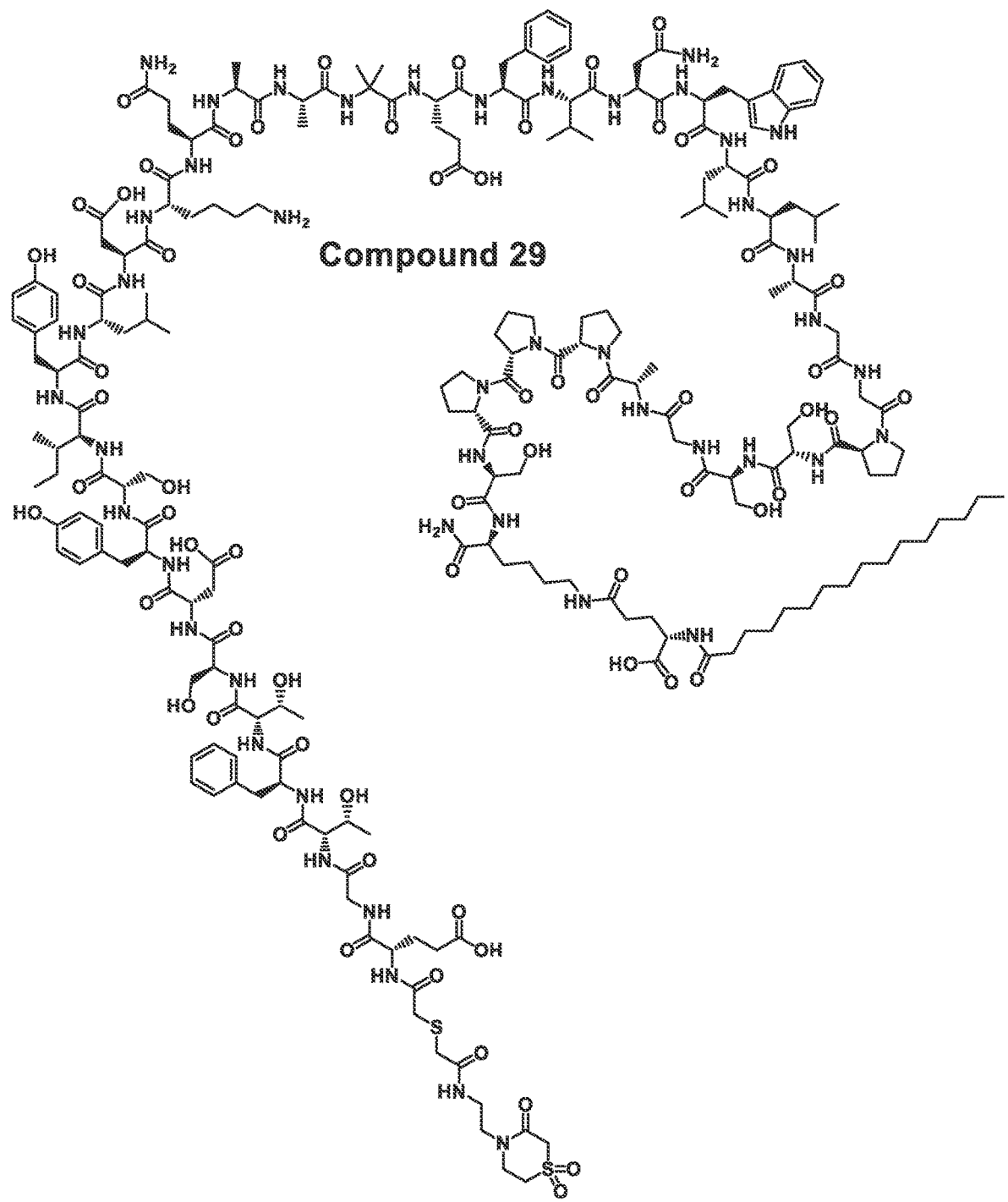
Compound 29
Cont'd

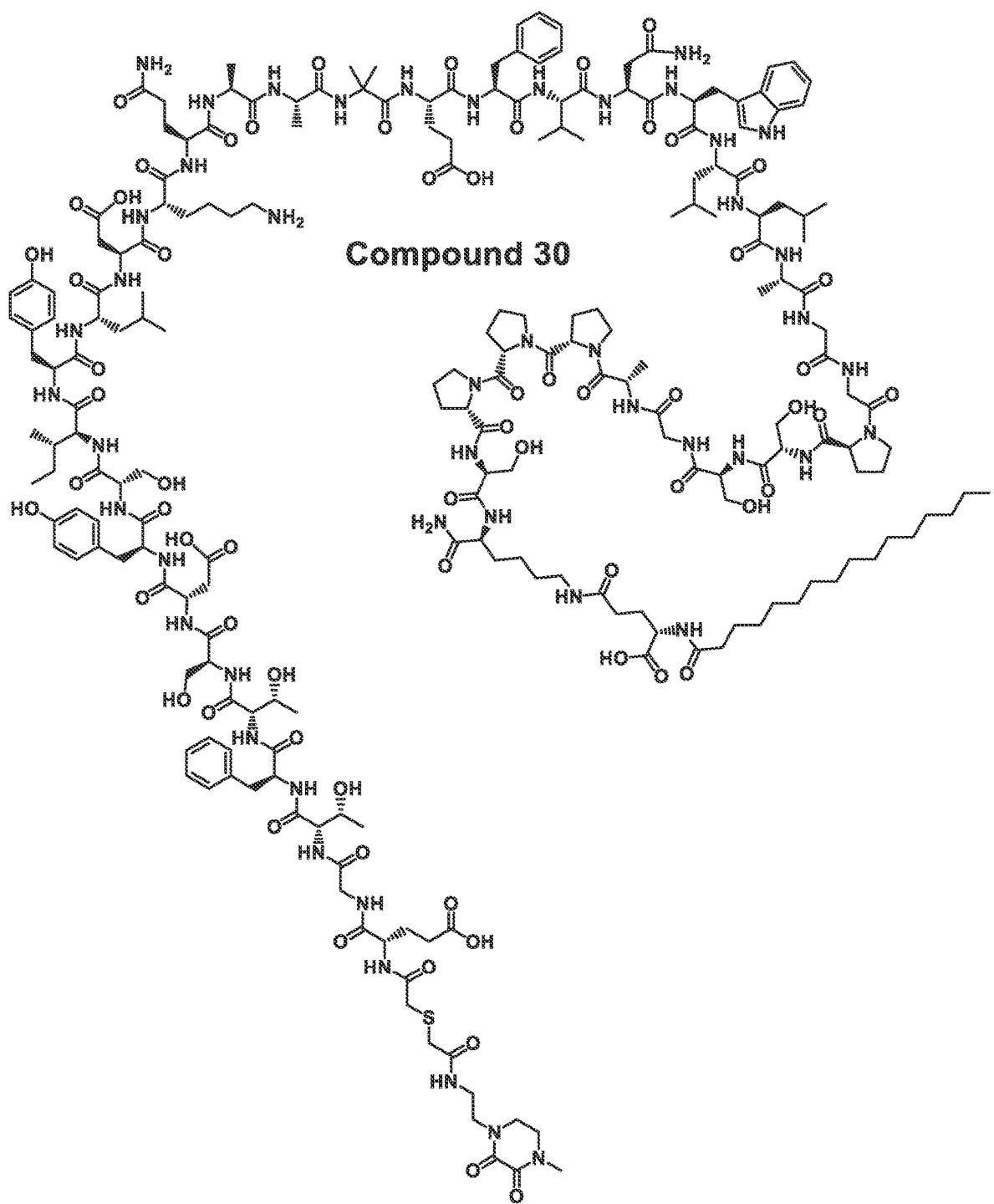
Compound 30
Cont'd

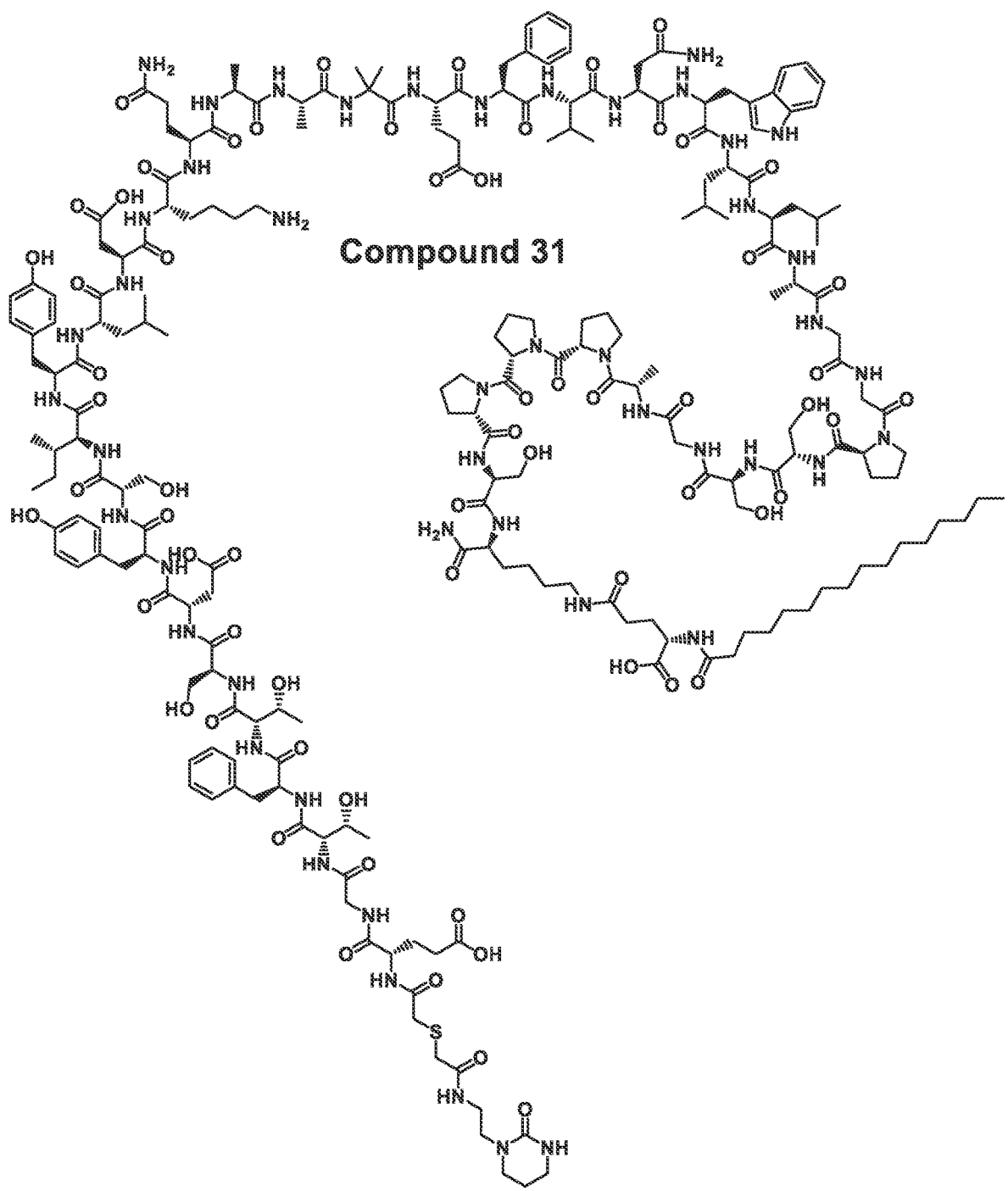
Compound 31
Cont'd

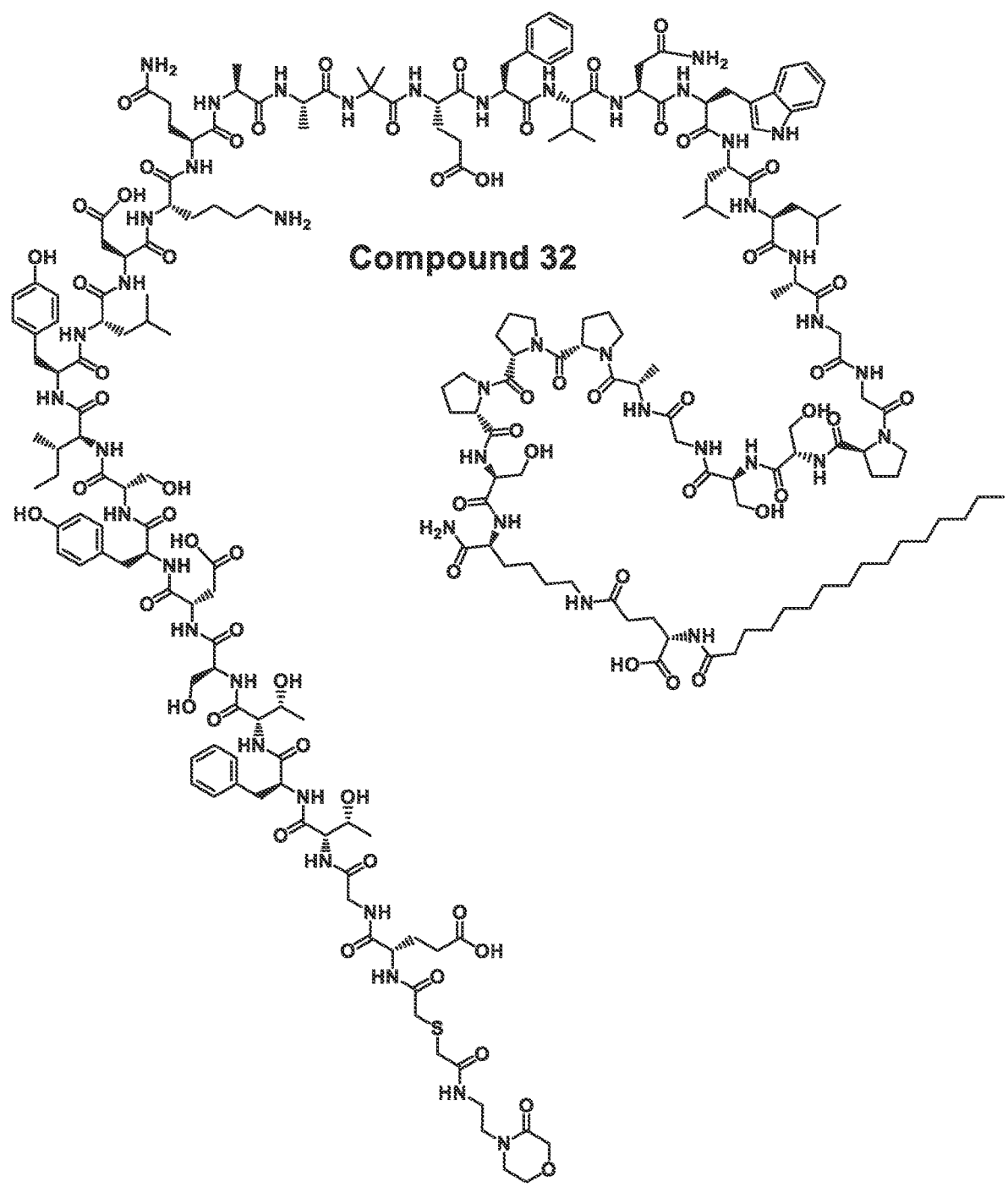
Compound 32
Cont'd

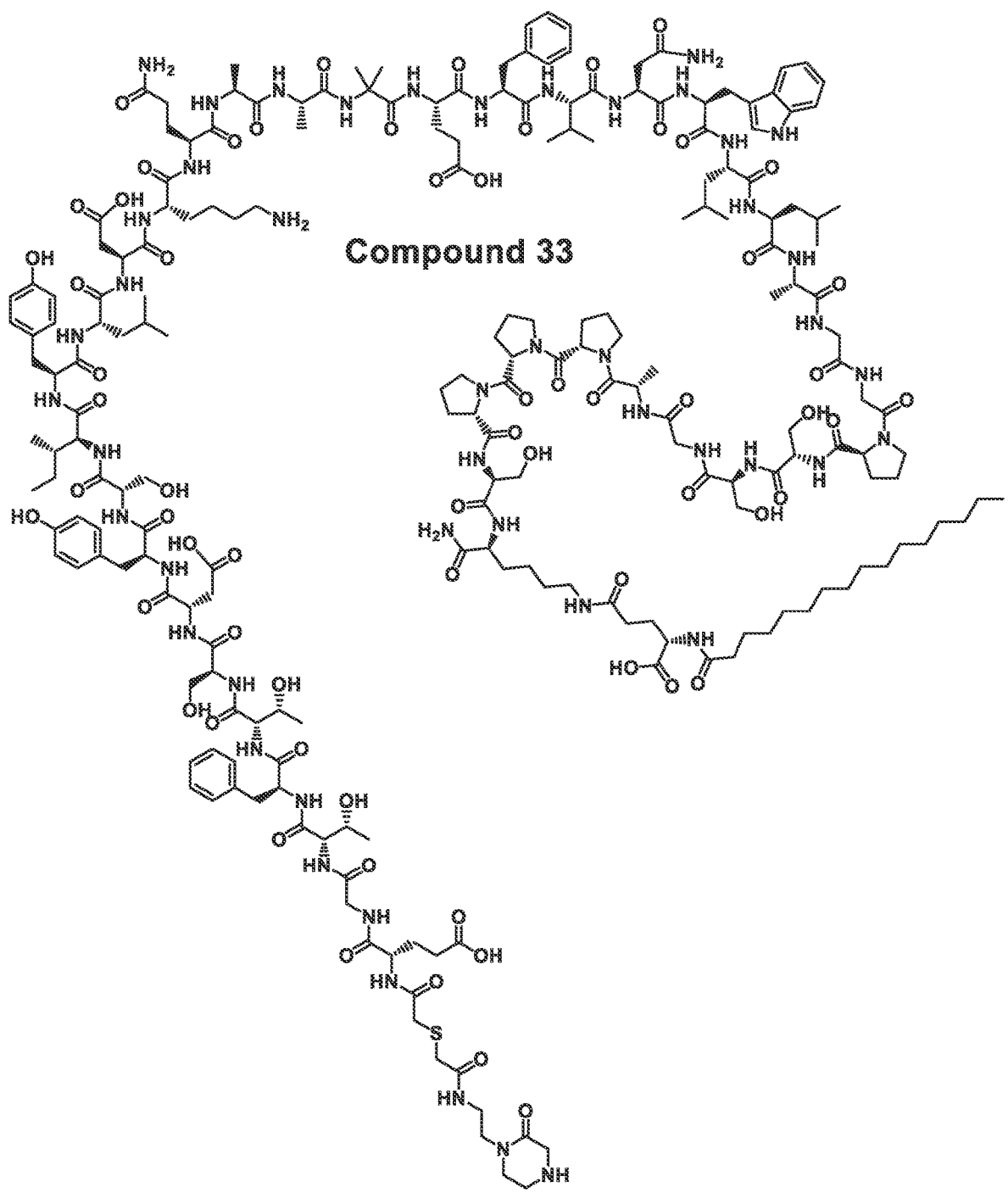
Compound 33
Cont'd

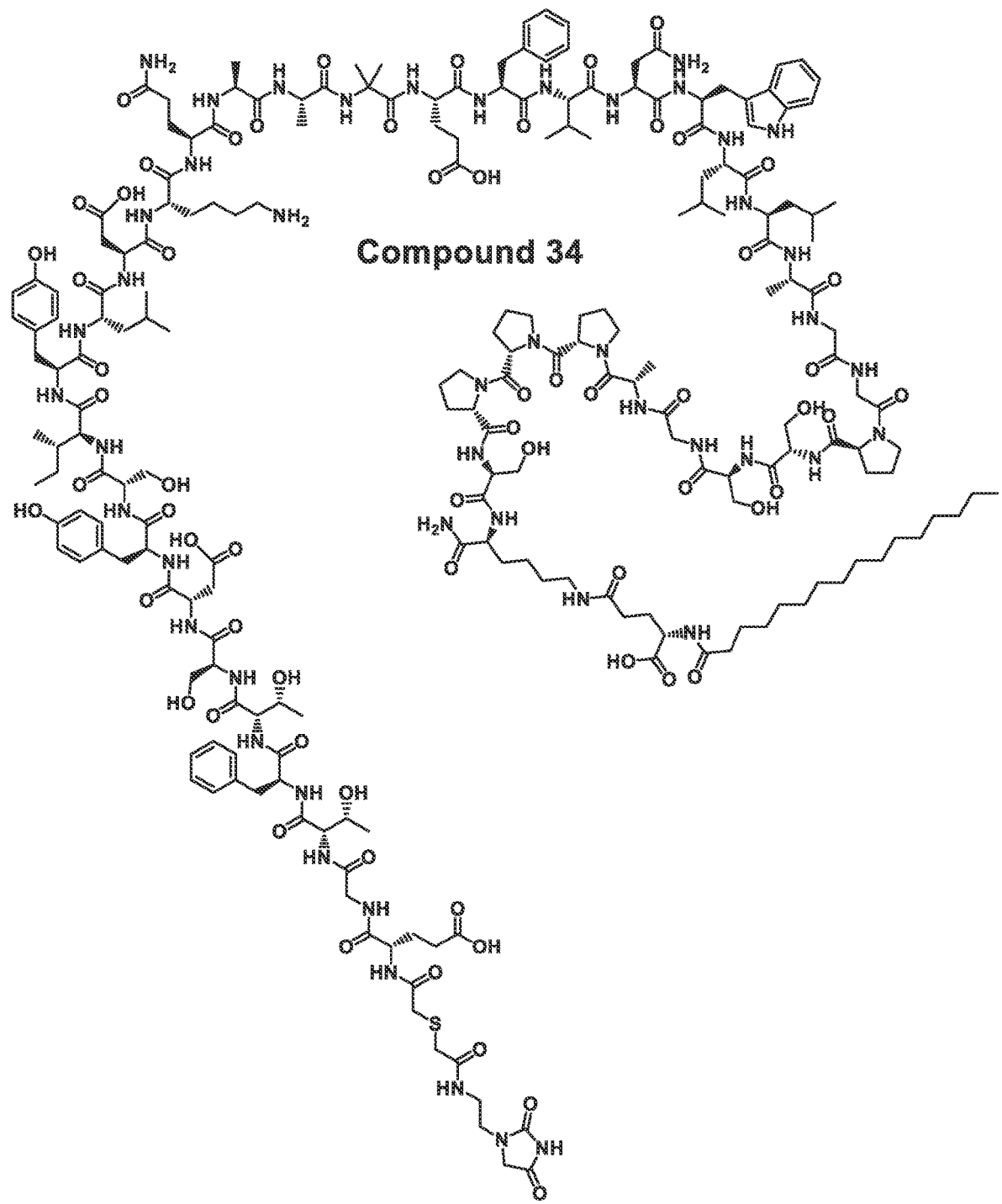
Compound 34
Cont'd

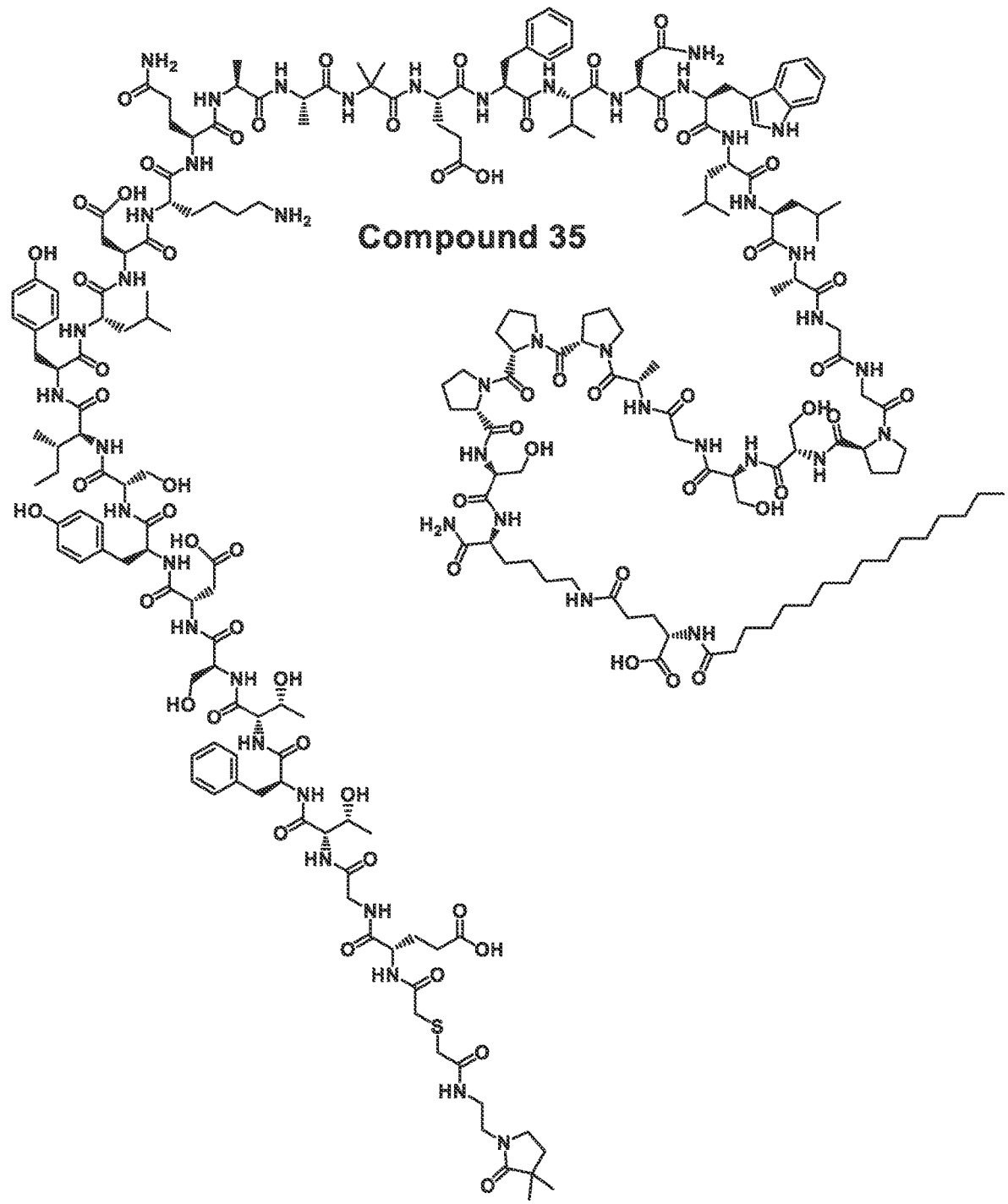
Compound 35
Cont'd

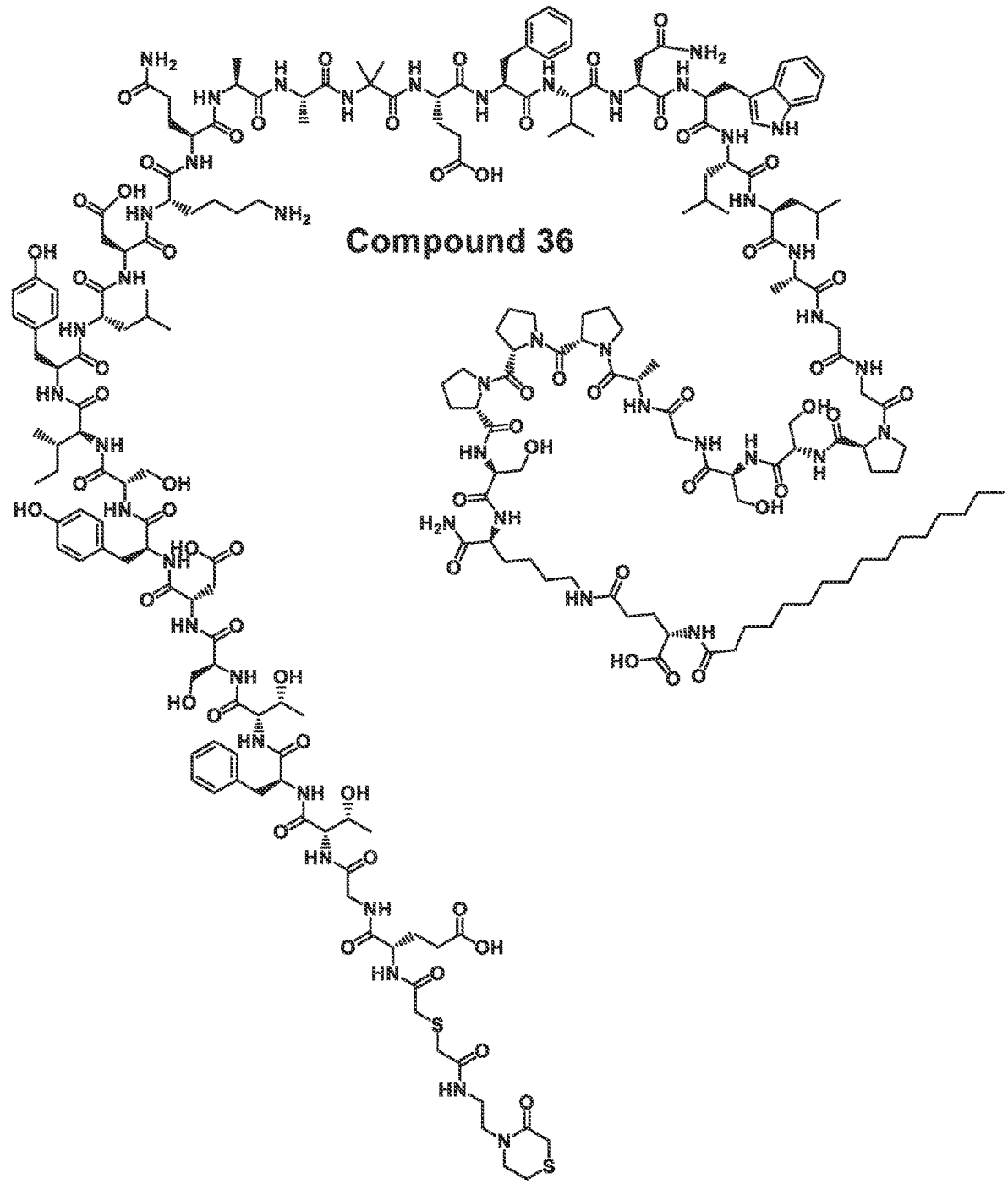
Compound 36
Cont'd

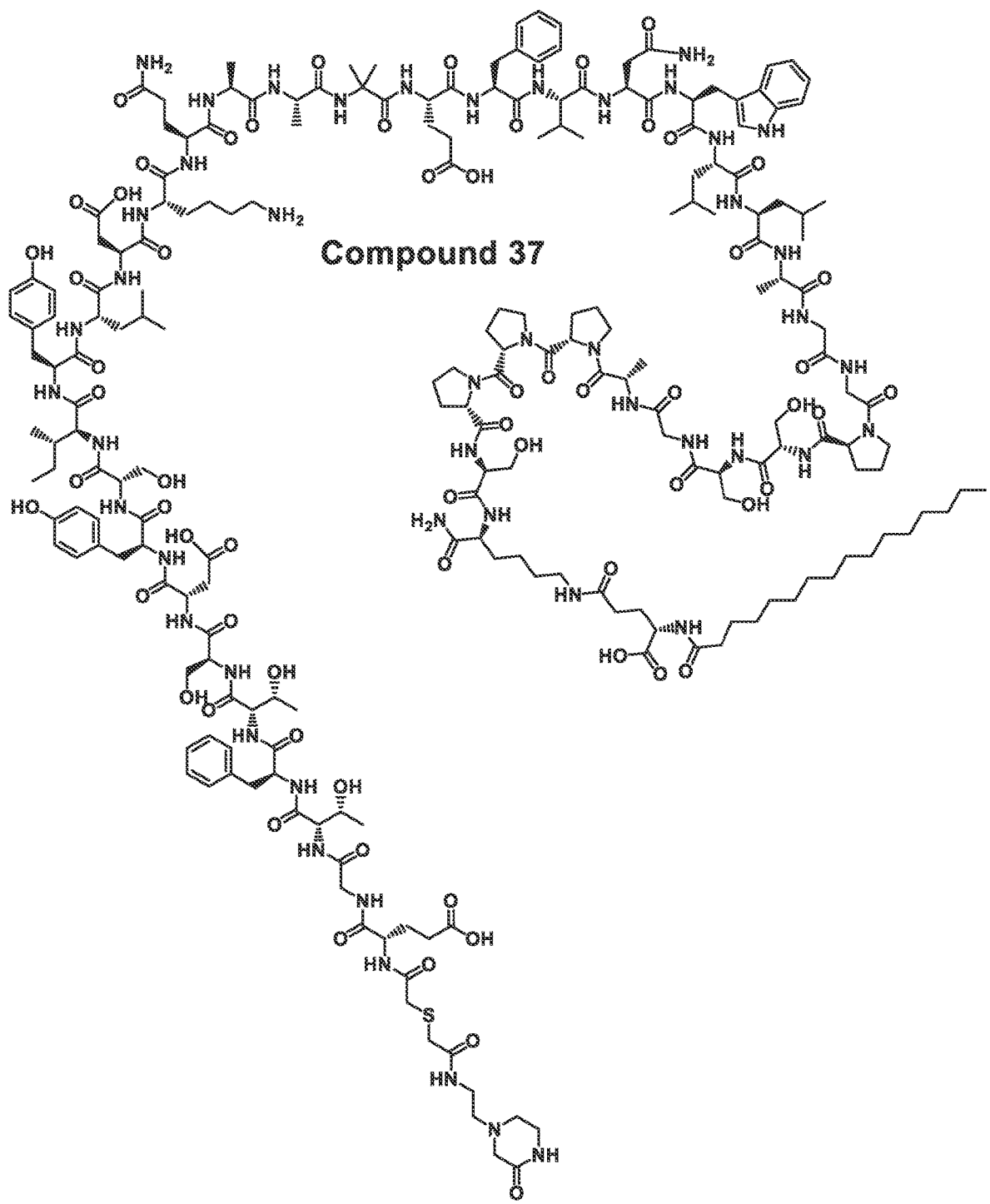
Compound 37
Cont'd

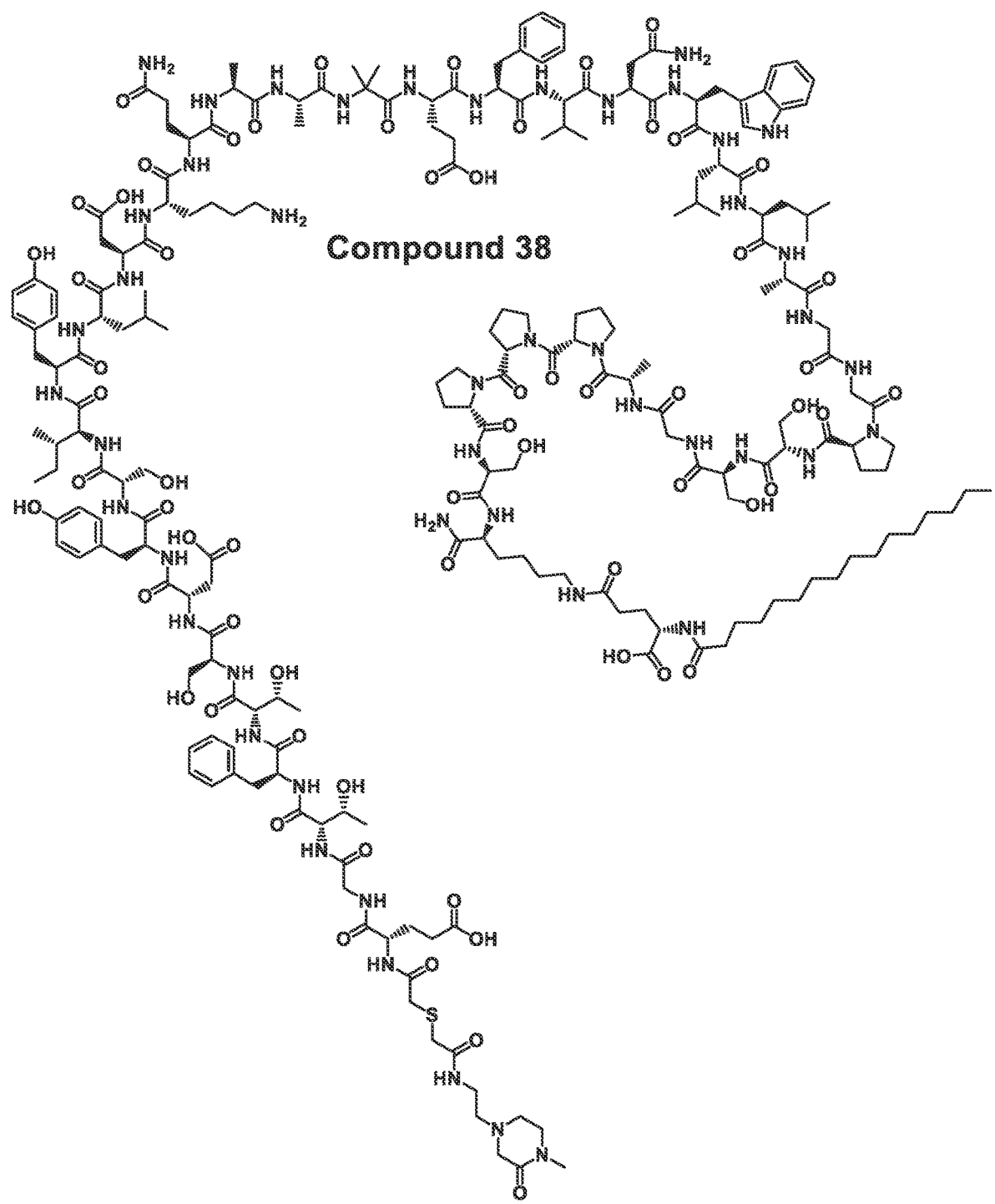
Compound 38
Cont'd

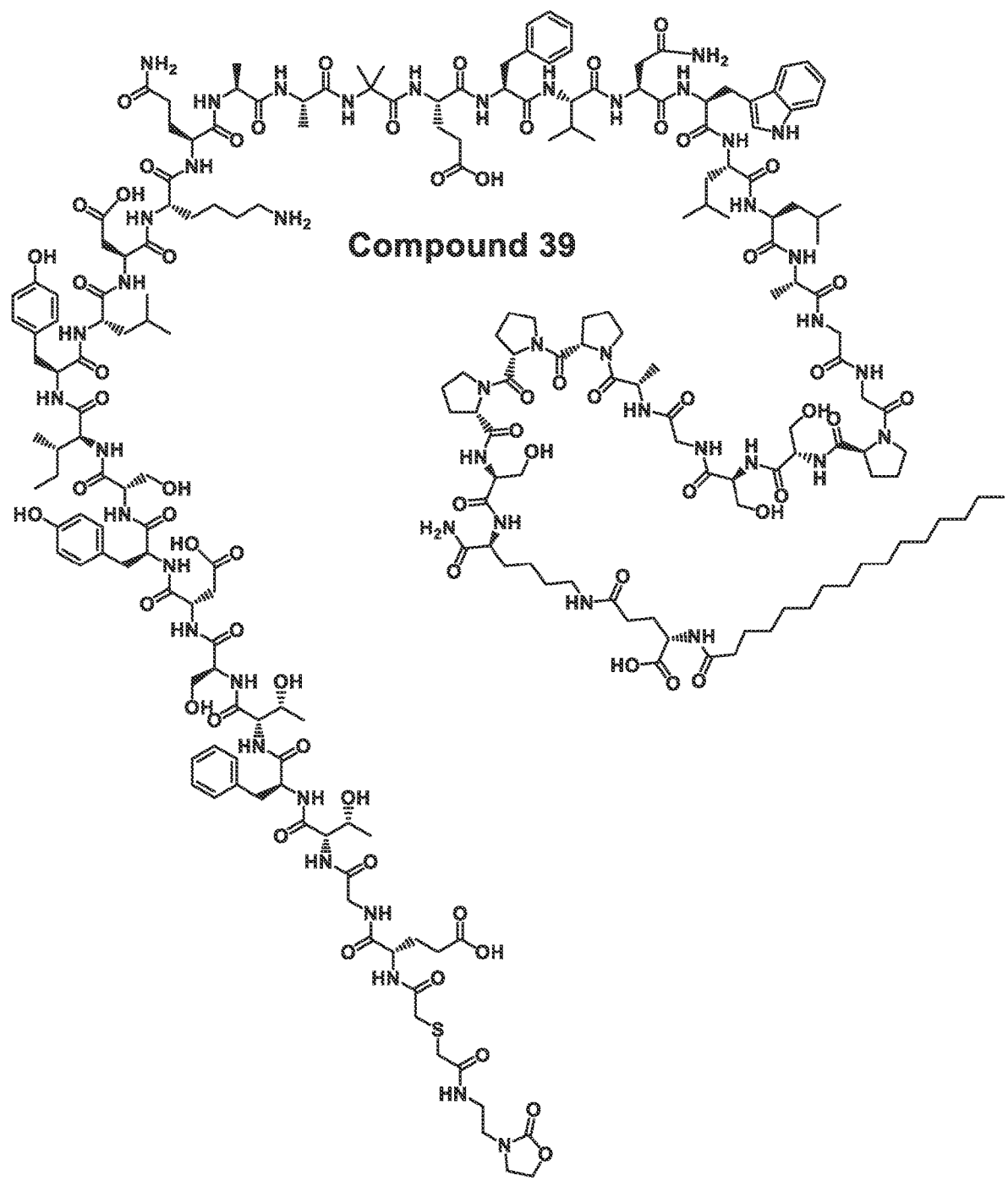
Compound 39
Cont'd

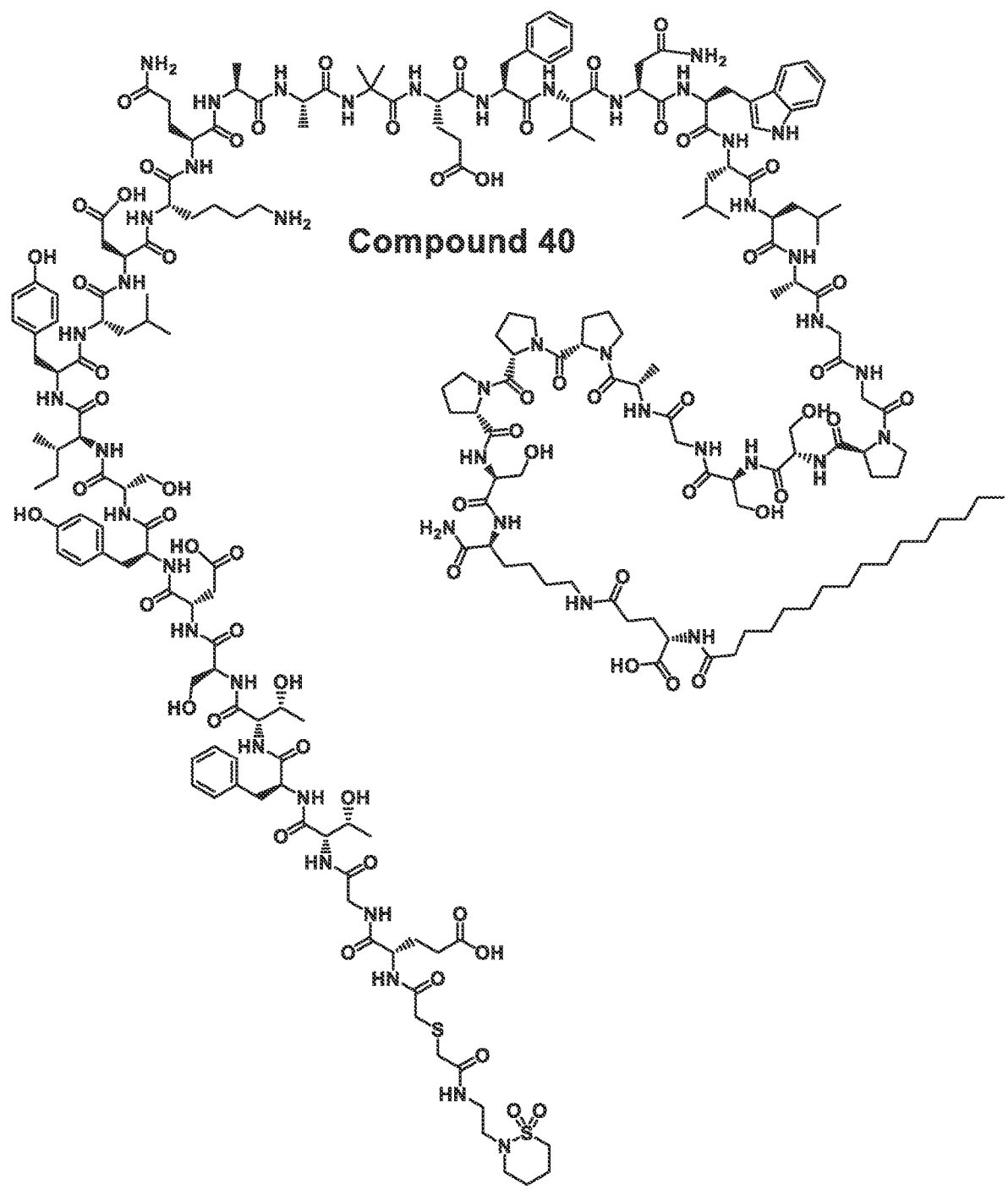
Compound 40
Cont'd

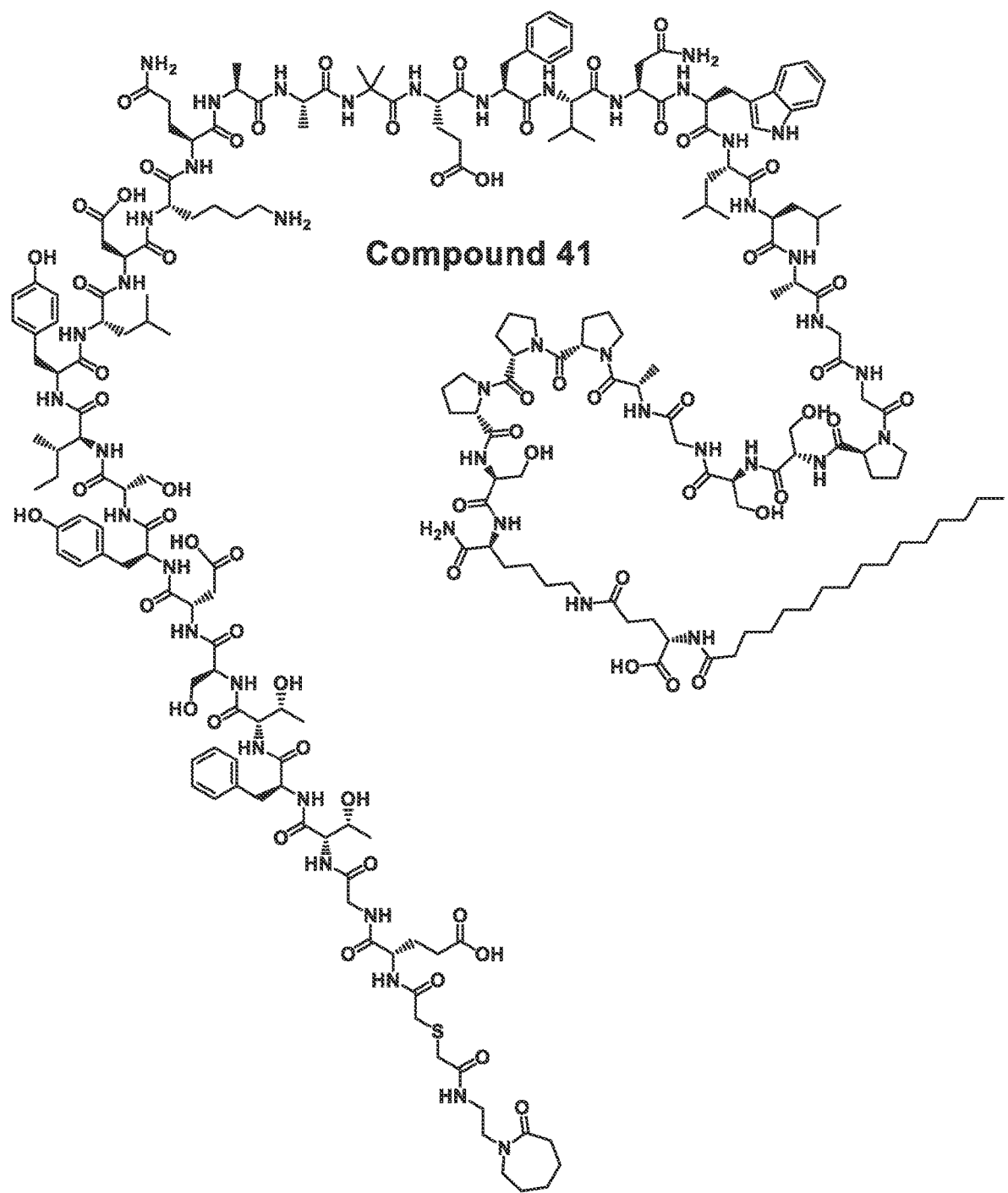
Compound 41
Cont'd

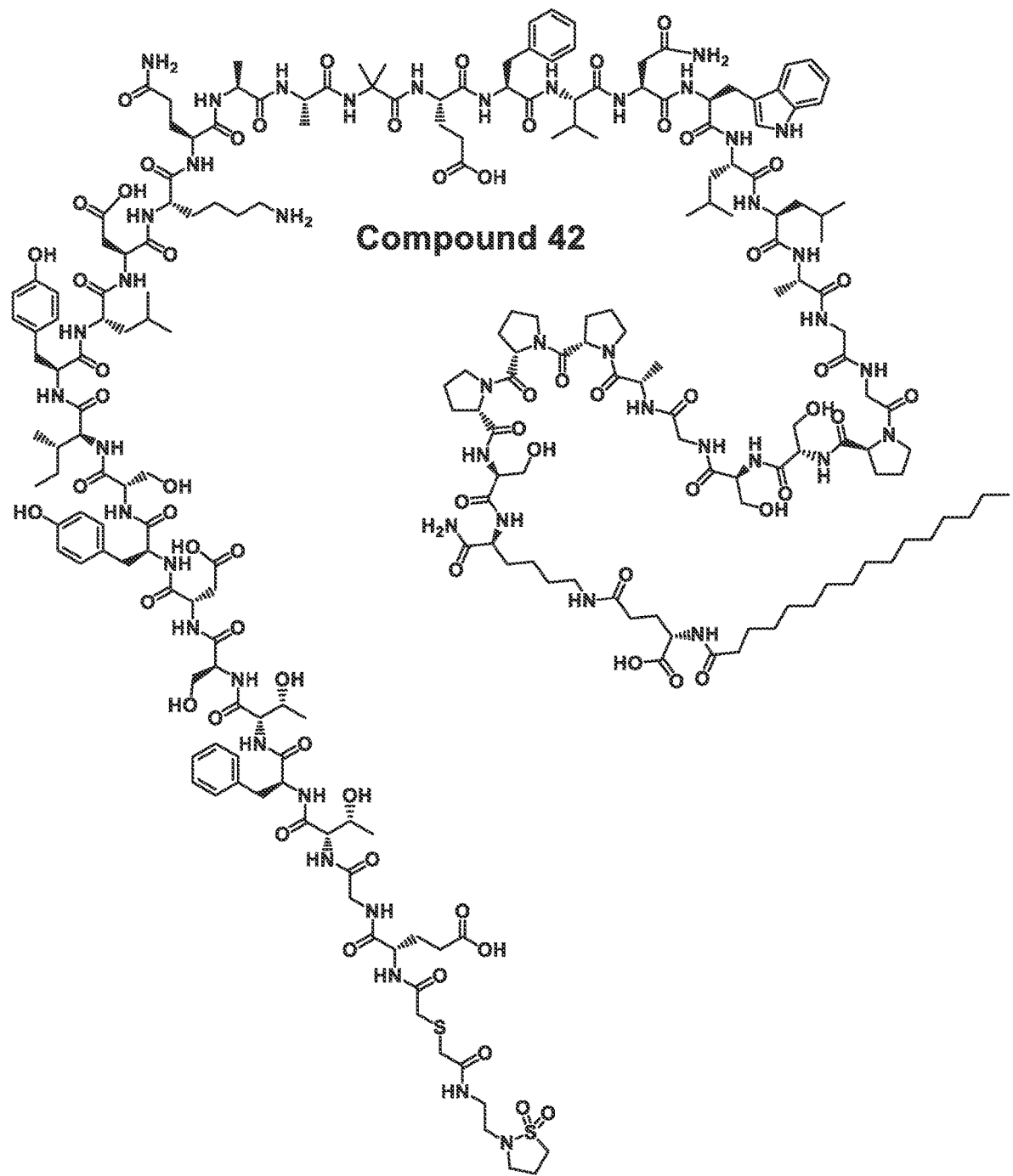
Compound 42
Cont'd

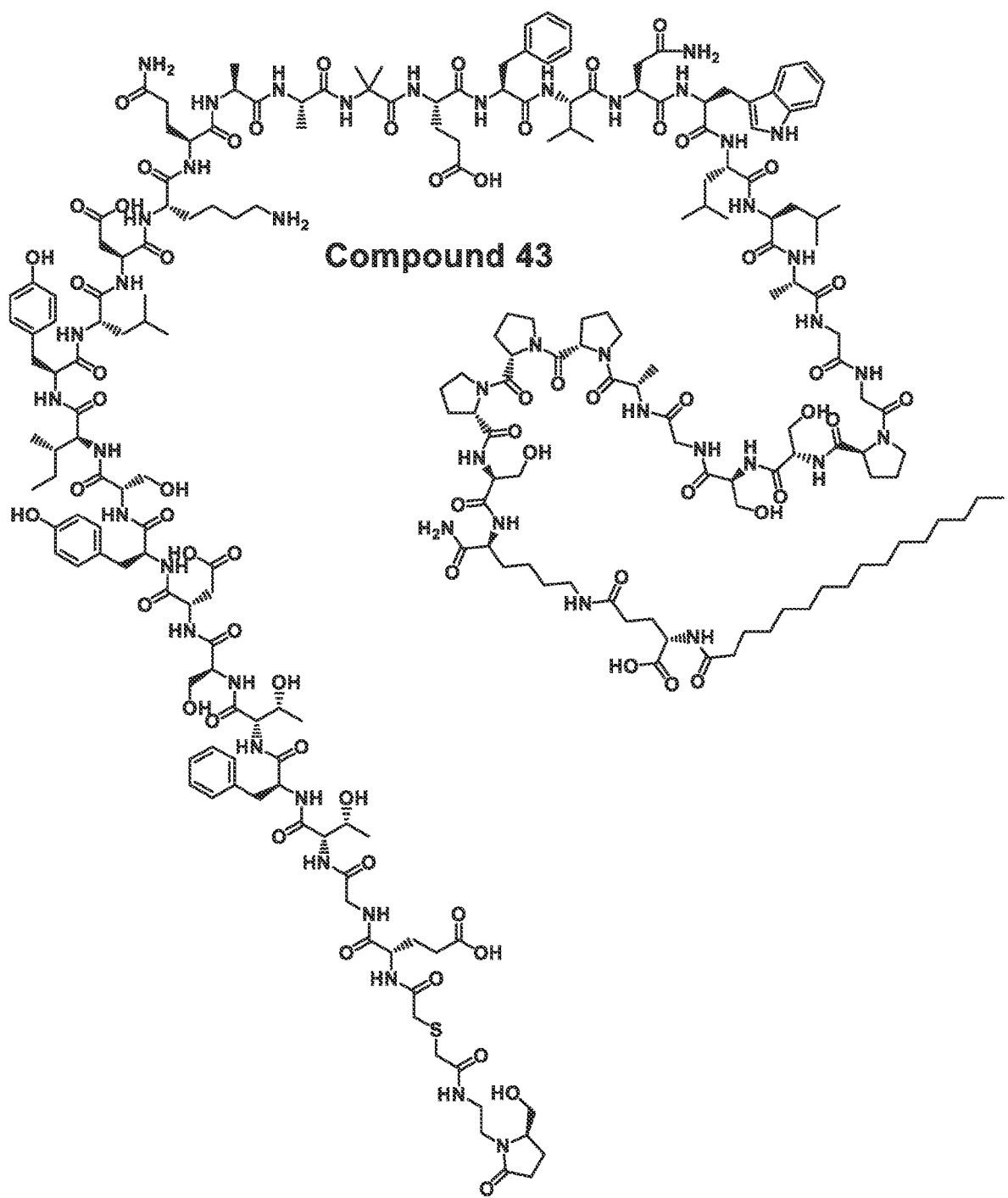
Compound 43
Cont'd

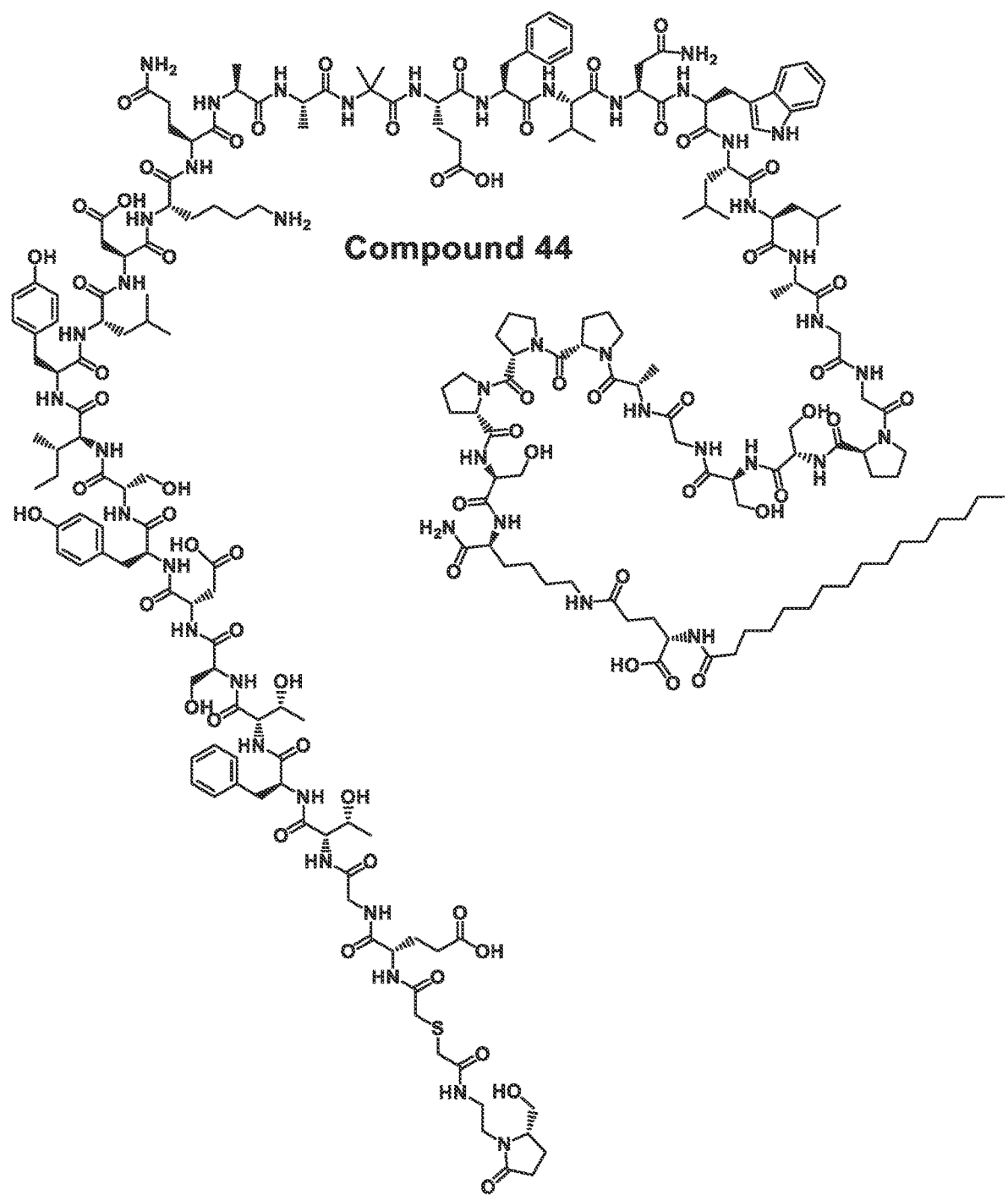
Compound 44
Cont'd

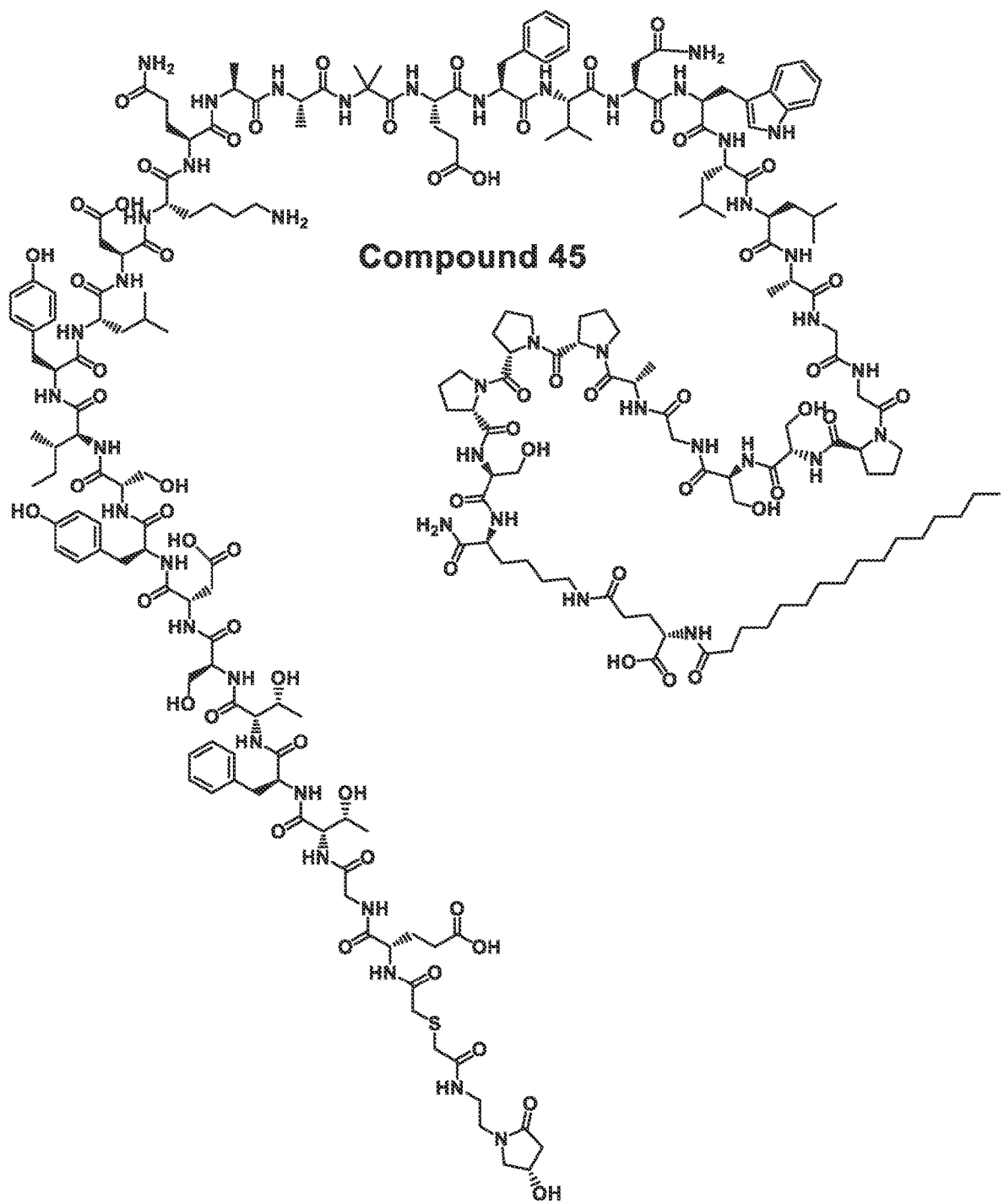
Compound 45
Cont'd

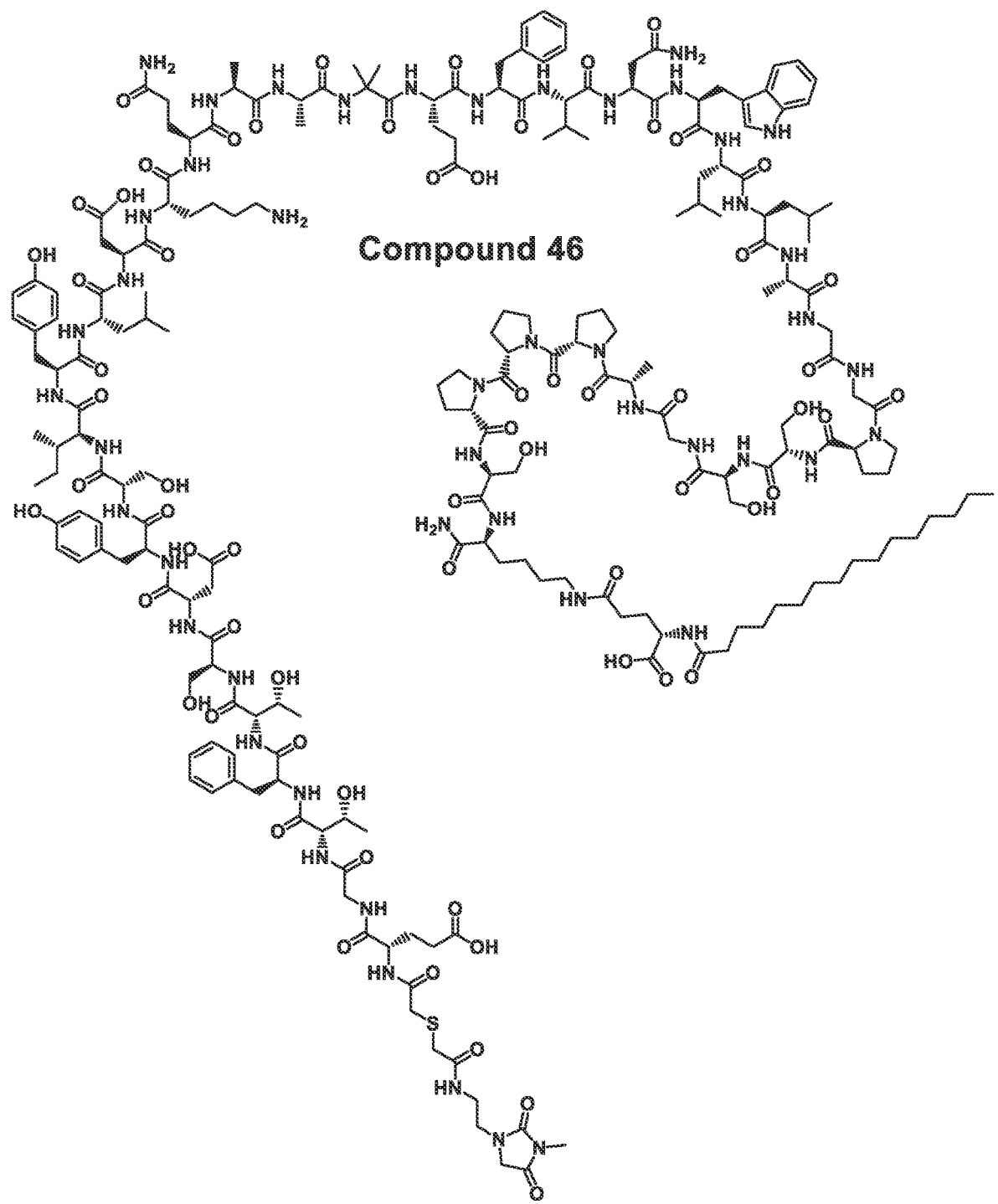
Compound 46
Cont'd

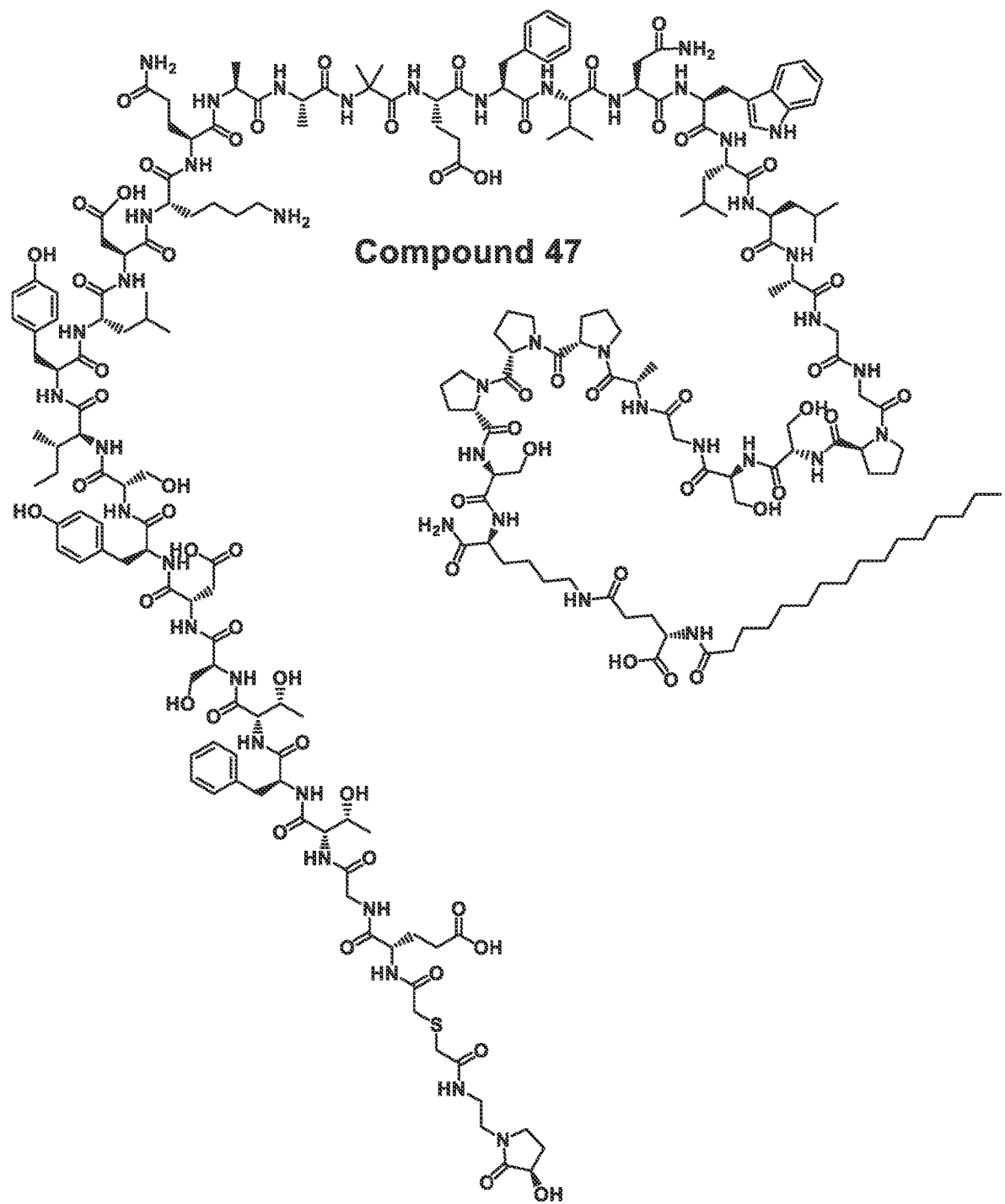
Compound 47
Cont'd

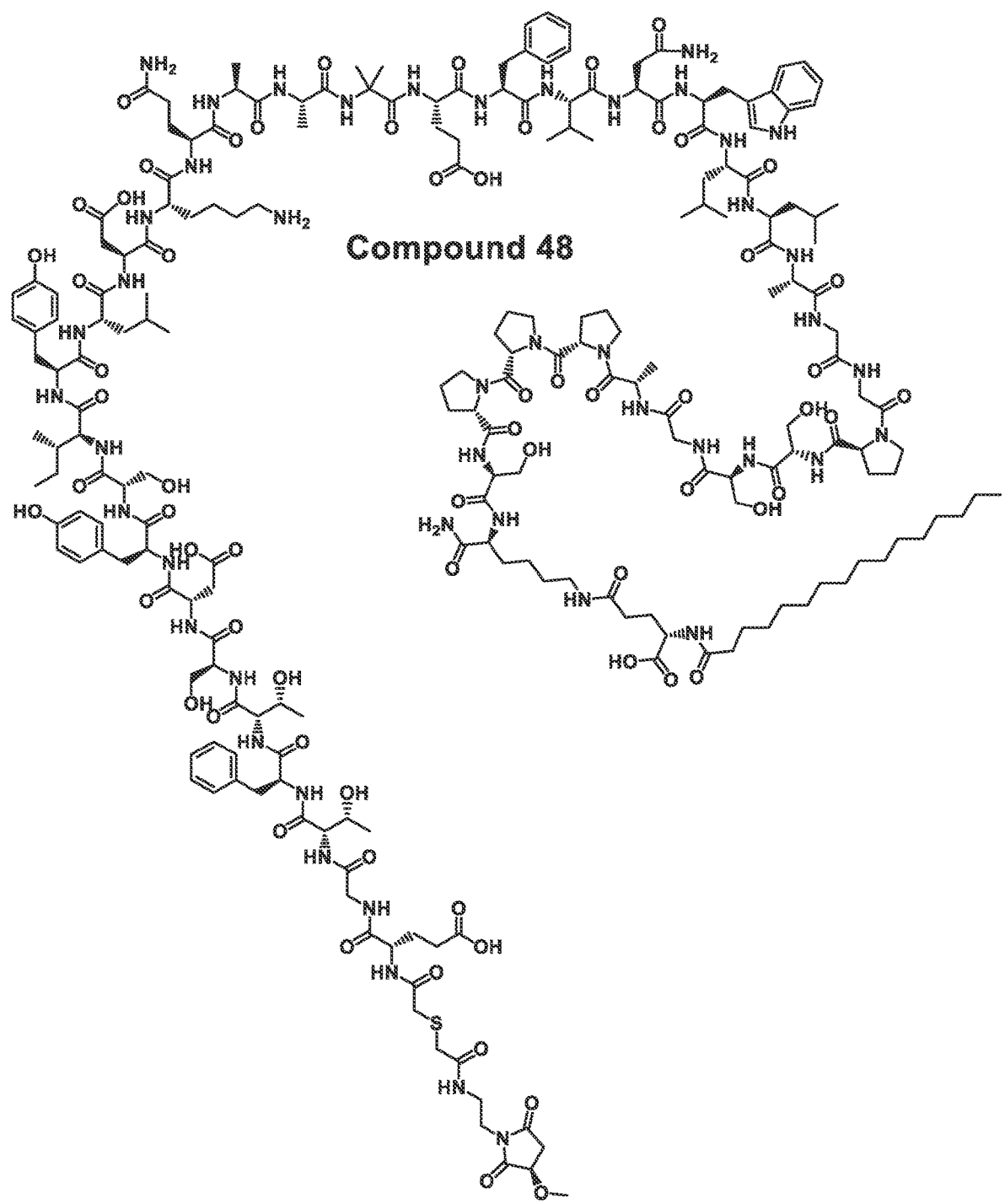
Compound 48
Cont'd

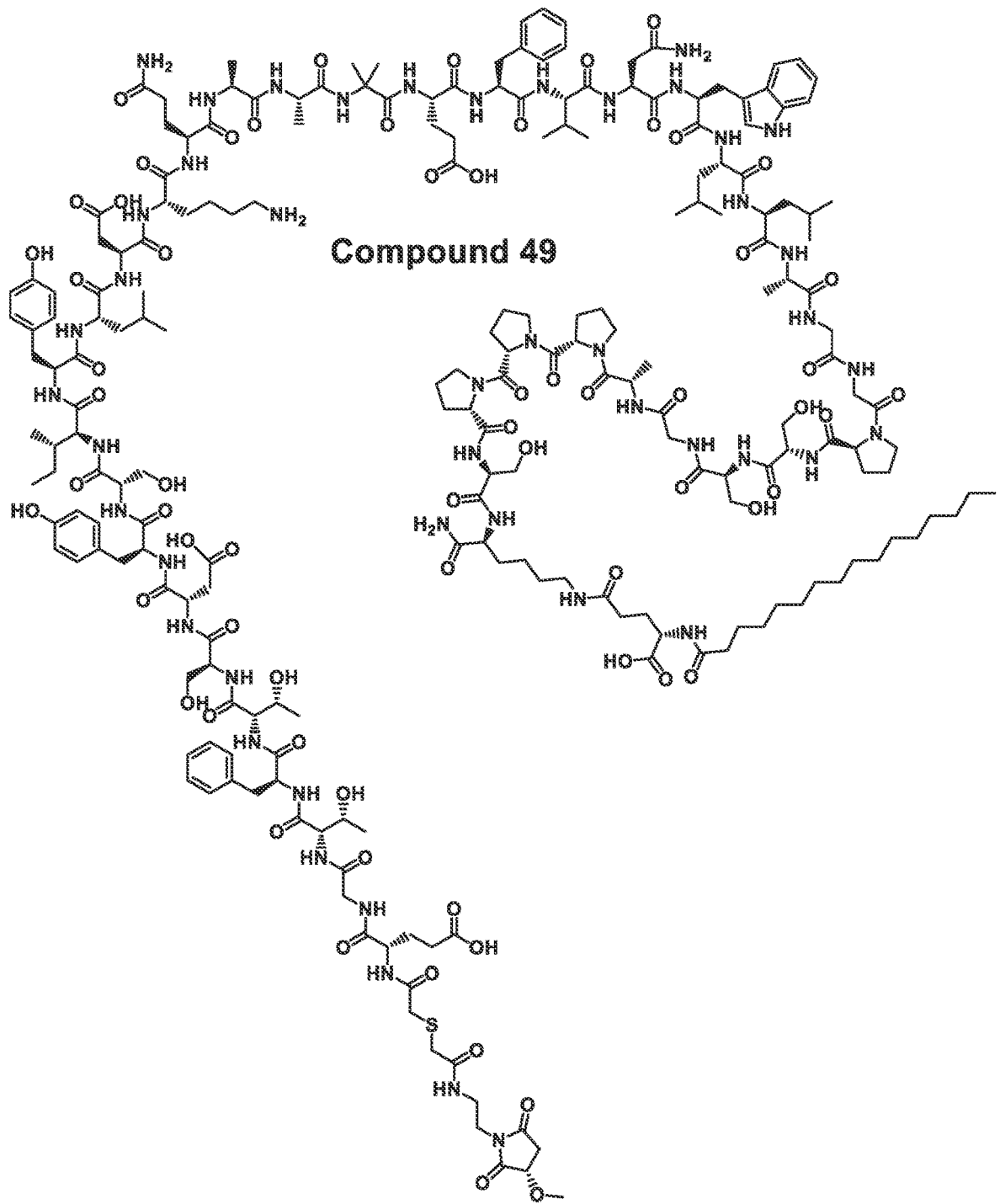
Compound 49
Cont'd

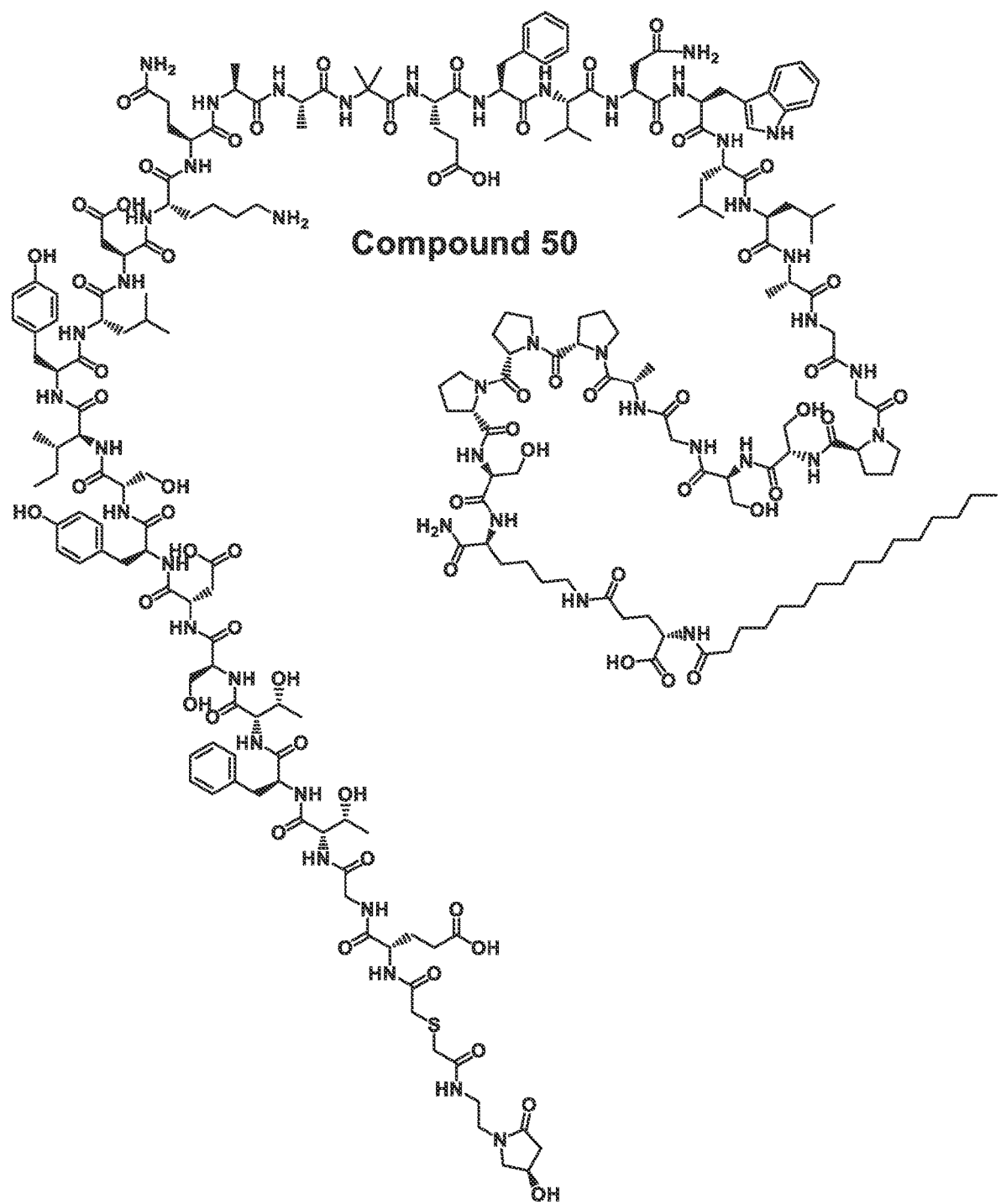
Compound 50
Cont'd

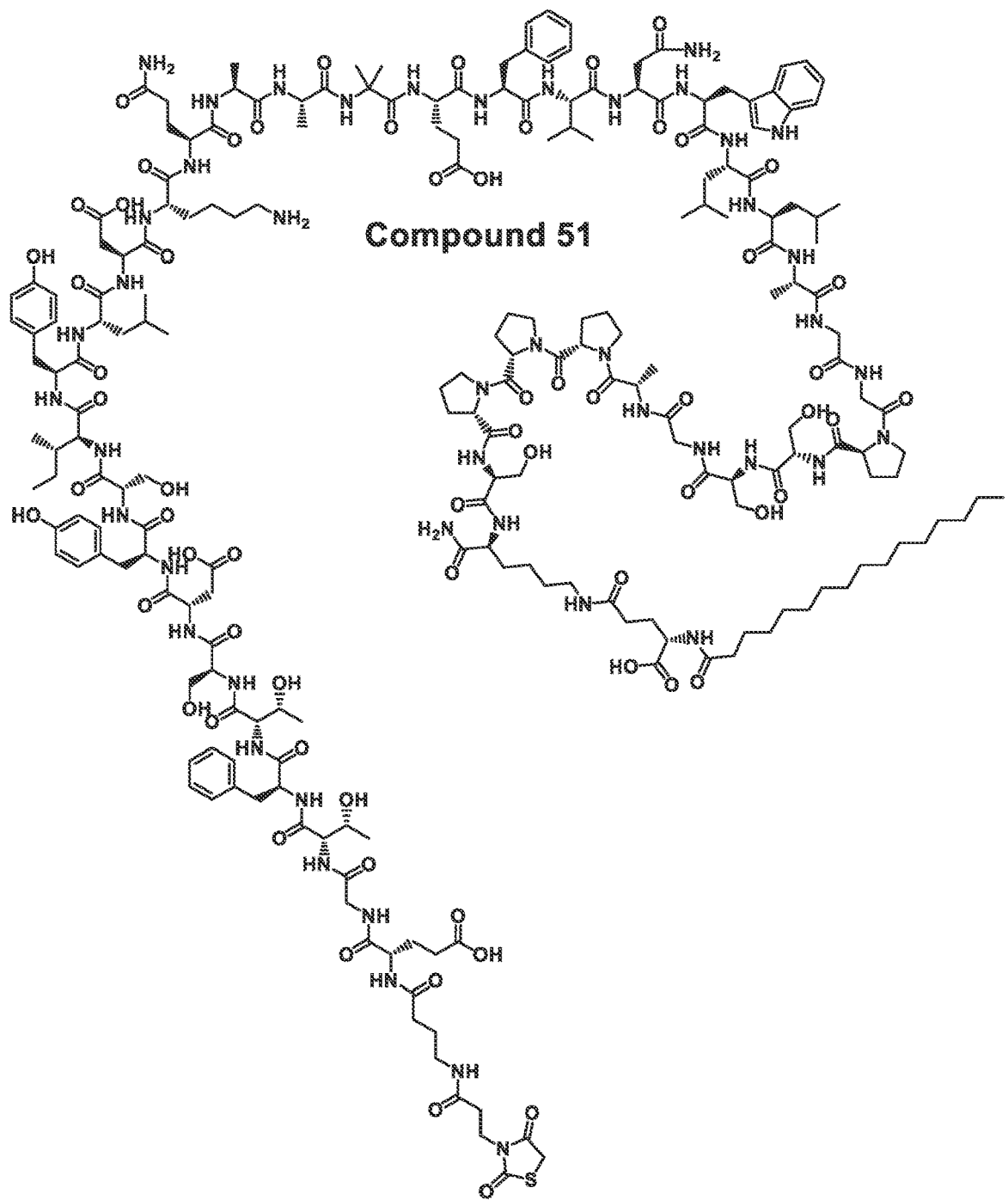
Compound 51
Cont'd

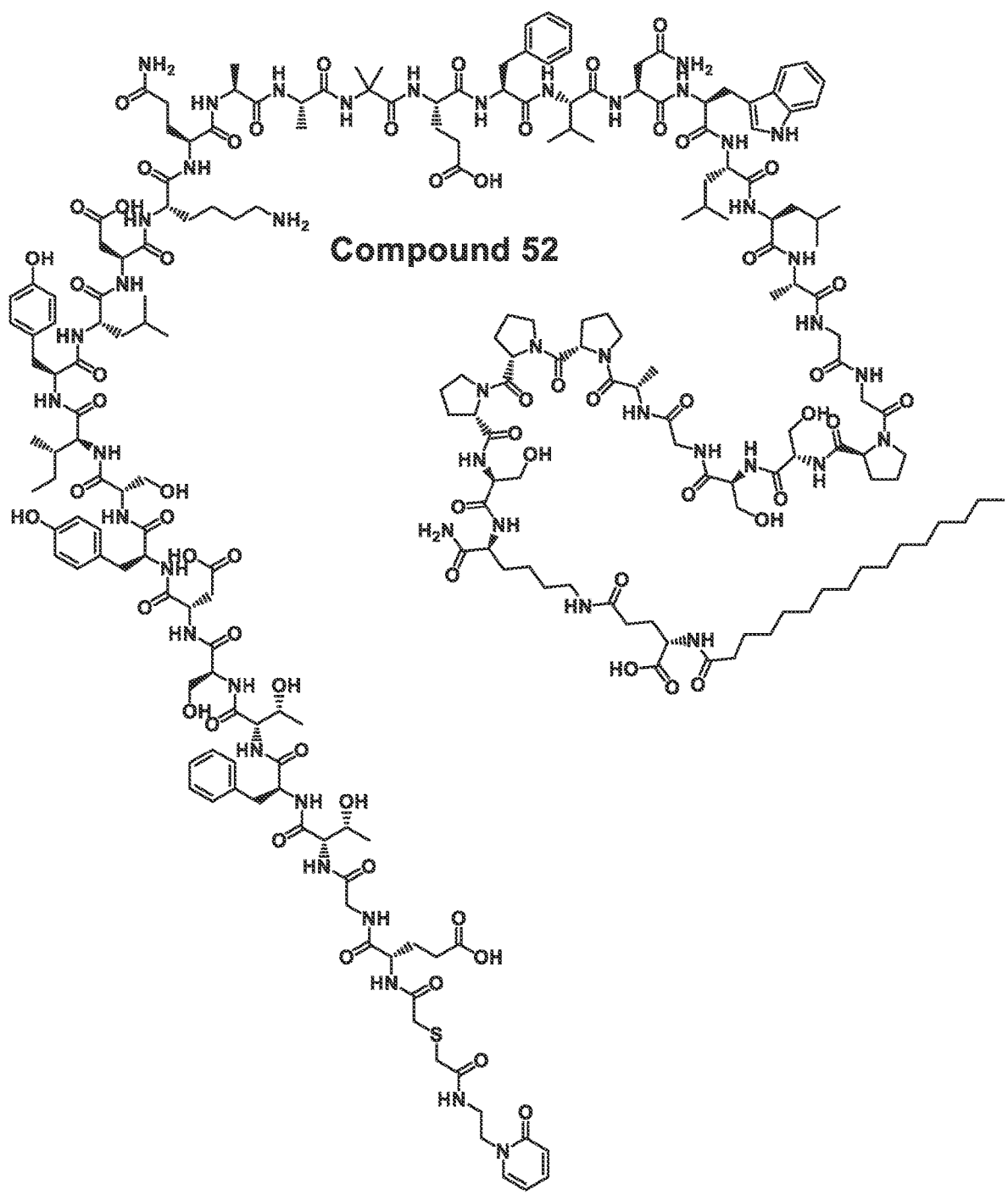
Compound 52
Cont'd

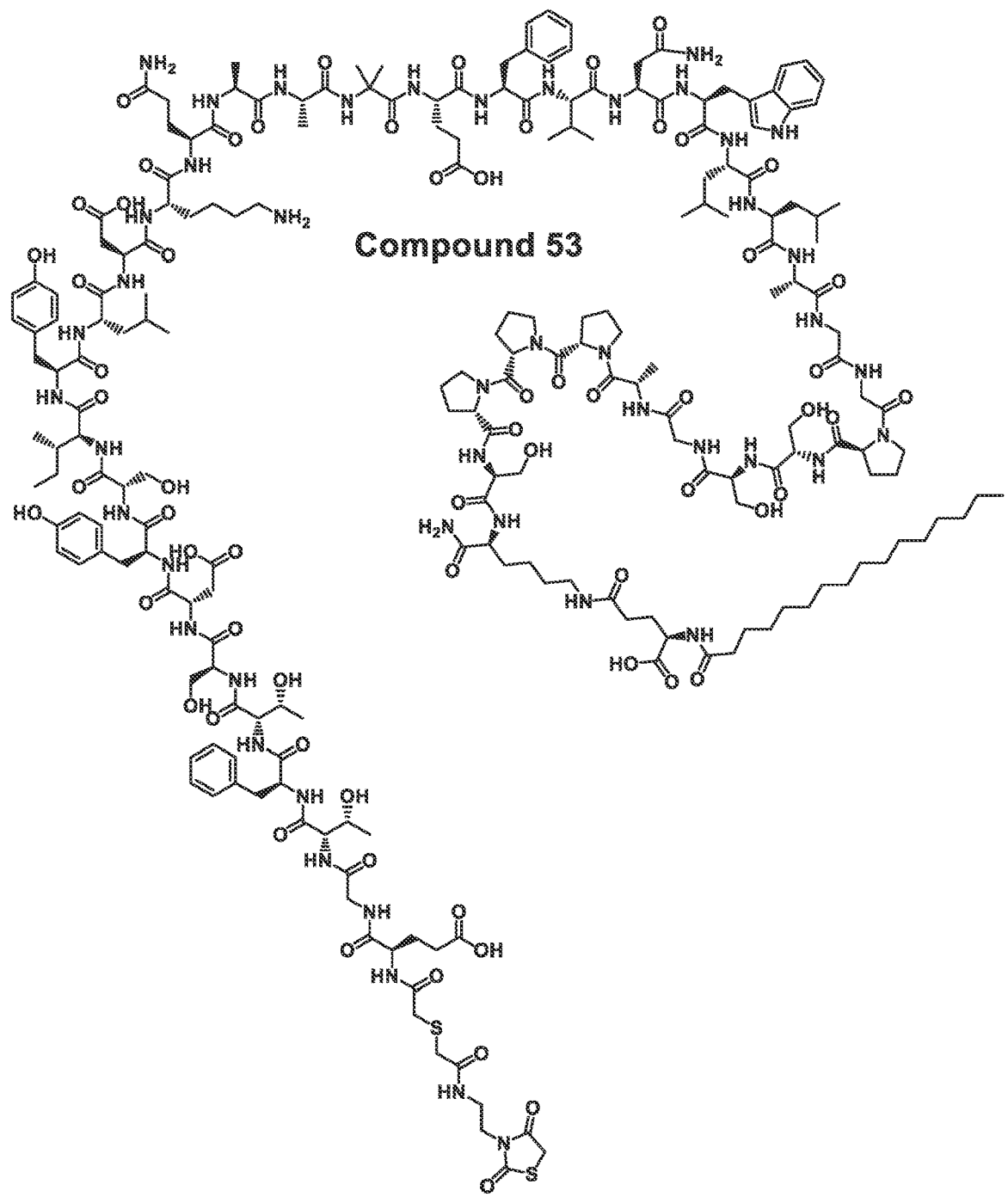
Compound 53
Cont'd

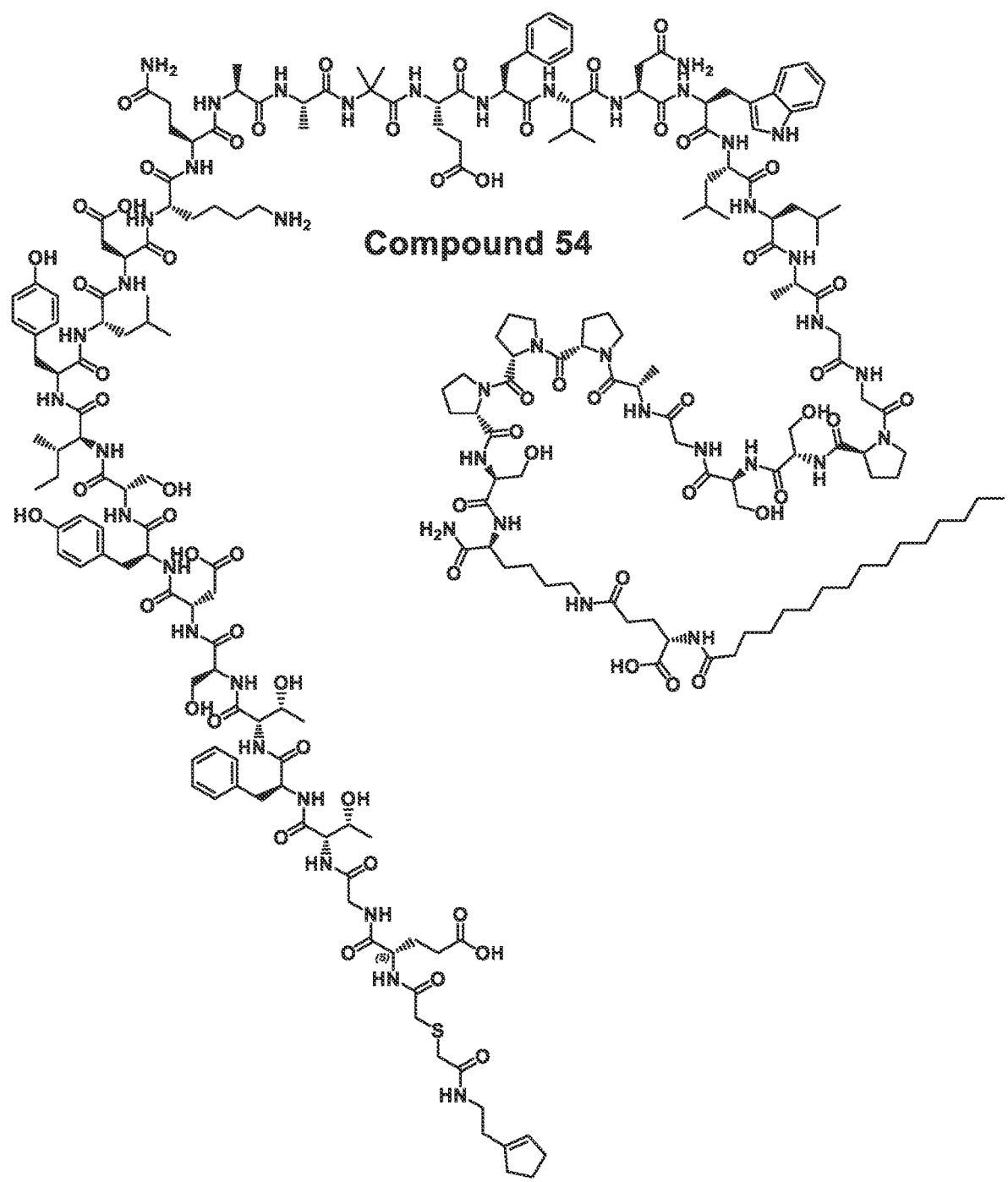
Compound 54
Cont'd

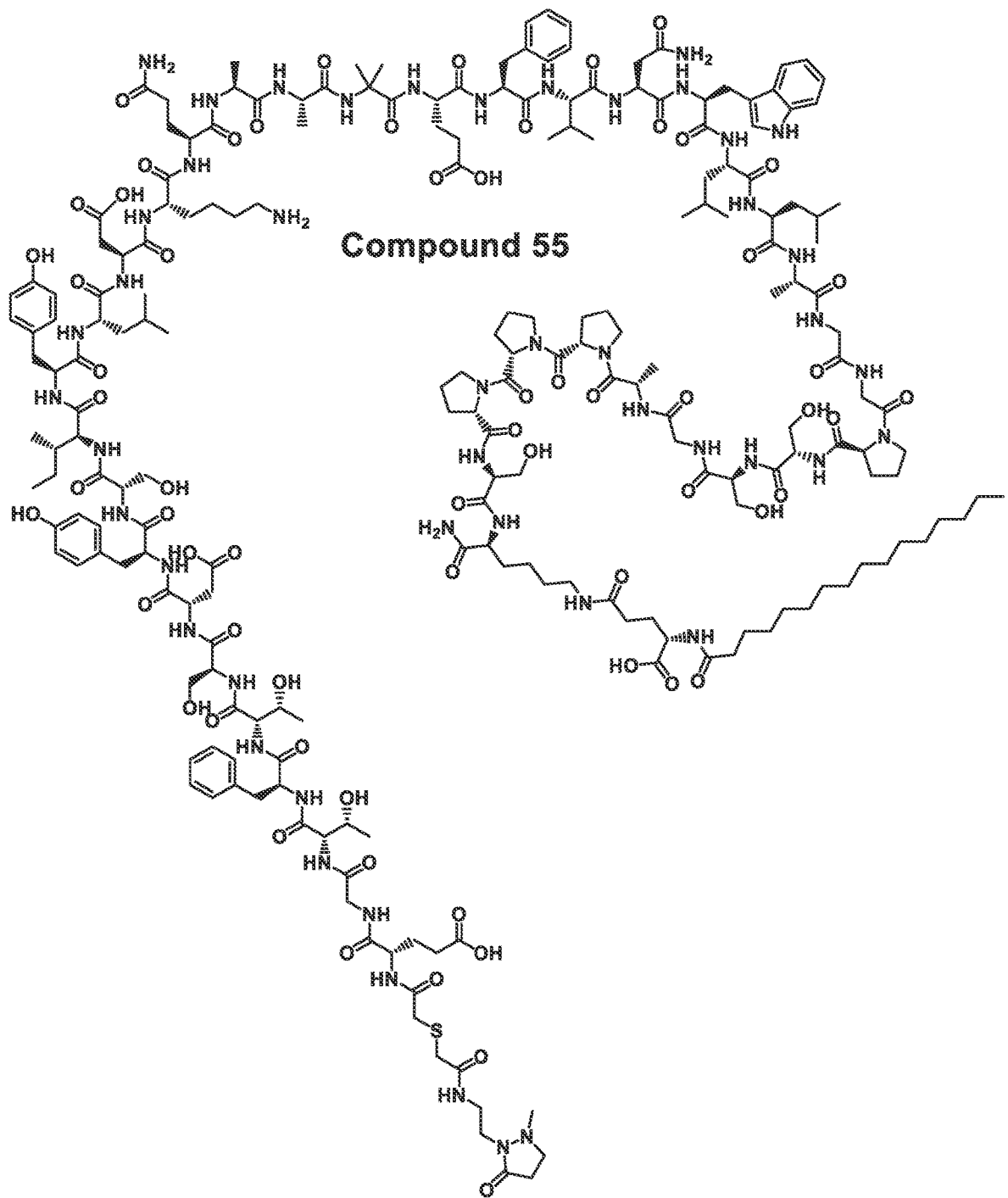
Compound 55
Cont'd

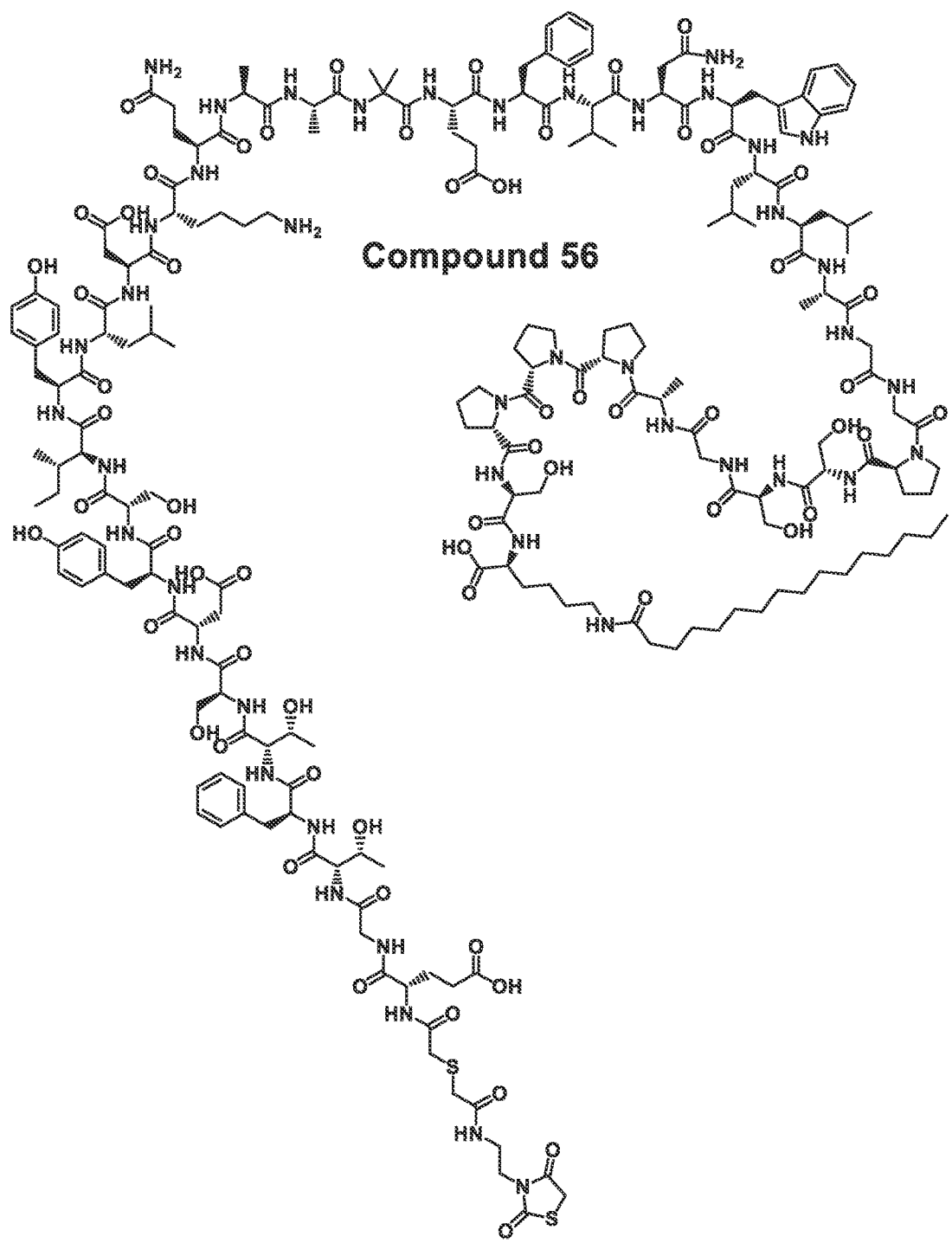
Compound 56
Cont'd

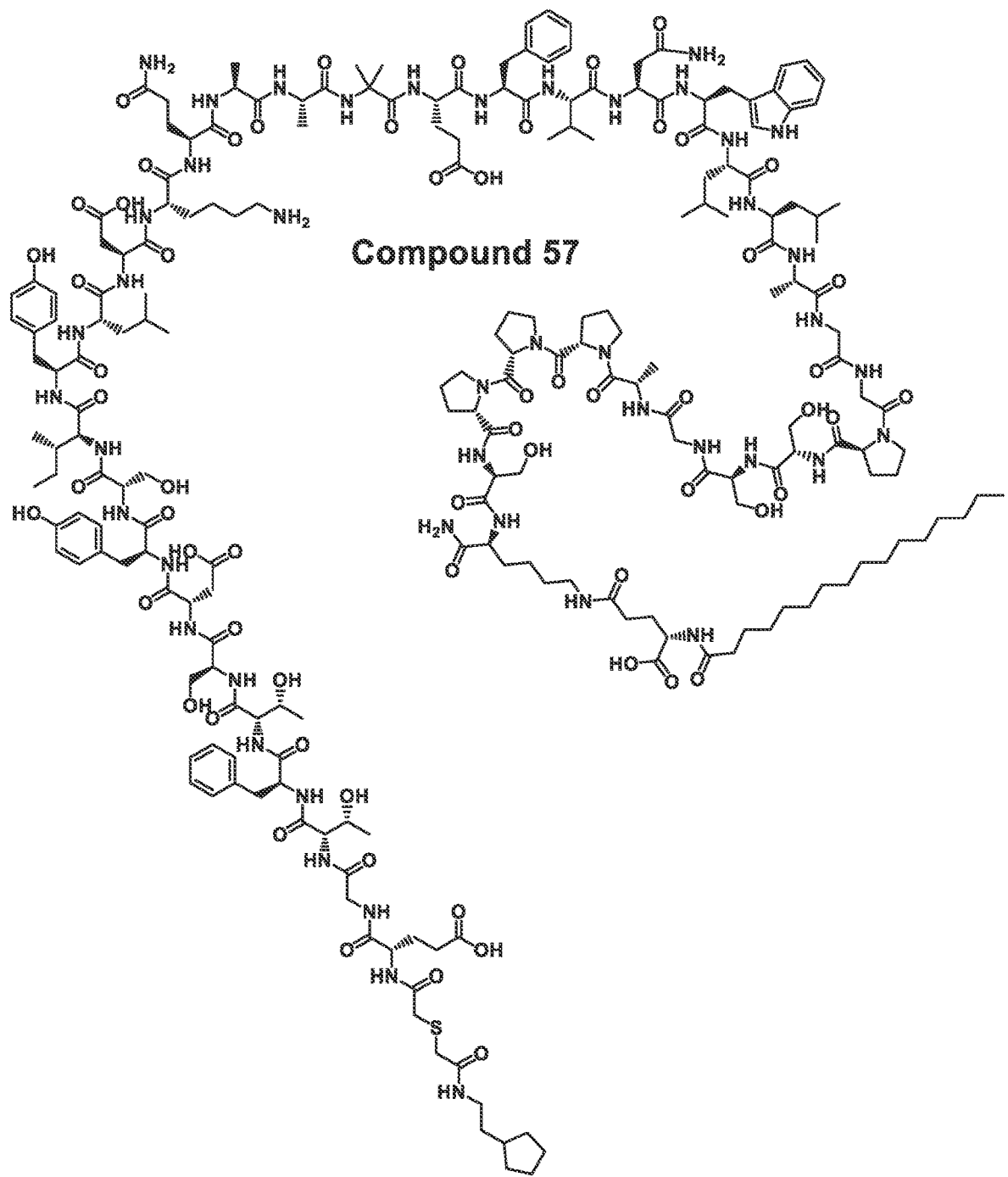
Compound 57
Cont'd

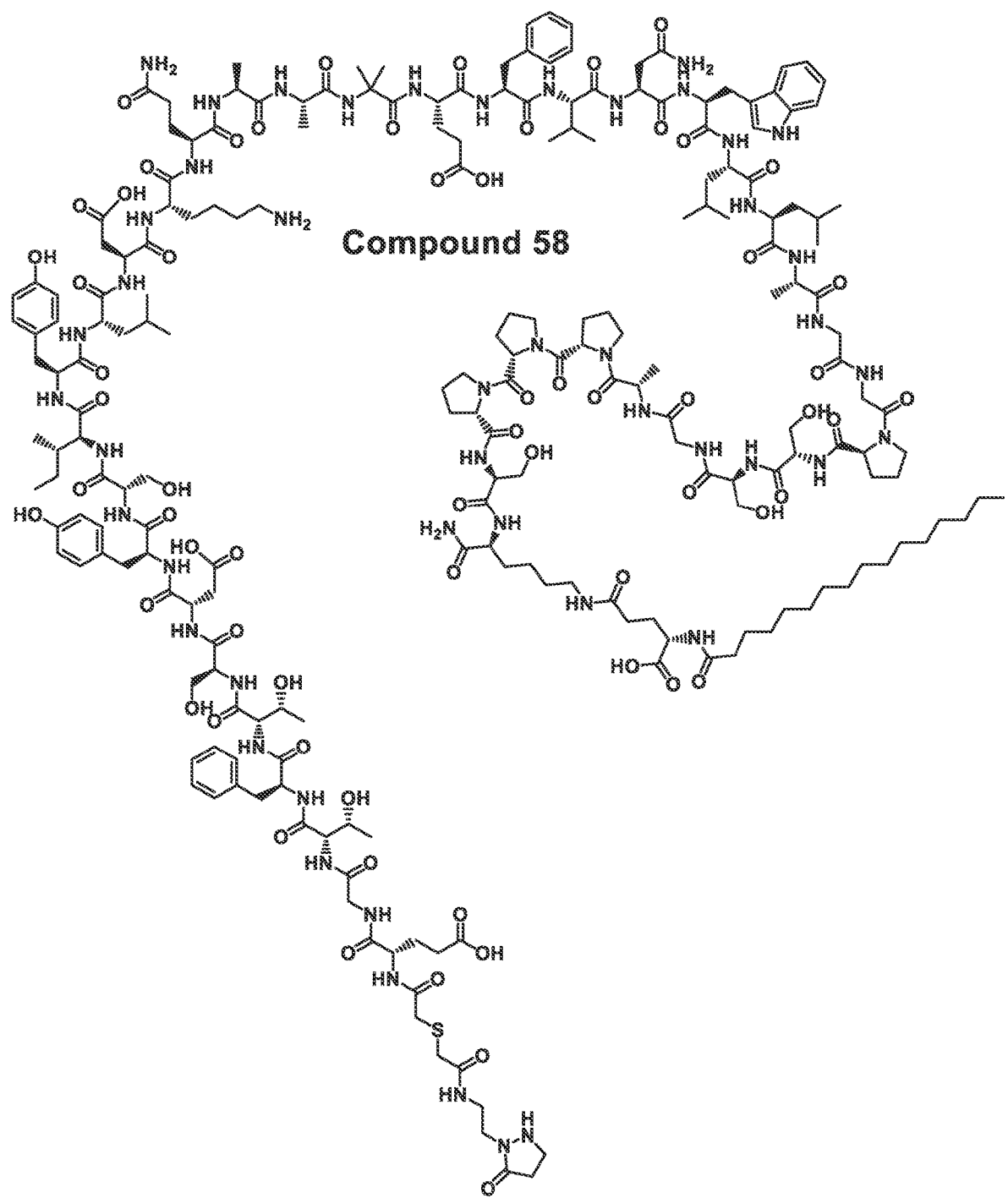
Compound 58
Cont'd

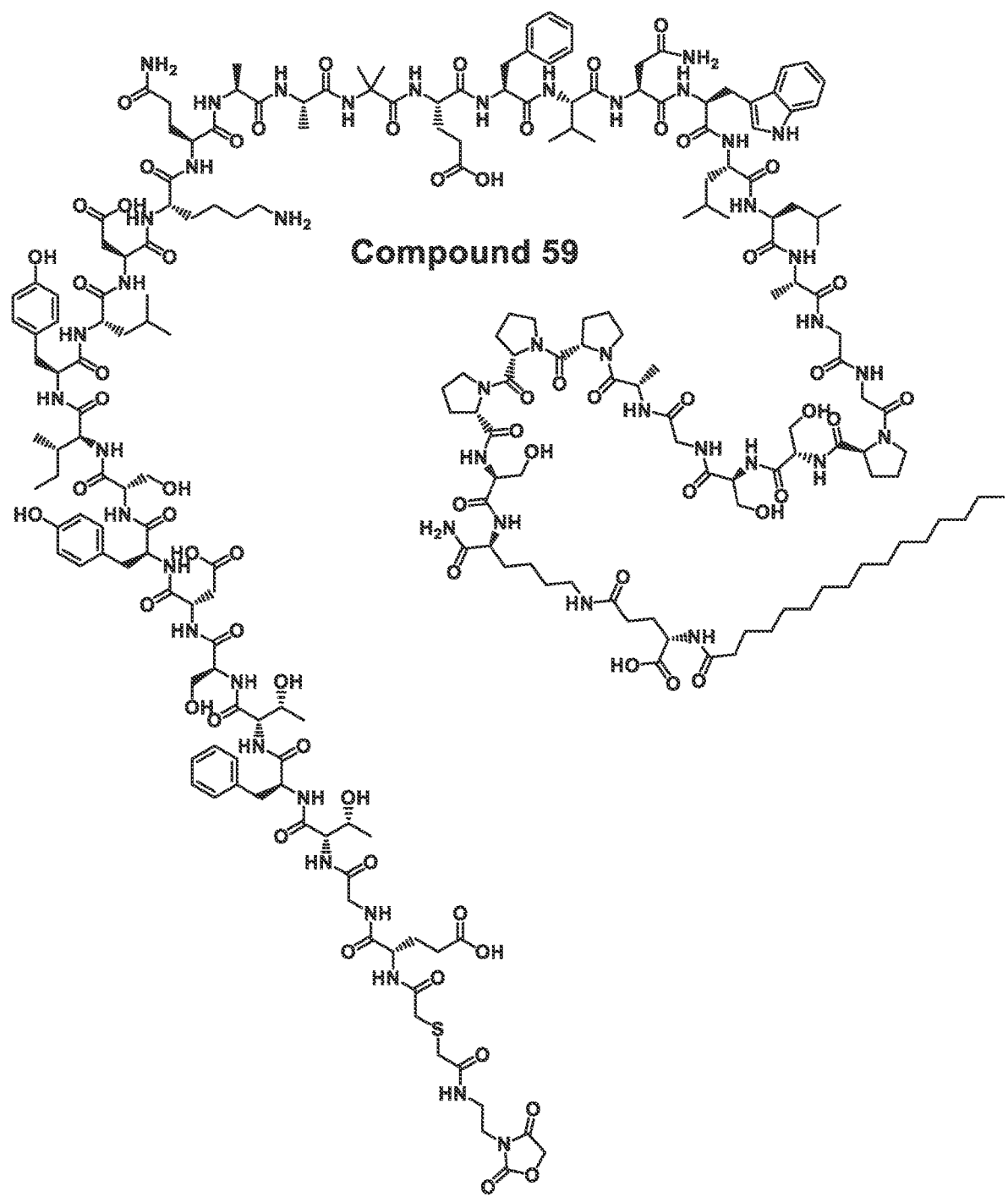
Compound 59
Cont'd

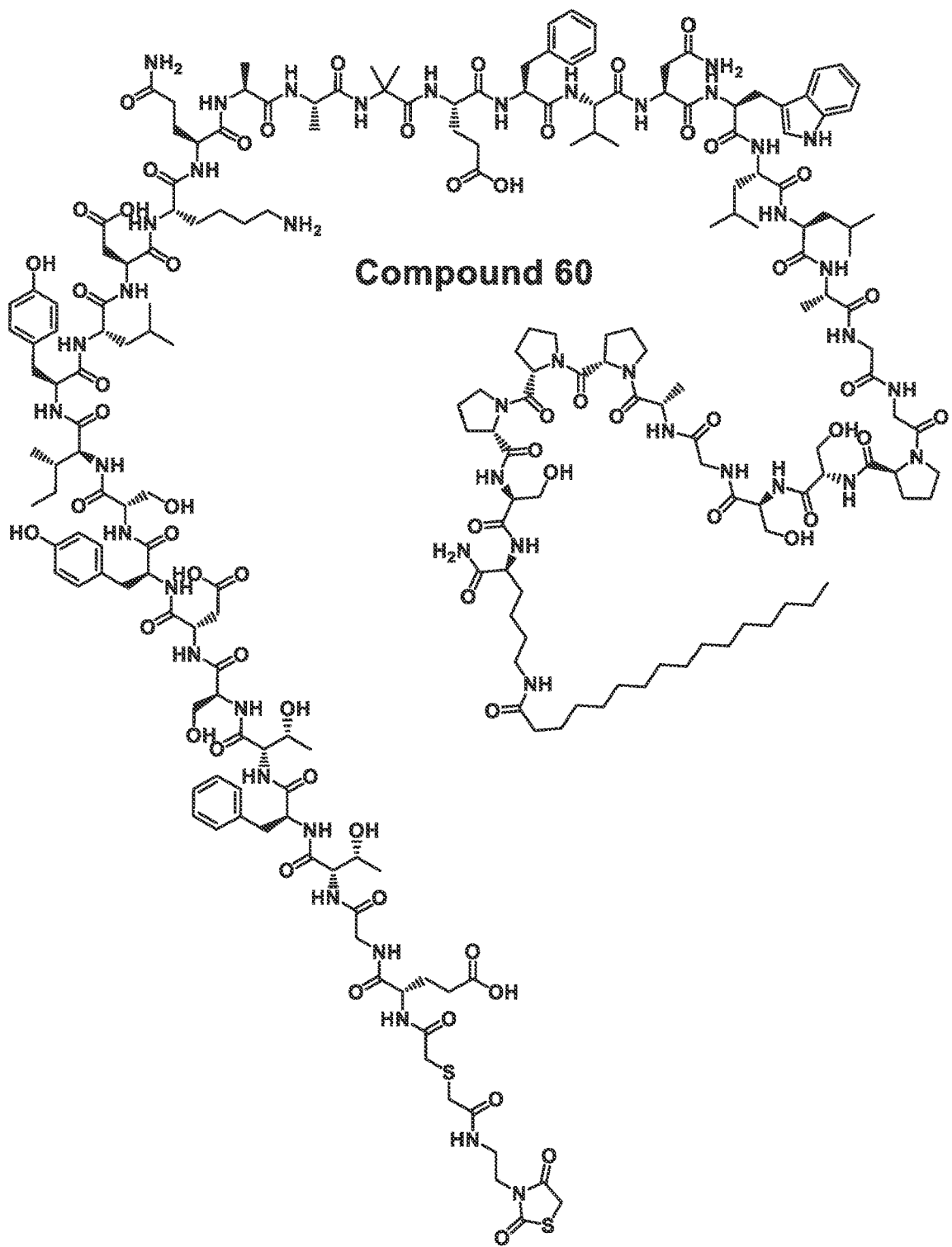
Compound 60
Cont'd

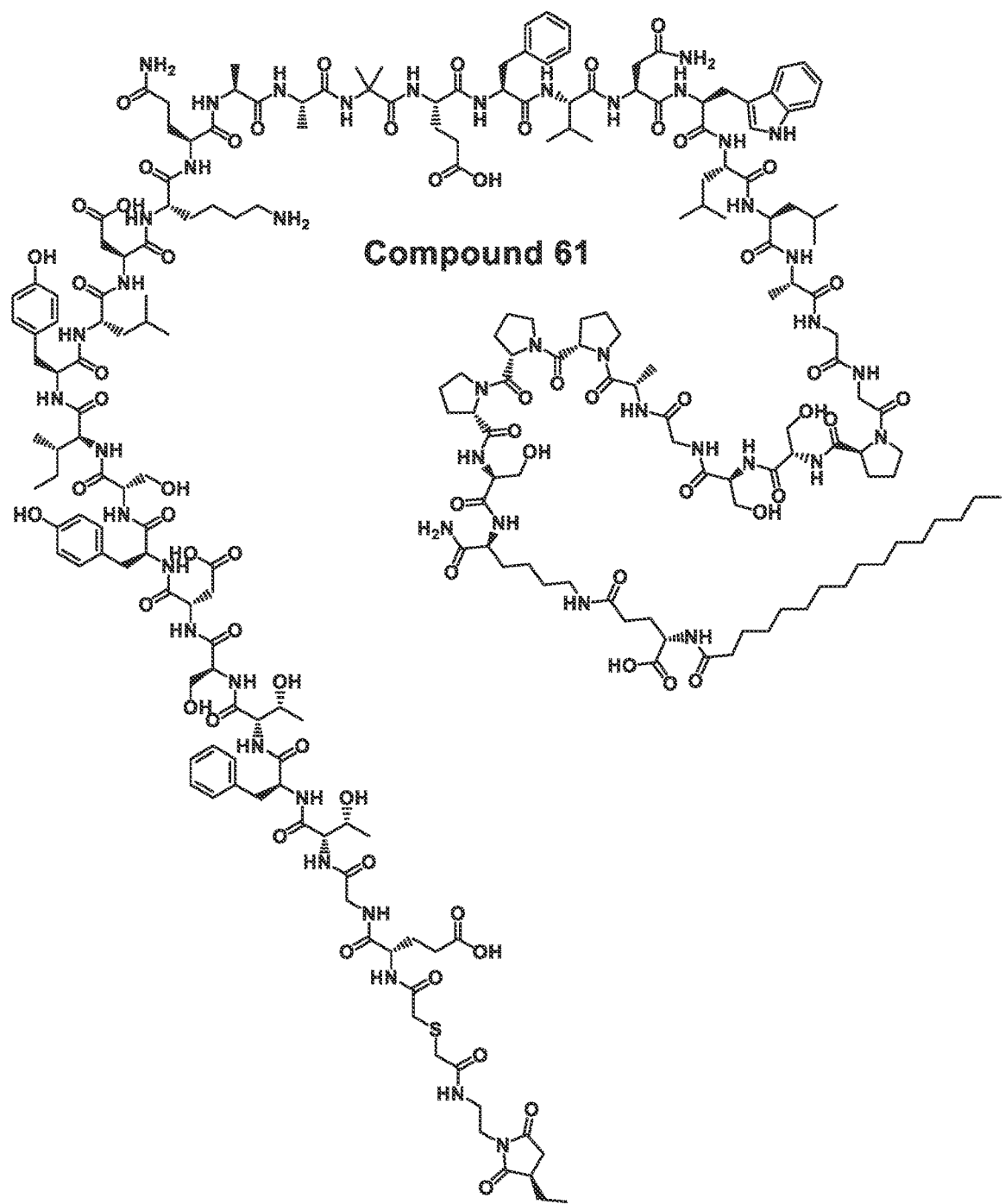
Compound 61
Cont'd

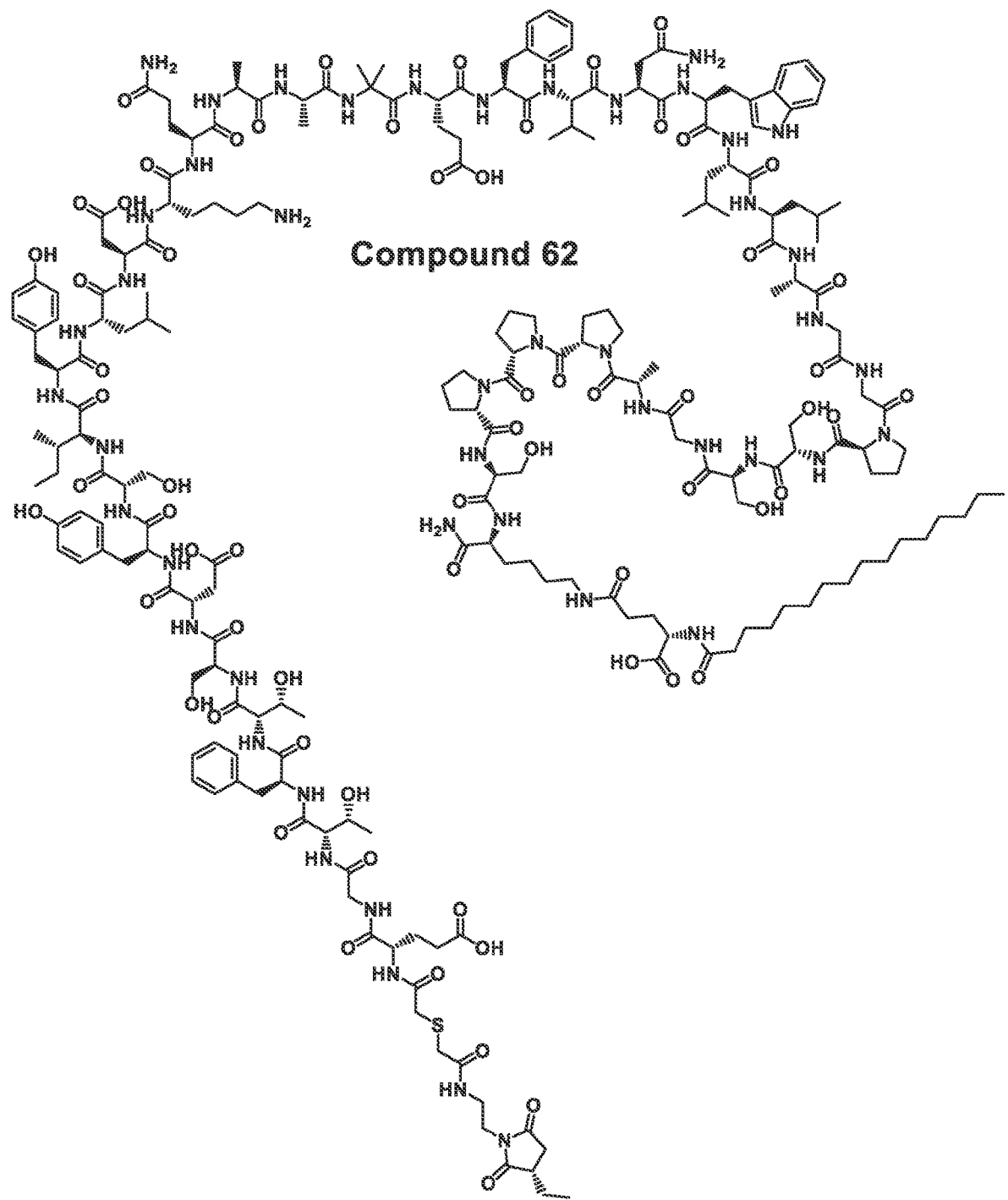
Compound 62
Cont'd

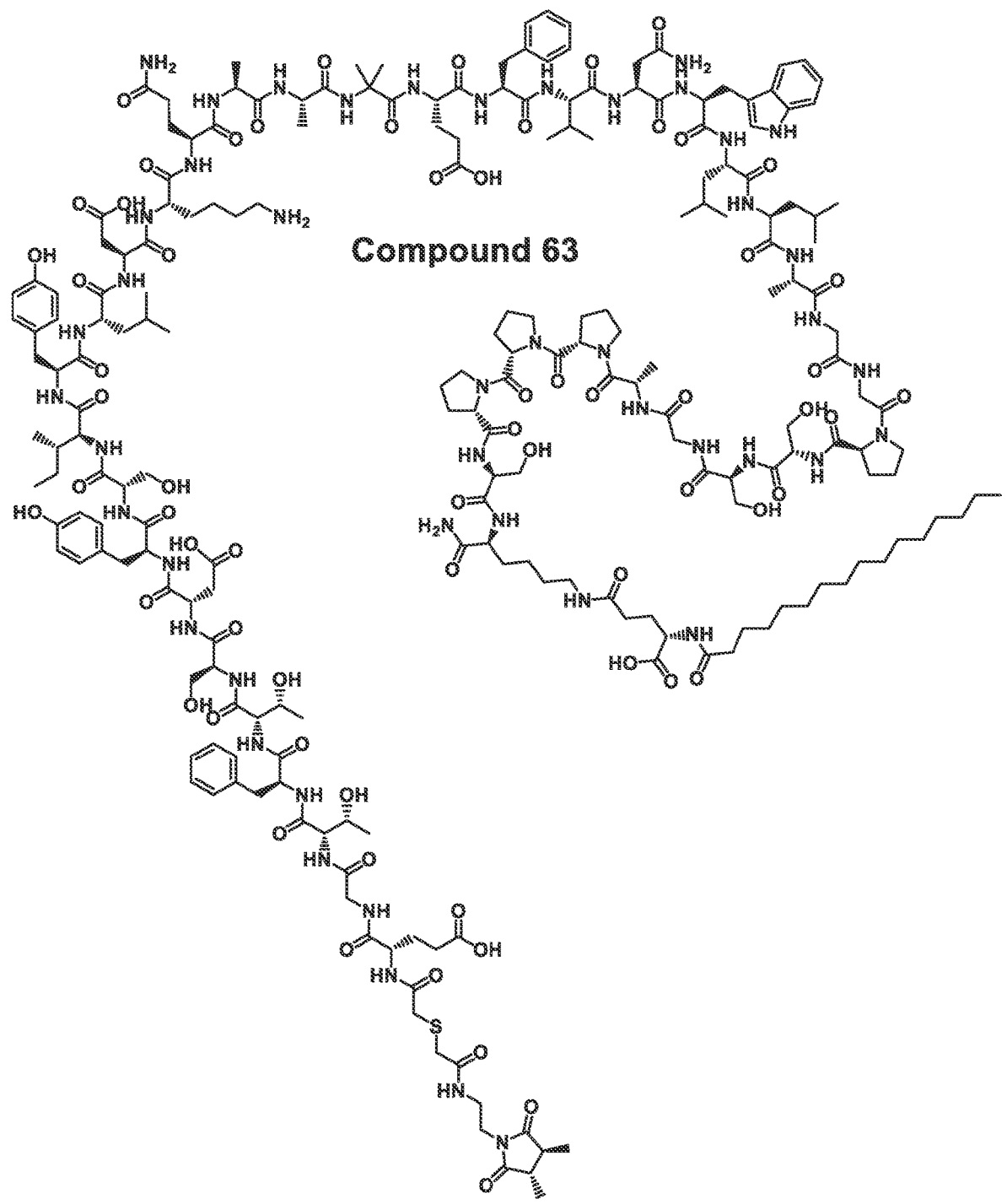
Compound 63
Cont'd

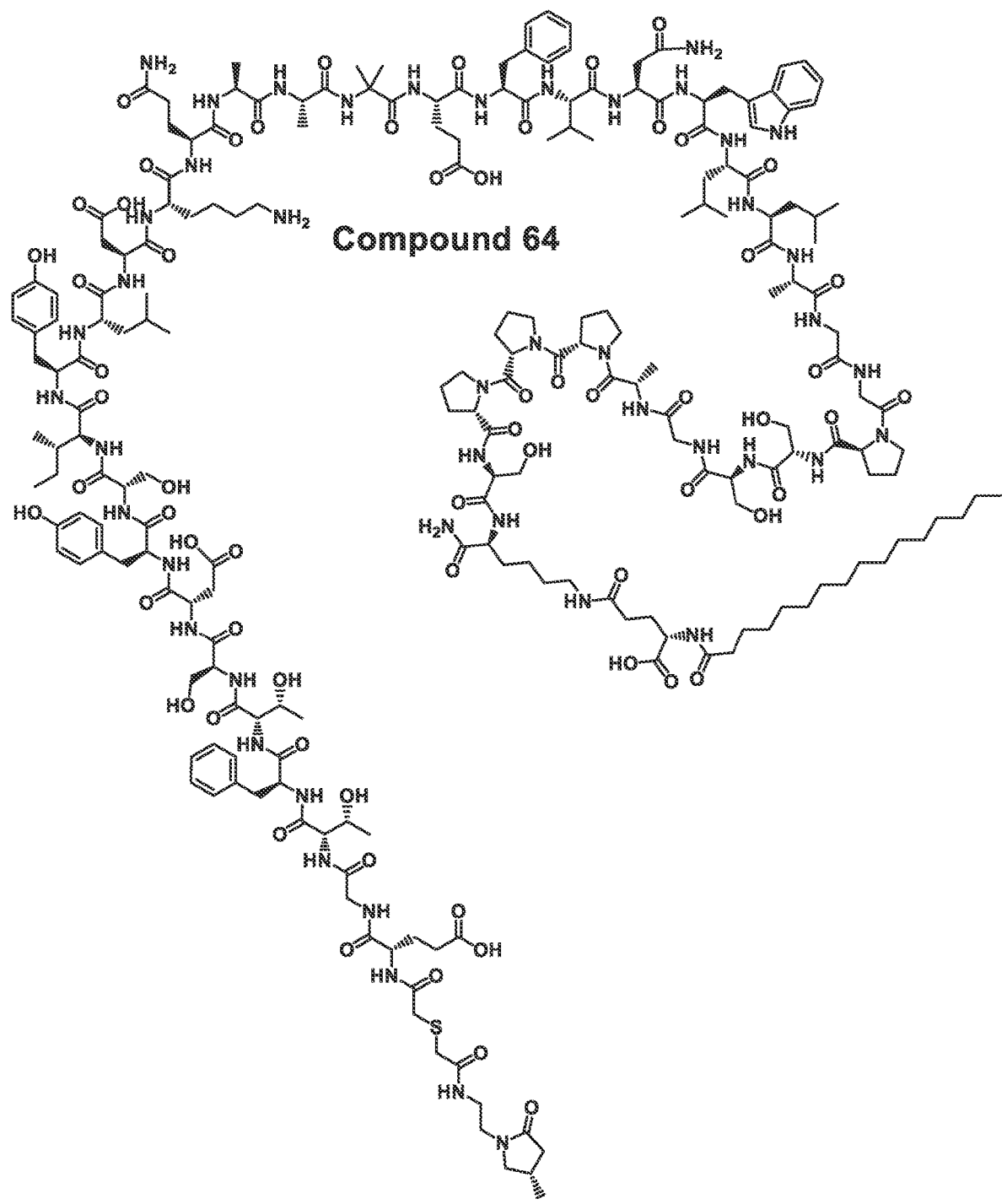
Compound 64
Cont'd

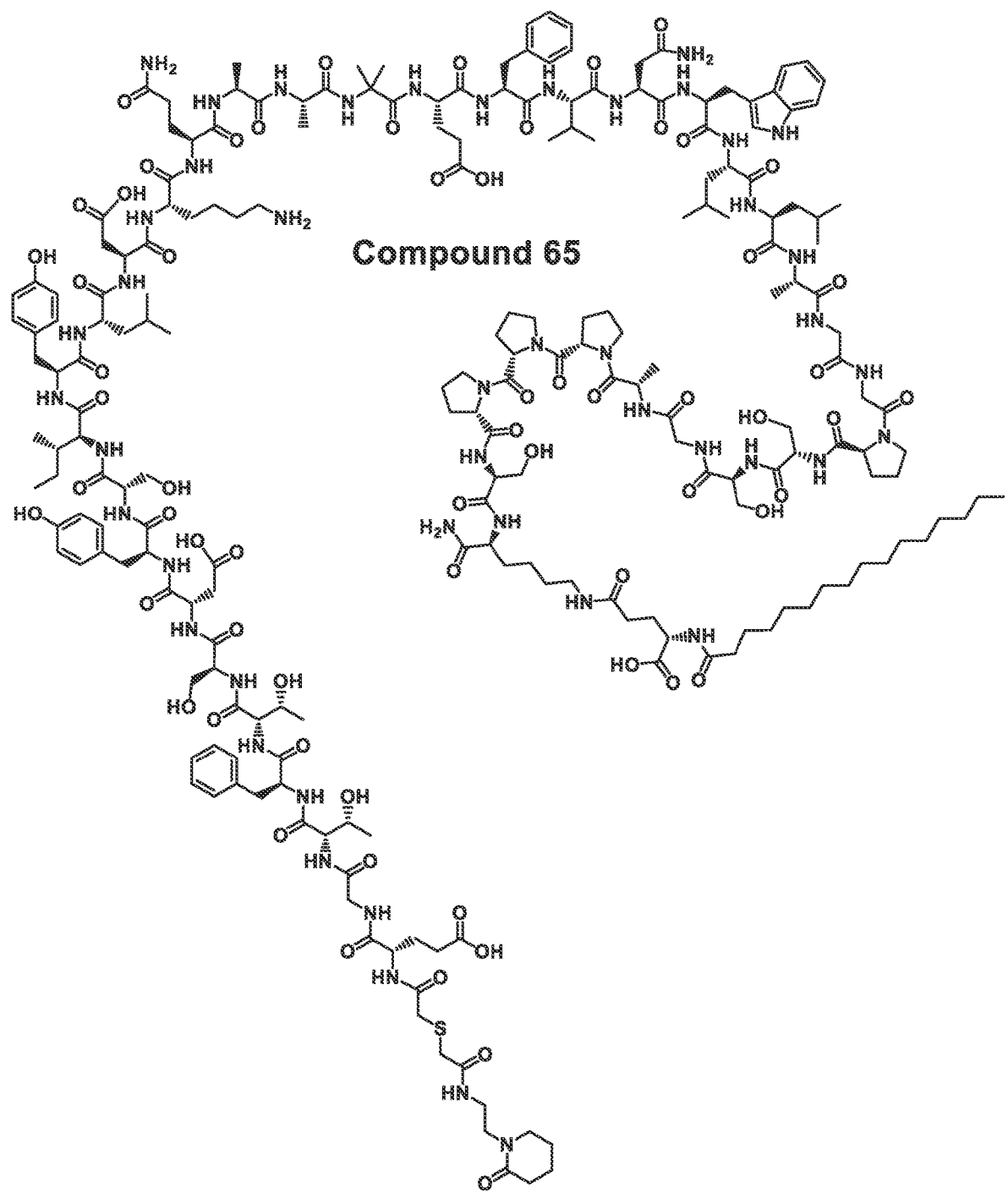
Compound 65
Cont'd

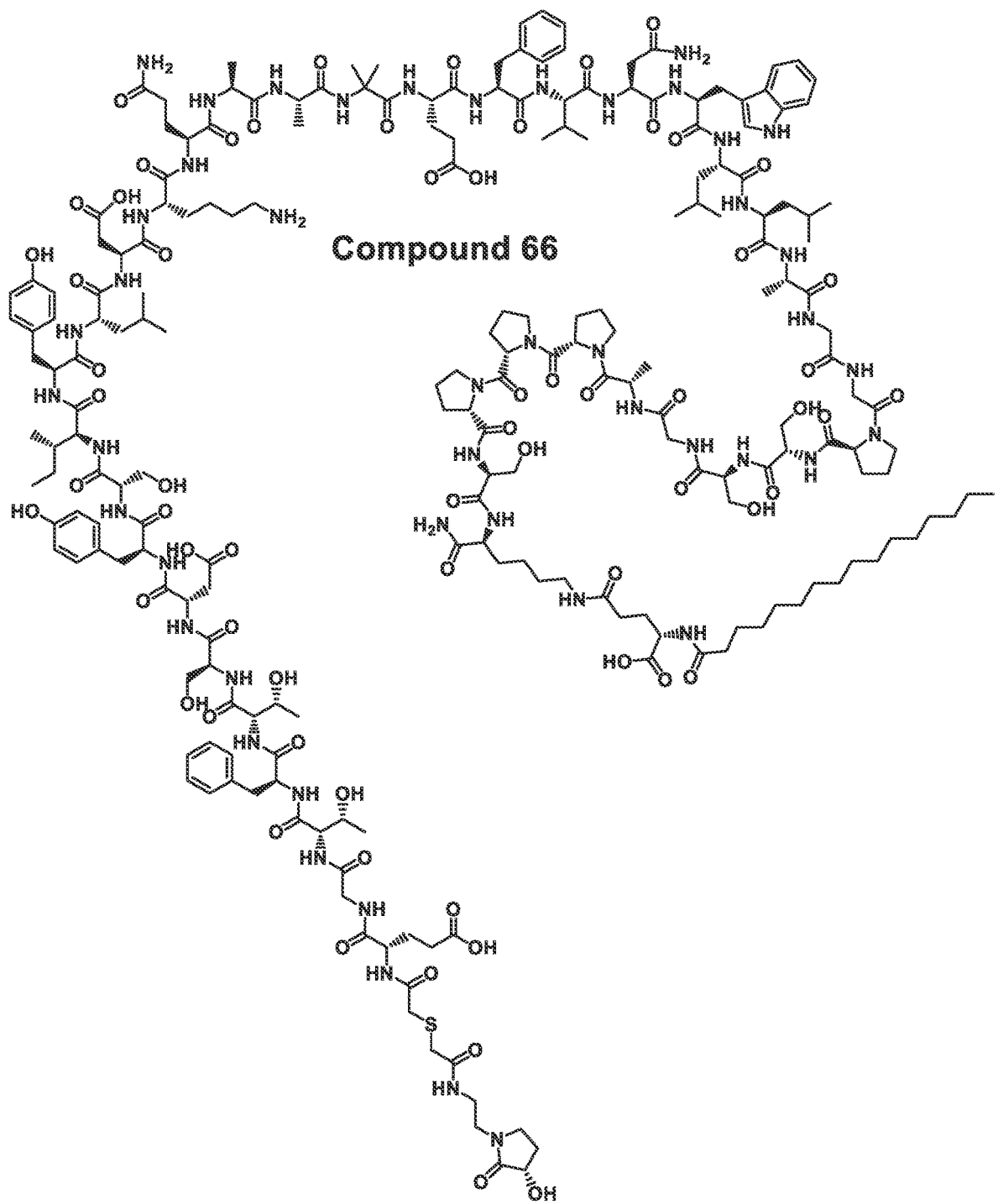
Compound 66
Cont'd

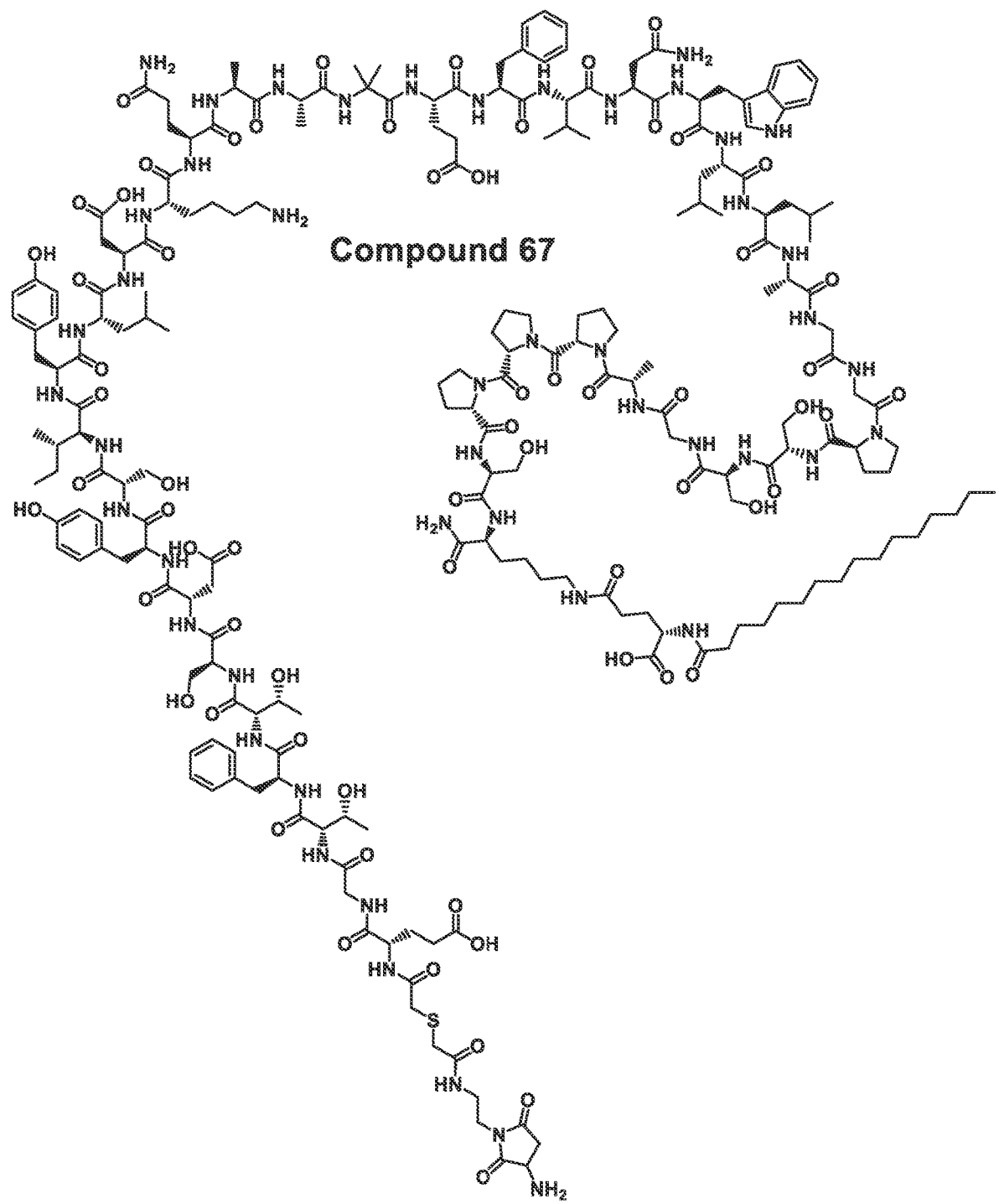
Compound 67
Cont'd

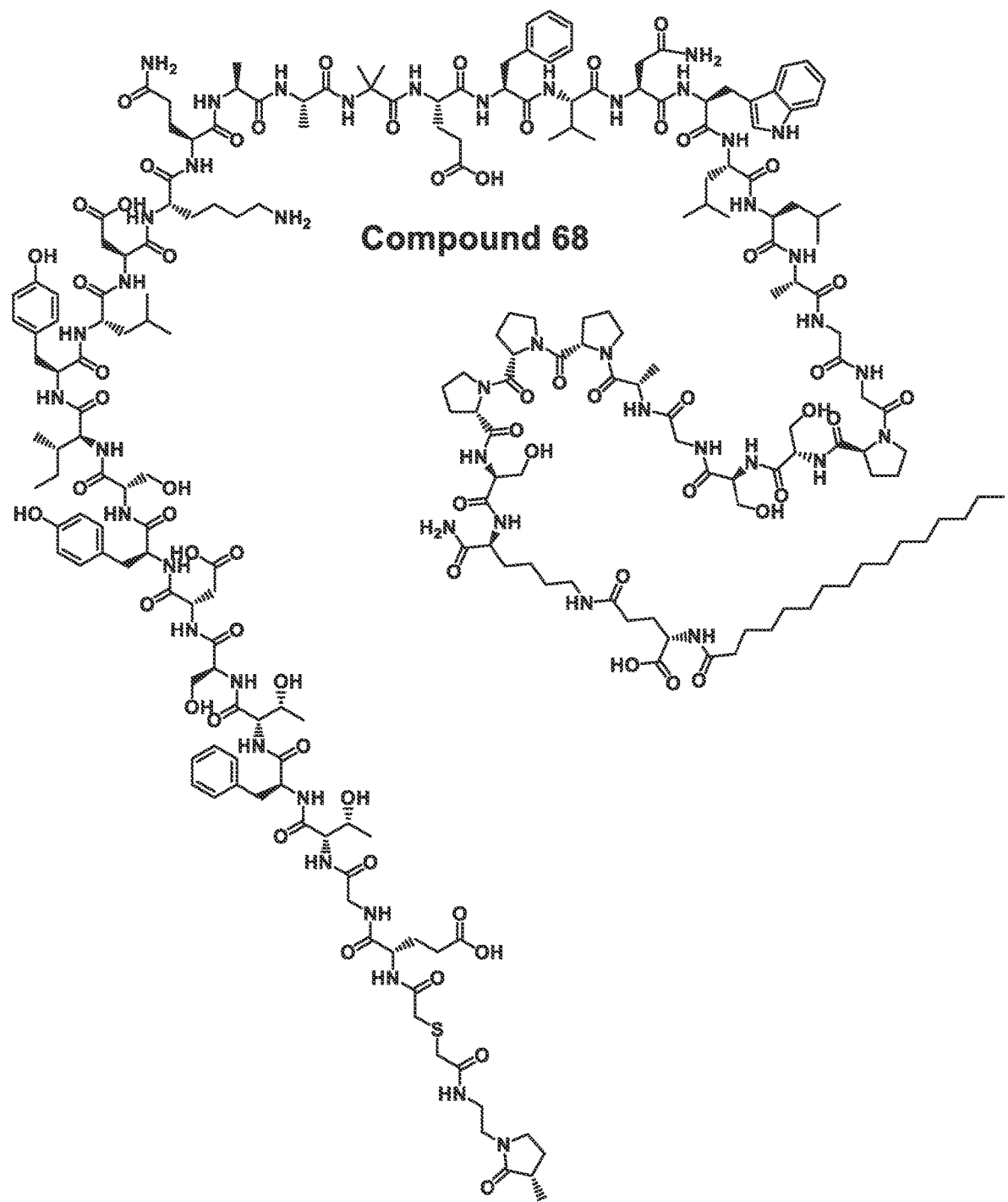
Compound 68
Cont'd

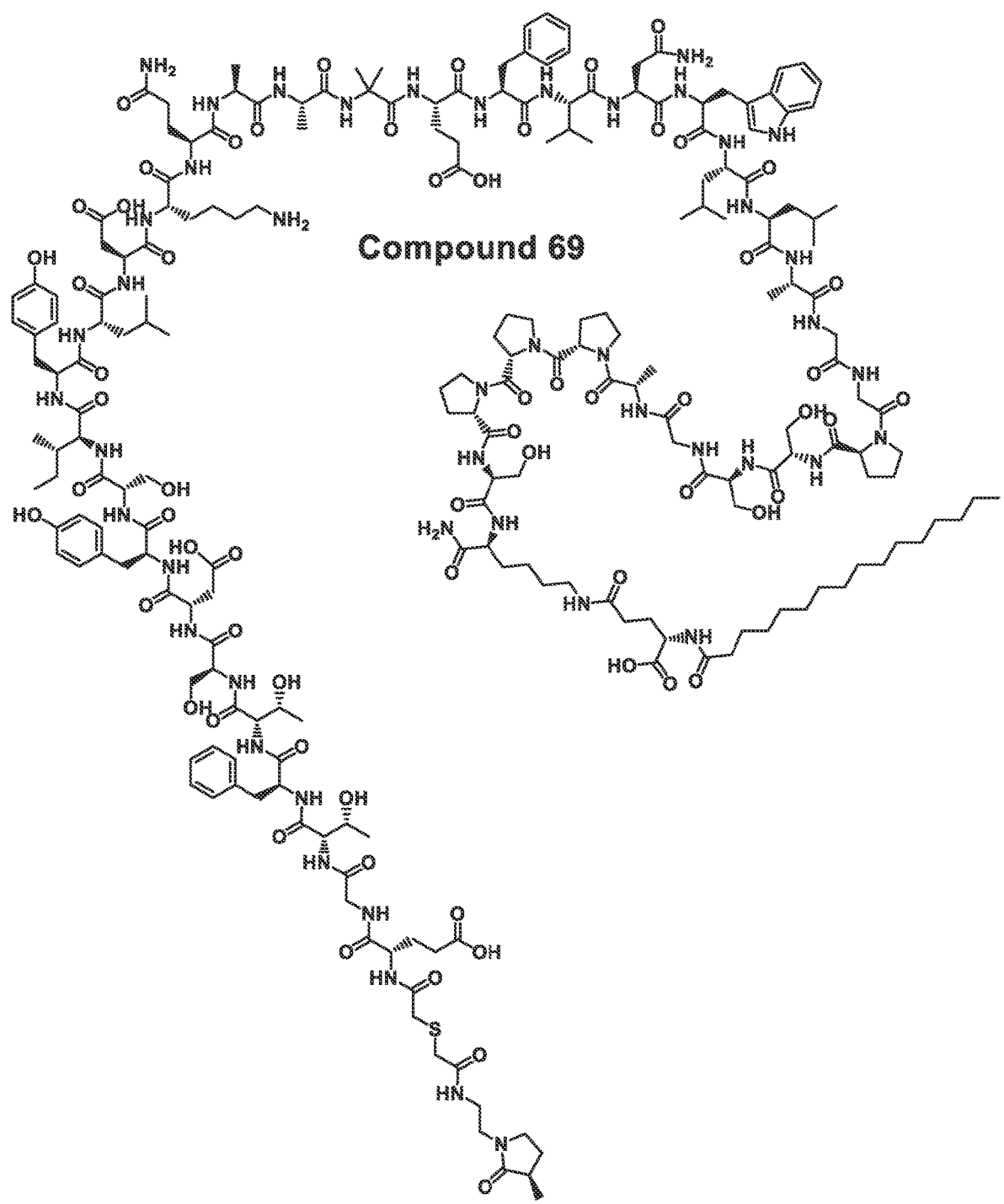
Cont'd

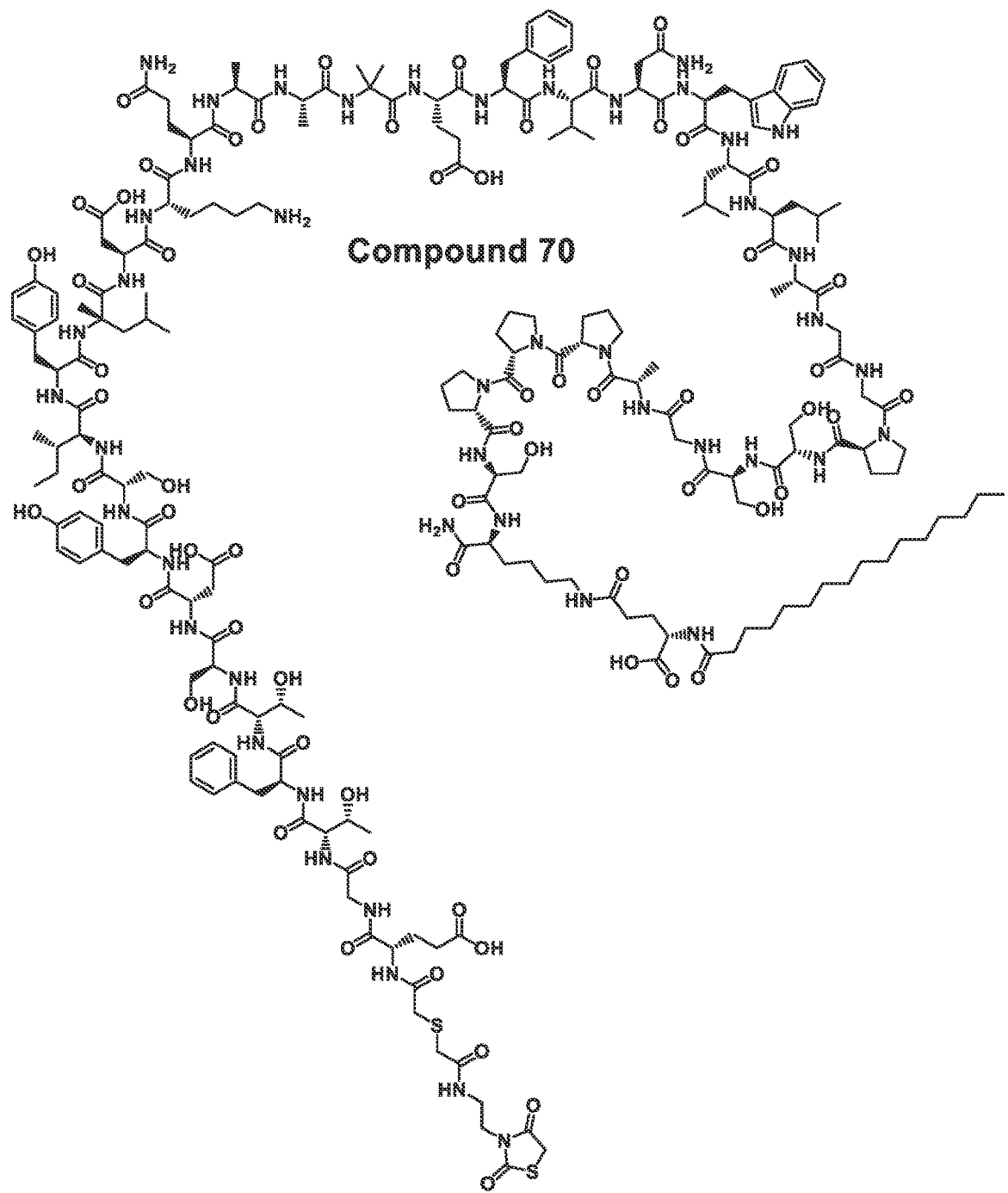
Compound 70

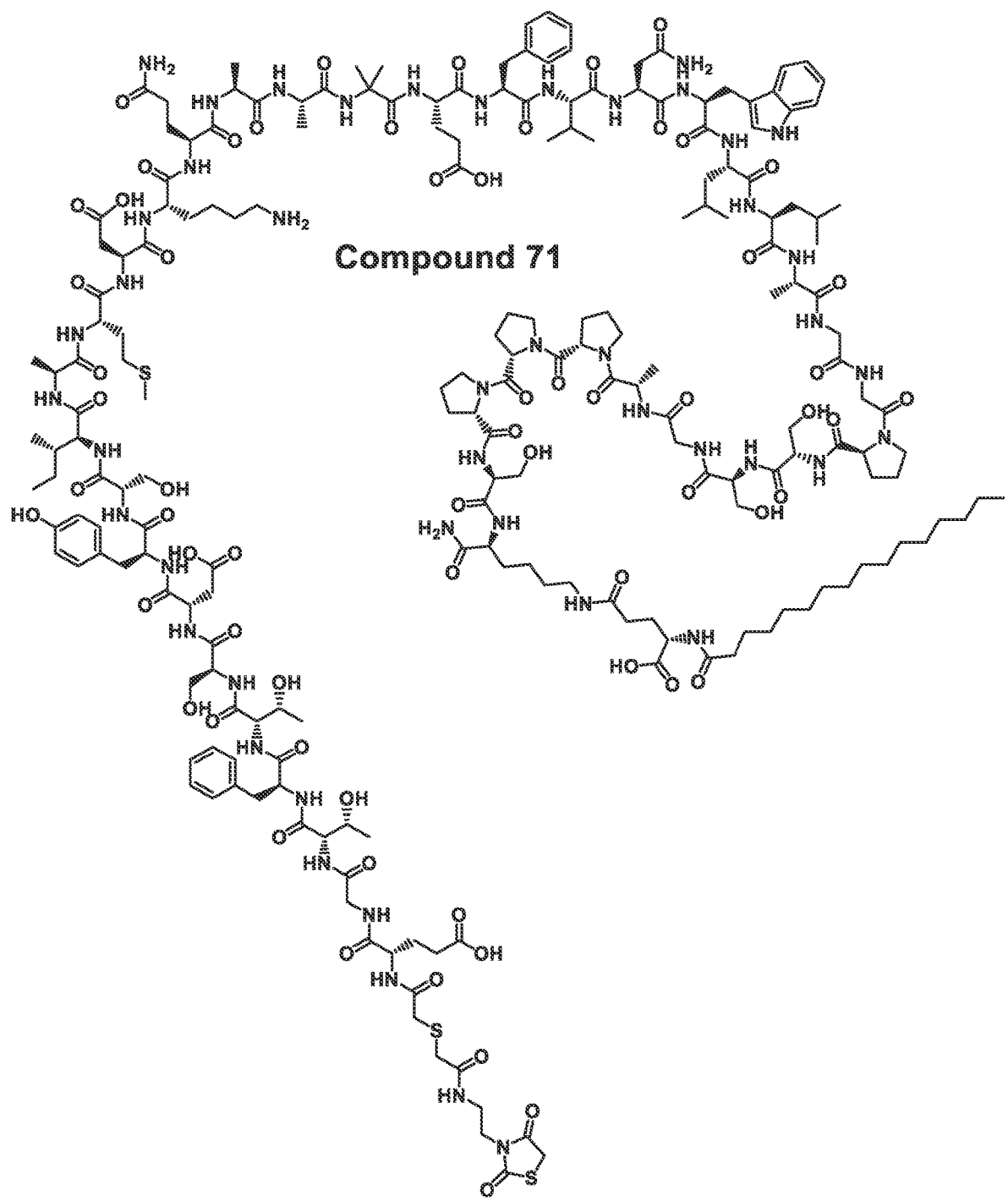
Compound 71
Cont'd

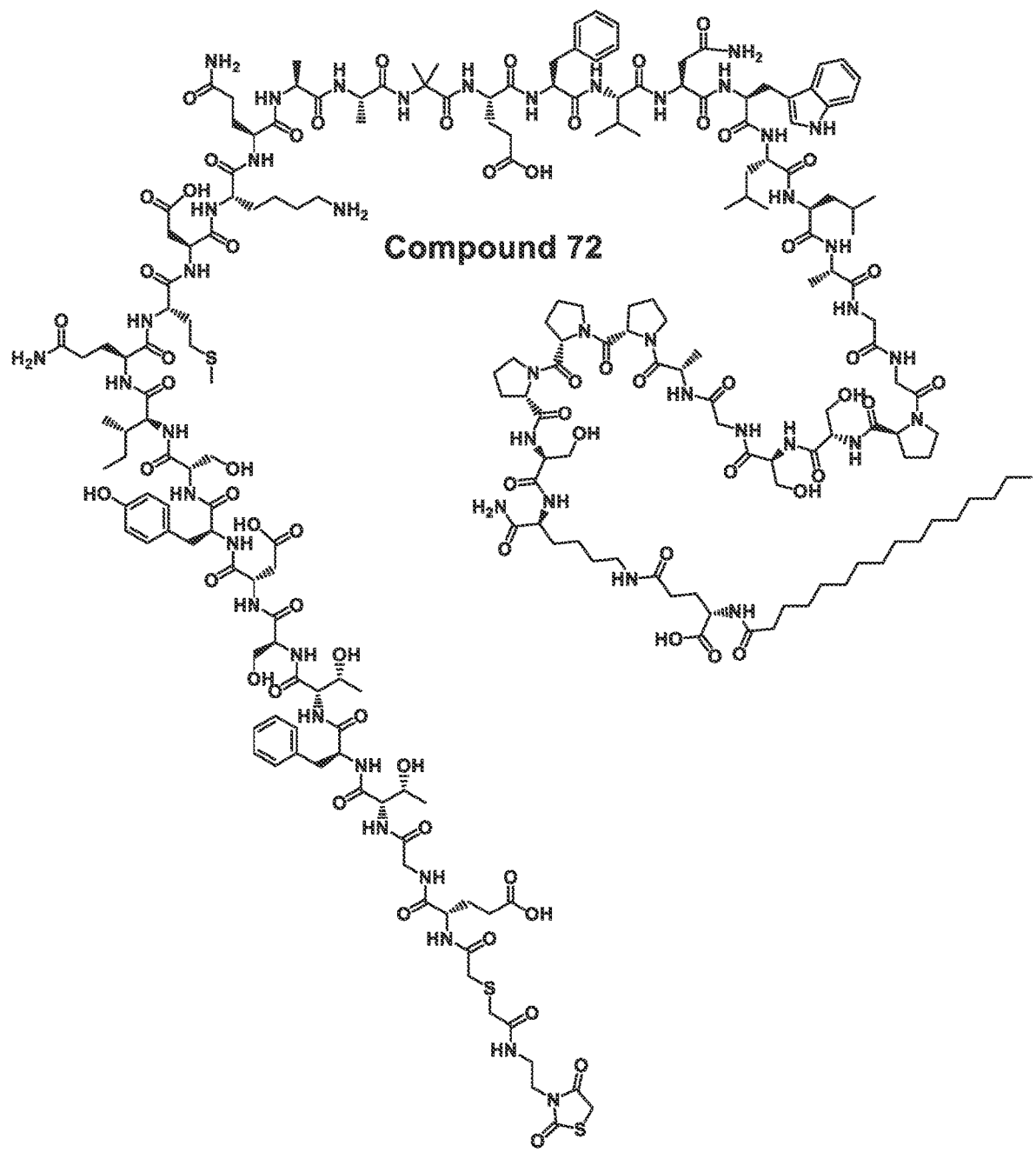
Compound 72
Cont'd

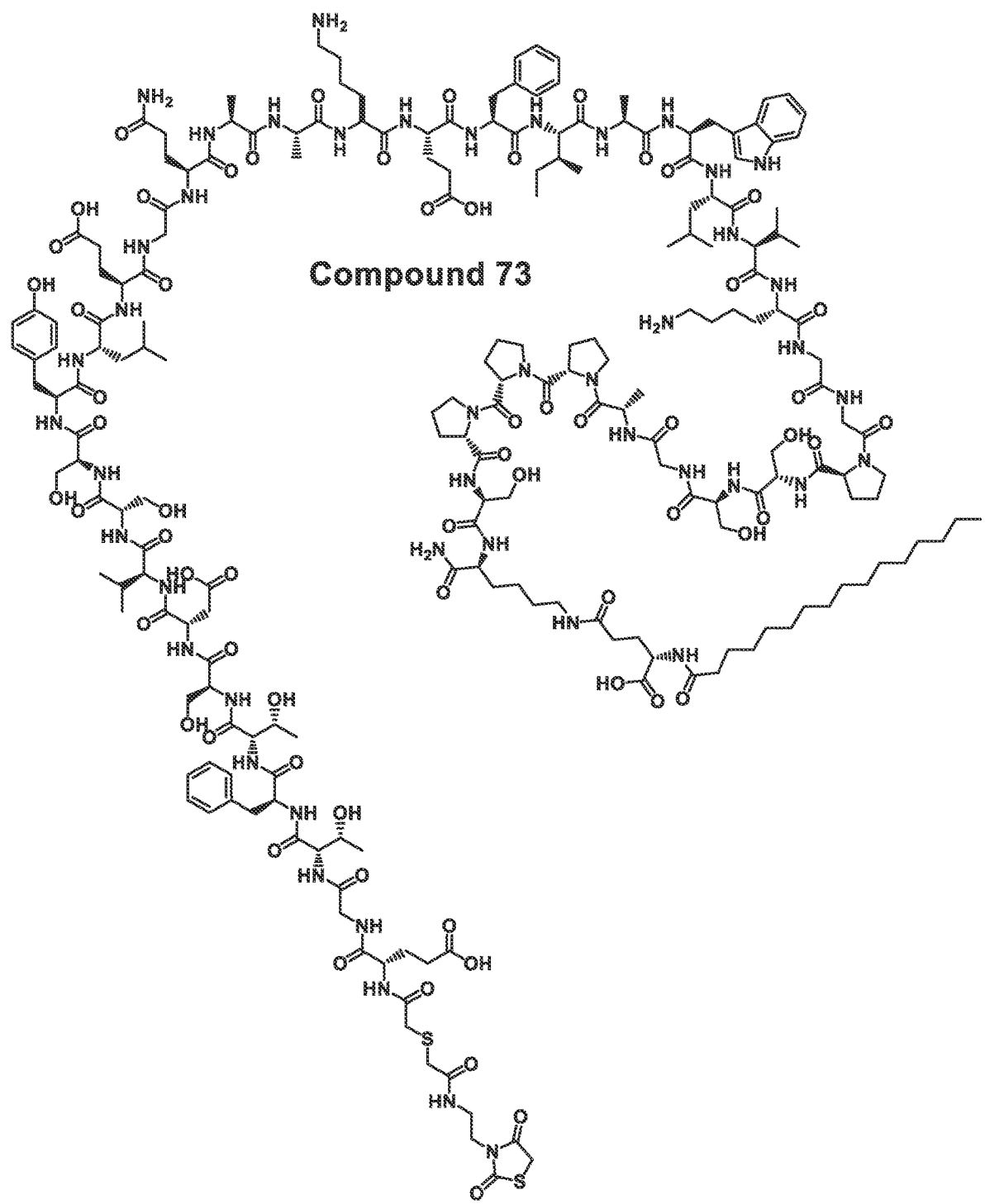
Compound 73
Cont'd

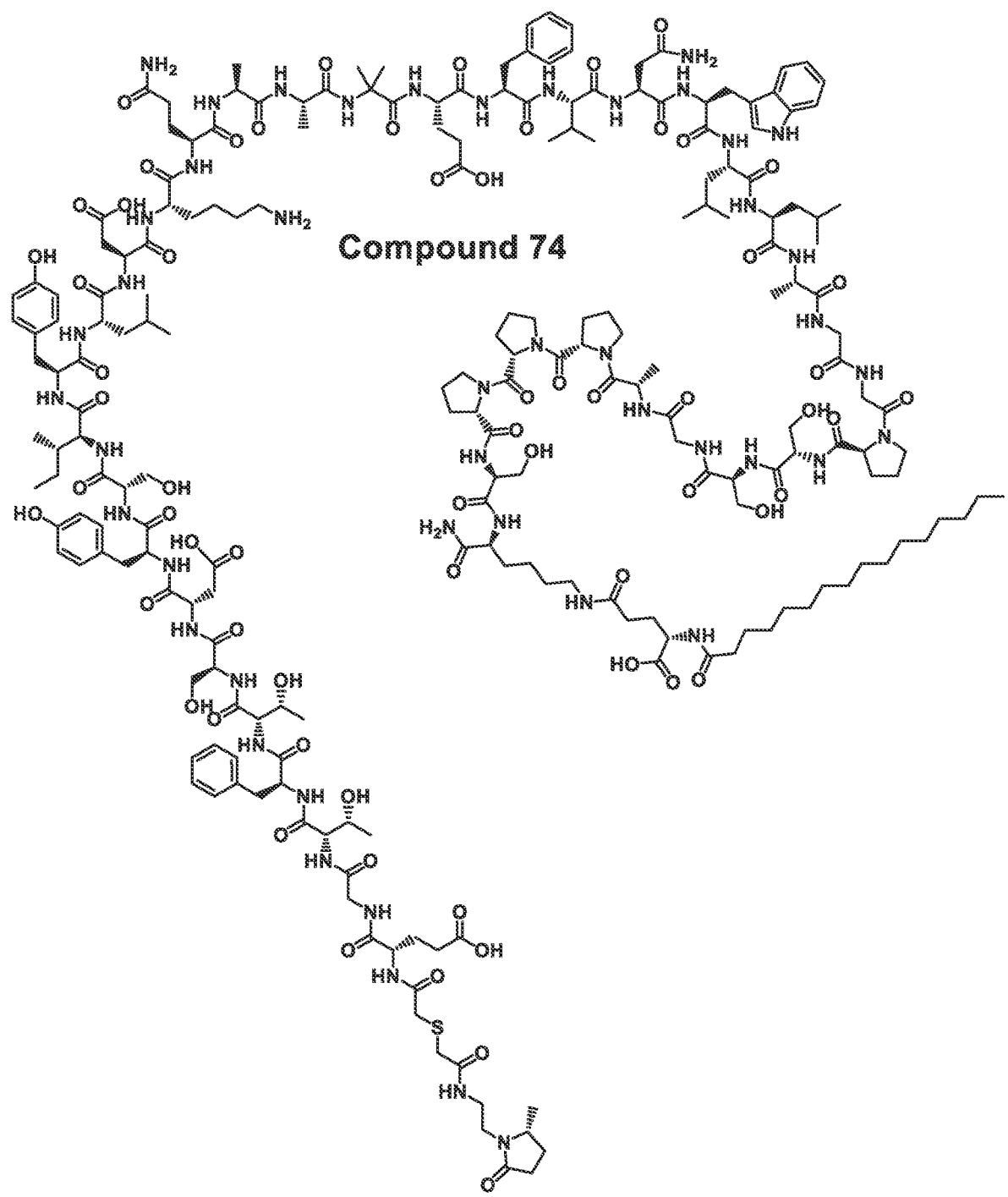
Compound 74
Cont'd

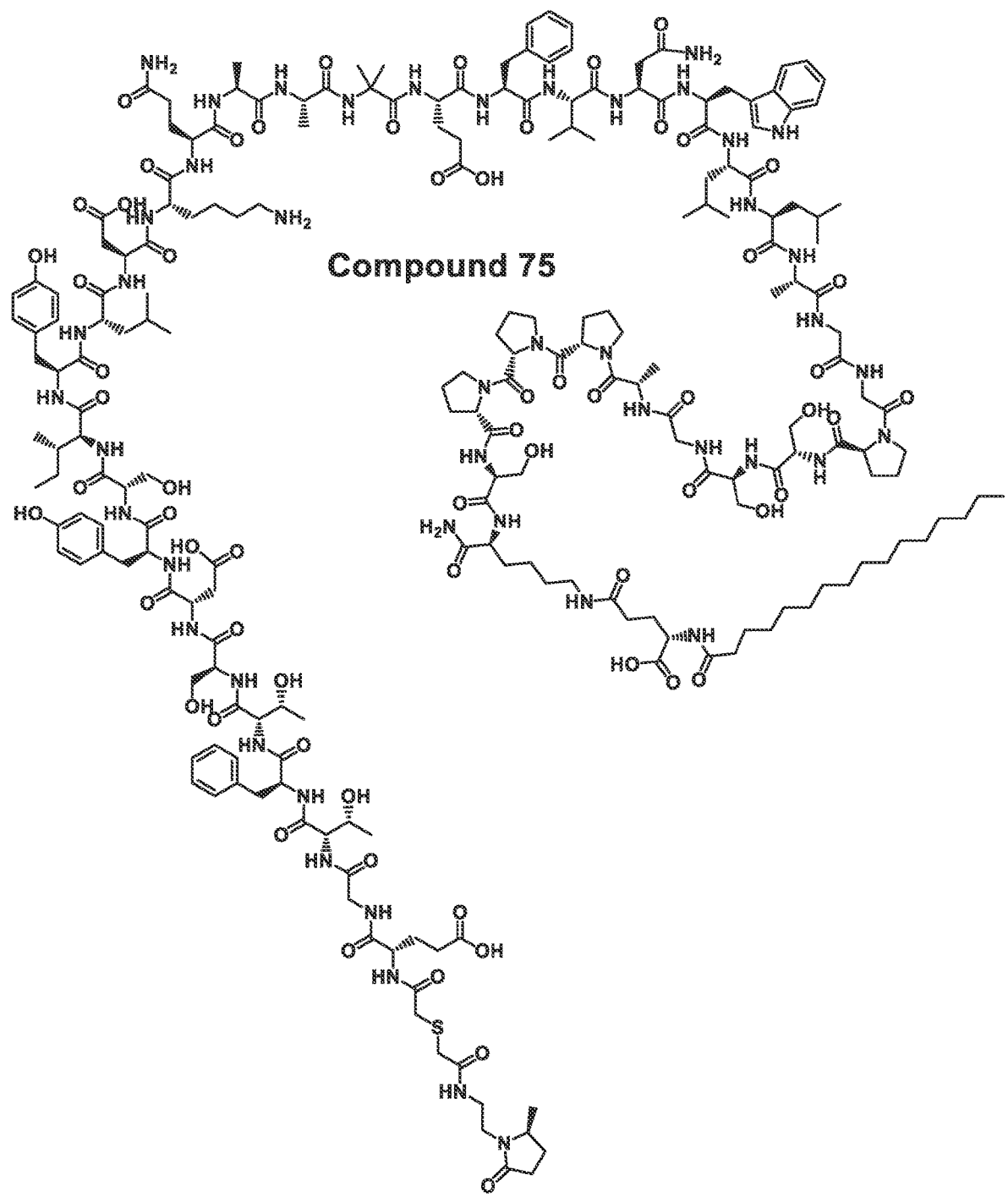
Compound 75
Cont'd

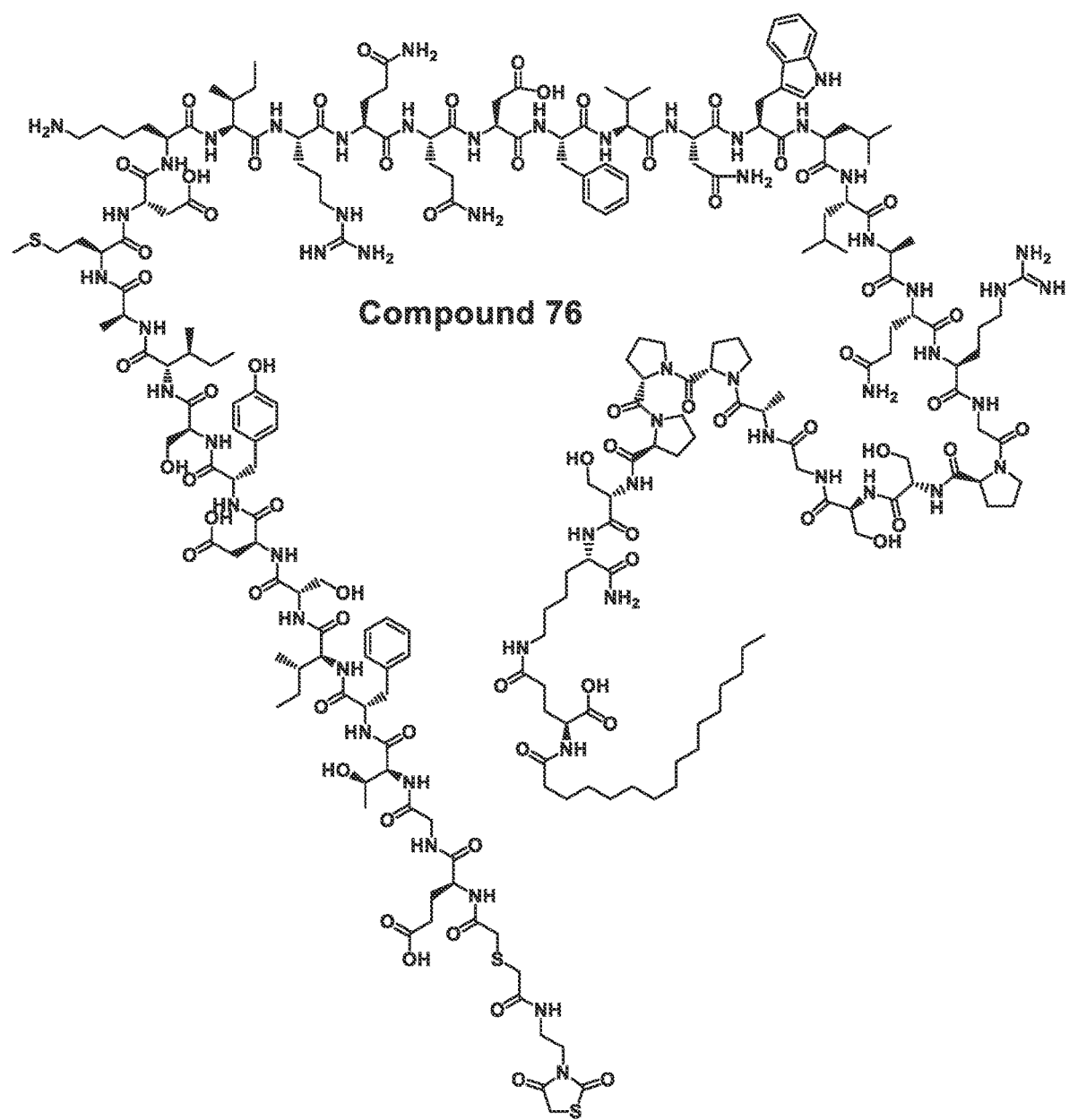
Compound 76
Cont'd

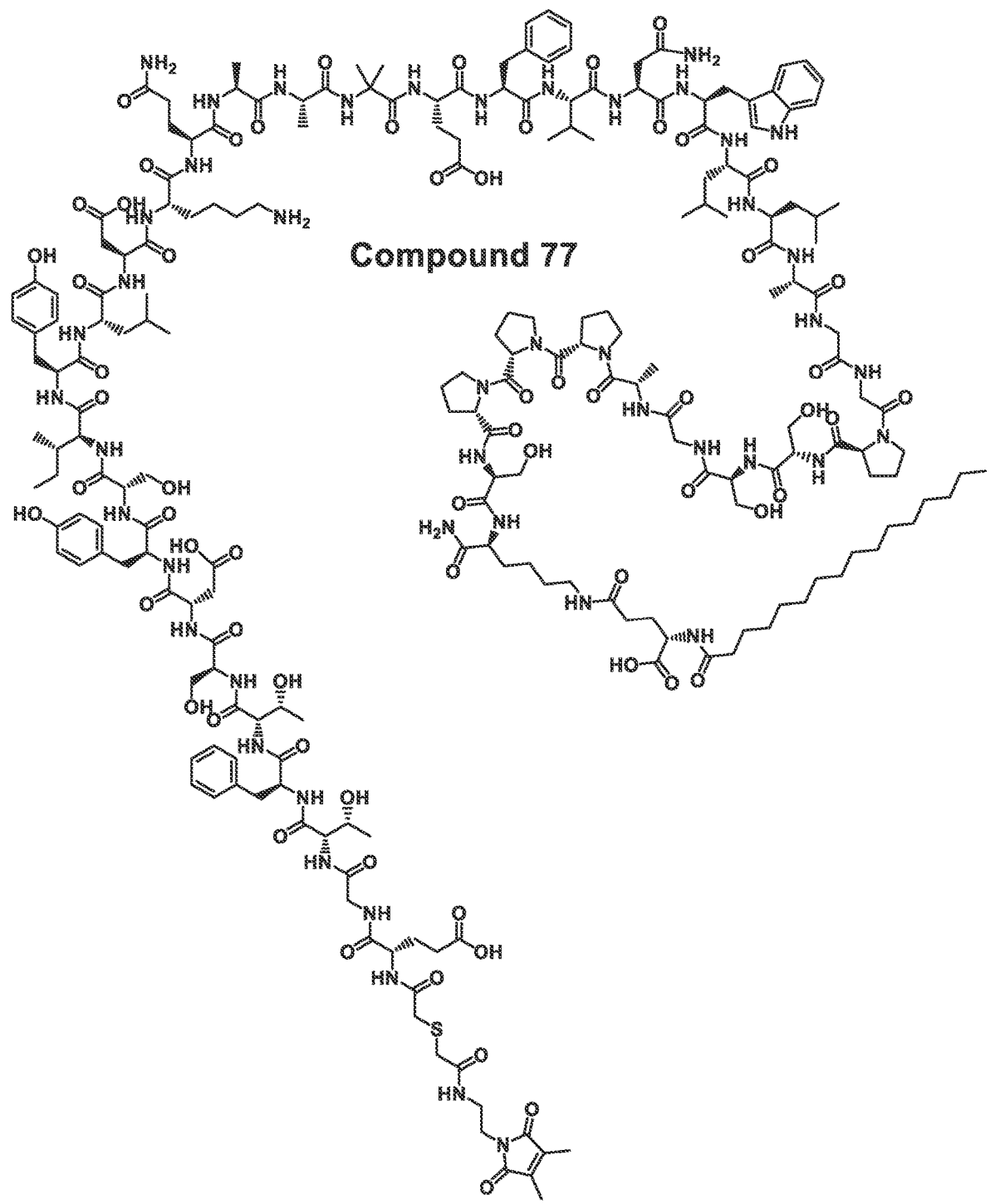
Compound 77
Cont'd

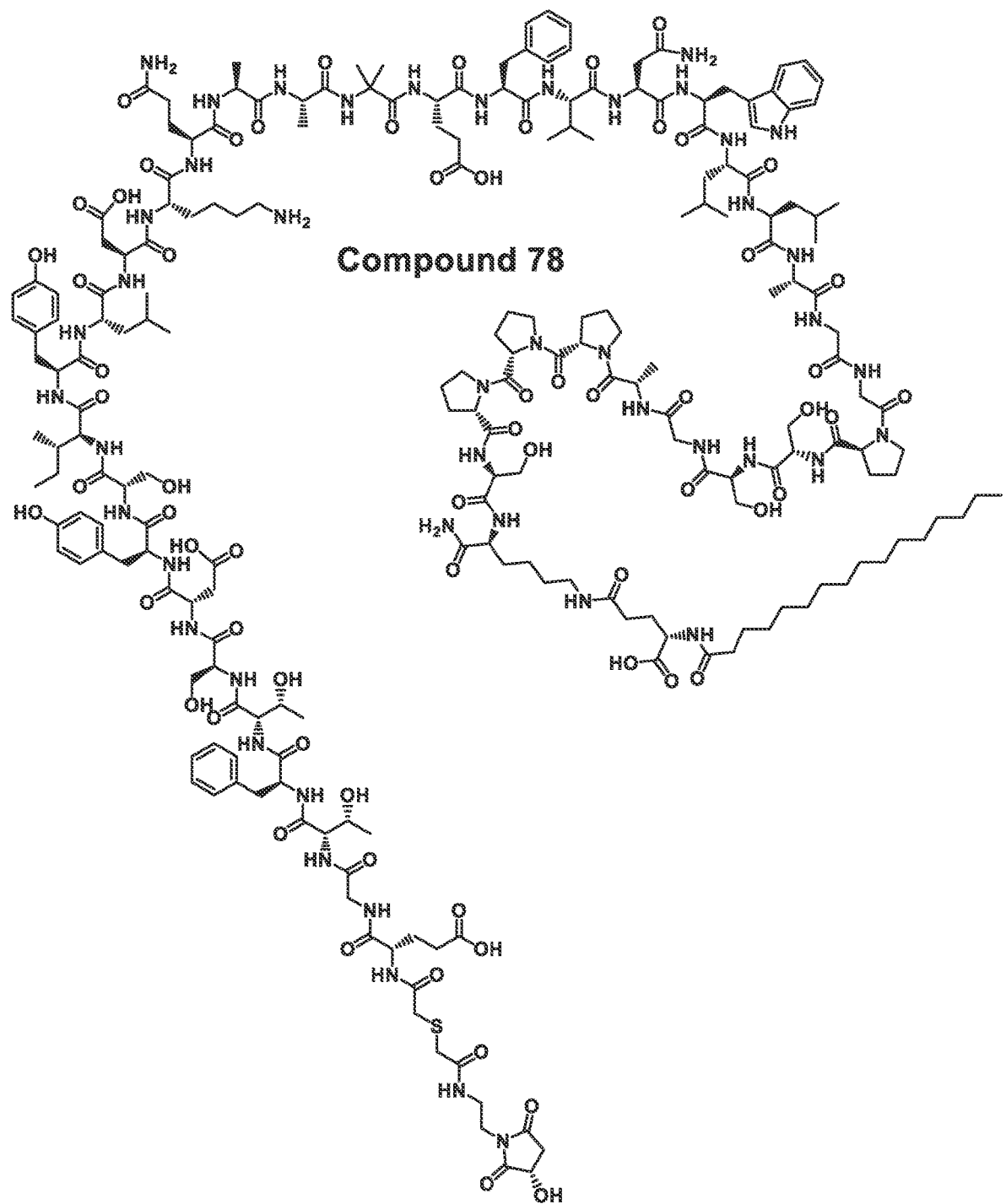
Compound 78
Cont'd

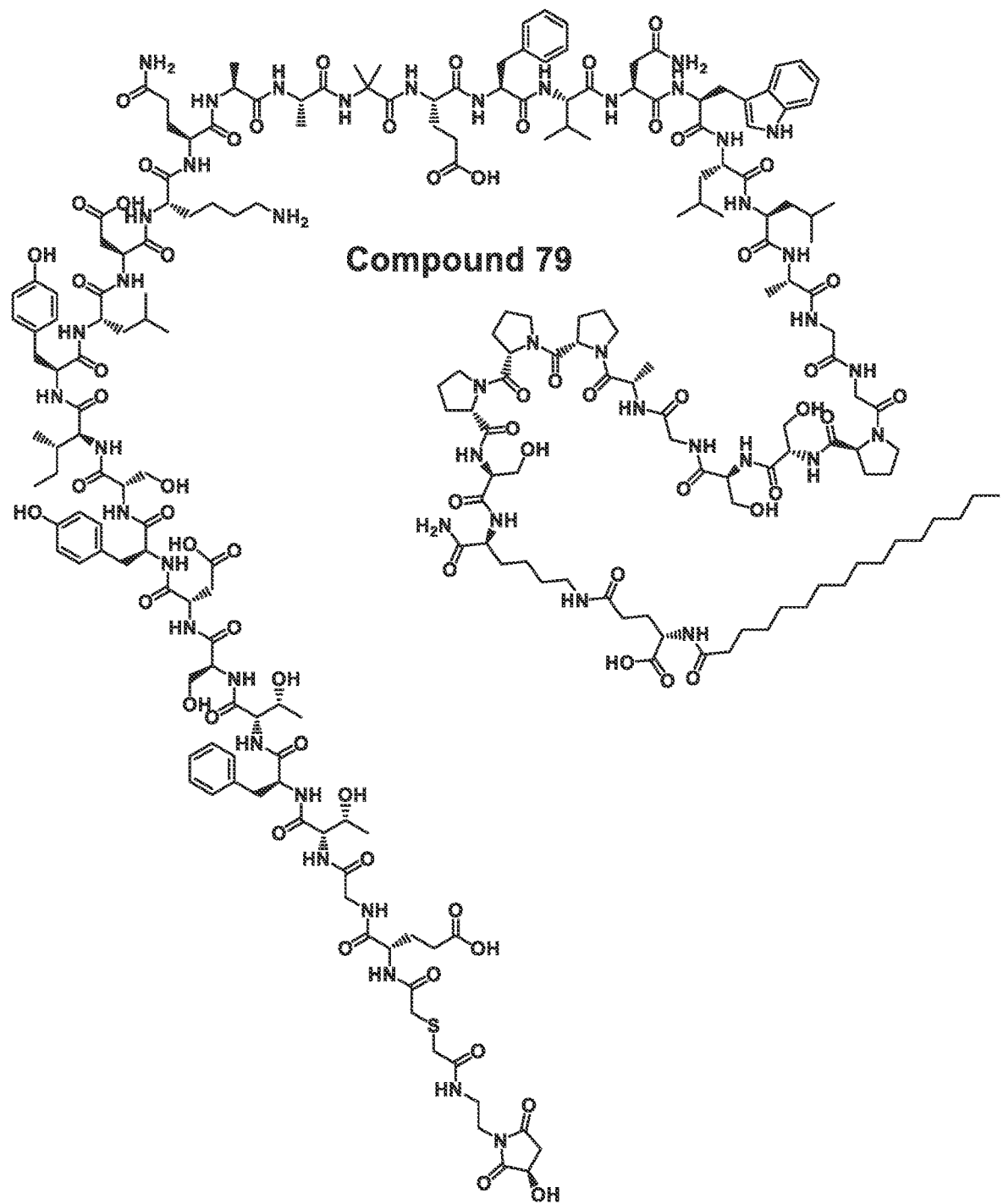
Compound 79
Cont'd

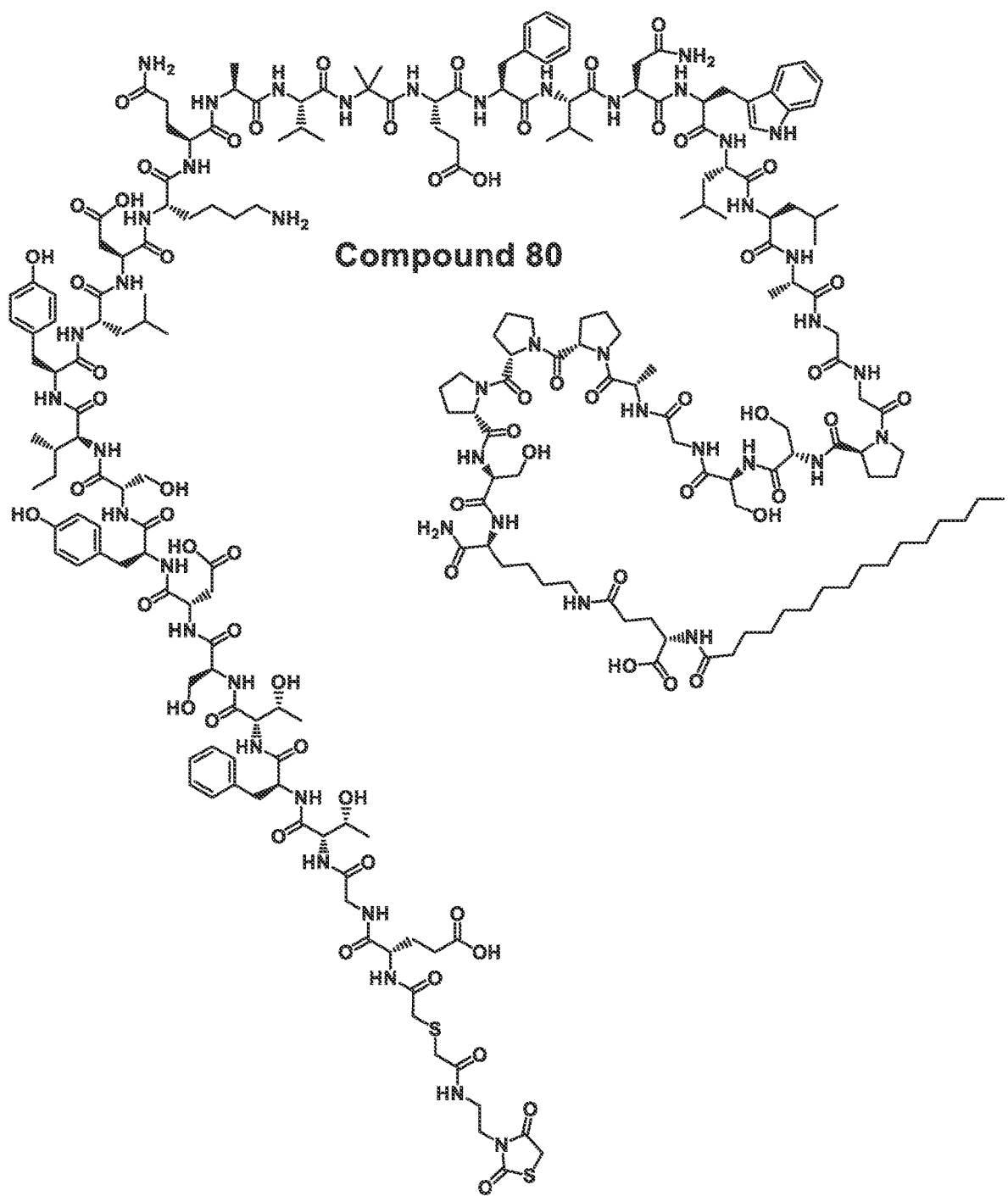
Compound 80
Cont'd

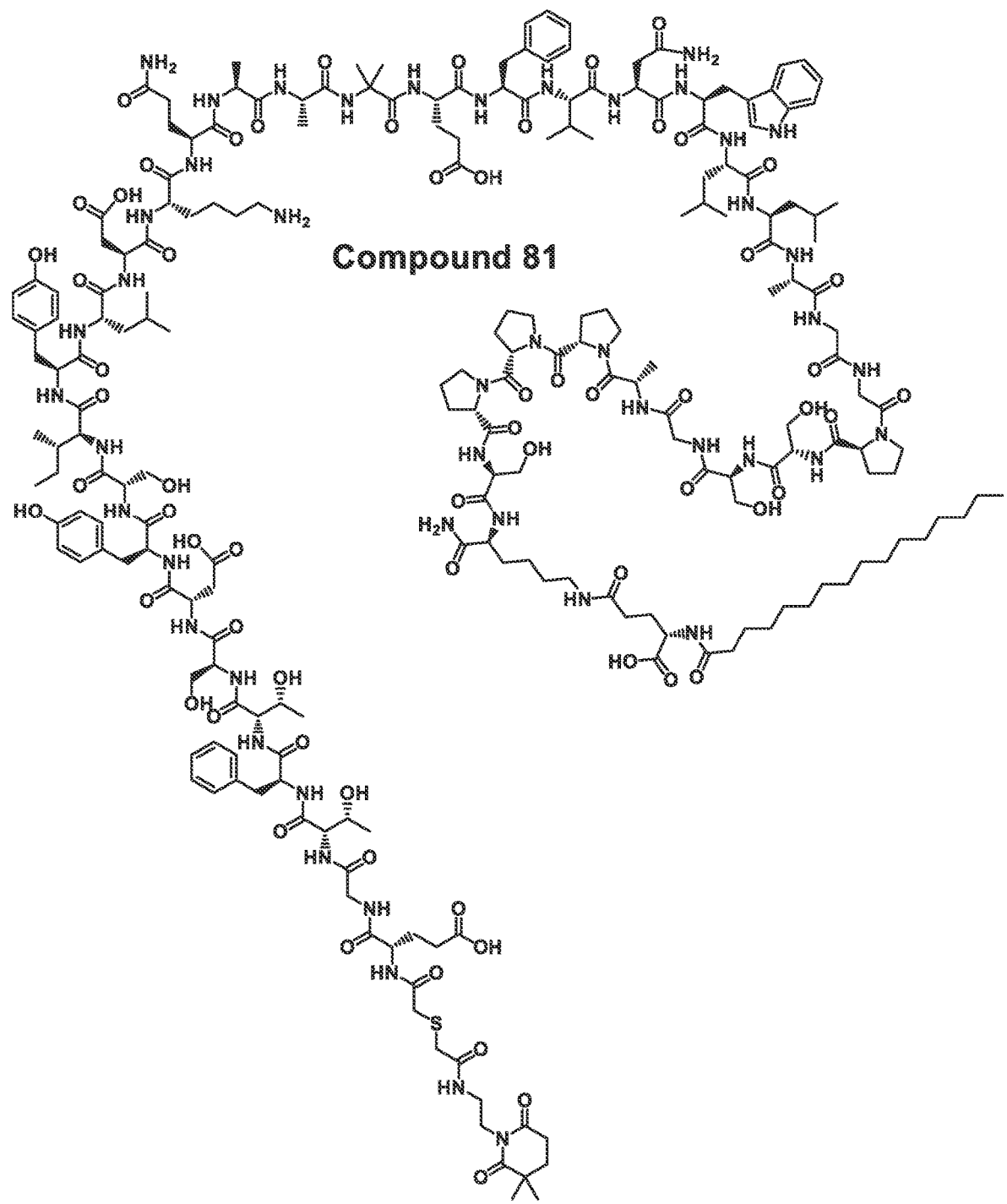
Compound 81
Cont'd

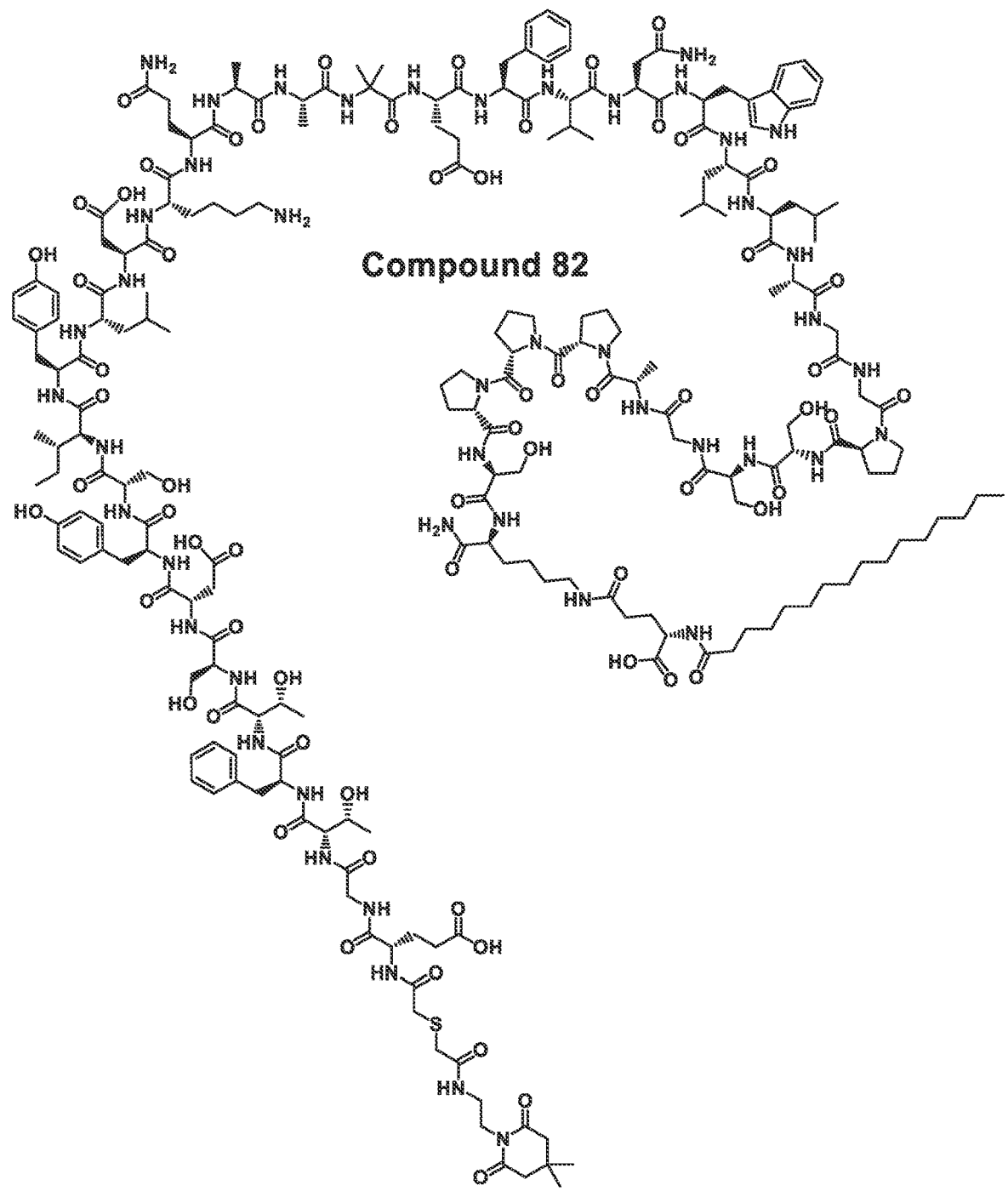
Compound 82
Cont'd

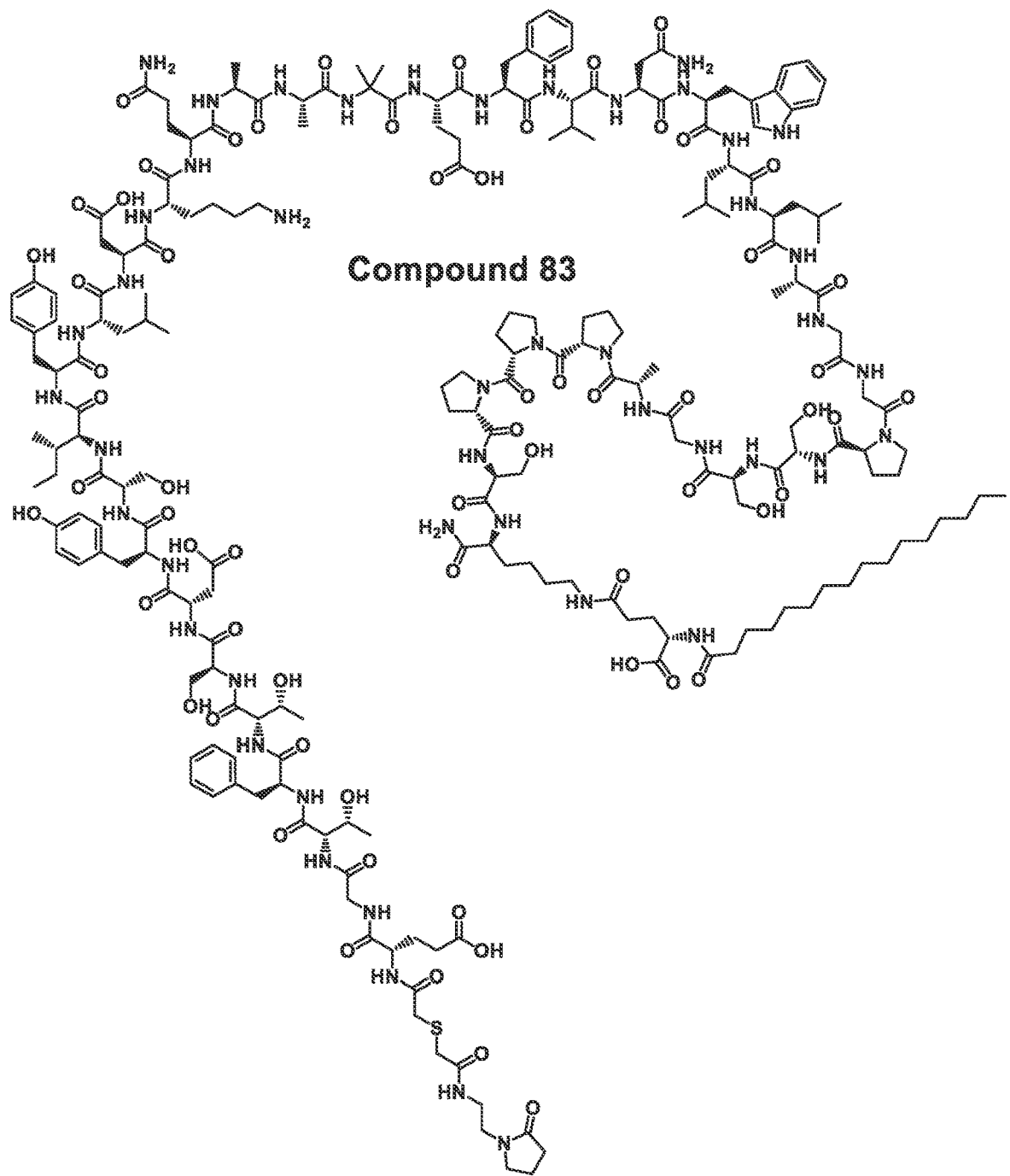
Compound 83
Cont'd

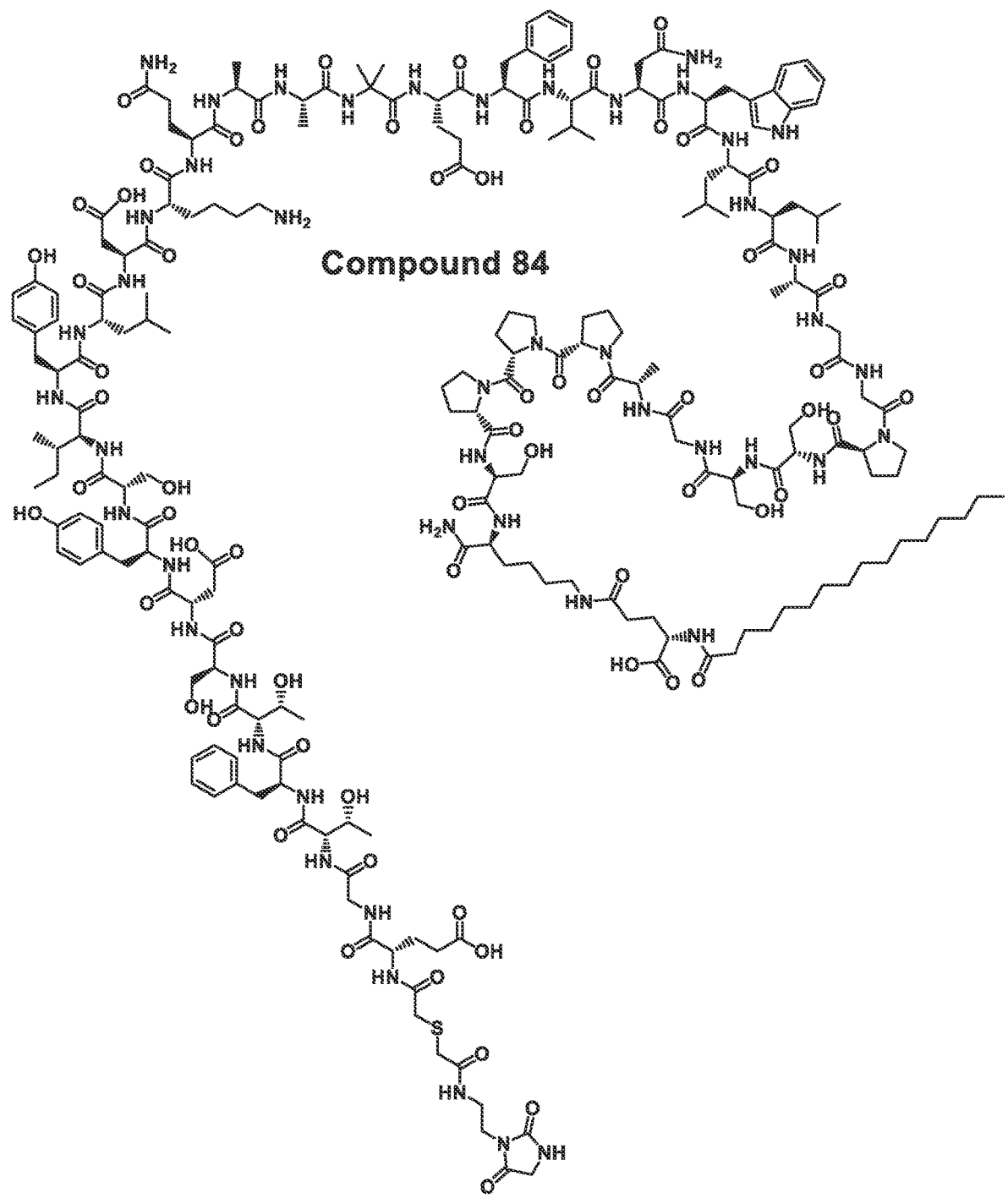
Compound 84
Cont'd

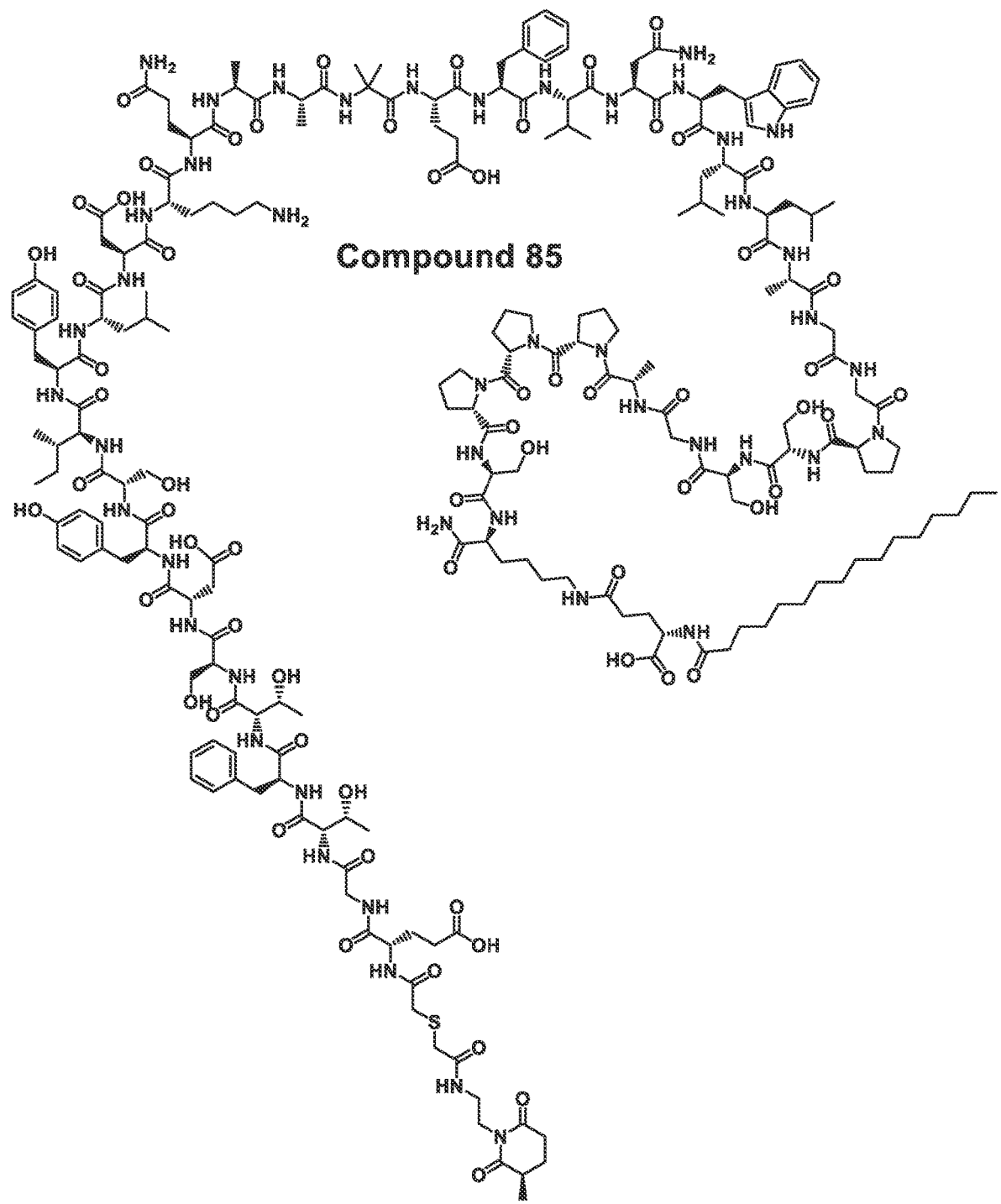
Compound 85
Cont'd

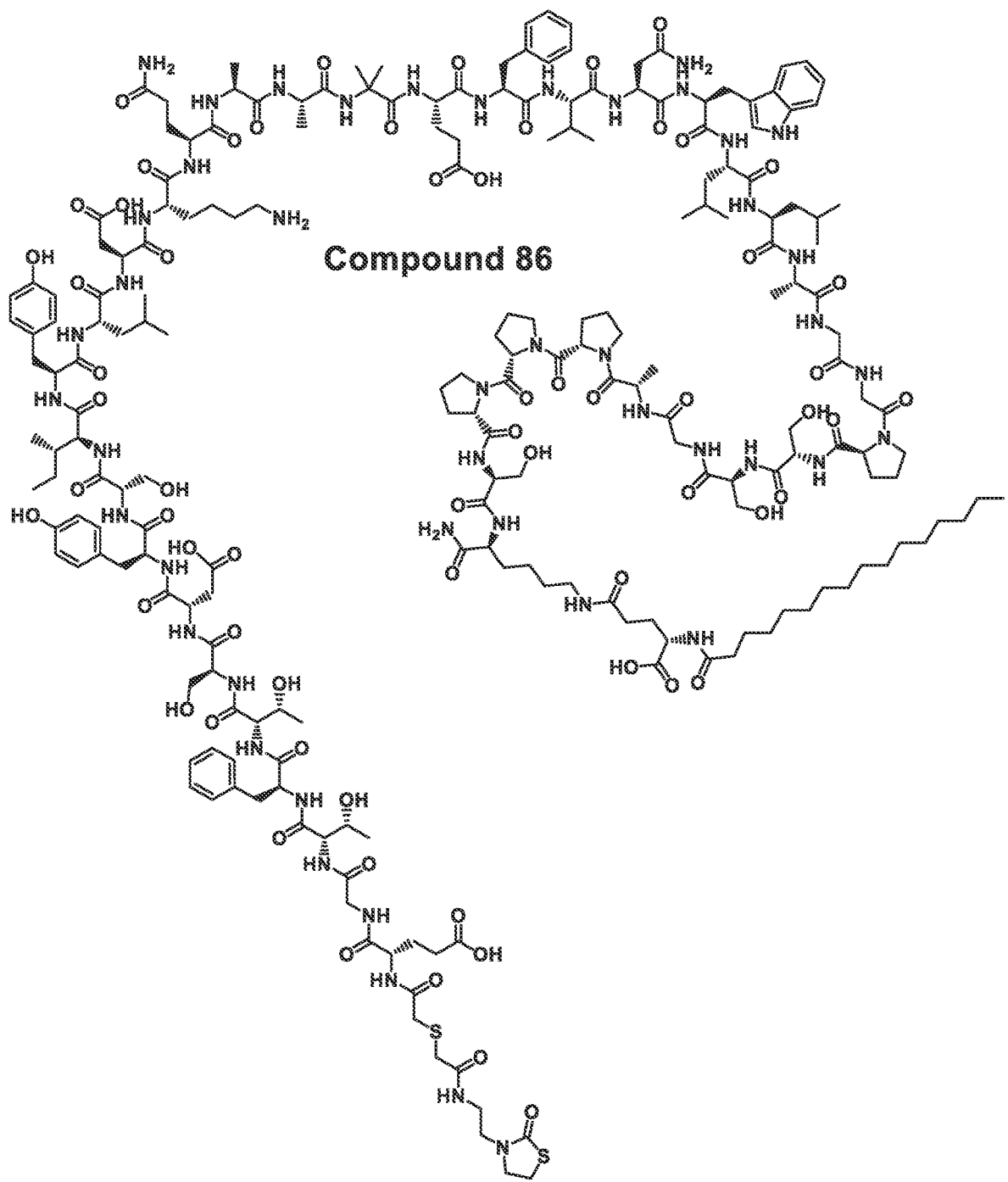
Compound 86
Cont'd

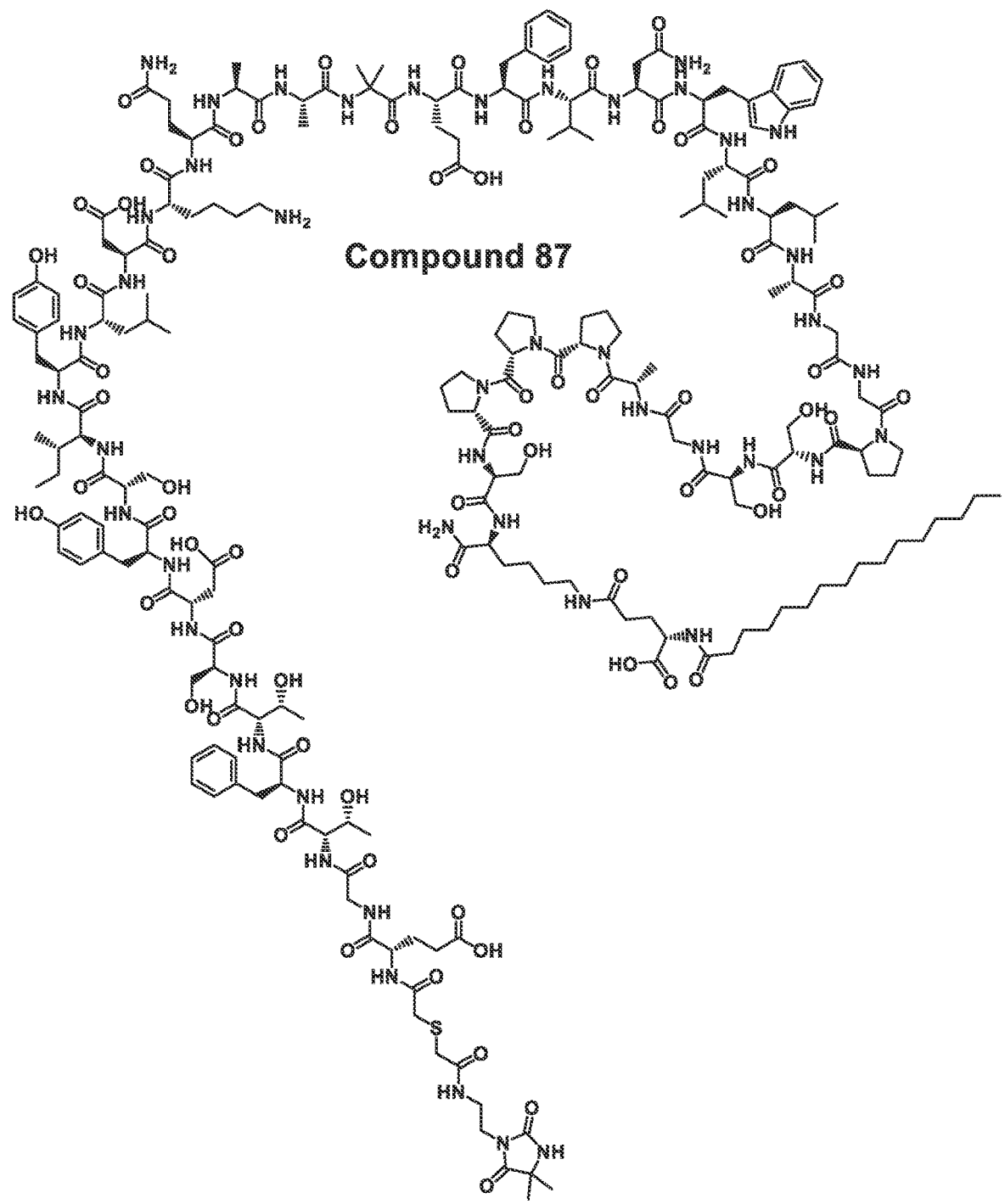
Compound 87
Cont'd

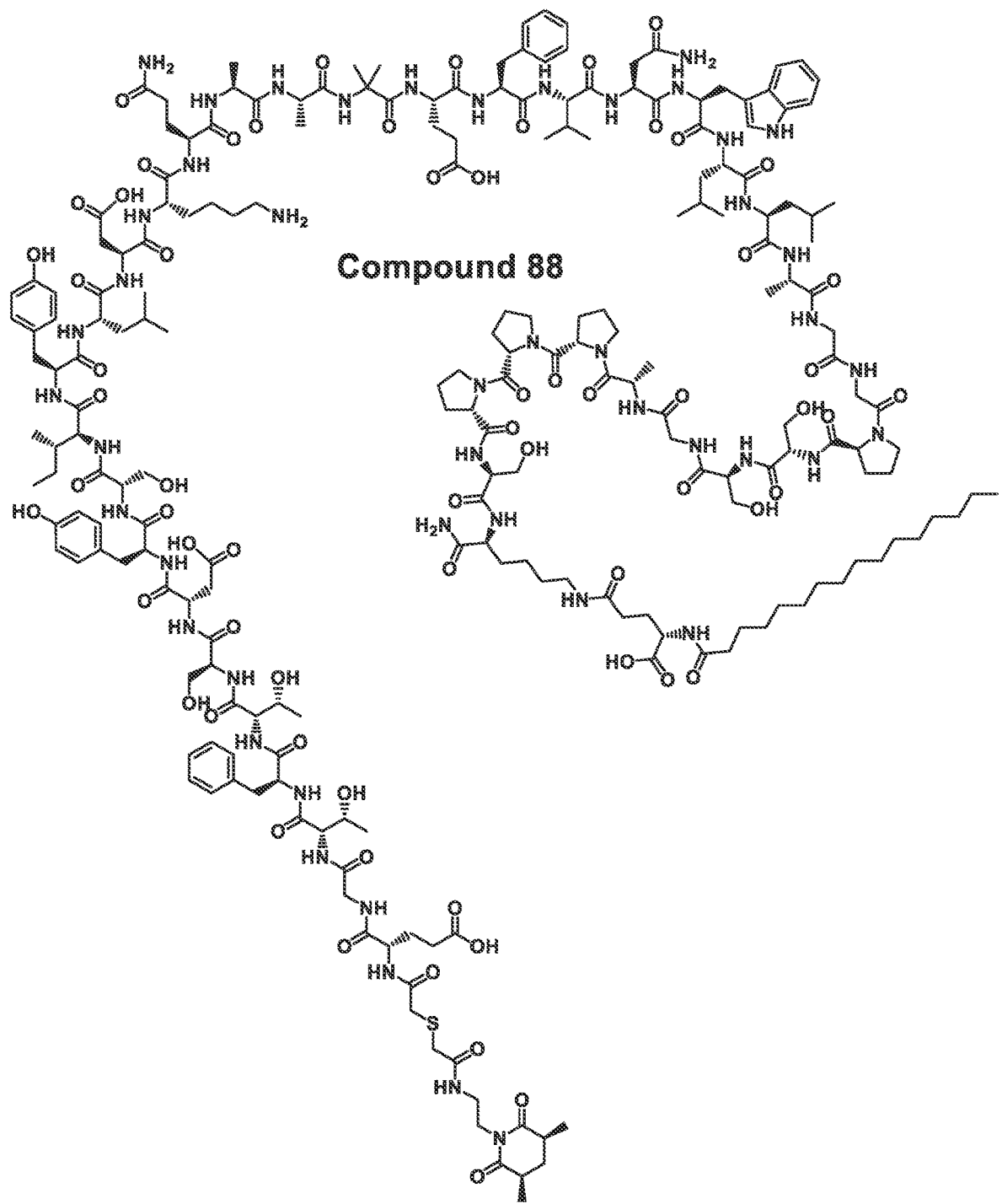
Compound 88
Cont'd

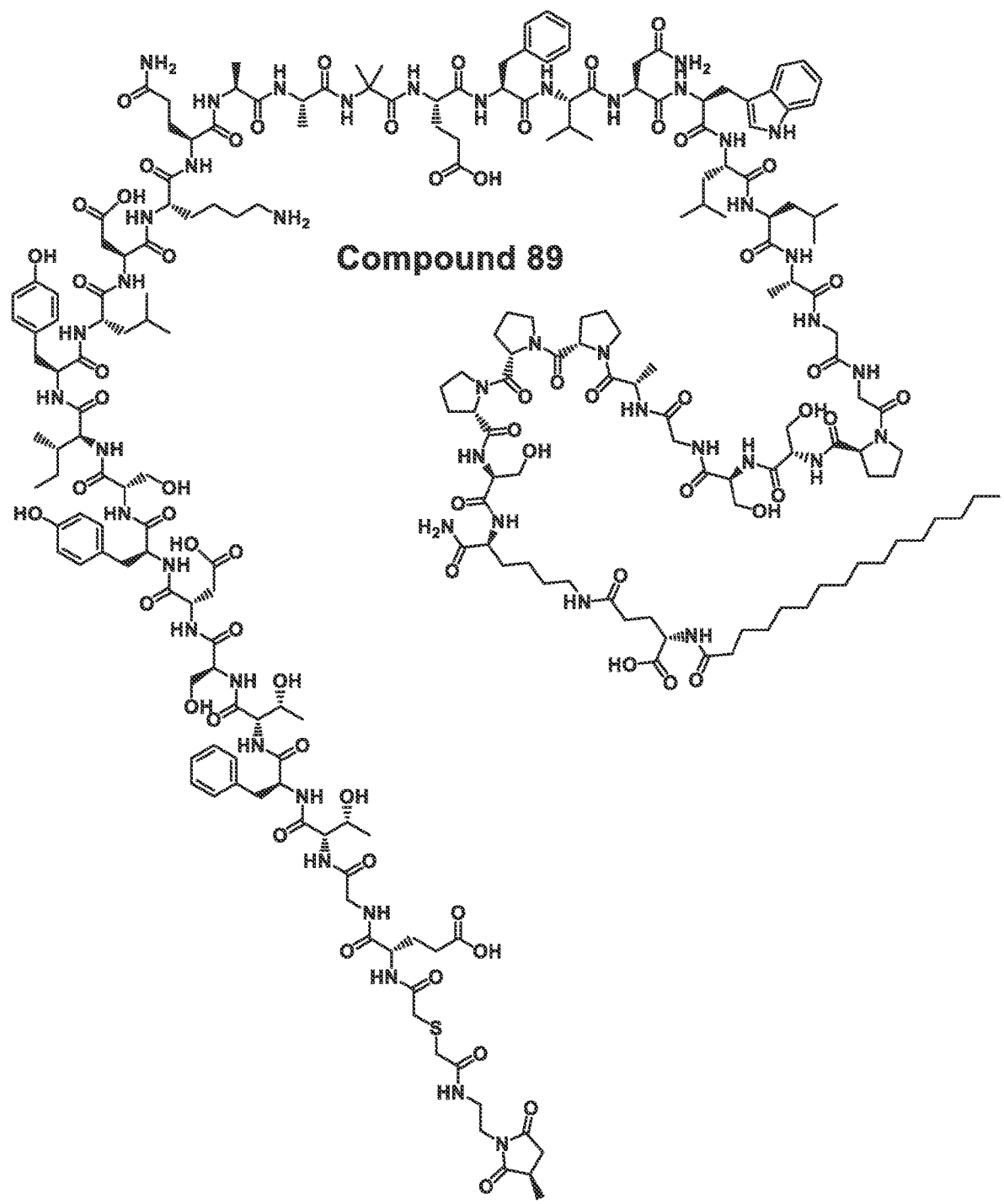
Compound 89
Cont'd

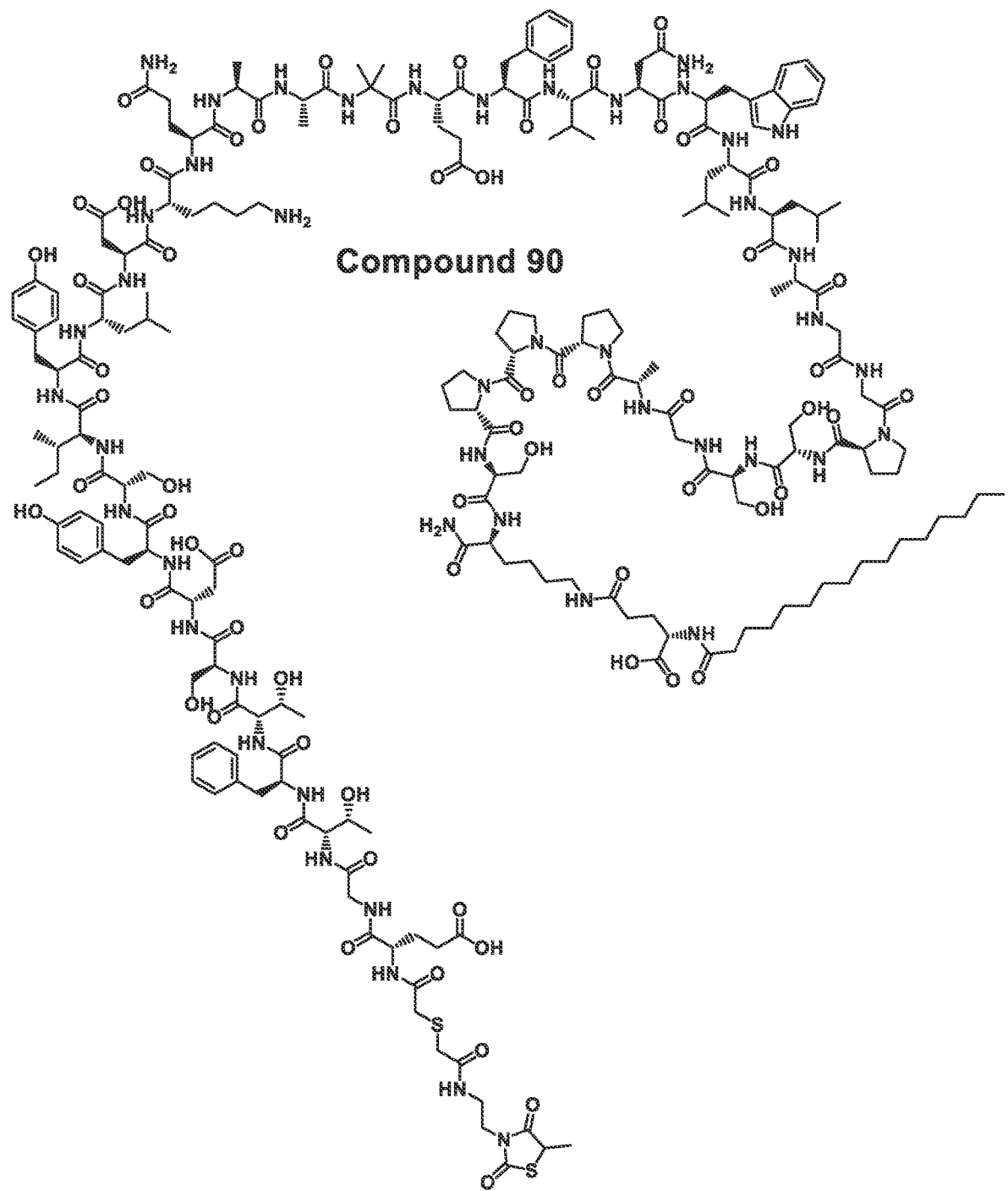
Compound 90
Cont'd

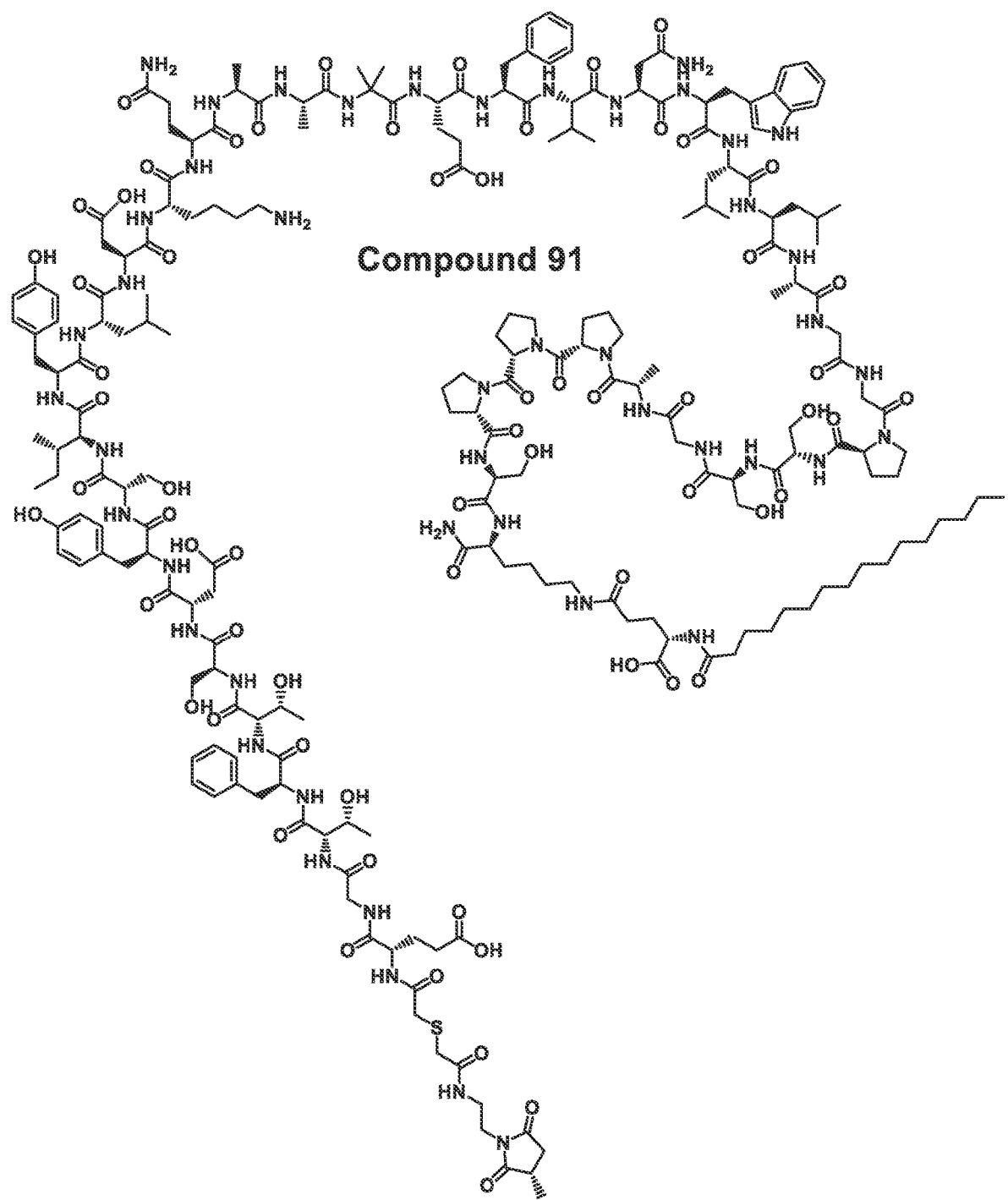
Compound 91
Cont'd

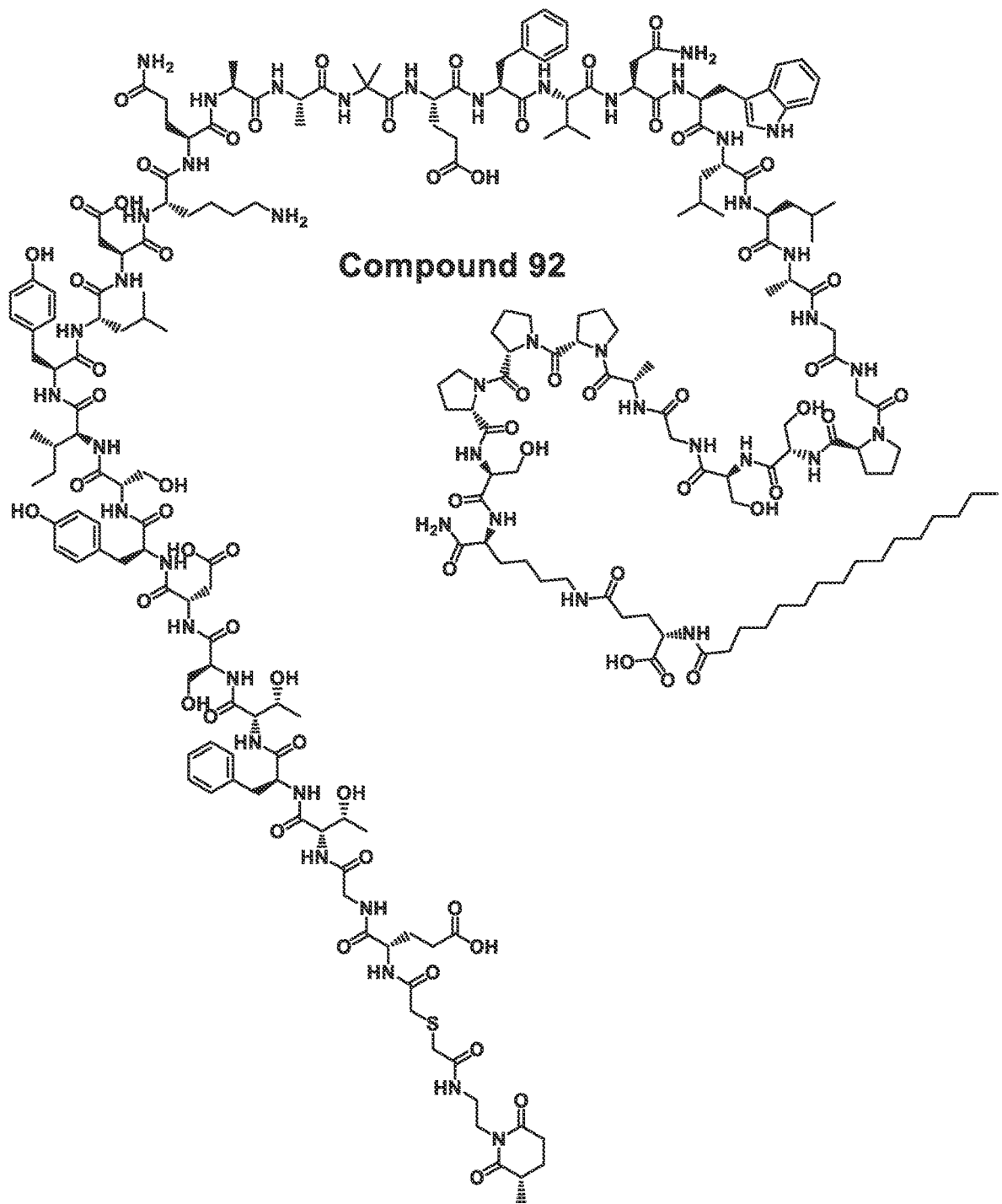
Compound 92
Cont'd

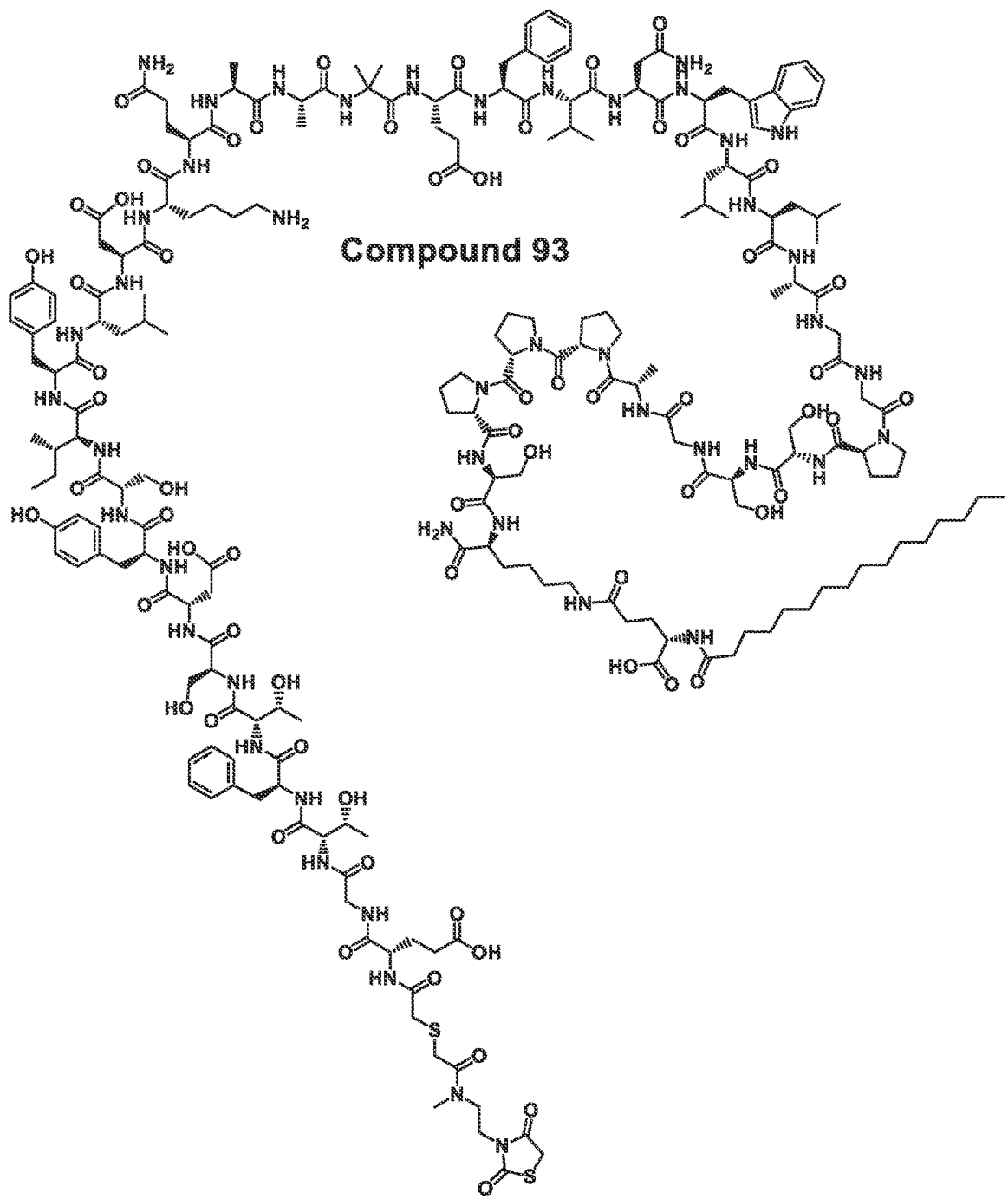
Compound 93
Cont'd

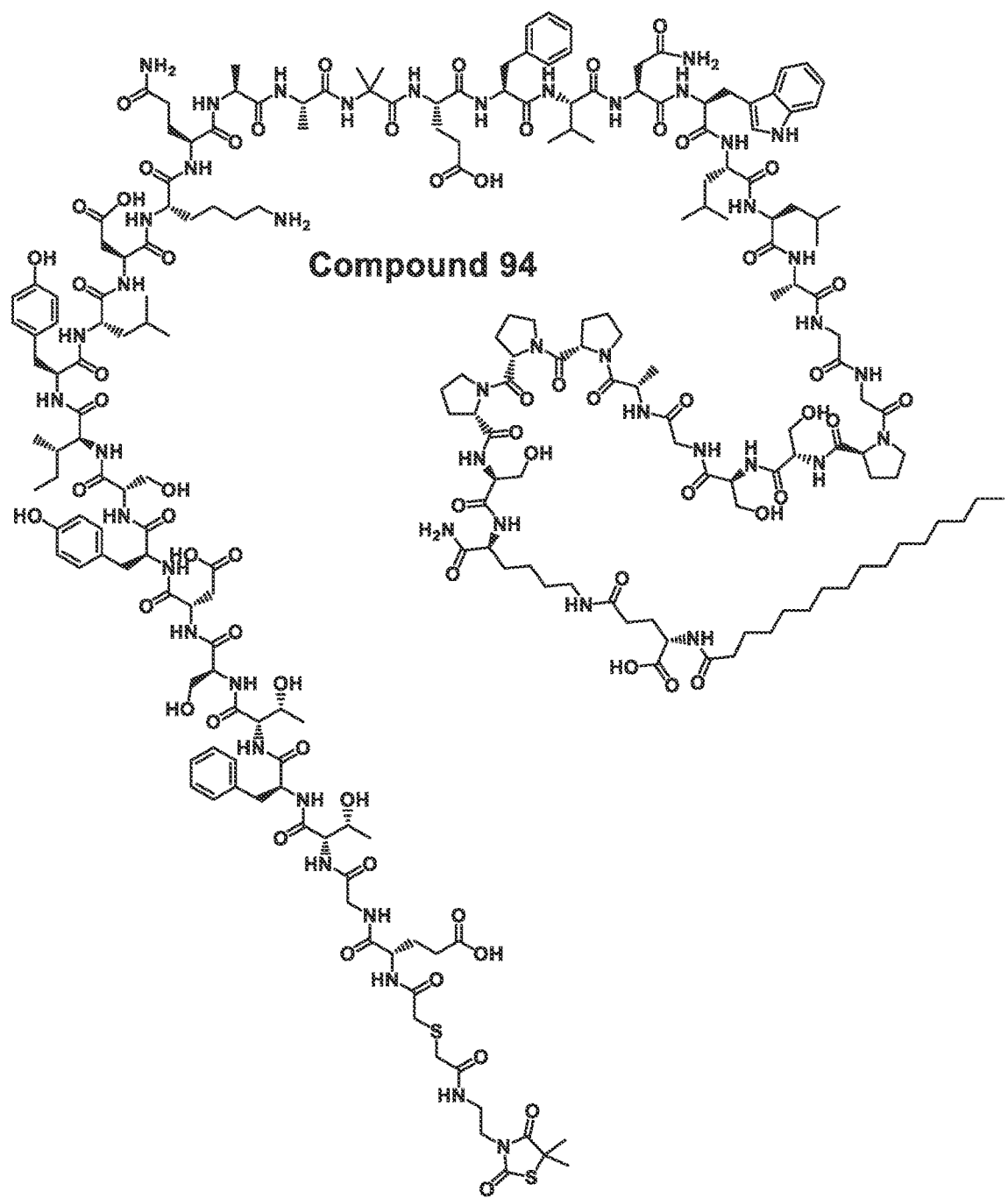
Compound 94
Cont'd

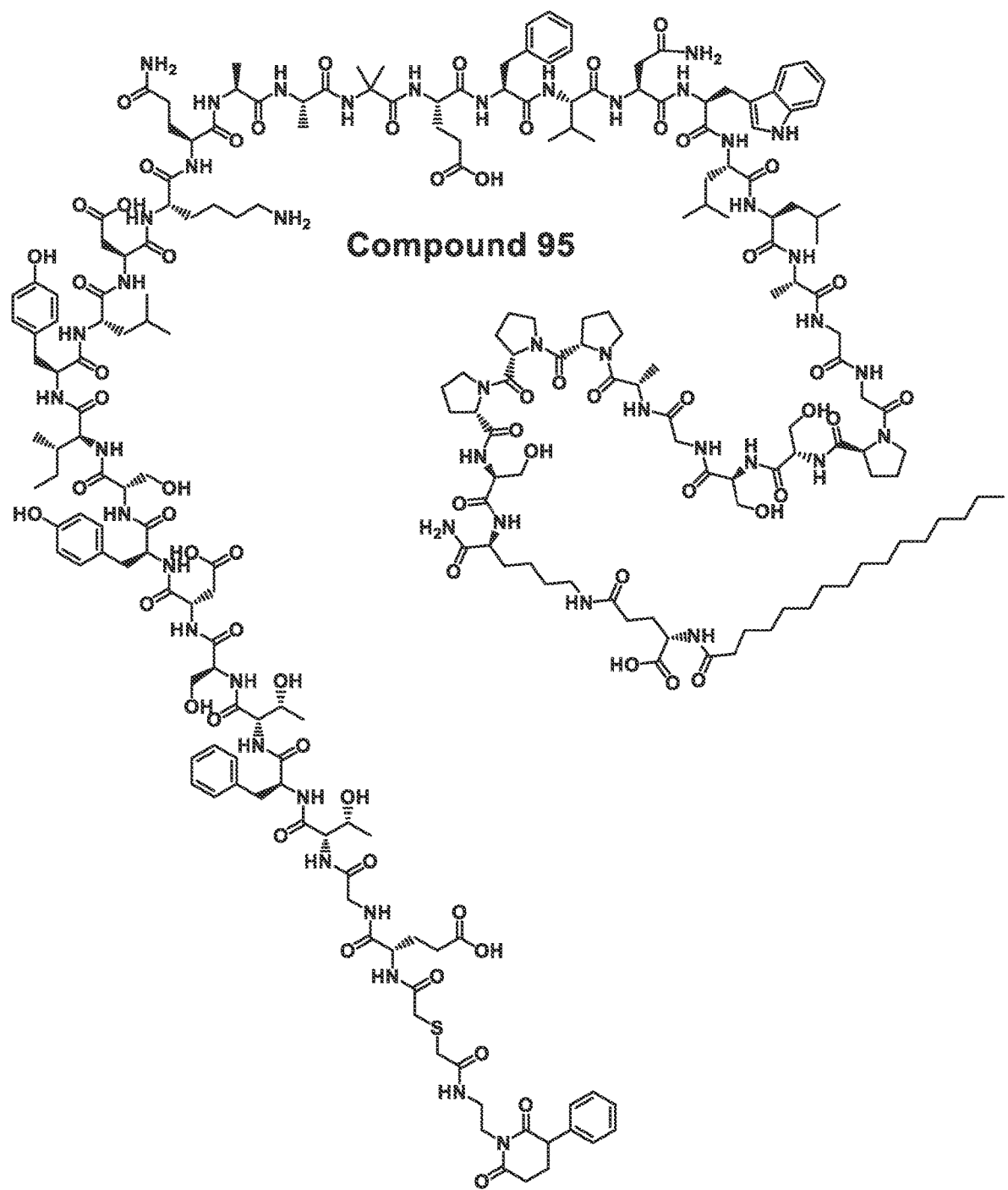
Compound 95
Cont'd

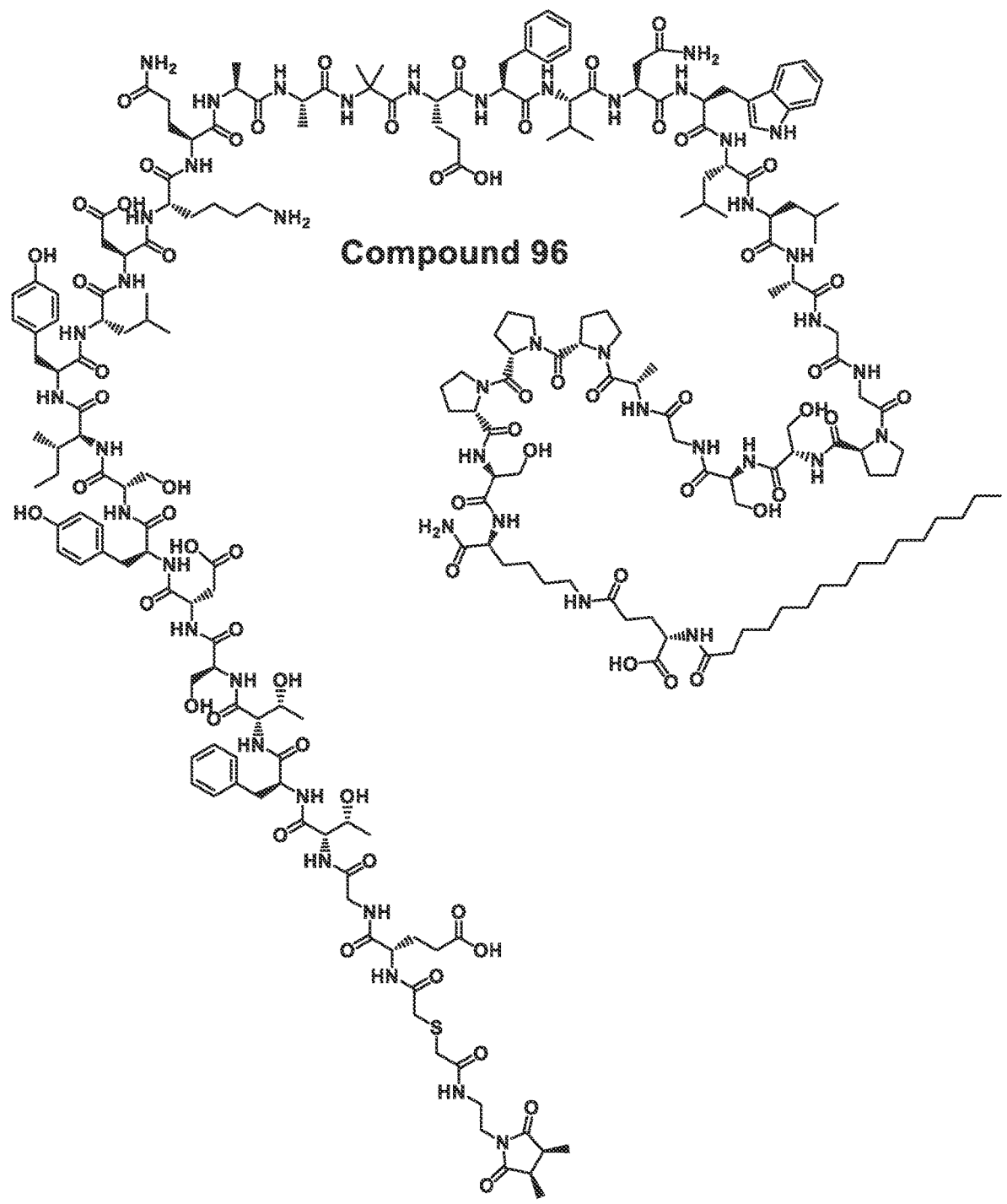
Compound 96
Cont'd

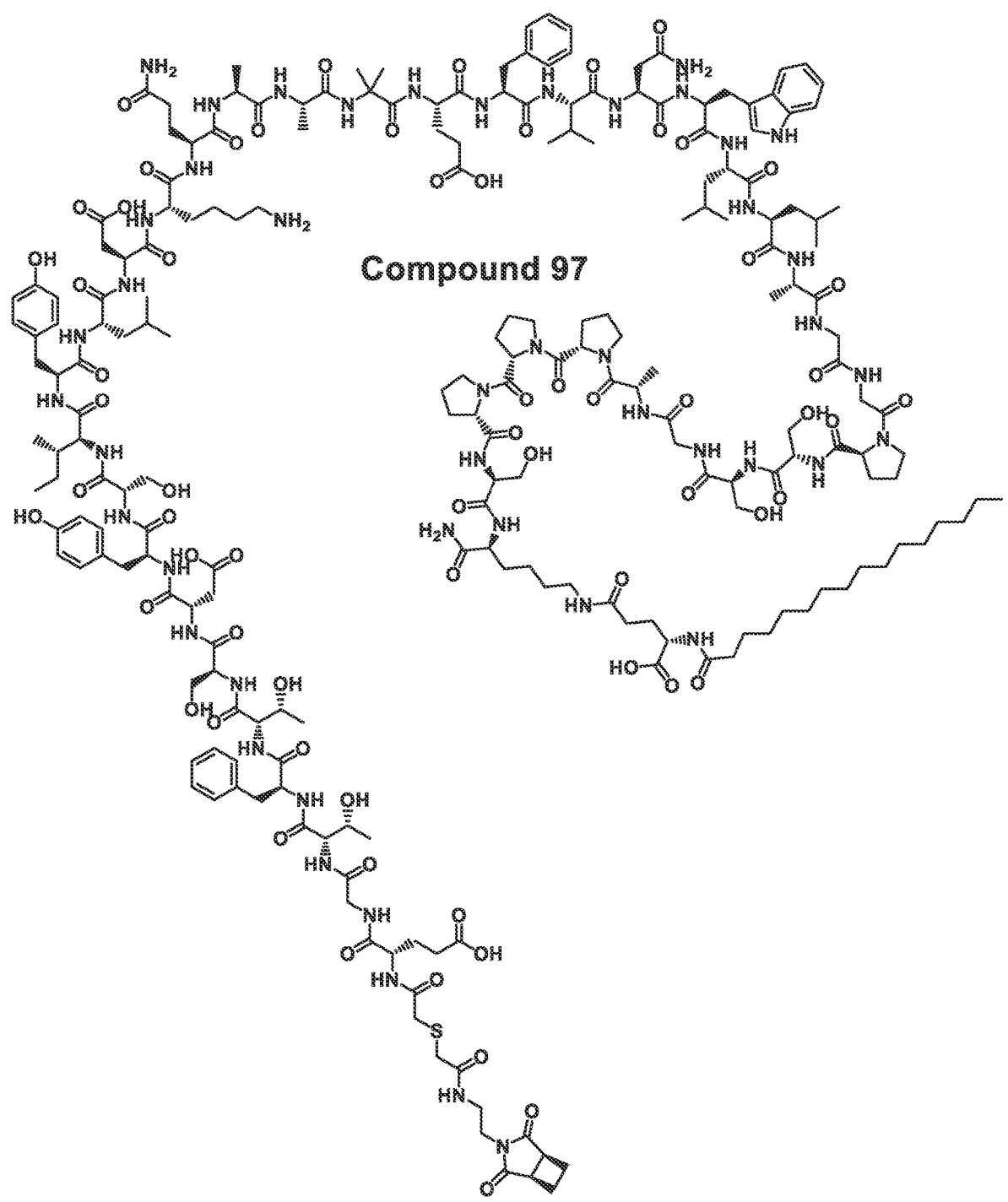
Compound 97
Cont'd

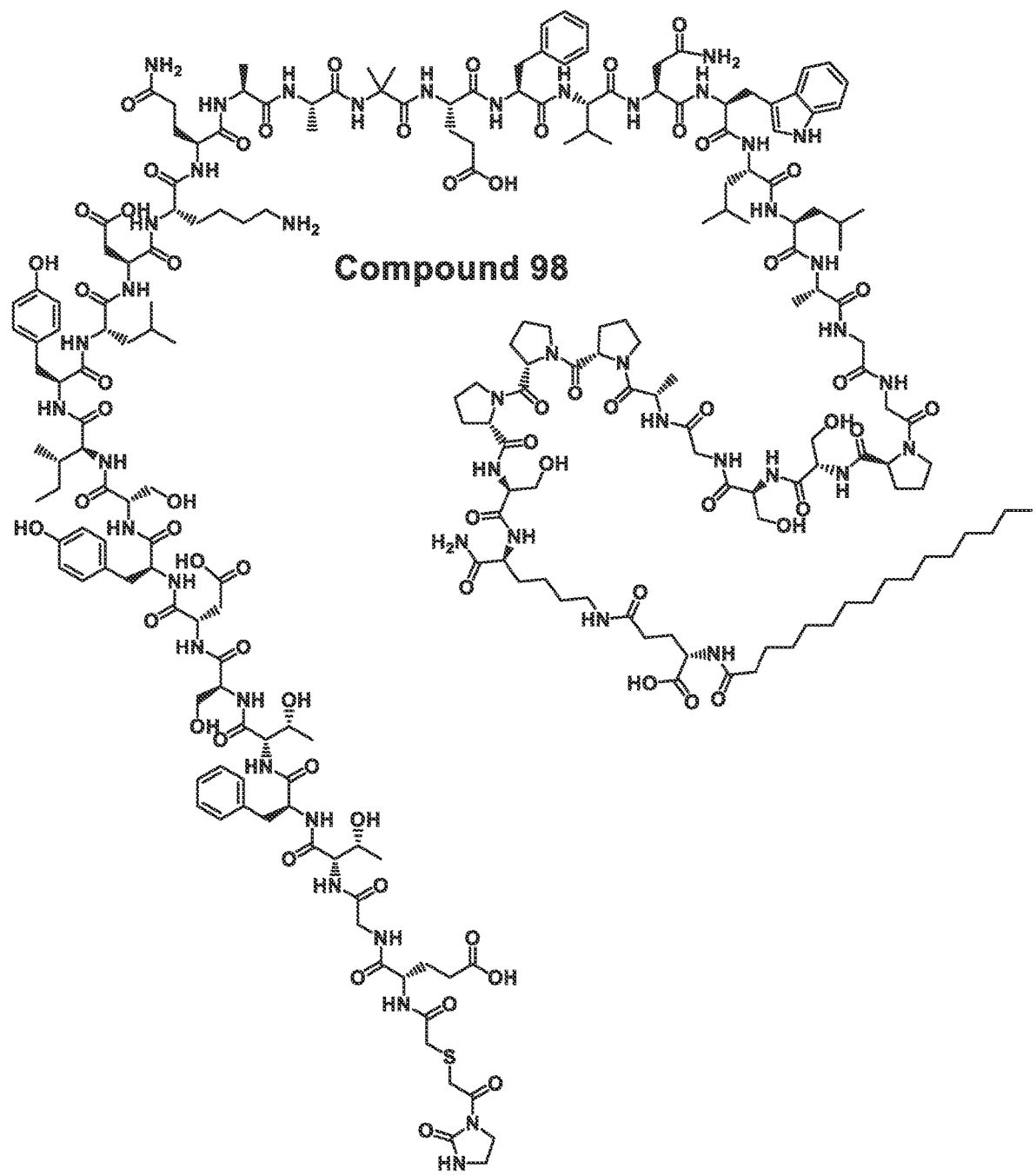
Compound 98
Cont'd

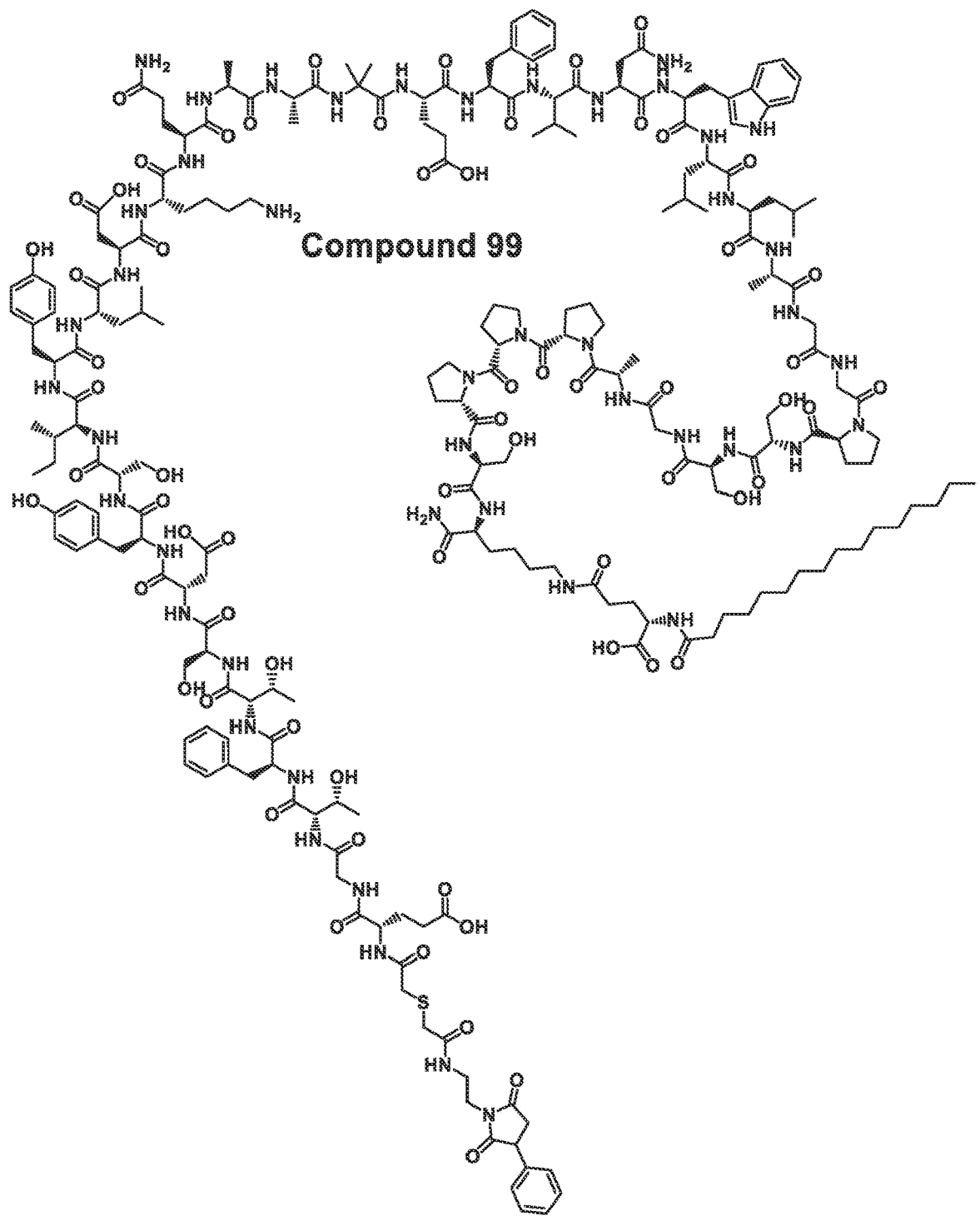
Compound 99
Cont'd

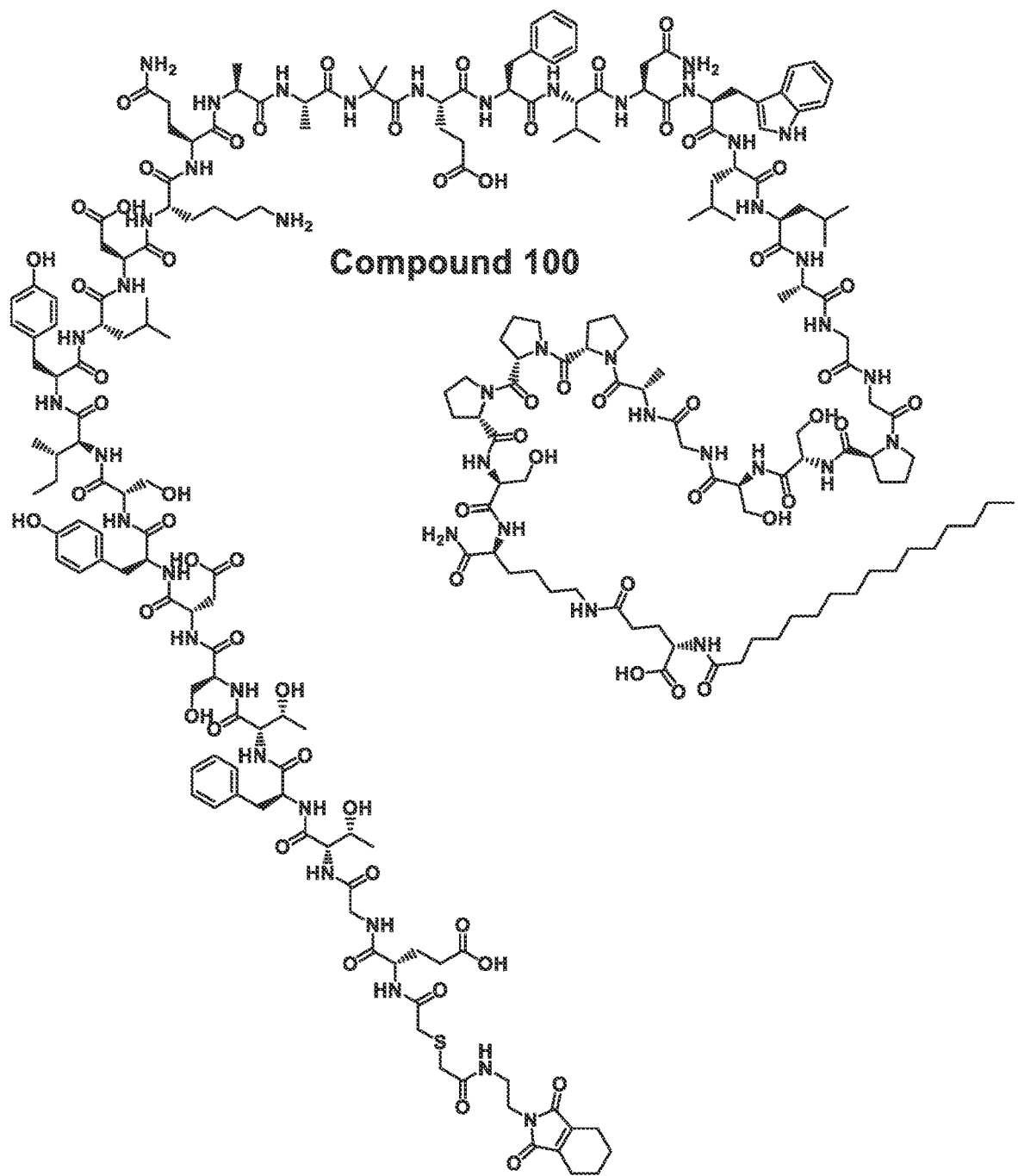
Compound 100
Cont'd

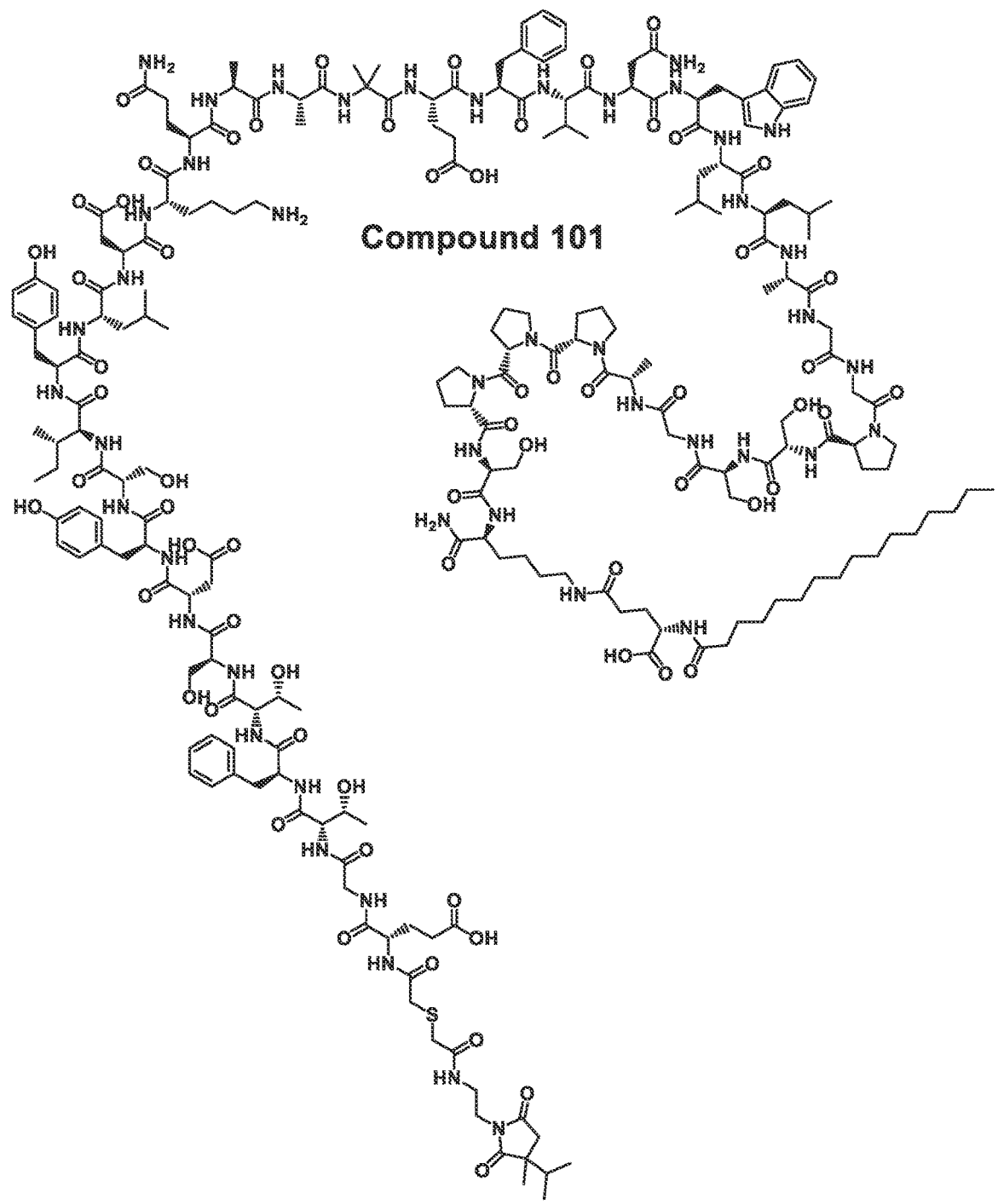
Compound 101
Cont'd

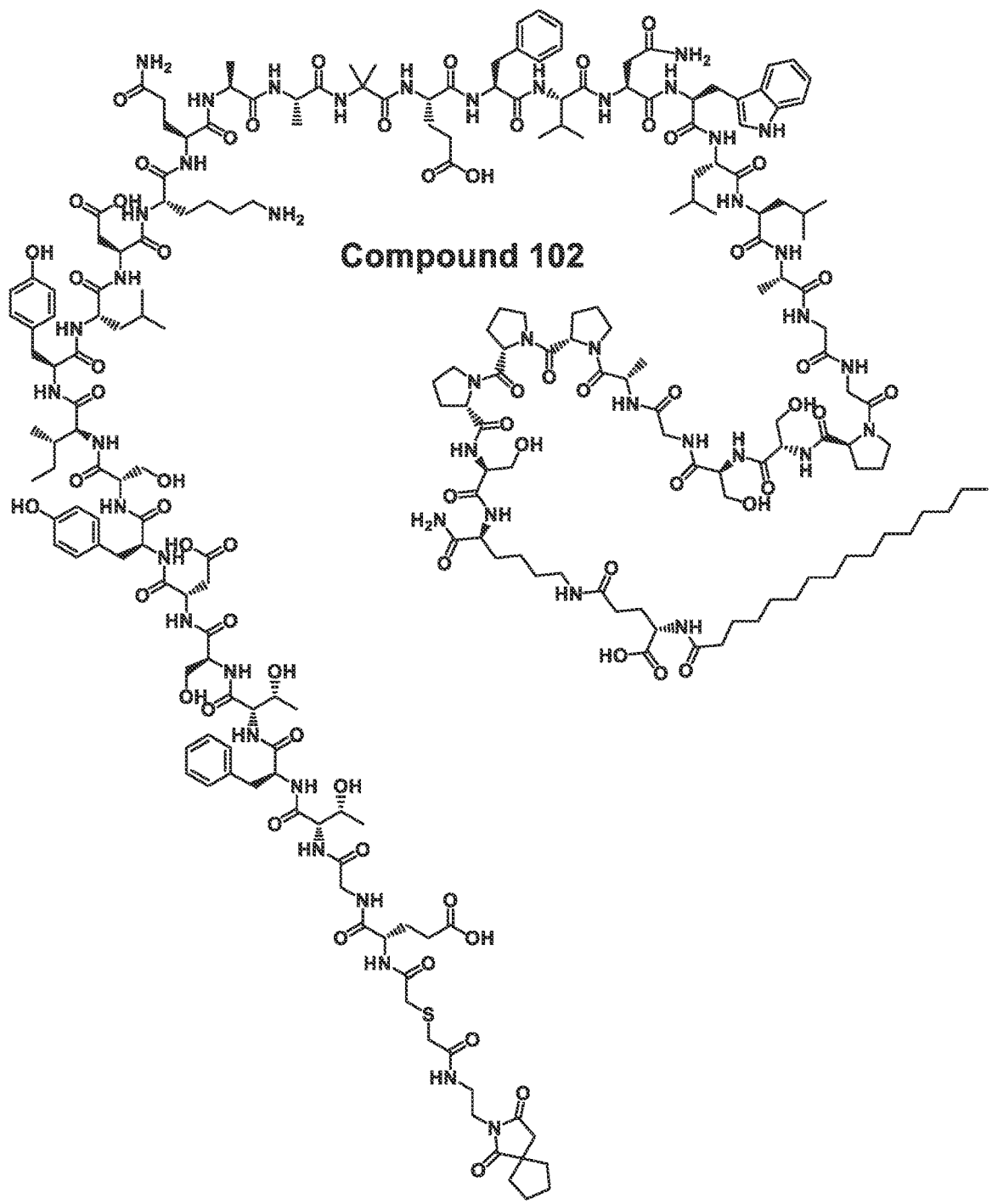
Compound 102
Cont'd

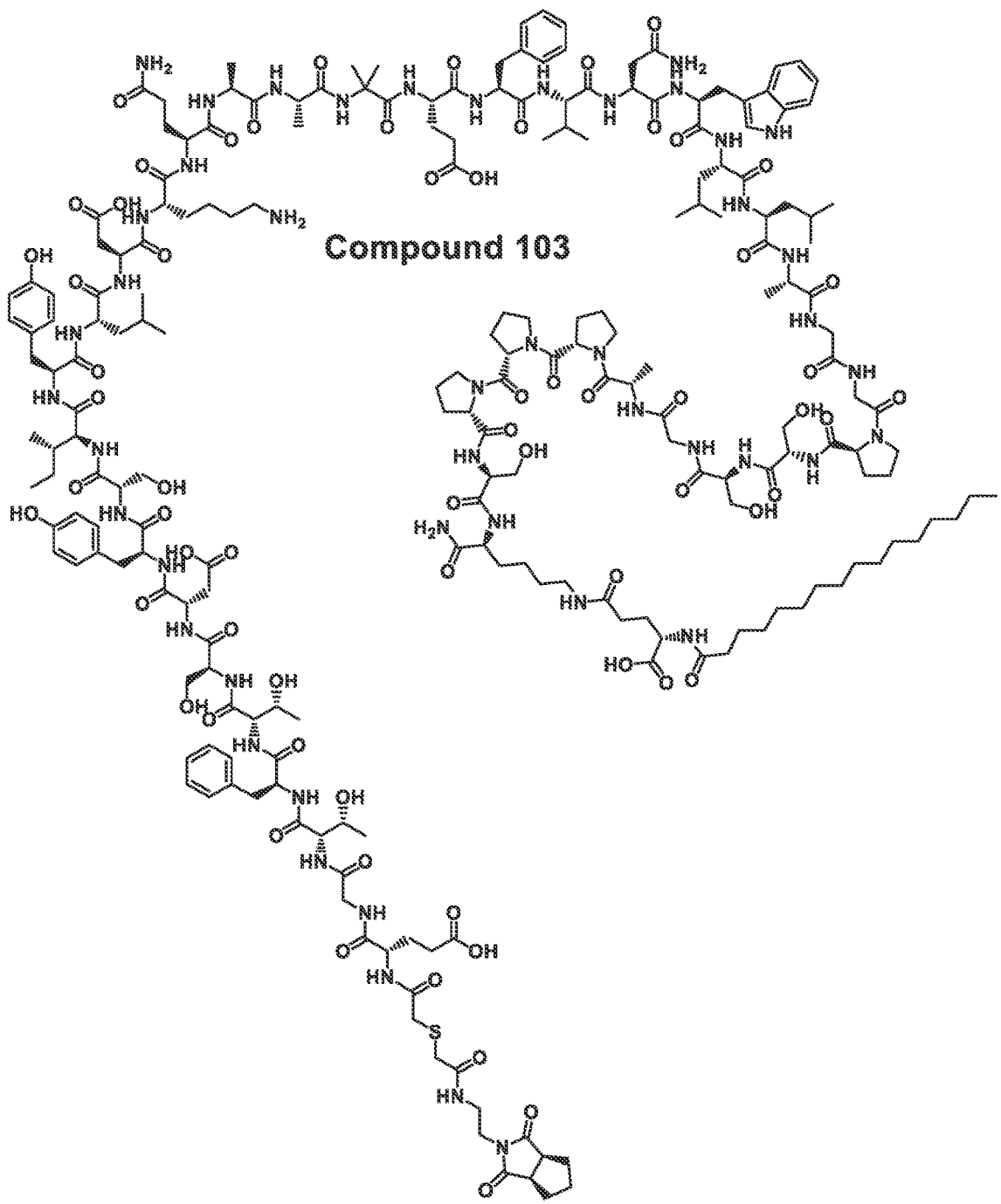
Compound 103
Cont'd

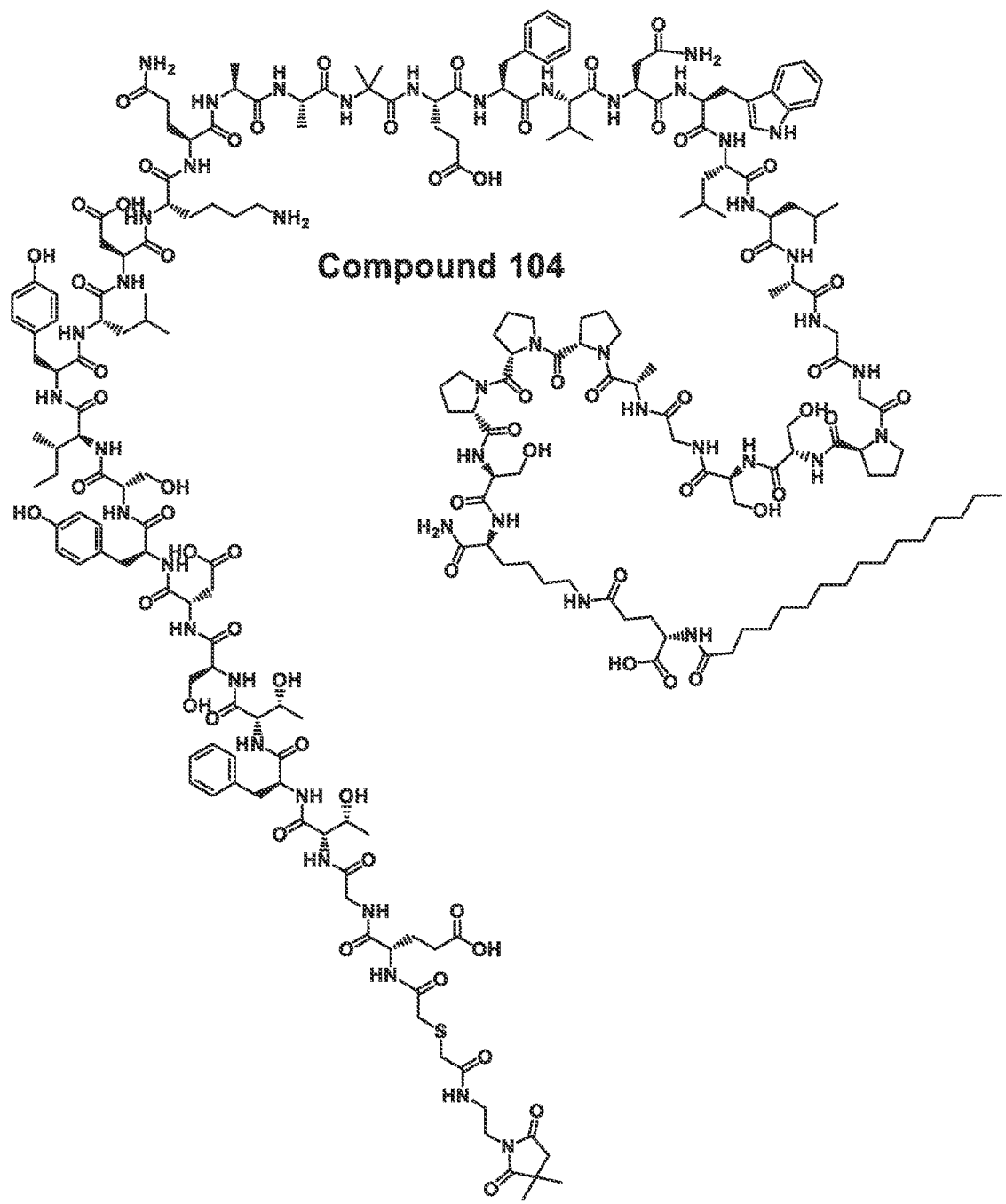
Compound 104
Cont'd

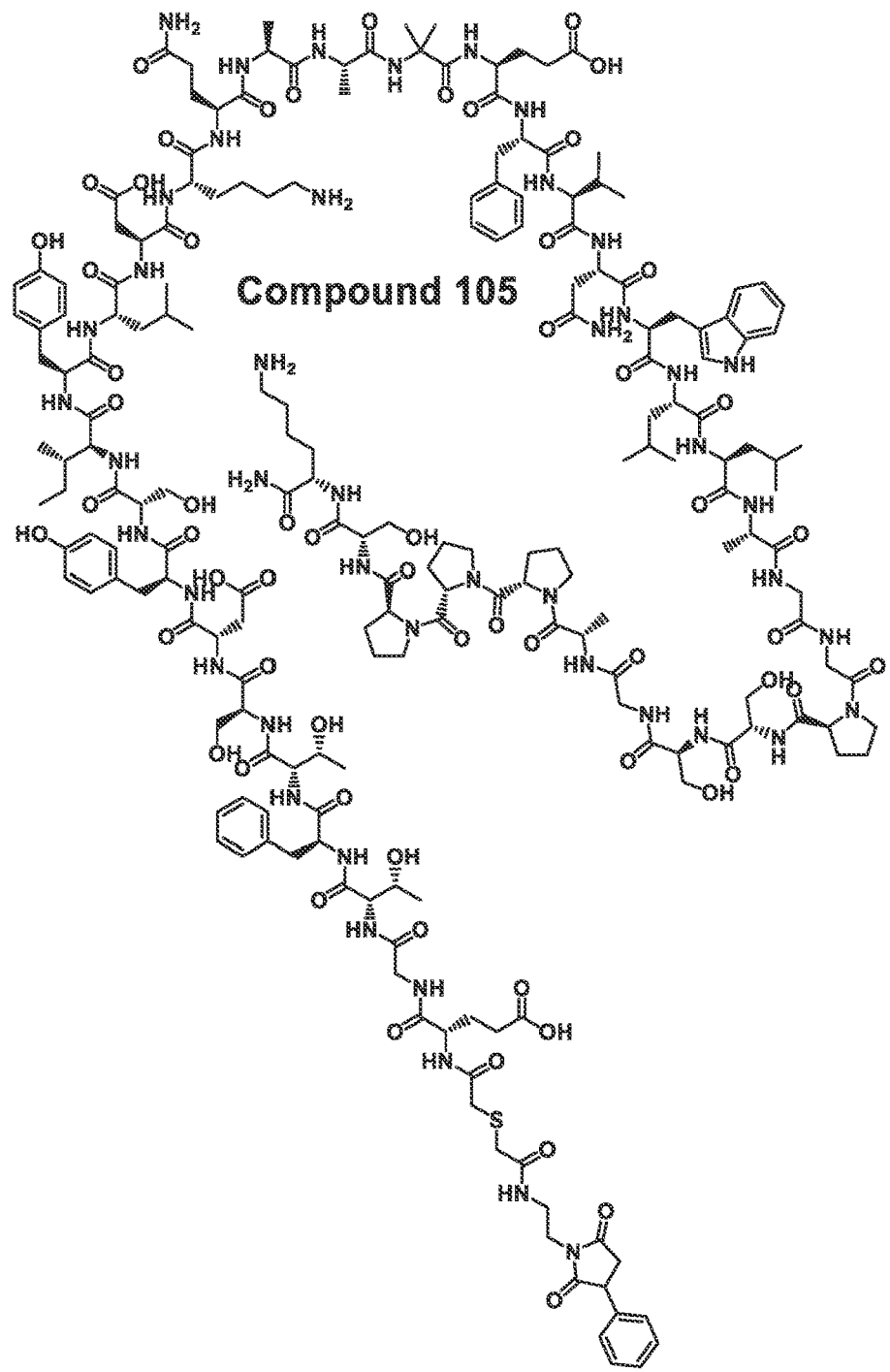

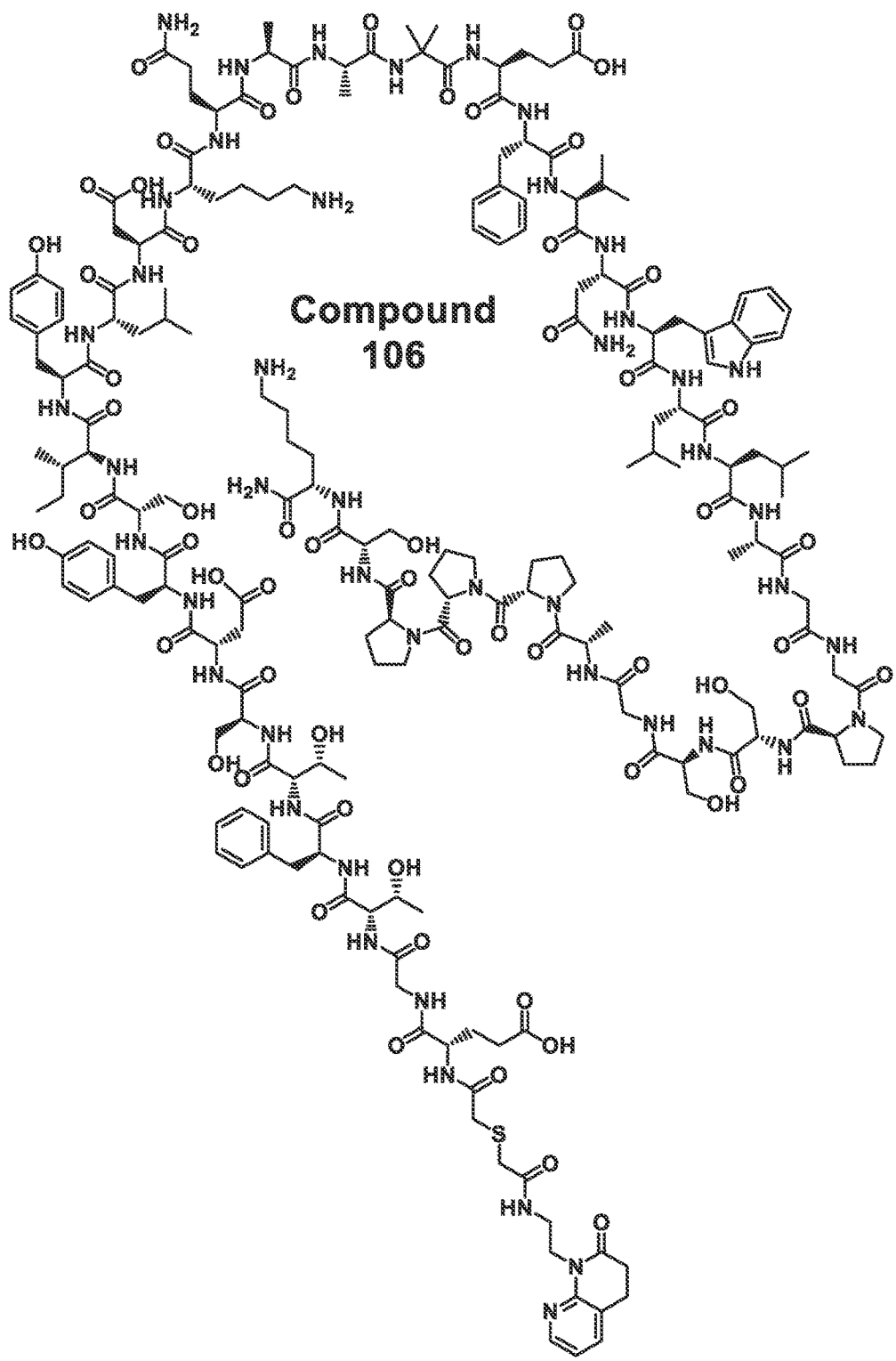
Compound 106
Cont'd

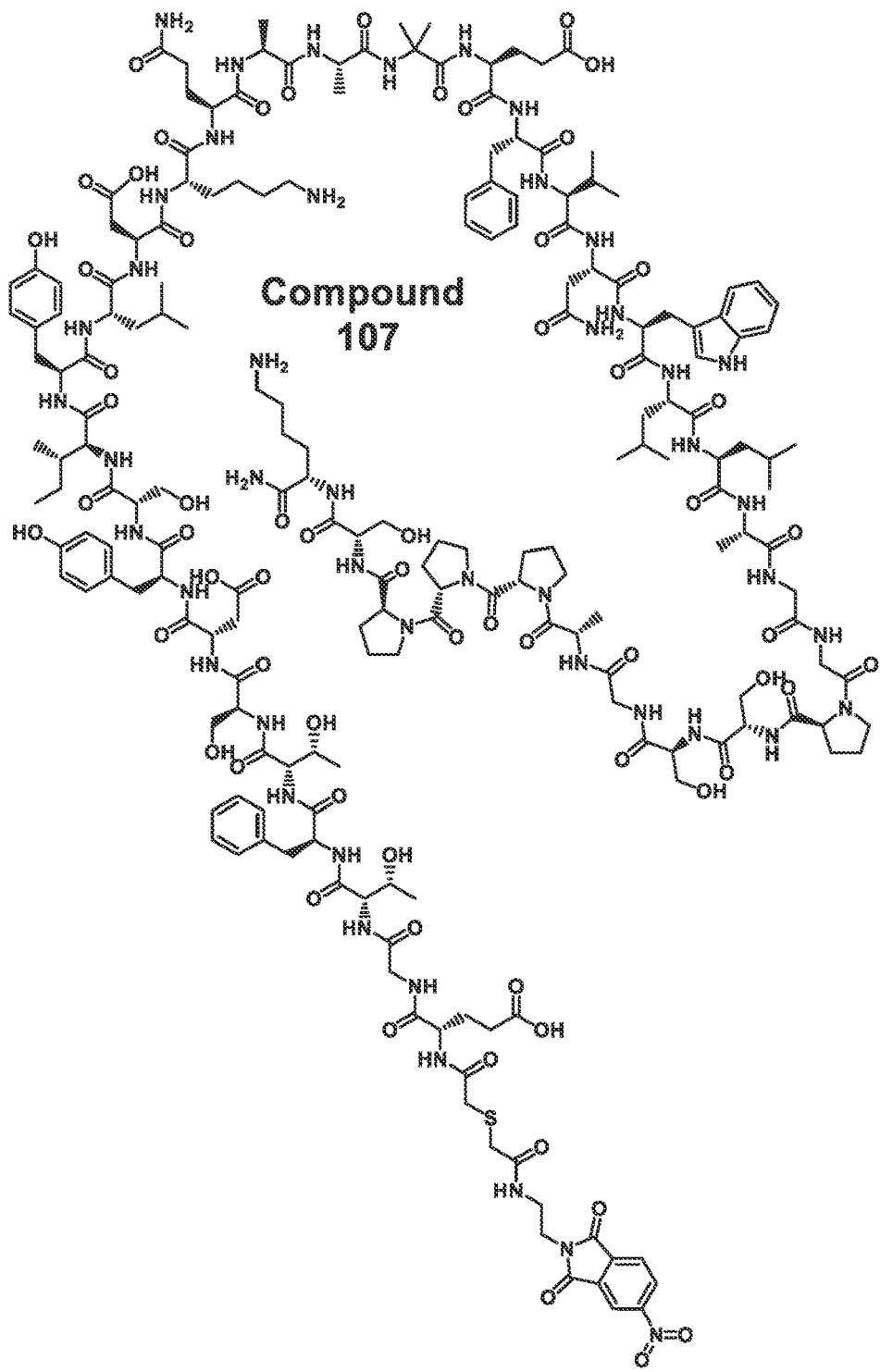
Cont'd

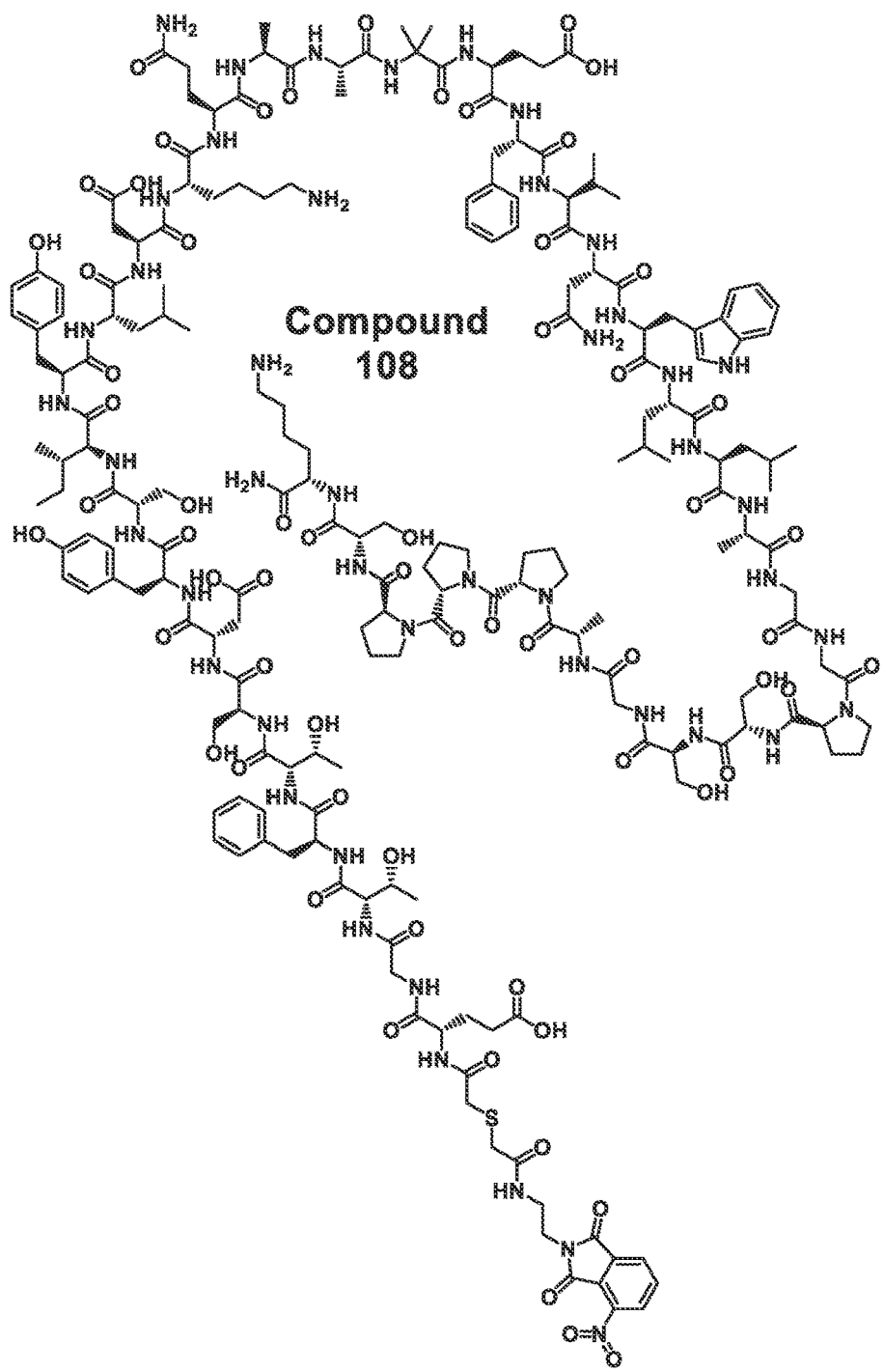
Compound 108
Cont'd

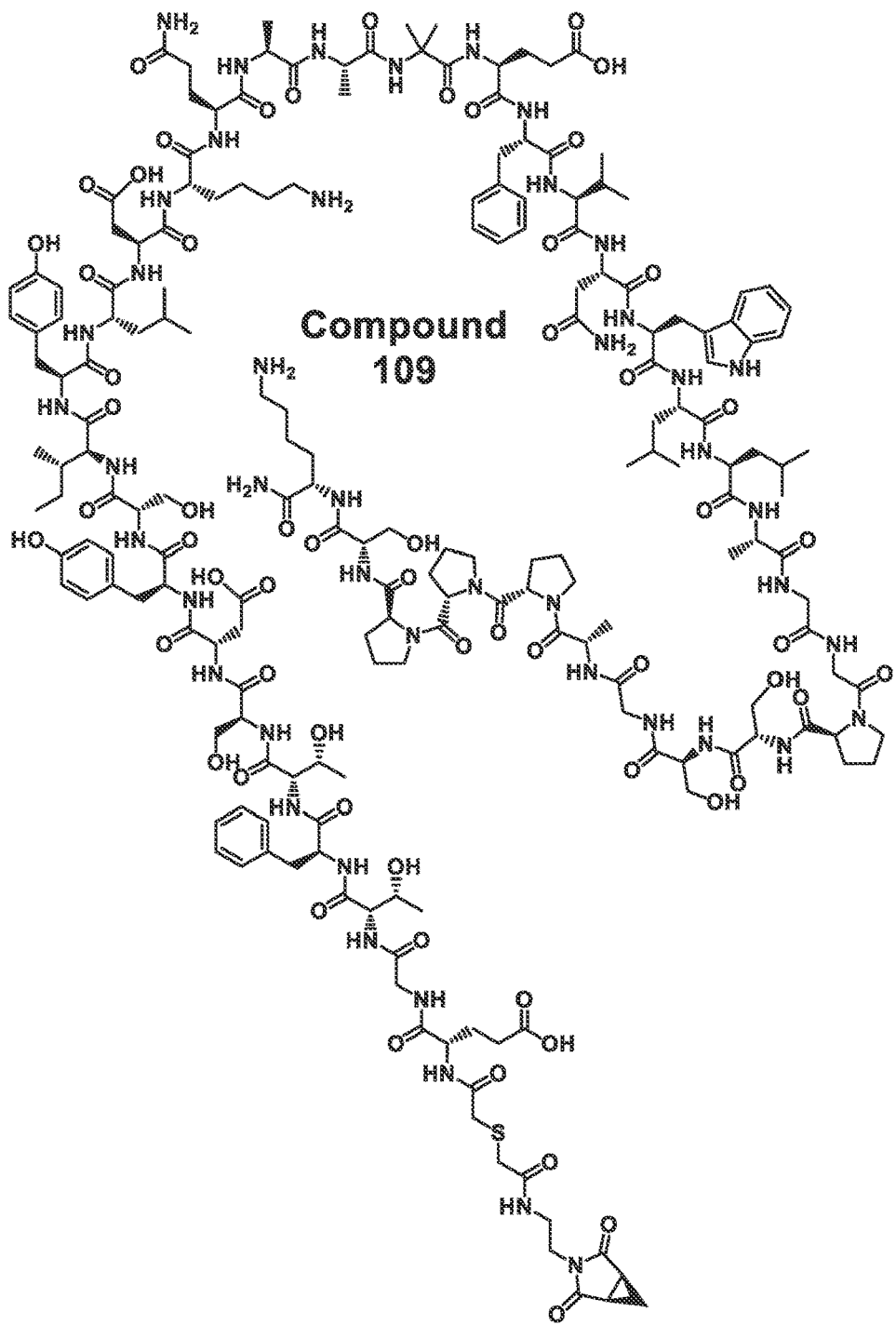
Compound 109
Cont'd

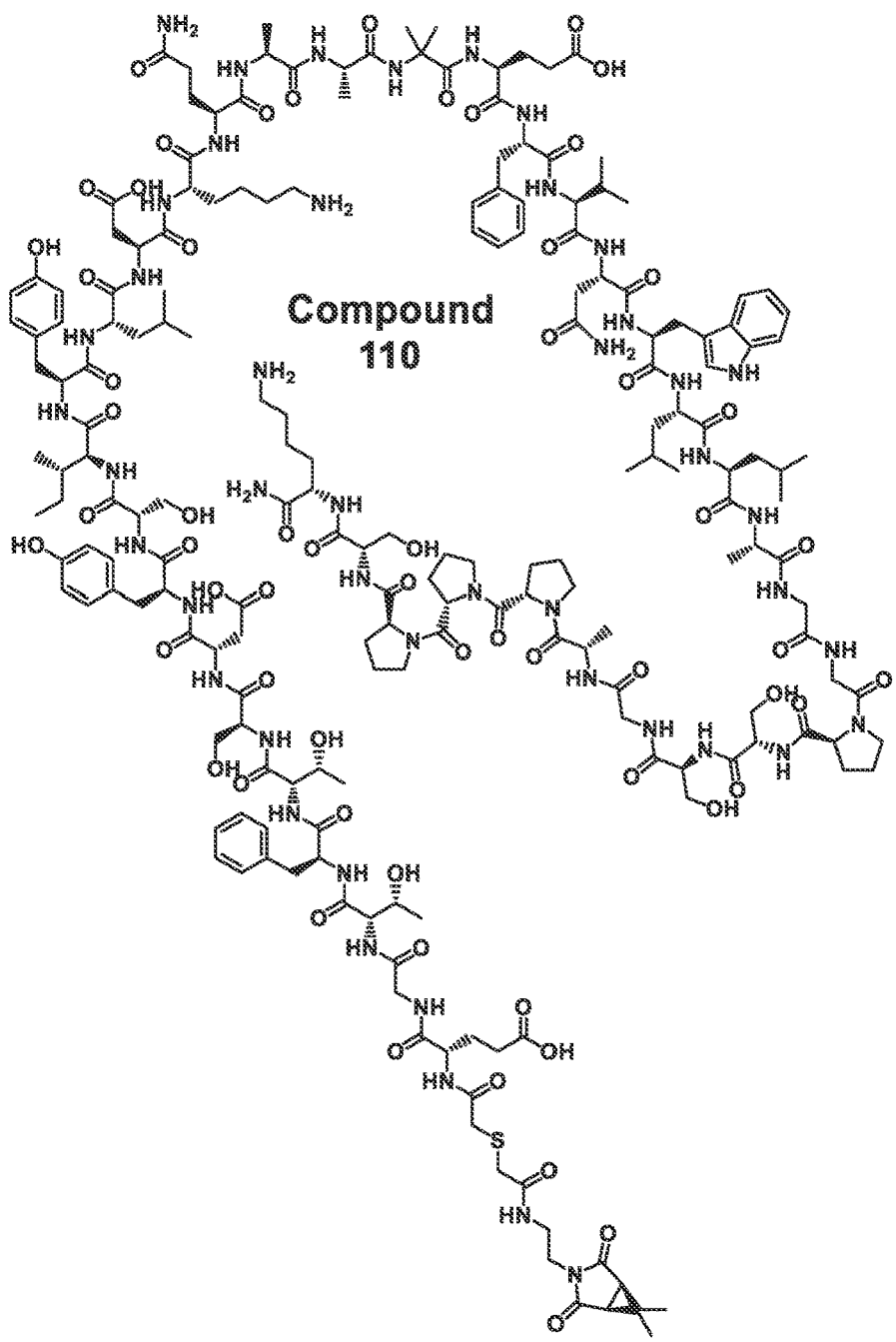
Compound 110
Cont'd

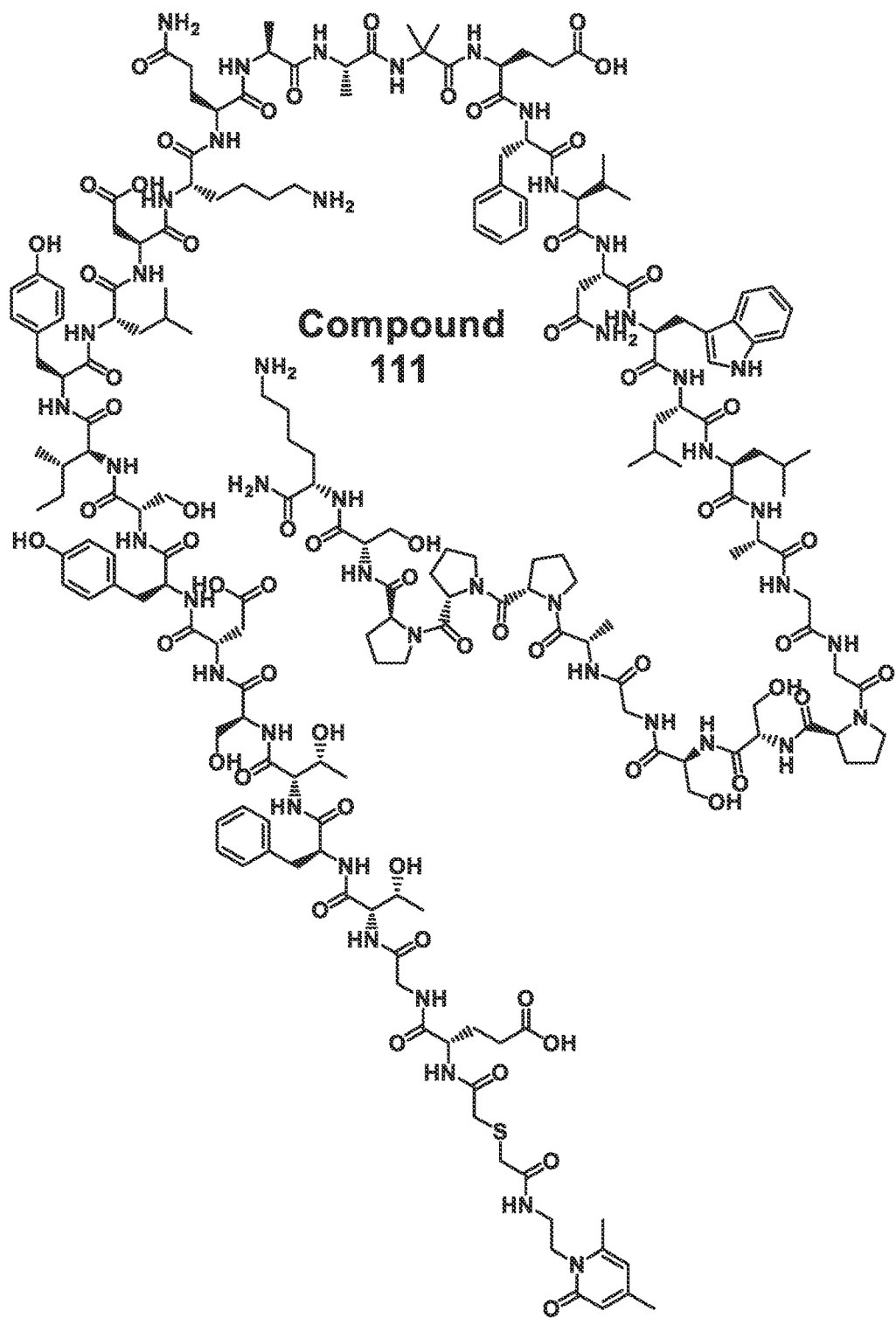
Compound 111
Cont'd

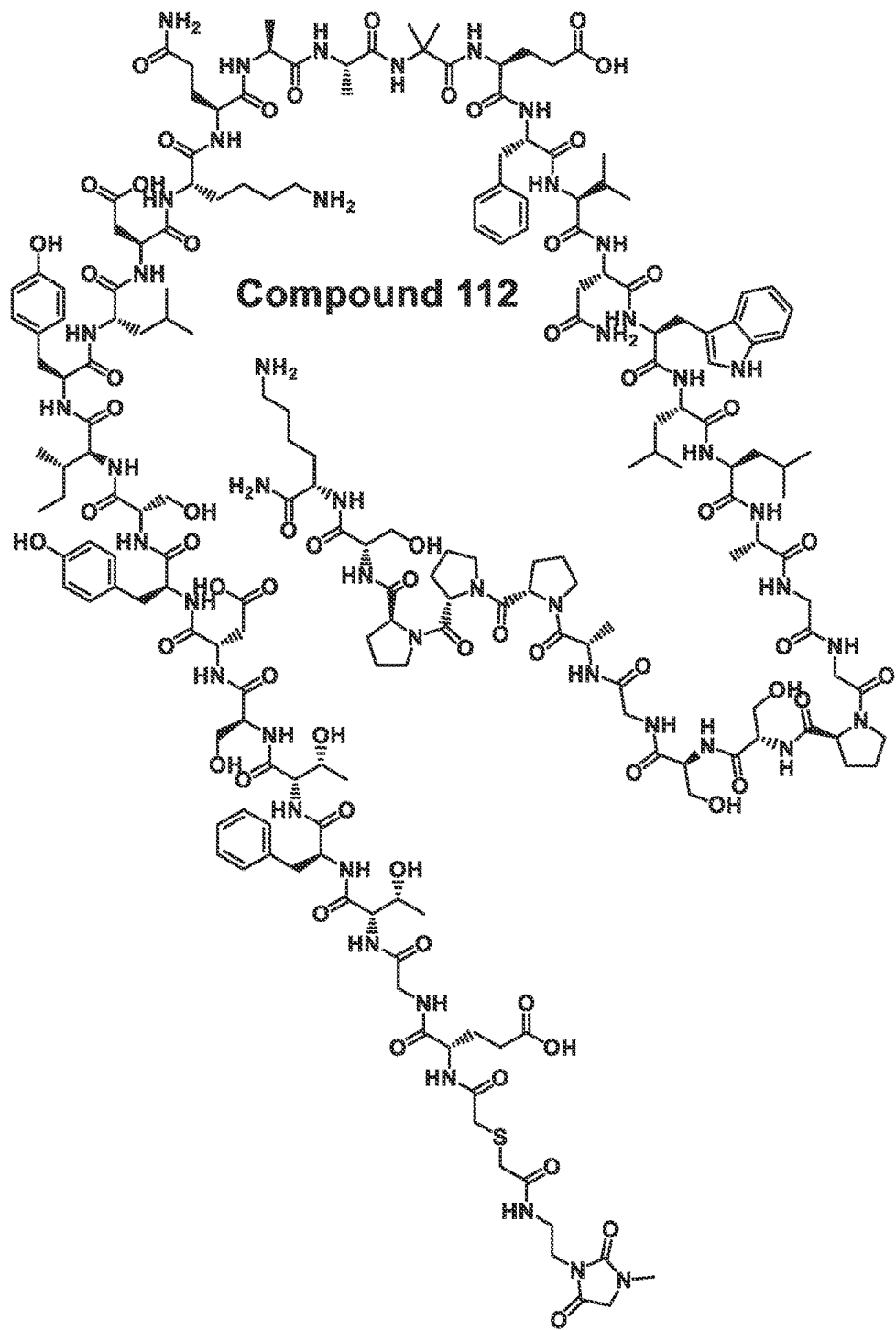
Compound 112
Cont'd

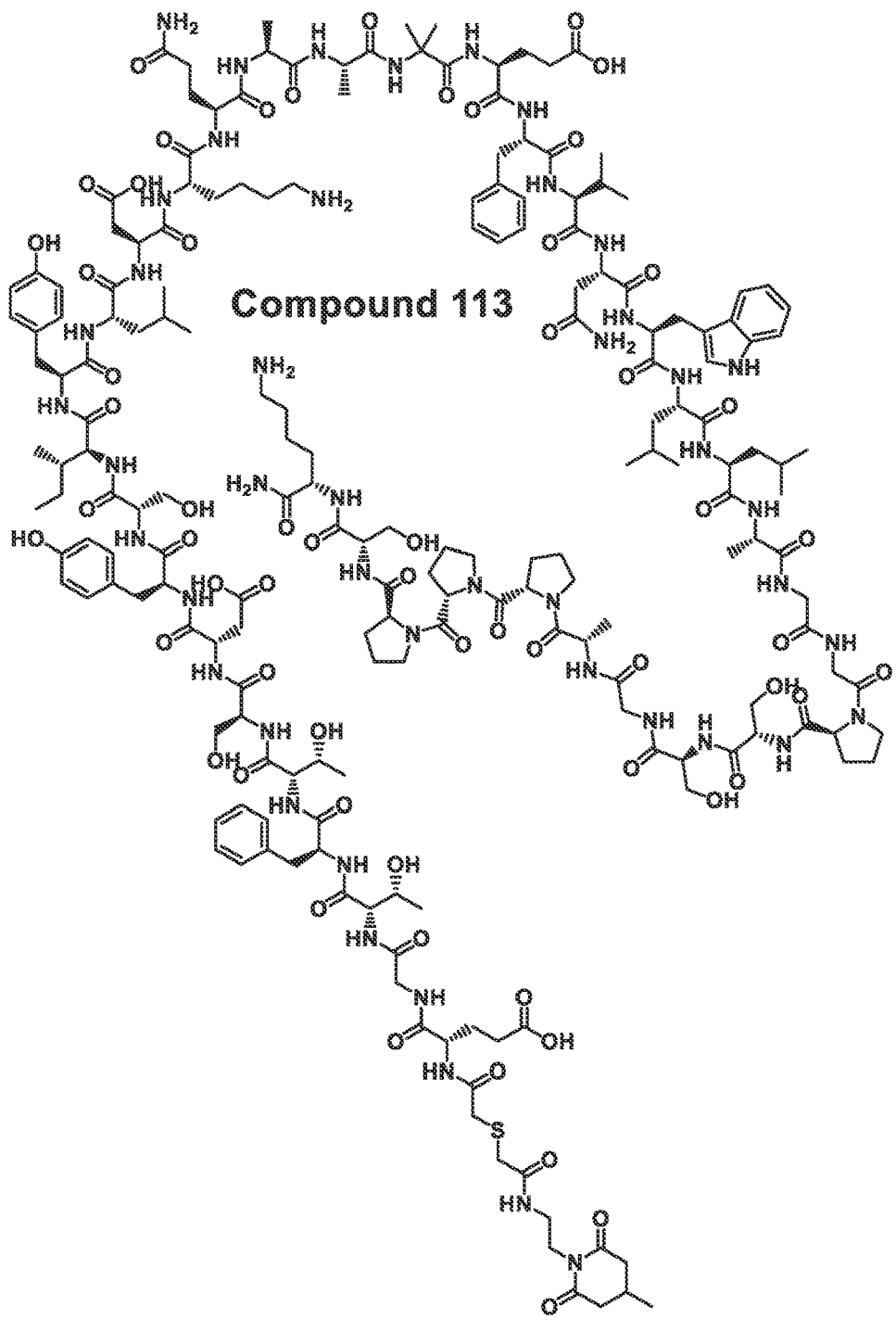
Compound 113
Cont'd

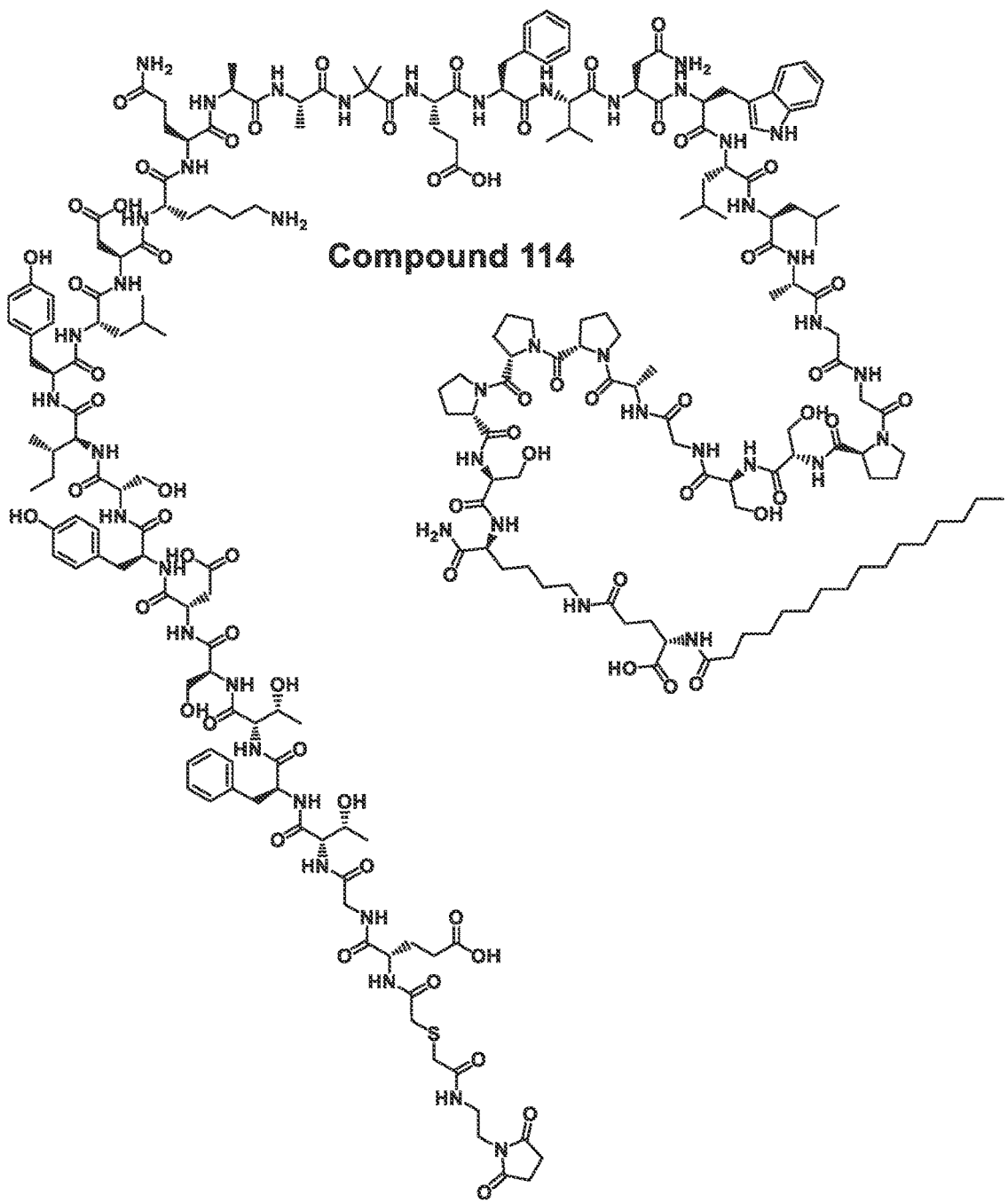
Compound 114
Cont'd

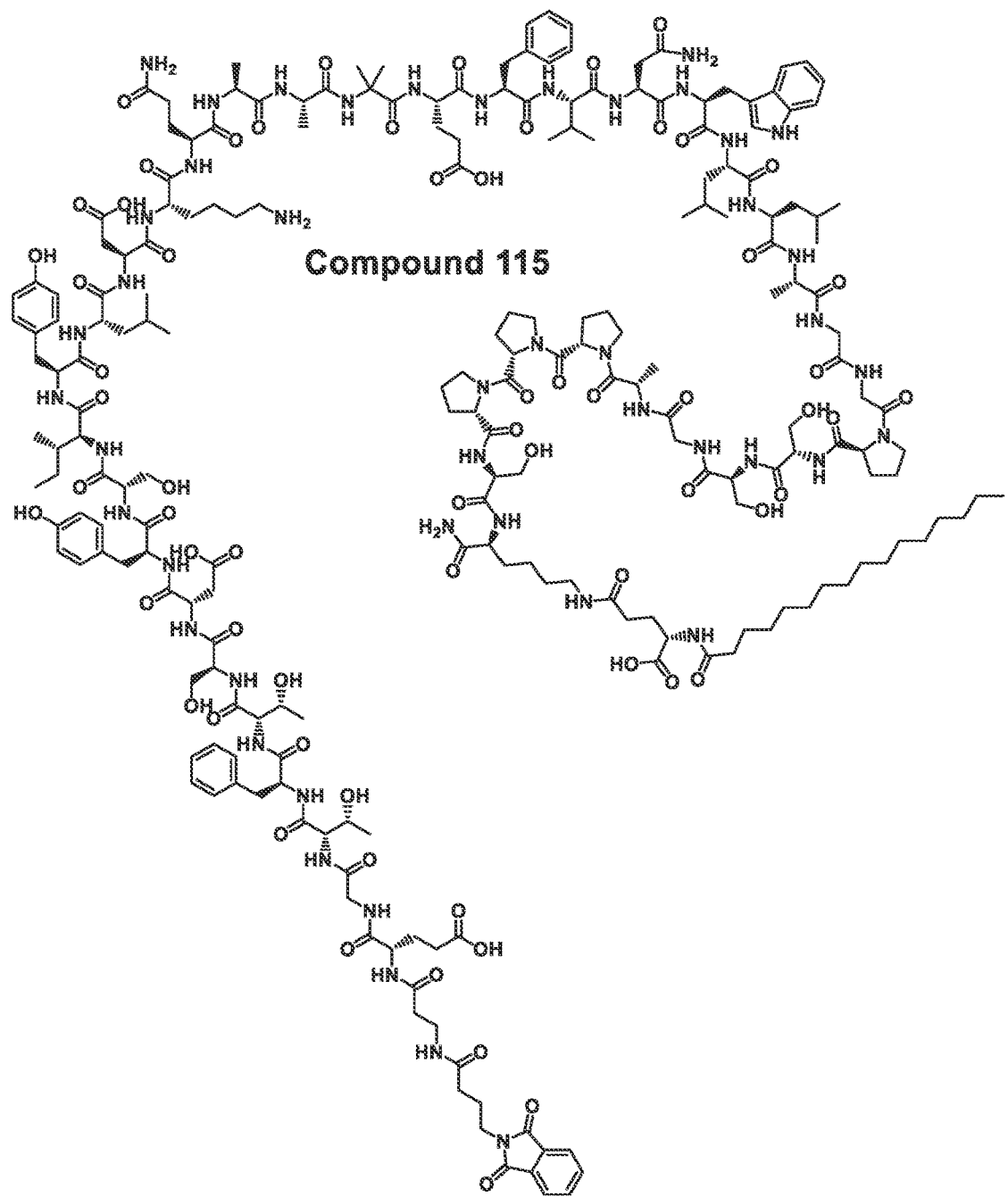
Compound 115
Cont'd

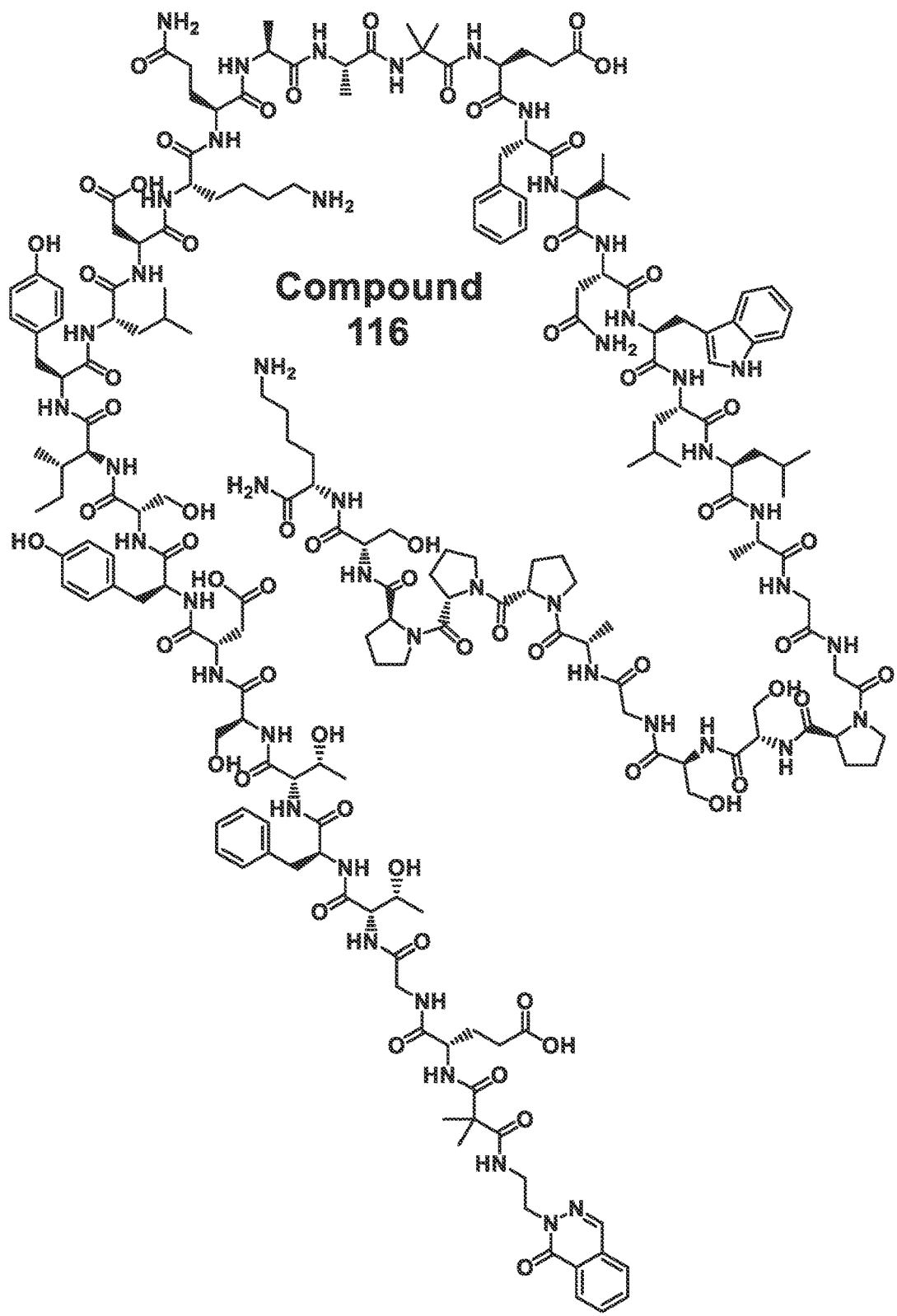

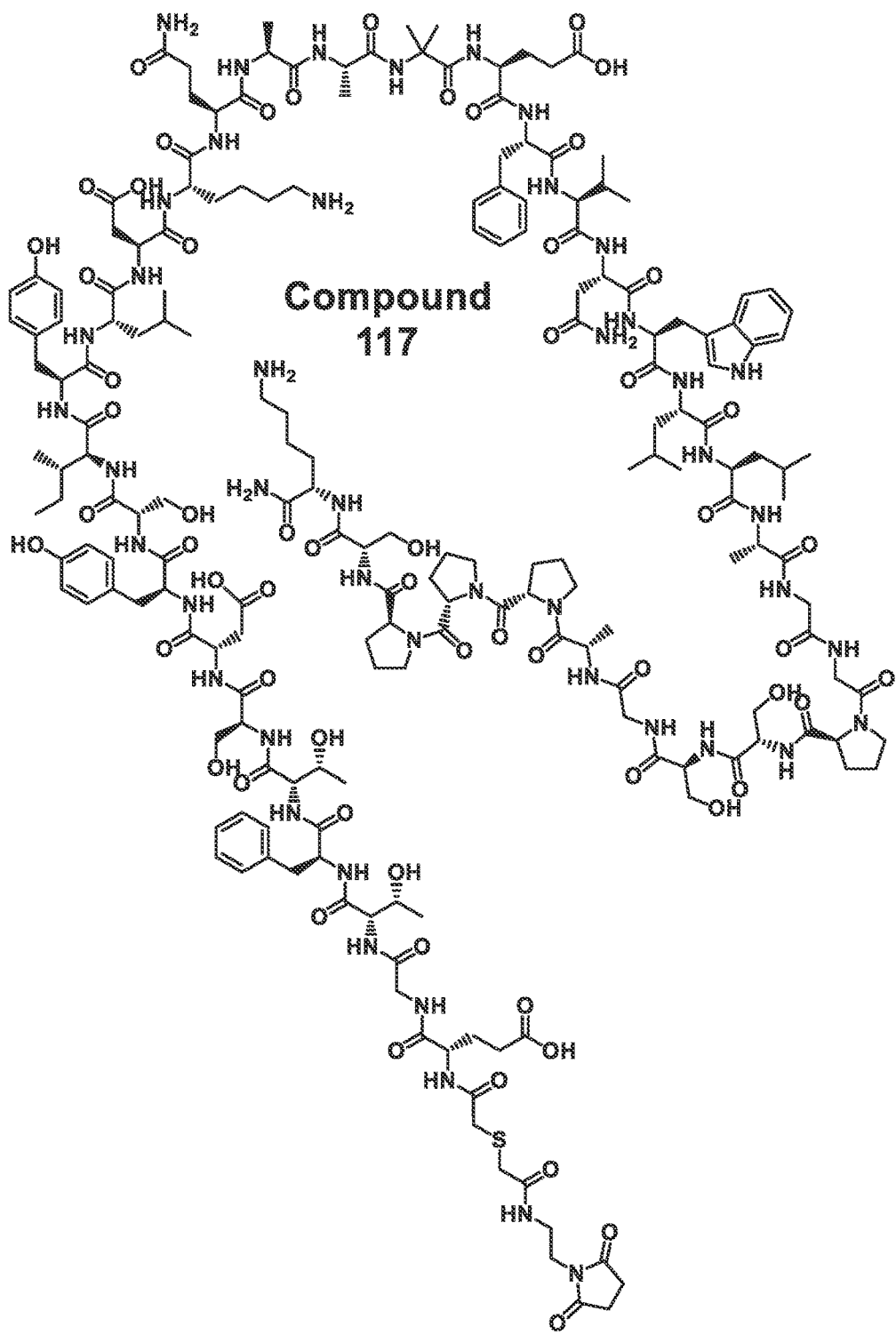
Compound 117
Cont'd

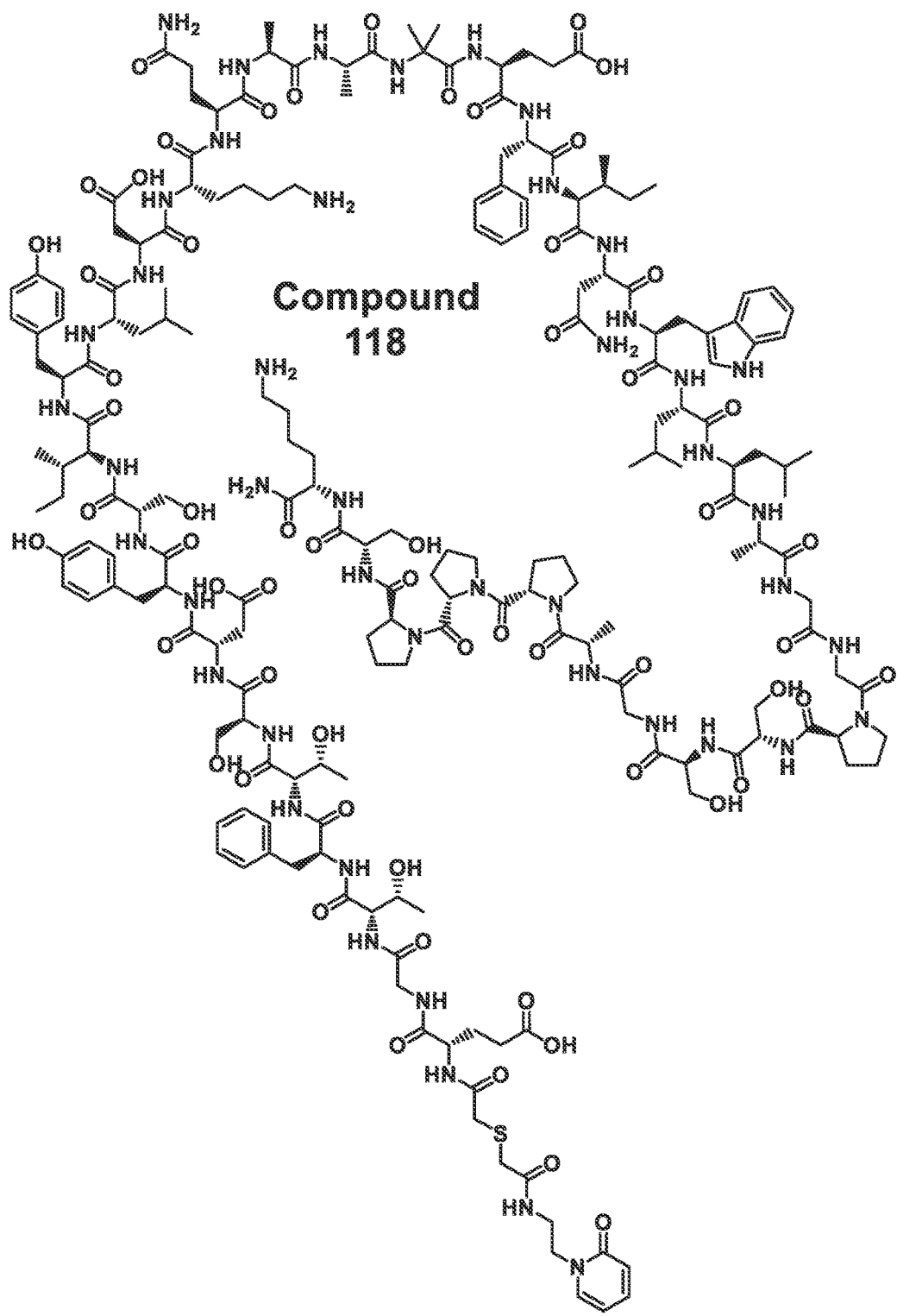
Compound 118
Cont'd

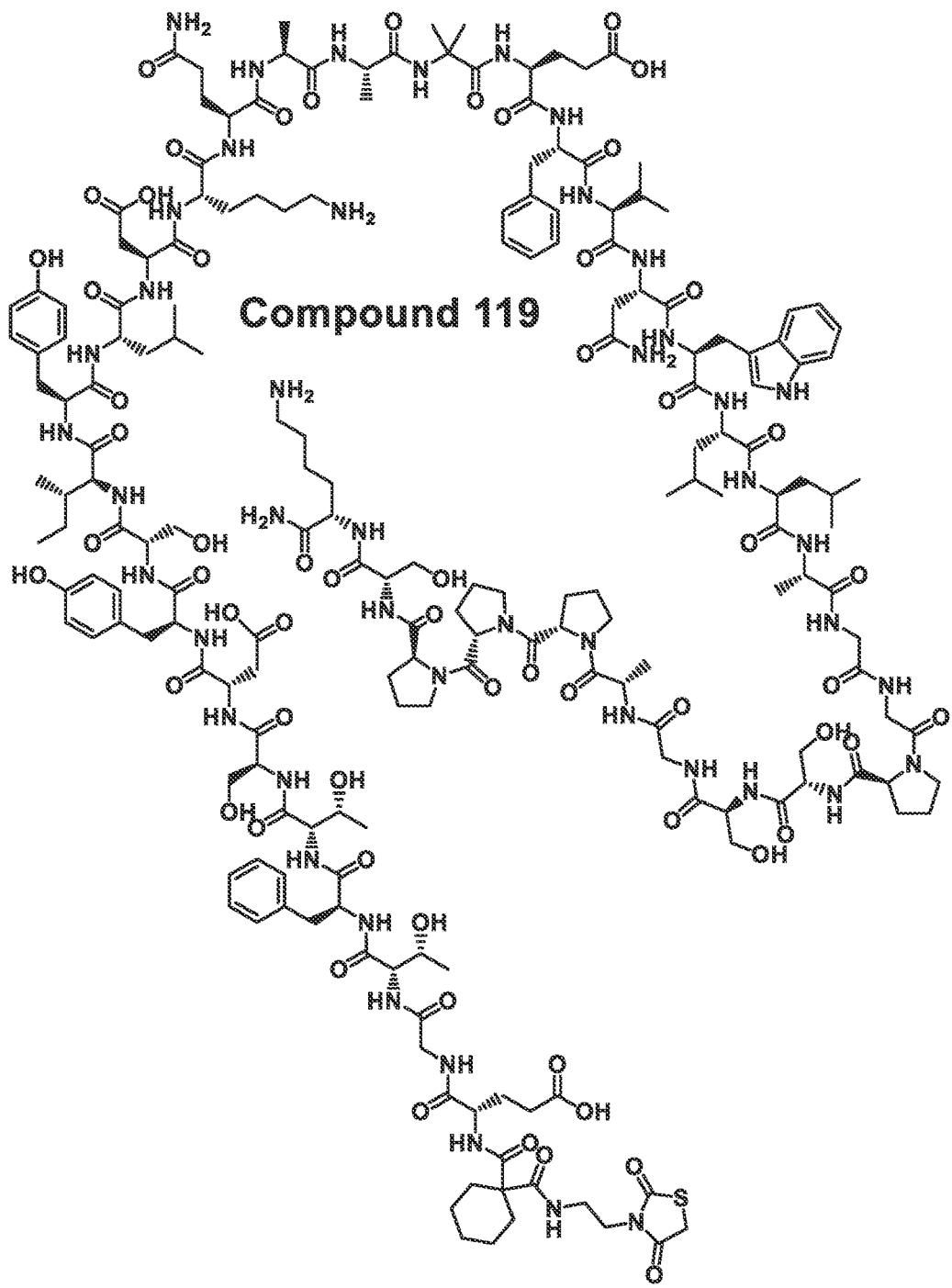
Compound 119
Cont'd

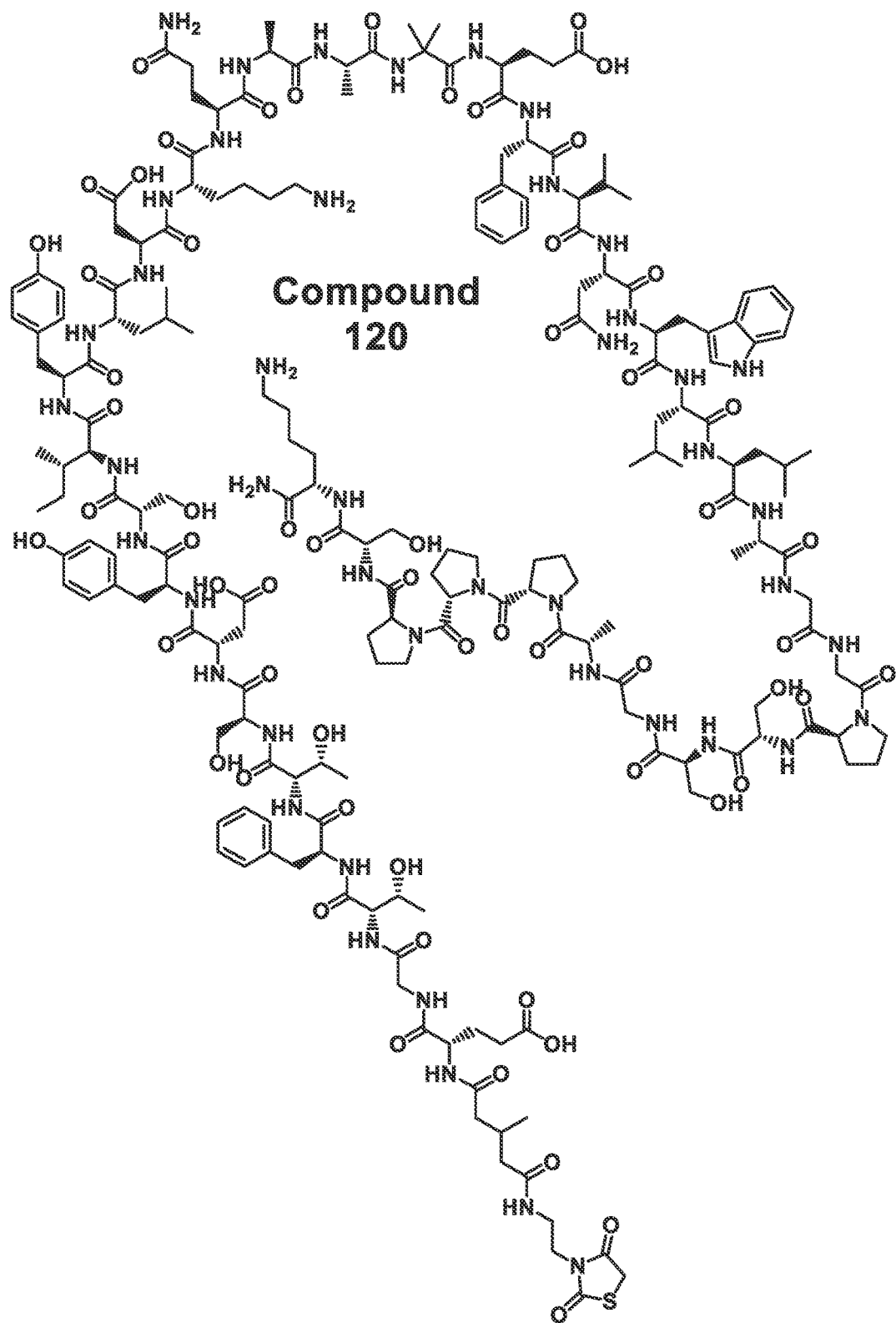
Compound 120
Cont'd

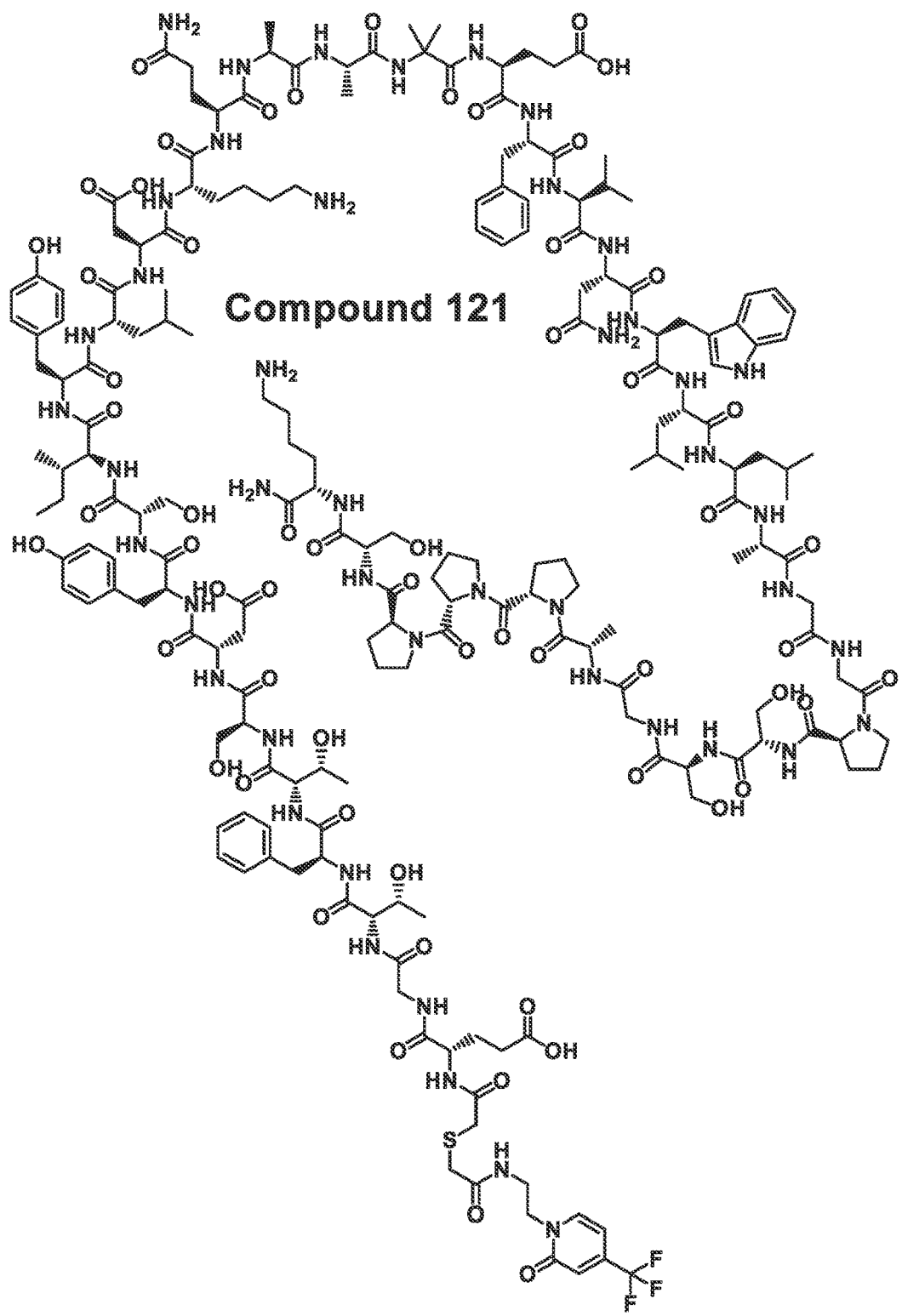
Compound 121
Cont'd

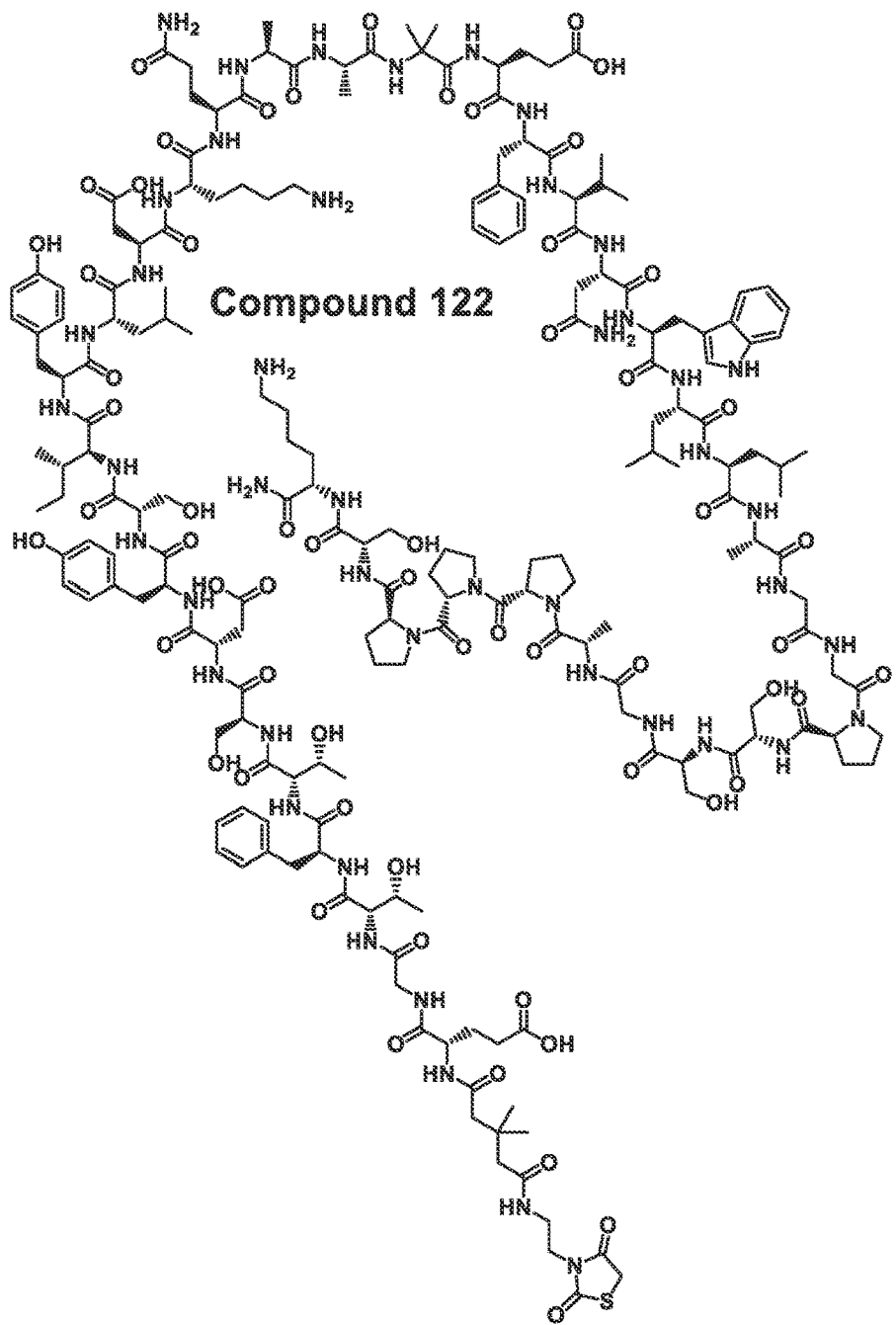
Compound 122
Cont'd

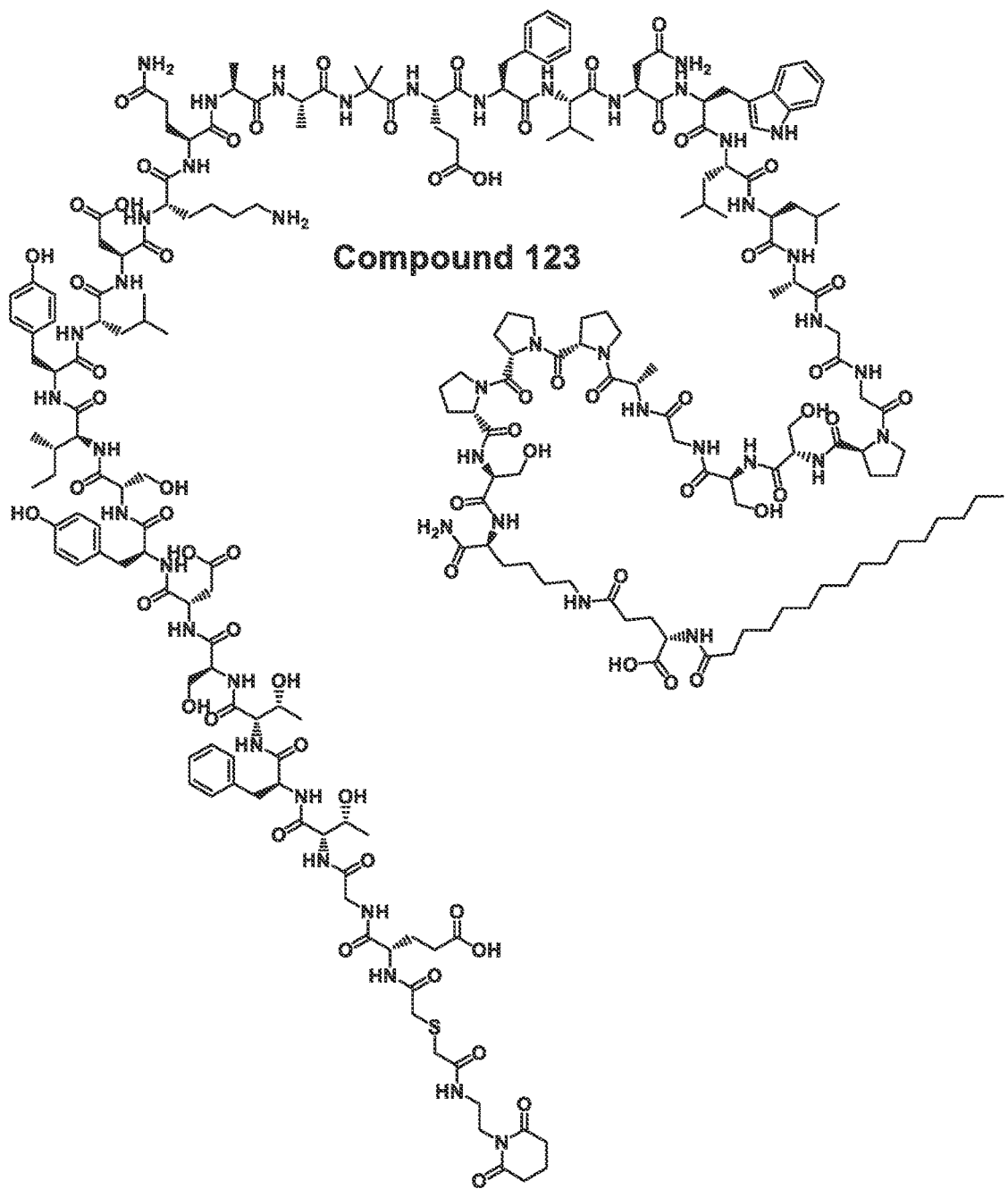
Compound 123
Cont'd

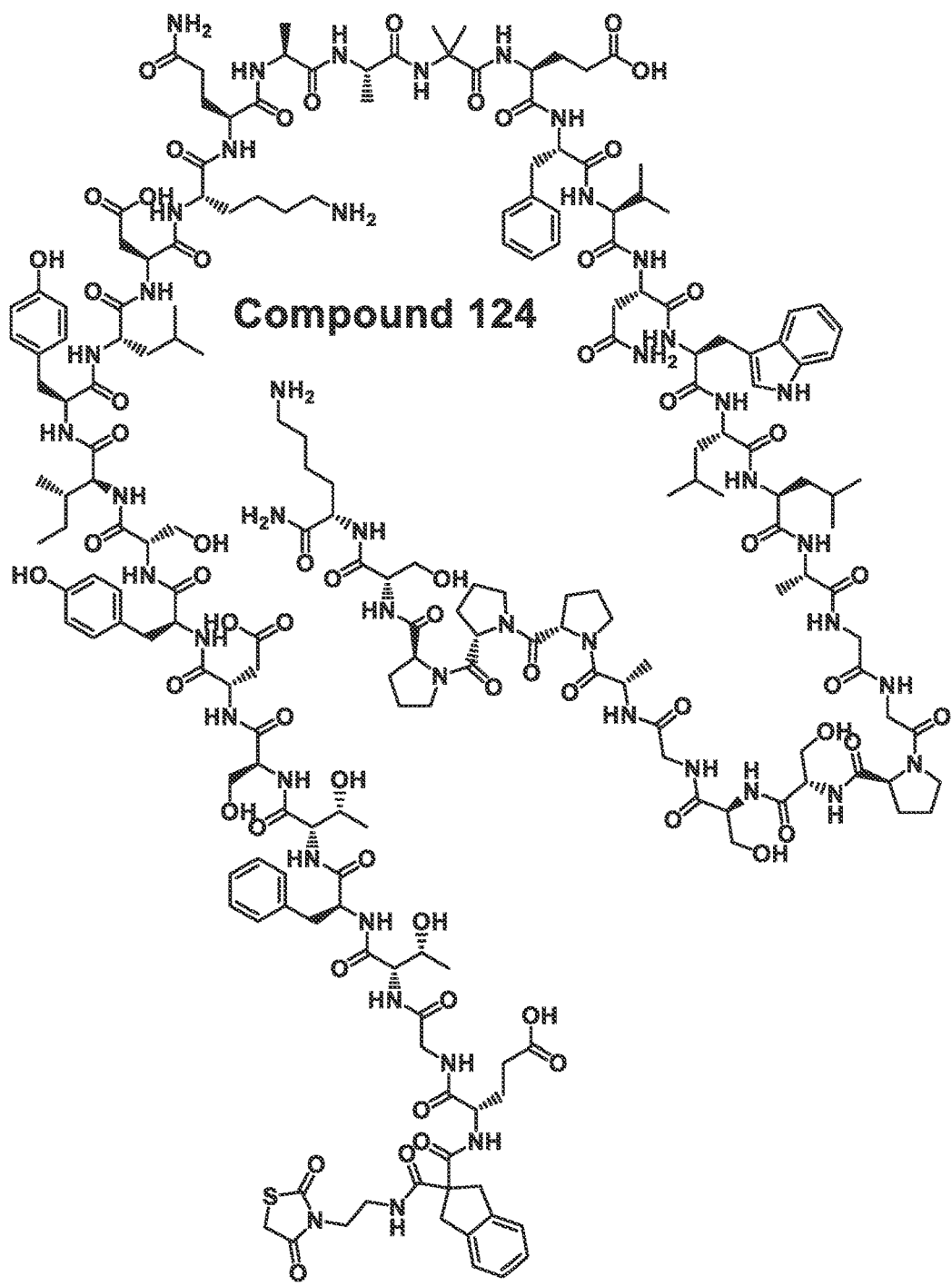
Compound 124
Cont'd

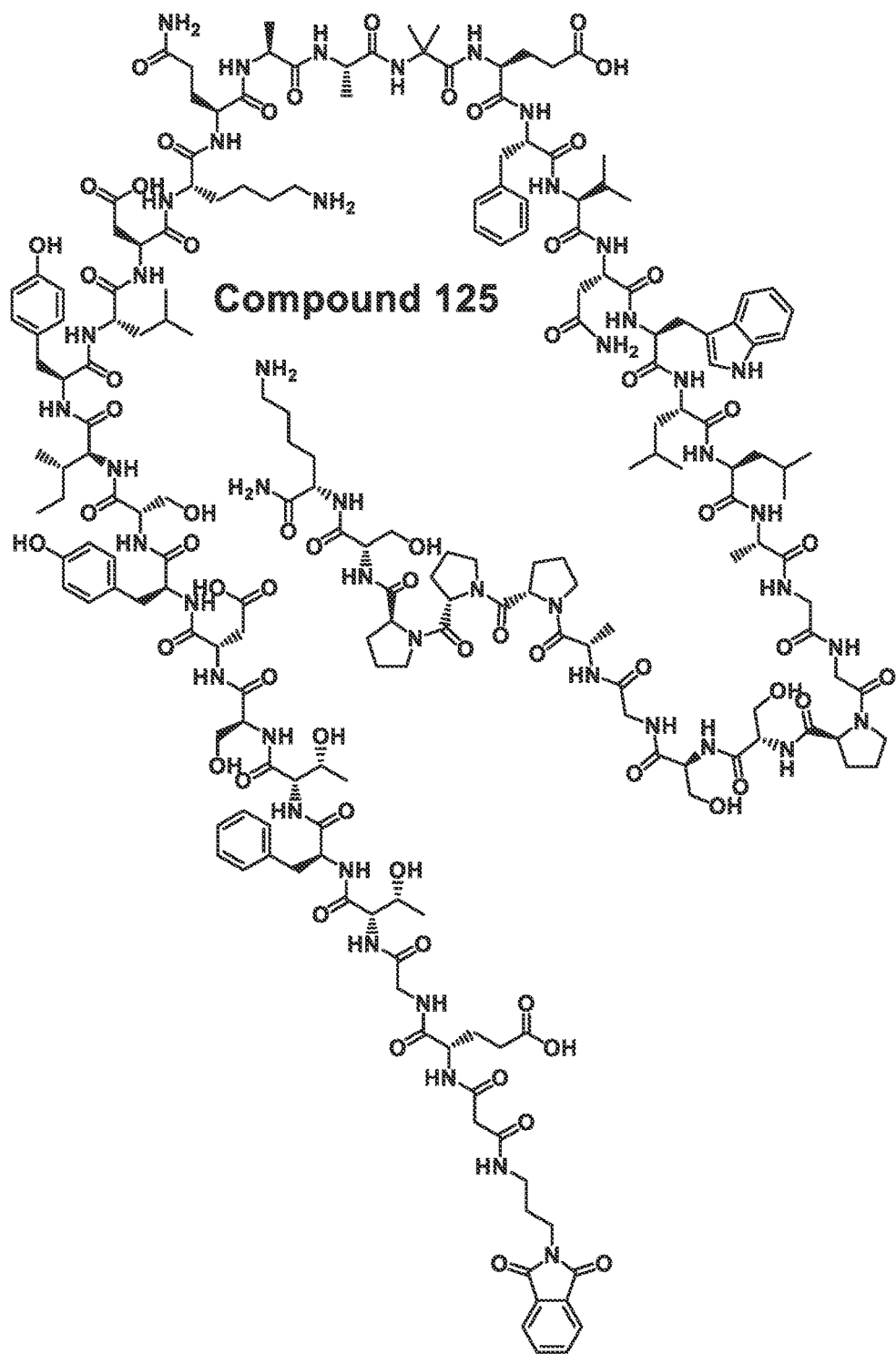
Compound 125
Cont'd

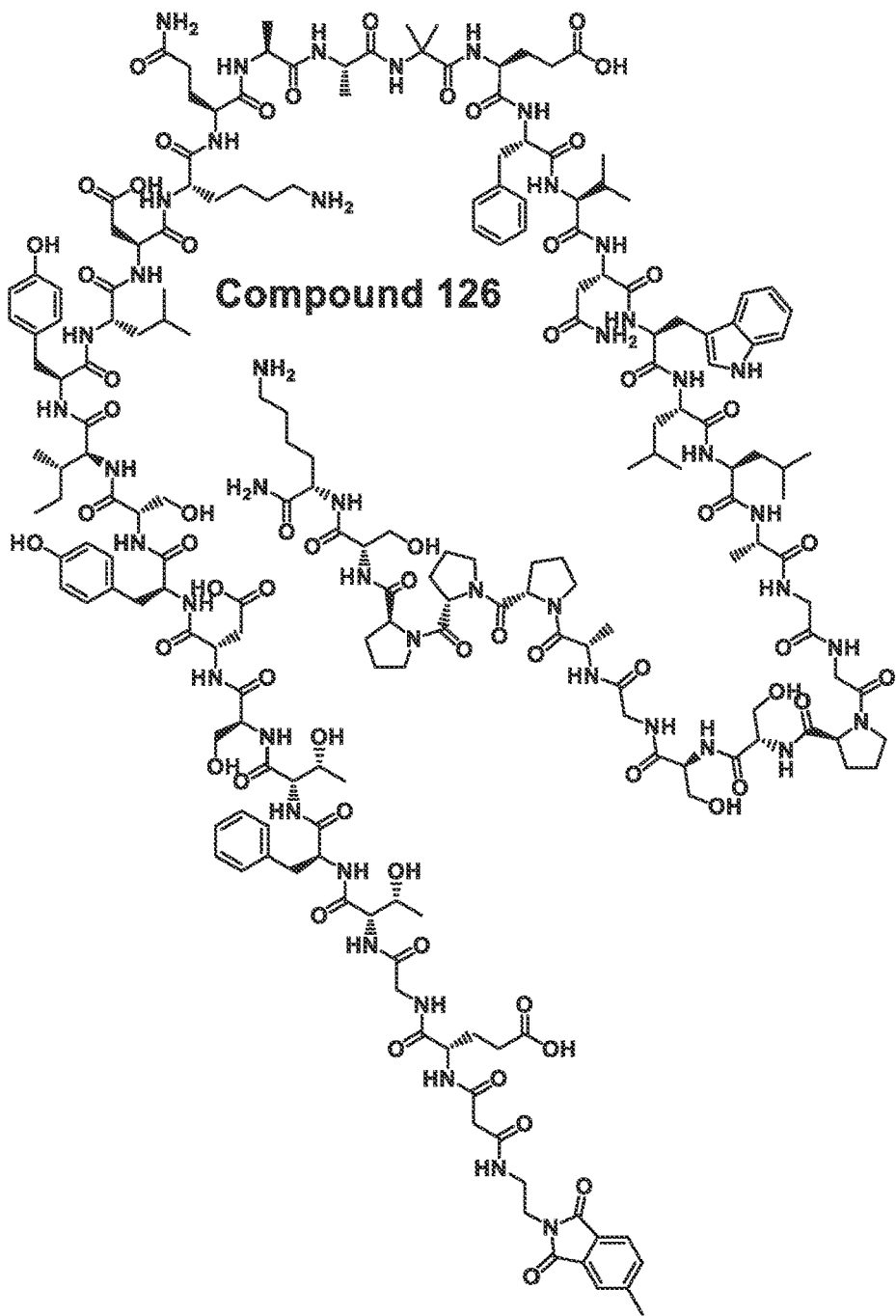
Compound 126
Cont'd

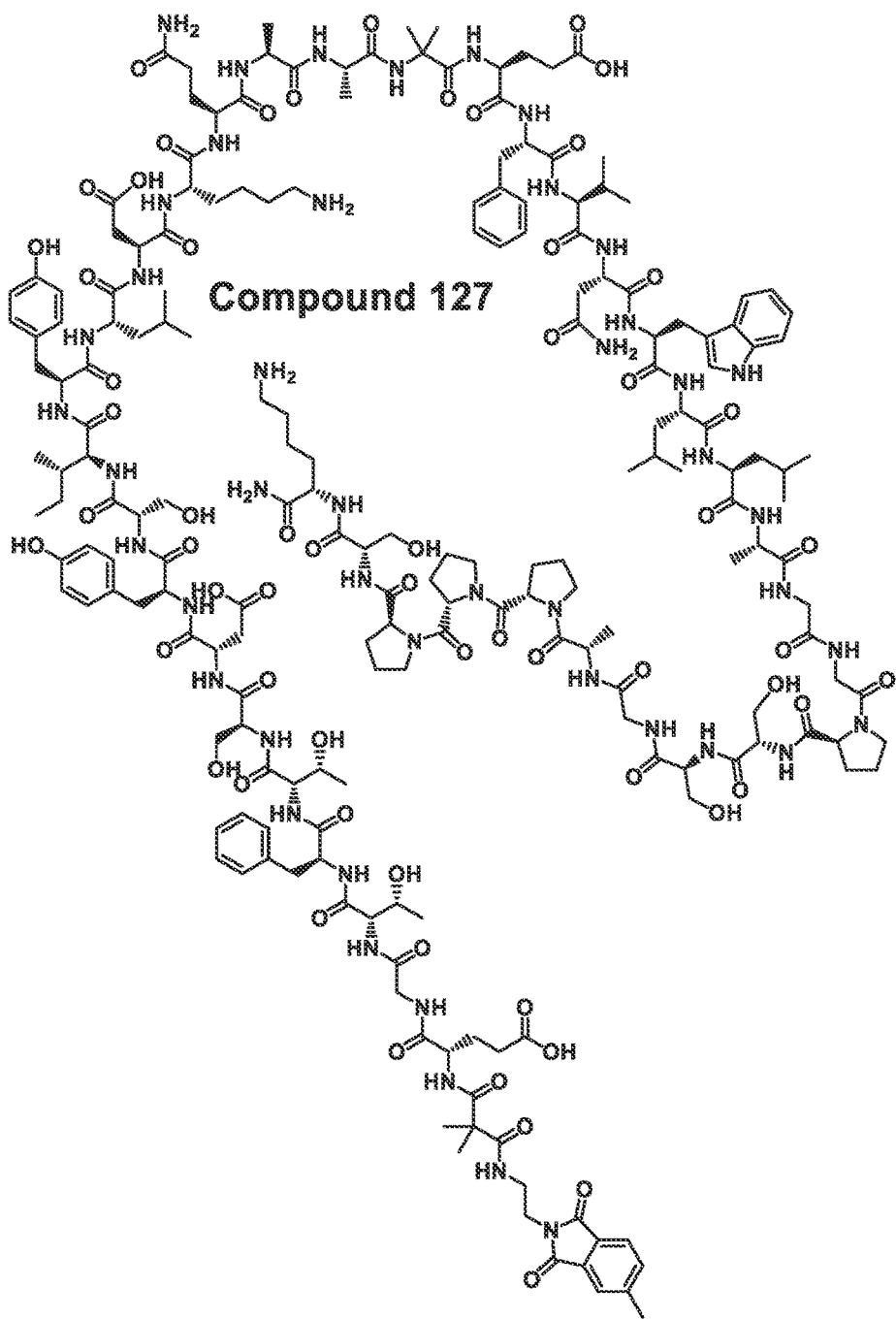

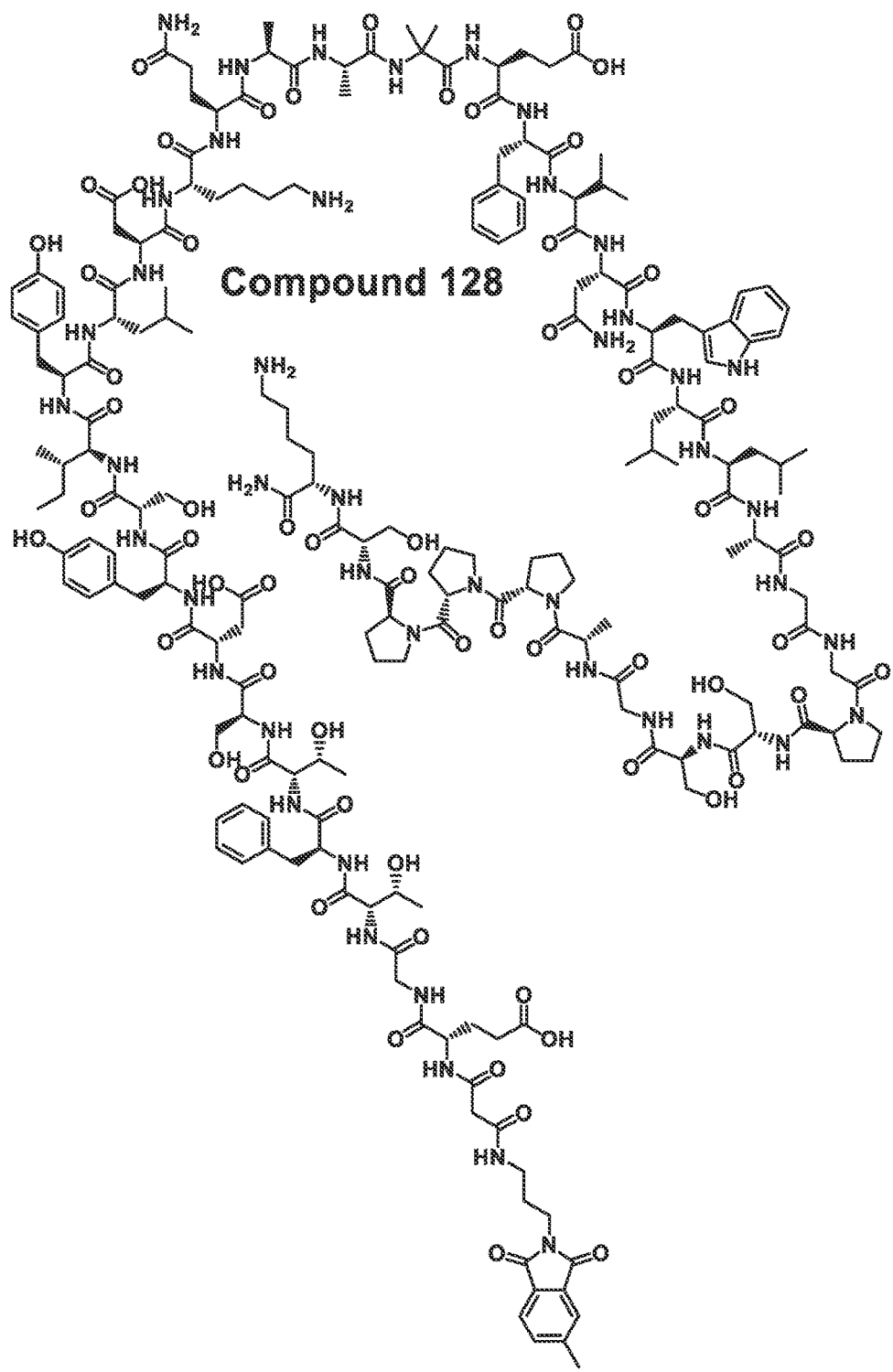
Cont'd

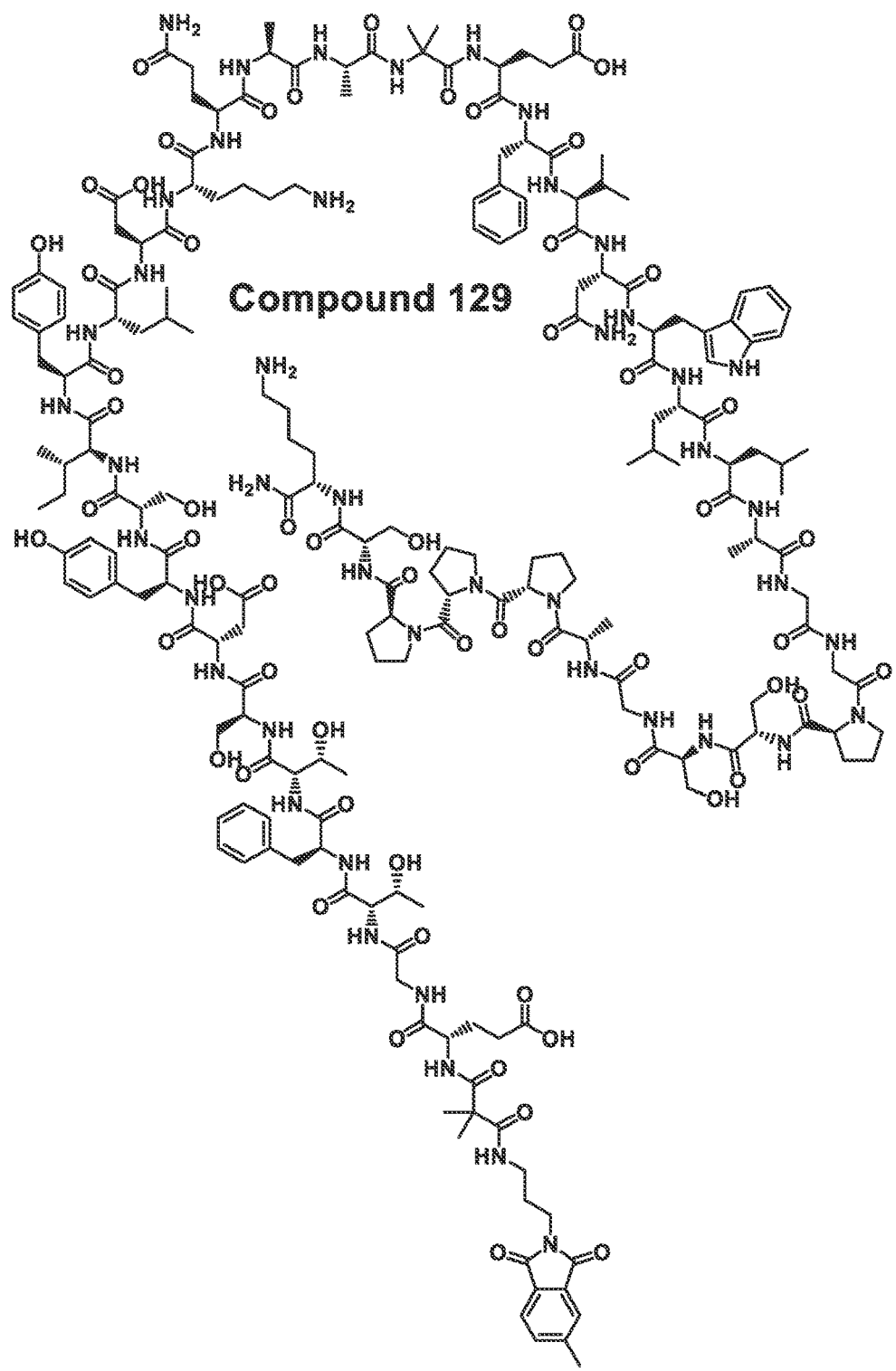
Compound 129
Cont'd

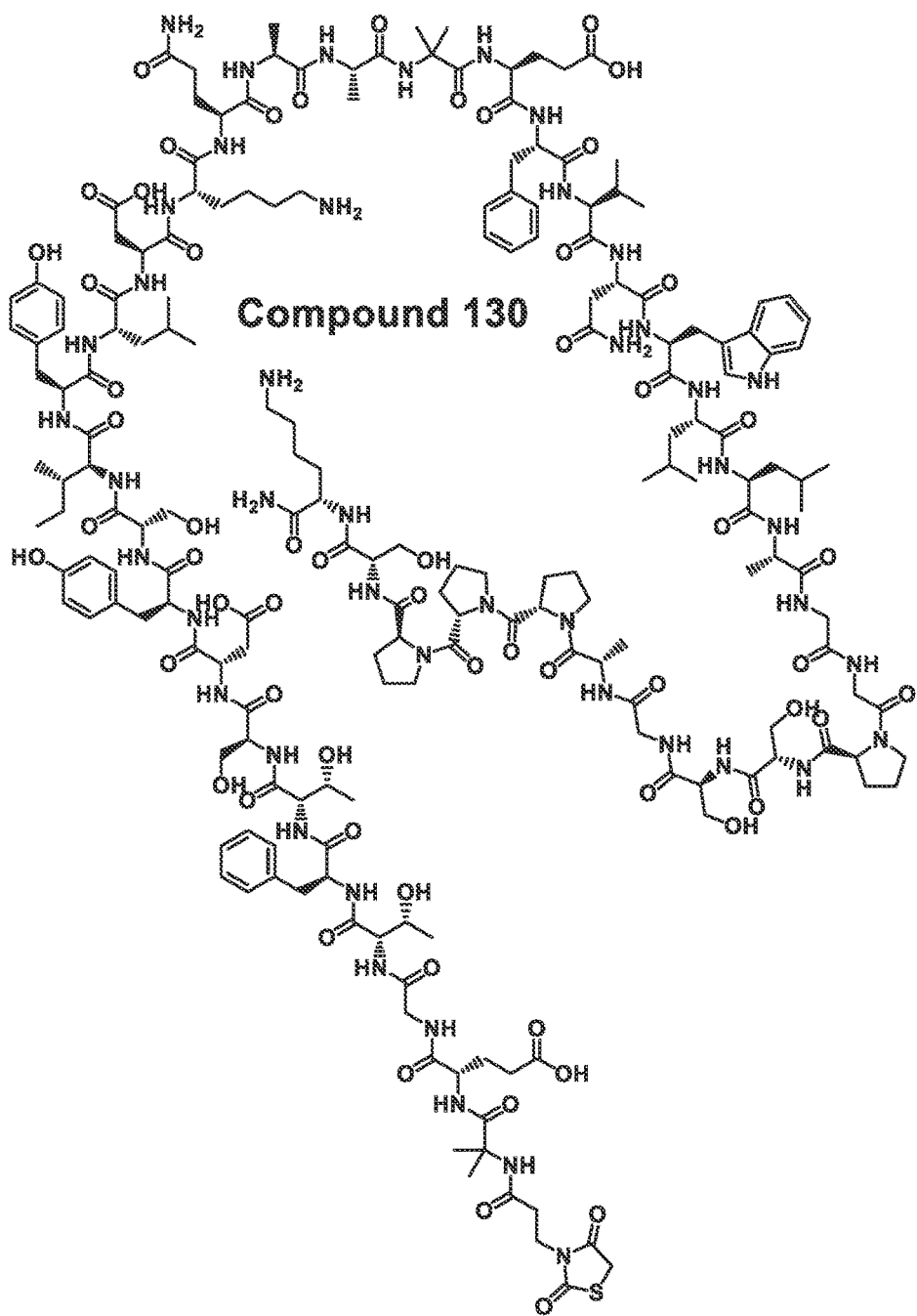
Compound 130
Cont'd

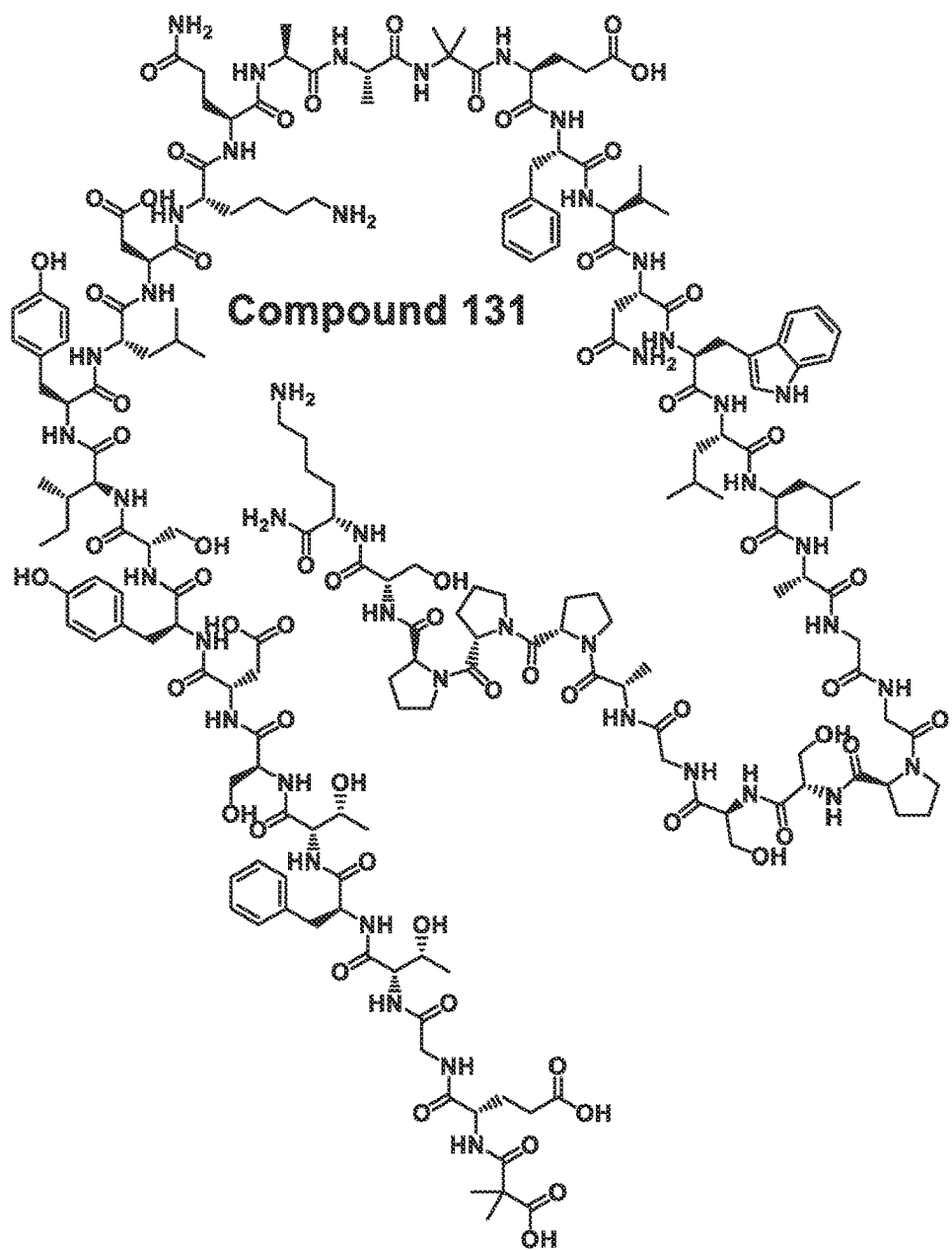
Compound 131
Cont'd

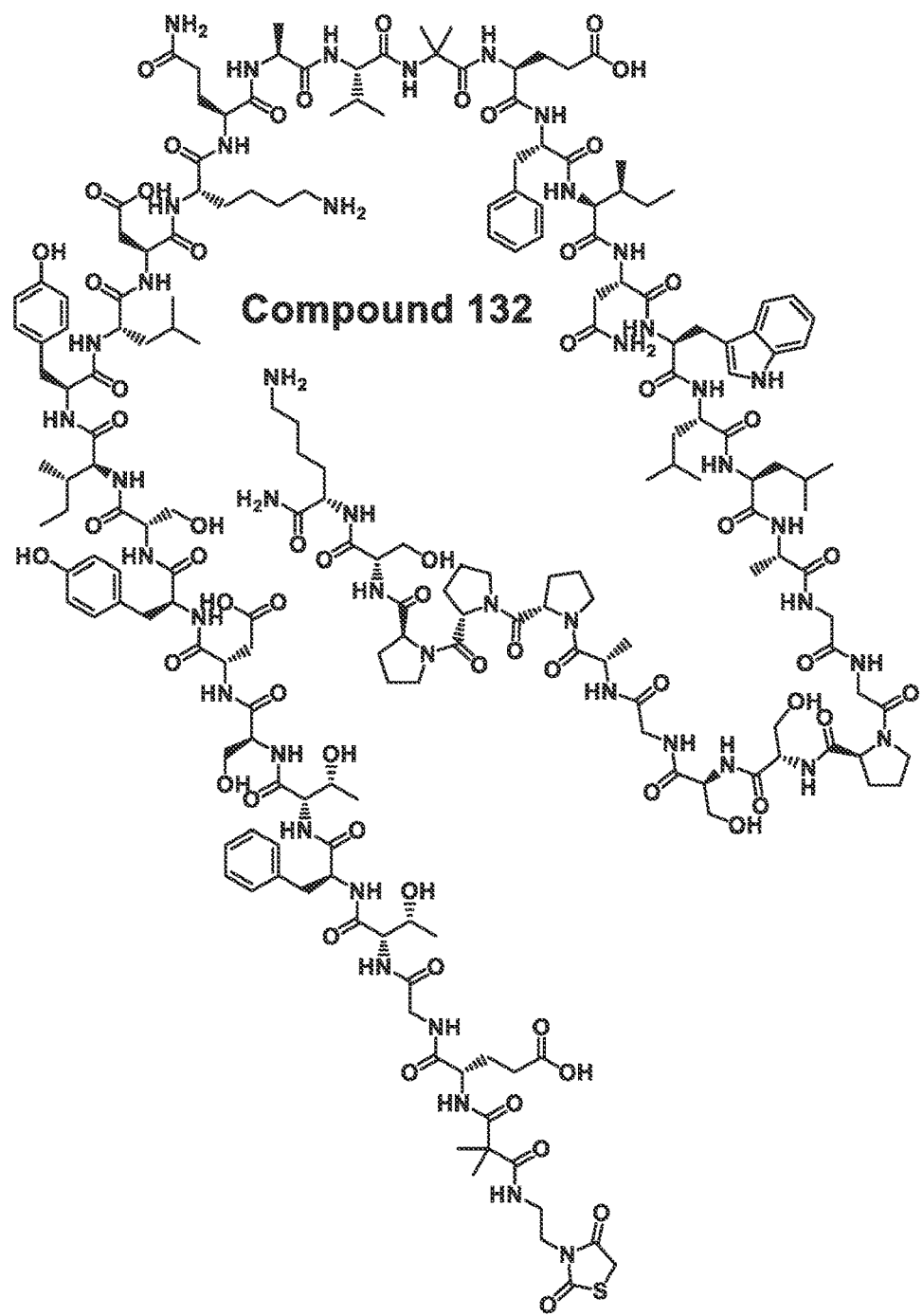

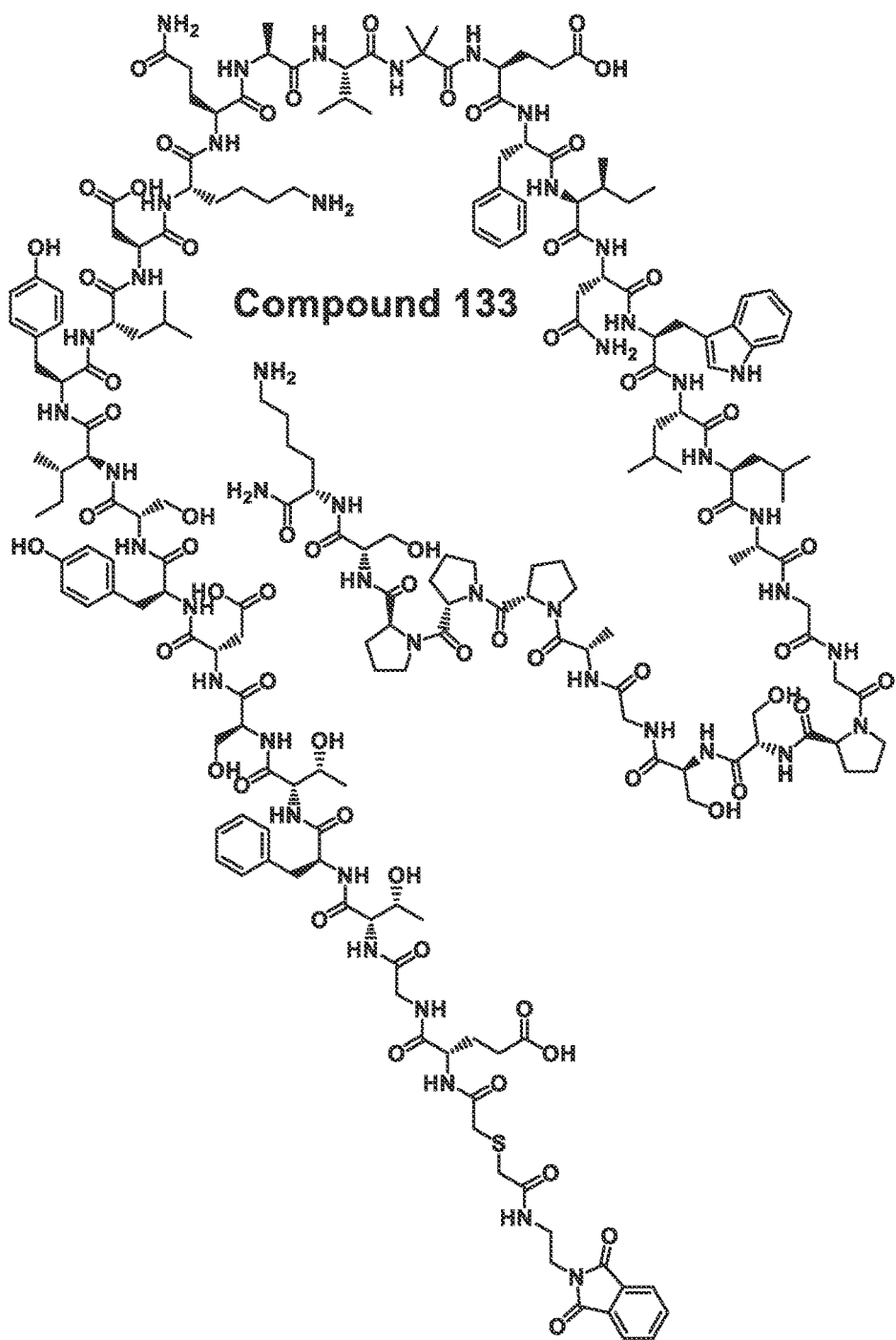
Compound 133
Cont'd

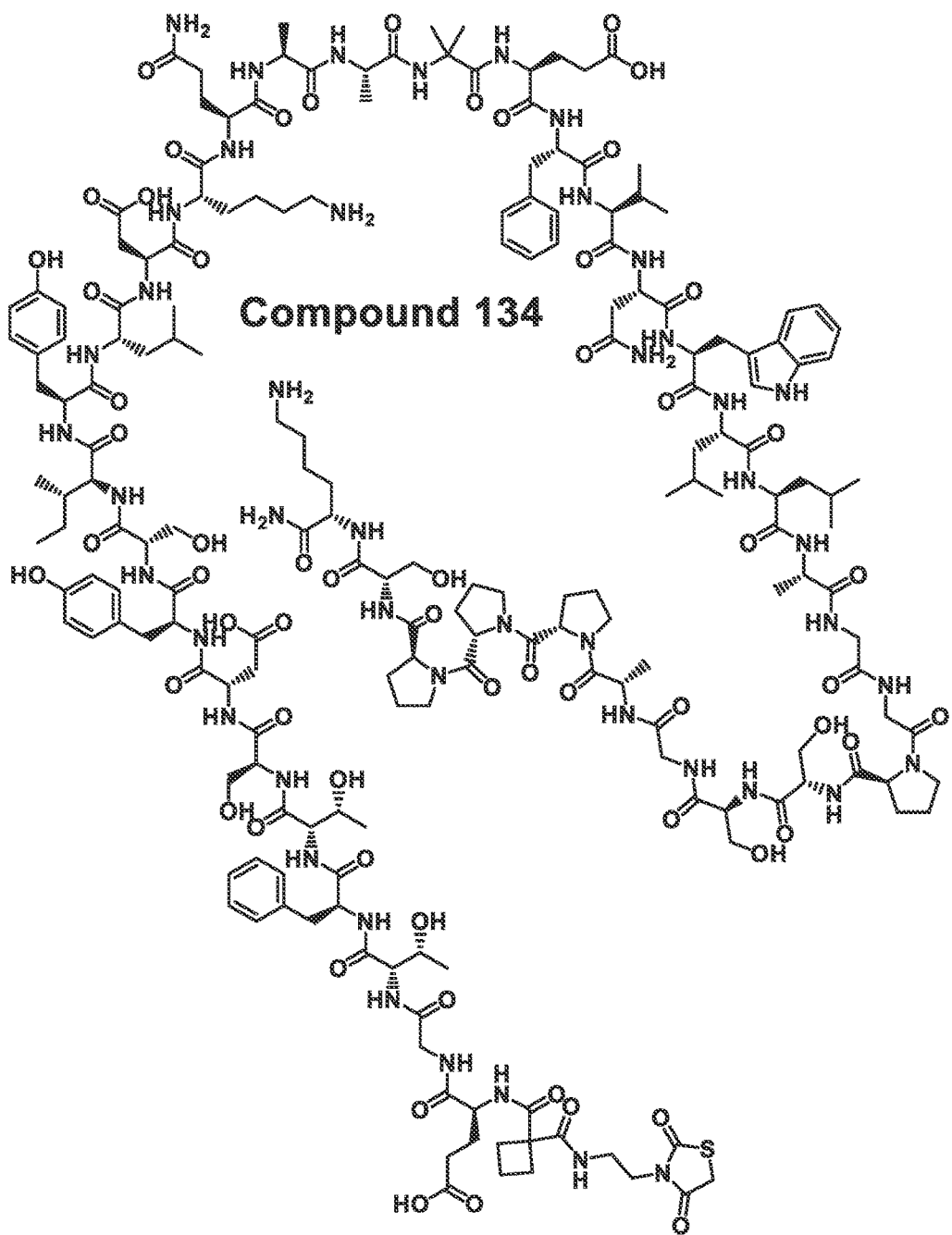
Compound 134
Cont'd

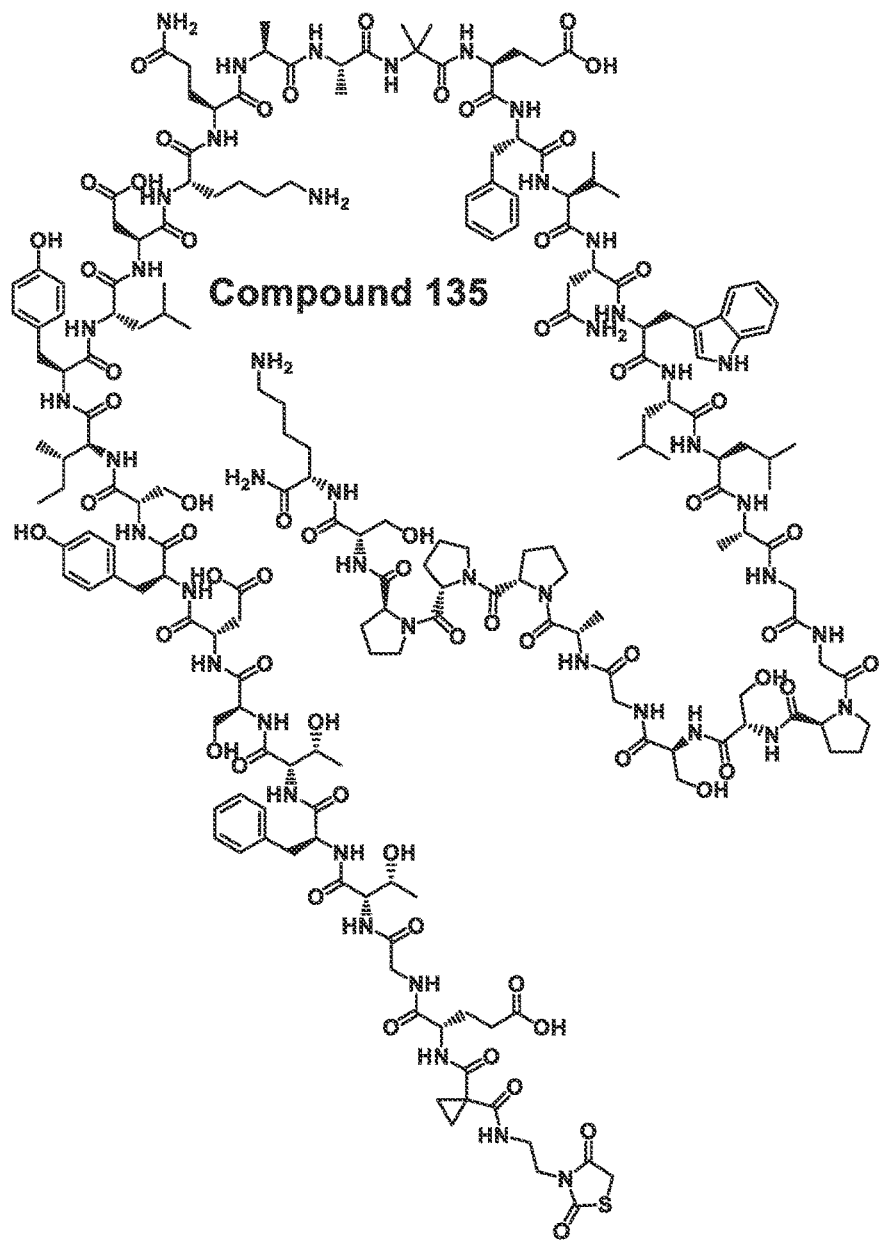

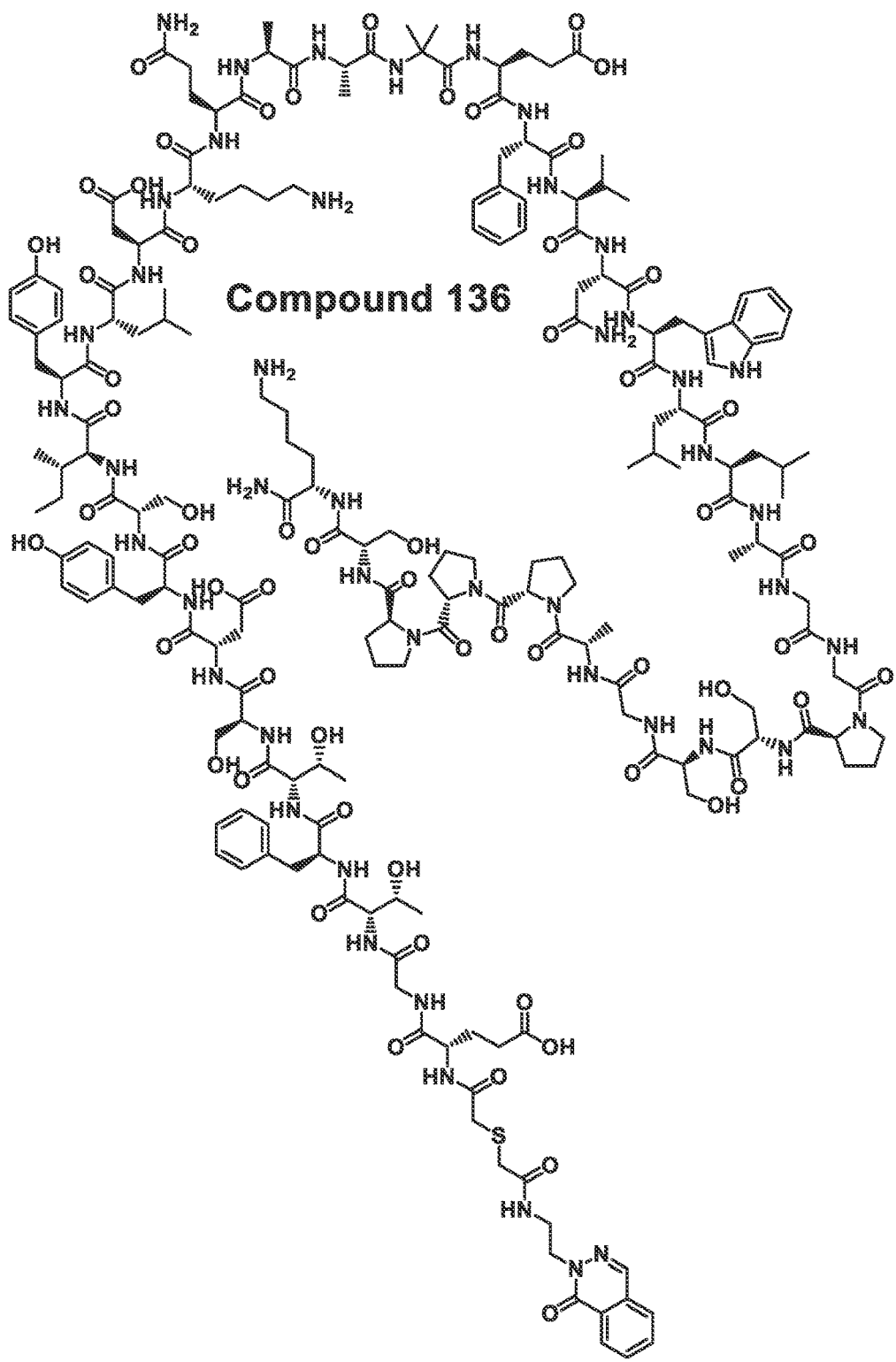
Compound 136
Cont'd

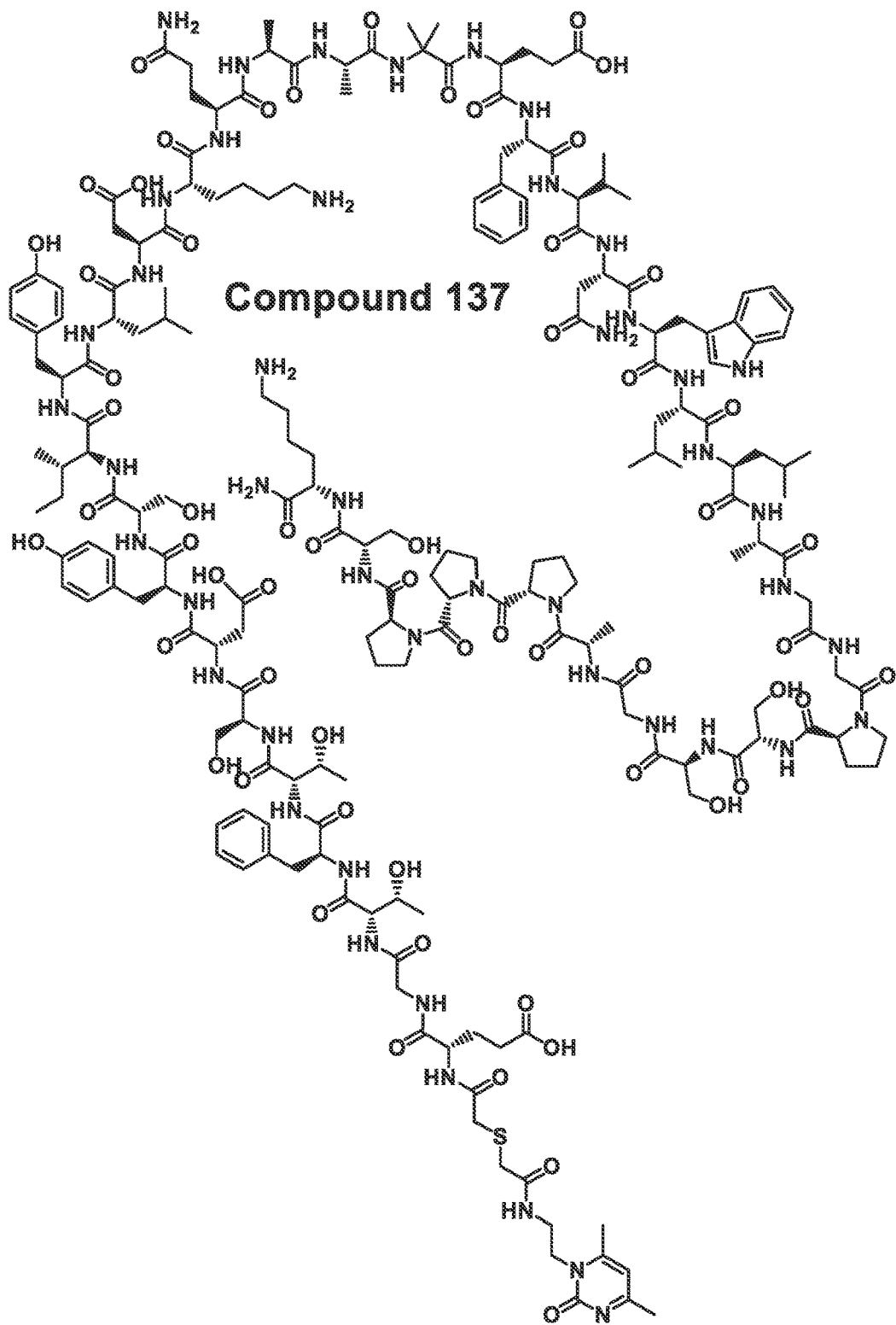
Compound 137
Cont'd

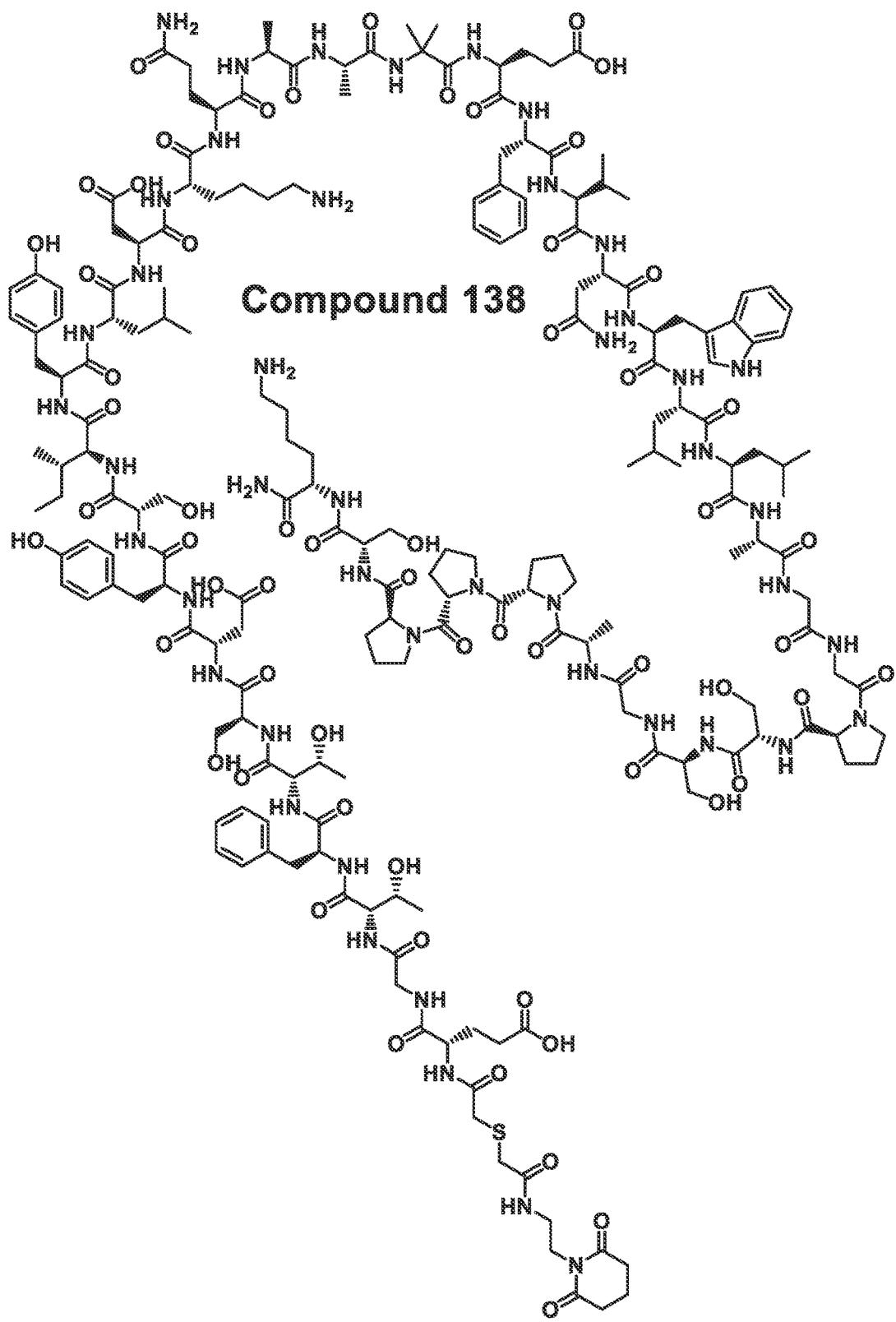
Compound 138
Cont'd

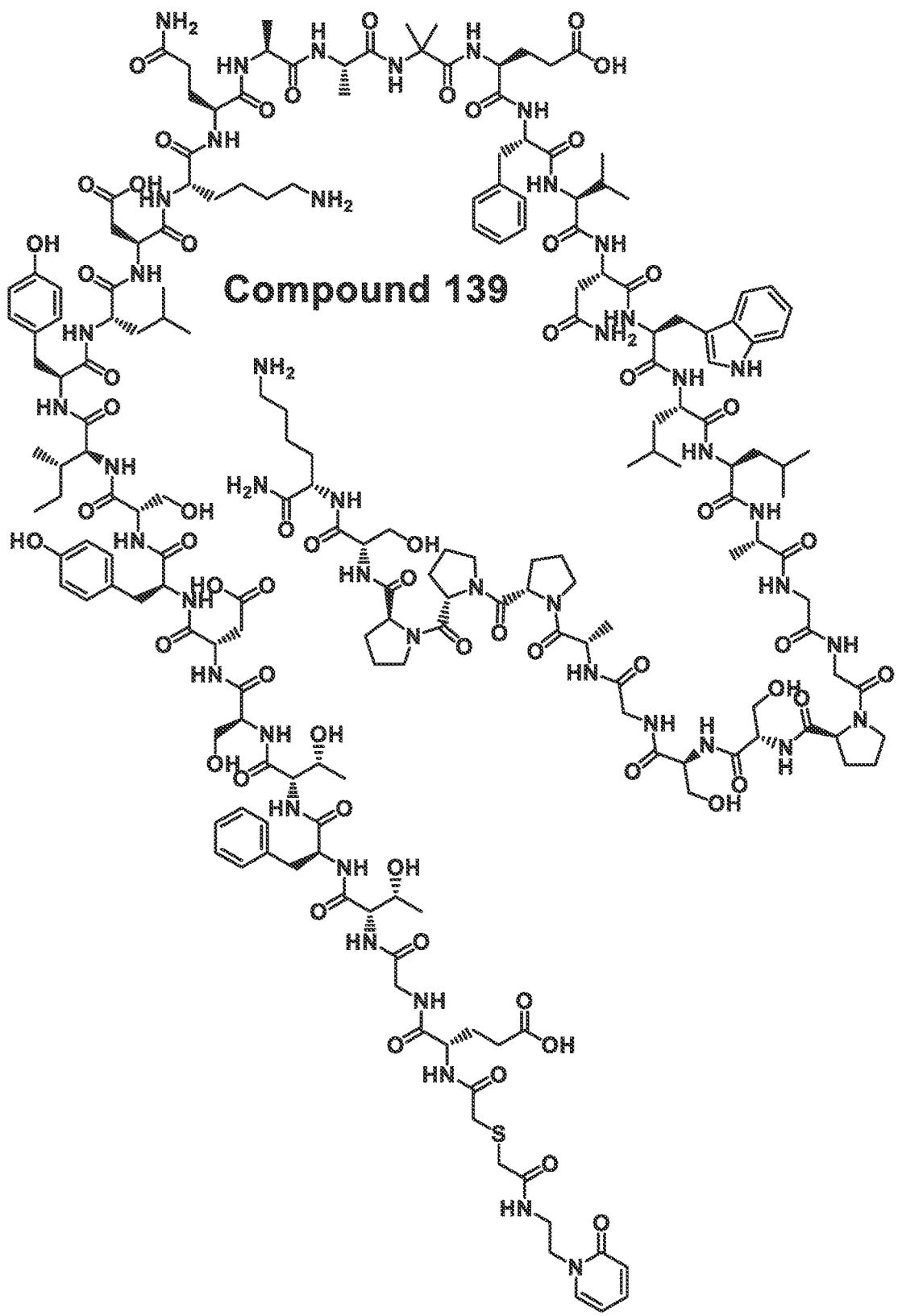
Cont'd

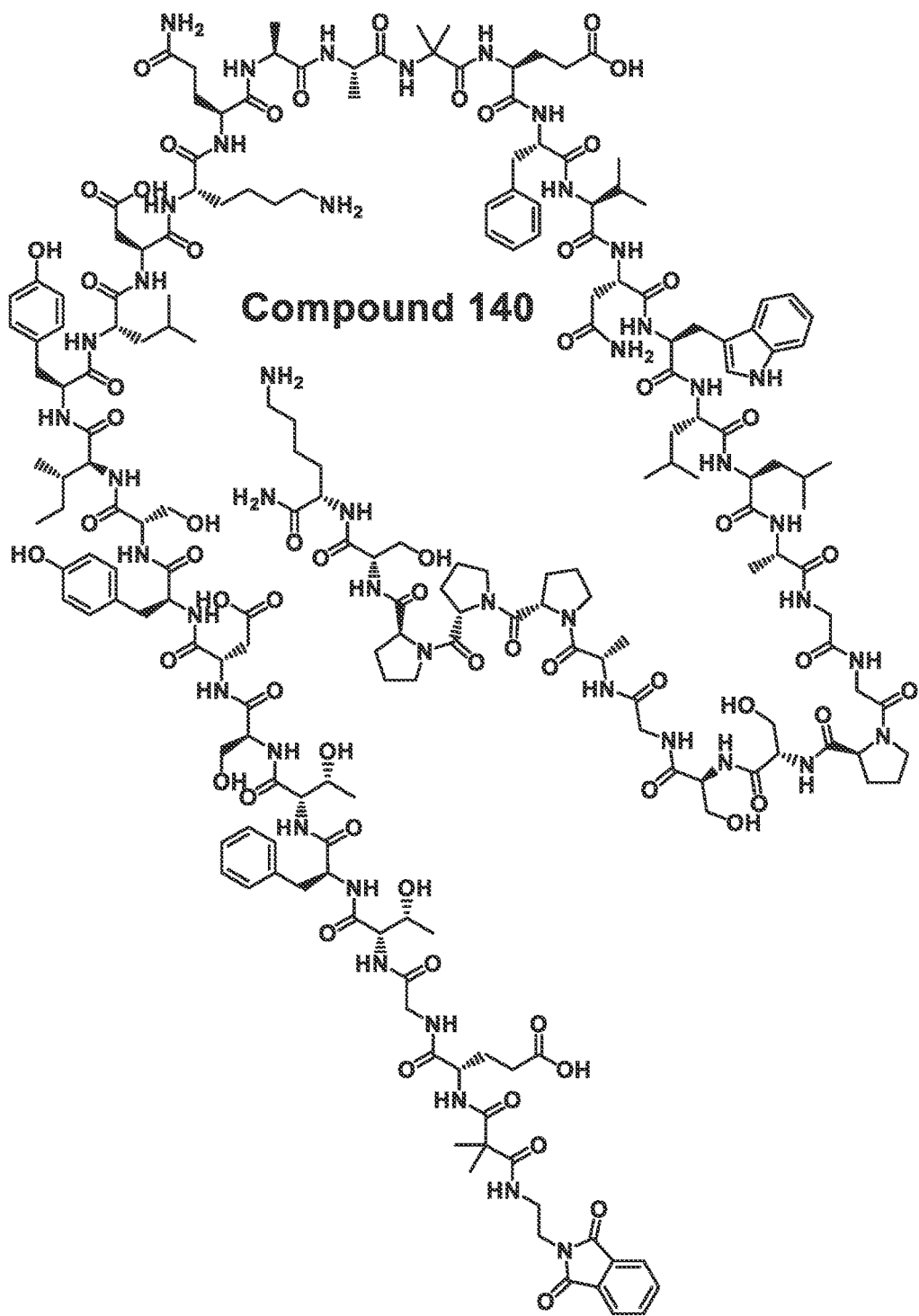
Compound 140
Cont'd

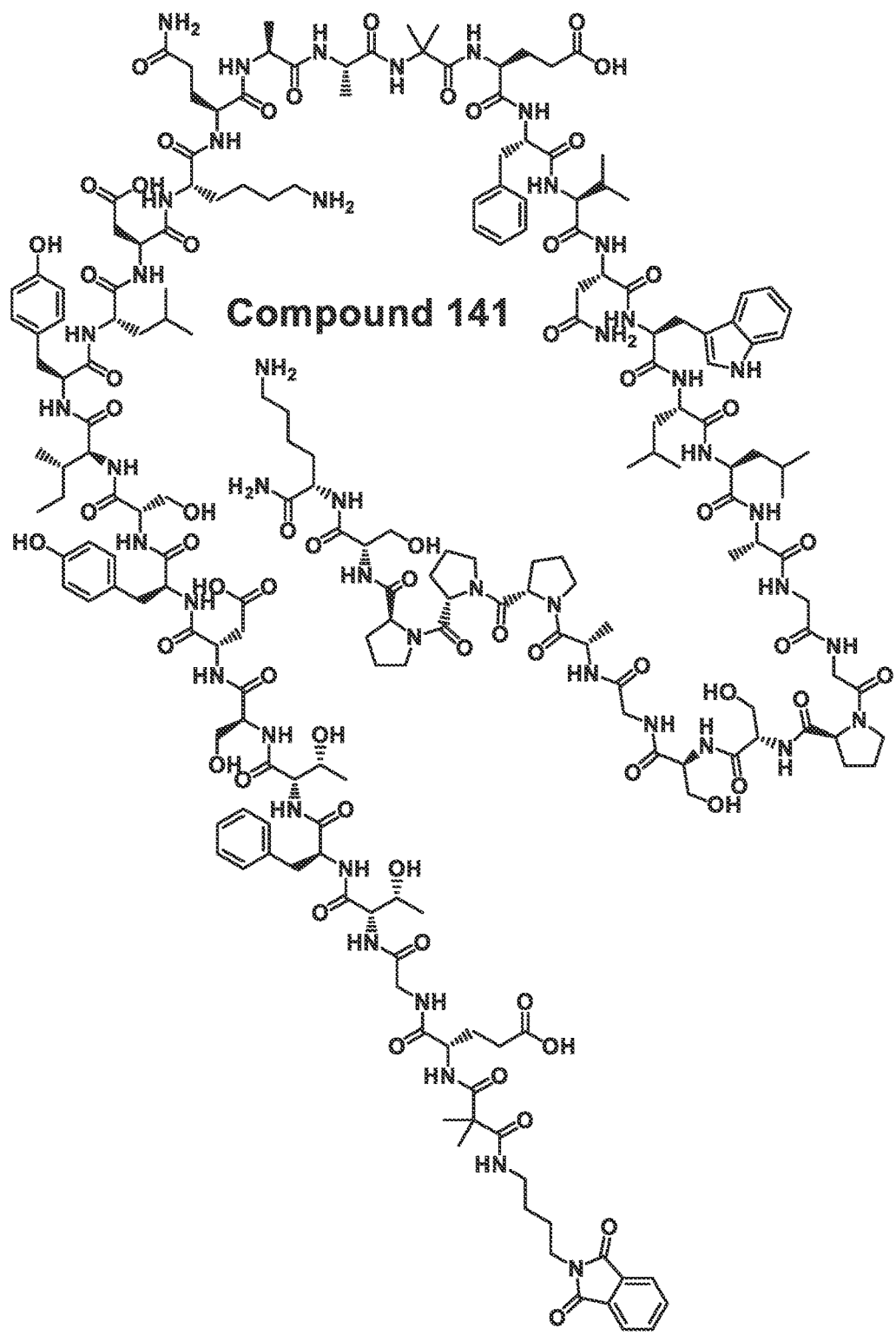
Compound 141
Cont'd

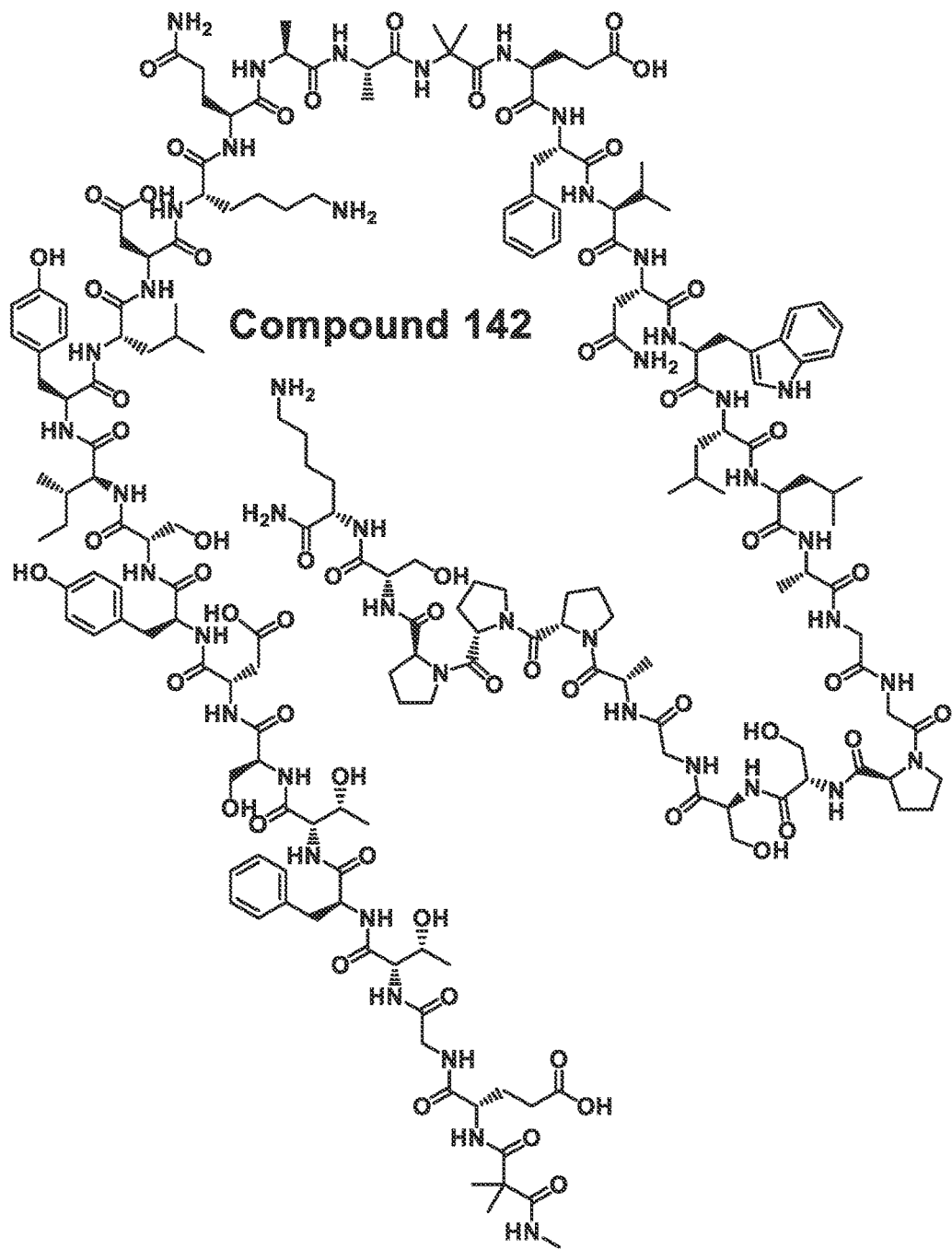
Compound 142
Cont'd

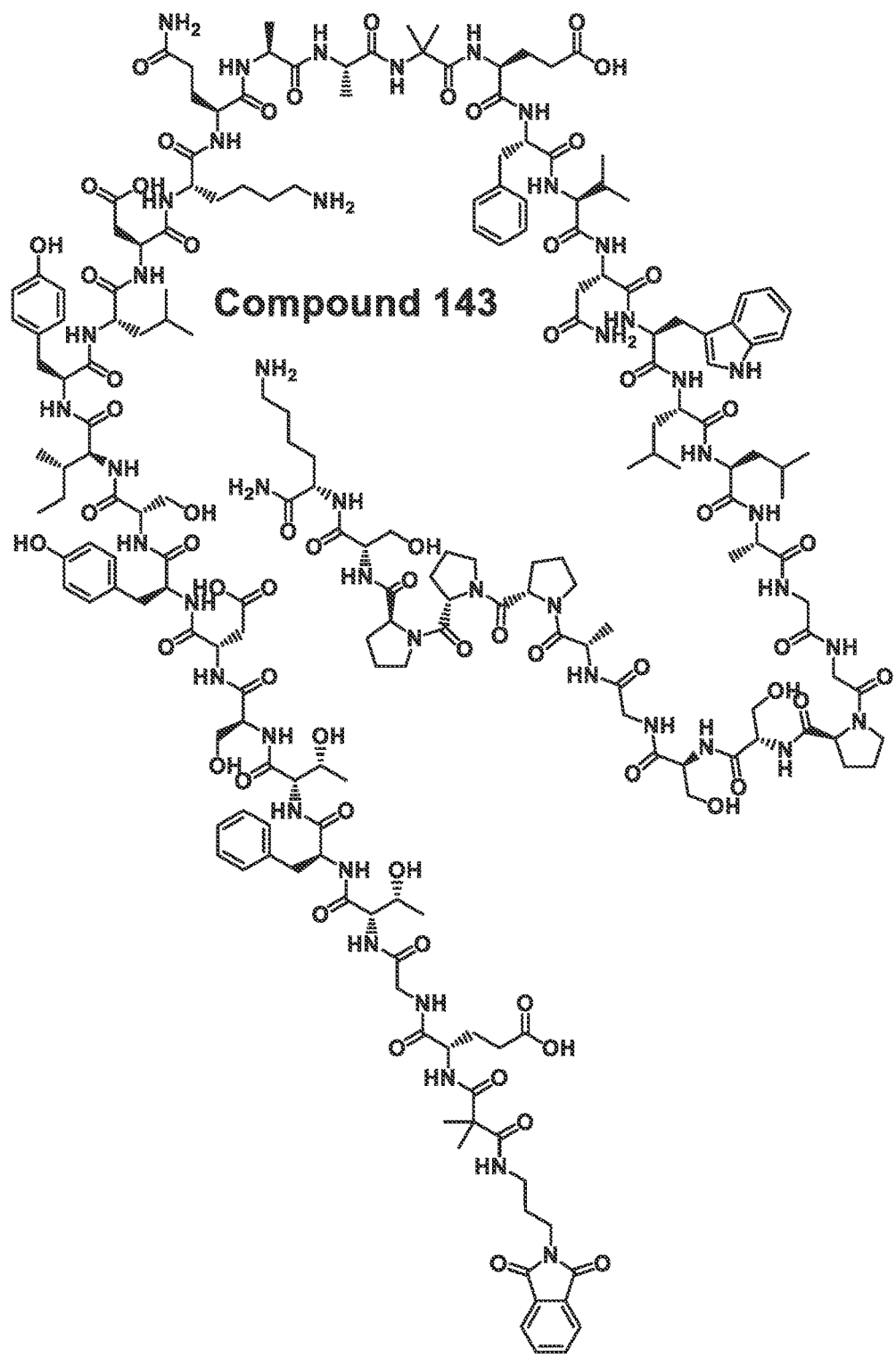
Compound 143
Cont'd

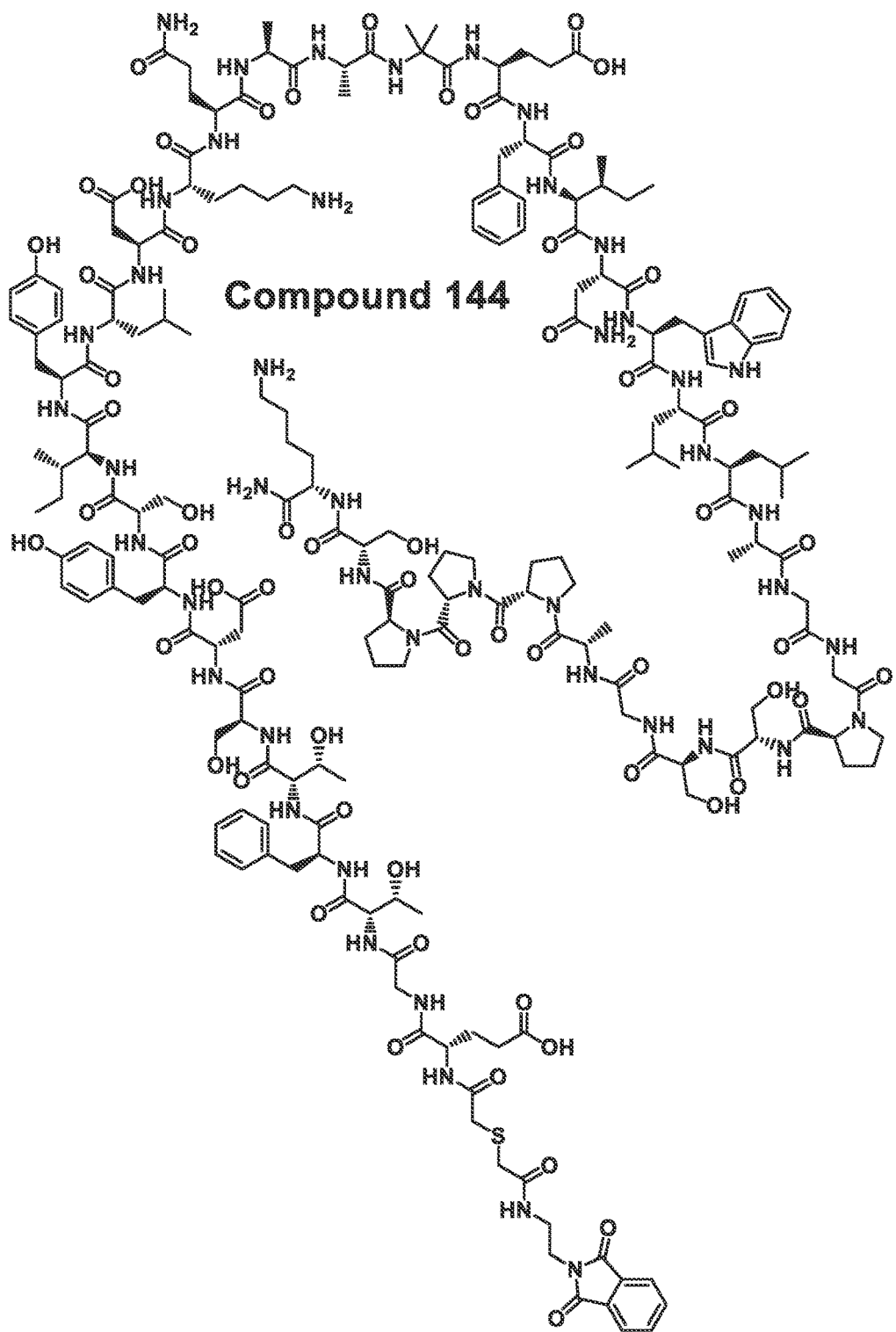
Compound 144
Cont'd

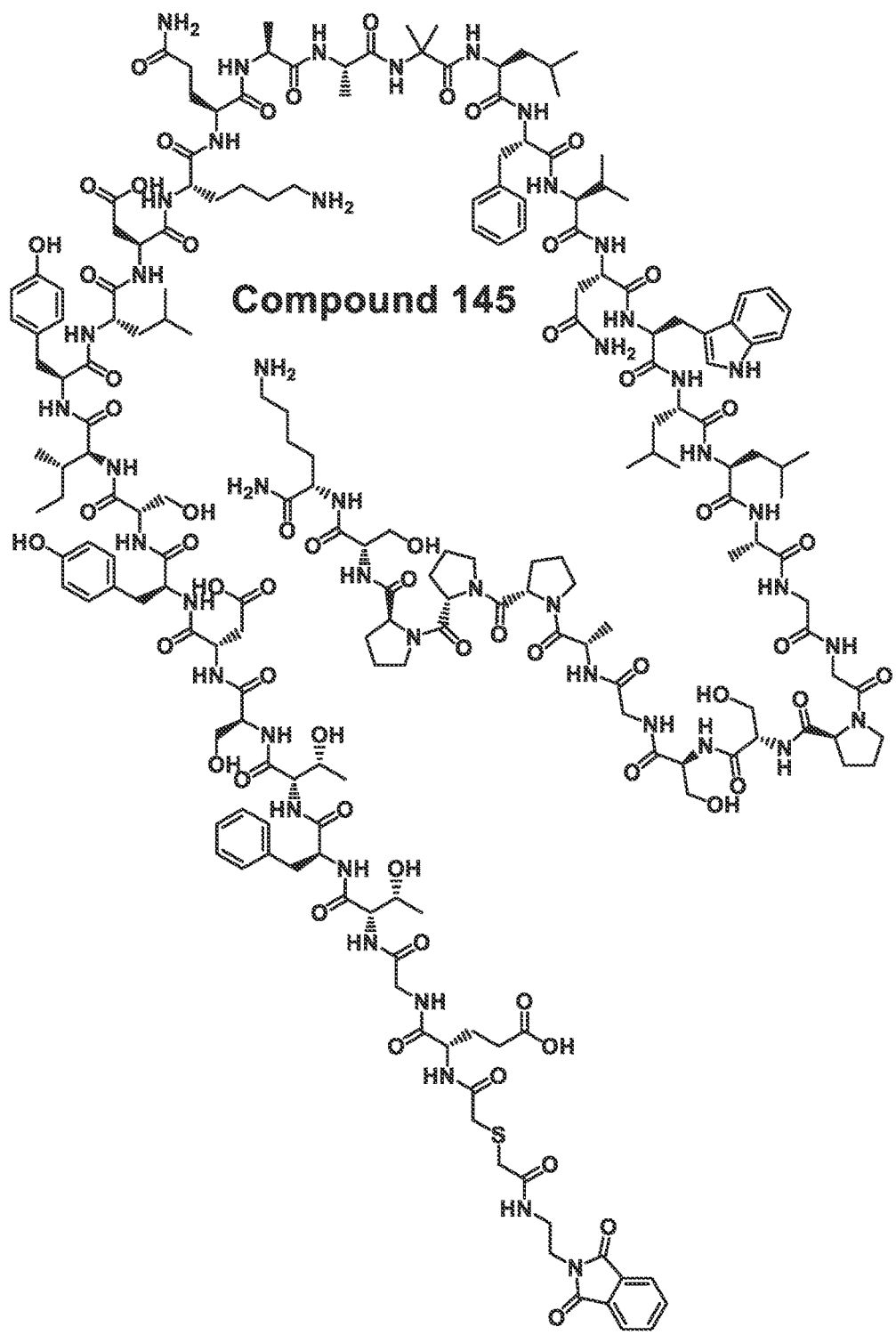
Compound 145
Cont'd

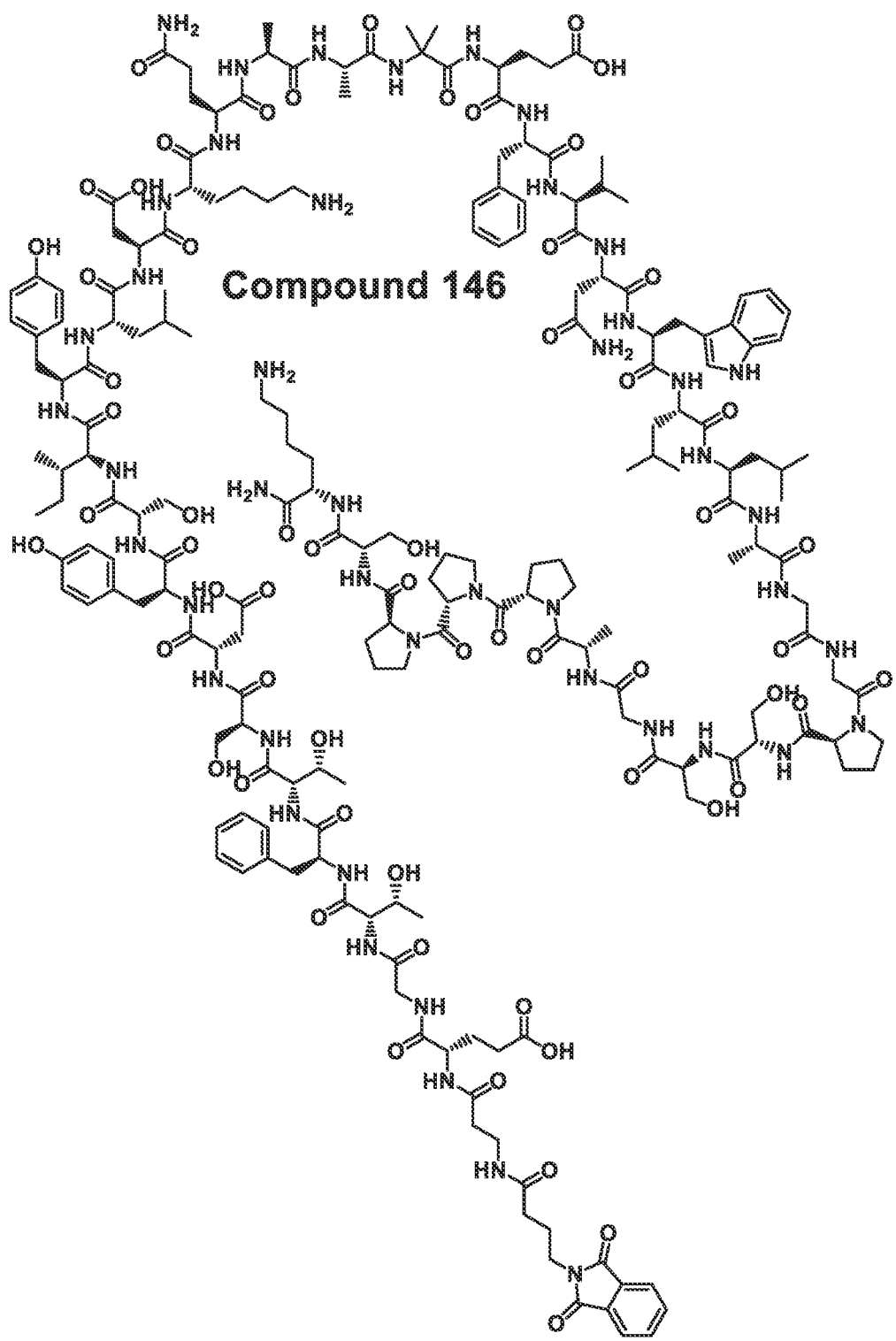
Compound 146
Cont'd

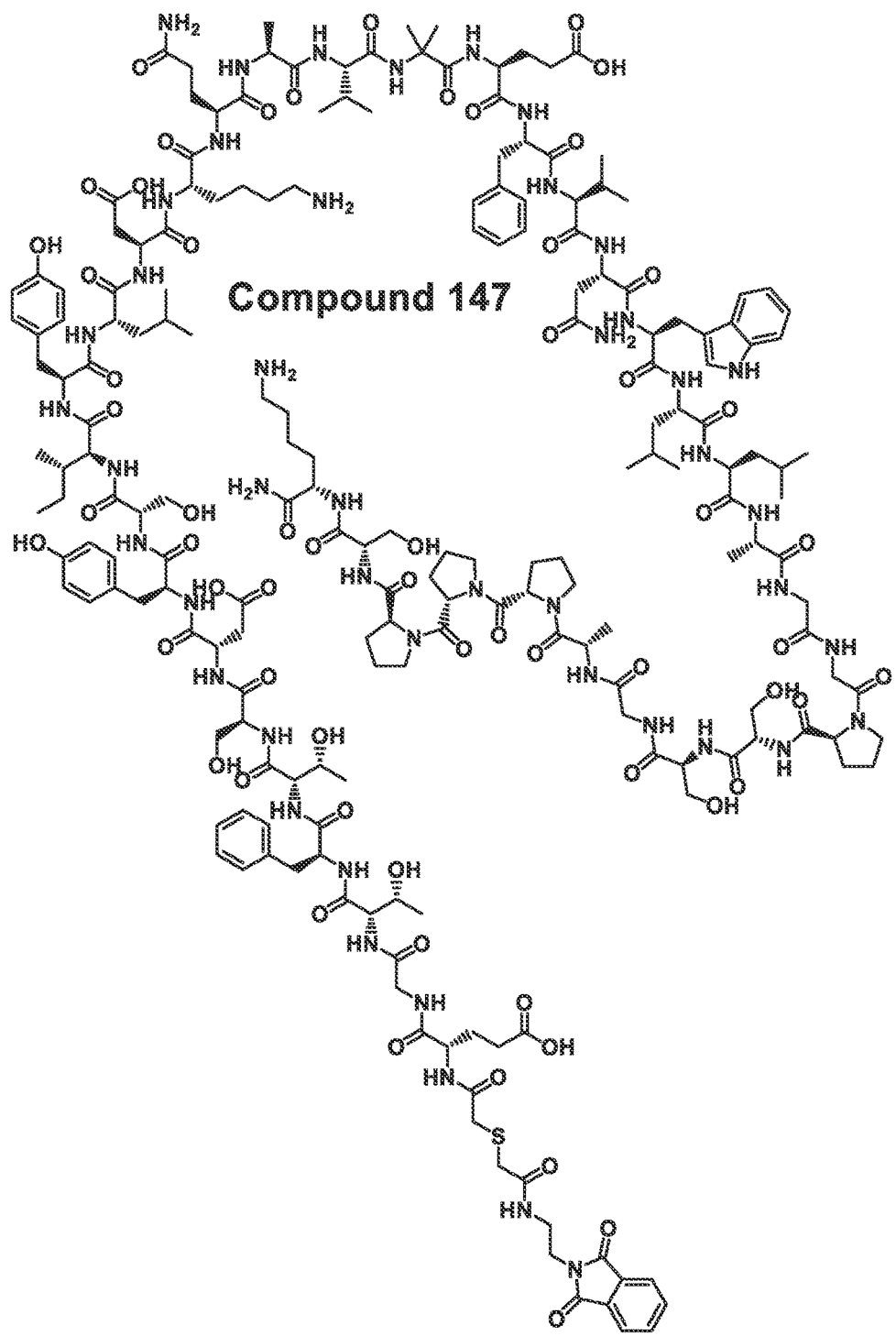
Compound 147
Cont'd

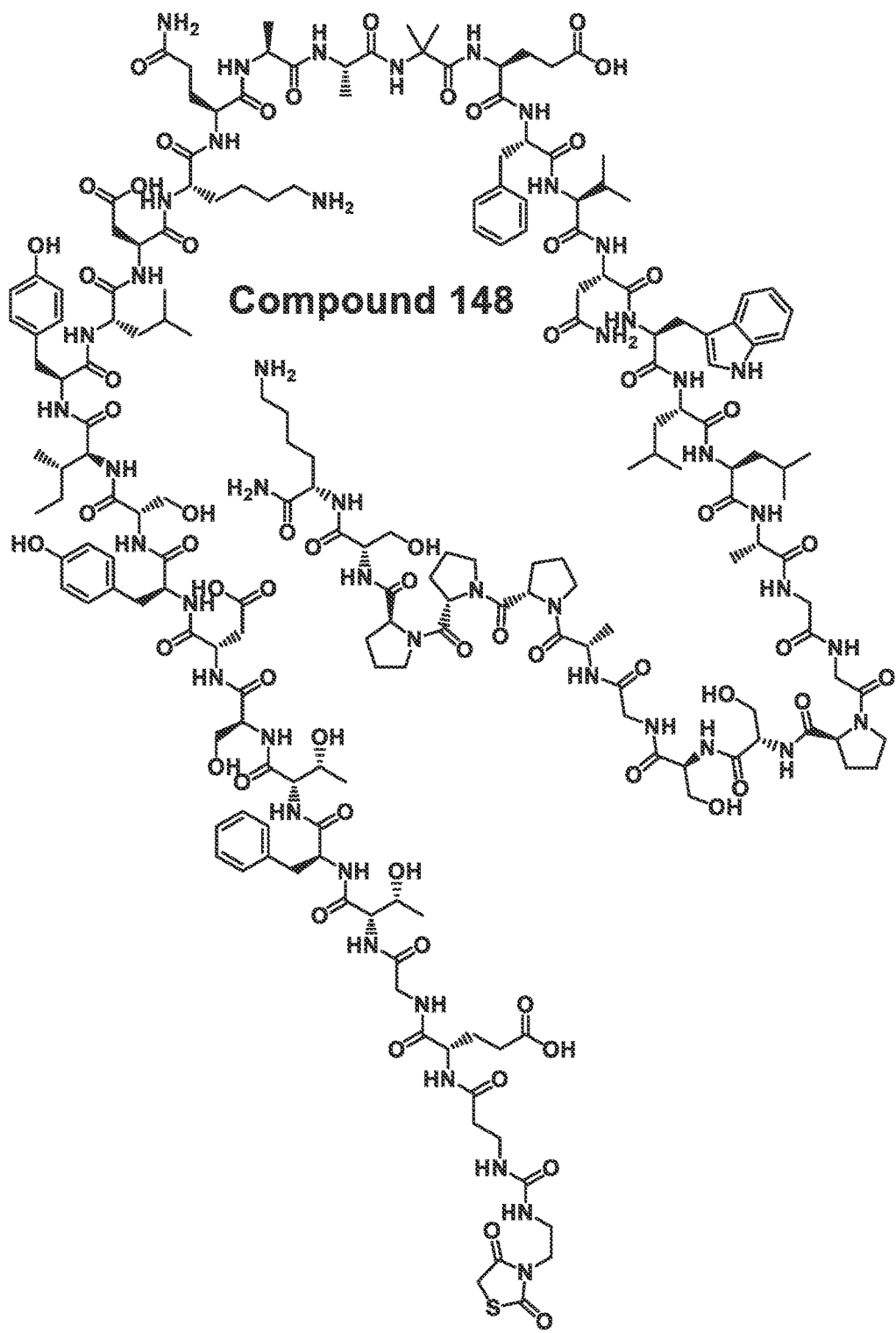
Compound 148
Cont'd

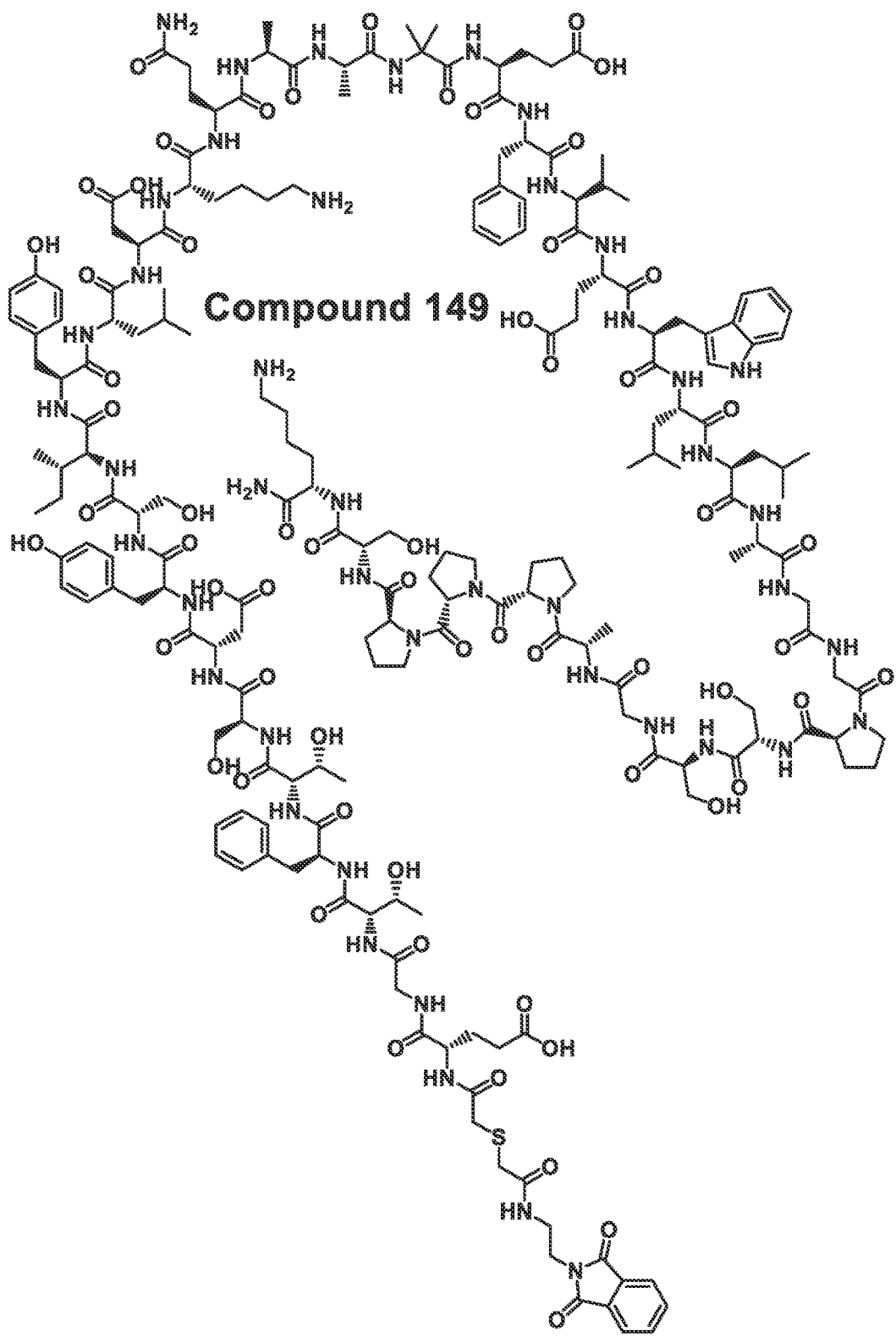
Compound 149
Cont'd

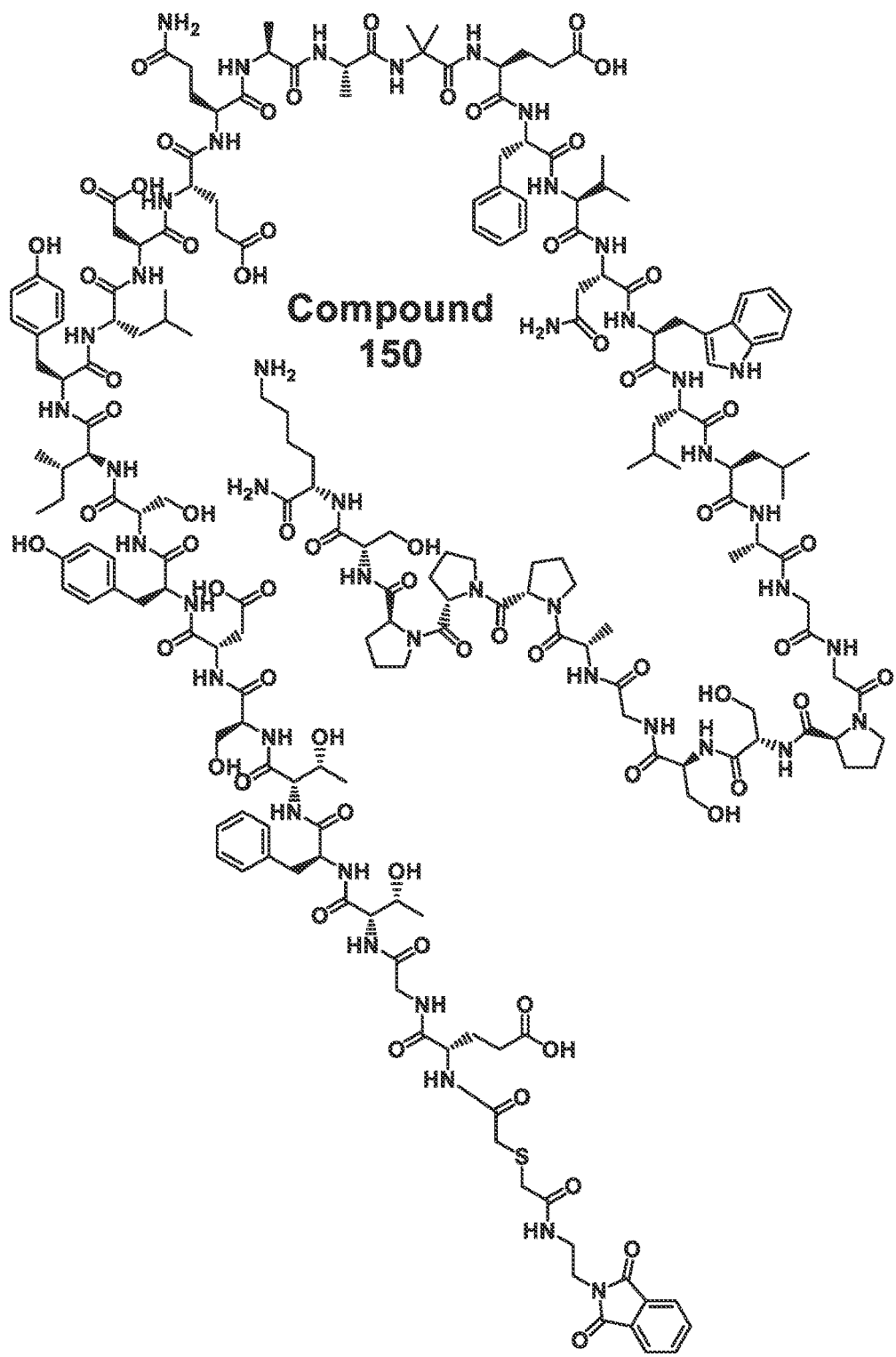
Compound 150
Cont'd

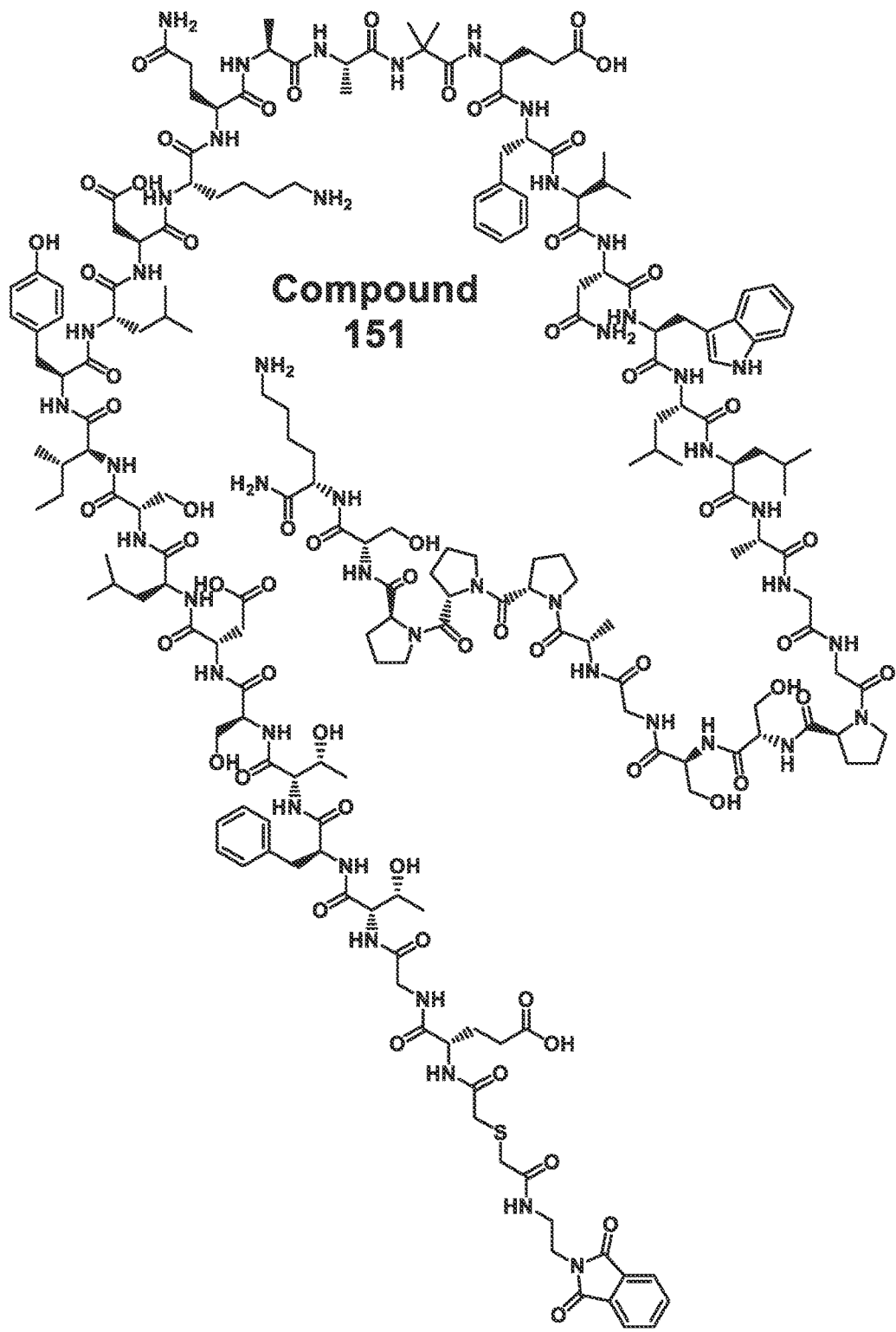
Compound 151
Cont'd

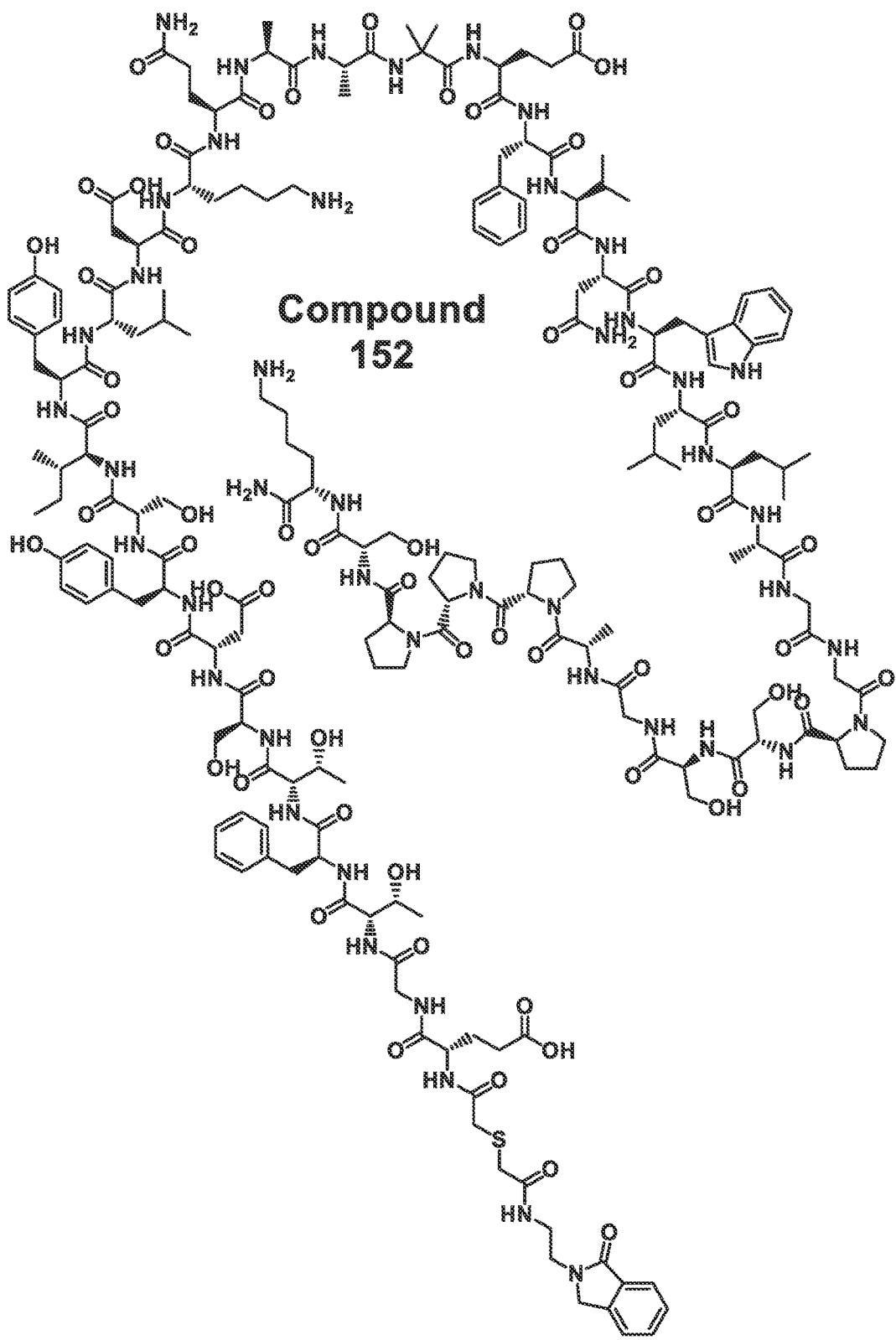
Compound 152
Cont'd

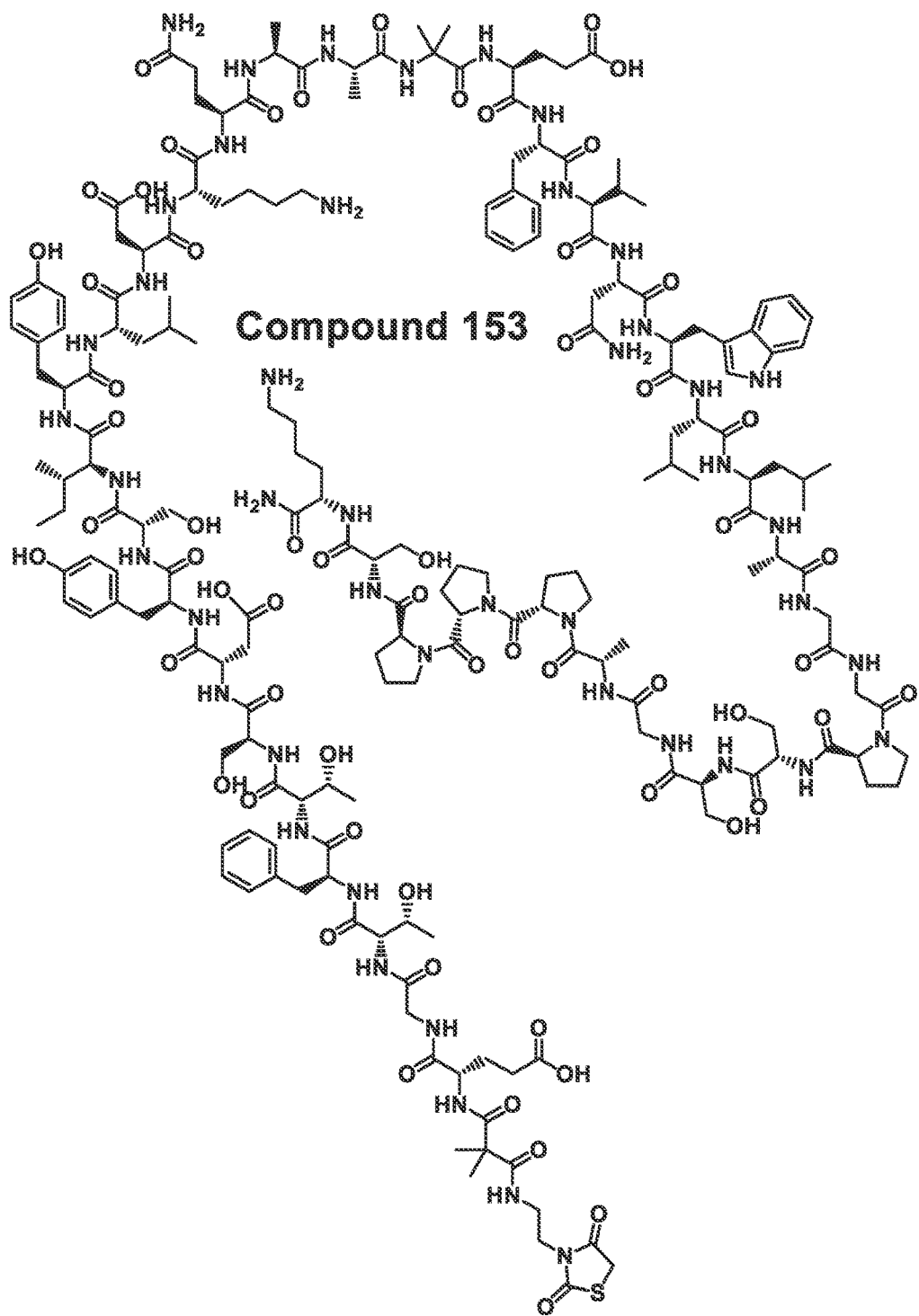
Compound 153
Cont'd

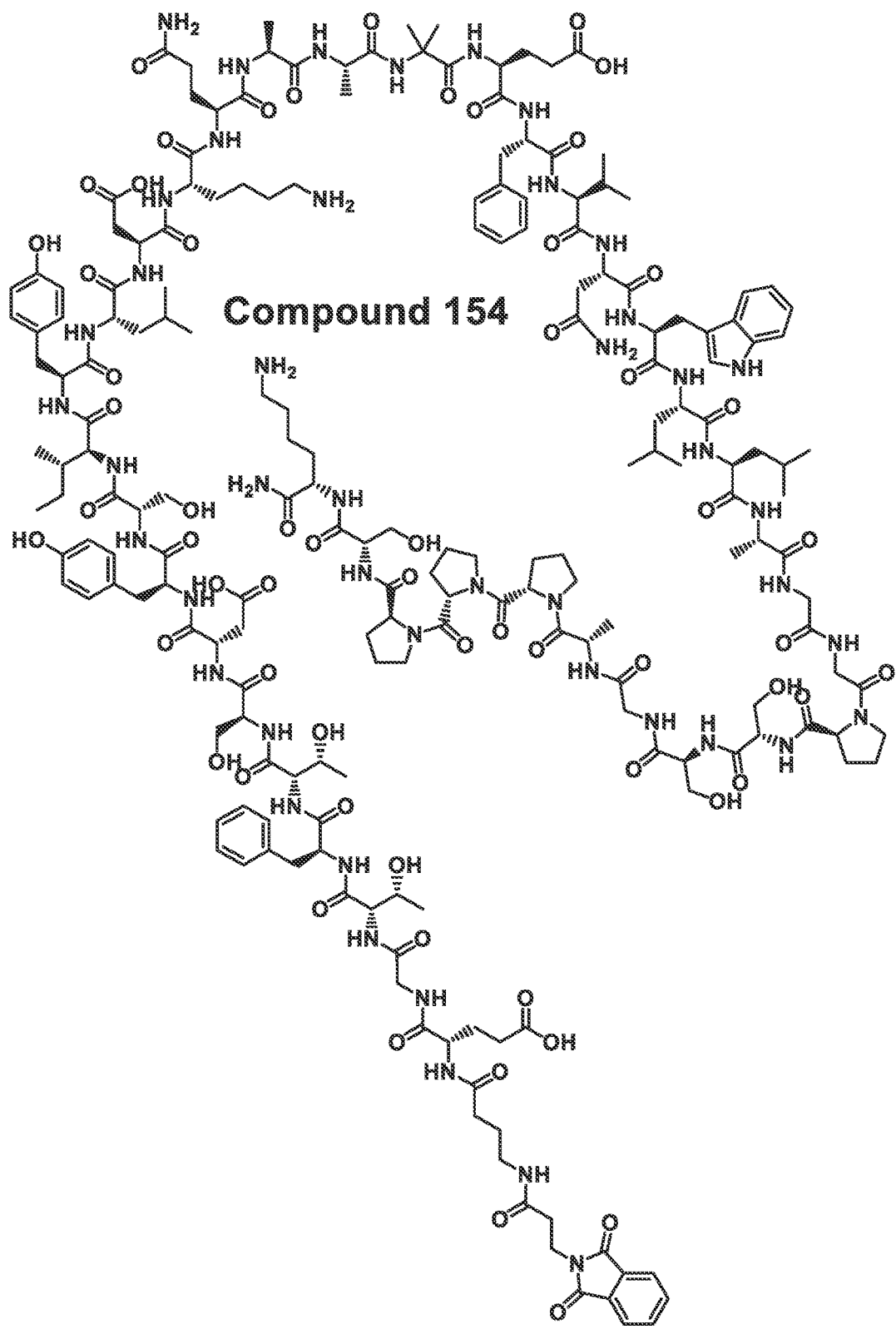
Compound 154
Cont'd

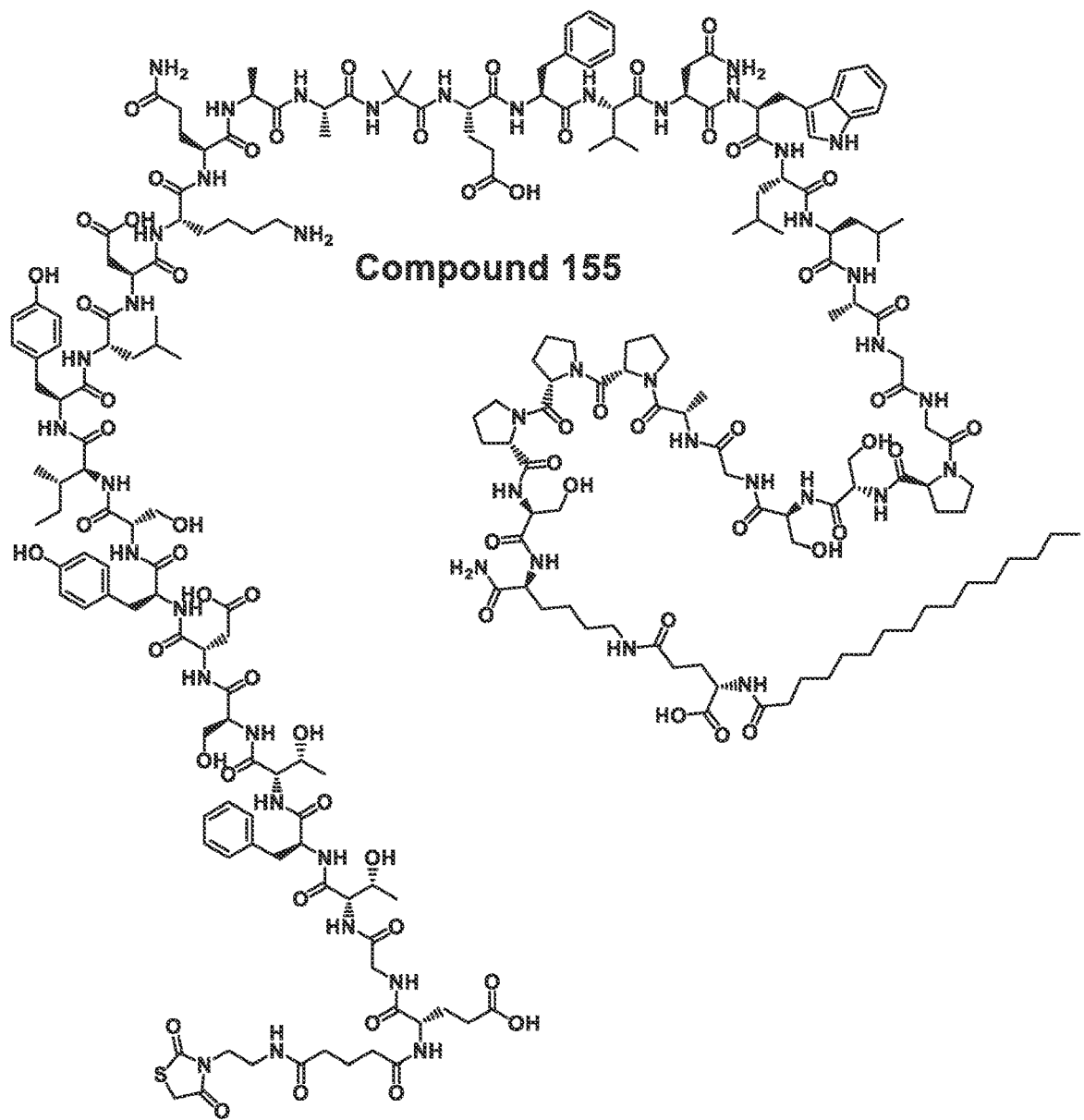
Compound 155
Cont'd

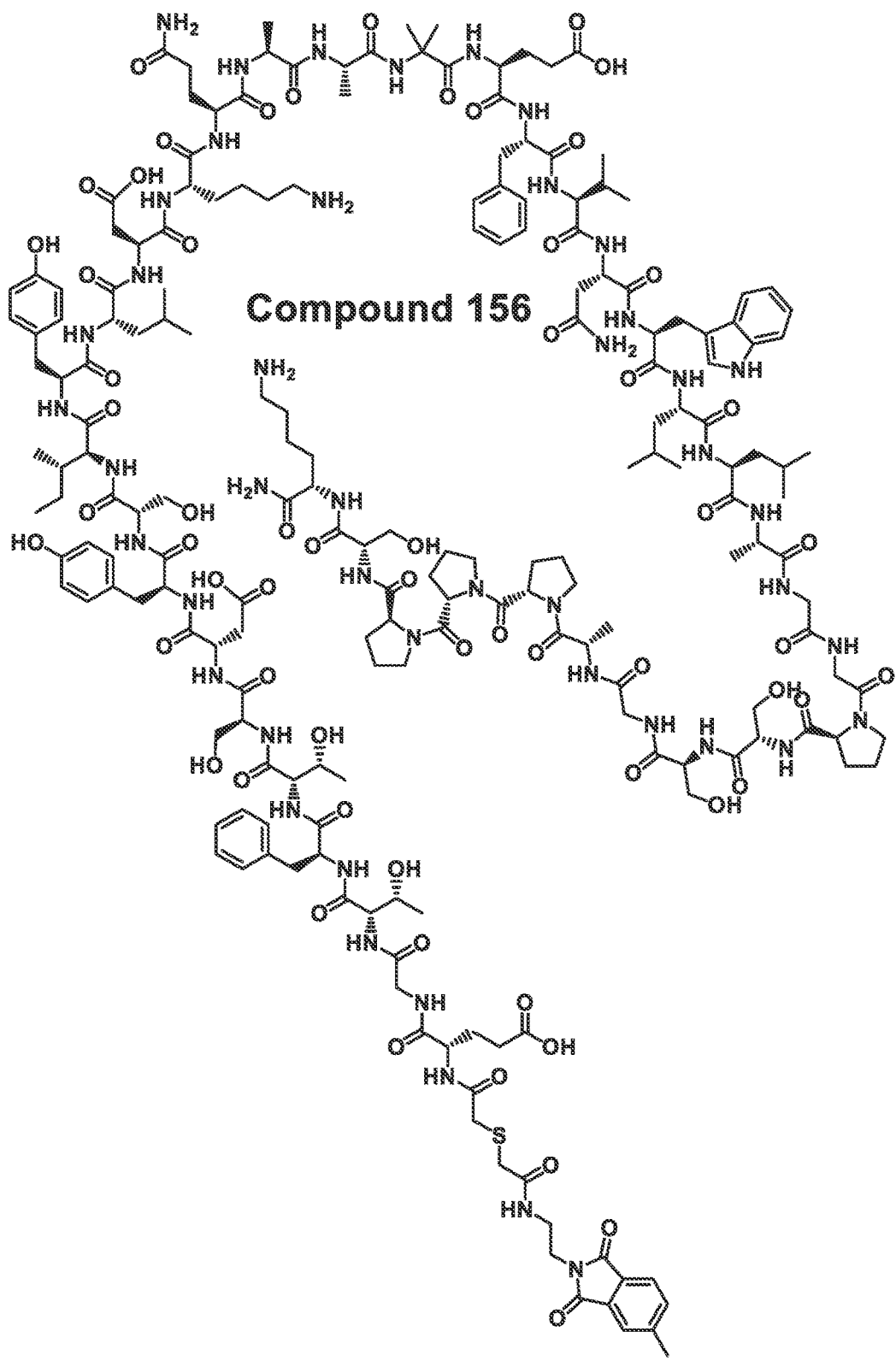
Compound 156
Cont'd

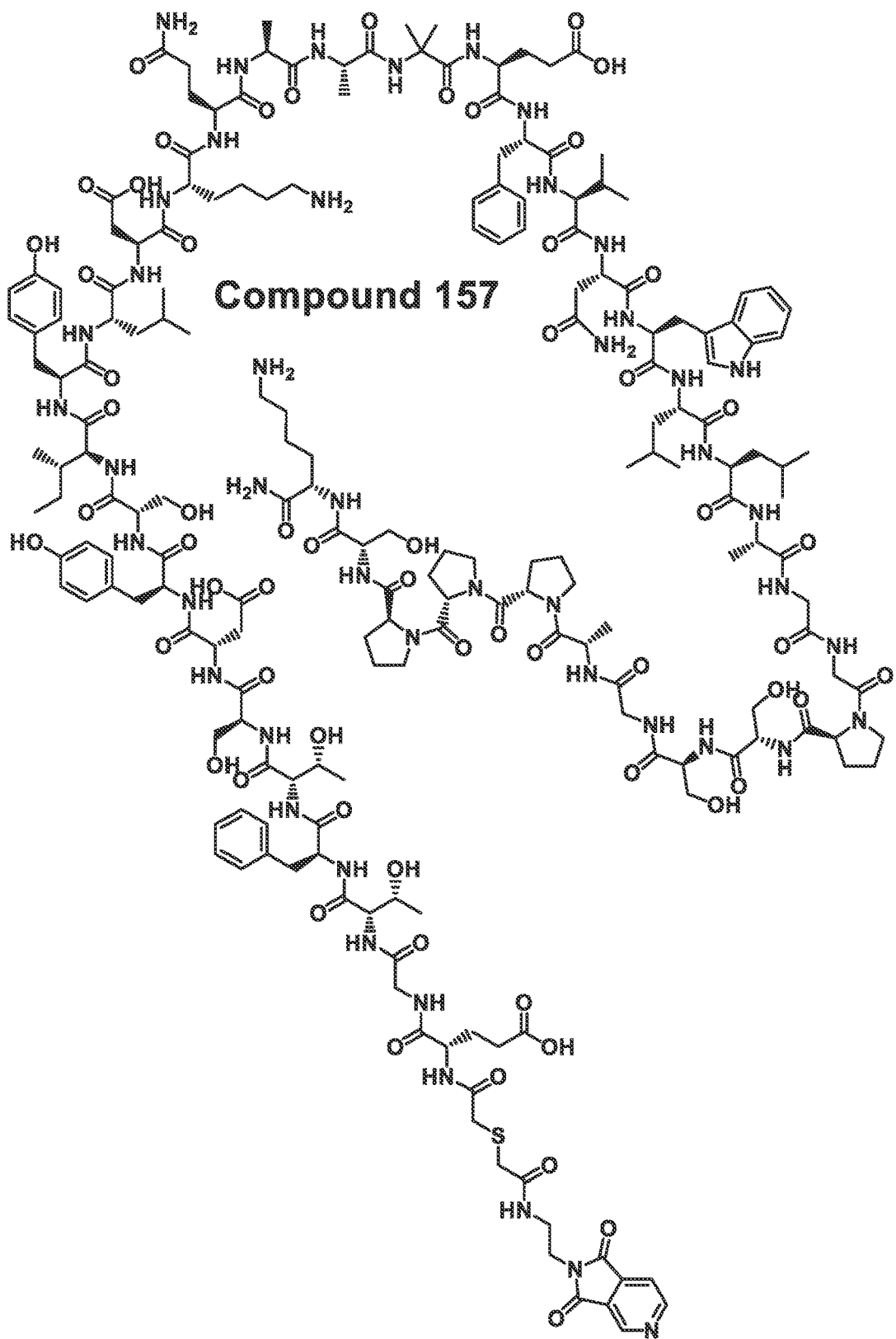
Compound 157
Cont'd

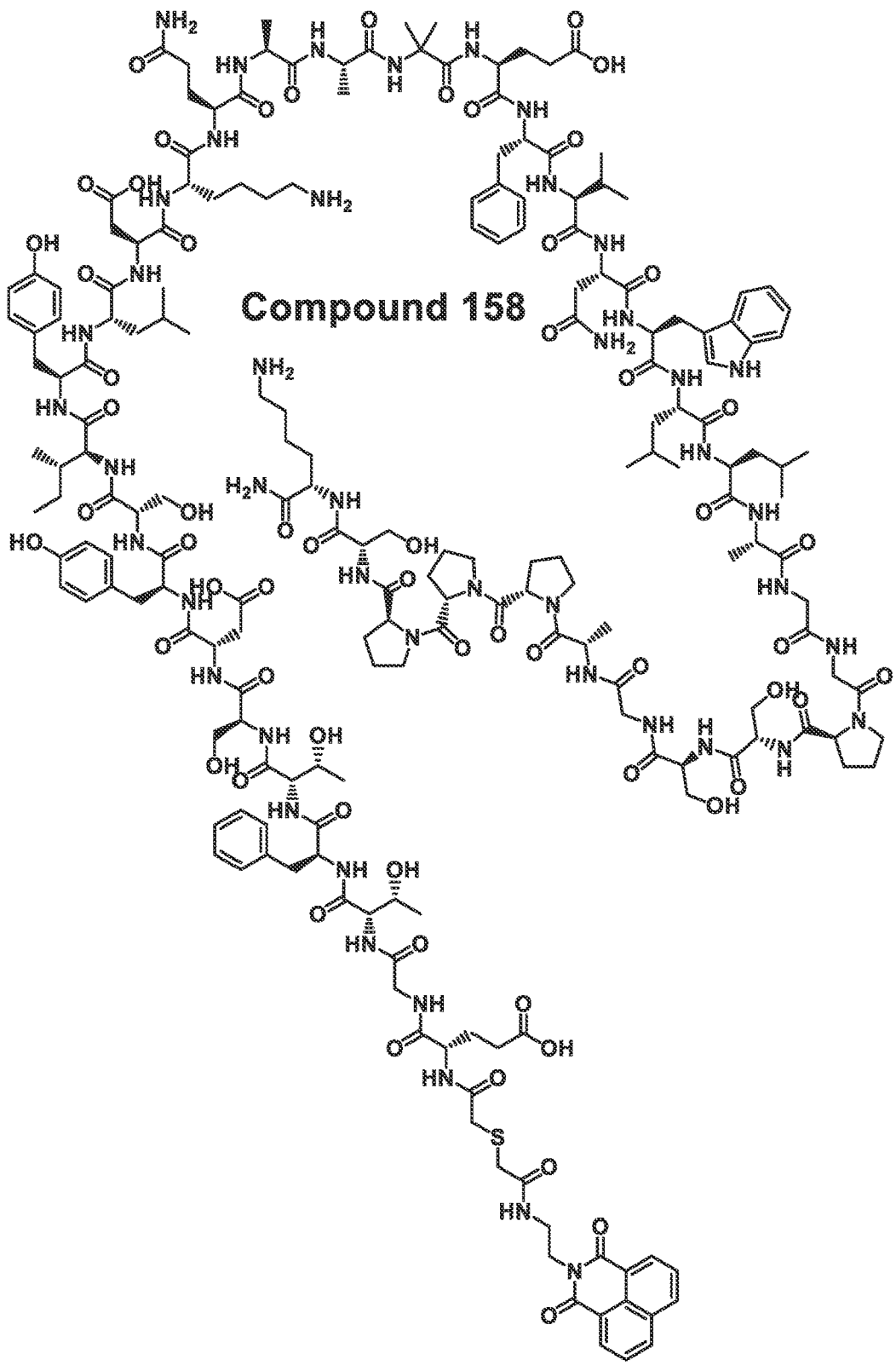
Compound 158
Cont'd

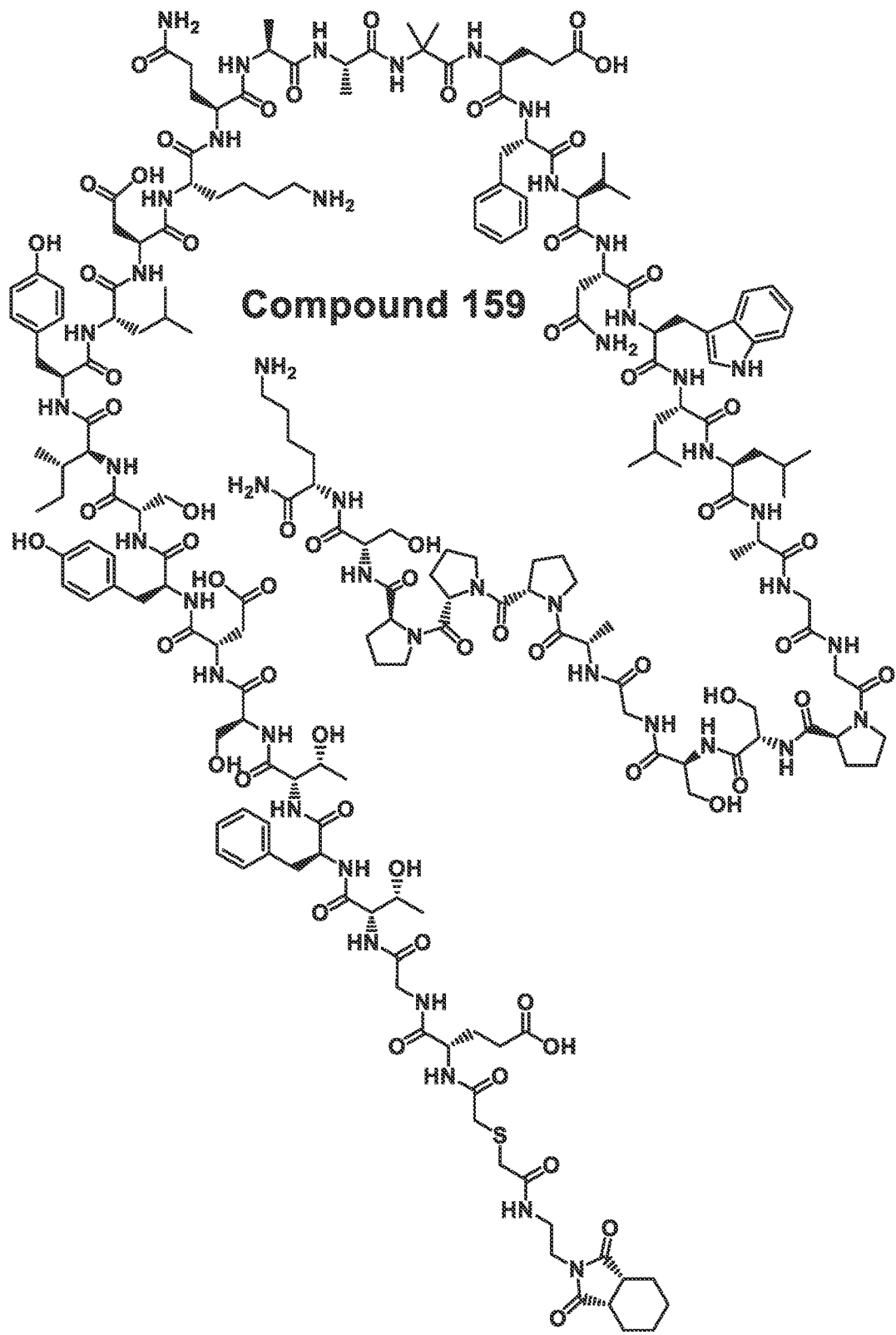
Compound 159
Cont'd

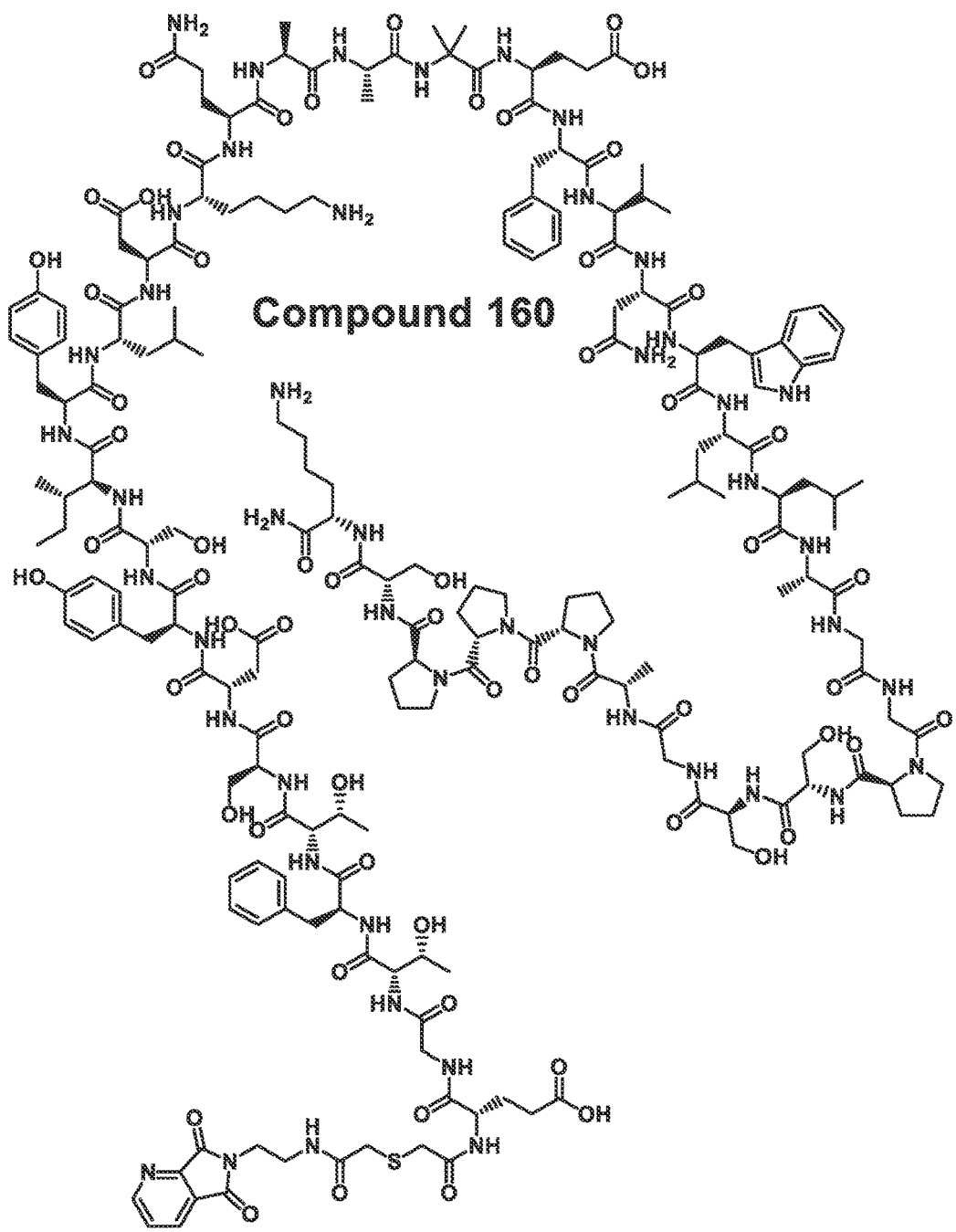
Compound 160
Cont'd

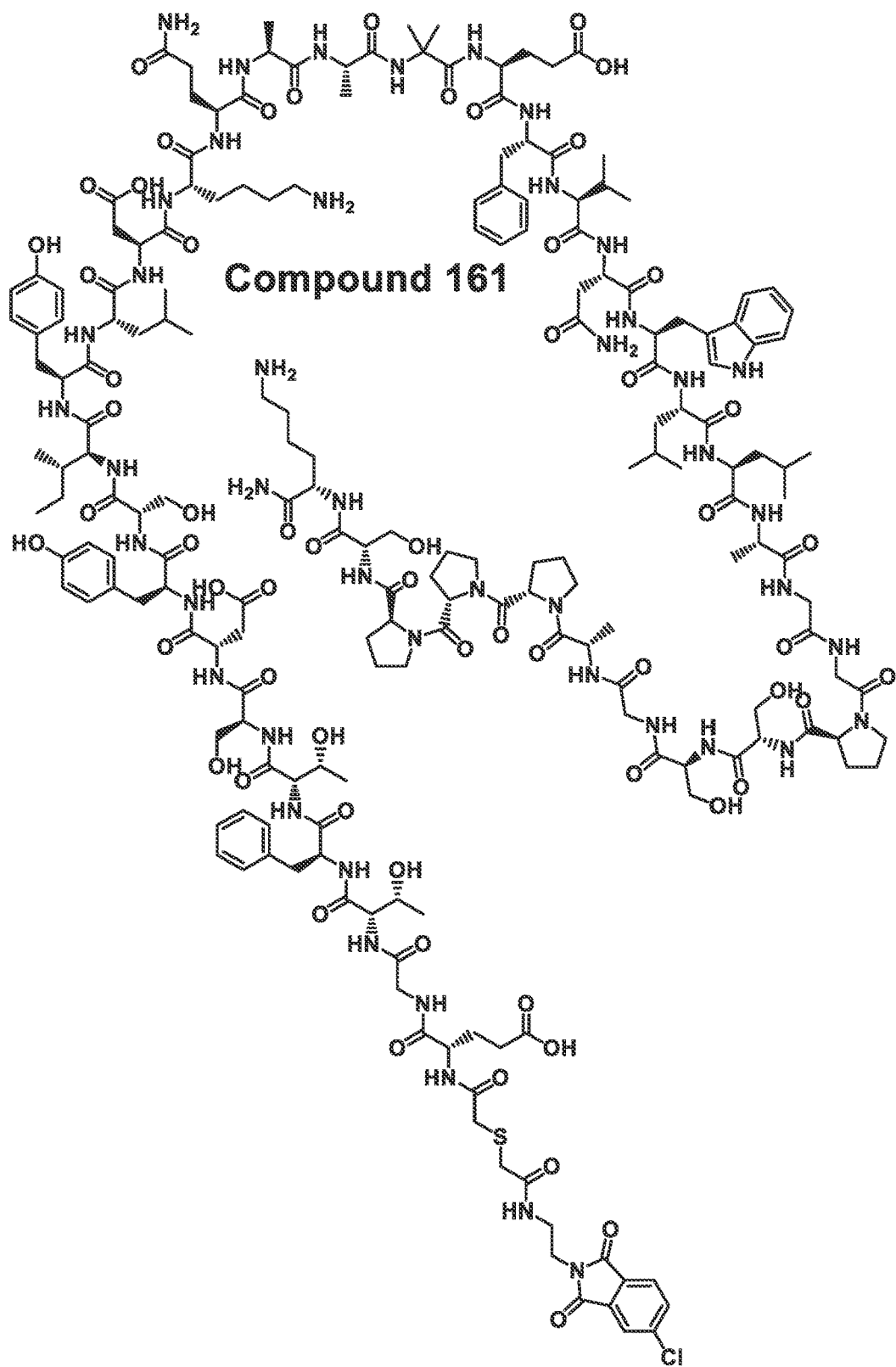
Compound 161
Cont'd

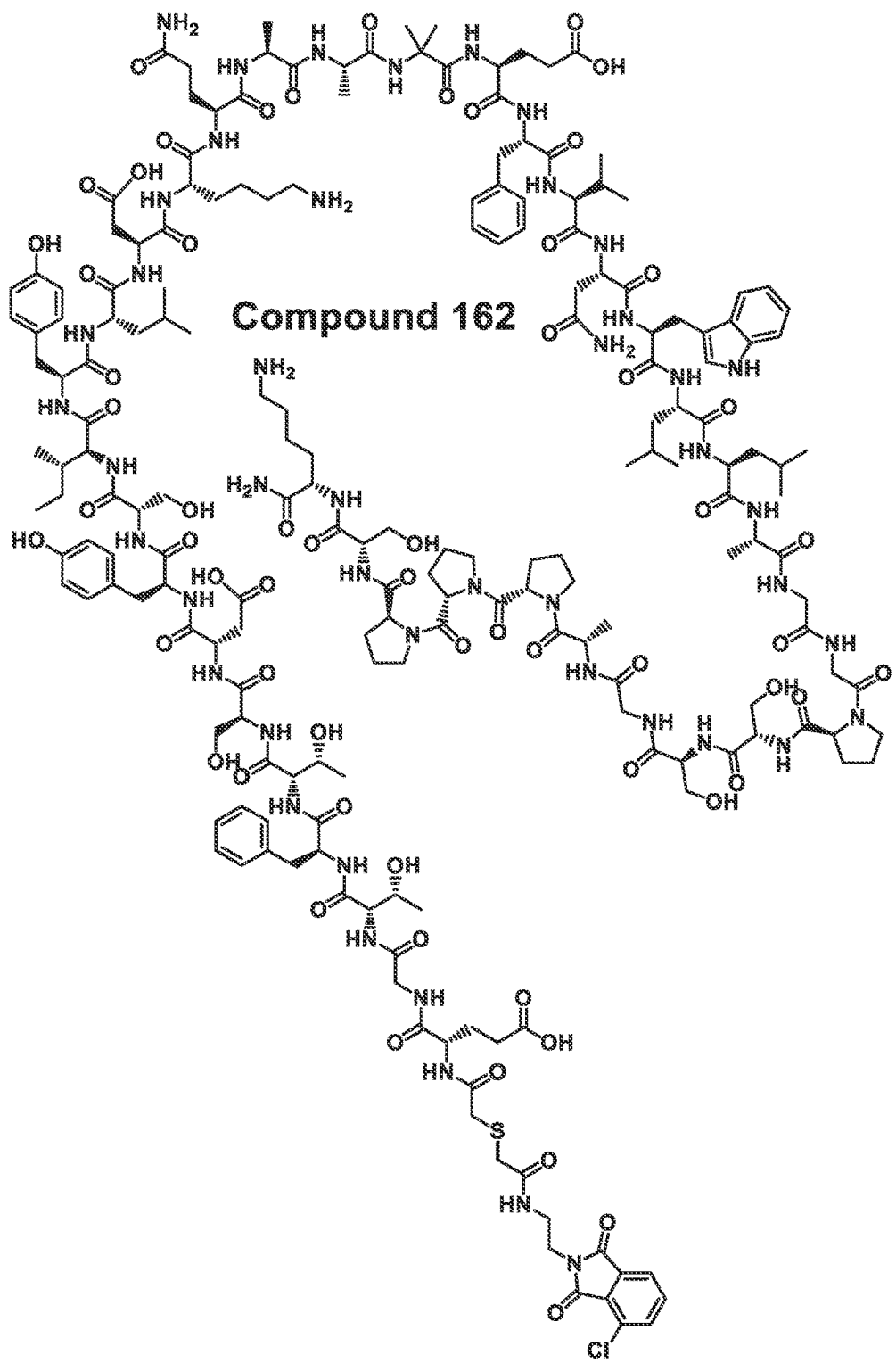
Compound 162
Cont'd

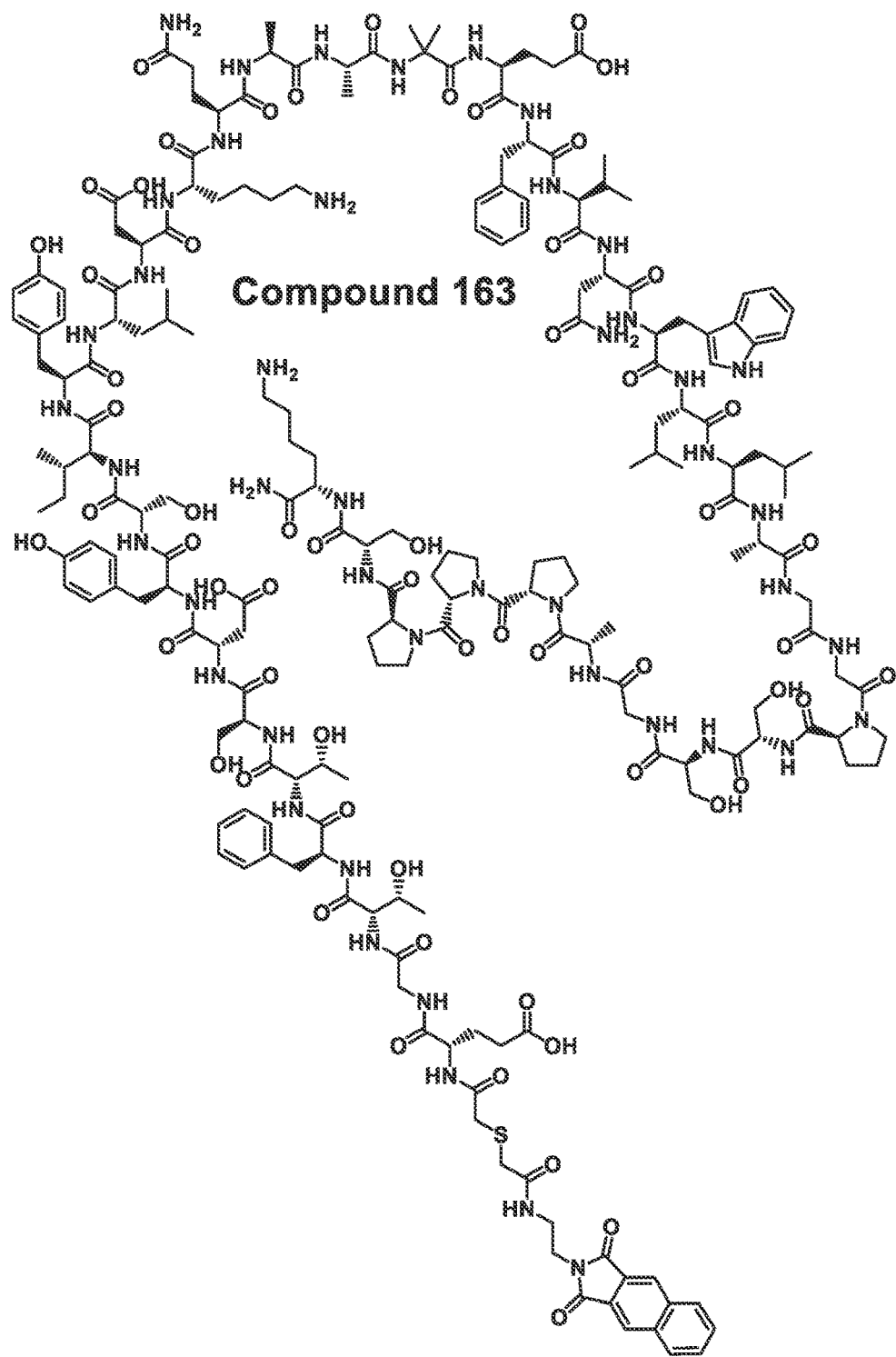
Compound 163
Cont'd

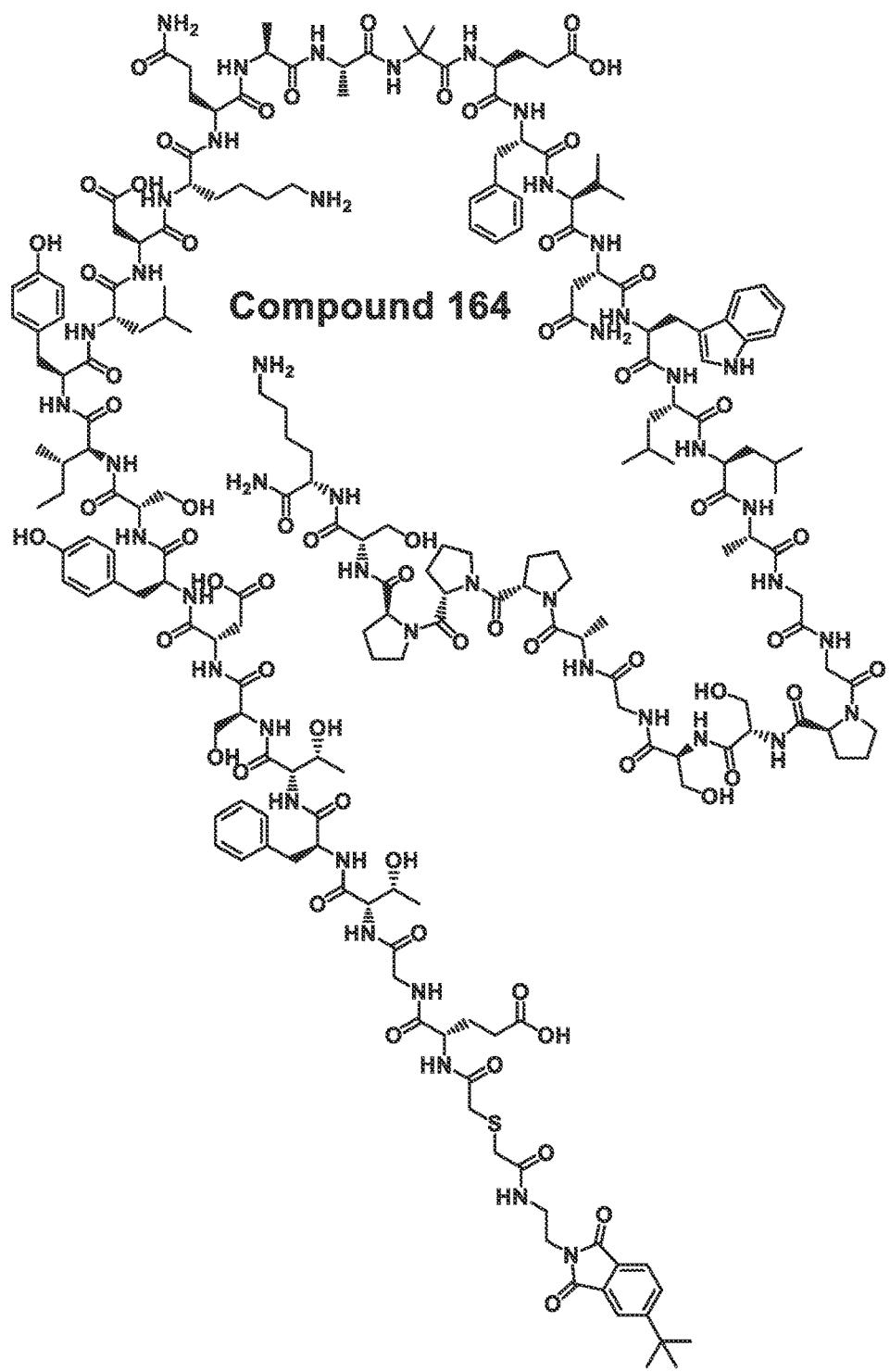
Cont'd

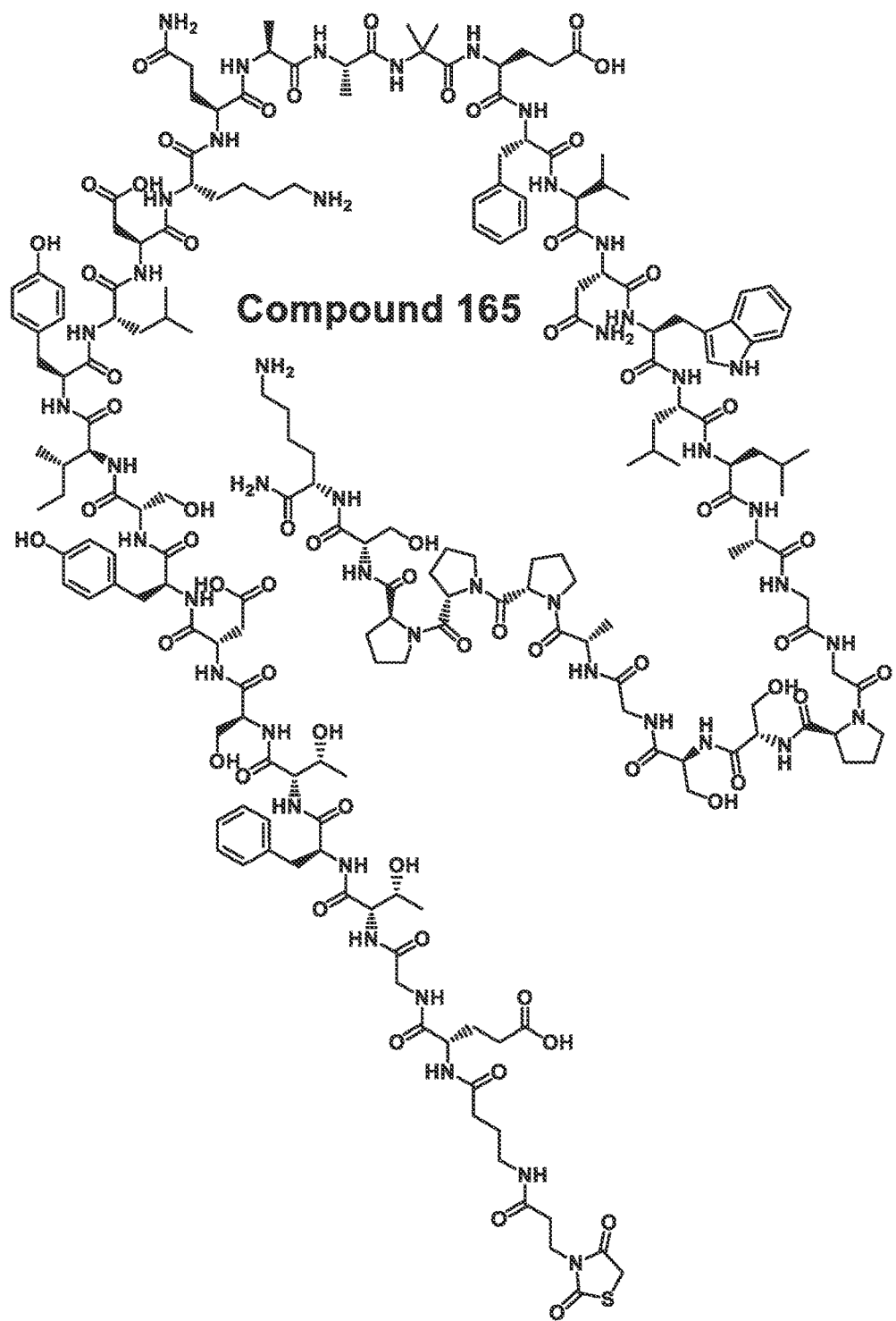
Compound 165
Cont'd

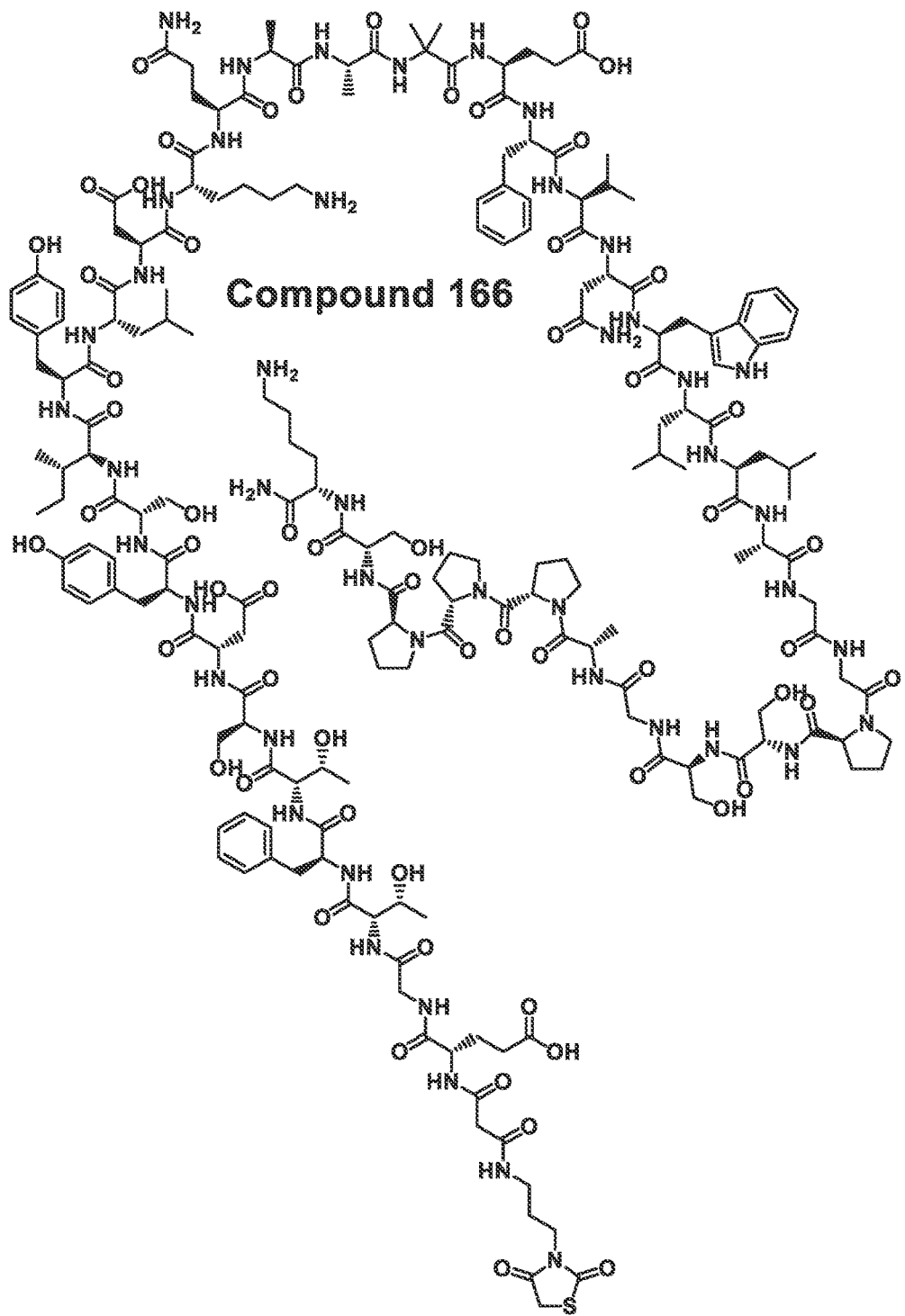
Compound 166
Cont'd

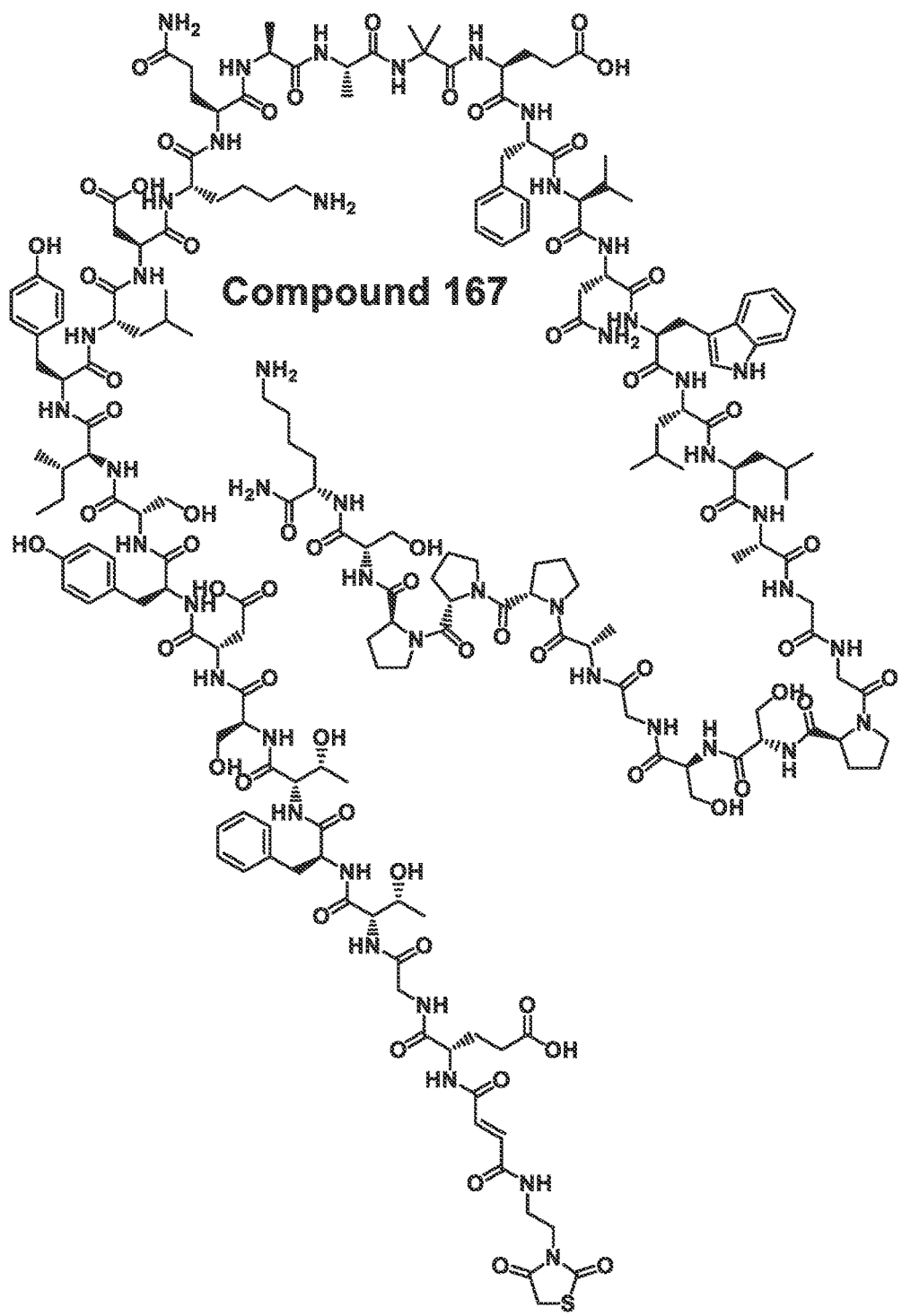
Compound 167
Cont'd

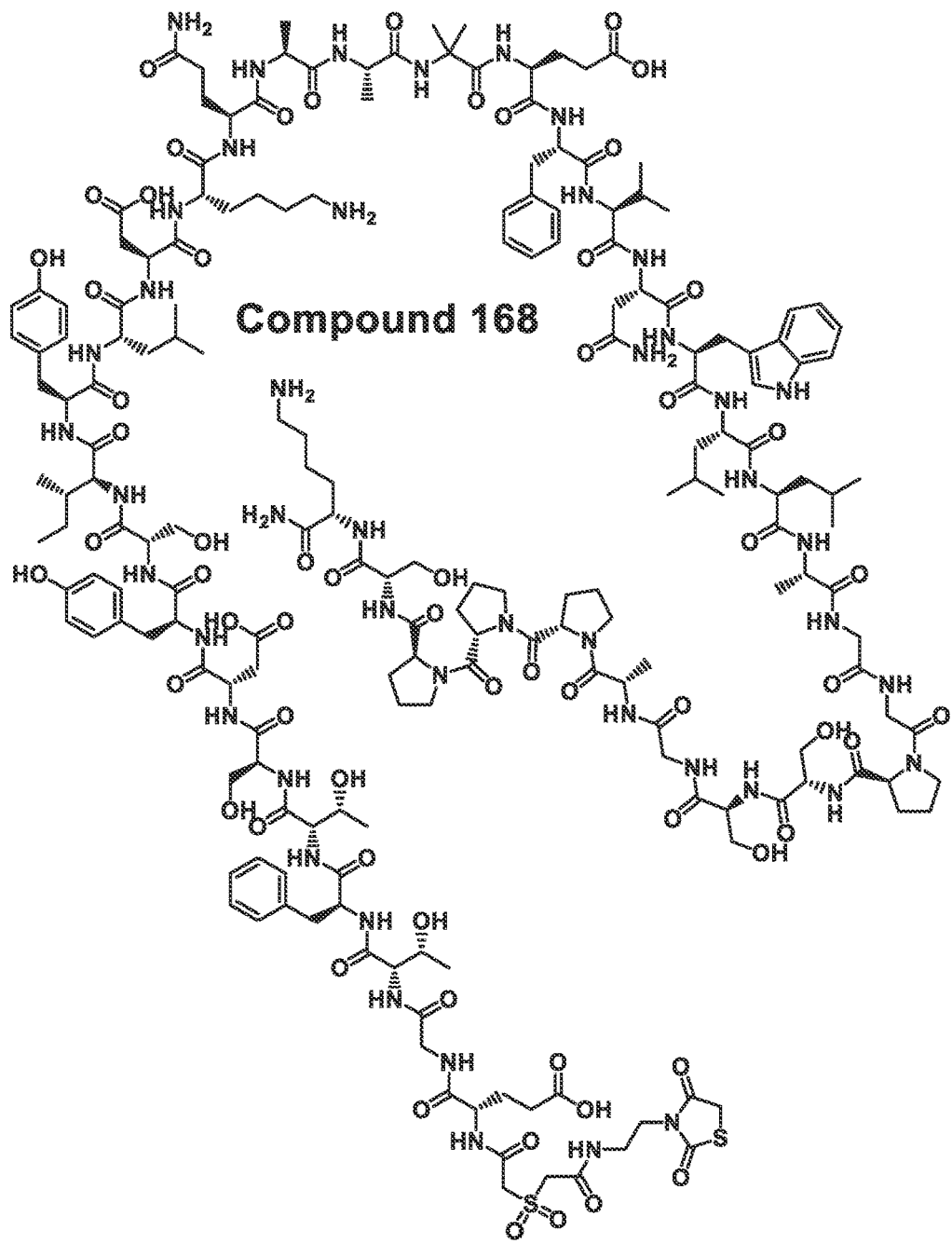
Cont'd

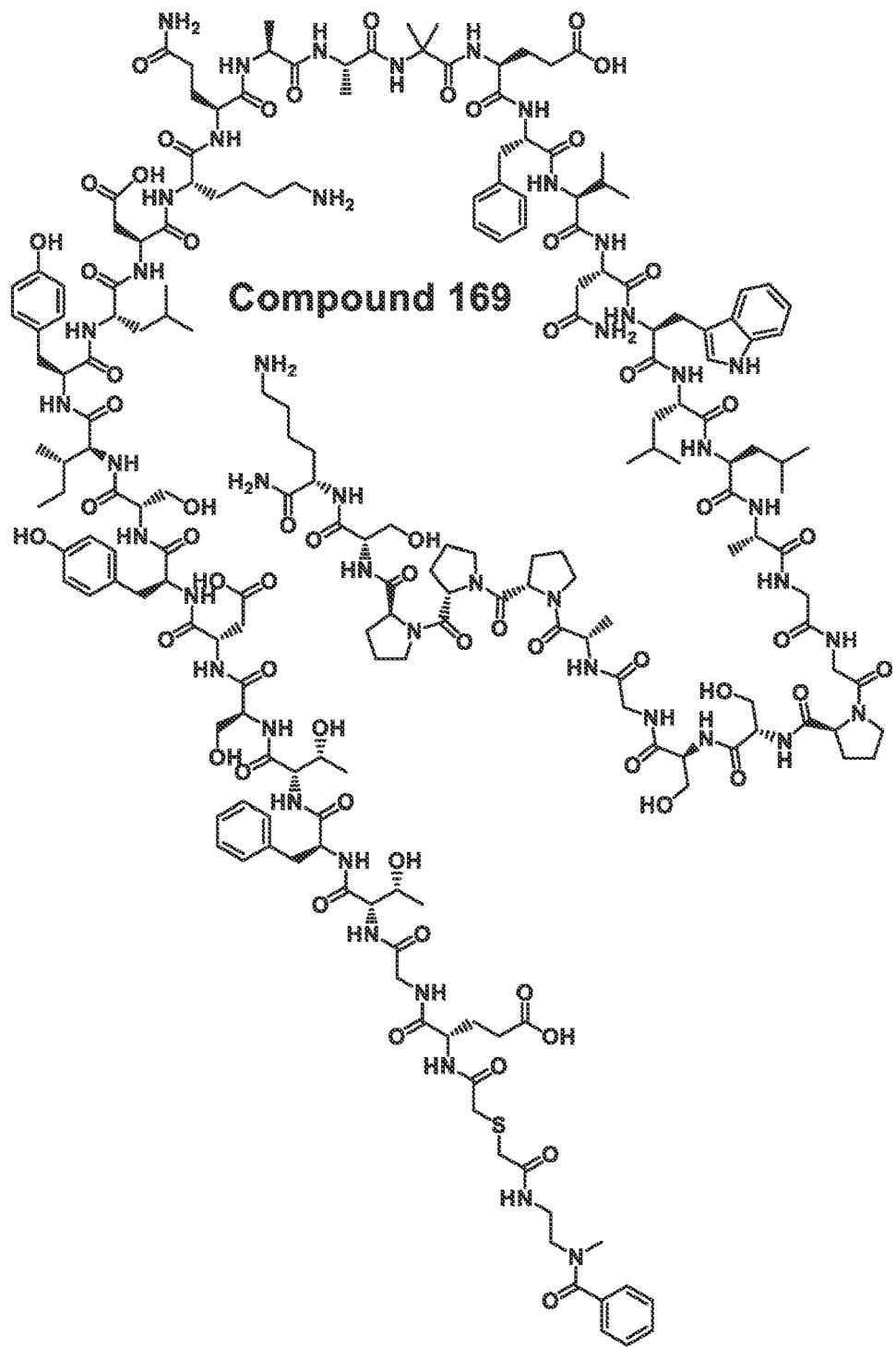
Compound 169
Cont'd

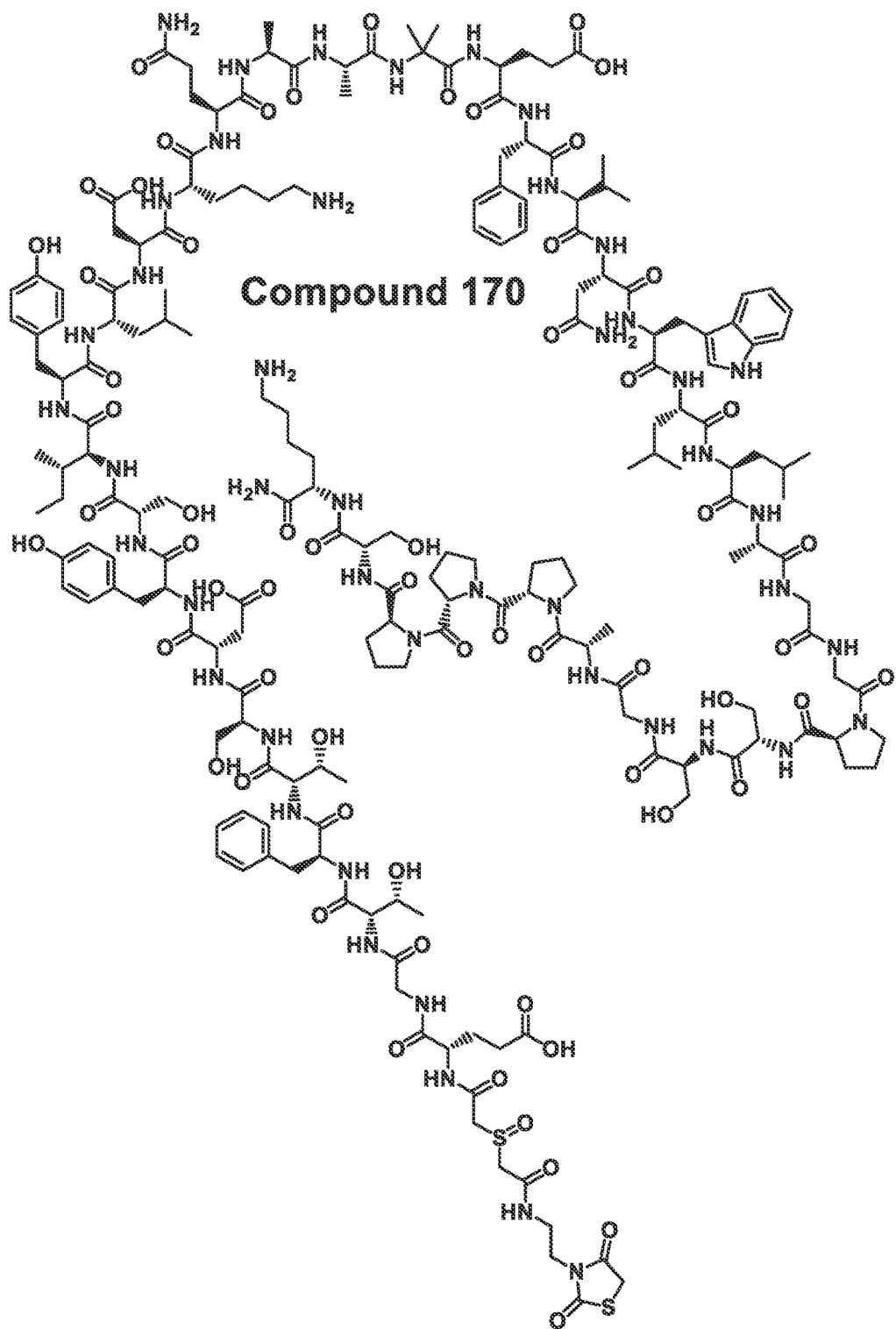
Compound 170
Cont'd

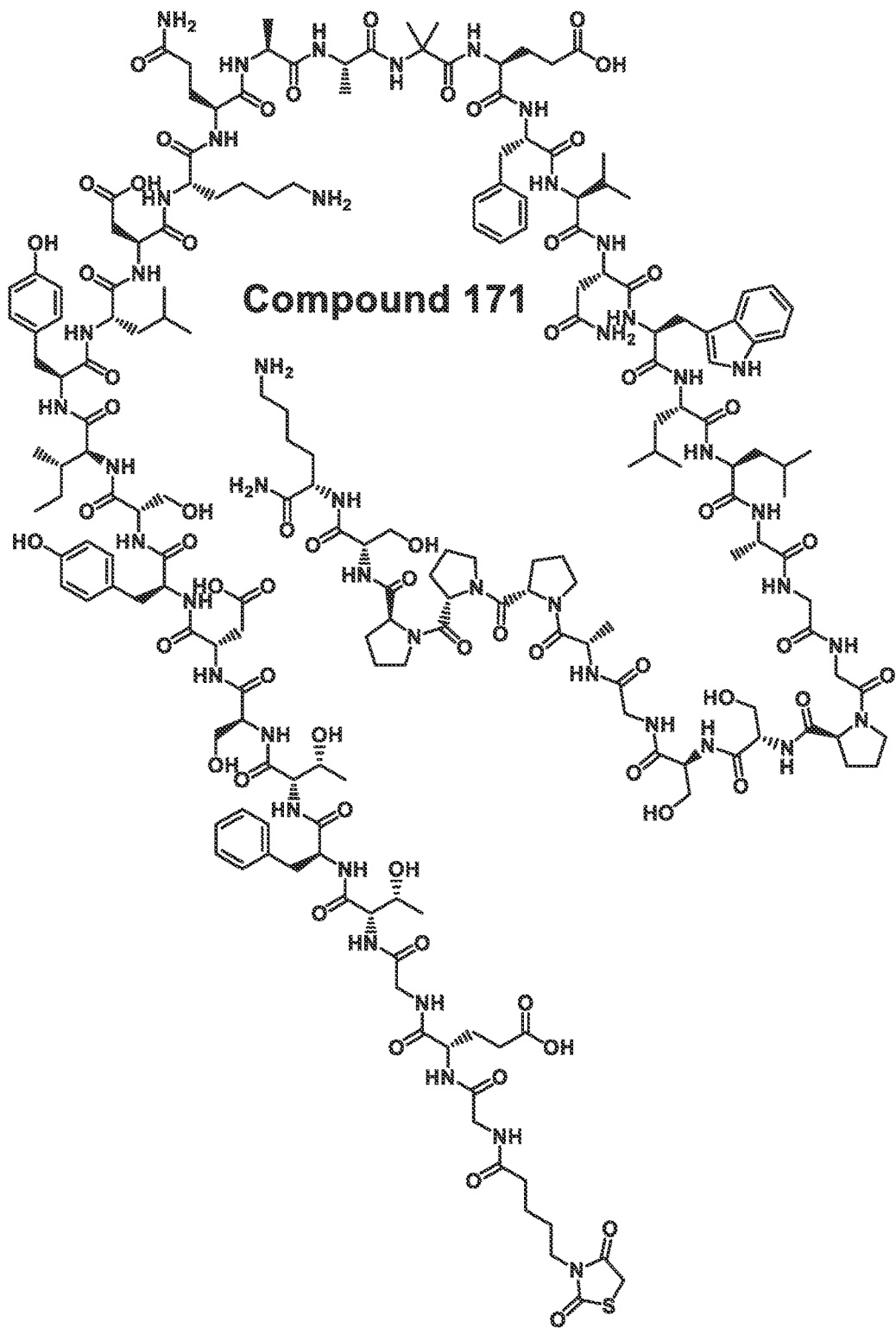
Compound 171
Cont'd

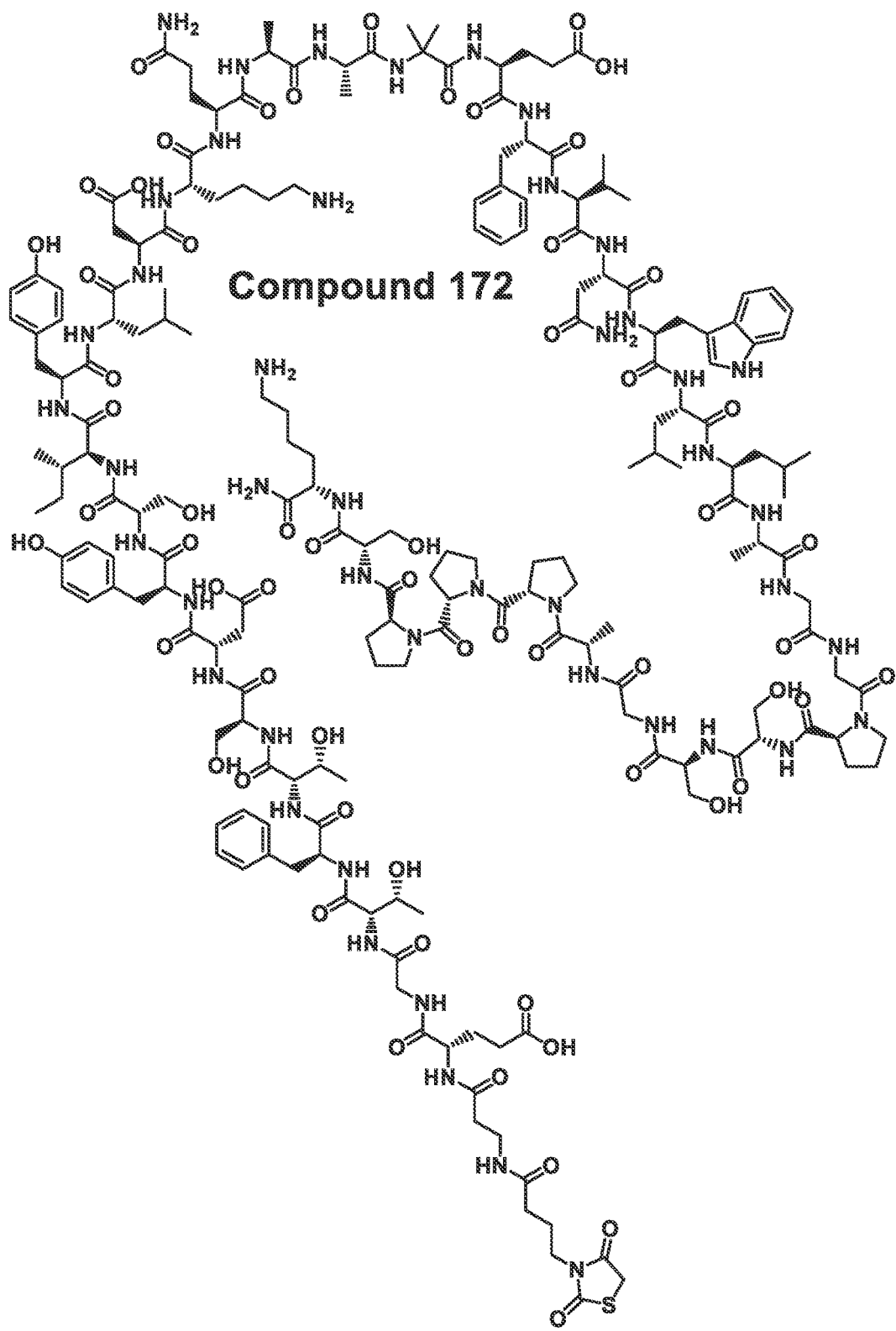
Compound 172
Cont'd

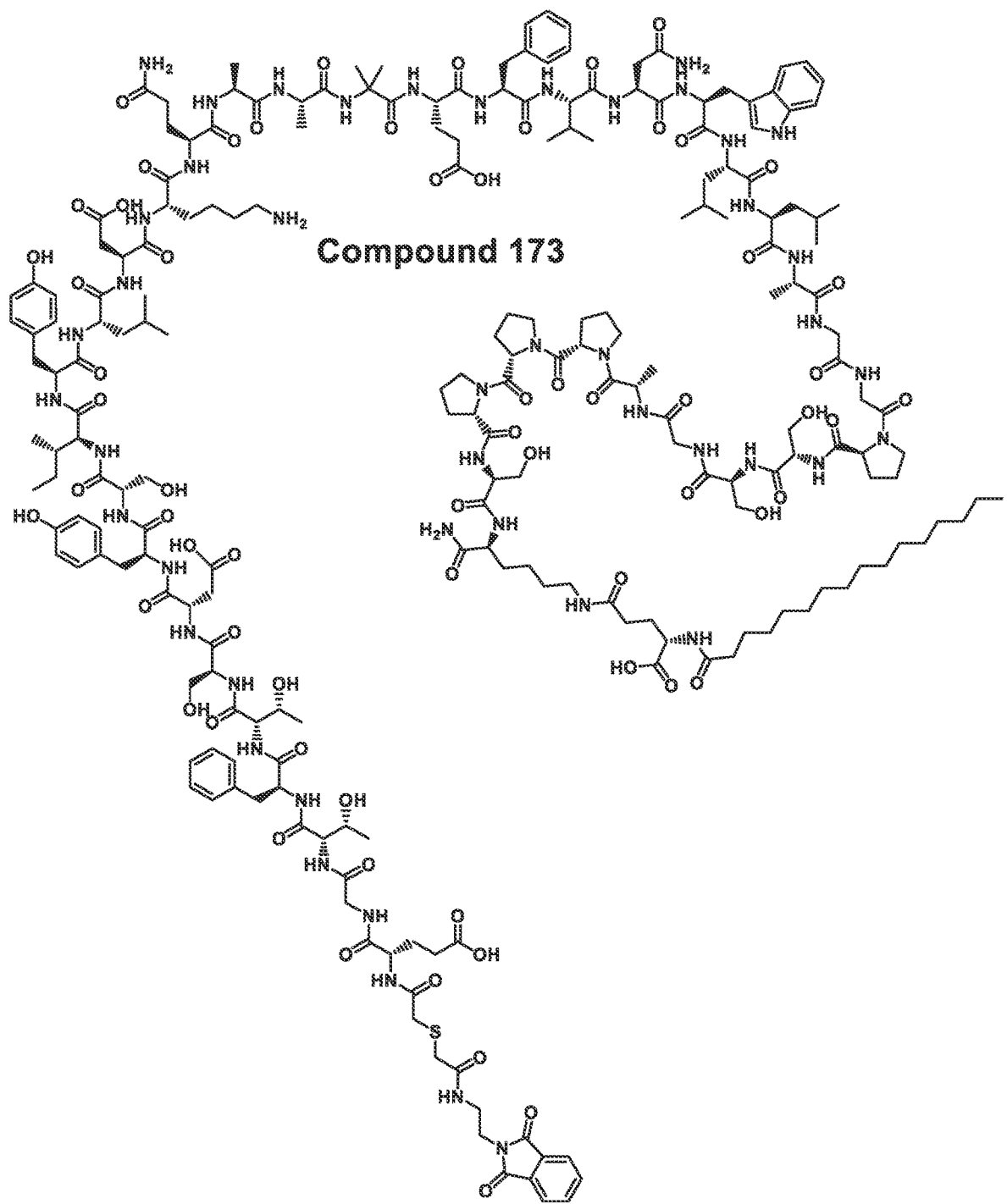
Compound 173
Cont'd

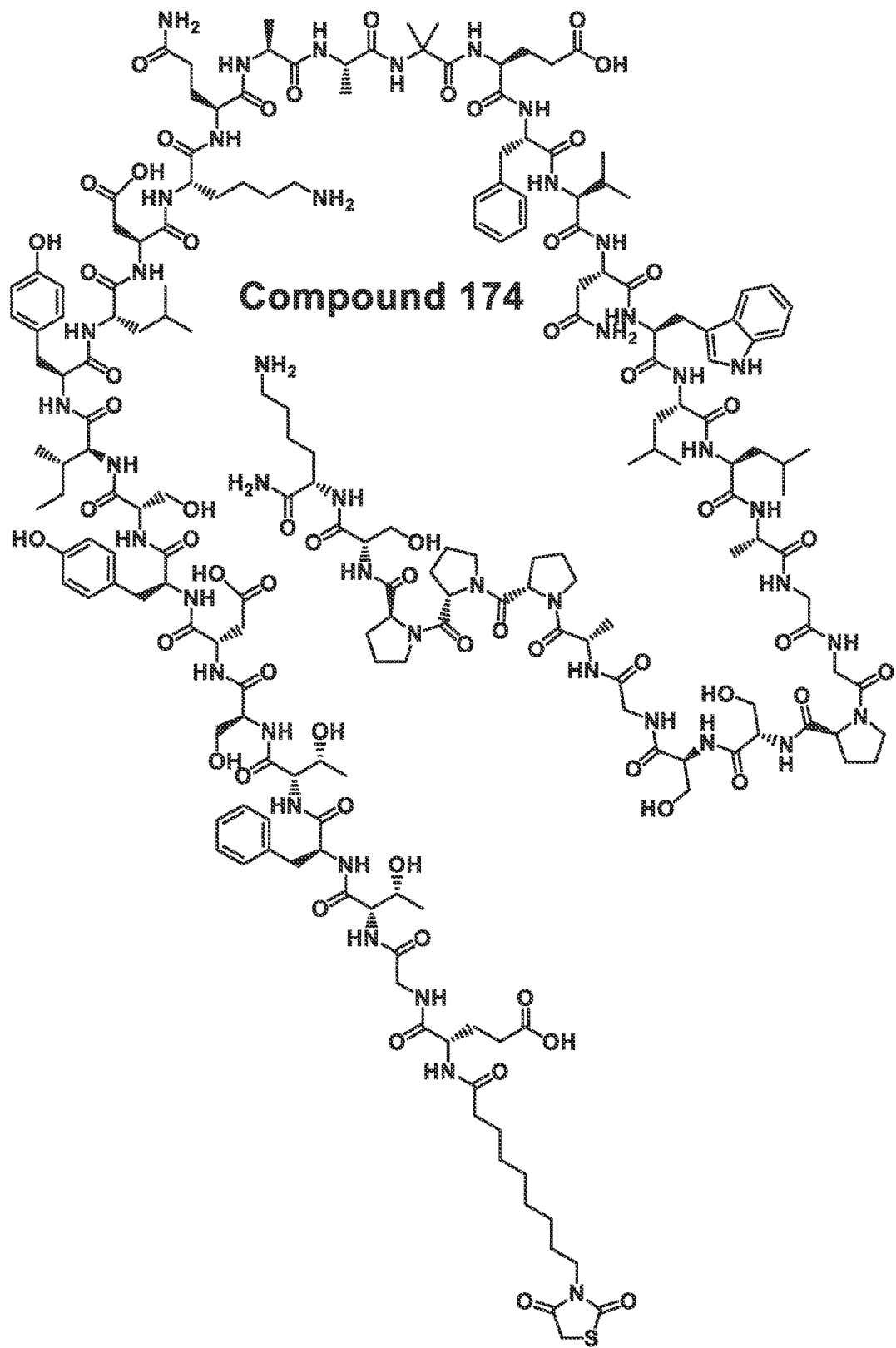
Compound 174
Cont'd

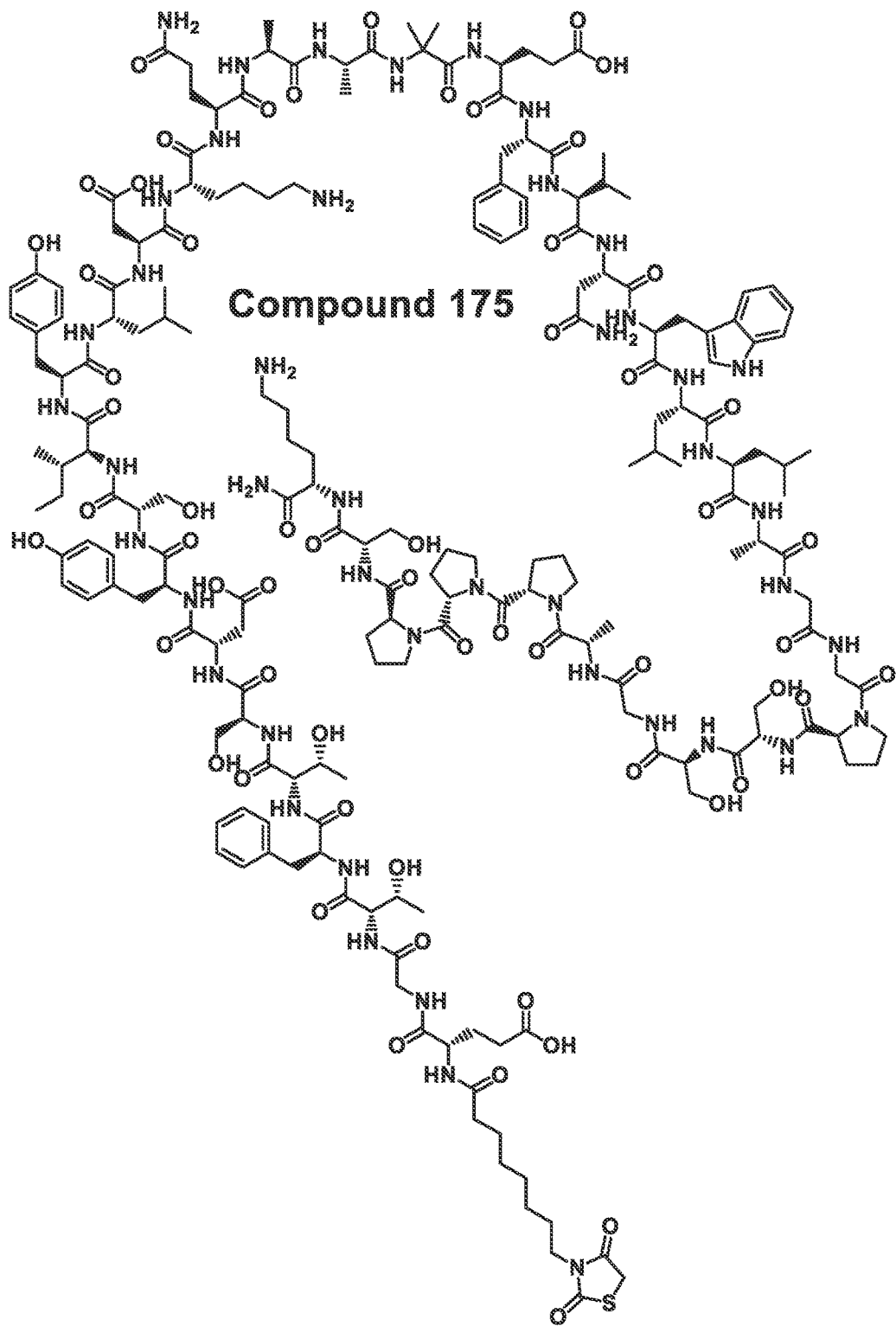
Compound 175
Cont'd

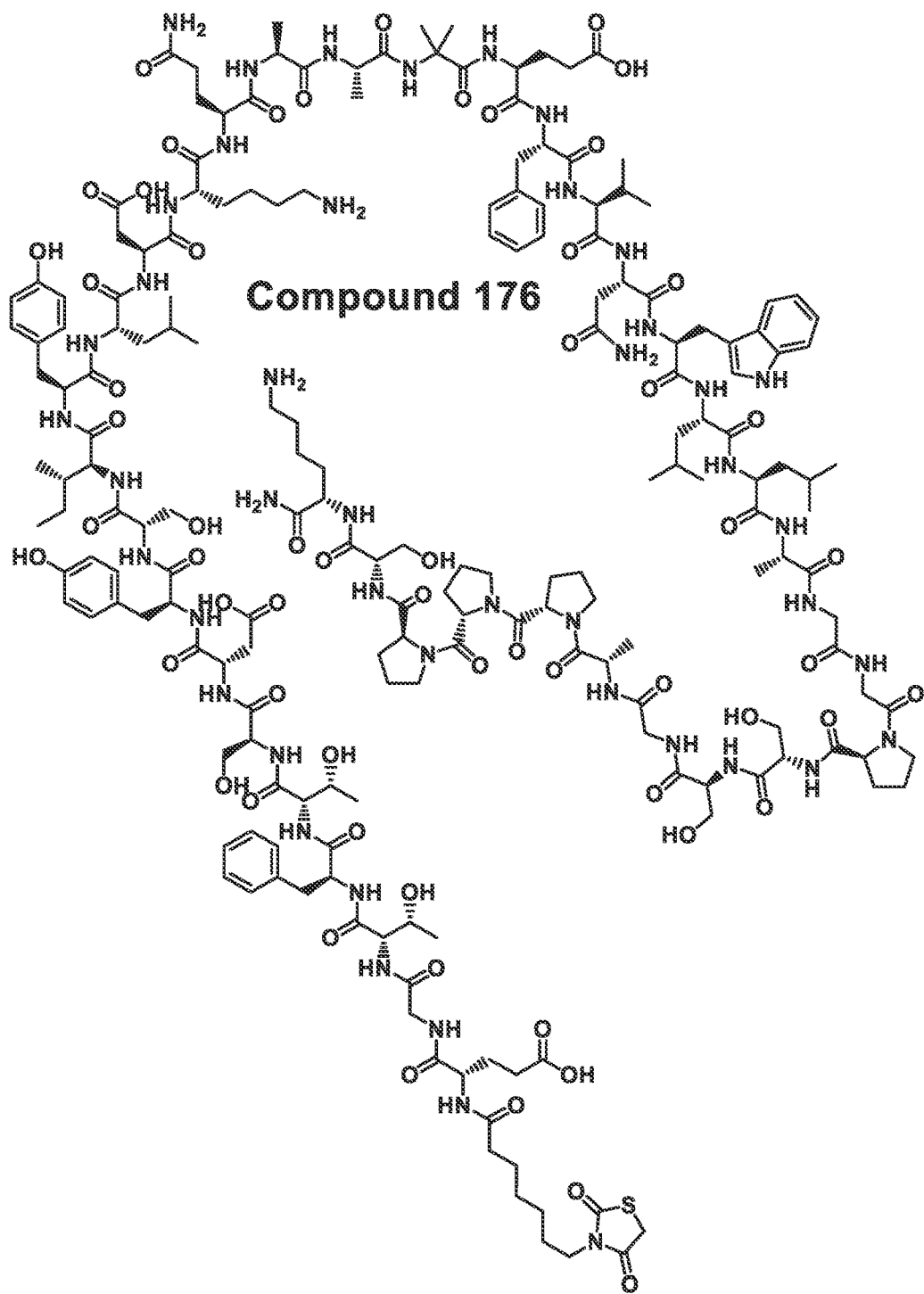
Compound 176
Cont'd

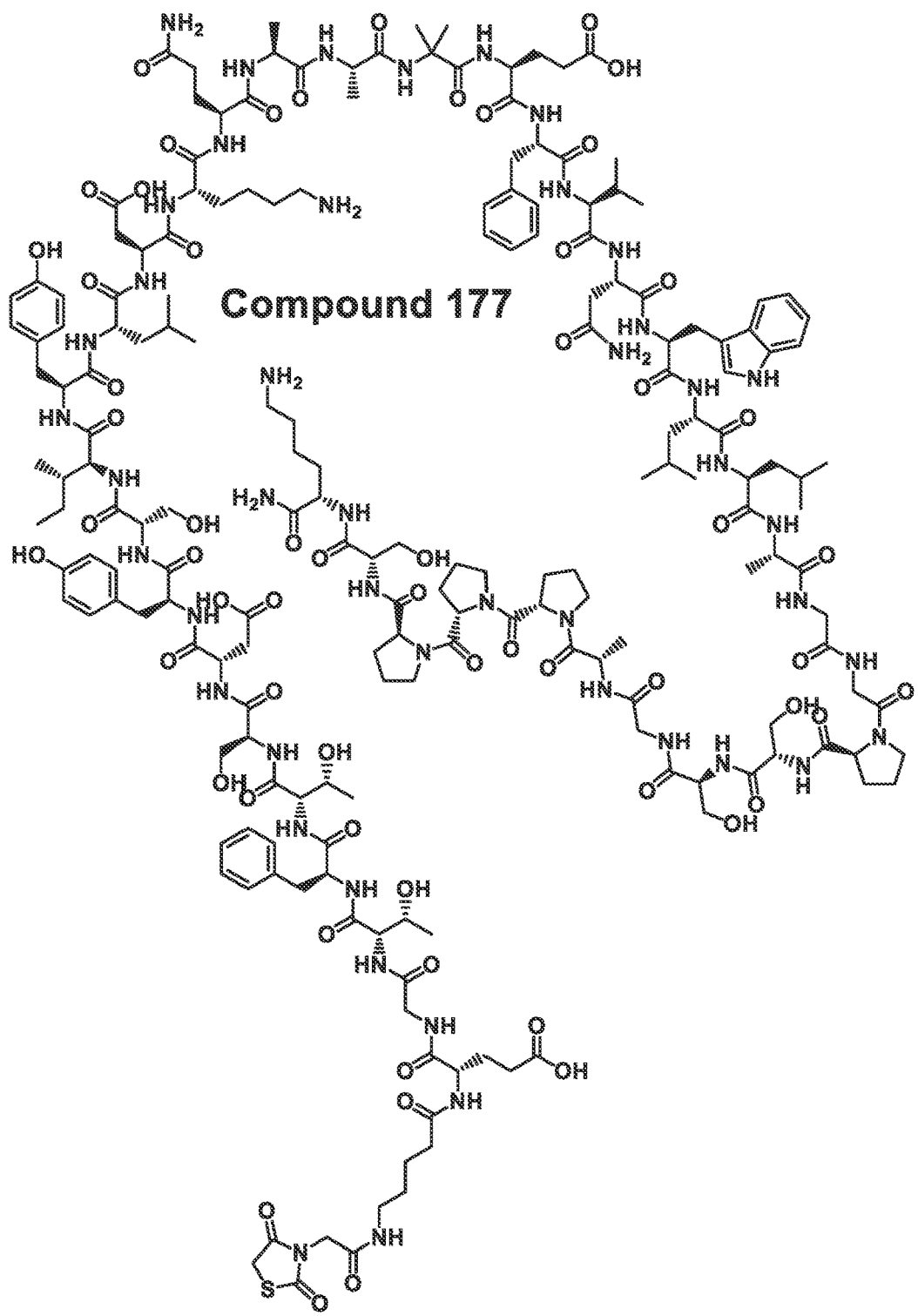

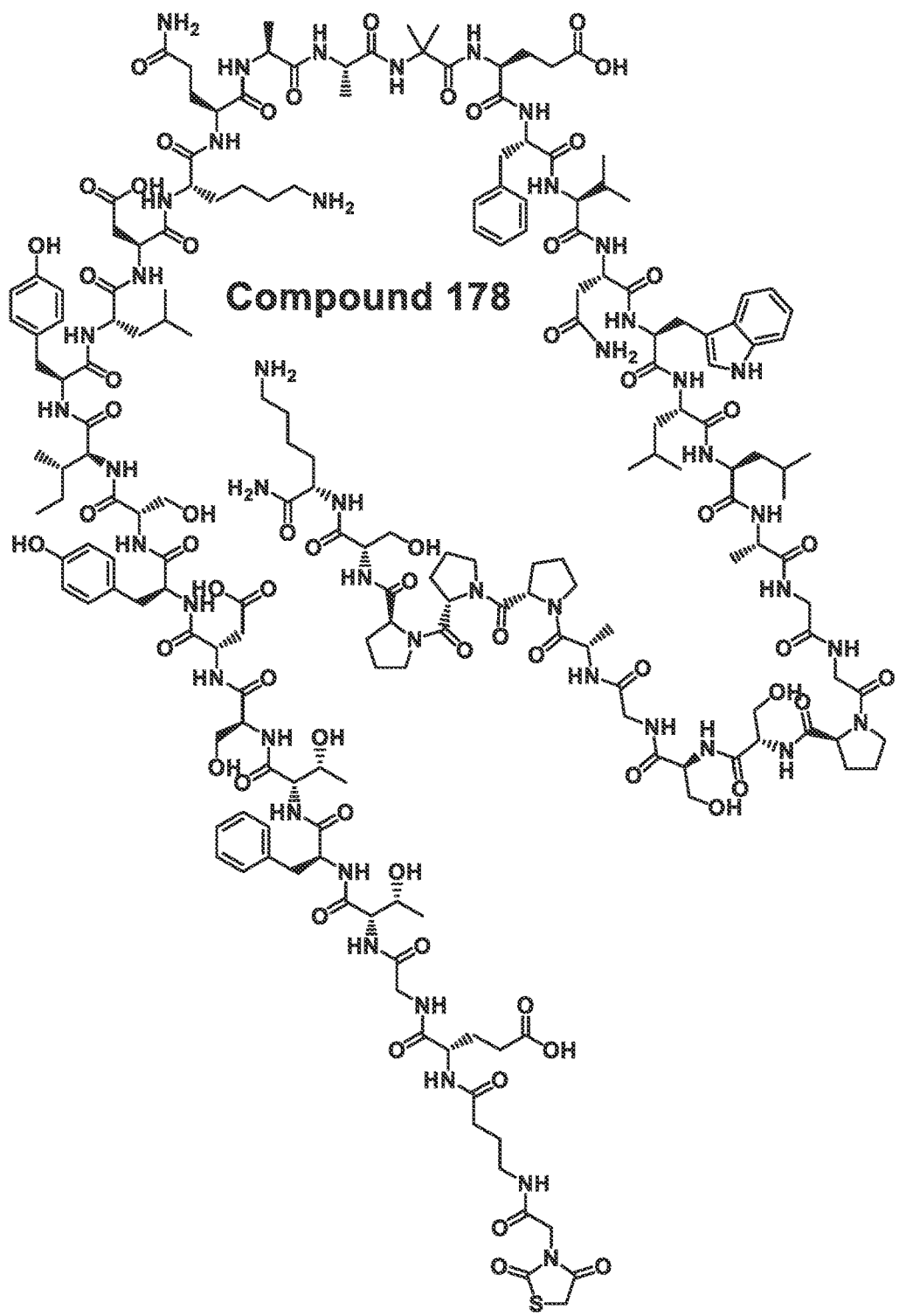
Compound 178
Cont'd

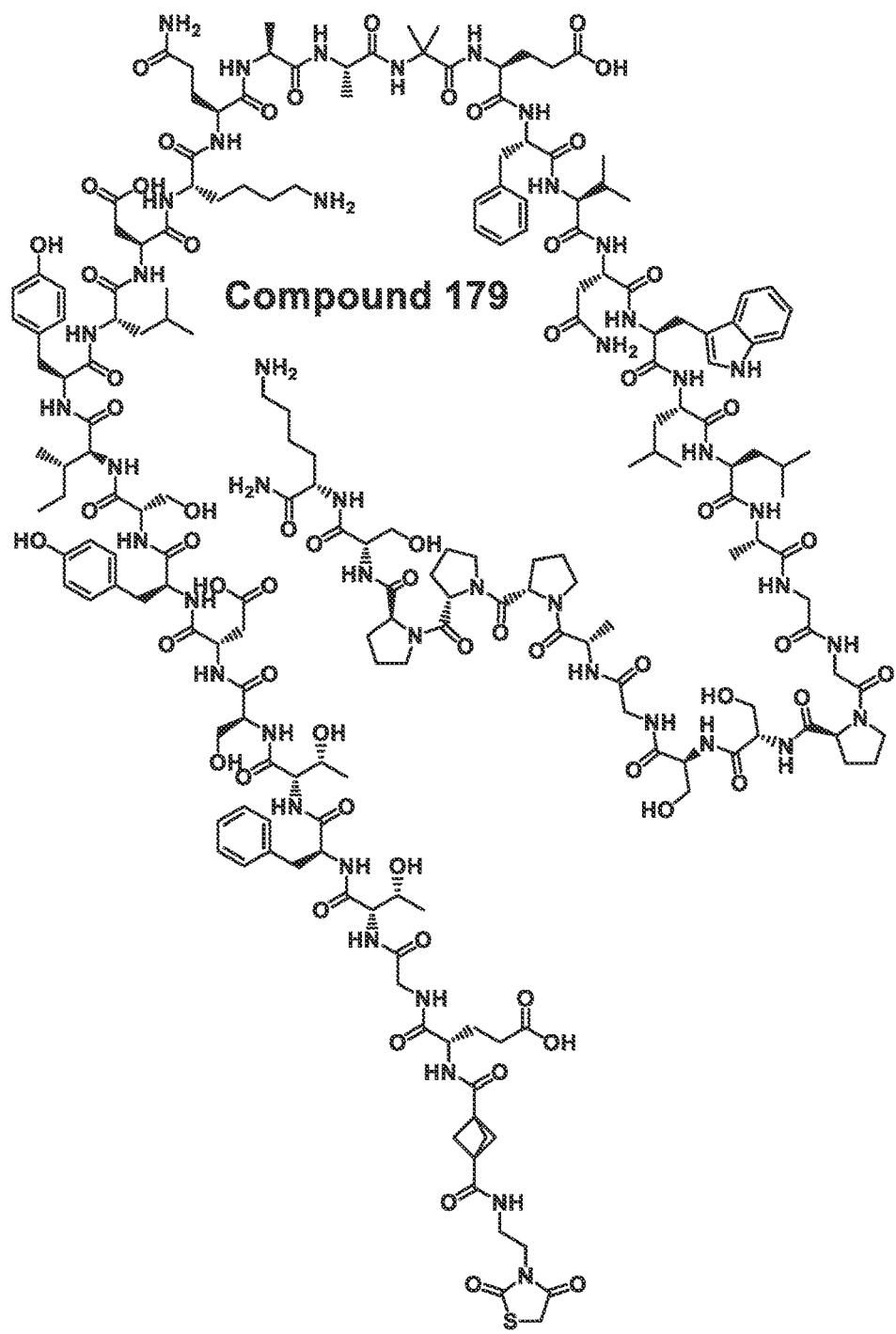

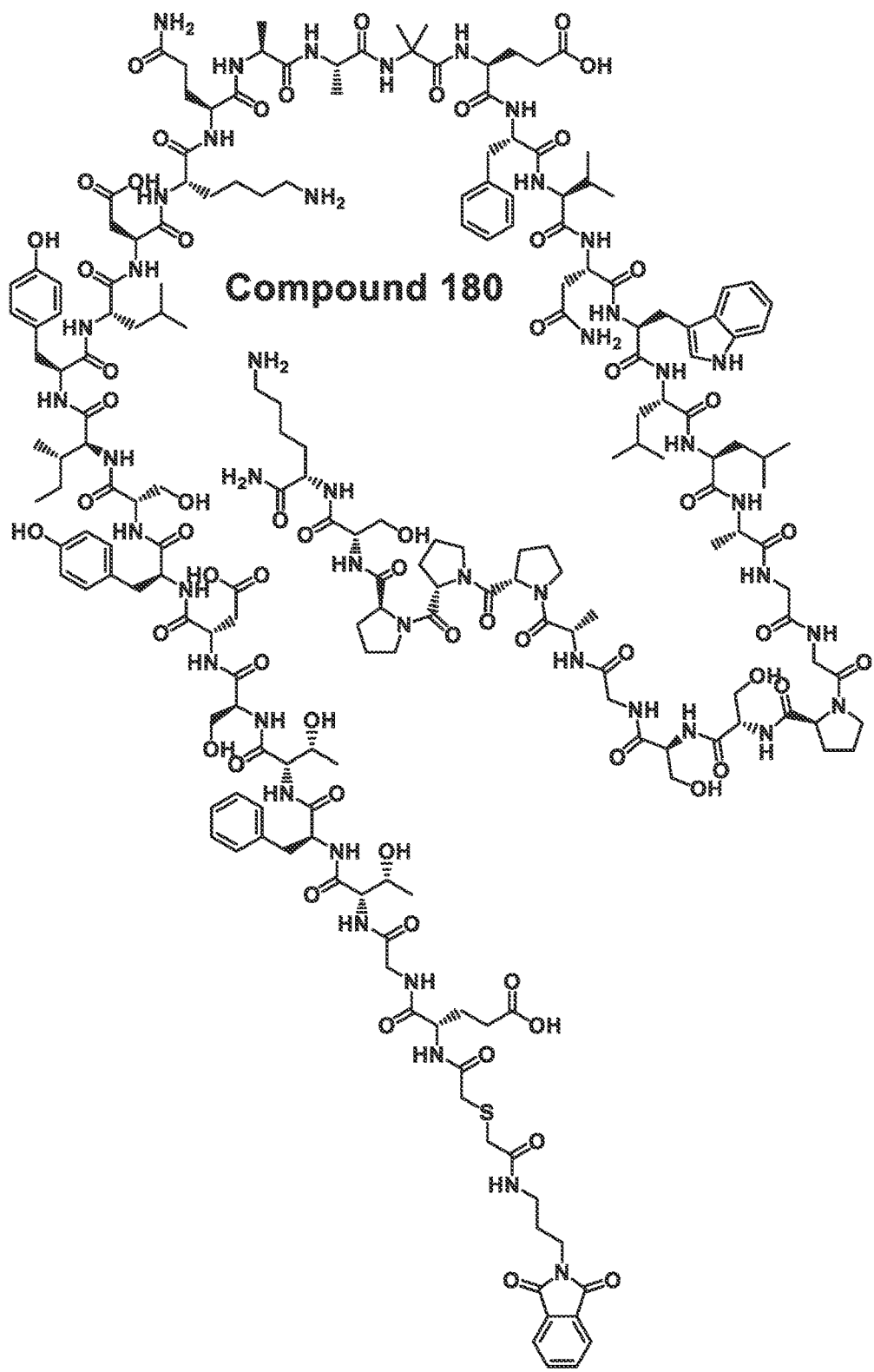
Compound 180
Cont'd

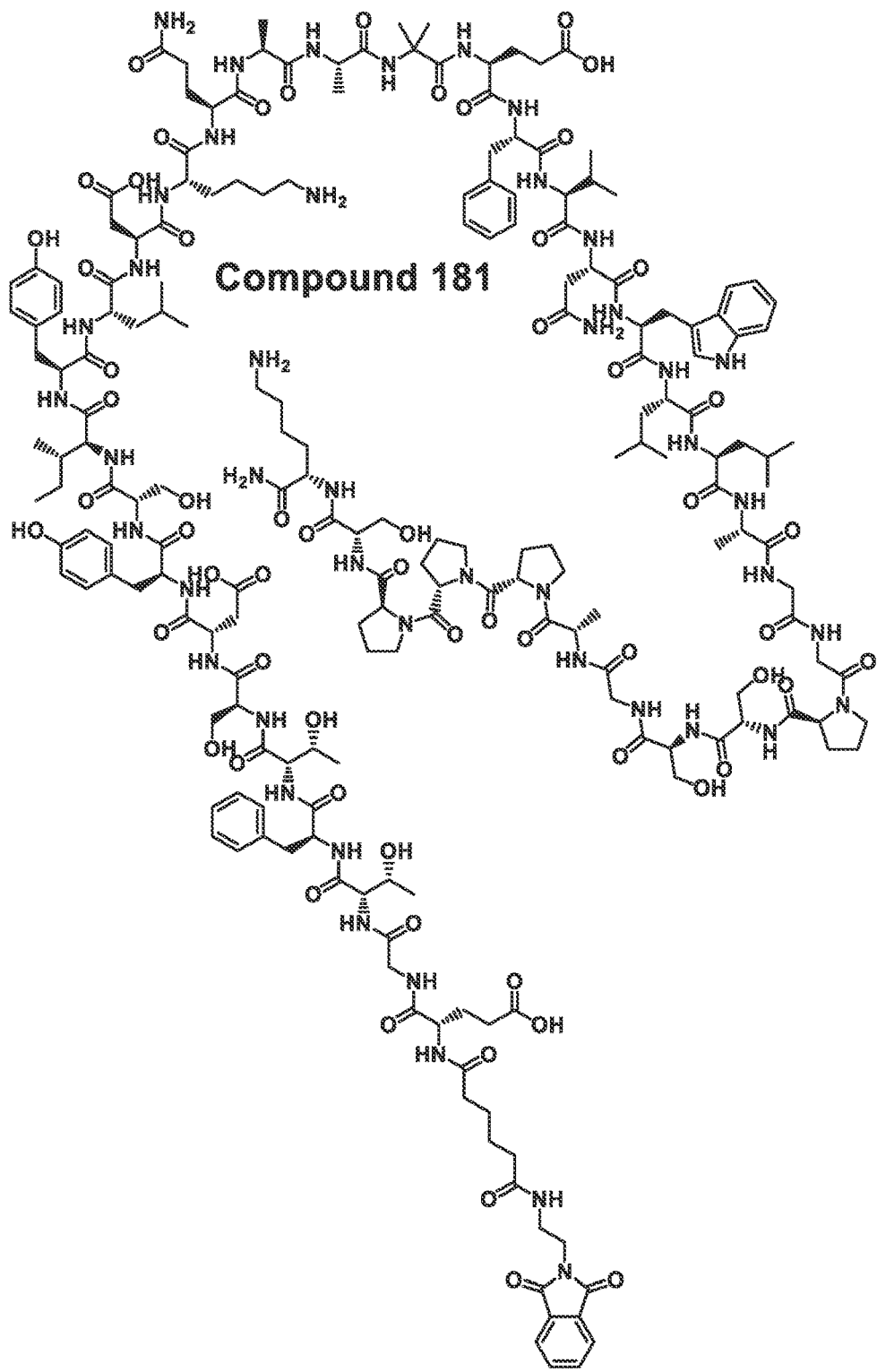
Compound 181
Cont'd

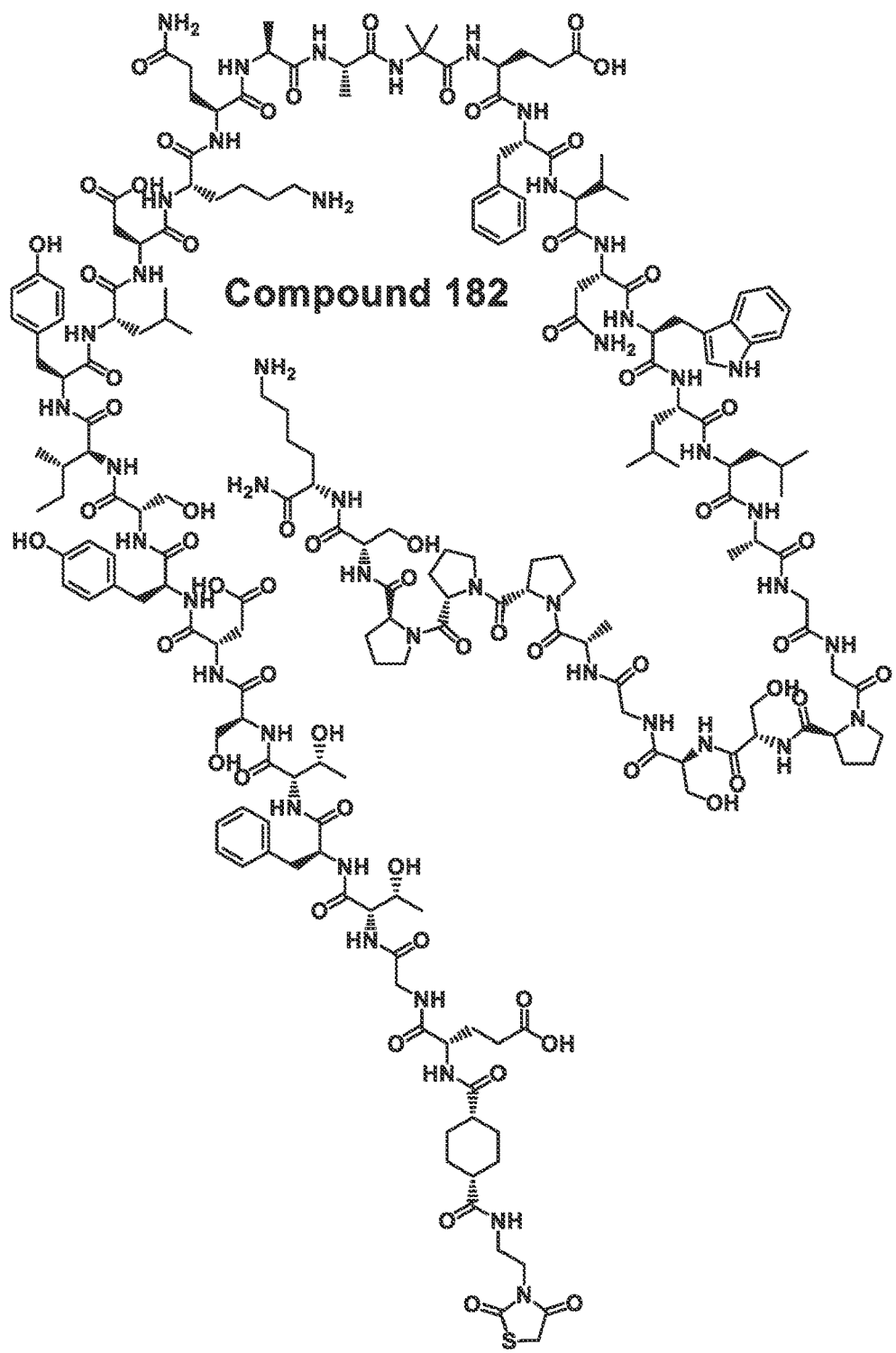
Compound 182
Cont'd

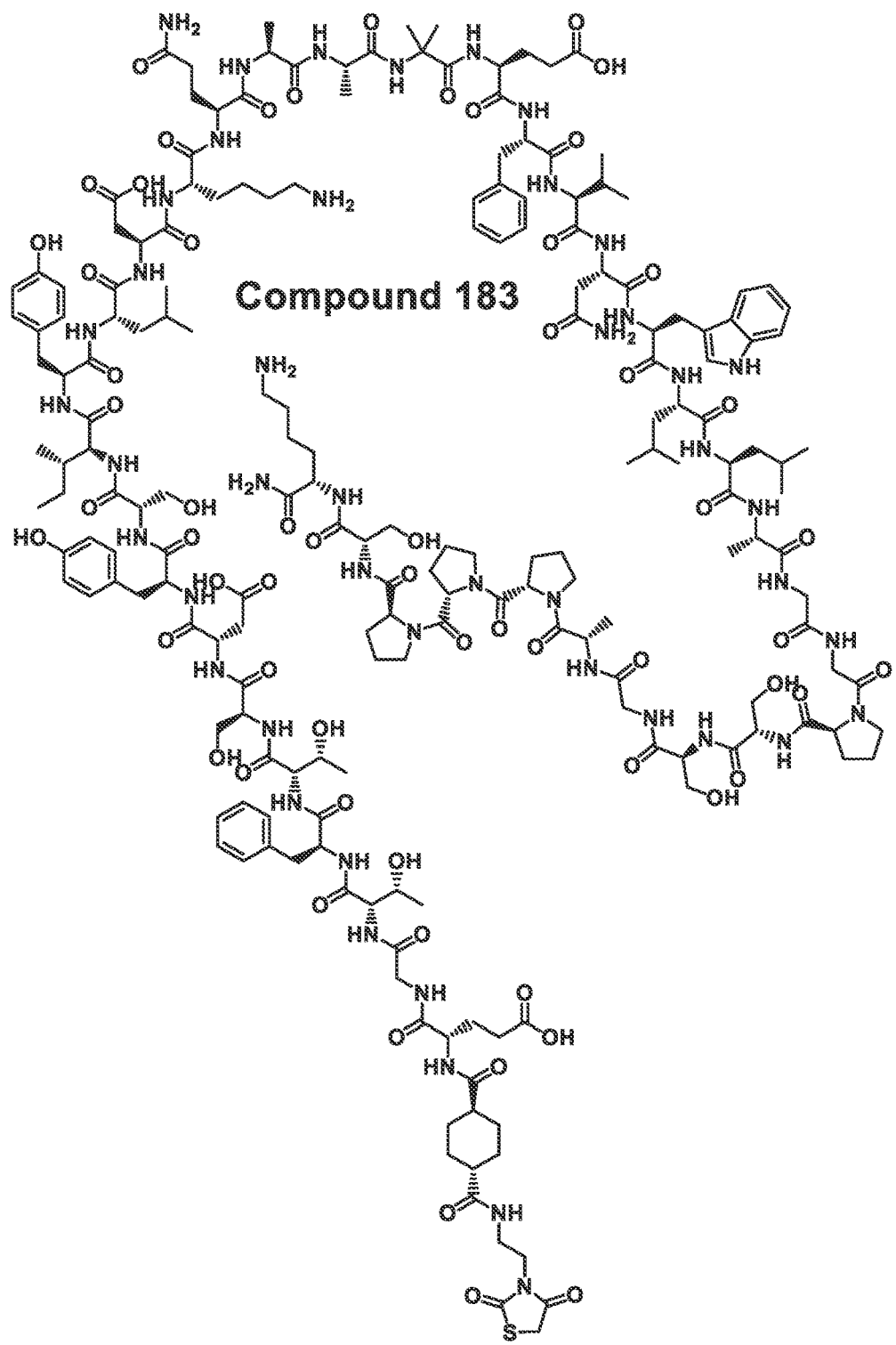
Compound 183
Cont'd

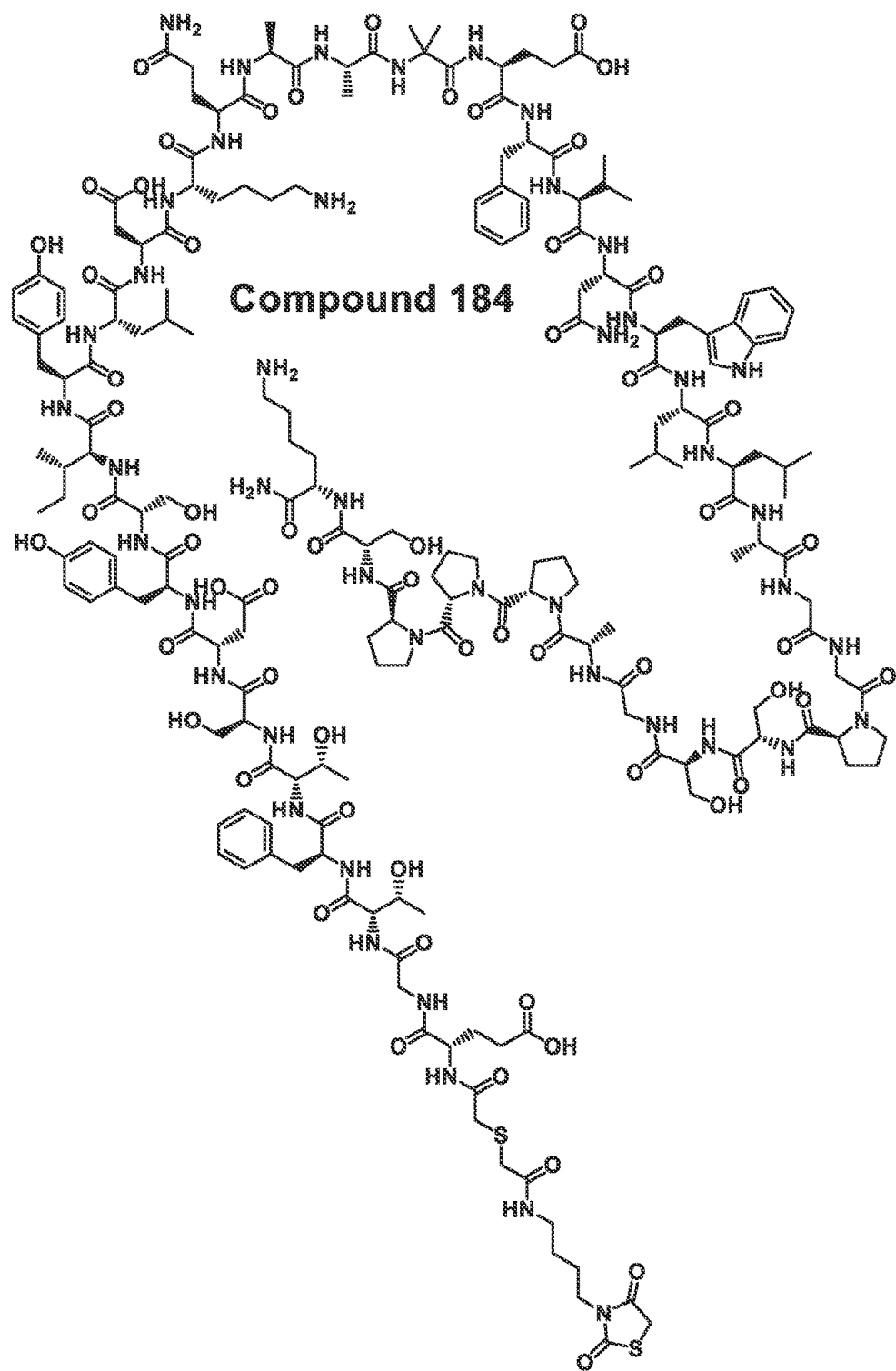

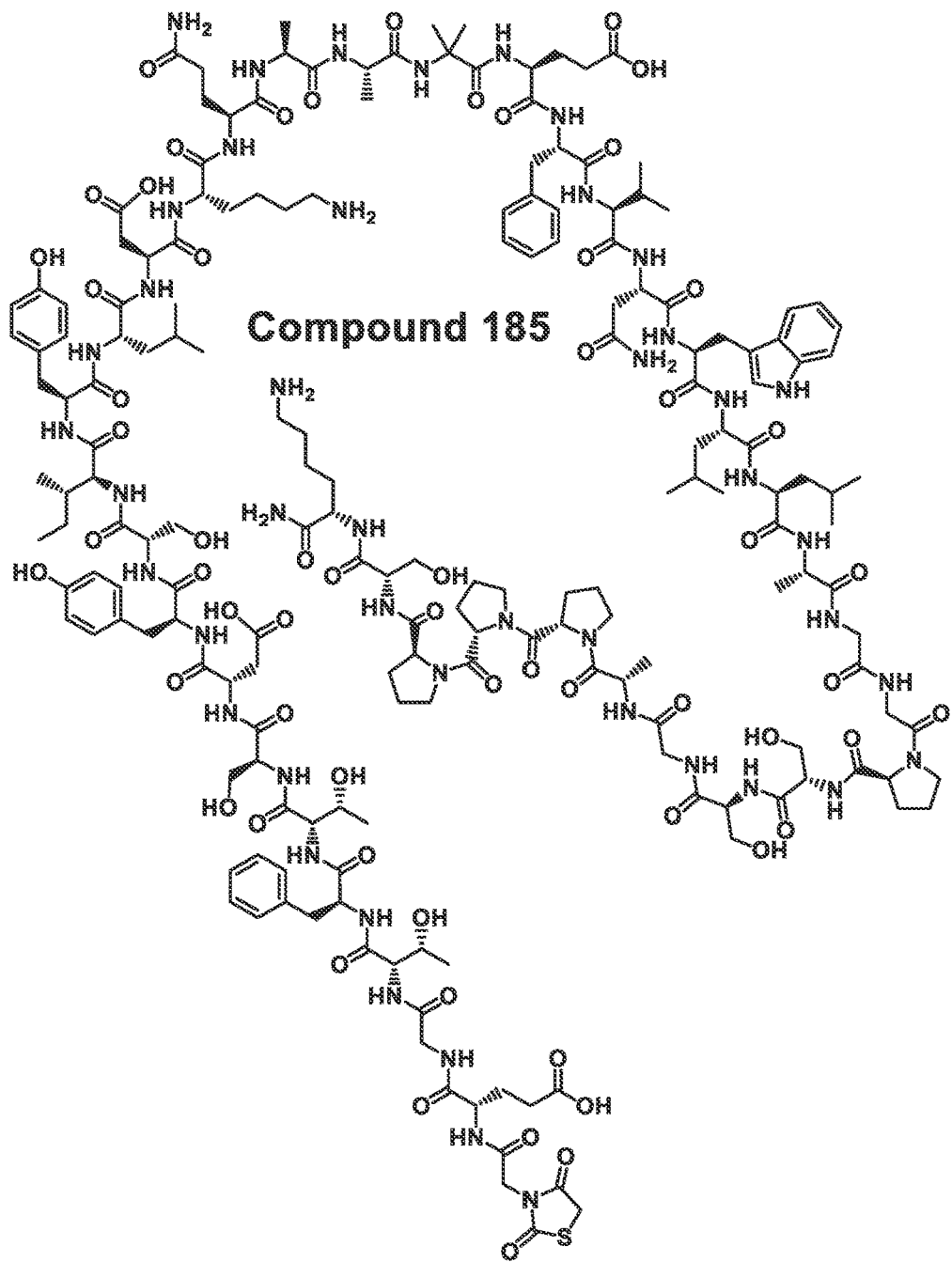

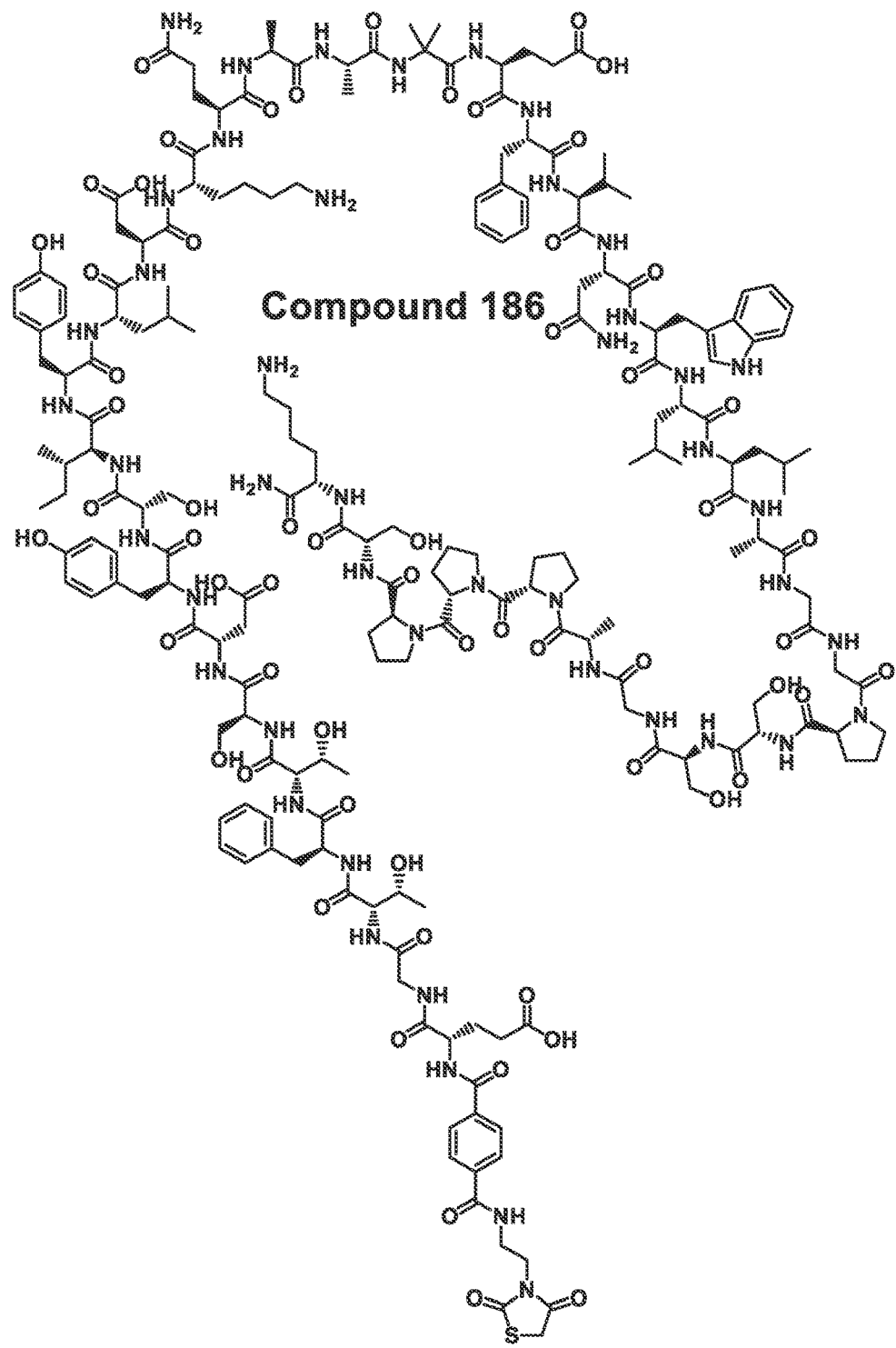
Compound 186
Cont'd

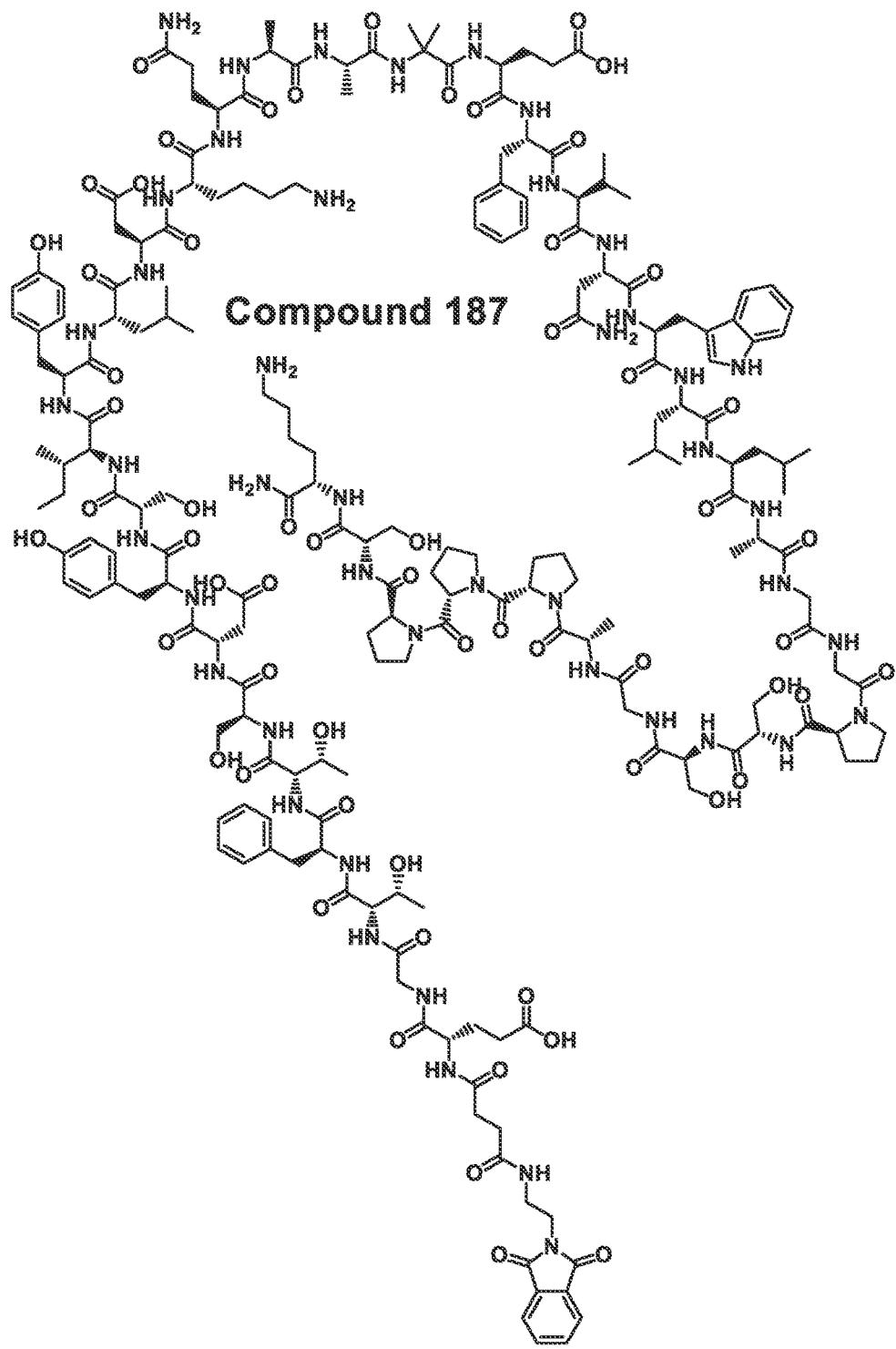
Compound 187

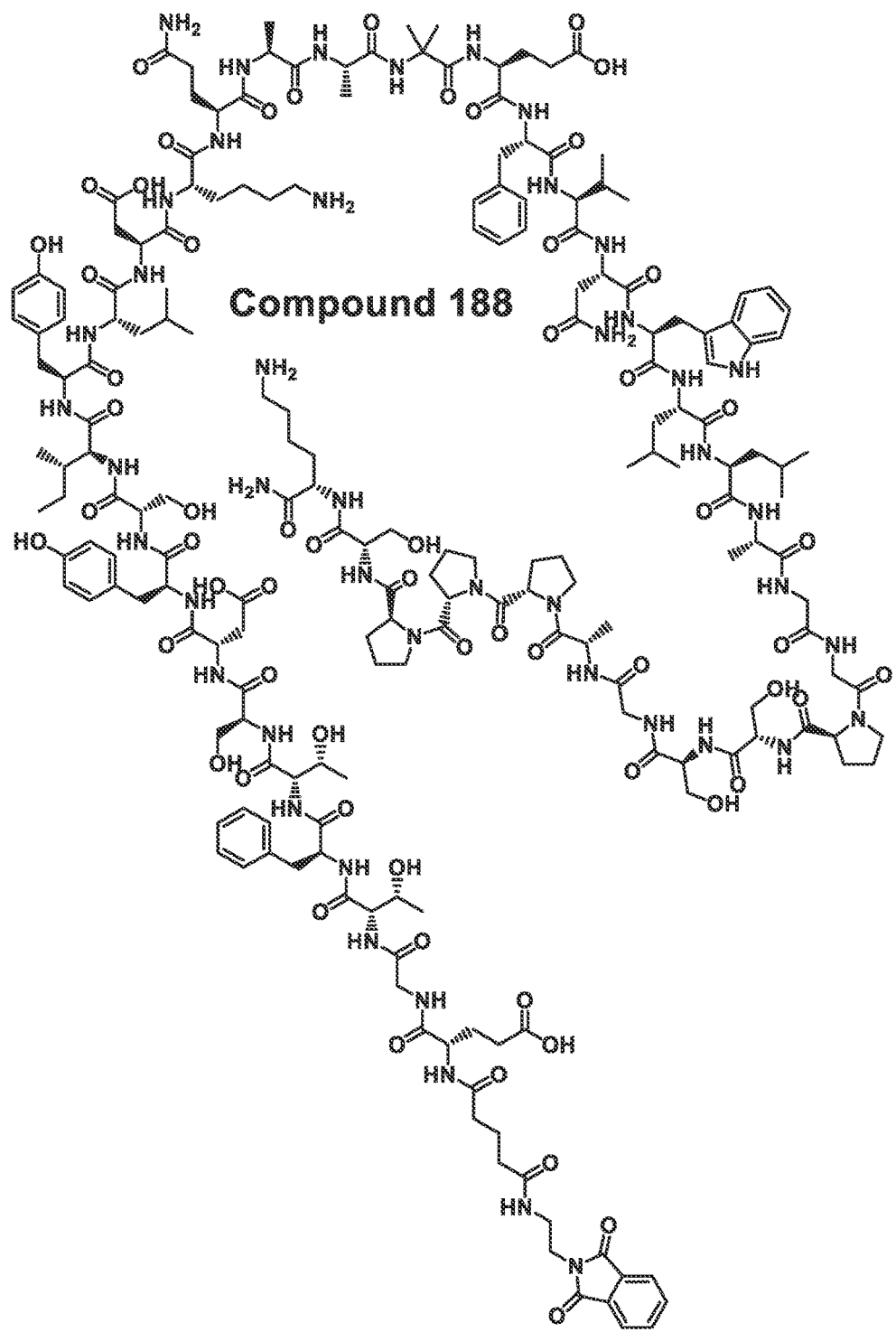
Compound 188
Cont'd

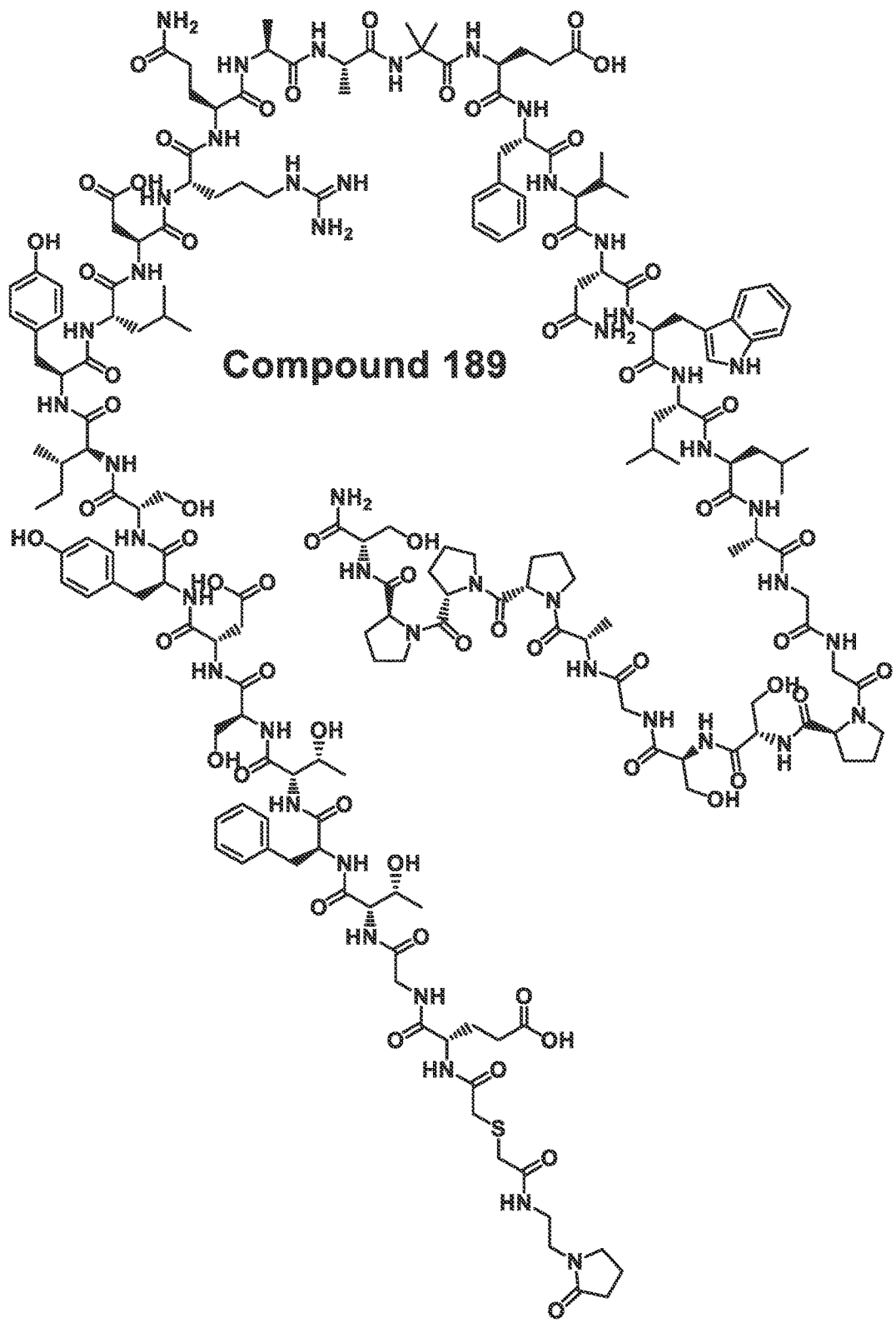
Compound 189
Cont'd

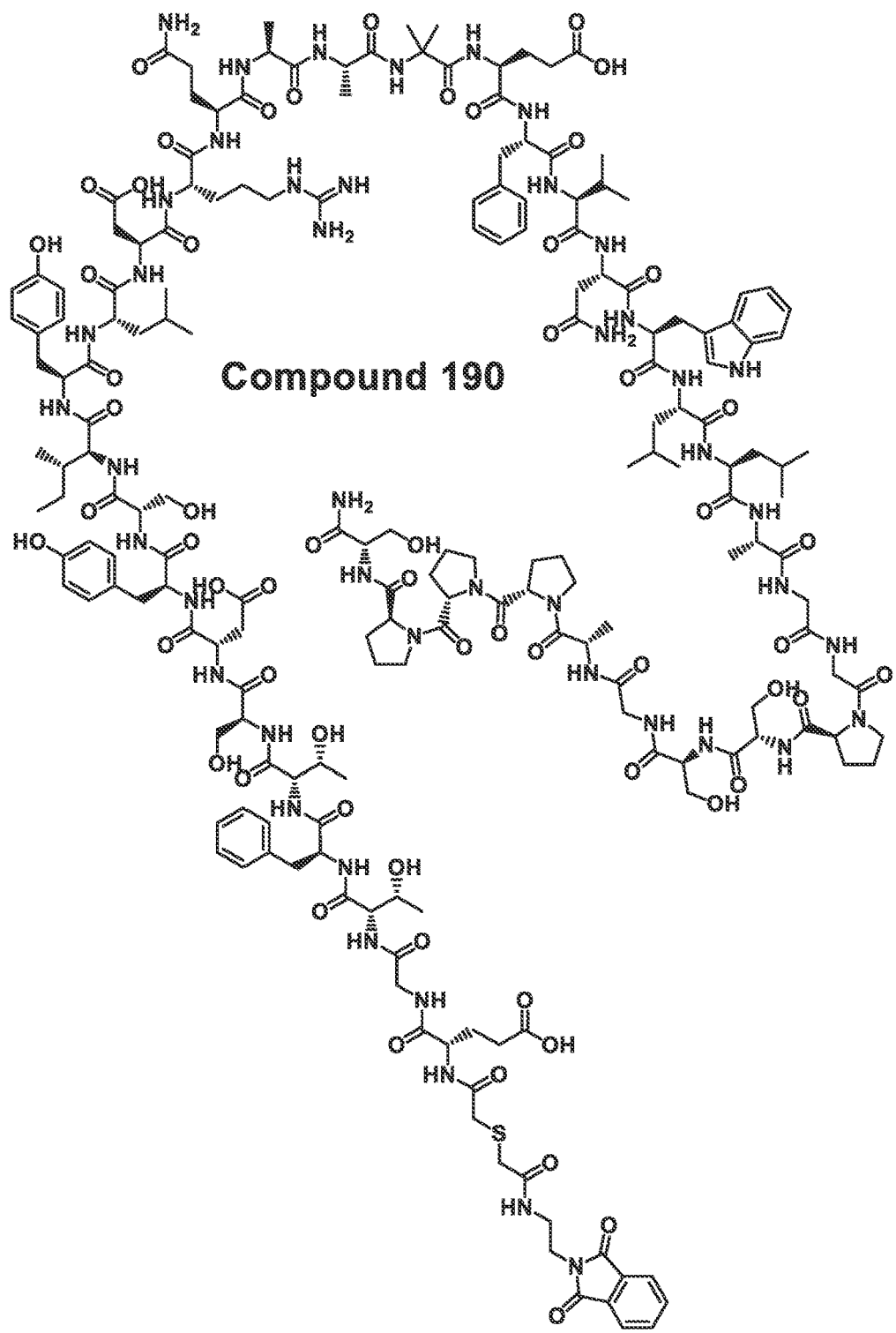
Compound 190
Cont'd

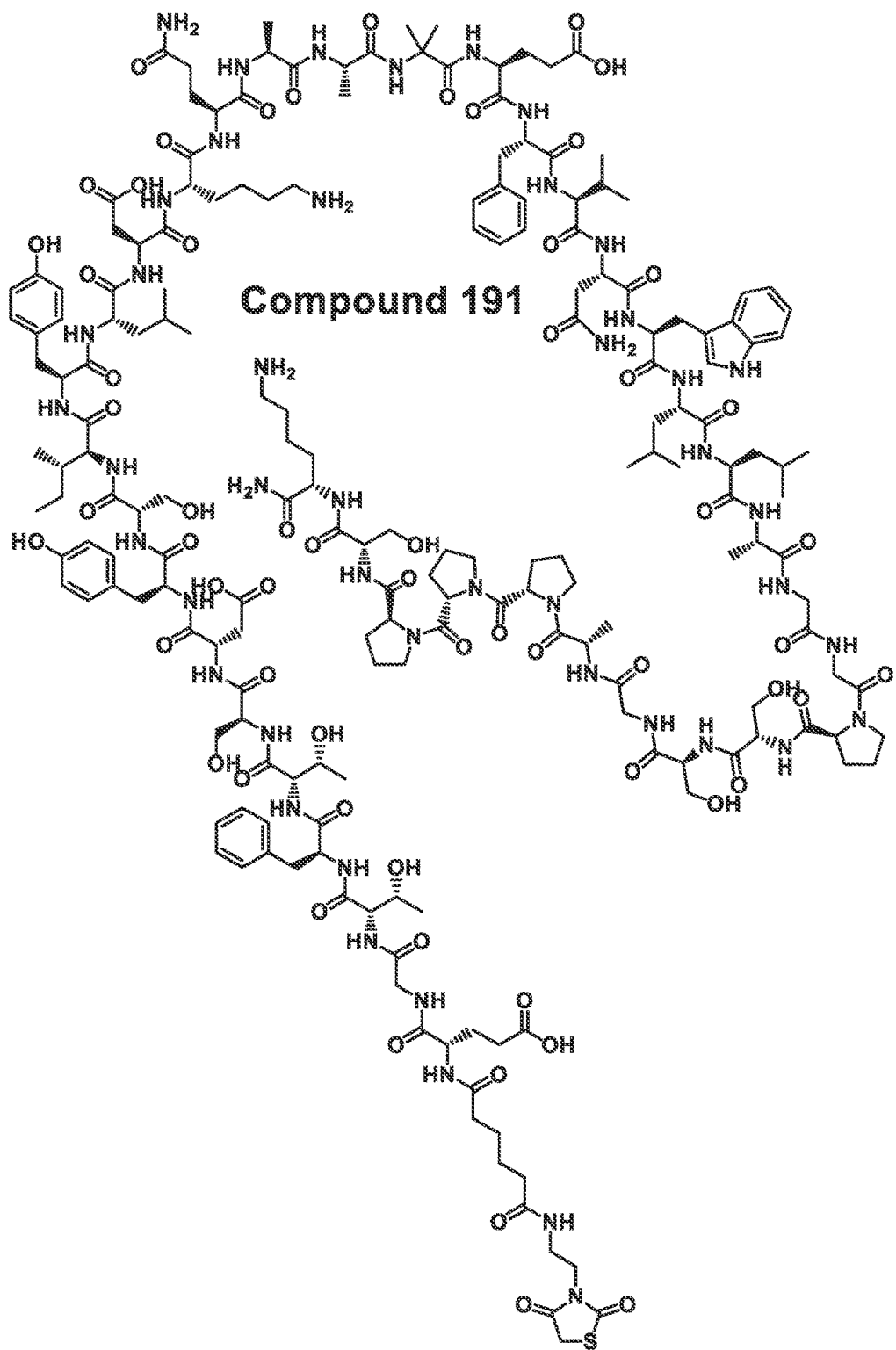
Compound 191
Cont'd

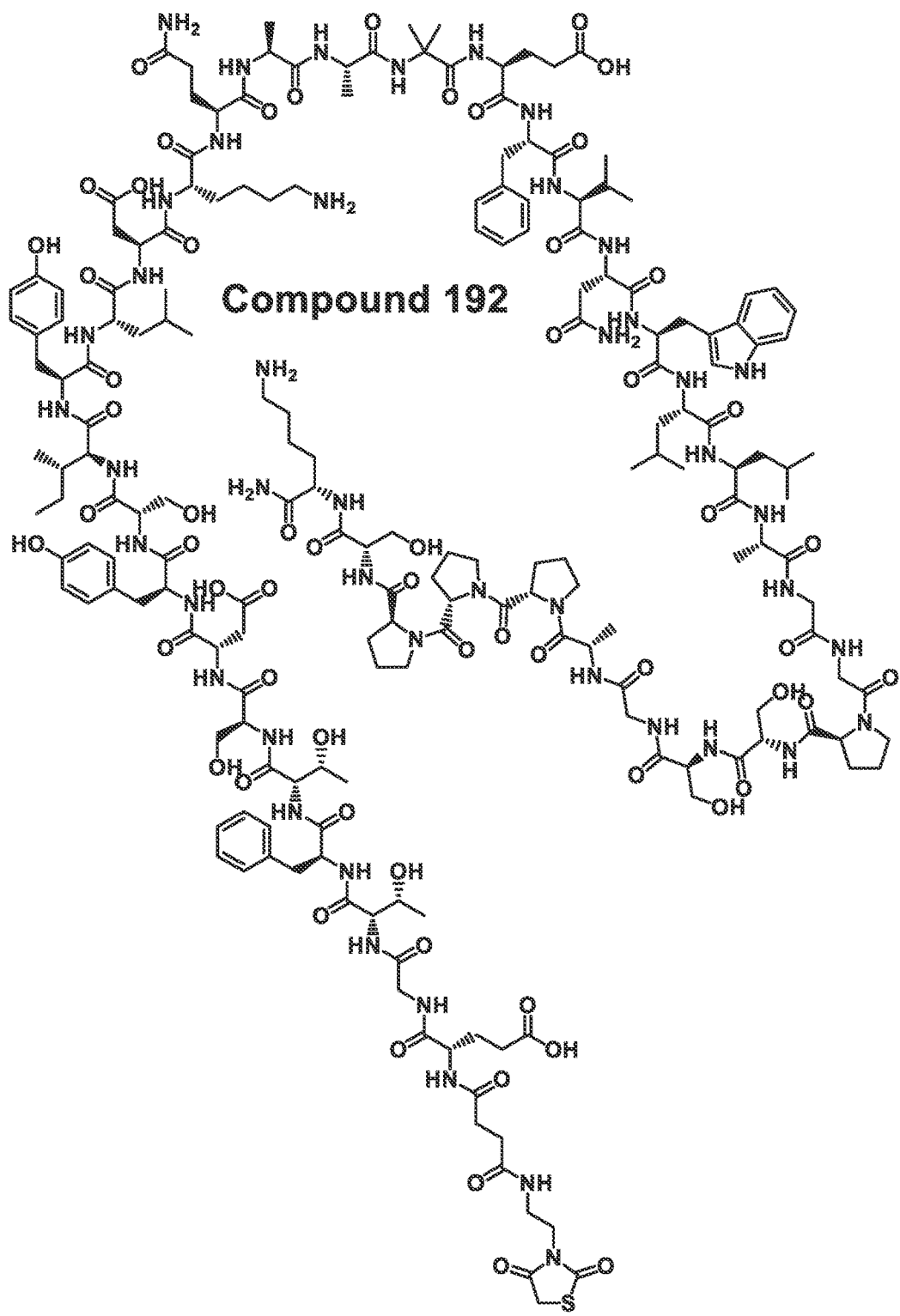
Compound 192
Cont'd

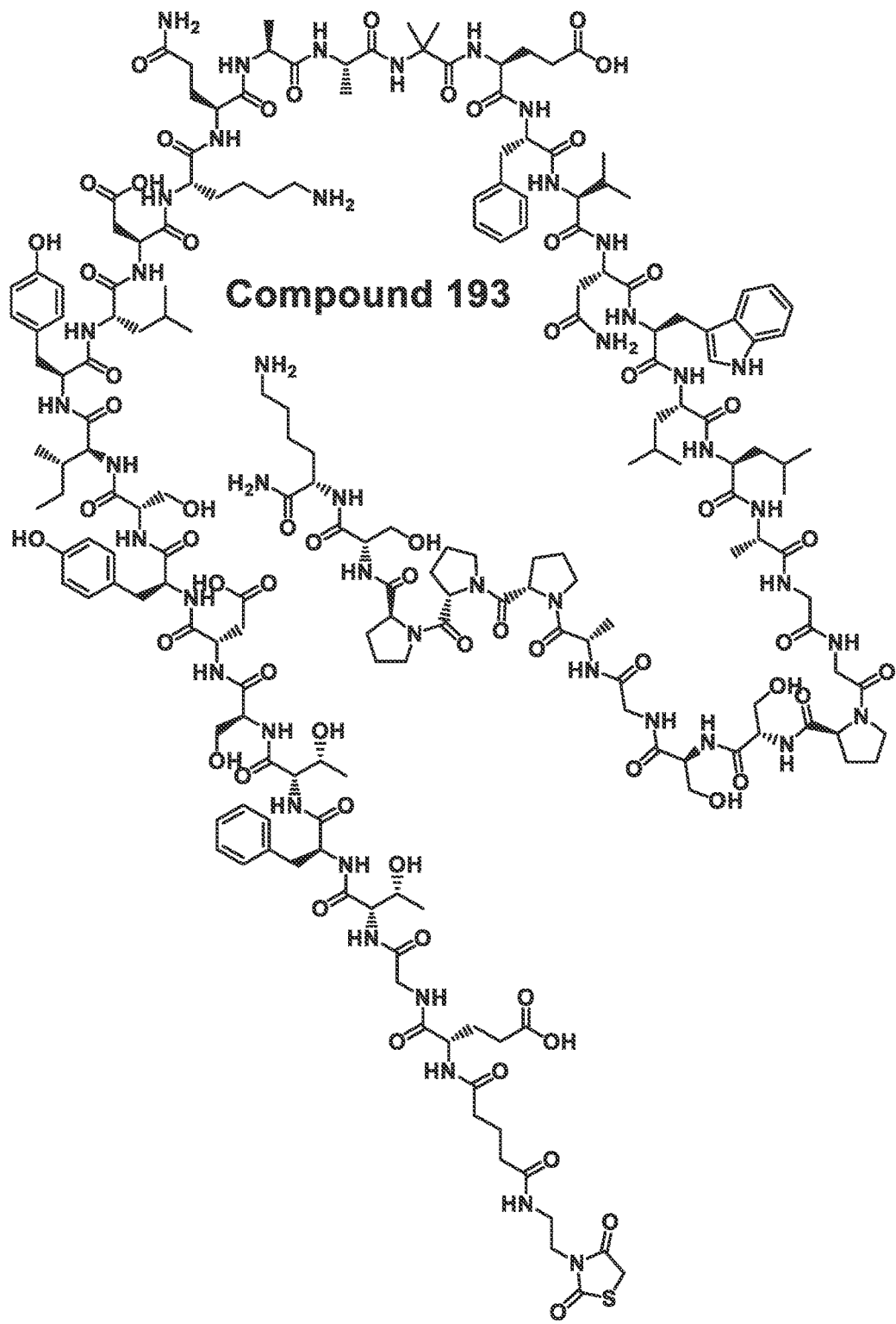
Compound 193
Cont'd

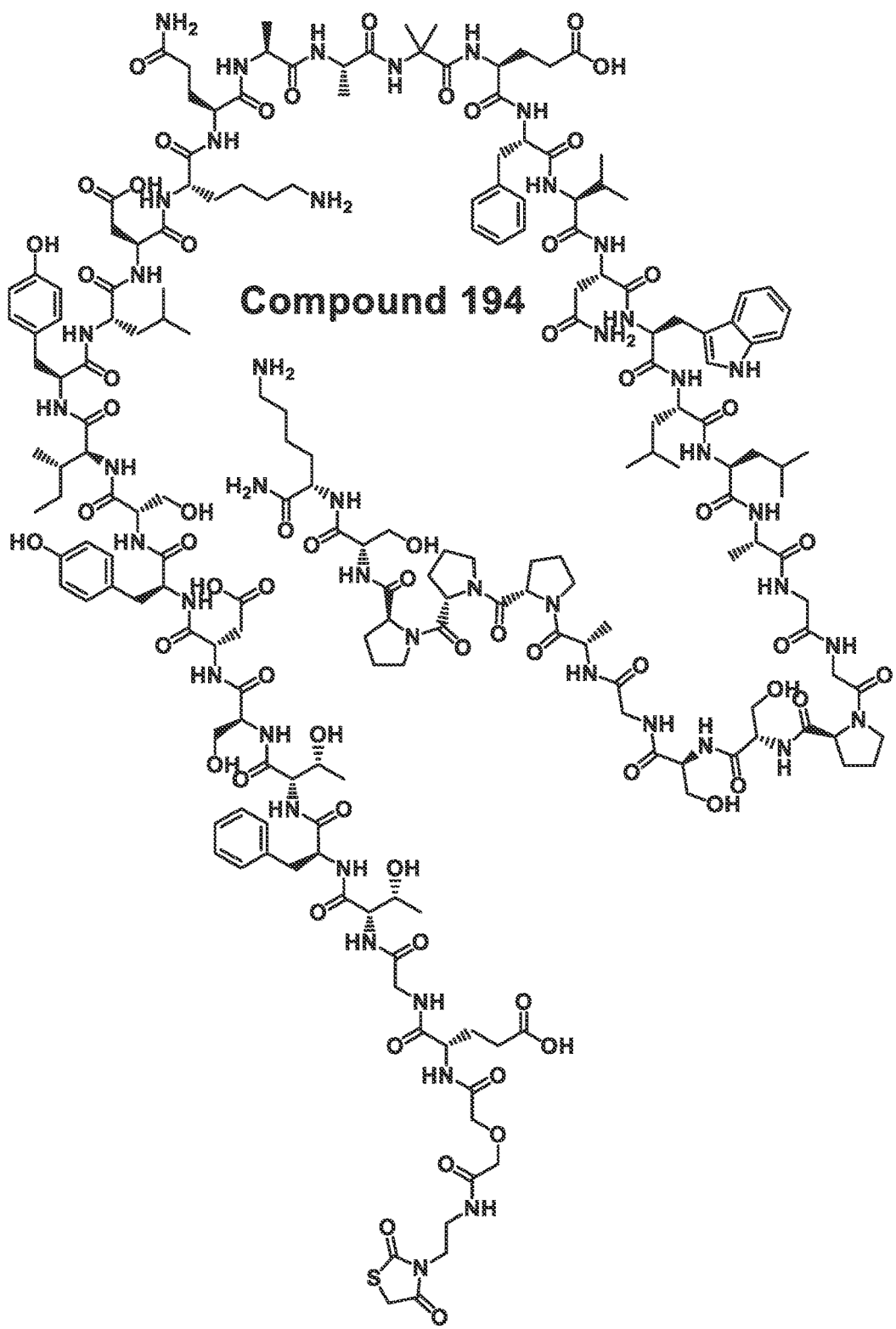
Cont'd

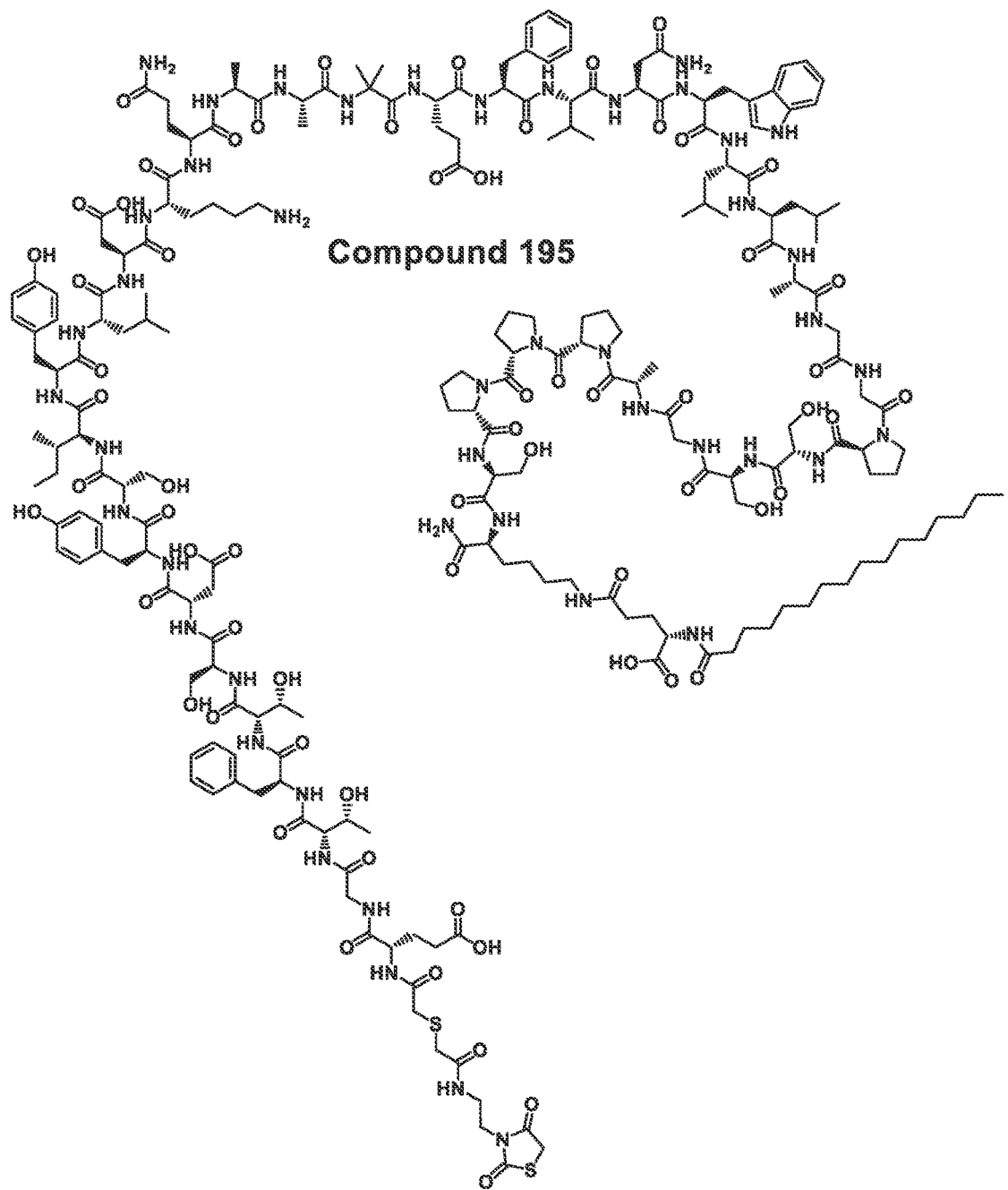
Compound 195
Cont'd

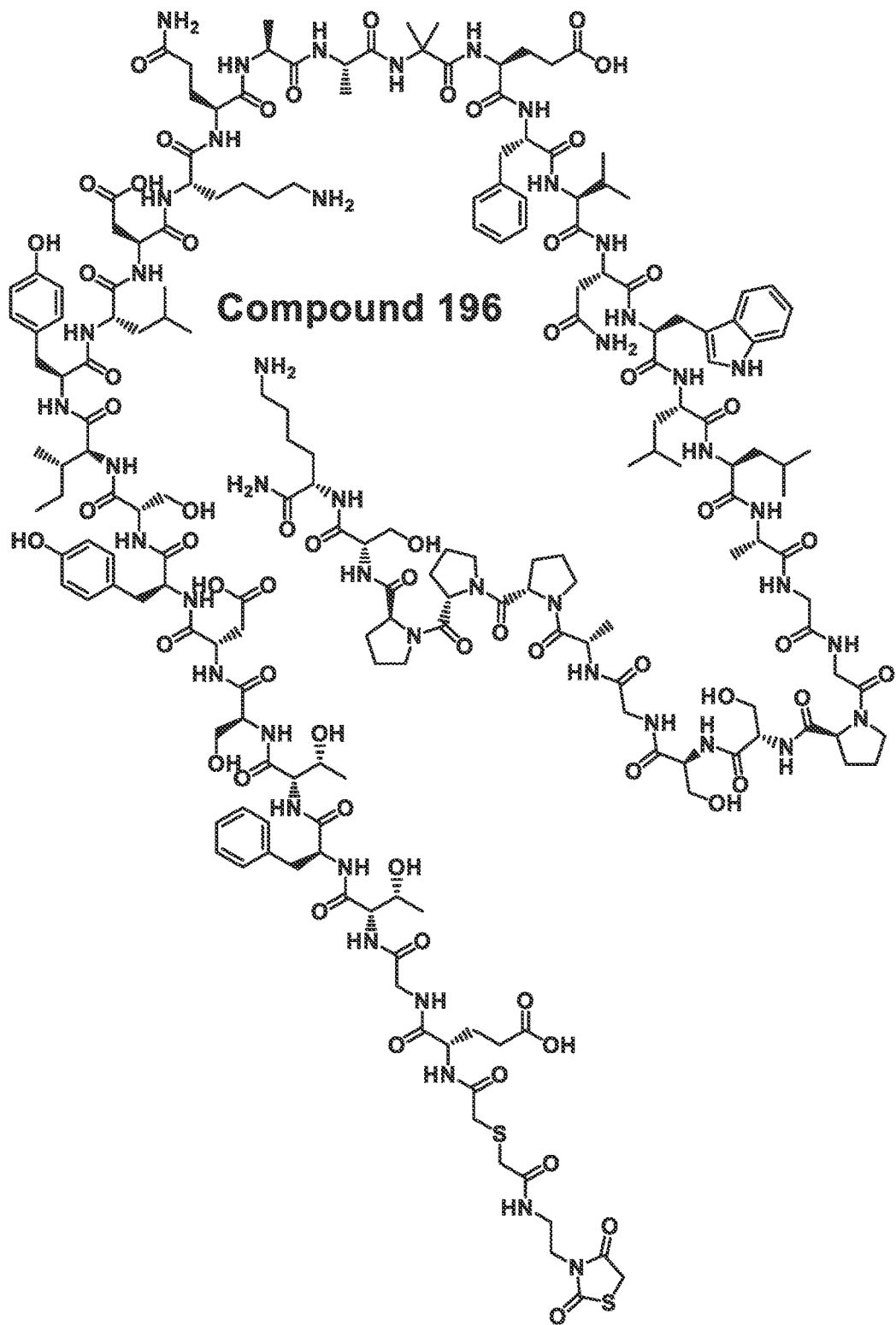
Compound 196
Cont'd

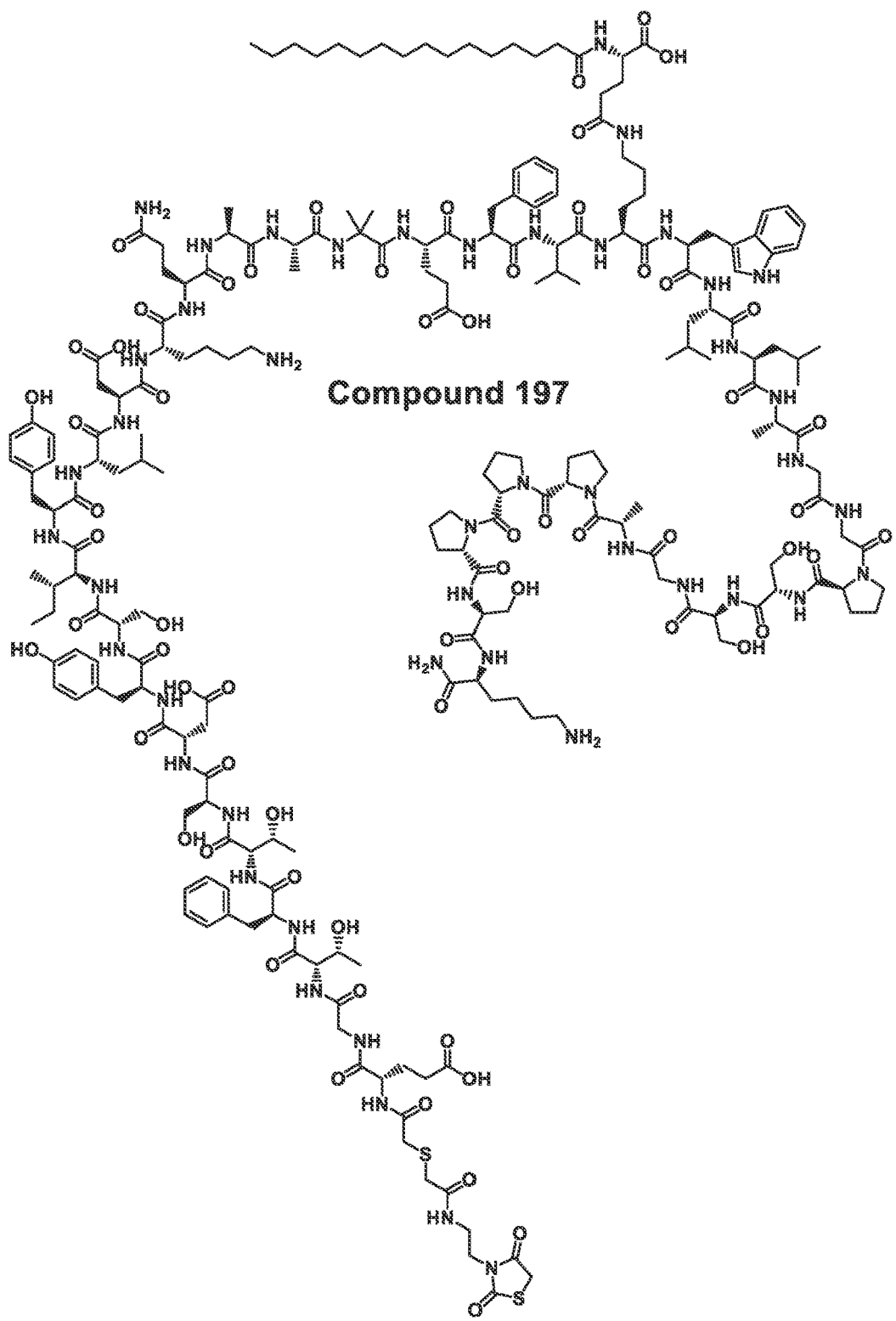
Compound 197
Cont'd

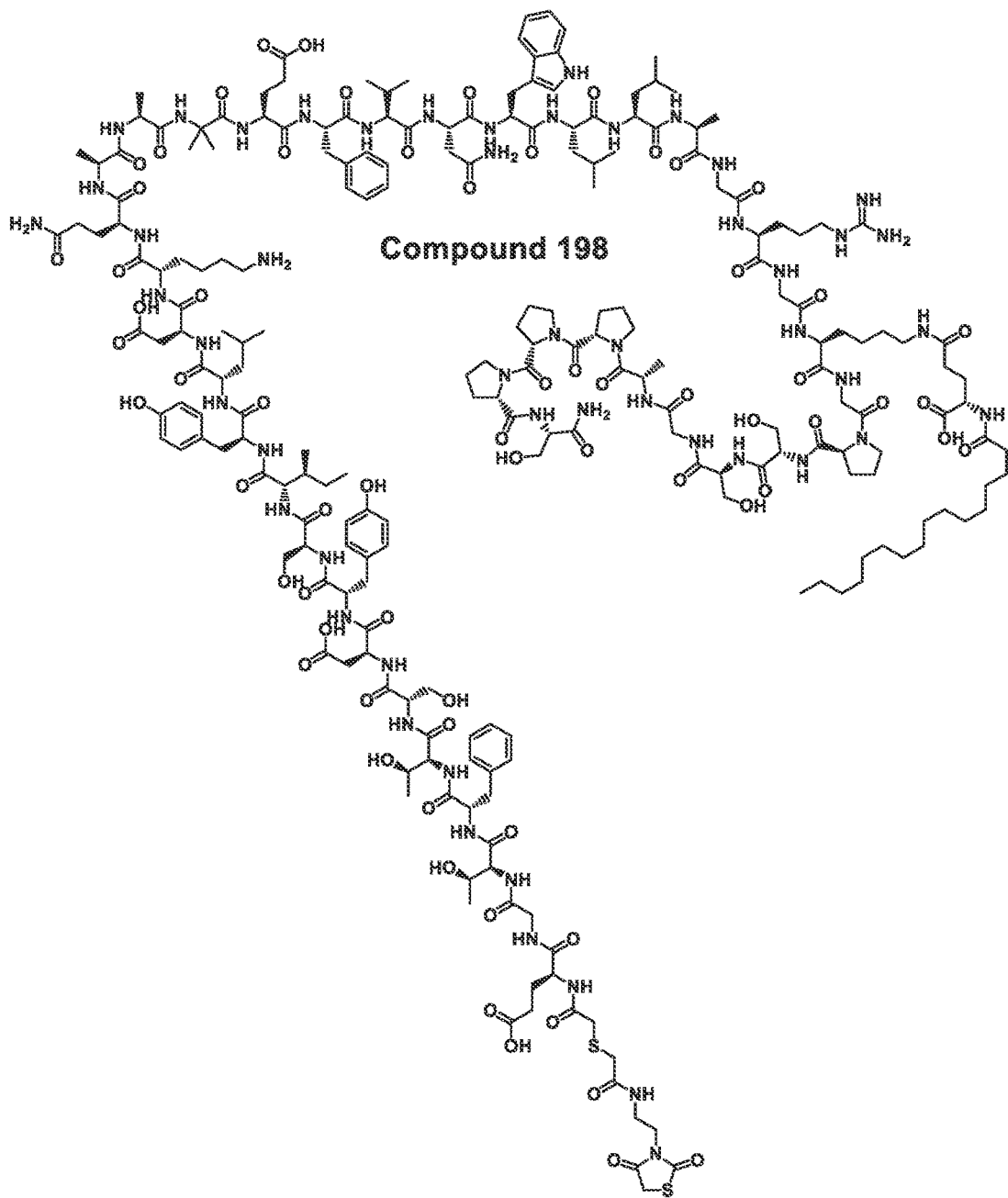
Compound 198
Cont'd

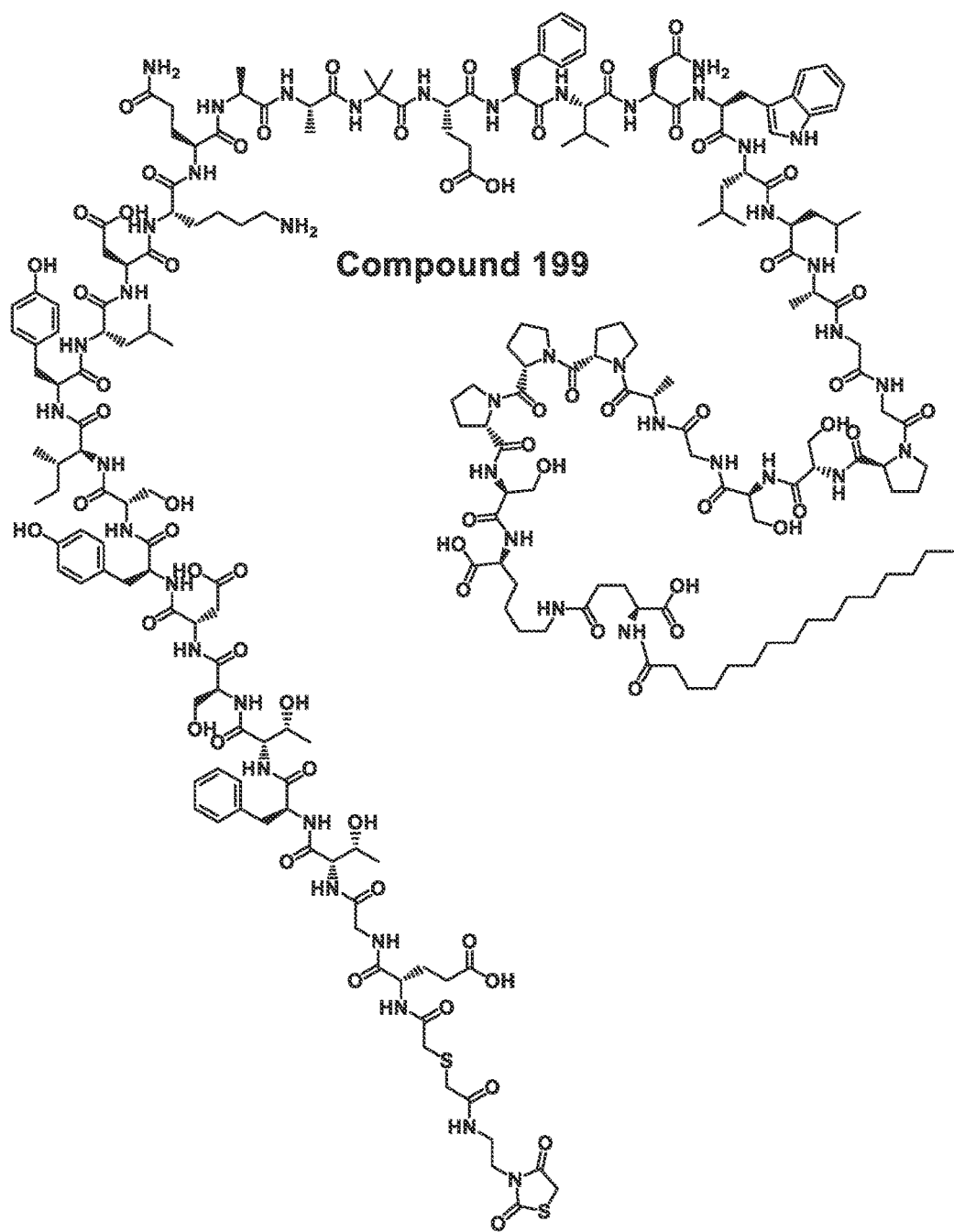
Compound 199
Cont'd

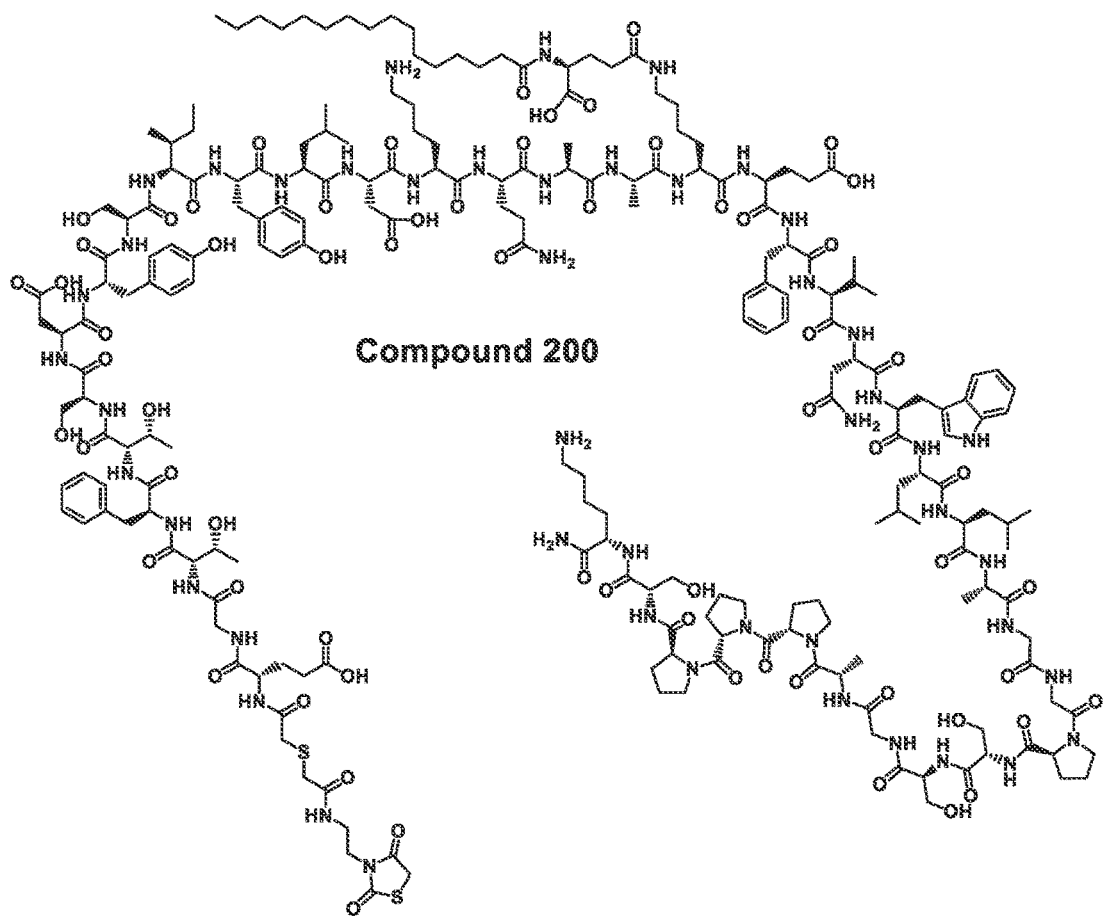
Compound 200
Cont'd

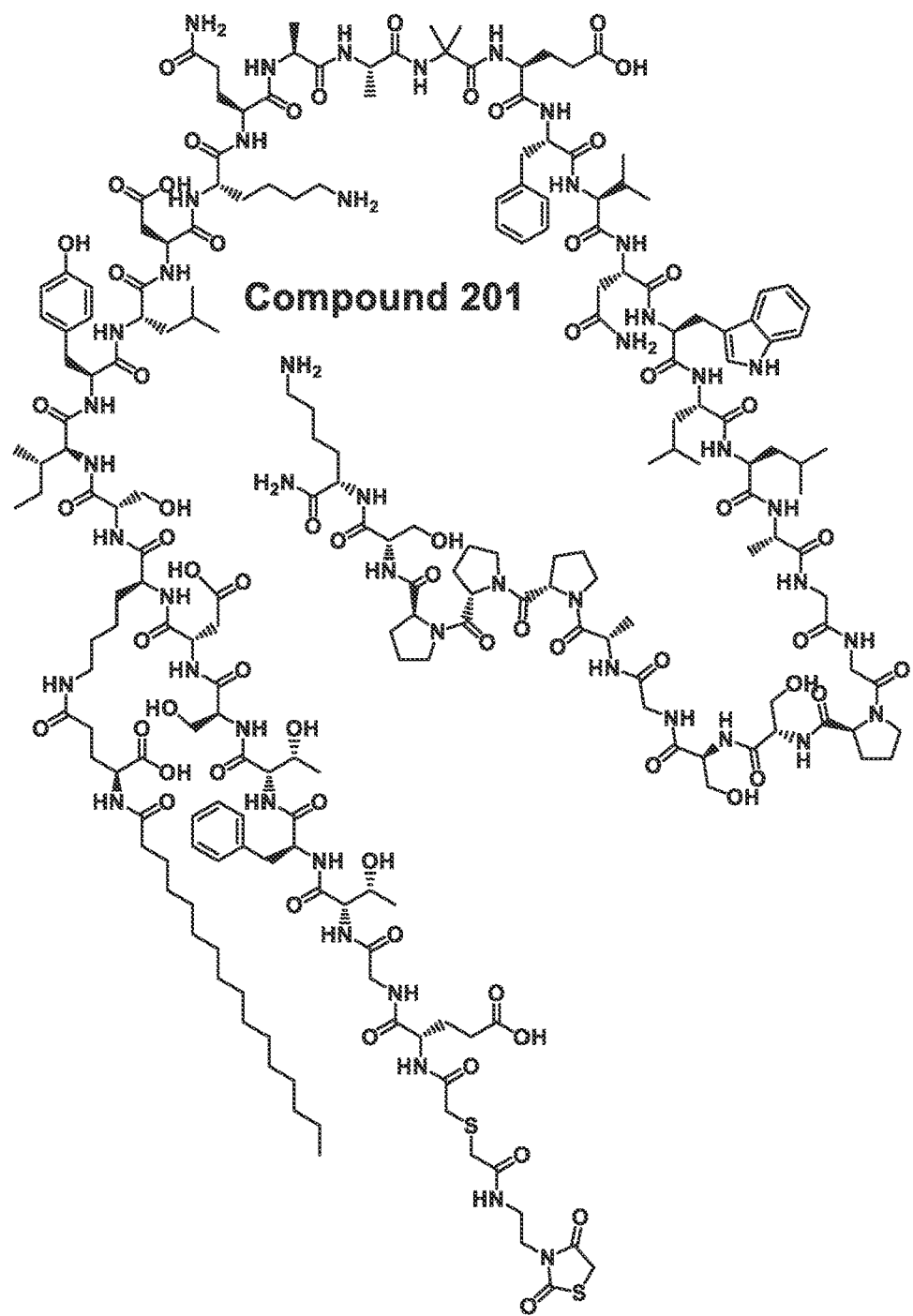

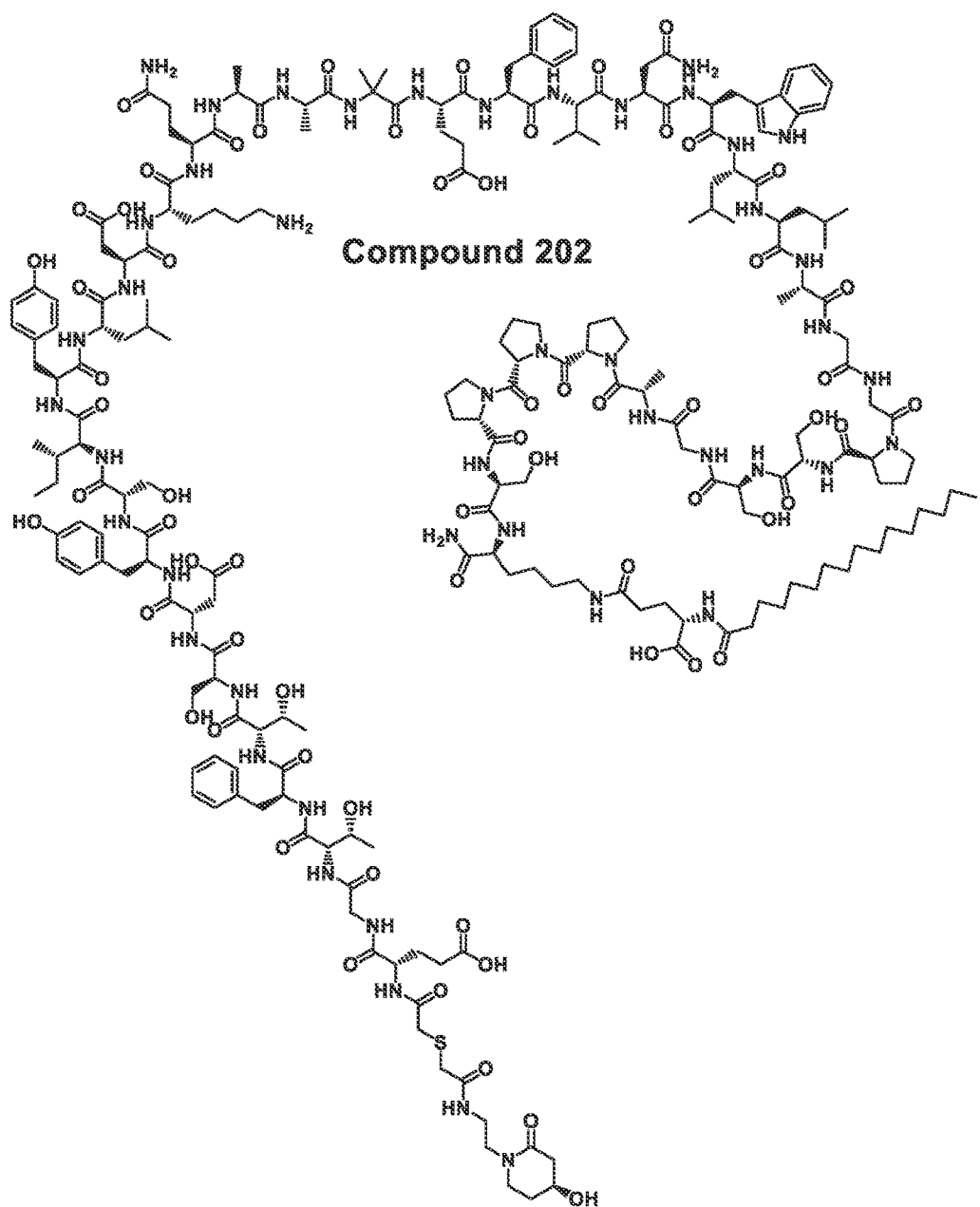
Compound 202
Cont'd

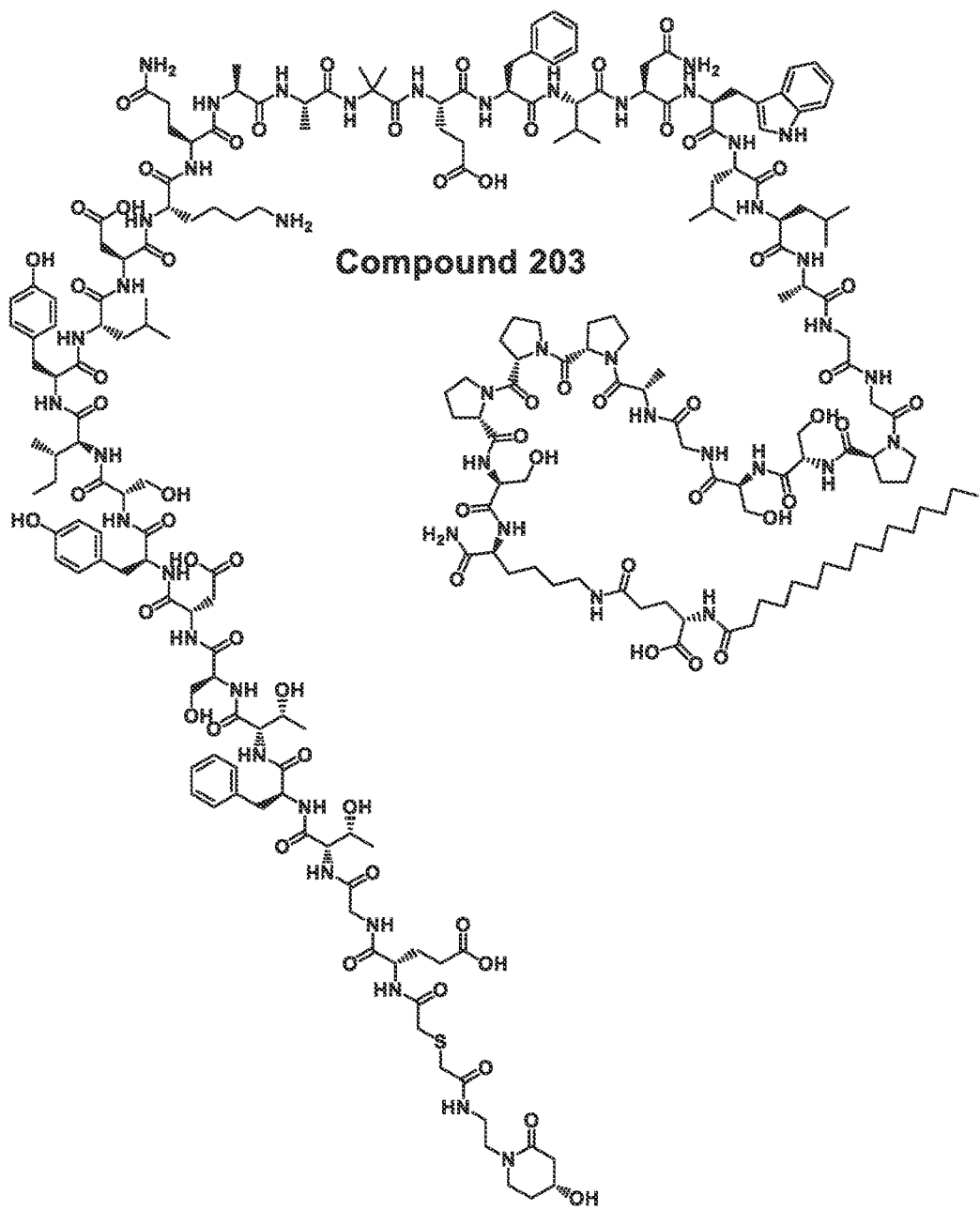
Compound 203
Cont'd

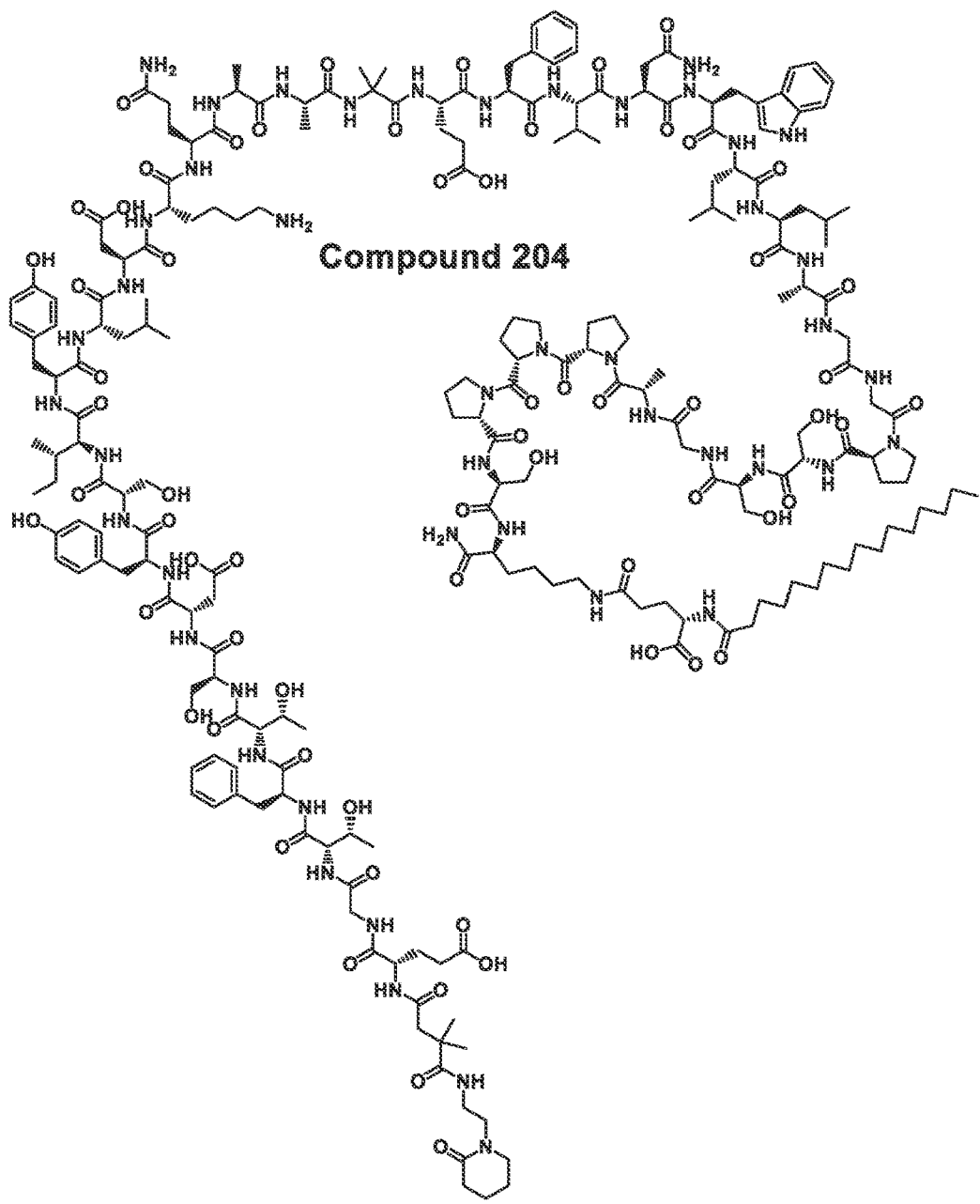

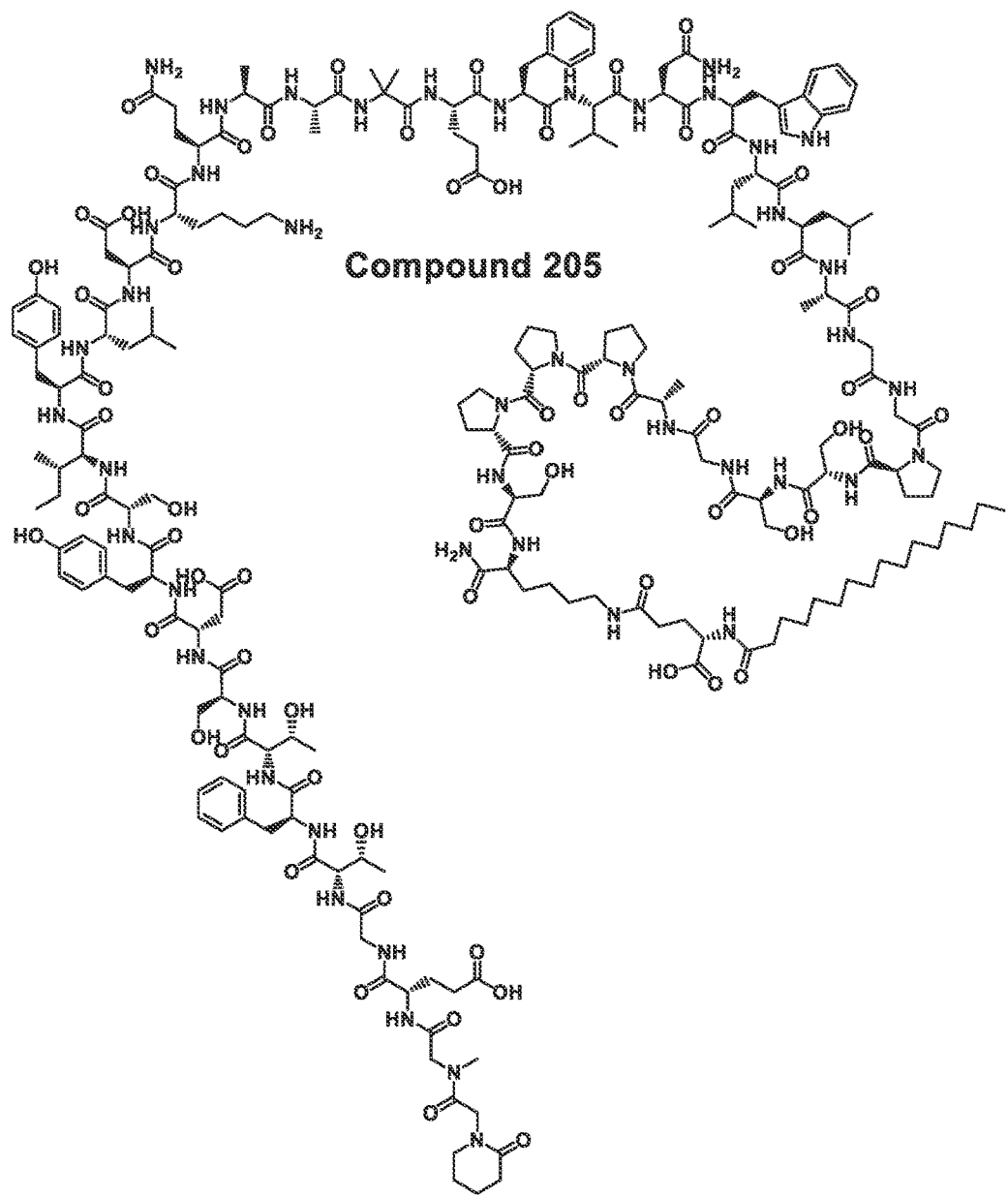
Compound 205
Cont'd

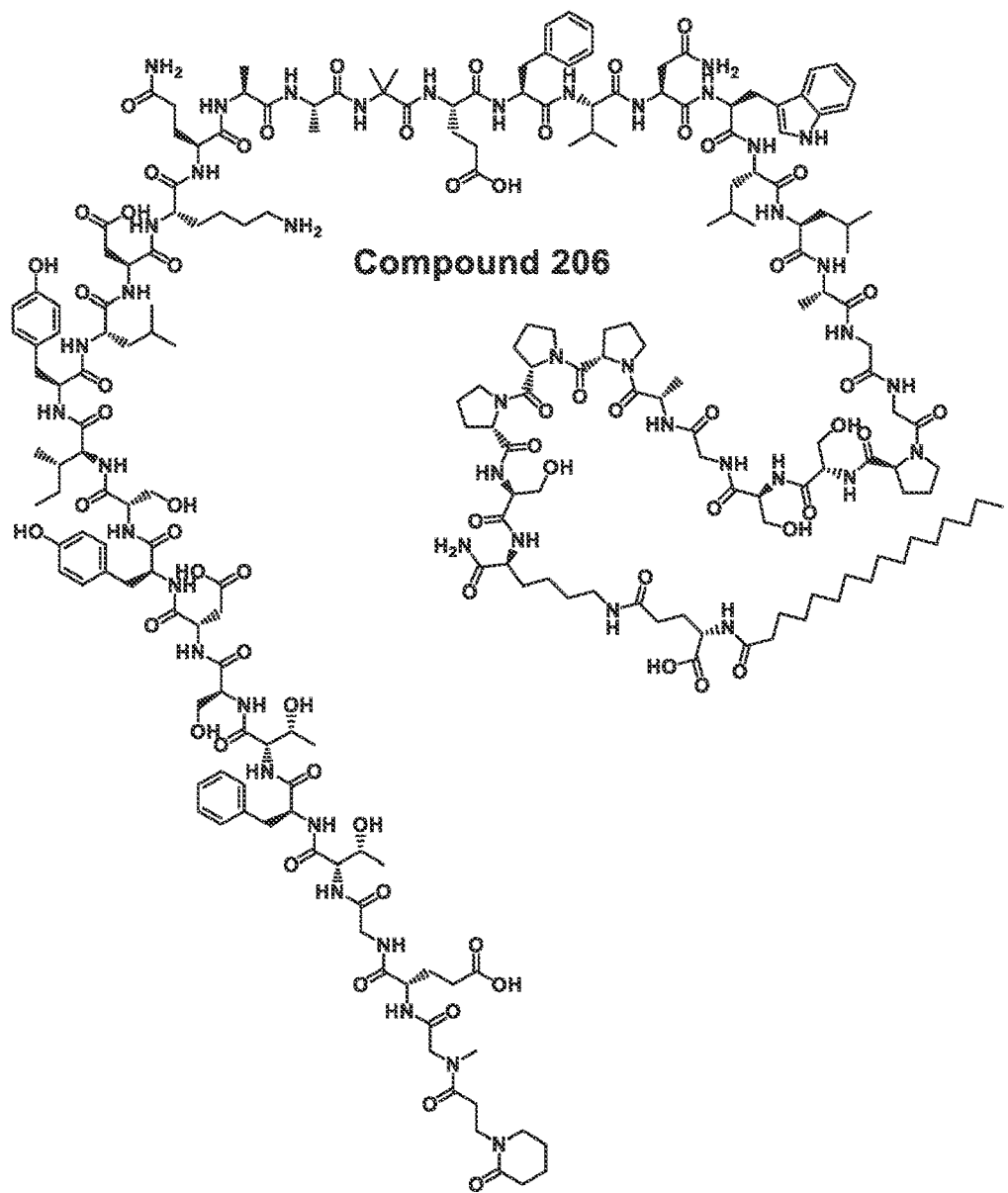
Compound 206
Cont'd

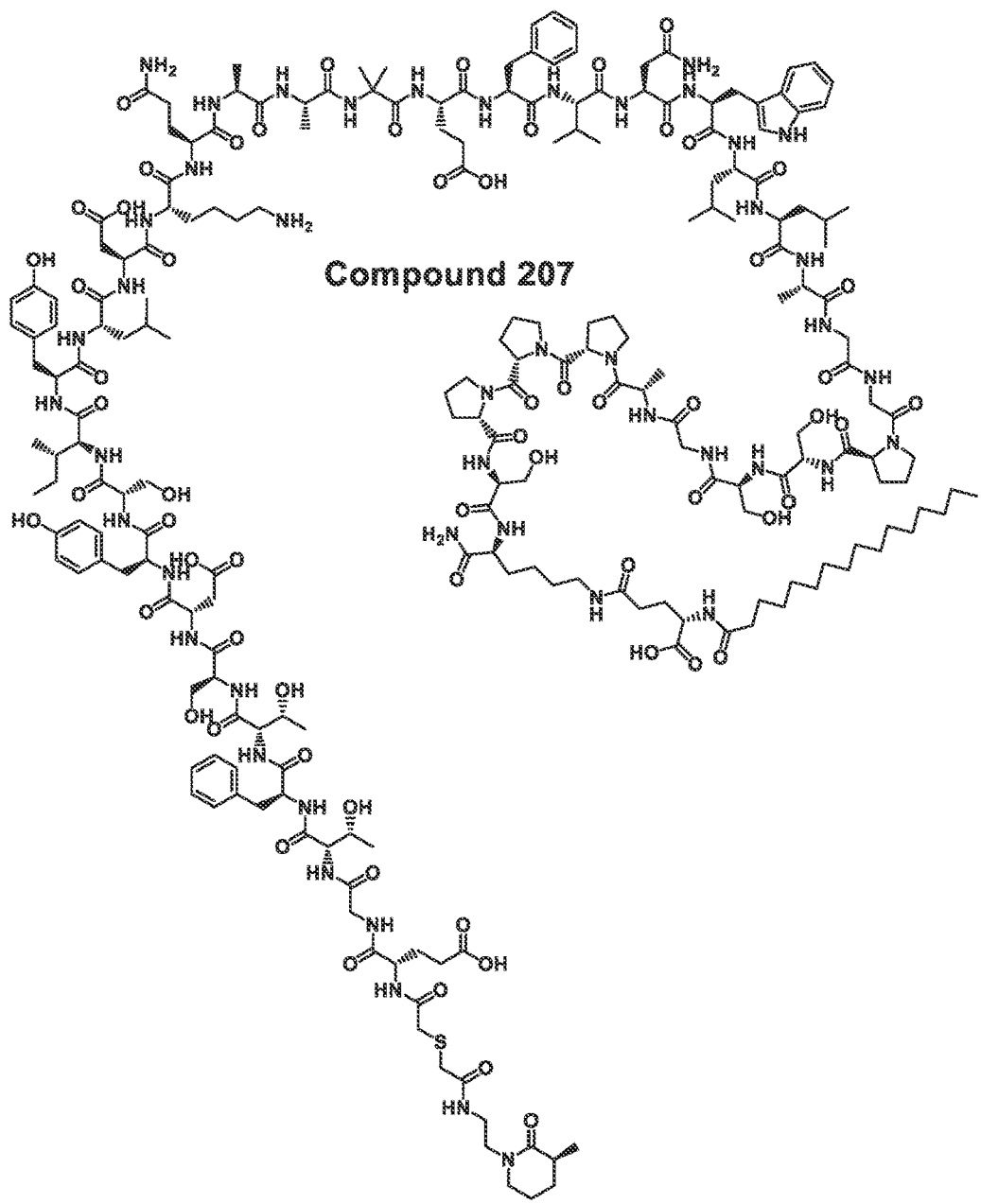
Compound 207
Cont'd

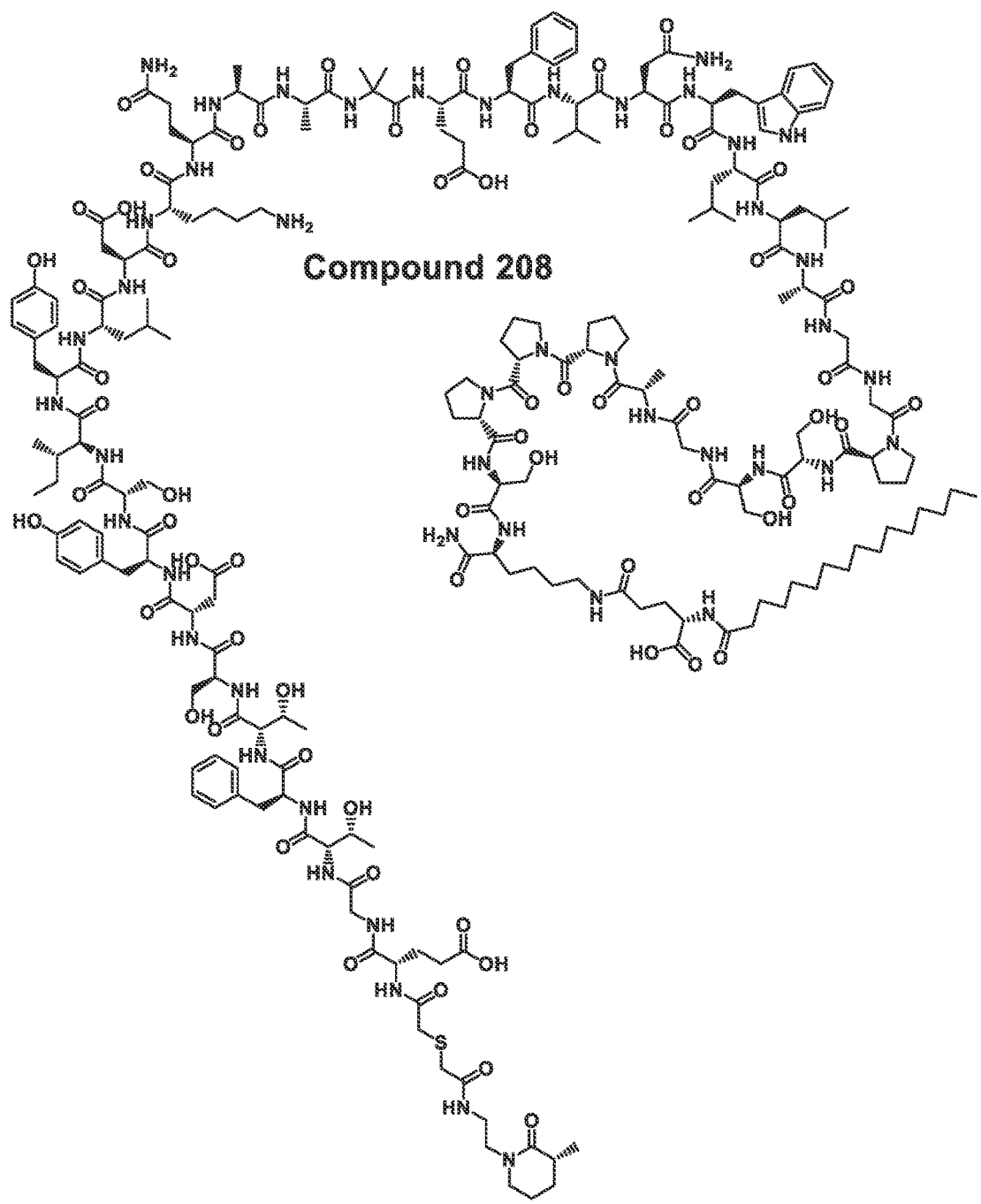
Compound 208
Cont'd

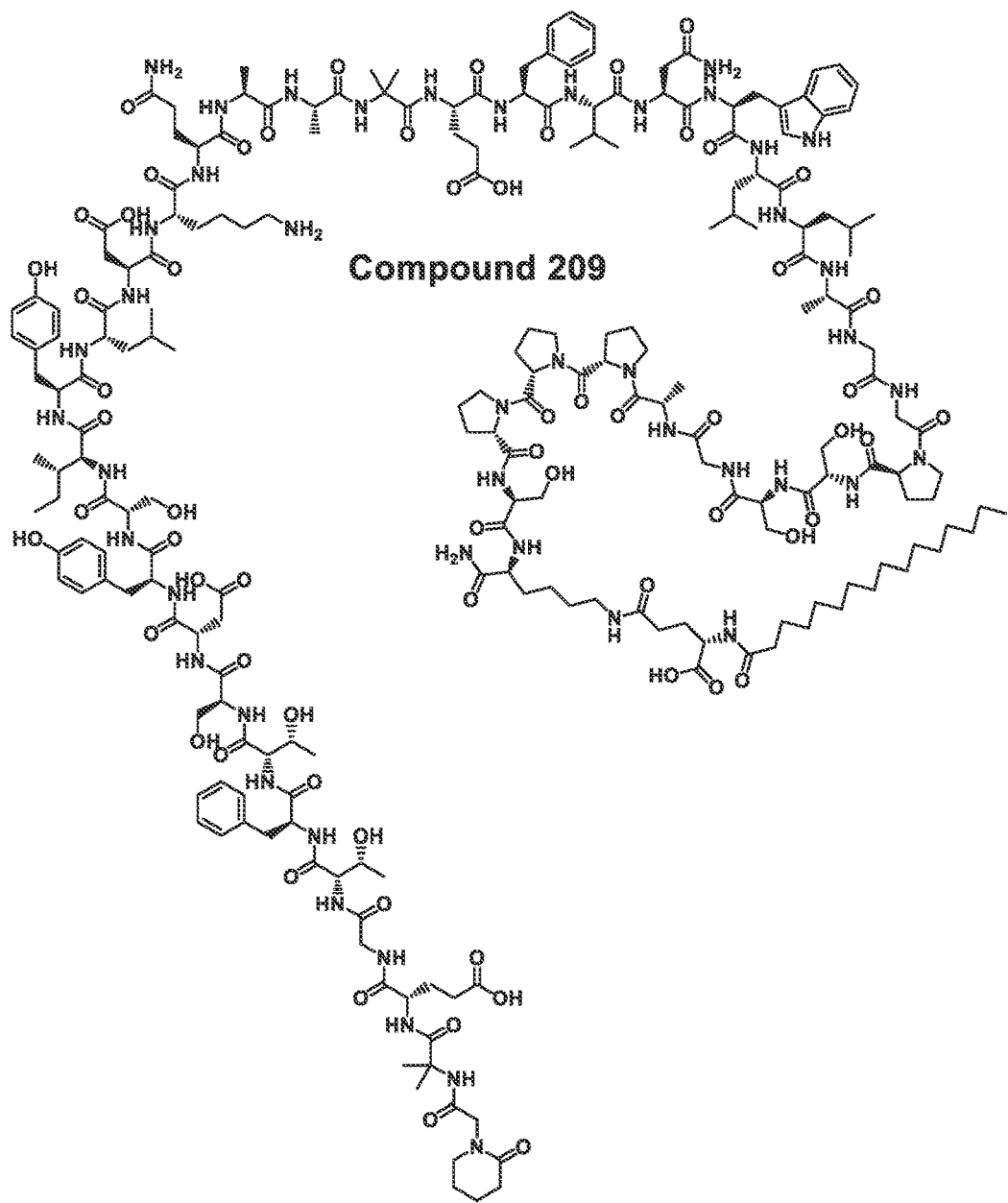
Compound 209
Cont'd

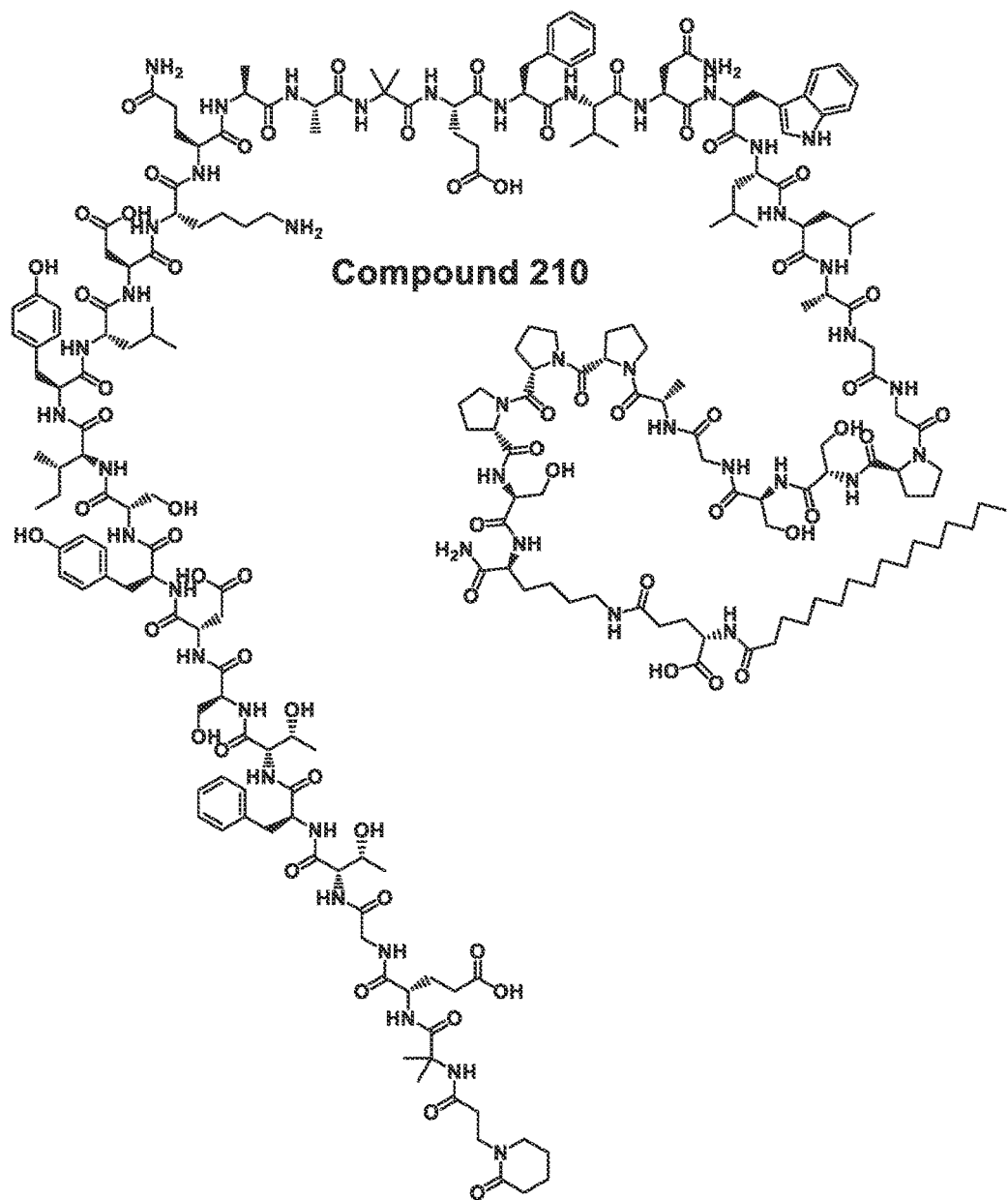

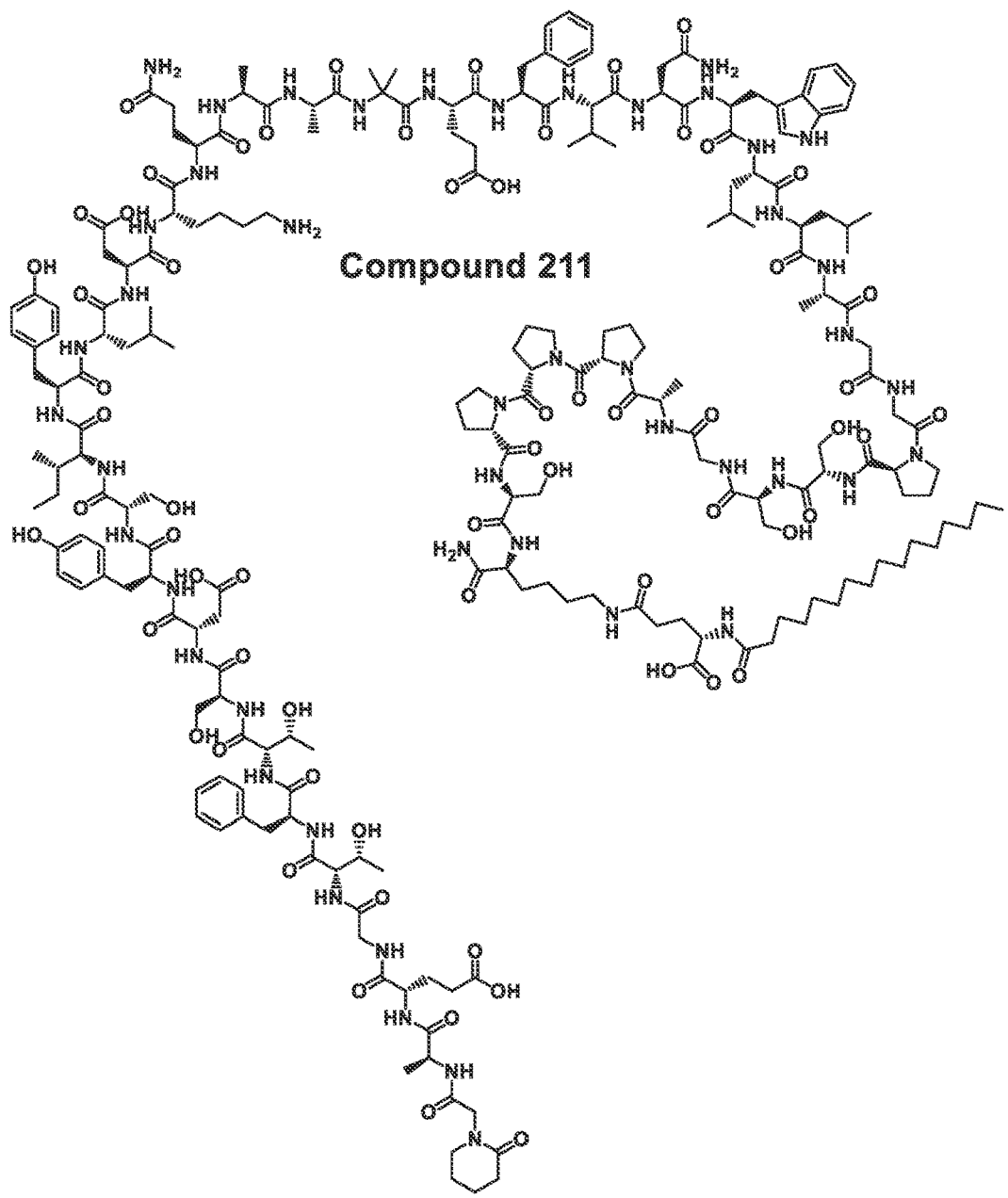
Compound 211
Cont'd

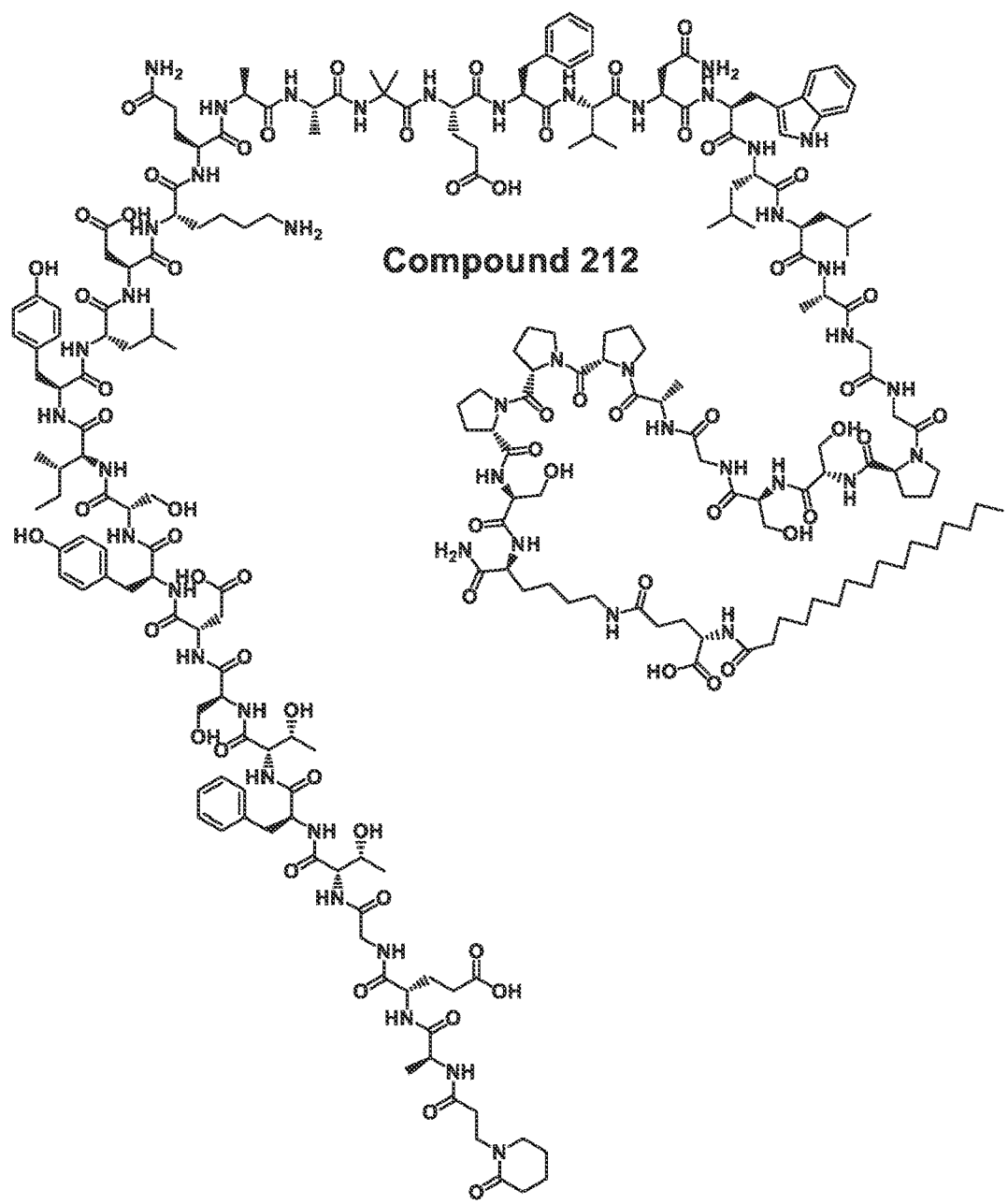
Compound 212
Cont'd

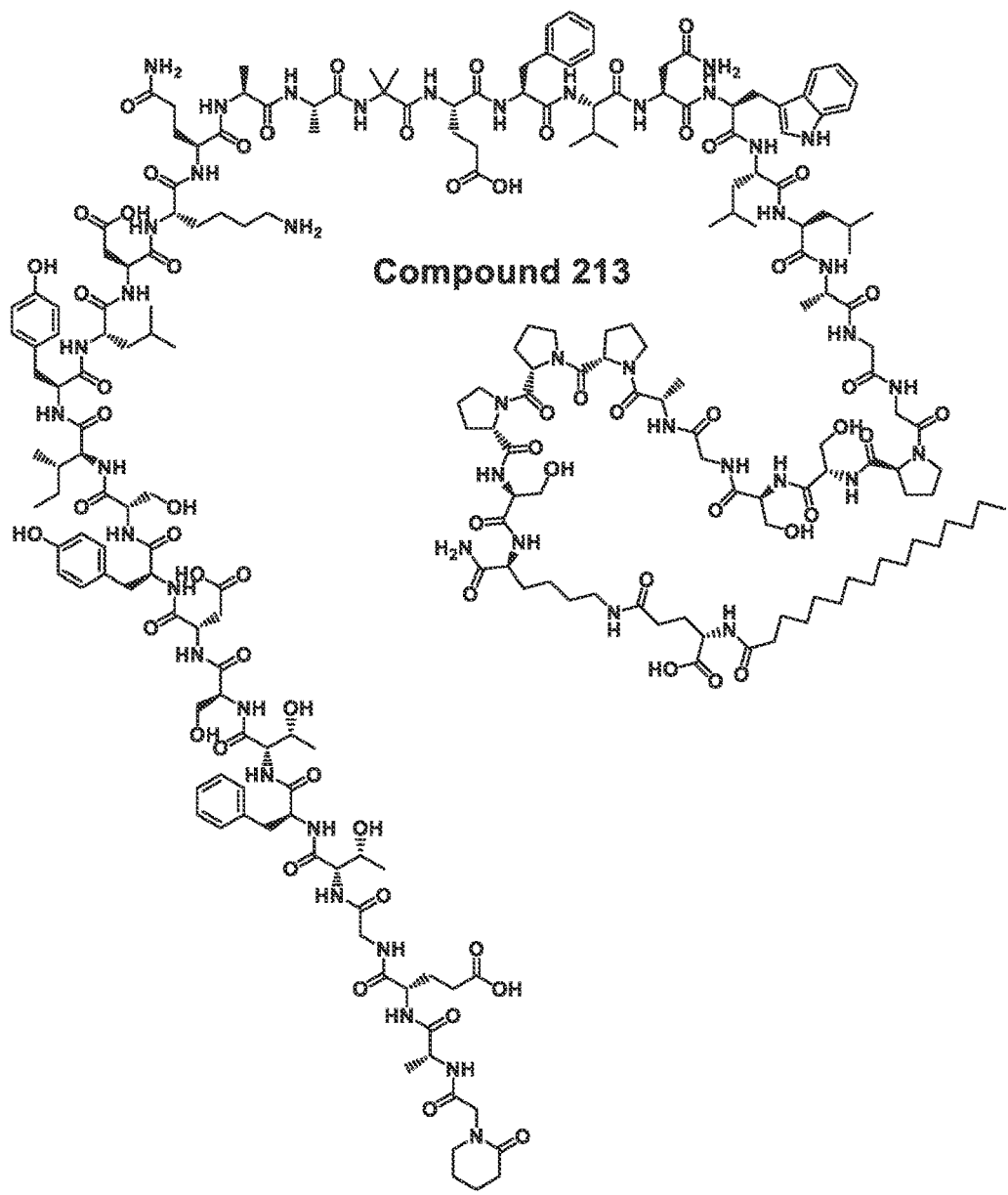
Compound 213
Cont'd

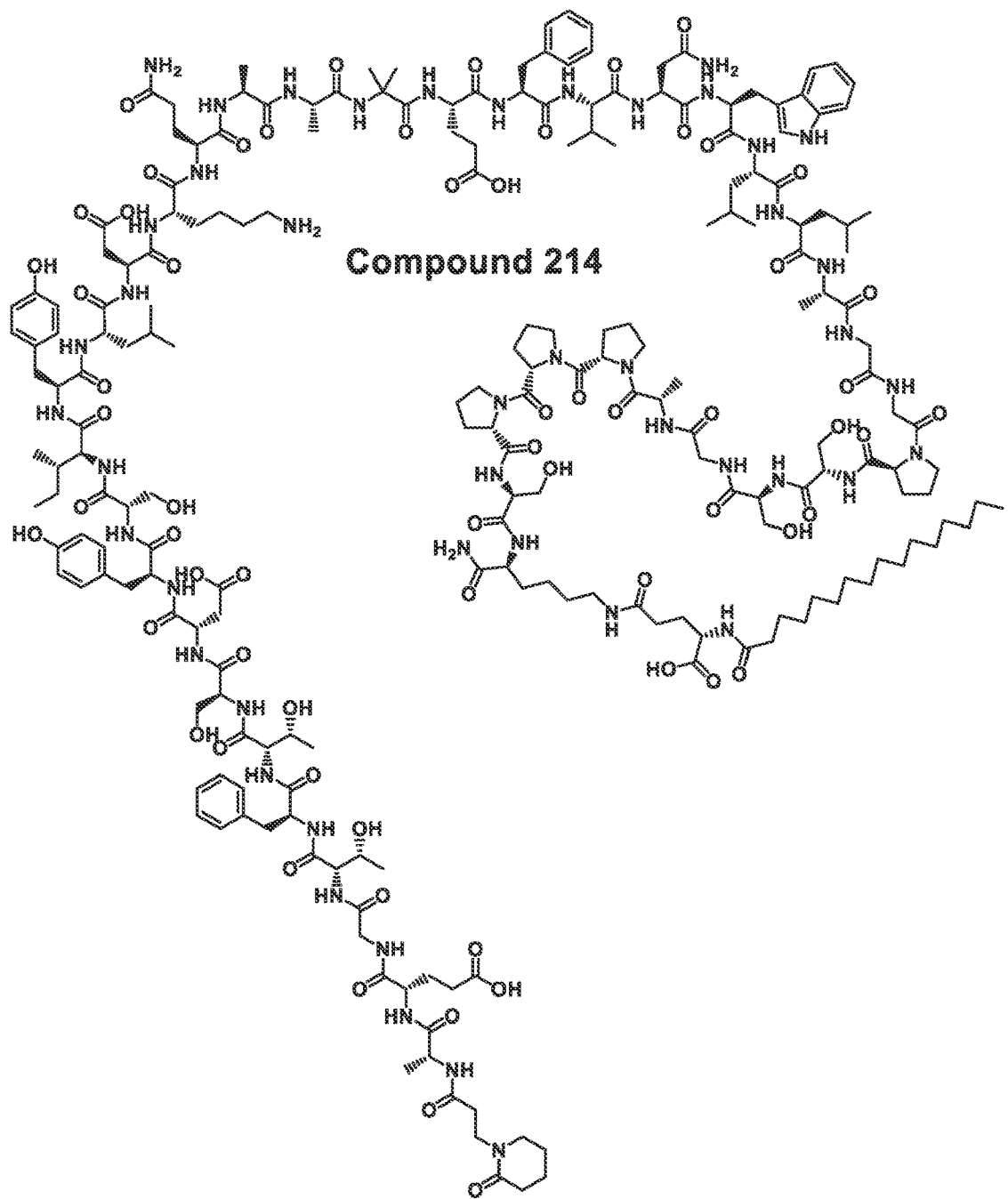
Compound 214
Cont'd

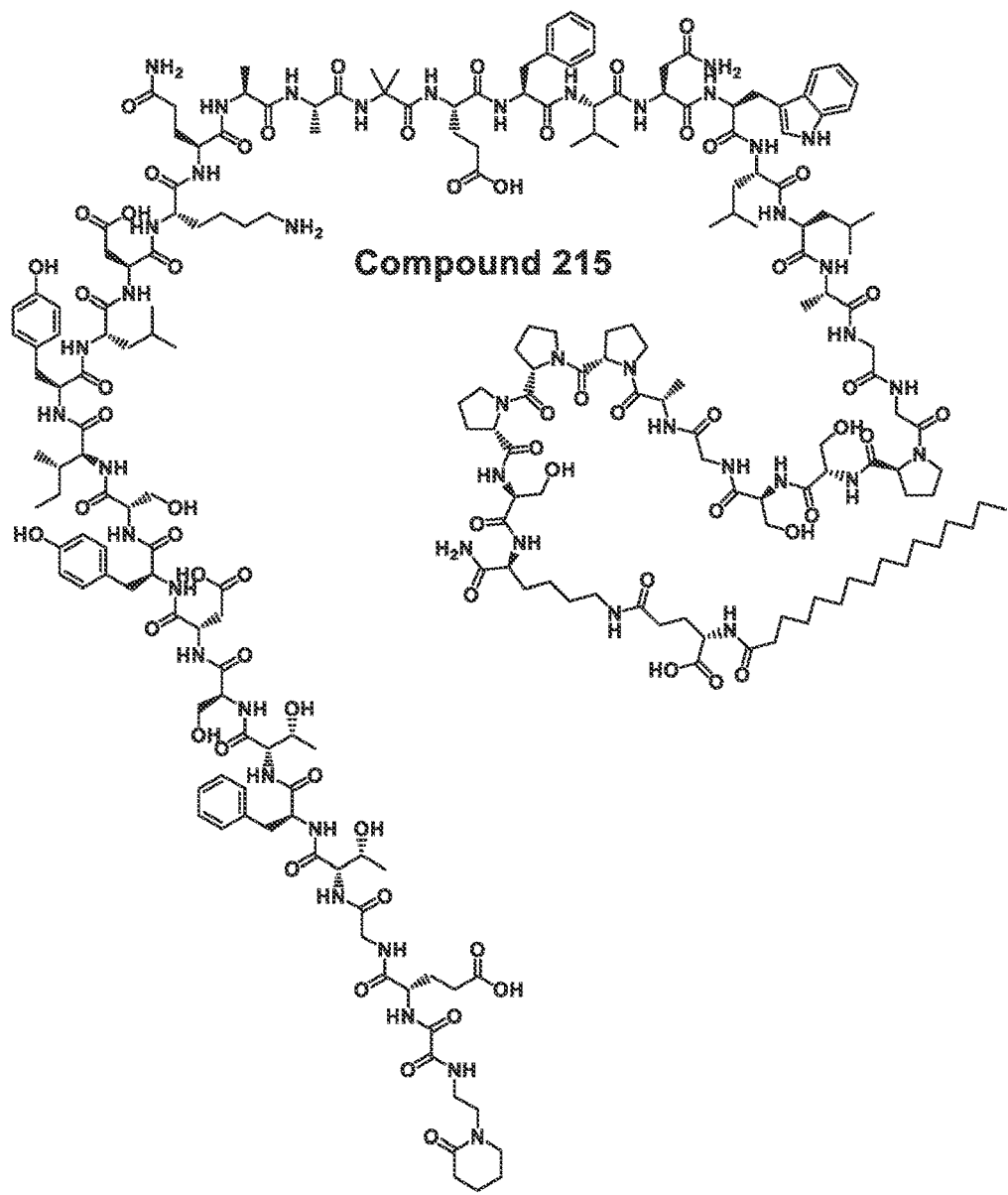
Compound 215
Cont'd

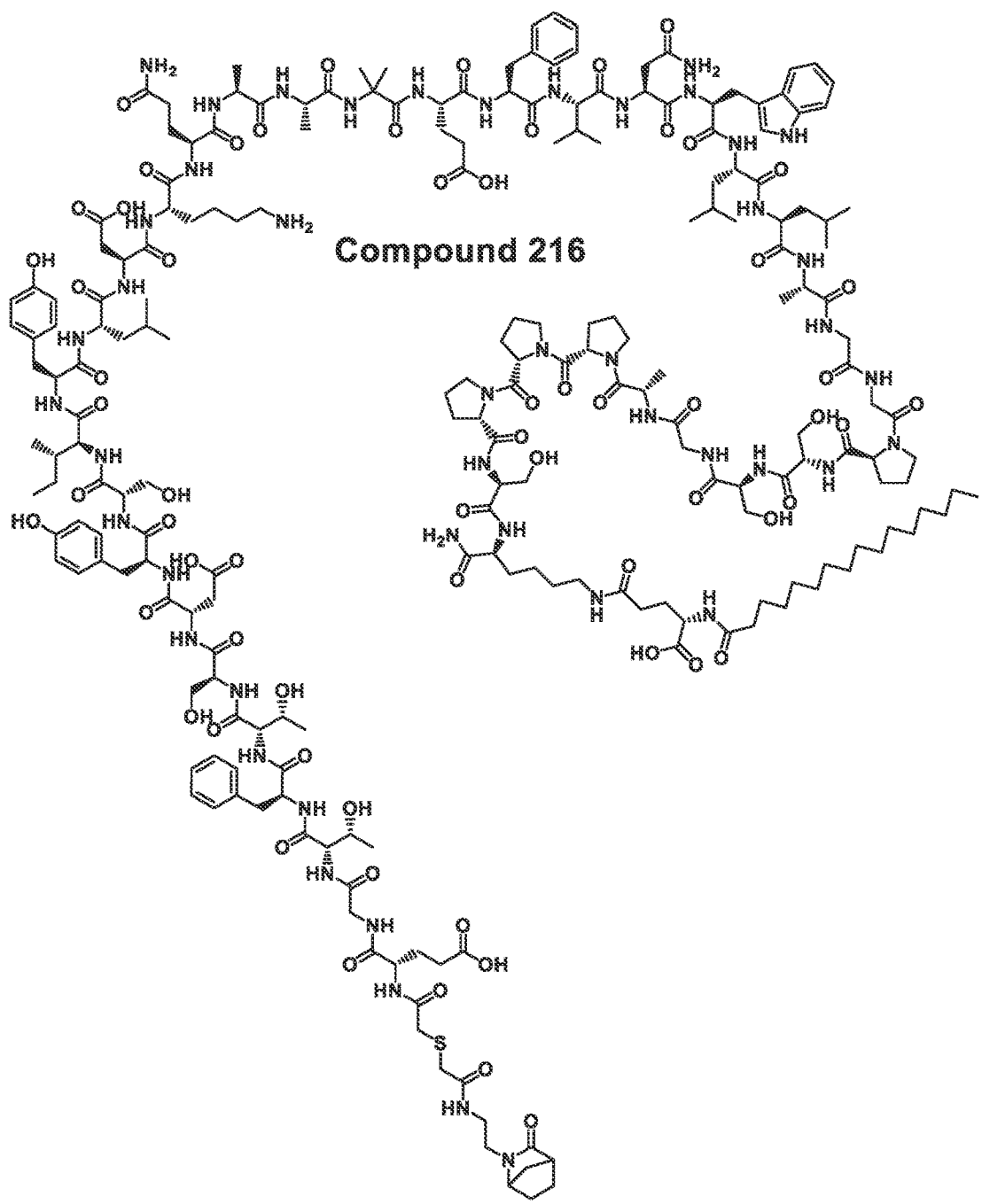
Compound 216
Cont'd

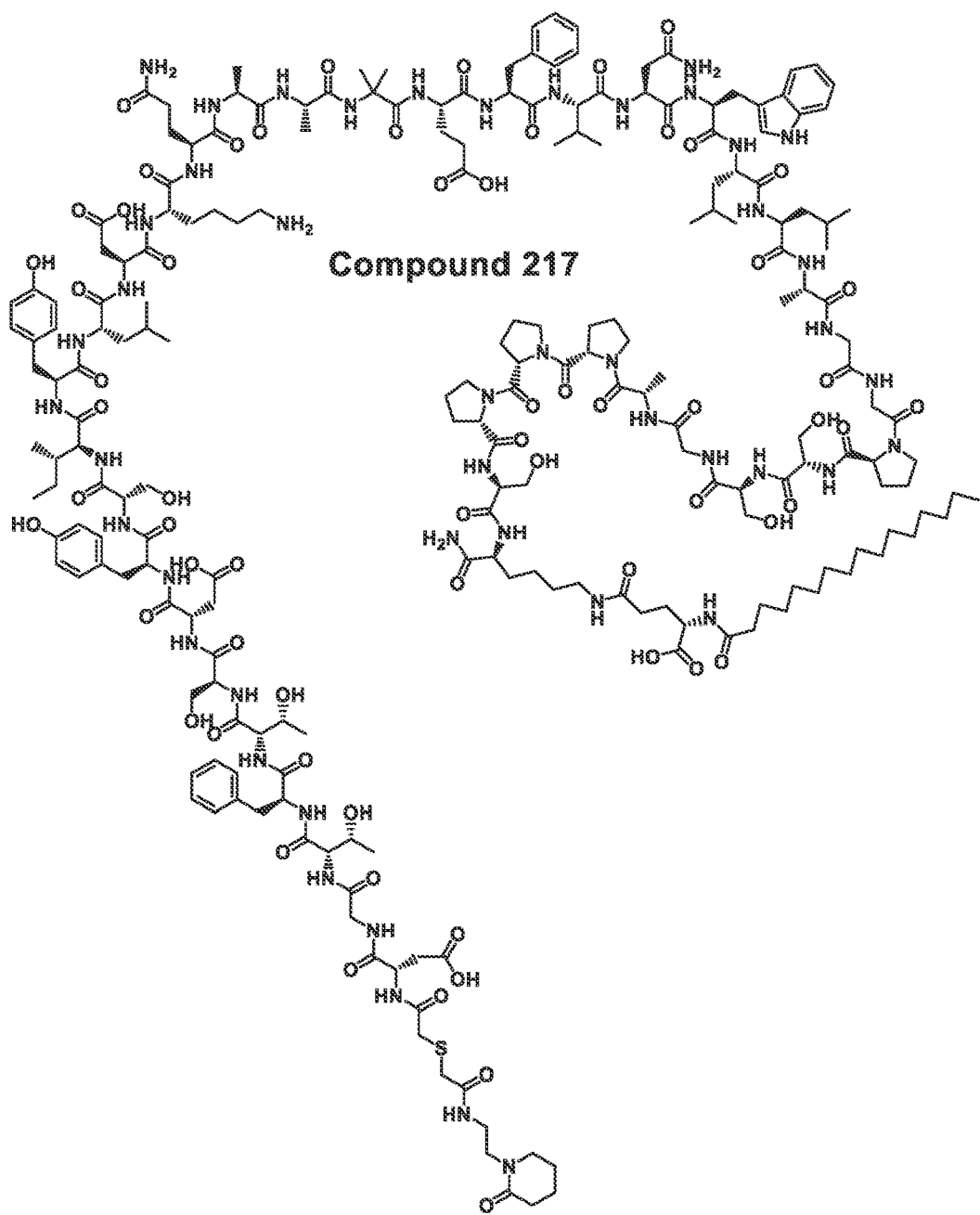
Compound 217
Cont'd

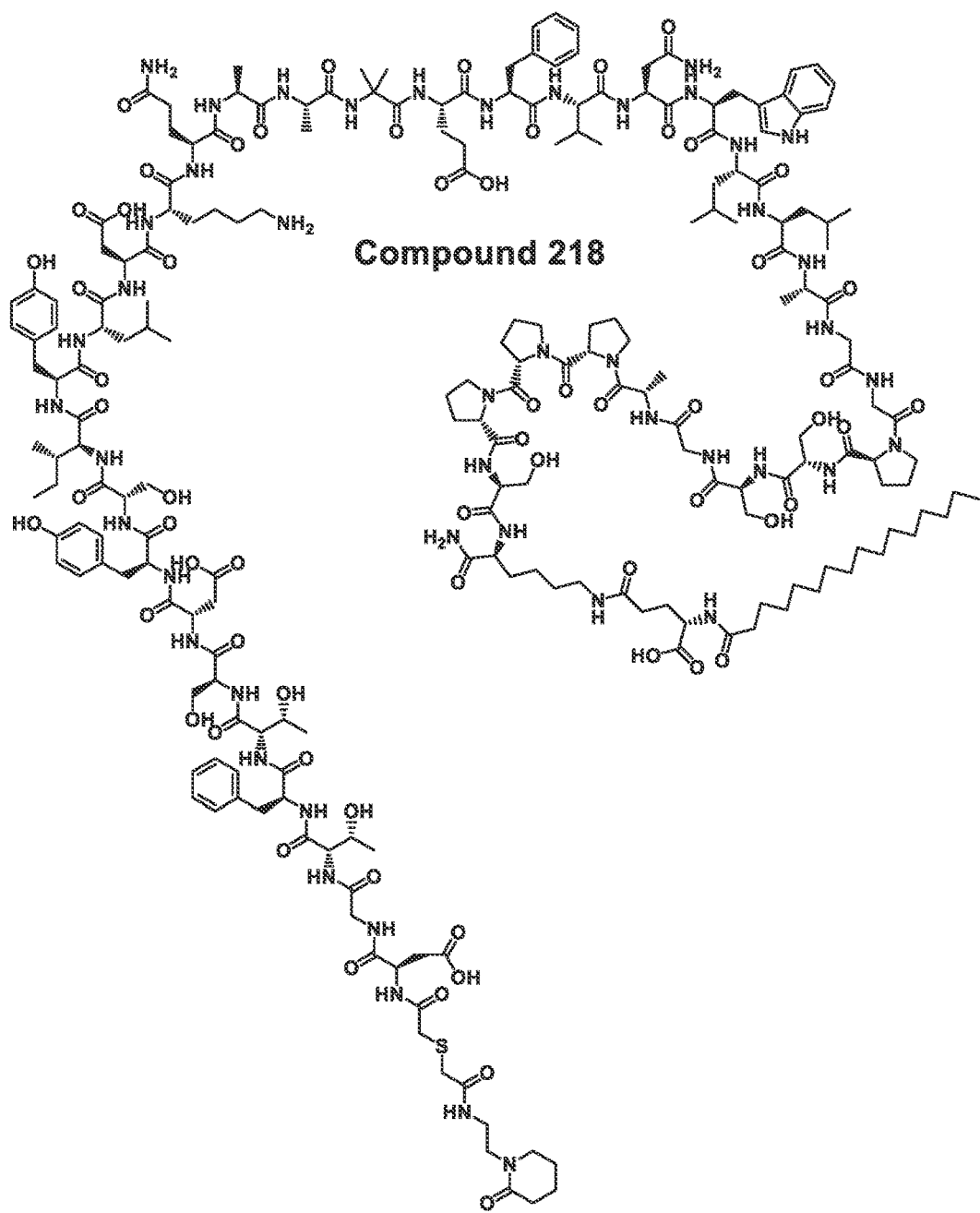
Compound 218
Cont'd

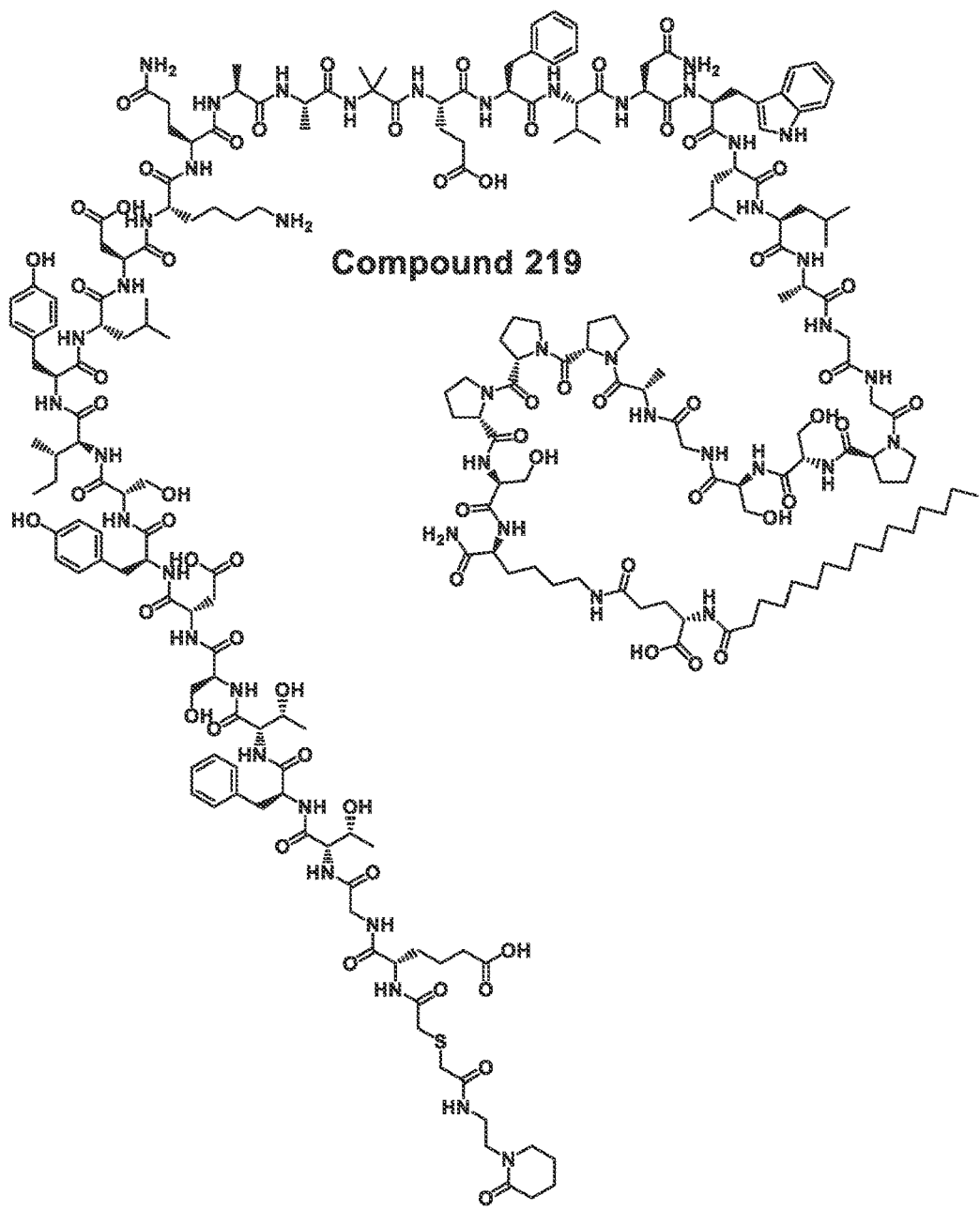
Compound 219
Cont'd

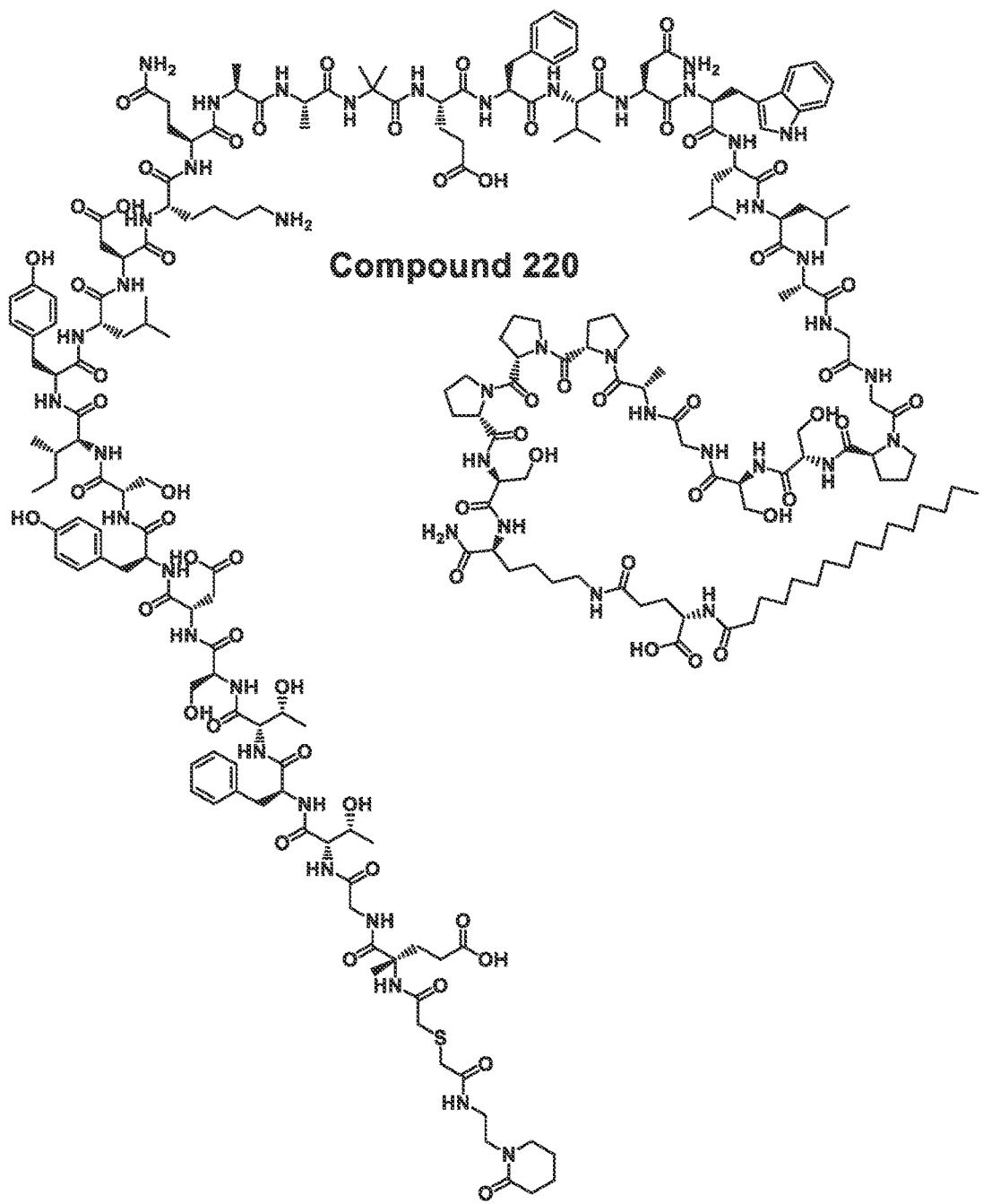
Compound 220
Cont'd

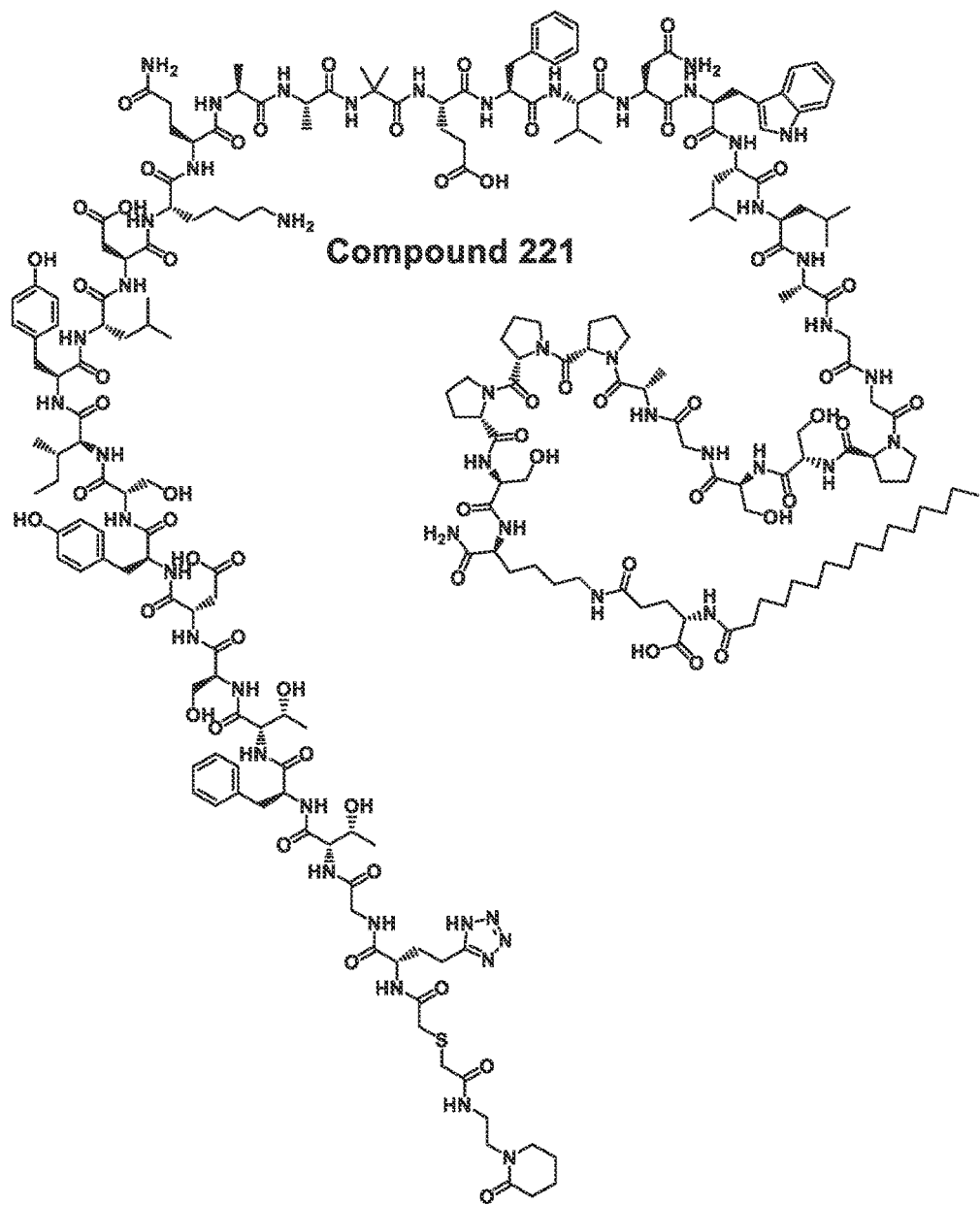
Compound 221
Cont'd

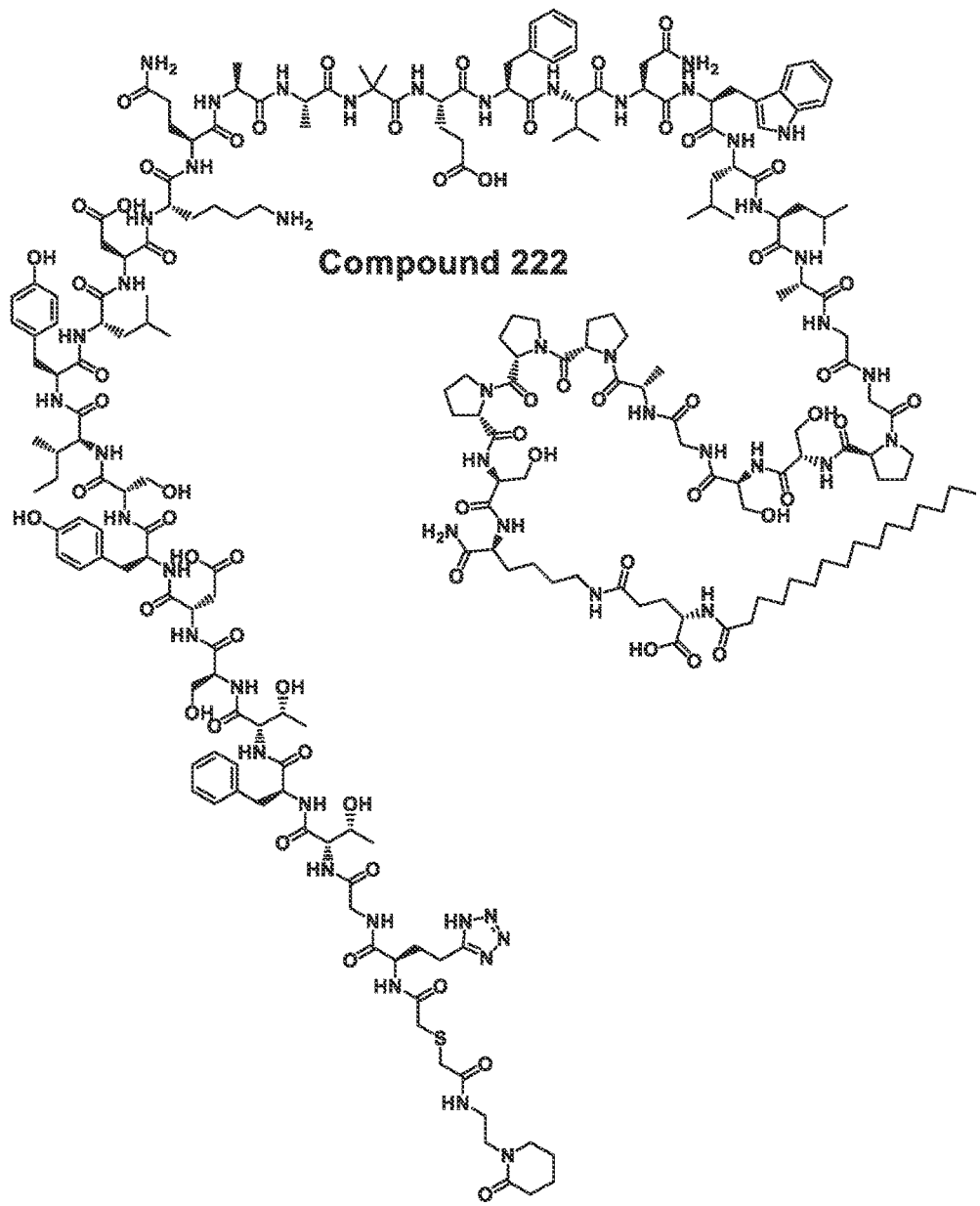
Compound 222
Cont'd

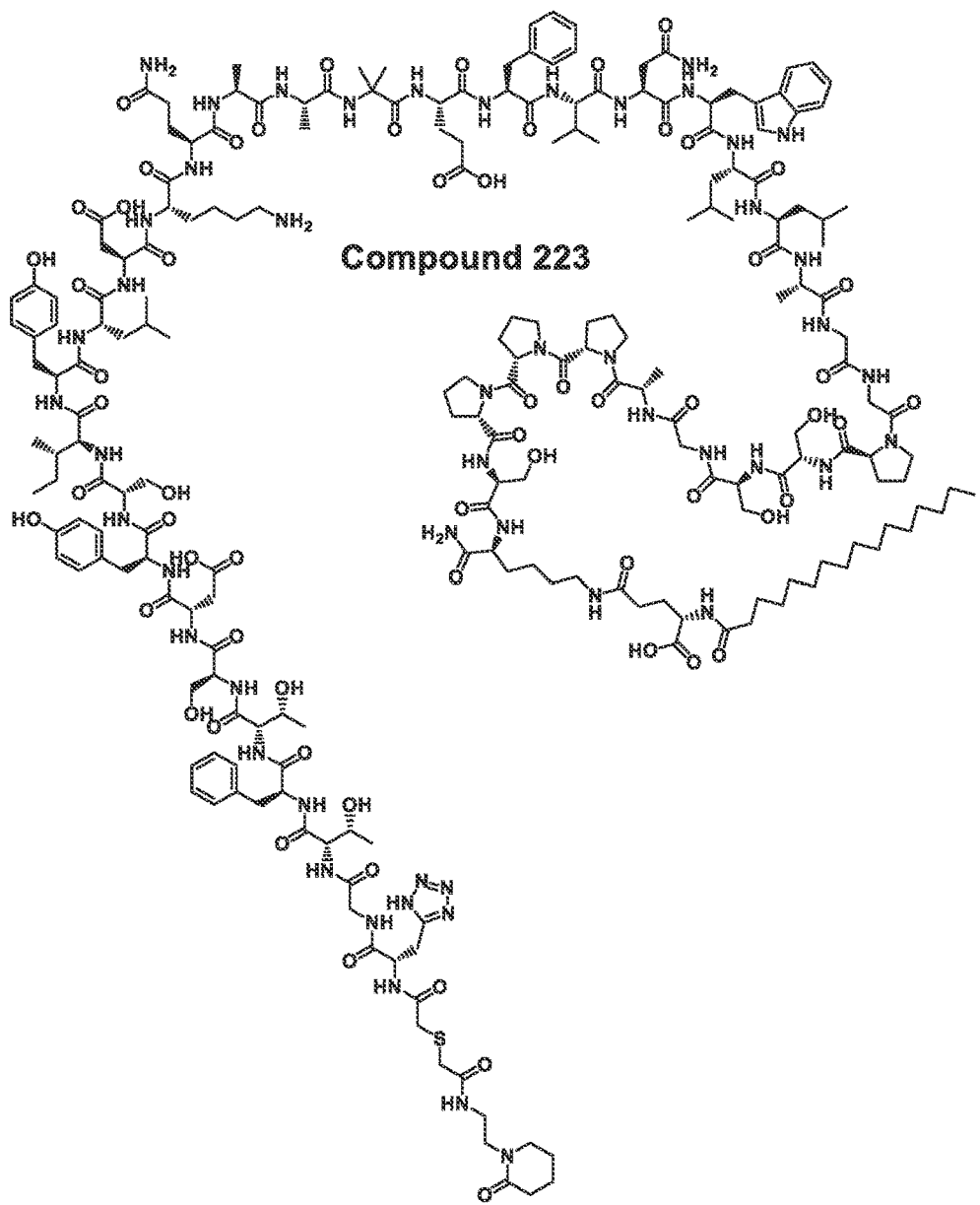
Compound 223
Cont'd

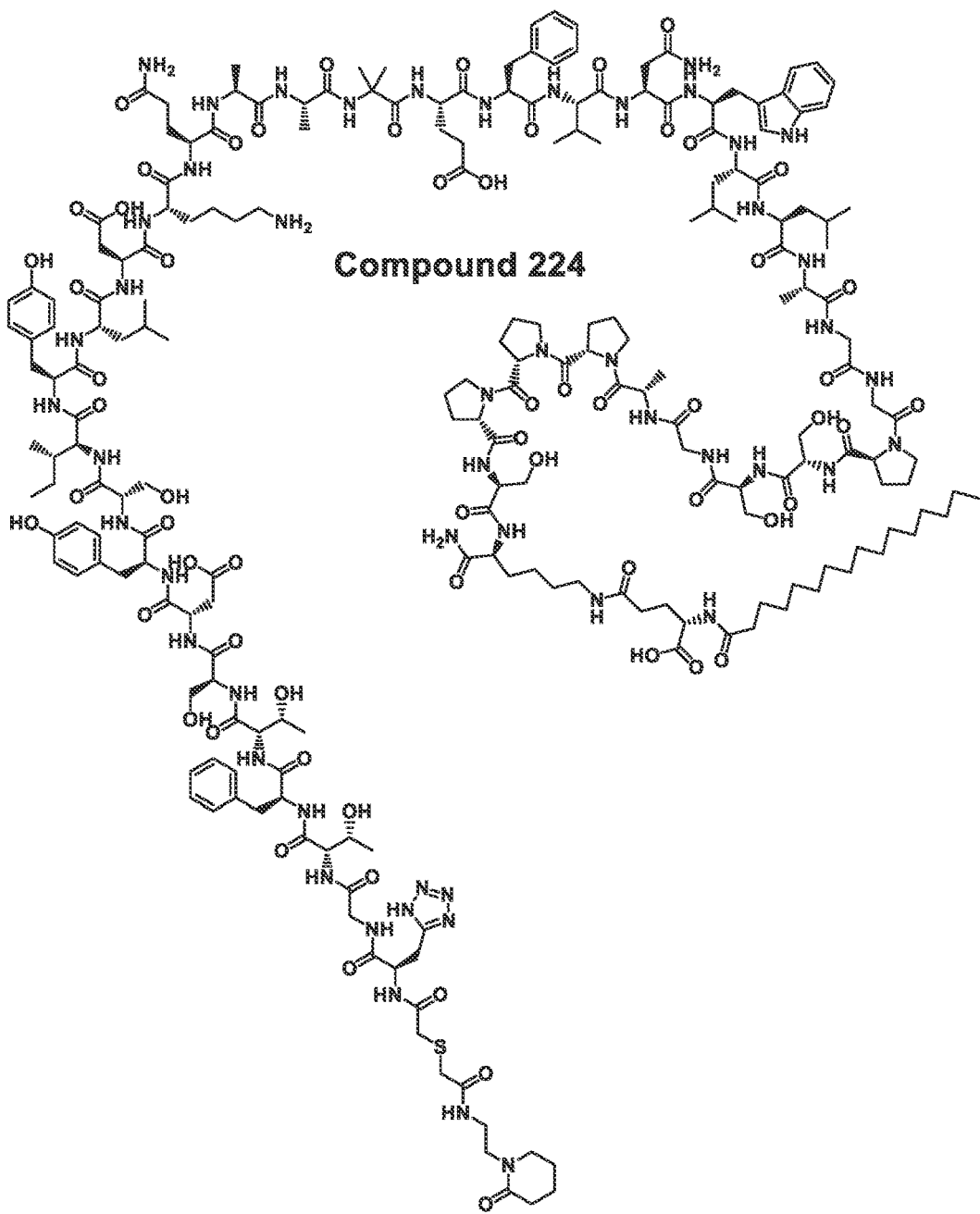
Compound 224
Cont'd

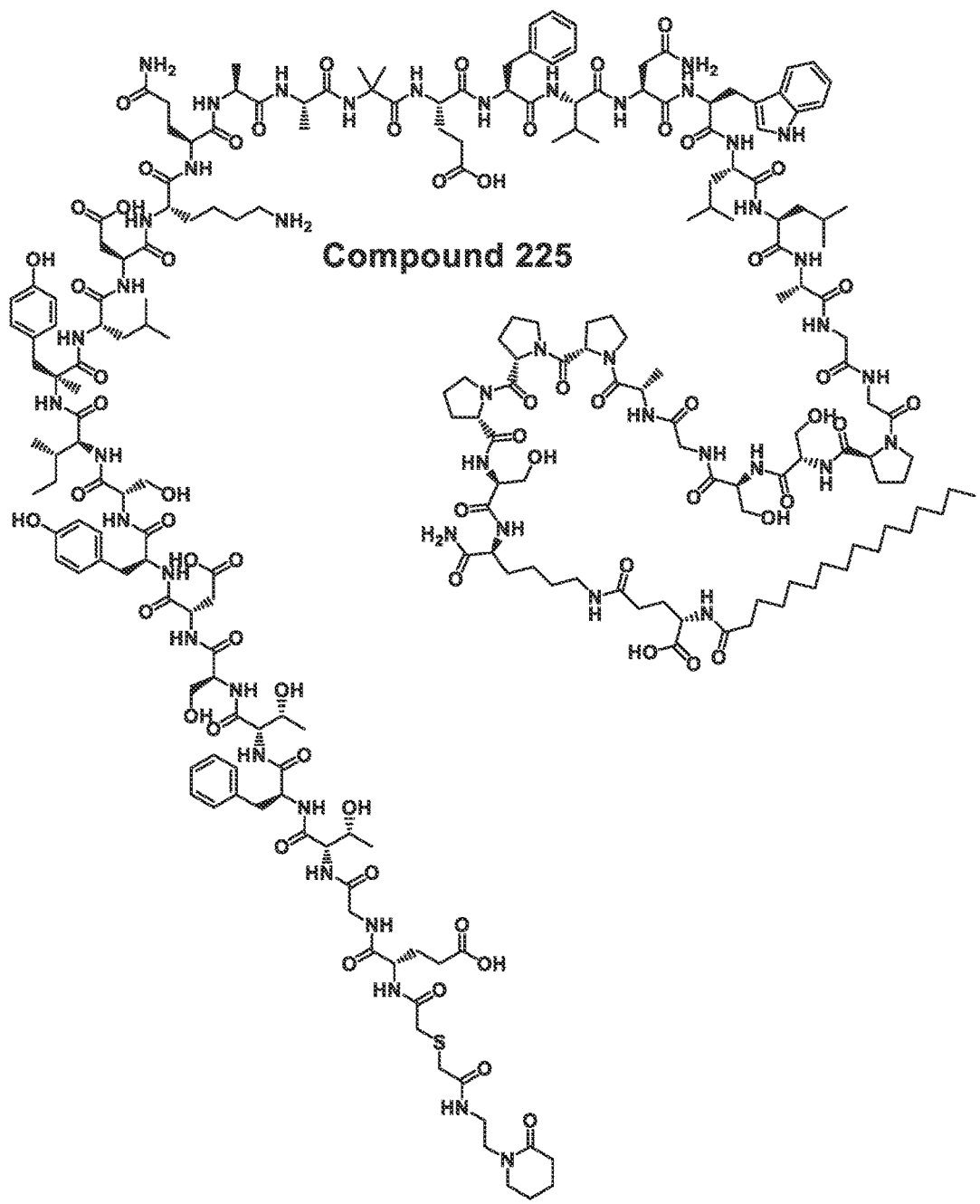
Compound 225
Cont'd

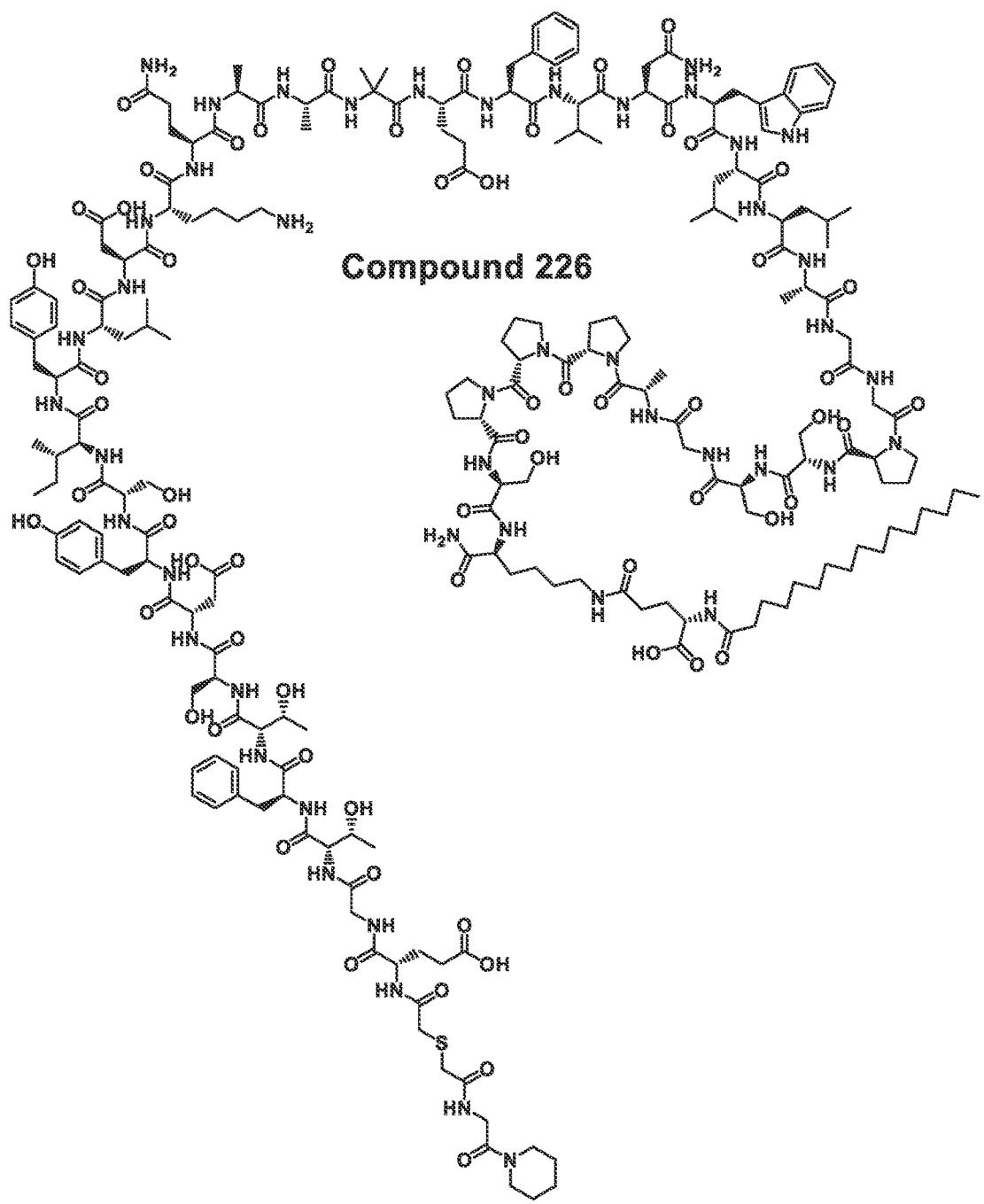
Compound 226
Cont'd

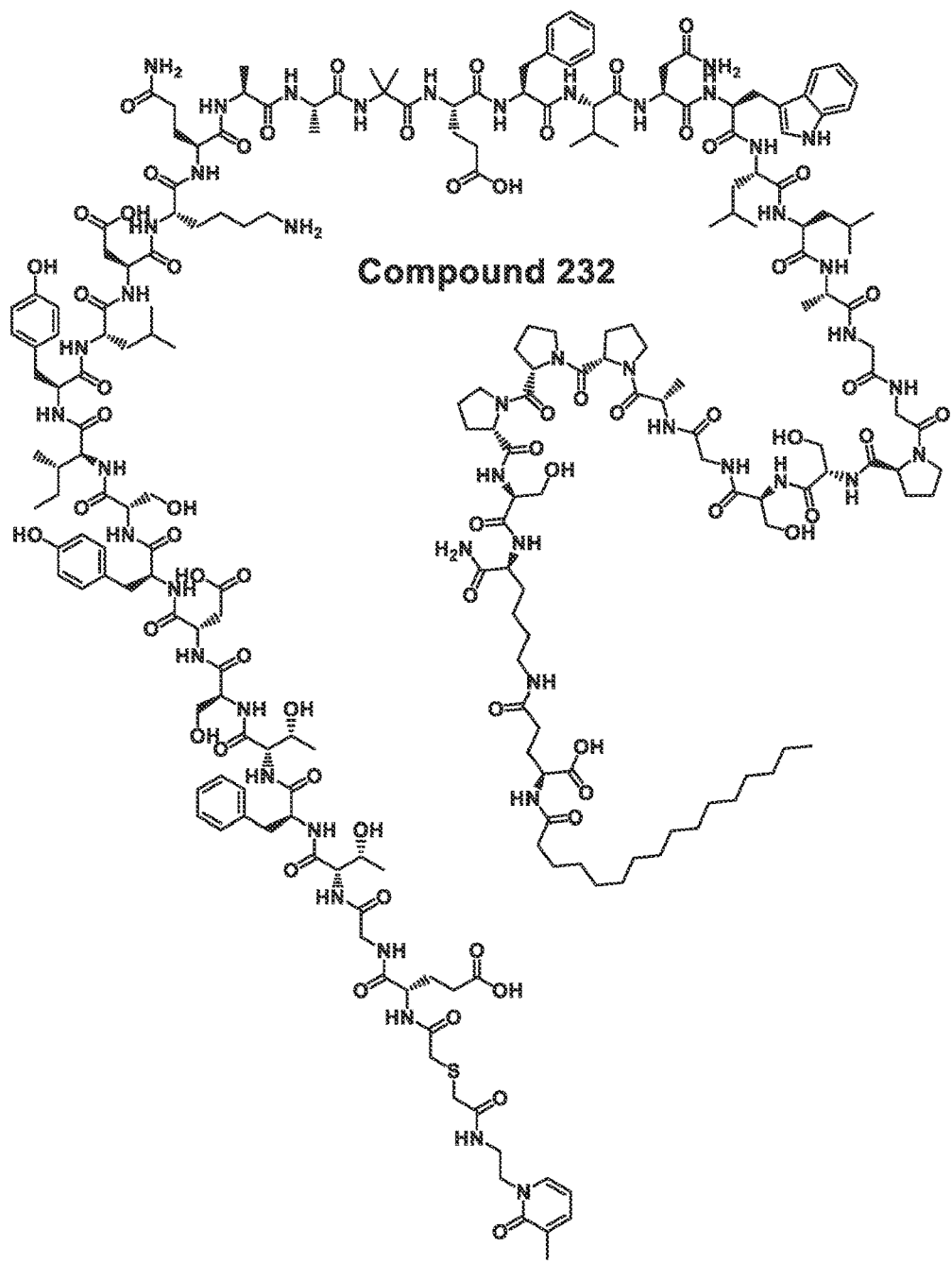
Compound 232
Cont'd

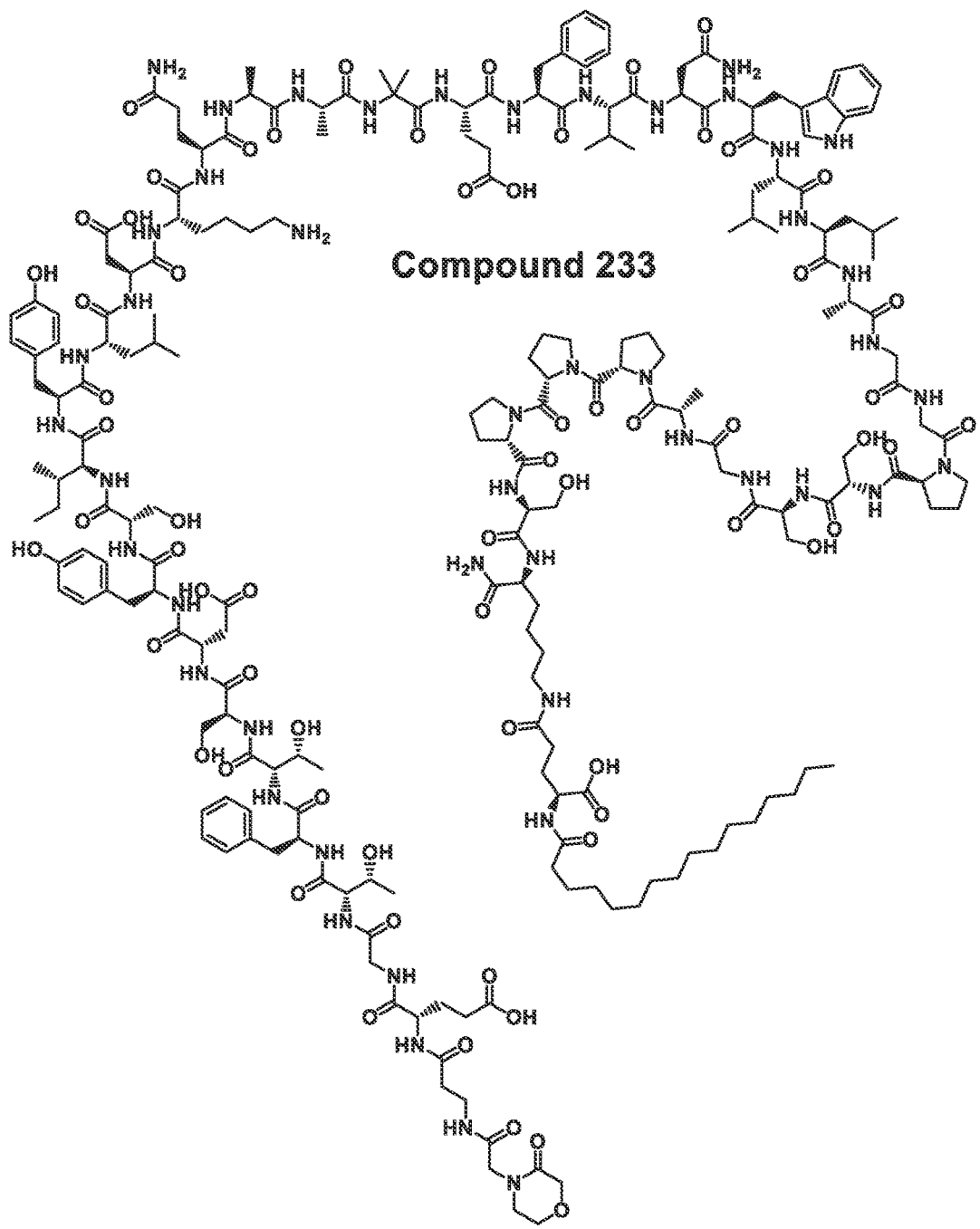
Compound 233
Cont'd

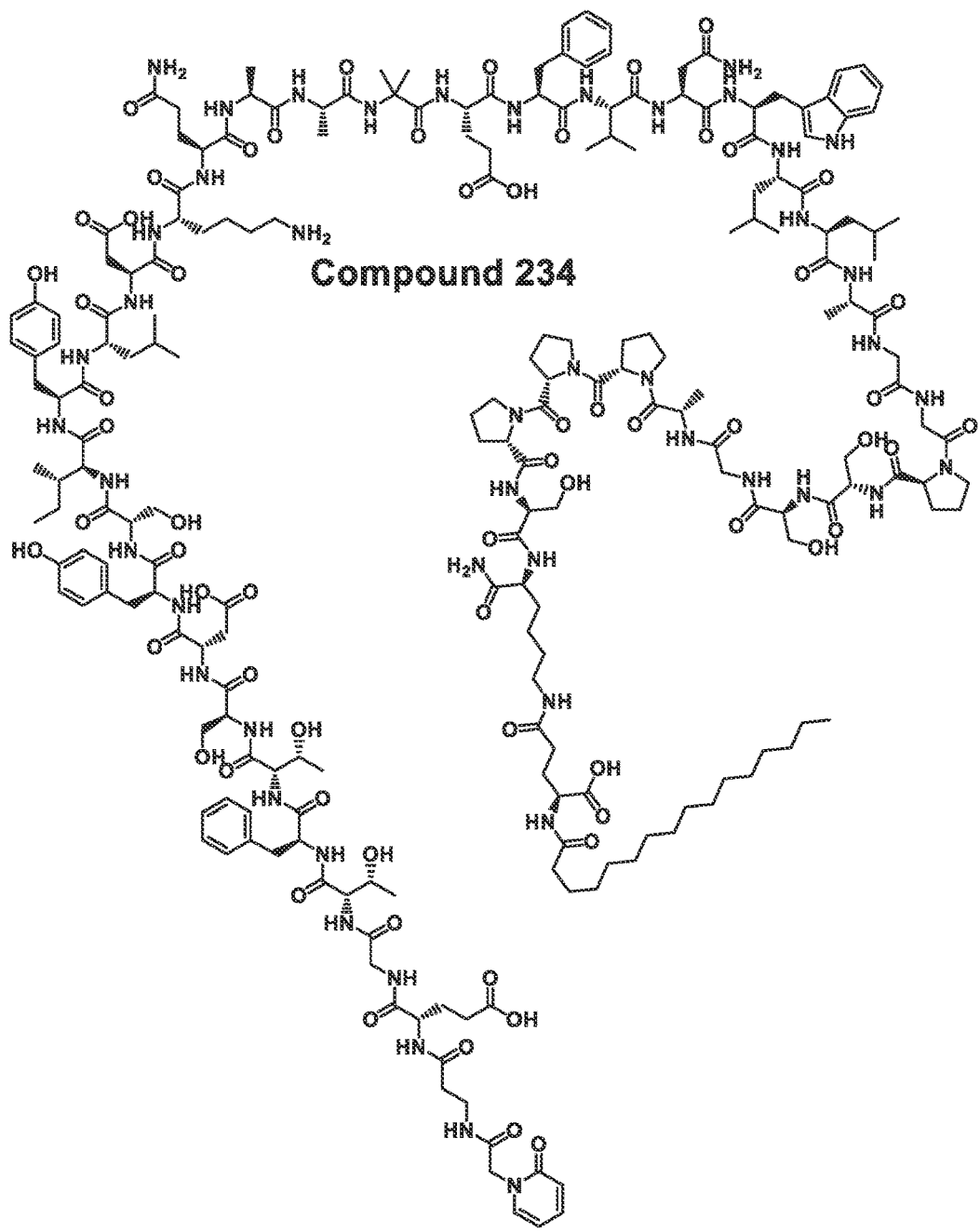
Compound 234
Cont'd

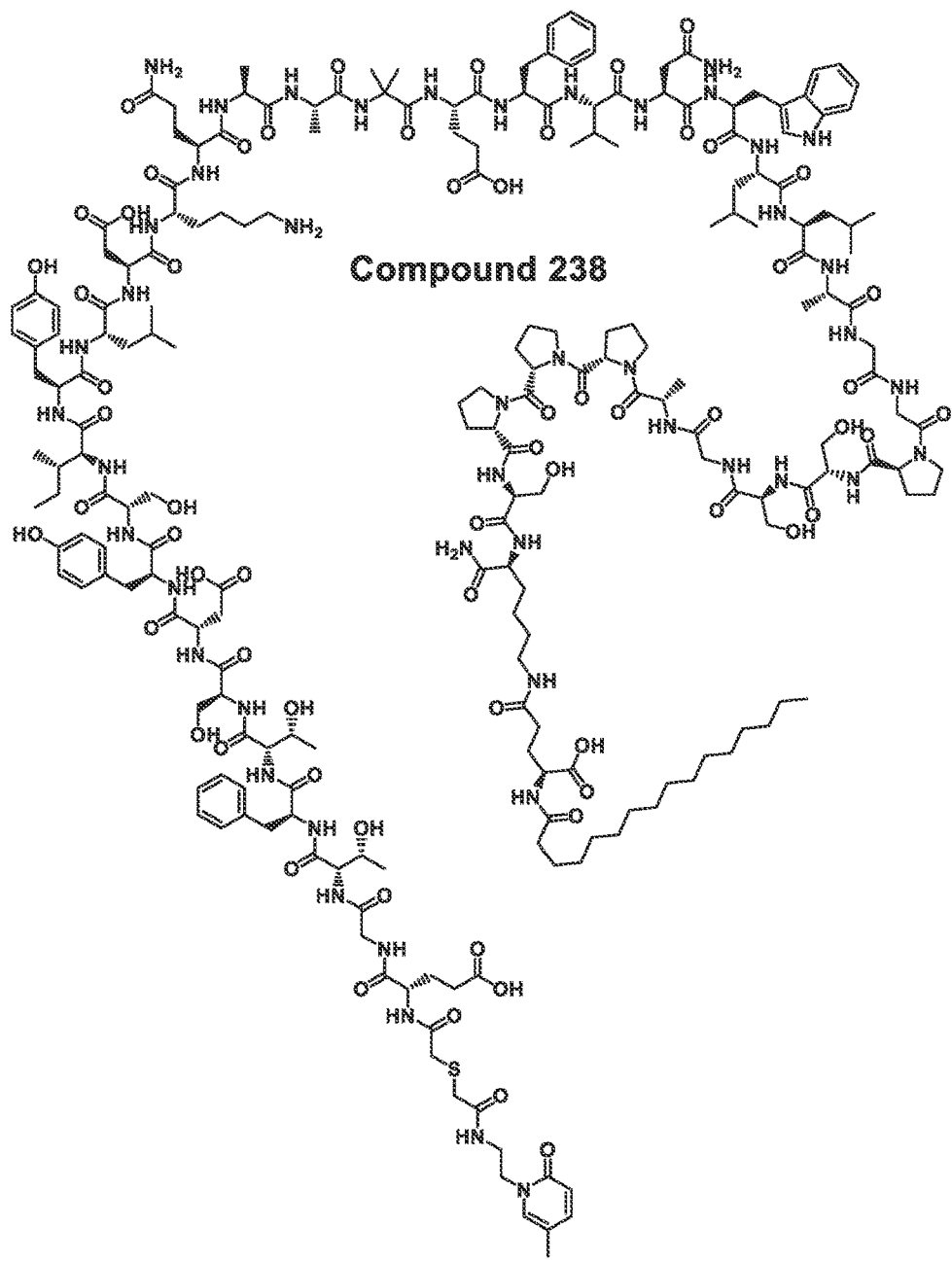
Compound 238
Cont'd

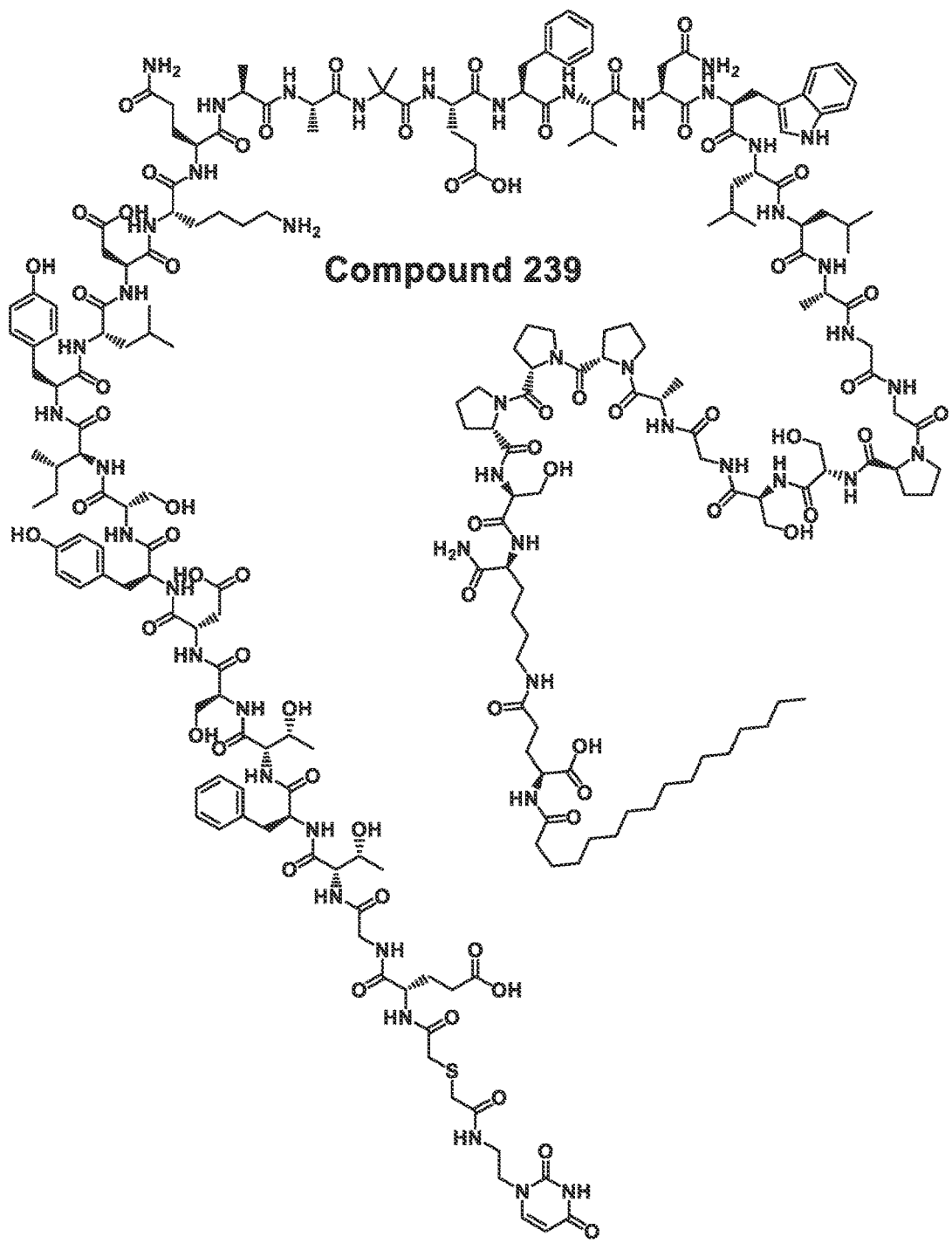
Compound 239
Cont'd

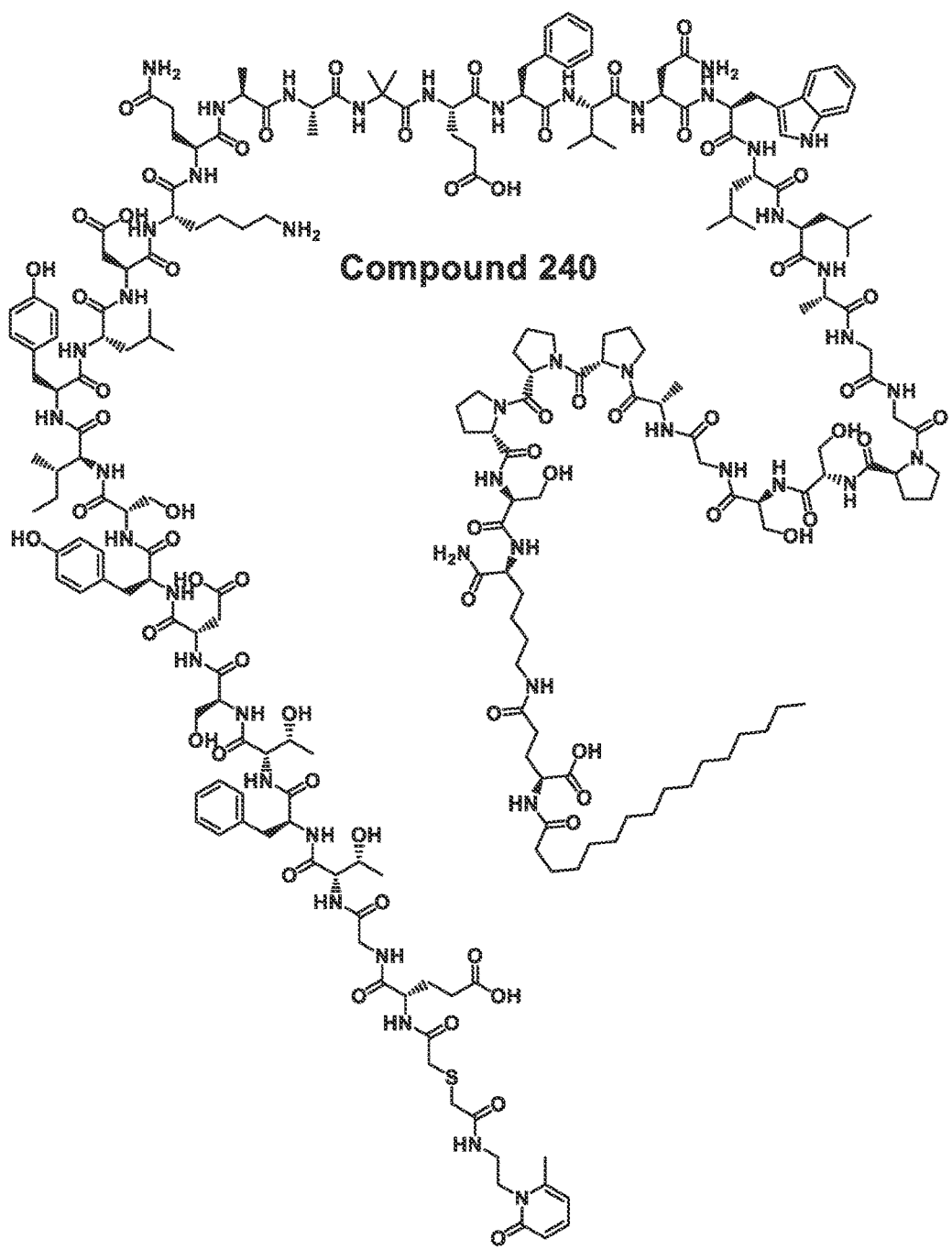
Compound 240
Cont'd

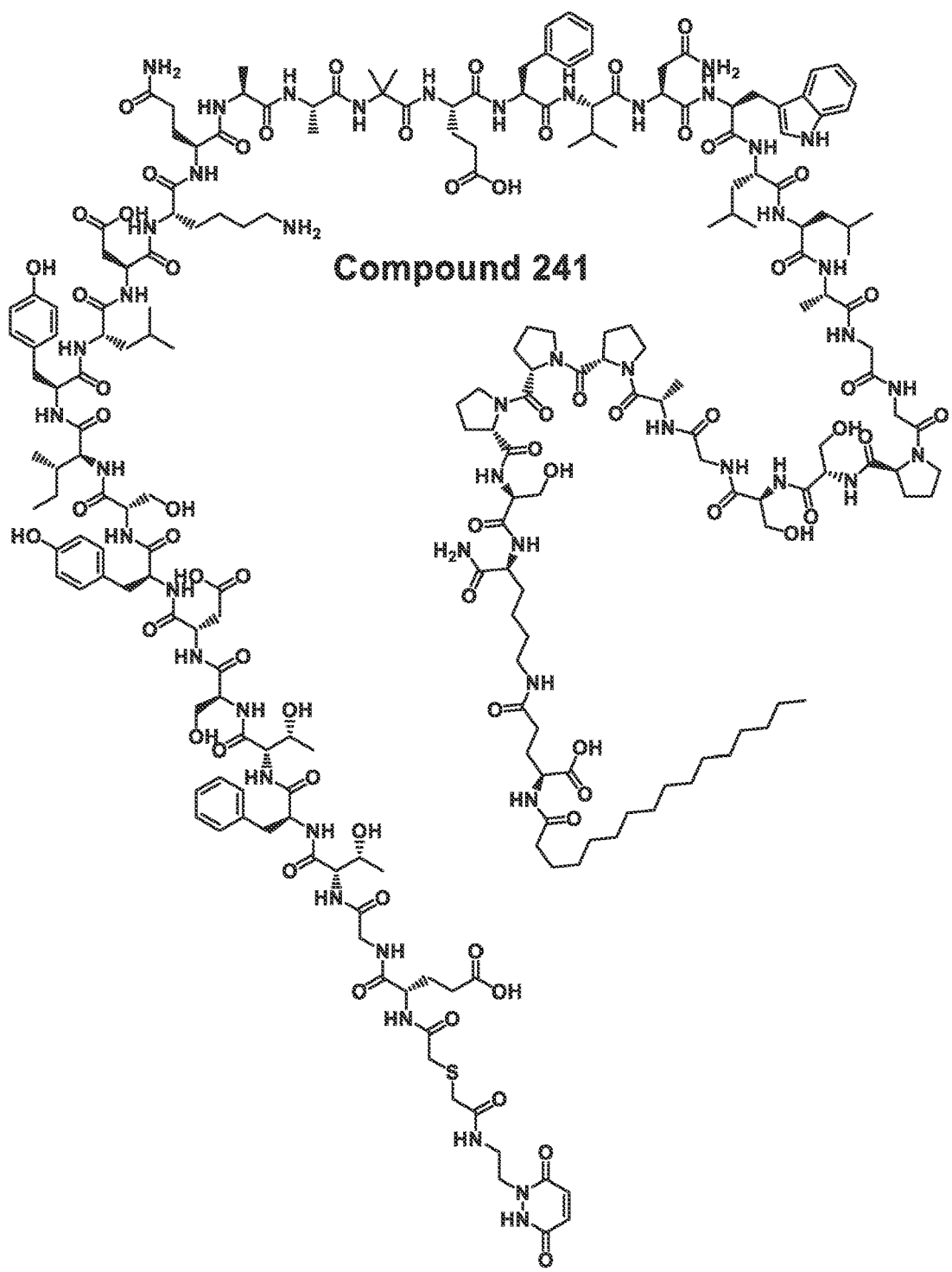
Compound 241
Cont'd

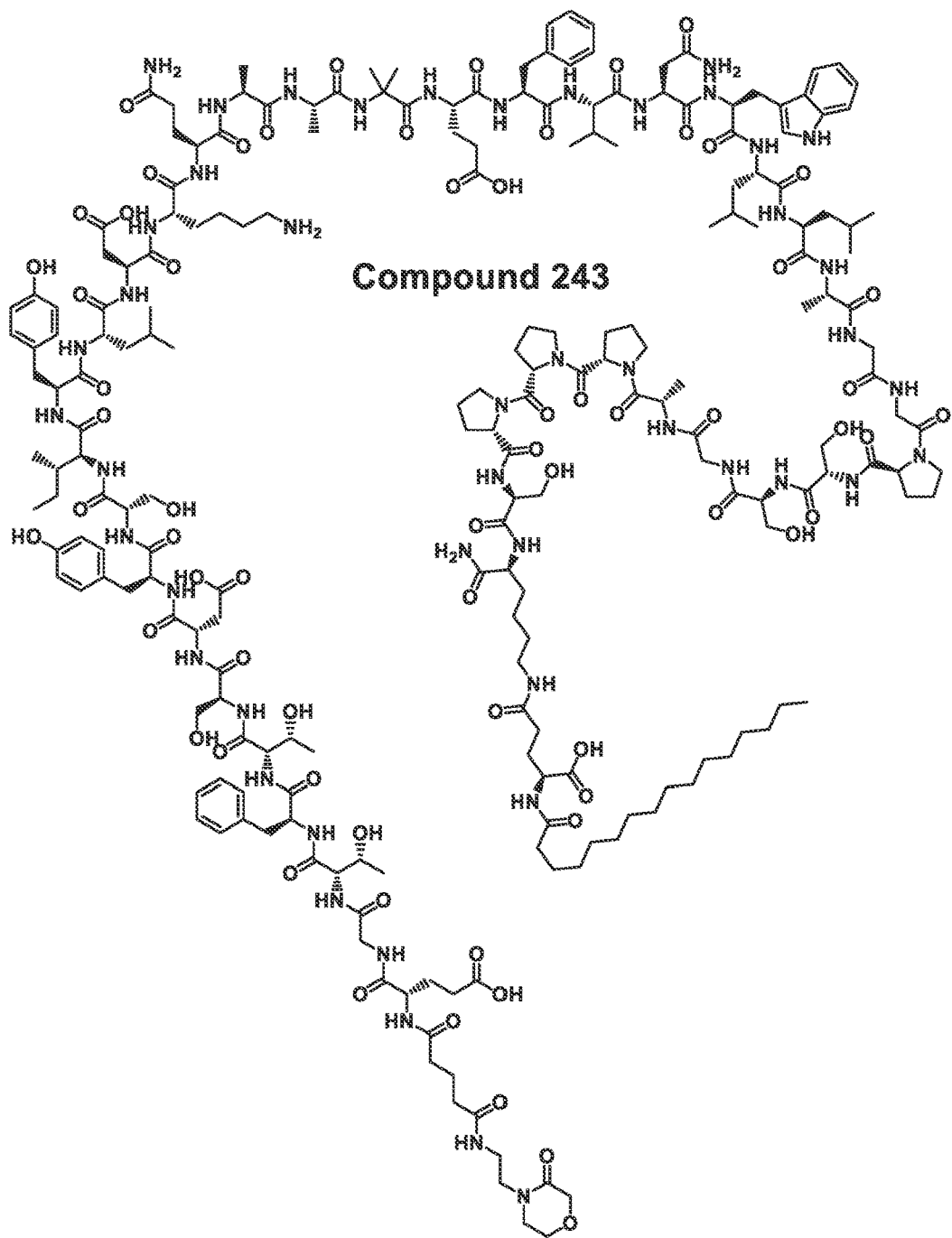
Compound 243
Cont'd

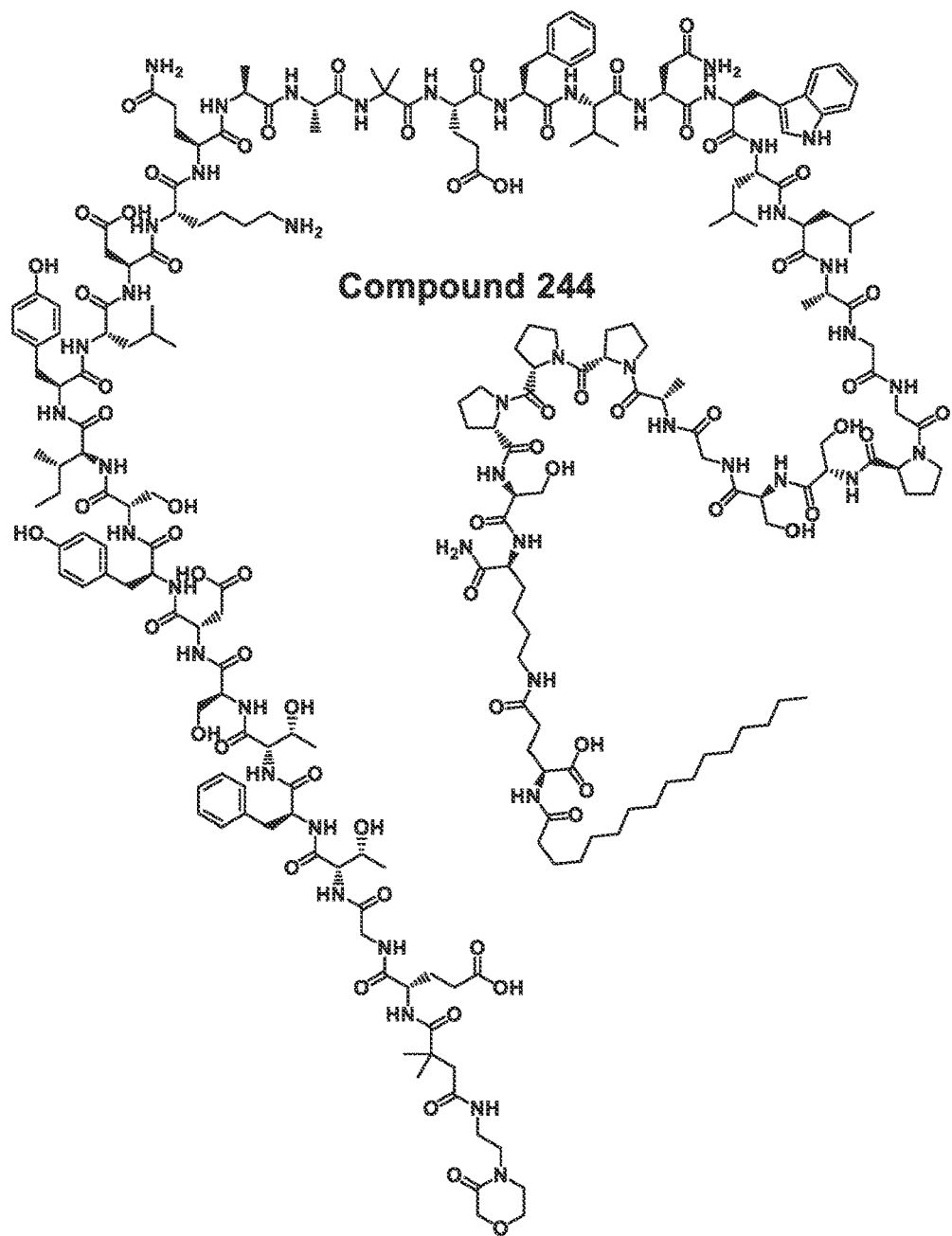
Compound 244
Cont'd

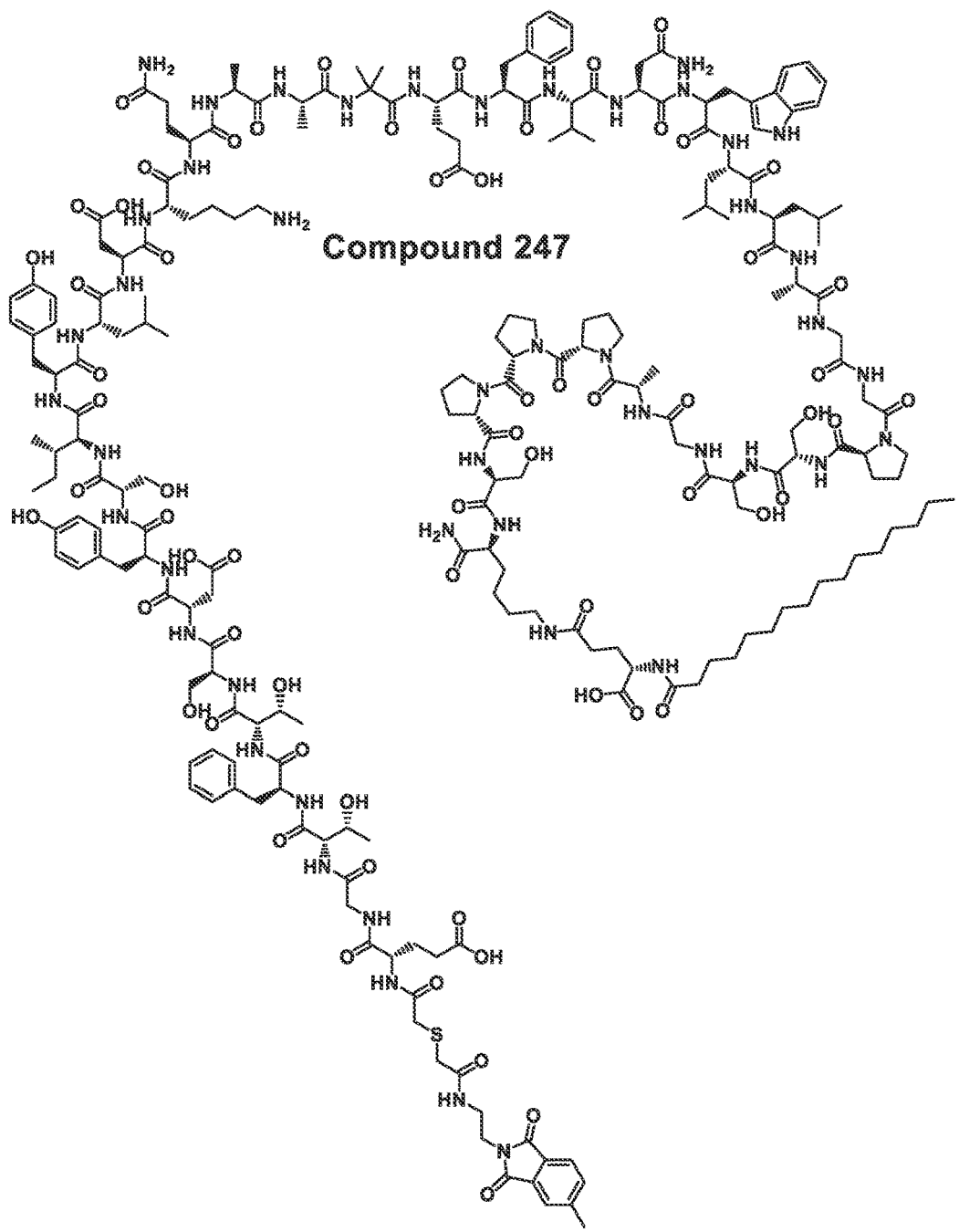
Compound 247
Cont'd

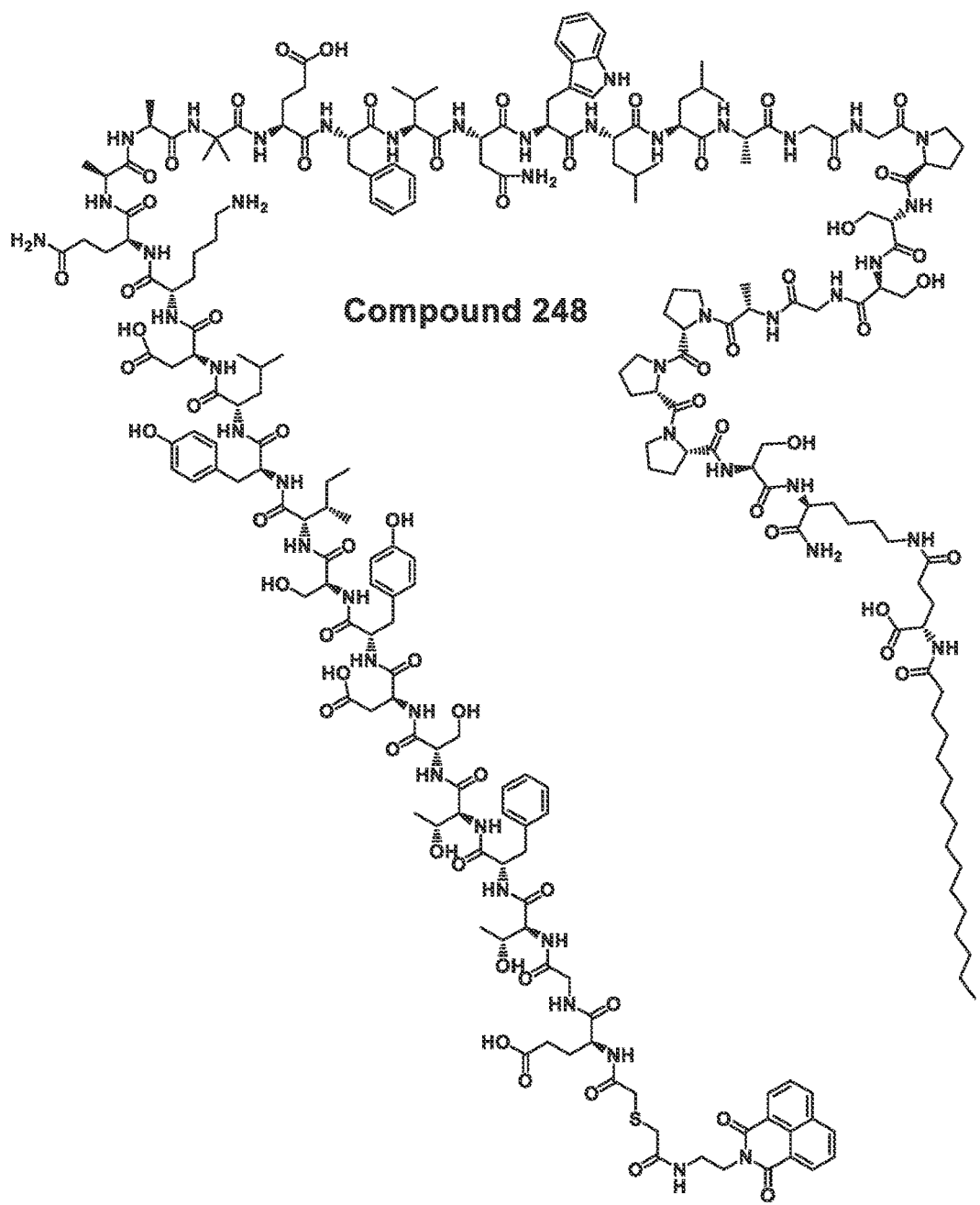
Compound 248
Cont'd

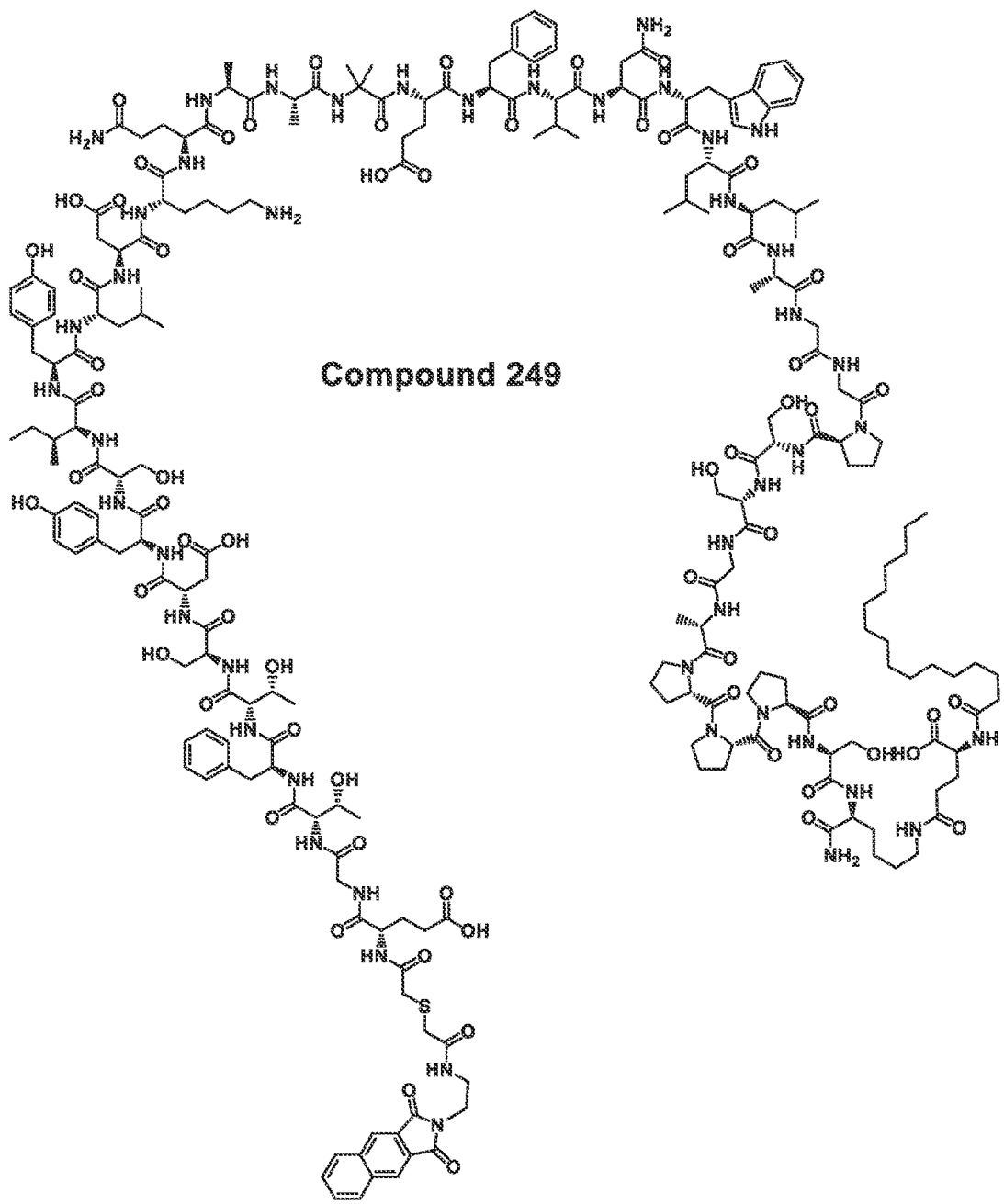
Compound 249
Cont'd

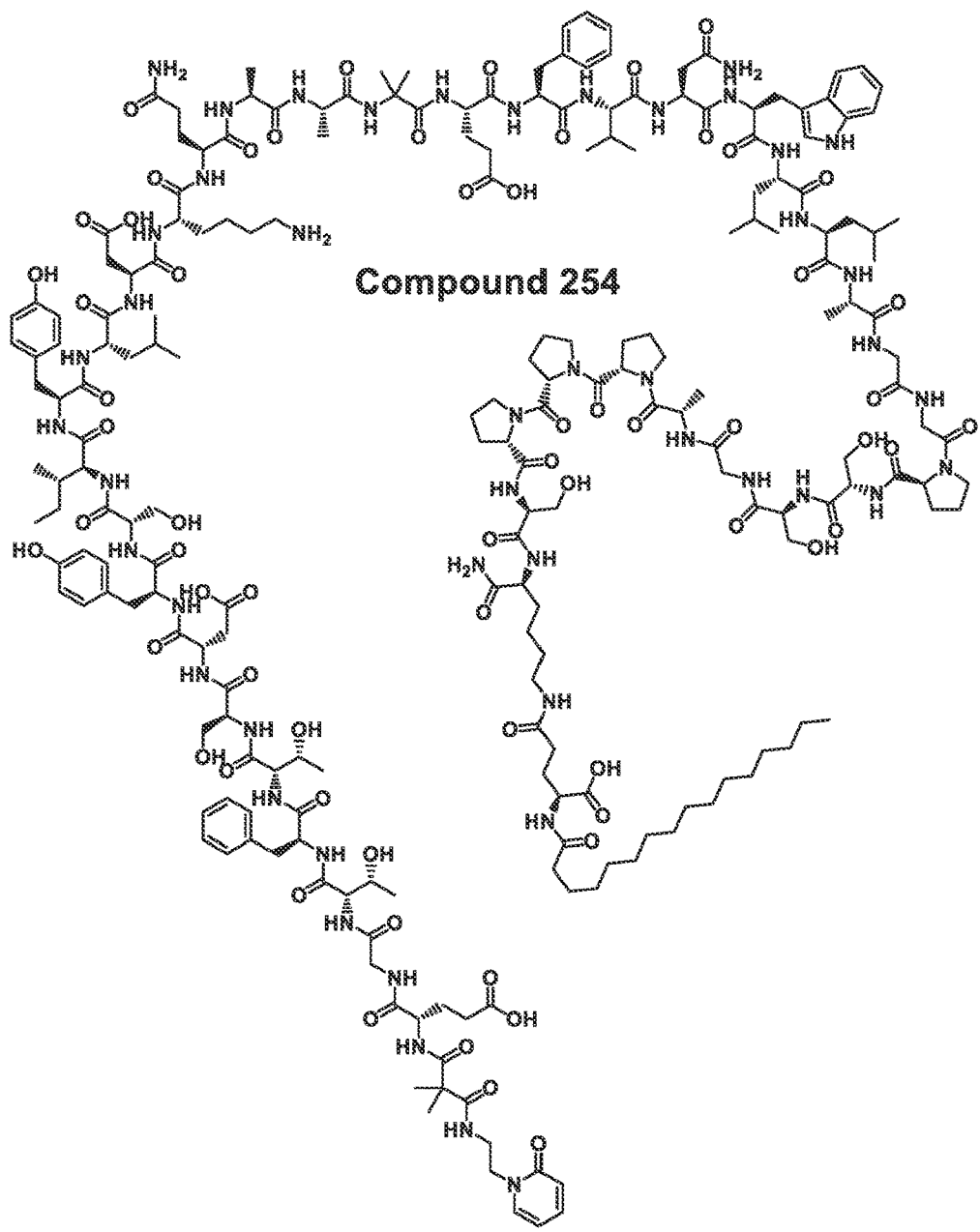
Compound 254
Cont'd

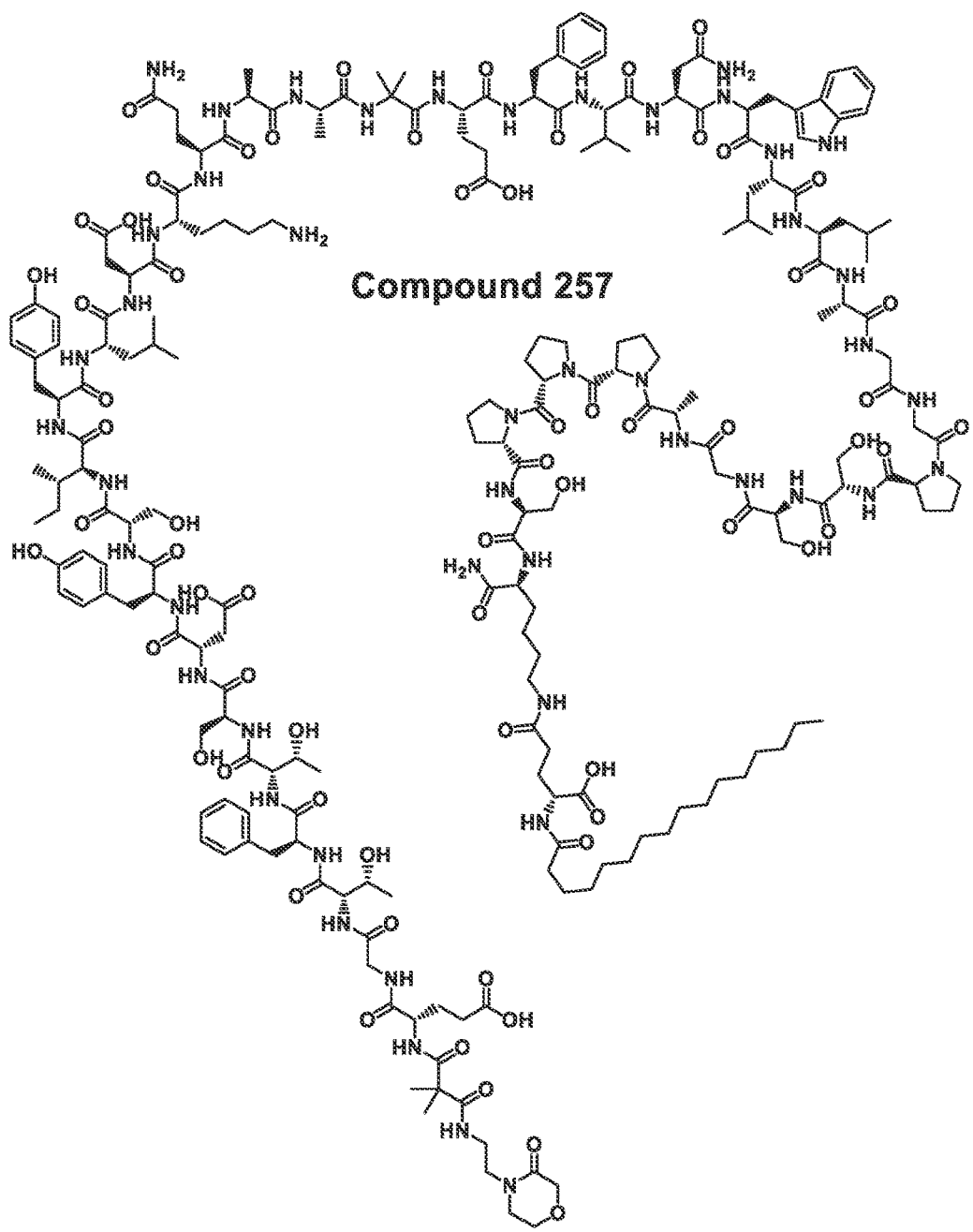
Compound 257
Cont'd

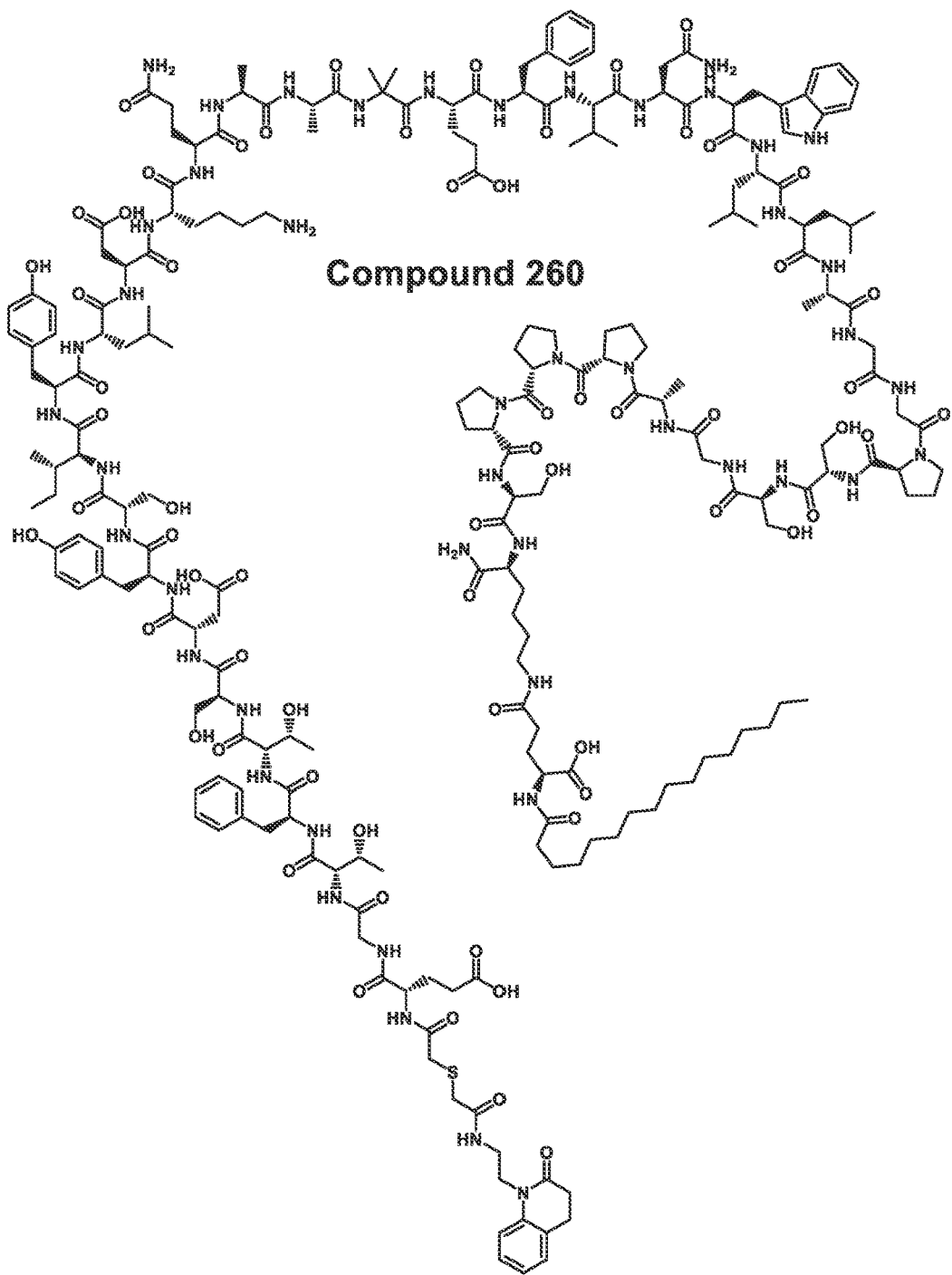
Compound 260
Cont'd

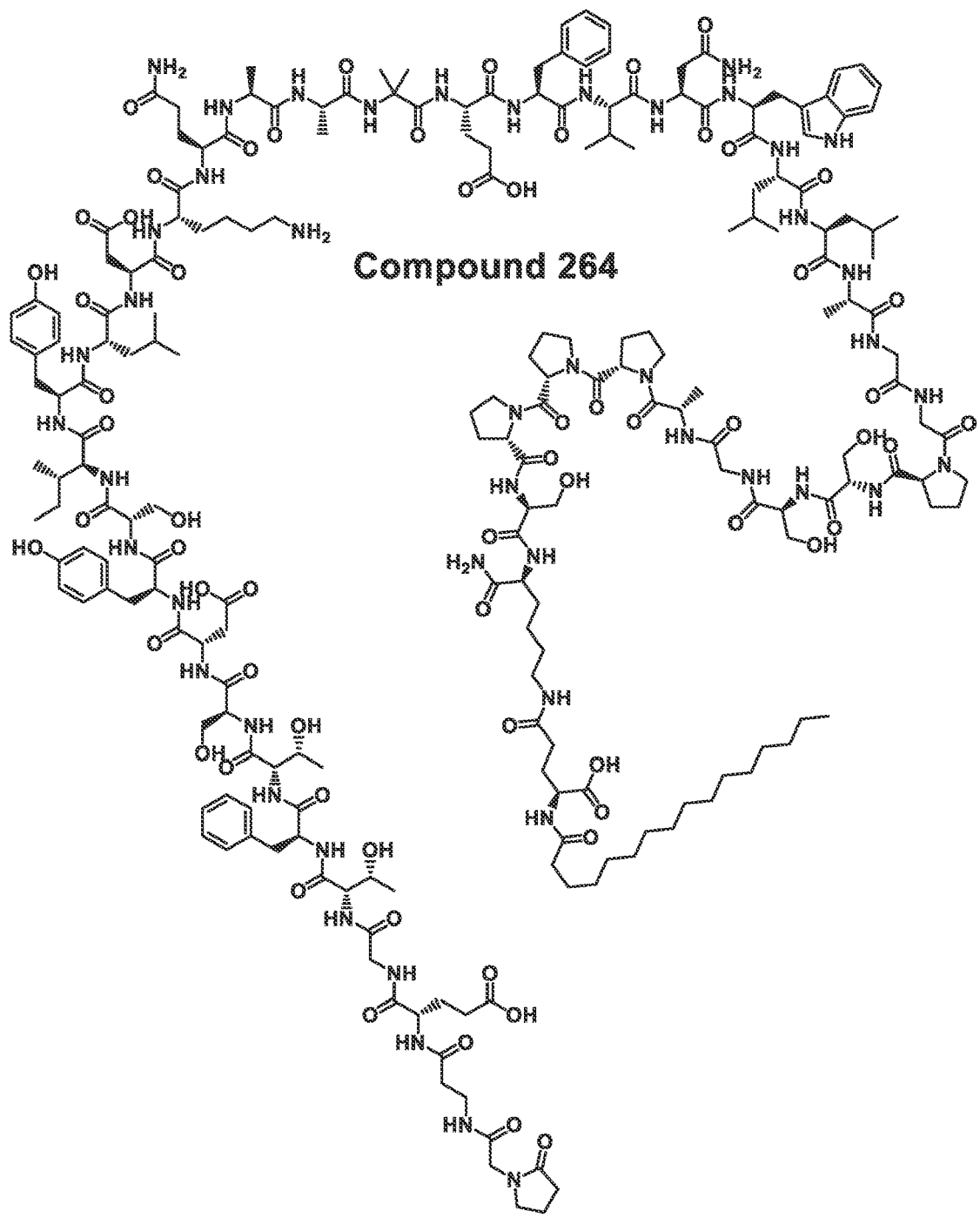
Compound 264
Cont'd

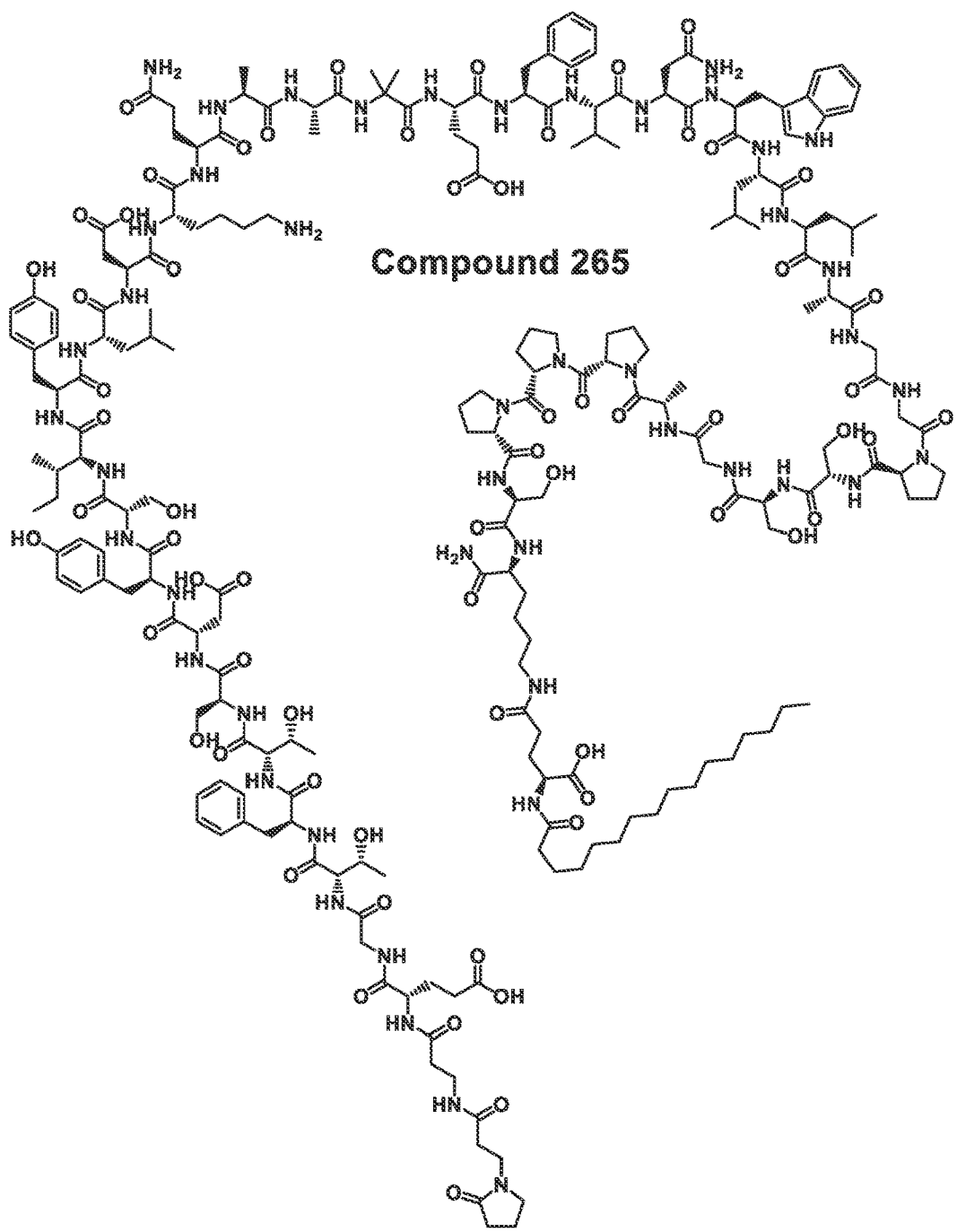
Compound 265

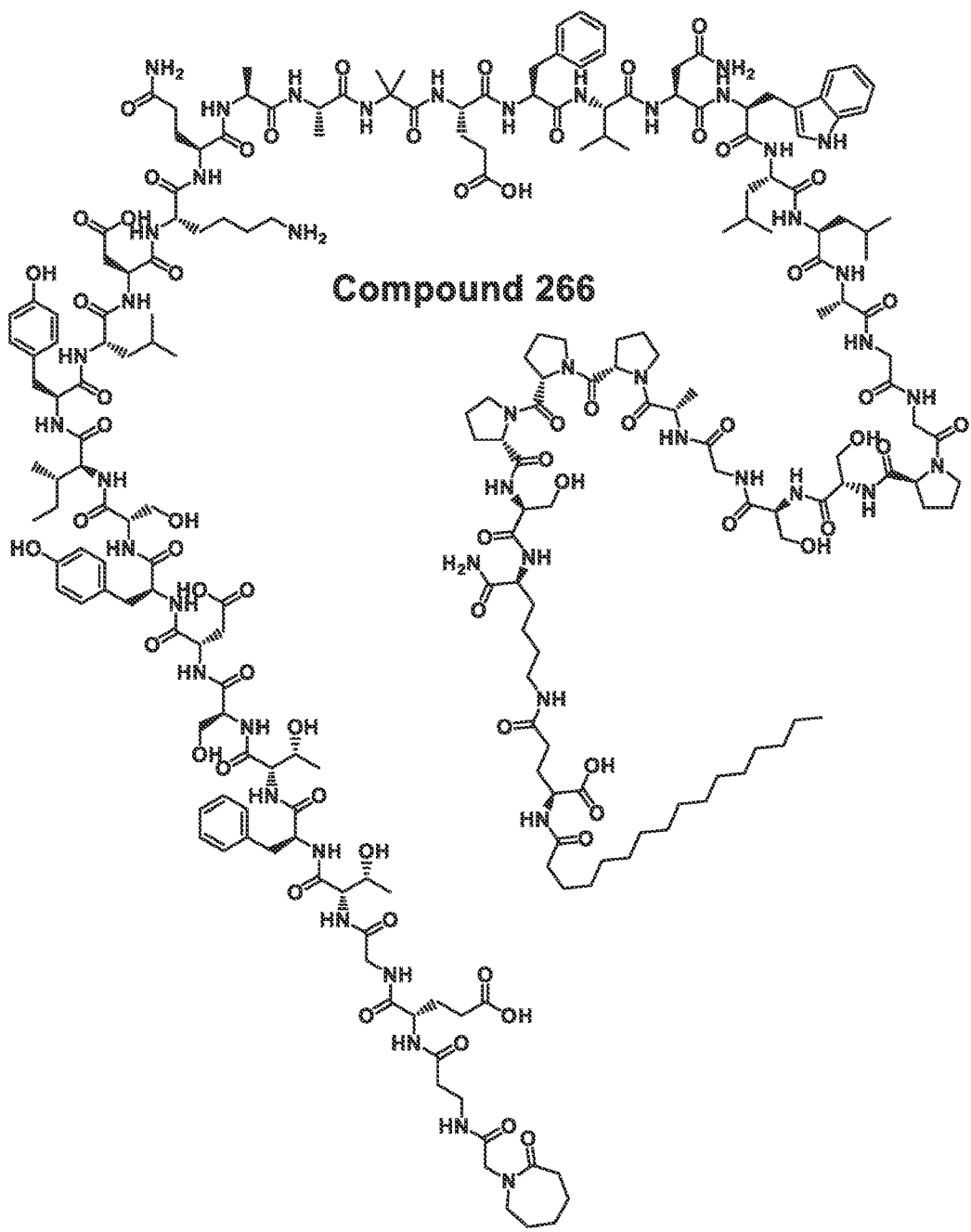
Compound 266

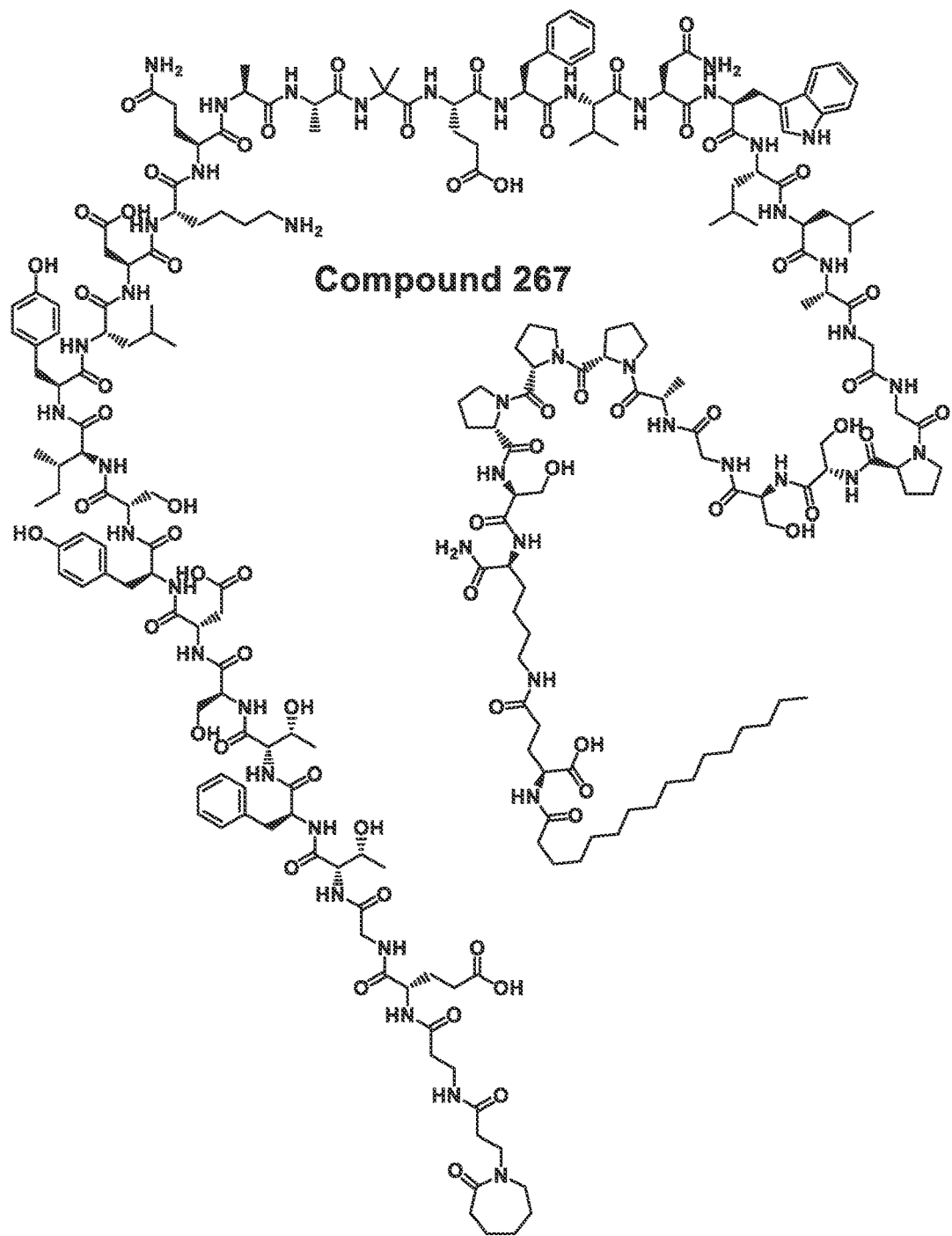
Compound 267
Cont'd

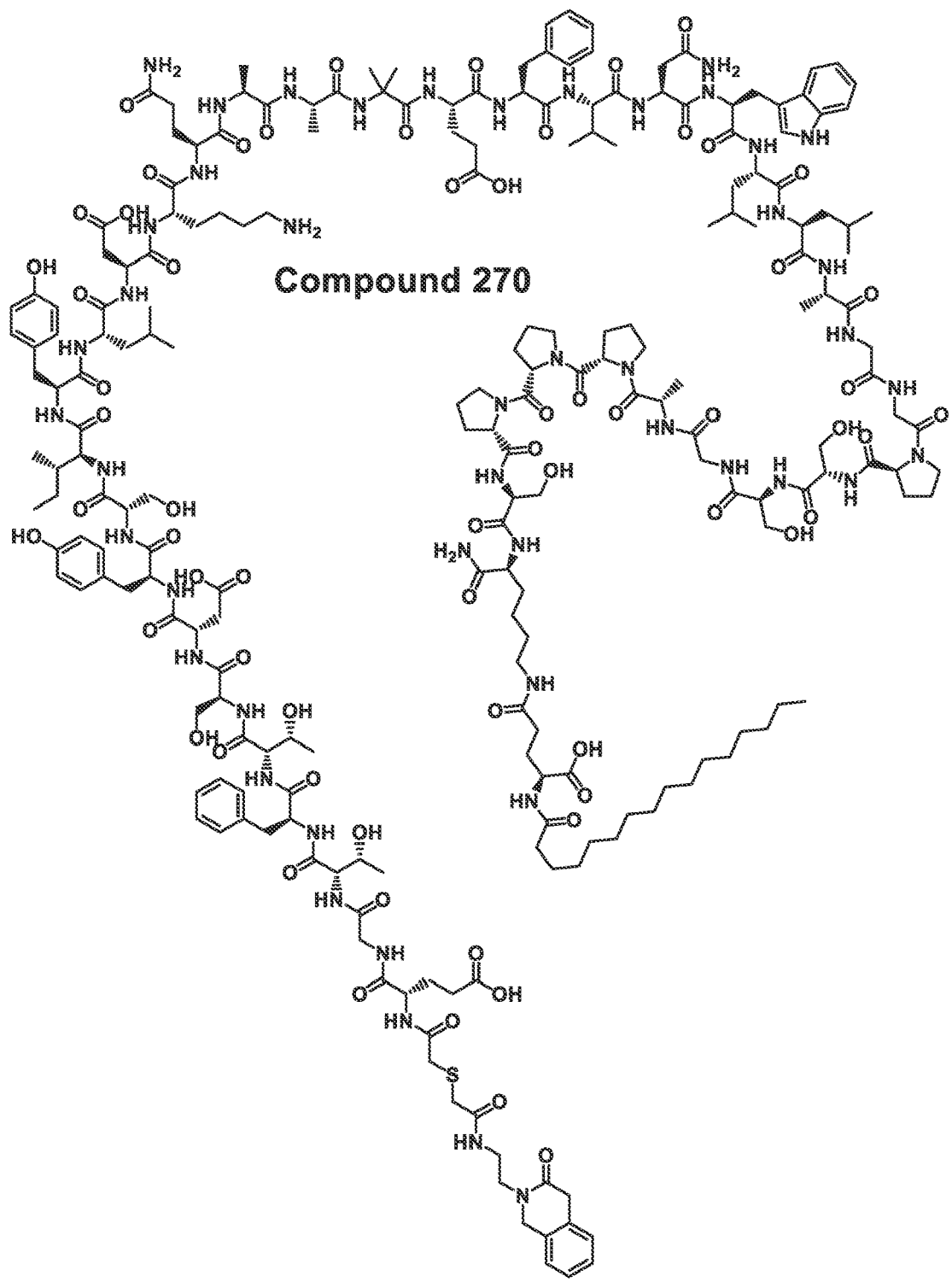
Compound 270
Cont'd

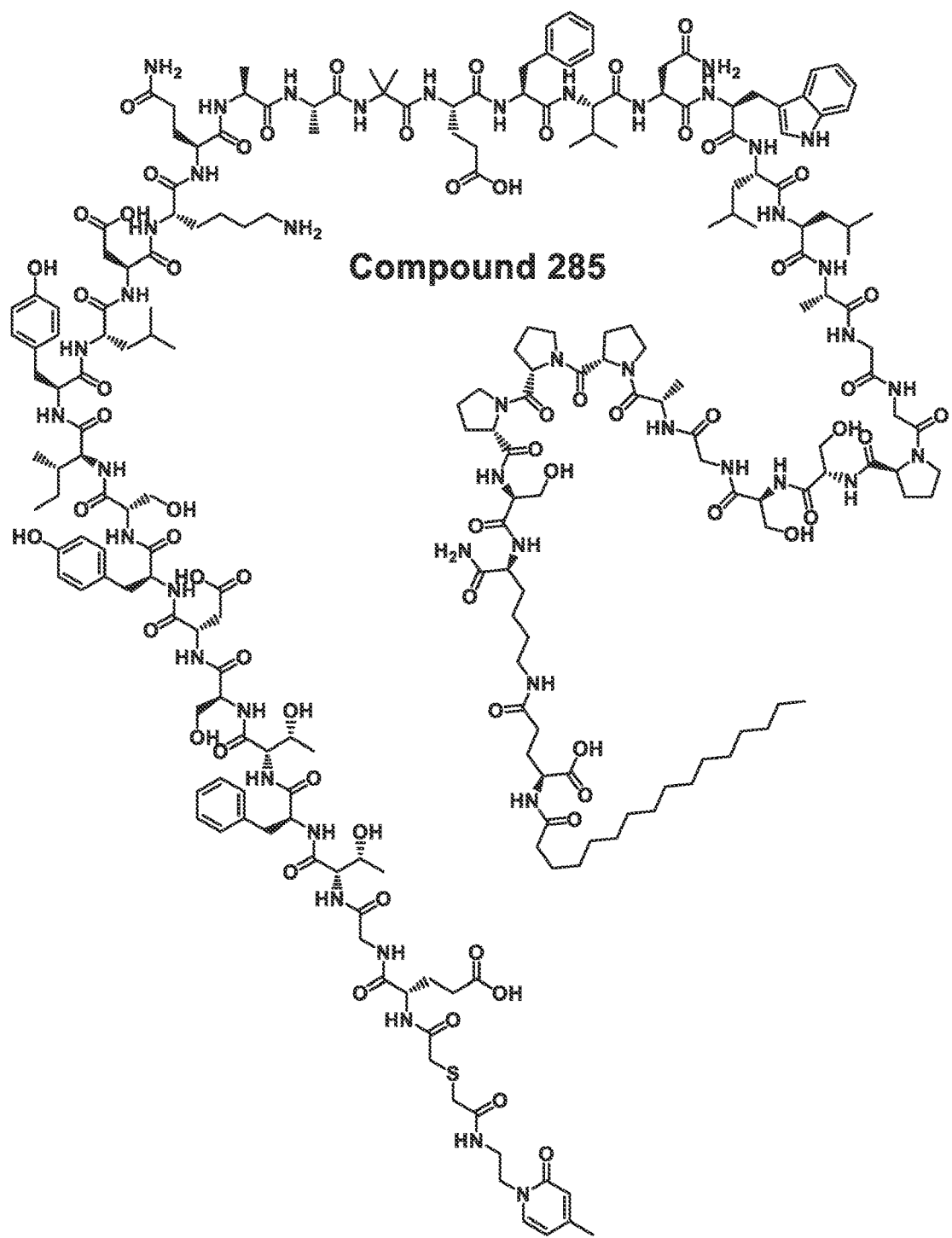
Compound 285
Cont'd

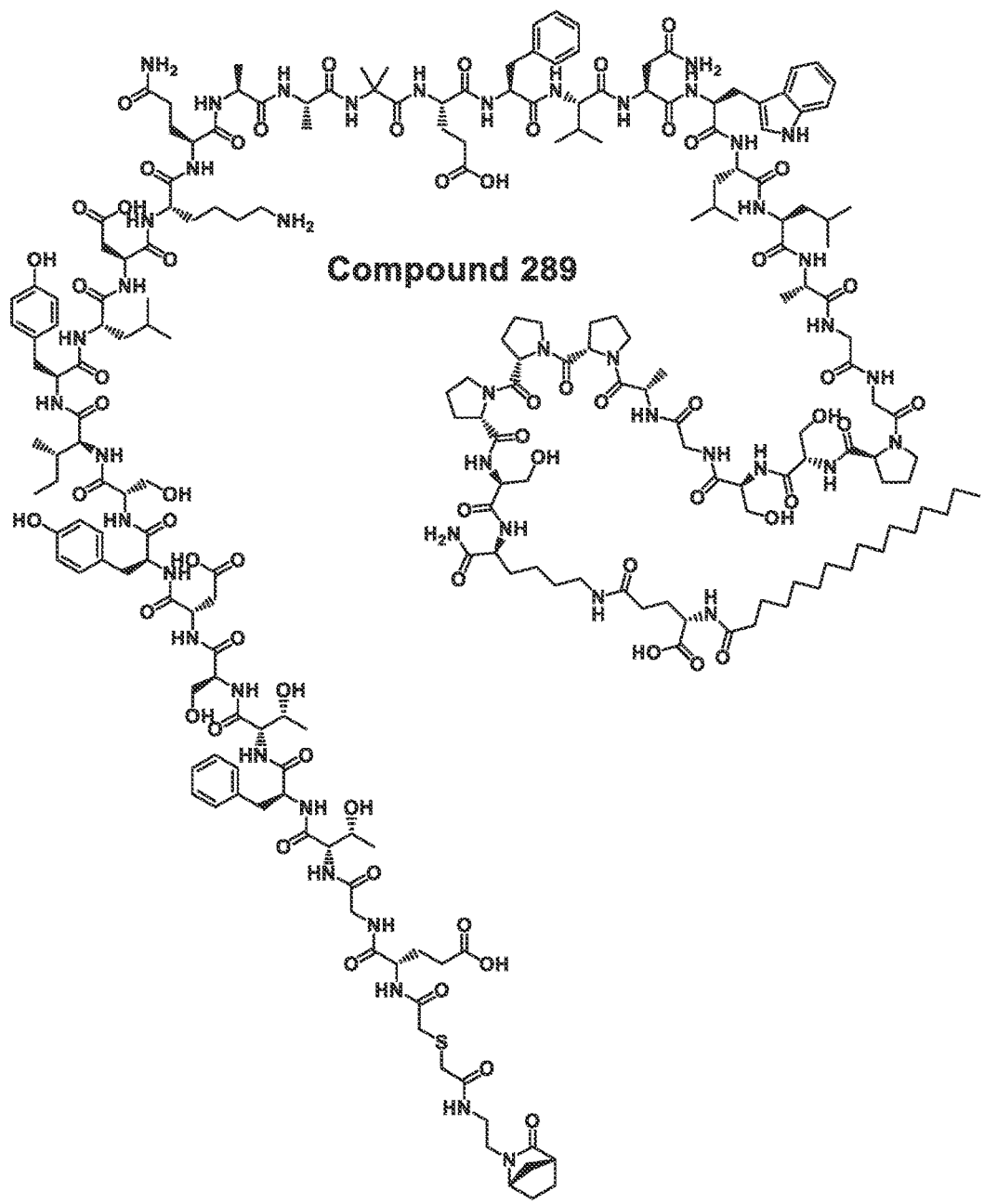
Compound 289
Cont'd

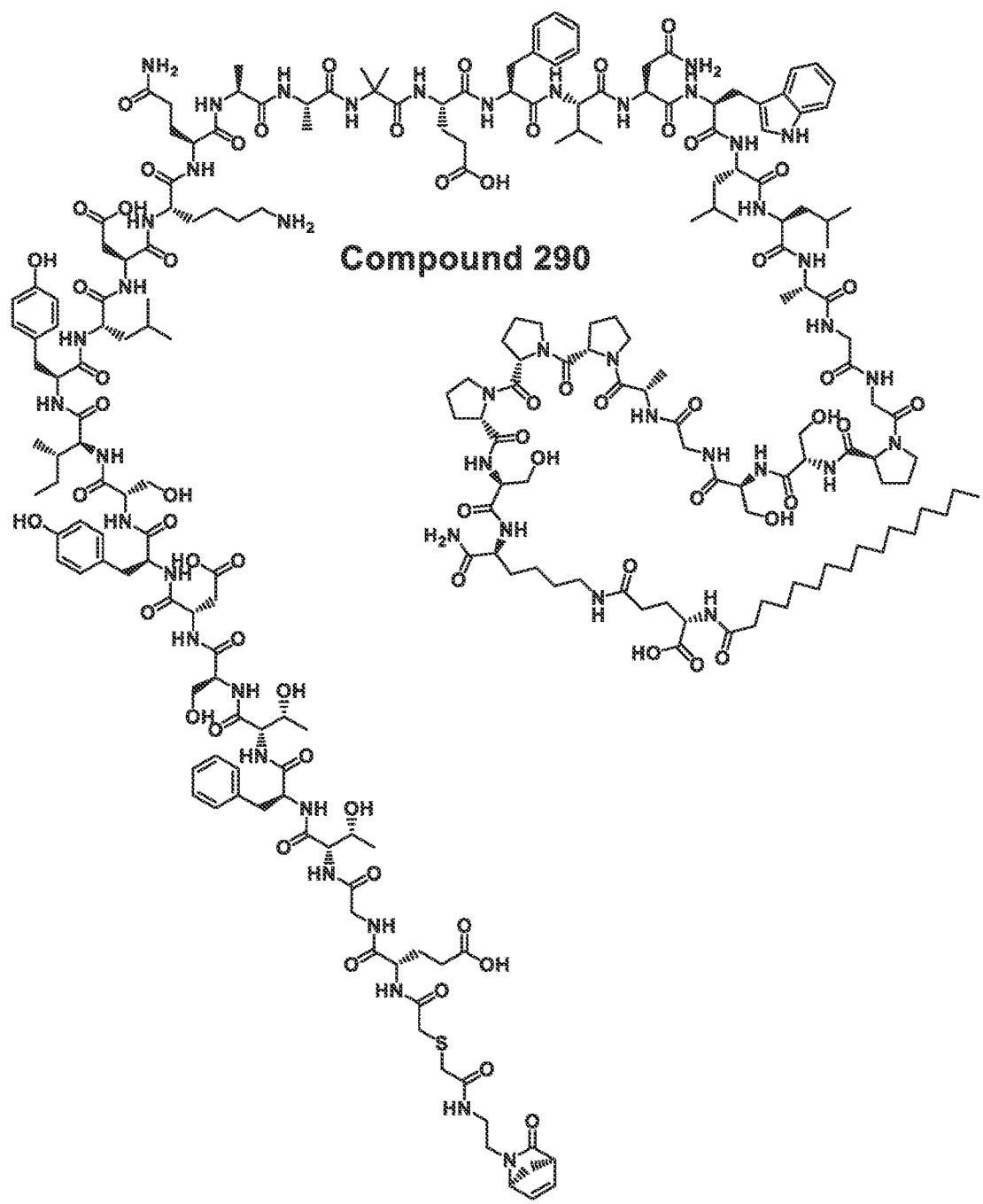
Compound 290
Cont'd

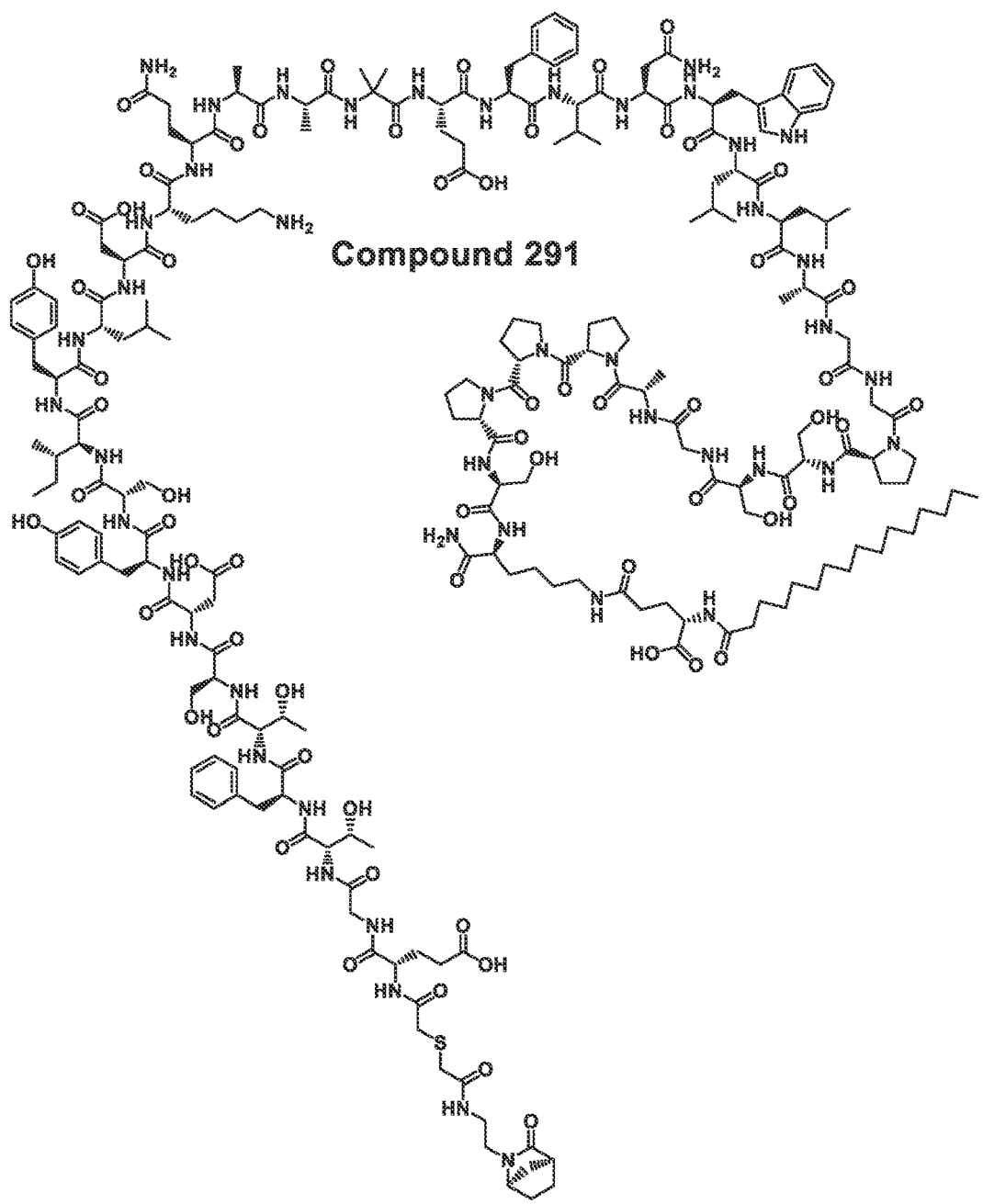
Compound 291
Cont'd

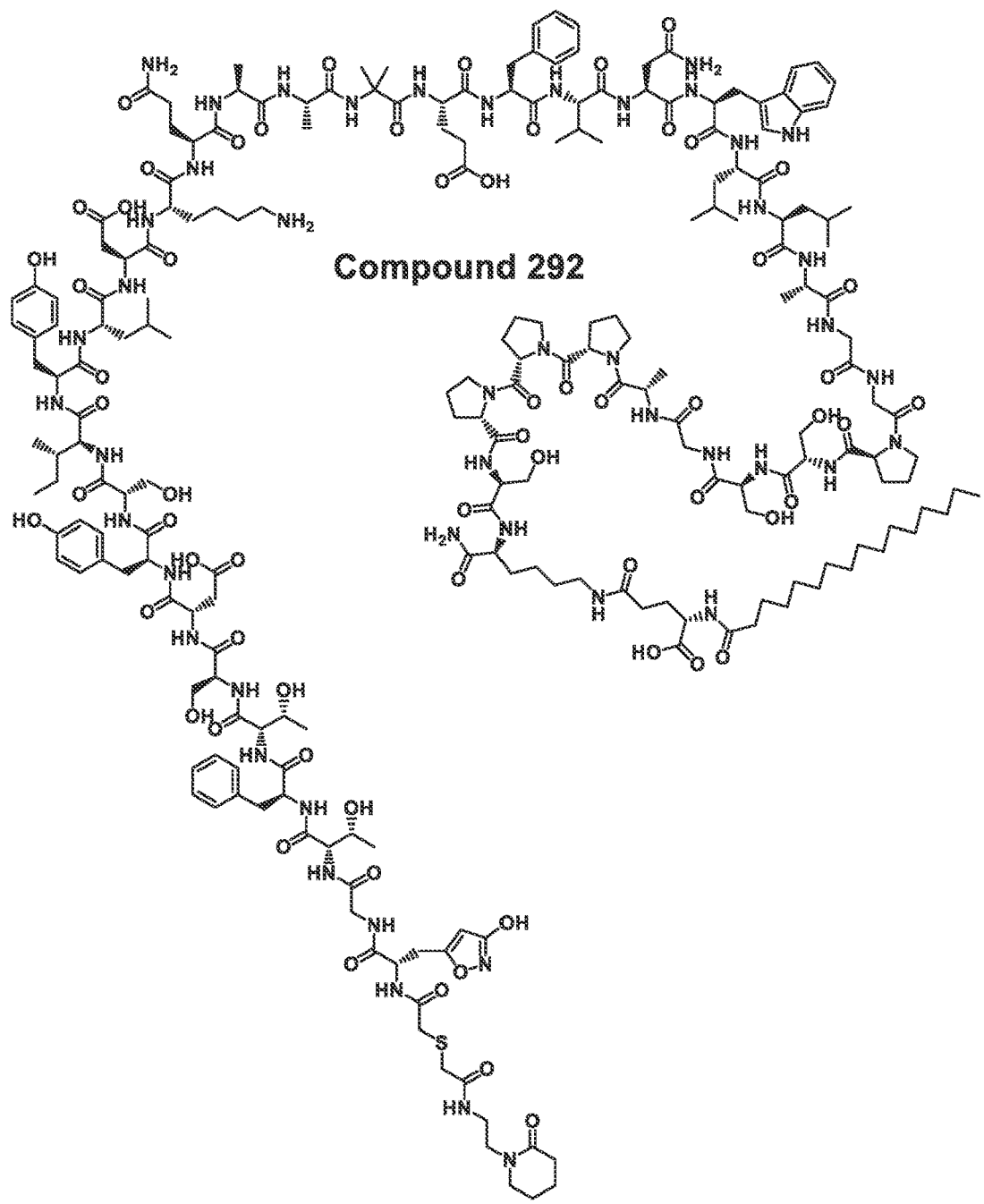

MODULATORS OF G-PROTEIN COUPLED RECEPTORS

CROSS-REFERENCE TO RELATED APPLICATIONS

This application is a National Stage application under 35 U.S.C. § 371 of International Application No. PCT/US2019/023726, having an International Filing Date of Mar. 22, 2019, which claims the benefit of U.S. Provisional Application Ser. No. 62/647,604, filed on Mar. 23, 2018, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 22, 2019, is named 41517-0002WO1_SL.txt and is 39,811 bytes in size.

TECHNICAL FIELD

This disclosure features chemical entities (e.g., a compound or a pharmaceutically acceptable salt and/or hydrate and/or prodrug of the compound) that modulate (e.g., agonize or partially agonize or antagonize) glucagon-like peptide-1 receptor ("GLP-1R") and/or the gastric inhibitory polypeptide receptor ("GIPR"). The chemical entities are useful, e.g., for treating a subject (e.g., a human) having a disease, disorder, or condition in which modulation (e.g., agonism, partial agonism or antagonism) of GLP-1R and/or GIPR activities is beneficial for the treatment or prevention of the underlying pathology and/or symptoms and/or progression of the disease, disorder, or condition. In some embodiments, the modulation results in an enhancement of (e.g., an increase in) existing levels (e.g., normal or below normal levels) of GLP-1R and/or GIPR activity (e.g., signaling). In some embodiments, the chemical entities described herein further modulate (e.g., attenuate, uncouple) β-arrestin signaling relative to what is observed with the native ligand. This disclosure also features compositions as well as other methods of using and making the said chemical entities.

BACKGROUND

Diabetes mellitus type 2 (type-2 diabetes) is characterized by high blood glucose and insulin resistance. Type 2 diabetes as well as conditions that are co-morbid or sequela with type-2 diabetes affect tens of millions of people in the United States alone. Type-2 diabetes is frequently associated with obesity.

Nonalcoholic steatohepatitis (NASH) is liver inflammation and damage caused by a buildup of fat in the liver. It is part of a group of conditions called nonalcoholic fatty liver disease (NAFLD). NASH and NAFLD tend to develop in patients having one of the following risk factors: obesity, dyslipidemia, and glucose intolerance and appears to be linked to insulin resistance (e.g., as in obesity or metabolic syndrome).

Incretin hormones are hormones that provide glycemic control in response to food intake. Gastric inhibitory polypeptide ("GIP") and glucagon-like peptide-1 ("GLP-1") are primary incretin hormones secreted from small intestinal L cells and K cells, respectively, on ingestion of glucose or nutrients to stimulate insulin secretion from pancreatic β cells. GIP and GLP-1 undergo degradation by dipeptidyl peptidase-4 (DPP-4), and rapidly lose their biological activities (see, e.g., Y Sieno, et. al, *Journal of Diabetes Investigation* 2013, 4, 108-130).

The actions of GIP and GLP-1 are believed to be mediated by their specific receptors, the GIP receptor (GIPR) and the GLP-1 receptor (GLP-1R), respectively, which both belong to the G-protein coupled receptor family and are expressed in pancreatic β-cells, as well as in various tissues and organs. GLP-1 activities include, without limitation, stimulation of insulin synthesis and secretion, inhibition of glucagon secretion, and inhibition of food intake. GIP activities include, without limitation, stimulation of glucose-dependent insulin secretion, an increase in β-cell mass, stimulation of glucagon secretion, and a decrease in gastric acid secretion. See, e.g., WO 2016/131893.

GLP-1 and GLP-1 analogues, acting as agonists at the GLP-1 receptor, have been shown to be effective in glycemic control, e.g., type-2 diabetes. See, e.g., WO 2016/131893. In addition to their insulinotropic effects, GIP and GLP-1 are believed to be involved in various biological processes in different tissues and organs that express GIPR and GLP-1R, including, e.g., the pancreas, fat, bone, brain, heart, kidney, eye, nerves, and liver. By way of example, investigations using mice lacking GIPR and/or GLP-1R, as well as mice lacking DPP-4, showed involvement of GIP and GLP-1 in divergent biological activities. The results of these investigations point to involvement of GIP and GLP-1 in treating and/or preventing diabetes-related microvascular complications (e.g., retinopathy, nephropathy and neuropathy) and macrovascular complications (e.g., coronary artery disease, peripheral artery disease and cerebrovascular disease), as well as diabetes-related comorbidity (e.g., obesity, non-alcoholic fatty liver disease, bone fracture and cognitive dysfunction). See, e.g., Sieno at page 108.

SUMMARY

This disclosure features chemical entities (e.g., a compound or a pharmaceutically acceptable salt and/or hydrate and/or prodrug of the compound) that modulate (e.g., agonize or partially agonize or antagonize) glucagon-like peptide-1 receptor ("GLP-1R") and/or the gastric inhibitory polypeptide receptor ("GIPR"). The chemical entities are useful, e.g., for treating a subject (e.g., a human) having a disease, disorder, or condition in which modulation (e.g., agonism, partial agonism or antagonism) of GLP-1R and/or GIPR activities is beneficial for the treatment or prevention of the underlying pathology and/or symptoms and/or progression of the disease, disorder, or condition. In some embodiments, the modulation results in an enhancement of (e.g., an increase in) existing levels (e.g., normal or below normal levels) of GLP-1R and/or GIPR activity (e.g., signaling). In some embodiments, the chemical entities described herein further modulate (e.g., attenuate, uncouple) β-arrestin signaling relative to what is observed with the native ligand. This disclosure also features compositions as well as other methods of using and making the said chemical entities.

An "agonist" of GLP-1R includes compounds that, at the protein level, directly bind or modify GLP-1R such that an activity of GLP-1R is increased, e.g., by activation, stabilization, altered distribution, or otherwise relative to GLP-1R activity in absence of ligand.

Certain compounds described herein that agonize GLP-1R to a lesser extent (partial agonists) than a GLP-1R full agonist (e.g native GLP-1) can function in assays as antagonists as well as agonists. These compounds antagonize activation of GLP-1R by a GLP-1R full agonist because they prevent the full effect of GLP-1R interaction. However, the compounds also, on their own, activate some GLP-1R activity, typically less than a corresponding amount of the GLP-1R full agonist. Such compounds are sometimes referred to herein as "partial agonists of GLP-1R".

An "antagonist" of GLP-1R includes compounds that, at the protein level, directly bind or modify GLP-1R such that an activity of GLP-1R is decreased, e.g., by inhibition, blocking or dampening agonist-mediated responses, altered distribution, or otherwise relative to GLP-1R activity in absence of ligand.

In some embodiments, the compounds described herein are agonists (e.g. full agonists) of GLP-1R. In other embodiments, the compounds described herein are partial agonists or antagonists of GLP-1R.

An "agonist" of GIPR includes compounds that, at the protein level, directly bind or modify GIPR such that an activity of GIPR is increased, e.g., by activation, stabilization, altered distribution, or otherwise relative to GIPR activity in absence of ligand.

Certain compounds described herein that agonize GIPR to a lesser extent than native GIP (s full agonist) can function as antagonists as well as agonists. These compounds are partial antagonists as they reduce activation of GIPR by native GIP because they reduce the full effect of native GIP. However, the compounds also, on their own, activate some GIPR activity, typically less than a corresponding amount of native GIP. Such compounds are sometimes referred to herein as "partial agonists of GIPR".

An "antagonist" of GIPR includes compounds that, at the protein level, directly bind or modify GIPR such that an activity of GIPR is decreased, e.g., by inhibition, blocking or dampening agonist-mediated responses, altered distribution, or otherwise relative to GIPR activity in absence of ligand.

In some embodiments, the compounds described herein are agonists (e.g. full agonists) of GIPR. In other embodiments, the compounds described herein are partial agonists of GIPR. In still other embodiments, the compounds described herein are or antagonists of GIPR.

In some embodiments, the compounds described herein are full agonists of both GLP-1R and GIPR. In some embodiments, the compounds described herein are partial agonists of both GLP-1R and GIPR. This disclosure also contemplates chemical entities that (i) agonize one of GLP-1R and GIPR (e.g., GLP-1R); and antagonize the other of GLP-1R and GIPR (e.g., GIPR). For example, this disclosure contemplates chemical entities that (i) fully agonize one of GLP-1R and GIPR (e.g., GLP-1R); and partially aginize or antagonize the other of GLP-1R and GIPR (e.g., GIPR). In certain embodiments, the chemical entities that are full agonists of GLP-1R and partial agonists or antagonists of GIPR; or that are partial agonists or antagonists of GLP-1R and full agonists of GIPR.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

In some embodiments, the chemical entities described herein further modulate (e.g., reduce, e.g., attenuate, disrupt, inhibit) β-arrestin coupling and/or b-arrestin signaling, and GLP-1R and/or GIPR internalization. In certain embodiments, the chemical entities described herein modulate (e.g., reduce, e.g., attenuate, disrupt, inhibit) recruitment of β-arrestin to a G-protein coupled receptor (e.g., GLP-1R). In certain embodiments, the chemical entities described herein modulate (e.g., reduce, e.g., attenuate, disrupt, inhibit) formation of a complex ("coupling") (e.g., a signaling complex) between β-arrestin and a G-protein coupled receptor (e.g., GLP-1R or GIPR). The effects of the chemical entities described herein on β-arrestin signaling and associated downstream processes (e.g., those delineated above) can be assessed using conventional methods, e.g., PathHunter β-arrestin Assay for determining β-arresting coupling (see Examples section). By way of example, a value of β-arrestin (GLP-1R) EC50<1 µM in the aforemented assay indicates a compound that induces β-arrestin recruitment to GLP-1R. GLP-1, the native ligand for GLP-1R, and therapeutic analogs thereof, such a liraglutide, are potent recruiters of β-arrestin. As another example, a value of β-arrestin (GLP1R) $EC_{50}$>1 µM (e.g., >10 µM) indicates a compound that does not substantially induce β-arrestin recruitment to GLP-1R. Therapeutic agents that modulate G-protein coupled receptors (e.g., GLP-1R and/or GIPR) can produce a variety of effects depending on the degree of cAMP activation versus β-arrestin-based signaling. It has been shown that b-arrestin coupling is a key strep in receptor internalization and subsequent de-sensitization and attenuation of signaling. Both GLP-1 (and the liraglutide analog) and GIP have been shown to produce rapid receptor internalization. Thus, compounds that activate GLP-1R and/or GIPR cAMP signaling but do not substantially couple to β-arrestin have the potential to prolong receptor signaling and extend pharmacological benefits. In some embodiments, the chemical entities described herein exhibit relatively strong GLP-1R and/or GIPR mediated cAMP activation with minimal or no detectable β-arrestin coupling. In some embodiments, the chemical entities described herein exhibit relatively strong GLP-1R mediated cAMP activation and no or little GIPR mediated cAMP activation with minimal or no detectable β-arrestin coupling.

In some embodiments, the compounds described herein show reduced activity in a rodent aversion model, while maintaining a relatively high potency in glucose clearance assay. Aversion models, such as conditioned taste aversion, are commonly used to identify compounds with adverse effects such as nausea. Nausea causing agents, such a Exendin-4 and liraglutide, are know to have a strong signal in conditioned taste aversion models. Advantageously, some of the chemical entities described herein are therefore expected to have a reduced likelihood of producing unwanted side effects, such as nausea, when administered to a patient, while maintaining full pharmacological benefit.

Accordingly, in one aspect, this disclosure features peptide-based chemical entities (e.g., N-protected peptide-based chemical entities; e.g., peptide-based chemical entities having from 30-50 amino acids, 30-45 amino acids, 30-40 amino acids, 35-40 amino acids; e.g., an N-protected peptide-based chemical entities having from 30-50 amino acids, 30-45 amino acids, 30-40 amino acids, 35-40 amino acids). The peptide-based chemical entities modulate (e.g., agonize or partially agonize or antagonize) glucagon-like peptide-1 receptor ("GLP-1R") and/or the gastric inhibitory polypeptide receptor ("GIPR") and optionally further modulate (e.g., uncouple, attenuate) β-arrestin signaling and/or aversion as described herein.

In some embodiments, the peptide-based chemical entities agonize or partially agonize GLP-1R.

In some embodiments, the peptide-based chemical entities agonize or partially agonize or antagonize GIPR.

In some embodiments, said peptide-based chemical entities reduce (e.g., uncouple, attenuate, inhibit) β-arrestin signaling; e.g., reduce (e.g., uncouple, attenuate, inhibit) the recruitment of β-arrestin to a G-protein coupled receptor (e.g., GLP-1R); e.g., reduce (e.g., attenuate, disrupt, inhibit) the formation of a complex (e.g., a signaling complex) between β-arrestin and a G-protein coupled receptor (e.g., GLP-1R).

In certain embodiments, the peptide-based chemical entities:
   agonize or partially agonize GLP-1R;
   agonize or partially agonize or antagonize GIPR;
   reduce (e.g., uncouple, attenuate, inhibit) β-arrestin signaling; e.g., reduce (e.g., attenuate, disrupt, inhibit) the recruitment of β-arrestin to a G-protein coupled receptor (e.g., GLP-1R and/or GIPR); e.g., reduce (e.g., attenuate, disrupt, inhibit) the formation of a complex (e.g., a signaling complex) between β-arrestin and a G-protein coupled receptor (e.g., GLP-1R and/or GIPR); and
   stimulate glucose clearance in vivo (GTT test) without causing aversion.

In some embodiments, the peptide-based chemical entities exhibit a value of cAMP (GLP1R) EC50 of less than about 10 nM, 5 nM, or 1 nM (e.g., less than about 1 nM).

In some embodiments, the peptide-based chemical entities exhibit a value of cAMP (GIPR) EC50 of less than about 100 nm, 50 nM, or 10 nM (e.g., less than about 10 nM).

In some embodiments, the peptide-based chemical entities inhibit GIP induced cAMP production (GIPR antagonism).

In some embodiments, the compounds described herein exhibit a value of β-arrestin (GLP1R) EC50>1 µM.

In some embodiments, the peptide-based chemical entities:
   exhibit a value of cAMP (GLP1R) EC50 of less than about 10 nM, 5 nM, or 1 nM (e.g., less than about 1 nM);
   exhibit a value of cAMP (GIPR) EC50 of less than about 100 nm, 50 nM, or 10 nM (e.g., less than about 10 nM) or are GIPR antagonists;
   exhibit a value of β-arrestin (GLP1R) EC50>1 µM; and
   stimulate glucose clearance in vivo (GTT test) without causing aversion (nausea)

In one aspect, the featured peptide-based chemical entities include compounds of Formula (IAA), or a pharmaceutically acceptable salt thereof:

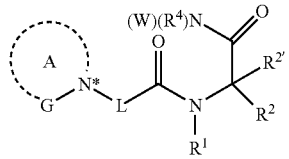

(IAA)

in which ring A, G, L, W, R$^1$, R$^2$, R$^{2'}$, and R$^4$ can be as defined anywhere herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing, partially agonizing, or antagonizing) GLP-1R and/or GIPR activities are featured that include contacting GLP-1R and/or GIPR with a chemical entity described herein (e.g., a compound described generically or specifically herein or a pharmaceutically acceptable salt thereof or compositions containing the same). Methods include in vitro methods, e.g., contacting a sample that includes one or more cells, each independently comprising one or more of GLP-1R and/or GIPR with the chemical entity. Methods can also include in vivo methods; e.g., administering the chemical entity to a subject (e.g., a human) having a disease, disorder, or condition in which modulation of GLP-1R and/or GIPR signaling is beneficial for the treatment of the underlying pathology and/or symptoms and/or progression of the disease, disorder, or condition (e.g., diabetes; e.g., NASH; e.g., obesity). In vivo methods include, but are not limited to modulating (e.g., increasing) insulin levels and modulating (e.g., decreasing) glucose levels in a subject (e.g., a human).

In some of the foregoing embodiments, said methods of modulating are achieved without substantially stimulating β-arrestin signaling; e.g., without stimulating the recruitment of β-arrestin to a G-protein coupled receptor (e.g., GLP-1R); e.g., without stimulating the formation of a complex (e.g., a signaling complex) between β-arrestin and a G-protein coupled receptor (e.g., GLP-1R). In some of the foregoing embodiments, said methods of modulating are achieved without causing aversion or nausea.

In a further aspect, methods of treatment of a disease, disorder, or condition are featured, in which modulation of GLP-1R and/or GIPR signaling is beneficial for the treatment of the underlying pathology and/or symptoms and/or progression of the disease, disorder, or condition. The methods include administering to a subject in need of such treatment an effective amount of a chemical entity described herein (e.g., a compound described generically or specifically herein, a pharmaceutically acceptable salt thereof, or compositions containing the same).

In another aspect, this disclosure features methods of treating a subject having a disease, disorder, or condition in which modulation of GLP-1R and/or GIPR signaling is beneficial for the treatment of the underlying pathology and/or symptoms and/or progression of the disease, disorder, or condition. The methods include administering a chemical entity described herein (e.g., a compound described generically or specifically herein, a pharmaceutically acceptable salt thereof or compositions containing the same) in an amount effective to treat the disease, disorder, or condition.

In a further aspect, methods of treatment are featured that include administering to a subject chemical entity described herein (e.g., a compound described generically or specifically herein, a pharmaceutically acceptable salt thereof, or compositions containing the same). The methods include administering the chemical entity in an amount effective to treat a disease, disorder, or condition, wherein modulation of GLP-1R and/or GIPR is beneficial for the treatment of the underlying pathology and/or symptoms and/or progression of the disease, disorder, or condition, thereby treating the disease, disorder, or condition.

In another aspect, methods of treatment can further include:
(i) administering a first therapeutic agent that modulates (e.g., agonizes, partially agonizes, or antagonizes) GLP-1R and/or GIPR to a subject as defined anywhere herein;
(ii) determining that the subject is suffering from one or more side effects (e.g., aversion, nausea or vomiting); and
(iii) ceasing administration of the first therapeutic agent and administering a chemical entity as described herein (e.g., a compound having formula (IAA), (IA), or (I)).

Non-limiting examples of such diseases, disorders, and conditions include metabolic syndrome; diabetes (e.g., type 2 diabetes); obesity; obesity-related disorders; impaired glucose tolerance; insulin resistance; non-alcoholic steatohepatitis (NASH); fatty liver disease; steatohepatitis; and other forms of inflammation in metabolically important tissues including, liver, fat, pancreas, kidney, and gut.

Other non-limiting examples of such diseases, disorders, and conditions include neurological disorders include brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeld-Jakob Disease, bovine spongiform encephalopathy (mad cow disease), and chronic wasting syndrome).

Still other non-limiting examples of such diseases, disorders, and conditions include bone disorder characterized by altered bone metabolism, such as osteoporosis, including post-menopausal osteoporosis, poor bone strength, osteopenia, Paget's disease, osteolytic metastasis in cancer patients, osteodistrophy in liver disease and the altered bone metabolism caused by renal failure or haemodialysis, bone fracture, bone surgery, aging, pregnancy, protection against bone fractures, and malnutrition.

In certain embodiments, the disease, disorder, or condition is diabetes.

In other embodiments, the disease, disorder, or condition is NASH.

In still other embodiments, the disease, disorder, or condition is obesity.

In other embodiments, the disease, disorder, or condition is Alzheimer's disease (AD) or Parkinson's disease (PD).

In still other embodiments, the disease, disorder, or condition is a bone disorder characterized by altered bone metabolism, such as osteoporosis, including post-menopausal osteoporosis, poor bone strength, osteopenia, Paget's disease, osteolytic metastasis in cancer patients, osteodistrophy in liver disease and the altered bone metabolism caused by renal failure or haemodialysis, bone fracture, bone surgery, aging, or pregnancy.

In certain embodiments, the chemical entities described herein are useful for protection against bone fractures.

The methods described herein can further include treating one or more conditions associated, co-morbid or sequela with any one or more of the conditions described herein. By way of non-limiting example, the methods can further include treating one or more conditions that are co-morbid or sequela with diabetes (e.g., type 2 diabetes), such as obesity, obesity-related disorders, metabolic syndrome, impaired glucose tolerance; insulin resistance; cardiovascular risk factors. (e.g., coronary artery disease, peripheral artery disease, cerebrovascular disease, hypertension, and risk factors related to unmanaged cholesterol and/or lipid levels, and/or inflammation), retinopathy, nephropathy, neuropathy, NASH, bone fracture and cognitive dysfunction.

In another aspect, this disclosure features methods for screening a candidate compound for treatment of a disease, disorder, or condition, in which modulation of GLP-1R and/or GIPR is beneficial for the treatment of the underlying pathology and/or symptoms and/or progression of the disease, disorder, or condition; the method comprising:
(a) contacting the candidate compound with (i) a β-Arrestin-coupled GPCR receptor signaling complex or (ii) one or more GPCR receptor signaling complexes that are not complexed with β-arrestin (e.g., uncoupled GLP-1R and/or uncoupled GIPR); and
(b) detecting (i) the disruption of the b-arrestin coupled complex; or (ii) detecting the formation of the signaling complex in the absence of b-arrestin coupling; wherein the candidate compound modulates (e.g., agonizes, partially agonizes) GLP-1R and/or GIPR.

In certain embodiments, the methods further include selecting a candidate compound that exhibits a value of β-arrestin (GLP-1R) EC50>1 μM.

The methods can further include identifying the subject.

The methods can further include administering one or more other therapeutic agents (e.g., in combination with a chemical entity described herein).

Embodiments can include one of more of the following advantageous properties.

In some embodiments, the compounds described herein exhibit a value of AUC Score of 0-25% of vehicle, which corresponds to a finding of maximal decrease in glucose excursion compared to control.

In some embodiments, the compounds described herein exhibit a value of cAMP (GLP-1R) EC50 of less than about 1 nM, which is indicative that the compound is a relatively potent GLP-1R agonist.

In some embodiments, the compounds described herein exhibit a value of cAMP (GLP-1R) Emax of greater than about 80%, which is indicative that the compound is an agonist that can fully activate GLP-1R.

In some embodiments, the compounds described herein exhibit a value of cAMP (GIPR) $EC_{50}$ of less than about 10 nM, which is indicative that the compound is a relatively potent GIPR agonist.

In some embodiments, the compounds described herein exhibit a value of cAMP (GIPR) $EC_{50}$ of less than about 10 nM, which is indicative that the compound is a relatively potent GIPR antagonist.

GLP-1 and GIP are susceptible to rapid degradation by dipeptidyl peptidease-IV (DPP-IV) (see, e.g., Deacon, et al. *Journal of Clinical Endocrinology & Metabolism,* 1995, 80, 952-957). As such, GLP-1 and GIP have been shown to exhibit relatively short half-life times in human due to DPP-IV degradation. Advantageously, the compounds described herein exhibit relatively long half-life times in the presence of DPP-IV when compared to those of GLP-1 and GIP.

In some embodiments, the compounds described herein exhibit a value of β-arrestin coupling (GLP-1R) EC50>1 μM in a β-arrestin (GLP1R) assay that measures the formation of a complex between GLP-1R and β-arrestin in cells. A value of β-arrestin (GLP1R) EC50>1 μM indicates a compound that does not substantially induce β-arrestin recruitment to GLP-1R.

In some embodiments, the compounds described herein exhibit a value of conditioned taste aversion ("CTA")=0.6-1.0, which indicates no measurable aversion to a compound, which is desired. A value of CTA=0.0-0.6 indicates significant aversion to a compound. The conditioned taste aversion assay measures the preference for a dilute saccharin solution that is associated with compound administration.

In some embodiments, the compounds described herein have a reduced likelihood of producing unwanted side effects when administered to a patient. A non-limiting example of such a side effect is nausea.

Other embodiments include those described in the Detailed Description, drawings, and/or in the claims.

DESCRIPTION OF DRAWINGS

FIG. 1 depicts representative compounds of Formula (IAA).

ADDITIONAL DEFINITIONS

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "GLP-1R" is meant to include, without limitation, nucleic acids, polynucleotides, oligonucleotides, sense and antisense polynucleotide strands, complementary sequences, peptides, polypeptides, proteins, homologous and/or orthologous GLP-1R molecules, isoforms, precursors, mutants, variants, derivatives, splice variants, alleles, different species, and active fragments thereof.

As used herein, the term "GIPR" is meant to include, without limitation, nucleic acids, polynucleotides, oligonucleotides, sense and antisense polynucleotide strands, complementary sequences, peptides, polypeptides, proteins, homologous and/or orthologous GIPR molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The term "IC50" or "EC50" refers an amount, concentration, or dosage of a compound that is required for 50% inhibition or activation of a maximal response observed for such compound (or that of a reference compound as the case may be) in an assay that measures such response.

The terms "effective amount" or "therapeutically effective amount," as used herein, refer to a sufficient amount of a chemical entity (e.g., a compound described generically or specifically herein, a pharmaceutically acceptable salt thereof, or compositions containing the same) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy, 21st ed.*; Lippincott Williams & Wilkins: Philadelphia, Pa., 2005; *Handbook of Pharmaceutical Excipients, 6th ed.*; Rowe et al., Eds.; The Pharmaceutical Press and the American Pharmaceutical Association: 2009; *Handbook of Pharmaceutical Additives, 3rd ed.*; Ash and Ash Eds.; Gower Publishing Company: 2007; *Pharmaceutical Preformulation and Formulation, 2nd ed.*; Gibson Ed.; CRC Press LLC: Boca Raton, Fla., 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "haloalkoxy" refers to an —O-haloalkyl radical (e.g., —OCH$_3$).

The term "alkylene" refers to a branched or unbranched divalent alkyl (e.g., —CH$_2$—).

The term "arylene" and the like refer to divalent forms of the ring system, here divalent aryl.

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Examples of heteroaryl groups also include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the description below and in the drawings. Other features and advantages will also be apparent from the claims.

DETAILED DESCRIPTION

This disclosure features chemical entities (e.g., a compound or a pharmaceutically acceptable salt and/or hydrate and/or prodrug of the compound) that modulate (e.g., agonize or partially agonize or antagonize) glucagon-like peptide-1 receptor ("GLP-1R") and/or the gastric inhibitory polypeptide receptor ("GIPR"). The chemical entities are useful, e.g., for treating a subject (e.g., a human) having a disease, disorder, or condition in which modulation (e.g., agonism, partial agonism or antagonism) of GLP-1R and/or GIPR activities is beneficial for the treatment or prevention of the underlying pathology and/or symptoms and/or progression of the disease, disorder, or condition. In some embodiments, the modulation results in an enhancement of (e.g., an increase in) existing levels (e.g., normal or below normal levels) of GLP-1R and/or GIPR activity (e.g., signaling). In some embodiments, the chemical entities described herein further modulate (e.g., attenuate, uncouple) β-arrestin signaling relative to what is observed with the native ligand. This disclosure also features compositions as well as other methods of using and making the said chemical entities.

In one aspect, the disclosure provides a compound having formula (IAA), or a pharmaceutically acceptable salt thereof:

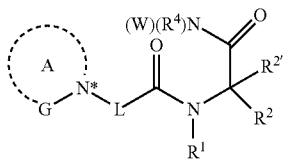

(IAA)

wherein:

ring A is:

(i) a saturated or unsaturated monocyclic ring that includes from 3-8 ring atoms (inclusive of G and the nitrogen atom labelled N*); or (ii) a saturated or unsaturated bicyclic or tricyclic ring that includes from 6-14 ring atoms (inclusive of G and the nitrogen atom labelled N*), wherein:

G is C(O), S(O), or $SO_2$; and the dotted, circular line connecting G and N* is a divalent group that includes from 1-6 ring atoms; wherein:

(a) from 0-2 of the divalent group's ring atoms are ring heteroatoms, which are each independently selected from the group consisting of N, $N(R^a)$, O, S, and $SO_2$; and (b) from 1-6 of the divalent group's ring atoms are ring carbon atoms, which are each independently selected from the group consisting of C, CH, $CH_2$, $CR^b$, $C(R^b)_2$, and $CHR^b$;

wherein:

(1) when ring A is a monocyclic ring, then each of the divalent group's 1-6 ring carbon atoms is independently selected from the group consisting of CH, $CH_2$, $CR^b$, $C(R^b)_2$, and $CHR^b$; and (2) when ring A is a bicyclic or tricyclic ring, then (A) or (B) applies:

(A) two or three adjacent ring carbon atoms of the divalent group are each independently selected from the group consisting of the group consisting of C, CH, $CH_2$, $CR^b$, $C(R^b)_2$, and $CHR^b$ and are fused to a second ring that is selected from the group consisting of:

(a) $C_{6-10}$ aryl optionally substituted with from 1-5 independently selected $R^c$;

(b) heteroaryl including from 5-10 ring atoms, wherein from 1-4 ring atoms are each independently selected from the group consisting of N, $N(R^a)$, O, and S, wherein the heteroaryl is optionally substituted with from 1-3 independently selected $R^c$;

(c) $C_{3-10}$ cycloalkyl optionally substituted with from 1-4 independently selected $R^d$;

(d) heterocyclyl including from 3-10 ring atoms, wherein from 1-3 ring atoms are each independently selected from the group consisting of $N(R^a)$, O, and S, wherein the heterocyclyl is optionally substituted with from 1-4 independently selected $R^d$; or (B) one of the divalent group's ring carbon atoms is C and is spiro-fused to a second ring that is selected from the group consisting of:

(a) $C_{3-10}$ cycloalkyl optionally substituted with from 1-4 independently selected $R^d$;

(b) heterocyclyl including from 3-10 ring atoms, wherein from 1-3 ring atoms are each independently selected from the group consisting of $N(R^a)$, O, and S, wherein the heterocyclyl is optionally substituted with from 1-4 independently selected $R^d$;

L is:

(i) —$(CH_2)_m$—$X^1$—$(CH_2)_n$—$X^2$—$(CH_2)_p$— (formula VIII), wherein m is from 1-6; n is from 0-2; and p is from 0-8;

(ii) —C(O)—$(CH_2)_n$—$X^3$—$(CH_2)_p$— (formula IX), wherein n is from 0-2; and p is from 0-8;

(iii) —$(CH_2)_q$—, wherein q is from 1-10;

(iv) —C(O)—; or (v) —$(CH_2)_m$—$X^1$—$(CH_2)_p$— (formula VIII), wherein m is from 1-6; and p is from 0-8;

$X^1$ is —C(O)—; —N(R')C(O)—; —C(O)N(R')—; or —N(R')C(O)NR')—; wherein each occurrence of R' is independently selected from the group consisting of: H and $C_{1-4}$ alkyl;

$X^2$ is:

(i) —O—;

(ii) —S—;

(iii) —$S(O)_t$—, wherein t is 1 or 2;

(iv) —$C(Q^1)(Q^2)$-, wherein each of $Q^1$ and $Q^2$ is independently selected from the group consisting of H and $C_{1-4}$ alkyl; or $Q^1$ and $Q^2$, together with the carbon atom to which each is attached forms $C_{3-10}$ cycloalkyl that is optionally substituted with from 1-4 independently selected $R^d$ and optionally fused to phenyl;

(v) $C_{6-10}$ arylene optionally substituted with from 1-5 independently selected $R^c$;

(vi) heteroarylene including from 5-10 ring atoms, wherein from 1-4 ring atoms are each independently selected from the group consisting of N, $N(R^a)$, O, and S; and which is optionally substituted with from 1-5 independently selected $R^c$;

(vii) $C_{3-10}$ cycloalkylene optionally substituted with from 1-4 independently selected $R^d$;

(viii) heterocycloalkylene including from 3-10 ring atoms, wherein from 1-3 ring atoms are each independently selected from the group consisting of $N(R^a)$, O, and S; and which is optionally substituted with from 1-5 independently selected $R^d$;

(ix) $C_2$-$C_4$ alkenylene optionally substituted with from 1-2 $R^e$; or (x) $C_2$-$C_4$ alkynylene optionally substituted with from 1-2 $R^e$;

$X^3$ is: —O—; —S—; or —$S(O)_t$—, wherein t is 1 or 2; each of $R^1$, $R^2$, and $R^4$ is independently selected from the group consisting of H and unsubstituted $C_{1-3}$ alkyl;

$R^{2'}$ is as defined according to (AA) or (BB) below:

(AA)

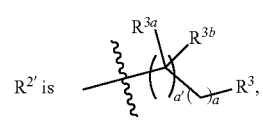

wherein:

$R^3$ is —C(O)OH, —C(O)$OR^{31}$, —CH(C(O)OH)$_2$ or a carboxylic acid isostere (e.g., amide or tetrazolyl);

a is 0-5;

a' is 0 or 1; and each of $R^{3a}$ and $R^{3b}$ is independently H or $C_{1-3}$ alkyl;

BB $R^{2'}$ and $R^4$ taken together with the atoms connecting them form a ring including from 5-8 ring atoms, wherein from 3-7 are ring carbon atoms each substituted with from 1-2 substituents independently selected from H, halo, hydroxy, oxo, and $C_{1-3}$ alkyl; and from 0-1 is a heteroatom (in addition to the N attached to Ri) selected from O, —NH, —N($C_{1-3}$ alkyl), and S (e.g., $R^4$ and $R^3$, taken together with the atoms to which each is attached form a ring including 5-8 ring atoms);

$R^{31}$ is:

(i) $C_{1-6}$ alkyl optionally substituted with from 1-2 independently selected $R^e$;

(ii) —($C_{0-3}$ alkylene)-$C_{3-10}$ cycloalkyl, wherein the cycloalkyl is optionally substituted with from 1-4 independently selected $R^d$;

(iii) —($C_{0-3}$ alkylene)-heterocyclyl including from 3-10 ring atoms, wherein from 1-3 ring atoms are each independently selected from the group consisting of N($R^a$), O, and S, wherein the heterocyclyl is optionally substituted with from 1-4 independently selected $R^d$;

(iv) —($C_{0-3}$ alkylene)-$C_{6-10}$ aryl, wherein the aryl is optionally substituted with from 1-5 independently selected $R^c$; or (v) —($C_{0-3}$ alkylene)-heteroaryl including from 5-10 ring atoms, wherein from 1-4 ring atoms are each independently selected from the group consisting of N, N($R^a$), O, and S, wherein the heteroaryl is optionally substituted with from 1-3 independently selected $R^c$;

each occurrence of $R^a$ is independently selected from the group consisting of: H; $C_{1-4}$ alkyl; $C_{3-6}$ cycloalkyl; —C(=O)($C_{1-6}$ alkyl); —C(=O)O($C_{1-6}$ alkyl); and —S(O)$_{1-2}$($C_{1-6}$ alkyl);

each occurrence of $R^b$ is independently selected from the group consisting of: $R^{31}$; $C_{1-4}$ haloalkyl; —OH; oxo; —F; —N($R^a$)(R"); $C_{1-4}$ alkoxy; $C_{1-4}$ haloalkoxy; —C(=O)($C_{1-4}$ alkyl); —C(=O)O($C_{1-6}$ alkyl); —C(=O)OH, —C(=O)N(R''')(R''''), —S(O)$_{1-2}$($C_{1-6}$ alkyl); and cyano;

each occurrence of $R^c$ is independently selected from the group consisting of: $C_{1-6}$ alkyl optionally substituted with from 1-2 independently selected $R^c$; $C_{3-6}$ cycloalkyl; $C_{1-4}$ haloalkyl; —OH; -halo; —NO$_2$; N$_3$; —N($R^a$)(R"); $C_{1-4}$ alkoxy; $C_{1-4}$ thioalkoxy; $C_{1-4}$ haloalkoxy; —OC(=O)($C_{1-6}$ alkyl); —C(=O)($C_{1-6}$ alkyl); —C(=O)O($C_{1-6}$ alkyl); —C(=O)OH, —C(=O)N(R''')(R''''), —S(O)$_{1-2}$($C_{1-6}$ alkyl); and cyano;

each occurrence of $R^d$ is independently selected from the group consisting of: $C_{1-6}$ alkyl optionally substituted with from 1-2 independently selected $R^e$; $C_{1-4}$ haloalkyl; —OH; —F; Cl; —N($R^a$)(R"); oxo; $C_{1-4}$ alkoxy; $C_{1-4}$ haloalkoxy; —OC(=O)($C_{1-6}$ alkyl); —C(=O)($C_{1-6}$ alkyl); —C(=O)O ($C_{1-6}$ alkyl); —C(=O)OH, —C(=O)N(R''')(R''''), —S(O)$_{1-2}$($C_{1-6}$ alkyl); and cyano;

each occurrence of $R^e$ is independently selected from the group consisting of: —OH; —N($R^a$)(R"); $C_{1-4}$ alkoxy; $C_{1-4}$ haloalkoxy; —OC(=O)($C_{1-6}$ alkyl); —C(=O)O($C_{1-6}$ alkyl); —C(=O)OH, —C(=O)N(R''')(R''''), —S(O)$_{1-2}$($C_{1-6}$ alkyl); and cyano;

each occurrence of R", R''', and R'''' is independently selected from the group consisting of: H and $C_{1-6}$ alkyl; and W is a peptide having the formula W'—$R^5$, wherein W' is a sequence of from 5-60 amino acids, and $R^5$ is a C-terminal amino acid, amino acid ester, or amino acid amide that is optionally substituted with from 1-2 modifying groups (e.g., 1-2 groups selected from an acyl group and a PEG group).

In some embodiments, the compound has Formula (IIAA):

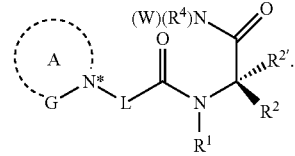

(IIAA)

In some embodiments, the compound has Formula (IIAA-B):

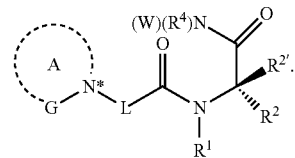

(IIAA-B)

In some embodiments, the compound has Formula (IA):

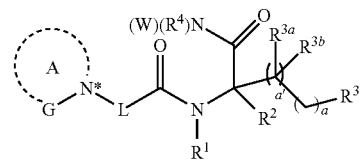

(IA)

wherein:

ring A is:

(i) a saturated or unsaturated monocyclic ring that includes from 3-8 ring atoms (inclusive of G and the nitrogen atom labelled N*); or (ii) a saturated or unsaturated bicyclic or tricyclic ring that includes from 6-14 ring atoms (inclusive of G and the nitrogen atom labelled N*), wherein:

G is C(O), S(O), or SO$_2$; and the dotted, circular line connecting G and N* is a divalent group that includes from 1-6 ring atoms; wherein:

(a) from 0-2 of the divalent group's ring atoms are ring heteroatoms, which are each independently selected from the group consisting of N, N($R^a$), O, S, and SO$_2$; and (b) from 1-6 of the divalent group's ring atoms are ring carbon atoms, which are each independently selected from the group consisting of C, CH, CH$_2$, CR$^b$, C(R$^b$)$_2$, and CHR$^b$;

wherein:

(1) when ring A is a monocyclic ring, then each of the divalent group's 1-6 ring carbon atoms is independently selected from the group consisting of CH, CH$_2$, CR$^b$, C(R$^b$)$_2$, and CHR$^b$; and (2) when ring A is a bicyclic or tricyclic ring, then (A) or (B) applies:

(A) two or three adjacent ring carbon atoms of the divalent group are each independently selected from the group consisting of C, CH, and, CR$^b$ and are fused to a second ring that is selected from the group consisting of:

(a) $C_{6-10}$ aryl optionally substituted with from 1-5 independently selected $R^c$;

(b) heteroaryl including from 5-10 ring atoms, wherein from 1-4 ring atoms are each independently selected from the group consisting of N, N($R^a$), O, and S, wherein the heteroaryl is optionally substituted with from 1-3 independently selected $R^c$;

(c) $C_{3-10}$ cycloalkyl optionally substituted with from 1-4 independently selected $R^d$;

(d) heterocyclyl including from 3-10 ring atoms, wherein from 1-3 ring atoms are each independently selected from the group consisting of N($R^a$), O, and S, wherein the heterocyclyl is optionally substituted with from 1-4 independently selected $R^d$; or (B) one of the divalent group's ring carbon atoms is C and is spiro-fused to a second ring that is selected from the group consisting of:

(a) $C_{3-10}$ cycloalkyl optionally substituted with from 1-4 independently selected $R^d$;

(b) heterocyclyl including from 3-10 ring atoms, wherein from 1-3 ring atoms are each independently selected from the group consisting of N($R^a$), O, and S, wherein the heterocyclyl is optionally substituted with from 1-4 independently selected $R^d$;

L is:
(i) —$(CH_2)_m$—$X^1$—$(CH_2)_n$—$X^2$—$(CH_2)_p$— (formula VIII), wherein m is from 1-6; n is from 0-2; and p is from 0-8;
(ii) —C(O)—$(CH_2)_n$—$X^3$—$(CH_2)_p$— (formula IX), wherein n is from 0-2; and p is from 0-8;
(iii) —$(CH_2)_q$—, wherein q is from 1-10;
(iv) —C(O)—; or
(v) —$(CH_2)_m$—$X^1$—$(CH_2)_p$— (formula VIII), wherein m is from 1-6; and p is from 0-8;

$X^1$ is —C(O)—; —N(R')C(O)—; —C(O)N(R')—; or —N(R')C(O)NR'—; wherein each occurrence of R' is independently selected from the group consisting of: H and $C_{1-4}$ alkyl;

$X^2$ is:
(i) —O—;
(ii) —S—;
(iii) —S(O)$_t$—, wherein t is 1 or 2;
(iv) —C($Q^1$)($Q^2$)-, wherein each of $Q^1$ and $Q^2$ is independently selected from the group consisting of H and $C_{1-4}$ alkyl; or $Q^1$ and $Q^2$, together with the carbon atom to which each is attached forms $C_{3-10}$ cycloalkyl that is optionally substituted with from 1-4 independently selected $R^d$ and optionally fused to phenyl;
(v) $C_{6-10}$ arylene optionally substituted with from 1-5 independently selected $R^c$;
(vi) heteroarylene including from 5-10 ring atoms, wherein from 1-4 ring atoms are each independently selected from the group consisting of N, N($R^a$), O, and S; and which is optionally substituted with from 1-5 independently selected $R^c$;
(vii) $C_{3-10}$ cycloalkylene optionally substituted with from 1-4 independently selected $R^d$;
(viii) heterocycloalkylene including from 3-10 ring atoms, wherein from 1-3 ring atoms are each independently selected from the group consisting of N($R^a$), O, and S; and which is optionally substituted with from 1-5 independently selected $R^d$;
(ix) $C_2$-$C_4$ alkenylene optionally substituted with from 1-2 $R^e$; or
(x) $C_2$-$C_4$ alkynylene optionally substituted with from 1-2 $R^e$;

$X^3$ is: —O—; —S—; or —S(O)$_t$—, wherein t is 1 or 2;
each of $R^1$, $R^2$, and $R^4$ is independently selected from the group consisting of H and unsubstituted $C_{1-3}$ alkyl;
$R^3$ is —C(O)OH, —C(O)O$R^{31}$, —CH(C(O)OH)$_2$ or a carboxylic acid isostere (e.g., amide or tetrazolyl);

a is 0-5;
a' is 0 or 1;
each of $R^{3a}$ and $R^{3b}$ is independently H or $C_{1-3}$ alkyl;
$R^{31}$ is:
(i) $C_{1-6}$ alkyl optionally substituted with from 1-2 independently selected $R^e$;
(ii) —($C_{0-3}$ alkylene)-$C_{3-10}$ cycloalkyl, wherein the cycloalkyl is optionally substituted with from 1-4 independently selected $R^d$;
(iii) —($C_{0-3}$ alkylene)-heterocyclyl including from 3-10 ring atoms, wherein from 1-3 ring atoms are each independently selected from the group consisting of N($R^a$), O, and S, wherein the heterocyclyl is optionally substituted with from 1-4 independently selected $R^d$;
(iv) —($C_{0-3}$ alkylene)-$C_{6-10}$ aryl, wherein the aryl is optionally substituted with from 1-5 independently selected $R^c$; or
(v) —($C_{0-3}$ alkylene)-heteroaryl including from 5-10 ring atoms, wherein from 1-4 ring atoms are each independently selected from the group consisting of N, N($R^a$), O, and S, wherein the heteroaryl is optionally substituted with from 1-3 independently selected $R^c$;

each occurrence of $R^a$ is independently selected from the group consisting of: H; $C_{1-4}$ alkyl; $C_{3-6}$ cycloalkyl; —C(=O)($C_{1-6}$ alkyl); —C(=O)O($C_{1-6}$ alkyl); and —S(O)$_{1-2}$($C_{1-6}$ alkyl);

each occurrence of $R^b$ is independently selected from the group consisting of: $R^{31}$; $C_{1-4}$ haloalkyl; —OH; oxo; —F; —N($R^a$)(R''); $C_{1-4}$ alkoxy; $C_{1-4}$ haloalkoxy; —C(=O)($C_{1-4}$ alkyl); —C(=O)O($C_{1-6}$ alkyl); —C(=O)OH, —C(=O)N(R''')(R''''), —S(O)$_{1-2}$($C_{1-6}$ alkyl); and cyano;

each occurrence of $R^c$ is independently selected from the group consisting of: $C_{1-6}$ alkyl optionally substituted with from 1-2 independently selected $R^e$; $C_{3-6}$ cycloalkyl; $C_{1-4}$ haloalkyl; —OH; -halo; —NO$_2$; N$_3$; —N($R^a$)(R''); $C_{1-4}$ alkoxy; $C_{1-4}$ thioalkoxy; $C_{1-4}$ haloalkoxy; —OC(=O)($C_{1-6}$ alkyl); —C(=O)($C_{1-6}$ alkyl); —C(=O)O($C_{1-6}$ alkyl); —C(=O)OH, —C(=O)N(R''')(R''''), —S(O)$_{1-2}$($C_{1-6}$ alkyl); and cyano;

each occurrence of $R^d$ is independently selected from the group consisting of: $C_{1-6}$ alkyl optionally substituted with from 1-2 independently selected $R^e$; $C_{1-4}$ haloalkyl; —OH; —F; Cl; —N($R^a$)(R''); oxo; $C_{1-4}$ alkoxy; $C_{1-4}$ haloalkoxy; —OC(=O)($C_{1-6}$ alkyl); —C(=O)($C_{1-6}$ alkyl); —C(=O)O ($C_{1-6}$ alkyl); —C(=O)OH, —C(=O)N(R''')(R''''), —S(O)$_{1-2}$($C_{1-6}$ alkyl); and cyano;

each occurrence of $R^e$ is independently selected from the group consisting of: —OH; —N($R^a$)(R''); $C_{1-4}$ alkoxy; $C_{1-4}$ haloalkoxy; —OC(=O)($C_{1-6}$ alkyl); —C(=O)O($C_{1-6}$ alkyl); —C(=O)OH, —C(=O)N(R''')(R''''), —S(O)$_{1-2}$ ($C_{1-6}$ alkyl); and cyano;

each occurrence of R'', R''', and R'''' is independently selected from the group consisting of: H and $C_{1-6}$ alkyl; and W is a peptide having the formula W'—$R^5$, wherein W' is a sequence of from 5-60 amino acids, and $R^5$ is a C-terminal amino acid, amino acid ester, or amino acid amide that is optionally substituted with from 1-2 modifying groups (e.g., 1-2 groups selected from an acyl group and a PEG group).

In some embodiments, the compound has Formula (IIA):

(IIA)

In some embodiments, the compound has Formula (I):

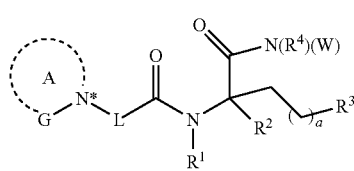

(I)

wherein:
ring A is:
(i) a saturated or unsaturated monocyclic ring that includes from 3-8 ring atoms (inclusive of G and the nitrogen atom labelled N*); or
(ii) a saturated or unsaturated bicyclic or tricyclic ring that includes from 6-14 ring atoms (inclusive of G and the nitrogen atom labelled N*), wherein:
G is C(O), S(O), or $SO_2$; and
the dotted, circular line connecting G and N* is a divalent group that includes from 1-6 ring atoms; wherein:
(a) from 0-2 of the divalent group's ring atoms are ring heteroatoms, which are each independently selected from the group consisting of N, N($R^a$), O, S, and $SO_2$; and
(b) from 1-6 of the divalent group's ring atoms are ring carbon atoms, which are each independently selected from the group consisting of C, CH, $CH_2$, $CR^b$, $C(R^b)_2$, and $CHR^b$;
wherein:
(1) when ring A is a monocyclic ring, then each of the divalent group's 1-6 ring carbon atoms is independently selected from the group consisting of CH, $CH_2$, $CR^b$, $C(R^b)_2$, and $CHR^b$; and
(2) when ring A is a bicyclic or tricyclic ring, then (A) or (B) applies:
(A) two or three adjacent ring carbon atoms of the divalent group are each independently selected from the group consisting of C, CH, and, $CR^b$ and are fused to a second ring that is selected from the group consisting of:
(a) $C_{6-10}$ aryl optionally substituted with from 1-5 independently selected $R^c$;
(b) heteroaryl including from 5-10 ring atoms, wherein from 1-4 ring atoms are each independently selected from the group consisting of N, N($R^a$), O, and S, wherein the heteroaryl is optionally substituted with from 1-3 independently selected $R^c$;
(c) $C_{3-10}$ cycloalkyl optionally substituted with from 1-4 independently selected $R^d$;
(d) heterocyclyl including from 3-10 ring atoms, wherein from 1-3 ring atoms are each independently selected from the group consisting of N($R^a$), O, and S, wherein the heterocyclyl is optionally substituted with from 1-4 independently selected $R^d$; or
(B) one of the divalent group's ring carbon atoms is C and is spiro-fused to a second ring that is selected from the group consisting of:
(a) $C_{3-10}$ cycloalkyl optionally substituted with from 1-4 independently selected $R^d$;
(b) heterocyclyl including from 3-10 ring atoms, wherein from 1-3 ring atoms are each independently selected from the group consisting of N($R^a$), O, and S, wherein the heterocyclyl is optionally substituted with from 1-4 independently selected $R^d$;

L is:
(i) —$(CH_2)_m$—$X^1$—$(CH_2)_n$—$X^2$—$(CH_2)_p$— (formula VIII), wherein m is from 1-6; n is from 0-2; and p is from 0-8;
(ii) —C(O)—$(CH_2)_n$—$X^3$—$(CH_2)_p$— (formula IX), wherein n is from 0-2; and p is from 0-8;
(iii) —$(CH_2)_q$—, wherein q is from 1-10;
(iv) —C(O)—; or
(v) —$(CH_2)_m$—$X^1$—$(CH_2)_p$— (formula VIII), wherein m is from 1-6; and p is from 0-8;
$X^1$ is —C(O)—; —N(R')C(O)—; —C(O)N(R')—; or —N(R')C(O)NR')—; wherein each occurrence of R' is independently selected from the group consisting of: H and $C_{1-4}$ alkyl;
$X^2$ is:
(i) —O—;
(ii) —S—;
(iii) —S(O)$_t$—, wherein t is 1 or 2;
(iv) —C($Q^1$)($Q^2$)-, wherein each of $Q^1$ and $Q^2$ is independently selected from the group consisting of H and $C_{1-4}$ alkyl; or $Q^1$ and $Q^2$, together with the carbon atom to which each is attached forms $C_{3-10}$ cycloalkyl that is optionally substituted with from 1-4 independently selected $R^d$ and optionally fused to phenyl;
(v) $C_{6-10}$ arylene optionally substituted with from 1-5 independently selected $R^c$;
(vi) heteroarylene including from 5-10 ring atoms, wherein from 1-4 ring atoms are each independently selected from the group consisting of N, N($R^a$), O, and S; and which is optionally substituted with from 1-5 independently selected $R^c$;
(vii) $C_{3-10}$ cycloalkylene optionally substituted with from 1-4 independently selected $R^d$;
(viii) heterocycloalkylene including from 3-10 ring atoms, wherein from 1-3 ring atoms are each independently selected from the group consisting of N($R^a$), O, and S; and which is optionally substituted with from 1-5 independently selected $R^d$;
(ix) $C_2$-$C_4$ alkenylene optionally substituted with from 1-2 $R^e$; or
(x) $C_2$-$C_4$ alkynylene optionally substituted with from 1-2 $R^e$;
$X^3$ is: —O—; —S—; or —S(O)$_t$—, wherein t is 1 or 2;
each of $R^1$, $R^2$, and $R^4$ is independently selected from the group consisting of H and unsubstituted $C_{1-3}$ alkyl;
$R^3$ is —C(O)OH, —C(O)$OR^{31}$, or a carboxylic acid isostere; wherein $R^{31}$ is:
(i) $C_{1-6}$ alkyl optionally substituted with from 1-2 independently selected $R^e$;
(ii) —($C_{0-3}$ alkylene)-$C_{3-10}$ cycloalkyl, wherein the cycloalkyl is optionally substituted with from 1-4 independently selected $R^d$;
(iii) —($C_{0-3}$ alkylene)-heterocyclyl including from 3-10 ring atoms, wherein from 1-3 ring atoms are each independently selected from the group consisting of N($R^a$), O, and S, wherein the heterocyclyl is optionally substituted with from 1-4 independently selected $R^d$;
(iv) —($C_{0-3}$ alkylene)-$C_{6-10}$ aryl, wherein the aryl is optionally substituted with from 1-5 independently selected $R^c$; or
(v) —($C_{0-3}$ alkylene)-heteroaryl including from 5-10 ring atoms, wherein from 1-4 ring atoms are each independently selected from the group consisting of N, N($R^a$), O, and S, wherein the heteroaryl is optionally substituted with from 1-3 independently selected $R^c$;

a is 0-5;

each occurrence of $R^a$ is independently selected from the group consisting of: H; $C_{1-4}$ alkyl; $C_{3-6}$ cycloalkyl; —C(=O)($C_{1-6}$ alkyl); —C(=O)O($C_{1-6}$ alkyl); and —S(O)$_{1-2}$($C_{1-6}$ alkyl);

each occurrence of $R^b$ is independently selected from the group consisting of: $R^{31}$; $C_{1-4}$ haloalkyl; —OH; oxo; —F; —N($R^a$)(R''); $C_{1-4}$ alkoxy; $C_{1-4}$ haloalkoxy; —C(=O)($C_{1-4}$ alkyl); —C(=O)O($C_{1-6}$ alkyl); —C(=O)OH, —C(=O)N (R''')(R''''), —S(O)$_{1-2}$($C_{1-6}$ alkyl); and cyano;

each occurrence of $R^c$ is independently selected from the group consisting of: $C_{1-6}$ alkyl optionally substituted with from 1-2 independently selected $R^e$; $C_{3-6}$ cycloalkyl; $C_{1-4}$ haloalkyl; —OH; -halo; —NO$_2$; N$_3$; —N($R^a$)(R''); $C_{1-4}$ alkoxy; $C_{1-4}$ thioalkoxy; $C_{1-4}$ haloalkoxy; —OC(=O)($C_{1-6}$ alkyl); —C(=O)($C_{1-6}$ alkyl); —C(=O)O($C_{1-6}$ alkyl); —C(=O)OH, —C(=O)N(R''')(R''''), —S(O)$_{1-2}$($C_{1-6}$ alkyl); and cyano;

each occurrence of $R^d$ is independently selected from the group consisting of: $C_{1-6}$ alkyl optionally substituted with from 1-2 independently selected $R^e$; $C_{1-4}$ haloalkyl; —OH; —F; Cl; —N($R^a$)(R''); oxo; $C_{1-4}$ alkoxy; $C_{1-4}$ haloalkoxy; —OC(=O)($C_{1-6}$ alkyl); —C(=O)($C_{1-6}$ alkyl); —C(=O)O ($C_{1-6}$ alkyl); —C(=O)OH, —C(=O)N(R''')(R''''), —S(O)$_{1-2}$($C_{1-6}$ alkyl); and cyano;

each occurrence of $R^e$ is independently selected from the group consisting of: —OH; —N($R^a$)(R''); $C_{1-4}$ alkoxy; $C_{1-4}$ haloalkoxy; —OC(=O)($C_{1-6}$ alkyl); —C(=O)O($C_{1-6}$ alkyl); —C(=O)OH, —C(=O)N(R''')(R''''), —S(O)$_{1-2}$ ($C_{1-6}$ alkyl); and cyano;

each occurrence of R'', R''', and R'''' is independently selected from the group consisting of: H and $C_{1-6}$ alkyl; and W is a peptide having the formula W'—$R^5$, wherein W' is a sequence of from 5-60 amino acids, and $R^5$ is a C-terminal amino acid, amino acid ester, or amino acid amide that is optionally substituted with from 1-2 modifying groups (e.g., 1-2 groups selected from an acyl group and a PEG group).

In some embodiments, one or more of the compound provisions delineated herein (e.g., as delineated in the section below) apply.

Compound Provisions

In some embodiments, the compound is other than CAS RN 1401463-49-7; and/or CAS RN 1116465-43-0; and/or CAS RN 1614237-35-2, and/or CAS RN 1614237-36-3; and/or CAS RN 1353718-57-6; and/or CAS Registry Number: 1083307-90-7, in which each of the registered chemical structures is incorporated herein by reference.

In some embodiments, the compound is not any of the compounds disclosed in Nacheva et al., *Organic & Biomolecular Chemistry*, 2012, 10 (38), 7840-7846, Chopra et al., *Bioconjugate Chemistry*, 2009, 20 (2), 231-240, and PCT application publication No. WO 2013/148579, each of which is incorporated by reference.

In some embodiments, ring A is other than unsubstituted maleimid-1-yl, i.e.:

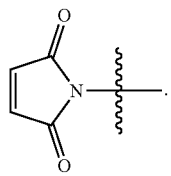 [SMILES: *N1C(=O)C=CC1=O]

In certain embodiments, when L is —(CH$_2$)$_2$—, —(CH$_2$)$_5$—C(O)NH—CH$_2$—, or —(CH$_2$)$_2$—C(O)NH—(CH$_2$)$_6$—, then ring A is other than unsubstituted maleimid-1-yl.

In certain embodiments, when L is —(CH$_2$)$_2$—, —(CH$_2$)$_5$—C(O)NH—CH$_2$—, or —(CH$_2$)$_2$—C(O)NH—(CH$_2$)$_6$—, and a is 1, then ring A is other than unsubstituted maleimid-1-yl.

In some embodiments, ring A is other than substituted maleimid-1-yl (e.g., other than 3,4-bis(2,4-difluorophenyl)-maleimid-1-yl, i.e.:

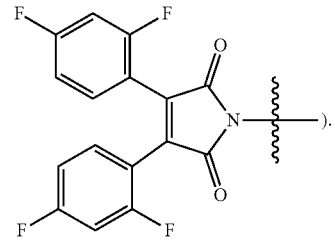 [SMILES: *N1C(=O)C(c2ccc(F)cc2F)=C(c2ccc(F)cc2F)C1=O]

In certain embodiments, when L is —(CH$_2$)$_3$—, then ring A is other than substituted maleimid-1-yl (e.g., other than 3,4-bis(2,4-difluorophenyl)-maleimid-1-yl).

In certain embodiments, when L is —(CH$_2$)$_3$—, and a is 1, then ring A is other than substituted maleimid-1-yl (e.g., other than 3,4-bis(2,4-difluorophenyl)-maleimid-1-yl).

In some embodiments, ring A is other than optionally substituted N-[2-(1,3-dioxo-1H-benz[de]isoquinolin-2(3H)-yl, (e.g., other than unsubstituted N-[2-(1,3-dioxo-1H-benz [de]isoquinolin-2(3H)-yl, i.e.:

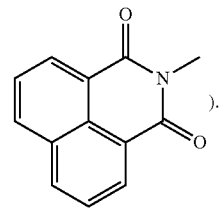 [SMILES: CN1C(=O)c2cccc3cccc(c23)C1=O]

In certain embodiments, when L is —(CH$_2$)$_3$—, then ring A is other than than optionally substituted N-[2-(1,3-dioxo-1H-benz[de]isoquinolin-2(3H)-yl, (e.g., other than unsubstituted N-[2-(1,3-dioxo-1H-benz[de]isoquinolin-2(3H)-yl).

In certain embodiments, when L is —(CH$_2$)$_3$—, and a is 0, then ring A is other than than optionally substituted N-[2-(1,3-dioxo-1H-benz[de]isoquinolin-2(3H)-yl, (e.g., unsubstituted N-[2-(1,3-dioxo-1H-benz[de]isoquinolin-2 (3H)-yl).

In some embodiments, ring A is other than:

(i) unsubstituted maleimid-1-yl; and (ii) substituted maleimid-1-yl (e.g., other than 3,4-bis(2, 4-difluorophenyl)-maleimid-1-yl).

In some embodiments, ring A is other than:

(i) unsubstituted maleimid-1-yl;

(ii) substituted maleimid-1-yl (e.g., other than 3,4-bis(2, 4-difluorophenyl)-maleimid-1-yl), and (iii) optionally substituted N-[2-(1,3-dioxo-1H-benz[de] isoquinolin-2(3H)-yl, (e.g., other than unsubstituted N-[2-(1,3-dioxo-1H-benz[de]isoquinolin-2(3H)-yl).

In some embodiments:

(i) when L is —(CH$_2$)$_2$—, —(CH$_2$)$_5$—C(O)NH—CH$_2$—, or —(CH$_2$)$_2$—C(O)NH—(CH$_2$)$_6$—, then ring A is other than unsubstituted maleimid-1-yl; and (ii) when L is —(CH$_2$)$_3$—, then ring A is other than substituted maleimid-1-yl (e.g., other than 3,4-bis(2,4-difluorophenyl)-maleimid-1-yl).

In some embodiments:

(i) when L is —(CH$_2$)$_2$—, —(CH$_2$)$_5$—C(O)NH—CH$_2$—, or —(CH$_2$)$_2$—C(O)NH—(CH$_2$)$_6$—, and a is 1, then ring A is other than unsubstituted maleimid-1-yl; and (ii) when L is —(CH$_2$)$_3$—, and a is 1, then ring A is other than substituted maleimid-1-yl (e.g., other than 3,4-bis(2,4-difluorophenyl)-maleimid-1-yl).

In some embodiments:

(i) when L is —(CH$_2$)$_2$—, —(CH$_2$)$_5$—C(O)NH—CH$_2$—, or —(CH$_2$)$_2$—C(O)NH—(CH$_2$)$_6$—, then ring A is other than unsubstituted maleimid-1-yl;

(ii) when L is —(CH$_2$)$_3$—, then ring A is other than substituted maleimid-1-yl (e.g., other than 3,4-bis(2,4-difluorophenyl)-maleimid-1-yl); and (iii) when L is —(CH$_2$)$_3$—, then ring A is other than optionally substituted N-[2-(1,3-dioxo-1H-benz[de]isoquinolin-2(3H)-yl, (e.g., other than unsubstituted N-[2-(1,3-dioxo-1H-benz[de]isoquinolin-2(3H)-yl).

In some embodiments:

(i) when L is —(CH$_2$)$_2$—, —(CH$_2$)$_5$—C(O)NH—CH$_2$—, or —(CH$_2$)$_2$—C(O)NH—(CH$_2$)$_6$—, and a is 1, then ring A is other than unsubstituted maleimid-1-yl;

(ii) when L is —(CH$_2$)$_3$—, and a is 1, then ring A is other than substituted maleimid-1-yl (e.g., other than 3,4-bis(2,4-difluorophenyl)-maleimid-1-yl); and (iii) when L is —(CH$_2$)$_3$—, and a is 0, then ring A is other than optionally substituted N-[2-(1,3-dioxo-1H-benz[de]isoquinolin-2(3H)-yl, (e.g., unsubstituted N-[2-(1,3-dioxo-1H-benz[de]isoquinolin-2(3H)-yl.

In some embodiments, the first three amino acids in W' must be glycine-threonine-phenylalanine (GTF).

In some embodiments, W' must include 11 or more amino acids (e.g., 12 or more, 13 or more, 14 or more, 15 or more, 16 or more, 17 or more, 18 or more, 19 or more, 20 or more, 25 or more, 30 or more amino acids).

In some embodiments, the first three amino acids in W' must be glycine-threonine-phenylalanine (GTF); and W' must include 11 or more amino acids (e.g., 12 or more, 13 or more, 14 or more, 15 or more, 16 or more, 17 or more, 18 or more, 19 or more, 20 or more, 25 or more, 30 or more amino acids).

In certain of these embodiments, one or more of the following applies. Ring A is unsubstituted maleimid-1-yl, and L is —(CH$_2$)$_2$—, —(CH$_2$)$_5$—C(O)NH—CH$_2$—, or —(CH$_2$)$_2$—C(O)NH—(CH$_2$)$_6$— (optionally, a is 1). Ring A is substituted maleimid-1-yl (e.g., 3,4-bis(2,4-difluorophenyl)-maleimid-1-yl), and L is —(CH$_2$)$_3$— (optionally, a is 1). Ring A is optionally substituted N-[2-(1,3-dioxo-1H-benz[de]isoquinolin-2(3H)-yl, (e.g., unsubstituted N-[2-(1,3-dioxo-1H-benz[de]isoquinolin-2(3H)-yl) (optionally, a is 0).

In certain embodiments, when L is (CH$_2$)$_q$, q is not 3. In certain embodiments, when ring A is substituted with 2 R$^b$ groups, the R$^b$ groups are not both o,p-(di-fluoro)phenyl, or ring A is substituted with 2 o,p-(di-fluoro)phenyl groups, the first amino acid in the sequence W' is not valine, or when ring A is substituted with 2 o,p-(di-fluoro)phenyl groups, L is not (CH$_2$)$_3$; or when L is (CH$_2$)$_3$, the first amino acid is the sequence W' is not valine.

In certain embodiments, when L is —(CH$_2$)$_m$—X$^1$—(CH$_2$)$_n$—X$^2$—(CH$_2$)$_p$—, m is 5, X$^1$ is —C(O)NH—, n and p are each zero, and X$^2$ is CQ$^1$Q$^2$, at least one of Q$^1$ and Q$^2$ is not H. In certain embodiments, when L is —(CH$_2$)$_m$—X$^1$—(CH$_2$)$_n$—X$^2$—(CH$_2$)$_p$—, m is 5, X$^1$ is —C(O)NH—, n and p are each zero, and X$^2$ is CH$_2$, ring A is not —N-maleimide. or In certain embodiments, when L is —(CH$_2$)$_m$—X$^1$—(CH$_2$)$_n$—X$^2$—(CH$_2$)$_p$—, m is 5, X$^1$ is —C(O)NH—, n and p are each zero, X$^2$ is CH$_2$, and ring A is —N-maleimide, the first amino acid is the sequence W' is not glycine.

In certain embodiments, when L is —(CH$_2$)$_m$—X$^1$—(CH$_2$)$_n$—X$^2$—(CH$_2$)$_p$—, m is 2, X$^1$ is —C(O)NH—, the sum of n and p is 5, and X$^2$ is CQ$^1$Q$^2$, at least one of Q$^1$ and Q$^2$ is not H. In certain embodiments, when L is —(CH$_2$)$_m$—X$^1$—(CH$_2$)$_n$—X$^2$—(CH$_2$)$_p$—, m is 2, X$^1$ is —C(O)NH—, the sum of n and p is 5, and X$^2$ is CH$_2$, ring A is not —N-maleimide. In certain embodiments, when L is —(CH$_2$)$_m$—X$^1$—(CH$_2$)$_n$—X$^2$—(CH$_2$)$_p$—, m is 2, X$^1$ is —C(O)NH—, the sum of n and p is 5, X$^2$ is CH$_2$, and ring A is —N-maleimide, the first amino acid in the sequence W' is not alanine.

In certain embodiments, when L is (CH$_2$)$_q$, q is not 2; or when L is (CH$_2$)$_2$, ring A is not —N-maleimide; or when L is (CH$_2$)$_2$ and ring A is —N-maleimide, the first amino acid in the sequence W' is not alanine.

Ring A

In some embodiments, G is C(O). By way of non-limiting example, such compounds can include those having formula (I-A), (I-AA), or (I-AB):

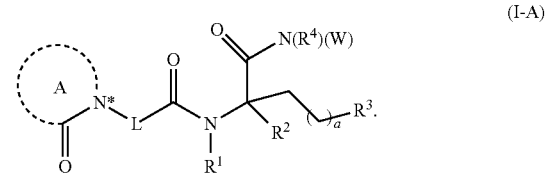

(I-A)

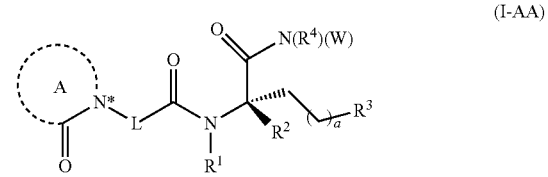

(I-AA)

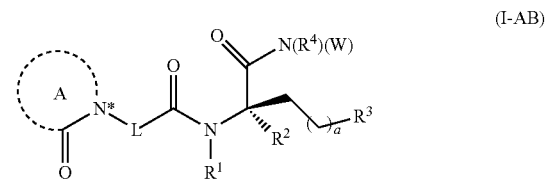

(I-AB)

Further non-limiting examples include compounds having formula (IA-A), (IA-AA), or (IA-AB).

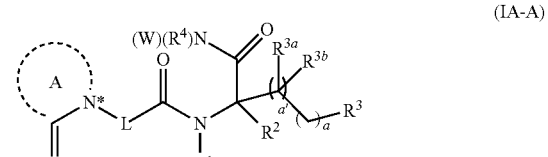

(IA-A)

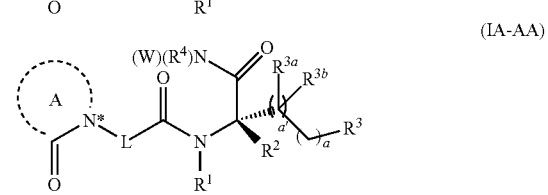

(IA-AA)

-continued

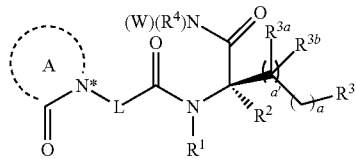

(IA-AB)

In some embodiments, G is S(O) or $SO_2$. By way of non-limiting example, such compounds can include those having formula (I-B), (I-BA), or (I-BB):

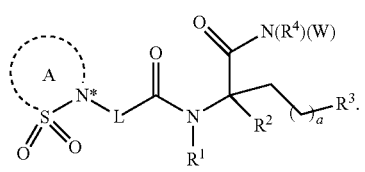

(I-B)

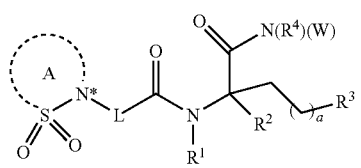

(I-BA)

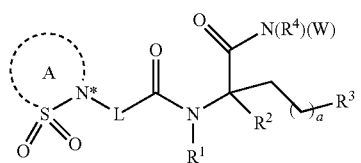

(I-BB)

Further non-limiting examples include compounds having formula (IA-B), (IA-BA), or (IA-BB):

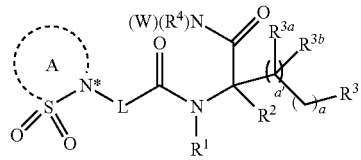

(IA-B)

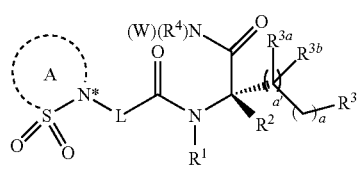

(IA-BA)

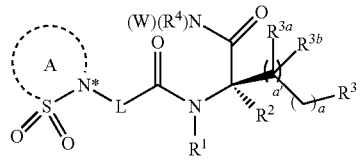

(IA-BB)

In some embodiments, ring A is a saturated or unsaturated monocyclic ring that includes from 3-8 (e.g., 4-8, 4-7, 5-6) ring atoms.

In certain of these embodiments, ring A is saturated. In other embodiments, ring A is unsaturated. In certain of these embodiments, ring A includes 4-7 ring atoms or 5-6 ring atoms.

In certain embodiments, ring A is a saturated monocyclic ring that includes from 3-8 (e.g., 4-8, 4-7, 5-6) ring atoms.

In certain embodiments, ring A is a saturated monocyclic ring that includes from 5-7 ring atoms.

In certain embodiments, ring A is a saturated monocyclic ring that includes from 5-6 ring atoms.

In certain embodiments, ring A has the following formula (III):

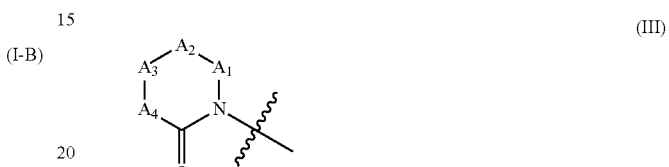

(III)

wherein:
$A_1$ is a bond, $A^{1A}$-$A^{1B}$, C(O), $CH_2$, $CHR^b$, or $C(R^b)_2$;
each of $A^{1A}$ and $A^{1B}$ is independently C(O), $CH_2$, $CHR^b$, or $C(R^b)_2$;
$A_2$ is C(O), $CH_2$, $CHR^b$, or $C(R^b)_2$;
$A_3$ is C(O), $CH_2$, $CHR^b$, or $C(R^b)_2$; O; S; $SO_2$, or $N(R^a)$;
$A_4$ is C(O), $CH_2$, $CHR^b$, or $C(R^b)_2$; O; S; or $N(R^a)$;
provided that $A_3$ and $A_4$ cannot both be O; S; or $N(R^a)$; or a combination thereof.

In certain embodiments, ring A has formula (III):

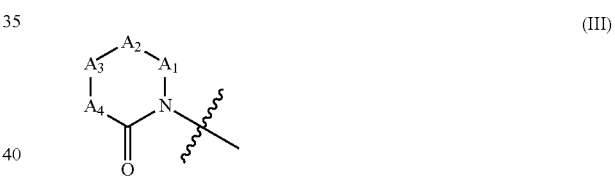

(III)

wherein:
$A_1$ is a bond, C(O), $CH_2$, $CHR^b$, or $C(R^b)_2$;
$A_2$ is C(O), $CH_2$, $CHR^b$, or $C(R^b)_2$;
$A_3$ is C(O), $CH_2$, $CHR^b$, or $C(R^b)_2$; O; S; $SO_2$; or $N(R^a)$; and
$A_4$ is $CH_2$, $CHR^b$, or $C(R^b)_2$; O; S; or $N(R^a)$; provided that $A_3$ and $A_4$ cannot both be O; S; or $N(R^a)$; or a combination thereof.

In certain embodiments of formula (III), $A_1$ is other than a bond (i.e., $A_1$ is C(O), $CH_2$, $CHR^b$, or $C(R^b)_2$), and ring A includes 6 ring atoms (i.e., ring A is a 6-membered ring).

In certain formula (III), 6-membered ring embodiments, $A_1$ is $CH_2$, $CHR^b$, or $C(R^b)_2$. For example, $A_1$ can be $CH_2$. In other embodiments, $A_1$ is C(O).

In certain formula (III), 6-membered ring embodiments, $A_2$ is $CH_2$, $CHR^b$, or $C(R^b)_2$. For example, $A_2$ can be $CH_2$.

In certain formula (III), 6-membered ring embodiments, $A_3$ is $CH_2$, $CHR^b$, or $C(R^b)_2$. For example, $A_3$ can be $CH_2$. In other embodiments, $A_3$ is O; S; $SO_2$; or $N(R^a)$.

In certain formula (III), 6-membered ring embodiments, $A_4$ is $CH_2$, $CHR^b$, or $C(R^b)_2$. For example, $A_4$ can be $CH_2$. In other embodiments, $A_4$ is O; S; or $N(R^a)$.

In certain formula (III), 6-membered ring embodiments, $A_2$, $A_3$ and $A_4$ are each independently selected from the group consisting of $CH_2$, $CHR^b$, or $C(R^b)_2$.

In certain embodiments, one or two (e.g., one) of $A_2$, $A_3$ and $A_4$ are independently selected from the group consisting of $CHR^b$ and $C(R^b)_2$, and the other(s) is/are $CH_2$.

In certain formula (III), 6-membered ring embodiments, $A_2$, $A_3$ and $A_4$ are each $CH_2$.

In certain formula (III), 6-membered ring embodiments, $A_2$ and $A_4$ are each independently selected from the group consisting of $CH_2$, $CHR^b$, and $C(R^b)_2$; and $A_3$ is O; S; $SO_2$; or $N(R^a)$. In certain of these embodiments, one or two (e.g., one) of $A_2$ and $A_4$ are independently selected from the group consisting of $CHR^b$ and $C(R^b)_2$, and the other (where applicable) is $CH_2$. In other embodiments, $A_2$ and $A_4$ are both $CH_2$. In certain of these embodiments, $A_3$ is $N(R^a)$ (e.g., $A_3$ can be NH). In other embodiments, $A_3$ is O. In still other embodiments, $A_3$ is $SO_2$.

In certain formula (III), 6-membered ring embodiments, $A_2$ and $A_3$ are each independently selected from the group consisting of $CH_2$, $CHR^b$, and $C(R^b)_2$; and $A_4$ is O; S; or $N(R^a)$. In certain of these embodiments, one or two (e.g., one) of $A_2$ and $A_3$ are independently selected from the group consisting of $CHR^b$ and $C(R^b)_2$, and the other (where applicable) is $CH_2$. In other embodiments, $A_2$ and $A_3$ are both $CH_2$. In certain of these embodiments, $A_4$ is $N(R^a)$ (e.g., $A_4$ can be NH). In other embodiments, $A_4$ is O.

In certain formula (III), 6-membered ring embodiments, $A_1$, $A_2$, $A_3$ and $A_4$ are each independently selected from the group consisting of $CH_2$, $CHR^b$, or $C(R^b)_2$.

In certain formula (III), 6-membered ring embodiments, one or two (e.g., one) of $A_1$, $A_2$, $A_3$ and $A_4$ are independently selected from the group consisting of $CHR^b$ and $C(R)_2$, and the others are $CH_2$.

In certain formula (III), 6-membered ring embodiments, $A_1$, $A_2$, $A_3$ and $A_4$ are each $CH_2$.

In certain formula (III), 6-membered ring embodiments, $A_1$, $A_2$ and $A_4$ are each independently selected from the group consisting of $CH_2$, $CHR^b$, and $C(R^b)_2$; and $A_3$ is O; S; $SO_2$; or $N(R^a)$. In certain of these embodiments, one or two (e.g., one) of $A_2$ and $A_4$ are independently selected from the group consisting of $CHR^b$ and $C(R^b)_2$, and the other (where applicable) is $CH_2$. In other embodiments, $A_2$ and $A_3$ are both $CH_2$. In certain of these embodiments, $A_1$ is $CH_2$. In certain of these embodiments, $A_3$ is $N(R^a)$ (e.g., $A_3$ can be NH). In other embodiments, $A_3$ is O. In still other embodiments, $A_3$ is $SO_2$.

In certain formula (III), 6-membered ring embodiments, $A_1$, $A_2$ and $A_3$ are each independently selected from the group consisting of $CH_2$, $CHR^b$, and $C(R^b)_2$; and $A_4$ is O; S; or $N(R^a)$. In certain of these embodiments, one or two (e.g., one) of $A_2$ and $A_4$ are independently selected from the group consisting of $CHR^b$ and $C(R^b)_2$, and the other (where applicable) is $CH_2$. In other embodiments, $A_2$ and $A_3$ are both $CH_2$. In certain of these embodiments, $A_1$ is $CH_2$. In certain of these embodiments, $A_4$ is $N(R^a)$ (e.g., $A_4$ can be NH). In other embodiments, $A_4$ is O.

In certain formula (III), 6-membered ring embodiments, $A_1$ is C(O); and $A_2$, $A_3$ and $A_4$ are each independently selected from the group consisting of $CH_2$, $CHR^b$, or $C(R^b)_2$. In certain of these embodiments, one or two (e.g., one) of $A_2$, $A_3$ and $A_4$ are independently selected from the group consisting of $CHR^b$ and $C(R^b)_2$, and the other(s) is/are $CH_2$.

In certain formula (III), 6-membered ring embodiments, $A_1$ is C(O); and $A_2$, $A_3$ and $A_4$ are each $CH_2$.

In certain formula (III), 6-membered ring embodiments, $A_1$ is C(O); $A_2$ and $A_4$ are each independently selected from the group consisting of $CH_2$, $CHR^b$, and $C(R^b)_2$; and $A_3$ is O; S; $SO_2$; or $N(R^a)$. In certain of these embodiments, one or two (e.g., one) of $A_2$ and $A_4$ are independently selected from the group consisting of $CHR^b$ and $C(R^b)_2$, and the other (where applicable) is $CH_2$. In other embodiments, $A_2$ and $A_4$ are both $CH_2$. In certain of these embodiments, $A_3$ is $N(R^a)$ (e.g., $A_3$ can be NH). In other embodiments, $A_3$ is O. In still other embodiments, $A_3$ is $SO_2$.

In certain formula (III), 6-membered ring embodiments, $A_1$ is C(O); $A_2$ and $A_3$ are each independently selected from the group consisting of $CH_2$, $CHR^b$, and $C(R^b)_2$; and $A_4$ is O; S; or $N(R^a)$. In certain of these embodiments, one or two (e.g., one) of $A_2$ and $A_3$ are independently selected from the group consisting of $CHR^b$ and $C(R^b)_2$, and the other (where applicable) is $CH_2$. In other embodiments, $A_2$ and $A_3$ are both $CH_2$. In certain of these embodiments, $A_4$ is $N(R^a)$ (e.g., $A_4$ can be NH). In other embodiments, $A_4$ is O.

In certain embodiments of formula (III), $A_1$ is a bond, and ring A includes 5 ring atoms (i.e., ring A is a 5-membered ring), and ring A has formula (III-A):

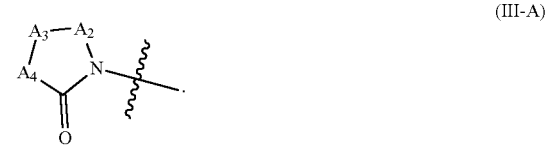

(III-A)

In certain formula (III-A) embodiments, $A_2$ is C(=O). In other embodiments, $A_2$ is $CH_2$, $CHR^b$, or $C(R^b)_2$; for example, $A_2$ can be $CH_2$.

In certain formula (III-A) embodiments, $A_3$ is O; S; or $N(R^e)$. For example, $A_3$ can be S. As another example, $A_3$ can be $N(R^a)$ (e.g., $A_3$ can be NH).

In certain formula (III-A) embodiments, $A_4$ is $CH_2$, $CHR^b$, or $C(R^b)_2$. For example, $A_4$ can be $CHR^b$ or $C(R^b)_2$. As another example, $A_4$ can be $CH_2$.

In certain formula (III-A) embodiments, $A_2$ is C(=O); $A_3$ is O; S; or $N(R^e)$; and $A_4$ is $CH_2$, $CHR^b$, or $C(R^b)_2$. In certain of these embodiments, $A_3$ is S. In other embodiments, $A_3$ is $N(R^a)$ (e.g., $A_3$ is NH). In certain of these embodiments, $A_4$ is $CH_2$. In other embodiments, $A_4$ is $CHR^b$ or $C(R^b)_2$.

In certain formula (III-A) embodiments, $A_2$ is C(=O); and each of $A_3$ and $A_4$ is independently selected from $CH_2$, $CHR^b$, or $C(R^b)_2$. In certain of these embodiments, each of $A_3$ and $A_4$ is $CH_2$. In other embodiments, one of $A_3$ and $A_4$ is $CH_2$, and the other of $A_3$ and $A_4$ is $CHR^b$ or $C(R^b)_2$. In still other embodiments, each of $A_3$ and $A_4$ is independently selected from $CHR^b$ or $C(R^b)_2$.

In certain formula (III-A) embodiments, $A_2$ is $CH_2$, $CHR^b$, or $C(R^b)_2$, e.g., $A_2$ can be $CH_2$; and each of $A_3$ and $A_4$ is independently selected from $CH_2$, $CHR^b$, or $C(R^b)_2$ (e.g., each of $A_3$ and $A_4$ is $CH_2$).

In certain of formula (III) embodiments, $A^1$ is $A^{1A}$-$A^{1B}$.

In certain of the foregoing formula (III) embodiments, each of $A^{1A}$ and $A^{1B}$ is independently $CH_2$, $CHR^b$, or $C(R^b)_2$. As a non-limiting example, each of $A^{1A}$ and $A^{1B}$ can be independently $CH_2$.

In certain of formula (III) embodiments (when $A^1$ is $A^{1A}$-$A^{1B}$), $A^2$ is $CH_2$, $CHR^b$, or $C(R^b)_2$. As a non-limiting example, $A^2$ can be $CH_2$.

In certain of formula (III) embodiments (when $A^1$ is $A^{1A}$-$A^{1B}$), $A^3$ is $CH_2$, $CHR^b$, or $C(R^b)_2$. As a non-limiting example, $A^3$ can be $CH_2$.

In certain of formula (III) embodiments (when $A^1$ is $A^{1A}$-$A^{1B}$), $A^4$ is $CH_2$, $CHR^b$, or $C(R^b)_2$. As a non-limiting example, $A^4$ is $CH_2$.

In certain of the foregoing formula (III) and (III-A) embodiments, each occurrence of $R^b$ is independently selected from the group consisting of:

(i) $C_{1-6}$ alkyl optionally substituted with from 1-2 independently selected $R^e$;

(ii) —($C_{0-3}$ alkylene)-$C_{6-10}$ aryl, wherein the aryl is optionally substituted with from 1-5 independently selected $R^c$;

(iii) —($C_{0-3}$ alkylene)-heteroaryl including from 5-10 ring atoms, wherein from 1-4 ring atoms are each independently selected from the group consisting of N, N($R^a$), O, and S, wherein the heteroaryl is optionally substituted with from 1-3 independently selected $R^c$;

(iv) —OH;

(v) —N($R^a$)(R″);

(vi) $C_{1-4}$ alkoxy; and (vii) $C_{1-4}$ haloalkoxy; and (viii) —F.

In certain of the formula (III) and (III-A) embodiments, each occurrence of $R^b$ is independently selected from the group consisting of:

(i) $C_{1-6}$ alkyl;

(iv) —OH;

(v) —N($R^a$)(R″);

(vi) $C_{1-4}$ alkoxy;

(vii) $C_{1-4}$ haloalkoxy; and (viii) —F.

In certain of the foregoing formula (III) embodiments, each occurrence of $R^b$ is independently selected from the group consisting of: $C_{1-6}$ alkyl optionally substituted with from 1-2 independently selected $R^e$; phenyl optionally substituted with from 1-5 independently selected $R^c$; —OH; —F; —N($R^a$)(R″); and $C_{1-4}$ alkoxy.

Non-limiting examples of ring A moities having formula (III) or (III-A) are delineated in tabular format in Table 1 below.

TABLE 1

| Example | $A_1$ | $A_2$ | $A_3$ | $A_4$ |
|---------|-------|-------|-------|-------|
| III-1 | Bond | C(O) | S | CH2 |
| III-2 | CH2 | CH2 | CH2 | CH2 |
| III-3 | Bond | C(O) | NH | CH2 |
| III-4 | CH2 | CH2 | S | CH2 |
| III-5 | CH2 | CH2 | SO2 | CH2 |
| III-6 | CH2—CH2 | CH2 | CH2 | CH2 |
| III-7 | CH2 | CH2 | CH2 | C(O) |
| III-8 | CH2 | CH2 | O | CH2 |

In some embodiments, ring A is an unsaturated monocyclic ring that includes from 4-8 (e.g., 4-7, 5-6) ring atoms.

In certain embodiments, ring A is an unsaturated monocyclic ring that includes from 4-7 ring atoms.

In certain embodiments, ring A is an unsaturated monocyclic ring that includes from 5-6 ring atoms.

In certain embodiments, ring A is an unsaturated monocyclic ring that includes 6 ring atoms.

In certain embodiments, ring A is other than an unsaturated monocyclic ring that includes 5 ring atoms (e.g., other than maleimide, e.g, unsubstituted or di-substituted maleimide).

In certain of these embodiments, ring A has formula (IV):

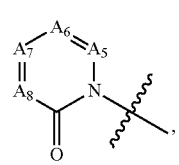

(IV)

wherein:
each of $A_6$, and $A_7$ is independently selected from CH and $CR^b$; and
each of $A_5$ and $A_8$ is independently N, CH, or $CR^b$.

In certain of these embodiments, ring A has formula (IV):

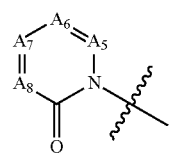

(IV)

wherein:
each of $A_5$, $A_6$, and $A_7$ is independently selected from CH and $CR^b$; and
$A_8$ is N, CH, or $CR^b$.

In certain formula (IV) embodiments, $A_5$, $A_6$, $A_7$, and $A_8$ are each independently selected from CH and $CR^b$. For example, one or two of $A_5$, $A_6$, $A_7$, and $A_8$ are an independently selected $CR^b$, and the others are CH. As another example, $A_5$, $A_6$, $A_7$, and $A_8$ are each CH.

In other formula (IV) embodiments, $A_5$, $A_6$, and $A_7$ are each independently selected from CH and $CR^b$, and $A_8$ is N. For example, one or two of $A_5$, $A_6$, and $A_7$ are an independently selected $CR^b$, and the others are CH. As another example, $A_5$, $A_6$, and $A_7$ are each CH.

In still other formula (IV) embodiments, $A_5$ is N; and each of $A_6$, $A_7$, and $A_8$ is independently selected from CH and $CR^b$ (e.g., one of $A_6$, $A_7$, and $A_8$ is $CR^b$ (e.g., C—OH)).

In certain of the foregoing formula (IV) embodiments, each occurrence of $R^b$ is independently selected from the group consisting of: $R^{31}$; $C_{1-4}$ haloalkyl; —OH; —N($R^a$)(R″); $C_{1-4}$ alkoxy; and $C_{1-4}$ haloalkoxy.

In certain of the foregoing formula (IV) embodiments, each occurrence of $R^b$ is independently selected from the group consisting of: $R^{31}$; —OH; —N($R^a$)(R″); $C_{1-4}$ alkoxy; and $C_{1-4}$ haloalkoxy.

In certain of the foregoing formula (IV) embodiments, each occurrence of $R^b$ is independently selected from the group consisting of:

(i) $C_{1-6}$ alkyl optionally substituted with from 1-2 independently selected $R^e$;

(ii) —($C_{0-3}$ alkylene)-$C_{6-10}$ aryl, wherein the aryl is optionally substituted with from 1-5 independently selected $R^c$;

(iii) —($C_{0-3}$ alkylene)-heteroaryl including from 5-10 ring atoms, wherein from 1-4 ring atoms are each independently selected from the group consisting of N, N($R^a$), O, and S, wherein the heteroaryl is optionally substituted with from 1-3 independently selected $R^c$;

(iv) —OH;

(v) —N($R^a$)(R″);

(vi) $C_{1-4}$ alkoxy;

(vii) $C_{1-4}$ haloalkoxy; and (viii) —F.

In certain of these embodiments, ring A has formula (V):

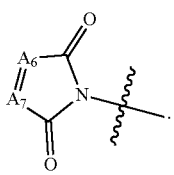

(V)

wherein:

each of $A_6$ and $A_7$ is independently selected from CH and $CR^b$; and $A_8$ is N, CH, or $CR^b$.

In other formula (V) embodiments, $A_6$ and $A_7$ are each CH. In other formula (IV) embodiments, $A_6$ and $A_7$ cannot both be CH.

In certain formula (V) embodiments, one of $A_6$ and $A_7$ is $CR^b$, the other of $A_6$ and $A_7$ is CH.

In other formula (IV) embodiments, $A_6$ and $A_7$ are each an independently selected $CR^b$. In other formula (IV) embodiments, $A_6$ and $A_7$ cannot both be an independently selected $CR^b$. In certain of these embodiments, when $A_6$ and $A_7$ are each an independently selected $CR^b$, then both $R^b$ substituents cannot be $C_{6-10}$ aryl (e.g., phenyl) substituted with from 1-5 independently selected $R^c$. As another example, both $R^b$ substituents cannot be $C_{6-10}$ aryl (e.g., phenyl) substituted with from 1-3 or 1-2 independently selected $R^c$. For example, both $R^b$ substituents cannot be $C_{6-10}$ aryl (e.g., phenyl), substituted with from 1-5 independently halo (e.g., fluoro). As another example, both $R^b$ substituents cannot be $C_{6-10}$ aryl (e.g., phenyl), substituted with from 1-3 or 1-2 independently selected halo (e.g., fluoro). For example, both both $R^b$ substituents cannot be difluorophenyl, e.g., o,p-(difluoro)phenyl.

In some embodiments, ring A is a saturated or unsaturated bicyclic or tricyclic ring that includes from 7-9 (e.g., 7-8, e.g, 7) ring atoms.

In certain of these embodiments, (A) applies (e.g., three adjacent ring carbon atoms of the divalent group are each independently selected from the group consisting of C, CH, $CR^b$, $CH_2$, $C(R^b)H$, $C(R^b)_2$ and are fused to a second ring).

In certain of these embodiments, ring A has the following formula:

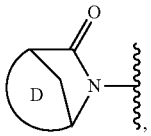

wherein D is:

(c) $C_{3-10}$ cycloalkyl optionally substituted with from 1-4 independently selected $R^d$; or (d) heterocyclyl including from 4-10 ring atoms, wherein from 1-3 ring atoms are each independently selected from the group consisting of $N(R^a)$, O, and S, wherein the heterocyclyl is optionally substituted with from 1-4 independently selected $R^d$.

As non-limiting examples of the foregoing embodiments, ring A can be:

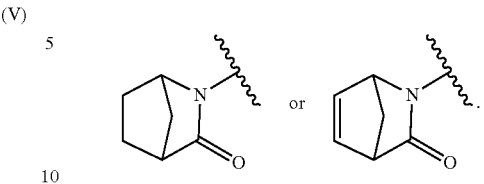

In some embodiments, ring A is a saturated or unsaturated bicyclic or tricyclic ring that includes from 8-10 ring atoms.

In certain of these embodiments, ring A is saturated. In other embodiments, ring A is unsaturated.

In certain of these embodiments, (A) applies (e.g., two adjacent ring carbon atoms of the divalent group are each independently selected from the group consisting of C, CH, and, $CR^b$ and are fused to a second ring). In other embodiments, (B) applies.

In certain embodiments, ring A is an unsaturated bicyclic or tricyclic ring that includes from 8-10 ring atoms. In certain of these embodiments, (A) applies. In certain of these embodiments, ring A is optionally further substituted with 1 oxo.

In certain embodiments, (A) applies, ring A is optionally further substituted with 1 oxo, and ring A has formula (VI):

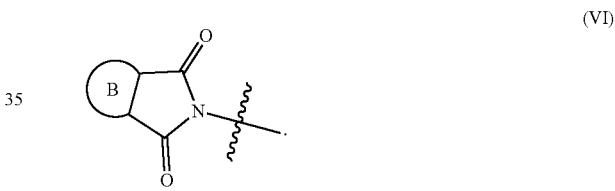

(VI)

In certain of these embodiments, fused ring B is fused $C_{6-10}$ aryl optionally substituted with from 1-5 independently selected $R^c$. For example, fused ring B can be fused phenyl optionally substituted with from 1-5 independently selected $R^c$. As a further example, ring A can have formula (VI-A):

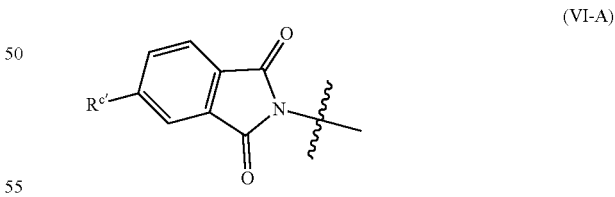

(VI-A)

wherein $R^{c'}$ is H or $R^c$ (e.g., $C_{1-6}$ alkyl, e.g., $CH_3$).

In certain of the formula (VI) embodiments, ring B is fused $C_{10}$ aryl optionally substituted with from 1-5 independently selected $R^c$ (e.g., unsubstituted).

In certain of the formula (VI) embodiments, ring B is fused heteroaryl including from 5-10 (e.g., 6) ring atoms, wherein from 1-4 (e.g., 1) ring atoms are each independently selected from the group consisting of N, $N(R^a)$, O, and S, wherein the heteroaryl is optionally substituted with from 1-3 independently selected $R^c$.

In certain embodiments, ring A is selected from one of the follows:

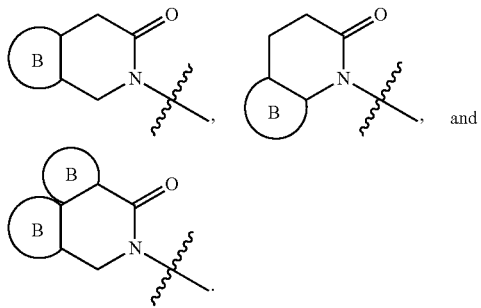

In certain of the foregoing embodiments, each fused ring B is independently selected from:

fused heteroaryl including from 5-10 (e.g., 6) ring atoms, wherein from 1-4 (e.g., 1) ring atoms are each independently selected from the group consisting of N, N($R^a$), O, and S, wherein the heteroaryl is optionally substituted with from 1-3 independently selected $R^c$; and fused $C_{6-10}$ (e.g., $C_6$) aryl optionally substituted with from 1-5 (e.g., from 1-2) independently selected $R^c$.

As a non-limiting example, each fused ring B can be independently a fused $C_{6-10}$ (e.g., $C_6$) aryl optionally substituted with from 1-5 (e.g., from 1-2) independently selected $R^c$.

In certain embodiments, ring A is a saturated bicyclic or tricyclic ring that includes from 8-10 ring atoms. In certain of these embodiments, (A) applies. In other embodiments, (B) applies. In certain of these embodiments, ring A is optionally further substituted with 1 oxo.

In certain embodiments, (A) applies, ring A is optionally further substituted with 1 oxo, and ring A has formula (VI):

(VI)

In certain of these embodiments, fused ring B is fused $C_{3-10}$ cycloalkyl optionally substituted with from 1-4 independently selected $R^d$. For example, fused ring B can be fused $C_{3-6}$ cycloalkyl (e.g., $C_{3-4}$ cycloalkyl) optionally substituted with from 1-4 independently selected $R^d$ (e.g., $R^d$ can be $C_{1-3}$ alkyl).

In other embodiments, (B) applies, ring A is optionally further substituted with 1 oxo, and ring A has formula (VII):

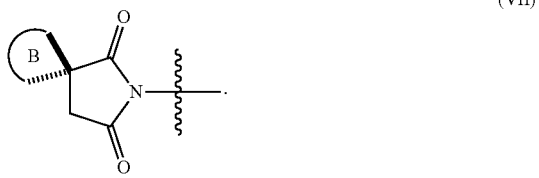

(VII)

In certain of these embodiments, the spiro-fused ring B is spiro-fused $C_{3-10}$ cycloalkyl optionally substituted with from 1-4 independently selected $R^d$. For example, the spiro-fused ring B is spiro-fused $C_{3-6}$ cycloalkyl (e.g., $C_{3-4}$ cycloalkyl) optionally substituted with from 1-4 independently selected $R^d$ (e.g., $R^d$ can be $C_{1-3}$ alkyl).

Variable L

In some embodiments, L has formula (VIII): —$(CH_2)_m$—$X^1$—$(CH_2)_n$—$X^2$—$(CH_2)_p$—.

In certain embodiments of formula (VIII), m is from 2-6 (e.g., m can be 2).

In certain embodiments of formula (VIII), m is 1.

In certain embodiments of formula (VIII), $X^1$ is —N(R')C(O)— (e.g., $X^1$ can be —N(H)C(O)—).

In certain embodiments of formula (VIII), n+p≥2. For example, n+p=2 (e.g., each of n and p is 1). As another example, n+p>2 (e.g., n+p=3, 4, 5, 6, 7, 8, 9, or 10).

In another embodiment, n+p<2.

In still other embodiments, n+p=0.

In certain embodiments of formula (VIII), $X^2$ is: —O—; —S—; or —S(O)$_t$—, wherein t is 1 or 2. For example, $X^2$ can be —S—.

In certain embodiments of formula (VIII), $X^2$ is —C($Q^1$)($Q^2$)—.

In certain of these embodiments, each of $Q^1$ and $Q^2$ is independently selected from the group consisting of H and $C_{1-4}$ alkyl. For example, one of $Q^1$ and $Q^2$ can be H, and the other of $Q^1$ and $Q^2$ can be $C_{1-4}$ alkyl (e.g., $CH_3$). For example, $Q^1$ can be H; and $Q^2$ can be $C_{1-4}$ alkyl. As another example, each of $Q^1$ and $Q^2$ can be H. As a further example, each of $Q^1$ and $Q^2$ can be an independently selected $C_{1-4}$ alkyl.

In other embodiments, $Q^1$ and $Q^2$, together with the carbon atom to which each is attached forms $C_{3-10}$ cycloalkyl that is optionally substituted with from 1-4 independently selected $R^d$ and optionally fused to phenyl. For example, $Q^1$ and $Q^2$, together with the carbon atom to which each is attached forms $C_{3-6}$ cycloalkyl that is optionally substituted with from 1-4 independently selected $R^d$ and optionally fused to phenyl.

In certain of the foregoing embodiments, $Q^1$ and $Q^2$, together with the carbon atom to which each is attached forms $C_{4-6}$ (e.g., $C_4$) cycloalkyl that is optionally substituted with from 1-2 independently selected $R^d$.

In certain embodiments of formula (VIII), $X^2$ is:

(v) $C_{6-10}$ arylene optionally substituted with from 1-5 independently selected $R^c$;

(vi) heteroarylene including from 5-10 ring atoms, wherein from 1-4 ring atoms are each independently selected from the group consisting of N, N($R^a$), O, and S; and which is optionally substituted with from 1-5 independently selected $R^c$;

(vii) $C_{3-10}$ cycloalkylene optionally substituted with from 1-4 independently selected $R^d$; or (viii) heterocycloalkylene including from 3-10 ring atoms, wherein from 1-3 ring atoms are each independently selected from the group consisting of N($R^a$), O, and S; and which is optionally substituted with from 1-5 independently selected $R^d$.

For example, $X^2$ can be:

(v) $C_{6-10}$ arylene optionally substituted with from 1-5 independently selected $R^c$; or (vii) $C_{3-10}$ cycloalkylene optionally substituted with from 1-4 independently selected $R^d$.

As another example, $X^2$ can be:

(v) phenylene optionally substituted with from 1-5 (e.g., 1-3, 1-2, 1) independently selected $R^c$; or (vii) $C_{3-6}$ cycloalkylene (e.g., $C_{3-4}$ cycloalkylene) optionally substituted with from 1-4 independently selected $R^d$ (e.g., $R^d$ can be $C_{1-3}$ alkyl).

In certain embodiments of formula (VIII), $X^2$ is (viii) heterocycloalkylene including from 3-10 ring atoms, wherein from 1-3 ring atoms are each independently selected from the group consisting of $N(R^a)$, O, and S; and which is optionally substituted with from 1-5 independently selected $R^d$.

In certain embodiments of formula (VIII), $X^2$ is (viii) heterocycloalkylene including from 4-6 (e.g., 4) ring atoms, wherein from 1-3 (e.g., 1) ring atoms are each independently selected from the group consisting of $N(R^a)$, O, and S; and which is optionally substituted with from 1-5 independently selected $R^d$ (e.g., $X^2$ can be

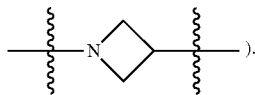 [SMILES: *C1CN(*)C1]

In some embodiments, L has formula (IX): L has formula (IX): —C(O)—$(CH_2)_n$—$X^3$—$(CH_2)_p$—. In certain of these embodiments, n+p>2. For example, n+p=2 (e.g., each of n and p is 1). As another example, n+p>2. In certain of these embodiments, $X^3$ is —S—.

Non-Limiting L Combinations

[1] In certain embodiments of formula (VIII):
m is from 2-6;
n+p≥2; and
$X^2$ is: —O—; —S—; or —S(O)$_t$—.
In certain of these embodiments, m is 2.
In certain of these embodiments, $X^1$ is —N(R')C(O)— (e.g., —N(H)C(O)—).
In certain of these embodiments, n+p>2.
In certain of these embodiments, n+p=2 (e.g., each of n and p is 1).
In certain of these embodiments $X^2$ is —S—.
In certain of these embodiments, m is 2-6 (e.g., 2), $X^1$ is —N(R')C(O)— (e.g., —N(H)C(O)—), and n+p>2.
In certain of these embodiments, m is 2-6 (e.g., 2), $X^1$ is —N(R')C(O)— (e.g., —N(H)C(O)—), and n+p>2, and $X^2$ is —S—.
In certain of these embodiments, m is 2-6 (e.g., 2), $X^1$ is —N(R')C(O)— (e.g., —N(H)C(O)—), and n+p=2 (e.g., each of n and p is 1).
In certain of these embodiments, m is 2-6 (e.g., 2), $X^1$ is —N(R')C(O)— (e.g., —N(H)C(O)—), and n+p=2 (e.g., each of n and p is 1), and $X^2$ is —S—.
For example, L can be —$CH_2CH_2NHC(O)CH_2SCH_2$—.

[2] In certain embodiments of formula (VIII):
m is from 2-6;
n+p<2; and
$X^2$ is:
(i) —$C(Q^1)(Q^2)$-, wherein each of $Q^1$ and $Q^2$ is an independently selected $C_{1-4}$ alkyl; or $Q^1$ and $Q^2$, together with the carbon atom to which each is attached forms $C_{3-10}$ cycloalkyl that is optionally substituted with from 1-4 independently selected $R^d$ and optionally fused to phenyl;
(v) $C_{6-10}$ arylene optionally substituted with from 1-5 independently selected $R^c$;
(vi) heteroarylene including from 5-10 ring atoms, wherein from 1-4 ring atoms are each independently selected from the group consisting of N, $N(R^a)$, O, and S; and which is optionally substituted with from 1-5 independently selected $R^c$;
(vii) $C_{3-10}$ cycloalkylene optionally substituted with from 1-4 independently selected $R^d$; or (viii) heterocycloalkylene including from 3-10 ring atoms, wherein from 1-3 ring atoms are each independently selected from the group consisting of $N(R^a)$, O, and S; and which is optionally substituted with from 1-5 independently selected $R^d$.

In certain of these embodiments, m is 2.
In certain of these embodiments, $X^1$ is —N(R')C(O)— (e.g., —N(H)C(O)—).
In certain of these embodiments, n+p=0.
In certain of these embodiments, $X^2$ is —$C(Q^1)(Q^2)$-.
In certain of these embodiments, each of $Q^1$ and $Q^2$ is H.
In certain of these embodiments, $Q^1$ is $C_{1-4}$ alkyl.
In certain of these embodiments, $Q^2$ is $C_{1-4}$ alkyl.
In certain of these embodiments, each of $Q^1$ and $Q^2$ is an independently selected $C_{1-4}$ alkyl (e.g., $CH_3$).
In certain of these embodiments, $Q^1$ and $Q^2$, together with the carbon atom to which each is attached forms $C_{3-6}$ cycloalkyl that is optionally substituted with from 1-4 independently selected $R^d$ and optionally fused to phenyl.
In certain of these embodiments, $X^2$ is:
(v) $C_{6-10}$ arylene optionally substituted with from 1-5 independently selected $R^c$; or
(vii) $C_{3-10}$ cycloalkylene optionally substituted with from 1-4 independently selected $R^d$.
In certain of these embodiments, $X^2$ is (viii) heterocycloalkylene including from 4-6 (e.g., 4) ring atoms, wherein from 1-3 (e.g., 1) ring atoms are each independently selected from the group consisting of $N(R^a)$, O, and S; and which is optionally substituted with from 1-5 independently selected $R^d$ (e.g., $X^2$ can be

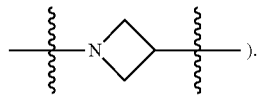

In certain of these embodiments, m is 2-6 (e.g., 2), $X^1$ is —N(R')C(O)— (e.g., —N(H)C(O)—), and n+p=0.
In certain of these embodiments, m is 2-6 (e.g., 2), $X^1$ is —N(R')C(O)— (e.g., —N(H)C(O)—), n+p=0, $X^2$ is —$C(Q^1)(Q^2)$-, and $Q^1$ and $Q^2$, together with the carbon atom to which each is attached forms $C_{3-6}$ cycloalkyl that is optionally substituted with from 1-4 independently selected $R^d$ and optionally fused to phenyl.
In certain of these embodiments, m is 2-6 (e.g., 2), $X^1$ is —N(R')C(O)— (e.g., —N(H)C(O)—), n+p=0, $X^2$ is —$C(Q^1)(Q^2)$-, and $Q^1$ and $Q^2$ is an independently selected $C_{1-4}$ alkyl (e.g., $CH_3$).
In certain of these embodiments, m is 2-6 (e.g., 2), $X^1$ is —N(R')C(O)— (e.g., —N(H)C(O)—), n+p=0, and $X^2$ is: (v) $C_{6-10}$ arylene (e.g., phenylene) optionally substituted with from 1-5 independently selected $R^c$; or (vii) $C_{3-10}$ cycloalkylene optionally substituted with from 1-4 independently selected $R^d$.

[3] In certain embodiments of formula (IX): n+p=2 (e.g., each of n and p is 1), and $X^3$ is —S—.

[4] In certain embodiments of formula (VIII):
m is 1;
n+p≤2; and
$X^2$ is: —O—; —S—; —S(O)$_t$—, or $C(Q^1)(Q^2)$.
In certain of these embodiments, n+p=2.
In certain of these embodiments, $X^2$ is —S—.
In certain of these embodiments, n+p<2 (e.g., n+p=0; or n+p=1).
In certain of these foregoing embodiments, $X^2$ is $C(Q^1)(Q^2)$.

In certain of these embodiments, each of $Q^1$ and $Q^2$ is H.

In certain of these embodiments, each of $Q^1$ and $Q^2$ is $C_{1-4}$ alkyl.

In certain of these embodiments, $Q^1$ is H; and $Q^2$ is $C_{1-4}$ alkyl.

Variables $R^1$, $R^2$, $R^{2'}$, and $R^4$

In some embodiments, Ri is H. In some embodiments, $R^2$ is H. In some embodiments, $R^4$ is H.

In some embodiments, two of $R^1$, $R^2$, and $R^4$ are H.

In some embodiments, each of $R^1$, $R^2$, and $R^4$ is H.

In some embodiments, $R^2$ is unsubstituted $C_{1-3}$ alkyl (e.g., methyl).

In some embodiments, $R^1$ and $R^4$ is H.

In some embodiments, $R^{2'}$ is as defined according to (AA).

In certain embodiments, a' is 1.

In certain of these embodiments, each of $R^{3a}$ and $R^{3b}$ is H.

In certain of these embodiments, each of $R^{3a}$ and $R^{3b}$ is $C_{1-3}$ alkyl (e.g., methyl).

In other embodiments, a' is 0.

In some embodiments, $R^3$ is —C(O)OH. In other embodiments, $R^3$ is a carboxylic acid isostere. Non-limiting examples of carboxylic acid isosteres include noncarbon acyclic acids such as phosphonic/phosphinic and sulfonic/sulfinic acids and sulfonamides; modified carbon-based acids such as hydroxamic acids, hydroxamic esters, acylureas, acyl sulfonamides, and sulfonyl ureas; optionally substituted heteroaryl and heterocyclyl-based isosteres, such as those based on optionally substituted tetrazole, oxadiazol-5(4H)-thione, thiadiazol-5(4H)-one, oxathiadiazole and oxidized forms thereof, isoxazole, thiazolidinedione, oxazolidinedione, tetramic acid, and derivatives thereof; and optionally substituted cycloalkyl and aryl-based isosteres, such as those based on optionally substituted cyclopentane-1,3-dione, phenol and squaric acid and derivatives thereof (e.g., tetrazolyl or amide). In certain embodiments, $R^3$ is an amide. In certain embodiments, $R^3$ is an optionally substituted tetrazolyl (e.g., unsubstituted tetrazolyl). In certain embodiments, $R^3$ is an optionally substituted isoxazolyl (e.g., isoxazolyl substituted with hydroxy (e.g.,

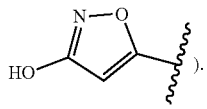

).

In some embodiments, a is 1-5 (e.g., 1-4, 1-3, 1-2). In some embodiments, a is 0. In some embodiments, a is 0, 1, or 2. In certain embodiments, a is 1. In other embodiments, a is 2. In still other embodiments, a is 0. In some embodiments, a is 0, 1, 2, or 3 (e.g., a=0; or a=1; or a=2).

Variables W, W', and $R^5$

W is a peptide having the formula W'—$R^5$, wherein W' is a sequence of from 5-60 amino acids, and $R^5$ is a C-terminal amino acid, amino acid ester, or amino acid amide that is optionally substituted with from 1-2 modifying groups (e.g., 1-2 groups selected from an acyl group and a PEG group). As used herein, "peptide" refers to a chain of amino acid monomers (sometimes termed "residues") linked by peptide (amide) bonds (or an isosteric replacement thereof), which have an N-terminal (N—$R^4$ in formulae (IAA), (IA), or (I)) and a C-terminal amino acid residue ($R^5$) at each of the ends of the peptide. The term peptide also includes modified peptides, including, e.g., any one or more of the modifications described herein.

Constituent Amino Acids and Modifications Thereof

In some embodiments, W includes one or more naturally occurring amino acids found, e.g., in polypeptides and/or proteins produced by living organisms, such as Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H).

In some embodiments, W includes one or more independently selected modifications that occur present in so-called modified peptides. Such modifications include, but not limited to: (i) the incorporation of lactam-bridge; (ii) head-to-tail cyclization; (iii) one or more alternative or non-naturally occurring (D or L) amino acids, such as synthetic non-native amino acids, substituted amino acids, and D-amino acids; (iv) peptide bond replacements; (v) targeting groups; and the like. In certain embodiments, W includes one modification in either the W' or $R^5$ component. In other embodiments, W includes more than one independently selected modification (e.g., 2 independently selected modifications, 3 independently selected modifications, 4 independently selected modifications, 5 independently selected modifications, 6 independently selected modifications, 7 independently selected modifications, 8 independently selected modifications, 9 independently selected modifications, or 10 independently selected modifications that occur in the W' and/or $R^5$ component (e.g., in the W' component only; or in the $R^5$ component only; or in both the W' and $R^5$ components).

Non-limiting examples of alternative or non-naturally amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citrulline, alpha-methylalanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, aminoisobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof (each which can be, where appropriate can each independently be D or L amino acids).

Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

Other non-limiting examples of modifications and/or moieties include PEGylation; glycosylation; HESylation; ELPylation; lipidation; acetylation; amidation; end-capping modifications (e.g., amidation at the C-terminus, introduction of C-terminal alcohol, aldehyde, ester, and thioester moieties); cyano groups; phosphorylation; cyclization, conjugation with targeting moieties and/or agents that increase retention in the body (e.g., agents such as cellulose, fatty acids, polyethylene glycol (PEG) or combinations thereof); incorporation of retro-inverso peptide motif (ie., a peptide with a reversal of the direction of the peptide bond on at least one position);

In certain embodiments, W includes only naturally occurring amino acids. In other embodiments, W includes only alternative or non-naturally occurring amino acids. In still other embodiments, W includes one or more naturally occurring amino acids and one or more alternative or non-naturally occurring amino acids. In certain of the foregoing embodiments, W includes only L amino acids; or W includes both D and L amino acids; or W includes only D amino acids. While not wishing to be bound by theory, it is believed that the incorporation of D amino acids can confer enhanced in vivo or intracellular stability to the compounds described herein.

In some embodiments, W includes amino acid residues each of Formula XAA:

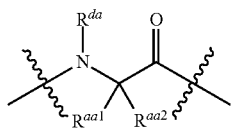

XAA wherein each of $R^{aa1}$ and $R^{aa2}$ is independently selected from:

(a) H;

(b) $C_{1-6}$ alkyl, which is optionally substituted with from 1-3 $R^{ba}$;

(c) $(C_{0-3}$ alkylene)-$C_{3-10}$ cycloalkyl, which is optionally substituted with from 1-4 $R^{ba}$;

(d) $(C_{0-3}$ alkylene)-heterocyclyl, wherein the heterocyclyl includes from 3-10 ring atoms, wherein from 1-3 ring atoms are heteroatoms, each independently selected from the group consisting of N($R^{da}$), O, and S, and wherein one or more of the heterocyclyl ring carbon atoms are optionally substituted with from 1-4 independently selected $R^{ba}$, (e) $(C_{0-3}$ alkylene)-$C_6$-$C_{10}$ aryl, which is optionally substituted with from 1-4 $R^{ca}$;

(f) $(C_{0-3}$ alkylene)-heteroaryl, wherein the heteroaryl includes from 5-10 ring atoms, wherein from 1-4 ring atoms are heteroatoms, each independently selected from the group consisting of N, N($R^{da}$), O, and S, and wherein one or more of the heteroaryl ring carbon atoms are optionally substituted with from 1-4 independently selected $R^{ca}$;

OR (g) $R^{aa1}$ and $R^{da}$, in the —C(=O)C$R^{aa1}$($R^{aa2}$)N($R^{da}$)— group, combine to form a ring including from 5-8 ring atoms, wherein the ring includes: (a) from 1-6 ring carbon atoms (in addition to C$R^{aa1}$($R^{aa2}$)), each of which is substituted with from 1-2 substituents independently selected from H and $C_{1-3}$ alkyl; and (b) from 0-3 ring heteroatoms (in addition to the nitrogen atom attached to $R^{da}$), which are each independently selected from the group consisting of N($R^{da}$), O, and S;

each occurrence of $R^{ba}$ is selected from the group consisting of —C(=O)(OH); —C(=O)(C$_{2-20}$ alkyl); —C(=O)NR'R''; —NHC(=NR')NR'R''; —C(=O)O(C$_{2-20}$ alkyl); —S(O)$_{0-2}$(C$_{1-6}$ alkyl); oxo; F; C$_{1-10}$ alkoxy; C$_{1-10}$ haloalkoxy; azido; —N($R^{ga}$)($R^{ha}$);

each occurrence of $R^{ca}$ is independently selected from the group consisting of: —OH; —SH; —F; —Cl; —Br; —NR'R''; C$_{1-4}$ alkyl; C$_{1-4}$ haloalkyl; C$_{1-4}$ alkoxy; C$_{1-4}$ haloalkoxy; —C(=O)O(C$_{1-4}$ alkyl); —C(=O)(C$_{1-4}$ alkyl); —C(=O)OH; —CON(R')(R''); —S(O)$_{1-2}$(NR'R'');

—S(O)$_{0-2}$(C$_{1-4}$ alkyl); cyano; —NR'C(=NR')NR'R''; C$_{6-10}$ aryl optionally substituted with 1-4 substituents independently selected from halo, C$_{1-4}$ alkyl, and C$_{1-4}$ haloalkyl; and C$_{3-6}$ cycloalkyl optionally substituted with from 1-4 independently selected C$_{1-4}$ alkyl;

each occurrence of $R^{da}$ is independently selected from the group consisting of: H, C$_{1-6}$ alkyl; C$_{3-6}$ cycloalkyl; —C(O)(C$_{1-4}$ alkyl); —C(O)O(C$_{1-4}$ alkyl); —CON(R')(R''); —S(O)$_{1-2}$(NR'R''); —S(O)$_{1-2}$(C$_{1-4}$ alkyl); —OH; and C$_{1-4}$ alkoxy; or $R^{aa1}$ and $R^{da}$, in the —C(=O)C$R^{aa1}$($R^{aa2}$)N($R^{da}$)— group, combine to form a ring including from 5-8 ring atoms as defined above;

each occurrence of $R^{ga}$ and $R^{ha}$ is independently selected from the group consisting of H; C$_{1-4}$ alkyl; —C(=O)O(C$_{2-20}$ alkyl); and —S(O)$_{1-2}$(C$_{1-6}$ alkyl); and each occurrence of R' and R'' is independently selected from the group consisting of: H and C$_{1-4}$ alkyl; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and C$_{1-3}$ alkyl; and (b) from 0-3 ring heteroatoms (in addition to the nitrogen atom attached to R' and R''), which are each independently selected from the group consisting of N(H), O, and S;

or a C-terminal amino acid or an amino acid ester or an amino acid amide thereof.

In some embodiments, W includes 25-45 amino acid residues of Formula XAA, wherein $R^{aa2}$ is H; or a C-terminal amino acid or an amino acid ester or an amino acid amide thereof.

In certain of these embodiments, $R^{aa1}$ is selected from the group consisting of:

H;

C$_1$-C$_6$ alkyl optionally substituted with 1-2 substituents selected from —NH$_2$, —OH, —SH, —SMe, —NH(C=NH)NH$_2$, CO$_2$H, and CO$_2$NH$_2$;

(C$_1$-C$_6$ alkylene)-phenyl, optionally substituted with 1-2 —OH;

(C$_1$-C$_6$ alkylene)-indolyl; and (C$_1$-C$_6$ alkylene)-imidazolyl; or $R^{aa1}$ and $R^{da}$, in the —CH($R^{aa1}$)N($R^{da}$)— group, combine to form a pyrrolidine ring.

As non-limiting examples of the foregoing, W can include from 25-45 naturally occurring amino acids found, e.g., in polypeptides and/or proteins produced by living organisms, such as Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H); or amino acid ester or amino acid amide thereof.

In certain embodiments, W includes from 1-2 (e.g., 1) amino acid residue of Formula XAA, wherein $R^{aa2}$ is H; $R^{aa1}$ is: C$_{1-6}$ alkyl, which is substituted with from 1-2 (e.g., 1) $R^{ba}$; and each occurrence of $R^{ba}$ is independently selected from:

—N($R^{ga}$)($R^{ha}$);

or a C-terminal amino acid or an amino acid ester or an amino acid amide thereof.

As non-limiting examples of the foregoing, W can include an amino acid residue selected from:

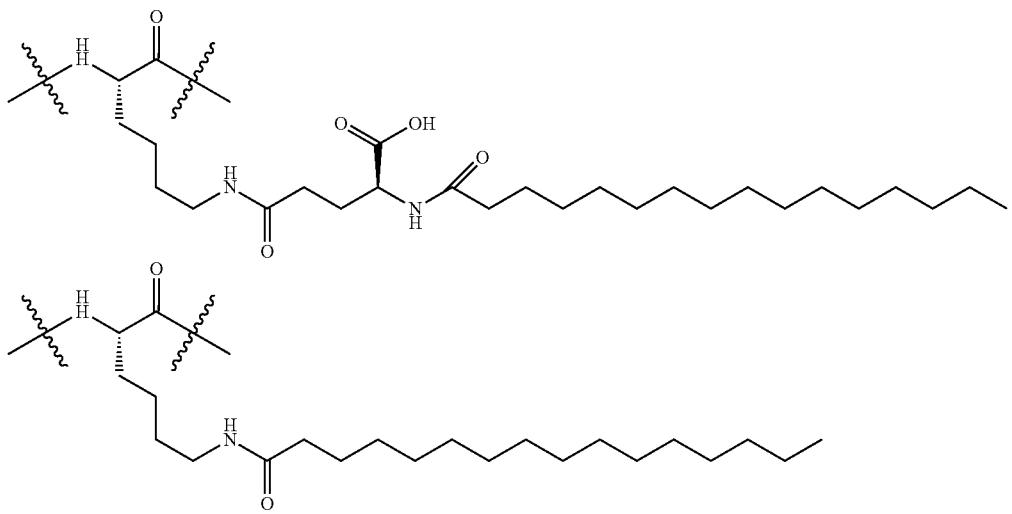

or a C-terminal amino acid or an amino acid ester or an amino acid amide thereof.

In certain embodiments, W includes from 1-2 (e.g., 1) amino acid residue of Formula XAA, wherein $R^{aa2}$ is $C_{1-3}$ alkyl (e.g., methyl); and $R^{aa1}$ is other than H;

or a C-terminal amino acid or an amino acid ester or an amino acid amide thereof.

Non-limiting examples include:

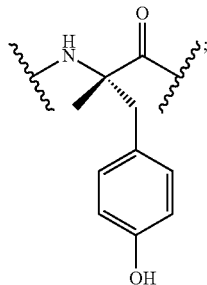 [SMILES: *N[C@@](C)(Cc1ccc(O)cc1)C(*)=O]

or a C-terminal amino acid or an amino acid ester or an amino acid amide thereof.

Variable W'

In some embodiments, W' is a sequence of from 20-60 (e.g., 20-55, 20-50, 20-45, 20-40, 20-30, 20-35) amino acids.

In some embodiments, W' is a sequence of from 30-60 (e.g., 30-55, 30-50, 30-45, 30-40) amino acids. In certain embodiments, W' is a sequence of from 25-45 (e.g., 30-45) amino acids. In certain embodiments, W' is a sequence of from 30-50 amino acids. For example, W' can be a sequence of from 30-45 amino acids or from 30-40 amino acids. In certain embodiments, W' can be a sequence of 34, 35, 36, 37, 38, or 39 amino acids; e.g., 36 or 37 amino acids; e.g., 36 amino acids. In certain embodiments, W' can be a sequence of 25-28 amino acids; e.g., 26 or 27 amino acids.

Variable $R^5$

In some embodiments, $R^5$ is a C-terminal amino acid amide that is optionally substituted with from 1-2 modifying groups. In other embodiments, $R^5$ is a C-terminal amino acid that is optionally substituted with from 1-2 modifying groups.

In certain embodiments, $R^5$ is a C-terminal lysyl residue, e.g., a lysyl amide residue that is optionally substituted with from 1-2 modifying groups. For example, $R^5$ can be a C-terminal L-lysyl amide residue that is optionally substituted with from 1-2 modifying groups. In certain embodiments, $R^5$ has formula (XI):

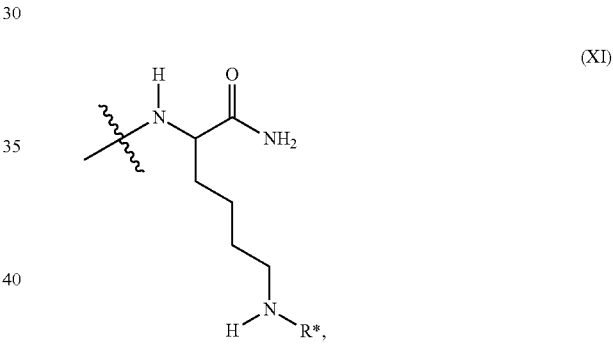

(XI)

wherein R* is H or a modifying group. In certain of these embodiments, formula (XI) is L. In other embodiments, formula (XI) is D.

In certain embodiments, R* is H.

In certain embodiments, the modifying group (e.g., R*) is an acyl group. For example, the acyl group can be a $C_{2-30}$ (e.g., $C_{2-20}$, $C_{2-10}$, $C_{2-6}$) acyl group that is optionally substituted with from 1-2 independently selected $R_f$. Each occurrence of $R_f$ is selected from the group consisting of —C(=O)(OH); —C(=O)($C_{2-20}$ alkyl); —C(=O)O($C_{2-20}$ alkyl); and —S(O)$_{1-2}$($C_{1-6}$ alkyl); oxo; F; $C_{1-10}$ alkoxy; $C_{1-10}$ haloalkoxy; and —N($R^g$)($R^h$). Each occurrence of $R^g$ and $R^h$ is independently selected from the group consisting of H; $C_{1-4}$ alkyl; —C(=O)($C_{2-20}$ alkyl); —C(=O)O($C_{2-20}$ alkyl); and —S(O)$_{1-2}$($C_{1-6}$ alkyl).

In certain embodiments, the modifying group (e.g., R*) is a $C_{2-30}$ (e.g., $C_{2-20}$, $C_{2-10}$, $C_{2-6}$) acyl group that is substituted with 1-2 (e.g., 2) independently selected $R_f$. In certain embodiments, each occurrence of $R_f$ can be independently selected from the group consisting of —C(=O)(OH) and —N($R^g$)($R^h$); e.g., in which one of $R^g$ and $R^h$ is independently selected from the group consisting of —C(=O)($C_{2-20}$ alkyl); —C(=O)O($C_{2-20}$ alkyl); and —S(O)$_{1-2}$($C_{1-6}$ alkyl), e.g., —C(=O)(C$_{2-20}$ alkyl). By way of example, the modifying group (e.g., R*) can be:

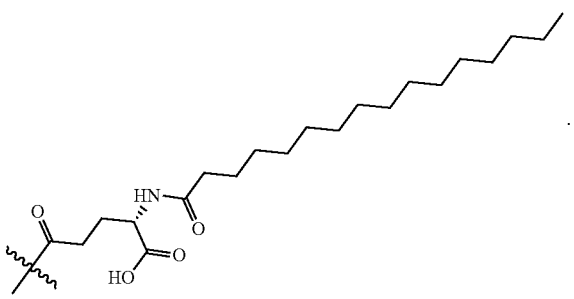 [SMILES: *C(=O)CC[C@H](NC(=O)CCCCCCCCCCCCCCC)C(=O)O]

As an additional example, R* can be:

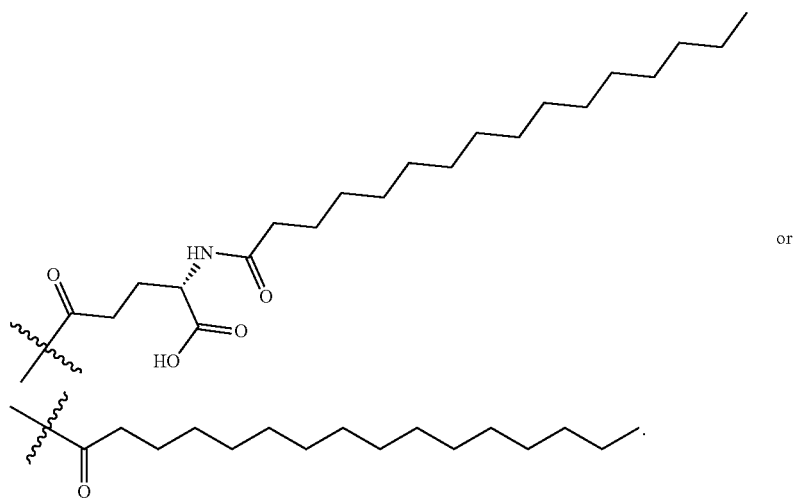

In some embodiments, R$^5$ is a a C-terminal amino acid that is optionally substituted with from 1-2 modifying groups (e.g., 1-2 groups selected from an acyl group and a PEG group).

In certain embodiments, R$^5$ is a C-terminal lysine that is optionally substituted with from 1-2 modifying groups (e.g., 1-2 groups selected from an acyl group and a PEG group). For example, R$^5$ can be a C-terminal L-lysine that is optionally substituted with from 1-2 modifying groups (e.g., 1-2 groups selected from an acyl group and a PEG group).

In certain embodiments, R$^5$ has formula (XI-OH):

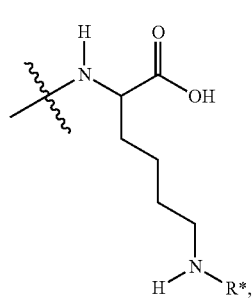

(XI-OH)

wherein R* is H or a modifying group (e.g., an acyl group and a PEG group). In certain of these embodiments, formula (XI-OH) is L. In other embodiments, formula (XI-OH) is D.

In certain embodiments of formula (XI) and (XI-OH), R* is H.

In certain embodiments, the modifying group (e.g., R*) is an acyl group. For example, the acyl group can be a C$_{2-30}$ (e.g., C$_{2-20}$, C$_{2-10}$, C$_{2-6}$) acyl group that is optionally substituted with from 1-2 independently selected R. Each occurrence of R$_f$ is selected from the group consisting of —C(=O)(OH); —C(=O)(C$_{2-20}$ alkyl); —C(=O)O(C$_{2-20}$ alkyl); and —S(O)$_{1-2}$(C$_{1-6}$ alkyl); oxo; F; C$_{1-10}$ alkoxy; C$_{1-10}$ haloalkoxy; and —N(R$^g$)(R$^h$). Each occurrence of R$^g$ and R$^h$ is independently selected from the group consisting of H; C$_{1-4}$ alkyl; —C(=O)(C$_{2-20}$ alkyl); —C(=O)O(C$_{2-20}$ alkyl); and —S(O)$_{1-2}$(C$_{1-6}$ alkyl).

In certain embodiments, the modifying group (e.g., R*) is a C$_{2-30}$ (e.g., C$_{2-20}$, C$_{2-10}$, C$_{2-6}$) acyl group that is substituted with 1-2 (e.g., 2) independently selected R$_f$. In certain embodiments, each occurrence of R$_f$ can independently selected from the group consisting of —C(=O)(OH) and —N(R$^g$)(R$^h$); e.g., in which one of R$^g$ and R$^h$ is independently selected from the group consisting of —C(=O)(C$_{2-20}$ alkyl); —C(=O)O(C$_{2-20}$ alkyl); and —S(O)$_{1-2}$(C$_{1-6}$ alkyl), e.g., —C(=O)(C$_{2-20}$ alkyl). By way of example, the modifying group (e.g., R*) can be:

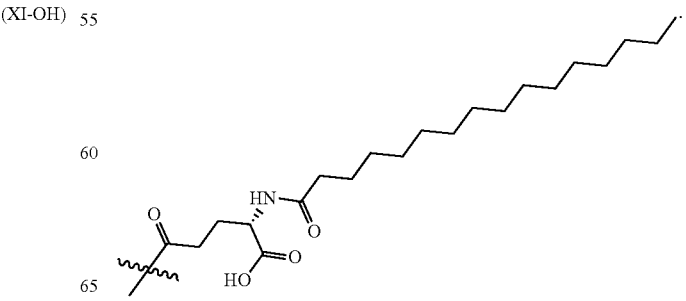

As an additional example, R* can be:

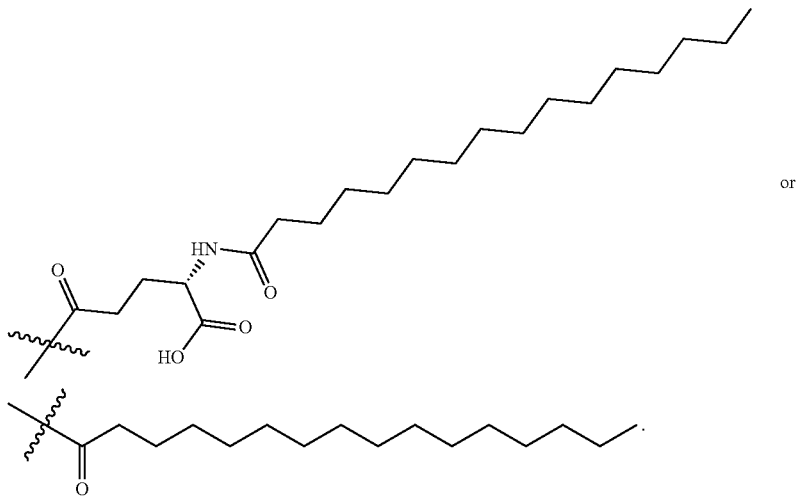

or

Other non-limiting, representative examples of acyl modifying groups are delineated, e.g., in Table 2.

In other embodiments, the modifying group is PEG. As used herein the general term "polyethylene glycol" or "PEG", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 5,000 to 40,000 Daltons. "Polyethylene glycol" or "PEG" is used in combination with a numeric suffix to indicate the approximate average molecular weight thereof. For example, PEG-5,000 refers to polyethylene glycol having a total molecular weight average of about 5,000. As used herein the term "PEGylated" or like terms refers to a compound that has been modified from its native state by linking a PEG chain to the peptide. A "PEGylated peptide" is a peptide that has a PEG chain covalently attached to the peptide itself.

In certain embodiments, $R^5$ is a C-terminal amino acid selected from serine, glycine, and arginine.

In certain embodiments, $R^5$ is a C-terminal amino acid amide selected from serinyl amide, glycyl amide, and argininyl amide.

In certain embodiments, $R^5$ is a C-terminal glycyl residue (e.g., C-terminal glycine or C-terminal glycyl amide).

In certain embodiments, $R^5$ is a C-terminal argininyl residue (e.g., C-terminal arginine or C-terminal argininyl amide).

In certain embodiments, $R^5$ is a C-terminal serinyl residue (e.g., C-terminal serine or C-terminal serinyl amide).

Non-Limiting Examples of W

In some embodiments, the amino acid sequence present in W is, or includes, the sequence that is present in native GLP-1-OH or GLP-1-NH$_2$. In other embodiments, the amino acid sequence present in W is, or includes, the sequence that is present in native GIP. In still other embodiments, the amino acid sequence present in W is, or includes, a hybrid sequence having one or more fragments (e.g., functional fragments) present in native GLP-1-OH or GLP-1-NH$_2$ and one or more fragments (e.g., functional fragments) present in native GIP. This disclosure further contemplates variations of the foregoing embodiments, e.g., W is, or includes, a conservatively substituted variation of the foregoing, meaning that one or more amino acid residues of an original peptide are replaced by different residues, and that the conservatively substituted peptide retains a desired biological activity. Examples of conservative substitutions include substitution of amino acids that tend not alter the secondary and/or tertiary structure of the compounds described herein, substitutions that do not change the overall or local hydrophobic character, substitutions that do not change the overall or local charge, substitutions by residues of equivalent side chain size, or substitutions by side chains with similar reactive groups.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics or substitutions of residues with similar side chain volume are also within the scope of this disclosure.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile, Phe, Trp; (2) neutral hydrophilic: Cys, Ser, Thr, Asn, Gln, Ala, Tyr, His, Pro, Gly; (3) acidic: Asp, Glu; (4) basic: His, Lys, Arg; (5) residues that influence chain orientation: Gly, Pro; (6) aromatic: Trp, Tyr, Phe, Pro, His, or hydroxyproline. Non-conservative substitutions will entail exchanging a member of one of these classes for another class.

In certain embodiments, conservative substitutions for use in the variants described herein are as follows: Ala into Gly or into Ser; Arg into Lys; Asn into Gln or into His; Asp into Glu or into Asn; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr or into Phe; Tyr into Phe or into Trp; and/or Phe into Val, into Tyr, into Ile or into Leu. In general, conservative substitutions encompass residue exchanges with those of similar physicochemical properties (i.e. substitution of a hydrophobic residue for another hydrophobic amino acid).

In still other embodiments, the amino acid sequence present in W is, or includes, or is based upon a sequence that is present in a peptide having at least 0.01% of the GLP-1 receptor activation activity of the native GLP-1, such as at least 0.1%, 0.2%, 0.5%, 0.8%, 1%, 3%, 5%, 10%, 20%, 30%, 40%, 50%, 60%, 70%, 80%, 90%, 95%, 99% of the GLP-1 receptor activation activity of the native GLP-1-OH or GLP-1-NH$_2$ and/or at least 0.01% of the GIP receptor activation activity of GIP, such as at least 0.1%, 0.2%, 0.5%, 0.8%, 1%, 3%, 5%, 10%, 20%, 30%, 40%, 50%, 60%, 70%, 80%, 90%, 95%, 99% of the GIP receptor activation activity of the native GIP.

As used herein the term "native GLP-1" refers to a peptide comprising the sequence of human GLP-1 (7-36, or 7-37), and term "native GIP" refers to a peptide comprising the sequence of human GIP (1-42). As used herein, a general reference to "GLP-1" or "GIP" in the absence of any further designation is intended to mean native GLP-1 or native GIP, respectively.

In some embodiments, W has formula (X): -GTF-W"—R$^5$, wherein W" is a sequence of 30-40 (e.g., 31-36, 33) amino acids.

In certain embodiments, W has formula (XII):

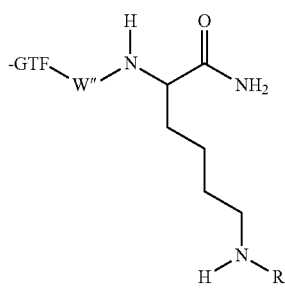

(XII)

wherein W" is a sequence of 30-40 (e.g., 31-35, e.g., 33) amino acids, and R* is H or a modifying group (e.g., an acyl group and a PEG group as described herein).

In certain embodiments, W has formula (XII-OH):

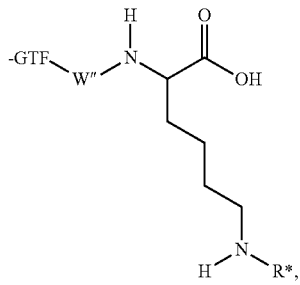

(XII)

wherein W" is a sequence of 30-40 (e.g., 31-35, e.g., 33) amino acids, and R* is H or a modifying group (e.g., an acyl group and a PEG group as described herein).

In some embodiments, W has formula (XIII):
-GTF-W'''-GPSSGAPPPS-R$^5$ (SEQ ID NO: 1); wherein W''' is a sequence of 20-30 (e.g., 21-25, e.g., 23) amino acids.

In some embodiments, W has formula (XIV-AA):
GT(Xaa3)(Xaa4)SD(Xaa7)S(Xaa9)(Xaa10)(Xaa11)(Xaa12)(Xaa13)(Xaa14)(Xaa15)(Xaa16)(Xaa17)(Xaa18)(Xaa19)(Xaa20)(Xaa21)WL(Xaa24)(Xaa25)(Xaa26)GPSSGAPPP(Xaa36)-R$^5$ (SEQ ID NO: 2A which is listed as SEQ ID NO: 35 in sequence listing);
wherein:
Xaa3 is F;
Xaa4 is T or I (e.g., T);
Xaa7 is Y, V, L, or K* (e.g., Y);
Xaa9 is I or S (e.g., I);
Xaa10 is Y, Y*, Q, A, or (Aib) (e.g., Y);
Xaa11 is L, M, or L* (e.g., L);
Xaa12 is D or E (e.g., D);
Xaa13 is K, G, R, or E (e.g., K);
Xaa14 is Q or I (e.g., Q);
Xaa15 is A, H, or R (e.g., A);
Xaa16 is A, Q, or V (e.g., A);
Xaa17 is A, (Aib), K*, K, or Q (e.g., (Aib));
Xaa18 is A, D, E, (Aib), or L (e.g., A, D, E, or L (e.g., E));
Xaa19 is F, or A (e.g., F);
Xaa20 is V or I (e.g., V);
Xaa21 is N, A, Q, K*, or E (e.g., N);
Xaa24 is I, L or V (e.g., L);
Xaa25 is A, K, or I (e.g., A);
Xaa26 is Q-R, G-R-G-K*, Q, or G (e.g., G); and
Xaa36 is S or absent (e.g., S).

In some embodiments (e.g., when W has formula (XIV-AA)), W has formula (XIV):
GTF(Xaa4)SD(Xaa7)S(Xaa9)(Xaa10)(Xaa11)(Xaa12)(Xaa13)QA(Xaa16)(Xaa 17)(Xaa18)F-(Xaa20)(Xaa21)WL(Xaa24)(Xaa25)GGPSSGAPPPS-R$^5$ (SEQ ID NO: 2);
wherein:
Xaa4 is T or I (e.g., T);
Xaa7 is Y, V, or L (e.g., Y);
Xaa9 is I or S (e.g., I);
Xaa10 is Y, Q, or A (e.g., Y);
Xaa11 is L, M, or L* (e.g., L);
Xaa12 is D or E (e.g., D);
Xaa13 is K, G, or E (e.g., K);
Xaa16 is A or V (e.g., A);
Xaa17 is (Aib) or K (e.g., (Aib));
Xaa18 is E or L (e.g., E);
Xaa20 is V or I (e.g., V);
Xaa21 is N, A, or E (e.g., N);
Xaa24 is L or V (e.g., L); and
Xaa25 is A or K (e.g., A).

In certain embodiments, W has formula (XIV-A):
GTF(Xaa4)SD(Xaa7)S(Xaa9)(Xaa10)(Xaa11)(Xaa12)(Xaa13)QA(Xaa16)(Aib)-(Xaa18)F(Xaa20)(Xaa21)WL(Xaa24)(Xaa25)GGPSSGAPPPS-R$^5$ (SEQ ID NO: 3), wherein each of the "Xaa" variables is as defined in conjunction with Formula (XIV). In certain of these embodiments, R$^5$ can be as defined anywhere herein (e.g., can have formula (XI); e.g., D or L formula (XI), and R* can be as defined anywhere herein).

In certain embodiments, W has formula (XIV-B):
GTFTSDYSIYLDKQAA(Aib)EFVNWL-LAGGPSSGAPPPS-R$^5$ (SEQ ID NO: 4). In certain of these embodiments, R$^5$ can be as defined anywhere herein (e.g., can have formula (XI); e.g., D or L formula (XI), and R* can be as defined anywhere herein).

As used herein "(Aib)" refers to 2-aminoisobutyric acid (also known as α-aminoisobutyric acid or α-methylalanine or 2-methylalanine).

As used herein, Y* refers to 2-amino-3-(4-hydroxyphenyl)-2-methylpropanoic acid (e.g., (S)-2-amino-3-(4-hydroxyphenyl)-2-methylpropanoic acid). As used herein, L* refers to 2-amino-2-methylpentanoic acid (e.g., (S)-2-amino-2-methylpentanoic acid).
or a C-terminal amino acid or an amino acid ester or an amino acid amide thereof.

As used herein K* is a lysine residue substituted with a modifying group, or a C-terminal amino acid or an amino acid ester or amino acid amide thereof.

Non-limiting examples of K* can include an amino acid residue selected from:

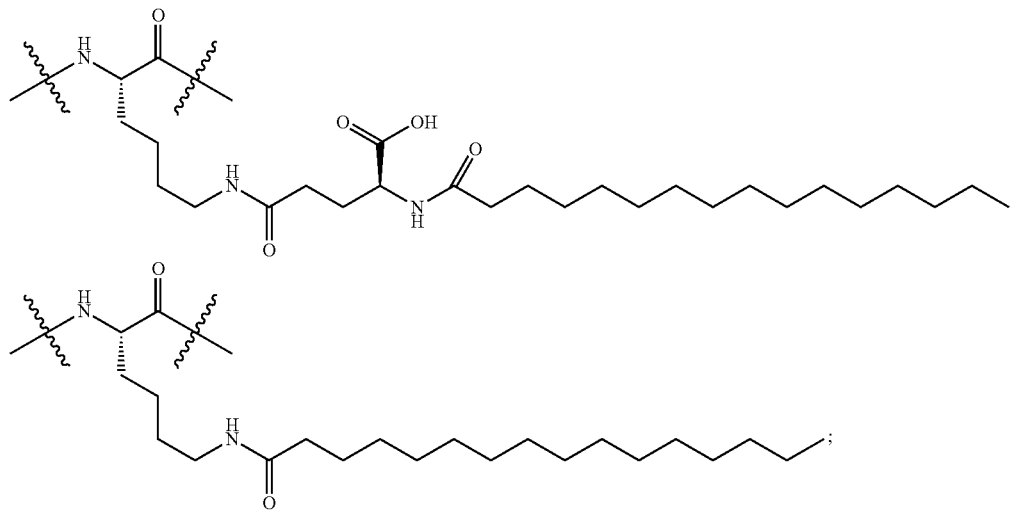

or a C-terminal amino acid or an amino acid ester or an amino acid amide thereof.

In some embodiments, W is represented by formula (X), (XII), (XIII), (XIV-AA), (XIV), (XIV-A), (XIV-B), (XV), or any of SEQ ID 1-34.

For example, W can have any of the sequences delineated in Table 2.

TABLE 2

| SEQ ID NO: | Sequence |
|---|---|
| 5 | GTFTSDYSIYLDKQAA(Aib)EFVNWLLAGGPSSGAPPPSK—NH$_2$ |
| 6 | GTFTSDYSIYLDKQAA(Aib)EFVNWLLAGGPSSGAPPPSK* |
| | K* = |
| 7 | GTFTSDYSIYLDKQAA(Aib)EFVNWLLAGGPSSGAPPPSK* |
| | K* = |

TABLE 2-continued

| SEQ ID NO: | Sequence |
|---|---|
| 8 | GTFTSDYSIYLDKQAA(Aib)EFVNWLLAGGPSSGAPPPSK\* <br> K* = lysine with ε-N-palmitoyl (C16 fatty acid) acylation; α-carboxamide |
| 9 | GTFTSDYSIYLDKQAA(Aib)EFVNWLLAGGPSSGAPPPSK\*, <br> K* = lysine with ε-N-palmitoyl (C16 fatty acid) acylation; α-carboxylic acid |
| 10 | **GTFTSDVSSYLEGQAAKEFIAWLVKGGPSSGAPPPSK\*—NH₂**, <br> K* = lysine with ε-N-(γ-Glu-palmitoyl) modification; α-carboxamide |
| 11 | **GTFISDYSIAMDKIRQQDFVNWLLAQRGPSSGAPPPSK\*—NH₂**, <br> K* = lysine with ε-N-(γ-Glu-palmitoyl) modification; α-carboxamide |
| 12 | GTFTSDLSIYLDKQAA(Aib)EFVNWLLAGGPSSGAPPPSK—NH₂ |
| 13 | GTFTSDYSIYLDEQAA(Aib)EFVNWLLAGGPSSGAPPPSK—NH₂ |
| 14 | GTFTSDYSIYLDKQAV(Aib)EFVNWLLAGGPSSGAPPPSK—NH₂ |
| 15 | GTFTSDYSIYLDKQAA(Aib)LFVNWLLAGGPSSGAPPPSK—NH₂ |
| 16 | GTFTSDYSIYLDKQAA(Aib)EFINWLLAGGPSSGAPPPSK—NH₂ |
| 17 | GTFTSDYSIYLDKQAA(Aib)EFVEWLLAGGPSSGAPPPSK—NH₂ |
| 18 | GTFTSDYSIYLDKQAV(Aib)EFINWLLAGGPSSGAPPPSK—NH₂ |
| 19 | **GTFTSDYSIQMDKQAA(Aib)EFVNWLLAGGPSSGAPPPSK\*—NH₂** <br> K* = lysine with ε-N-(γ-Glu-palmitoyl) modification; α-carboxamide |

| SEQ ID NO: | Sequence |
|---|---|
| 20 | **GTFTSDYSIAMDKQAA(Aib)EFVNWLLAGGPSSGAPPPSK\*—NH₂**<br>K\* = 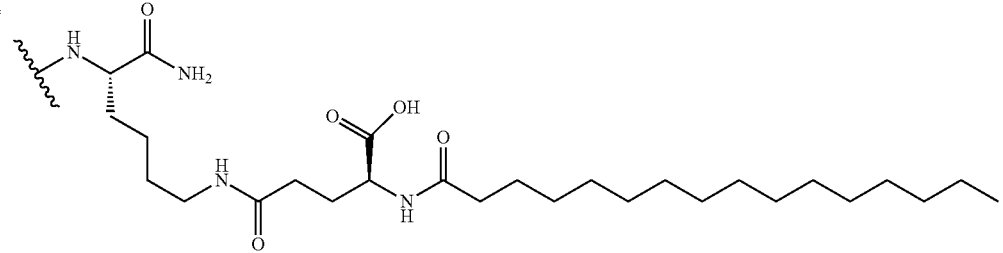 |
| 21 | **GTFTSDYSIYL\*DKQAA(Aib)EFVNWLLAGGPSSGAPPPSK\*—NH₂**<br>K\* = <br>L\* = 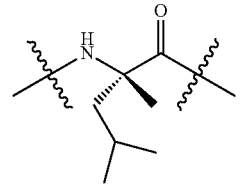 |
| 22 | GTFTSDYSIYLDRQAA(Aib)EFVNWLLAGGPSSGAPPPS—NH₂ |
| 23 | **R—N(H)—EGTFTSDYSIYLDKQAV(Aib)EFVNWLLAGGPSSGAPPPSK\*—NH₂**<br>Sequence Ga<br>= K\*<br>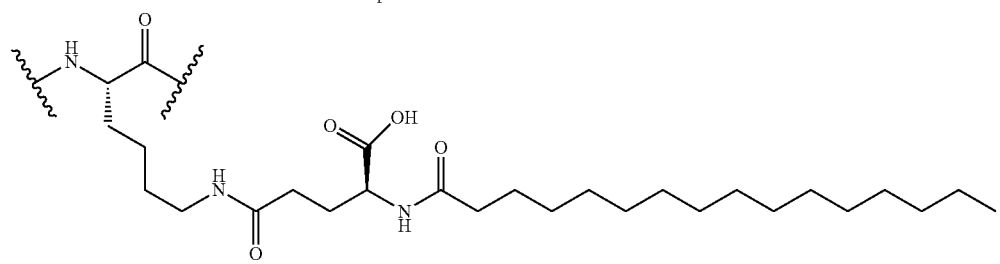 |
| 24 | **R—N(H)—EGTFTSDYSIYLDKQAA(Aib)EFVK\*WLLAGGPSSGAPPPSK—NH₂**<br>Sequence Pa<br>= K\*<br>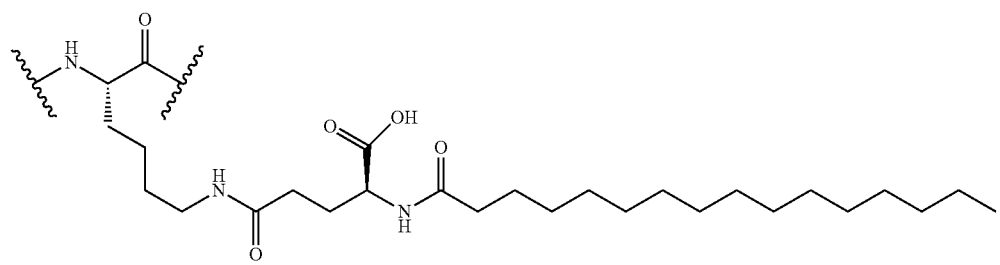 |

TABLE 2-continued
| SEQ ID NO: | Sequence |
|---|---|
| 25 | R—NH—EGTFTSDYSIYLDKQAA(Aib)EFVNWLLAGRGK*GPSSGAPPPS—NH$_2$<br>Sequence Qa<br>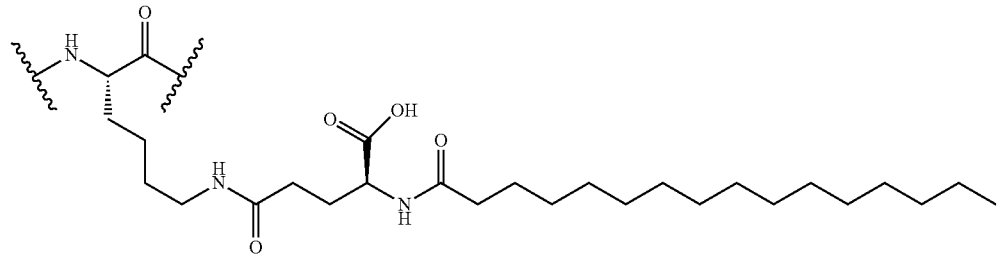 = K* |
| 26 | R—NH—EGTFTSDYSIYLDKQAAK*EFVNWLLAGGPSSGAPPPSK—NH$_2$<br>Sequence Ra<br>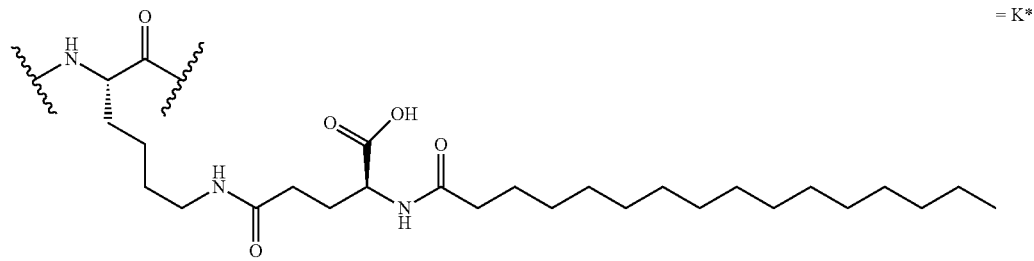 [SMILES: *N[C@@H](CCCCNC(=O)CC[C@H](NC(=O)CCCCCCCCCCCCCCC)C(=O)O)C(*)=O] = K* |
| 27 | R—NH—EGTFTSDK*SIYLDKQAA(Aib)EFVNWLLAGGPSSGAPPPSK—NH$_2$<br>Sequence Sa<br>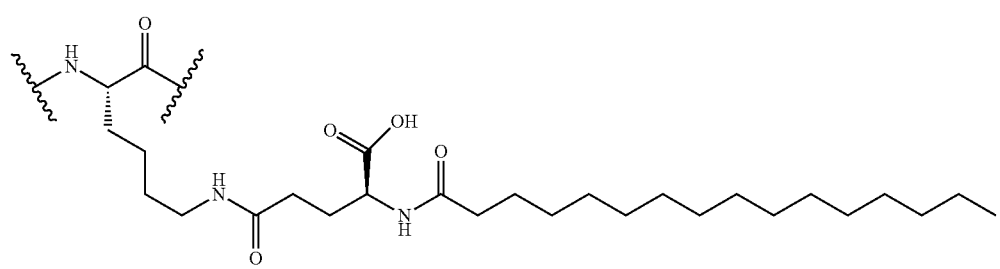 = K* |
| 28 | GTFTSDYSIYLDKQAA(Aib)EFVNWLLAGGPSSGAPPPSK*—NH$_2$<br>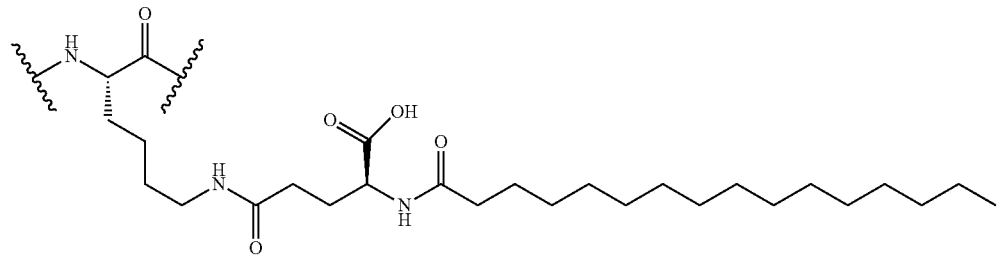 = K* |

TABLE 2-continued
| SEQ ID NO: | Sequence |
|---|---|
| 29 | **GTFTSDYSIY\*LDKQAA(Aib)EFVNWLLAGGPSSGAPPPSK\*—NH₂** |
K* = 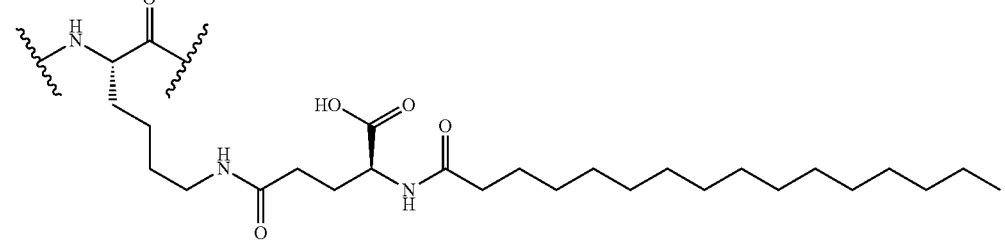
Y* = 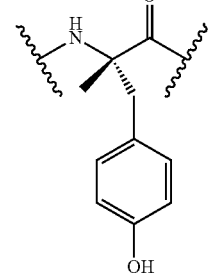
| 30 | **GTFTSDYSIYLDKQAV(Aib)EFVNWLLAGGPSSGAPPPSK\*—NH₂** |
= K* 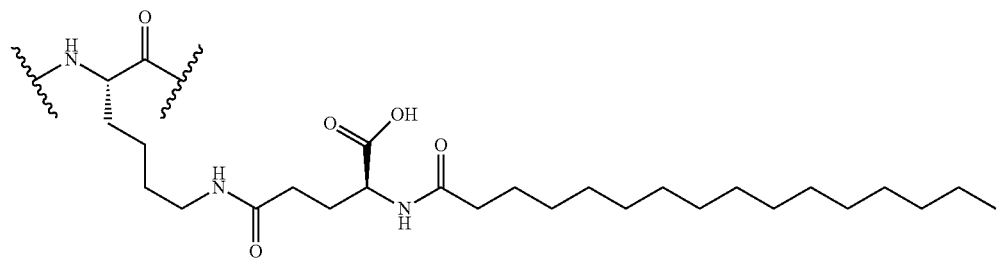
| 31 | **GTFTSDYSIYLDKQAA(Aib)EFVK\*WLLAGGPSSGAPPPSK—NH₂** |
= K* 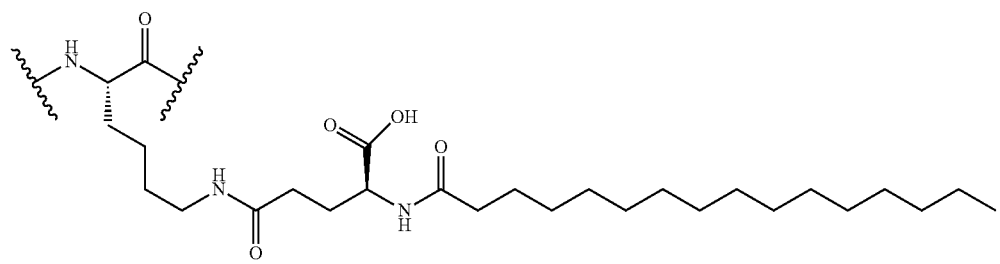
| 32 | **GTFTSDYSIYLDKQAA(Aib)EFVNWLLAGRGK\*GPSSGAPPPS—NH₂** |
= K* 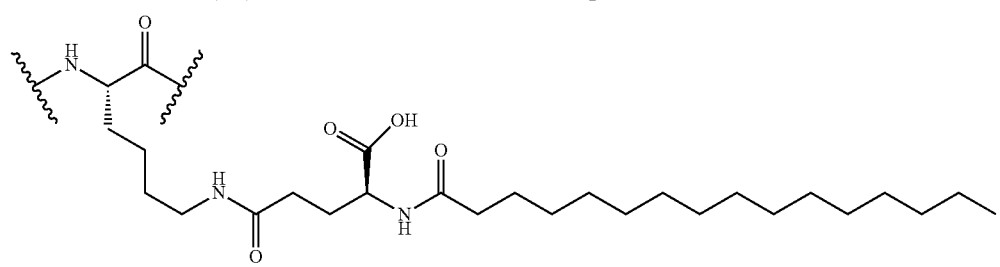

TABLE 2-continued

| SEQ ID NO: | Sequence |
|---|---|
| 33 | **GTFTSDYSIYLDKQAAK\*EFVNWLLAGGPSSGAPPPSK—NH$_2$** |
| 34 | **GTFTSDK\*SIYLDKQAA(Aib)EFVNWLLAGGPSSGAPPPSK—NH$_2$** |

= K* (structures shown for both, depicting a lysine side chain modified with a γ-glutamate linker and a long fatty acyl chain)

In some embodiments, W is represented by any one of SEQ ID 1-34 (e.g., SEQ. ID 5-27; e.g., SEQ ID 5-29; (e.g., SEQ ID 6); e.g., SEQ ID 28-29; e.g., SEQ ID 30-34).

In some embodiments, W is represented by any one of SEQ ID 1-27 (e.g., SEQ. ID 5-27; e.g., SEQ ID 6).

In some embodiments, W is represented by any one of SEQ ID 28-29 (e.g., 28, 29).

In certain embodiments, W has the sequence of SEQ ID 6.

Non-Limiting Combinations of Formulae (IAA), (IA), and (I)

[1] In some embodiments, the compound has formula (I-A), (I-AA, or (I-AB), ring A is a saturated or unsaturated monocyclic ring that includes from 3-8 (e.g., 4-8, 4-7, 5-6) ring atoms, and L has formula (VIII): —(CH$_2$)$_m$—X$^1$—(CH$_2$)$_n$—X$^2$—(CH$_2$)$_p$—. In certain embodiments, one, two, or three of R$^1$, R$^2$, and R$^4$ are H. In certain embodiments, R$^3$ is —C(O)OH. In certain embodiments, a is 0, 1, or 2 (e.g., 1). In certain embodiments, each of R$^1$, R$^2$, and R$^4$ is H, a is 0, 1, or 2 (e.g., 1), and R$^3$ is —C(O)OH.

[1A] In some embodiments, the compound has formula (IA-A), (IA-AA), or (IA-AB), ring A is a saturated or unsaturated monocyclic ring that includes from 3-8 (e.g., 4-8, 4-7, 5-6) ring atoms, and L has formula (VIII): —(CH$_2$)$_m$—X$^1$—(CH$_2$)$_n$—X$^2$—(CH$_2$)$_p$—. In certain embodiments, one, two, or three of R$^1$, R$^2$, and R$^4$ are H. In certain embodiments, R$^3$ is —C(O)OH. In certain embodiments, a is 0, 1, or 2 (e.g., 1). In certain embodiments, each of R$^1$, R$^2$, and R$^4$ is H, a is 0, 1, or 2 (e.g., 1), and R$^3$ is —C(O)OH. In certain embodiments, a' is 1; each of R$^{3a}$ and R$^{3b}$ is H.

[2] In some embodiments, the compound has formula (I-A), (I-AA), or (I-AB), (I-A), (I-AA), or (I-AB), ring A is a saturated monocyclic ring that includes from 3-8 (e.g., 4-8, 4-7, 5-6) ring atoms, and L has formula (VIII): —(CH$_2$)$_m$—X$^1$—(CH$_2$)$_n$—X$^2$—(CH$_2$)$_p$—. In certain embodiments, one, two, or three of R$^1$, R$^2$, and R$^4$ are H. In certain embodiments, R$^3$ is —C(O)OH. In certain embodiments, a is 0, 1, or 2 (e.g., 1). In certain embodiments, each of R$^1$, R$^2$, and R$^4$ is H, a is 0, 1, or 2 (e.g., 1), and R$^3$ is —C(O)OH.

[2A] In some embodiments, the compound has formula (IA-A), (IA-AA), or (IA-AB), (IA-B), (IA-BA, or (IA-BB), ring A is a saturated monocyclic ring that includes from 3-8 (e.g., 4-8, 4-7, 5-6) ring atoms, and L has formula (VIII): —(CH$_2$)$_m$—X$^1$—(CH$_2$)$_n$—X$^2$—(CH$_2$)$_p$—. In certain embodiments, one, two, or three of R$^1$, R$^2$, and R$^4$ are H. In certain embodiments, R$^3$ is —C(O)OH. In certain embodiments, a is 0, 1, or 2 (e.g., 1). In certain embodiments, each of R$^1$, R$^2$, and R$^4$ is H, a is 0, 1, or 2 (e.g., 1), and R$^3$ is —C(O)OH. In certain embodiments, a' is 1; each of R$^{3a}$ and R$^{3b}$ is H.

[3] In some embodiments, the compound has formula (I-A), (I-AA), or (I-AB), ring A is a saturated, monocyclic, 6-membered ring having formula (III) (i.e., A$^1$ is not a bond), and L has formula (VIII): —(CH$_2$)$_m$—X$^1$—(CH$_2$)$_n$—X$^2$—(CH$_2$)$_p$—. In certain embodiments, one, two, or three of R$^1$, R$^2$, and R$^4$ are H. In certain embodiments, R$^3$ is —C(O)OH. In certain embodiments, a is 0, 1, or 2 (e.g., 1). In certain embodiments, each of R$^1$, R$^2$, and R$^4$ is H, a is 0, 1, or 2 (e.g., 1), and R$^3$ is —C(O)OH.

[3A] In some embodiments, the compound has formula (IA-A), (IA-AA), or (IA-AB), ring A is a saturated, monocyclic, 6-membered ring having formula (III) (i.e., A$^1$ is not a bond), and L has formula (VIII): —(CH$_2$)$_m$—X$^1$—(CH$_2$)$_n$—X$^2$—(CH$_2$)$_p$—. In certain embodiments, one, two, or three of R$^1$, R$^2$, and R$^4$ are H. In certain embodiments, R$^3$ is —C(O)OH. In certain embodiments, a is 0, 1, or 2 (e.g., 1). In certain embodiments, each of R$^1$, R$^2$, and R$^4$ is H, a is 0, 1, or 2 (e.g., 1), and R$^3$ is —C(O)OH. In certain embodiments, a' is 1; each of R$^{3a}$ and R$^{3b}$ is H.

[4] In some embodiments, the compound has formula (I-A), (I-AA), or (I-AB), ring A is a saturated, monocyclic, 5-membered ring having formula (III-A) (i.e., A$^1$ in formula (III) is a bond), and L has formula (VIII): —(CH$_2$)$_m$—X$^1$—(CH$_2$)$_n$—X$^2$—(CH$_2$)$_p$—. In certain embodiments, one, two, or three of R$^1$, R$^2$, and R$^4$ are H. In certain embodiments, R$^3$ is —C(O)OH. In certain embodiments, a is 0, 1, or 2 (e.g., 1). In certain embodiments, each of R$^1$, R$^2$, and R$^4$ is H, a is 0, 1, or 2 (e.g., 1), and R$^3$ is —C(O)OH.

[4A] In some embodiments, the compound has formula (IA-A), (IA-AA), or (IA-AB), ring A is a saturated, monocyclic, 5-membered ring having formula (III-A) (i.e., $A^1$ in formula (III) is a bond), and L has formula (VIII): —$(CH_2)_m$—$X^1$—$(CH_2)_n$—$X^2$—$(CH_2)_p$—. In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, each of $R^1$, $R^2$, and $R^4$ is H, a is 0, 1, or 2 (e.g., 1), and $R^3$ is —C(O)OH. In certain embodiments, a' is 1; each of $R^{3a}$ and $R^{3b}$ is H.

[5] In some embodiments, the compound has formula (I-A), (I-AA), or (I-AB), ring A is a saturated or unsaturated bicyclic or tricyclic ring that includes from 6-14 (e.g., 8-10) ring atoms, and L has formula (VIII): —$(CH_2)_m$—$X^1$—$(CH_2)_n$—$X^2$—$(CH_2)_p$—. In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, each of $R^1$, $R^2$, and $R^4$ is H, a is 0, 1, or 2 (e.g., 1), and $R^3$ is —C(O)OH.

[5A] In some embodiments, the compound has formula (IA-A), (IA-AA), or (IA-AB), ring A is a saturated or unsaturated bicyclic or tricyclic ring that includes from 6-14 (e.g., 8-10) ring atoms, and L has formula (VIII): —$(CH_2)_m$—$X^1$—$(CH_2)_n$—$X^2$—$(CH_2)_p$—. In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, each of $R^1$, $R^2$, and $R^4$ is H, a is 0, 1, or 2 (e.g., 1), and $R^3$ is —C(O)OH. In certain embodiments, a' is 1; each of $R^{3a}$ and $R^{3b}$ is H.

[6] In some embodiments, the compound has formula (I-A), (I-AA), or (I-AB), ring A is a saturated or unsaturated monocyclic ring that includes from 3-8 (e.g., 4-8, 4-7, 5-6) ring atoms, L has formula (VIII): —$(CH_2)_m$—$X^1$—$(CH_2)_n$—$X^2$—$(CH_2)_p$—, and W is represented by formula (X), (XII), (XIII), (XIV), (XIV-A), (XIV-B), or any of SEQ ID 1-27 (e.g., SEQ ID 5-27, e.g., SEQ ID 6). In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI).

[6A] In some embodiments, the compound has formula (IA-A), (IA-AA), or (IA-AB), ring A is a saturated or unsaturated monocyclic ring that includes from 3-8 (e.g., 4-8, 4-7, 5-6) ring atoms, L has formula (VIII): —$(CH_2)_m$—$X^1$—$(CH_2)_n$—$X^2$—$(CH_2)_p$—, and W is represented by formula (X), (XII), (XIII), (XIV-AA), (XIV), (XIV-A), (XIV-B), (XV), or any of SEQ ID 1-34 (e.g., SEQ ID 5-27; e.g., SEQ ID 5-29; (e.g., SEQ ID 6); e.g., SEQ ID 28-29; e.g., SEQ ID 30-34). In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI). In certain embodiments, a' is 1; each of $R^{3a}$ and $R^{3b}$ is H.

[7] In some embodiments, the compound has formula (I-A), (I-AA), or (I-AB), ring A is a saturated monocyclic ring that includes from 3-8 (e.g., 4-8, 4-7, 5-6) ring atoms, L has formula (VIII): —$(CH_2)_m$—$X^1$—$(CH_2)_n$—$X^2$—$(CH_2)_p$—, and W is represented by (X), (XII), (XIII), (XIV), (XIV-A), (XIV-B), or any of SEQ ID 1-27 (e.g., SEQ ID 5-27, e.g., SEQ ID 6). In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI).

[7A] In some embodiments, the compound has formula (I-A), (I-AA), or (I-AB), ring A is a saturated monocyclic ring that includes from 3-8 (e.g., 4-8, 4-7, 5-6) ring atoms, L has formula (VIII): —$(CH_2)_m$—$X^1$—$(CH_2)_n$—$X^2$—$(CH_2)_p$—, and W is represented by formula (X), (XII), (XIII), (XIV-AA), (XIV), (XIV-A), (XIV-B), (XV), or any of SEQ ID 1-34 (e.g., SEQ. ID 5-27; e.g., SEQ ID 5-29; (e.g., SEQ ID 6); e.g., SEQ ID 28-29; e.g., SEQ ID 30-34). In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI). In certain embodiments, a' is 1; each of $R^{3a}$ and $R^{3b}$ is H.

[8] In some embodiments, the compound has formula (I-A), (I-AA), or (I-AB), ring A is a saturated, monocyclic, 6-membered ring having formula (III) (i.e., $A^1$ is not a bond), L has formula (VIII): —$(CH_2)_m$—$X^1$—$(CH_2)_n$—$X^2$—$(CH_2)_p$—, and W is represented by formula (X), (XII), (XIII), (XIV), (XIV-A), (XIV-B), or any of SEQ ID 1-27 (e.g., SEQ ID 5-27, e.g., SEQ ID 6). In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI).

[8A] In some embodiments, the compound has formula (IA-A), (IA-AA), or (IA-AB), ring A is a saturated, monocyclic, 6-membered ring having formula (III) (i.e., $A^1$ is not a bond), L has formula (VIII): —$(CH_2)_m$—$X^1$—$(CH_2)_n$—$X^2$—$(CH_2)_p$—, and W is represented by formula (X), (XII), (XIII), (XIV-AA), (XIV), (XIV-A), (XIV-B), (XV), or any of SEQ ID 1-34 (e.g., SEQ. ID 5-27; e.g., SEQ ID 5-29; (e.g., SEQ ID 6); e.g., SEQ ID 28-29; e.g., SEQ ID 30-34). In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI). In certain embodiments, a' is 1; each of $R^{3a}$ and $R^{3b}$ is H.

[9] In some embodiments, the compound has formula (I-A), (I-AA), or (I-AB), ring A is a saturated, monocyclic, 5-membered ring having formula (III-A) (i.e., $A^1$ in formula (III) is a bond), L has formula (VIII): —$(CH_2)_m$—$X^1$—$(CH_2)_n$—$X^2$—$(CH_2)_p$—, and W is represented by formula (X), (XII), (XIII), (XIV), (XIV-A), (XIV-B), or any of SEQ ID 1-27 (e.g., SEQ ID 5-27, e.g., SEQ ID 6). In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI).

[9A] In some embodiments, the compound has formula (IA-A), (IA-AA), or (IA-AB), ring A is a saturated, monocyclic, 5-membered ring having formula (III-A) (i.e., $A^1$ in formula (III) is a bond), L has formula (VIII): —$(CH_2)_m$—$X^1$—$(CH_2)_n$—$X^2$—$(CH_2)_p$—, and W is represented by formula (X), (XII), (XIII), (XIV-AA), (XIV), (XIV-A), (XIV-B), (XV), or any of SEQ ID 1-34 (e.g., SEQ. ID 5-27; e.g., SEQ ID 5-29; (e.g., SEQ ID 6); e.g., SEQ ID 28-29; e.g., SEQ ID 30-34). In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI). In certain embodiments, a' is 1; each of $R^{3a}$ and $R^{3b}$ is H.

[10] In some embodiments, the compound has formula (I-A), (I-AA), or (I-AB), ring A is a saturated or unsaturated bicyclic or tricyclic ring that includes from 6-14 (e.g., 8-10) ring atoms, L has formula (VIII): —$(CH_2)_m$—$X^1$—$(CH_2)_n$—$X^2$—$(CH_2)_p$—, and W is represented by formula (X), (XII), (XIII), (XIV), (XIV-A), (XIV-B), or any of SEQ ID 1-27 (e.g., SEQ ID 5-27, e.g., SEQ ID 6). In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI).

[10A] In some embodiments, the compound has formula (IA-A), (IA-AA), or (IA-AB), ring A is a saturated or unsaturated bicyclic or tricyclic ring that includes from 6-14 (e.g., 8-10) ring atoms, L has formula (VIII): —$(CH_2)_m$—$X^1$—$(CH_2)_n$—$X^2$—$(CH_2)_p$—, and W is represented by formula (X), (XII), (XIII), (XIV-AA), (XIV), (XIV-A), (XIV-B), (XV), or any of SEQ ID 1-34 (e.g., SEQ. ID 5-27; e.g., SEQ ID 5-29; (e.g., SEQ ID 6); e.g., SEQ ID 28-29; e.g., SEQ ID 30-34). In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI). In certain embodiments, a' is 1; each of $R^{3a}$ and $R^{3b}$ is H.

[11] In some embodiments:
the compound has formula (I-A), (I-AA), or (I-AB);
ring A is a saturated monocyclic ring that includes from 3-8 (e.g., 4-8, 4-7, 5-6) ring atoms;
L has formula (VIII): —$(CH_2)_m$—$X^1$—$(CH_2)_n$—$X^2$—$(CH_2)_p$—,
W is represented by formula (X), (XII), (XIII), (XIV), (XIV-A), (XIV-B), or any of SEQ ID 1-27 (e.g., SEQ ID 5-27, e.g., SEQ ID 6); and
m is 2-6 (e.g., 2), $X^1$ is —N(R')C(O)— (e.g., —N(H)C(O)—), and n+p=2 (e.g., each of n and p is 1), and $X^2$ is —S—; or
m is 2-6 (e.g., 2), $X^1$ is —N(R')C(O)— (e.g., —N(H)C(O)—), n+p=0, $X^2$ is —C($Q^1$)($Q^2$)-, and $Q^1$ and $Q^2$, together with the carbon atom to which each is attached forms $C_{3-6}$ cycloalkyl that is optionally substituted with from 1-4 independently selected $R^d$ and optionally fused to phenyl; or
m is 2-6 (e.g., 2), $X^1$ is —N(R')C(O)— (e.g., —N(H)C(O)—), n+p=0, $X^2$ is —C($Q^1$)($Q^2$)-, and $Q^1$ and $Q^2$ is an independently selected $C_{1-4}$ alkyl (e.g., $CH_3$); or
m is 2-6 (e.g., 2), $X^1$ is —N(R')C(O)— (e.g., —N(H)C(O)—), n+p=0, and $X^2$ is: (v) $C_{6-10}$ arylene (e.g., phenylene) optionally substituted with from 1-5 independently selected $R^c$; or (vii) $C_{3-10}$ cycloalkylene optionally substituted with from 1-4 independently selected $R^d$.

In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI).

In certain of these embodiments, m is 2-6 (e.g., 2), $X^1$ is —N(R')C(O)— (e.g., —N(H)C(O)—), and n+p=2 (e.g., each of n and p is 1), and $X^2$ is —S—. For example, L can be —$CH_2CH_2NHC(O)CH_2SCH_2$—.

In certain of these embodiments, any one of SEQ ID 5-27 (e.g., SEQ ID 6) represents W.

[11A] In some embodiments:
the compound has formula (IA-A), (IA-AA), or (IA-AB);
ring A is a saturated monocyclic ring that includes from 3-8 (e.g., 4-8, 4-7, 5-6) ring atoms;
L has formula (VIII): —$(CH_2)_m$—$X^1$—$(CH_2)_n$—$X^2$—$(CH_2)_p$—, and
W is represented by formula (X), (XII), (XIII), (XIV-AA), (XIV), (XIV-A), (XIV-B), (XV), or any of SEQ ID 1-34 (e.g., SEQ. ID 5-27; e.g., SEQ ID 5-29; (e.g., SEQ ID 6); e.g., SEQ ID 28-29; e.g., SEQ ID 30-34).

In certain embodiments, m is 2-6 (e.g., 2), $X^1$ is —N(R')C(O)— (e.g., —N(H)C(O)—), and n+p=2 (e.g., each of n and p is 1), and $X^2$ is —S—; or
m is 2-6 (e.g., 2), $X^1$ is —N(R')C(O)— (e.g., —N(H)C(O)—), n+p=0, $X^2$ is —C($Q^1$)($Q^2$)-, and $Q^1$ and $Q^2$, together with the carbon atom to which each is attached forms $C_{3-6}$ cycloalkyl that is optionally substituted with from 1-4 independently selected $R^d$ and optionally fused to phenyl; or
m is 2-6 (e.g., 2), $X^1$ is —N(R')C(O)— (e.g., —N(H)C(O)—), n+p=0, $X^2$ is —C($Q^1$)($Q^2$)-, and $Q^1$ and $Q^2$ is an independently selected $C_{1-4}$ alkyl (e.g., $CH_3$); or
m is 2-6 (e.g., 2), $X^1$ is —N(R')C(O)— (e.g., —N(H)C(O)—), n+p=0, and $X^2$ is: (v) $C_{6-10}$ arylene (e.g., phenylene) optionally substituted with from 1-5 independently selected $R^c$; or (vii) $C_{3-10}$ cycloalkylene optionally substituted with from 1-4 independently selected $R^d$.

In certain embodiments, m is 2-6 (e.g., 2), $X^1$ is —N(R') C(O)— (e.g., —N(H)C(O)—), n+p=0, and $X^2$ is: heterocycloalkylene including from 4-6 (e.g., 4) ring atoms, wherein from 1-3 (e.g., 1) ring atoms are each independently selected from the group consisting of N($R^a$), O, and S; and which is optionally substituted with from 1-5 independently selected $R^d$ (e.g., $X^2$ can be

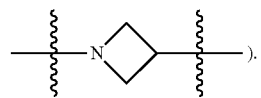 [SMILES: *C1CN(*)C1]

).

In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI). In certain embodiments, a' is 1; each of $R^{3a}$ and $R^{3b}$ is H.

In certain of these embodiments, m is 2-6 (e.g., 2), $X^1$ is —N(R')C(O)— (e.g., —N(H)C(O)—), and n+p=2 (e.g., each of n and p is 1), and $X^2$ is —S—. For example, L can be —$CH_2CH_2NHC(O)CH_2SCH_2$—.

In certain of these embodiments, any one of SEQ ID 5-34 (e.g., SEQ ID 6) represents W.

[12] In some embodiments:
the compound has formula (I-A), (I-AA), or (I-AB);
ring A is a saturated, monocyclic, 6-membered ring having formula (III) (i.e., $A^1$ is not a bond);
L has formula (VIII): —$(CH_2)_m$—$X^1$—$(CH_2)_n$—$X^2$—$(CH_2)_p$—;
W is represented by formula (X), (XII), (XIII), (XIV), (XIV-A), (XIV-B), or any of SEQ ID 1-27 (e.g., SEQ ID 5-27, e.g., SEQ ID 6); and m is 2-6 (e.g., 2), $X^1$ is —N(R')C(O)— (e.g., —N(H)C(O)—), and n+p=2 (e.g., each of n and p is 1), and $X^2$ is —S—; or m is 2-6 (e.g., 2), $X^1$ is —N(R')C(O)— (e.g., —N(H)C(O)—), n+p=0, $X^2$ is —C($Q^1$)($Q^2$)-, and $Q^1$ and $Q^2$, together with the carbon atom to which each is attached forms $C_{3-6}$ cycloalkyl that is optionally substituted with from 1-4 independently selected $R^d$ and optionally fused to phenyl; or m is 2-6 (e.g., 2), $X^1$ is —N(R')C(O)— (e.g., —N(H)C(O)—), n+p=0, $X^2$ is —C($Q^1$)($Q^2$)-, and $Q^1$ and $Q^2$ is an independently selected $C_{1-4}$ alkyl (e.g., $CH_3$); or m is 2-6 (e.g., 2), $X^1$ is —N(R')C(O)— (e.g., —N(H)C(O)—), n+p=0, and $X^2$ is: (v) $C_{6-10}$ arylene (e.g., phenylene) optionally substituted with from 1-5 independently selected $R^c$; or (vii) $C_{3-10}$ cycloalkylene optionally substituted with from 1-4 independently selected $R^d$.

In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI).

In certain of these embodiments, m is 2-6 (e.g., 2), $X^1$ is —N(R')C(O)— (e.g., —N(H)C(O)—), and n+p=2 (e.g., each of n and p is 1), and $X^2$ is —S—. For example, L can be —$CH_2CH_2NHC(O)CH_2SCH_2$—.

In certain of these embodiments, any one of SEQ ID 5-27 (e.g., SEQ ID 6) represents W.

In certain formula (III), 6-membered ring embodiments, $A_1$, $A_2$, $A_3$ and $A_4$ are each independently selected from the group consisting of $CH_2$, $CHR^b$, or $C(R^b)_2$.

In certain formula (III), 6-membered ring embodiments, one or two (e.g., one) of $A_1$, $A_2$, $A_3$ and $A_4$ are independently selected from the group consisting of $CHR^b$ and $C(R^b)_2$, and the others are $CH_2$.

In certain formula (III), 6-membered ring embodiments, $A_1$, $A_2$, $A_3$ and $A_4$ are each $CH_2$.

In certain formula (III), 6-membered ring embodiments, $A_1$, $A_2$ and $A_4$ are each independently selected from the group consisting of $CH_2$, $CHR^b$, and $C(R^b)_2$; and $A_3$ is O; S; $SO_2$; or N($R^a$). In certain of these embodiments, one or two (e.g., one) of $A_2$ and $A_4$ are independently selected from the group consisting of $CHR^b$ and $C(R^b)_2$, and the other (where applicable) is $CH_2$. In other embodiments, $A_2$ and $A_3$ are both $CH_2$. In certain of these embodiments, $A_1$ is $CH_2$. In certain embodiments, $A_3$ is N($R^a$) (e.g., $A_3$ can be NH). In other embodiments, $A_3$ is O. In still other embodiments, $A_3$ is $SO_2$.

In certain formula (III), 6-membered ring embodiments, $A_1$, $A_2$ and $A_3$ are each independently selected from the group consisting of $CH_2$, $CHR^b$, and $C(R^b)_2$; and $A_4$ is O; S; or N($R^a$). In certain of these embodiments, one or two (e.g., one) of $A_2$ and $A_4$ are independently selected from the group consisting of $CHR^b$ and $C(R^b)_2$, and the other (where applicable) is $CH_2$. In other embodiments, $A_2$ and $A_3$ are both $CH_2$. In certain of these embodiments, $A_1$ is $CH_2$. In certain of these embodiments, $A_4$ is N($R^a$) (e.g., $A_4$ can be NH). In other embodiments, $A_4$ is O.

In certain formula (III), 6-membered ring embodiments, $A_1$ is C(O); and $A_2$, $A_3$ and $A_4$ are each independently selected from the group consisting of $CH_2$, $CHR^b$, or $C(R^b)_2$. In certain of these embodiments, one or two (e.g., one) of $A_2$, $A_3$ and $A_4$ are independently selected from the group consisting of $CHR^b$ and $C(R^b)_2$, and the other(s) is/are $CH_2$.

In certain formula (III), 6-membered ring embodiments, $A_1$ is C(O); and $A_2$, $A_3$ and $A_4$ are each $CH_2$.

In certain formula (III), 6-membered ring embodiments, $A_1$ is C(O); $A_2$ and $A_4$ are each independently selected from the group consisting of $CH_2$, $CHR^b$, and $C(R^b)_2$; and $A_3$ is O; S; $SO_2$; or N($R^a$). In certain of these embodiments, one or two (e.g., one) of $A_2$ and $A_4$ are independently selected from the group consisting of $CHR^b$ and $C(R^b)_2$, and the other (where applicable) is $CH_2$. In other embodiments, $A_2$ and $A_4$ are both $CH_2$. In certain of these embodiments, $A_3$ is N($R^a$) (e.g., $A_3$ can be NH). In other embodiments, $A_3$ is O. In still other embodiments, $A_3$ is $SO_2$.

In certain formula (III), 6-membered ring embodiments, $A_1$ is C(O); $A_2$ and $A_3$ are each independently selected from the group consisting of $CH_2$, $CHR^b$, and $C(R^b)_2$; and $A_4$ is O; S; or N($R^a$). In certain of these embodiments, one or two (e.g., one) of $A_2$ and $A_3$ are independently selected from the group consisting of $CHR^b$ and $C(R^b)_2$, and the other (where applicable) is $CH_2$. In other embodiments, $A_2$ and $A_3$ are both $CH_2$. In certain of these embodiments, $A_4$ is N($R^a$) (e.g., $A_4$ can be NH). In other embodiments, $A_4$ is O. In certain formula (III), 6-membered ring embodiments, $A_1$, $A_2$, $A_3$ and $A_4$ are each independently selected from the group consisting of $CH_2$, $CHR^b$, or $C(R^b)_2$.

[12A] In some embodiments:
the compound has formula (IA-A), (IA-AA), or (IA-AB);
ring A is a saturated, monocyclic, 6-membered ring having formula (III) (i.e., $A^1$ is not a bond);
L has formula (VIII): —$(CH_2)_m$—$X^1$—$(CH_2)_n$—$X^2$—$(CH_2)_p$—; and
W is represented by formula (X), (XII), (XIII), (XIV-AA), (XIV), (XIV-A), (XIV-B), (XV), or any of SEQ ID 1-34 (e.g., SEQ. ID 5-27; e.g., SEQ ID 5-29; (e.g., SEQ ID 6); e.g., SEQ ID 28-29; e.g., SEQ ID 30-34).

In certain embodiments, m is 2-6 (e.g., 2), $X^1$ is —N(R')C(O)— (e.g., —N(H)C(O)—), and n+p=2 (e.g., each of n and p is 1), and $X^2$ is —S—; or m is 2-6 (e.g., 2), $X^1$ is —N(R')C(O)— (e.g., —N(H)C(O)—), n+p=0, $X^2$ is —C($Q^1$)($Q^2$)-, and $Q^1$ and $Q^2$, together with the carbon atom to which each is attached forms $C_{3-6}$ cycloalkyl that is optionally substituted with from 1-4 independently selected $R^d$ and optionally fused to phenyl; or m is 2-6 (e.g., 2), $X^1$ is —N(R')C(O)— (e.g., —N(H)C(O)—), n+p=0, $X^2$ is —C($Q^1$)($Q^2$)-, and $Q^1$ and $Q^2$ is an independently selected $C_{1-4}$ alkyl (e.g., $CH_3$); or m is 2-6 (e.g., 2), $X^1$ is —N(R')C(O)— (e.g., —N(H)C(O)—), n+p=0, and $X^2$ is: (v) $C_{6-10}$ arylene (e.g., phenylene) optionally substituted with from 1-5 independently selected $R^c$; or (vii) $C_{3-10}$ cycloalkylene optionally substituted with from 1-4 independently selected $R^d$.

In certain embodiments, m is 2-6 (e.g., 2), $X^1$ is —N(R')C(O)— (e.g., —N(H)C(O)—), n+p=0, and $X^2$ is: heterocycloalkylene including from 4-6 (e.g., 4) ring atoms, wherein from 1-3 (e.g., 1) ring atoms are each independently selected from the group consisting of N($R^a$), O, and S; and which is optionally substituted with from 1-5 independently selected $R^d$ (e.g., $X^2$ can be

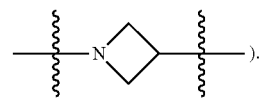).

In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI). In certain embodiments, a' is 1; each of $R^{3a}$ and $R^{3b}$ is H.

In certain of these embodiments, m is 2-6 (e.g., 2), $X^1$ is —N(R')C(O)— (e.g., —N(H)C(O)—), and n+p=2 (e.g., each of n and p is 1), and $X^2$ is —S—. For example, L can be —CH$_2$CH$_2$NHC(O)CH$_2$SCH$_2$—.

In certain of these embodiments, any one of SEQ ID 5-34 (e.g., SEQ ID 6) represents W.

In certain formula (III), 6-membered ring embodiments, $A_1$, $A_2$, $A_3$ and $A_4$ are each independently selected from the group consisting of CH$_2$, CHR$^b$, or C(R$^b$)$_2$.

In certain formula (III), 6-membered ring embodiments, one or two (e.g., one) of $A_1$, $A_2$, $A_3$ and $A_4$ are independently selected from the group consisting of CHR$^b$ and C(R$^b$)$_2$, and the others are CH$_2$.

In certain formula (III), 6-membered ring embodiments, $A_1$, $A_2$, $A_3$ and $A_4$ are each CH$_2$.

In certain formula (III), 6-membered ring embodiments, $A_1$, $A_2$ and $A_4$ are each independently selected from the group consisting of CH$_2$, CHR$^b$, and C(R$^b$)$_2$; and $A_3$ is O; S; SO$_2$; or N(R$^a$). In certain of these embodiments, one or two (e.g., one) of $A_2$ and $A_4$ are independently selected from the group consisting of CHR$^b$ and C(R$^b$)$_2$, and the other (where applicable) is CH$_2$. In other embodiments, $A_2$ and $A_3$ are both CH$_2$. In certain of these embodiments, $A_1$ is CH$_2$. In certain of these embodiments, $A_3$ is N(R$^a$) (e.g., $A_3$ can be NH). In other embodiments, $A_3$ is O. In still other embodiments, $A_3$ is SO$_2$.

In certain formula (III), 6-membered ring embodiments, $A_1$, $A_2$ and $A_3$ are each independently selected from the group consisting of CH$_2$, CHR$^b$, and C(R$^b$)$_2$; and $A_4$ is O; S; or N(R$^a$). In certain of these embodiments, one or two (e.g., one) of $A_2$ and $A_4$ are independently selected from the group consisting of CHR$^b$ and C(R$^b$)$_2$, and the other (where applicable) is CH$_2$. In other embodiments, $A_2$ and $A_3$ are both CH$_2$. In certain of these embodiments, $A_1$ is CH$_2$. In certain of these embodiments, $A_4$ is N(R$^a$) (e.g., $A_4$ can be NH). In other embodiments, $A_4$ is O.

In certain formula (III), 6-membered ring embodiments, $A_1$ is C(O); and $A_2$, $A_3$ and $A_4$ are each independently selected from the group consisting of CH$_2$, CHR$^b$, or C(R$^b$)$_2$. In certain of these embodiments, one or two (e.g., one) of $A_2$, $A_3$ and $A_4$ are independently selected from the group consisting of CHR$^b$ and C(R$^b$)$_2$, and the other(s) is/are CH$_2$.

In certain formula (III), 6-membered ring embodiments, $A_1$ is C(O); and $A_2$, $A_3$ and $A_4$ are each CH$_2$.

In certain formula (III), 6-membered ring embodiments, $A_1$ is C(O); $A_2$ and $A_4$ are each independently selected from the group consisting of CH$_2$, CHR$^b$, and C(R$^b$)$_2$; and $A_3$ is O; S; SO$_2$; or N(R$^a$). In certain of these embodiments, one or two (e.g., one) of $A_2$ and $A_4$ are independently selected from the group consisting of CHR$^b$ and C(R$^b$)$_2$, and the other (where applicable) is CH$_2$. In other embodiments, $A_2$ and $A_4$ are both CH$_2$. In certain of these embodiments, $A_3$ is N(R$^a$) (e.g., $A_3$ can be NH). In other embodiments, $A_3$ is O. In still other embodiments, $A_3$ is SO$_2$.

In certain formula (III), 6-membered ring embodiments, $A_1$ is C(O); $A_2$ and $A_3$ are each independently selected from the group consisting of CH$_2$, CHR$^b$, and C(R$^b$)$_2$; and $A_4$ is O; S; or N(R$^a$). In certain of these embodiments, one or two (e.g., one) of $A_2$ and $A_3$ are independently selected from the group consisting of CHR$^b$ and C(R$^b$)$_2$, and the other (where applicable) is CH$_2$. In other embodiments, $A_2$ and $A_3$ are both CH$_2$. In certain of these embodiments, $A_4$ is N(R$^a$) (e.g., $A_4$ can be NH). In other embodiments, $A_4$ is O. In certain formula (III), 6-membered ring embodiments, $A_1$, $A_2$, $A_3$ and $A_4$ are each independently selected from the group consisting of CH$_2$, CHR$^b$, or C(R$^b$)$_2$.

[13] In some embodiments:
the compound has formula (IA-A), (IA-AA), or (IA-AB);
ring A is a saturated, monocyclic, 5-membered ring having formula (III-A) (i.e., $A^1$ in formula (III) is a bond);
L has formula (VIII): —(CH$_2$)$_m$—X$^1$—(CH$_2$)$_n$—X$^2$—(CH$_2$)$_p$—,
W is represented by formula (X), (XII), (XIII), (XIV), (XIV-A), (XIV-B), or any of SEQ ID 1-27 (e.g., SEQ ID 5-27, e.g., SEQ ID 6); and
m is 2-6 (e.g., 2), $X^1$ is —N(R')C(O)— (e.g., —N(H)C(O)—), and n+p=2 (e.g., each of n and p is 1), and $X^2$ is —S—; or
m is 2-6 (e.g., 2), $X^1$ is —N(R')C(O)— (e.g., —N(H)C(O)—), n+p=0, $X^2$ is —C(Q$^1$)(Q$^2$)-, and Q$^1$ and Q$^2$, together with the carbon atom to which each is attached forms C$_{3-6}$ cycloalkyl that is optionally substituted with from 1-4 independently selected R$^d$ and optionally fused to phenyl; or
m is 2-6 (e.g., 2), $X^1$ is —N(R')C(O)— (e.g., —N(H)C(O)—), n+p=0, $X^2$ is —C(Q$^1$)(Q$^2$)-, and Q$^1$ and Q$^2$ is an independently selected C$_{1-4}$ alkyl (e.g., CH$_3$); or
m is 2-6 (e.g., 2), $X^1$ is —N(R')C(O)— (e.g., —N(H)C(O)—), n+p=0, and $X^2$ is: (v) C$_{6-10}$ arylene (e.g., phenylene) optionally substituted with from 1-5 independently selected R$^c$; or (vii) C$_{3-10}$ cycloalkylene optionally substituted with from 1-4 independently selected R$^d$.

In certain embodiments, one, two, or three of $R^1$, $R^2$, and $R^4$ are H. In certain embodiments, $R^3$ is —C(O)OH. In certain embodiments, a is 0, 1, or 2 (e.g., 1). In certain embodiments, $R^5$ has formula (XI). In certain embodiments, each of $R^1$, $R^2$, and $R^4$ is H, a is 0, 1, or 2 (e.g., 1), $R^3$ is —C(O)OH, and $R^5$ has formula (XI).

In certain of these embodiments, m is 2-6 (e.g., 2), $X^1$ is —N(R')C(O)— (e.g., —N(H)C(O)—), and n+p=2 (e.g., each of n and p is 1), and $X^2$ is —S—. For example, L can be —CH$_2$CH$_2$NHC(O)CH$_2$SCH$_2$—.

In certain of these embodiments, any one of SEQ ID 5-27 (e.g., SEQ ID 6) represents W.

[13A] In some embodiments:
the compound has formula (IA-A), (IA-AA), or (IA-AB);
ring A is a saturated, monocyclic, 5-membered ring having formula (III-A) (i.e., $A^1$ in formula (III) is a bond);
L has formula (VIII): —(CH$_2$)$_m$—X$^1$—(CH$_2$)$_n$—X$^2$—(CH$_2$)$_p$—, and
W is represented by formula (X), (XII), (XIII), (XIV-AA), (XIV), (XIV-A), (XIV-B), (XV), or any of SEQ ID 1-34 (e.g., SEQ. ID 5-27; e.g., SEQ ID 5-29; (e.g., SEQ ID 6); e.g., SEQ ID 28-29; e.g., SEQ ID 30-34).

In certain embodiments, m is 2-6 (e.g., 2), $X^1$ is —N(R')C(O)— (e.g., —N(H)C(O)—), and n+p=2 (e.g., each of n and p is 1), and $X^2$ is —S—; or
m is 2-6 (e.g., 2), $X^1$ is —N(R')C(O)— (e.g., —N(H)C(O)—), n+p=0, $X^2$ is —C(Q$^1$)(Q$^2$)-, and Q$^1$ and Q$^2$, together with the carbon atom to which each is attached forms C$_{3-6}$ cycloalkyl that is optionally substituted with from 1-4 independently selected R$^d$ and optionally fused to phenyl; or
m is 2-6 (e.g., 2), $X^1$ is —N(R')C(O)— (e.g., —N(H)C(O)—), n+p=0, $X^2$ is —C(Q$^1$)(Q$^2$)-, and Q$^1$ and Q$^2$ is an independently selected C$_{1-4}$ alkyl (e.g., CH$_3$); or
m is 2-6 (e.g., 2), $X^1$ is —N(R')C(O)— (e.g., —N(H)C(O)—), n+p=0, and $X^2$ is: (v) C$_{6-10}$ arylene (e.g., phenylene) optionally substituted with from 1-5 independently selected R$^c$; or (vii) C$_{3-10}$ cycloalkylene optionally substituted with from 1-4 independently selected R$^d$.

In certain embodiments, m is 2-6 (e.g., 2), $X^1$ is —N(R')C(O)— (e.g., —N(H)C(O)—), n+p=0, and $X^2$ is: heterocycloalkylene including from 4-6 (e.g., 4) ring atoms, wherein from 1-3 (e.g., 1) ring atoms are each independently selected from the group consisting of N(R$^a$), O, and S; and which is optionally substituted with from 1-5 independently selected R$^d$ (e.g., X$^2$ can be

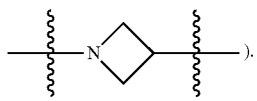 [SMILES: *C1CN(*)C1]

In certain embodiments, one, two, or three of R$^1$, R$^2$, and R$^4$ are H. In certain embodiments, R$^3$ is —C(O)OH. In certain embodiments, a is 0, 1, or 2 (e.g., 1). In certain embodiments, R$^5$ has formula (XI). In certain embodiments, each of R$^1$, R$^2$, and R$^4$ is H, a is 0, 1, or 2 (e.g., 1), R$^3$ is —C(O)OH, and R$^5$ has formula (XI). In certain embodiments, a' is 1; each of R$^{3a}$ and R$^{3b}$ is H.

In certain of these embodiments, m is 2-6 (e.g., 2), X$^1$ is —N(R')C(O)— (e.g., —N(H)C(O)—), and n+p=2 (e.g., each of n and p is 1), and X$^2$ is —S—. For example, L can be —CH$_2$CH$_2$NHC(O)CH$_2$SCH$_2$—.

In certain of these embodiments, any one of SEQ ID 5-34 (e.g., SEQ ID 6) represents W.

Embodiments of combinations [1]-[13] can also include any one or more of the features delineated in the Detailed Descriptions and/or claims.

Embodiments of combinations [1A]-[13A] can also include any one or more of the features delineated in the Detailed Descriptions and/or claims.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are contemplated within the scope of this disclosure, though such resonance forms or tautomers are not explicitly represented herein.

Pharmaceutical Compositions and Administration

General

In some embodiments, a chemical entity (e.g., a compound or a pharmaceutically acceptable salt and/or hydrate and/or prodrug of the compound) that modulates (e.g., agonizes or partially agonizes or antagonizes) glucagon-like peptide-1 receptor ("GLP-1R") and/or the gastric inhibitory polypeptide receptor ("GIPR"), is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-a-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22$^{nd}$ Edition (Pharmaceutical Press, London, U K. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In general, the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules, sterility is not required. The USP/NF standard is usually sufficient.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Proper dosage for a particular situation can be determined by one skilled in the medical arts. In some cases, the total daily dosage may be divided and administered in portions throughout the day or by means providing continuous delivery.

In some embodiments, the compounds described herein are administered at a dosage of from about 0.0002 mg/Kg to about 100 mg/Kg (e.g., from about 0.0002 mg/Kg to about 50 mg/Kg; from about 0.0002 mg/Kg to about 25 mg/Kg; from about 0.0002 mg/Kg to about 10 mg/Kg; from about 0.0002 mg/Kg to about 5 mg/Kg; from about 0.0002 mg/Kg to about 1 mg/Kg; from about 0.0002 mg/Kg to about 0.5 mg/Kg; from about 0.0002 mg/Kg to about 0.1 mg/Kg; from about 0.001 mg/Kg to about 50 mg/Kg; from about 0.001 mg/Kg to about 25 mg/Kg; from about 0.001 mg/Kg to about 10 mg/Kg; from about 0.001 mg/Kg to about 5 mg/Kg; from about 0.001 mg/Kg to about 1 mg/Kg; from about 0.001 mg/Kg to about 0.5 mg/Kg; from about 0.001 mg/Kg to about 0.1 mg/Kg; from about 0.01 mg/Kg to about 50 mg/Kg; from about 0.01 mg/Kg to about 25 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 50 mg/Kg; from about 0.1 mg/Kg to about 25 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

This disclosure features methods for treating a subject (e.g., a human) having a disease, disorder, or condition in which modulation of GLP-1R and/or GIPR activities (e.g., repressed or impaired and/or elevated or unwanted GLP-1R and/or GIPR signaling) is beneficial for the treatment of the underlying pathology and/or symptoms and/or progression of the disease, disorder, or condition. In certain embodiments, the methods described herein can include or further include treating one or more conditions associated, co-morbid or sequela with any one or more of the conditions described herein.

In certain embodiments, the chemical entities described herein induce blood glucose reduction (e.g., reduce blood glucose levels), promote insulin synthesis, stimulate insulin secretion, increase the mass of $\beta$-cells, modulate gastric acid secretion, modulate gastric emptying, and/or decrease glucagon production. In certain embodiments, the chemical entities described herein stabilize serum glucose and serum insulin levels.

Indications

Obesity

In some embodiments, the condition, disease or disorder is obesity and conditions, diseases or disorders that are associated with obesity. Non-limiting examples of obesity and obesity related conditions include symptomatic obesity, simple obesity, childhood obesity, morbid obesity and abdominal obesity (central obesity characterized by abdominal adiposity). Non-limiting examples of symptomatic obesity include endocrine obesity (e.g., Cushing syndrome, hypothyroidism, insulinoma, obese type II diabetes, pseudo-hypoparathyroidism, hypogonadism), hypothalamic obesity, hereditary obesity (e.g., Prader-Willi syndrome, Laurence-Moon-Biedl syndrome), and drug-induced obesity (e.g., steroid, phenothiazine, insulin, sulfonylurea agent, or P-blocker-induced obesity).

In some embodiments, the condition, disease or disorder is associated with obesity. Examples of such conditions, disease or disorders include, without limitation, glucose tolerance disorders, diabetes (e.g., type 2 diabetes, obese diabetes), lipid metabolism abnormality, hyperlipidemia, hypertension, cardiac failure, hyperuricemia, gout, fatty liver (including non-alcoholic steatohepatitis (NASH)), coronary heart disease (e.g., myocardial infarction, angina pectoris), cerebral infarction (e.g., brain thrombosis, transient cerebral ischemic attack), bone or articular disease (e.g., knee osteoarthritis, hip osteoarthritis, spondylitis deformans, lumbago), sleep apnea syndrome, obesity hypoventilation syndrome (Pickwickian syndrome), menstrual disorder (e.g., abnormal menstrual cycle, abnormality of menstrual flow and cycle, amenorrhea, abnormal catamenial symptom), visceral obesity syndrome, and metabolic syndrome. In certain embodiments, the chemical entities described herein can be used to treat subjects exhibiting symptoms of both obesity and insulin deficiency.

Diabetes

In some embodiments, the condition, disease or disorder is diabetes. Non-limiting examples of diabetes include type 1 diabetes, type 2 diabetes (e.g., diet-treated type 2-diabetes, sulfonylurea-treated type 2-diabetes, a far-advanced stage type 2-diabetes, long-term insulin-treated type 2-diabetes), diabetes mellitus (e.g., non-insulin-dependent diabetes mellitus, insulin-dependent diabetes mellitus), gestational diabetes, obese diabetes, autoimmune diabetes, and borderline type diabetes.

In some embodiments, the condition, disease or disorder is associated with diabetes (e.g., a complication of diabetes). Non-limiting examples of disorders associated with diabetes include obesity, obesity-related disorders, metabolic syndrome, neuropathy, nephropathy (e.g., diabetic nephropathy), retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, diabetic cachexia, delayed wound healing, diabetic dyslipidemia peripheral blood circulation disorder, cardiovascular risk factors. (e.g., coronary artery disease, peripheral artery disease, cerebrovascular disease, hypertension, and risk factors related to unmanaged cholesterol and/or lipid levels, and/or inflammation), NASH, bone fracture and cognitive dysfunction Other non-limiting examples of disorders related to diabetes include pre-diabetes, hyperlipidemia (e.g., hypertriglyceridemia, hypercholesterolemia, high LDL-cholesterolemia, low HDL-cholesterolemia, postprandial hyperlipemia), metabolic syndrome (e.g., metabolic disorder where activation of GLP-1R is beneficial, metabolic syndrome X), hypertension, impaired glucose tolerance (IGT), insulin resistance, and sarcopenia.

In some embodiments, the condition, disease or disorder is diabetes and obesity (diabesity). In certain embodiments, the compounds described herein are also useful in improving the therapeutic effectiveness of metformin.

Disorders of Metabolically Important Tissues

In some embodiments, the condition, disease or disorder is a disorder of a metabolically important tissue.

In some embodiments, the condition, disease or disorder is a fatty liver disease. Fatty liver diseases include, but are not limited to, non-alcoholic fatty acid liver disease (NAFLD), steatohepatitis, non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

Non-alcoholic fatty liver disease (NAFLD) represents a spectrum of disease occurring in the absence of alcohol abuse and is typically characterized by the presence of steatosis (fat in the liver). NAFLD is believed to be linked to a variety of conditions, e.g., metabolic syndrome (including obesity, diabetes and hypertriglyceridemia) and insulin resistance. It can cause liver disease in adults and children and may ultimately lead to cirrhosis (Skelly et al., J Hepatol 2001; 35: 195-9; Chitturi et al., Hepatology 2002; 35(2): 373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., J Gastroenterol Hepatol 2002; 17 Suppl: S186-90). In certain embodiments, the subject is a pediatric subject (e.g., 6-16 years old; or 6-12 years old; or 6-10 years old). In certain embodiments, the subject is a adult subject.

Other non-limiting examples of disorders in metabolically important tissues include joint disorders (e.g., osteoarthritis, secondary osteoarthritis), steatosis (e.g. in the liver); gall stones; gallbladder disorders; gastroesophageal reflux; sleep apnea; hepatitis; fatty liver; bone disorder characterized by altered bone metabolism, such as osteoporosis, including post-menopausal osteoporosis, poor bone strength, osteopenia, Paget's disease, osteolytic metastasis in cancer patients, osteodistrophy in liver disease and the altered bone metabolism caused by renal failure or haemodialysis, bone fracture, bone surgery, aging, pregnancy, protection against bone fractures, and malnutritionpolycystic ovary syndrome; renal disease (e.g., chronic renal failure, glomerulonephritis, glomerulosclerosis, nephrotic syndrome, hypertensive nephrosclerosis, end-stage renal disease); muscular dystrophy, angina pectoris, acute or chronic diarrhea, testicular dysfunction, respiratory dysfunction, frailty, sexual dysfunction (e.g., erectile dysfunction) and geriatric syndrome. In certain embodiments, the chemical entities described herein can be used for treating surgical trauma by improving recovery after surgery and/or by preventing the catabolic reaction caused by surgical trauma.

Cardiovascular Diseases

In some embodiments, the condition, disease or disorder is a cardiovascular disease. Non-limiting examples of cardiovascular disease include congestive heart failure, atherosclerosis, arteriosclerosis, coronary heart disease, or peripheral artery disease, stroke, coronary artery disease, congestive heart failure, coronary heart disease, hypertension, cardiac failure, cerebrovascular disorder (e.g., cerebral infarction), vascular dysfunction, myocardial infarction, elevated blood pressure (e.g., 130/85 mm Hg or higher), and prothrombotic state (exemplified by high fibrinogen or plasminogen activator inhibitor in the blood).

Neurological Diseases

In some embodiments, the condition, disease or disorder is a neurological disorder (e.g., neurodegenerative disorder) or a psychiatric disorder. Non-limiting examples of neurological disorders include brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeld-Jakob Disease, bovine spongiform encephalopathy (mad cow disease), chronic wasting syndrome). See, e.g., US20060275288A1.

Non-limiting examples of psychiatric disorders include drug dependence/addiction (narcotics and amphetamines and attention deficit/hyperactivity disorder (ADHD). The chemical entities described herein can be useful in improving behavioral response to addictive drugs, decreasing drug dependence, prevention drug abuse relapse, and relieving anxiety caused by the absence of a given addictive substance. See, e.g., US20120021979A1.

In certain embodiments, the chemical entities described herein are useful in improving learning and memory by enhancing neuronal plasticity and facilitation of cellular differentiation, and also in preserving dopamine neurons and motor function in Morbus Parkinson.

Insulin-Related

In some embodiments, the condition, disease or disorder is impaired fasting glucose (IFG), impaired fasting glycemia (IFG), hyperglycemia, insulin resistance (impaired glucose homeostasis), hyperinsulinemia, elevated blood levels of fatty acids or glycerol, a hypoglycemic condition, insulin resistant syndrome, paresthesia caused by hyperinsulinemia, hyperlipidaemia, hypercholesteremia, impaired wound healing, leptin resistance, glucose intolerance, increased fasting glucose, dyslipidemia (e.g., hyperlipidemia, atherogenic dyslipidemia characterized by high triglycerides and low HDL cholesterol), glucagonoma, hyperuricacidemia, hypoglycemia (e.g., nighttime hypoglycemia), and concomitant comatose endpoint associated with insulin.

In certain embodiments, the chemical entities described herein can reduce or slow down the progression of borderline type, impaired fasting glucose or impaired fasting glycemia into diabetes.

Autoimmune Disorders

In some embodiments, the condition, disease or disorder is an autoimmune disorder. Non-limiting examples of autoimmune disorders include multiple sclerosis, experimental autoimmune encephalomyelitis, autoimmune disorder is associated with immune rejection, graft versus host disease, uveitis, optic neuropathies, optic neuritis, transverse myelitis, inflammatory bowel disease, rheumatoid arthritis, ankylosing spondylitis, systemic lupus erythematosus, myasthenia gravis, and Graves disease. See, e.g., US20120148586A1.

Stomach and Intestine-Related Disorders

In some embodiments, the condition, disease or disorder is a stomach or intestine related disorder. Non-limiting examples of these disorders include ulcers of any etiology (e.g. peptic ulcers, Zollinger-Ellison syndrome, drug-induced ulcers, ulcers related to infections or other pathogens), digestion disorders, malabsorption, short bowel syndrome, cul-de-sac syndrome, inflammatory bowel diseases (Crohn's disease and ulcerative colitis), celiac sprue, hypogammaglobulinemic sprue, chemotherapy and/or radiation therapy-induced mucositis and diarrhea, gastrointestinal inflammation, short bowel syndrome, colitis ulcerosa, gastric mucosal injury (e.g., gastric mucosal injury caused by aspirin), small intestinal mucosal injury, and cachexia (e.g., cancerous cachexia, tuberculous cachexia, cachexia associated with blood disease, cachexia associated with endocrine disease, cachexia associated with infectious disease, cachexia caused by acquired immunodeficiency syndrome).

Body Weight

In some embodiments, the chemical entities described herein can be used to reduce body weight (e.g., excess body weight), prevent body weight gain, induce weight loss, decrease body fat, or reduce food intake in a subject (e.g., a subject in need thereof). In certain embodiments, the weight increase in a subject may be attributed to excessive ingestion of food or unbalanced diets, or may be weight increase derived from a concomitant drug (e.g., insulin sensitizers having a PPARγ agonist-like action, such as troglitazone, rosiglitazone, englitazone, ciglitazone, pioglitazone and the like). Alternatively, the weight increase may be weight increase before reaching obesity, or may be weight increase in an obese subject. The weight increase may also be medication-induced weight gain or weight gain subsequent to cessation of smoking.

In some embodiments, the condition, disease or disorder is an eating disorder, such as hyperphagia, binge eating, bulimia, or compulsive eating.

Inflammatory Diseases

In some embodiments, the condition, disease or disorder is an inflammatory disorder. Non-limiting examples of inflammatory disorders include chronic rheumatoid arthritis, spondylitis deformans, arthritis deformans, lumbago, gout, post-operational or post-traumatic inflammation, bloating, neuralgia, laryngopharyngitis, cystitis, pneumonia, pancreatitis, enteritis, inflammatory bowel disease (including inflammatory large bowel disease), inflammation in metabolically important tissues including liver, fat, pancreas, kidney and gut, and a proinflammatory state (e.g., elevated levels of proinflammatory cytokines or markers of inflammation-like C-reactive protein in the blood).

Cancer

In some embodiments, the condition, disease or disorder is cancer. Suitable examples of cancer include breast cancer (e.g., invasive ductal breast cancer, noninvasive ductal breast cancer, inflammatory breast cancer), prostate cancer (e.g., hormone-dependent prostate cancer, hormone-independent prostate cancer), pancreatic cancer (e.g., ductal pancreatic cancer), gastric cancer (e.g., papillary adenocarcinoma, mucous adenocarcinoma, adenosquamous carcinoma), lung cancer (e.g., non-small cell lung cancer, small-cell lung cancer, malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, gastrointestinal stromal tumor), small intestinal cancer (e.g., non-Hodgkin's lymphoma, gastrointestinal stromal tumor), esophageal cancer, duodenal cancer, tongue cancer, pharyngeal cancer (e.g., nasopharyngeal cancer, oropharynx cancer, hypopharyngeal cancer), salivary gland cancer, brain tumor (e.g., pineal astrocytoma, pilocytic astrocytoma, diffuse astrocytoma, anaplastic astrocytoma), neurilemmoma, liver cancer (e.g., primary liver cancer, extrahepatic bile duct cancer), renal cancer (e.g., renal cell cancer, transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential), bladder cancer, urethral cancer, skin cancer (e.g., intraocular (ocular) melanoma, Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, soft tissue sarcoma), angiofibroma, sarcoma of the retina, penis cancer, testicular tumor, pediatric solid tumor (e.g., Wilms' tumor, childhood kidney tumor), Kaposi's sarcoma, Kaposi's sarcoma caused by AIDS, tumor of maxillary sinus, fibrous histiocytoma, leiomyosarcoma, rhabdomyosarcoma, and leukemia (e.g., acute myeloid leukemia, acute lymphoblastic leukemia).

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the methods described herein include administering a compound described herein in combination with one or more of a diet therapy (e.g., diet therapy for diabetes), an exercise therapy, blood sugar monitoring, and diet modifications.

In some embodiments, the compound described herein can be administered in combination with one or more of additional therapeutic agents.

Representative additional therapeutic agents include, but are not limited to, anti-obesity agents, therapeutic agents for diabetes, therapeutic agents for diabetic complications, therapeutic agents for hyperlipidemia, antihypertensive agents, diuretics, chemotherapeutics, immunotherapeutics, anti-inflammatory drugs, antithrombotic agents, anti-oxidants, therapeutic agents for osteoporosis, vitamins, antidementia drugs, erectile dysfunction drugs, therapeutic drugs for urinary frequency or urinary incontinence, therapeutic agents for NAFLD, and therapeutic agents for dysuria.

In some embodiments, the one or more additional therapeutic agents include those useful, e.g., as anti-obesity agents. Non-limiting examples include:
- monoamine uptake inhibitors (e.g., tramadol, phentermine, sibutramine, mazindol, fluoxetine, tesofensine);
- serotonin 2C receptor agonists (e.g., lorcaserin);
- serotonin 6 receptor antagonists;
- histamine H3 receptor modulator;
- GABA modulator (e.g., topiramate), including GABA receptor agonists (e.g., gabapentin, pregabalin);
- neuropeptide Y antagonists (e.g., velneperit);
- cannabinoid receptor antagonists (e.g., rimonabant, taranabant);
- ghrelin antagonists;
- ghrelin receptor antagonists;
- ghrelin acylation enzyme inhibitors;
- opioid receptor antagonists (e.g., GSK-1521498);
- orexin receptor antagonists;
- melanocortin 4 receptor agonists;
- 11β-hydroxysteroid dehydrogenase inhibitors (e.g., AZD-4017, BVT-3498, INCB-13739);
- pancreatic lipase inhibitors (e.g., orlistat, cetilistat);
- β3 agonists (e.g., N-5984);
- diacylglycerol acyltransferase 1 (DGAT1) inhibitors;
- acetylCoA carboxylase (ACC) inhibitors;
- stearoyl-CoA desaturated enzyme inhibitors;
- microsomal triglyceride transfer protein inhibitors (e.g., R-256918);
- Na-glucose cotransporter 2 (SGLT-2) inhibitors (e.g., JNJ-28431754, dapagliflozin, AVE2268, TS-033, YM543, TA-7284, ASP1941, remogliflozin);
- NFK inhibitors (e.g., HE-3286);
- PPAR agonists (e.g., GFT-505, DRF-11605, gemfibrozil and fenofibrate);
- phosphotyrosine phosphatase inhibitors (e.g., sodium vanadate, trodusquemin);
- GPR119 agonists (e.g., PSN-821, MBX-2982, APD597);
- glucokinase activators (e.g., piragliatin, AZD-1656, AZD6370, TTP-355, compounds described in W0006/112549, W0007/028135, W0008/047821, W0008/050821, W0008/136428 and W0008/156757);
- leptin, leptin derivatives (e.g., metreleptin), leptin resistance improving drugs;
- CNTF (ciliary neurotrophic factor);
- BDNF (brain-derived neurotrophic factor);
- cholecystokinin agonists, amylin preparations (e.g., pramlintide, AC-2307);
- neuropeptide Y agonists (e.g., PYY3-36, derivatives of PYY3-36, obineptide, TM-30339, TM-30335);
- oxyntomodulin (OXM) preparations;
- appetite suppressants (e.g. ephedrine);
- FGF21 preparations (e.g., animal FGF21 preparations extracted from the pancreas of bovine or swine; human FGF21 preparations genetically synthesized using *Escherichia coli* or yeast; fragments or derivatives of FGF21); and
- anorexigenic agents (e.g., P-57).

In some embodiments, the one or more additional therapeutic agents include those useful, e.g., as anti-diabetic agents. Non-limiting examples include:
- insulin and insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation, synthetic human insulin);
- insulin sensitizers (e.g., pioglitazone or a salt thereof);
- biguanides (e.g., metformin, buformin or a salt thereof (e.g., hydrochloride, fumarate, succinate));
- glucagon analogs (e.g., any of glucagon analogs described, e.g., in WO 2010/011439);
- agents which antagonize the actions of or reduce secretion of glucagon;
- sulfonylurea agents (e.g., chlorpropamide, tolazamide, gliclazide, glimepiride, tolbutamide, glibenclamide, gliclazide, acetohexamide, glyclopyramide, glybuzole, glyburide);
- thiazolidinedione agents (e.g. rosiglitazone or pioglitazone);
- α-glucosidase inhibitors (e.g., voglibose, acarbose, miglitol, emiglitate);
- insulin secretagogues, such as prandial glucose regulators (sometimes called "short-acting secretagogues"), e.g., meglitinides (e.g. repaglinide and nateglinide);
- cholinesterase inhibitors (e.g., donepezil, galantamine, rivastigmine, tacrine);
- NMDA receptor antagonists;
- dual GLP-1/GIP receptor agonists (e.g., LBT-2000, ZPD1-70);
- GLP-1R agonists (e.g., exenatide, liraglutide, albiglutide, dulaglutide, AVE-0010, S4P and Boc5); and
- dipeptidyl peptidase IV (DPP-4) inhibitors (e.g., vildagliptin, dutogliptin, gemigliptin, alogliptin, saxagliptin, sitagliptin, linagliptin, berberine, adogliptin, BI1356, GRC8200, MP-513, PF-00734200, PHX1149, SK-0403, ALS2-0426, TA-6666, TS-021, KRP-104, trelagliptin).

In some embodiments, the one or more additional therapeutic agents include those useful, e.g., for treating NAFL and NASH. Non-limiting examples include glycyrrhizin, schisandra extract, ascorbic acid, glutathione, silymarin, lipoic acid, and d-alpha-tocopherol, ascorbic acid, glutathione, vitamin B-complex, glitazones/thiazolidinediones (e.g., troglitazone, rosiglitazone, pioglitazone), metformin, cysteamine, sulfonylureas, alpha-glucosidase inhibitors, meglitinides, vitamin E, tetrahydrolipstatin, milk thistle protein, anti-virals, and anti-oxidants.

In some embodiments, the one or more additional therapeutic agents include those useful, e.g., for treating diabetic complications. Non-limiting examples include:
- aldose reductase inhibitors (e.g., tolrestat, epalrestat, zopolrestat, fidarestat, CT-112, ranirestat, lidorestat);
- neurotrophic factor and increasing agents thereof (e.g., NGF, NT-3, BDNF, neurotrophic production/secretion promoting agents described in WO01/14372 (e.g., 4-(4-chlorophenyl)-2-(2-methyl-1-imidazolyl)-5-[3-(2- methylphenoxyl)propyl]oxazole), compounds described in WO2004/039365);

PKC inhibitors (e.g., ruboxistaurin mesylate);

AGE inhibitors (e.g., ALT946, N-phenacylthiazolium bromide (ALT766), EXO-226, pyridorin, pyridoxamine);

serotonin and noradrenalin reuptake inhibitors (e.g., duloxetine);

sodium channel inhibitors (e.g., lacosamide);

active oxygen scavengers (e.g., thioctic acid);

cerebral vasodilators (e.g., tiapuride, mexiletine);

somatostatin receptor agonists (e.g., BIM23190); and apoptosis signal regulating kinase-1 (ASK-1) inhibitors.

In some embodiments, the one or more additional therapeutic agents include those useful, e.g., for treating hyperlipidemia. Non-limiting examples include:

HMG-COA reductase inhibitors (e.g., pravastatin, simvastatin, lovastatin, atorvastatin, fluvastatin, rosuvastatin, pitavastatin or a salt thereof (e.g., sodium salt, calcium salt));

squalene synthase inhibitors (e.g., compounds described in WO97/10224, e.g., N-[[(3R,5S)-1-(3-acetoxy-2,2-dimethylpropyl)-7-chloro-5-(2,3-dimethoxyphenyl)-2-oxo-1,2,3,5-tetrahydro-4, 1-benzoxazepin-3-yl]acetyl] piperidin-4-acetic acid);

fibrate compounds (e.g., bezafibrate, clofibrate, simfibrate, clinofibrate);

anion exchange resin (e.g., colestyramine);

nicotinic acid drugs (e.g., nicomol, niceritrol, niaspan);

phytosterols (e.g., soysterol, gamma oryzanol (γ-oryzanol));

cholesterol absorption inhibitors (e.g., zechia);

CETP inhibitors (e.g., dalcetrapib, anacetrapib); and

ω-3 fatty acid preparations (e.g., ω-3-fatty acid ethyl esters 90).

In some embodiments, the one or more additional therapeutic agents include those useful, e.g., as anti-hypertensive agents. Non-limiting examples include:

angiotensin converting enzyme inhibitors (e.g., captopril, enalapril, delapril);

angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil);

calcium antagonists (e.g., manidipine, nifedipine, amlodipine, efonidipine, nicardipine, cilnidipine); and β-blockers (e.g., metoprolol, atenolol, propranolol, carvedilol, pindolol).

In some embodiments, the one or more additional therapeutic agents include those useful, e.g., as diuretics. Non-limiting examples include:

xanthine derivatives (e.g., theobromine sodium salicylate, theobromine calcium salicylate);

thiazide preparations (e.g., ethiazide, cyclopenthiazide, trichloromethiazide, hydrochlorothiazide, hydroflumethiazide, benzylhydrochlorothiazide, penfluthiazide, polythiazide, methyclothiazide);

antialdosterone preparations (e.g., spironolactone, triamterene);

carbonic anhydrase inhibitors (e.g., acetazolamide); and chlorobenzenesulfonamide agents (e.g., chlortalidone, mefruside, indapamide).

In some embodiments, the one or more additional therapeutic agents include those useful, e.g., as immunotherapeutic agents. Non-limiting examples include: microbial or bacterial compounds (e.g., muramyl dipeptide derivative, picibanil); polysaccharides having immunoenhancing activity (e.g., lentinan, sizofiran, krestin); cytokines obtained by genetic engineering approaches (e.g., interferon, interleukin (IL) such as IL-1, IL-2, IL-12); and colony-stimulating factors (e.g., granulocyte colony-stimulating factor, erythropoietin).

In some embodiments, the one or more additional therapeutic agents include those useful, e.g., as anti-thrombotic agents. Non-limiting examples include: heparins (e.g., heparin sodium, heparin calcium, enoxaparin sodium, dalteparin sodium); warfarin (e.g., warfarin potassium); anti-thrombin drugs (e.g., aragatroban, dabigatran); FXa inhibitors (e.g., rivaroxaban, apixaban, edoxaban, YM150, compounds described in WO02/06234, WO2004/048363, WO2005/030740, WO2005/058823, and WO2005/113504); thrombolytic agents (e.g., urokinase, tisokinase, alteplase, nateplase, monteplase, pamiteplase); and platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride).

In some embodiments, the one or more additional therapeutic agents include those useful, e.g., for treating osteoporosis. Non-limiting examples include: alfacalcidol, calcitriol, elcatonin, calcitonin salmon, estriol, ipriflavone, pamidronate disodium, alendronate sodium hydrate, incadronate disodium, and risedronate disodium. Suitable examples of vitamins include vitamin B1 and vitamin B12. Suitable examples of erectile dysfunction drugs include apomorphine and sildenafil citrate. Suitable examples of therapeutic agents for urinary frequency or urinary incontinence include flavorxate hydrochloride, oxybutynin hydrochloride and propiverine hydrochloride. Suitable examples of therapeutic agents for dysuria include acetylcholine esterase inhibitors (e.g., distigmine). Suitable examples of anti-inflammatory agents include nonsteroidal anti-inflammatory drugs such as aspirin, acetaminophen, indomethacin.

Other additional therapeutic agents include:

agents that modulate hepatic glucose balance (e.g., fructose 1,6-bisphosphatase inhibitors, glycogen phosphorylase inhibitors, glycogen synthase kinase inhibitors, glucokinase activators);

agents designed to treat the complications of prolonged hyperglycemia, such as aldose reductase inhibitors (e.g. epalrestat and ranirestat);

agents used to treat complications related to micro-angiopathies;

anti-dyslipidemia agents, such as HMG-CoA reductase inhibitors (statins, e.g. rosuvastatin);

cholesterol-lowering agents;

bile acid sequestrants (e.g., cholestyramine);

cholesterol absorption inhibitors (e.g. plant sterols such as phytosterols);

cholesteryl ester transfer protein (CETP) inhibitors;

inhibitors of the ileal bile acid transport system (BAT inhibitors);

bile acid binding resins;

nicotinic acid (niacin) and analogues thereof;

anti-oxidants, such as probucol;

omega-3 fatty acids;

antihypertensive agents, including adrenergic receptor antagonists, such as beta blockers (e.g. atenolol), alpha blockers (e.g. doxazosin), and mixed alpha/beta blockers (e.g. labetalol);

adrenergic receptor agonists, including alpha-2 agonists (e.g. clonidine);

angiotensin converting enzyme (ACE) inhibitors (e.g. lisinopril);

calcium channel blockers, such as dihydropridines (e.g. nifedipine), phenylalkylamines (e.g. verapamil), and benzothiazepines (e.g. diltiazem);

angiotensin II receptor antagonists (e.g. candesartan);

aldosterone receptor antagonists (e.g. eplerenone);

centrally acting adrenergic drugs, such as central alpha agonists (e.g. clonidine);

diuretic agents (e.g. furosemide);

haemostasis modulators, including antithrombotics (e.g., activators of fibrinolysis), thrombin antagonists, factor VIIa inhibitors, anticoagulants (e.g., vitamin K antagonists such as warfarin), heparin and low molecular weight analogues thereof, factor Xa inhibitors, and direct thrombin inhibitors (e.g. argatroban);

antiplatelet agents (e.g., cyclooxygenase inhibitors (e.g. aspirin));

adenosine diphosphate (ADP) receptor inhibitors (e.g. clopidogrel);

phosphodiesterase inhibitors (e.g. cilostazol);

glycoprotein IIB/IIA inhibitors (e.g. tirofiban);

adenosine reuptake inhibitors (e.g. dipyridamole);

noradrenergic agents (e.g. phentermine);

serotonergic agents (e.g. sibutramine);

diacyl glycerolacyltransferase (DGAT) inhibitors;

feeding behavior modifying agents;

pyruvate dehydrogenase kinase (PDK) modulators;

serotonin receptor modulators;

monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), and monoamine oxidase inhibitors (MAOI) (e.g. toloxatone and amiflamine);

compounds described in W0007/013694, WO2007/018314, WO2008/093639 and WO2008/099794;

GPR40 agonists (e.g., fasiglifam or a hydrate thereof, compounds described in WO2004/041266, WO2004/106276, WO2005/063729, WO2005/063725, WO2005/087710, WO2005/095338, WO2007/013689 and WO2008/001931);

SGLT1 inhibitors;

adiponectin or agonist thereof;

IKK inhibitors (e.g., AS-2868);

somatostatin receptor agonists;

ACC2 inhibitors;

cachexia-ameliorating agents, such as a cyclooxygenase inhibitors (e.g., indomethacin), progesterone derivatives (e.g., megestrol acetate), glucocorticoids (e.g., dexamethasone), metoclopramide agents, tetrahydrocannabinol agents, agents for improving fat metabolism (e.g., eicosapentaenoic acid), growth hormones, IGF-1, antibodies against a cachexia-inducing factor TNF-α, LIF, IL-6, and oncostatin M;

metabolism-modifying proteins or peptides such as glucokinase (GK), glucokinase regulatory protein (GKRP), uncoupling proteins 2 and 3 (UCP2 and UCP3), peroxisome proliferator-activated receptor α (PPARα);

MC4r agonists;

insulin receptor agonist;

PDE 5 inhibitors;

glycation inhibitors (e.g., ALT-711);

nerve regeneration-promoting drugs (e.g., Y-128, VX853, prosaptide);

antidepressants (e.g., desipramine, amitriptyline, imipramine);

antiepileptic drugs (e.g., lamotrigine, trileptal, keppra, zonegran, pregabalin, harkoseride, carbamazepine);

antiarrhythmic drugs (e.g., mexiletine);

acetylcholine receptor ligands (e.g., ABT-594);

endothelin receptor antagonists (e.g., ABT-627);

narcotic analgesics (e.g., morphine);

α2 receptor agonists (e.g., clonidine);

local analgesics (e.g., capsaicin);

antianxiety drugs (e.g., benzothiazepine);

phosphodiesterase inhibitors (e.g., sildenafil);

dopamine receptor agonists (e.g., apomorphine);

cytotoxic antibodies (e.g., T-cell receptor and IL-2 receptor-specific antibodies);

B cell depleting therapies (e.g., anti-CD20 antibody (e.g., rituxan), i-BLyS antibody);

drugs affecting T cell migration (e.g., anti-integrin alpha 4/beta 1 antibody (e.g., tysabri);

drugs that act on immunophilins (e.g., cyclosporine, tacrolimus, sirolimus, rapamicin);

interferons (e.g., IFN-β);

immunomodulators (e.g., glatiramer);

TNF-binding proteins (e.g., circulating receptors);

immunosupressants (e.g., mycophenolate); and metaglidasen, AMG-131, balaglitazone, MBX-2044, rivoglitazone, aleglitazar, chiglitazar, lobeglitazone, PLX-204, PN-2034, GFT-505, THR-0921, exenatide, exendin-4, memantine, midazolam, ketoconazole, ethyl icosapentate, clonidine, azosemide, isosorbide, ethacrynic acid, piretanide, bumetanide, etoposide.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art).

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

In some embodiments, intermediates useful for preparing the compounds described herein can be prepared using the chemistries delineated in any one or more of the following schemes and non-limiting examples.

A. ABBREVIATIONS

AcOH=Acetic acid
BOP=(Benzotriazol-1-yloxy)tris(dimethylamino)phosphonium hexafluorophosphate
CDI=1,1-carbonyldiimidazole
DCC=N,N-dicyclohexylcarbodiimide
DCM=Dichloromethane
DIAD=Diisopropylazodicarboxylate
DIPEA=N,N-diisopropylethylamine
DMAP=4-Dimethylaminopyridine
DMF=N,N-dimethylformamide
DMSO=Dimethylsulfoxide
EDC=1-Ethyl-3-(3-dimethylaminopropyl)carbodiimide hydrochloride
ESI-MS=Electrospray ionization mass spectrometry
Et$_2$O=Diethyl ether
EtOAc=EtOAc
EtOH=Ethanol
HATU=1-[Bis(dimethylamino)methylene]-1H-1,2,3-triazolo[4,5-b]pyridinium 3-oxide hexafluorophosphate
HOSu=N-hydroxysuccinimide
HPLC=High performance liquid chromatography
LC-MS=Liquid chromatography-mass spectrometry
MeCN=Acetonitrile
MeOH=Methanol
NMR=Nuclear magnetic resonance
Proton sponge=1,8-Bis(dimethylamino)naphthalene
TBAB=Tetrabutylammonium bromide
TBAF=Tetrabutylammonium fluoride
TBAI=Tetrabutylammonium iodide
TBSCl=tert-Butyldimethylsilyl chloride
TEA=Triethylamine
TFA=Trifluoroacetic acid
TFAA=Trifluoroacetic anhydride
THF=Tetrahydrofuran
TIS=Triisopropylsilane
TIPS=Triisopropylsilyl
T3P=Propylphosphonic anhydride
TLC=Thin layer chromatography

B. PEPTIDE SEQUENCES OF COMPOUNDS DESCRIBED IN THIS INVENTION (SEQ ID NOS 36-58 DISCLOSED BELOW, RESPECTIVELY, IN ORDER OF APPEARANCE)

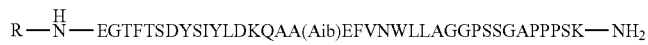

Sequence A

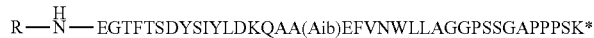

Sequence Aa

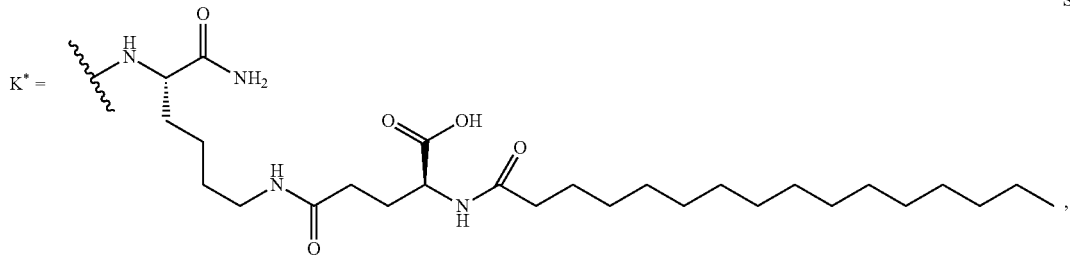

Sequence Aa-OH

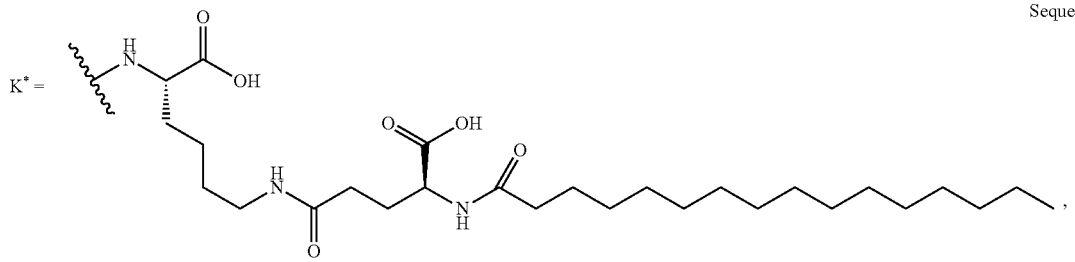

Sequence Aa2

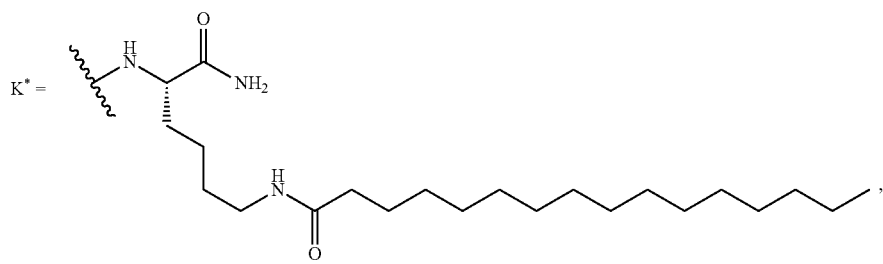

-continued

Sequence Aa2-OH

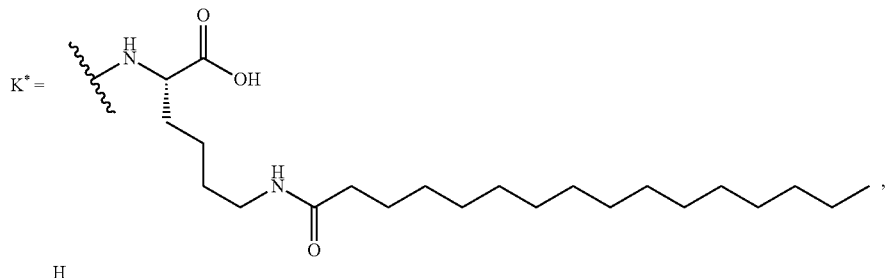

R—NH—(dE)GTFTSDYSIYLDKQAA(Aib)EFVNWLLAGGPSSGAPPPSK*—NH$_2$

Sequence Ba

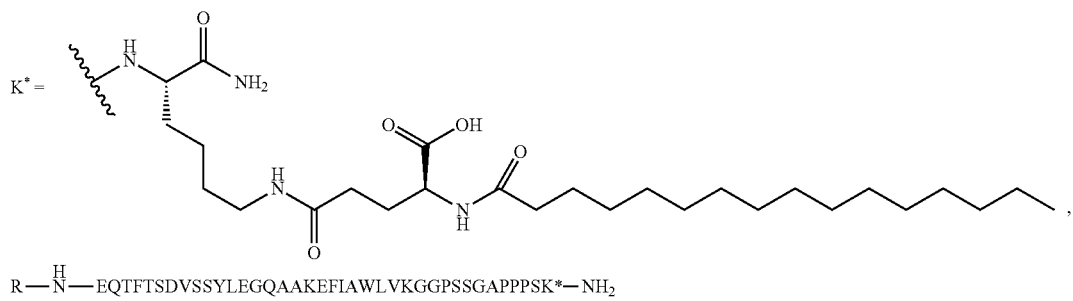

R—NH—EQTFTSDVSSYLEGQAAKEFIAWLVKGGPSSGAPPPSK*—NH$_2$

Sequence Ca

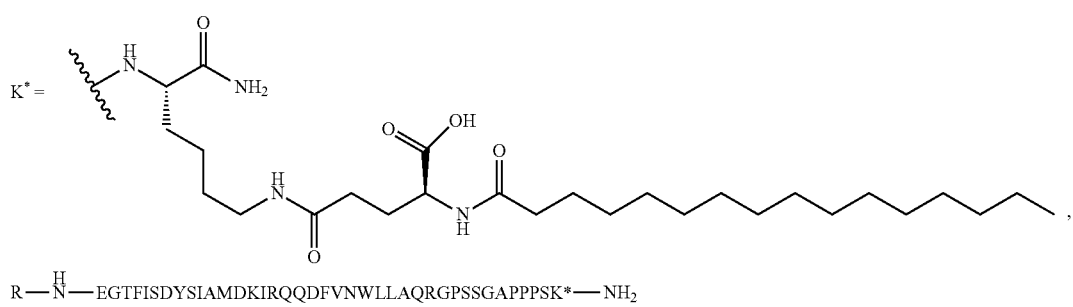

R—NH—EGTFISDYSIAMDKIRQQDFVNWLLAQRGPSSGAPPPSK*—NH$_2$

Sequence Da

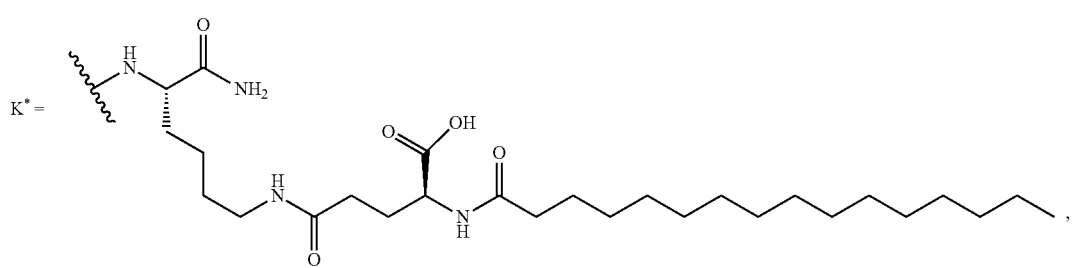

Sequence E

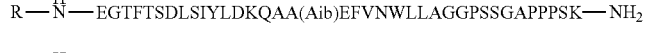

R—NH—EGTFTSDLSIYLDKQAA(Aib)EFVNWLLAGGPSSGAPPPSK—NH$_2$

Sequence F

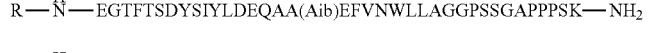

R—NH—EGTFTSDYSIYLDEQAA(Aib)EFVNWLLAGGPSSGAPPPSK—NH$_2$

Sequence G

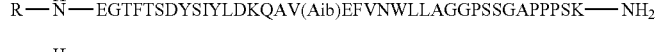

R—NH—EGTFTSDYSIYLDKQAV(Aib)EFVNWLLAGGPSSGAPPPSK—NH$_2$

Sequence H

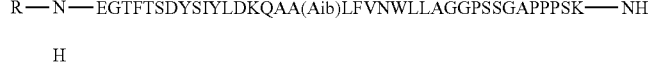

R—NH—EGTFTSDYSIYLDKQAA(Aib)LFVNWLLAGGPSSGAPPPSK—NH$_2$

Sequence I

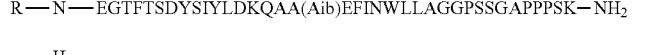

R—NH—EGTFTSDYSIYLDKQAA(Aib)EFINWLLAGGPSSGAPPPSK—NH$_2$

Sequence J

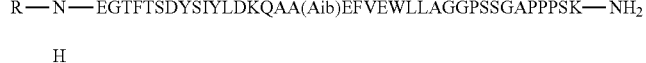

R—NH—EGTFTSDYSIYLDKQAA(Aib)EFVEWLLAGGPSSGAPPPSK—NH$_2$

Sequence K

R—NH—EGTFTSDYSIYLDKQAV(Aib)EFINWLLAGGPSSGAPPPSK—NH$_2$

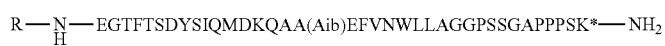
Sequence La
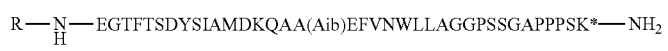
Sequence Ma
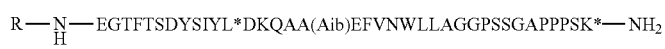
Sequence Na
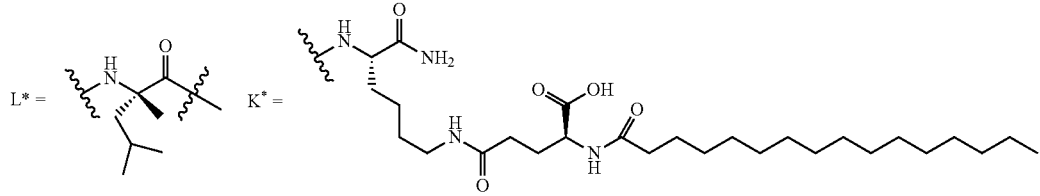
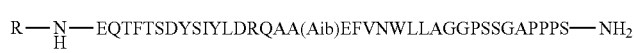
Sequence O
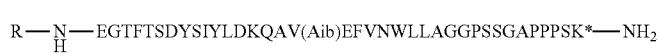
Sequence Ga
Sequence Pa
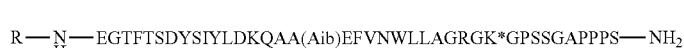
Sequence Qa
Sequence Ra
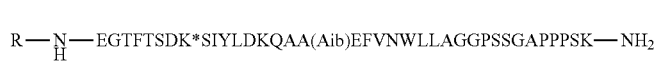
Sequence Sa
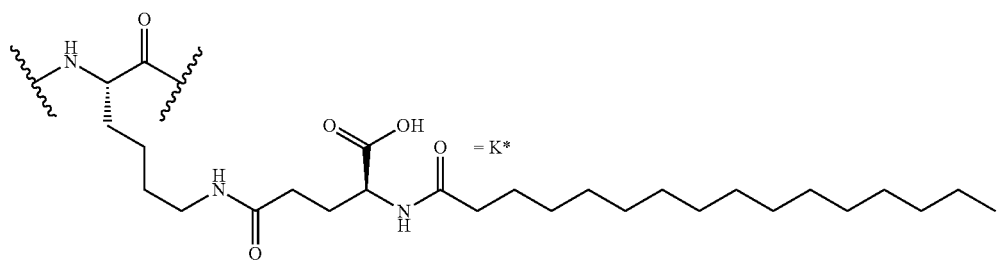
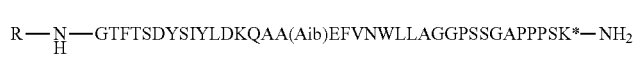
Sequence Ta
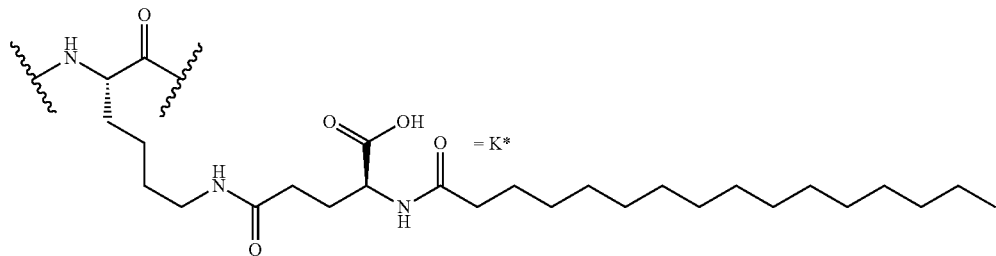
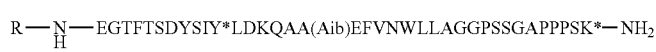
Sequence ACa
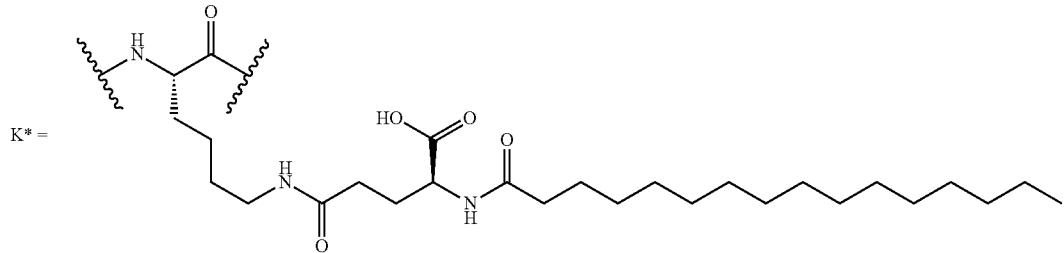

Y* = 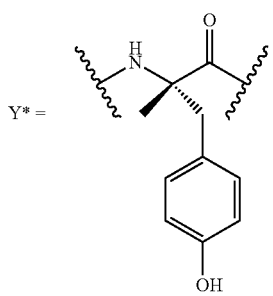

In the sequences depicted above with the exception of Sequence Ta,

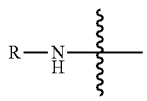

corresponds to the

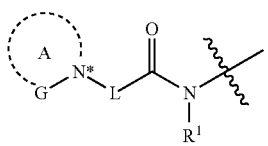

moiety in any of the formulae described herein (wherein $R^1$ is H).

In sequence Ta above,

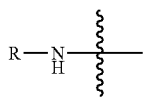

corresponds to the

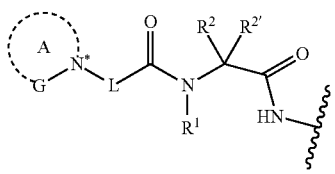

moiety in any of the formulae described herein (wherein $R^4$ is H).

C. SYNTHESIS OF INTERMEDIATES TO COMPOUNDS DESCRIBED IN THIS INVENTION

General Procedure 1 (GP1): Preparation of Carboxylic Acid Building Blocks for Peptide N-Terminal Derivatization To amine or amine salt (1.0 equiv.) in DMF (1-2 mL) was added thiodiglycolic anhydride, 3-methylglutaric anhydride, or 3,3-dimethylglutaric anhydride (1.1-1.2 equiv), followed by DIPEA (2-5 equiv.). After 0.5-16 hours at ambient temperature, the reaction product was isolated by preparative HPLC (Phenomenex Jupiter 10 µM Proteo 90 Å LC column, 250×21.2 mm, with flow rate—15 mL/min, H₂O/MeCN with 0.1% TFA).

General Procedure 2 (GP2): Preparation of bis-pentafluorophenyl) Esters

Scheme 1

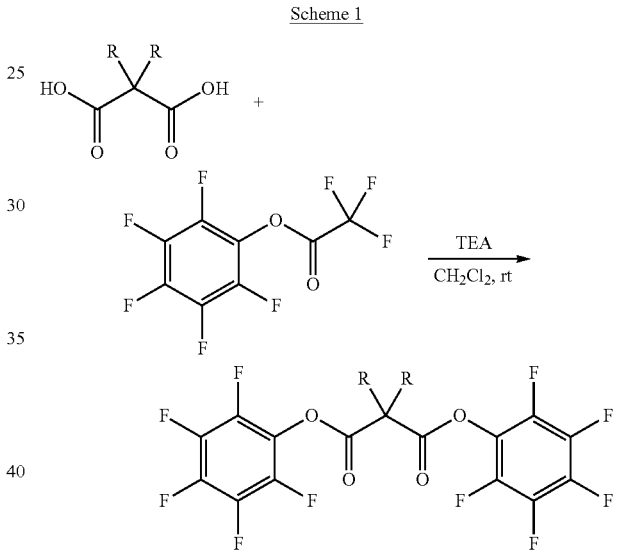

To a slurry of diacid (1.8-3.9 mmol) and triethylamine (2.1-3.0 equiv.) in DCM (5-20 mL) was added pentafluorophenyl trifluoroacetate (2.0-2.1 equiv.). The reaction mixture was stirred at ambient temperature for 5-18 hours, then concentrated and purified by silica gel chromatography to afford the desired diester.

General Procedure 3 (GP3): Preparation of Pentafluorophenyl Ester Building Blocks from bis-(pentafluorophenyl) esters (as Depicted in Scheme 2)

Scheme 2

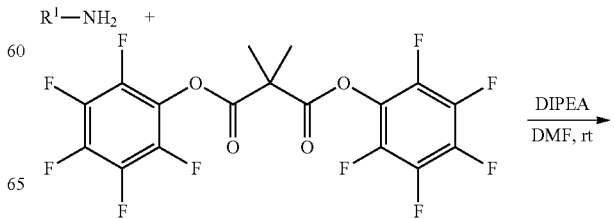

-continued

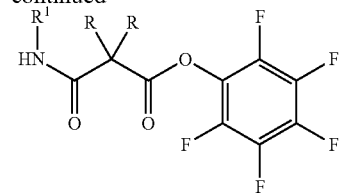

To amine (0.1-0.4 mmol) and bis-(pentafluorophenyl) ester (1.0 equiv.) in DMF (1 mL), added DIPEA (3.0 equiv.). After 3 hours at ambient temperature, the reaction mixture was purified by preparative HPLC (Phenomenex Jupiter 10 μM Proteo 90 Å LC column, 250×21.2 mm, with flow rate—15 mL/min, H₂O/MeCN with 0.1% TFA) to afford the desired substitution product.

Synthesis of I-3 is Depicted in Scheme 3

Scheme 3

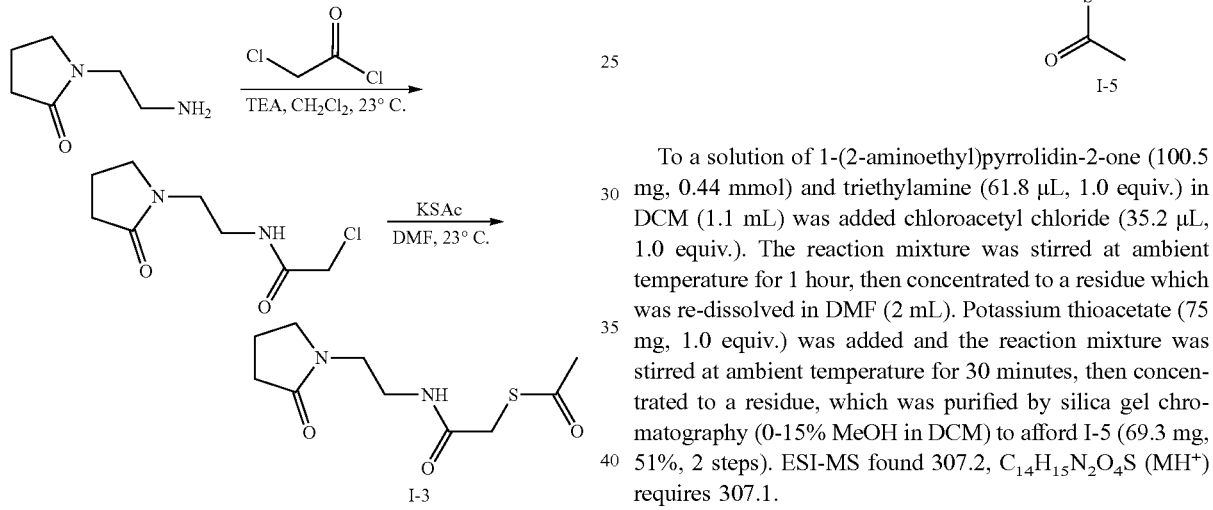

To a solution of 1-(2-aminoethyl)pyrrolidin-2-one (103.1 mg, 0.80 mmol) and triethylamine (0.11 mL, 1.0 equiv.) in DCM (2.3 mL) was added chloroacetyl chloride (63.9 μL, 1.0 equiv.). The reaction mixture was stirred at ambient temperature for 1 hour, then concentrated to a residue which was re-dissolved in DMF (2 mL). Potassium thioacetate (137.7 mg, 1.0 equiv.) was added and the reaction mixture was stirred at ambient temperature for 30 minutes, then concentrated to a residue, which was purified by silica gel chromatography (0-15% MeOH in DCM) to afford I-3. ESI-MS found 245.2, $C_{10}H_{17}N_2O_3S$ (MH⁺) requires 245.1.

Synthesis of I-5 is Depicted in Scheme 4

Scheme 4

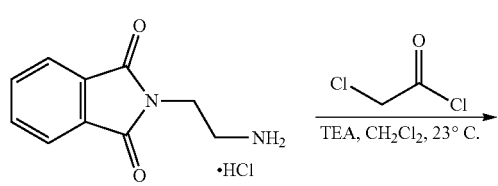

-continued

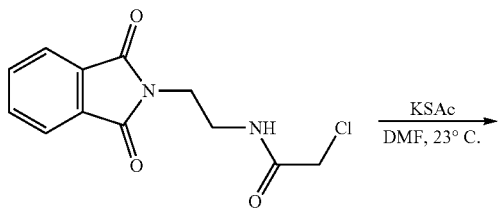

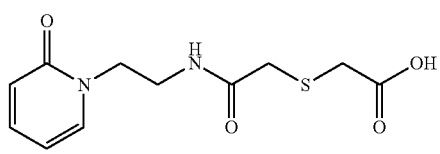

I-5

To a solution of 1-(2-aminoethyl)pyrrolidin-2-one (100.5 mg, 0.44 mmol) and triethylamine (61.8 μL, 1.0 equiv.) in DCM (1.1 mL) was added chloroacetyl chloride (35.2 μL, 1.0 equiv.). The reaction mixture was stirred at ambient temperature for 1 hour, then concentrated to a residue which was re-dissolved in DMF (2 mL). Potassium thioacetate (75 mg, 1.0 equiv.) was added and the reaction mixture was stirred at ambient temperature for 30 minutes, then concentrated to a residue, which was purified by silica gel chromatography (0-15% MeOH in DCM) to afford I-5 (69.3 mg, 51%, 2 steps). ESI-MS found 307.2, $C_{14}H_{15}N_2O_4S$ (MH⁺) requires 307.1.

I-6

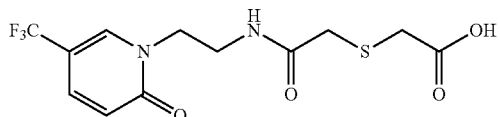

Prepared according to GP1. Yield: 57.8 mg (64%). ESI-MS found 271.2, $C_{11}H_{15}N_2O_4S$ (MH⁺) requires 271.1.

I-7

I-7

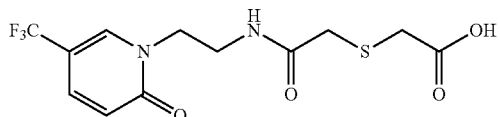

Prepared according to GP1. Yield: 28.6 mg (69%). ESI-MS found 339.2, $C_{12}H_{14}F_3N_2O_4S$ (MH⁺) requires 339.1.

I-8

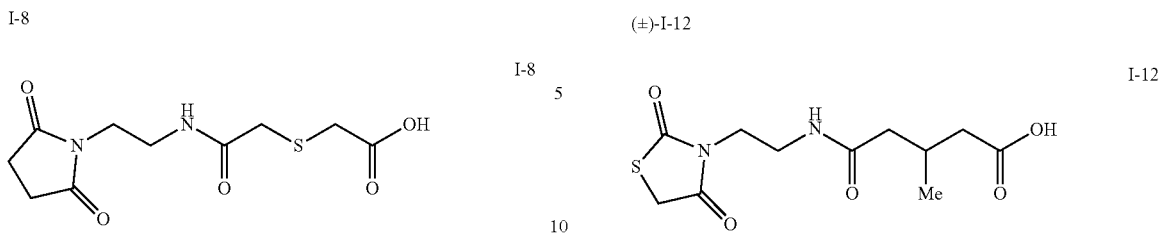

Prepared according to GP1. Yield: 70.1 mg (100%). ESI-MS found 275.2, $C_{10}H_{15}N_2O_5S$ (MH$^+$) requires 275.1.

I-9

Prepared according to GP1. Yield: 188.4 mg (73%). ESI-MS found 292.2, $C_9H_{13}N_2O_5S_2$(MH$^+$) requires 292.1.

I-1

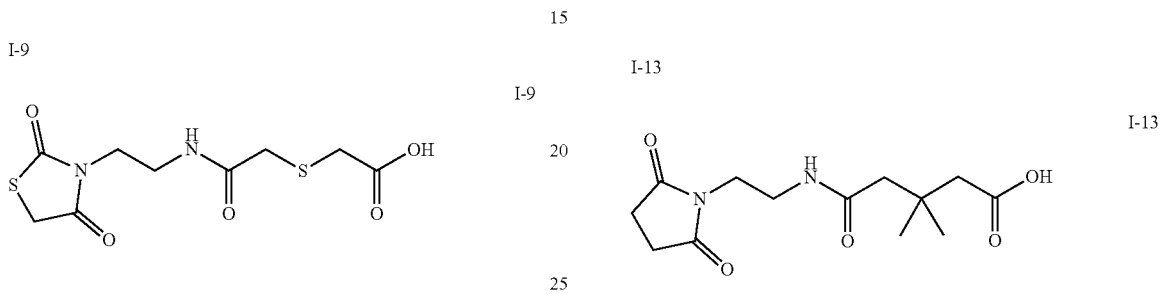

Prepared according to GP1. Yield: 92.7 mg (68%). ESI-MS found 259.3, $C_{10}H_{15}N_2O_4S$ (M–H$^+$) requires 259.1.

I-10

Prepared according to GP1. Yield: 73 mg. ESI-MS found 300.2, $C_{12}H_{18}N_3O_4S$ (MH$^+$) requires 300.1.

I-11

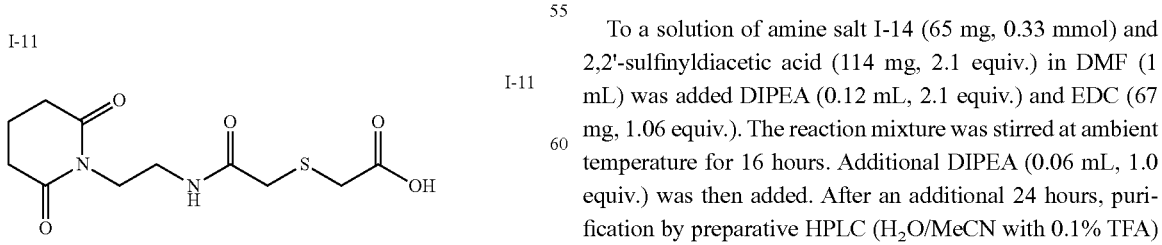

Prepared according to GP1. Yield: 60.1 mg (87%). ESI-MS found 289.2, $C_{11}H_{17}N_2O_5S$ (MH$^+$) requires 289.1.

(±)-I-12

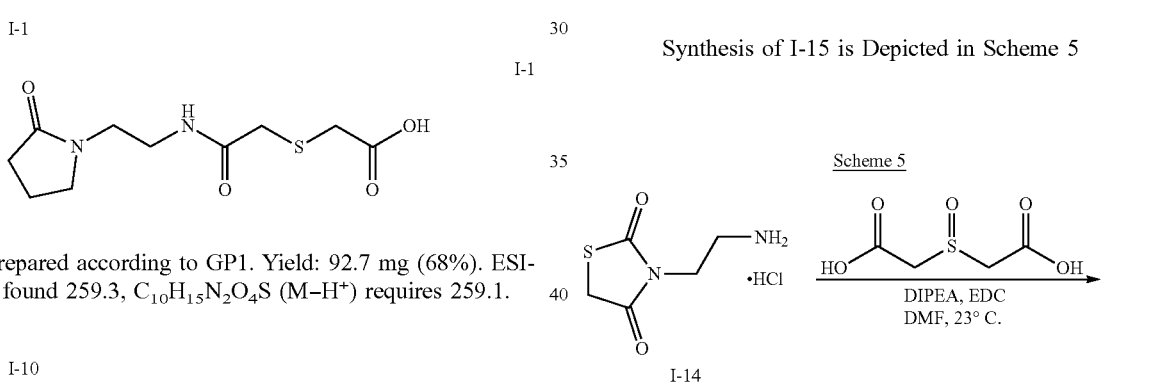

Prepared according to GP1. Yield: 68.5 mg (98%). ESI-MS found 289.2, $C_{11}H_{17}N_2O_5S$ (MH$^+$) requires 289.1.

I-13

Prepared according to GP1. Yield: 73.1 mg (95%). ESI-MS found 303.2, $C_{12}H_{19}N_2O_5S$ (MH$^+$) requires 303.1.

Synthesis of I-15 is Depicted in Scheme 5

Scheme 5

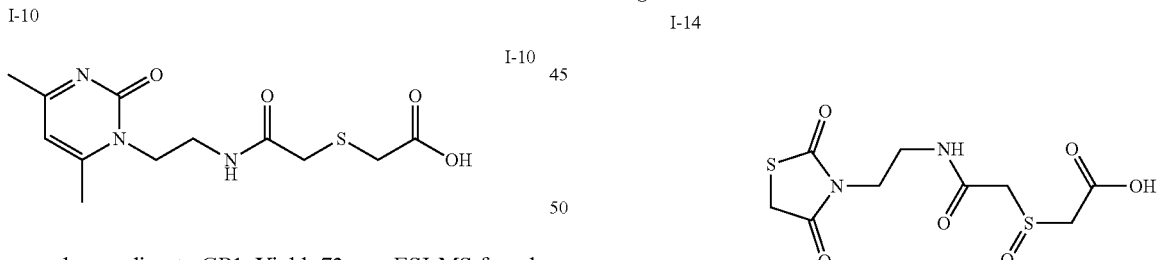

To a solution of amine salt I-14 (65 mg, 0.33 mmol) and 2,2'-sulfinyldiacetic acid (114 mg, 2.1 equiv.) in DMF (1 mL) was added DIPEA (0.12 mL, 2.1 equiv.) and EDC (67 mg, 1.06 equiv.). The reaction mixture was stirred at ambient temperature for 16 hours. Additional DIPEA (0.06 mL, 1.0 equiv.) was then added. After an additional 24 hours, purification by preparative HPLC (H$_2$O/MeCN with 0.1% TFA) afforded 106.9 mg (quantitative yield) of I-15 as a colorless oil. ESI-MS found 306.9, $C_9H_{11}N_2O_6S_2$ (M–H$^+$) requires 307.0.

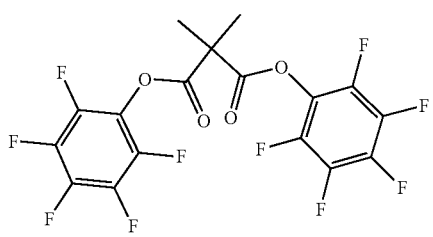

I-16

Diester I-16: Prepared according to GP2. Yield: 1.16 g (65%).

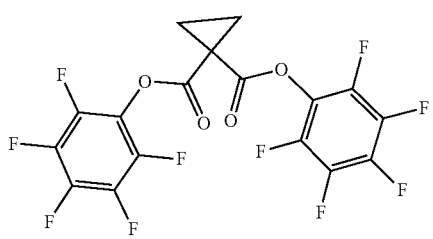

I-17

Diester I-17: Prepared according to GP2. Yield: 599 mg (29%)

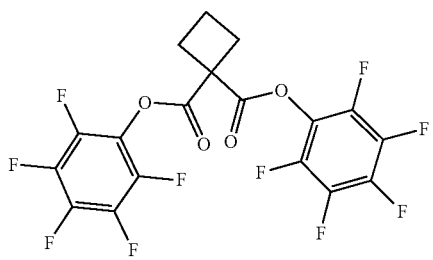

I-18

Diester I-18: Prepared according to GP2. Yield: 778 mg (46%)

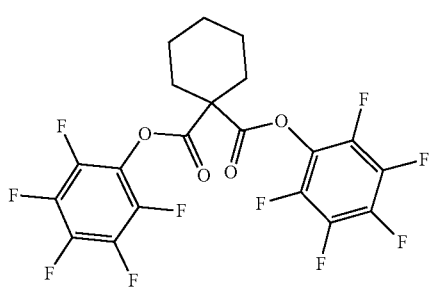

I-19

Diester I-19: Prepared according to GP2. Yield: 569.8 mg (64%).

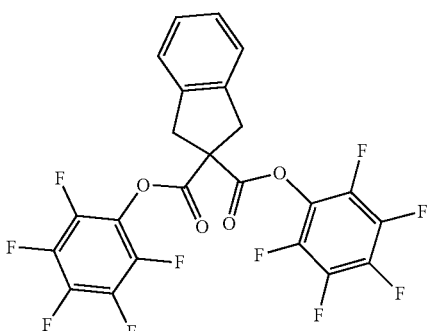

I-20

Diester I-20: Prepared according to GP2. Yield: 399.3 mg (48%).

I-21

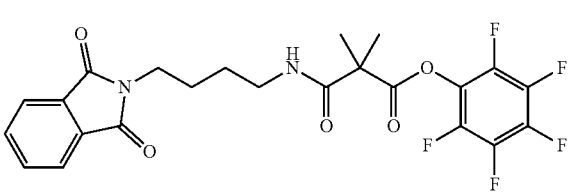

I-21

Prepared according to GP3 from diester I-16. Yield: 43.2 mg (50%). ESI-MS found 485.1, $C_{22}H_{18}F_5N_2O_5$ (MH$^+$) requires 485.1.

I-22

I-22

Prepared according to GP3 from diester I-16. Yield: 25.8 mg (33%). ESI-MS found 312.1, $C_{12}H_{18}F_5NO_3$ (MH$^+$) requires 312.1.

I-23

I-23

Prepared according to GP3 from diester I-16. Yield: 53.4 mg (55%). ESI-MS found 499.1, $C_{23}H_{20}F_5N_2O_5(MH^+)$ requires 499.1.

I-24

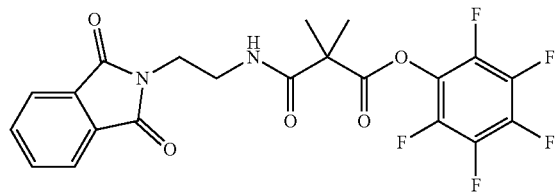

I-24

Prepared according to GP3 from diester I-16. Yield: 56.7 mg (58%). ESI-MS found 471.1, $C_{21}H_{16}F_5N_2O_5(MH^+)$ requires 471.1.

I-25

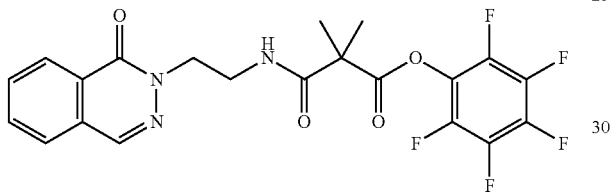

I-25

Prepared according to GP3 from diester I-16. Yield: 28.7 mg (33%). ESI-MS found 470.3, $C_{21}H_{17}F_5N_3O_4(MH^+)$ requires 470.1.

I-26

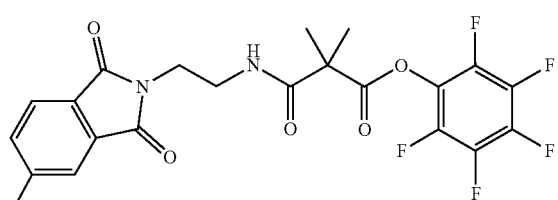

I-26

Prepared according to GP3 from diester I-16. Yield: 57.4 mg (86%). ESI-MS found 485.3, $C_{22}H_{18}F_5N_2O_5$ (MH$^+$) requires 485.1.

I-27

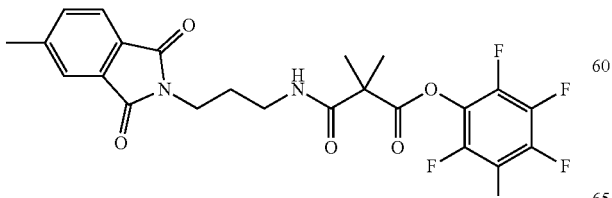

I-27

Prepared according to GP3 from diester I-16. Yield: 18.1 mg (27%).

I-28

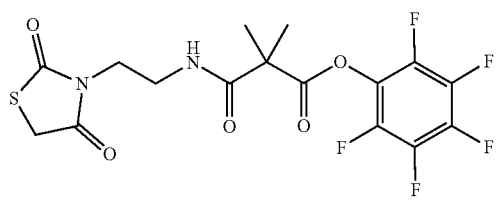

I-28

Prepared according to GP3 from diester I-16. Yield: 48 mg (33%). ESI-MS found 441.1, $C_{16}H_{14}F_5N_2O_5S$ (MH$^+$) requires 441.1.

I-29

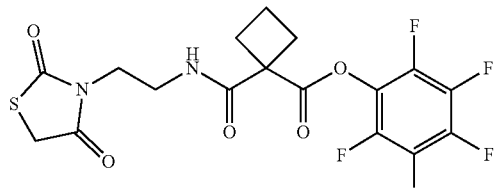

I-29

Prepared according to GP3 from diester I-18. Yield: 66.1 mg (59%). ESI-MS found 453.1, $C_{17}H_{14}F_5N_2O_5S$ (MH$^+$) requires 453.1.

I-30

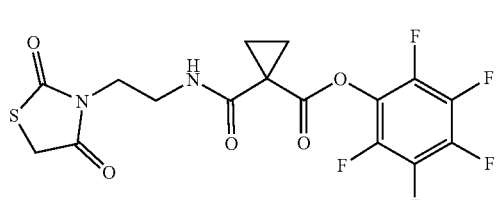

I-30

Prepared according to GP3 from diester I-17. Yield: 58.8 mg (48%). ESI-MS found 439.1, $C_{16}H_{12}F_5N_2O_5S$ (MH$^+$) requires 439.1.

I-31

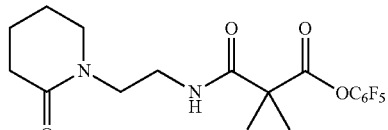

I-31

Prepared according to GP3 from diester I-16. Yield: 47.9 mg (61%). ESI-MS found 423.1, $C_{18}H_{20}F_5N_2O_4(MH^+)$ requires 423.1.

I-32

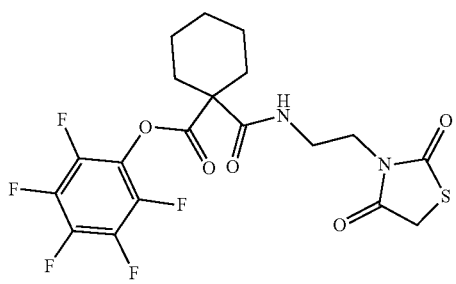

Prepared according to GP3 from diester I-19. Yield: 40 mg (30% yield). ESI-MS found 481.2, $C_{19}H_{18}F_5N_2O_5S$ (MH$^+$) requires 481.1.

I-33

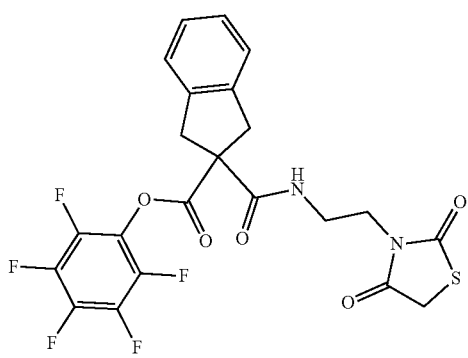

I-33: Prepared according to GP3 from diester I-20. Yield: 8.6 mg (9% yield).

Synthesis of I-34 is Depicted in Scheme 6

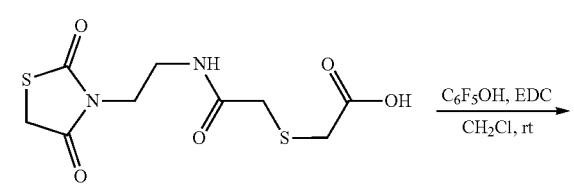

Scheme 6

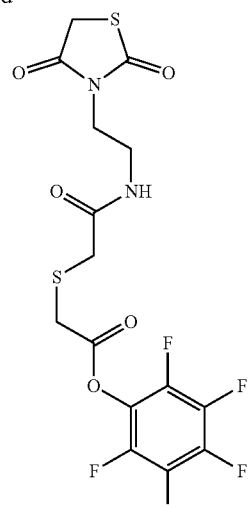

I-34

To a slurry of 3-(2-aminoethyl)thiazolidine-2,4-dione hydrochloride (100 mg, 0.51 mmol) and thiodiglycolic anhydride (69 mg, 1.0 equiv.) in DCM (1 mL) was added DIPEA (0.18 mL, 2.0 equiv.). The reaction mixture was stirred at ambient temperature for 2 hours. Pentafluorophenol (98 mg, 1.0 equiv.) was then added, followed by EDC (100 mg, 1.0 equiv.). The reaction mixture was stirred for 16 hours, then concentrated and purified by silica gel chromatography (0-60% EtOAc in Hexanes) to afford 69.1 mg (30% yield) of I-34 as a white solid. ESI-MS found 459.1. $C_{15}H_{12}F_5N_2O_5S2$ (MH$^+$) requires 459.0.

Synthesis of I-35 is Depicted in Scheme 7

Scheme 7

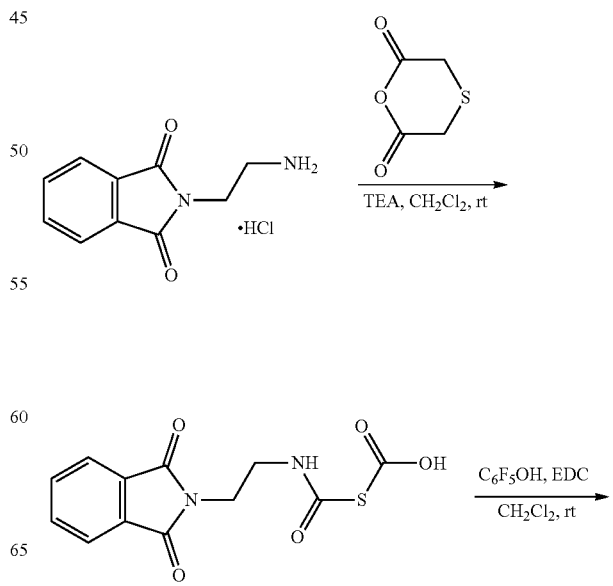

-continued

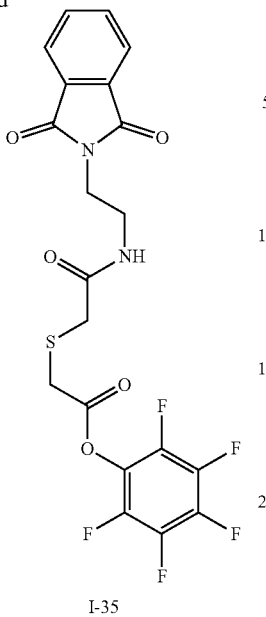

I-35

To a slurry of 2-(2-aminoethyl)isoindoline-1,3-dione hydrochloride (200 mg, 0.82 mmol) and thiodiglycolic anhydride (122 mg, 1.05 equiv.) in DCM (5 mL) and DMF (2 mL) was added TEA (0.27 mL, 2.2 equiv.). The reaction mixture was stirred at ambient temperature for 16 hours. Additional thiodiglycolic anhydride (23 mg, 0.2 equiv.) was added for completion of the reaction. The reaction mixture was concentrated and diluted with DCM (30 mL). The organic phase was washed with 1M HCl (30 mL) and the aqueous phase was back-extracted with EtOAc (30 mL). The combined organic extracts were dried (MgSO$_4$) and concentrated to a residue, which was purified by silica gel chromatography (10:1 DCM/MeOH with 1% AcOH) to afford 400 mg of intermediate acid, This acid was re-dissolved in DCM (5 mL). Pentafluorophenol (215 mg, 1.3 equiv.) was then added, followed by EDC (224 mg, 1.3 equiv.). The reaction mixture was stirred for 1 hour, and additional pentafluorophenol (108 mg, 0.65 equiv.) and EDC (112 mg, 0.65 equiv.) were added. After an additional 30 minutes, the reaction mixture was concentrated and purified by silica gel chromatography (0-100% EtOAc in Hexanes) to afford 250 mg (58% yield, 2 steps) of I-35 as a white solid. ESI-MS found 489.1. $C_{20}H_{14}F_5N_2O_5S$ (MH$^+$) requires 489.1.

Synthesis of I-36 is Depicted in Scheme 8

Scheme 8

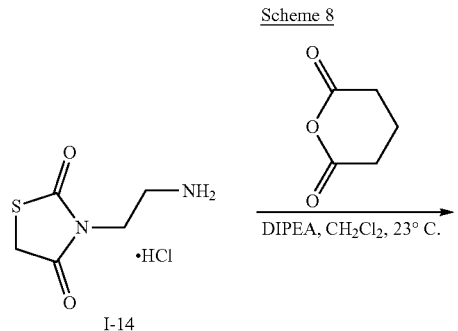

-continued

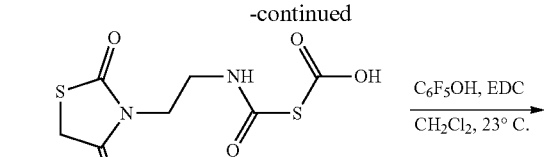

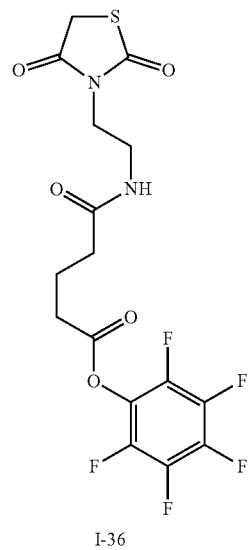

I-36

Amine salt I-14 (81 mg, 0.41 mmol) and glutaric anhydride (49 mg, 1.04 equiv.) were suspended in DCM (4 mL), and DIPEA (0.14 mL, 2.0 equiv.) was added. The reaction mixture was stirred at ambient temperature for 15 hours, whereupon pentafluorophenol (80 mg, 1.06 equiv.) and EDC (81 mg, 1.02 equiv.) were added to the homogeneous solution. After an additional 4 hours, the reaction mixture was diluted with DCM (20 mL) and washed with 1M HCl (5 mL) and brine (8 mL). The organic extracts were dried (Na$_2$SO$_4$) and concentrated to a residue, which was purified by silica gel chromatography (Hexanes/EtOAc) to afford 105 mg (58% yield) of I-36 as a white solid. ESI-MS found 441.0. $C_{16}H_{14}F_5N_2O_5S$ (MH$^+$) requires 441.1.

Synthesis of I-37 is Depicted in Scheme 9

Scheme 9

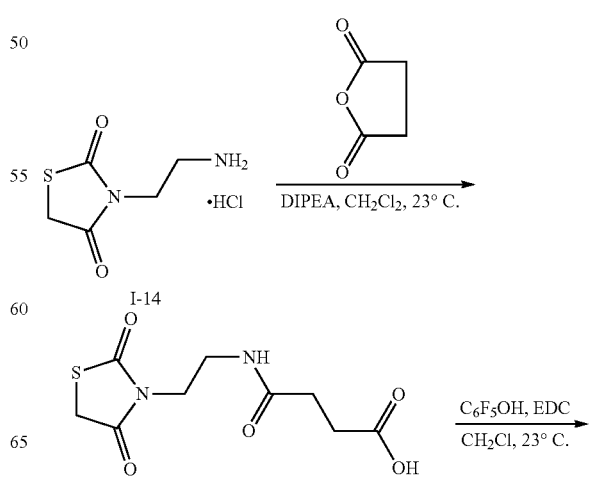

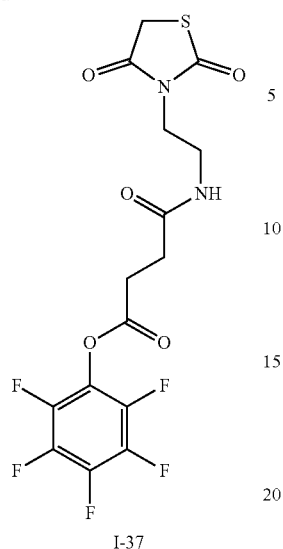

I-37

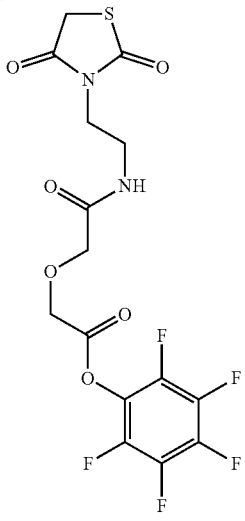

I-38

Amine salt I-14 (69 mg, 0.35 mmol) and succinic anhydride (35 mg, 1.0 equiv.) were suspended in DCM (5 mL), and DIPEA (0.12 mL, 2.0 equiv.) was added. The reaction mixture was stirred at ambient temperature for 16 hours, whereupon pentafluorophenol (80 mg, 1.24 equiv.) and EDC (74 mg, 1.1 equiv.) were added to the homogeneous solution. After an additional 4 hours, the reaction mixture was diluted with DCM (20 mL) and washed with 1M HCl (5 mL) and brine (8 mL). The organic extracts were dried ($Na_2SO_4$) and concentrated to a residue, which was purified by silica gel chromatography (Hexanes/EtOAc) to afford 64 mg (43% yield) of I-37 as a white solid. ESI-MS found 427.0. $C_{15}H_{12}F_5N_2O_5S$ ($MH^+$) requires 427.1.

Amine salt I-14 (73 mg, 0.37 mmol) and diglycolic anhydride (43 mg, 1.0 equiv.) were suspended in DCM (5 mL), and DIPEA (0.14 mL, 2.2 equiv.) was added. The reaction mixture was stirred at ambient temperature for 17 hours, whereupon pentafluorophenol (86 mg, 1.26 equiv.) and EDC (78 mg, 1.1 equiv.) were added to the homogeneous solution. After an additional 6 hours, the reaction mixture was diluted with DCM (20 mL) and washed with 1M HCl (5 mL) and brine (8 mL). The organic extracts were dried ($Na_2SO_4$) and concentrated to a residue, which was purified by silica gel chromatography (Hexanes/EtOAc) to afford 22 mg (14% yield) of I-38 as a white solid. ESI-MS found 443.0. $C_{15}H_{12}F_5N_2O_6S$ ($MH^+$) requires 443.0.

Synthesis of I-38 is Depicted in Scheme 10

Synthesis of I-39 is Depicted in Scheme 11

Scheme 10

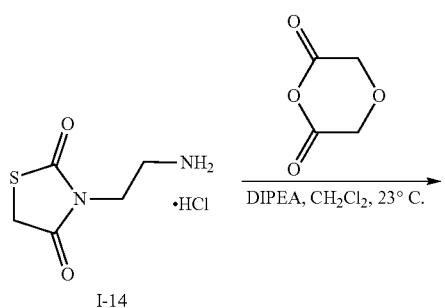

Scheme 11

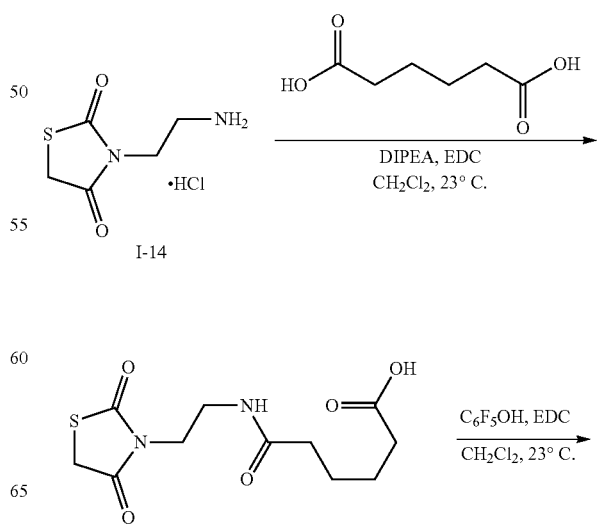

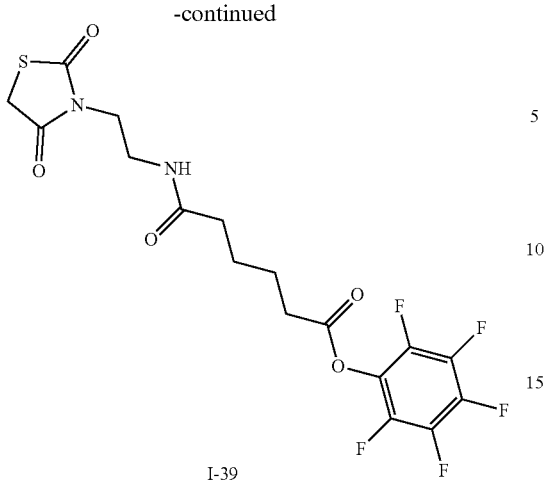

I-39

To a suspension of amine salt I-14 (99 mg, 0.50 mmol), adipic acid (73.7 mg, 1.0 equiv.) and EDC (98 mg, 1.02 equiv.) in DCM (5 mL) was added DIPEA (0.27 mL, 3.1 equiv.). The reaction mixture was stirred at ambient temperature for 60 hours at which point pentafluorophenol (98 mg, 1.06 equiv.) and additional EDC (102 mg, 1.05 equiv.) were added to the homogeneous solution. After an additional 4.5 hours, the reaction mixture was diluted with DCM (20 mL) and washed with 1M HCl (5 mL) and brine (8 mL). The organic extracts were dried (Na$_2$SO$_4$) and concentrated to a residue, which was purified by silica gel chromatography (Hexanes/EtOAc) to afford 90 mg (39% yield) of I-39 as a white solid. ESI-MS found 455.0. C$_{17}$H$_{16}$F$_5$N$_2$O$_5$S (MH$^+$) requires 455.1.

Synthesis of I-40 is Depicted in Scheme 12

Scheme 12

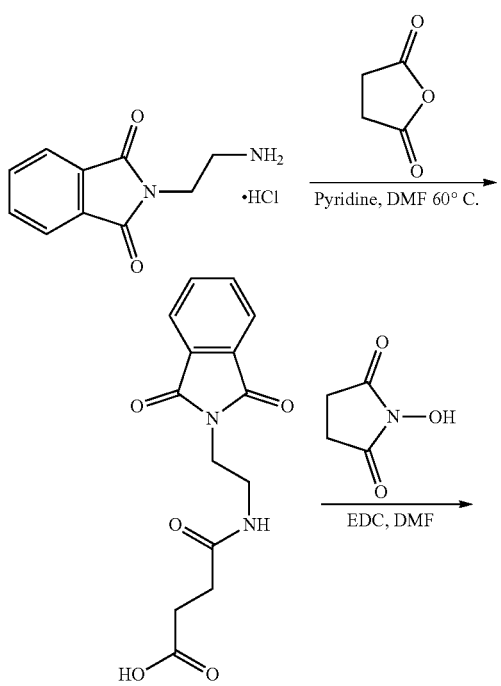

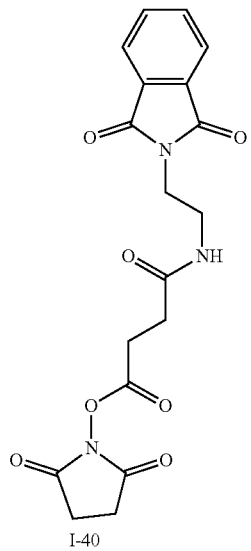

I-40

To a slurry of 2-(2-aminoethyl)isoindoline-1,3-dione hydrochloride (74.3 mg, 0.33 mmol) and succinic anhydride (39.4 mg, 1.2 equiv.) in DMF (1.5 mL) was added pyridine (79 µL, 3.0 equiv.). The reaction mixture was heated to 60° C. for 1 hour at which point acylation was complete. The reaction mixture was cooled to ambient temperature, and HOSu (75.5 mg, 2.0 equiv.) was added, followed by EDC (125.8 mg, 2.0 equiv.) The reaction mixture was stirred at ambient temperature for 4 hours. The reaction mixture was diluted saturated aqueous NH$_4$Cl (8 mL) and H$_2$O (5 mL) and extracted with EtOAc (3×5 mL). The organic extracts were combined, dried (MgSO$_4$), and concentrated to afford a white solid. Silica gel chromatography (EtOAc) afforded 22.9 mg (18% yield) of ester I-40.

Synthesis of I-41 is Depicted in Scheme 13

Scheme 13

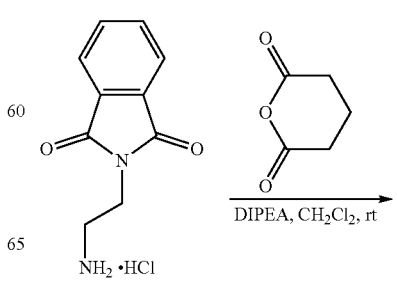

-continued

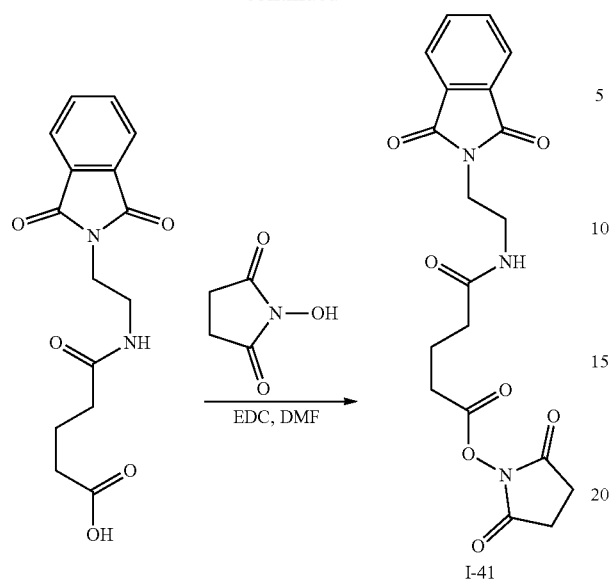

I-41

To a solution of 2-(2-aminoethyl)isoindoline-1,3-dione hydrochloride (102.2 mg, 0.45 mmol) and glutaric anhydride (61.7 mg, 1.2 equiv.) in DMF (2 mL) was added DIPEA (196 µL, 2.5 equiv.). The reaction mixture was stirred for 22.5 hours at ambient temperature and HOSu (103.8 mg, 2.0 equiv.) was added, followed by EDC (172.8 mg, 2.0 equiv.). The reaction mixture was maintained at ambient temperature for an additional 16 hours, then diluted with $H_2O$ (10 mL) and extracted with EtOAc (3×5 mL). The combined organic extracts were dried ($MgSO_4$) and concentrated to afford a residue, which was purified by silica gel chromatography (EtOAc) to afford 85.8 mg (47% yield, 2 steps) of I-41 as a white solid. ESI-MS found 402.3. $C_{19}H_{20}N_3O_7$ ($MH^+$) requires 402.1.

Synthesis of I-42 is Depicted in Scheme 14

-continued

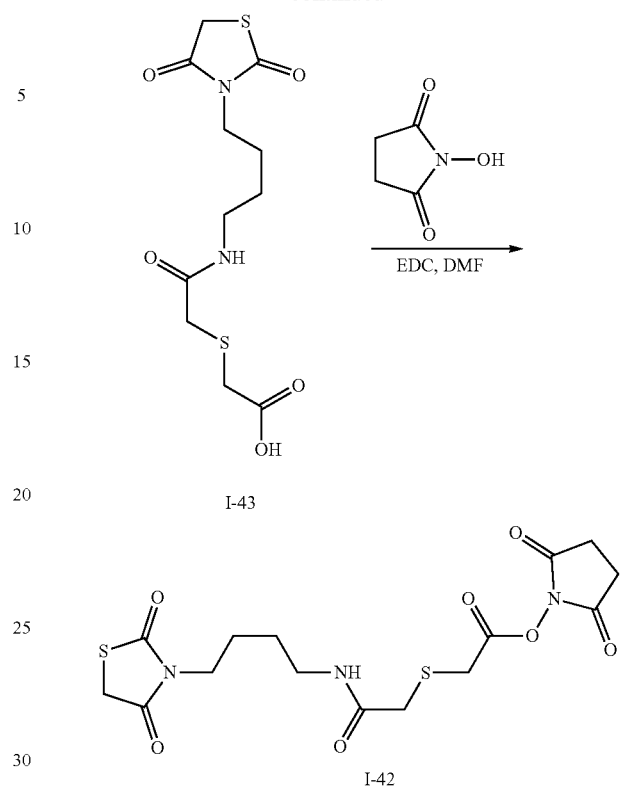

I-43

I-42

To amine salt I-14 (63.4 mg, 0.28 mmol) in DMF (1 mL) was added thiodiglycolic anhydride (44.7 mg, 1.2 equiv), followed by DIPEA (123 µL, 2.5 equiv.). After stirring at ambient temperature for 3 hours, purification by preparative HPLC ($H_2O$/MeCN with 0.1% TFA) afforded 70.5 mg (78% yield) of carboxylic acid I-43 as a white solid. Carboxylic acid I-43 was dissolved in DMF (2 mL), and HOSu (38 mg, 1.5 equiv.) was added, followed by EDC (63.3 mg, 1.5 equiv.) The reaction mixture was stirred at ambient temperature for 18 hours, then subjected to preparative HPLC ($H_2O$/MeCN with 0.1% TFA) to afford 89.8 mg (98% yield) of ester I-42 as a white solid. ESI-MS found 418.2. $C_{15}H_{20}N_3O_7S_2$($MH^+$) requires 418.1.

Synthesis of I-44 is Depicted in Scheme 15

Scheme 14

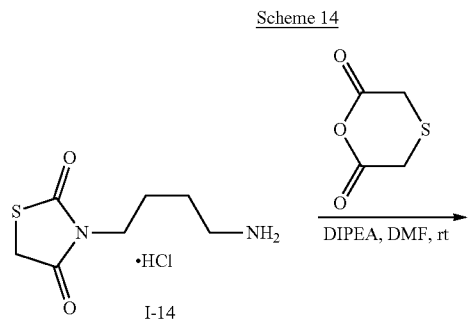

Scheme 15

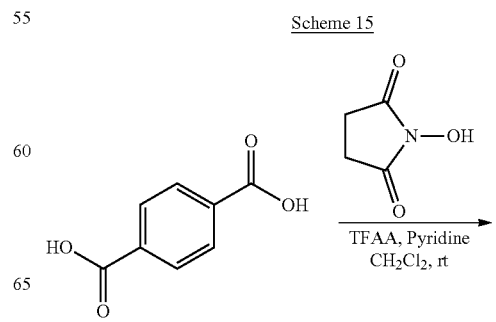

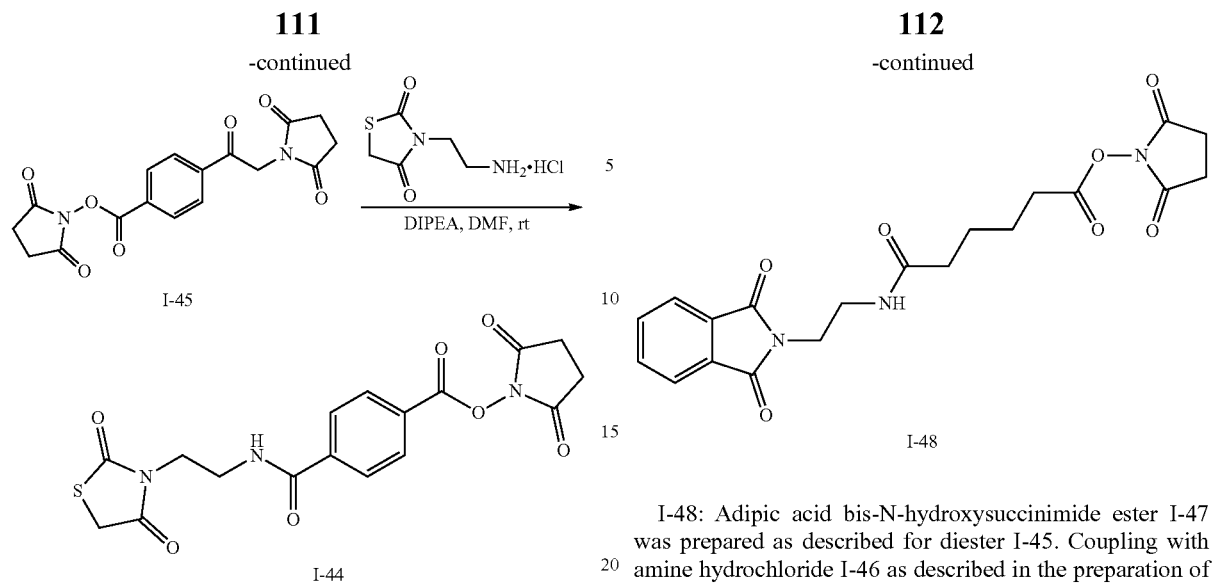

To a slurry of terephthalic acid (216.7 mg, 1.304 mmol) and HOSu (547.9 mg, 2.0 equiv.) in DCM (10 mL) was added pyridine (420 mL, 4.0 equiv.). The reaction mixture was cooled to 0-5° C. and trifluoroacetic anhydride (368 mL, 2.0 equiv.) was added. The reaction mixture was allowed to warm to ambient temperature, stirred for 16 hours, and then concentrated. EtOH (20 mL) was added to the residue and the slurry was filtered and dried to afford the crude bis-N-hydroxysuccinimide ester I-45 (403 mg, 86% yield), which was taken forward without further purification.

To a solution of 3-(2-aminoethyl)thiazolidine-2,4-dione hydrochloride (34.3 mg, 0.174 mmol) in DMF (1 mL) was added diester I-45 (125.7 mg, 2.0 equiv.) and DIPEA (91 mL, 3.0 equiv.). The reaction mixture was maintained at ambient temperature for 17 hours and then purified by HPLC to afford 54 mg (76% yield) of I-44.

Synthesis of I-48 is Depicted in Scheme 16

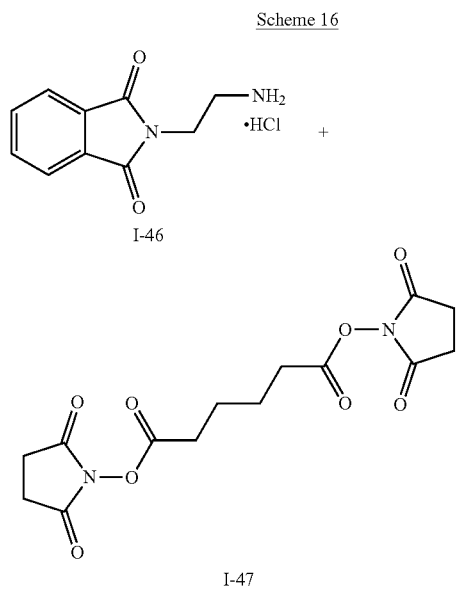

I-48: Adipic acid bis-N-hydroxysuccinimide ester I-47 was prepared as described for diester I-45. Coupling with amine hydrochloride I-46 as described in the preparation of I-44 afforded 69.8 mg (69% yield) of I-48 after purification by preparative HPLC (H$_2$O/MeCN with 0.1% TFA).

Synthesis of I-51 is Depicted in Scheme 17

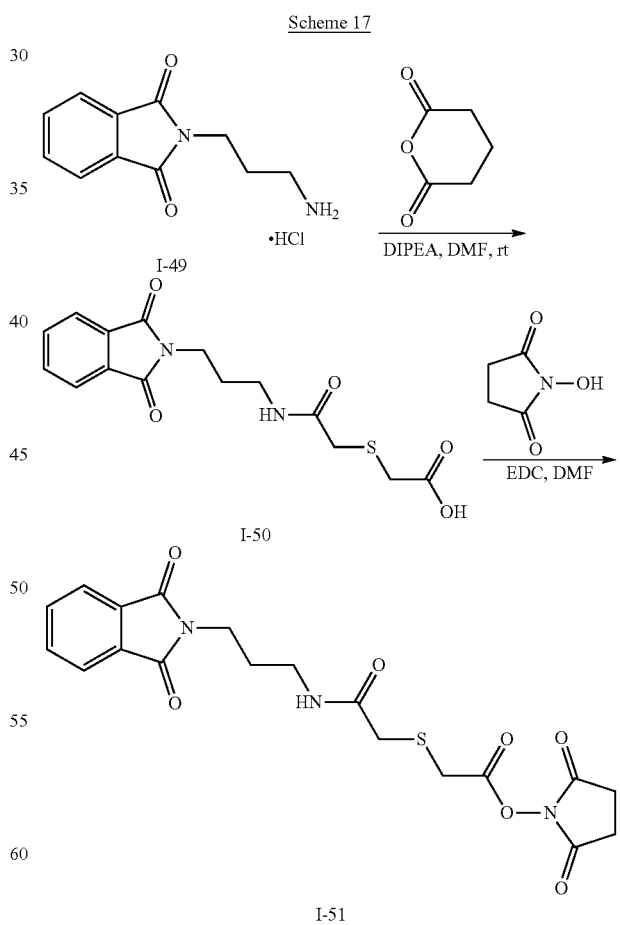

Using a procedure similar to that described for the preparation of I-42, amine hydrochloride I-49 (85 mg, 0.353 mmol) afforded 62.5 mg (38% yield, 2 steps) of I-51.

Synthesis of I-53 is Depicted in Scheme 18

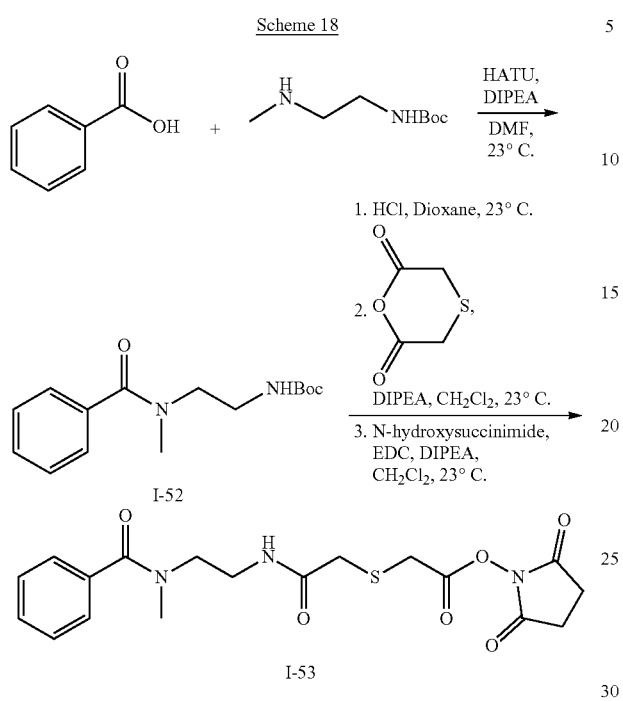

Scheme 18

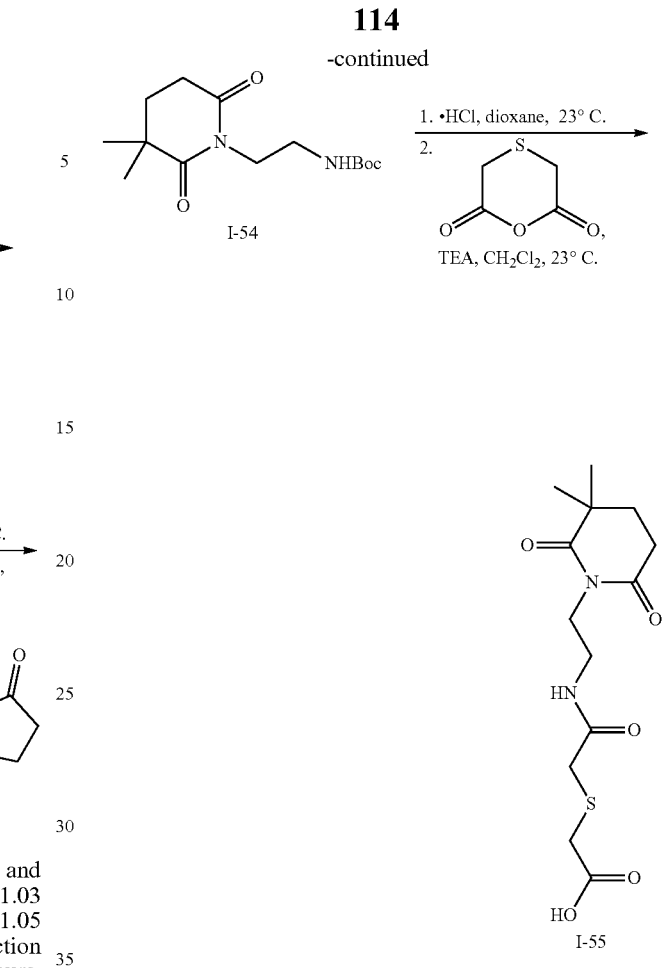

To a solution of benzoic acid (66.2 mg, 0.54 mmol) and tert-butyl (2-(methylamino)ethyl)carbamate (97.5 mg, 1.03 equiv.) in DMF (3 mL) was added HATU (216.8 mg, 1.05 equiv.) and DIPEA (0.1 mL, 1.06 equiv.). The reaction mixture was stirred at ambient temperature for 16 hours, then diluted with EtOAc (20 mL) and washed with water (10 mL), 1M HCl (10 mL), 1M NaOH (10 mL) and brine (10 mL). The combined organic extracts were dried ($Na_2SO_4$) and concentrated to afford intermediate amide I-52 (130.8 mg), which was then dissolved in 4M HCl in dioxane (3 mL). After 1 hour, the reaction mixture was concentrated to afford the deprotected amine as a solid. This amine was suspended in DCM (3 mL) along with thiodiglycolic anhydride (60.4 mg, 0.97 equiv.), and DIPEA (0.17 mL, 2.1 equiv.) was added. The reaction mixture was stirred at ambient temperature for 2.5 hours, at which point HOSu (55.1 mg, 1.02 equiv.) and EDC (90 mg, 1.0 equiv.) were added. After 16 hours, the reaction mixture was diluted with DCM (20 mL) and washed with 1M HCl (2×10 mL) and brine (8 mL). The organic extracts were dried ($Na_2SO_4$) and concentrated to a residue, which was purified by silica gel chromatography (EtOAc) to afford 34.5 mg (18% yield) of I-53. ESI-MS found 408.2. $C_{18}H_{22}N_3O_6S$ (MH$^+$) requires 408.1.

Synthesis of I-55 is Depicted in Scheme 19

Scheme 19

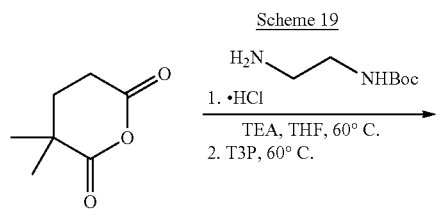

To a solution of 3,3-dimethyldihydro-2H-pyran-2,6(3H)-dione (98.7 mg, 0.69 mmol) and tert-butyl (2-aminoethyl)carbamate hydrochloride (140 mg, 1.02 equiv.) in THF (6 mL) was added TEA (0.2 mL, 2.1 equiv.). The reaction mixture was heated to 60° C. for 48 hours. T3P (50% solution in EtOAc, 0.27 g, 0.6 equiv.) was added, followed by additional THF (3 mL). The reaction mixture was heated to 60° C. for 8 hours, at which time additional T3P (0.47 g, 1.1 equiv.) was added and the reaction mixture was heated to 60° C. for an additional 16 hours. The reaction mixture was diluted with EtOAc (20 mL) and washed with $H_2O$ (2×10 mL), saturated aqueous $NaHCO_3$ (10 mL), 1M HCl (10 mL), and brine (10 mL). The organic extracts were dried ($Na_2SO_4$) and concentrated to afford a residue, which was purified by silica gel chromatography to afford the glutarimide I-54 (59 mg, 30% yield).

Glutarimide I-54 (59 mg, 0.21 mmol) was dissolved in 4M HCl in dioxane (3 mL). After 2 hours, the reaction mixture was concentrated to afford a white solid. This solid and thiodiglycolic anhydride (28.3 mg, 1.03 equiv.) were dissolved in DCM (3 mL), and TEA (90 µL, 3.1 equiv.) was added. After 25 minutes, the reaction mixture was concentrated and purified by preparative HPLC ($H_2O$/MeCN with 0.1% TFA) to afford 40.5 mg (62% yield) of I-55. ESI-MS found 317.2, $C_{13}H_{21}N_2O_5S$ (MH$^+$) requires 317.1.

Synthesis of I-56 is Depicted in Scheme 20

Synthesis of I-60 is Depicted in Scheme 22

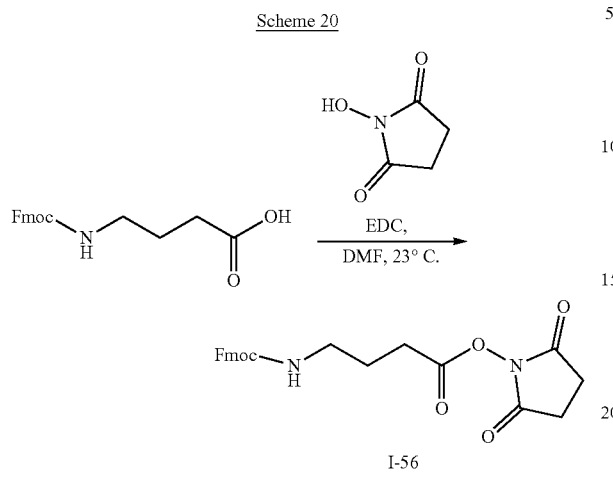

To a solution of N-Fmoc-4-aminobutanoic acid (111.3 mg, 0.34 mmol) in DMF (1 mL) was added HOSu (59.1 mg, 1.5 equiv.) and EDC (98.3 mg, 1.5 equiv.). The reaction mixture was stirred at ambient temperature for 1.5 hours and then purified by preparative HPLC ($H_2O$/MeCN with 0.1% TFA) to afford 126.2 mg (87% yield) of ester I-56 as a white solid.

Synthesis of I-57 is Depicted in Scheme 21

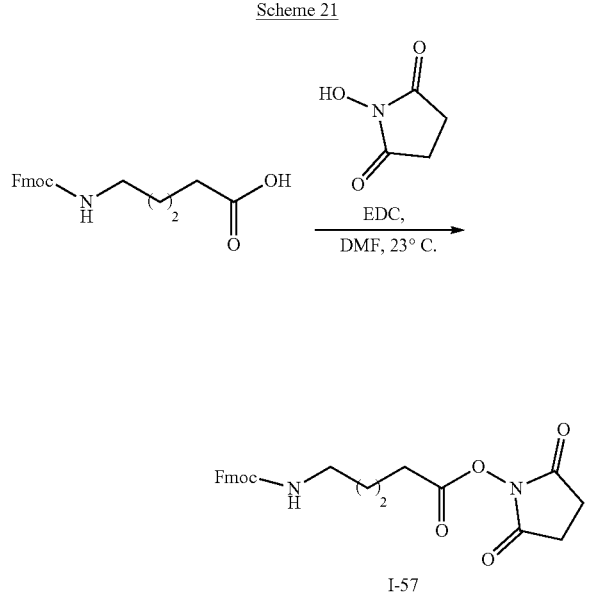

To a solution of N-Fmoc-4-aminopentanoic acid (106.4 mg, 0.31 mmol) in DMF (1 mL) was added HOSu (54.1 mg, 1.5 equiv.) and EDC (90.1 mg, 1.5 equiv.). The reaction mixture was stirred at ambient temperature for 4 hours, then purified by preparative HPLC ($H_2O$/MeCN with 0.1% TFA) to afford 131.2 mg (96% yield) of ester I-57 as a white solid.

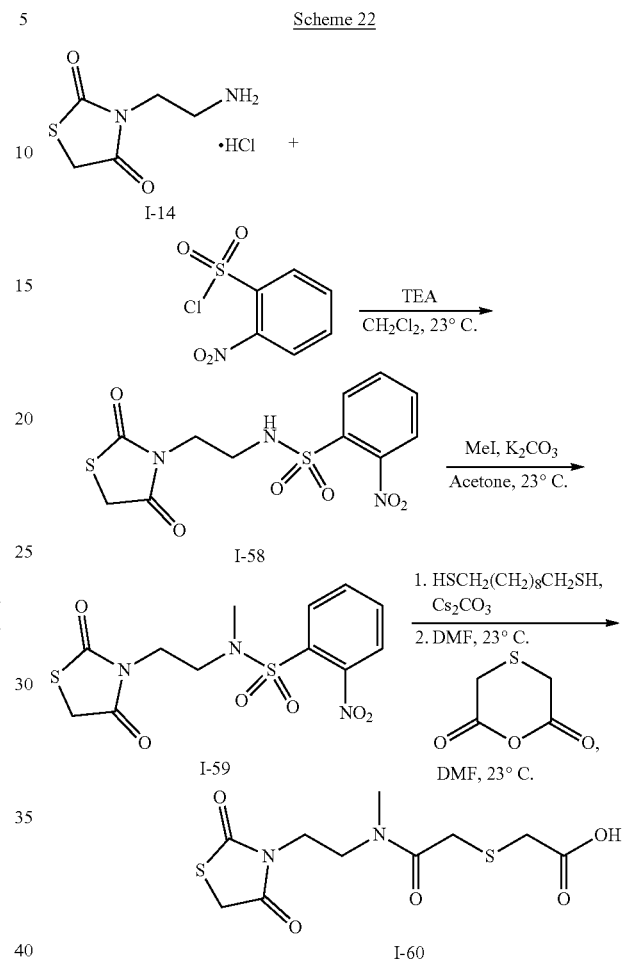

To a solution of amine salt I-14 (202.3 mg, 1.03 mmol) and TEA (0.43 mL, 3.0 equiv.) in DCM (5 mL) was added 2-nitrobenzenesulfonyl chloride (273.6 mg, 1.2 equiv.). The reaction mixture was stirred at ambient temperature for 3 hours, then concentrated and the residue purified by silica gel chromatography (40% EtOAc in hexanes) to afford sulfonamide I-58 (217.7 mg, 61% yield) as a pale yellow solid.

Sulfonamide I-58 (79.7 mg, 0.23 mmol) was dissolved in acetone (3 mL). Potassium carbonate (65.5 mg, 2.0 equiv.) was added, followed by methyl iodide (29 μL, 2.0 equiv.). The reaction mixture was stirred at ambient temperature for 1 hour, then carefully acidified by addition of 1M HCl (5 mL) and extracted with EtOAc (2×7 mL). The combined organic extracts were dried ($MgSO_4$) and concentrated to a residue, which was purified by preparative TLC (5:1 Toluene/MeCN, 3 elutions) to afford N-methylsulfonamide I-59 (47.7 mg, 58% yield) as a colorless oil.

To N-methylsulfonamide I-59 (47.7 mg, 0.13 mmol) in DMF (1.6 mL) was added 1,10-decanedithiol (41.1 mg, 1.5 equiv.) and cesium carbonate (64.8 mg, 1.5 equiv.). The reaction mixture was stirred at ambient temperature for 4 hours and then filtered. Thiodiglycolic anhydride (26.3 mg, 1.5 equiv.) was added to the filtrate and the reaction mixture maintained at ambient temperature for 2 hours and then diluted with H$_2$O (0.5 mL). The slurry was clarified by centrifugation and the supernatant was purified directly by preparative HPLC (H$_2$O/MeCN with 0.1% TFA) to afford 14.4 mg (35% yield) of I-60. ESI-MS found 307.1, C$_{10}$H$_{15}$N$_2$O$_5$S$_2$(MH$^+$) requires 307.0.

Synthesis of I-61 is Depicted in Scheme 23

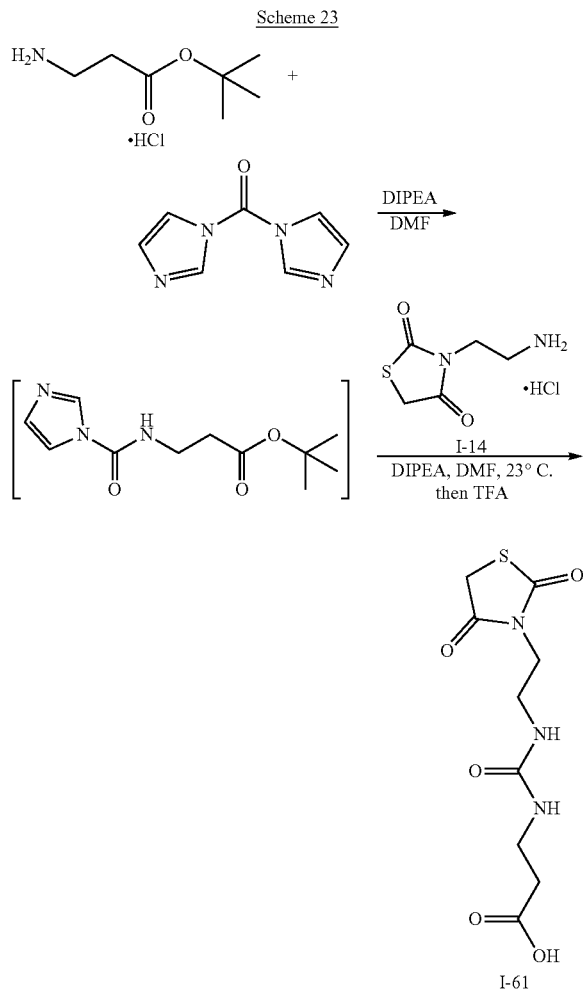

To a solution of beta-alanine-tert-butyl ester hydrochloride (221.3 mg, 1.22 mmol) and CDI (197.5 mg, 1.0 equiv.) in DMF (3 mL) was added DIPEA (1.1 mL, 5.0 equiv). The reaction mixture was stirred for 2 hours, and amine hydrochloride I-14 (239.5 mg, 1.0 equiv.) was added. The reaction mixture was heated to 40° C. for 18 hours, and then concentrated under reduced pressure. TFA (5 mL) was added to the residue. The reaction mixture was maintained at ambient temperature for 2 hours, then concentrated under reduced pressure, and purified by preparative HPLC (H$_2$O/MeCN with 0.1% TFA) to afford 17 mg (5% yield) of I-61 as a colorless oil. ESI-MS found 276.3, C$_9$H$_{14}$N$_3$O$_5$S (MH$^+$) requires 276.1.

Synthesis of I-62 is Depicted in Scheme 24

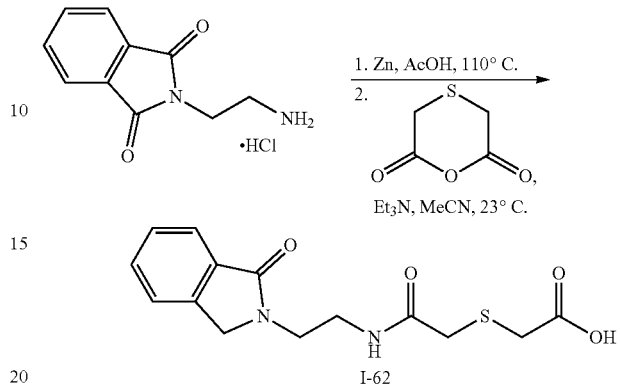

2-(2-Aminoethyl)isoindoline-1,3-dione hydrochloride (316.1 mg, 1.395 mmol) was dissolved in glacial AcOH (7 mL). Zinc dust (912.2 mg, 10 equiv.) was added, and the reaction mixture was heated to 110° C. for 18.5 hours, filtered hot, and concentrated under reduced pressure to afford the crude reduction product (900 mg). Half of this material was dissolved in MeCN (5 mL). Thiodiglycolic anhydride (120 mg, 0.91 mmol) was added, followed by triethylamine (486 µL, 5 equiv.). The reaction mixture was stirred at ambient temperature for 16 hours, concentrated, and purified by preparative HPLC (H$_2$O/MeCN with 0.1% TFA) to afford 20.4 mg (10% yield) of I-62 as a colorless oil. ESI-MS found 309.2, C$_{14}$H$_{17}$N$_2$O$_4$S (MH$^+$) requires 309.1.

Synthesis of I-64 is Depicted in Scheme 25

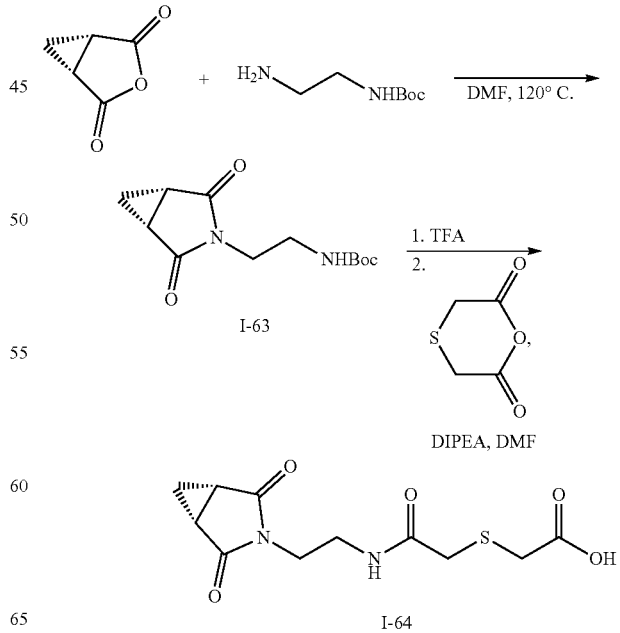

To a solution of (1R,5S)-3-oxabicyclo[3.1.0]hexane-2,4-dione (168.3 mg, 1.50 mmol) in DMF (5 mL) was added N-tert-butyloxycarbonyl ethylenediamine (360.8 mg, 1.5 equiv.). The reaction mixture was stirred at ambient temperature for 30 minutes, and then heated at 120° C. for 4.5 hours. The reaction mixture was then cooled and diluted with EtOAc (50 mL). The solution was washed with saturated aqueous NH$_4$Cl (20 mL) and water (3×20 mL). The combined washes were back-extracted with EtOAc (30 mL). The combined organic extracts were washed with brine (20 mL), dried (MgSO$_4$), and concentrated to afford a residue, which was purified by silica gel chromatography (0-60% EtOAc in hexanes) to afford 174.3 mg (46% yield) of carbamate I-63 as a white solid.

To 34.8 mg (0.137 mmol) of carbamate I-63 was added TFA (1 mL). The reaction mixture was maintained at ambient temperature for 30 minutes and then concentrated. The residue was re-dissolved in DMF (0.8 mL), and DIPEA (119.2 µL, 5.0 equiv.) was added, followed by thiodiglycolic anhydride (21.7 mg, 1.2 equiv.). The reaction mixture was maintained at ambient temperature for 2 hours and then purified by preparative HPLC (H$_2$O/MeCN with 0.1% TFA) to afford 31.6 mg (81% yield) of I-64. ESI-MS found 287.0, C$_{11}$H$_{15}$N$_2$O$_5$S (MH$^+$) requires 287.1.

Synthesis of I-66 is Depicted in Scheme 26

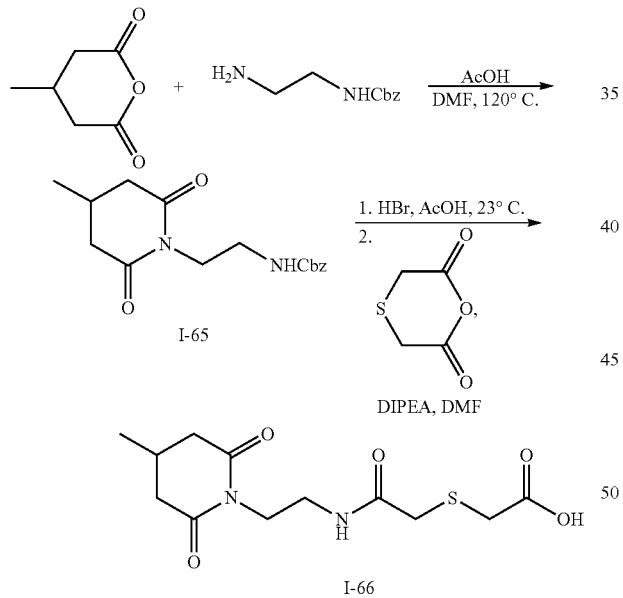

Scheme 26

I-65

I-66

To a solution of 3-methylglutaric anhydride (247 mg, 1.93 mmol) in DMF (1 mL) was added N-benzyloxycarbonyl ethylenediamine (374.4 mg, 1.0 equiv.). The reaction mixture was stirred at ambient temperature for 1.5 hours. AcOH (2 mL) was then added. The reaction mixture was heated to 110° C. for 21.5 hours and then cooled to ambient temperature. The reaction mixture was diluted with water (10 mL) and extracted with EtOAc (3×5 mL). The combined extracts were dried (MgSO$_4$) and concentrated to a residue. Purification by silica gel chromatography (0-63% EtOAc in hexanes) afforded carbamate I-65 (432.8 mg, 74% yield) as a white solid.

A solution of HBr in AcOH (33% v/v, 3 mL) was added to carbamate I-65 (104 mg, 0.34 mmol). The reaction mixture was sonicated for 5 minutes to solubilize the solids and then maintained at ambient temperature for 45 minutes, after which it was concentrated under reduced pressure. The residue was triturated with Et$_2$O (10 mL) and the supernatant was discarded. The residue was dissolved in DMF (1.2 mL). DIPEA (179 µL, 3.0 equiv.) was added, followed by thiodiglycolic anhydride (49.7 mg, 1.1 equiv.). The reaction mixture was maintained at ambient temperature for 1.5 hours and then purified by preparative HPLC (H$_2$O/MeCN with 0.1% TFA) to afford 69 mg (67% yield) of I-66. ESI-MS found 303.3, C$_{12}$H$_{18}$N$_2$O$_5$S (MH$^+$) requires 303.1.

Synthesis of (±)-I-67 is Depicted in Scheme 27

Scheme 27

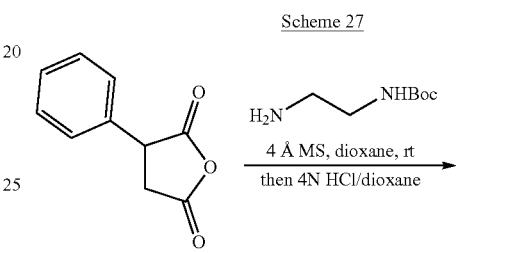

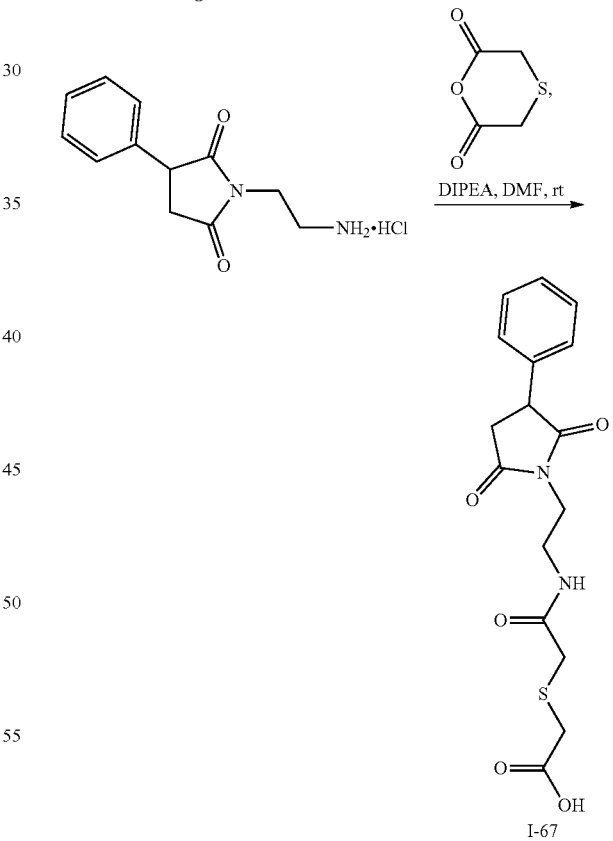

I-67

A solution of 3-phenyldihydrofuran-2,5-dione (71.2 mg, 0.40 mmol) and (2-aminoethyl)carbamate (64.1 mg, 1.0 equiv.) in 1 mL of anhydrous dioxane was stirred over 4 Å molecular sieves for 5.5 hours at ambient temperature. The reaction mixture was filtered and concentrated under reduced pressure. The residue obtained was dissolved in 4N HCl in dioxane (3 mL). After stirring at ambient temperature for 16 hours, the reaction mixture was concentrated under reduced pressure to afford the crude amine hydrochloride. Amine hydrochloride (39 mg, 0.153 mmol) was converted to 17.6 mg of acid I-67 (33% yield) following GP1. ESI-MS: Found 348.9, $C_{16}H_{18}N_2O_5S$ (MH⁻) requires 349.1.

I-68

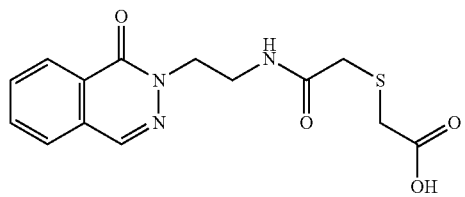

Prepared according to GP1. Yield: 68.1 mg (97%). ESI-MS found 322.2, $C_{14}H_{16}N_3O_4S$ (MH⁺) requires 322.1.

I-69

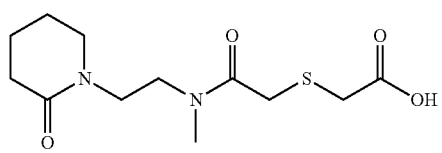

Prepared according to GP1. Yield: 48.1 mg (55%). ESI-MS found 289.2, $C_{15}H_{19}N_2O_4S$ (MH⁺) requires 289.1.

I-70

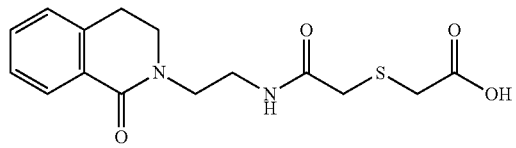

Prepared according to GP1. Yield: 37.7 mg (73%). ESI-MS found 323.2, $C_{12}H_{21}N_2O_4S$ (MH⁺) requires 323.1.

I-71

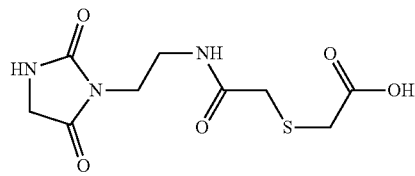

Prepared according to GP1. Yield: 9.9 mg (20%). ESI-MS found 276.1, $C_9H_{14}N_3O_5S$ (MH⁺) requires 276.1.

I-72

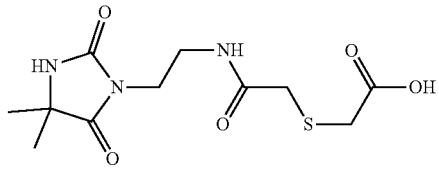

Prepared according to GP1. Yield: 60 mg (88%). ESI-MS found 304.2, $C_{11}H_{18}N_3O_5S$ (MH⁺) requires 304.1.

Synthesis of (±)-I-74 is Depicted in Scheme 28

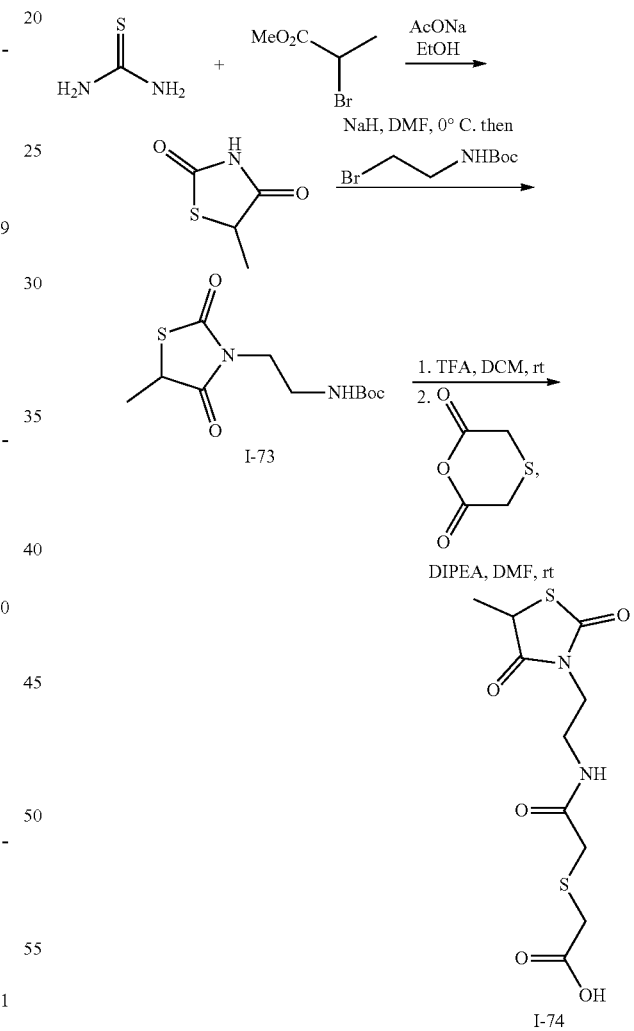

To a solution of methyl 2-bromopropanoate (200 µL, 1.79 mmol) in THF (9 mL) were added thiourea (177 mg, 1.3 equiv.) and sodium acetate (293 mg, 2.0 equiv.). The reaction mixture was heated under reflux for 20 hours. 6N HCl (4 mL) was then added. The reaction mixture was heated under reflux for an additional 16 hours and then allowed to cool to ambient temperature. Water was then added, and the reaction mixture was extracted with EtOAc. The combined organic extracts were washed with brine, dried (sodium sulfate), and concentrated. The residue obtained was subjected to silica gel chromatography (0 to 7% MeOH in DCM) to afford 235 mg of 5-methylthiazolidine-2,4-dione as a clear oil (>95% yield).

To a solution of 5-methylthiazolidine-2,4-dione (112 mg, 0.854 mmol) in DMF (6 mL) at 0° C. was added sodium hydride (41 mg of a 60% dispersion in mineral oil, 1.2 equiv.), and the resulting slurry was stirred for 30 minutes. A solution of tert-butyl (2-bromoethyl)carbamate (304 mg, 1.6 equiv.) in DMF (1 mL) was then added and the reaction mixture was allowed to warm to ambient temperature and stirred for two hours. The reaction was quenched with 45 mL of saturated NH$_4$Cl solution and then extracted three times with EtOAc. The combined organic extracts were washed with brine, dried (Na$_2$SO$_4$), and concentrated in vacuo to afford a residue, which was purified by silica gel chromatography to afford 202 mg (86% yield) of carbamate I-73. Deprotection of carbamate I-73 in TFA/DCM (1:1 v/v) for 2 hours at ambient temperature was followed by concentration of the reaction mixture in vacuo to give a crude trifluoroacetate salt, which was converted to 99.9 mg of acid I-74 (44% yield) following GP1. ESI-MS: Found 305.1, C$_{10}$H$_{13}$N$_2$O$_5$S$_2$(M−H)$^-$ requires 305.0.

Synthesis of I-74 is Depicted in Scheme 29

To a solution of 5,5-dimethylthiazolidine-2,4-dione (163 mg, 1.12 mmol) and tert-butyl (2-bromoethyl)carbamate (377 mg, 1.5 equiv.) in 5 mL of anhydrous DMF was added potassium carbonate (309 mg, 2.0 equiv.), and the resulting suspension was stirred for 18 hours at ambient temperature. The reaction mixture was diluted with 50 mL of EtOAc. The organic phase was washed twice with water, brine, dried over sodium sulfate, and concentrated in vacuo to afford a residue, which was purified by silica gel chromatography to afford 275 mg (83% yield) of carbamate I-75. Deprotection of carbamate I-73 in TFA/DCM (1:1 v/v) for two hours at ambient temperature was followed by concentration of the reaction mixture in vacuo to give a crude trifluoroacetate salt. This amine TFA salt (66 mg, ca. 0.218 mmol) was converted to 36 mg of acid I-76 (52% yield) following GP1. ESI-MS: Found 319.0, C$_{11}$H$_{15}$N$_2$O$_5$S$_2$(M−H)$^-$ requires 319.1.

Synthesis of I-79 and I-80 is Depicted in Scheme 30

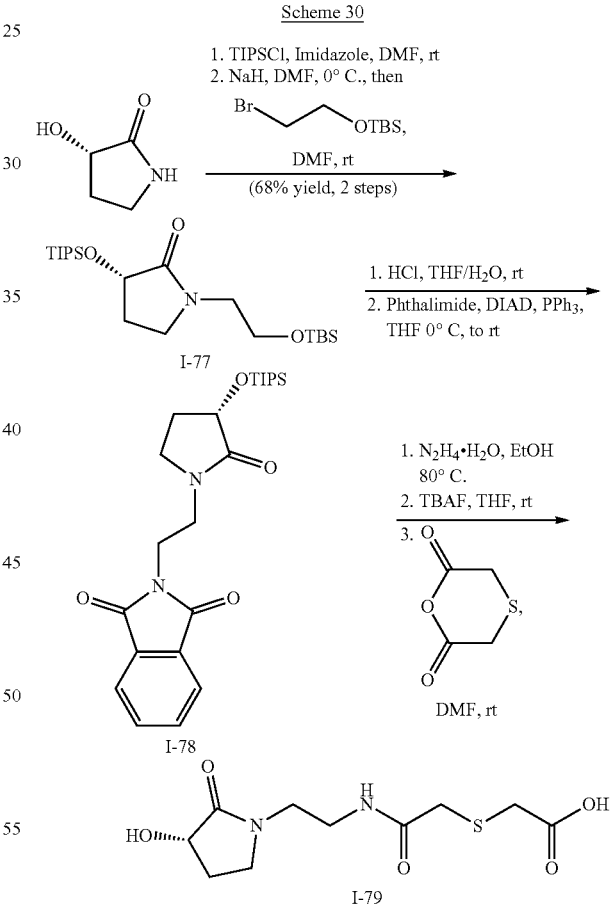

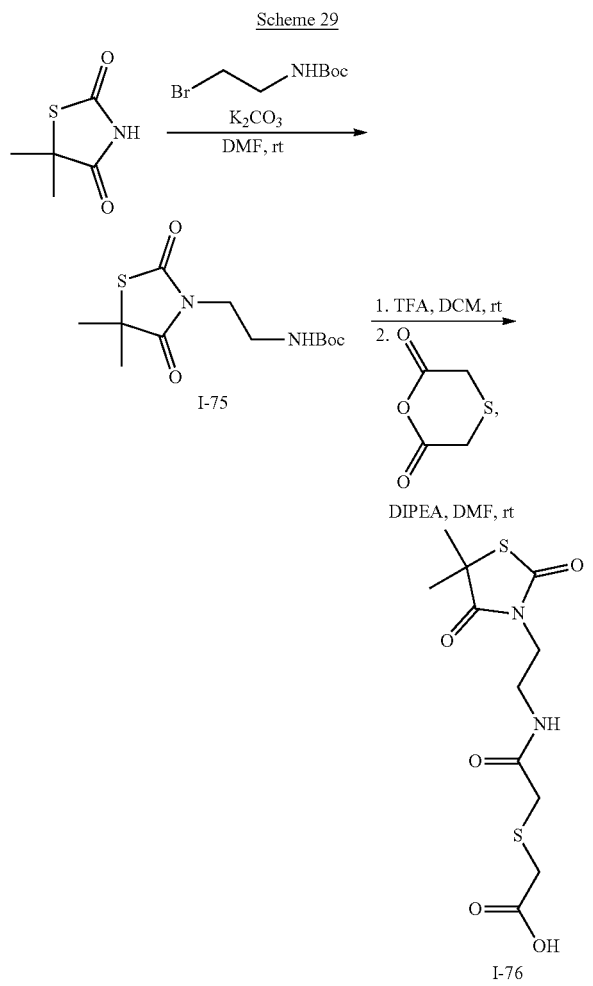

I-79: to a solution of (S)-3-hydroxypyrrolidinone (488 mg, 4.83 mmol) in DMF (10 mL), was added imidazole (493 mg, 1.5 equiv.), followed by triisopropylsilyl chloride (1.12 g, 1.2 equiv.). The reaction mixture was stirred at ambient temperature. On completion of the reaction, the reaction mixture was diluted with EtOAc (100 mL) and washed with H$_2$O (5×20 mL). The aqueous washes were combined and back-extracted with EtOAc (50 mL). The combined organic extracts were washed with brine (50 mL), dried (MgSO$_4$) and concentrated to afford a colorless oil. Purification by silica gel chromatography (12 g pre-packed column, eluting with 35-60% EtOAc in Hexanes) afforded 1.23 g (99% yield) of the TIPS-protected alcohol as a colorless oil.

The silyl ether was then dissolved in DMF (7 mL). This solution was added to a suspension of NaH (574 mg of 60% dispersion in mineral oil, 3.0 equiv.) in DMF (15 mL) that had been pre-cooled to 0-5° C. After 4 minutes, (2-bromoethoxy)(tert-butyl)dimethylsilane (1.37 g, 1.2 equiv.) was added. The reaction mixture was allowed to warm to ambient temperature. After 1.5 hours, the reaction mixture was quenched with saturated aqueous NH$_4$Cl (20 mL), and diluted with brine (100 mL). The aqueous phase was extracted with EtOAc (3×70 mL). The combined EtOAc extracts were dried (MgSO$_4$) and concentrated to afford a colorless oil. Purification by silica gel chromatography (24 g pre-packed column, eluting with 30% EtOAc in Hexanes) afforded 1.38 g (69% yield) of the bis-silyl ether I-77 as a colorless oil. This bis-silyl ether was dissolved in THF (12 mL). 1N HCl (4 mL) was then added. The reaction mixture was stirred at ambient temperature for 2 hours, then diluted with H$_2$O (100 mL) and extracted with EtOAc (3×60 mL). The combined organic extracts were dried (Na$_2$SO$_4$) and concentrated to afford a colorless oil. Purification by silica gel chromatography (24 g pre-packed column, eluting with 80-100% EtOAc in Hexanes) afforded 0.85 g (85% yield) of the deprotection product. This deprotected silyl ether was dissolved in THF (20 mL) in the presence of triphenylphosphine (1.11 g, 1.5 equiv.) and phthalimide (622 mg, 1.5 equiv.). The solution was cooled to 0-5° C., and DIAD (833 μL, 1.5 equiv.) was added. After 1.5 hours, the reaction mixture was concentrated to a yellow oil, which was purified by silica gel chromatography (40 g pre-packed column, eluting with 44% EtOAc in Hexanes) to afford 2.3 g of phthalimide I-78 (50% pure, with diisopropylhydrazine-1,2-dicarboxylate as impurity).

To a solution of phthalimide I-78 (254 mg, 0.59 mmol, ~50% pure, with diisopropylhydrazine-1,2-dicarboxylate as impurity) in EtOH (3 mL) was added hydrazine hydrate (183 μL, 10.0 equiv.). The reaction mixture was heated to 80° C. for 20 minutes, cooled and concentrated. The residue was re-suspended in MeOH (5 mL) and filtered. The filtrate was concentrated to a residue and TBAF (1 M in THF, 1.2 mL, 2.0 equiv. based on phthalimide I-78) was added. The reaction mixture was stirred at ambient temperature for 19 hours, then concentrated. The residue was re-dissolved in DMF (2 mL) and thiodiglycolic anhydride (78 mg, 1.0 equiv. based on phthalimide I-78) was added. After 2 hours, the reaction mixture was subjected to purification by preparative HPLC (H$_2$O/MeCN with 0.1% TFA) to afford 10.6 mg of the desired carboxylic acid I-79 as a colorless oil. ESI-MS: Found 277.2, C$_{10}$H$_{17}$N$_2$O$_5$S (MH$^+$) requires 277.1.

I-80: Analogous procedure was used for the preparation of the enantiomer, I-80. ESI-MS: Found 277.2, C$_{10}$H$_{17}$N$_2$O$_5$S (MH$^+$) requires 277.1.

Synthesis of I-82 is Depicted in Scheme 31

Scheme 31

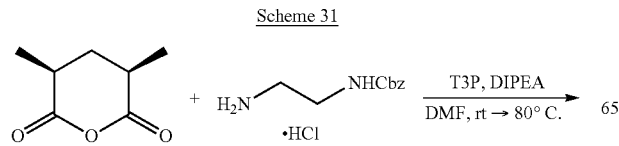

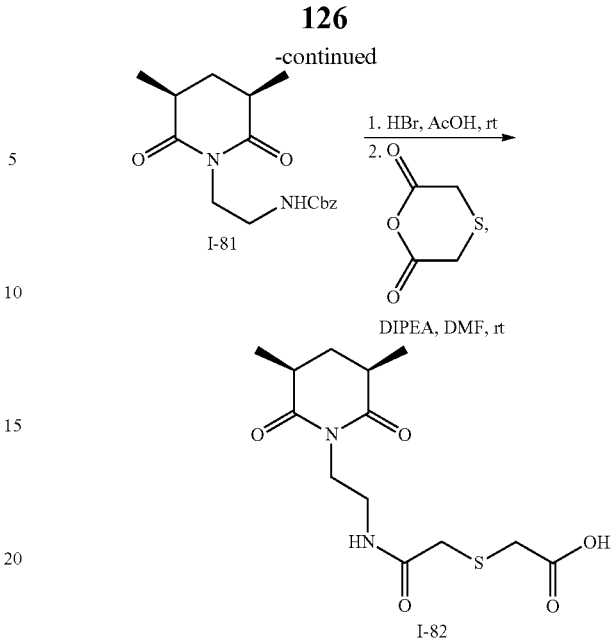

A slurry of (3R,5S)-3,5-dimethyldihydro-2H-pyran-2,6 (3H)-dione (102.8 mg, 0.723 mmol), benzyl (2-aminoethyl) carbamate hydrochloride (166.8 mg, 1.0 equiv.), T3P (50% w/v solution in DMF, 0.92 mL, 2.0 equiv.) and DIPEA (378 μL, 3.0 equiv.) in DMF (2 mL) was stirred at ambient temperature for 1 hour, then heated to 80° C. for 2 hours. The reaction mixture was cooled to ambient temperature, diluted with brine (10 mL), and then extracted with EtOAc (3×15 mL). The combined organic extracts were dried (MgSO$_4$) and concentrated to afford an oil, which was purified by silica gel chromatography (12 g pre-packed column, eluting at 51% EtOAc/Hexanes) to afford imide I-81 (77 mg, 33% yield) as a colorless oil.

To imide I-81 (77 mg, 0.24 mmol) was added 33% v/v HBr/AcOH (3 mL). The reaction mixture was maintained at ambient temperature for 1 hour and then concentrated. The residue was triturated with Et$_2$O (10 mL) and the Et$_2$O was discarded. The remaining residue was dissolved in DMF (1.5 mL). Thiodiglycolic anhydride (32 mg, 1.0 equiv. based on imide I-81) was added, followed by DIPEA (126 μL, 3.0 equiv.). The reaction mixture was maintained at ambient temperature for 20 hours and then purified by preparative HPLC (H$_2$O/MeCN with 0.1% TFA) to afford 59.4 mg (78% yield) of I-82 as a colorless oil. ESI-MS: Found 317.3, C$_{13}$H$_{21}$N$_2$O$_5$S (MH$^+$) requires 317.1.

Synthesis of I-85 is Depicted in Scheme 32

Scheme 32

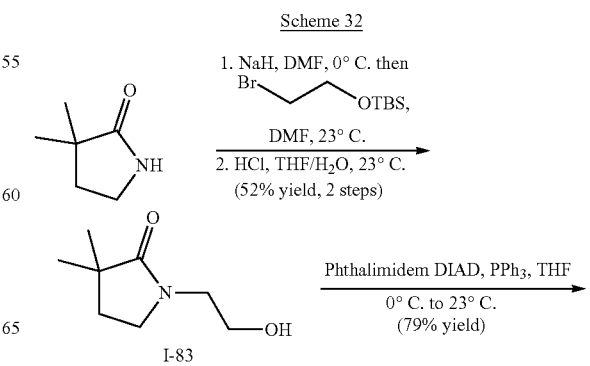

Synthesis of I-87 is Depicted in Scheme 33

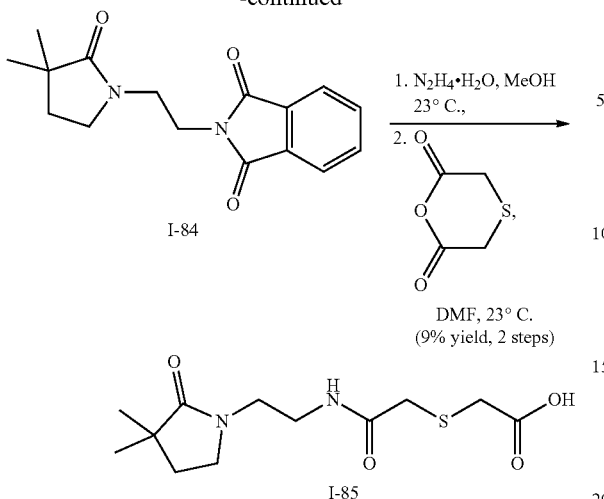

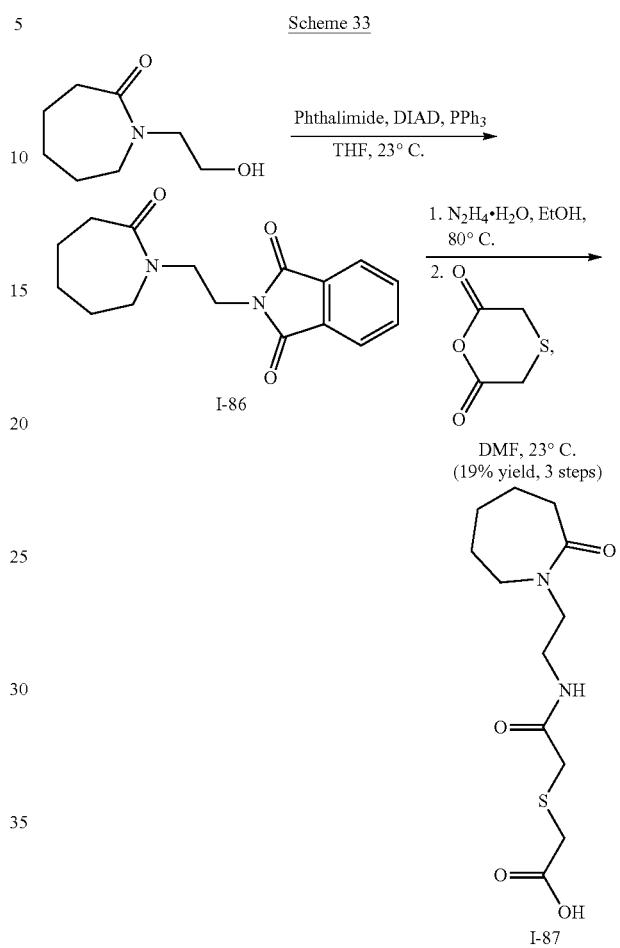

To a slurry of 447.7 mg (5.0 equiv.) of sodium hydride (60% dispersion in mineral oil) in DMF (5 mL) that had been cooled to 0-5° C. was added a solution of 2,2-dimethylpyrollidinone (253.3 mg, 2.238 mmol) in DMF (7 mL). The reaction mixture was stirred at 0-5° C. for 10 minutes and (2-bromoethoxy)(tert-butyl)dimethylsilane (642.5 mg, 1.2 equiv.) was added in one portion. The reaction mixture was stirred for 10 minutes at 0-5° C., then allowed to warm to ambient temperature. After 18 hours, the reaction mixture was cooled to 0-5° C., and the reaction was quenched with saturated aqueous $NH_4Cl$ (10 mL). The reaction mixture was diluted with 50% brine (100 mL) and extracted with EtOAc (3×50 mL). The organic extracts were combined, dried ($Na_2SO_4$), and concentrated to afford a colorless oil which was then dissolved in THF (12 mL). Aqueous HCl (1M, 4 mL) was added, and the reaction mixture was stirred at ambient temperature for 5 hours. The reaction was quenched with saturated aqueous $NaHCO_3$ (10 mL) and diluted with brine (50 mL), then extracted with EtOAc (3×50 mL). The organic extracts were combined, dried ($Na_2SO_4$) and concentrated to afford a colorless oil, which was purified by silica gel chromatography (Hexanes/Acetone 0-100% gradient) to afford intermediate alcohol I-83 (183.8 mg, 52% yield over 2 steps) as a colorless oil.

To a solution of alcohol I-83 (183.8 mg, 1.17 mmol), phthalimide (258 mg, 1.5 equiv.) and triphenylphosphine (460 mg, 1.5 equiv.) in THF (6 mL) that had been cooled to 0-5° C. was added DIAD (0.35 mL, 1.5 equiv.). The reaction mixture was allowed to warm to ambient temperature and concentrated after 2.5 hours. Purification of the resulting residue by silica gel chromatography (EtOAc) afforded phthalimide I-84 (263.2 mg, 79% yield) as a colorless oil.

To a solution of phthalimide I-84 (263.2 mg, 0.92 mmol) in MeOH (5 mL) was added hydrazine hydrate (0.29 mL, 10.0 Equiv). The reaction mixture was stirred at ambient temperature for 24 hours and then filtered. The filter cake was washed with MeOH (10 mL). The combined filtrate and wash were concentrated to a residue, which was re-dissolved in DMF (3 mL). Thiodiglycolic anhydride (121.5 mg, 1.0 equiv.) was added and the reaction mixture was stirred at ambient temperature for 4 hours, then purified by preparative HPLC (0-30% MeCN/25 mM $NH_4OAc$ gradient over 35 minutes) to afford 22.8 mg (9% yield, 2 steps) of I-85 as a colorless oil. ESI-MS: Found 289.2, $C_{12}H_{21}N_2O_4S$ (MH+) requires 289.1.

To a solution of 1-(2-hydroxyethyl)azepan-2-one (97 mg, 0.62 mmol), triphenylphosphine (242.9 mg, 1.5 equiv.), and phthalimide (136.1 mg, 1.5 equiv.) in THF (3 mL) at ambient temperature was added DIAD (0.18 mL, 1.5 equiv.). The reaction mixture was allowed to warm to ambient temperature and concentrated after 2.5 hours. Purification of the resulting residue by silica gel chromatography (EtOAc) afforded phthalimide I-86, which co-eluted with triphenylphosphine oxide. The phthalimide was dissolved in EtOH (10 mL) and hydrazine hydrate (0.19 mL, 10 equiv.) was added. The reaction mixture was heated to 80° C. for 1.5 hours and then cooled to ambient temperature and filtered. The filtrate was concentrated to afford a residue. DMF (3 mL) was added, and the suspension afforded was clarified by centrifugation. Thiodiglycolic anhydride (81.5 mg, 1.0 equiv.) was added to the supernatant and the reaction mixture was maintained at ambient temperature for 24 hours. Purification by preparative HPLC ($H_2O$/MeCN with 0.1% TFA) to afford 34.1 mg (19% yield, 3 steps) of I-87 as a colorless oil. ESI-MS: Found 289.2, $C_{12}H_{21}N_2O_4S$ (MH+) requires 289.1.

Synthesis of I-89 and I-90 is Depicted in Scheme 34

Synthesis of I-92 is Depicted in Scheme 35

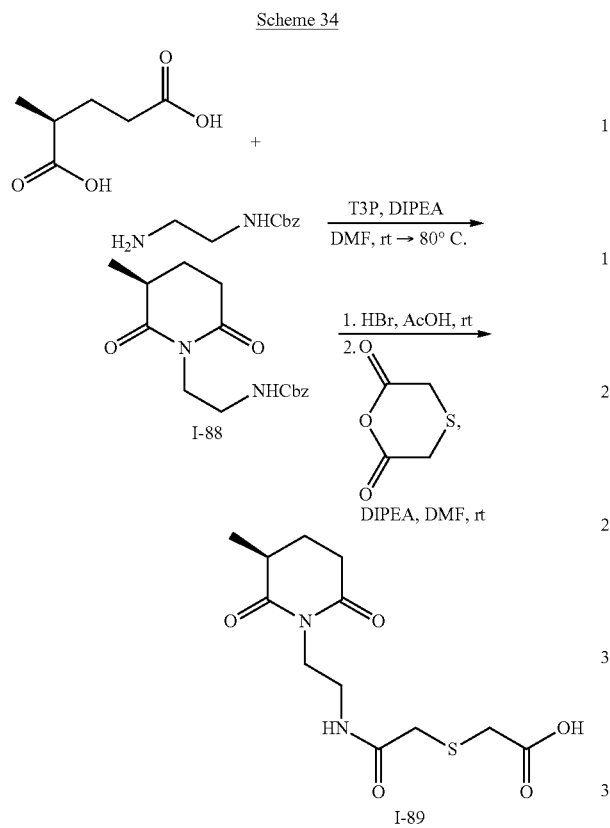

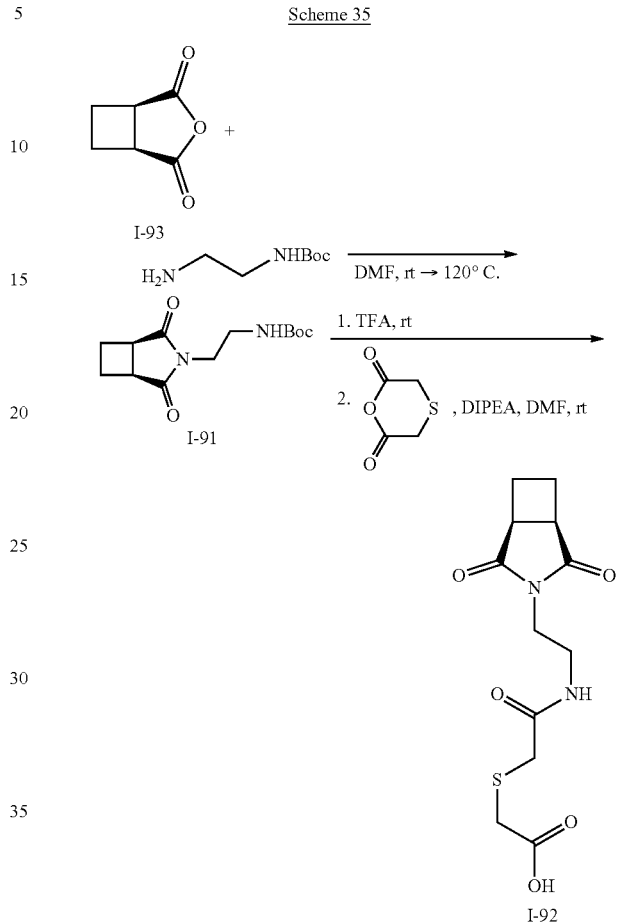

I-89: a slurry of (S)-2-methylglutaric acid (68.5 mg, 0.469 mmol), benzyl (2-aminoethyl)carbamate (91.1 mg, 1.0 equiv.), T3P (50% w/v solution in DMF, 1.5 mL, 5.0 equiv.), and DIPEA (817 µL, 10.0 equiv.) in DMF (3 mL) was stirred at ambient temperature for 63 hours and then heated to 80° C. for 4 hours. The reaction mixture was cooled and diluted with EtOAc (10 mL) and saturated aqueous NaHCO$_3$ (10 mL). The phases were separated, and the aqueous phase was extracted with EtOAc (2×10 mL). The combined organic extracts were dried (MgSO$_4$) and concentrated to afford a colorless oil, which was purified by silica gel chromatography to afford imide I-88 (25.8 mg, 18% yield) as a colorless oil.

To imide I-88 (25.8 mg, 0.085 mmol) was added 33% v/v HBr/AcOH (2 mL). The reaction mixture was maintained at ambient temperature for 1 hour and then concentrated. The residue was triturated with Et$_2$O (10 mL) and the Et$_2$O was discarded. The remaining residue was dissolved in DMF (1 mL). Thiodiglycolic anhydride (13.4 mg, 1.2 equiv. based on imide I-88) was added, followed by DIPEA (74 µL, 5.0 equiv.). The reaction mixture was maintained at ambient temperature for 16 hours and then purified by preparative HPLC (H$_2$O/MeCN with 0.1% TFA) to afford 20.6 mg (81% yield) of I-89 as a colorless oil. ESI-MS: Found 303.2, C$_{12}$H$_{19}$N$_2$O$_5$S (MH$^+$) requires 303.1.

I-90: an analogous procedure was used to prepare enantiomeric building block I-90. Yield: 43 mg (62%). ESI-MS: Found 303.2, C$_{12}$H$_{19}$N$_2$O$_5$S (MH$^+$) requires 303.1.

To a solution of anhydride I-93 (106.8 mg, 0.85 mmol) in DMF (2 mL) was added tert-butyl (2-aminoethyl)carbamate (203.5 mg, 1.5 equiv.). The reaction mixture was maintained at ambient temperature for 1.5 hours and then heated to 120° C. for 6 hours and 90° C. for 60 hours. The reaction mixture was cooled, diluted with H$_2$O (10 mL), and then extracted with EtOAc (3×6 mL). The combined organic extracts were dried (MgSO$_4$) and concentrated to afford a brown solid, which was purified by silica gel chromatography (12 g pre-packed column, 63% EtOAc/Hexanes) to afford imide I-91 (165.3 mg, 73% yield) as a colorless oil.

To imide I-91 (43.3 mg, 0.161 mmol) was added TFA (2 mL). After 15 minutes at ambient temperature the reaction mixture was concentrated to a residue, which was redissolved in DMF (1 mL). Thiodiglycolic anhydride (23.5 mg, 1.1 equiv. based on imide I-91) was added, followed by DIPEA (84 µL, 3.0 equiv.). The reaction mixture was maintained at ambient temperature for 24 hours and then purified by preparative HPLC (H$_2$O/MeCN with 0.1% TFA) to afford 42.4 mg (87% yield) of I-92 as a colorless oil. ESI-MS: Found 301.2, C$_{12}$H$_{17}$N$_2$O$_5$S (MH$^+$) requires 301.1.

Synthesis of I-94 is Depicted in Scheme 36

Scheme 36

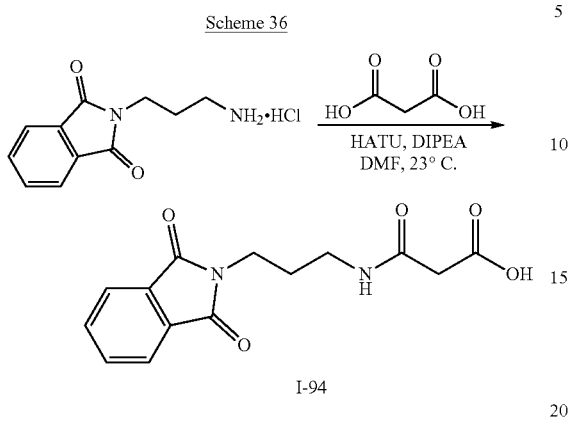

I-94

To a solution of 2-(3-aminopropyl)isoindoline-1,3-dione hydrochloride (49.8 mg, 0.207 mmol), malonic acid (43.1 mg, 2.0 equiv.), and DIPEA (0.11 mL, 3.0 equiv.) in DMF (0.9 mL) was added HATU (157.3 mg, 2.0 equiv.). The reaction mixture was agitated at ambient temperature for 3 hours and then purified by preparative HPLC (H$_2$O/MeCN with 0.1% TFA) to afford 6.7 mg (11% yield) of I-94 as a colorless oil. ESI-MS: Found 291.1, $C_{14}H_{15}N_2O_5$ (MH$^+$) requires 291.1.

Synthesis of I-96 is Depicted in Scheme 37

Scheme 37

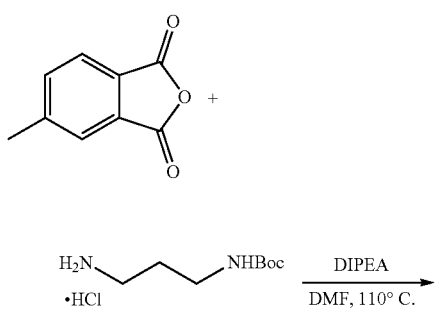

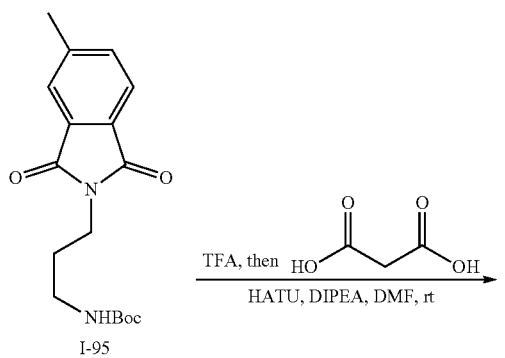

I-95

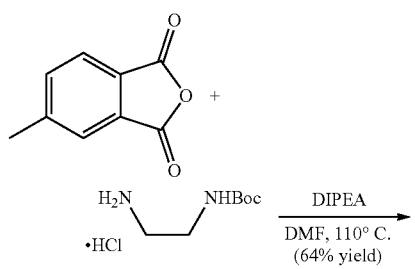

I-96

5-methylisobenzofuran-1,3-dione (305 mg, 1.88 mmol) was dissolved in DMF (5 mL). Tert-butyl (3-aminopropyl) carbamate hydrochloride (595 mg, 1.5 equiv.) was added, followed by DIPEA (983 µL, 3.0 equiv.). The reaction mixture was heated to 110° C. for 18 hours. The reaction mixture was then cooled and diluted with EtOAc (50 mL). The EtOAc solution was washed with saturated aq. NH$_4$Cl (20 mL) and H$_2$O (3×20 mL). The aqueous washes were back-extracted with EtOAc (30 mL). The combined organic extracts were washed with brine (20 mL), dried (MgSO$_4$), and concentrated to a solid which was purified by silica gel chromatography (39% EtOAc/Hexanes) to afford 481 mg (80% yield) of intermediate carbamate I-95 as a white solid.

To carbamate I-95 (40.6 mg, 0.128 mmol) was added TFA (1 mL). After 30 minutes at ambient temperature, the TFA was removed in vacuo. Malonic acid (26.5 mg, 2.0 equiv.) was added, followed by DIPEA (67 µL, 3.0 equiv.) and HATU (97 mg, 2.0 equiv.) The reaction mixture was stirred at ambient temperature for 1 hour, then purified directly by HPLC (H$_2$O/MeCN with 0.1% TFA) to afford 13.1 mg (34% yield) of I-96. ESI-MS found 305.3, $C_{15}H_{17}N_2O_5$ (MH$^+$) requires 305.1.

Synthesis of I-98 is Depicted in Scheme 38

Scheme 38

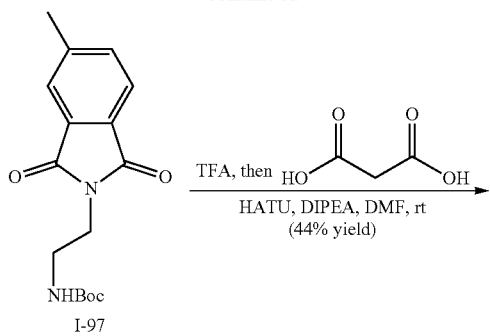

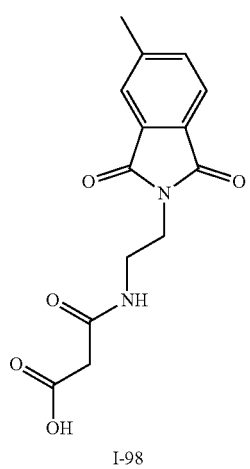

Using a procedure similar to that described for the preparation of I-96, 295 mg (1.82 mmol) of 5-methylisobenzofuran-1,3-dione afforded 356.7 mg (64% yield) of phthalimide I-97. Phthalimide I-97 (44.2 mg, 0.145 mmol) then afforded 18.5 mg (44% yield, 2 steps) of I-98. ESI-MS found 291.2, $C_{14}H_{15}N_2O_5$ (MH$^+$) requires 291.1.

Synthesis of I-100 is Depicted in Scheme 39

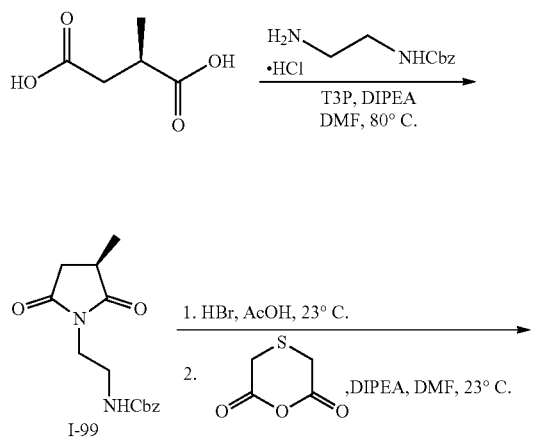

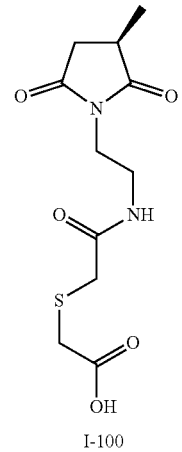

To (R)-2-methylsuccinic acid (174.5 mg, 1.32 mmol) in DMF (2 mL) was added benzyl (2-aminoethyl)carbamate hydrochloride (304.7 mg, 1.0 equiv.), DIPEA (0.69 mL, 3.0 equiv.), and propylphosphonic anhydride (50% in DMF, 2.5 mL, 3.0 equiv.). The reaction mixture was heated to 80° C. for 1.5 hours, then cooled and concentrated. The resulting residue was purified by silica gel chromatography to afford 48 mg (13%) of the intermediate succinimide I-99. HBr (33% solution in AcOH, 2 mL) was added to I-99. The reaction mixture was maintained at ambient temperature for 45 minutes, then concentrated under reduced pressure. The residue afforded was triturated with Et$_2$O (10 mL) and then redissolved in DMF (0.7 mL). DIPEA (86 μL, 3.0 equiv) was added, followed by thiodiglycolic anhydride (21.8 mg, 1.0 equiv.). The reaction mixture was maintained at ambient temperature for 3 hours and then purified by preparative HPLC (0-100% acetonitrile in water with 0.1% TFA) to afford 15.3 mg (32% yield) of I-100. ESI-MS found 289.2, $C_{11}H_{17}N_2O_5S$ (MH$^+$) requires 289.1.

I-101: an analogous procedure was used to synthesize enantiomeric building block I-101. Yield 16.2 mg (6% yield, 3 steps). ESI-MS found 289.2, $C_{11}H_{17}N_2O_5S$ (MH$^+$) requires 289.1.

Synthesis of I-104 is Depicted in Scheme 40

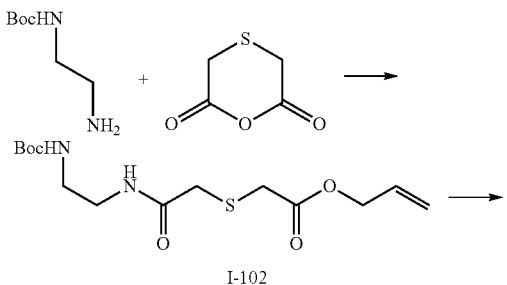

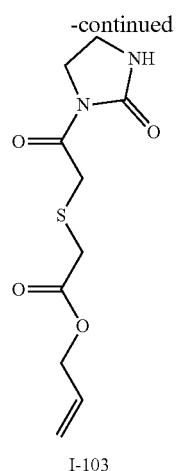

I-103

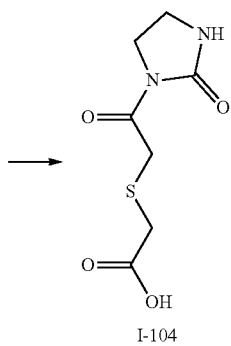

I-104

A solution of tert-butyl (2-aminoethyl)carbamate (415 mg, 2.6 mmol) and thiodiglycolic anhydride (376 mg, 1.1 equiv.) in 5 mL of DMF was treated with TEA (1.27 mL, 1.4 equiv.). The reaction mixture was stirred for 3 hours at ambient temperature at which time allyl bromide (336 μL, 1.5 equiv.) was added and the reaction mixture was stirred for an additional 72 hours. The reaction mixture was then diluted with EtOAc (40 mL). The organic phase was washed with saturated aqueous $NaHCO_3$, brine, dried ($Na_2SO_4$), and concentrated in vacuo. Purification by flash chromatography (0% to 70% EtOAc in hexanes) afforded 250 mg of I-102 as a clear oil (75% yield). ESI-MS found 331.2, $C_{14}H_{23}N_2O_5S$ (M–H)$^-$ requires 331.1

A solution of I-102 (135 mg, 0.406 mmol) in 1 mL of dioxane was treated with 3 mL of 4N HCl/dioxane and stirred for 2 hours. The reaction mixture was concentrated under reduced pressure and then placed under high vacuum for 8 hours to afford 112 mg of intermediate hydrochloride salt, a portion of which (84.1 mg, 0.313 mmol) was suspended in 5 mL of DCM, treated with DIPEA (223 μL, 4.0 equiv.) and sonicated for 5 minutes. The resulting suspension was filtered through a plug of cotton, treated with proton sponge (201 mg, 3.0 equiv.), and added to a solution of triphosgene (56 mg, 0.6 equiv.) in 5 mL of DCM at 0° C. under $N_2$. After stirring for 4 hours at 0-5° C., the reaction mixture was allowed to warm to ambient temperature, and stirring was continued another 24 hours. The reaction mixture was then diluted with 45 mL of DCM. The organic phase was washed twice with 1M aqueous $NaHSO_4$, brine, dried over $Na_2SO_4$ and concentrated in vacuo. The resulting residue was purified by preparative HPLC (0-100% acetonitrile in water with 0.1% TFA) to afford 32 mg of I-103 as a white solid (31% yield). ESI-MS found 259.2, $C_{10}H_{13}N_2O_4S$ (MH$^+$) requires 259.1

A solution of I-103 (42 mg, 0.161 mmol) in 4 mL of DCM was treated with Pd(PPh$_3$)$_4$ (46.6 mg, 0.25 equiv.) and phenylsilane (79 μL, 4.0 equiv.) and the reaction mixture was stirred at ambient temperature for one hour. The reaction mixture was then concentrated in vacuo and the residue was suspended in 2.5 mL of 3:1 v/v DMSO/$H_2O$ and filtered to give a clear solution, which was then purified directly by preparative HPLC (0-100% acetonitrile in water with 0.1% TFA) to afford 18.5 mg of I-104 as a white solid (53% yield). ESI-MS found 217.1, $C_7H_9N_2O_4S$ (MH$^-$) requires 217.0.

Synthesis of I-106 is Depicted in Scheme 41

Scheme 41

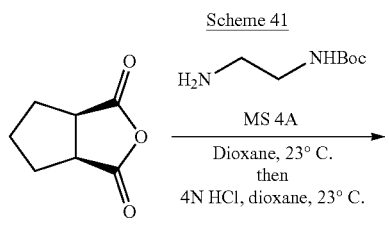

I-107

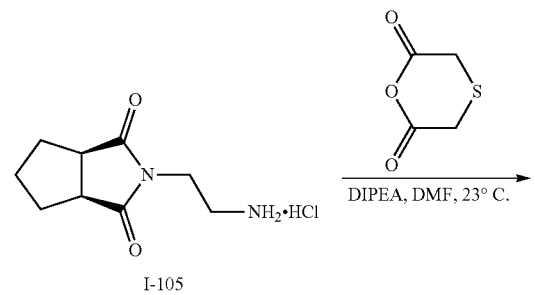

I-105

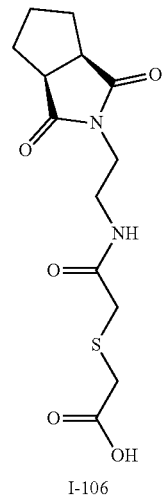

I-106

A solution of anhydride I-107 (42 mg, 0.300 mmol) and tert-butyl (2-aminoethyl)carbamate (57.6 mg, 1.2 equiv.) in 3 mL of anhydrous dioxane were stirred over 4 Å molecular sieves for 1 hour and then decanted. 4N hydrogen chloride in dioxane (2 mL) was added to the supernatant and the reaction mixture was stirred for 16 hours and then concentrated in vacuo to afford the crude hydrochloride salt I-105. The crude hydrochloride salt was converted to 27.3 mg of acid I-106 (29% yield over 3 steps) using GP1. ESI-MS found 312.9, $C_{13}H_{18}N_2O_5S$ (MH$^-$) requires 313.1.

Synthesis of I-109 is Depicted in Scheme 42

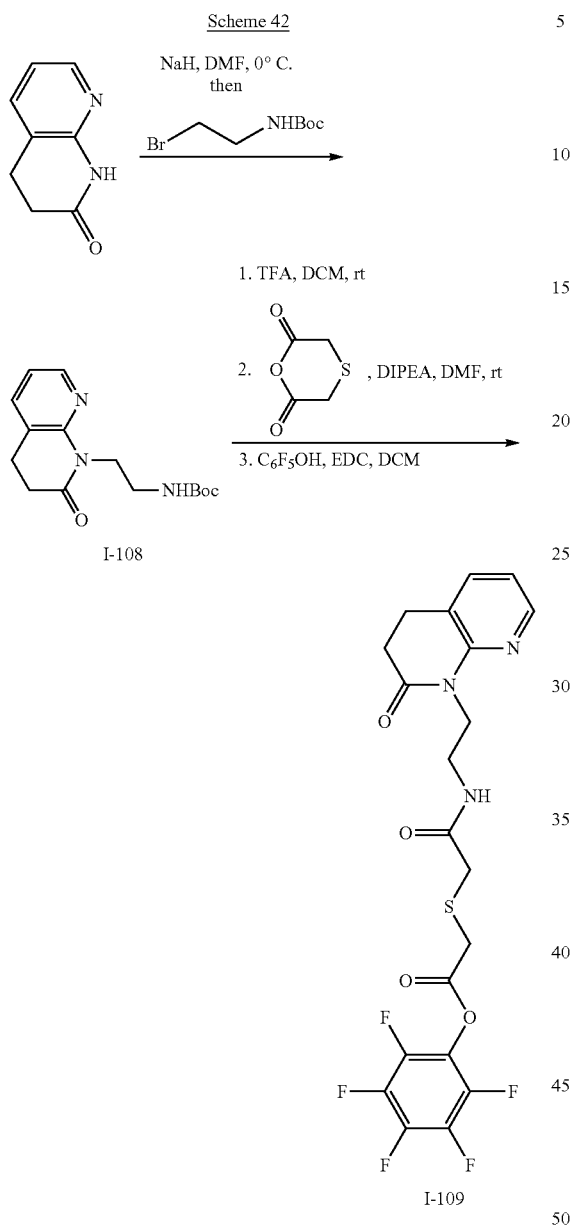

To a solution of 3,4-dihydro-1,8-naphthyridin-2(1H)-one (106 mg, 0.714 mmol) in 2.4 mL of anhydrous DMF at 0° C. was added sodium hydride (34.4 mg of a 60% dispersion in mineral oil, 1.2 equiv.), and the resulting suspension was stirred 10 minutes. Tert-butyl (2-bromoethyl)carbamate (176 mg, 1.1 equiv.) was added in two portions and the solution was allowed to warm to ambient temperature and stirred for two hours. The reaction was quenched with 25 mL of saturated ammonium chloride solution and then extracted three times with EtOAc. The combined organic extracts were washed with brine, dried over sodium sulfate and concentrated in vacuo to afford a residue, which was purified by silica gel chromatography to afford 104 mg (50% yield) of carbamate I-108. Carbamate I-108 (84 mg, 0.287 mmol) was deprotected with TFA/DCM (1:1 v/v) for two hours at ambient temperature. The reaction mixture was concentrated under reduced pressure to afford a crude trifluoroacetate salt, which was dissolved in 1 mL of DMF and 5 mL of DCM and treated with a solution of thiodiglycolic anhydride (37 mg, 1.0 equiv. based on carbamate I-108) and DIPEA (200 μL, 4.0 equiv.) in 1 mL of DMF. The reaction mixture was stirred for 2 hours. A solution of EDC (72 mg, 1.3 equiv.) and pentafluorophenol (67 mg, 1.3 equiv.) in 1 mL of DMF was then added; stirring was continued for 18 hours. The reaction mixture was then diluted with 50 mL of DCM. the organic phase was washed with 1 N aqueous NaHSO$_4$ then brine, dried over Na$_2$SO$_4$ and concentrated under reduced pressure to afford a residue, which was purified by flash chromatography (0 to 80% ethyl acetate in hexanes) to afford 97 mg of ester I-109 (69% yield). ESI-MS found 489.9, C$_{20}$H$_{15}$F$_5$N$_3$O$_4$S (M–H)$^-$ requires 490.1.

Synthesis of I-111 is Depicted in Scheme 43

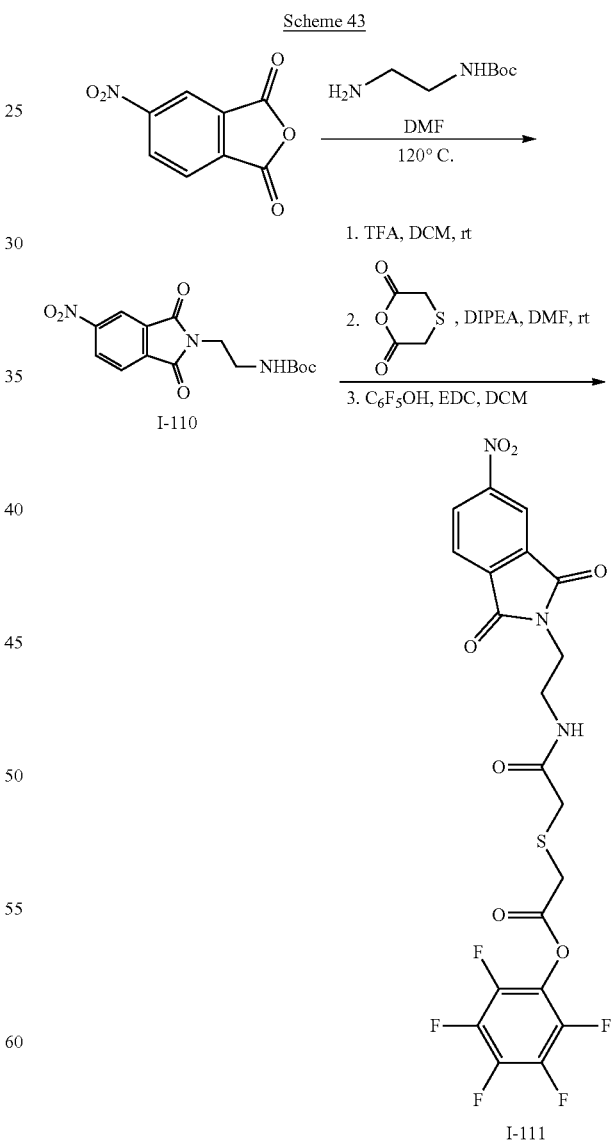

A solution of 5-nitroisobenzofuran-1,3-dione (295 mg, 1.53 mmol) and tert-butyl (2-aminoethyl)carbamate (367 mg, 1.5 equiv.) in 9 mL of anhydrous DMF was stirred for 30 minutes at ambient temperature and then for 2 hours at 120° C. The reaction mixture was allowed to cool to ambient temperature and diluted with 40 mL of EtOAc. The organic phase was washed with water and brine. The combined organic phase was then dried over sodium sulfate and concentrated under reduced pressure to a residue, which was purified by silica gel chromatography to afford 302 mg (90% yield) of carbamate I-110.

Carbamate I-110 (132 mg, 0.395 mmol) was deprotected with TFA/DCM (1:1 v/v) for two hours at ambient temperature, and the reaction mixture was concentrated under reduced pressure to afford the crude trifluoroacetate salt. The crude triflouroacetate salt was dissolved in 4 mL of DMF and treated with a solution of thiodiglycolic anhydride (58.5 mg, 1.1 equiv. based on carbamate I-110) and DIPEA (85 µL, 1.2 equiv.) in 1 mL of DCM. The reaction mixture was stirred for 18 hours and then a solution of EDC (68 mg, 0.8 equiv.) and pentafluorophenol (58 mg, 0.8 equiv.) in 1 mL of DMF was added and stirring was continued for 1 hour. The reaction mixture was then diluted with 30 mL of DCM. The organic phase was washed with 1 N aqueous NaHSO$_4$ and brine, dried over Na$_2$SO$_4$, and concentrated under reduced pressure to afford a residue which was purified by flash chromatography (0 to 60% ethyl acetate in hexanes) to afford 111 mg of ester I-111 (46% yield). ESI-MS found 533.8, C$_{20}$H$_{12}$F$_5$N$_3$O$_7$S (MH$^+$) requires 534.0.

Synthesis of I-113 is Depicted in Scheme 44

Scheme 44

A suspension of 4-nitroisobenzofuran-1,3-dione (145 mg, 0.765 mmol) and tert-butyl (2-aminoethyl)carbamate (184 mg, 1.5 equiv.) were stirred over 4 Å molecular sieves in a sealed tube at 130° C. for 16 hours. The reaction mixture was filtered, concentrated in vacuo, and purified by silica gel chromatography to afford 82 mg (32% yield) of carbamate I-112 which was deprotected in 1:1 DCM/TFA for two hours at ambient temperature followed by concentration in vacuo to give a crude trifluoroacetate salt. The salt was dissolved in 4 mL of DMF and treated with a solution of thiodiglycolic anhydride (32 mg, 0.24 mmol) and DIPEA (48 µL, 0.27 mmol) in 1 mL of DMF. The reaction mixture was stirred for 2 hours and then a solution of EDC (68 mg, 0.32 mmol) and pentafluorophenol (58 mg, 0.32 mmol) in 1 mL of DMF was added; stirring was continued for one hour. The reaction mixture was then diluted with 30 mL DCM, and the organic phase was washed with 1 N NaHSO$_4$ and brine, dried over Na$_2$SO$_4$, and concentrated under reduced pressure to afford a residue which was purified by flash chromatography (0 to 60% ethyl acetate in hexanes) to afford 50 mg of I-113 (39% yield). ESI-MS found 533.8, C$_{20}$H$_{12}$F$_5$N$_3$O$_7$S (MH$^+$) requires 534.0.

Synthesis of I-115 is Depicted in Scheme 45

Scheme 45

-continued

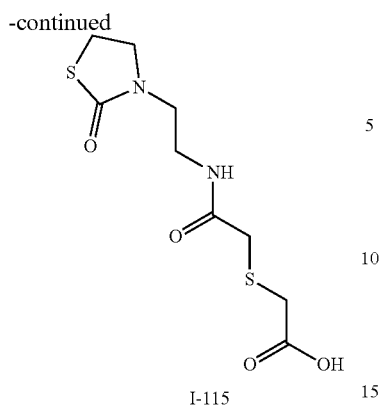

I-115

To a solution of thiazolidin-2-one (103 mg, 1.0 mmol) in 2 mL of anhydrous DMF at 0° C. was added sodium hydride (48 mg of a 60% dispersion in mineral oil, 1.2 equiv.) and the resulting suspension was stirred for 10 minutes. Tert-butyl (2-bromoethyl)carbamate (356 mg, 1.6 equiv.) in 2 mL of anhydrous DMF was added, and the solution was allowed to warm to ambient temperature and stirred for two hours. The reaction was quenched with 45 mL of saturated ammonium chloride solution. The reaction mixture was extracted three times with EtOAc. The combined organic extracts were washed with brine, dried over sodium sulfate, and concentrated in vacuo to afford a residue which was purified by silica gel chromatography to afford 125 mg (51% yield) of carbamate I-114. I-114 was deprotected in TFA/DCM (1:1 v/v) for two hours at ambient temperature followed by concentration in vacuo to give a crude trifluoroacetate salt, which was converted to 107 mg of acid I-115 (76% yield) following GP1. ESI-MS found 279.1 $C_9H_{14}N_2O_4S_2(MH^+)$ requires 279.0.

Synthesis of I-118 is Depicted in Scheme 46

Scheme 46

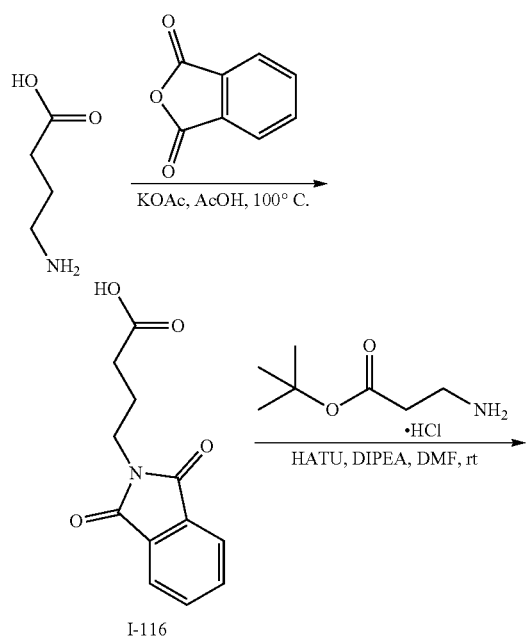

I-116

-continued

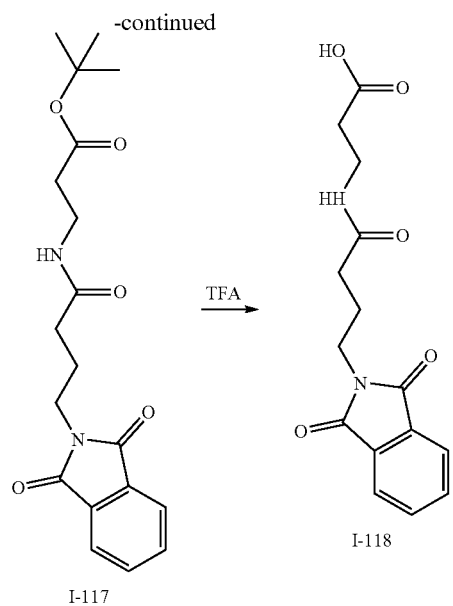

I-117

I-118

To 4-aminobutanoic acid (100 mg, 0.97 mmol) in AcOH was added phthalic anhydride (151 mg, 1.05 equiv.) and potassium acetate (286 mg, 3.0 equiv.). The reaction mixture was heated to 100° C. for 16 hours when LC-MS analysis indicated complete formation of phthalimide I-116. The reaction mixture was cooled and concentrated. The resulting residue was taken up in EtOAc; the organic extract was washed with 1M HCl, dried, and concentrated to afford the crude phthalimide I-116 which was re-dissolved in DMF. HATU (400 mg, 1.1 equiv.) was added, followed by DIPEA (607 µL, 3.5 equiv.) and β-alanine-tert-butyl ester hydrochloride (200 mg, 1.1 equiv.) The reaction mixture was stirred at ambient temperature until the reaction was deemed complete by LC-MS. The reaction mixture was concentrated to a residue, which was taken up in EtOAc and the organic extract was washed with 1M HCl, dried and concentrated. The resulting residue was purified by silica gel chromatography to afford 167 mg (48% yield, 2 steps) of phthalimide I-117. The tert-butyl ester of Phthalimide I-117 was deprotected to afford I-118 using TFA prior to coupling to the resin-bound peptide, MS (ESI) m/z calcd for $C_{15}H_{15}N_2O_5$ [M–H]$^-$: 303.1; found 302.9.

Synthesis of I-120 is Depicted in Scheme 47

Scheme 47

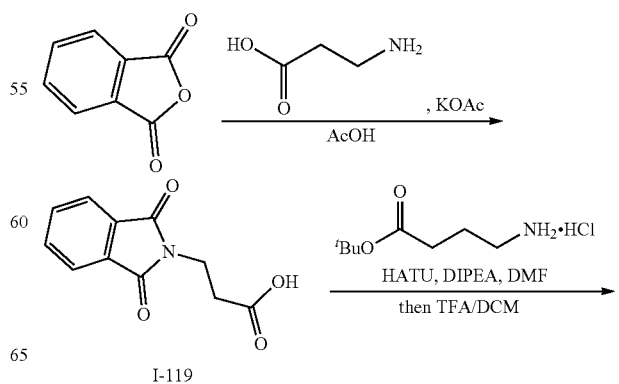

I-119

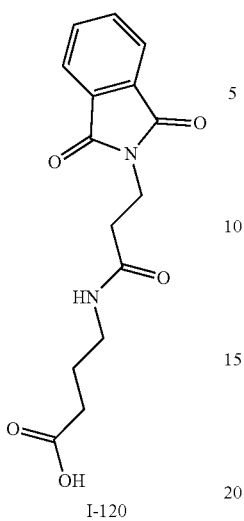

I-120

A solution of phthalic anhydride (2.26 g., 20.0 mmol), 3-aminopropanoic acid (1.87 g., 21.0 mmol) and potassium acetate (3.32 g., 1.9 equiv.) in AcOH was stirred 4 hours at 100° C., cooled to ambient temperature, and concentrated in vacuo. The resulting residue was dissolved in EtOAc, washed with 1 N HCl then brine, dried over sodium sulfate, and concentrated in vacuo to afford 4.25 g of the crude acid I-119 (97% yield). A portion of this material (59 mg, ca. 0.270 mmol) was dissolved in DMF and HATU (113 mg, 1.1 equiv.), tert-butyl 4-aminobutanoate hydrochloride (58 mg, 1.1 equiv.), and DIPEA (156 μL, 3.5 equiv.) were added. The reaction mixture was stirred at ambient temperature for 18 hours and then concentrated in vacuo. The residue was dissolved in EtOAc, and the resulting solution was washed with 1 M HCl, dried over sodium sulfate, and concentrated in vacuo. Purification by flash chromatography using hexanes/EtOAc followed by treatment with 1:1 DCM/TFA for 2 hours, concentration in vacuo and flash chromatography of the resulting residue with 20% MeOH and 1% AcOH in DCM afforded 39 mg of I-120 (108 mmol, 40% over two steps).

Synthesis of I-122 is Depicted in Scheme 48

Scheme 48

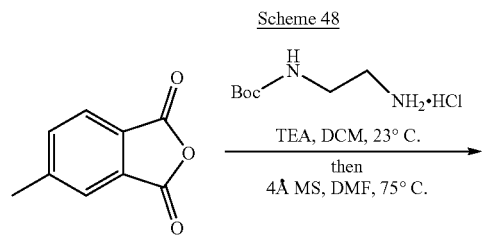

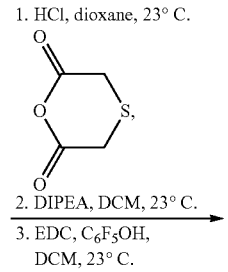

I-121

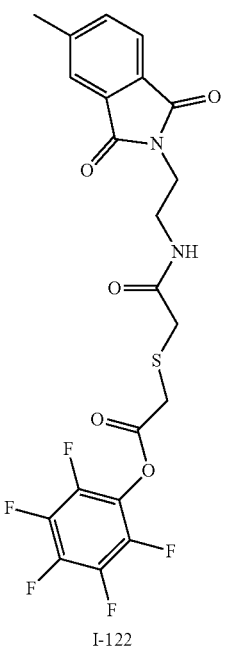

I-122

A solution of 5-methylisobenzofuran-1,3-dione (162 mg, 1.0 mmol), tert-butyl (2-aminoethyl)carbamate hydrochloride (207 mg, 1.05 equiv.) and TEA (278 μL, 2.0 equiv.) in DCM was stirred for 18 hours at ambient temperature. Then 4 Å molecular sieves and DMF were added and the reaction mixture was stirred at 75° C. for 18 hours. The reaction mixture was diluted with EtOAc, filtered, washed with saturated sodium bicarbonate and brine, then dried over sodium sulfate, and concentrated in vacuo to afford 300 mg of the intermediate imide I-121 (99% yield). This material was deprotected by treatment with 4 N HCl in dioxane followed by concentration in vacuo. A portion of the crude amine hydrochloride (30 mg, 0.125 mmol) was suspended in DCM and treated with thiodiglycolic anhydride (20 mg, 1.2 equiv.) and DIPEA (48 μL, 2.2 equiv.). The reaction mixture was stirred for 4 hours, concentrated in vacuo, and the residue was dissolved in EtOAc. The solution was washed with 1 M HCl and brine, dried over sodium sulfate, and concentrated in vacuo to afford 43 mg of the crude acid. A solution of this material, pentafluorophenol (35 mg, 0.188 mmol) and EDC (36 mg, 0.188 mmol) in DCM was stirred for one hour and then concentrated in vacuo. The residue obtained was dissolved in EtOAc, and the solution was washed with 1 M HCl, brine, dried over sodium sulfate and concentrated in vacuo. Purification by flash chromatography using EtOAc in hexanes afforded 66 mg of I-122 (quantitative yield).

145

Synthesis of I-124 is Depicted in Scheme 19

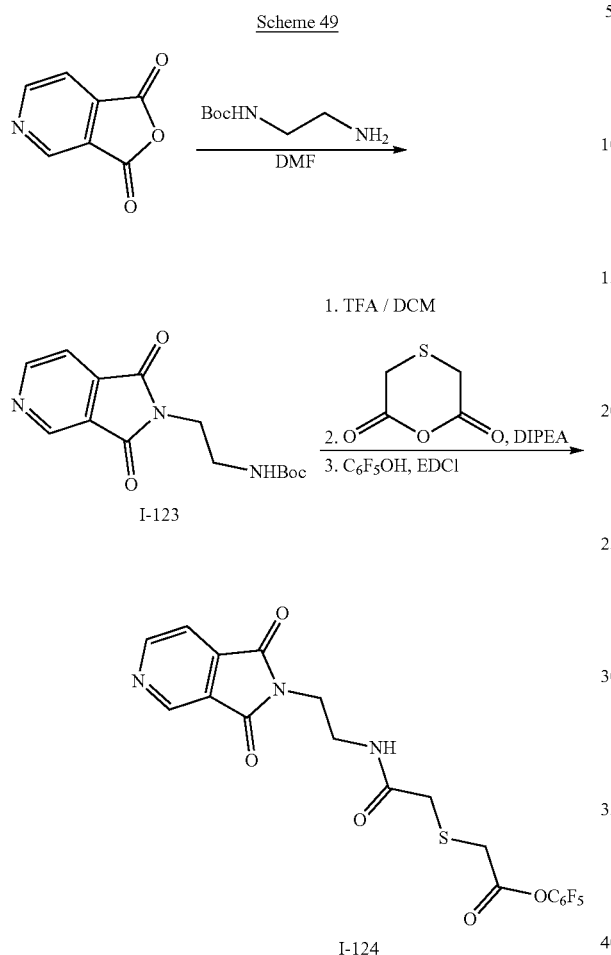

I-123

I-124

A solution of furo[3,4-c]pyridine-1,3-dione (100 mg, 0.671 mmol) and tert-butyl (2-aminoethyl)carbamate (112 mg, 1.05 equiv.) in DMF was stirred at 130° C. for 18 hours and then allowed to cool to ambient temperature. The reaction mixture was diluted with EtOAc and washed with 1 M HCl and brine. The combined aqueous washes were back-extracted with EtOAc. The combined organic extracts were dried over sodium sulfate and concentrated in vacuo. The resulting crude carbamate I-123 was stirred in 1:1 DCM/TFA for 2 hours, after which removal of the solvent afforded a primary amine salt, which was suspended in DCM and treated with thiodiglycolic anhydride (98 mg, 1.1 equiv.) and DIPEA (388 µL, 1.1 equiv.). The reaction mixture was stirred 4 hours. Pentafluorophenol (184 mg, 1.5 equiv.) and EDC (194 mg, 1.5 equiv.) were added; stirring was continued for 2 hours. The reaction mixture was diluted with EtOAc and the solution was washed with 1 M HCl then brine, dried over sodium sulfate and concentrated in vacuo. Purification by flash chromatography using EtOAc in hexanes afforded 200 mg of I-124 (61% yield).

146

Synthesis of I-126 is Depicted in Scheme 50

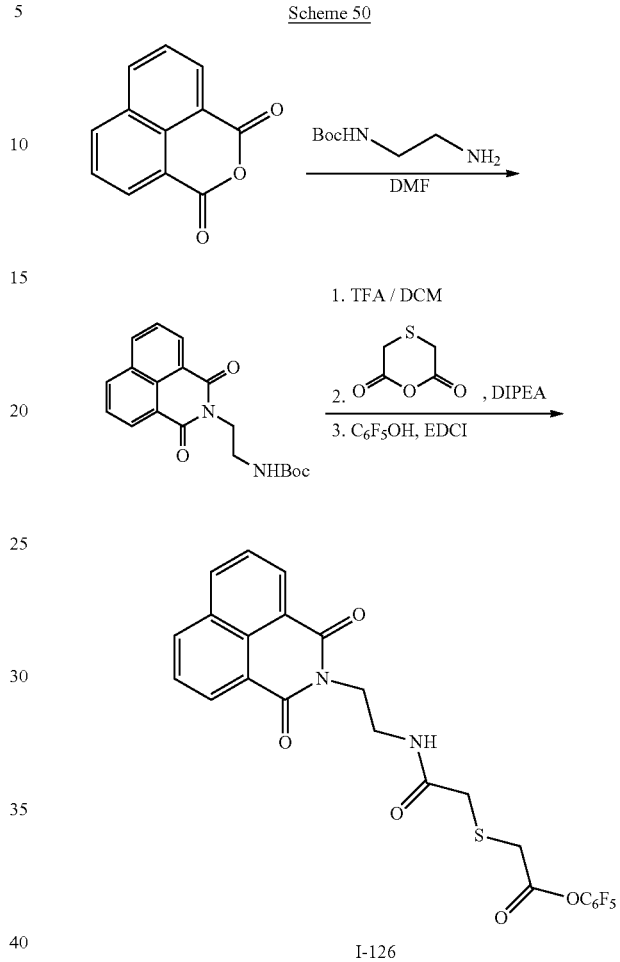

I-126

A solution of 1H,3H-benzo[de]isochromene-1,3-dione (100 mg, 0.505 mmol) and tert-butyl (2-aminoethyl)carbamate (85 mg, 1.05 equiv.) in DMF was stirred at 130° C. for 3 hours and allowed to cool to ambient temperature. The reaction mixture was diluted with EtOAc and washed with 1 M HCl and brine. The combined aqueous washes were extracted with EtOAc. The combined organic extracts were dried over sodium sulfate and concentrated in vacuo. The resulting crude carbamate I-125 was stirred in 1:1 DCM/TFA for 2 hours, after which removal of the solvent afforded a primary amine salt. The amine salt was suspended in DCM and treated with thiodiglycolic anhydride (73 mg, 1.1 equiv.) and DIPEA (219 µL, 2.5 equiv.). The reaction mixture was stirred 4 hours. Pentafluorophenol (139 mg, 1.5 equiv.) and EDC (207 mg, 2.0 equiv.) were added; stirring was continued for 2 hours. The reaction mixture was diluted with EtOAc and the solution was washed with 1 M HCl then brine, dried over sodium sulfate and concentrated in vacuo. Purification by flash chromatography using EtOAc in hexanes afforded I-126.

Synthesis of I-127 is Depicted in Scheme 51

Scheme 51

A solution of tert-butyl (2-aminoethyl)carbamate hydrochloride (207 mg, 1.05 mmol), thiodiglycolic anhydride (132 mg, 0.95 equiv.) and DIPEA (365 μL, 2.0 equiv.) in DCM was stirred 2 hours, concentrated in vacuo. The residue obtained was dissolved in EtOAc. This solution was washed with 1 M HCl and brine, dried over sodium sulfate and concentrated in vacuo to afford 366 mg of the crude carbamate, which was deprotected by treatment with 1:1 v/v TFA/DCM to afford the crude amine-TFA salt, I-127.

Synthesis of I-129 is Depicted in Scheme 52

Scheme 52

A solution of amine salt I-127 (34 mg, 0.111 mmol), (meso)-hexahydroisobenzofuran-1,3-dione (21 mg, 1.2 equiv.), and potassium acetate (33 mg, 3.0 equiv.) in AcOH was heated to 100° C. for 18 hours. The resulting mixture was cooled to ambient temperature and concentrated in vacuo. The residue was dissolved in EtOAc and washed with 1 M HCl then brine, and the combined aqueous washes were back-extracted with EtOAc. The combined organic extracts were dried over sodium sulfate and concentrated in vacuo. The resulting residue was purified by flash chromatography using 15% MeOH in DCM with 1% AcOH to afford 32 mg of intermediate acid I-128 (88% yield). This material was dissolved in DCM along with pentafluorophenol (18.4 mg, 0.100 mmol) and EDC (19 mg, 0.100 mmol). The resulting reaction mixture was stirred for 2 hours and concentrated in vacuo. The residue was dissolved in EtOAc. The resulting solution was washed with 1 M HCl and brine, then dried over sodium sulfate and concentrated in vacuo. Purification of the residue by flash chromatography using EtOAc in hexanes afforded 43 mg of I-129 (78% yield over two steps).

Synthesis of I-131 is Depicted in Scheme 53

Scheme 53

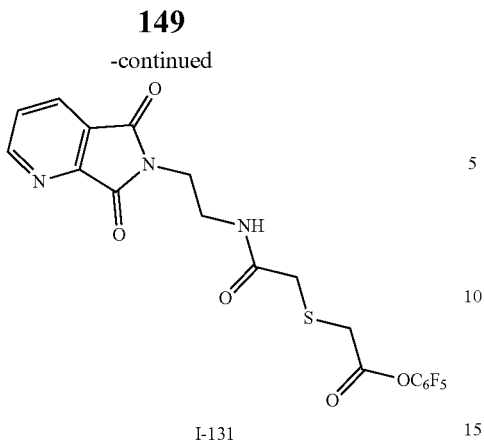

I-131

A solution of amine salt I-127 (34 mg, 0.111 mmol), furo[3,4-b]pyridine-5,7-dione (20 mg, 1.2 equiv.) and potassium acetate (33 mg, 3.0 equiv.) in AcOH was heated to 100° C. for 18 hours then cooled to ambient temperature and concentrated in vacuo. The residue was dissolved in EtOAc and the solution was washed with 1 M HCl and then brine. The combined aqueous washes were back-extracted with EtOAc. The combined organic extracts were dried over sodium sulfate and concentrated in vacuo. The resulting residue was purified by flash chromatography using 15% MeOH in DCM with 1% AcOH to afford 14 mg of intermediate acid I-130 (39% yield). This material was dissolved in DCM along with pentafluorophenol (12 mg, 0.065 mmol) and EDC (16 mg, 0.086 mmol). The resulting solution was stirred for 2 hours, concentrated in vacuo and the residue was dissolved in EtOAc. The resulting solution was washed with 1 M HCl and brine, then dried over sodium sulfate and concentrated in vacuo. Purification of the residue by flash chromatography using EtOAc in hexanes afforded 17 mg of I-131 (81% yield).

Synthesis of I-133 is Depicted in Scheme 54

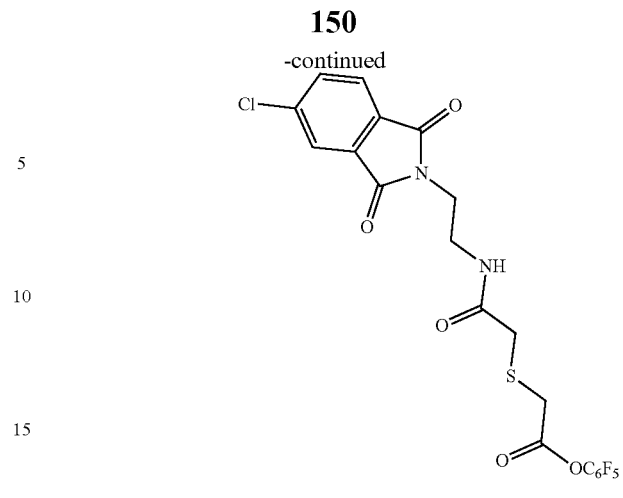

I-133

A solution of amine salt I-127 (30 mg, 0.098 mmol), 5-chloroisobenzofuran-1,3-dione (21 mg, 1.2 equiv.), and potassium acetate (29 mg, 3.0 equiv.) in AcOH was heated to 100° C. for 18 hours then cooled to ambient temperature and concentrated in vacuo. The residue was dissolved in EtOAc and the solution was washed with 1 M HCl and then brine. The combined aqueous washes were extracted with EtOAc. The combined organic extracts were dried over sodium sulfate and concentrated in vacuo. The resulting residue was purified by flash chromatography using 15% MeOH in DCM with 1% AcOH to afford 29 mg of intermediate acid I-132 (69%). This material was dissolved in DCM along with pentafluorophenol (18 mg, 0.100 mmol) and EDC (26 mg, 0.139 mmol). The resulting reaction mixture was stirred for 2 hours and concentrated in vacuo; the residue was re-dissolved in EtOAc. The resulting solution was washed with 1 M HCl and brine, dried over sodium sulfate, concentrated in vacuo. Purification of the residue by flash chromatography using EtOAc in hexanes afforded 21 mg of I-133 (60% yield).

Synthesis of I-135 is Depicted in Scheme 55

Scheme 54

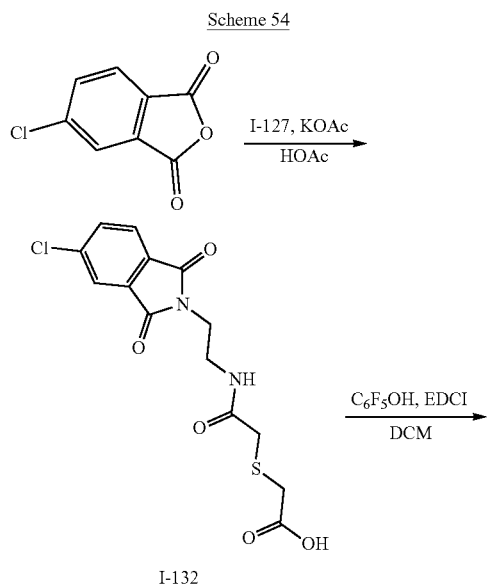

I-132

Scheme 55

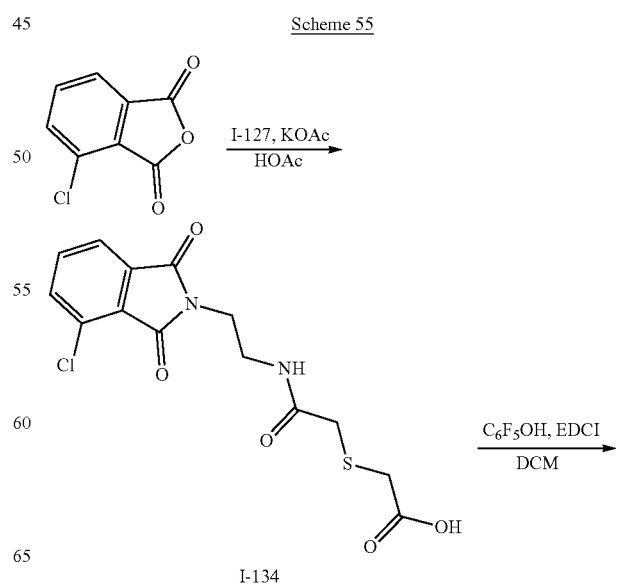

I-134

151

-continued

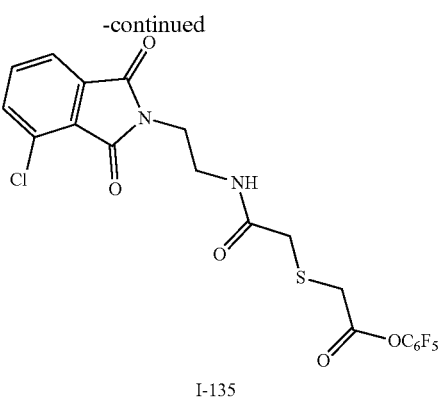

I-135

152

-continued

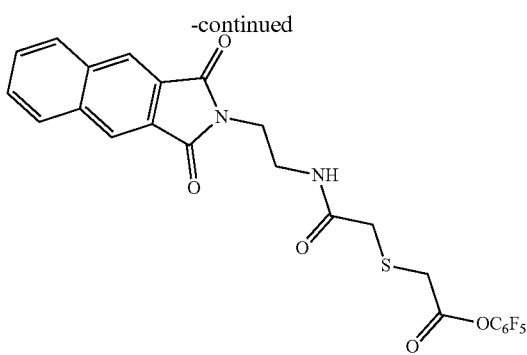

I-137

A solution of amine salt I-127 (23 mg, 0.075 mmol), 4-chloroisobenzofuran-1,3-dione (16 mg, 1.2 equiv.) and potassium acetate (22 mg, 3.0 equiv.) in AcOH was heated to 100° C. for 18 hours, cooled to ambient temperature, and concentrated in vacuo. The residue was dissolved in EtOAc and washed with 1 M HCl then brine, and the combined aqueous washes were back-extracted with EtOAc. The combined organic extracts were dried over sodium sulfate and concentrated in vacuo. The resulting residue was purified by flash chromatography using 15% MeOH in DCM with 1% AcOH to afford 21 mg of intermediate acid I-134 (79% yield). This material was dissolved in DCM along with pentafluorophenol (16 mg, 0.089 mmol) and EDC (23 mg, 0.118 mmol). The resulting reaction mixture was stirred for 2 hours and concentrated in vacuo. The residue was dissolved in EtOAc. The resulting solution was washed with 1 M HCl and brine, then dried over sodium sulfate and concentrated in vacuo. Purification of the residue by flash chromatography using EtOAc in hexanes afforded 20 mg of I-135 (0.038 mmol, 65% yield).

Synthesis of I-137 is Depicted in Scheme 56

A solution of amine salt I-127 (43 mg, 0.14 mmol), naphtho[2,3-c]furan-1,3-dione (33 mg, 1.2 equiv.), and potassium acetate (42 mg, 3.0 equiv.) in AcOH was heated to 100° C. for 18 hours. The reaction mixture was then cooled to ambient temperature and concentrated in vacuo. The residue afforded was dissolved in EtOAc, and the solution was washed with 1 M HCl and brine. The combined aqueous washes were back-extracted with EtOAc. The combined organic extracts were dried over sodium sulfate and concentrated in vacuo. The resulting residue was purified by flash chromatography using 15% MeOH in DCM with 1% AcOH to afford 20 mg of intermediate acid I-136 (38% yield). This material was dissolved in DCM along with pentafluorophenol (15 mg, 0.081 mmol) and EDC (16 mg, 0.081 mmol). The resulting reaction mixture was stirred for 2 hours, concentrated in vacuo and the residue was re-dissolved in EtOAc. The resulting solution was washed with 1 M HCl and brine, then dried over sodium sulfate and concentrated in vacuo. Purification of the residue by flash chromatography using EtOAc in hexanes afforded 31 mg of I-137 (98% yield).

Synthesis of I-139 is Depicted in Scheme 57

Scheme 56

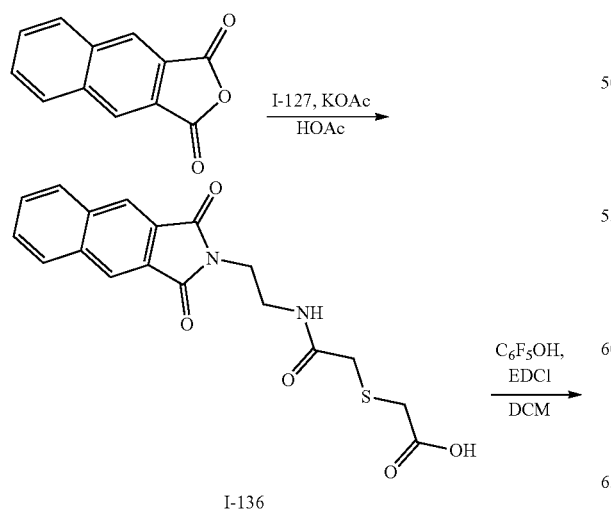

I-136

Scheme 57

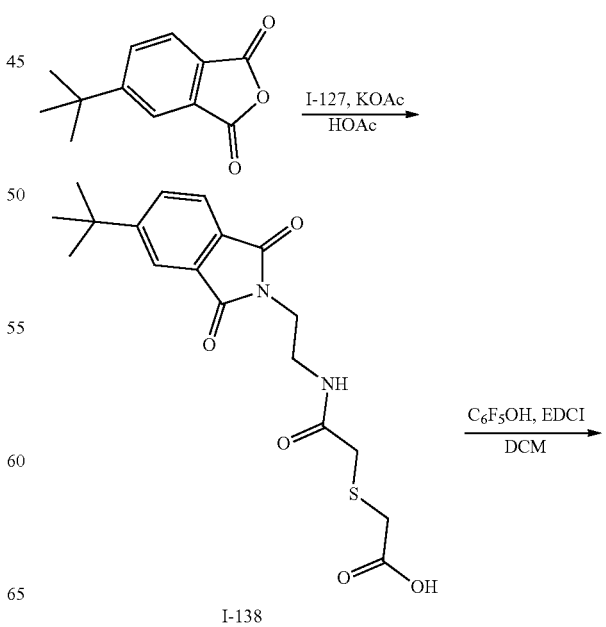

I-138

153

-continued

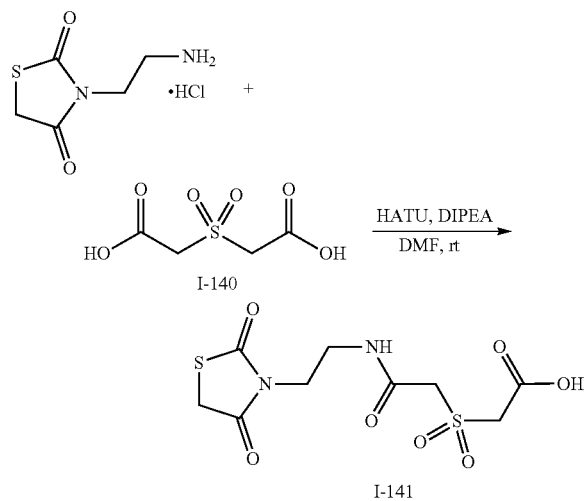

I-139

A solution of amine salt I-127 (36 mg, 0.117 mmol), 5-(tert-butyl)isobenzofuran-1,3-dione (29 mg, 1.2 equiv.) and potassium acetate (11 mg, 1.0 equiv.) in AcOH was heated to 100° C. for 18 hours. The reaction mixture was then cooled to ambient temperature and concentrated in vacuo. The residue was dissolved in EtOAc and the solution was washed with 1 M HCl then brine, and the combined aqueous washes were back-extracted with EtOAc. The combined organic extracts were dried over sodium sulfate and concentrated in vacuo. The resulting residue was purified by flash chromatography using 15% MeOH in DCM with 1% AcOH to afford 49 mg of intermediate acid I-138 containing dicarboxylic acid impurities. This material was dissolved in DCM along with pentafluorophenol (18.4 mg, 0.100 mmol) and EDC (19 mg, 0.100 mmol). The resulting reaction mixture was stirred for 2 hours, concentrated in vacuo, and the residue was re-dissolved in EtOAc. The resulting solution was washed with 1 M HCl and brine, dried over sodium sulfate, and concentrated in vacuo. Purification of the residue by flash chromatography using EtOAc in hexanes afforded 22 mg of I-139 (37% yield over two steps).

Synthesis of I-141 is Depicted in Scheme 58

Scheme 58

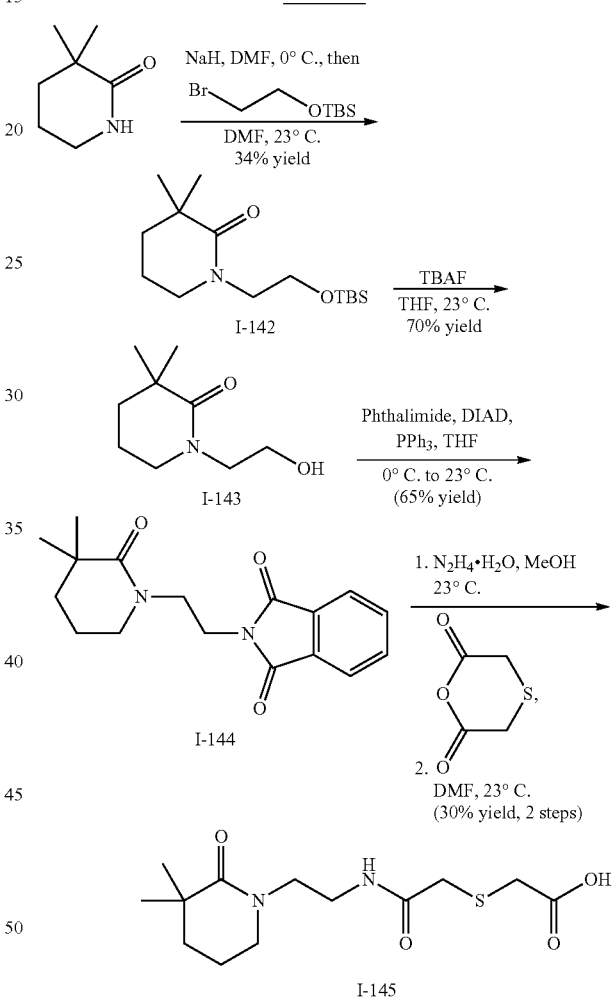

154

To a slurry of 3-(2-aminoethyl)thiazolidine-2,4-dione hydrochloride (43.8 mg, 0.22 mmol) and dicarboxylic acid I-140 (81.1 mg, 2.0 equiv.) in DMF (1 mL) was added DIPEA (117 µL, 3.0 equiv.) and HATU (127.2 mg, 1.5 equiv.). The reaction mixture was agitated at ambient temperature for 2.5 hours and then purified directly by preparative HPLC (0-100% acetonitrile in water with 0.1% TFA) to afford 62.1 mg (86% yield) of I-141 as a white solid. ESI-MS found 325.1, $C_9H_{13}N_2O_7S_2(MH^+)$ requires 325.1.

Synthesis of I-145 is Depicted in Scheme 59

To a solution of 3,3-dimethylpiperidin-2-one (240 mg, 1.88 mmol) in DMF (5 mL) at 0° C. under $N_2$ was added a slurry of NaH (574 mg of 60% dispersion in mineral oil, 3.0 equiv.) in DMF (15 mL). After 20 minutes, (2-bromoethoxy)(tert-butyl)dimethylsilane (673 mg, 1.5 equiv.) was added. The reaction mixture was allowed to warm to ambient temperature. After 18 hours, the reaction mixture was quenched with saturated aqueous $NH_4Cl$ (10 mL) and diluted with water (50 mL). The aqueous phase was extracted with EtOAc (3×50 mL). The combined EtOAc extracts were dried ($Na_2SO_4$) and concentrated to afford a colorless oil. Purification by silica gel chromatography (12 g pre-packed column, 0 to 25% EtOAc in Hexanes) afforded 181 mg (34% yield) of the silyl ether I-142 as a colorless oil. This material (90 mg, 0.315 mmol) was dissolved in THF (3 mL) and treated with 1M TBAF solution in THF (0.95 mL, 3 equiv.) and the resulting solution was stirred at ambient temperature for 2 hours. The reaction mixture was then concentrated under reduced pressure to afford a residue, which was purified by preparative HPLC (H$_2$O/MeCN with 0.1% TFA) to provide 37.7 mg of alcohol I-143 (70% yield).

Alcohol I-143 was dissolved in THF (6 mL) in the presence of triphenylphosphine (85.7 mg, 1.5 equiv.) and phthalimide (48.1 mg, 1.5 equiv.). The solution was cooled to 0-5° C., and DIAD (64 µL, 1.5 equiv.) was added; the reaction mixture was allowed to warm to ambient temperature. After 1.5 hours, the reaction mixture was concentrated to a yellow oil, which was purified by silica gel chromatography (12 g pre-packed column, eluting with 0 to 35% Acetonitrile in DCM) to afford 42.5 mg of phthalimide I-144 (65% yield) as a colorless oil.

To a solution of phthalimide I-144 (42.5 mg, 0.142 mmol) in MeOH (2 mL) was added hydrazine hydrate (44.2 µL, 10.0 equiv.). The reaction mixture was heated to 45° C. for 2 hours, cooled and concentrated under reduced pressure. The residue was re-dissolved in DMF (2 mL) and thiodiglycolic anhydride (22.5 mg, 1.2 equiv. based on phthalimide I-144) was added. After 2 hours, the reaction mixture was subjected to purification by preparative HPLC (H$_2$O/MeCN with 0.1% TFA) to afford 13.0 mg (30% yield) of the desired carboxylic acid I-145 as a colorless oil. ESI-MS: Found 301.2, $C_{13}H_{21}N_2O_4S$ (M–H)$^-$ requires 301.1.

Synthesis of I-146 is Depicted in Scheme 60

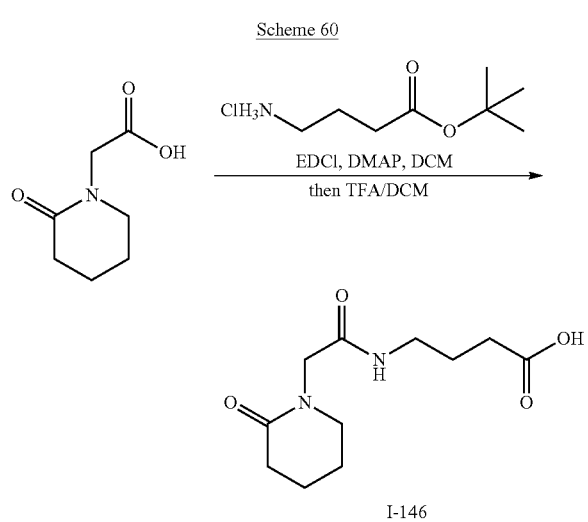

I-146

A suspension of 2-(2-oxopiperidin-1-yl)acetic acid (46 mg, 0.292 mmol) and tert-butyl 4-aminobutanoate hydrochloride (68 mg, 1.2 equiv.) in 0.5 mL of DCM was treated with DMAP (78 mg, 2.2 equiv.) and then EDC (67 mg, 1.2 equiv.). The mixture was allowed to stir at ambient temperature for 72 hours. The reaction mixture was diluted with 8 mL of DCM, and the organic phase was washed with 1 N NaHSO$_3$, brine, dried over Na$_2$SO$_4$, and concentrated in vacuo. The resulting crude ester was dissolved in 1 mL of DCM and treated with 1 mL of TFA, and the resulting solution was concentrated under a stream of nitrogen and held under high vacuum for 2 hours. Half of the crude product was purified by preparative HPLC (H$_2$O/MeCN with 0.1% TFA) to afford 27.6 mg (78% yield based on 0.146 mmol) of carboxylic acid I-146. ESI-MS: Found 243.3, $C_{11}H_{19}N_2O_4$ (MH$^+$) requires 243.3.

Synthesis of I-147 is Depicted in Scheme 61

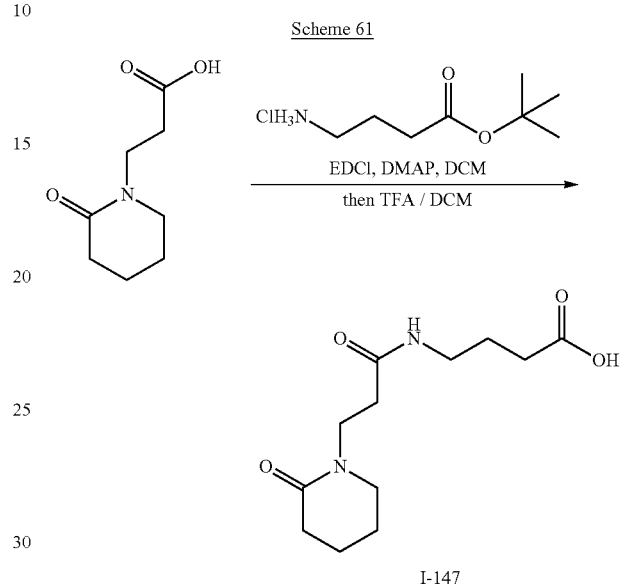

I-147

A suspension of 3-(2-oxopiperidin-1-yl)propanoic acid (50 mg, 0.292 mmol) and tert-butyl 4-aminobutanoate hydrochloride (68 mg, 1.2 equiv.) in 0.5 mL of DCM was treated with DMAP (78 mg, 2.2 equiv.) and then EDC (67 mg, 1.2 equiv.). The mixture was allowed to stir at ambient temperature for 72 hours. The reaction mixture was diluted with 8 mL of DCM, and the organic phase was washed with 1 N NaHSO$_3$, brine, dried over Na$_2$SO$_4$ and concentrated in vacuo. The resulting crude ester was dissolved in 1 mL of DCM and treated with 1 mL of TFA and the resulting solution was concentrated under a stream of nitrogen and held under high vacuum for 2 hours. Half of the crude product was then purified by preparative HPLC (H$_2$O/ MeCN with 0.1% TFA) to afford 32.8 mg (87% yield based on 0.146 mmol) of carboxylic acid I-147. ESI-MS: Found 255.1, $C_{12}H_{19}N_2O_4$ (M–H)$^-$ requires 255.3.

Synthesis of I-148 is Depicted in Scheme 62

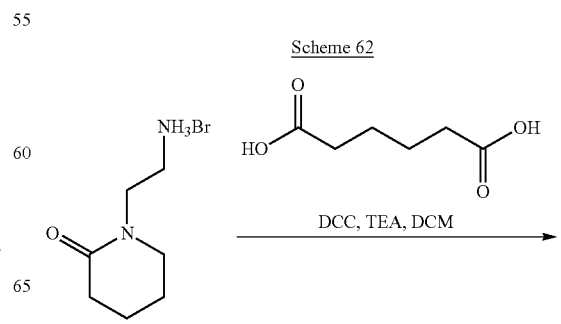

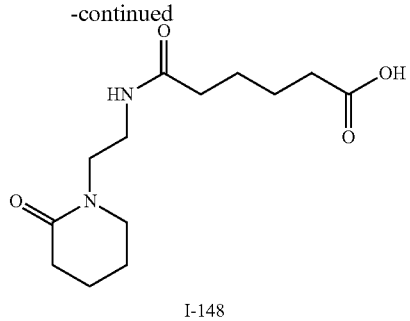

I-148

To a suspension of 1-(2-aminoethyl)piperidin-2-one hydrobromide (71.2 mg, 0.319 mmol), adipic acid (54.0 mg, 1.2 equiv.) and DCC (78.8 mg, 1.2 equiv.) was added TEA (53 µL, 1.2 equiv.). The resulting solution was stirred at ambient temperature for 72 hours, then filtered through celite, and concentrated in vacuo. Purification by preparative HPLC ($H_2O$/MeCN with 0.1% TFA) afforded 24 mg (23% yield) of carboxylic acid I-148. ESI-MS: Found 269.3, $C_{13}H_{21}N_2O_4$ (M–H)⁻ requires 269.3.

Synthesis of I-150 is Depicted in Scheme 63

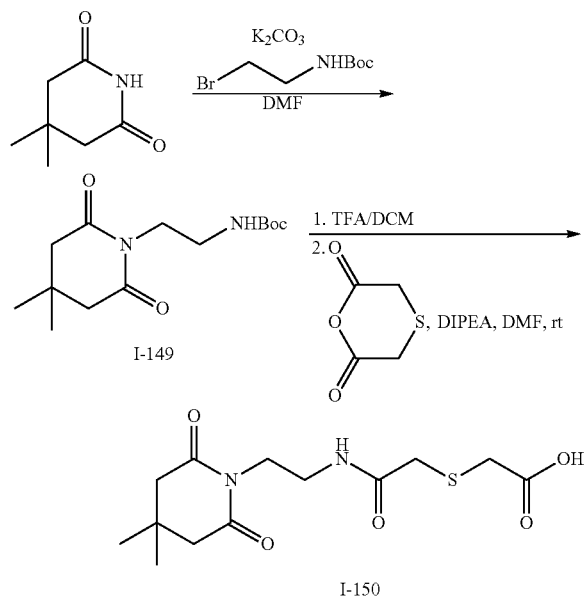

To a solution of 4,4-dimethylpiperidine-2,6-dione (28 mg, 0.20 mmol) and tert-butyl (2-bromoethyl)carbamate (45 mg, 1.0 equiv.) in 1 mL of anhydrous DMF was added potassium carbonate (41 mg, 1.5 equiv.), and the resulting suspension was stirred for 22 hours at ambient temperature. The reaction mixture was filtered and purified directly by preparative HPLC to afford 23 mg (40% yield) of carbamate I-149. Carbamate I-149 was subjected to deprotection in 2:1 DCM/TFA for 10 minutes at ambient temperature. The reaction mixture was then concentrated in vacuo to give a crude trifluoroacetate salt, which was converted to 19 mg (74% yield) of acid I-150 using GP1. ESI-MS found 317.0, $C_{13}H_{20}N_2O_5S$ (MH⁺) requires 317.1.

Synthesis of I-152 is Depicted in Scheme 64

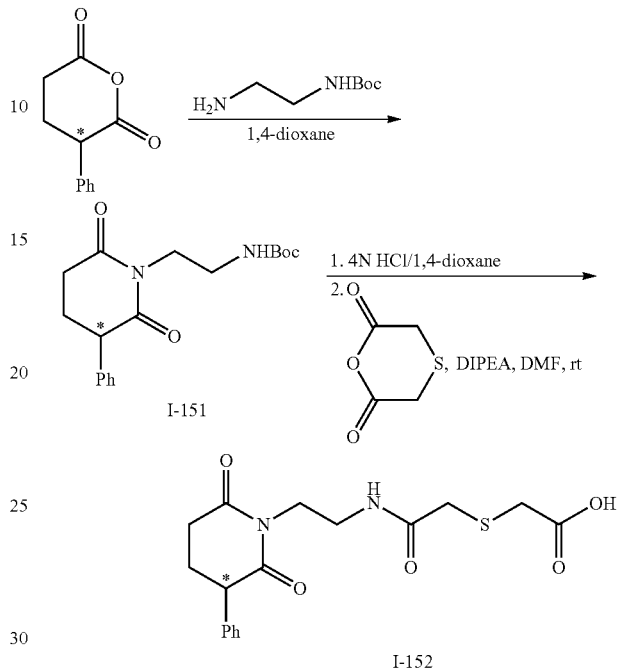

*Mixture of diastereomers

A solution of rac-3-phenyldihydro-2H-pyran-2,6(3H)-dione (38 mg, 0.20 mmol) and tert-butyl (2-aminoethyl)carbamate (38 mg, 1.2 equiv.) in 0.6 mL of anhydrous 1,4-dioxane was stirred for 35 minutes at ambient temperature. HCl in 1,4-dioxane (4N, 1.5 mL) was then added and the reaction mixture was stirred for an additional 8 days. The reaction mixture was then concentrated in vacuo to give a crude hydrochloride salt, which was converted to 17.5 mg of I-152 (39% yield overall) following GP1. ESI-MS found 365.0, $C_{17}H_{20}N_2O_5S$ (MH⁺) requires 365.1.

Synthesis of I-155 is Depicted in Scheme 65

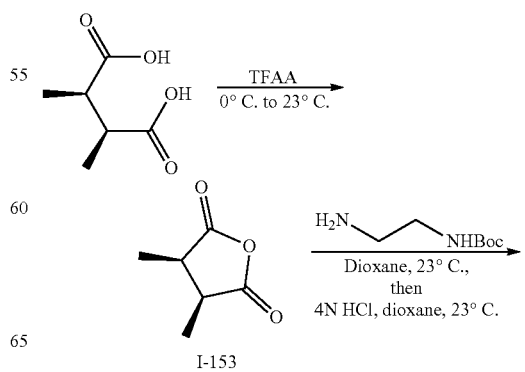

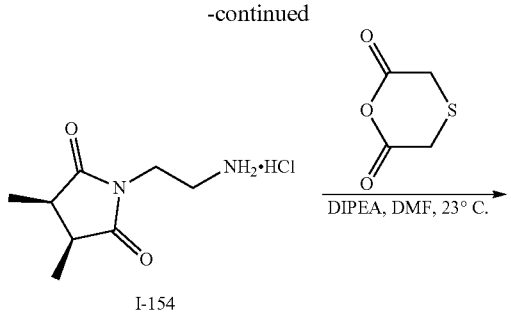

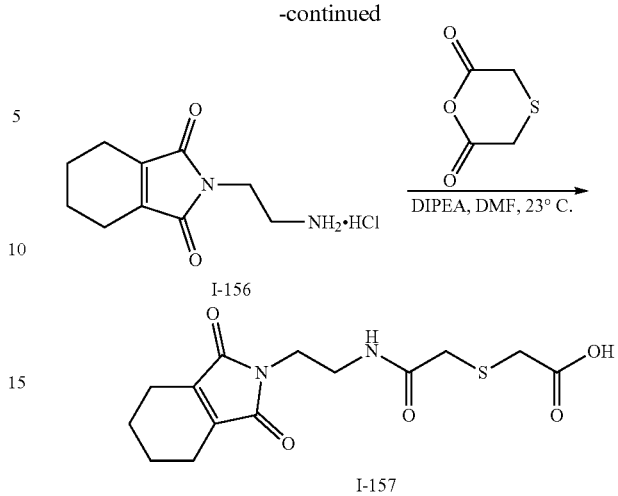

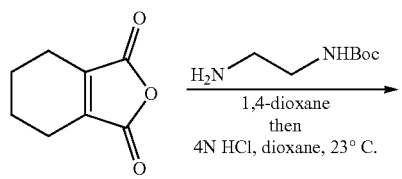

A solution of 4,5,6,7-tetrahydroisobenzofuran-1,3-dione (46 mg, 0.30 mmol) and tert-butyl (2-aminoethyl)carbamate (58 mg, 1.2 equiv.) in 0.8 mL of anhydrous 1,4-dioxane was stirred 50 minutes at ambient temperature. 4N HCl in 1,4-dioxane (1 mL) was then added, and the reaction mixture was stirred for an additional 5 hours and then concentrated in vacuo to give a crude hydrochloride salt I-156, which was converted to 55.5 mg of I-157 (57% yield overall) following GP1. ESI-MS found 327.0, $C_{14}H_{18}N_2O_5S$ (MH$^+$) requires 327.1.

Synthesis of I-159 is Depicted in Scheme 67

Meso-2,3-dimethylsuccinic acid (44 mg, 0.30 mmol) was dissolved in 0.2 mL of TFAA at 0° C. The solution was allowed to slowly warm to room temperature and stirred for 70 minutes. Concentration of the reaction mixture in vacuo gave the crude anhydride I-153, which was dissolved in 1 mL of anhydrous 1,4-dioxane and treated with tert-butyl (2-aminoethyl)carbamate (58 mg, 1.2 equiv.). The reaction mixture was stirred for 40 minutes at ambient temperature. 4N HCl in 1,4-dioxane (1.5 mL) was then added, and the reaction mixture was stirred for an additional 136 hours and then concentrated in vacuo to give a crude hydrochloride salt I-154 which was converted to 52 mg of carboxylic acid I-155 (57% yield overall) following GP1. ESI-MS found 303.0, $C_{12}H_{18}N_2O_5S$ (MH$^+$) requires 303.1.

Synthesis of I-157 is Depicted in Scheme 66

Scheme 67

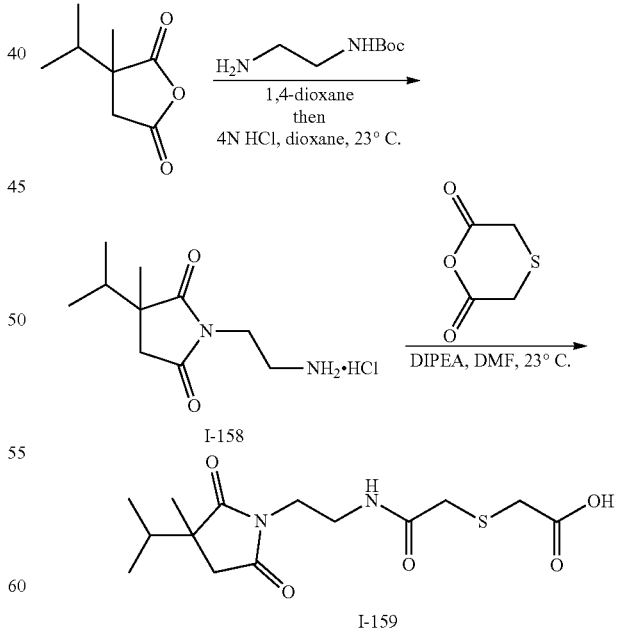

A solution of rac-3-isopropyl-3-methyldihydrofuran-2,5-dione (47 mg, 0.30 mmol) and tert-butyl (2-aminoethyl) carbamate (58 mg, 1.2 equiv.) in 0.8 mL anhydrous 1,4-dioxane was stirred for 15 minutes at ambient temperature.

4N HCl in 1,4-dioxane (0.8 mL) was then added, and the reaction mixture was stirred for an additional 41 hours and then concentrated in vacuo to give a crude hydrochloride salt I-158, which was converted to 82.0 mg of I-159 (83% yield overall) following GP1. ESI-MS found 331.0, $C_{14}H_{22}N_2O_5S$ (MH$^+$) requires 331.1.

Synthesis of I-161 is Depicted in Scheme 68

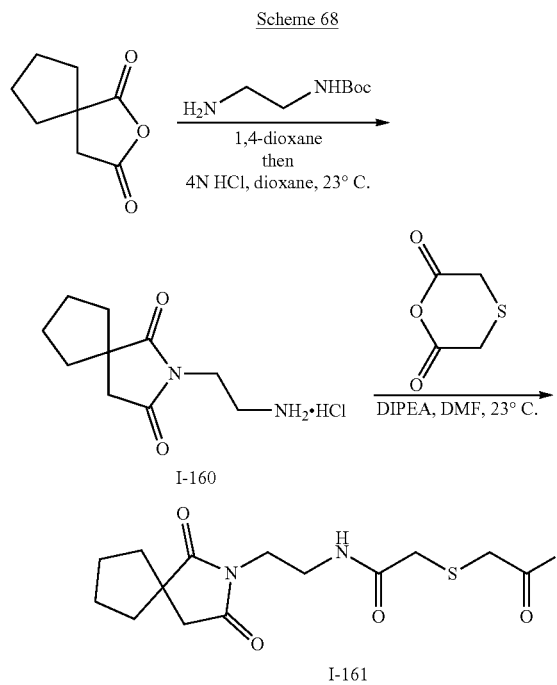

A solution of 2-oxaspiro[4.4]nonane-1,3-dione (46 mg, 0.30 mmol) and tert-butyl (2-aminoethyl)carbamate (58 mg, 1.2 equiv.) in 0.8 mL of anhydrous 1,4-dioxane was stirred for 70 minutes at ambient temperature. 4N HCl in 1,4-dioxane (1 mL) was then added, and the reaction mixture was stirred for an additional 66 hours and then concentrated in vacuo to give a crude hydrochloride salt I-160, which was converted to 66.0 mg of I-161 (67% yield overall) following GP1. ESI-MS found 329.0, $C_{14}H_{20}N_2O_5S$ (MH$^+$) requires 329.1.

Synthesis of I-163 is Depicted in Scheme 69

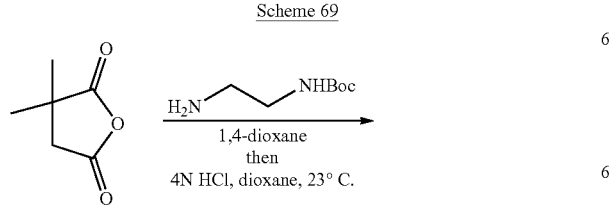

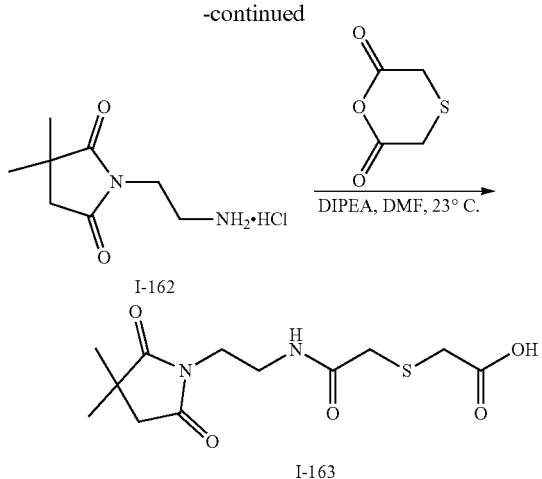

A solution of 3,3-dimethyldihydrofuran-2,5-dione (38 mg, 0.30 mmol) and tert-butyl (2-aminoethyl)carbamate (58 mg, 1.2 equiv.) in 0.8 mL of anhydrous 1,4-dioxane was stirred for 100 minutes at ambient temperature. Then 4N HCl in 1,4-dioxane (0.8 mL) was then added, and the reaction mixture was stirred for an additional 69 hours and then concentrated in vacuo to give a crude hydrochloride salt I-162, which was converted to 62.5 mg of I-163 (69% yield overall) following GP1. ESI-MS found 303.0, $C_{12}H_{18}N_2O_5S$ (MH$^+$) requires 303.1.

Synthesis of I-165 is Depicted in Scheme 70

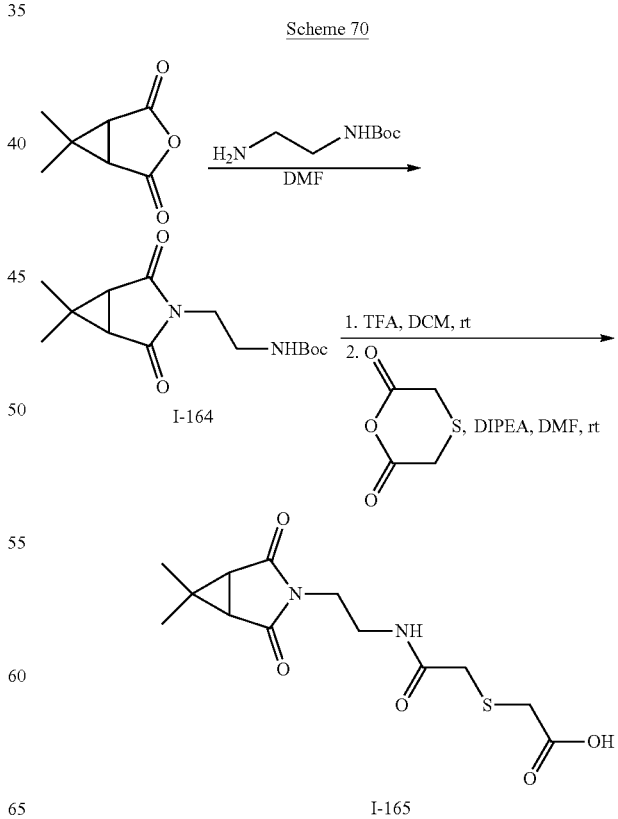

A solution of 6,6-dimethyl-3-oxabicyclo[3.1.0]hexane-2,4-dione (70 mg, 0.50 mmol) and tert-butyl (2-aminoethyl) carbamate (120 mg, 1.5 equiv.) in 3 mL of anhydrous DMF was stirred for 30 minutes at ambient temperature and then for 91 hours at 120° C. The reaction mixture was purified directly by preparative HPLC to afford 99 mg (0.35 mmol, 70% yield) of carbamate I-164. A portion of the carbamate I-164 (56 mg, 0.20 mmol) was deprotected in 2:1 v/v DCM/TFA for twenty minutes at ambient temperature. The reaction mixture was concentrated in vacuo to give a crude trifluoroacetate salt, which was converted to 56 mg of I-165 (89% yield) following GP1. ESI-MS found 315.0, $C_{13}H_{18}N_2O_5S$ (MH$^+$) requires 315.1.

Synthesis of I-167 is Depicted in Scheme 71

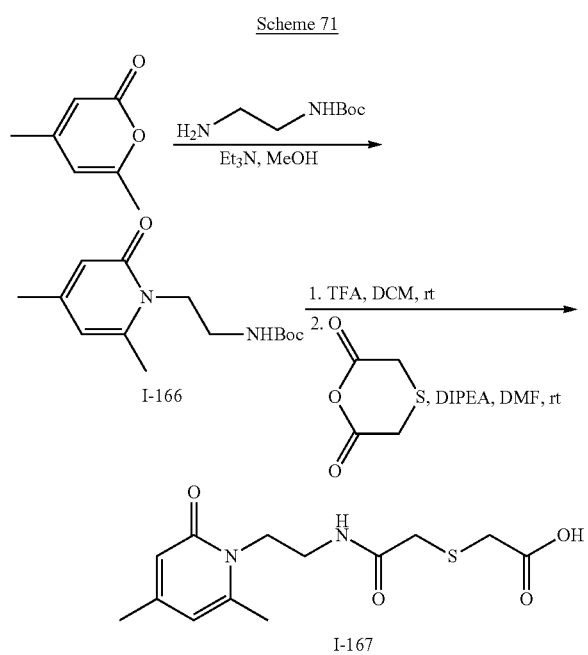

I-166

I-167

To 4,6-dimethyl-2H-pyran-2-one (222.8 mg, 1.79 mmol) in MeOH (5 mL) was added N-tert-butyloxycarbonylethylene diamine (496 mg, 1.7 equiv.) and TEA (0.75 mL, 3.0 equiv.). The reaction mixture was heated to 60° C. for 48 hours, then to 100° C. for a further 5 hours to ensure completion of the reaction. The reaction mixture was concentrated and purified by silica gel chromatography to afford the intermediate carbamate, I-166.

Carbamate I-166 (33 mg, 0.12 mmol) was treated with TFA for deprotection. After concentration of the reaction mixture, the resulting amine salt was converted to 33.4 mg of I-167 (90% yield) following GP1. ESI-MS found 299.8, $C_{13}H_{19}N_2O_4S$ (MH$^+$) requires 299.1.

Synthesis of I-168 is Depicted in Scheme 72

Scheme 72

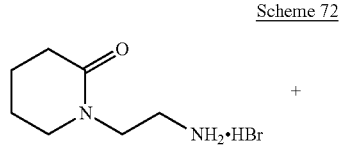

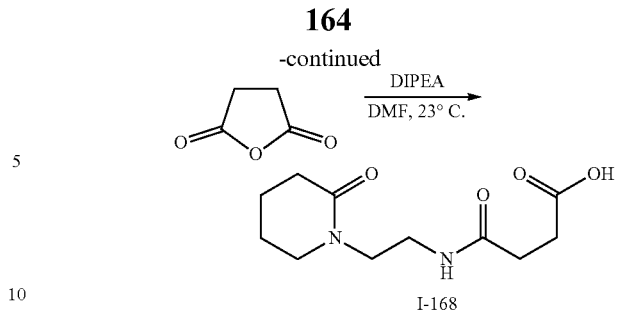

I-168

1-(2-aminoethyl)piperidin-2-one hydrobromide (54.5 mg, 0.24 mmol) was dissolved in DMF (1 mL). DIPEA (128 µL, 3.0 equiv.) was added, followed by succinic anhydride (26.9 mg, 1.1 equiv.). The reaction mixture was agitated at ambient temperature for 3 hours and then directly purified by preparative HPLC (H$_2$O/MeCN with 0.1% TFA) to afford 48.2 mg (81% yield) of acid I-168 as a white solid. ESI-MS found 243.3. $C_{11}H_{19}N_2O_4$ (MH$^+$) requires 243.1.

Synthesis of I-169 is Depicted in Scheme 73

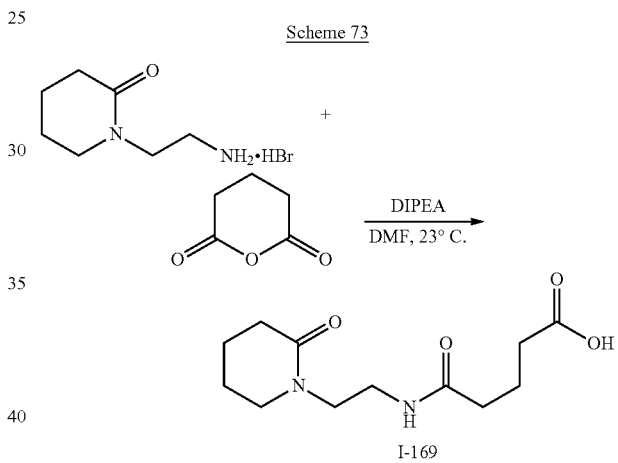

I-169

1-(2-aminoethyl)piperidin-2-one hydrobromide (64.9 mg, 0.29 mmol) was dissolved in DMF (1 mL). DIPEA (152 µL, 3.0 equiv.) was added, followed by glutaric anhydride (36.5 mg, 1.1 equiv.). The reaction mixture was agitated at ambient temperature for 3 hours and then directly purified by preparative HPLC (H$_2$O/MeCN with 0.1% TFA) to afford 76.8 mg (quantitative yield) of acid I-169 as a white solid. ESI-MS found 256.1. $C_{12}H_{21}N_2O_4$ (MH$^+$) requires 256.1.

Synthesis of I-170 is Depicted in Scheme 74

Scheme 74

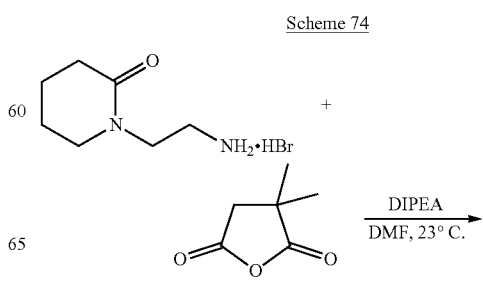

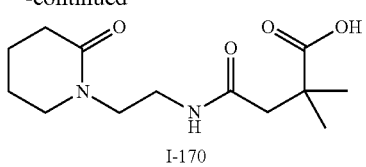

I-170

1-(2-aminoethyl)piperidin-2-one hydrobromide (178.2 mg, 0.8 mmol) was dissolved in DMF (0.9 mL). DIPEA (417 µL, 3.0 equiv.) was added, followed by 2,2-dimethylsuccinic anhydride (133 mg, 1.3 equiv.). The reaction mixture was agitated at ambient temperature for 12 hours and then directly purified by preparative HPLC (H$_2$O/MeCN with 0.1% TFA) to afford 51.7 mg (24% yield) of acid I-170 as a white solid. ESI-MS found 271.2. C$_{13}$H$_{23}$N$_2$O$_4$ (MH$^+$) requires 271.2.

Synthesis of I-172 is Depicted in Scheme 75

Scheme 75

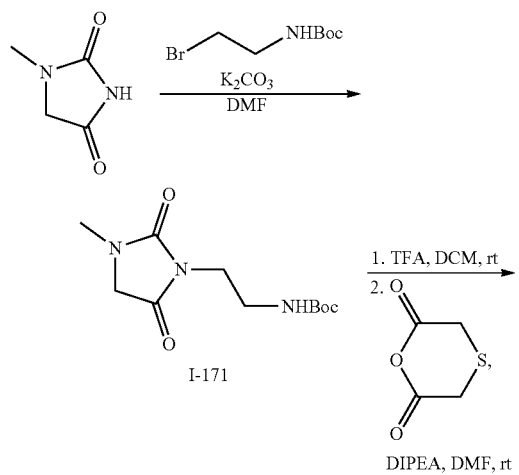

I-172

To a solution of 1-methylimidazolidine-2,4-dione (44 mg, 0.20 mmol) and tert-butyl (2-bromoethyl)carbamate (377 mg, 8.4 equiv.) in 1.5 mL of anhydrous DMF was added potassium carbonate (41 mg, 0.30 mmol) and the resulting suspension was stirred for 20 hours at ambient temperature. The reaction mixture was then filtered, and the filtrate was subjected to preparative HPLC to afford 23 mg (0.089 mmol, 45% yield) of carbamate I-171 which was deprotected in 2:1 v/v DCM/TFA for 15 minutes at ambient temperature. The reaction mixture was concentrated under reduced pressure to give a crude trifluoroacetate salt. A portion of this salt (66 mg, 0.218 mmol) was converted to 9 mg of acid I-172 using GP1 (35% yield). ESI-MS found 290.0, C$_{10}$H$_{15}$N$_3$O$_5$S (MH$^+$) requires 290.1.

Synthesis of I-174 is Depicted in Scheme 76

Scheme 76

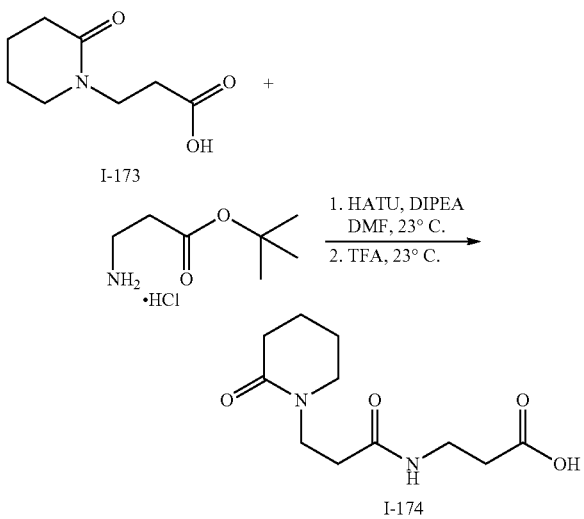

I-174

To a solution of carboxylic acid I-173 (125.3 mg, 0.73 mmol) and beta-alanine tert-butyl ester hydrochloride (146.3 mg, 1.1 equiv.) in DMF (3 mL) was added DIPEA (382 µL, 3.0 equiv.), followed by HATU (417.4 mg, 1.5 equiv.). The reaction mixture was stirred at ambient temperature for 16 hours, then diluted with H$_2$O (30 mL) and extracted with EtOAc (3×30 mL). The combined organic extracts were washed with brine (30 mL), dried (MgSO$_4$), and concentrated to afford a brown oil. TFA (5 mL) was added to this oil and the reaction mixture was stirred for 1 hour at ambient temperature. The reaction mixture was then concentrated and purified by preparative HPLC (H$_2$O/MeCN with 0.1% TFA) to afford I-174 (153.4 mg, 87% yield over 2 steps) as a colorless oil. ESI-MS found 243.3, C$_{11}$H$_{19}$N$_2$O$_4$ (MH$^+$) requires 243.1.

Synthesis of I-176 is Depicted in Scheme 77

Scheme 77

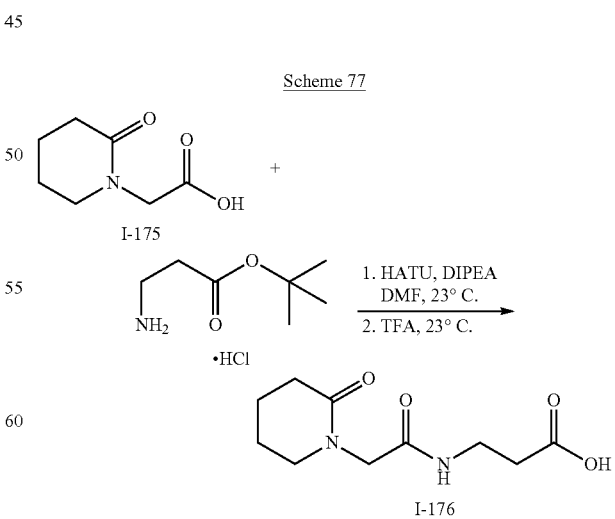

I-176

Using a procedure similar to that employed for the synthesis of I-174, carboxylic acid I-175 (102.4 mg, 0.65 mmol) afforded 123.5 mg (83% yield, 2 steps) of I-176 as a white solid. ESI-MS found 229.2, $C_{10}H_{17}N_2O_4$ (MH$^+$) requires 229.1.

Synthesis of I-180 is Depicted in Scheme 78

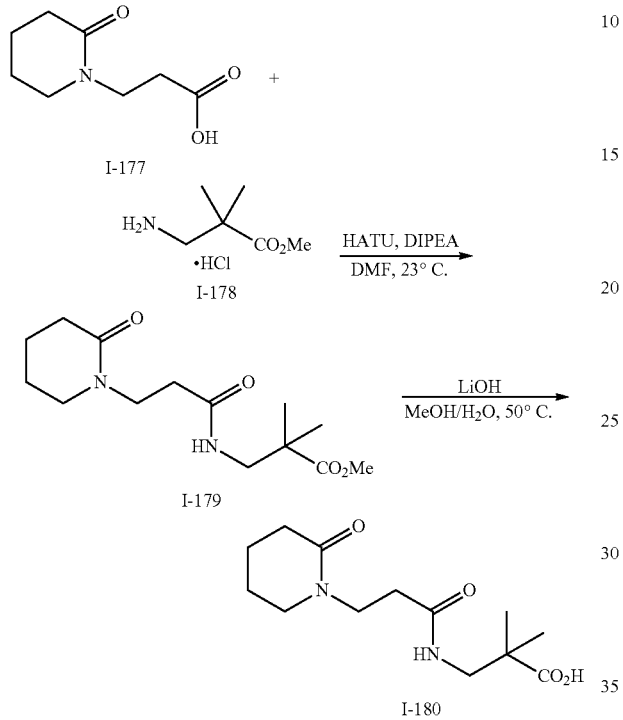

To a solution of carboxylic acid I-177 (79.1 mg, 0.46 mmol) and amine hydrochloride I-178 (77.5 mg, 1.0 equiv.) in DMF (1 mL) was added DIPEA (241 µL, 3.0 equiv.), followed by HATU (263.5 mg, 1.5 equiv.). The reaction mixture was stirred at ambient temperature for 3 hours, and then purified by preparative HPLC (H$_2$O/MeCN with 0.1% TFA) to afford the intermediate amide I-179 (190.2 mg) as a brown oil. This oil was redissolved in MeOH (3 mL). A solution of LiOH (22.1 mg, 2 equiv. based on carboxylic acid I-177) in H$_2$O (1 mL) was added. The reaction mixture was heated to 50° C. for 18 hours and then concentrated to remove MeOH. HCl (6M) was added to acidify the solution to pH<2, and the crude material was purified by preparative HPLC (H$_2$O/MeCN with 0.1% TFA) to afford I-180 (110.4 mg, 88% yield over 2 steps) as a colorless oil. ESI-MS found 271.2, $C_{13}H_{23}N_2O_4$ (MH$^+$) requires 271.2.

Synthesis of I-183 is Depicted in Scheme 79

Scheme 79

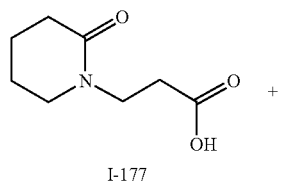

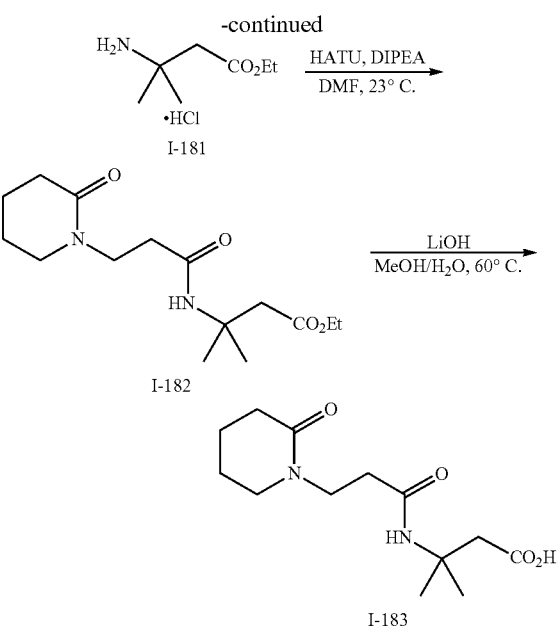

Using a procedure similar to that employed for the synthesis of I-180, carboxylic acid I-177 (77 mg, 0.45 mmol) afforded 62.4 mg (51% yield, 2 steps) of I-183 as a colorless oil. ESI-MS found 271.2, $C_{13}H_{23}N_2O_4$ (MH$^+$) requires 271.2.

Synthesis of I-184 is Depicted in Scheme 80

Scheme 80

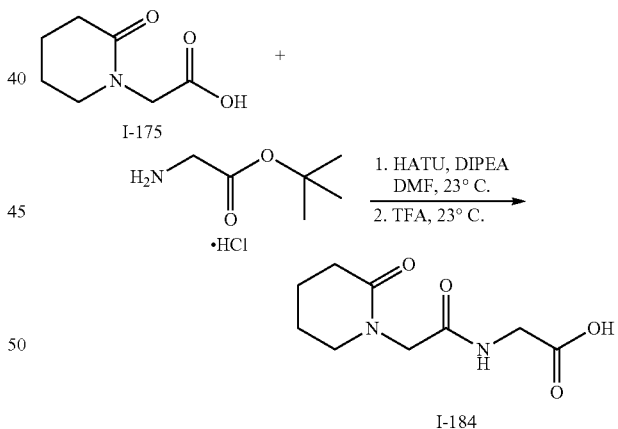

To a solution of carboxylic acid I-175 (72 mg, 0.46 mmol) and glycine tert-butyl ester hydrochloride (76.8 mg, 1.0 equiv.) in DMF (1.1 mL) was added DIPEA (240 µL, 3.0 equiv.), followed by HATU (261.5 mg, 1.5 equiv.). The reaction mixture was stirred at ambient temperature for 21 hours, then diluted with H$_2$O (1 mL), and purified by preparative HPLC (H$_2$O/MeCN with 0.1% AcOH) to afford the amide coupling product. TFA (5 mL) was added to this amide, and the reaction mixture was maintained at ambient temperature for 2 hours. The reaction mixture was then concentrated and purified by preparative HPLC (H$_2$O/MeCN with 0.1% TFA) to afford I-184 (84 mg, 86% yield over 2 steps) as a colorless oil. ESI-MS found 213.1 $C_9H_{13}N_2O_4$ (M–H)⁻ requires 213.1.

Synthesis of I-185 is Depicted in Scheme 81

Scheme 81

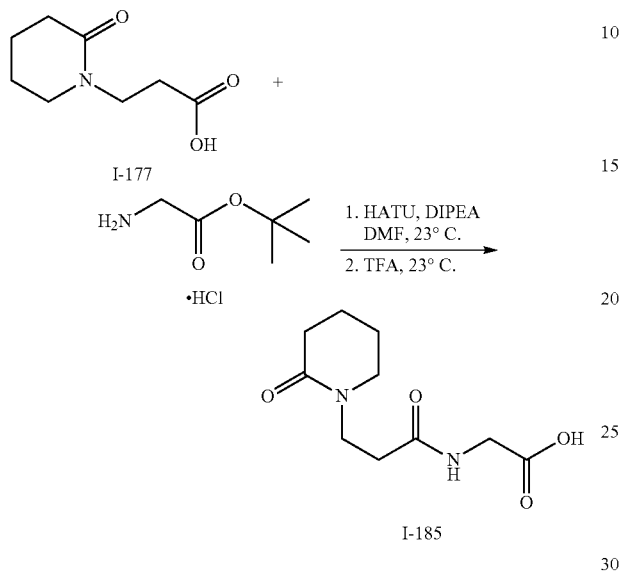

I-185

Using a procedure similar to that employed for the synthesis of I-184, carboxylic acid I-177 (72.4 mg, 0.42 mmol) afforded 104.1 mg (quant., 2 steps) of I-185 as a colorless oil. ESI-MS found 229.2 $C_{10}H_{17}N_2O_4$ (MH⁺) requires 229.1.

Synthesis of I-187 is Depicted in Scheme 82

Scheme 82

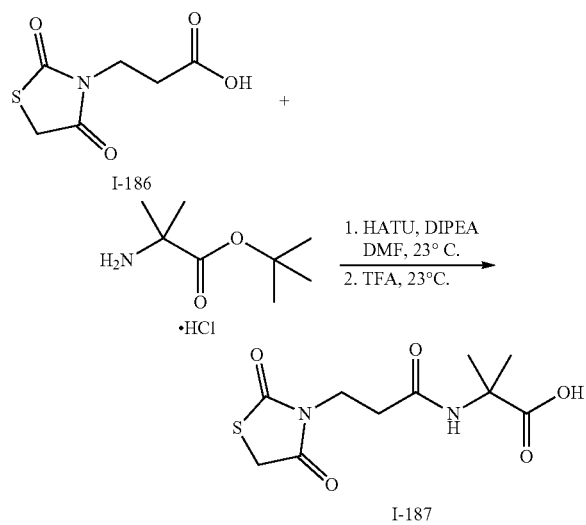

I-187

To a solution of carboxylic acid I-186 (96.4 mg, 0.51 mmol) and Q-aminoisobutyric acid tert-butyl ester hydrochloride (119.7 mg, 1.2 equiv.) in DMF (2 mL) was added DIPEA (178 µL, 2.0 equiv.), followed by HATU (290.6 mg, 1.5 equiv.). The reaction mixture was stirred at ambient temperature for 3 hours, then concentrated. TFA (5 mL) was added to the residue. The reaction mixture was stirred at ambient temperature for 1 hour and then concentrated under reduced pressure. The residue was purified by preparative HPLC (H₂O/MeCN with 0.1% TFA) to afford 74 mg (53% yield, 2 steps) of I-187 as a white solid. ESI-MS found 273.1, $C_{10}H_{13}N_2O_5S$ (M–H)⁻ requires 273.1.

Synthesis of I-188 is Depicted in Scheme 83

Scheme 83

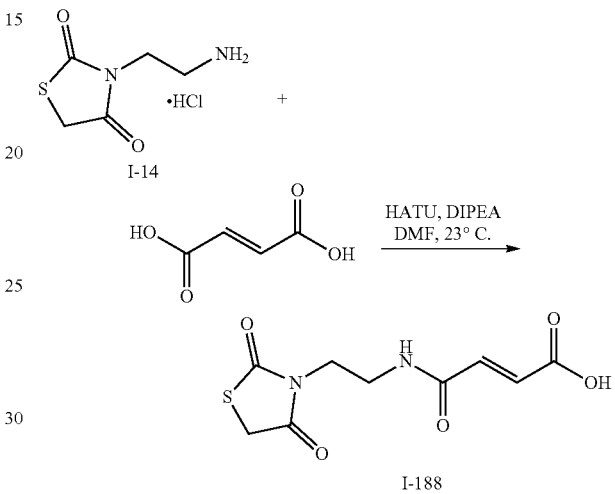

I-188

To a solution of amine hydrochloride I-14 (46.8 mg, 0.24 mmol) and fumaric acid (55.2 mg, 2.0 equiv.) in DMF (1.2 mL) was added DIPEA (124 µL, 3.0 equiv.), followed by HATU (135.7 mg, 1.5 equiv.). The reaction mixture was stirred at ambient temperature for 3.5 hours, then diluted with H₂O (0.3 mL), and purified by preparative HPLC (H₂O/MeCN with 0.1% TFA) to afford 45 mg (73% yield) of I-188 as a white solid. ESI-MS found 257.1, $C_9H_9N_2O_5S$ (M–H⁺) requires 257.1.

Synthesis of I-191 is Depicted in Scheme 84

Scheme 84

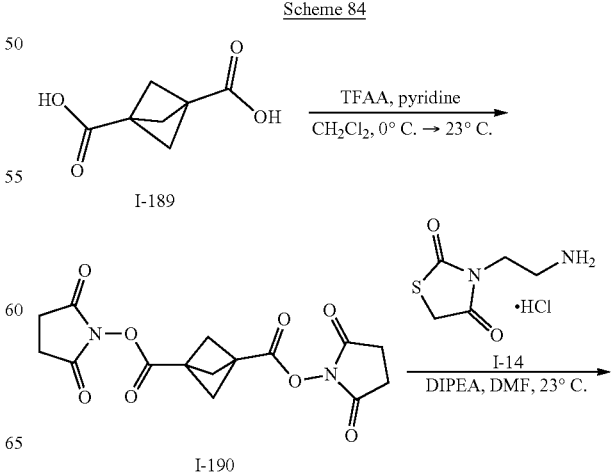

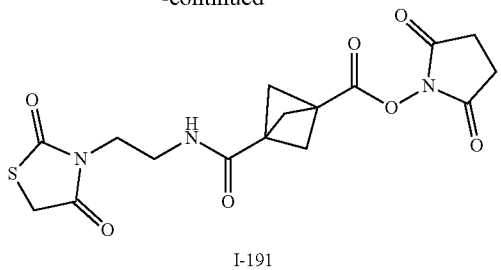
I-191

To a solution of dicarboxylic acid I-189 (101.5 mg, 0.65 mmol) and HOSu (149.6 mg, 2.0 equiv.) in DCM (4 mL) was added pyridine (209 µL, 4.0 equiv.). The solution was cooled to 0-5° C. and TFAA (183 µL, 2.0 equiv.) was added. The reaction mixture was allowed to warm to ambient temperature, stirred for 16 hours, and then concentrated. EtOH (10 mL) was added and the precipitated solids were collected by filtration and dried in vacuo to afford 218 mg of crude diester I-190, which was taken forward to the next step without further purification.

To a solution of amine salt I-14 (42.6 mg, 0.22 mmol) and diester I-190 (151.7 mg, ca. 2.0 equiv.) in DMF (1.3 mL) was added DIPEA (76 µL, 2.0 equiv.). The reaction mixture was agitated for 16 hours and then purified by preparative HPLC ($H_2O$/MeCN with 0.1% TFA) to afford 29 mg (34% yield) of I-191 as a colorless oil.

Synthesis of I-194 is Depicted in Scheme 85

Synthesis of I-197 is Depicted in Scheme 86

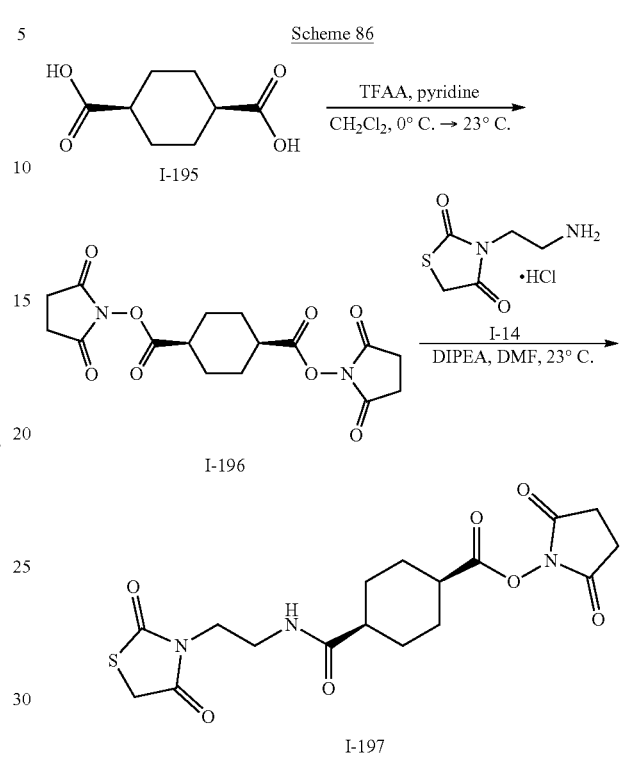

Diester I-196 and activated ester I-194 were prepared as described for I-191. Yield: 33.8 mg (31% yield) of 1-197 as a white solid.

Synthesis of I-200 is Depicted in Scheme 87

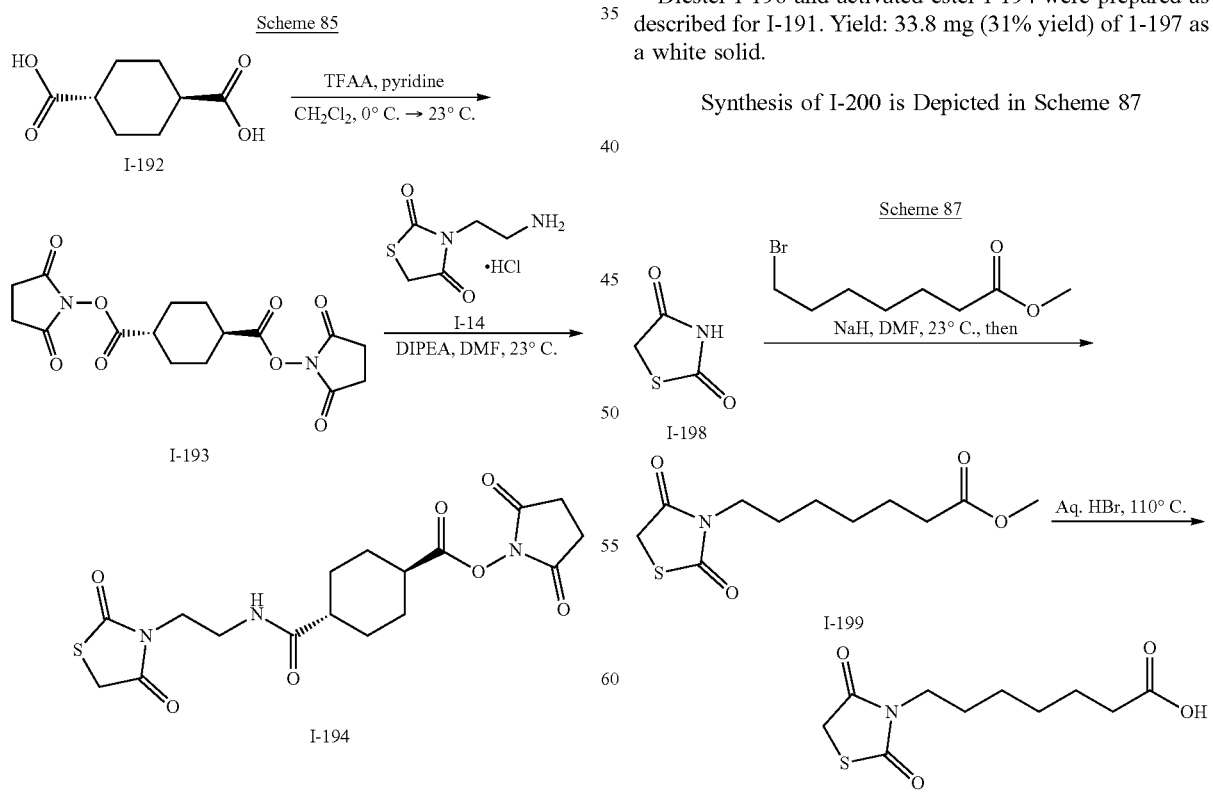

Diester I-193 and activated ester I-194 were prepared as described for I-191. Yield: 13 mg (10% yield) of 1-194 as a colorless oil.

To a solution of thiazolidinedione I-198 (1.0 g, 8.55 mmol) in anhydrous DMF (10 mL) was added NaH (376.7 mg, 9.41 mmol, 1.1 equiv.), and the reaction mixture was stirred for 30 minutes at ambient temperature. Methyl-7-bromoheptanoate (2.09 g, 1.1 equiv.) was added dropwise, and the mixture was stirred at ambient temperature for 16 hours. The reaction was monitored by TLC. The reaction mixture was quenched with H$_2$O (20 mL) and extracted with EtOAc (3×20 mL). The combined organic extracts were concentrated and the residue obtained was purified by preparative TLC (Petroleum ether/EtOAc=1:1) to afford 1-199 (900 mg, 41%) as a white solid.

TLC: (Petroleum ether/EtOAc=1:1), UV 254 nm
R$_f$ (compound I-198)=0.4
R$_f$ (compound I-199)=0.5

A solution of thiazolidinedione I-199 (900 mg, 3.47 mmol) in 40% aqueous HBr (10 mL) was refluxed at 110° C. for 4 hours. The reaction was monitored by TLC. Water (10 mL) was added and the reaction mixture was extracted with EtOAc (3×40 mL). The combined organic extracts were dried over Na$_2$SO$_4$, filtered, concentrated and the residue obtained was purified by preparative TLC (Petroleum ether/EtOAc=1:1) to afford I-200 (360 mg, 42%) as a white solid.

TLC: Petroleum ether/EtOAc=1:1, UV 254 nm
R$_f$ (compound I-199)=0.5
R$_f$ (I-200)=0.1
$^1$H NMR (400 MHz, d$_6$-DMSO) δ 11.92 (s, 1H), 4.17 (s, 2H), 3.47 (t, J=6.8 Hz, 2H), 2.18 (t, J=7.2 Hz, 2H), 1.57-1.37 (m, 4H), 1.34-1.12 (m, 4H).

Synthesis of I-202 is Depicted in Scheme 88

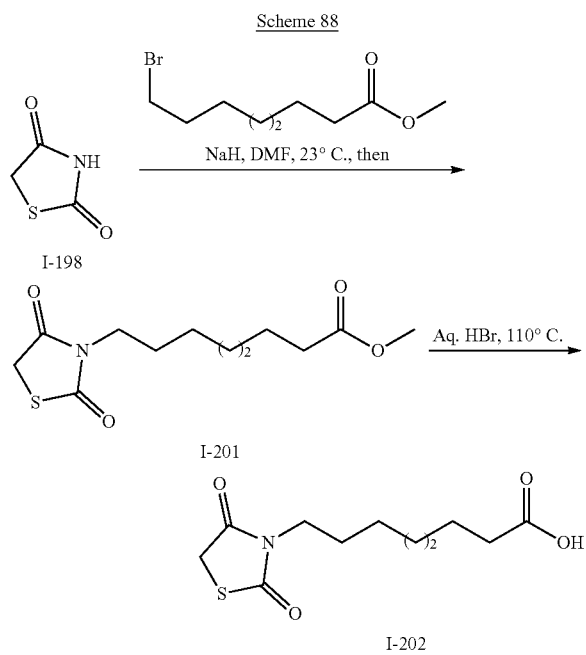

was monitored by TLC. The reaction mixture was quenched with H$_2$O (20 mL) and extracted with EtOAc (3×20 mL). The combined organic extracts were dried over Na$_2$SO$_4$, concentrated and the residue obtained was purified by preparative TLC (Petroleum ether/EtOAc=1:1) to afford intermediate ester I-201 (300 mg, 52%) as a white solid.

TLC: Petroleum ether/EtOAc=1:1, UV 254 nm
R$_f$ (compound I-198)=0.4
R$_f$ (compound I-201)=0.5

A solution of ester I-201 (300 mg, 1.1 mmol) in 40% aqueous HBr (5 mL) was refluxed at 110° C. for 4 hours. The reaction was monitored by TLC. Water (20 mL) was added and the reaction mixture was extracted with EtOAc (3×20 mL). The combined organic extracts were dried over Na$_2$SO$_4$, filtered, and concentrated to a residue, which was purified by preparative TLC (Petroleum Ether/EtOAc=1:1) to afford I-202 (144 mg, 51%) as a white solid.

TLC: Petroleum Ether/EtOAc=1:1, UV 254 nm
R$_f$ (compound I-202)=0.5
R$_f$ (I-202)=0.1
$^1$H NMR (400 MHz, d$_6$-DMSO) δ 11.96 (s, 1H), 4.17 (s, 2H), 3.46 (t, J=6.8 Hz, 2H), 2.18 (t, J=7.6 Hz, 2H), 1.52-1.43 (m, 4H), 0.39-1.13 (m, 6H).

Synthesis of I-204 is Depicted in Scheme 89

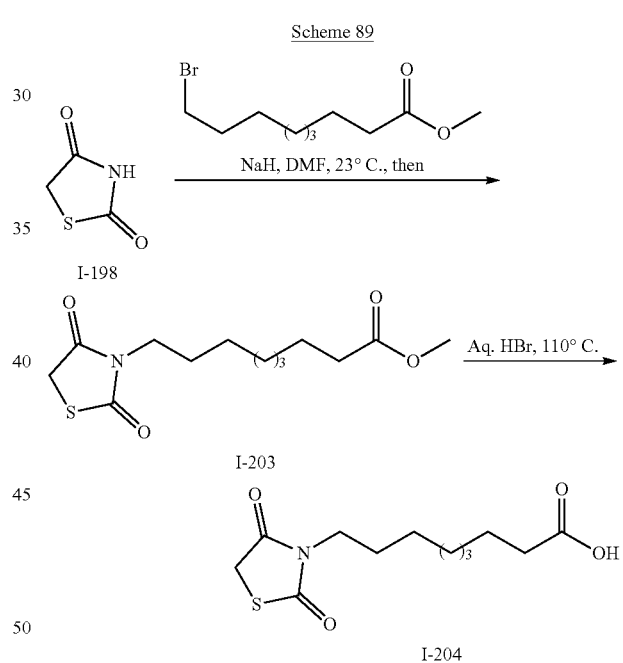

To a solution of thiazolidinedione I-198 (246 mg, 2.1 mmol) in anhydrous DMF (5 mL) was added NaH (53 mg, 1.1 equiv.) and the mixture was stirred for 30 minutes at ambient temperature. Methyl-9-bromononanoate (500 mg, 0.95 equiv.) was added dropwise and the mixture was stirred at ambient temperature for 4 hours. The reaction was monitored by TLC. The reaction mixture was quenched with H$_2$O (20 mL) and extracted with EtOAc (3×20 mL). The combined organic extracts were dried over Na$_2$SO$_4$, concentrated, and the residue obtained was purified by preparative TLC (Petroleum Ether/EtOAc=1:1) to afford ester I-203 (287 mg, 48%) as a white solid.

TLC: Petroleum Ether/EtOAc=1:1, UV 254 nm
R$_f$ (compound I-198)=0.4
R$_f$ (ester I-203)=0.5

To a solution of thiazolidinedione I-198 (246 mg, 2.1 mmol) in anhydrous DMF (5 mL) was added NaH (53 mg, 1.1 equiv.) and the reaction mixture was stirred for 30 minutes at ambient temperature. Methyl-8-bromooctanoate (500 mg, 1.0 equiv.) was added dropwise. The mixture was stirred at ambient temperature for 16 hours. The reaction A solution of ester I-203 (287 mg, 1.0 mmol) in 40% aqueous HBr (5 mL) was refluxed at 110° C. for 4 hours. The reaction was monitored by TLC. Water (10 mL) was added, and the reaction mixture was extracted with EtOAc (3×20 mL). The combined organic extracts were dried over Na$_2$SO$_4$, filtered, concentrated, and the residue obtained was purified by preparatory TLC (Petroleum Ether/EtOAc=1:1) to afford I-204 (122 mg, 45%) as a white solid.

TLC: Petroleum Ether/EtOAc=1:1, UV 254 nm

R$_f$ (compound I-203)=0.5

R$_f$ (I-204)=0.1

$^1$H NMR (400 MHz, DMSO) δ 11.98 (s, 1H), 4.17 (s, 2H), 3.44 (t, J=6.0 Hz, 2H), 2.48 (t, J=6.0 Hz, 2H), 1.55-1.36 (m, 4H), 1.32-1.09 (m, 8H).

Synthesis of I-209 is Depicted in Scheme 90

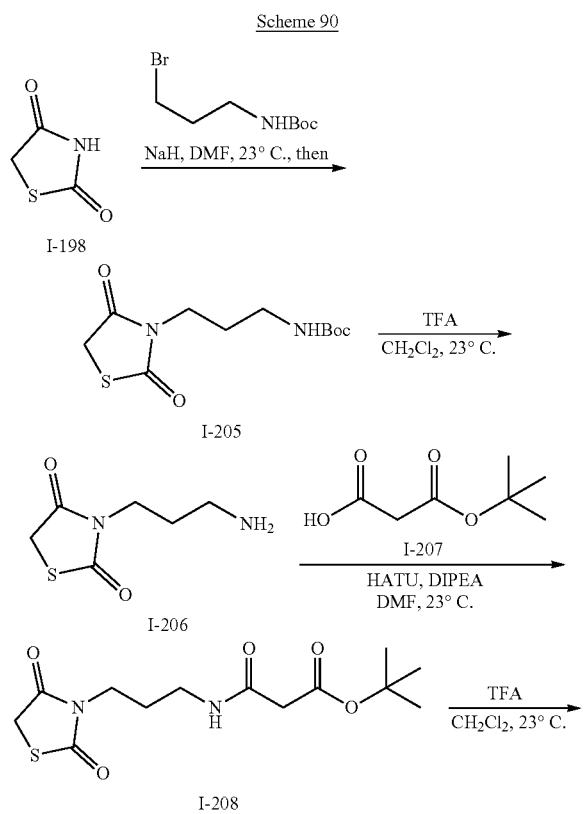

To a solution of thiazolidinedione I-198 (1.0 g, 8.55 mmol) in anhydrous DMF (10 mL) was added 60% NaH (376 mg, 1.1 equiv.) and the reaction mixture was stirred at ambient temperature for 1 hour. Tert-butyl (3-bromopropyl) carbamate (2.24 g, 1.1 equiv.) was added and the reaction mixture was stirred at ambient temperature for 3 hours. The reaction was monitored by TLC. The reaction mixture was quenched with H$_2$O (20 mL) and extracted with EtOAc (3×20 mL). The combined organic extracts were washed with brine, dried over Na$_2$SO$_4$, concentrated, and the residue obtained was purified by preparative TLC (Petroleum Ether/EtOAc=1:1) to afford carbamate I-205 (889 mg, 38%) as a light yellow solid.

TLC: Petroleum Ether/EtOAc=1:1, UV 254 nm

R$_f$ (compound I-198)=0.5

R$_f$ (carbamate I-205)=0.6

To a solution of carbamate I-205 (500 mg, 1.82 mmol) in DCM (5 mL) was added TFA (0.5 mL). The reaction mixture was stirred at ambient temperature for 1 hour. The reaction was monitored by TLC. The reaction mixture was concentrated under reduced pressure to afford amine I-206 (315 mg, 99%) as a light yellow solid.

TLC: Petroleum Ether/EtOAc=1:1, UV 254 nm

R$_f$ (compound I-205)=0.6

R$_f$ (compound amine I-206)=0.1

A solution of amine I-206 (315 mg, 1.81 mmol), carboxylic acid I-207 (263 mg, 1.0 equiv.), HATU (688 mg, 1.1 equiv.), and DIPEA (851 mg, 4.0 equiv.) in anhydrous DMF (3 mL) was stirred at ambient temperature for 16 hours. The reaction was monitored by TLC. The reaction mixture was quenched with H$_2$O (5 mL) and extracted with EtOAc (3×5 mL). The combined organic extracts were dried over Na$_2$SO$_4$, and concentrated to a residue that was purified by preparative TLC (Petroleum Ether/EtOAc=1:1) to afford amide I-208 (250 mg, 48%) as a light yellow solid.

TLC: Petroleum Ether/EtOAc=1:1, UV 254 nm

R$_f$ (amine I-206)=0.1

R$_f$ (amide I-208)=0.6

To a solution of amide I-208 (250 mg, 0.79 mmol) in DCM (3 mL) was added TFA (0.3 mL). The mixture was stirred at ambient temperature for 4 hours. The reaction was monitored by TLC. The reaction mixture was concentrated to afford a residue, which was purified by preparative HPLC to yield acid I-209 (50 mg, 24%) as a white solid.

TLC: Petroleum Ether/EtOAc=1:1, UV 254 nm

R$_f$ (amide I-208)=0.6

R$_f$ (I-209)=0.1

$^1$H NMR (400 MHz, DMSO): δ 12.48 (br. s, 1H), 8.06 (s, 1H), 4.16 (s, 2H), 3.49 (t, J=6.8 Hz, 2H), 3.08 (s, 2H), 3.06-3.00 (m, 2H), 1.65-1.57 (m, 2H).

Synthesis of I-213 is Depicted in Scheme 91

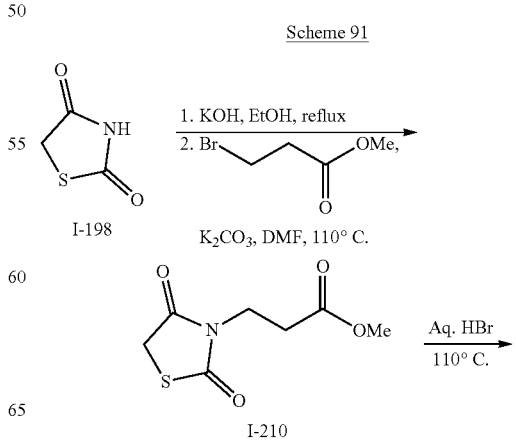

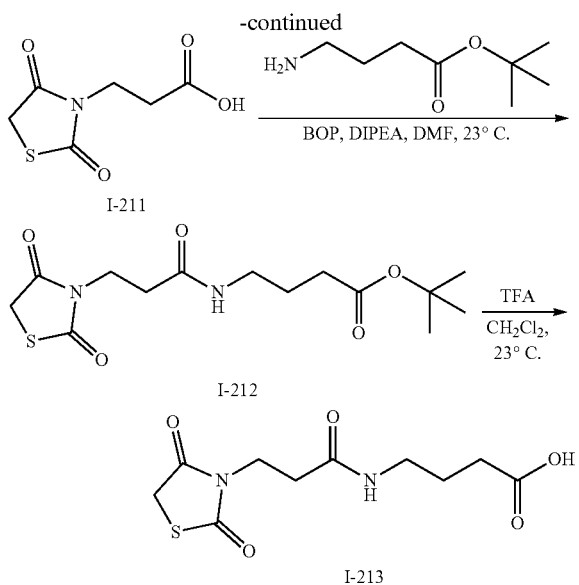

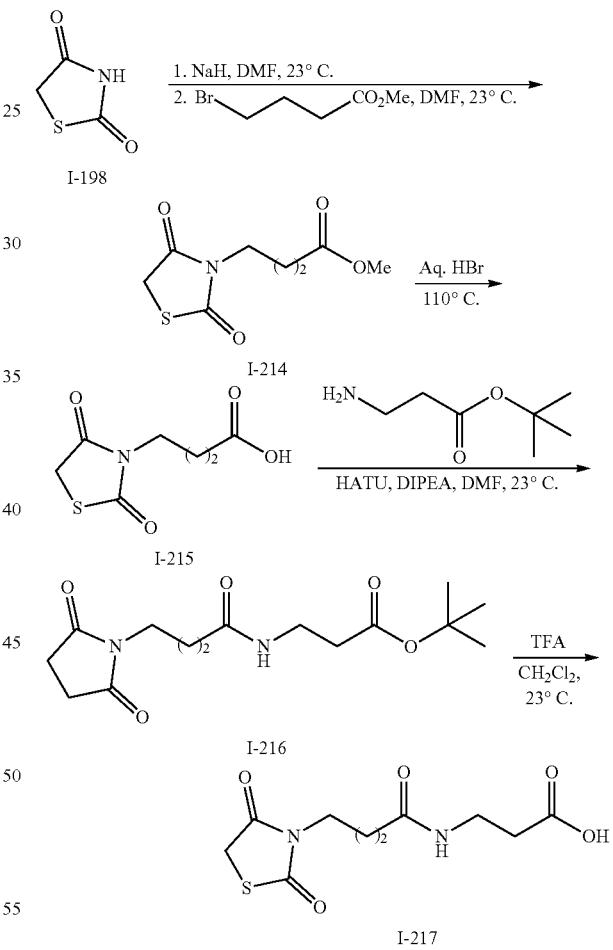

To a solution of amide I-212 (300 mg, 0.91 mmol) in DCM (3 mL) was added TFA (0.3 mL). The reaction mixture was stirred at ambient temperature for 2 hours. The reaction was monitored by TLC. The reaction mixture was concentrated and the residue obtained was purified by preparative HPLC to afford I-213 (52 mg, 21%) as a white solid.

TLC: Petroleum Ether/EtOAc=1:1, UV 254 nm $R_f$ (carboxylic acid I-211)=0.5

$R_f$ (I-213)=0.1

$^1$H NMR (400 MHz, DMSO) δ 12.05 (s, 1H), 7.98 (t, J=5.2 Hz, 1H), 4.14 (s, 2H), 3.66 (t, J=7.6 Hz, 2H), 3.02-2.96 (m, 2H), 2.31 (t, J=7.2 Hz, 2H), 2.20 (t, J=7.6 Hz, 2H), 1.61-1.53 (m, 2H).

Synthesis of I-217 is Depicted in Scheme 92

A solution of thiazolidinedione I-198 (5.0 g, 42.7 mmol) and KOH (2.63 g, 1.1 equiv.) in EtOH (50 mL) was refluxed for 4 hours. The reaction mixture was concentrated to give the crude potassium salt (6.62 g) as a white solid. To a solution of this salt (6.62 g, 42.7 mmol) in DMF (70 mL) was added $K_2CO_3$ (25 g, 170.8 mmol, 4.0 equiv.) and methyl-3-bromopropionate (21.4 g, 3.0 equiv.). The reaction mixture was stirred at ambient temperature for 16 hours. The reaction was monitored by TLC and quenched with $H_2O$ (100 mL), then extracted with EtOAc (3×80 mL). The combined organic extracts were washed with brine, dried over $Na_2SO_4$ and concentrated under reduced pressure to a residue, which was purified by flash chromatography on silica (Petroleum Ether/EtOAc=20:1-5:1) to afford ester I-210 (2.8 g, 32%) as a light yellow oil.

TLC: Petroleum Ether/EtOAc=1:1, UV 254 nm $R_f$ (compound I-198)=0.1

$R_f$ (compound I-210)=0.5

A solution of ester I-210 (3.16 g, 15.56 mmol) in 45% HBr (25 mL) was refluxed at 110° C. for 4 hours. The reaction was monitored by TLC. Water (25 mL) was added and the reaction mixture was extracted with EtOAc (3×20 mL). The combined extracts were washed with brine, dried over $Na_2SO_4$, filtered, and concentrated to a residue, which was purified by preparative TLC (Petroleum Ether/EtOAc=1:1) to afford carboxylic acid I-211 (2.73 g, 93%) as a white solid.

TLC: Petroleum Ether/EtOAc=1:1, UV 254 nm $R_f$ (ester I-210)=0.5

$R_f$ (carboxylic acid I-211)=0.1

A solution of carboxylic acid I-211 (719 mg, 3.8 mmol), gamma-aminobutyric acid tert-butyl ester (550 mg, 3.45 mmol, 1.0 equiv.), BOP (2.52 g, 1.1 equiv.) and DIPEA (2.25 g, 4.0 equiv.) in anhydrous DMF (8 mL) was stirred at ambient temperature for 16 hours. The reaction was monitored by TLC. The reaction mixture was quenched with $H_2O$ (10 mL) and extracted with EtOAc (3×10 mL). The combined organic extracts were dried over $Na_2SO_4$, concentrated and the residue obtained was purified by preparative TLC (Petroleum Ether/EtOAc=1:1) to afford amide I-212 (600 mg, 52%) as a light yellow solid.

TLC: Petroleum Ether/EtOAc=1:1, UV 254 nm $R_f$ (carboxylic acid I-211)=0.1

$R_f$ (amide I-212)=0.5

To a solution of thiazolidinedione I-198 (1.62 g, 13.8 mmol) in anhydrous DMF (15 mL) was added NaH (552 mg, 1.0 equiv.) and the reaction mixture was stirred for 10 min at ambient temperature. Methyl-4-bromobutanoate (2.5 g, 1.0 equiv.) was added dropwise, and the reaction mixture was stirred at ambient temperature for 4 hours. The reaction was monitored by TLC. $H_2O$ (20 mL) was added and the mixture was extracted with EtOAc (3×20 mL). The combined organic extracts were washed with 5% HCl solution, dried over Na$_2$SO$_4$, and concentrated; the residue obtained was purified by preparative TLC (Petroleum Ether/EtOAc=2:1) to afford ester I-214 (1.8 g, 60% yield) as a colorless oil.

TLC: Petroleum Ether/EtOAc=1:1, UV 254 nm

R$_f$ (compound I-198)=0.2

R$_f$ (ester I-214)=0.5

A solution of ester I-214 (1.8 g, 8.29 mmol) in 40% HBr (15 mL) was refluxed at 110° C. for 4 hours. The reaction was monitored by TLC. Water (15 mL) was added, and the reaction was extracted with EtOAc (3×50 mL). The combined organic extracts were dried over Na$_2$SO$_4$, filtered, and concentrated; the residue obtained was purified by preparative TLC (EtOAc) to afford carboxylic acid I-215 (1.3 g, 77%) as a white solid.

TLC: Petroleum Ether/EtOAc=2:1, UV 254 nm

R$_f$ (ester I-214)=0.6

R$_f$ (carboxylic acid I-215)=0.3

A solution of carboxylic acid I-215 (200 mg, 1.0 mmol), DIPEA (387 mg, 3.0 equiv.), β-alanine-tert-butyl ester (143 mg, 1.0 equiv.) and HATU (564 mg, 1.5 equiv.) in anhydrous DMF (2 mL) was stirred at ambient temperature for 16 hours. The reaction was monitored by TLC. H$_2$O (10 mL) was added and the reaction mixture was extracted with DCM (3×10 mL). The combined organic extracts were dried over Na$_2$SO$_4$, and concentrated; the residue obtained was purified by preparative TLC (Petroleum Ether/EtOAc=1:2) to afford amide I-216 (150 mg, 46%) as a light yellow oil.

TLC: Petroleum Ether/EtOAc=1:1, UV 254 nm

R$_f$ (carboxylic acid I-215)=0.2

R$_f$ (amide I-216)=0.7

To a solution of amide I-216 (150 mg, 0.455 mmol) in DCM (2 mL) was added TFA (2 mL). The reaction mixture was stirred at ambient temperature for 2 hours. The reaction was monitored by LC-MS. The reaction mixture was concentrated, and the residue obtained was purified by preparative HPLC to afford I-217 (30 mg, 24%) as a colorless oil.

LC-MS: 275 (M+1)

$^1$H NMR (400 MHz, CD$_3$OD): δ 4.06 (s, 2H), 3.63 (t, J=6.4 Hz, 2H), 3.42-3.38 (m, 2H), 2.50 (t, J=7.6 Hz, 2H), 2.20 (t, J=7.2 Hz, 2H), 1.90-1.85 (m, 2H).

Synthesis of I-221 is Depicted in Scheme 93

Scheme 93

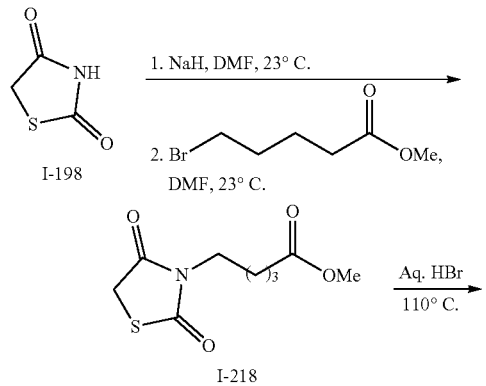

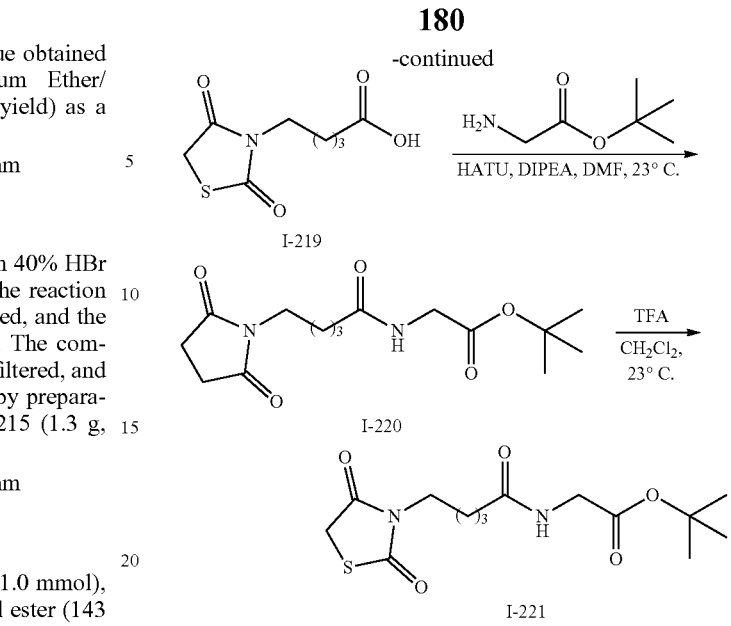

To a solution of thiazolidinedione I-198 (2 g, 17.1 mmol) in anhydrous DMF (25 mL) was added NaH (820 mg, 1.2 equiv.), and the reaction mixture was stirred for 10 minutes at ambient temperature. Methyl-5-bromopentanoate (3.66 g, 1.1 equiv.) was added dropwise to the reaction and the mixture was stirred at ambient temperature for 4 hours. The reaction was monitored by TLC. H$_2$O (40 mL) was added, and the reaction mixture was extracted with EtOAc (3×30 mL). The combined organic extracts were washed with 5% HCl solution, dried over MgSO$_4$, and concentrated. The residue obtained was purified by preparative TLC (Petroleum Ether/EtOAc=2:1) to afford ester I-218 (1.23 g, 31%) as a colorless oil.

TLC: Petroleum Ether/EtOAc=2:1, UV 254 nm

R$_f$ (compound I-198)=0.2

R$_f$ (ester I-218)=0.5

A solution of ester I-218 (1.23 g, 5.32 mmol) in 40% HBr (12 mL) was refluxed at 110° C. for 4 hours. The reaction was monitored by TLC. Water (12 mL) was added, and the reaction mixture was extracted with EtOAc (3×50 mL). The combined organic extracts were dried over MgSO$_4$, filtered, and concentrated; the residue obtained was purified by preparative TLC (EtOAc) to afford carboxylic acid I-219 (777 mg, 67%) as a white solid.

TLC: Petroleum Ether/EtOAc=2:1, UV 254 nm

R$_f$ (ester I-218)=0.6

R$_f$ (carboxylic acid I-219)=0.3

A solution of carboxylic acid I-219 (200 mg, 0.922 mmol), DIPEA (142 mg, 1.2 equiv.), glycine-tert-butyl ester (145 mg, 1.2 equiv.) and HATU (420 mg, 1.2 equiv.) in anhydrous DMF (5 mL) was stirred at ambient temperature for 4 hours. The reaction was monitored by TLC. H$_2$O (10 mL) was added and the reaction mixture was extracted with DCM (3×10 mL). The combined organic extracts were dried over Na$_2$SO$_4$, and concentrated. The residue obtained was purified by preparative TLC (Petroleum Ether/EtOAc=1:2) to give amide I-220 (200 mg, 66%) as a yellow oil.

TLC: Petroleum Ether/EtOAc=1:1, UV 254 nm

R$_f$ (carboxylic acid I-219)=0.2

R$_f$ (amide I-220)=0.7

To a solution of amide I-220 (200 mg, 0.606 mmol) in DCM (2 mL) was added TFA (2 mL). The reaction mixture was stirred at ambient temperature for 2 hours. The reaction was monitored by LC-MS. The reaction mixture was concentrated, and the residue obtained was purified by preparative HPLC to give I-221 (77 mg, 46%) as a white solid.

LC-MS: 275 (M+1)

$^1$H NMR (400 MHz, CD$_3$OD): δ 4.07 (s, 2H), 3.88 (s, 2H), 3.63 (t, J=6.4 Hz, 2H), 2.29 (t, J=6.4 Hz, 2H), 1.63-1.30 (m, 4H).

The Synthesis of Compound I-225 Involved 4 Steps as Depicted in the Following Scheme 94.

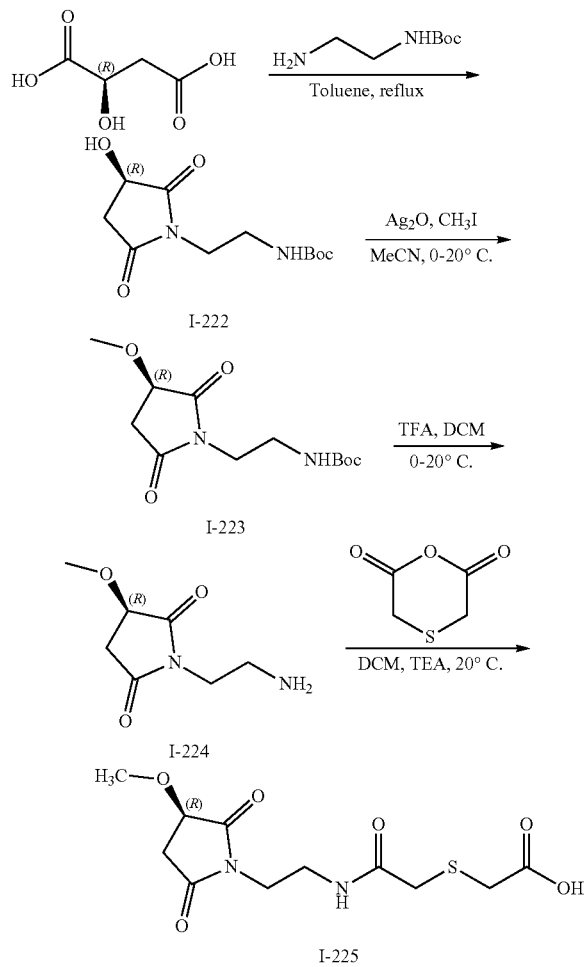

Scheme 94

The chemical structure of the target compound was confirmed by $^1$H NMR and LC-MS with the purity >95% (HPLC 214 & 254 nm).

Step 1: tert-butyl (R)-(2-(3-hydroxy-2,5-dioxopyrrolidin-1-yl)ethyl)carbamate (I-222)

A mixture of (R)-2-hydroxysuccinic acid (cas: 636-61-3, 2 g, 14.92 mmol), tert-butyl (2-aminoethyl)carbamate (cas: 57260-73-8, 2 g, 1.0 equiv.) in toluene (25 mL) was refluxed at 130° C. for 2 hours. The reaction mixture was then cooled to ambient temperature and concentrated to give the crude product. The crude product was purified by silica gel chromatography to provide I-222 as a pale yellow oil (0.624 g, 17% yield). MS (ESI, pos. ion) m/z: 281 (M+Na).

Step 2: tert-butyl (R)-(2-(3-methoxy-2,5-dioxopyrrolidin-1-yl)ethyl)carbamate (I-223)

To a solution of tert-butyl (R)-(2-(3-hydroxy-2,5-dioxopyrrolidin-1-yl)ethyl)carbamate (0.624 g, 2.42 mmol) in anhydrous MeCN (10 mL) at 0-5° C. was added Ag$_2$O (1.12 g, 2.0 equiv.) under N$_2$. The reaction mixture was then stirred for 5 minutes and MeI (0.309 g, 0.9 equiv.) was added to the reaction. The reaction mixture was allowed to warm to ambient temperature and stirred for another 10 hours, then filtered. The filtrate was concentrated in vacuo to give the crude product, which was purified by preparative TLC (Petroleum ether:EtOAc=1:2) to provide I-223 as a pale oil (0.2 g, 30% yield). MS (ESI, pos. ion) m/z: 295 (M+Na).

Step 3: (R)-1-(2-aminoethyl)-3-methoxypyrrolidine-2,5-dione (I-224)

A solution of tert-butyl (R)-(2-(3-methoxy-2,5-dioxopyrrolidin-1-yl)ethyl)carbamate (200 mg, 0.735 mmol) in TFA/DCM (1:3 v/v, 8 mL) was stirred at 25° C. for 1 hour. When LC-MS analysis indicated that the reaction was complete, the reaction mixture was concentrated under reduced pressure to afford the crude amine TFA salt I-224 (390 mg) as a pale oil, which was used directly in next step. MS (ESI, pos. ion) m/z: 173 (M+1)

Step 4: (R)-2-((2-((2-(3-methoxy-2,5-dioxopyrrolidin-1-yl)ethyl)amino)-2-oxoethyl)thio)acetic acid (I-225)

To a solution of (R)-1-(2-aminoethyl)-3-methoxypyrrolidine-2,5-dione (390 mg, 1.37 mmol) and thiodiglycolic anhydride (217 mg, 1.2 equiv.) in 5 mL of DCM was added TEA (166 mg, 1.2 equiv.). The reaction mixture was stirred for 2 hours, and then concentrated in vacuo to give the crude product. The crude product was purified by preparative HPLC (Mobile Phase: MeCN/H$_2$O (0.1% TFA)) to afford I-225 (130 mg, 19% yield) as a pale oil. MS (ESI, pos. ion) m/z: 305 (M+1). $^1$H NMR (400 MHz, DMSO) δ 8.14 (m, 1H), 4.31 (m, 1H), 3.47-3.39 (m, 5H), 3.33 (s, 2H), 3.28-3.17 (m, 2H), 3.14 (s, 2H), 2.96 (m, 1H), 2.55 (m, 1H).

The Synthesis of Compound I-229 Involved 4 Steps as Depicted in the Following Scheme 95.

Scheme 95(S)-2-((2-((2-(3-methoxy-2,5-dioxopyrrolidin-1-yl)ethyl)amino)-2-oxoethyl)thio)acetic acid (I-229)

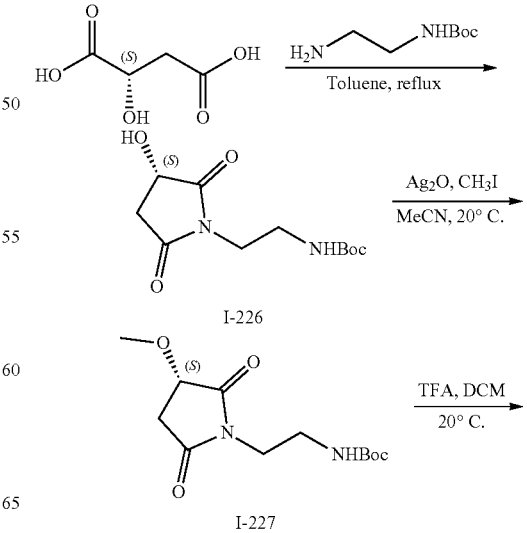

183

-continued

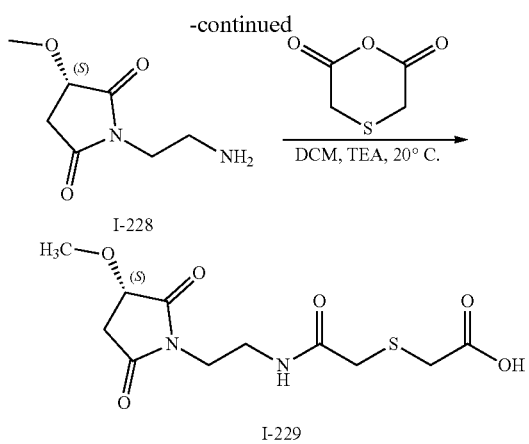

I-228

I-229

The synthetic route for I-229 was similar with I-225 and commenced with (S)-2-hydroxysuccinic acid (cas: 97-67-6). I-229 (pale oil, 120 mg, 15% yield) was isolated by preparative HPLC (Mobile Phase: MeCN/H$_2$O (0.1% TFA)). MS (ESI, pos. ion) m/z: 305 (M+1). $^1$H NMR (400 MHz, CDCl$_3$) δ 7.41 (s, 1H), 5.68 (s, 1H), 4.28 (m, 1H), 3.71 (m, 2H), 3.60 (s, 3H), 3.56-3.50 (m, 2H), 3.33 (m, 4H), 3.05 (m, 1H), 2.70-2.62 (m, 1H).

E-149 (from (R*)-I-234) and E-150 (from (S*)-I-234)

The Syntheses of Both Enantiomers of I-234 Involved 5 Steps as Depicted in Scheme 96:

Scheme 96

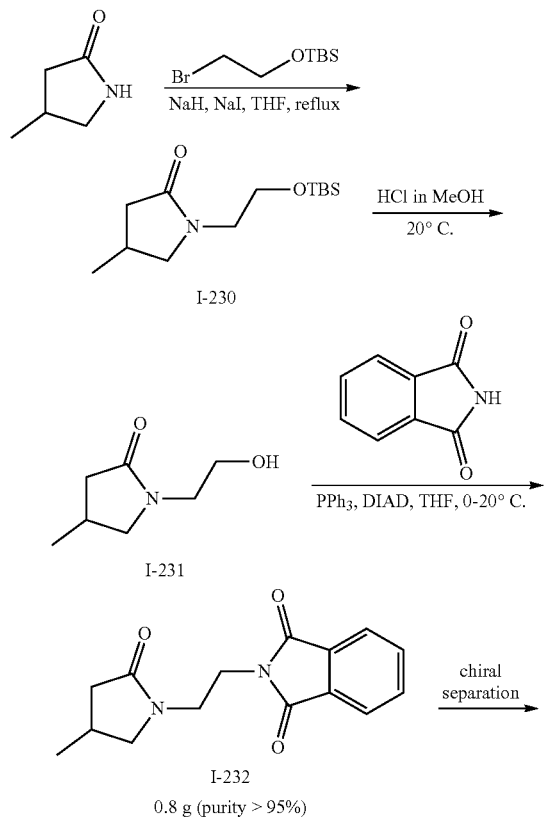

I-230

I-231

I-232

0.8 g (purity > 95%)

184

-continued

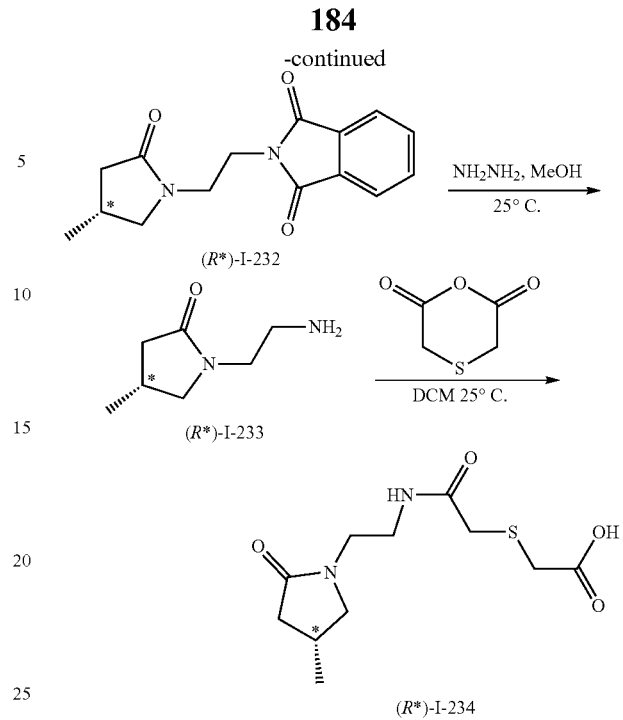

(R*)-I-232

(R*)-I-233

(R*)-I-234

(S*)-I-232

(S*)-I-233

(S*)-I-234

Step 1: 1-(2-((tert-butyldimethylsilyl)oxy)ethyl)-4-methylpyrrolidin-2-one (I-230)

(2-bromoethoxy)(tert-butyl)dimethylsilane (cas: 86864-60-0, 3.18 g, 15 mmol) in 20 mL of THF was added dropwise to an ice-cooled suspension of 4-methylpyrrolidin-2-one (cas: 2996-58-9, 1 g, 1.0 equiv.), NaI (1.5 g, 1.0 equiv.) and NaH (2.4 g, 6.0 equiv.) in THF (50 mL) with stirring under N$_2$. After 2 hours, the ice bath was removed and the reaction mixture was heated to reflux overnight. The reaction was quenched with H$_2$O (50 mL). After removal of the solvent under reduced pressure, the residue was partitioned between EtOAc and H$_2$O. The aqueous layer was extracted with EtOAc (3×20 mL). The combined organic extracts were dried over MgSO$_4$, concentrated and the residue obtained was purified by silica gel chromatography to afford 360 mg (14%) of I-230 as a pale oil. MS (ESI, pos. ion) m/z: 258 (M+1).

Step 2: 1-(2-hydroxyethyl)-4-methylpyrrolidin-2-one (I-231)

To 1-(2-((tert-butyldimethylsilyl)oxy)ethyl)-methylpyrrolidin-2-one I-230 (550 mg, 2.14 mmol) in MeOH (5 ml) was added 10 mL of HCl (4 M in MeOH). After 10 min, MeOH was removed under reduced pressure to afford 300 mg of the crude alcohol I-231 as a light yellow oil, which was taken forward to the next step without purification.

Step 3: 2-(2-(4-methyl-2-oxopyrrolidin-1-yl)ethyl)isoindoline-1,3-dione (I-232)

To a stirred solution of 1-(2-hydroxyethyl)-4-methylpyrrolidin-2-one I-231 (96 mg, 0.66 mmol), phthalimide (cas: 85-41-6, 105 mg, 1.0 equiv.) and triphenylphosphine (260 mg, 1.0 equiv.) in anhydrous THF (10 mL) was added a solution of DIAD (400 mg, 3.0 equiv.) in anhydrous THF (2 mL) dropwise at 0° C. The reaction mixture was allowed to warm to ambient temperature and stirred for 8 hours. The reaction was monitored by LC-MS. Upon completion of the reaction, the reaction mixture was filtered. The filtrate was concentrated, and the resulting residue was purified by silica gel chromatography (10-80% EtOAc in hexanes) to give 145 mg of I-232 (60% purity) as light oil. MS (ESI, pos. ion) m/z: 273.1 (M+1).

The racemic mixture I-232 was subjected to chromatographic separation using a chiral column to afford the two enantiomers (CHIRALPAK AD column, (Hexane/EtOH=50/50 (v/v)), but their absolute configuration was not established.

Step 4: 1-(2-aminoethyl)-4-methylpyrrolidin-2-one (I-233)

To a stirred solution of each enantiomer of 2-(2-(4-methyl-2-oxopyrrolidin-1-yl)ethyl)isoindoline-1,3-dione, I-232 (145 mg, 0.53 mmol) in MeOH (10 mL) was added hydrazine monohydrate (40 mg, 1.5 equiv.). The reaction mixture was stirred at ambient temperature for 18 hours and then filtered. The filtrate was concentrated. The residue was dissolved in DCM, and the precipitate was again filtered off. After concentration of the filtrate, the 72 mg (78%) of crude amine I-233 was used in the next step without purification. MS (ESI, pos. ion) m/z: 143.1 (M+1).

Step 5: 2-((2-((2-(4-methyl-2-oxopyrrolidin-1-yl)ethyl)amino)-2-oxoethyl)thio) acetic acid (I-234)

To a stirred solution of each enantiomer of 1-(2-aminoethyl)-4-methylpyrrolidin-2-one, I-233 (144 mg, 1.06 mmol) in DCM (10 mL) at ambient temperature was added thiodiglycolic anhydride (cas: 3261-87-8, 210 mg, 1.6 mmol), and the resulting solution was stirred at ambient temperature for 1 hour. The reaction mixture was concentrated and purified by preparative HPLC to give 150 mg (55%) of I-234 as a light oil. MS (ESI, pos. ion) m/z: 275.1 (M+1).

(R*)-I-234: $^1$H NMR (400 MHz, CDCl$_3$) δ 7.30 (s, 1H), 3.71-3.61 (m, 1H), 3.58-3.39 (m, 4H), 3.36 (s, 2H), 3.20 (d, 2H), 3.10 (dd, 1H), 2.65 (dd, 1H), 2.49 (td, 1H), 2.13 (dd, 1H), 1.14 (s, 3H).

(S*)-I-234: $^1$H NMR (400 MHz, CDCl$_3$) δ 7.35 (s, 1H), 3.71-3.61 (m, 1H), 3.58-3.39 (m, 4H), 3.36 (s, 2H), 3.20 (d, 2H), 3.10 (dd, 1H), 2.65 (dd, 1H), 2.49 (td, 1H), 2.13 (dd, 1H), 1.12 (s, 3H).

The Synthesis of I-240 Involved 6 Steps as Depicted in the Following Scheme 97.

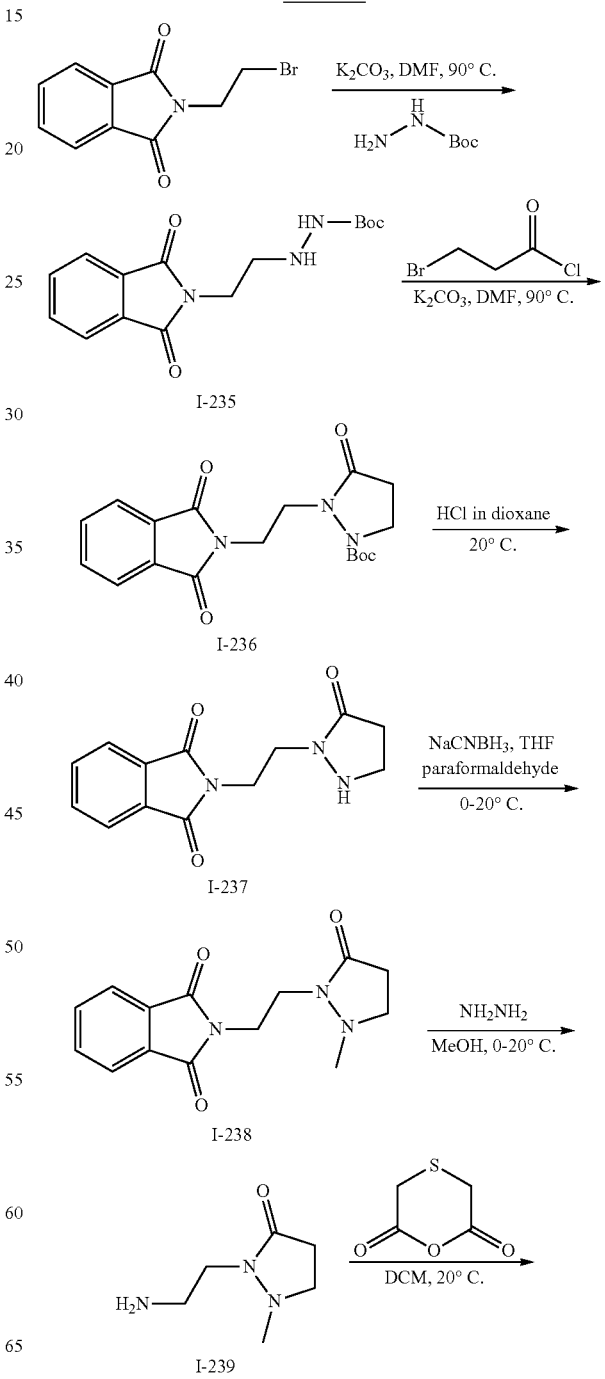

Scheme 97

-continued

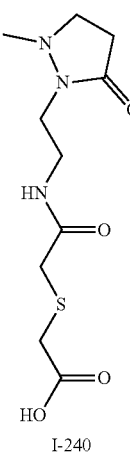

I-240

Step 1: tert-butyl 2-(2-(1,3-dioxoisoindolin-2-yl)ethyl)hydrazine-1-carboxylate (I-235)

To a solution of 2-(2-bromoethyl)isoindoline-1,3-dione (cas: 574-98-1, 20 g, 79 mmol) and tert-butyl hydrazinecarboxylate (cas: 870-46-2, 16 g, 1.5 equiv.) in DMF (100 mL) was added $K_2CO_3$ (28 g, 2 equiv.). The solution was heated to 90° C. and stirred for 12 hours. Upon completion of the reaction, the reaction was quenched with water (100 mL) and extracted with EtOAc (3×100 mL). After drying with $Na_2SO_4$, the combined organic extracts were concentrated, and the crude product was purified by silica gel chromatography to provide 5 g of I-235 as a pale oil (21% yield). MS (ESI, pos. ion) m/z: 328.2 (M+23).

Step 2: tert-butyl 2-(2-(1,3-dioxoisoindolin-2-yl)ethyl)-3-oxopyrazolidine-1-carboxylate (I-236)

A solution of tert-butyl 2-(2-(1,3-dioxoisoindolin-2-yl)ethyl)hydrazine-1-carboxylate (5 g, 16.4 mmol), 3-bromopropanoyl chloride (3.6 g, 1.5 equiv.) and $K_2CO_3$ (37 g, 2 equiv.) in DMF (80 mL) was heated to 90° C. for 16 hours. Upon completion of the reaction, the reaction was quenched with water (80 mL) and extracted with EtOAc (3×80 mL). After drying with $Na_2SO_4$, the combined organic extracts were concentrated, and the crude product was purified by silica gel chromatography to afford 3.2 g (54% yield) of I-236 as a pale oil. MS (ESI, pos. ion) m/z: 382.2 (M+23).

Step 3: 2-(2-(5-oxopyrazolidin-1-yl)ethyl)isoindoline-1,3-dione I-237)

A solution of tert-butyl 2-(2-(1,3-dioxoisoindolin-2-yl)ethyl)-3-oxopyrazolidine-1-carboxylate (3.2 g, 8.9 mmol) in HCl (4M in dioxane, 15 mL) was stirred at ambient temperature for 0.5 hours. Upon completion of the reaction, the reaction mixture was concentrated to afford the crude pyrazolone I-237 (3.5 g) as a white solid, which was used directly in the next step. MS (ESI, pos. ion) m/z: 260.2 (M+1).

Step 4: 2-(2-(2-methyl-5-oxopyrazolidin-1-yl)ethyl)isoindoline-1,3-dione (I-238)

To a solution of 2-(2-(5-oxopyrazolidin-1-yl)ethyl)isoindoline-1,3-dione (3.5 g, ca. 8.9 mmol) and paraformaldehyde (2.7 g, 10 equiv.) in THF was added 2 drops of AcOH.

After 1 hour, $NaCNBH_3$ (cas: 25895-60-7, 2.8 g, 5 equiv.) was added to the reaction mixture at 0° C. The reaction mixture was stirred for 12 hours, then quenched with water (30 mL), and extracted with DCM:MeOH (10:1) (3×40 mL). The combined organic extracts were dried over $Na_2SO_4$, and concentrated to a residue which was purified by silica gel chromatography to afford I-238 (0.6 g, 24% yield over 2 steps) as a yellow solid. MS (ESI, pos. ion) m/z: 274.2 (M+1).

Step 5: 2-(2-aminoethyl)-1-methylpyrazolidin-3-one (I-239)

To a solution of 2-(2-(2-methyl-5-oxopyrazolidin-1-yl)ethyl)isoindoline-1,3-dione (600 mg, 2.2 mmol) in MeOH (50 mL) at 0-5° C. was added $NH_2NH_2$ (85% in $H_2O$, 1.5 mL, 2.5 equiv.). The reaction mixture was allowed to warm to ambient temperature, stirred for 12 hours, and then filtered. The filtrate was concentrated to afford the crude amine I-239 (0.4 g) as a pale oil, which was used directly for the next step. MS (ESI, pos. ion) m/z: 144.2 (M+23).

Step 6: 2-((2-((2-(2-methyl-5-oxopyrazolidin-1-yl)ethyl)amino)-2-oxoethyl)thio)acetic acid (I-240)

A solution of 2-(2-aminoethyl)-1-methylpyrazolidin-3-one (400 mg, 2.8 mmol) and thiodiglycolic anhydride (990 mg, 2.5 equiv.) in 10 mL of DCM was stirred for 0.5 hours and then concentrated in vacuo to afford the crude product. Half of this crude product was purified by preparative HPLC (Mobile Phase: MeCN/$H_2O$ with 0.1% TFA), gradient: 5-15% MeCN) to afford 56 mg (15% yield) of I-240 as a white solid. MS (ESI, pos. ion) m/z: 276.2 (M+1). $^1$H NMR (400 MHz, D2O) δ 3.75-3.70 (m, 2H), 3.38-3.34 (m, 4H), 3.29 (s, 2H), 3.25 (s, 2H), 3.02-2.85 (m, 1H), 2.81-2.77 (m, 3H), 2.55-2.42 (m, 1H).

The Synthesis of I-243 Involved 5 Steps as Depicted in the Following Scheme 98.

Scheme 98

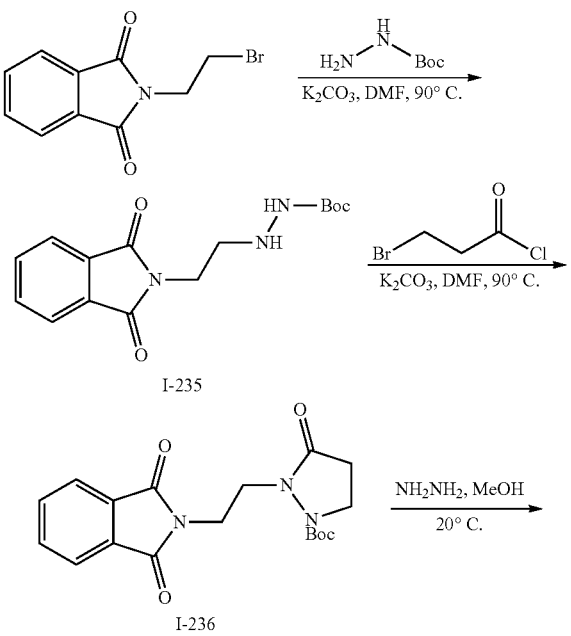

I-235

I-236

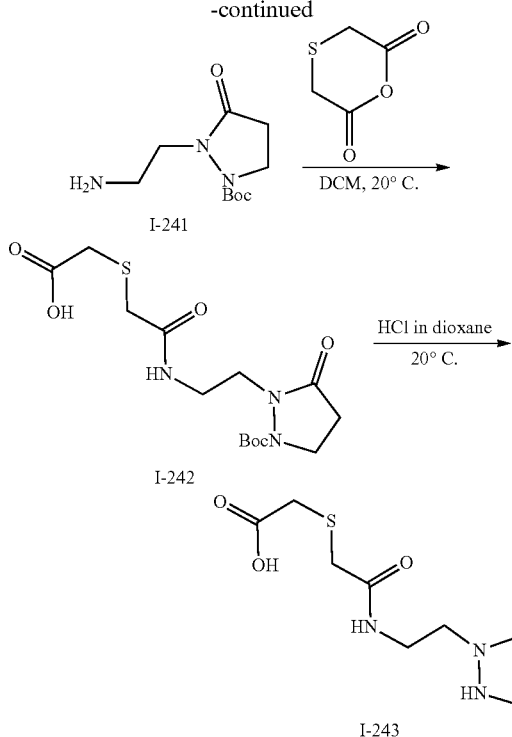

Step 3: tert-butyl 2-(2-aminoethyl)-3-oxopyrazolidine-1-carboxylate (I-241)

To a solution of tert-butyl 2-(2-(1,3-dioxoisoindolin-2-yl)ethyl)-3-oxopyrazolidine-1-carboxylate, I-236 (2 g, 5.5 mmol) in MeOH (50 mL) at 0-5° C. was added $NH_2NH_2$ (85% in $H_2O$, 1 mL, 2.5 equiv.). The reaction mixture was allowed to warm to ambient temperature, stirred for 12 hours, and then filtered. The filtrate was concentrated under reduced pressure to afford the crude amine I-241 (0.7 g) as a pale oil, which was used directly for next step. MS (ESI, pos. ion) m/z: 252.2 (M+23).

Step 4: 2-((2-((2-(2-(tert-butoxycarbonyl)-5-oxopyrazolidin-1-yl)ethyl)amino)-2-oxoethyl)thio)acetic acid (I-242)

A solution of tert-butyl 2-(2-aminoethyl)-3-oxopyrazolidine-1-carboxylate I-241 (700 mg, 3 mmol), thiodiglycolic anhydride (990 mg, 2.5 equiv.), and TEA (0.8 mL, 2 equiv.) in 10 mL of DCM was stirred for 0.5 hours. The reaction mixture was then concentrated in vacuo to afford the crude product as a pale oil. Half of this crude product was purified by preparative HPLC to afford 270 mg (49% yield) of I-242 as a white solid. MS (ESI, pos. ion) m/z: 384.2 (M+23).

Step 5: 2-((2-oxo-2-((2-(5-oxopyrazolidin-1-yl)ethyl)amino)ethyl)thio)acetic acid (I-243)

A solution of 2-((2-((2-(2-(tert-butoxycarbonyl)-5-oxopyrazolidin-1-yl)ethyl)amino)-2-oxoethyl)thio)acetic acid I-242 (270 mg, 0.74 mmol) in HCl (4 M in dioxane) (10 mL) was stirred at 20° C. for 0.5 hours. The reaction mixture was then concentrated and the residue obtained was purified by preparative HPLC (MeCN/$H_2O$ with 0.1% TFA), gradient: 10-20% MeCN) to afford 160 mg (81% yield) of I-243 as a pale oil. MS (ESI, pos. ion) m/z: 262.2 (M+1). $^1$H NMR (400 MHz, DMSO) δ 8.19 (s, 1H), 3.39 (dd, 2H), 3.34 (d, 4H), 3.25 (dd, 2H), 3.20 (s, 2H), 2.44 (t, 3H).

The Synthesis of I-248 Involved 5 Steps as Depicted in the Following Scheme 99.

Scheme 99

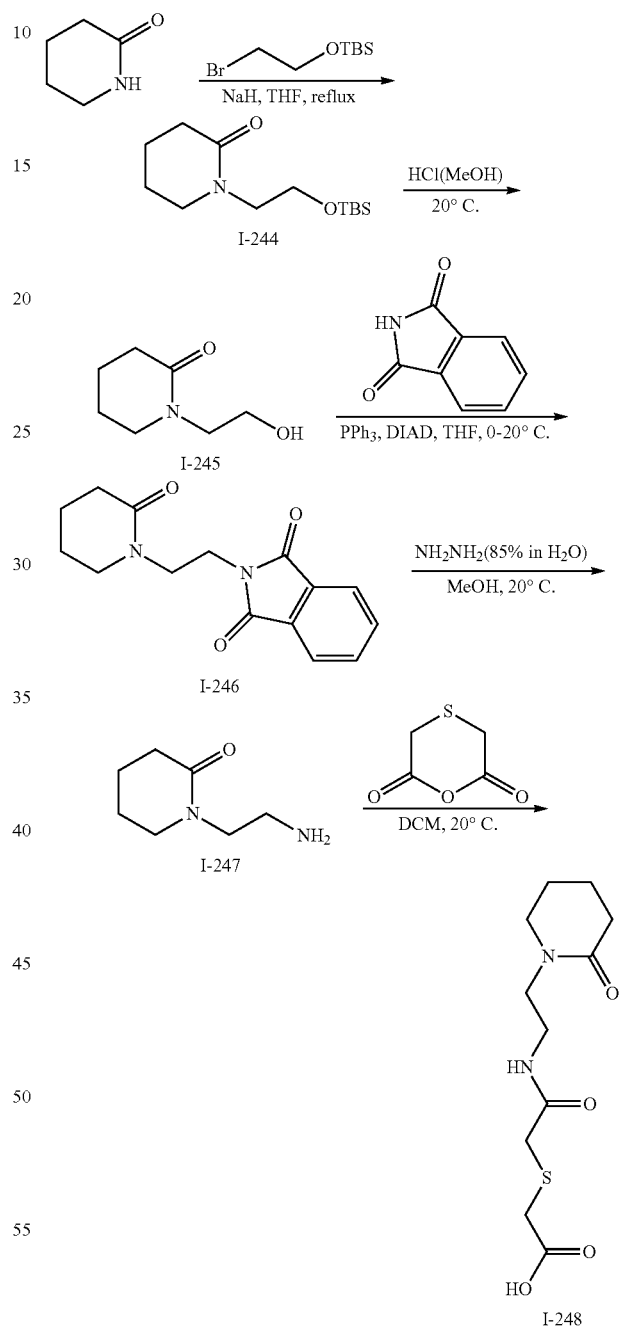

Step 1: 1-(2-((tert-butyldimethylsilyl)oxy)ethyl)piperidin-2-one (I-244)

To a solution of piperidin-2-one (cas: 675-20-7, 6 g, 60 mmol) in THF (200 mL) at 0-5° C. was added NaH (4.8 g, 2 equiv., 60% dispersion in mineral oil) in portions under N₂. The reaction mixture was stirred for 0.5 hours. (2-bromoethoxy)(tert-butyl)dimethylsilane (cas: 86864-60-0, 4.9 g, 1.2 equiv.) was then added and the reaction mixture was heated to reflux for 6 hours. The reaction was then quenched with water (50 mL), and extracted with EtOAc (3×80 mL). The combined organic extracts were washed with water (50 mL), brine (50 mL), dried with Na₂SO₄, and concentrated under reduced pressure to a residue, which was purified by silica gel chromatography to afford I-244 as a pale oil (2 g, 13% yield). MS (ESI, pos. ion) m/z: 258 (M+1).

Step 2: 1-(2-hydroxyethyl)piperidin-2-one (I-245)

To a solution of 1-(2-((tert-butyldimethylsilyl)oxy)ethyl) piperidin-2-one I-244 (2 g, 7.8 mmol) in MeOH (15 mL) at 0-5° C. was added HCl in MeOH (30% v/v, 10 mL) under N₂. The reaction mixture was stirred for 0.5 hours, then concentrated under reduced pressure to afford the crude alcohol I-245 as a pale oil (1.2 g), which was used directly for next step. MS (ESI, pos. ion) m/z: 144 (M+1).

Step 3: 2-(2-(2-oxopiperidin-1-yl)ethyl)isoindoline-1,3-dione (I-246)

To a solution of 1-(2-hydroxyethyl)piperidin-2-one I-245 (1.2 g, 8.4 mmol) in THF (15 mL) at 0-5° C. was added phthalimide (1.85 g, 1.5 equiv.) and PPh₃ (3.9 g, 1.8 equiv.) and the reaction mixture was stirred for 0.5 hours under N₂. DIAD (3.4 g, 2.0 equiv.) was added and the reaction mixture was allowed to warm to ambient temperature and stirred for 2 hours. The reaction mixture was then filtered, and the filtrate was concentrated under reduced pressure to afford a pale oil, which was purified by silica gel chromatography to afford I-246 (purity: 60%, 0.7 g, 35% yield). MS (ESI, pos. ion) m/z: 273 (M+1).

Step 4: 1-(2-aminoethyl)piperidin-2-one (I-247)

To a solution of 2-(2-(2-oxopiperidin-1-yl)ethyl)isoindoline-1,3-dione I-246 (0.7 g, 2.6 mmol) in MeOH (10 mL) at 0-5° C. was added NH₂NH₂ (85% in H₂O, 0.2 mL, 1.2 equiv.). The reaction mixture was allowed to warm to ambient temperature and stirred for 12 hours, then filtered, and the filtrate was concentrated under reduced pressure to afford the crude amine I-247 (0.4 g) as a pale oil, which was used directly for next step. MS (ESI, pos. ion) m/z: 143 (M+1).

Step 5: 2-((2-oxo-2-((2-(2-oxopiperidin-1-yl)ethyl)amino)ethyl)thio)acetic acid (I-248)

A solution of 1-(2-aminoethyl)piperidin-2-one I-247 (400 mg, 2.8 mmol) and thiodiglycolic anhydride (924 mg, 2.5 equiv.) in 20 mL of DCM was stirred for 0.5 hours, and then concentrated in vacuo to give the crude product as a pale oil. The crude product was purified by preparative HPLC (Mobile Phase: MeCN/H₂O (0.1% formic acid), Gradient: 5-15% MeCN) to afford 200 mg of I-248 (26% yield) as a pale oil. MS (ESI, pos. ion) m/z: 275.2 (M+1). ¹H NMR (400 MHz, CDCl₃): δ 7.57 (s, 1H), 6.48 (s, 2H), 3.83-3.07 (m, 10H), 2.44 (s, 2H), 1.82 (s, 4H).

The Synthesis of I-249 Involved 1 Step as Depicted in the Following Scheme 100.

Scheme 100

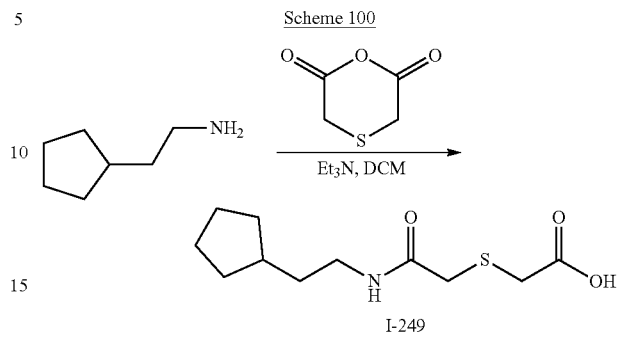

Step 1: 2-((2-((2-cyclopentylethyl)amino)-2-oxoethyl)thio) acetic acid (I-249)

A solution of 2-cyclopentylethan-1-amine (cas: 5763-55-3, 200 mg, 1.8 mmol) and thiodiglycolic anhydride (594 mg, 2.5 equiv.) in 5 mL of DCM was stirred for 0.5 hours, and then concentrated in vacuo to afford a pale oil, which was purified by preparative HPLC (Mobile Phase: MeCN/H₂O (0.1% TFA), Gradient: 30-40% MeCN) to provide 250 mg (56% yield) of I-249 as a white solid. MS (ESI, pos. ion) m/z: 246.2 (M+1). ¹H NMR (400 MHz, CDCl₃): δ 6.64 (s, 1H), 3.47-3.22 (m, 6H), 1.79 (s, 3H), 1.68-1.47 (m, 6H), 1.11 (d, 2H).

The Synthesis of Compound I-250 Involved 1 Step as Depicted in the Following Scheme 101.

Scheme 101

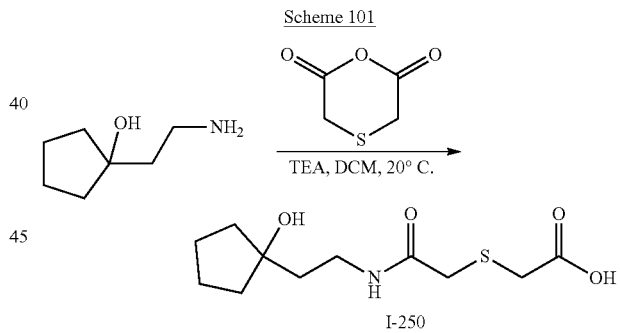

The chemical structure of the target compound was confirmed by ¹H NMR and LC-MS with the purity >95% (HPLC 214 & 254 nm).

Step 1. 2-((2-((2-(1-hydroxycyclopentyl) ethyl) amino)-2-oxoethyl)thio) acetic acid (I-250)

To a solution of 1-(2-aminoethyl) cyclopentan-1-ol (cas: 859629-83-7, 0.1 g, 0.774 mmol) and thiodiglycolic anhydride (0.102 g, 1.0 equiv.) in DCM (5 mL) was added TEA (93 mg, 1.2 equiv.) and the reaction mixture was stirred for 4 hours at ambient temperature, then concentrated under reduced pressure to afford the crude product. The crude product was purified by preparative HPLC (Mobile Phase: MeCN/H₂O (0.1% TFA)) to afford I-250 (50 mg, 24% yield) as a pale oil. MS (ESI, pos. ion) m/z: 262.2 (M+1). ¹H NMR (400 MHz, DMSO): δ 12.63 (s, 1H), 7.97 (s, 1H), 4.09 (m, 1H), 3.35 (s, 2H), 3.20-3.12 (m, 4H), 1.75-1.35 (m, 10H).

The Synthesis of I-257 Involved 7 Steps as Depicted in the Following Scheme 102.

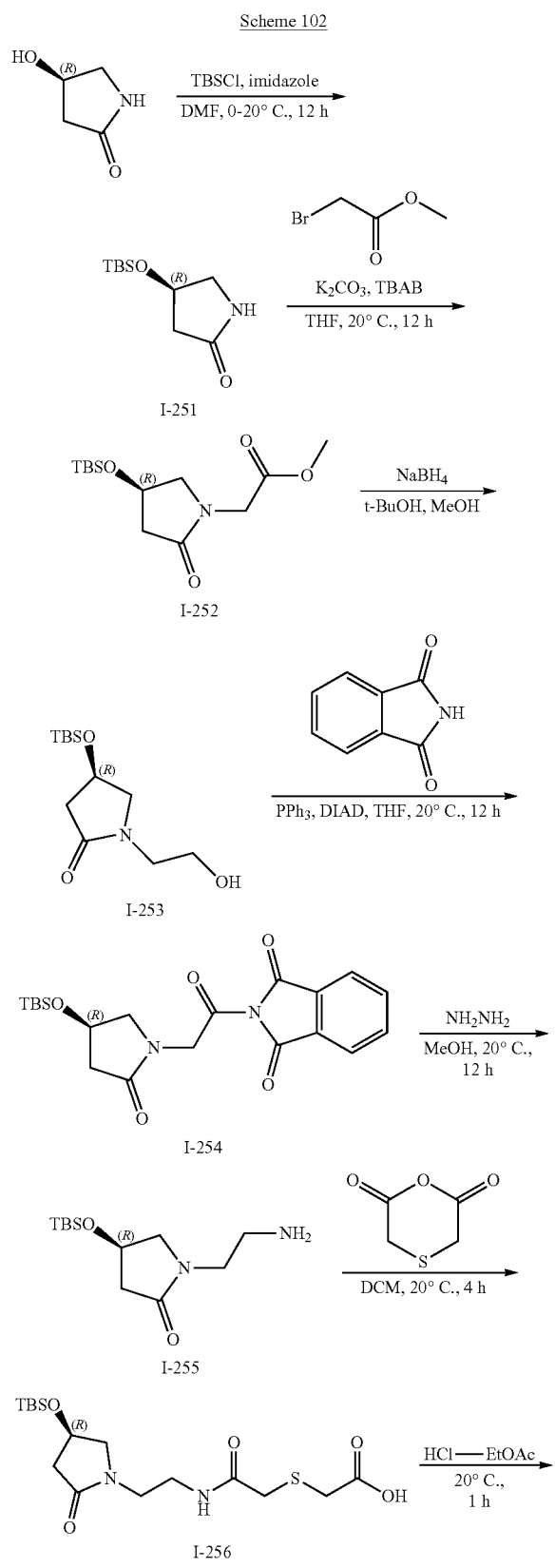

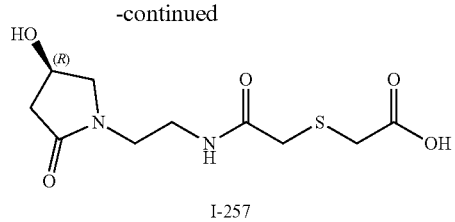

Step 1: (R)-4-((tert-butyldimethylsilyl)oxy)pyrrolidin-2-one (I-251)

To a solution of (R)-4-hydroxypyrrolidin-2-one (cas: 22677-21-0, 2.02 g, 20 mmol) in DMF (10 ml) at 0-5° C. was added tert-butylchlorodimethylsilane (3.62 g, 24 mmol, 1.2 equiv.) and imidazole (3.40 g, 50 mmol, 2.5 equiv.). The reaction mixture was allowed to warm to ambient temperature and stirred for 12 hours. Water (50 mL) was then added, and the reaction mixture was stirred for 10 minutes. The white solid that precipitated was filtered and washed with water (10 mL) and dried under high vacuum to afford I-251 (4.05 g, 95% yield). MS (ESI, pos. ion) m/z: 216.1 (M+1).

Step 2: methyl (R)-2-(4-((tert-butyldimethylsilyl)oxy)-2-oxopyrrolidin-1-yl)acetate (I-252)

To a solution of (R)-4-((tert-butyldimethylsilyl)oxy)pyrrolidin-2-one, I-251 (3.8 g, 17.37 mmol) in THF (30 mL) was added methyl 2-bromoacetate (cas: 96-32-2, 4.03 g, 1.5 equiv.), potassium carbonate (0.84 g, 2.5 equiv.) and TBAB (4.94 g, 0.2 equiv.) under $N_2$. The reaction mixture was stirred at ambient temperature for 12 hours. The reaction was then quenched with water (10 mL), extracted with EtOAc (3×50 mL). The combined organic extracts were then washed with water (20 mL), brine (20 mL), dried ($Na_2SO_4$), and concentrated under reduced pressure to a residue, which was purified by silica gel chromatography to afford I-252 (0.71 g, 27% yield) as a pale oil. MS (ESI, pos. ion) m/z: 288.1 (M+1).

Step 3: (R)-4-((tert-butyldimethylsilyl)oxy)-1-(2-hydroxyethyl)pyrrolidin-2-one (I-253)

To a solution of methyl (R)-2-(4-((tert-butyldimethylsilyl)oxy)-2-oxopyrrolidin-1-yl)acetate, I-252 (0.71 g, 2.47 mmol) in t-BuOH (10 mL) was added sodium borohydride (0.38 g, 4.0 equiv.) in MeOH (0.5 mL) under $N_2$. The reaction mixture was stirred for 2 hours at 80° C., then concentrated under reduced pressure to a residue. The residue was diluted with water (2 mL), and extracted with EtOAc (3×20 mL). The combined organic extracts were then washed with water (20 mL), brine (20 mL), dried ($Na_2SO_4$), and concentrated under reduced pressure to a residue, which was purified by silica gel chromatography to afford I-253 as a pale oil (0.43 g, 69% yield). MS (ESI, pos. ion) m/z: 260.2 (M+1).

Step 4: (R)-2-(2-(4-((tert-butyldimethylsilyl)oxy)-2-oxopyrrolidin-1-yl)ethyl)isoindoline-1,3-dione (I-254)

To a solution of (R)-4-((tert-butyldimethylsilyl)oxy)-1-(2-hydroxyethyl)pyrrolidin-2-one, I-253 (0.43 g, 1.66 mmol) in THF (5 mL) at at 0-5° C. was added phthalimide (0.27 g, 1.1 equiv.) and $PPh_3$ (0.76 g, 1.5 equiv.). The reaction mixture was stirred for 0.5 hours under N$_2$, and DIAD (1.01 g, 3.0 equiv.) was added to the solution. The reaction mixture was allowed to warm to ambient temperature and stirred for 12 hours. The resulting mixture was quenched with water (5 mL) and extracted with DCM (3×20 mL). The combined organic extracts were washed with water (20 mL), brine (20 mL), dried (Na$_2$SO$_4$), and concentrated under reduced pressure to a residue, which was purified by silica gel chromatography to afford I-254 as a pale oil (0.48 g, 75% yield). MS (ESI, pos. ion) m/z: 389.2 (M+1).

Step 5: (R)-1-(2-aminoethyl)-4-((tert-butyldimethylsilyl)oxy)pyrrolidin-2-one (I-255)

To a solution of (R)-2-(2-(4-((tert-butyldimethylsilyl)oxy)-2-oxopyrrolidin-1-yl)ethyl)isoindoline-1,3-dione, I-254 (0.48 g, 1.24 mmol) in MeOH (10 mL) at 0-5° C. was added NH$_2$NH$_2$ (85% in H$_2$O, 0.06 g, 1.2 equiv.). The reaction mixture was allowed to warm to ambient temperature and stirred for 12 hours and then filtered. The filtrate was concentrated under reduced pressure to afford the crude amine, I-255 (0.3 g) as a pale oil, which was used directly for next step. MS (ESI, pos. ion) m/z: 259.2 (M+1).

Step 6: (R)-2-((2-((2-(4-((tert-butyldimethylsilyl)oxy)-2-oxopyrrolidin-1-yl)ethyl)amino)-2-oxoethyl)thio) acetic acid (I-256)

To a solution of (R)-1-(2-aminoethyl)-4-((tert-butyldimethylsilyl)oxy)pyrrolidin-2-one, I-255 (0.302 mg, 1.17 mmol) in DCM (10 mL) was added thiodiglycolic anhydride (0.20 mg, 1.52 mmol, 1.3 equiv.). The reaction mixture was stirred for 2 hours at 20° C. and then concentrated under reduced pressure to afford the crude product (0.5 g) as a pale oil. The crude product I-256 was used directly for the next step. MS (ESI, pos. ion) m/z: 391.2 (M+1).

Step 6: (R)-2-((2-((2-(4-hydroxy-2-oxopyrrolidin-1-yl)ethyl)amino)-2-oxoethyl)thio) acetic acid (I-257)

To a solution of (R)-2-((2-((2-(4-((tert-butyldimethylsilyl)oxy)-2-oxopyrrolidin-1-yl)ethyl)amino)-2-oxoethyl)thio) acetic acid (0.50 g, 1.28 mmol) in DCM (5 mL) at 0-5° C. was added HCl in EtOAc (2M, 1.5 mL) under N$_2$. The reaction mixture was stirred for 1 hour. The reaction mixture was then concentrated under reduced pressure to afford the crude product as a pale oil. The crude product was purified by preparative HPLC (Mobile Phase: MeCN/H$_2$O with 0.1% TFA), Gradient: 2-8% MeCN) to give 33.3 mg (9% yield) of I-257 as a pale oil. MS (ESI, pos. ion) m/z: 277.1 (M+1). $^1$H NMR (400 MHz, CDCl$_3$): 7.46 (s, 1H), 4.49-4.45 (m, 1H), 4.01 (ddd, 1H), 3.80 (ddd, 1H), 3.70 (dt, 2H), 3.39 (s, 2H), 3.35-3.28 (m, 1H), 3.20 (q, 2H), 3.08 (d, 1H), 2.81-2.74 (m, 1H), 2.57 (s, 1H).

The Synthesis of I-264 Involved 7 Steps as Depicted in the Following Scheme 103.

Scheme 103

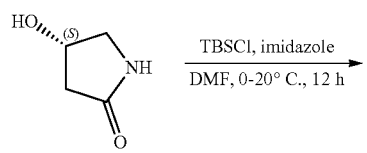

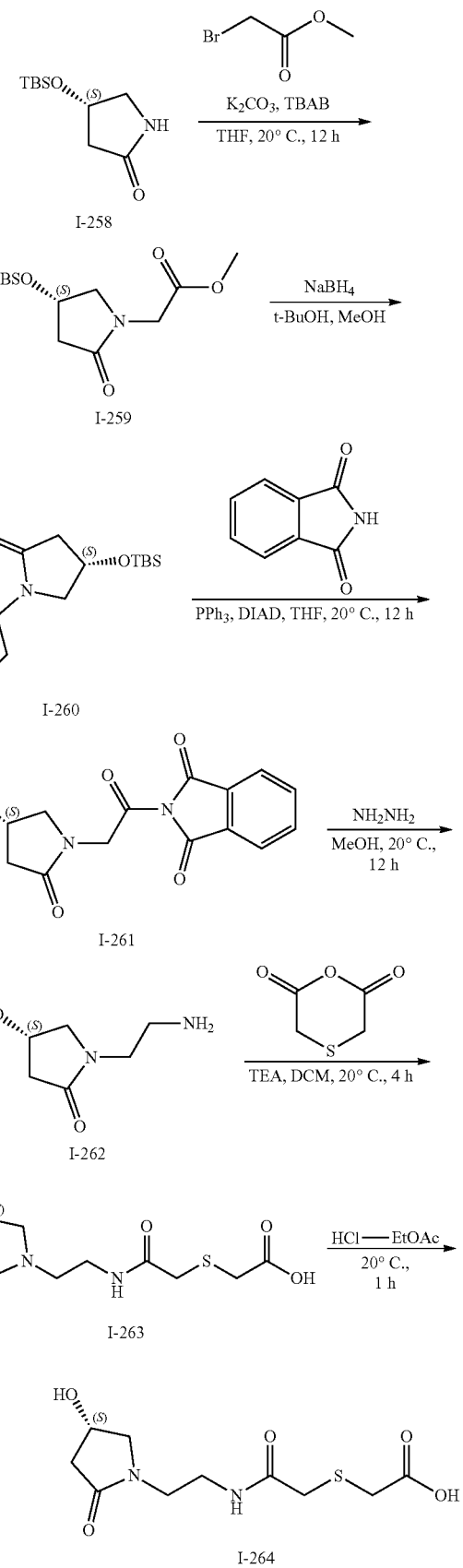

Step 1: (S)-4-((tert-butyldimethylsilyl)oxy)pyrrolidin-2-one (I-258)

To a solution of (S)-4-hydroxypyrrolidin-2-one (cas: 68108-18-9, 5.0 g, 49.5 mmol) in DMF (20 mL) at 0-5° C. was added tert-butylchlorodimethylsilane (8.9 g, 1.2 equiv.) and imidazole (8.4 g, 2.5 equiv.). The reaction mixture was allowed to warm to ambient temperature and stirred for 12 hours. Water (50 mL) was then added and the reaction mixture was stirred for 10 minutes. The white precipitate that was formed was filtered and washed with water (15 mL) and then dried under high vacuum to afford I-258 (9.8 g, 92% yield). MS (ESI, pos. ion) m/z: 216.1 (M+1).

Step 2: methyl (S)-2-(4-((tert-butyldimethylsilyl)oxy)-2-oxopyrrolidin-1-yl)acetate (I-259)

To a solution of (S)-4-((tert-butyldimethylsilyl)oxy)pyrrolidin-2-one, I-258 (4.9 g, 22.79 mmol) in THF (40 mL) was added methyl 2-bromoacetate (5.2 g, 1.5 equiv.), potassium carbonate (7.9 g, 2.5 equiv.) and TBAB (1.47 g, 0.2 equiv.) under $N_2$. The reaction mixture was stirred for 12 hours at 20° C., quenched with water (10 mL), and extracted with EtOAc (3×50 mL). The combined organic extracts were washed with water (20 mL), brine (20 mL), dried ($Na_2SO_4$), and concentrated under reduced pressure to afford a residue, which was purified by silica gel chromatography to afford I-259 as a pale oil (1.1 g, 29% yield). MS (ESI, pos. ion) m/z: 288.1 (M+1).

Step 3: (S)-4-((tert-butyldimethylsilyl)oxy)-1-(2-hydroxyethyl)pyrrolidin-2-one (I-260)

To a solution of methyl (S)-2-(4-((tert-butyldimethylsilyl)oxy)-2-oxopyrrolidin-1-yl)acetate, I-259 (1.1 g, 3.8 mmol) in t-BuOH (15 mL) was added sodium borohydride (0.58 g, 4.0 equiv.) in MeOH (1 mL) under $N_2$. The reaction mixture was stirred for 2 hours at 80° C. and then concentrated under reduced pressure to afford a residue. The residue was diluted with water (2 mL) and extracted with EtOAc (3×50 mL). The combined organic extracts were washed with water (20 mL), brine (20 mL), dried ($Na_2SO_4$), and concentrated under reduced pressure to afford a residue, which was purified by silica gel chromatography to afford I-260 as a pale oil (0.82 g, 83% yield). MS (ESI, pos. ion) m/z: 260.2 (M+1).

Step 4: (S)-2-(2-(4-((tert-butyldimethylsilyl)oxy)-2-oxopyrrolidin-1-yl)ethyl)isoindoline-1,3-dione (I-261)

To a solution of (S)-4-((tert-butyldimethylsilyl)oxy)-1-(2-hydroxyethyl)pyrrolidin-2-one, I-260 (0.82 g, 3.17 mmol) in THF (10 mL) at 0-5° C. was added phthalimide (0.51 g, 1.1 equiv.) and $PPh_3$ (1.45 g, 1.5 equiv.). The reaction mixture was stirred for 0.5 hours under $N_2$ and DIAD (1.92 g, 3.0 equiv.) was added to the solution. The reaction mixture was allowed to warm to ambient temperature and stirred for 12 hours. The reaction was quenched with water (5 mL) and extracted with DCM (3×50 mL). The combined organic extracts were washed with water (20 mL), brine (20 mL), dried ($Na_2SO_4$) and concentrated under reduced pressure to afford a residue, which was purified by silica gel chromatography to afford I-261 as a pale oil (1.15 g, 94% yield). MS (ESI, pos. ion) m/z: 389.2 (M+1).

Step 5: (S)-1-(2-aminoethyl)-4-((tert-butyldimethylsilyl)oxy)pyrrolidin-2-one (I-262)

To a solution of (S)-2-(2-(4-((tert-butyldimethylsilyl)oxy)-2-oxopyrrolidin-1-yl)ethyl)isoindoline-1,3-dione, I-261 (1.05 g, 1.24 mmol) in MeOH (10 mL) at 0-5° C. was added $NH_2NH_2$ (85% in $H_2O$, 0.12 g, 1.2 equiv.). The reaction mixture was allowed to warm to ambient temperature, stirred for 12 hours, and then filtered. The filtrate was concentrated under reduced pressure to afford the crude amine, I-262 (0.71 g) as a pale oil, which was used directly for the next step. MS (ESI, pos. ion) m/z: 259.2 (M+1).

Step 6: (S)-2-((2-((2-(4-((tert-butyldimethylsilyl)oxy)-2-oxopyrrolidin-1-yl)ethyl)amino)-2-oxoethyl)thio) acetic acid (I-263)

To a solution of (S)-1-(2-aminoethyl)-4-((tert-butyldimethylsilyl)oxy)pyrrolidin-2-one (0.61 mg, 2.36 mmol) in DCM (10 mL) was added thiodiglycolic anhydride (0.41 mg, 1.3 equiv.) and TEA (0.05 g, 0.2 equiv.). The reaction mixture was stirred for 2 hours at 20° C. and was then concentrated under reduced pressure to give the crude product, I-263 (0.89 g) as a pale oil. The crude product was used directly for next step. MS (ESI, pos. ion) m/z: 391.2 (M+1).

Step 6: (S)-2-((2-((2-(4-hydroxy-2-oxopyrrolidin-1-yl)ethyl)amino)-2-oxoethyl)thio) acetic acid (I-264)

To a solution of (S)-2-((2-((2-(4-((tert-butyldimethylsilyl)oxy)-2-oxopyrrolidin-1-yl)ethyl)amino)-2-oxoethyl)thio) acetic acid, I-263 (0.89 g, ca. 2.97 mmol) in DCM (10 mL) at 0-5° C. was added HCl in EtOAc (2M, 2.5 mL) under $N_2$. The reaction mixture was stirred for 1 hour and then concentrated under reduced pressure to afford the crude product as a pale oil. The crude product was purified by preparative HPLC (Mobile Phase: MeCN/$H_2O$ (0.1% TFA), Gradient: 2-8% MeCN) to give 90 mg (11% yield) of I-264 as a pale oil. MS (ESI, pos. ion) m/z: 277.1 (M+1). $^1$H NMR (400 MHz, $CDCl_3$): 7.40 (s, 1H), 4.44 (dd, 1H), 3.99 (dd, 1H), 3.76 (s, 1H), 3.69 (dt, 2H), 3.37 (s, 2H), 3.33-3.26 (m, 1H), 3.19 (q, 2H), 3.06 (d, J=14.4 Hz, 1H), 2.75 (ddd, 1H), 2.52 (d, 1H).

The Synthesis of Compound I-271 Involved 7 Steps as Depicted in the Following Scheme 104.

Scheme 104

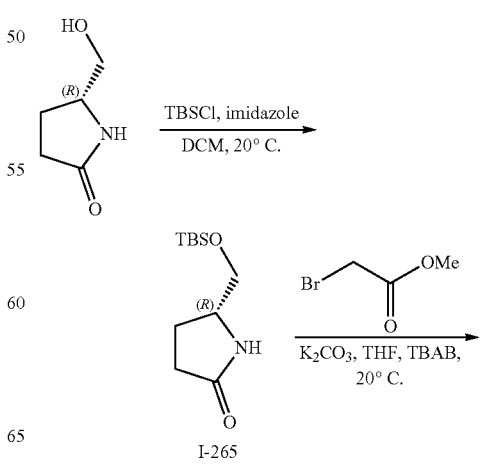

-continued

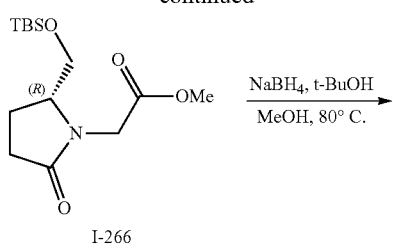

I-266

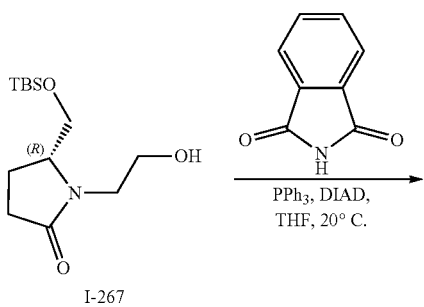

I-267

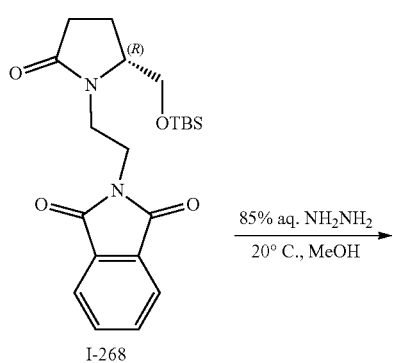

I-268

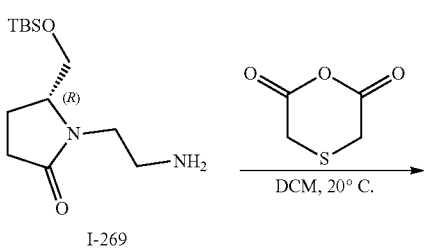

I-269

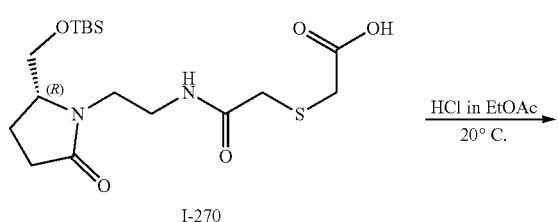

I-270

-continued

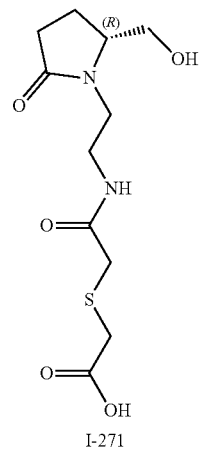

I-271

The chemical structure of the target compound was confirmed by $^1$H NMR and LC-MS with the purity >95% (HPLC 214 & 254 nm).

(R)-2-((2-((2-(2-(hydroxymethyl)-5-oxopyrrolidin-1-yl)ethyl)amino)-2-oxoethyl)thio) acetic acid (I-271)

Step 1. (R)-5-(((tert-butyldimethylsilyl)oxy)methyl) pyrrolidin-2-one (I-265)

To a solution of (R)-5-(hydroxymethyl)pyrrolidin-2-one (cas: 66673-40-3, 2 g, 17.4 mmol) in DCM (15 mL) was added imidazole (2.36 g, 2.0 equiv.) and TBSCl (3.14 g, 1.2 equiv.). The reaction mixture was stirred for 7 hours and was then quenched with water (20 mL). The aqueous phase was extracted with EtOAc (3×20 mL). The combined organic extracts were washed with water, brine, dried ($Na_2SO_4$), and concentrated under reduced pressure to afford a residue, which was purified by silica gel chromatography to provide silyl ether I-265 (2.9 g, 73% yield) as a pale yellow oil. MS (ESI, pos. ion) m/z: 230 (M+1).

Step 2. methyl (R)-2-(2-(((tert-butyldimethylsilyl) oxy)methyl)-5-oxopyrrolidin-1-yl)acetate (I-266)

To a solution of (R)-5-(((tert-butyldimethylsilyl)oxy) methyl)pyrrolidin-2-one, I-265 (0.4 g, 1.75 mmol) in THF (10 mL) were added methyl 2-bromoacetate (0.4 g, 1.5 equiv.), $K_2CO_3$ (0.605 g, 2.5 equiv.), and TBAB (0.112 g, 2.0 equiv.). The reaction mixture was then stirred at ambient temperature for 10 hours and then quenched with water (20 mL). The aqueous phase was extracted with EtOAc (3×20 mL). The combined organic extracts were washed with water, brine, dried ($Na_2SO_4$), and concentrated under reduced pressure to a residue, which was purified by silica gel chromatography to provide ester I-266 (100 mg, 19%) as a pale yellow oil. MS (ESI, pos. ion) m/z: 302 (M+1).

Step 3. (R)-5-(((tert-butyldimethylsilyl)oxy)methyl)- 1-(2-hydroxyethyl)pyrrolidin-2-one (I-267)

To a solution of methyl (R)-2-(2-(((tert-butyldimethylsilyl)oxy)methyl)-5-oxopyrrolidin-1-yl)acetate, I-266 (0.2 g, 0.66 mmol) in t-BuOH (5 mL) and MeOH (0.2 mL) was added $NaBH_4$ (0.1 g, 4.0 equiv.) in one portion. The reaction mixture was heated to 80° C. for 2 hours and then cooled to ambient temperature and quenched with water (20 mL). The aqueous phase was then extracted with EtOAc (3×20 mL). The combined organic extracts were washed with water, brine, dried (Na₂SO₄) and concentrated under reduced pressure to a residue (220 mg), which was used directly for next step. MS (ESI, pos. ion) m/z: 274 (M+1).

Step 4. (R)-2-(2-(2-(((tert-butyldimethylsilyl)oxy) methyl)-5-oxopyrrolidin-1-yl)ethyl)isoindoline-1,3-dione (I-268)

To a solution of (R)-5-(((tert-butyldimethylsilyl)oxy) methyl)-1-(2-hydroxyethyl) pyrrolidin-2-one, I-267 (0.22 g, 0.81 mmol), phthalimide (0.13 g, 1.1 equiv.) and PPh₃ (0.318 g, 1.5 equiv.) in anhydrous THF (5 mL) at 0-5° C. was added DIAD (0.49 g, 3.0 equiv.) under N₂. The reaction mixture was allowed to warm to ambient temperature and stirred for 7 hours and then concentrated under reduced pressure to a residue, which was and purified by preparative HPLC to afford the imide I-268 (145 mg, 28% yield). MS (ESI, pos. ion) m/z: 403 (M+1).

Step 5. (R)-1-(2-aminoethyl)-5-(((tert-butyldimethylsilyl)oxy)methyl)pyrrolidin-2-one (I-269)

To a solution of (R)-2-(2-(2-(((tert-butyldimethylsilyl) oxy)methyl)-5-oxopyrrolidin-1-yl)ethyl)isoindoline-1,3-dione, I-268 (0.345 g, 0.858 mmol) in MeOH (10 mL) was added hydrazine hydrate (85% in H₂O, 0.05 g, 1.5 equiv.). The reaction mixture was stirred for 12 hours at ambient temperature and then filtered. The filtrate was concentrated under reduced pressure to give the crude product, I-269 (307 mg), which was used directly in next step. MS (ESI, pos. ion) m/z: 273 (M+1).

Step 6. (R)-2-((2-((2-(2-(((tert-butyldimethylsilyl) oxy)methyl)-5-oxopyrrolidin-1-yl)ethyl)amino)-2-oxoethyl)thio) acetic acid (I-270)

To a solution of (R)-1-(2-aminoethyl)-5-(((tert-butyldimethylsilyl)oxy)methyl)pyrrolidin-2-one, I-269 (0.307 g, ca. 1.13 mmol) in DCM (5 mL) was added thiodiglycolic anhydride (178 mg, 1.2 equiv.) and TEA (22.8 mg, 0.2 equiv.). The reaction mixture was stirred for 2 hours and then concentrated in vacuo to give crude acid I-270 as a pale oil (0.5 g). The crude product was used directly for next step. MS (ESI, pos. ion) m/z: 405 (M+1).

Step 7. (R)-2-((2-((2-(2-(hydroxymethyl)-5-oxopyrrolidin-1-yl)ethyl)amino)-2-oxoethyl)thio)acetic acid (I-271)

To a solution of (R)-2-((2-((2-(2-(((tert-butyldimethylsilyl)oxy)methyl)-5-oxopyrrolidin-1-yl)ethyl)amino)-2-oxoethyl)thio)acetic acid, I-270 (0.5 g, ca. 1.23 mmol) was added HCl in EtOAc (2M, 5 mL) and the reaction mixture was stirred for 2 hours and then concentrated in vacuo to afford the crude product. The crude product was purified by preparative HPLC (Mobile Phase: MeCN/H₂O (0.1% TFA)) to afford I-271 (0.1 g, 28% yield). MS (ESI, pos. ion) m/z: 291 (M+1). ¹H NMR (400 MHz, DMSO) δ 12.64 (s, 1H), 8.08 (m, 1H), 4.84 (s, 1H), 3.66 (m, 4.0 Hz, 1H), 3.56-3.47 (m, 2H), 3.41 (s, 3H), 3.28-3.09 (m, 4H), 3.02 m, 1H), 2.22 (m, 1H), 2.14 (m, 1H), 1.96 (m, 1H), 1.76 (m, 1H).

The Synthesis of Compound I-278 Involved 7 Steps as Depicted in the Following Scheme 105.

Scheme 105

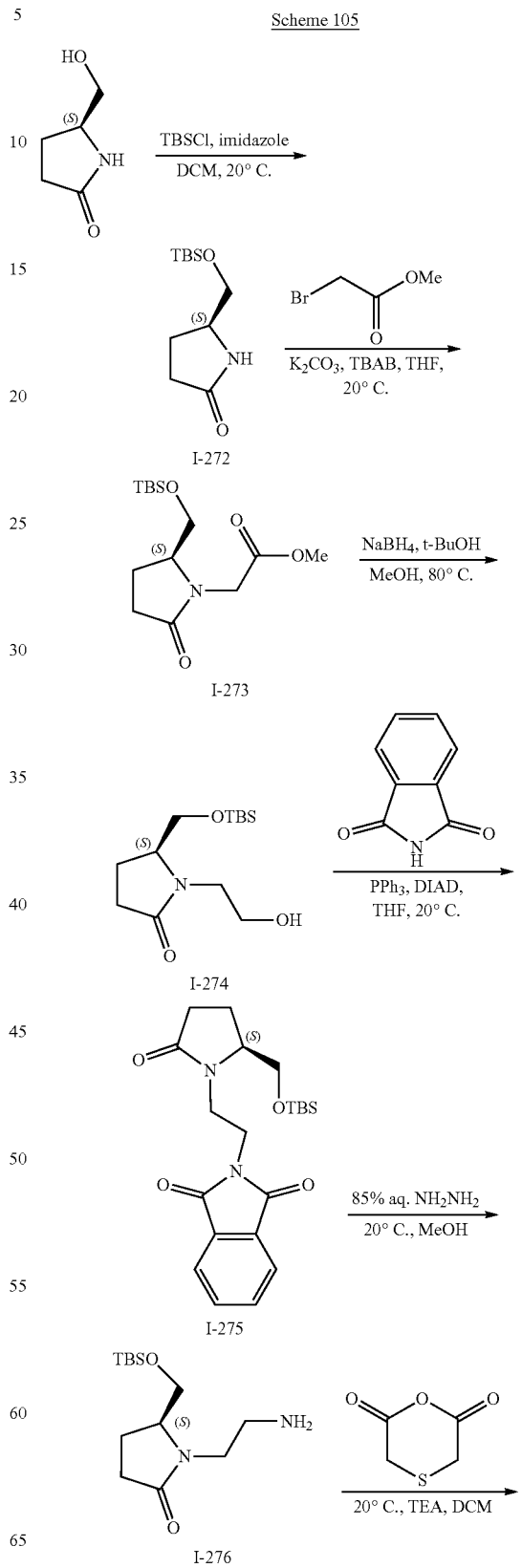

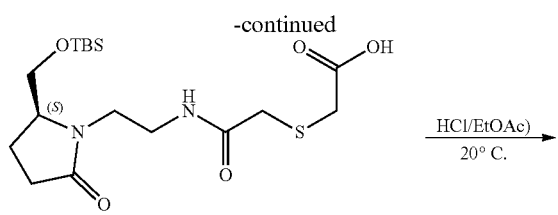

I-277

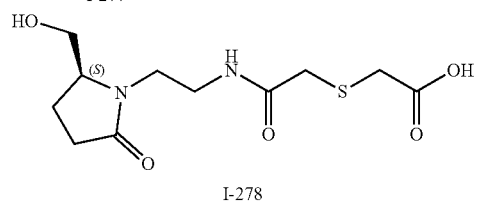

I-278

The chemical structure of the target compound was confirmed by ¹H NMR and LC-MS with the purity >95% (HPLC 214 & 254 nm).

(S)-2-((2-((2-(2-(hydroxymethyl)-5-oxopyrrolidin-1-yl)ethyl)amino)-2-oxoethyl)thio)acetic acid (I-278)

The synthetic route for I-278 was similar to that for the synthesis of I-271 and commenced with (S)-5-(hydroxymethyl)pyrrolidin-2-one (cas: 17342-08-4). (S)-2-((2-((2-(2-(hydroxymethyl)-5-oxopyrrolidin-1-yl)ethyl)amino)-2-oxoethyl)thio)acetic acid, I-278 (pale oil, 120 mg, 15% yield) was isolated by preparative HPLC (Mobile Phase: MeCN/H₂O with 0.1% TFA). MS (ESI, pos. ion) m/z: 291 (M+1). ¹H NMR (400 MHz, DMSO) δ 12.59 (s, 1H), 8.08 (m, 1H), 4.80 (s, 1H), 3.66 (m, 1H), 3.56-3.48 (m, 2H), 3.40 (m, 3H), 3.28-3.10 (m, 4H), 3.06-2.96 (m, 1H), 2.28-2.17 (m, 1H), 2.17-2.06 (m, 1H), 1.96 (m, 1H), 1.80-1.70 (m, 1H).

Synthesis of I-279 is Depicted in Scheme 106

Scheme 106 2-((2-oxo-2-((2-(2-oxoxazolidin-3-yl)ethyl)amino)ethyl)thio) acetic acid (I-279)

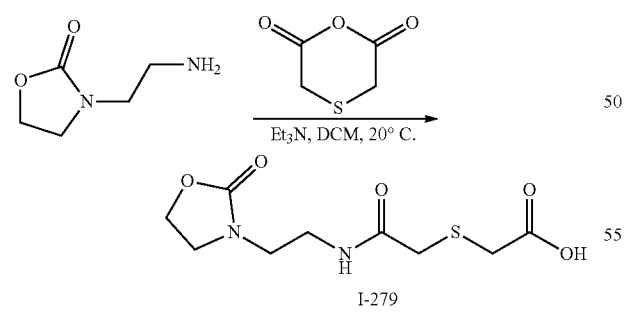

I-279

To a solution of 3-(2-aminoethyl)oxazolidin-2-one (cas: 141778-93-0, 300 mg, 1.8 mmol) in DCM (20 mL) was added thiodiglycolic anhydride (360 mg, 1.5 equiv.) and TEA (90 mg, 0.5 equiv.). The reaction mixture was stirred at ambient temperature for 1 hour and then concentrated in vacuo. The residue obtained was purified by preparative HPLC (Mobile Phase: MeCN/H₂O (0.1% TFA), Gradient: 1-3% MeCN) to afford 87 mg (27% yield) of I-279 as a white solid. MS (ESI, pos. ion) m/z: 263.1 (M+1). ¹H NMR (400 MHz, DMSO) δ 12.58 (s, 1H), 8.15 (m, 1H), 4.26-4.20 (m, 2H), 3.59-3.52 (m, 2H), 3.35 (s, 2H), 3.26-3.17 (m, 6H). The Synthesis of Compound I-282 Involved 3 Steps as Depicted in the Following Scheme 107.

Scheme 107

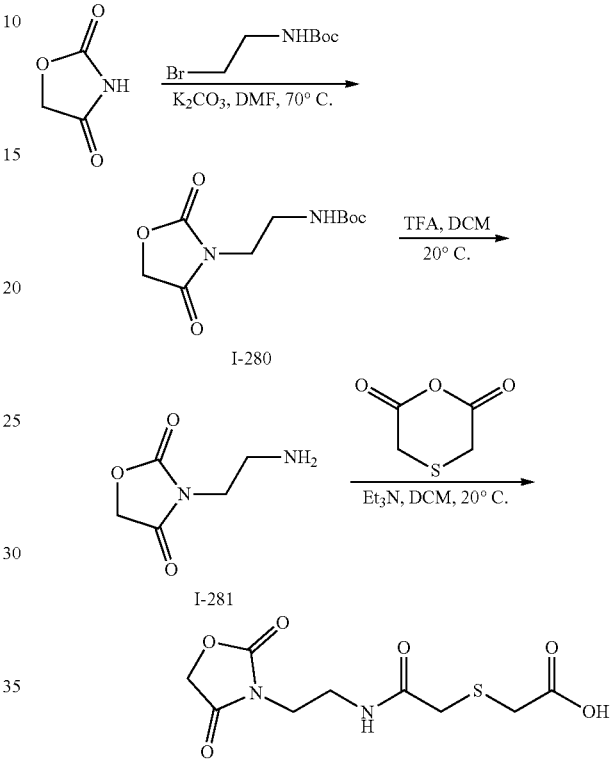

I-282

The chemical structure of the target compound was confirmed by ¹H NMR and LC-MS with the purity >95% (HPLC 214 & 254 nm).

2-((2-((2-(2,4-dioxooxazolidin-3-yl)ethyl)amino)-2-oxoethyl)thio) acetic acid (I-282)

Step 1: Tert-butyl (2-(2,4-dioxooxazolidin-3-yl)ethyl)carbamate (I-280)

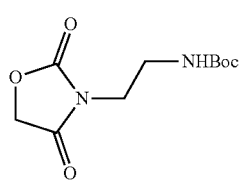 [SMILES: CC(C)(C)OC(=O)NCCN1C(=O)COC1=O]

To a solution of oxazolidine-2,4-dione (cas: 2346-26-1, 0.1 g, 0.99 mmol) in DMF (5 mL) was added tert-butyl (2-bromoethyl) carbamate (cas: 39684-80-5, 0.265 g, 1.2 equiv.) and K₂CO₃ (0.274 g, 2.0 equiv.). The reaction mixture was heated to 70° C. for 2 hours. The reaction mixture was then cooled to ambient temperature, and quenched with water (20 mL). The aqueous phase was extracted with EtOAc (3×20 mL). The combined organic extracts were washed with water, brine, dried (Na$_2$SO$_4$), and concentrated under reduced pressure to afford a residue, which was purified by preparative TLC (Petroleum: EtOAc=1:1) to provide carbamate I-280 as a pale yellow oil (0.1 g, 41% yield). MS (ESI, pos. ion) m/z: 267 (M+Na).

Step 2: 3-(2-aminoethyl)oxazolidine-2,4-dione (I-281)

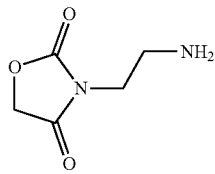

To a solution of tert-butyl (2-(2,4-dioxooxazolidin-3-yl) ethyl)carbamate, I-280 (0.1 g, 0.41 mmol) in DCM (2 ml) that had been pre-cooled to 0-5° C. was added a solution of TFA/DCM (1:1 v/v, 2 mL). The reaction mixture was then stirred at ambient temperature for 2 hours. When LC-MS showed that the reaction went to completion, the reaction solution was concentrated under reduced pressure to give the crude product, I-281 (pale oil, 176 mg). The crude product was used directly for next step. MS (ESI, pos. ion) m/z: 145 (M+1).

Step 3: 2-((2-((2-(2,4-dioxooxazolidin-3-yl)ethyl) amino)-2-oxoethyl)thio) acetic acid (I-282)

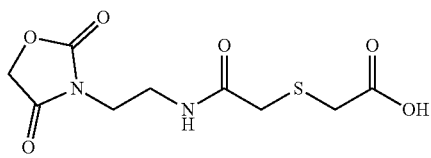 [SMILES: O=C(O)CSCC(=O)NCCN1C(=O)COC1=O]

To a solution of 3-(2-aminoethyl)oxazolidine-2,4-dione, I-281 (0.17 g, 1.17 mmol) and thiodiglycolic anhydride (0.087 g, 1.6 equiv. based on carbamate I-280) in DCM (5 mL) was added TEA (80 mg, 0.792 mmol). After 4 hours, the reaction mixture was concentrated to give the crude product. The crude product was purified by preparative HPLC (Mobile Phase: MeCN/H$_2$O with 0.1% TFA) to afford I-282 as a pale oil (50 mg, 2% yield). MS (ESI, pos. ion) m/z: 277.1 (M+1). $^1$H NMR (400 MHz, DMSO): δ 8.21 (m, 1H), 4.77 (s, 2H), 3.47 (m, 2H), 3.33 (s, 2H), 3.28 (m, 2H), 3.16 (s, 2H).

The Synthesis of Compound I-289 Involved 7 Steps as Depicted in the Following Scheme 108.

Scheme 108

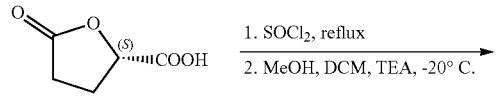

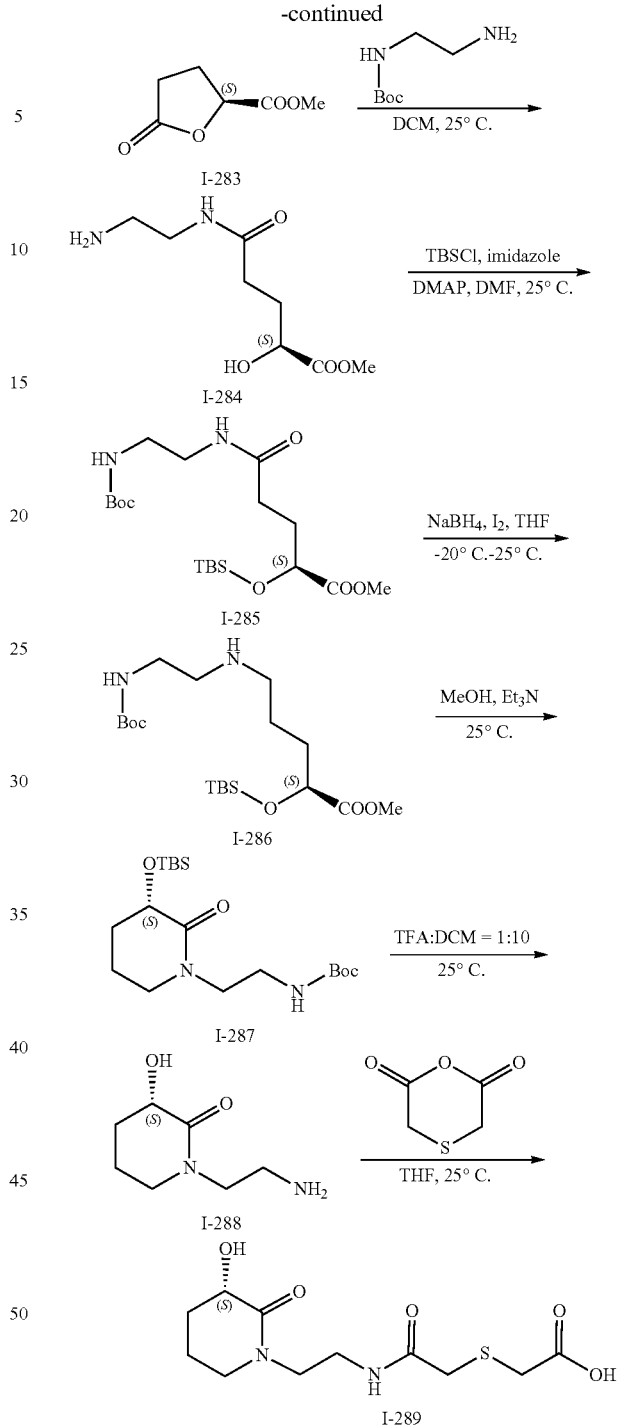

The chemical structure of the target compound was confirmed by $^1$H NMR and LC-MS with the purity >95% (HPLC 214 & 254 nm).

Step 1: Methyl-(S)-5-oxotetrahydrofuran-2-carboxylate (I-283)

To a solution of (S)-5-oxotetrahydrofuran-2-carboxylic acid (cas: 21461-84-7, 7 g, 53.8 mmol) was added SOCl$_2$ (17.95 g, 2.8 equiv., 11 mL) and the reaction mixture was refluxed at 80° C. for 4 hours under $N_2$. The reaction mixture was then allowed to cool to ambient temperature and stirred for 12 hours. The excess $SOCl_2$ was removed under reduced pressure. The residue was diluted with DCM (70 mL); a solution of MeOH (2.1 mL, 53.8 mmoL) and TEA (6.56 g, 64.5 mmoL) was added at 20° C. The reaction mixture was warmed to ambient temperature and stirred for 12 hours. The reaction was then quenched with $H_2O$ (40 mL) and extracted with EtOAc (20 mL×3). The combined organic extracts were dried over $MgSO_4$ and concentrated under reduced pressure to give the crude product. The crude product was purified by silica gel chromatography (Petroleum ether:EtOAc=1:1) to afford I-283 as a pale oil (4.5 g, 58% yield). MS (ESI, pos. ion) m/z: 236 (M+1).

Step 2: Methyl-(S)-5-((2-aminoethyl)amino)-2-hydroxy-5-oxopentanoate (I-284)

To a solution of methyl (S)-5-oxotetrahydrofuran-2-carboxylate, I-283 (3 g, 20.83 mmol) in DCM (20 mL) was added tert-butyl (2-aminoethyl)carbamate (cas: 57260-73-8, 230 mg). The reaction mixture was then stirred at ambient temperature for 48 hours. When the LC-MS showed the reaction went to completion, the reaction mixture was concentrated under reduced pressure to give the crude product, I-284. The crude product (3.5 g, 83% yield) was used directly in next step. MS (ESI, pos. ion) m/z: 205 (M+1).

Step 3: Methyl-(S)-5-((2-((tert-butoxycarbonyl)amino)ethyl)amino)-2-((tert-butyldimethylsily)oxy)-5-oxopentanoate (I-285)

To a solution of methyl (S)-5-((2-aminoethyl)amino)-2-hydroxy-5-oxopentanoate, I-284 (3.5 g, 13.98 mmol) in anhydrous DMF (30 mL) was added imidazole (2.38 g, 2.5 equiv.) and TBSCl (3.79 g, 1.8 equiv.). The reaction mixture was stirred at ambient temperature for 3 hours. The reaction was quenched with $H_2O$ (20 mL) and extracted with EtOAc (20 mL×3). The combined organic extracts were concentrated to afford the crude product. The crude product was purified by silica gel chromatography (Petroleum ether:EtOAc=1:3) to provide I-285 as a pale oil (3.6 g, 49% yield). MS (ESI, pos. ion) m/z: 419 (M+1).

Step 4: Methyl (S)-8-((tert-butoxycarbonyl)amino)-2-((tert-butyldimethylsilyl)oxy)octanoate (I-286)

A solution of methyl (S)-5-((2-((tert-butoxycarbonyl)amino)ethyl)amino)-2-((tert-butyldimethylsilyl)oxy)-5-oxopentanoate, I-285 (2 g, 5.48 mmol) and $NaBH_4$ (0.373 g, 1.8 equiv.) in THF (anhydrous, 26 mL) was added to a solution of iodine (1.25 g, 0.9 equiv.) in THF (anhydrous, 10 mL) at −20° C. under $N_2$. The reaction mixture was gradually warmed to ambient temperature over 8 hours. When the LC-MS showed that the reaction went to completion, the reaction was quenched with $H_2O$ (20 mL) and extracted with EtOAc (30 mL×3). The combined organic extracts were dried over $MgSO_4$ and concentrated to give the crude product. The crude product, I-286 (1.8 g, 93% yield) was used directly in next step. MS (ESI, pos. ion) m/z: 404 (M+1).

Step 5: Tert-butyl (S)-(2-(3-((tert-butyldimethylsilyl)oxy)-2-oxopiperidin-1-yl)ethyl)carbamate (I-287)

To a solution of methyl (S)-8-((tert-butoxycarbonyl)amino)-2-((tert-butyldimethylsilyl)oxy)octanoate, I-286 (3.6 g, 8.9 mmol) in DCM (30 mL) was added TEA (0.27 g, 0.3 mmol). The reaction mixture was stirred for 48 hours and was concentrated under reduced pressure to give the crude product. The crude product was purified by silica gel chromatography (Petroleum ether:EtOAc=3:1) to provide lactam I-287 as a pale oil (1.2 g, 36% yield). MS (ESI, pos. ion) m/z: 373 (M+1), 395 (M+Na).

Step 6: (S)-1-(2-aminoethyl)-3-hydroxypiperidin-2-one (I-288)

A solution of tert-butyl (S)-(2-(3-((tert-butyldimethylsilyl)oxy)-2-oxopiperidin-1-yl)ethyl)carbamate, I-287 (1.2 g, 3.22 mmol) was added to a solution of TFA/DCM (1 mL/3 mL) at 0° C. The reaction mixture was stirred for 2 hours and concentrated under reduced pressure to afford the crude product. The crude product, I-288 (0.8 g, pale oil) was used directly for next step. MS (ESI, pos. ion) m/z: 159 (M+1).

Step 7: (S)-2-((2-((2-(3-hydroxy-2-oxopiperidin-1-yl)ethyl)amino)-2-oxoethyl)thio) acetic acid (I-289)

To a solution of (S)-1-(2-aminoethyl)-3-hydroxypiperidin-2-one, I-288 (0.89 g, 5.6 mmol) and thiodiglycolic anhydride (1.11 g, ca. 1.5 equiv.) in 10 mL of DCM was added TEA (0.114 g, 0.2 equiv.). The reaction mixture was stirred for 2 hours and concentrated under reduced pressure to give the crude product. The crude product was purified by preparative HPLC (Mobile Phase:MeCN/$H_2O$ (0.1% TFA), Gradient: 5-15% MeCN) to give I-289 (50 mg, 3% yield) as a pale oil. MS (ESI, pos. ion) m/z: 291.1 (M+1). $^1$H NMR (400 MHz, DMSO) δ 12.63 (s, 1H), 8.11 (m, 1H), 3.84 (m, 1H), 3.45-3.37 (m, 2H), 3.35 (s, 2H), 3.30-3.24 (m, 2H), 3.24-3.19 (m, 3H), 3.18 (s, 2H), 1.99-1.89 (m, 1H), 1.81 (m, 1H), 1.70 (m, 1H), 1.64-1.52 (m, 1H).

The Synthesis of I-296 Involved 7 Steps as Depicted in the Following Scheme 109.

Scheme 109
(R)-2-((2-((2-(3-hydroxy-2-oxopiperidin-1-yl)ethyl)amino)-2-oxoethyl)thio) acetic acid (I-296)

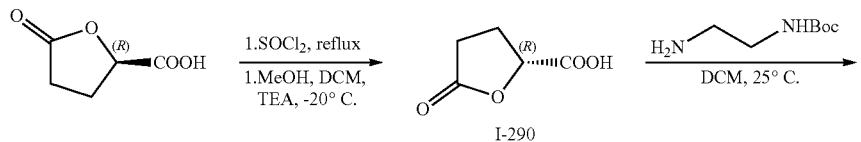

I-290

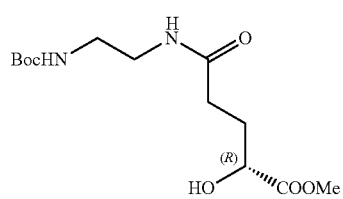
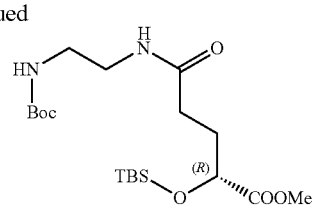
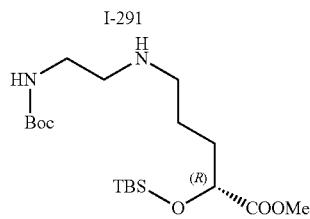
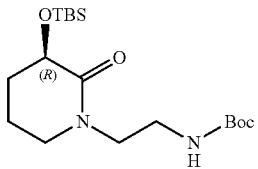
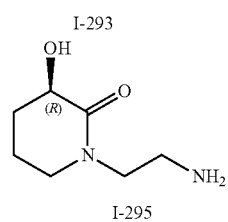
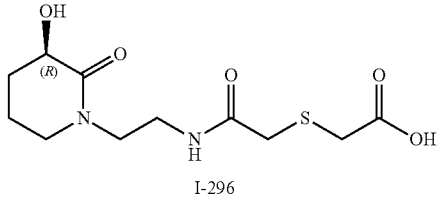

The synthetic route for I-296 was similar to that of I-288 and commenced with (R)-5-oxotetrahydrofuran-2-carboxylic acid (cas: 53558-93-3). I-296 (pale oil, 39 mg, 3% yield) was isolated by preparative HPLC (Mobile Phase: MeCN/H$_2$O (0.1% TFA), Gradient: 5-15% MeCN). MS (ESI, pos. ion) m/z: 291.1 (M+1). $^1$H NMR (400 MHz, DMSO) δ 12.59 (s, 1H), 8.10 (s, 1H), 5.00 (s, 1H), 3.84 (m, 1H), 3.42 (s, 2H), 3.28 (m, 3H), 3.21 (m, 3H), 3.18 (s, 2H), 1.95 (m, 1H), 1.87-1.76 (m, 1H), 1.75-1.65 (m, 1H), 1.58 (m, 1H).

The Synthesis of I-301 Involved 5 Steps as Depicted in the Following Scheme 110.

Scheme 110

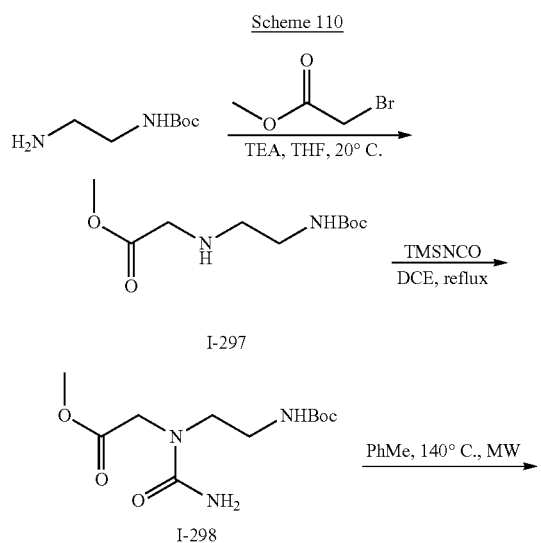

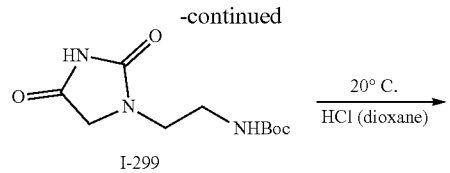
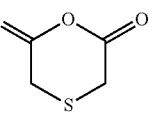
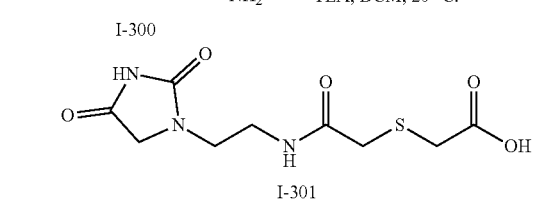

Step 1: Methyl (2-((tert-butoxycarbonyl)amino)ethyl)glycinate (I-297)

A solution of tert-butyl (2-aminoethyl)carbamate (cas: 57260-73-8, 3.2 g, 20 mmol), methyl 2-bromoacetate (cas: 96-32-2, 3.0 g, 1 equiv.) and TEA (4 mL, 2.9 equiv.) in 100 mL of THF was stirred at ambient temperature for 4 hours. Upon completion of the reaction, the reaction mixture was filtered and the filtrate was concentrated and the crude product, I-297 (5.3 g) was used in next step directly. MS (ESI, pos. ion) m/z: 255.2 (M+23).

Step 2: Methyl N-(2-((tert-butoxycarbonyl)amino)ethyl)-N-carbamoylglycinate (I-298)

A solution of methyl (2-((tert-butoxycarbonyl)amino)ethyl)glycinate, I-297 and trimethylsilyl isocyanate (cas:

1118-02-1, 4.5 mL, 1.7 equiv.) in DCE (50 mL) was heated to 90° C. for 48 hours. LC-MS at this point indicated that the reaction was not complete. The reaction mixture was concentrated, and purified by silica gel chromatography to afford I-298 as a pale oil (4.2 g, 76% over 2 steps). MS (ESI, pos. ion) m/z: 298.2 (M+23).

Step 3: Tert-butyl (2-(2,4-dioxoimidazolidin-1-yl)ethyl)carbamate (I-299)

Methyl N-(2-((tert-butoxycarbonyl)amino)ethyl)-N-carbamoylglycinate, I-298 (4.2 g, 15 mmol) in toluene (20 mL) was heated to 140° C. under Microwave irradiation for 30 minutes. The reaction mixture was then concentrated and purified by silica gel chromatography to afford I-299 as a pale oil (1.5 g, 41% yield). MS (ESI, pos. ion) m/z: 266.2 (M+23).

Step 4: 1-(2-aminoethyl)imidazolidine-2,4-dione (I-300)

A solution of tert-butyl (2-(2,4-dioxoimidazolidin-1-yl)ethyl)carbamate, I-299 (1.2 g, 4.9 mmol) in HCl (4M in dioxane) (18 mL) was stirred at ambient temperature for 2 hours. Upon completion of the reaction, the reaction mixture was concentrated and the crude amine I-300 was used in the next step directly. MS (ESI, pos. ion) m/z: 144.2 (M+1).

Step 5: 2-((2-((2-(2,4-dioxoimidazolidin-1-yl)ethyl)amino)-2-oxoethyl)thio) acetic acid (I-301)

A solution of 1-(2-aminoethyl)imidazolidine-2,4-dione, I-300 (crude, ca. 4.9 mmol) and thiodiglycolic anhydride (1.2 g, 1.8 equiv.) in 30 mL of DCM was stirred for 15 min. Upon completion of the reaction, the reaction mixture was concentrated in vacuo to give the crude product as a pale oil. Half the crude product was purified by preparative HPLC (Mobile Phase: MeCN/H$_2$O with 0.1% TFA), Gradient: 1-3% MeCN) to give 130 mg of I-301 as a white solid (19% yield). MS (ESI, pos. ion) m/z: 276.2 (M+1). $^1$H NMR (400 MHz, DMSO) δ 12.61 (s, 1H), 10.72 (s, 1H), 8.15 (t, 1H), 3.94 (s, 2H), 3.33 (s, 2H), 3.31-3.25 (m, 2H), 3.25-3.20 (m, 2H), 3.18 (s, 2H).

The Synthesis of I-307 Involved 6 Steps as Depicted in the Following Scheme 111.

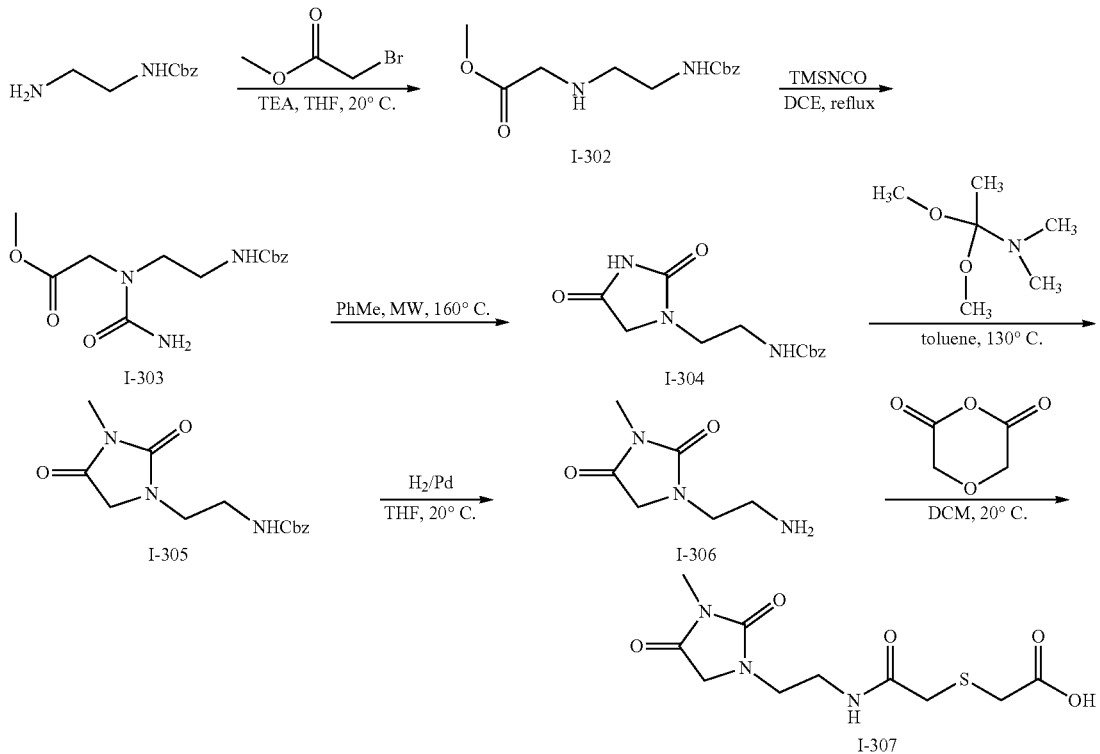

Steps 1-3 were similar to those used in the preparation of carboxylic acid I-301.

Step 4: Benzyl (2-(3-methyl-2,4-dioxoimidazolidin-1-yl)ethyl)carbamate (I-305)

To a solution of benzyl (2-(2,4-dioxoimidazolidin-1-yl)ethyl)carbamate, I-304 (600 mg, 2.17 mmol) in toluene (20 mL) was added N,N-dimethylacetamide dimethyl acetal (cas: 18871-66-4, 1.3 mL, 4.0 equiv.) in one portion at 25° C. The resulting mixture was heated to 130° C. for 2 hours. After cooling to ambient temperature, the reaction mixture was concentrated in vacuo. The residue was purified by preparative TLC to give 500 mg (79% yield) of carbamate I-305 as a pale yellow oil. MS (ESI, pos. ion) m/z: 292.1 (M+1).

Step 5: Tert-butyl 1-(((benzyloxy)carbonyl)amino)cyclopropane-1-carboxylate (I-306)

To a solution of benzyl (2-(3-methyl-2,4-dioxoimidazolidin-1-yl)ethyl)carbamate, I-305 (500 mg, 1.72 mmol) in 20 mL of THF was added 50 mg of 10% Pd/C. The reaction was stirred at 25° C. for 10 hours under H₂. Upon completion of the reaction, the reaction mixture was filtered and the filtrate was concentrated in vacuo. The residue was used in next step directly without purification. MS (ESI, pos. ion) m/z: 158.1 (M+1).

Step 6: 2-((2-((2-(3-methyl-2,4-dioxoimidazolidin-1-yl)ethyl)amino)-2-oxoethyl)thio)acetic acid (I-307)

To a solution of tert-butyl 1-(((benzyloxy)carbonyl)amino)cyclopropane-1-carboxylate, I-306 (500 mg, 3.18 mmol) in DCM (20 mL) was added thiodiglycolic anhydride (630 mg, 1.5 equiv.). The reaction mixture was then stirred at 25° C. for 1 hour. Upon completion of the reaction, the solvent was removed in vacuo, and the crude product was purified by preparative HPLC (Mobile Phase: MeCN/H₂O with 0.1% TFA), gradient: 1-3% MeCN) to give 250 mg (27% yield) of I-307 as a pale oil. MS (ESI, pos. ion) m/z: 290.1 (M+1). ¹H NMR (400 MHz, DMSO) δ 8.15 (s, 1H), 3.98 (s, 2H), 3.34 (d, 2H), 3.33 (s, 2H), 3.25 (t, 2H), 3.17 (s, 2H), 2.83 (s, 3H).

The Synthesis of I-311 Involved 5 Steps as Depicted in the Following Scheme 112.

Scheme 112 2-((2-((2-(2,5-dioxopiperazin-1-yl)ethyl)amino)-2-oxoethyl)thio)acetic acid (I-311):

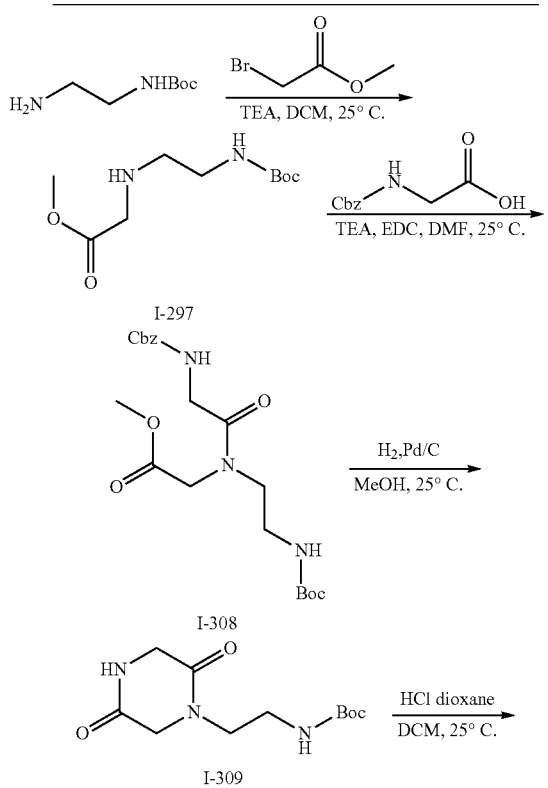

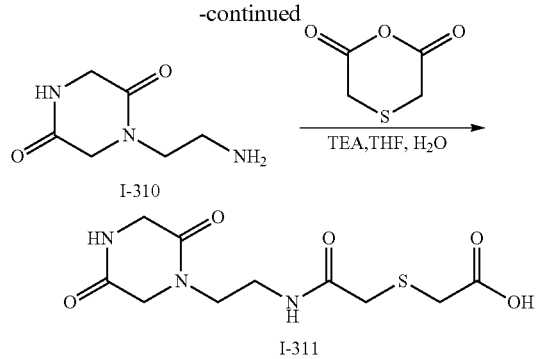

Step 2: Methyl N-(((benzyloxy)carbonyl)glycyl)-N-(2-((tert-butoxycarbonyl) amino) ethyl) glycinate (I-308)

To a solution of benzyloxycarbonylglycine (3.1 g, 15 mmol, cas: 1138-80-3) in DMF (30 mL) and methyl (2-((tert-butoxycarbonyl)amino)ethyl)glycinate, I-297 (1.8 g, 7.8 mmol) was added TEA (2.4 g, 24 mmol), EDC (4.6 g, 24 mmol), and then the reaction mixture was stirred at 25° C. for 15 hours. The reaction mixture was then diluted with EtOAc (100 mL) and was sequentially washed with aqueous 5% NaHCO₃ (100 mL×3), aqueous 5% citric acid solution (100 mL×3) and brine (100 mL×3). The EtOAc extracts were dried over anhydrous magnesium sulfate and purified by silica gel column chromatography (3% MeOH/DCM) to give 2.1 g of I-308 as a pale oil. Yield: 64%. MS (ESI, pos. ion) m/z: 446.1 (M+23).

Step 3: Tert-butyl (2-(2,5-dioxopiperazin-1-yl)ethyl) carbamate (I-309)

To a solution of methyl N-(((benzyloxy)carbonyl)glycyl)-N-(2-((tert-butoxycarbonyl)amino)ethyl)glycinate, I-308 (2.1 g, 5 mmol) in 30 mL of MeOH was added 500 mg of 10% Pd/C. The reaction mixture was stirred at ambient temperature for 10 hours under H₂ (1 atm). Upon completion of the reaction, Pd/C was filtered and the filtrate was concentrated in vacuo. The residue was purified by silica gel column chromatography (3% MeOH/DCM) to give 800 mg of I-309 as a pale oil. Yield: 64%. MS (ESI, pos. ion) m/z: 280.1 (M+23).

Step 4: Benzyl (2-(3-methyl-2,4-dioxoimidazolidin-1-yl)ethyl)carbamate (I-310)

To a solution of tert-butyl (2-(2,5-dioxopiperazin-1-yl)ethyl)carbamate, I-309 (400 mg, 1.6 mmol) in 15 mL of DCM was added 15 mL of 4 M HCl in dioxane. The reaction mixture was stirred at 25° C. for 1 hour. Upon completion of the reaction, the mixture was concentrated under reduced pressure to give 360 mg of crude amine I-310 as a white solid, which was used in next step. MS (ESI, pos. ion) m/z: 158.1 (M+1).

Step 5: 2-((2-((2-(2,5-dioxopiperazin-1-yl)ethyl)amino)-2-oxoethyl)thio)acetic acid (I-311)

To a solution of benzyl (2-(3-methyl-2,4-dioxoimidazolidin-1-yl)ethyl)carbamate (300 mg, 1.91 mmol) in THF/H₂O (10 mL/1 mL) was added TEA (200 mg, 2 mmol) and thiodiglycolic anhydride (504 mg, 3.82 mmol). The reaction mixture was stirred at 25° C. for 1 hour. Upon completion of the reaction, the solvent was removed under reduced pressure and the resulting residue was purified by preparative HPLC (Mobile Phase:MeCN/H₂O (with 0.1% formic acid) Gradient: 2-8% MeCN) to give 65 mg of carboxylic acid I-311 as a pale oil. Yield: 12%. MS (ESI, pos. ion) m/z: 290.1 (M+1). ¹H NMR (400 MHz, DMSO) δ 8.12 (dd, J=12.1, 6.1 Hz, 2H), 3.92 (s, 2H), 3.76 (s, 1H), 3.38-3.31 (m, 4H), 3.23 (dd, J=11.8, 5.9 Hz, 1H).

The Synthesis of I-320 Involved 9 Steps as Depicted in the Following Scheme 113.

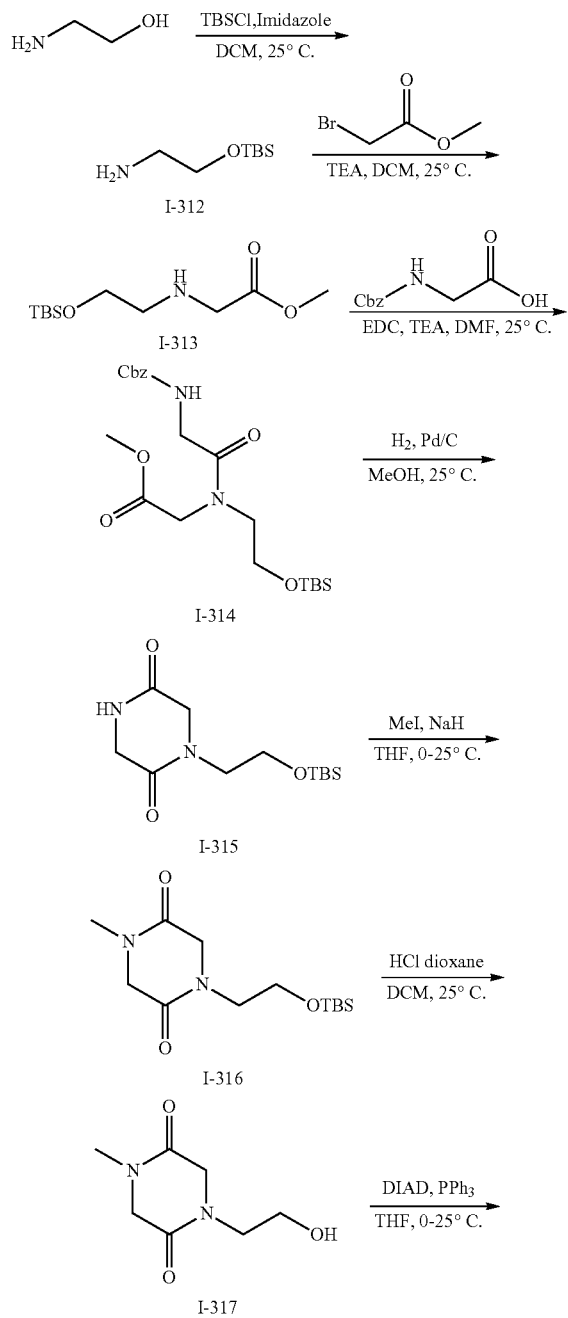

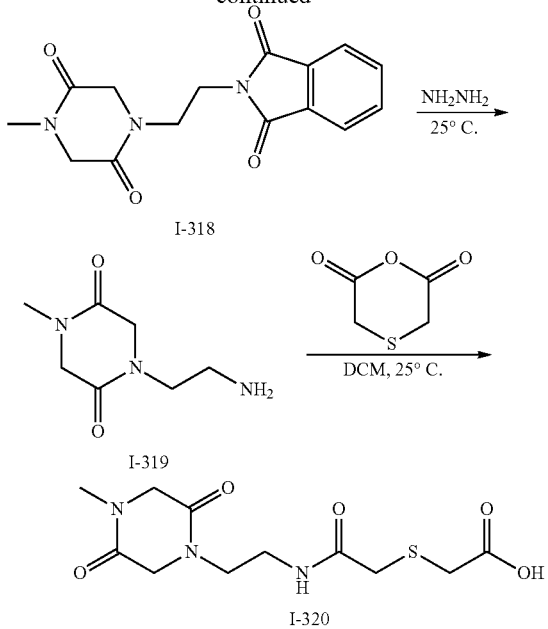

Step 1: 2-((tert-butyldimethylsilyl)oxy)ethan-1-amine (I-312)

To a solution of 2-aminoethan-1-ol (1.2 g, 20 mmol), DMAP (220 mg, 1.8 mmol) and imidazole (2.7 g, 40 mmol) in 30 ml of DCM was added TBSCl (3.1 g, 21 mmol). The resulting mixture was stirred at ambient temperature for 16 hours. Upon completion of the reaction, 50 mL of water was added to the reaction mixture, which was then extracted with DCM (30 mL×3). The combined organic extracts were dried over Na₂SO₄, then concentrated in vacuo to give 3.1 g of I-312 as a pale oil. Yield: 89%. MS (ESI, pos. ion) m/z: 176.1 (M+1).

Step 2: Methyl (2-((tert-butyldimethylsilyl)oxy)ethyl)glycinate (I-313)

To a solution of 2-((tert-butyldimethylsilyl)oxy)ethan-1-amine, I-312 (1.75 g, 10 mmol) in 30 mL of DCM was added methyl 2-bromoacetate (1.6 g, 1.1 equiv., cas #: 96-32-2) and TEA (2.0 g, 2.0 equiv.). The reaction mixture was stirred at ambient temperature for 10 hours under N₂. Upon completion of the reaction, the solvent was removed in vacuo and the mixture was purified by column chromatography (5-10% MeOH in DCM) to give 2 g of I-313 as a yellow oil. Yield: 62%. MS (ESI, pos. ion) m/z: 248.1 (M+1).

Step 3: Methyl N-(((benzyloxy)carbonyl)glycyl)-N-(2-((tert-butoxycarbonyl) amino) ethyl) glycinate (I-314)

To a solution of benzyloxycarbonylglycine (3.1 g, 15 mmol, cas #: 1138-80-3) and amine I-313 (1.8 g, 7.28 mmol) in 30 mL of DMF was added TEA (2.4 g, 24 mmol) and the reaction mixture was stirred at 0° C. To this reaction mixture was added EDC (3.5 g, 18 mmol) and stirring continued at 0° C. for 2 hours, after which the reaction mixture was allowed to warm to ambient temperature and stirred for 15 hours. The reaction mixture was diluted with EtOAc (100 mL) and sequentially washed with aqueous 5% sodium bicarbonate solution (100 mL×3), aqueous 5% citric acid solution (100 mL×3), aqueous saturated sodium chloride solution (100 mL×3). The EtOAc extracts were dried over $Na_2SO_4$ and purified by silica gel column chromatography (3.8% MeOH/DCM) to give 3 g of amide I-314 as a yellow oil. Yield: 43%. MS (ESI, pos. ion) m/z: 461.1 (M+23).

Step 4: 1-(2-((tert-butyldimethylsilyl)oxy)ethyl) piperazine-2,5-dione (I-315)

To a solution of methyl N-(((benzyloxy)carbonyl)glycyl)-N-(2-((tert-butoxycarbonyl) amino) ethyl) glycinate, I-314 (2.1 g, 4.8 mmol) in 30 mL of MeOH was added 500 mg of 10% Pd/C, The reaction mixture was stirred at ambient temperature for 10 hours under $H_2$ (1 atm). Upon completion of the reaction, Pd/C was filtered and the filtrate was concentrated under reduced pressure. The residue was purified by silica gel column chromatography (3% MeOH/DCM) to give 720 mg of diketopiperazine I-315 as a pale oil. Yield: 55%. MS (ESI, pos. ion) m/z: 273.1 (M+1).

Step 5: 1-(2-((tert-butyldimethylsilyl)oxy)ethyl)-4-methylpiperazine-2,5-dione (I-316)

To a solution of 1-(2-((tert-butyldimethylsilyl)oxy)ethyl) piperazine-2,5-dione, I-315 (720 mg, 2.64 mmol) and NaH (500 mg, 8.3 equiv., 60% dispersion in mineral oil) in 20 mL of THF at 0° C. was added MeI (1.1 g, 3.0 equiv.). The reaction mixture was stirred at ambient temperature for 1 hour. Upon completion of the reaction, the solvent was removed in vacuo, and the residue obtained was purified by column chromatography (DCM) to give 680 mg of diketopiperazine I-316 as a yellow oil, yield: 90%. MS (ESI, pos. ion) m/z: 287.1 (M+1).

Step 6: 1-(2-hydroxyethyl)-4-methylpiperazine-2,5-dione (I-317)

To a solution of 1-(2-((tert-butyldimethylsilyl)oxy)ethyl)-4-methylpiperazine-2,5-dione, I-316 (800 mg, 2.8 mmol) in DCM (8 mL) cooled in an ice-water bath was added HCl in Dioxane (30% v/v, 8 mL) under $N_2$. The reaction mixture was stirred for 0.5 hours. Upon completion of the reaction, the reaction mixture was concentrated under reduced pressure to give 608 mg of I-317 as a pale oil, which was used directly for next step. MS (ESI, pos. ion) m/z: 173.1 (M+1).

Step 7: 2-(2-(4-methyl-2,5-dioxopiperazin-1-yl) ethyl)isoindoline-1,3-dione (I-318)

To a solution of 1-(2-hydroxyethyl)-4-methylpiperazine-2,5-dione, I-317 (600 mg, 3.8 mmol) in THF (20 mL) was added phthalimide (cas: 85-41-6, 592 mg, 1.05 equiv.) and $PPh_3$ (1.5 g, 1.5 equiv.). The reaction mixture was stirred for 0.5 h in ice bath under $N_2$. DIAD (2.3 g, 3.0 equiv.) was the added dropwise to the solution. The reaction mixture was allowed to warm to ambient temperature and stirred for 6 hours. Upon completion of the reaction, the reaction mixture was quenched with water (5 mL) and extracted with DCM (3×20 mL). The combined organic extracts were washed with water (20 mL), brine (20 mL), and dried over $Na_2SO_4$, then concentrated and the residue obtained was purified by column chromatography (50-100% EtOAc) to give 480 mg of I-318 as a yellow solid, yield: 42%. MS (ESI, pos. ion) m/z: 302.1 (M+1).

Step 8: 1-(2-aminoethyl)-4-methylpiperazine-2,5-dione (I-319)

To a solution of 2-(2-(4-methyl-2,5-dioxopiperazin-1-yl) ethyl)isoindoline-1,3-dione, I-318 (300 mg, 1 mmol) in MeOH (5 mL) that had been cooled in an ice-water bath was added $NH_2NH_2$ (85% in $H_2O$, 300 mg, 5.5 equiv.). The reaction mixture was allowed to warm to ambient temperature and stirred for 12 hours. Upon completion of the reaction, the slurry was filtered and the filtrate was concentrated to afford crude amine I-319, which was used directly for the next step (pale oil, 280 mg). MS (ESI, pos. ion) m/z: 172.1 (M+1).

Step 9: 2-((2-((2-(4-methyl-2,5-dioxopiperazin-1-yl) ethyl)amino)-2-oxoethyl)thio) acetic acid (I-320)

A solution of 1-(2-aminoethyl)-4-methylpiperazine-2,5-dione, I-319 (280 mg, 1.27 mmol) and thiodiglycolic anhydride (300 mg, 1.8 equiv.) in 5 mL of DCM was stirred for 2 hours, and then was concentrated in vacuo to give the crude product as a pale oil. The crude product was purified by preparative HPLC (Mobile Phase: $MeCN/H_2O$ (0.1% formic acid) Gradient: 5-15% MeCN) to give 50 mg of carboxylic acid I-320 as a white solid, yield: 13%. $^1$H NMR (400 MHz, CDCl3) δ 7.34 (s, 1H), 4.14 (s, 2H), 4.06 (s, 2H), 3.64 (dd, 2H), 3.55 (dd, 2H), 3.36 (s, 2H), 3.25 (s, 2H), 3.00 (s, 3H).

The Synthesis of I-325 Involved 5 Steps as Depicted in the Following Scheme 114.

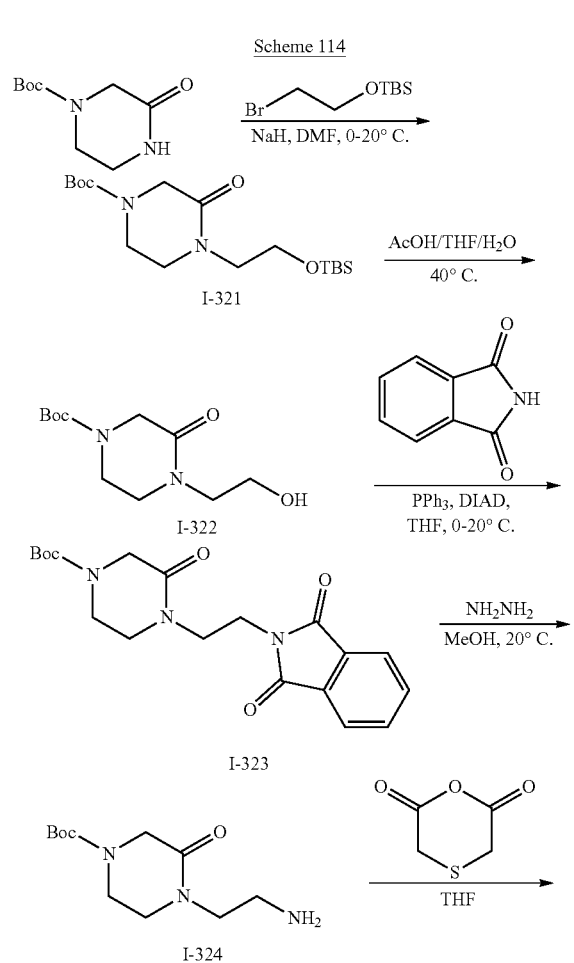

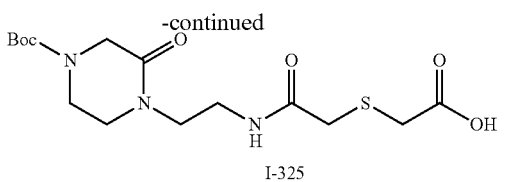

I-325

Step 1: tert-butyl 4-(2-((tert-butyldimethylsilyl)oxy) ethyl)-3-oxopiperazine-1-carboxylate (I-321)

To a solution of tert-butyl 3-oxopiperazine-1-carboxylate (cas: 76003-29-7, 2 g, 10 mmol) in DMF (20 mL) that had been pre-cooled in an ice-water bath was added NaH (800 mg, 2.0 equiv.) in portions under $N_2$. The mixture was stirred for 0.5 hours. (2-bromoethoxy)(tert-butyl)dimethylsilane (cas: 86864-60-0, 5.3 mL, 2.5 equiv.) was added to the solution at 0° C. The reaction mixture was stirred at 25° C. for 12 hours. The reaction mixture was then diluted with water (50 mL) and extracted with EtOAc (3×80 mL). The combined organic extracts was then washed with water (50 mL), brine (50 mL), and dried over $Na_2SO_4$, then concentrated under reduced pressure to a residue. The residue was purified by silica gel chromatography to afford ketopiperazine I-321 as a pale oil (1.8 g, 50% yield, pale oil). MS (ESI, pos. ion) m/z: 381 (M+23).

Step 2: tert-butyl 4-(2-hydroxyethyl)-3-oxopiperazine-1-carboxylate (I-322)

A solution of tert-butyl 4-(2-((tert-butyldimethylsilyl)oxy)ethyl)-3-oxopiperazine-1-carboxylate, I-321 (1.8 g, 5 mmol) in AcOH/THF/$H_2O$ (40 mL/13 mL/13 mL) was stirred at 40° C. for 2 hours. Upon completion of the reaction, the solvent was removed under reduced pressure. The crude product was purified by silica gel chromatography to give the alcohol I-322 (0.95 g, 78%, pale oil). MS (ESI, pos. ion) m/z: 267 (M+23).

Step 3: tert-butyl 4-(2-(1,3-dioxoisoindolin-2-yl) ethyl)-3-oxopiperazine-1-carboxylate (I-323)

To a solution of tert-butyl 4-(2-hydroxyethyl)-3-oxopiperazine-1-carboxylate, I-322 (0.82 g, 3.4 mmol) in THF (8 mL) was added phthalimide (cas: 85-41-6, 0.75 g, 1.5 equiv.), $PPh_3$ (1.6 g, 1.8 equiv.) in sequence at 0° C. under $N_2$. Then DIAD (1.4 mL, 2.0 equiv.) was added dropwise. The mixture was then stirred at 25° C. for 1.5 hours. After LC-MS showed the reaction went to completion, the mixture solution was filtered. The filtrate was concentrated under reduced pressure to afford the crude product. The crude product was purified by silica gel chromatography to give phthalimide I-323 as a white solid (purity: 40%, 2.8 g, 88% yield). MS (ESI, pos. ion) m/z: 396 (M+23).

Step 4: tert-butyl 4-(2-aminoethyl)-3-oxopiperazine-1-carboxylate (I-324)

To a solution of tert-butyl 4-(2-(1,3-dioxoisoindolin-2-yl)ethyl)-3-oxopiperazine-1-carboxylate, I-323 (0.58 g, ca. 0.77 mmol) in MeOH (8 mL) that had been pre-cooled in an ice-water bath was added $NH_2NH_2$ (85% in $H_2O$, 0.1 mL, 2 equiv.). The reaction mixture was allowed to warm to ambient temperature and then stirred for 18 hours. Upon completion of the reaction, the slurry was filtered and the filtrate was concentrated to afford a pale oil. The crude product, I-324 was used directly for next step. MS (ESI, pos. ion) m/z: 266 (M+23).

Step 5: 2-((2-((2-(4-(tert-butoxycarbonyl)-2-oxopiperazin-1-yl)ethyl)amino)-2-oxoethyl)thio) acetic acid (I-325)

A solution of tert-butyl 4-(2-aminoethyl)-3-oxopiperazine-1-carboxylate, I-324 (crude product, ca. 0.77 mmol) and 1,4-thiodiglycolic anhydride (100 mg, 1.0 equiv.) in THF (5 mL) was stirred for 5 min and concentrated under reduced pressure. The crude product was purified by preparative HPLC (Mobile Phase: MeCN/$H_2O$ (0.10% formic acid), Gradient: 20-30% MeCN) to afford carboxylic acid I-325 as a white solid (54 mg, 19% yield). MS (ESI, pos. ion) m/z: 398.2 (M+23). $^1$H NMR (400 MHz, CDCl3) δ 4.14 (s, 2H), 3.67 (dd, 4H), 3.59-3.50 (m, 2H), 3.44 (d, 2H), 3.35 (s, 2H), 3.27 (s, 2H), 1.47 (s, 9H).

The Synthesis of I-328 Involved 3 Steps as Depicted in the Following Scheme 115.

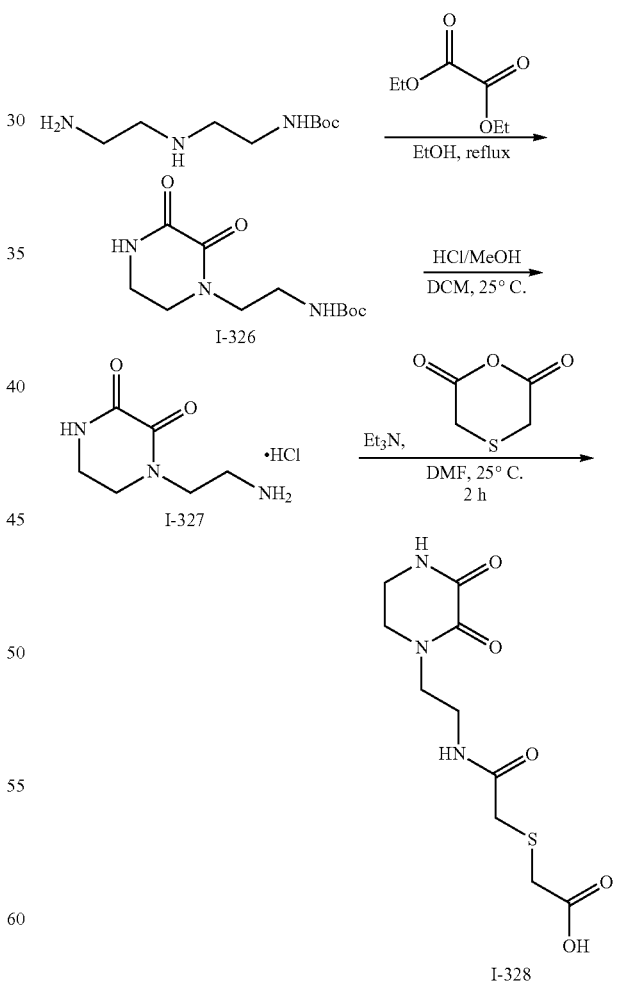

Scheme 115

The chemical structure of the target compound was confirmed by $^1$H NMR and LC-MS with the purity >95% (HPLC 214 & 254 nm).

2-((2-((2-(2,3-dioxopiperazin-1-yl)ethyl)amino)-2-oxoethyl)thio) acetic acid (I-328)

Step 1. tert-butyl (2-(2,3-dioxopiperazin-1-yl)ethyl)carbamate (I-326)

To a solution of tert-butyl (2-((2-aminoethyl)amino)ethyl)carbamate (cas: 193206-49-4, 1 g, 5 mmol) in EtOH (50 mL) was added diethyl oxalate (cas: 95-92-1, 0.73 g, 1.0 equiv.). The reaction mixture was heated to reflux for 18 hours, then concentrated under reduced pressure. The residue obtained was purified by silica gel chromatography to provide carbamate I-326 as a colorless foam. (330 mg, 26% yield). MS (ESI, pos. ion) m/z: 280 (M+23).

Step 2. 1-(2-aminoethyl)piperazine-2,3-dione hydrochloride (I-327)

To a solution of tert-butyl (2-(2,3-dioxopiperazin-1-yl)ethyl)carbamate, I-326 (280 mg, 1.1 mmol) in DCM (20 ml) was added HCl/MeOH (5 mL). The reaction mixture was then stirred at ambient temperature for 1 hour, then concentrated under reduced pressure to afford 210 mg of the crude product I-327, which was directly used without further purification. MS (ESI, pos. ion) m/z: 158 (M+1).

Step 3. 2-((2-((2-(2,3-dioxopiperazin-1-yl)ethyl)amino)-2-oxoethyl)thio) acetic acid (I-328)

To a solution of 1-(2-aminoethyl)piperazine-2,3-dione hydrochloride, I-327 (210 mg, 1.1 mmol) and thiodiglycolic anhydride (cas: 3261-87-8, 144 mg, 1.1 equiv.) in DMF (10 mL) was added TEA (222 mg, 2.2 equiv.). The reaction mixture was stirred at ambient temperature for 2 hours and then was concentrated under reduced pressure to afford the crude product. The crude product was purified by preparative HPLC (Mobile Phase: MeCN/H$_2$O (with 0.1% TFA)) to give afford acid I-328 (56 mg, 18% yield) as a white solid). MS (ESI, pos. ion) m/z: 290 (M+1). $^1$H NMR (400 MHz, DMSO) δ 8.54 (s, 1H), 8.18 (t, 1H), 3.55-3.45 (m, 2H), 3.41 (t, 2H), 3.32 (d, 2H), 3.25 (dd, 2H), 3.18 (s, 2H).
The Synthesis of I-332 Involved 4 Steps as Depicted in the Following Scheme 116.

Scheme 116

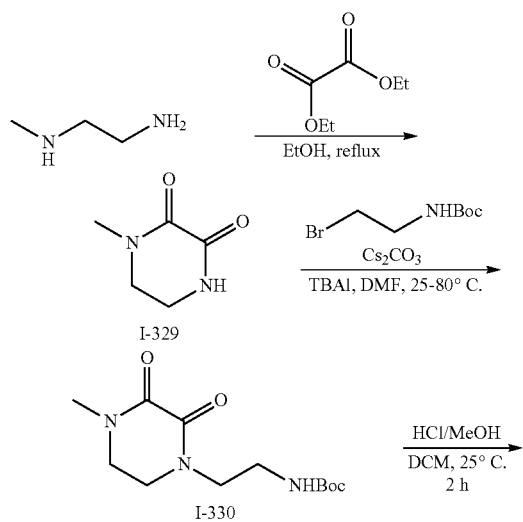

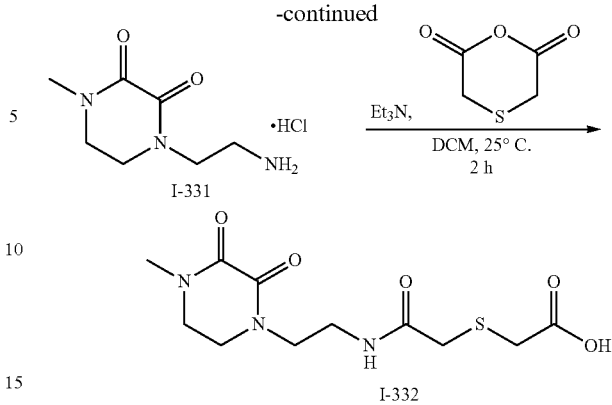

The chemical structure of the target compound was confirmed by $^1$H NMR and LC-MS with the purity >95% (HPLC 214 & 254 nm).

(S)-2-((2-((2-(2-(hydroxymethyl)-5-oxopyrrolidin-1-yl)ethyl)amino)-2-oxoethyl)thio) acetic acid (I-332)

Step 1: 1-Methylpiperazine-2,3-dione (I-329)

To a solution of N-methylethylene-1,2-diamine (cas: 109-81-9, 1 g, 13.5 mmol) in EtOH (80 mL) was added diethyl oxalate (cas: 95-92-1, 2 g, 5 mmol). The reaction was heated to reflux for 18 hours, then concentrated under reduced pressure. The residue obtained was purified by silica gel chromatography to provide (1.4 g, 80% yield) of I-329 as a colorless foam. MS ESI, pos. ion) m/z: 129 (M+1).

Step 2: Tert-butyl (2-(4-methyl-2,3-dioxopiperazin-1-yl)ethyl)carbamate (I-330)

To a slurry of 1-methylpiperazine-2,3-dione, I-329 (1 g, 7.8 mmol), Cs$_2$CO$_3$ (12.7 g, 5.0 equiv.) and TBAI (288 mg, 0.1 equiv.) in DMF (50 mL) was added tert-butyl (2-bromoethyl)carbamate (3.5 g, 2.0 equiv.). The reaction mixture was heated to 80° C. for 24 hours. The reaction mixture was then concentrated and the residue obtained was purified by silica gel chromatography to provide 1.4 g (67% yield) of carbamate I-330 as a colorless oil. MS (ESI, pos. ion) m/z: 294 (M+23).

Step 3: 1-(2-Aminoethyl)-4-methylpiperazine-2,3-dione hydrochloride (I-331)

To a solution of tert-butyl (2-(4-methyl-2,3-dioxopiperazin-1-yl)ethyl)carbamate, I-330 (100 mg, 0.37 mmol) in DCM (12 mL) was added HCl/MeOH (2 mL). The reaction was then stirred at ambient temperature for 1 hour. The reaction mixture was then concentrated and the crude product (77 mg, colorless oil) obtained was directly used without purification. MS (ESI, pos. ion) m/z: 172 (M+1).

Step 4: 2-((2-((2-(4-Methyl-2,3-dioxopiperazin-1-yl)ethyl)amino)-2-oxoethyl)thio) acetic acid (I-332)

To a solution of 1-(2-aminoethyl)-4-methylpiperazine-2,3-dione hydrochloride, I-331 (77 mg, 0.37 mmol) and thiodiglycolic anhydride (49 mg, 1.0 equiv.) in DCM (10 mL) was added TEA (75 mg, 0.74 mmol). The reaction mixture was stirred at ambient temperature for 1 hour and then was concentrated under reduced pressure to give the crude product. The crude product was purified by preparative HPLC (Mobile Phase: MeCN/H$_2$O (0.1% TFA)) to afford acid I-332 (40 mg, 37% yield). MS (ESI, pos. ion) m/z: 304 (M+1). $^1$H NMR (400 MHz, DMSO) δ 8.21 (s, 1H), 3.52 (d, J=4.9 Hz, 4H), 3.39 (t, J=5.5 Hz, 2H), 3.31 (s, 2H), 3.26 (d, J=5.5 Hz, 2H), 3.17 (s, 2H), 2.91 (s, 3H).

The Synthesis of Compound I-335 Involved 3 Steps as Depicted in the Following Scheme 117.

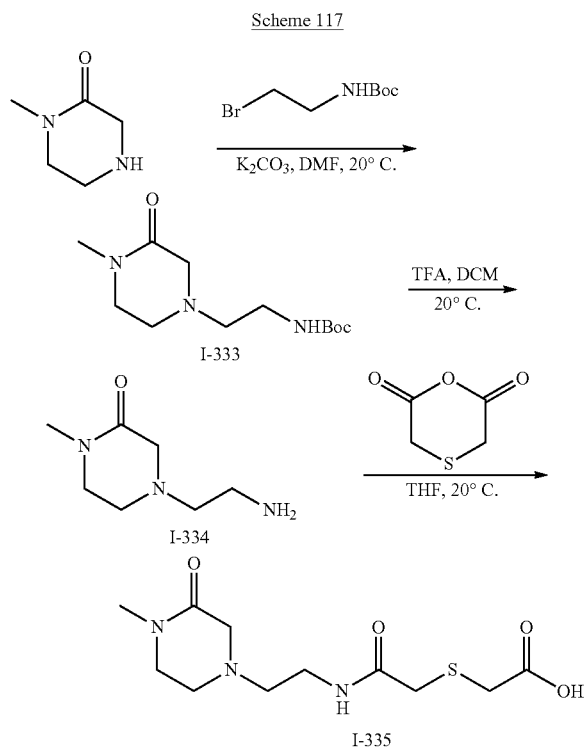

The chemical structure of the target compound was confirmed by $^1$H NMR and LC-MS with the purity >95% (HPLC 214 & 254 nm).

Step 1: Tert-butyl (2-((3-chloropropyl)sulfonamido) ethyl)carbamate (I-333)

A solution of 1-methylpiperazin-2-one (cas: 5625-67-2, 1 g, 9.99 mmol), tert-butyl (2-bromoethyl)carbamate (cas: 39684-80-5, 2 g, 0.9 equiv.) in anhydrous DMF (15 mL) was added K$_2$CO$_3$ (8.28 g, 6.0 equiv.). The reaction mixture was stirred for 8 hours at ambient temperature. Once LC-MS analysis indicated reaction completion, the reaction was quenched with H$_2$O (20 mL) and the aqueous phase was extracted with EtOAc (20 mL×3). The combined organic extracts was concentrated under reduced pressure to give the crude product. The crude product was purified by silica gel chromatography (Petroleum ether:EtOAc=1:10) to provide carbamate I-333 as a pale oil (0.65 g, 22%). MS (ESI, pos. ion) m/z: 258 (M+1).

Step 2: 4-(2-Aminoethyl)-1-methylpiperazin-2-one (I-334)

A solution of tert-butyl (2-(4-methyl-3-oxopiperazin-1-yl)ethyl)carbamate, 1-333 (0.25 g, 0.97 mmol) in DCM (2 mL) that had been pre-cooled in an ice-water bath was added a solution of TFA/DCM (1:1 v/v, 2 mL). The reaction mixture was then stirred at ambient temperature for 2 hours. When the LC-MS showed the reaction went to completion, the reaction mixture was concentrated in vacuo to afford the crude amine, I-334 (pale oil, 200 mg). The crude product was used directly for next step. MS (ESI, pos. ion) m/z: 158 (M+1).

Step 3: 2-((2-((2-(4-Methyl-3-oxopiperazin-1-yl) ethyl)amino)-2-oxoethyl)thio) acetic acid (I-335)

A solution of 4-(2-aminoethyl)-1-methylpiperazin-2-one, I-334 (0.2 g, 1.27 mmol) and thiodiglycolic anhydride (0.185 g, 1.1 equiv.) in THF (5 mL) was stirred at ambient temperature for 4 hours, and then the reaction mixture was concentrated to give the crude product. The crude product was purified by preparative HPLC (Mobile Phase: MeCN/H$_2$O (0.1% TFA)) to afford the acid I-335 as a pale oil (50 mg, 2% yield). MS (ESI, pos. ion) m/z: 290.1 (M+1). $^1$H NMR (400 MHz, DMSO) δ 8.26 (s, 1H), 3.75 (s, 2H), 3.48 (s, 3H), 3.44-3.36 (m, 5H), 3.26 (s, 2H), 3.12 (m, 2H), 2.87 (s, 3H).

The Synthesis of Compound I-338 Involved 3 Steps as Depicted in the Following Scheme 118.

Scheme 118
2-((2-oxo-2-((2-(3-oxopiperazin-1-yl)ethyl)amino)ethyl)thio) acetic acid (I-338)

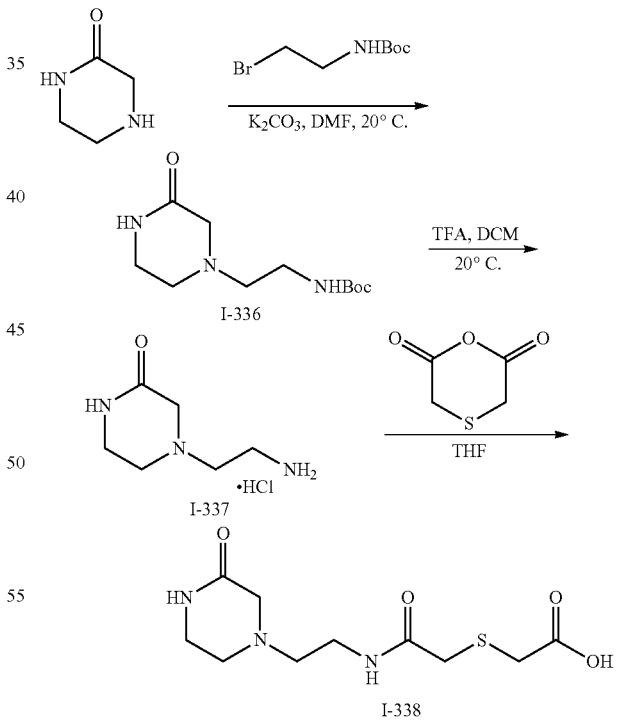

The synthetic route for I-338 was similar to that of I-335 and commenced with piperazin-2-one (cas: 5625-67-2). 2-((2-oxo-2-((2-(3-oxopiperazin-1-yl)ethyl)amino)ethyl) thio)acetic acid (pale oil, 50 mg, 15% yield) was isolated by preparative HPLC (Mobile Phase: MeCN/H$_2$O (with 0.1% TFA)). MS (ESI, pos. ion) m/z: 276.1 (M+1). $^1$H NMR (400

MHz, MeOD) δ 3.82 (s, 2H), 3.60-3.53 (m, 4H), 3.47 (m, 2H), 3.38 (s, 2H), 3.35 (s, 2H), 3.23 (m, 2H).
The Synthesis of I-343 is Depicted in Scheme 119.

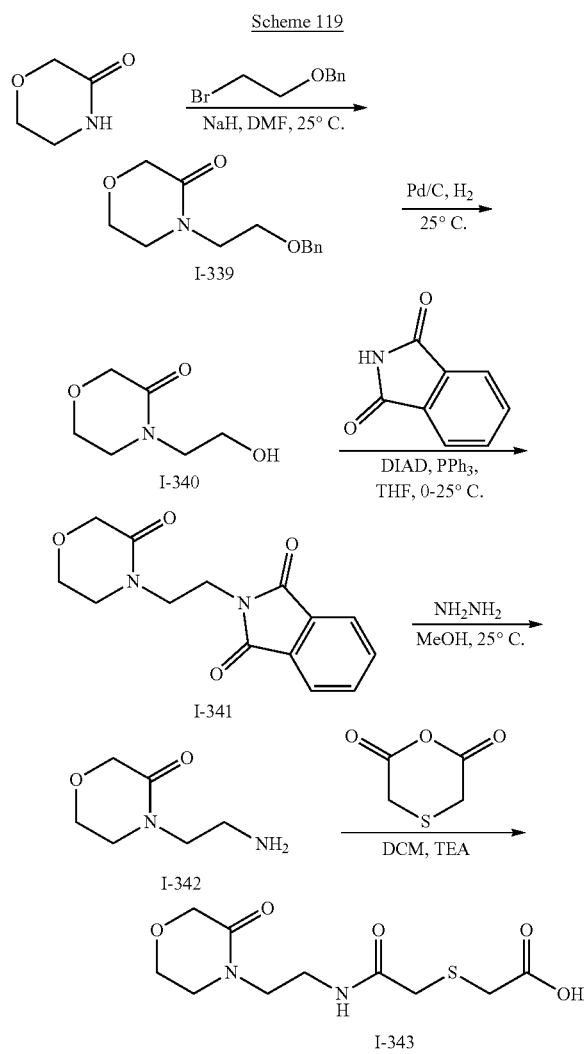

The chemical structure of the target compound was confirmed by $^1$H NMR and LC-MS with the purity >95% (HPLC 214 & 254 nm).

Step 1: 4-(2-(benzyloxy)ethyl)morpholin-3-one (I-339)

To a solution of morpholin-3-one (cas: 109-11-5, 2 g, 19.8 mmol) in anhydrous DMF (25 mL) was added NaH (60% dispersion in mineral oil, 1.98 g, 2.5 equiv.) at 0° C. under $N_2$. The reaction mixture was stirred for 30 minutes and then ((2-bromoethoxy)methyl)benzene (cas: 1462-37-9, 1.98 g, 2.5 equiv.) was added to the reaction mixture, which was then allowed to warm to ambient temperature. After 12 hours, analysis by LC-MS indicated completion of the reaction. The reaction mixture was quenched with $H_2O$ (20 mL) and extracted with EtOAc (20 mL×3). The combined organic extracts were concentrated under reduced pressure to give the crude product, which was purified by silica gel chromatography (Petroleum ether:EtOAc=1:4) to provide morpholinone 1-339 as a pale oil (2.3 g, 49% yield). MS (ESI, pos. ion) m/z: 236 (M+1).

Step 2: 4-(2-hydroxyethyl)morpholin-3-one (I-340)

To a solution of 4-(2-(benzyloxy)ethyl)morpholin-3-one, I-339 (2.35 g, 9.79 mmol) in MeOH (10 mL) was added Pd/C (230 mg) quickly under $H_2$(1 atm). The reaction mixture was then stirred at ambient temperature for 48 hours, when analysis by LC-MS showed the reaction was complete. The reaction mixture was filtered and the filtrate was concentrated under reduced pressure to afford the crude product, 1-340 (pale oil, 1.35 g, 93% yield). The crude product was used directly in next step. MS (ESI, pos. ion) m/z: 146 (M+1).

Step 3: 2-(2-(3-oxomorpholino)ethyl)isoindoline-1,3-dione (I-341)

A solution of 4-(2-hydroxyethyl)morpholin-3-one, I-340 (1.37 g, 9.45 mmol), phthalimide (cas: 85-41-6, 1.53 g, 1.1 equiv.) and PPh$_3$ (3.72 g, 1.5 equiv.) in anhydrous THF (30 mL) was stirred at 0° C. for 0.5 hours. Then DIAD (5.73 g, 3.0 equiv.) was added and the reaction mixture was allowed to warm to ambient temperature and stirred for 7 hours. The reaction mixture was concentrated and the residue obtained was purified by silica gel chromatography (Petroleum ether: EtOAc=1:5) to provide I-341 as a pale oil (2.5 g, 50% purity, 50% yield). MS (ESI, pos. ion) m/z: 275 (M+1).

Step 4: 4-(2-aminoethyl)morpholin-3-one (I-342)

A solution of 2-(2-(3-oxomorpholino)ethyl)isoindoline-1,3-dione, I-341 (1.25 g, 4.56 mmol) in MeOH (10 mL) was added hydrazine hydrate (80% aqueous solution, 0.291 g, 1.5 equiv.). The reaction mixture was stirred for 12 hours at ambient temperature, then filtered and the filtrate was then concentrated to give the crude product, I-342 (1 g), which was taken forward to the next step without further purification. MS (ESI, pos. ion) m/z: 145 (M+1).

Step 5: 2-((2-oxo-2-((2-(3-oxomorpholino)ethyl)amino)ethyl)thio) acetic acid (I-343)

A solution of 4-(2-aminoethyl)morpholin-3-one, I-342 (1 g, 6.94 mmol) and thiodiglycolic anhydride (cas: 3261-87-8, 1.09 g, 1.2 equiv.) in 10 mL of DCM was stirred for 2 hours, and then concentrated under reduced pressure to afford a residue, which was purified by preparative HPLC (Mobile Phase:MeCN/H$_2$O (with 0.1% Formic Acid), Gradient: 5-15% MeCN) to obtain I-343 (50 mg, 3% yield) as a pale oil. MS (ESI, pos. ion) m/z: 277 (M+1). $^1$H NMR (400 MHz, DMSO) δ 12.65 (s, 1H), 8.14 (m, 1H), 4.00 (s, 2H), 3.82-3.75 (m, 2H), 3.40-3.34 (m, 6H), 3.24 (m, 2H), 3.18 (s, 2H).
The Synthesis of 1-348 Involved 5 Steps as Depicted in the Following Scheme 120.

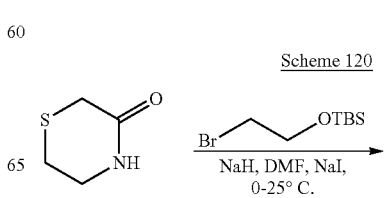

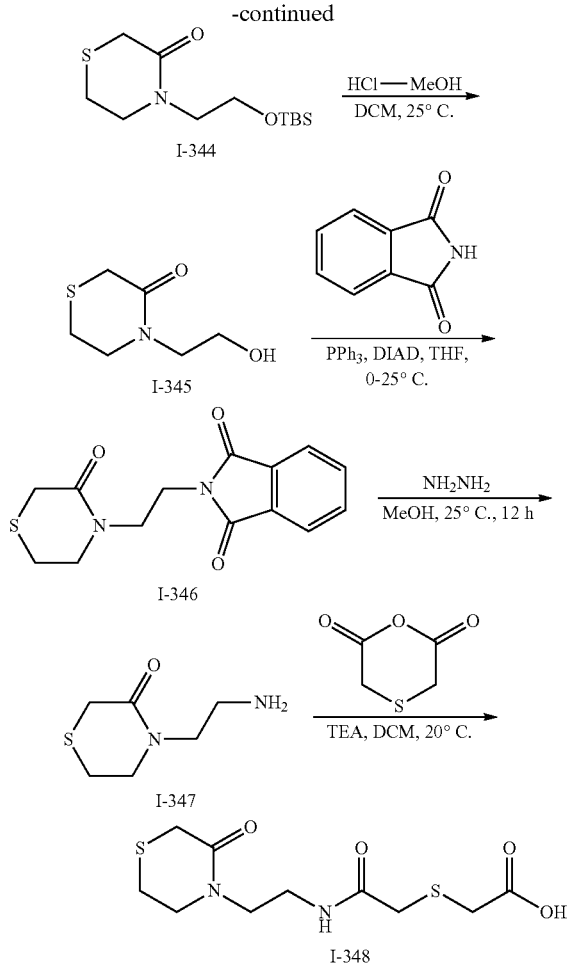

Step 1: 4-(2-((tert-butyldimethylsilyl)oxy)ethyl)thiomorpholin-3-one (I-344)

To a solution of thiomorpholin-3-one (cas: 20196-21-8, 1.17 g, 10 mmol) in anhydrous DMF (10 mL) was added sodium hydride (cas: 7646-69-7, 1.20 g, 30 mmol, 3.0 equiv.) in ice bath under $N_2$. After 30 minutes, (2-bromoethoxy)(tert-butyl)dimethylsilane (cas: 86864-60-0, 3.59 g, 1.5 equiv.) was added to the solution at 0° C. The reaction mixture was allowed to warm to ambient temperature and stirred for 5 hours. Once complete, the reaction was quenched with water (5 mL), extracted with EtOAc (3×500 mL). The combined organic extracts were then washed with water (50 mL), brine (50 mL), and dried with $Na_2SO_4$, then concentrated under reduced pressure to a residue, which was purified by silica gel chromatography to afford I-344 (1.40 g, 54% yield) as a pale yellow oil. MS (ESI, pos. ion) m/z: 276.1 (M+1).

Step 2: 4-(2-hydroxyethyl)thiomorpholin-3-one (I-345)

To a solution of 4-(2-((tert-butyldimethylsilyl)oxy)ethyl)thiomorpholin-3-one, I-344 (1.40 g, 5.09 mmol) in DCM (15 mL) that had been pre-cooled in an ice-water bath was added HCl in MeOH (30% v/v, 10 mL) under $N_2$. The reaction mixture was stirred for 3 hours. Upon completion of the reaction, the resulting solution was concentrated under reduced pressure to a residue. The residue was purified by silica gel chromatography to afford I-345 (0.71 g, 87% yield) as a pale yellow oil. MS (ESI, pos. ion) m/z: 162.1 (M+1).

Step 3: 2-(2-(3-oxothiomorpholino)ethyl)isoindoline-1,3-dione (I-346)

To a solution of 4-(2-hydroxyethyl)thiomorpholin-3-one, I-345 (0.71 g, 4.41 mmol) in anhydrous THF (10 mL) at 0-5° C. was added phthalimide (cas: 85-41-6, 0.72 g, 1.1 equiv.) and $PPh_3$ (1.74 g, 1.5 equiv.) under $N_2$. After 30 minutes, DIAD (2.67 g, 3.0 equiv.) was added. The reaction mixture was allowed to warm to ambient temperature and stirred for 12 hours. Upon completion of the reaction, the reaction mixture was concentrated under reduced pressure to a residue, which was purified by silica gel chromatography to afford imide I-346 (0.90 g, 70% yield, about 50% purity, contaminated with $PPh_3O$) as a white solid. MS (ESI, pos. ion) m/z: 291.1 (M+1).

Step 4: 4-(2-aminoethyl)thiomorpholin-3-one (I-347)

To a solution of 2-(2-(3-oxothiomorpholino)ethyl)isoindoline-1,3-dione, I-346 (0.9 g, 1.24 mmol) in MeOH (10 mL) at 0-5° C. was added $NH_2NH_2$ (85% in $H_2O$, 0.14 g, 1.2 equiv.). The reaction mixture was allowed to warm to ambient temperature and stirred for 12 hours. Upon completion of the reaction, the reaction mixture was concentrated under reduced pressure. The residue obtained was purified by reversed-phase chromatography to afford the amine I-347 as a pale oil (0.41 g, 82% yield, about 40% purity). MS (ESI, pos. ion) m/z: 162.1 (M+1).

Step 5: 2-((2-oxo-2-((2-(3-oxothiomorpholino)ethyl)amino)ethyl)thio) acetic acid (I-348)

A solution of 4-(2-aminoethyl)thiomorpholin-3-one, I-347 (0.41 g, 2.56 mmol) and thiodiglycolic anhydride (cas: 3261-87-8, 0.405 g, 3.07 mmol, 1.2 equiv.) in DCM (5 ml) and DMF (2.0 ml) was stirred for 16 hours at 25° C. Upon completion of the reaction, the mixture was concentrated by vacuum to afford a residue, which was purified by preparative HPLC (Mobile Phase: MeCN/$H_2O$ (0.1% TFA), Gradient: 20-30% MeCN) to obtain 22.8 mg (3% yield) of I-348 as a pale oil. MS (ESI, pos. ion) m/z: 293.1 (M+1). $^1$H NMR (400 MHz, $CDCl_3$): $^1$H NMR (400 MHz, CDCl3): 7.41 (s, 1H), 3.70 (ddd, 4H), 3.55 (d, 2H), 3.39 (d, 4H), 3.28 (s, 2H), 2.93-2.89 (m, 2H).

The Synthesis of I-351 Involved 3 Steps from the Previously Described Intermediate I-346 as Depicted in the Following Scheme 121.

Scheme 121

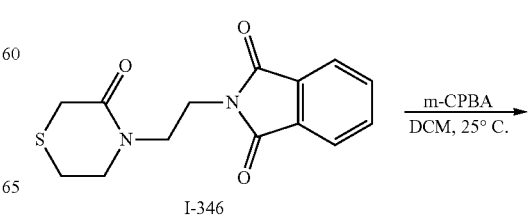

Step 3: 2-((2-oxo-2-((2-(3-oxothiomorpholino)ethyl)amino)ethyl)thio) acetic acid (I-351)

A solution of 4-(2-aminoethyl)thiomorpholin-3-one 1,1-dioxide, I-350 (0.1 g, 0.52 mmol) and thiodiglycolic anhydride (cas: 3261-87-8, 0.082 g, 0.62 mmol, 1.2 equiv.) in DMF (4 mL) was stirred for 3 hours at 25° C. The reaction mixture was then concentrated under reduced pressure to afford a pale oil. The crude product was purified by preparative HPLC (Mobile Phase: MeCN/H$_2$O (0.1% TFA), Gradient: 1-3% MeCN) to afford 63.4 mg (38% yield) of acid I-351 as a pale oil. MS (ESI, pos. ion) m/z: 325.1 (M+1). $^1$H NMR (400 MHz, D$_2$O) δ 4.19 (s, 1H), 3.87 (dd, 1H), 3.59-3.53 (m, 2H), 3.41-3.37 (m, 1H), 3.32 (s, 2H), 3.25 (s, 2H).

The Synthesis of I-356 Involved 5 Steps as Depicted in the Following Scheme 122.

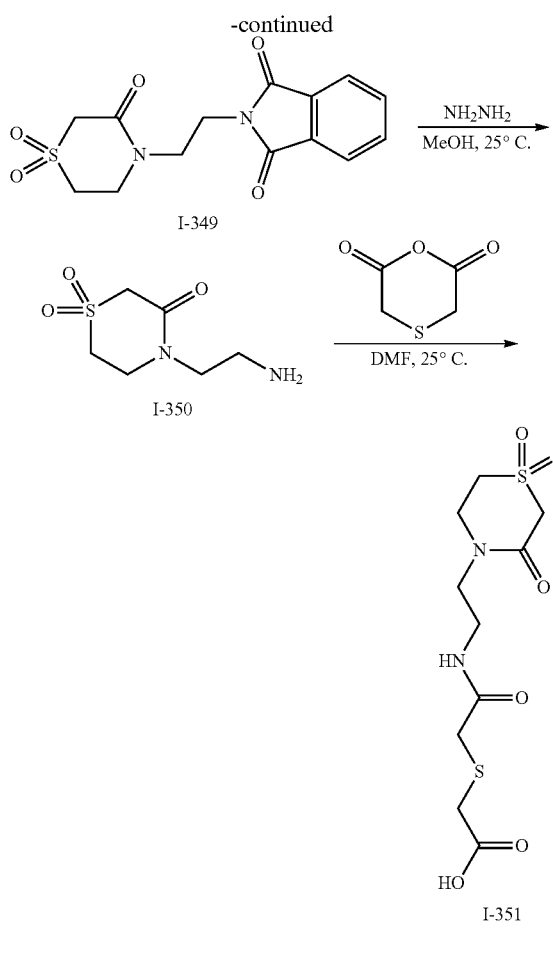

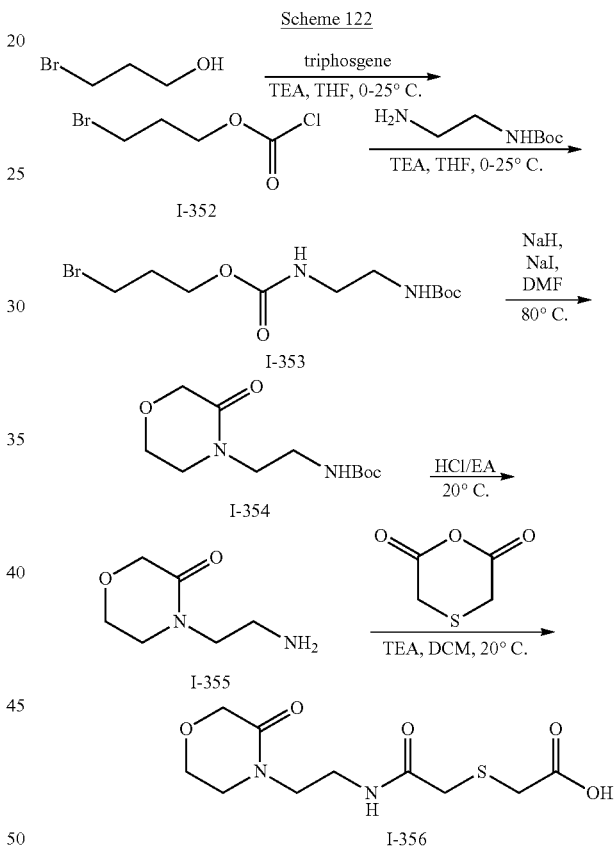

Step 1: 2-(2-(1,1-dioxido-3-oxothiomorpholino)ethyl)isoindoline-1,3-dione (I-349)

To a solution of 2-(2-(3-oxothiomorpholino)ethyl)isoindoline-1,3-dione, I-346 (2.3 g, purity 50%, 7.9 mmol) in DCM (10 mL) at 0-5° C. was added m-chloroperbenzoic acid (4.08 g, 3.0 equiv.). The mixture was allowed to warm to ambient temperature and stirred for 12 hours. Upon completion of the reaction, the reaction mixture was washed with saturated aqueous Na$_2$SO$_3$ (10 ml), saturated aqueous NaHCO$_3$ (10 ml), brine (10 ml), dried, and concentrated under reduced pressure. The residue was purified by silica gel chromatography to afford sulfone I-349 as a white solid (0.3 g, 23% yield, about 80% purity). MS (ESI, pos. ion) m/z: 323.1 (M+1).

Step 2: 4-(2-aminoethyl)thiomorpholin-3-one 1,1-dioxide (I-350)

To a solution of 2-(2-(1, 1-dioxido-3-oxothiomorpholino)ethyl)isoindoline-1,3-dione, I-349 (0.3 g, 0.93 mmol) in MeOH (10 mL) was added hydrazine (85% solution in H$_2$O, 0.042 g, 1.2 equiv.). The reaction mixture was stirred for 12 hours. Upon completion of the reaction, the reaction mixture was concentrated under reduced pressure to a residue, which was purified by reversed-phase chromatography to afford amine I-350 (0.1 g, 56% yield, about 80% purity) as a pale oil. MS (ESI, pos. ion) m/z: 193.1 (M+1).

Step 1: 3-bromopropyl carbonochloridate (I-352)

To a solution of 3-bromopropan-1-ol (cas: 627-18-9, 600 mg, 4.3 mmol) in 15 mL of THF that had been pre-cooled to 0° C. was added TEA (0.9 mL) and a solution of triphosgene (600 mg, 0.5 equiv.) in 5 mL of THF under N$_2$. The reaction mixture was monitored by LC-MS (the reaction aliquot was treated with BnNH$_2$ prior to analysis). After 30 minutes, the reaction mixture was used directly in next step. MS (ESI, pos. ion) m/z: 272.2 (M+1).

Step 2: 3-bromopropyl tert-butyl ethane-1,2-diyldicarbamate (I-353)

To the reaction mixture from previous step, was added tert-butyl (2-aminoethyl)carbamate (1 g, 1.5 equiv.) in one portion. The reaction mixture was stirred at 25° C. for 15 hours. Upon completion of the reaction, the reaction was quenched with water (50 mL), and extracted with EtOAc (3×50 mL). The combined organic extracts were concentrated to a residue, which was purified by silica gel chromatography (Petroleum ether:EtOAc=1:1) to afford 1.2 g (86% yield, 2 steps) of carbamate I-353 as a white solid. MS (ESI, pos. ion) m/z: 347.2 (M+23).

Step 3: tert-butyl (2-(2-oxo-1,3-oxazinan-3-yl)ethyl) carbamate (I-354)

A solution of 3-bromopropyl tert-butyl ethane-1,2-diyldicarbamate, I-353 (1.1 g, 3.4 mmol), NaH (360 mg, 2.5 equiv., 60% dispersion in mineral oil), NaI (350 mg, 1 equiv.) in DMF (60 mL) was heated to 80° C. for 2 hours. On completion, the reaction mixture was quenched with water (30 mL) and extracted with EtOAc (3×30 mL). The combined organic extracts were concentrated to a residue, which was purified by silica gel chromatography (EtOAc), to afford oxazinone I-354 (100 mg, 12%) as a pale oil. MS (ESI, pos. ion) m/z: 267.2 (M+23).

Step 4: 3-(2-aminoethyl)-1,3-oxazinan-2-one (I-355)

A solution of tert-butyl (2-(2-oxo-1,3-oxazinan-3-yl) ethyl)carbamate (100 mg, 0.4 mmol) in HCl (2M in EtOAc, 3 mL) was stirred at 25° C. for 2 hours. Upon completion of the reaction, the reaction mixture was concentrated and purified by preparative HPLC (Mobile Phase: MeCN/H₂O (0.1% TFA) to afford amine I-355 (30 mg, 50% yield) as a pale oil. MS (ESI, pos. ion) m/z: 145.2 (M+1).

Step 5: 2-((2-oxo-2-((2-(2-oxo-1,3-oxazinan-3-yl) ethyl)amino)ethyl)thio) acetic acid (I-356)

To a stirred solution of 3-(2-aminoethyl)-1,3-oxazinan-2-one, I-355 (30 mg, 0.2 mmol) in DCM (2 mL), was added thiodiglycolic anhydride (cas: 3261-87-8, 27 mg, 1 equiv.), TEA (4 drops) at 25° C. The reaction mixture was stirred for 2 hours, and then concentrated and purified by preparative HPLC (Mobile Phase: MeCN/H₂O (0.1% TFA), gradient: 2-8% MeCN) to afford acid I-356 (15 mg, 27%) as a pale oil. MS (ESI, pos. ion) m/z: 277.2 (M+1). ¹H NMR (400 MHz, CDCl₃) δ 7.38 (s, 1H), 4.33-4.28 (m, 2H), 3.63-3.58 (m, 2H), 3.57-3.52 (m, 2H), 3.45 (t, 2H), 3.37 (s, 2H), 3.27 (s, 2H), 2.11-2.07 (m, 2H).

The Synthesis of 1-363 Involved 7 Steps as Depicted in the Following Scheme 123.

Scheme 123 2-((2-((2-(3-methyl-2-oxotetrahydropyrimidin-1(2H)-yl)ethyl)amino)-2-oxoethyl)thio acetic acid (I-363):

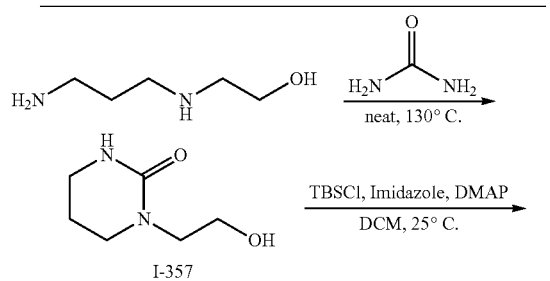

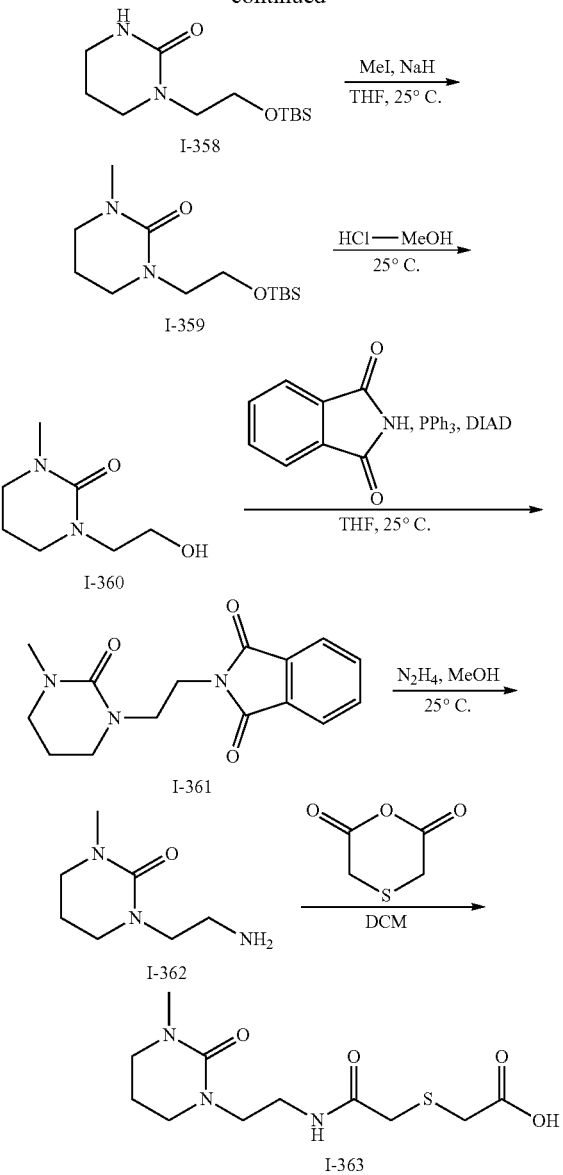

Step 1: 1-(2-hydroxyethyl)tetrahydropyrimidin-2 (1H)-one (I-357)

2-((3-aminopropyl)amino)ethan-1-ol (5.9 g, 50 mmol, cas #: 4461-39-6) and urea (4.5 g, 1.5 equiv., cas #: 57-13-6) in a sealed tube was heated at 130° C. for 10 hours. After reaction completion, the residue was purified by silica gel column chromatography (20% MeOH in dichloromethane) to afford alcohol I-357 (1 g, 14% yield) as a white solid. MS (ESI, pos. ion) m/z: 145.1 (M+1).

Step 2: 1-(2-((tert-butyldimethylsilyl)oxy)ethyl) tetrahydropyrimidin-2(1H)-one (I-358)

To a solution of 1-(2-hydroxyethyl)tetrahydropyrimidin-2(1H)-one, I-357 (2.6 g, 18 mmol), DMAP (220 mg, 0.1 equiv.) and imidazole (2.5 g, 2.0 equiv.) in 30 mL of DCM was added TBSCl (2.7 g, 1.0 equiv.). The reaction mixture was stirred at ambient temperature for 16 hours, then diluted with 50 mL of water and extracted with DCM (30 mL×3). The combined organic extracts were dried over Na$_2$SO$_4$ and concentrated in vacuo to afford 3.1 g (67% yield) of silyl ether I-358 as a pale oil. MS (ESI, pos. ion) m/z: 259.1 (M+1).

Step 3: 1-(2-((tert-butyldimethylsilyl)oxy)ethyl)-3-methyltetrahydropyrimidin-2(1H)-one (I-359)

To a solution of 1-(2-((tert-butyldimethylsilyl)oxy)ethyl) tetrahydropyrimidin-2(1H)-one, I-358 (2.1 g, 8 mmol) and NaH (960 mg, 5.0 equiv.) in THF (30 mL) at 0° C. was added MeI (3.4 g, 3.0 equiv.). The reaction mixture was stirred at ambient temperature for 1 hour, then the solvent was removed in vacuo, and the residue obtained was purified by column chromatography (DCM) to afford silyl ether I-359 (1.1 g, 50% yield) as a white solid. MS (ESI, pos. ion) m/z: 273.1 (M+1).

Step 3: 1-(2-((tert-butyldimethylsilyl)oxy)ethyl)-3-methyltetrahydropyrimidin-2(1H)-one (I-360)

To a solution of 1-(2-((tert-butyldimethylsilyl)oxy)ethyl)-3-methyltetrahydropyrimidin-2(1H)-one, I-359 (1.1 g, 4 mmol) in MeOH (10 mL) at 0-5° C. was added HCl in MeOH (30% v/v, 10 mL) under N$_2$. The reaction mixture was stirred for 0.5 hours, then concentrated under reduced pressure to afford alcohol I-360 (600 mg, 95% yield) as a pale oil, which was used directly for next step. MS (ESI, pos. ion) m/z: 159.1 (M+1).

Step 4: 2-(2-(3-methyl-2-oxotetrahydropyrimidin-1(2H)-yl)ethyl)isoindoline-1,3-dione (I-361)

To a solution of 1-(2-((tert-butyldimethylsilyl)oxy)ethyl)-3-methyltetrahydropyrimidin-2(1H)-one, I-360 (600 mg, 3.8 mmol) in THF (20 mL) at 0-5° C. was added phthalimide (cas: 85-41-6, 592 mg, 1.05 equiv.), PPh$_3$ (1.5 g, 1.5 equiv) under N$_2$. After 30 minutes, DIAD (2.3 g, 3.0 equiv.) was added and the reaction mixture was allowed to warm to ambient temperature and stirred for 6 hours. The reaction was then quenched with water (5 mL), and extracted with DCM (3×20 mL). The combined organic extracts were washed with water (20 mL), brine (20 mL), and dried with Na$_2$SO$_4$, then concentrated under reduced pressure. The residue obtained was purified by column chromatography (50% EtOAc in Petroleum Ether) to afford phthalimide I-361 (280 mg, 26% yield) as a yellow solid. MS (ESI, pos. ion) m/z: 288.1 (M+1).

Step 5: 1-(2-aminoethyl)-3-methyltetrahydropyrimidin-2(1H)-one (I-362)

To a solution of 2-(2-(3-methyl-2-oxotetrahydropyrimidin-1(2H)-yl)ethyl)isoindoline-1,3-dione, I-361 (280 mg, 0.98 mmol) in MeOH (5 mL) at 0-5° C. was added NH$_2$NH$_2$ (85% solution in H$_2$O, 200 mg, 5.6 equiv.). The reaction mixture was allowed to warm to ambient temperature and stirred for 12 hours. The slurry was then filtered, and the filtrate was concentrated to afford the crude amine I-362 (0.2 g) as a pale oil, which was taken forward to the next step. MS (ESI, pos. ion) m/z: 158.1 (M+1).

Step 6: 2-((2-oxo-2-((2-(2-oxotetrahydropyrimidin-1(2H)-yl)ethyl)amino)ethyl)thio) acetic acid (I-363)

A solution of 1-(2-aminoethyl)-3-methyltetrahydropyrimidin-2(1H)-one, I-362 (200 mg, 1.27 mmol) and thio-diglycolic anhydride (cas: 3261-87-8, 300 mg, 1.8 equiv.) in 5 mL DCM was stirred for 2 hours, and then concentrated in vacuo to afford the crude product as a pale oil. Purification by preparative HPLC (Mobile Phase: MeCN/H$_2$O (with 0.1% Formic Acid) Gradient: 5-15% MeCN) afforded I-363 (50 mg, 14% yield) as a white solid. MS (ESI, pos. ion) m/z: 290.1 (M+1). $^1$H NMR (400 MHz, CDCl$_3$) δ 7.47 (s, 1H), 3.59-3.56 (m, 2H), 3.5-3.42 (m, 2H), 3.36 (s, 2H), 3.36-3.31 (m, 2H), 3.31-3.26 (m, 2H), 3.20 (s, 2H), 2.94 (s, 3H), 2.01-1.96 (m, 2H).

The Synthesis of I-366 Involved 3 Steps from Previously Described Intermediate I-357 as Depicted in the Following Scheme 124.

Scheme 124
2-((2-oxo-2-((2-(2-oxotetrahydropyrimidin-1(2H)-yl)ethyl)amino)ethyl)thio)acetic acid (I-366)

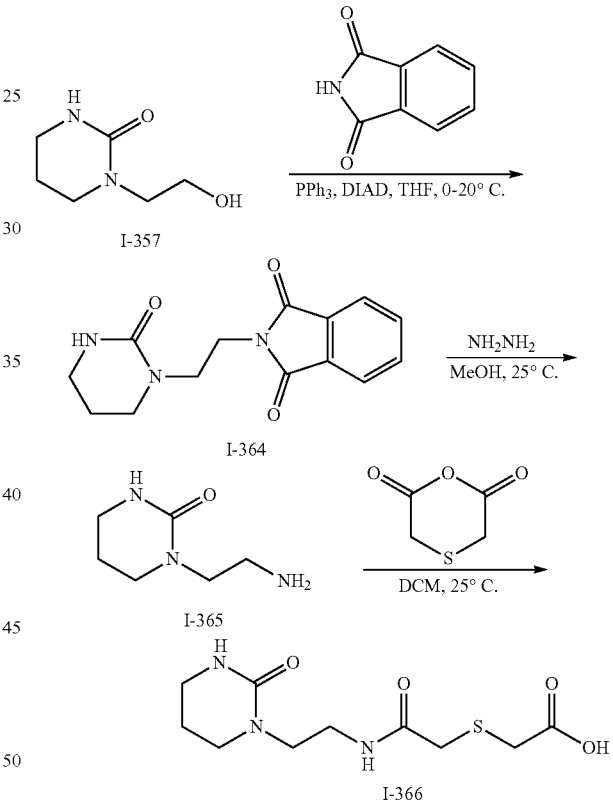

Step 1: 2-(2-(2-oxotetrahydropyrimidin-1(2H)-yl)ethyl)isoindoline-1,3-dione (I-364)

To a solution of 1-(2-hydroxyethyl)tetrahydropyrimidin-2(1H)-one, I-357 (1 g, 6.9 mmol) in THF (30 mL) at 0-5° C. was added phthalimide (cas: 85-41-6, 1 g, 1.05 equiv.) and PPh$_3$ (2.7 g, 1.5 equiv.). After 30 minutes, DIAD (4.2 g, 3.0 equiv.) was added and the reaction mixture was allowed to warm to ambient temperature and stirred for 6 hours. The reaction was then quenched with water (5 mL), extracted with DCM (3×20 mL). The combined organic extracts were washed with water (20 mL), brine (20 mL), and dried with Na$_2$SO$_4$, then concentrated under reduced pressure. The residue obtained was purified by silica gel column chromatography (50% EtOAc in Petroleum Ether) to afford 800 mg (43% yield) of phthalimide I-364 as a yellow solid. MS (ESI, pos. ion) m/z: 274.1 (M+1).

Step 2: 1-(2-aminoethyl)-3-methylpyrrolidin-2-one (I-365)

To a solution of 2-(2-(2-oxotetrahydropyrimidin-1(2H)-yl)ethyl)isoindoline-1,3-dione, I-364 (0.2 g, 0.7 mmol) in MeOH (5 mL) at 0-5° C. was added $NH_2NH_2$ (85% in $H_2O$, 200 mg, 5.5 mmol). The reaction mixture was allowed to warm to ambient temperature and stirred for 7 hours, then filtered, and the filtrate was concentrated to afford crude amine I-365 (0.12 g) as a pale oil. The crude product was used directly for the next step. MS (ESI, pos. ion) m/z: 145.1 (M+1).

Step 3: 2-((2-oxo-2-((2-(2-oxotetrahydropyrimidin-1 (2H)-yl)ethyl)amino)ethyl)thio) acetic acid (I-366)

A solution of 1-(2-aminoethyl)-3-methylpyrrolidin-2-one, I-365 (120 mg, 0.83 mmol) and thiodiglycolic anhydride (cas: 3261-87-8, 167 mg, 1.5 equiv.) in 5 mL of DCM was stirred for 2 hours, and then concentrated in vacuo to give the crude product as a pale oil. The crude product was purified by preparative HPLC (Mobile Phase: MeCN/$H_2O$ (0.1% TFA), gradient: 5-15% MeCN) to afford 80 mg (35% yield) of I-366 as a white solid. MS (ESI, pos. ion) m/z: 276.2 (M+1). $^1$H NMR (400 MHz, $CDCl_3$) δ 7.54 (s, 1H), 6.71 (s, 1H), 3.59-3.52 (m, 2H), 3.51 (d, J=5.1 Hz, 2H), 3.42-3.36 (m, 3H), 3.34-3.29 (m, 3H), 1.99 (s, 2H), 1.25 (s, 2H).

The Synthesis of Compound I-373 Involved 8 Steps as Depicted in the Following Scheme 125.

Scheme 125

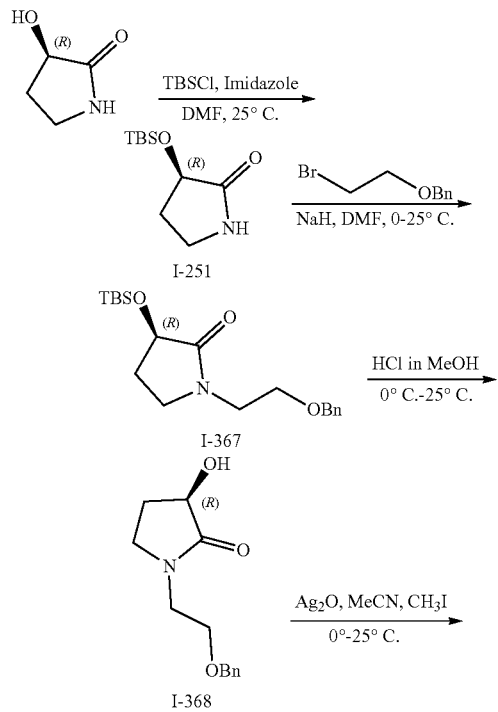

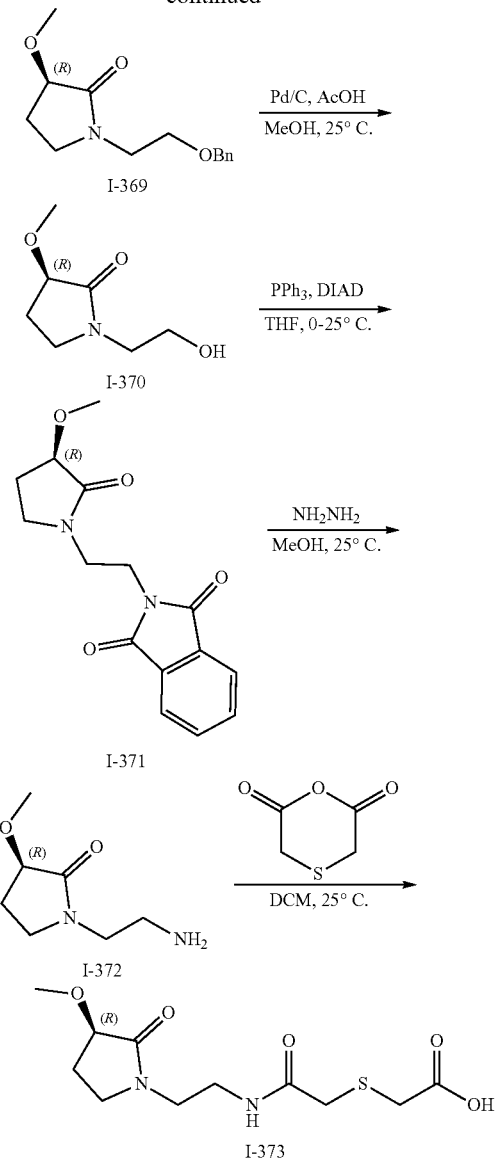

The chemical structure of the target compound was confirmed by $^1$H NMR and LC-MS with the purity >95% (HPLC 214 & 254 nm).

Step 1: (R)-1-(2-(benzyloxy)ethyl)-3-((tert-butyldimethylsilyl)oxy)pyrrolidin-2-one (I-367)

To a solution of (R)-3-((tert-butyldimethylsilyl)oxy)pyrrolidin-2-one, I-251 (8 g, 37.2 mmol) in anhydrous DMF (80 mL) at 0-5° C. was added NaH (60% dispersion in mineral oil, 3.72 g, 2.5 equiv.) under $N_2$. The reaction mixture was stirred for 30 minutes at at 0-5° C. and ((2-bromoethoxy) methyl)benzene (cas: 1462-37-9, 11.9 g, 1.5 equiv.) was added. The reaction mixture was allowed to warm to ambient temperature. After 12 hours, LC-MS indicated that the reaction was complete. $H_2O$ (20 mL) was added and the reaction mixture was extracted with EtOAc (20 mL×3). The combined organic extracts were concentrated under reduced pressure and the crude product was purified by silica gel chromatography (Petroleum ether:EtOAc=1:1) to provide I-367 (5 g, 39% yield) as a pale oil. MS (ESI, pos. ion) m/z: 350 (M+1).

Step 2: (R)-1-(2-(benzyloxy)ethyl)-3-hydroxypyrrolidin-2-one (I-368)

To a solution of (R)-1-(2-(benzyloxy)ethyl)-3-((tert-butyldimethylsilyl)oxy)pyrrolidin-2-one, I-367 (5 g, 14.32 mmol) was added HCl in MeOH (30% v/v, 30 mL) and the reaction mixture was stirred at 0-5° C. for 0.5 hours. Once LC-MS analysis indicated reaction completion, the reaction mixture was concentrated and the crude product was purified by silica gel chromatography (Petroleum ether:EtOAc=1:10) to afford I-368 (2.36 g, 70% yield) as a pale oil. MS (ESI, pos. ion) m/z: 236 (M+1).

Step 3: (R)-1-(2-(benzyloxy)ethyl)-3-methoxypyrrolidin-2-one (I-369)

To a solution of (R)-1-(2-(benzyloxy)ethyl)-3-hydroxypyrrolidin-2-one, I-368 (2.36 g, 10.0 mmol) in anhydrous MeCN (30 ml) at 0-5° C. was added Ag$_2$O (4.65 g, 2.0 equiv.) under N$_2$. The reaction mixture was then stirred for 5 minutes and CH$_3$I (1.28 g, 0.9 equiv.) was added. The reaction mixture was was allowed to warm to ambient temperature and stirred for 10 hours. When LC-MS analysis indicated that the reaction was complete, the reaction mixture was filtered and the filtrate was concentrated under reduced pressure to afford the crude product, which was purified by silica gel chromatography (Petroleum ether:EtOAc=1:1) to provide I-369 (1.7 g, 68%) as a pale oil. MS (ESI, pos. ion) m/z: 250 (M+1).

Step 4: (R)-1-(2-hydroxyethyl)-3-methoxypyrrolidin-2-one (I-370)

To a solution of (R)-1-(2-(benzyloxy)ethyl)-3-methoxypyrrolidin-2-one, I-369 (1.7 g, 6.82 mmol) in MeOH (10 mL) was added Pd/C (170 mg) quickly under H$_2$ (1 atm). The reaction mixture was then stirred at ambient temperature for 48 hours. When LC-MS analysis indicated that the reaction was complete, the reaction mixture was filtered, and the filtrate was concentrated under reduced pressure to a residue. The crude product was purified by silica gel chromatography (Petroleum ether:EtOAc=1:10) to provide I-370 (0.15 g, 14% yield) as a pale oil. MS (ESI, pos. ion) m/z: 160 (M+1).

Step 5: (R)-2-(2-(3-methoxy-2-oxopyrrolidin-1-yl)ethyl)isoindoline-1,3-dione (I-371)

A solution of (R)-1-(2-hydroxyethyl)-3-methoxypyrrolidin-2-one, I-370 (0.15 g, 0.94 mmol), phthalimide (cas: 85-41-6, 0.148 g, 1.1 equiv.) and PPh$_3$ (0.369 g, 1.5 equiv.) in anhydrous THF (3 mL) was stirred at 0-5° C. for 0.5 hours. Then DIAD (0.569 g, 3.0 equiv.) was added and the reaction mixture was allowed to warm to ambient temperature and stirred for 7 hours. The reaction mixture was then concentrated to afford the crude product, which was purified by silica gel chromatography (Petroleum ether:EtOAc=1:10) to provide I-371 (0.5 g, 50% purity, 50% yield) as a pale oil. MS (ESI, pos. ion) m/z: 275 (M+1).

Step 6: (R)-1-(2-aminoethyl)-3-methoxypyrrolidin-2-one (I-372)

To a solution of (R)-2-(2-(3-methoxy-2-oxopyrrolidin-1-yl)ethyl)isoindoline-1,3-dione, I-371 (0.5 g, 1.74 mmol) in MeOH (5 mL) was added hydrazine hydrate (80% solution, 0.130 g, 1.5 equiv.). The reaction mixture was stirred for 12 hours at ambient temperature, then filtered. The filtrate was concentrated and the crude product, I-372 (0.5 g) was used directly in the next step. MS (ESI, pos. ion) m/z: 159 (M+1).

Step 7: (R)-2-((2-((2-(3-methoxy-2-oxopyrrolidin-1-yl)ethyl)amino)-2-oxoethyl)thio) acetic acid (I-373)

To a solution of (R)-1-(2-aminoethyl)-3-methoxypyrrolidin-2-one, I-372 (0.5 g, 3.3 mmol) and thiodiglycolic anhydride (cas: 3261-87-8, 0.653 g, 1.5 equiv.) in 5 mL of DCM was added TEA (0.066 g, 0.2 equiv.). The reaction mixture was stirred for 2 hours, and then concentrated under reduced pressure to give the crude product, which was purified by preparative HPLC (Mobile Phase: MeCN/H$_2$O (0.1% TFA), Gradient: 5-15% MeCN) to afford I-373 (50 mg, 5% yield) as a pale oil. MS (ESI, pos. ion) m/z: 291.1 (M+1). $^1$H NMR (400 MHz, DMSO) δ 12.68 (s, 1H), 8.10 (s, 1H), 3.88 (s, 1H), 3.38 (s, 3H), 3.35 (s, 2H), 3.33-3.26 (m, 3H), 3.19 (m, 5H), 2.32-2.20 (m, 1H), 1.76 (m, 1H).

The Synthesis of Compound I-380 Involved 8 Steps as Depicted in the Following Scheme 126.

Scheme 126 (S)-2-((2-((2-(3-methoxy-2-oxopyrrolidin-1-yl)ethyl)amino)-2-oxoethyl)thio)acetic acid (I-380)

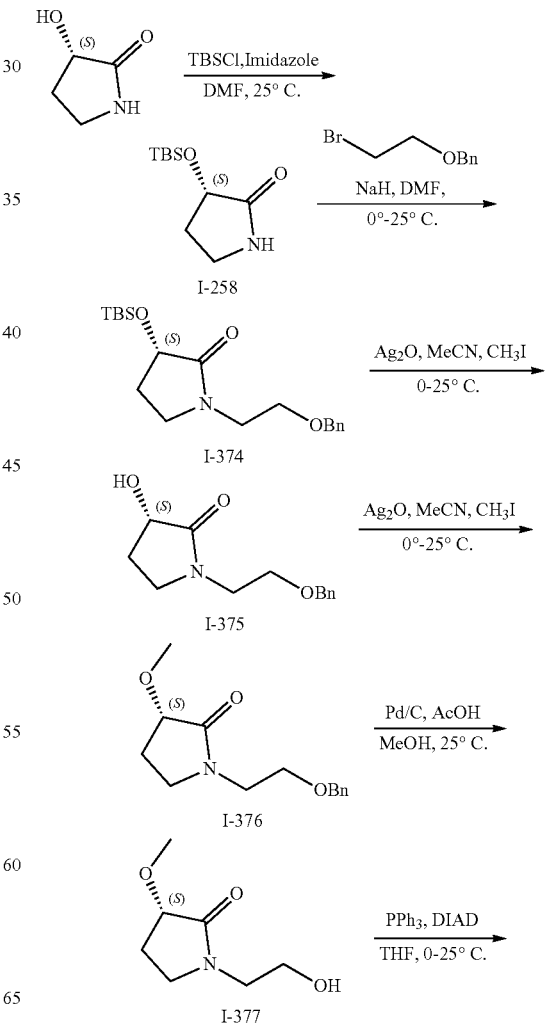

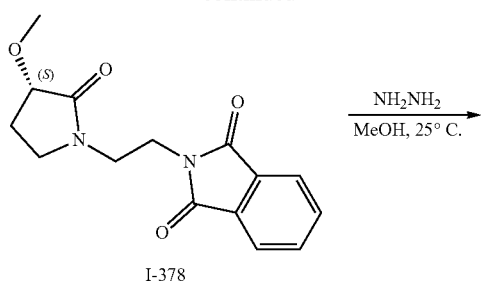

I-378

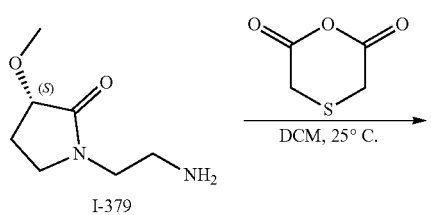

I-379

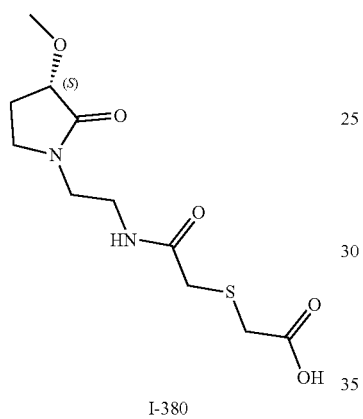

I-380

The synthetic route for I-380 is similar to that of I-373 and commenced with (S)-3-hydroxypyrrolidin-2-one (cas: 34368-52-0). Carboxylic acid I-380 (pale oil, 50 mg, 3% yield) was isolated by preparative HPLC (Mobile Phase: MeCN/H$_2$O (with 0.1% TFA), Gradient: 5-15% MeCN). MS (ESI, pos. ion) m/z: 291.1 (M+1). $^1$H NMR (400 MHz, DMSO) δ 8.11 (s, 1H), 3.89 (m, 1H), 3.38 (s, 3H), 3.35 (s, 2H), 3.33-3.25 (m, 3H), 3.25-3.14 (m, 5H), 2.31-2.21 (m, 1H), 1.82-1.70 (m, 1H).

The Synthesis of I-386 Involved 6 Steps from Previously Described Intermediate I-259 as Depicted in the Following Scheme 127.

Scheme 127

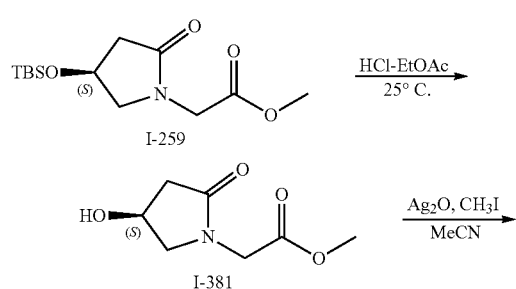

I-382

I-383

I-384

I-385

I-386

Step 1: Methyl (S)-2-(4-hydroxy-2-oxopyrrolidin-1-yl)acetate (I-381)

To a solution of methyl (S)-2-(4-((tert-butyldimethylsilyl)oxy)-2-oxopyrrolidin-1-yl)acetate, I-259 (2.1 g, 7.32 mmol) in MeOH (15 mL) at 0-5° C. was added HCl in EtOAc (2M, 15 mL) under N$_2$. The reaction mixture was allowed to warm to ambient temperature and stirred for 4 hours. After reaction completion, ammonium hydroxide (ca. 0.2 mL) was added to adjust the pH to 7, and then the reaction mixture was concentrated under reduced pressure. The residue obtained was purified by silica gel chromatography to afford ester I-381 (1.3 g, 102% yield) as a pale oil. MS (ESI, pos. ion) m/z: 174.1 (M+1).

Step 2: Methyl (S)-2-(4-methoxy-2-oxopyrrolidin-1-yl)acetate (I-382)

To a solution of methyl (S)-2-(4-hydroxy-2-oxopyrrolidin-1-yl)acetate, I-381 (1.3 g, 7.51 mmol) in acetonitrile (15 ml) at 0-5° C. was added silver oxide (cas: 260667-12-3, 2.62 g, 1.5 equiv.) and iodomethane (0.96 g, 0.9 equiv.) under N$_2$. The reaction mixture was allowed to warm to ambient temperature and stirred for 12 hours. Upon completion of the reaction, the reaction mixture was filtered through celite. The filtrate was concentrated under reduced pressure and the residue obtained was purified by silica gel chromatography to afford ester I-382 (0.48 g, 35% yield) as a pale oil. MS (ESI, pos. ion) m/z: 184.1 (M+1).

Step 3: (S)-1-(2-hydroxyethyl)-4-methoxypyrrolidin-2-one (I-383)

To a solution of methyl (S)-2-(4-methoxy-2-oxopyrrolidin-1-yl)acetate, I-382 (0.25 g, 1.50 mmol) in t-BuOH (10 mL) was added sodium borohydride (0.228 g, 4.0 equiv.) in MeOH (0.5 mL) under $N_2$. The reaction mixture was stirred for 0.5 hours at 85° C. Upon completion of the reaction, the reaction mixture was concentrated under reduced pressure. The residue afforded was quenched with water (2 mL), and extracted with DCM (3×20 mL). The combined organic extracts were then washed with water (20 mL), brine (20 mL), and dried with $Na_2SO_4$, then concentrated and the residue obtained was purified by silica gel chromatography to afford alcohol I-383 (0.11 g, 46% yield) as a pale oil. MS (ESI, pos. ion) m/z: 160.1 (M+1).

Step 4: (S)-2-(2-(4-methoxy-2-oxopyrrolidin-1-yl)ethyl)isoindoline-1,3-dione (I-384)

To a solution of (S)-1-(2-hydroxyethyl)-4-methoxypyrrolidin-2-one, I-383 (0.31 g, 1.95 mmol) in THF (5 mL) was added phthalimide (0.32 g, 1.1 equiv.), and $PPh_3$ (0.77 g, 1.5 equiv.). The reaction mixture was stirred for 0.5 h at 0-5° C. under $N_2$ and DIAD (1.18 g, 3.0 equiv.) was added. The reaction mixture was allowed to warm to ambient temperature and stirred at ambient temperature for 12 hours, then concentrated under reduced pressure. The residue obtained was purified by silica gel chromatography to afford phthalimide I-384 as a yellow oil (0.40 g, 71% yield). MS (ESI, pos. ion) m/z: 289.1 (M+1).

Step 5: (S)-1-(2-aminoethyl)-4-methoxypyrrolidin-2-one (I-385)

To a solution of (S)-2-(2-(4-methoxy-2-oxopyrrolidin-1-yl)ethyl)isoindoline-1,3-dione, I-384 (0.40 g, 1.39 mmol) in MeOH (10 mL) at 05° C. was added hydrazine (85% in $H_2O$, 0.06 g, 1.2 equiv.). The reaction mixture was allowed to warm to ambient temperature and stirred for 12 hours, then concentrated under reduced pressure. DCM (10 ml) was added to the residue and the slurry was filtered. The filtrate was concentrated to afford the crude amine I-385 as a pale oil, 0.18 g, 82% yield), which was used directly in the next step. MS (ESI, pos. ion) m/z: 159.1 (M+1).

Step 6: (S)-2-((2-((2-(4-methoxy-2-oxopyrrolidin-1-yl)ethyl)amino)-2-oxoethyl)thio) acetic acid (I-386)

A solution of (S)-1-(2-aminoethyl)-4-methoxypyrrolidin-2-one, I-385 (0.18 g, 1.13 mmol) and thiodiglycolic anhydride (0.19 g, 1.3 equiv.) in DMF (5 mL) was stirred for 2 hours at 25° C., then concentrated under reduced pressure to give the crude product as a pale oil. The crude product was purified by preparative HPLC (Mobile Phase: $MeCN/H_2O$ (0.1% TFA), Gradient: 1-3% MeCN) to afford 137 mg (42% yield) of I-386 as a pale oil. MS (ESI, pos. ion) m/z: 291.1 (M+1). $^1H$ NMR (400 MHz, $CDCl_3$) δ 7.56 (s, 1H), 4.06 (t, 1H), 3.82 (dd, 1H), 3.68-3.59 (m, 2H), 3.46-3.36 (m, 5H), 3.32 (s, 3H), 3.27 (s, 2H), 2.72 (dd, 6.7 Hz, 1H), 2.53 (dd, 1.6 Hz, 1H).

The Synthesis of I-392 Involved 6 Steps from Previously Described Intermediate I-252 as Depicted in the Following Scheme 128.

Scheme 128

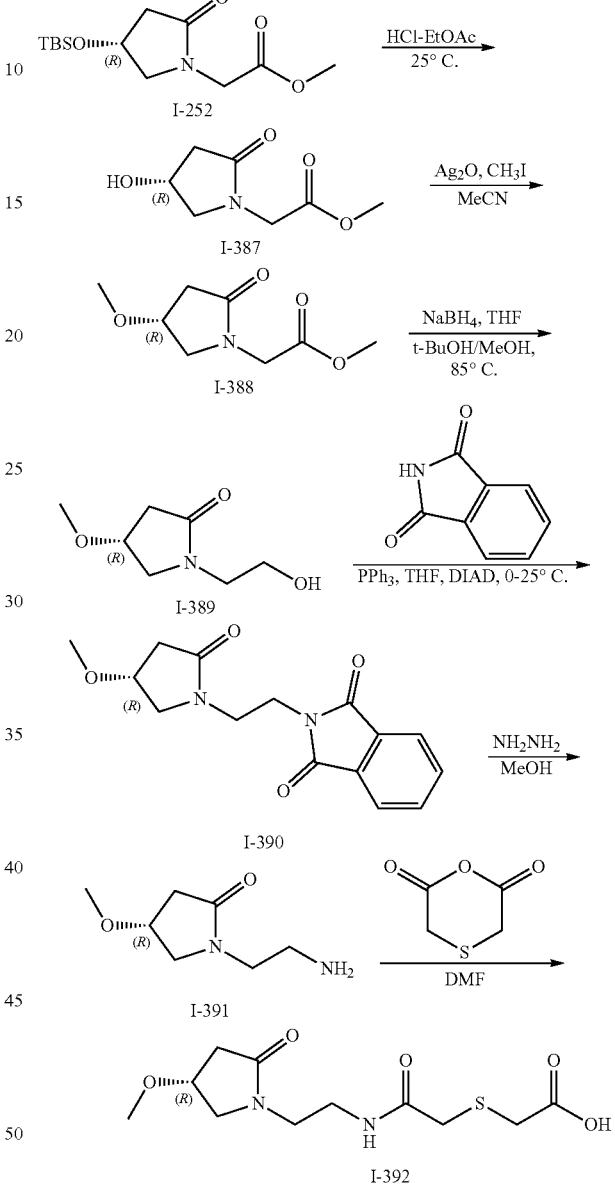

Step 1: Methyl (R)-2-(4-hydroxy-2-oxopyrrolidin-1-yl)acetate (I-387)

To a solution of methyl (R)-2-(4-((tert-butyldimethylsilyl)oxy)-2-oxopyrrolidin-1-yl)acetate, 1-252 (3.7 g, 12.89 mmol) in MeOH (20 mL) at 0-5° C. was added HCl in EtOAc (2M, 20 mL) under $N_2$. The reaction mixture was stirred for 4 hours. Upon completion of the reaction, ammonium hydroxide (about 0.4 ml) was added to adjust pH 7, and then the reaction mixture was concentrated under reduced pressure. The residue obtained was purified by silica gel chromatography to afford alcohol 1-387 as a pale oil (2.1 g, 94% yield). MS (ESI, pos. ion) m/z: 174.1 (M+1).

Step 2: Methyl (R)-2-(4-methoxy-2-oxopyrrolidin-1-yl)acetate (I-388)

To a solution of methyl (R)-2-(4-hydroxy-2-oxopyrrolidin-1-yl)acetate, 1-387 (2.1 g, 12.14 mmol) in acetonitrile (20 ml) at 0-5° C. was added silver oxide (4.22 g, 1.5 equiv.) and iodomethane (1.55 g, 0.9 equiv.) under $N_2$. The reaction mixture was allowed to warm to ambient temperature and stirred for 12 hours, then filtered through celite. The filtrate was concentrated under reduced pressure. The residue obtained was purified by silica gel chromatography to afford ester 1-388 as a pale oil (0.83 g, 37% yield). MS (ESI, pos. ion) m/z: 184.1 (M+1).

Step 3: (R)-1-(2-hydroxyethyl)-4-methoxypyrrolidin-2-one (I-389)

To a solution of methyl (R)-2-(4-methoxy-2-oxopyrrolidin-1-yl)acetate, I-388 (1.2 g, 6.42 mmol) in t-BuOH (10 mL) was added sodium borohydride (0.73 g, 3.0 equiv.) under $N_2$. The reaction mixture was stirred for 0.5 hours at 80° C., then cooled and concentrated under reduced pressure. The residue was quenched with water (2 mL) and extracted with DCM (3×20 mL). The combined organic extracts were then washed with water (20 mL), brine (20 mL), and dried with $Na_2SO_4$, then concentrated and the residue obtained was purified by silica gel chromatography to afford alcohol I-389 as a pale oil (0.52 g, 51% yield). MS (ESI, pos. ion) m/z: 160.1 (M+1).

Step 4: (R)-2-(2-(4-methoxy-2-oxopyrrolidin-1-yl)ethyl)isoindoline-1,3-dione (I-390)

To a solution of (R)-1-(2-hydroxyethyl)-4-methoxypyrrolidin-2-one, I-389 (0.58 g, 3.64 mmol) in THF (6 mL) was added phthalimide (0.59 g, 1.1 equiv.) and $PPh_3$ (1.43 g, 1.5 equiv.). The reaction mixture was stirred for 0.5 hours in an ice-water bath under $N_2$. Then DIAD (2.21 g, 3.0 equiv.) was added and the reaction mixture was allowed to warm to ambient temperature and stirred for 12 hours, then concentrated under reduced pressure. The residue obtained was purified by silica gel chromatography to afford phthalimide I-390 as a yellow oil (0.45 g, 43% yield). MS (ESI, pos. ion) m/z: 289.1 (M+1).

Step 5: (R)-1-(2-aminoethyl)-4-methoxypyrrolidin-2-one (I-391)

To a solution of (S)-2-(2-(4-methoxy-2-oxopyrrolidin-1-yl)ethyl)isoindoline-1,3-dione, I-390 (0.45 g, 1.56 mmol) in MeOH (10 mL) at 05° C. was added hydrazine (85% in $H_2O$, 0.07 g, 1.87 mmol, 1.2 equiv.). The reaction mixture was allowed to warm to ambient temperature and stirred for 12 hours, then concentrated. The residue was diluted in DCM (10 mL) and the slurry was filtered. The filtrate was concentrated to afford the crude amine I-391 as a pale oil (0.21 g, 85% yield, 85% purity), which was used directly in the next step. MS (ESI, pos. ion) m/z: 159.1 (M+1).

Step 6: (R)-2-((2-((2-(4-methoxy-2-oxopyrrolidin-1-yl)ethyl)amino)-2-oxoethyl)thio) acetic acid (I-392)

A solution of (R)-1-(2-aminoethyl)-4-methoxypyrrolidin-2-one, I-391 (0.21 g, 1.33 mmol) and thiodiglycolic anhydride (0.23 g, 1.3 equiv.) in DMF (5 mL) was stirred for 2 hours at 25° C., then the reaction mixture was concentrated under reduced pressure and the crude product was purified by preparative HPLC (Mobile Phase: MeCN/$H_2O$ (0.1% TFA), Gradient: 1-3% MeCN) to give 117.5 mg (41% yield) of acid I-392 as a pale oil. MS (ESI, pos. ion) m/z: 291.1 (M+1). $^1$H NMR (400 MHz, $CDCl_3$) δ 7.52 (s, 1H), 4.04 (t, 1H), 3.78 (dd, 1H), 3.63-3.55 (m, 2H), 3.42-3.32 (m, 5H), 3.30 (s, 3H), 3.27 (s, 2H), 2.67 (dd, 1H), 2.47 (dd, 1H).

The Synthesis of Compounds (S*)-I-395 and (R*)-I-395 Involved 4 Steps as Depicted in Scheme 129.

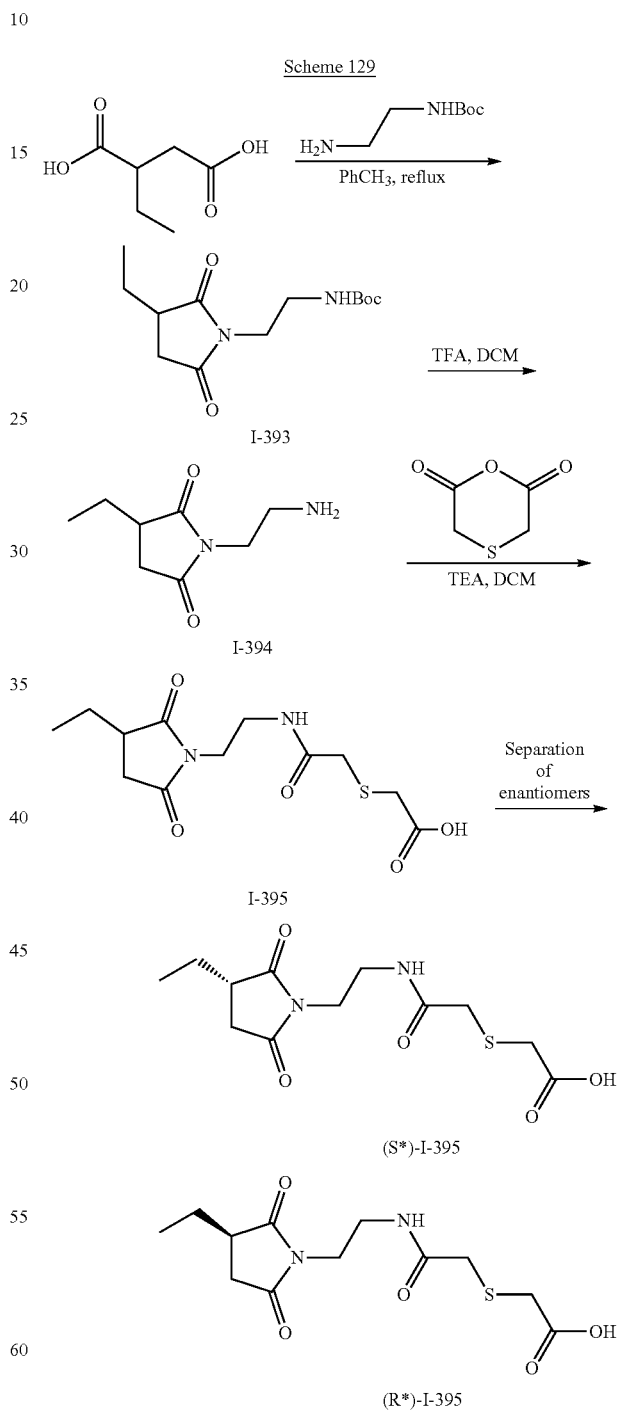

The chemical structure of the target compound was confirmed by $^1$H NMR and LC-MS with the purity >95% (HPLC 214 & 254 nm).

Step 1: Tert-butyl (2-(3-ethyl-2,5-dioxopyrrolidin-1-yl)ethyl)carbamate (I-393)

A solution of 2-ethylsuccinic acid (cas: 636-48-6, 0.2 g, 1.37 mmol) and tert-butyl (2-aminoethyl)carbamate (0.26 g, 1.2 equiv.) in 5 mL of PhCH₃ was heated to reflux for 7 hours. After LC-MS analysis indicated that the reaction was complete, the reaction mixture was concentrated under reduced pressure to give the crude product, which was purified by preparative TLC (EtOAc:Petroleum ether-2:1) to afford imide I-393 (0.15 g, 41% yield) a pale oil. MS (ESI, pos. ion) m/z: 293 (M+Na).

Step 2: 1-(2-aminoethyl)-3-ethylpyrrolidine-2,5-dione (I-394)

A solution of tert-butyl (2-(3-ethyl-2,5-dioxopyrrolidin-1-yl)ethyl)carbamate, I-393 (250 mg, 0.93 mmol) in TFA/DCM (1:3 v/v, 8 mL) was stirred at 25° C. for 1 hour. When LC-MS analysis indicated that the reaction was complete, the reaction mixture was concentrated under reduced pressure to give 1-(2-aminoethyl)-3-ethylpyrrolidine-2,5-dione, I-394 (500 mg) as a pale oil, which was used directly for next step. MS (ESI, pos. ion) m/z: 171 (M+1).

Step 3: 2-((2-((2-(3-ethyl-2,5-dioxopyrrolidin-1-yl)ethyl)amino)-2-oxoethyl)thio) acetic acid (I-395)

To a solution of (S)-1-(2-aminoethyl)-3-hydroxypyrrolidine-2, 5-dione, I-394 (500 mg, 1.77 mmol) and thiodiglycolic anhydride (257 mg, 1.1 equiv.) in 5 mL DCM was added TEA (257 mg, 1.1 equiv.). The reaction mixture was stirred for 2 hours and was concentrated in vacuo to give the crude product. The crude product was purified by preparative HPLC (Mobile Phase: MeCN/H₂O (0.1% formic acid)) to afford the racemic carboxylic acid I-395 as a pale oil (220 mg, 41% yield). MS (ESI, pos. ion) m/z: 303.1 (M+1).

(S)-2-((2-((2-(3-ethyl-2,5-dioxopyrrolidin-1-yl)ethyl)amino)-2-oxoethyl)thio) acetic acid ((S*)-I-395)

(S*)-I-395 (pale oil, 80 mg, 36% yield) was isolated by chiral separation (Superchiral S-AD (Chiralway), 2 cm I.D.*25 cm Length, 5 um, CO₂/EtOH=70/30 (v/v)) from racemic acid I-395. MS (ESI, pos. ion) m/z: 303.1 (M+1). ¹H NMR (400 MHz, CDCl₃) δ 7.22 (s, 1H), 3.74-3.61 (m, 2H), 3.58-3.45 (m, 2H), 3.33 (m, 4H), 2.93-2.72 (m, 2H), 2.40 (m, 1H), 1.99-1.86 (m, 1H), 1.65-1.53 (m, 1H), 0.99 (m, 3H).

(R)-2-((2-((2-(3-ethyl-2,5-dioxopyrrolidin-1-yl)ethyl)amino)-2-oxoethyl)thio) acetic acid ((R*)-I-395)

(R*)-I-395 (pale oil, 80 mg, 36% yield) is isolated by chiral separation (Superchiral S-AD (Chiralway), 2 cm I.D.*25 cm Length, 5 um, CO₂/EtOH=70/30 (v/v)) from racemic acid I-395. MS (ESI, pos. ion) m/z: 303.1 (M+1). ¹H NMR (400 MHz, CDCl₃) δ 7.48 (s, 1H), 3.66 (m, 2H), 3.47 (m, 2H), 3.31 (s, 4H), 2.94-2.67 (m, 2H), 2.37 (m, 1H), 1.88 (m, 1H), 1.56 (m, 1H), 0.95 (m 3H).

The Synthesis of Compound I-398 Involved 3 Steps as Depicted in Scheme 130. I-399, the Enantiomer of I-398, was Made Using a Similar Route.

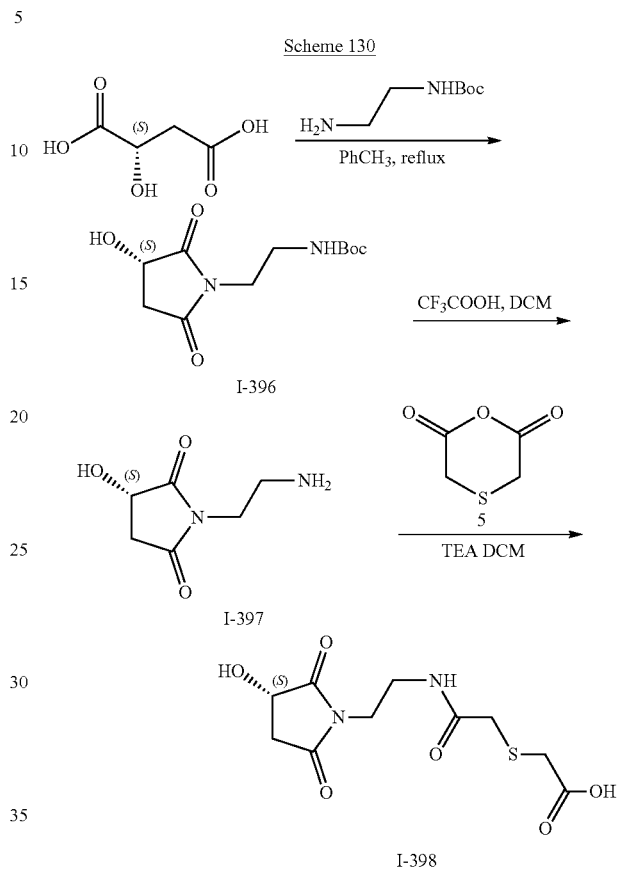

Scheme 130

Step 1: Tert-butyl (S)-(2-(3-hydroxy-2,5-dioxopyrrolidin-1-yl)ethyl)carbamate (I-396)

A solution of (S)-2-hydroxysuccinic acid (cas: 97-67-6, 2 g, 14.9 mmol) and tert-butyl (2-aminoethyl)carbamate (2.88 g, 1.2 equiv.) in 10 mL of toluene was heated to reflux for 7 hours. When LC-MS analysis indicated that the reaction was complete, the reaction mixture was concentrated under reduced pressure to give the crude product, which was purified by silica gel chromatography (EtOAc:Petroleum ether=2:1) to afford 1.9 g (49% yield) of intermediate tert-butyl (S)-(2-(3-hydroxy-2,5-dioxopyrrolidin-1-yl)ethyl) carbamate 1-396 as a pale oil. MS (ESI, pos. ion) m/z: 281 (M+Na).

Step 2: (S)-1-(2-aminoethyl)-3-hydroxypyrrolidine-2, 5-dione (I-397)

A solution of tert-butyl (S)-(2-(3-hydroxy-2,5-dioxopyrrolidin-1-yl)ethyl)carbamate, 1-396 (300 mg, 1.06 mmol) in TFA/DCM (1:3 v/v, 8 mL) was stirred at 25° C. for 1 hour. When LC-MS analysis indicated that the reaction was complete, the reaction mixture was concentrated under reduced pressure to afford (S)-1-(2-aminoethyl)-3-hydroxy-pyrrolidine-2, 5-dione, 1-397 (400 mg) as a pale oil, which was used directly for next step. MS (ESI, pos. ion) m/z: 159 (M+1).

Step 3: (S)-2-((2-((2-(3-hydroxy-2,5-dioxopyrroli-din-1-yl)ethyl)amino)-2-oxoethyl)thio) acetic acid (I-398)

A solution of (S)-1-(2-aminoethyl)-3-hydroxypyrrolidine-2,5-dione, I-397 (200 mg, 1.3 mmol) and thiodiglycolic anhydride (167 mg, 1.3 mmol) in 5 mL of DCM was added TEA (157 mg, 1.2 equiv.). The reaction mixture was stirred for 2 hours, then concentrated under reduced pressure to give the crude product. The crude product was purified by preparative HPLC to give the carboxylic acid I-398 (83 mg, 22% yield) as a pale oil. MS (ESI, pos. ion) m/z: 291.2 (M+1). $^1$H NMR (400 MHz, DMSO-$d_6$): δ 8.16-8.13 (m, 1H), 4.48-4.45 (m, 1H), 3.45-3.42 (m, 2H), 3.35 (s, 2H), 3.26-3.17 (m, 2H), 3.14 (s, 2H), 2.98-2.91 (m, 1H), 2.55 (s, 1H), 2.44-2.39 (m, 1H).

R-2-((2-((2-(3-hydroxy-2,5-dioxopyrrolidin-1-yl)ethyl)amino)-2-oxoethyl)thio) acetic acid (I-399)

I-399 was prepared from (2R)-malic acid as a pale oil in 79% yield. MS (ESI, pos. ion) m/z: 291.2 (M+1). $^1$H NMR (400 MHz, DMSO-$d_6$): δ 8.15-8.12 (m, 1H), 4.47-4.44 (m, 1H), 3.45-3.42 (m, 2H), 3.34 (s, 2H), 3.26-3.16 (m, 2H), 3.14 (s, 2H), 2.97-2.91 (m, 1H), 2.54 (s, 1H), 2.44-2.36 (m, 1H).

The Synthesis of Racemic Compound (±)-I-403 Involved 3 Steps as Depicted in the Following Scheme 131. The Intermediate I-404 was then Isolated by Chiral Separation.

Scheme 131
2-((2-((2-(3,4-dimethyl-2,5-dioxopryrrolidin-1-yl)ethyl)amino)-2-oxoethyl)thio) acetic acid (I-404)

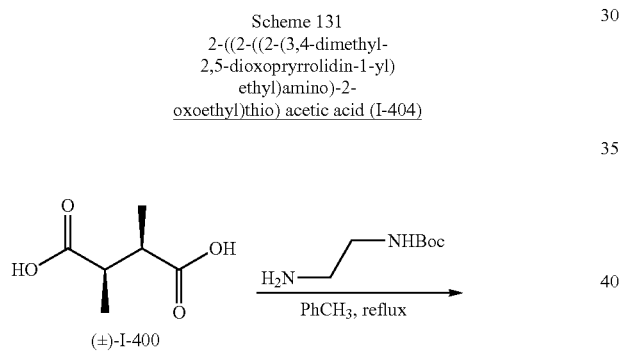

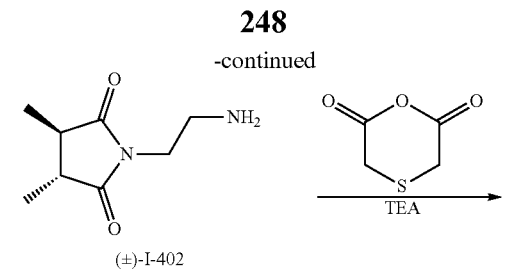

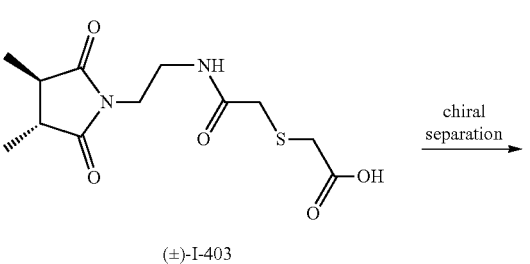

The synthetic route for I-404 was similar to that of I-398 and commenced with (±)-(2R*,3R*)-2,3-dimethylsuccinic acid, (±)-I-400 (cas: 13545-04-5). I-404 (pale oil, 30 mg, 15% yield) was isolated by chiral separation (Superchiral S-AD (Chiralway), 2 cm I.D.*25 cm Length, 5 um, Hexane/EtOH=60/40 (v/v)) from racemic acid I-403. MS (ESI, pos. ion) m/z: 303.1 (M+1). $^1$H NMR (400 MHz, CDCl$_3$): δ 7.34 (s, 1H), 5.6 (s, 1H), 3.67 (m, 2H), 3.5 (s, 2H), 3.31 (m, 4H), 2.4 (m, 2H), 1.3 (m, 6H).

The Synthesis of (R*)-I-409 and (S*)-I-409 Involved 5 Steps as Depicted in the Following Scheme 132.

Scheme 132

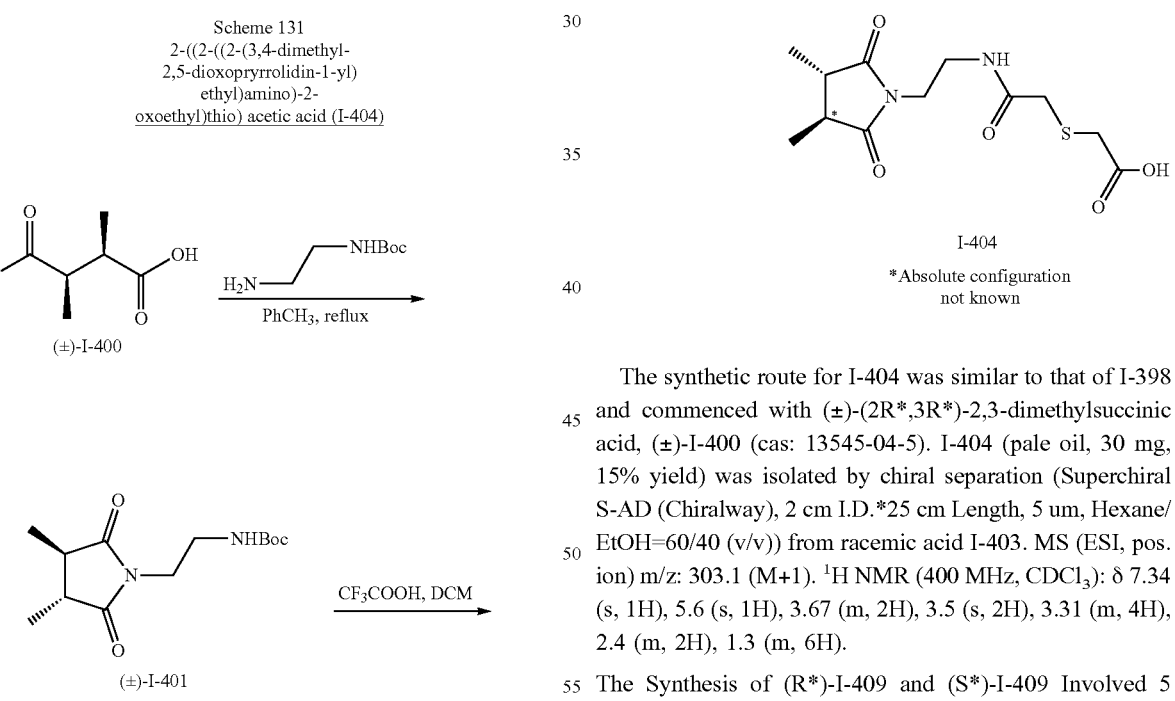

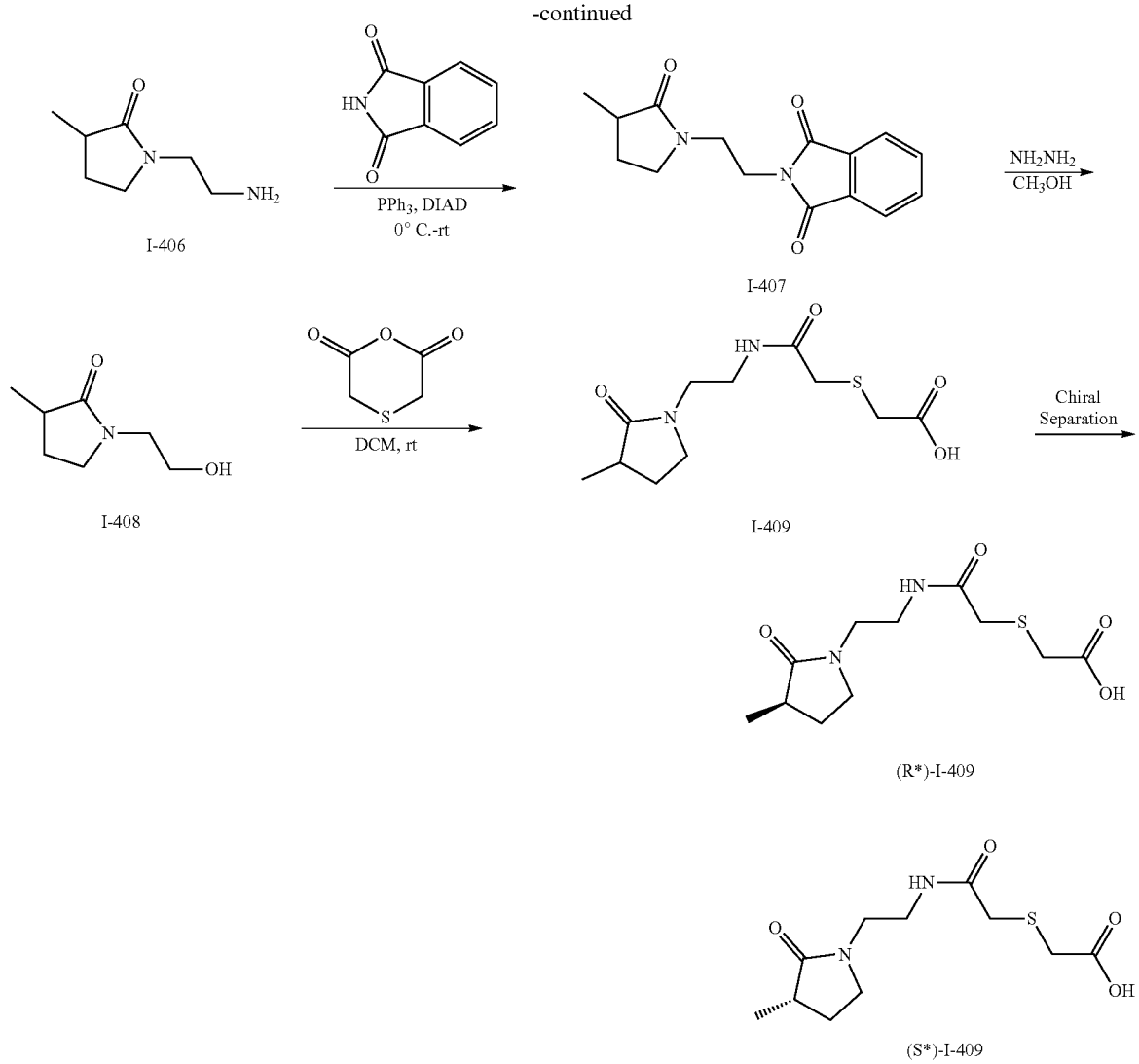

Step 1: 1-(2-((tert-butyldimethylsilyl) oxy)ethyl)-3-methylpyrrolidin-2-one (I-405)

To a solution of 3-methylpyrrolidin-2-one (cas: 2555-05-7, 0.3 g, 3 mmol) in THF (10 mL) at 0-5° C. was added NaH (0.242 g, 2 equiv.) under $N_2$. The reaction mixture was stirred for 0.5 hours, then (2-bromoethoxy)(tert-butyl)dimethylsilane (cas: 86864-60-0, 0.86 g, 1.2 equiv.) was added. The reaction mixture was allowed to warm to ambient temperature and stirred for 5 hours. The reaction was then quenched with water (5 mL), and extracted with DCM (3×20 mL). The combined organic extracts were then washed with water (20 mL), brine (20 mL), dried with $Na_2SO_4$ and concentrated under reduced pressure. The residue obtained was purified by silica gel chromatography to afford 1-405 (0.25 g, 32% yield) as a pale oil. MS (ESI, pos. ion) m/z: 258 (M+1).

Step 2: 1-(2-Hydroxy-ethyl)-3-methyl-pyrrolidin-2-one (I-406)

To a solution of 1-(2-((tert-butyldimethylsilyl)oxy)ethyl)-3-methylpyrrolidin-2-one, I-405 (0.3 g, 3 mmol) in MeOH (10 mL) at 0-5° C. was added HCl in MeOH (30%, 3 mL) under $N_2$. The mixture was stirred for 0.5 hours. The reaction mixture was then concentrated under reduced pressure to afford the crude alcohol I-406 as a pale oil (0.25 g), which was used directly in the next step. MS (ESI, pos. ion) m/z: 144 (M+1).

Step 3: 2-(2-(3-Methyl-2-oxopyrrolidin-1-yl) ethyl) isoindoline-1,3-dione (I-407)

To a solution of 1-(2-hydroxyethyl)-3-methylpyrrolidin-2-one, I-406 (0.25 g, 1.75 mmol) in THF (5 mL) was added phthalimide (cas: 85-41-6, 0.25 g, 1.5 equiv.) and $PPh_3$ (0.68 g, 1.5 equiv.). The reaction mixture was cooled to 0-5° C. and DIAD (1.059 g, 3.0 equiv.) was added. The reaction mixture was allowed to warm to ambient temperature and stirred for 6 hours, then quenched with water (5 mL), and extracted with DCM (3×20 mL). The combined organic extracts were then washed with water (20 mL), brine (20 mL), dried with $Na_2SO_4$ and concentrated under reduced pressure to afford the crude product, I-407 (purity: 67%, 0.3 g, 48% yield), which was taken to the next step without further purification. MS (ESI, pos. ion) m/z: 273 (M+1).

Step 4: 1-(2-aminoethyl)-3-methylpyrrolidin-2-one (I-408)

To a solution of 2-(2-(3-methyl-2-oxopyrrolidin-1-yl)ethyl)isoindoline-1,3-dione, I-407 (0.3 g, 3 mmol) in MeOH (10 mL) at 0-5° C. was added NH$_2$NH$_2$ (85% in H$_2$O, 1.03 mL, 1.2 equiv.). The reaction mixture was allowed to warm to ambient temperature, stirred for 7 hours, and then filtered. The filtrate was concentrated to afford a pale oil. The crude product, I-408 (0.35 g) was used directly in the next step. MS (ESI, pos. ion) m/z: 143 (M+1).

Step 5: 2-((2-((2-(3-methyl-2-oxopyrrolidin-1-yl)ethyl)amino)-2-oxoethyl)thio) acetic acid (I-409)

To a solution of 1-(2-aminoethyl)-3-methylpyrrolidin-2-one, I-408 (350 mg, 1.3 mmol) and thiodiglycolic anhydride (167 mg, 1.0 equiv.) in 5 mL of DCM was added TEA (157 mg, 1.56 mmol). The reaction mixture was stirred for 2 hours and was concentrated in vacuo to give the crude acid, which was purified by preparative HPLC to afford racemic acid I-409. (R*)-I-409 (30 mg, 5%, absolute configuration not known) was isolated by chiral separation (CHIRALPAK AD-H column, Mobile phase: Hexane/EtOH/AcOH=80/20/0.1 (v/v/v)) from racemic I-409. MS (ESI, pos. ion) m/z: 275.2 (M+1). $^1$H NMR (400 MHz, CDCl$_3$): δ 7.38 (s, 1H), 3.5 (m, 6H), 3.4 (s, 2H), 3.2 (s, 2H), 2.6 (m, 1H), 2.3 (m, 1H), 1.6 (m, 1H), 1.1 (m, 3H).

2-((2-((2-(3-methyl-2-oxopyrrolidin-1-yl)ethyl)amino)-2-oxoethyl)thio) acetic acid (S*)-I-409

Isolated as a pale oil in 5% yield by chiral separation (CHIRALPAK AD-H column, Mobile phase: Hexane/EtOH/HOAc=80/20/0.1 (v/v/v)) from racemic I-409. The absolute configuration at the stereocenter was not established. MS (ESI, pos. ion) m/z: 275.2 (M+1). $^1$H NMR (400 MHz, CDCl$_3$): δ 7.4 (s, 1H), 3.5 (m, 6H), 3.4 (s, 2H), 3.2 (s, 2H), 2.58 (m, 1H), 2.28 (m, 1H), 1.7 (m, 1H), 1.1 (m, 3H). The Synthesis of 1-412 Involved 3 Steps as Depicted in the Following Scheme 133.

Scheme 133

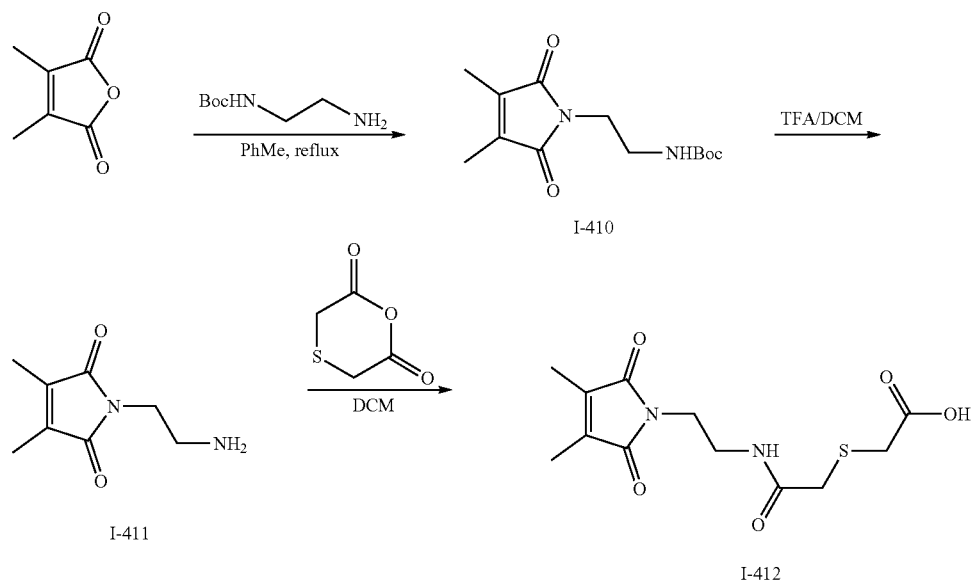

Step 1: tert-butyl (2-(3,4-dimethyl-2,5-dioxo-2,5-dihydro-1H-pyrrol-1-yl)ethyl)carbamate (I-410)

A solution of 3,4-dimethylfuran-2,5-dione (cas: 766-39-2, 600 mg, 4.76 mmol) and tert-butyl (2-aminoethyl)carbamate (cas: 57260-73-8, 1.1 g, 1.5 equiv.) in toluene (30 mL) was heated to reflux for 2 hours. The reaction mixture was then concentrated and purified by silica gel chromatography (Hexane:EtOAc=5:1) to afford tert-butyl (2-(3,4-dimethyl-2,5-dioxo-2,5-dihydro-1H-pyrrol-1-yl)ethyl)carbamate, I-410 as a yellow solid (700 mg, 55%). MS (ESI, pos. ion) m/z: 291.1 (M+23).

Step 2: 1-(2-aminoethyl)-3,4-dimethyl-1H-pyrrole-2,5-dione (I-411)

To a solution tert-butyl (2-(3,4-dimethyl-2,5-dioxo-2,5-dihydro-1H-pyrrol-1-yl)ethyl)carbamate (700 mg, 2.61 mmol) in DCM (10 mL) was added TFA (2 mL). The reaction mixture was stirred at ambient temperature for 1 hour, then concentrated to afford the crude 1-(2-aminoethyl)-3,4-dimethyl-1H-pyrrole-2,5-dione TFA salt, I-411 as a brown oil (500 mg, 108%). MS (ESI, pos. ion) m/z: 169.1 (M+1).

Step 3: 2-((2-((2-(3,4-dimethyl-2,5-dioxo-2,5-dihydro-1H-pyrrol-1-yl)ethyl)amino)-2-oxoethyl) thio) acetic acid (I-412)

A solution of 1-(2-aminoethyl)-3,4-dimethyl-1H-pyrrole-2,5-dione (0.4 g, 2.38 mmol) and thiodiglycolic anhydride (1.2 g, 4 equiv.) in DCM (5 mL) was stirred at ambient temperature overnight. The reaction was monitored by LC- MS. Upon completion of the reaction, the reaction mixture was concentrated and purified by preparative TLC to afford acid I-412 (100 mg, 14%) as a white solid. MS (ESI, pos. ion) m/z: 301.1 (M+1). $^1$H NMR (400 MHz, CDCl3): δ 8.28 (s, 1H), 3.70 (m, 2H), 3.50 (m, 2H), 3.39 (s, 2H), 3.36 (s, 1H), 3.32 (s, 2H), 1.96 (s, 6H).

(S*)-I-413 and (R*)-I-413

The synthetic route for (S*)-I-413 and (R*)-I-413 was similar to the route for (R*)- and (S*)-I-234. The synthesis started with 5-methylpyrrolidin-2-one. The final target compounds were purified by preparative HPLC to afford 200 mg (55%) of racemic I-413 as a pale oil. Preparative chiral separation (CHIRALPAK AD column (Hexane/EtOH/AcOH=70/30/0.1)) of the racemate afforded the two enantiomers.

(S*)-I-413

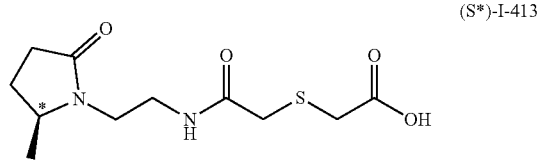

(R*)-I-413

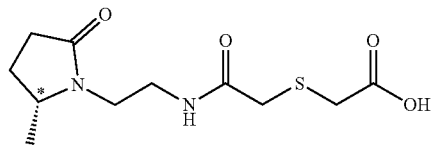

*Absolute configuration not known (S*)-I-413
After chiral HPLC purification, 30 mg of (S*)-I-413 (absolute configuration not determined) was obtained as a yellow oil. MS (ESI, pos. ion) m/z: 275.1 (M+1). $^1$H NMR (400 MHz, CDCl$_3$): δ 7.50 (s, 1H), 6.81 (s, 1H), 3.96-3.84 (m, 1H), 3.77-3.67 (m, 1H), 3.71-3.58 (m, 1H), 3.36 (s, 2H), 3.29-3.19 (m, 2H), 3.28-3.23 (m, 1H), 3.18-3.08 (m, 1H), 2.51-2.37 (m, 2H), 2.26-2.16 (m, 1H), 1.72-1.53 (m, 1H), 1.26-1.22 (m, 3H).

(R*)-I-413
After chiral HPLC purification, 41 mg of (R*)-I-413 (absolute configuration not determined) was obtained as a yellow oil. MS (ESI, pos. ion) m/z: 275.1 (M+1). $^1$H NMR (400 MHz, CDCl$_3$): δ 7.39 (s, 1H), 3.96-3.88 (m, 1H), 3.88-3.79 (m, 1H), 3.73 (s, 1H), 3.36 (s, 2H), 3.29-3.19 (m, 3H), 3.15-3.07 (m, 1H), 2.47-2.37 (m, 2H), 2.27-2.19 (m, 1H), 1.67-1.56 (m, 1H), 1.26-1.24 (m, 3H).

The Synthesis of Compound I-417 Involved 4 Steps as Depicted in the Following Scheme 134.

Scheme 134

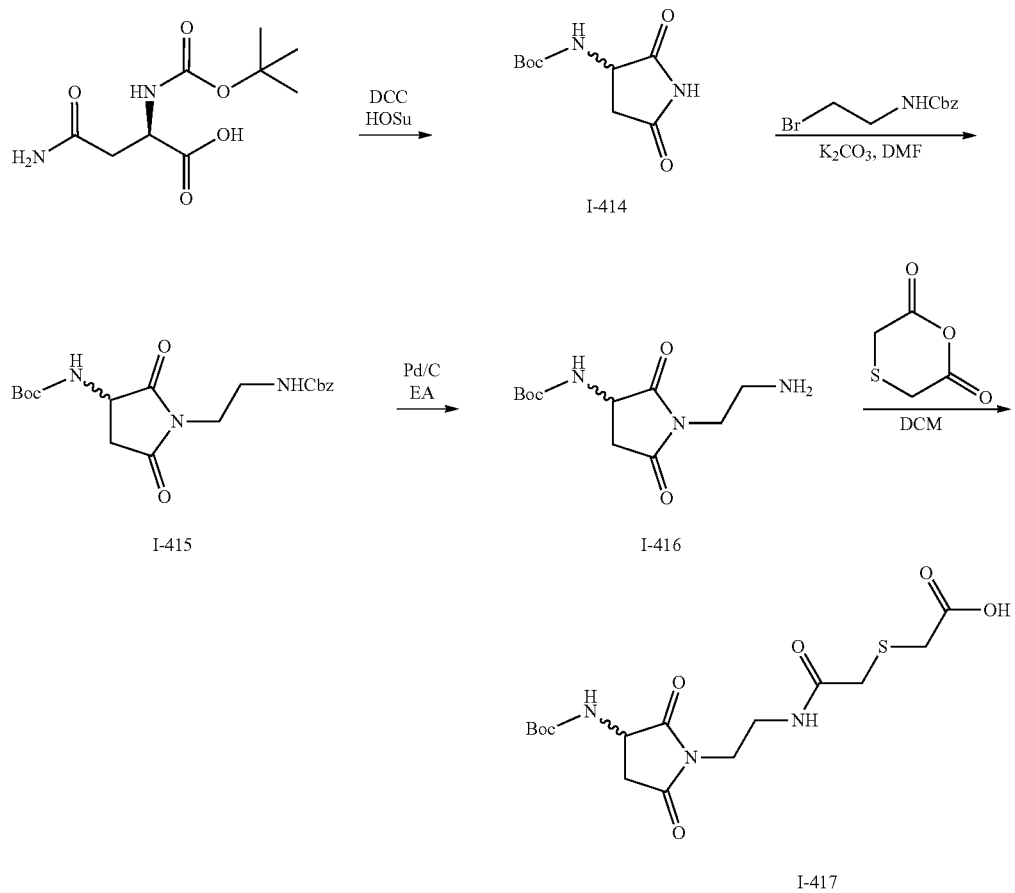

The chemical structure of the target compound was confirmed by ¹H NMR and LC-MS with the purity >95% (HPLC 214 & 254 nm).

(R)-2-((2-((2-(3-((tert-butoxycarbonyl)amino)-2,5-dioxopyrrolidin-1-yl)ethyl)amino)-2-oxoethyl)thio)acetic acid (I-417)

Step 1: tert-butyl (2,5-dioxopyrrolidin-3-yl)carbamate (I-414)

To a stirred solution of (tert-butoxycarbonyl)-D-asparagine (cas: 75647-01-7, 1.0 g, 4.3 mmol) in DMF (7 mL) was added DCC (0.8 g, 1.0 equiv.) and HOSu (0.5 g, 1.0 equiv.). The reaction mixture was heated to 80° C. for 6 hours and then concentrated under reduced pressure. The residue was dissolved in EtOAc (10 mL) and filtered. The filtrate was washed with water, brine, dried with Na₂SO₄, and then concentrated under reduced pressure. The resulting residue was purified by column chromatography (EtOAc:Petroleum ether=1:1) to afford imide I-414 as a pale yellow solid (0.5 g, 53% yield). MS (ESI, pos. ion) m/z: 237.1 (M+23).

Step 2: tert-butyl (1-(2-(((benzyloxy)carbonyl)amino)ethyl)-2,5-dioxopyrrolidin-3-yl)carbamate (I-415)

To a solution of tert-butyl(2,5-dioxopyrrolidin-3-yl)carbamate, I-414 (0.5 g, 2.3 mmol) and benzyl (2-bromoethyl)carbamate (cas: 53844-02-3, 890 mg, 1.5 equiv.) in DMF (5 mL) was added potassium carbonate (800 mg, 2.5 equiv.). The reaction mixture was heated to 90° C. for 12 hours. The reaction was then quenched with water (5 mL), and extracted with EtOAc (3×20 mL). The combined organic extracts were then washed with water (20 mL), brine (20 mL), dried with Na₂SO₄ and concentrated under reduced pressure. The residue was purified by column chromatography (EtOAc:Petroleum ether=1:1) to provide carbamate I-415 as a pale yellow oil (0.9 g, 100%). MS (ESI, pos. ion) m/z: 414.1 (M+23).

Step 3: tert-butyl-(1-(2-aminoethyl)-2,5-dioxopyrrolidin-3-yl)carbamate (I-416)

To a solution of tert-butyl (1-(2-(((benzyloxy)carbonyl)amino)ethyl)-2,5-dioxopyrrolidin-3-yl)carbamate, I-415 (0.9 g, 2.3 mmol) in EtOAc (15 ml), was added 100 mg of Pd/C under H₂ (14 Psi). The reaction mixture was stirred at ambient temperature overnight then filtered, and the filtrate was concentrated to afford the crude tert-butyl-(1-(2-aminoethyl)-2,5-dioxopyrrolidin-3-yl)carbamate I-416 as brown oil (0.5 g, 84%). MS (ESI, pos. ion) m/z: 280.1 (M+23).

Step 4: 2-((2-((2-(3-((tert-butoxycarbonyl)amino)-2,5-dioxopyrrolidin-1-yl)ethyl)amino)-2-oxoethyl)thio) acetic acid (I-417)

A solution of tert-butyl-(1-(2-aminoethyl)-2,5-dioxopyrrolidin-3-yl)carbamate, I-416 (0.1 g, 0.4 mmol) and thiodiglycolic anhydride (211 mg, 4 equiv.) in DCM (5 mL) was stirred at ambient temperature for 4 hours. The reaction was monitored by LC-MS. Upon completion of the reaction, the reaction mixture was concentrated, and the resulting residue was purified by preparative HPLC to afford I-417 (racemic) (39 mg, 25% yield). MS (ESI, pos. ion) m/z: 412.2 (M+23). ¹H NMR (400 MHz, CDCl₃): δ 7.34 (s, 1H), 5.62 (m, 1H), 4.36 (s, 1H), 3.72 (m, 1H), 3.57 (m, 1H), 3.45 (m, 3H), 3.31 (1H), 3.05 (m, 1H), 2.80 (s, 2H), 2.01 (s, 2H), 1.44 (s, 9H). The Synthesis of Compound I-421 Involved 4 Steps as Depicted in the Following Scheme 135.

Scheme 135

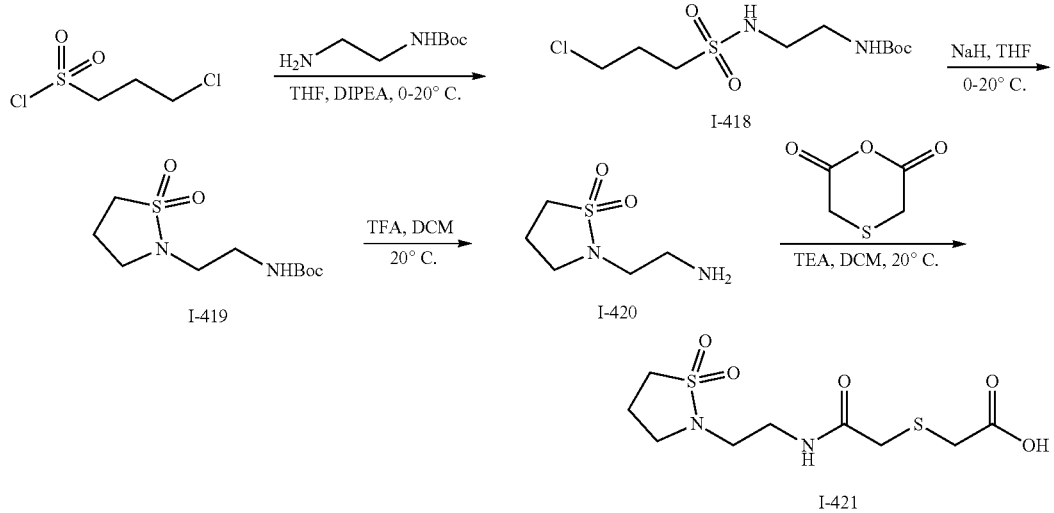

The chemical structure of the target compound was confirmed by ¹H NMR and LC-MS with the purity >95% (HPLC 214 & 254 nm).

Step 1: Tert-butyl (2-((3-chloropropyl)sulfonamido)ethyl)carbamate (I-418)

A solution of 3-chloropropane-1-sulfonyl chloride (cas: 1633-82-5, 1.22 g, 6.9 mmol) in anhydrous THF (5 mL) was added to a solution of tert-butyl (2-aminoethyl)carbamate (1 g, 6.25 mmol) and DIPEA (1.30 mL) in anhydrous THF (62 mL) at 0-5° C. The reaction mixture was was allowed to warm to ambient temperature and stirred for 8 hours. When LC-MS analysis indicated that the reaction was complete, H₂O (20 mL) was added, and the reaction mixture was extracted with EtOAc (20 mL×3). The combined organic extracts were concentrated under reduced pressure to give the crude product. The crude product was purified by silica gel chromatography (Petroleum ether:EtOAc=1:2) to provide I-418 (2.0 g, 96%) as a pale oil. MS (ESI, pos. ion) m/z: 323 (M+Na).

Step 2: Tert-butyl (2-(1,1-dioxidoisothiazolidin-2-yl)ethyl)carbamate (I-419)

To a solution of tert-butyl (2-aminoethyl)carbamate, I-418 (2 g, 6.67 mmol) in anhydrous THF (70 mL) at 0-5° C. was added NaH (60% dispersion in mineral oil, 0.4 g, 1.5 equiv.) in portions. The reaction was allowed to warm to ambient temperature and stirred for 8 hours. When LC-MS analysis indicated that the reaction was complete, H₂O (20 mL) was added and the reaction mixture was extracted with EtOAc (20 mL×3). The combined organic extracts were concentrated in vacuo to provide the crude product. The crude product was purified by silica gel chromatography (Petroleum Ether:EtOAc=2:1) to provide I-419 (0.15 g, 9% yield) as a pale oil. MS (ESI, pos. ion) m/z: 287 (M+Na).

Step 3: 2-(2-aminoethyl)isothiazolidine 1,1-dioxide (I-420)

A solution of tert-butyl (2-(1,1-dioxidoisothiazolidin-2-yl)ethyl)carbamate, I-419 (150 mg, 0.57 mmol) in TFA/DCM (1:3 v/v, 4 mL) was stirred at 25° C. for 2 hours. When LC-MS analysis indicated that the reaction was complete, the reaction mixture was concentrated in vacuo to give the crude amine TFA salt, I-420 as a pale oil (337 mg), which was used directly in the next step. MS (ESI, pos. ion) m/z: 165 (M+1).

Step 4. 2-((2-((2-(1,1-dioxidoisothiazolidin-2-yl)ethyl)amino)-2-oxoethyl)thio) acetic acid (I-421)

To a solution of 2-(2-aminoethyl)isothiazolidine-1,1-dioxide (337 mg, 1.22 mmol) and thiodiglycolic anhydride (193 mg, 1.2 equiv.) in 5 mL of DCM was added TEA (24 mg, 0.244 mmol). The reaction mixture was stirred for 2 hours and then concentrated under reduced pressure to give the crude product. The crude product was purified by preparative HPLC (Mobile Phase: MeCN/H₂O (0.1% TFA), Gradient: 1-5% MeCN) to afford I-421 as a pale oil (50 mg, 14% yield). MS (ESI, pos. ion) m/z: 297.1 (M+1). ¹H NMR (400 MHz, DMSO) δ 12.60 (s, 1H), 8.11 (m, 1H), 3.36 (s, 2H), 3.27-3.19 (m, 6H), 3.19-3.12 (m, 2H), 2.95 (m, 2H), 2.25-2.15 (m, 2H).

I-425:
The Synthesis of Compound I-425 Involved 4 Steps as Depicted in the Following Scheme 136.

Scheme 136 2-((2-((2-(1,1-dioxido-1,2-thiazinan-2-yl)ethyl)amino)-2-oxoethyl)thio) acetic acid (I-425)

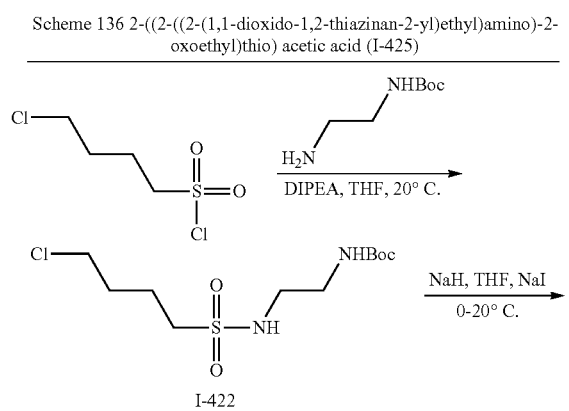

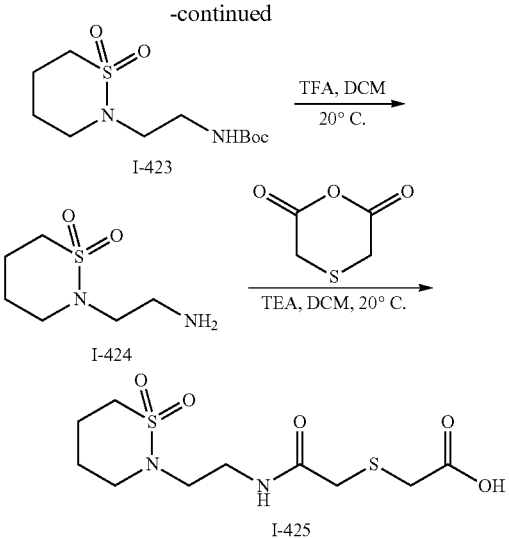

The synthetic route for I-425 was similar to that used for the synthesis of I-421 and commenced with 4-chlorobutane-1-sulfonyl chloride (cas: 1633-84-7). 2-((2-((2-(1,1-dioxido-1,2-thiazinan-2-yl)ethyl)amino)-2-oxoethyl)thio)acetic acid, I-425 (pale oil, 50 mg, 15% yield) was isolated by preparative HPLC (Mobile Phase: MeCN/H₂O (with 0.1% TFA), Gradient: 10-20% MeCN). MS (ESI, pos. ion) m/z: 311.1 (M+1). ¹H NMR (400 MHz, DMSO) δ 12.57 (s, 1H), 8.13 (m, 1H), 3.37 (s, 2H), 3.34-3.30 (m, 2H), 3.21 (s, 2H), 3.18 (m, 2H), 3.11 (m, 2H), 3.08-3.03 (m, 2H), 2.06-1.95 (m, 2H), 1.54 (m, 3.7 Hz, 2H).

Synthesis of I-426 was Depicted in Scheme 137

Scheme 137

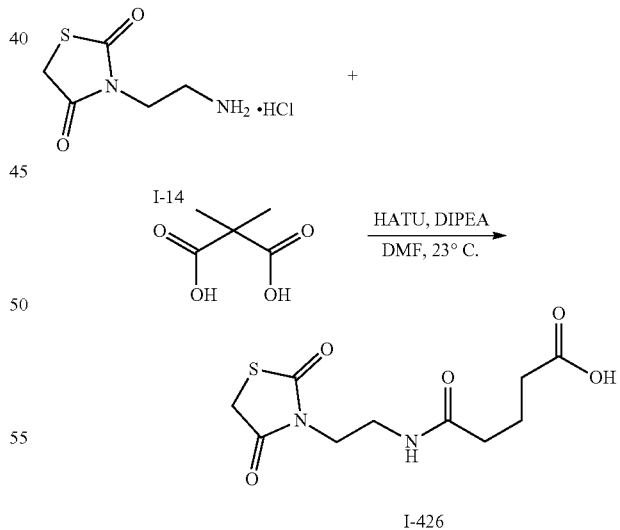

To a solution of amine salt I-14 (44.5 mg, 0.226 mmol), 2,2-dimethylmalonic acid (59.8 mg, 2.0 equiv.) and DIPEA (118 μL, 3.0 equiv.) in DMF (1 mL) was added HATU (129.1 mg, 1.5 equiv.). The reaction mixture was maintained at ambient temperature for 2 hours and was then purified by preparative HPLC (Mobile Phase: MeCN/H₂O with 0.1% TFA) to afford I-426 (8.6 mg, 14% yield).

D. EXAMPLES OF COMPOUNDS DESCRIBED IN THIS INVENTION

General Procedure 4 (GP4): Solid Phase Synthesis of Peptides Utilizing Carboxylic Acid Building Blocks

Example 1: Compound 83

Scheme 138

1. 20% piperidine/DMF, 23° C.

2. 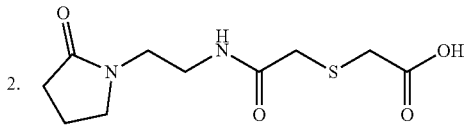

I-1

HATU, DIPEA, DMF, 23° C.

3. TFA/TIS/H$_2$O (95:2.5:2.5 v/v/v), 23° C.

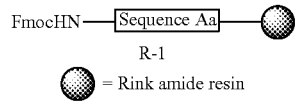

R-1

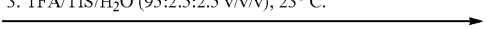

= Rink amide resin

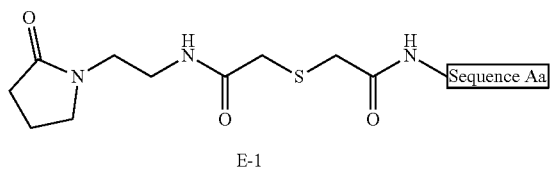

E-1

E-1 was synthesized as depicted in Scheme 138.

To Rink-amide resin R-1 (0.125 mmol/g, 140.5 mg, 17.6 µmol) in a 6 mL polypropylene tube with an end-cap was added 20% v/v piperidine/DMF (2 mL). The tube was capped and agitated at ambient temperature for 30 minutes, then drained. The resin was washed with DMF (5×3 mL). A solution of carboxylic acid building block I-1 (36.6 mg, 8.0 equiv.) in DMF (2.8 mL) was added to the resin, followed by DIPEA (61 µL, 20 equiv.). HATU (80 mg, 12.0 equiv.) was then added and the reaction mixture was agitated at ambient temperature for 18 hours. The reaction mixture was drained and the resin washed with DMF (5×3 mL), DCM (5×3 mL) and dried in vacuo for 30 minutes.

The resin was transferred to a 15 mL Falcon tube and 3 mL of cleavage reagent (95:2.5:2.5 v/v/v TFA/TIS/H$_2$O) was added. The reaction mixture was agitated at ambient temperature for 1 hour. The resin was filtered and washed with TFA (2×3 mL). The combined filtrate and washes were concentrated under reduced pressure to afford a residue, which was triturated with Et$_2$O (3 mL) to precipitate the peptide. The peptide was re-dissolved in glacial AcOH (2 mL) and purified by preparative HPLC (Phenomenex Jupiter 10 µM Proteo 90 Å LC column, 250×21.2 mm, with flow rate—15 mL/min, gradient of 0-100% acetonitrile in 25 mM aqueous ammonium acetate over 30 minutes) to afford 25.8 mg of E-1 as a white solid. ESI-MS (positive ionization) found 1149.7, [C$_{213}$H$_{325}$N$_{47}$O$_{64}$S]$^{4+}$ calculated 1149.3.

General Procedure 5 (GP5): Solid Phase Synthesis of Peptides Utilizing Pentafluorophenyl or N-hydroxysuccinimide Ester Building Blocks Scheme 139

1. 20% piperidine/DMF, 23° C.

2. 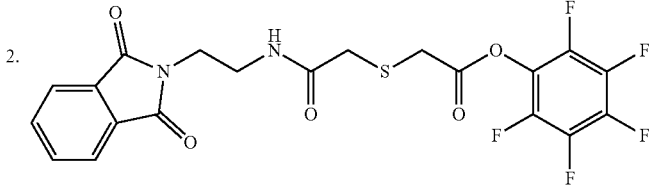

I-2

HATU, DIPEA, DMF, 23° C.

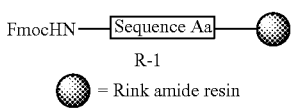

R-1

3. TFA/TIS/H$_2$O (95:2.5:2.5 v/v/v), 23° C.

= Rink amide resin

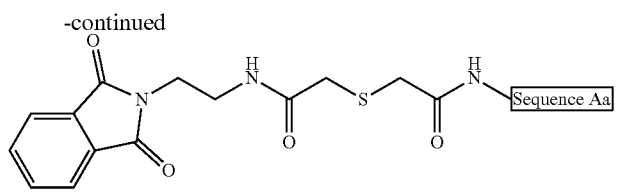

E-2

Example 2: Compound 173

E-2 was synthesized as depicted in Scheme 139.

To Rink-amide resin (0.125 mmol/g, 107.8 mg, 13.5 μmol) in a 6 mL polypropylene tube with an end-cap was added 20% v/v piperidine/DMF (2 mL). The tube was capped, agitated at ambient temperature for 30 minutes, and then drained. The resin was washed with DMF (5×3 mL). A solution of pentafluorophenyl ester I-2 (32.9 mg, 5.0 equiv.) in DMF (1 mL) was added to the resin, followed by DIPEA (24 μL, 10 equiv.) and the reaction mixture was agitated at ambient temperature for 24 hours. The reaction mixture was drained. The resin was washed with DMF (5×3 mL), DCM (5×3 mL), and dried in vacuo for 30 minutes.

The resin was transferred to a 15 mL falcon tube and 3 mL of cleavage reagent (95:2.5:2.5 v/v/v TFA/TIS/H$_2$O) was added. The reaction mixture was agitated at ambient temperature for 3 hours. The resin was filtered and washed with TFA (2×0.5 mL). The combined filtrate and washes were concentrated under reduced pressure to afford a residue, which was triturated with Et$_2$O (2 mL) to precipitate the peptide. The peptide was re-dissolved in glacial AcOH (1.2 mL) and purified by preparative HPLC (Phenomenex Jupiter 10 μM Proteo 90 Å LC column, 250×21.2 mm, with flow rate—15 mL/min, gradient of 0-100% acetonitrile in 25 mM aqueous ammonium acetate over 30 minutes) to afford 9.4 mg of E-2 as a white solid. ESI-MS (positive ionization) found 1165.3, $[C_{217}H_{323}N_{47}O_{65}S]^{4+}$ calculated 1164.8.

Example 3: Compound 189

Scheme 140

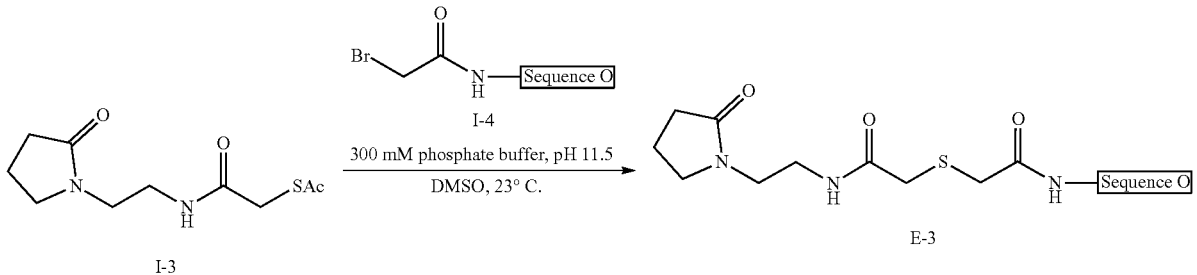

E-3 was synthesized as depicted in Scheme 140.

To peptide I-4 (0.25 mL of a 5 mM stock solution in DMSO, 1.2 μmol) was added I-3 (50 μL of a 50 mM stock solution in DMSO, 2.0 equiv.), followed by 300 mM sodium phosphate buffer, pH 11.5 (50 μL). The reaction mixture was agitated at ambient temperature for 16 hours and then purified by preparative HPLC (H$_2$O/MeCN with 0.1% TFA) to afford E-3 (4.3 mg) as a white solid. ESI-MS found 1374.3, $C_{186}H_{269}N_{46}O_{59}S$ (M−3H) requires 1374.3.

Example 4: Compound 190

Scheme 141

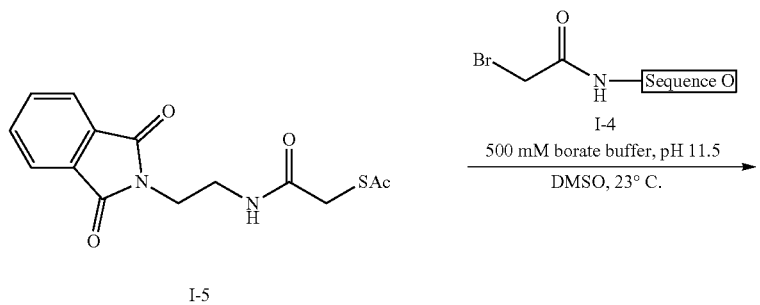

I-5

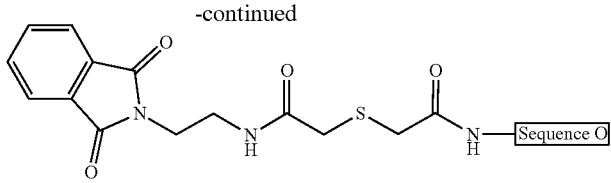

E-4

E-4 was synthesized as depicted in Scheme 141.

To peptide I-4 (0.25 mL of a 5 mM stock solution in DMSO, 1.2 µmol) was added I-5 (50 µL of a 50 mM stock solution in DMSO, 2.0 equiv.), followed by 500 mM borate buffer, pH 9.5 (25 µL). The reaction mixture was agitated at ambient temperature for 16 hours and then purified by preparative HPLC (H$_2$O/MeCN with 0.1% TFA) to afford E-4 (1.8 mg) as a white solid. ESI-MS found 1395.0, $C_{190}H_{267}N_{46}O_{60}S$ (M−3H) requires 1395.0.

Example 5: Compound 139

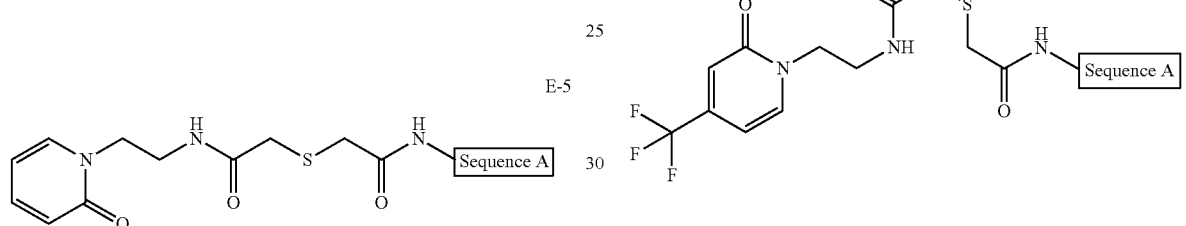

E-5

E-5 was prepared according to GP4 using 24 mg of resin (estimated loading 0.18 mmol/g) and I-6 to afford 2.3 mg of E-5 as a white solid. ESI-MS found 1058.5, $C_{193}H_{278}N_{46}O_{60}S$ (M−4H$^+$) requires 1058.0.

Example 6: Compound 118

E-6

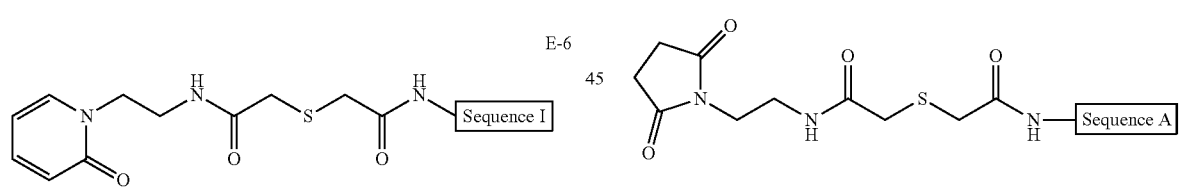

E-6 was prepared according to GP4 using 30.9 mg of resin (estimated loading 0.15 mmol/g) and I-6 to afford 0.9 mg of E-6 as a white solid. ESI-MS found 1063.5, $C_{194}H_{288}N_{46}O_{60}S$ (M+4H$^+$) requires 1063.5.

Example 7: Compound 52

E-7

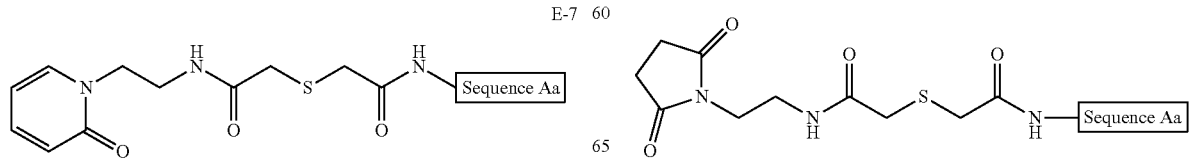

E-7 was prepared according to GP4 using 43.3 mg of resin (estimated loading 0.125 mmol/g) and I-6 to afford 2.5 mg of E-7 as a white solid. ESI-MS found 1152.3, $C_{214}H_{323}N_{47}O_{64}S$ (M+4H$^+$) requires 1151.8.

Example 8: Compound 121

E-8

E-8 was prepared according to GP4 using 30.8 mg of resin (estimated loading 0.18 mmol/g) and I-7 to afford 2.4 mg of E-8 as a white solid. ESI-MS found 1077.6, $C_{194}H_{285}FN_{46}O_{60}S$ (M+4H$^+$) requires 1077.0.

Example 9: Compound 117

E-9

E-9 was prepared according to GP4 using 30.3 mg of resin (estimated loading 0.18 mmol/g) and I-8 to afford 3.1 mg of E-9 as a white solid. ESI-MS found 1061.0, $C_{192}H_{286}N_{46}O_{61}S$ (M+4H$^+$) requires 1061.0.

Example 10: Compound 114

E-10

E-10 was prepared according to GP4 using 40.1 mg of resin (estimated loading 0.125 mmol/g) and I-8 to afford 1.5 mg of E-10 as a white solid. ESI-MS found 1152.8, $C_{213}H_{323}N_{47}O_{65}S$ (M+4H$^+$) requires 1152.8.

Example 11: Compound 53

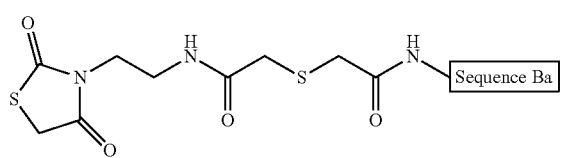

E-11 was prepared according to GP4 using 67 mg of resin (estimated loading 0.08 mmol/g) and I-9 to afford 2.5 mg of E-11 as a white solid. ESI-MS found 1157.9, $C_{212}H_{321}N_{47}O_{65}S_2$ (M+4H$^+$) requires 1157.3.

Example 12: Compound 56

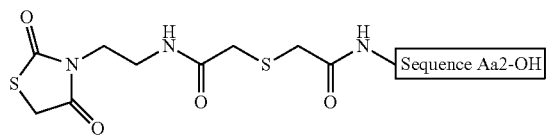

E-12 was prepared according to GP4 using 55.6 mg of resin (estimated loading 0.15 mmol/g) and I-9 to afford 1.7 mg of E-12 as a white solid. ESI-MS found 1125.8, $C_{207}H_{313}N_{45}O_{63}S_2$ (M+4H$^+$) requires 1125.3.

Example 13: Compound 60

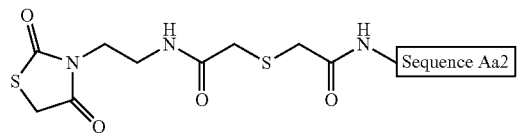

E-13 was prepared according to GP4 using 53.3 mg of resin (estimated loading 0.18 mmol/g) and I-9 to afford 5.0 mg of E-13 as a white solid. ESI-MS found 1125.4, $C_{207}H_{314}N_{46}O_{62}S_2$ (M+4H$^+$) requires 1125.1.

Example 14: Compound 76

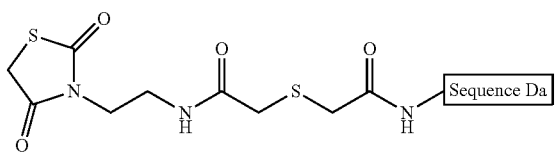

E-14 was prepared according to GP4 using 41.3 mg of resin (estimated loading 0.11 mmol/g) and I-9 to afford 0.5 mg of E-14 as a white solid. ESI-MS found 1238.2, $C_{222}H_{348}N_{56}O_{66}S_3$ (M+4H$^+$) requires 1237.6.

Example 15: Compound 73

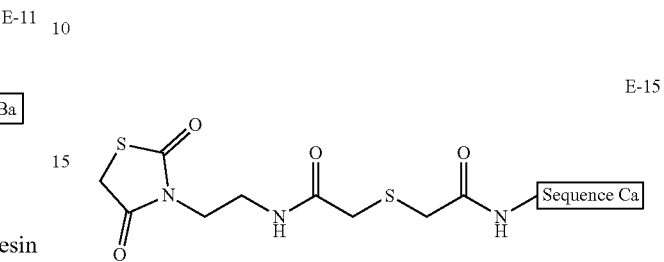

E-15 was prepared according to GP4 using 40.4 mg of resin (estimated loading 0.06 mmol/g) and I-9 to afford 0.8 mg of E-15 as a white solid. ESI-MS found 1135.3, $C_{206}H_{319}N_{47}O_{64}S_2$ (M+4H$^+$) requires 1134.8.

Example 16: Compound 70

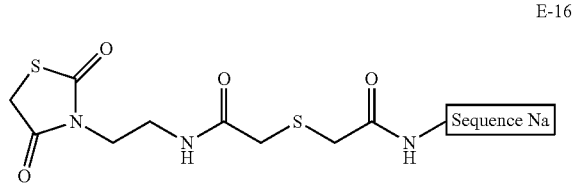 [SMILES: CNC(=O)CSCC(=O)NCCN1C(=O)CSC1=O]

E-16 was prepared according to GP4 using 56.5 mg of resin (estimated loading 0.18 mmol/g) and I-9 to afford 1.1 mg of E-16 as a white solid. ESI-MS found 1161.2, $C_{213}H_{323}N_{47}O_{65}S2$ (M+4H$^+$) requires 1160.8.

Example 17: Compound 71

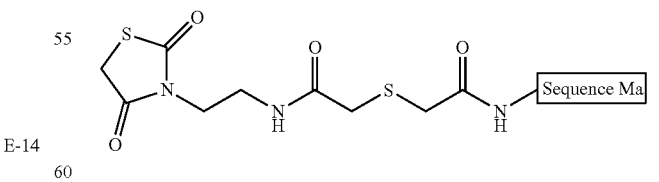

E-17 was prepared according to GP4 using 68 mg of resin (estimated loading 0.16 mmol/g) and I-9 to afford 3.3 mg of E-17 as a white solid. ESI-MS found 1139.3, $C_{205}H_{315}N_{47}O_{64}S_3$(M+4H$^+$) requires 1138.8.

Example 18: Compound 72

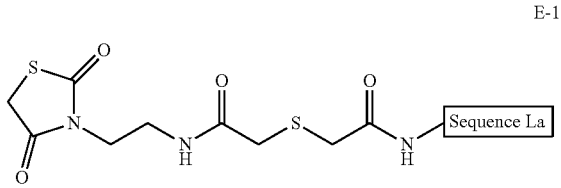

E-18

E-18 was prepared according to GP4 using 56.9 mg of resin (estimated loading 0.17 mmol/g) and I-9 to afford 0.7 mg of E-18 as a white solid. ESI-MS found 1153.4, $C_{207}H_{318}N_{48}O_{65}S_3$ (M+4H$^+$) requires 1153.1.

Example 19: Compound 137

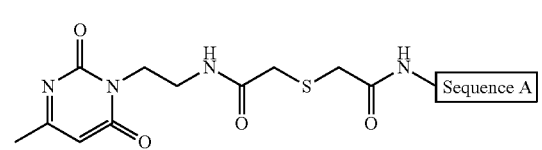

E-19

E-19 was prepared according to GP4 using 27.3 mg of resin (estimated loading 0.18 mmol/g) and I-10 to afford 0.7 mg of E-19 as a white solid. ESI-MS found 1065.8, $C_{194}H_{281}N_{47}O_{60}S$ (M−4H)$^−$ requires 1065.3.

Example 20: Compound 138

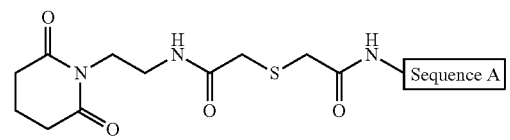

E-20

E-20 was prepared according to GP4 using 29 mg of resin (estimated loading 0.18 mmol/g) and I-11 to afford 3.0 mg of E-20 as a white solid. ESI-MS found 1063.0, $C_{193}H_{280}N_{46}O_{61}S$ (M−4H)$^−$ requires 1062.5.

Example 21: Compound 123

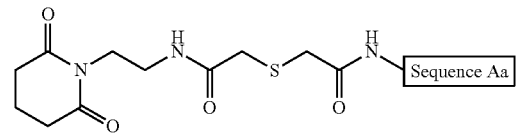

E-21

E-21 was prepared according to GP4 using 108.5 mg of resin (estimated loading 0.125 mmol/g) and I-11 to afford 9.7 mg of E-21 as a white solid. ESI-MS found 1156.8, $C_{214}H_{325}N_{47}O_{65}S$ (M+4H$^+$) requires 1156.3.

Example 22: Compound 120

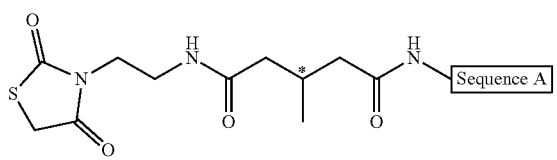

E-22

*Mixture of diastereomers

E-22 was prepared according to GP4 using 31.5 mg of resin (estimated loading 0.18 mmol/g) and I-12 to afford 1.8 mg of E-22 as a white solid. ESI-MS found 1065.1, $C_{193}H_{288}N_{46}O_{61}S$ (M+4H$^+$) requires 1064.5.

Example 23: Compound 122

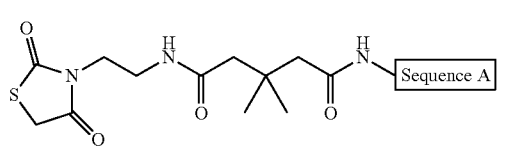

E-23

E-23 was prepared according to GP4 using 29.4 mg of resin (estimated loading 0.18 mmol/g) and I-13 to afford 4.2 mg of E-23 as a white solid. ESI-MS found 1068.6, $C_{194}H_{290}N_{46}O_{61}S$ (M+4H$^+$) requires 1068.0.

Example 24: Compound 170

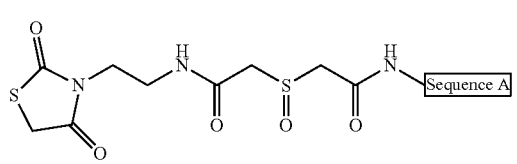

E-24

E-24 was prepared according to GP4 using 26.9 mg of resin (estimated loading 0.15 mmol/g) and I-15 to afford 3.3 mg of E-24 as a white solid. ESI-MS found 1068.0, $C_{191}H_{276}N_{46}O_{62}S_2$ (M−4H)$^−$ requires 1067.5.

Example 25: Compound 131

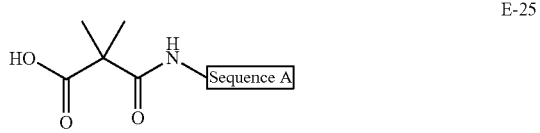

E-25

E-25 was prepared according to GP3 using 29.1 mg of resin (estimated loading 0.18 mmol/g) and diester I-16 to afford 2.1 mg of E-25 as a white solid. ESI-MS found 1024.0, $C_{187}H_{272}N_{44}O_{60}$ (M−4H)⁻ requires 1023.5.

Example 26: Compound 143

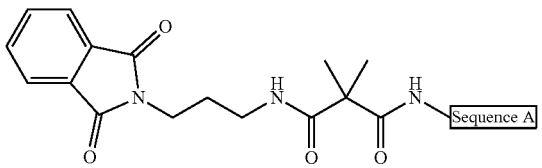

E-26 was prepared according to GP5 using 28.7 mg of resin (estimated loading 0.18 mmol/g) and I-21 to afford 3.4 mg of E-26 as a white solid. ESI-MS found 1070.5, $C_{198}H_{282}N_{46}O_{61}$ (M−4H)⁻ requires 1070.0.

Example 27: Compound 142

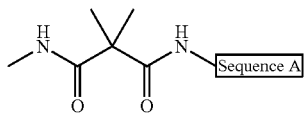

E-27 was prepared according to GP5 using 24.7 mg of resin (estimated loading 0.18 mmol/g) and I-22 to afford 2.5 mg of E-27 as a white solid. ESI-MS found 1027.3, $C_{188}H_{275}N_{45}O_{59}$ (M−4H)⁻ requires 1026.8.

Example 28: Compound 141

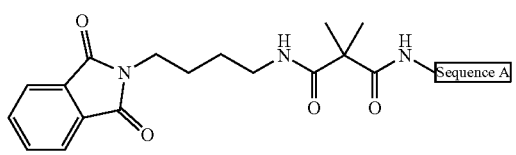

E-28 was prepared according to GP5 using 26.1 mg of resin (estimated loading 0.18 mmol/g) and I-23 to afford 1.8 mg of E-28 as a white solid. ESI-MS found 1074.0, $C_{199}H_{284}N_{46}O_{61}$ (M−4H)⁻ requires 1073.5.

Example 29: Compound 140

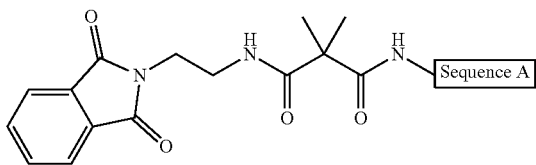

E-29 was prepared according to GP5 using 23.5 mg of resin (estimated loading 0.18 mmol/g) and I-24 to afford 0.5 mg of E-29 as a white solid. ESI-MS found 1067.0, $C_{197}H_{280}N_{46}O_{61}$ (M−4H)⁻ requires 1066.5.

Example 30: Compound 116

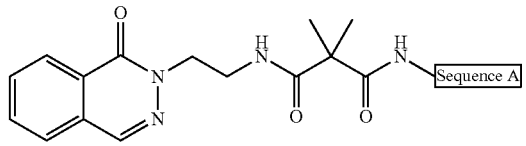

E-30 was prepared according to GP5 using 24.9 mg of resin (estimated loading 0.18 mmol/g) and I-25 to afford 1.4 mg of E-30 as a white solid. ESI-MS found 1068.7, $C_{197}H_{289}N_{47}O_{60}$ (M+4H⁺) requires 1068.3.

Example 31: Compound 127

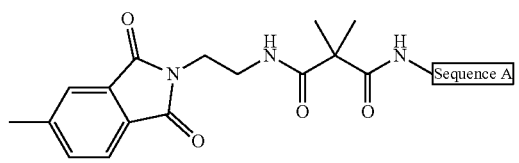

E-31 was prepared according to GP5 using 28.4 mg of resin (estimated loading 0.18 mmol/g) and I-26 to afford 2.4 mg of E-31 as a white solid. ESI-MS found 1070.5, $C_{198}H_{282}N_{46}O_{61}$ (M−4H)⁻ requires 1070.0.

Example 32: Compound 129

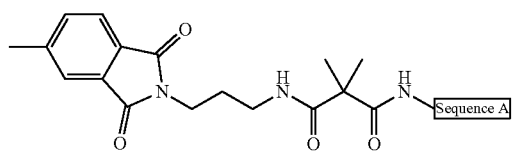

E-32 was prepared according to GP5 using 26.4 mg of resin (estimated loading 0.18 mmol/g) and I-27 to afford 5.5 mg of E-32 as a white solid. ESI-MS found 1074.0, $C_{199}H_{284}N_{46}O_{61}$ (M−4H)⁻ requires 1073.5.

Example 33: Compound 132

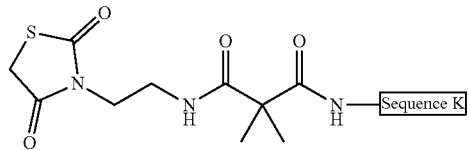

E-33 was prepared according to GP5 using 27.1 mg of resin (estimated loading 0.2 mmol/g) and I-28 to afford 3.1 mg of E-33 as a white solid. ESI-MS found 1070.0, $C_{195}H_{284}N_{46}O_{61}S$ (M–4H)⁻ requires 1069.5.

Example 34: Compound 134

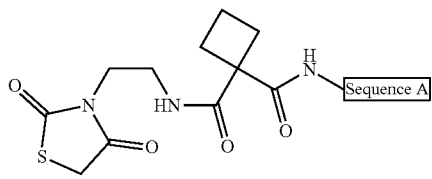
E-34

E-34 was prepared according to GP5 using 28 mg of resin (estimated loading 0.18 mmol/g) and I-29 to afford 3.0 mg of E-34 as a white solid. ESI-MS found 1062.5, $C_{193}H_{278}N_{46}O_{61}S$ (M–4H)⁻ requires 1149.8.

Example 35: Compound 135

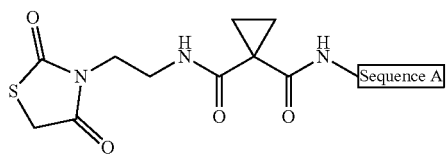
E-35

E-35 was prepared according to GP5 using 25.8 mg of resin (estimated loading 0.18 mmol/g) and I-30 to afford 2.4 mg of E-35 as a white solid. ESI-MS found 1059.0, $C_{192}H_{276}N_{46}O_{61}S$ (M–4H)⁻ requires 1058.5.

Example 36: Compound 19

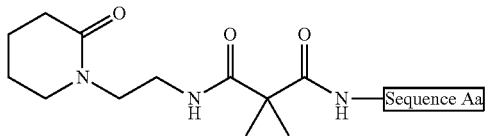
E-36

E-36 was prepared according to GP5 using 39.7 mg of resin (estimated loading 0.125 mmol/g) and I-31 to afford 5.9 mg of E-36 as a white solid. ESI-MS found 1148.9, $C_{215}H_{329}N_{47}O_{64}$ (M+4H⁺) requires 1148.3.

Example 37: Compound 119

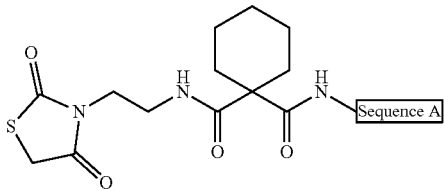
E-37

E-37 was prepared according to GP5 using 34 mg of resin (estimated loading 0.18 mmol/g) and I-32 to afford 5.2 mg of E-37 as a white solid. ESI-MS found 1071.6, $C_{195}H_{290}N_{46}O_{61}S$ (M+4H⁺) requires 1071.0.

Example 38: Compound 124

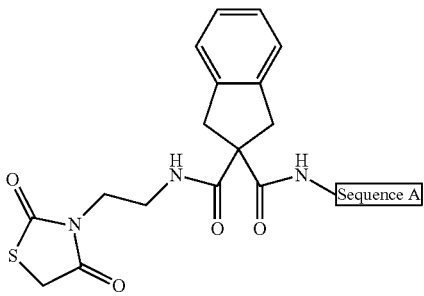
E-38

E-38 was prepared according to GP5 using 21.6 mg of resin (estimated loading 0.18 mmol/g) and I-33 to afford 3.5 mg of E-38 as a white solid. ESI-MS found 1080.0, $C_{198}H_{288}N_{46}O_{61}S$ (M+4H⁺) requires 1079.5.

Example 39: Compound 80

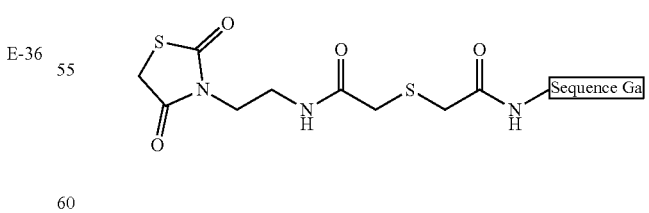
E-39

E-39 was prepared according to GP5 using 51.5 mg of resin (estimated loading 0.14 mmol/g) and I-9 to afford 0.8 mg of E-39 as a white solid. ESI-MS found 1164.9, $C_{214}H_{325}N_{47}O_{65}S_2$ (M+4H⁺) requires 1164.3.

Example 40: Compound 196

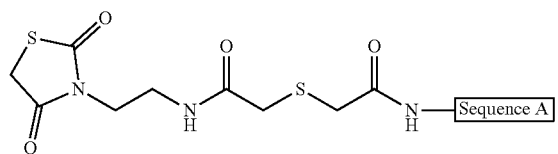

E-40

E-40 was prepared according to GP5 using 26.2 mg of resin (estimated loading 0.38 mmol/g) and I-34 to afford 3.3 mg of E-40 as a white solid. ESI-MS found 1064.0, $C_{191}H_{276}N_{46}O_{61}S_2$ (M−4H)⁻ requires 1063.5.

Example 41: Compound 195

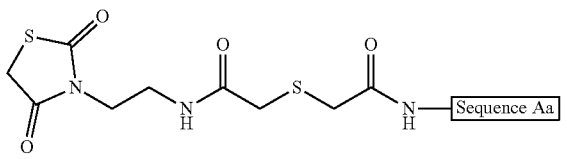

E-41

E-41 was prepared according to GP5 using 109.9 mg of resin (estimated loading 0.125 mmol/g) and I-34 to afford 7.3 mg of E-41 as a white solid. ESI-MS found 1156.1, $C_{212}H_{313}N_{47}O_{65}S2$ (M−4H) requires 1155.3.

Example 42: Compound 147

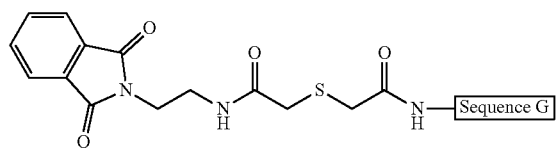

E-42

Peptide E-42 was prepared from 39 mg of resin (approximate loading 0.18 mmol/g) using I-35 and GP5 to afford E-42 as a white solid. ESI-MS found 1078.5, $C_{198}H_{282}N_{46}O_{61}S$ (M−4H)⁻ requires 1078.0.

Example 43: Compound 145

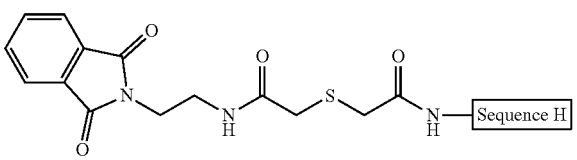

E-43

Peptide E-43 was prepared from 36 mg of resin (approximate loading 0.18 mmol/g) using I-35 and GP5 to afford E-43 as a white solid. ESI-MS found 1067.5, $C_{197}H_{282}N_{46}O_{59}S$ (M−4H)⁻ requires 1067.0.

Example 44: Compound 144

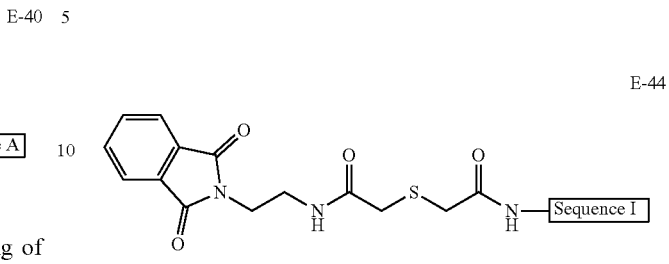

E-44

Peptide E-44 was prepared from 36 mg of resin (approximate loading 0.18 mmol/g) using I-35 and GP5 to afford E-44 as a white solid. ESI-MS found 1075.0, $C_{197}H_{280}N_{46}O_{61}S$ (M−4H)⁻ requires 1074.5.

Example 45: Compound 133

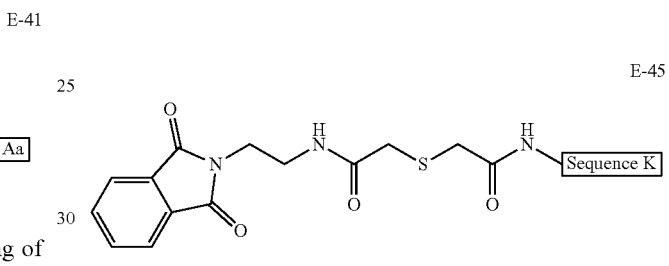

E-45

Peptide E-45 was prepared from 27.9 mg of resin (approximate loading 0.2 mmol/g) using I-35 and GP5 to afford 2.3 mg of E-45 as a white solid. ESI-MS found 1082.0, $C_{199}H_{284}N_{46}O_{61}S$ (M−4H)⁻ requires 1081.5.

Example 46: Compound 149

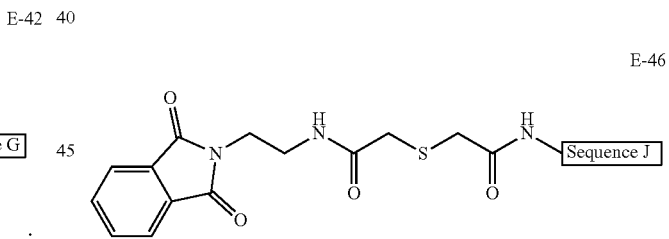

E-46

Peptide E-46 was prepared from 32 mg of resin (approximate loading 0.17 mmol/g) using I-35 and GP5 to afford 4.7 mg of E-46 as a white solid. ESI-MS found 1075.3, $C_{197}H_{279}N_{45}O_{62}S$ (M−4H)⁻ requires 1074.8.

Example 47: Compound 150

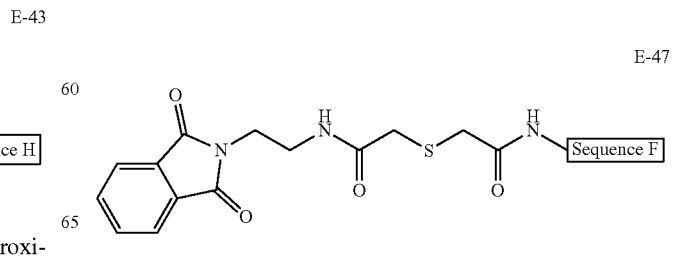

E-47

Peptide E-47 was prepared from 32.6 mg of resin (approximate loading 0.17 mmol/g) using I-35 and GP5 to afford 4.8 mg of E-47 as a white solid. ESI-MS found 1071.7, $C_{195}H_{273}N_{45}O_{63}S$ (M−4H)⁻ requires 1071.2.

Example 48: Compound 151

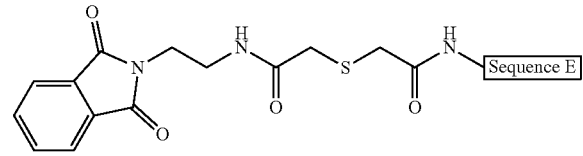

Peptide E-48 was prepared from 30.2 mg of resin (approximate loading 0.19 mmol/g) using I-35 and GP5 to afford 5.4 mg of E-48 as a white solid. ESI-MS found 1059.0, $C_{193}H_{280}N_{46}O_{60}S$ (M−4H)⁻ requires 1058.5.

Example 49: Compound 193

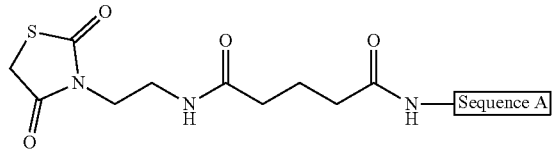

E-49 was prepared according to GP5 using 50 mg of resin (estimated loading 0.18 mmol/g) and I-36 to afford 7.7 mg of E-49 as a white solid. ESI-MS found 1059.5, $C_{192}H_{278}N_{46}O_{61}S$ (M−4H)⁻ requires 1059.0.

Example 50: Compound 155

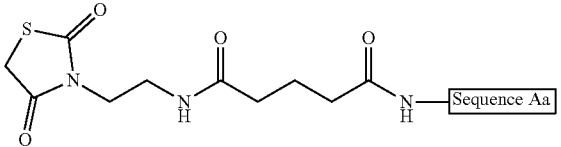

E-50 was prepared according to GP5 using 52.9 mg of resin (estimated loading 0.15 mmol/g) and I-36 to afford E-50 as a white solid. ESI-MS found 1151.3, $C_{212}H_{323}N_{47}O_{64}S$ (M−4H)⁻ requires 1150.8.

Example 51: Compound 192

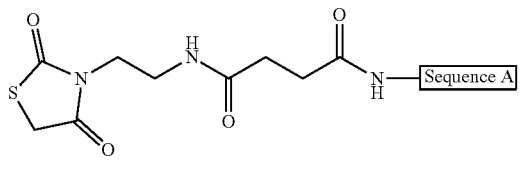

E-51 was prepared according to GP5 using 50 mg of resin (estimated loading 0.18 mmol/g) and I-37 to afford 5.9 mg of E-51 as a white solid. ESI-MS found 1056.0, $C_{191}H_{276}N_{46}O_{61}S$ (M−4H)⁻ requires 1055.5.

Example 52: Compound 194

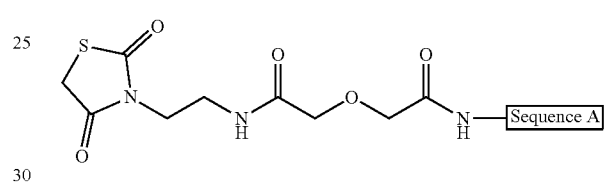

E-52 was prepared according to GP5 using 50 mg of resin (estimated loading 0.18 mmol/g) and I-38 to afford 3.1 mg of E-52 as a white solid. ESI-MS found 1060.0, $C_{191}H_{276}N_{46}O_{62}S$ (M−4H)⁻ requires 1059.5.

Example 53: Compound 191

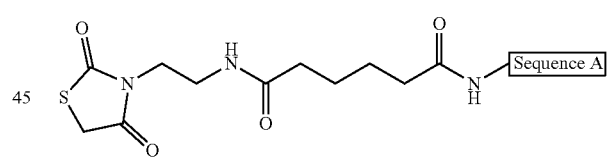

E-53 was prepared according to GP5 using 50 mg of resin (estimated loading 0.18 mmol/g) and I-39 to afford 7.8 mg of E-53 as a white solid. ESI-MS found 1063.0, $C_{193}H_{280}N_{46}O_{61}S$ (M−4H)⁻ requires 1062.5.

Example 54: Compound 187

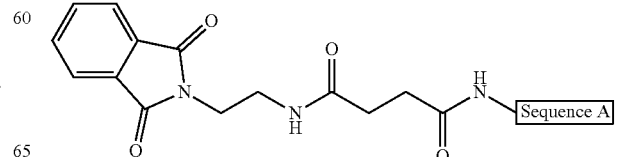

E-54 was prepared according to GP5 using 22 mg of resin (estimated loading 0.5 mmol/g) and I-40 to afford 1.8 mg of E-54 as a white solid. ESI-MS found 1063.5, $C_{196}H_{278}N_{46}O_{61}$ (M−4H)$^-$ requires 1063.0.

Example 55: Compound 188

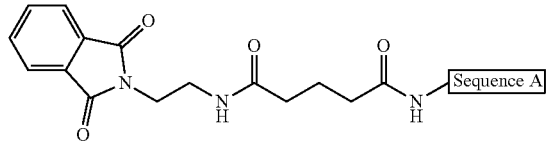
E-55

E-55 was prepared according to GP5 using 21.3 mg of resin (estimated loading 0.5 mmol/g) and I-41 to afford 1.0 mg of E-55 as a white solid. ESI-MS found 1067.0, $C_{197}H_{280}N_{46}O_{61}$ (M−4H)$^-$ requires 1066.5.

Example 56: Compound 184

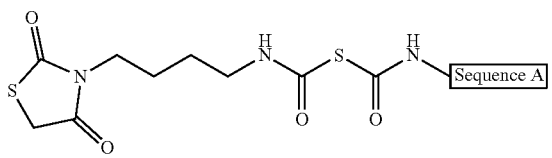
E-56

E-56 was prepared according to GP5 using 13.6 mg of resin (estimated loading 0.5 mmol/g) and I-42 to afford 0.8 mg of E-56 as a white solid. ESI-MS found 1071.0, $C_{193}H_{280}N_{46}O_{61}S_2$(M−4H)$^-$ requires 1070.5.

Example 57: Compound 186

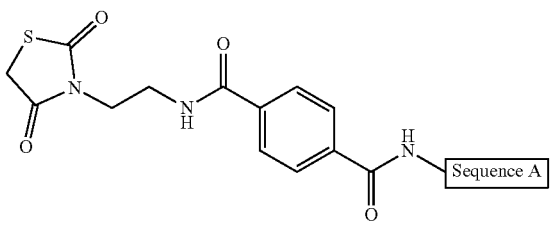
E-57

E-57 was prepared according to GP5 using 16.1 mg of resin (estimated loading 0.5 mmol/g) and I-44 to afford 0.4 mg of E-57 as a white solid. ESI-MS found 1068.0, $C_{195}H_{276}N_{46}O_{61}S$ (M−4H)$^-$ requires 1067.5.

Example 58: Compound 181

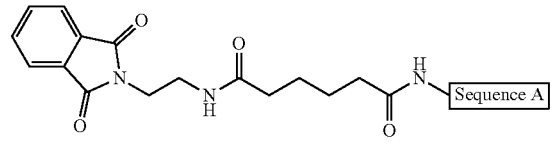
E-58

E-58 was prepared according to GP5 using 20.7 mg of resin (estimated loading 0.5 mmol/g) and I-48 to afford 0.3 mg of E-58 as a white solid. ESI-MS found 1070.5, $C_{198}H_{282}N_{46}O_{61}$ (M−4H)$^-$ requires 1070.0.

Example 59: Compound 180

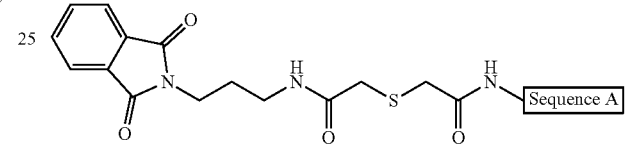
E-59

E-59 was prepared according to GP5 using 13.6 mg of resin (estimated loading 0.5 mmol/g) and I-51 to afford 0.6 mg of E-59 as a white solid. ESI-MS found 1075.0, $C_{197}H_{280}N_{46}O_{61}S$ (M−4H)$^-$ requires 1074.5.

Example 60: Compound 169

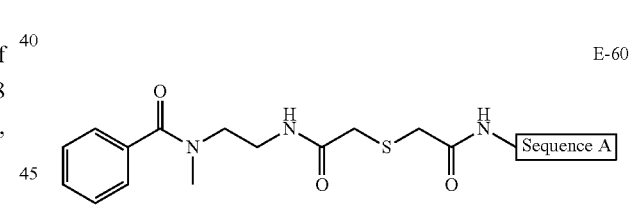
E-60

E-60 was prepared according to GP5 using 30.5 mg of resin (estimated loading 0.15 mmol/g) and I-53 to afford 3.6 mg of E-60 as a white solid. ESI-MS found 1068.5, $C_{196}H_{282}N_{46}O_{60}S$ (M−4H)$^-$ requires 1068.0.

Example 61: Compound 81

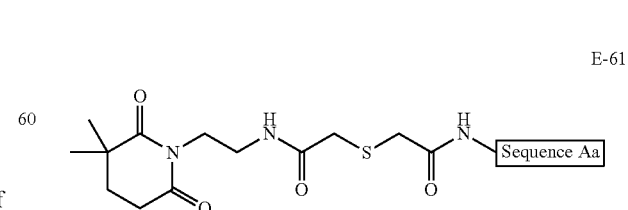
E-61

E-61 was prepared according to GP4 using 36.9 mg of resin (estimated loading 0.125 mmol/g) and I-55 to afford 5.1 mg of E-61 as a white solid. ESI-MS found 1163.8, $C_{216}H_{329}N_{47}O_{65}S$ (M+4H$^+$) requires 1163.3.

Example 62: Compound 185

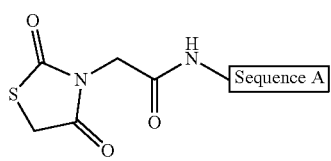

E-62

E-62 was prepared according to GP4 using 22 mg of resin (estimated loading 0.5 mmol/g) and commercially available 2-(2,4-dioxothiazolidin-3-yl)acetic acid to afford 0.8 mg of E-62 as a white solid. ESI-MS found 1034.7, $C_{187}H_{269}N_{45}O_{60}S$ (M−4H)$^-$ requires 1034.2.

Example 63: Compound 178 and washed with DMF (5×1 mL). A solution of ester I-56 (23.9 mg, 5.0 equiv.) in DMF (0.6 mL) was added, followed by DIPEA (19.7 µL, 10.0 equiv.) and the reaction mixture was agitated at ambient temperature for 16 hours. The resin was then drained and washed with DMF (5×) and DCM (5×) and then dried in vacuo. The resin was treated with 20% piperidine/DMF (3×5 min×1 mL) for Fmoc deprotection. The resin was drained and washed with DMF (5×1 mL). A solution of 2-(2,4-dioxothiazolidin-3-yl)acetic acid (9.9 mg, 5.0 equiv.) in DMF (0.6 mL) was added, followed by DIPEA (23.6 µL, 12.0 equiv.) and HATU (34.4 mg, 8.0 equiv.) and the reaction mixture was agitated at ambient temperature for 16 hours. The resin was then drained and washed with DMF (5×) and DCM (5×) and then dried in vacuo. Resin cleavage was performed with TFA/TIPS/H$_2$O (95:2.5:2.5 v/v/v, 1 mL) at ambient temperature for 1 hour. The reaction mixture was filtered and the resin was washed with TFA (2×1 mL). The combined filtrate and washes were concentrated. The residue was triturated with Et$_2$O (2 mL) and the supernatant was discarded. The residue was dissolved in AcOH (1 mL) and Scheme 142

1. 20% piperidine/DMF, 23° C.

2. 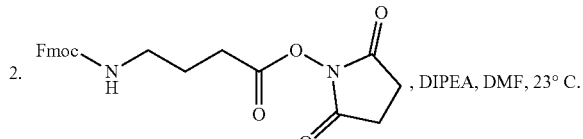, DIPEA, DMF, 23° C.

I-56

FmocHN—[Sequence A]—●
R-2

● = Rink amide resin 3. 20% piperidine/DMF, 23° C.

4. 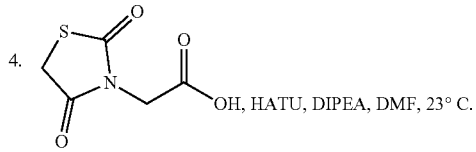OH, HATU, DIPEA, DMF, 23° C.

5. TFA/TIPS/H$_2$O (95:2.5:2.5 v/v/v), 23° C.

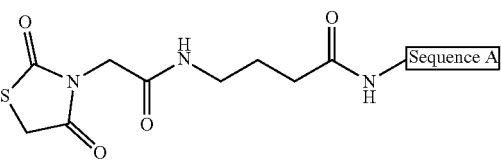

E-63

E-63 was synthesized as depicted in Scheme 142.
Resin R-2 (29.2 mg, approximate loading 0.39 mmol/g, 11.3 µmol) was treated with 20% piperidine/DMF (3×5 min×1 mL) for Fmoc deprotection. The resin was drained and purified by preparative HPLC (25 mM NH$_4$OAc/MeCN, 0-100% gradient over 30 minutes) to afford 1.6 mg of peptide E-63 as a white solid. ESI-MS found 1056.0, $C_{191}H_{276}N_{46}O_{61}S$ (M−4H)$^-$ requires 1055.5.

Example 64: Compound 177

Scheme 143

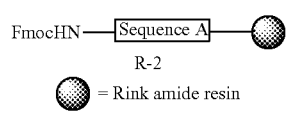

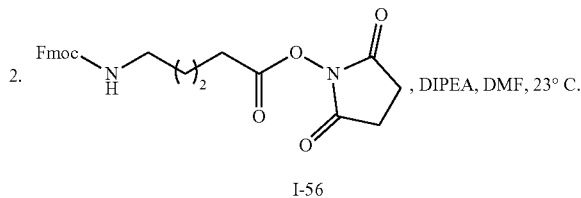

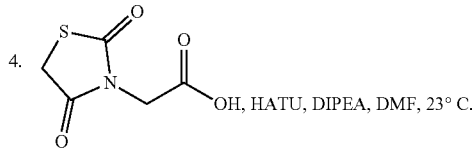

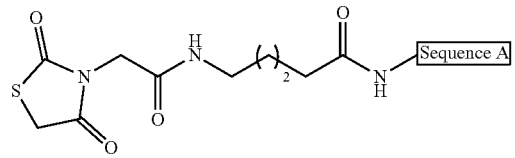

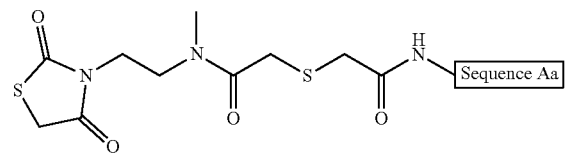

E-64

E-64 was synthesized as depicted in Scheme 143.

Resin R-2 (36.1 mg, approximate loading 0.39 mmol/g, 14.1 µmol) was treated with 20% piperidine/DMF (3×5 min×1 mL) for Fmoc deprotection. The resin was drained and washed with DMF (5×1 mL). A solution of ester I-57 (30.7 mg, 5.0 equiv.) in DMF (0.6 mL) was added, followed by DIPEA (24.5 µL, 10.0 equiv.) and the reaction mixture was agitated at ambient temperature for 16 hours. The resin was then drained and washed with DMF (5×) and DCM (5×) and then dried in vacuo. The resin was treated with 20% piperidine/DMF (3×5 min×1 mL) for Fmoc deprotection. The resin was drained and washed with DMF (5×1 mL). A solution of 2-(2,4-dioxothiazolidin-3-yl)acetic acid (12.3 mg, 5.0 equiv.) in DMF (0.6 mL) was added, followed by DIPEA (29.4 µL, 12.0 equiv.) and HATU (42.8 mg, 8.0 equiv.) and the reaction mixture was agitated at ambient temperature for 16 hours. The resin was then drained and washed with DMF (5×) and DCM (5×) and then dried in vacuo. Resin cleavage was performed with TFA/TIPS/H$_2$O (95:2.5:2.5 v/v/v, 1 mL) at ambient temperature for 1 hour. The reaction mixture was filtered and the resin was washed with TFA (2×1 mL). The combined filtrate and washes were concentrated. The residue was triturated with Et$_2$O (2 mL) and the supernatant was discarded. The residue was dissolved in AcOH (1 mL) and purified by preparative HPLC (25 mM NH$_4$OAc/MeCN, 0-100% gradient over 30 minutes) to afford 1.2 mg of peptide E-64 as a white solid. ESI-MS found 1059.5, C$_{192}$H$_{278}$N$_{46}$O$_{61}$S (M–4H)$^-$ requires 1059.0.

Example 65: Compound 93

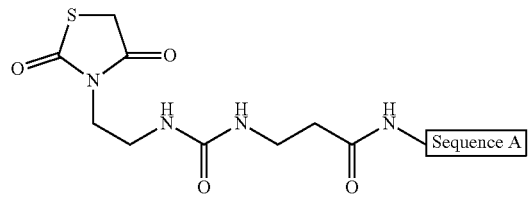

E-65 was prepared according to GP4 using 49.4 mg of resin (estimated loading 0.125 mmol/g) and I-60 to afford 5.8 mg of E-65 as a white solid. ESI-MS found 1161.4, C$_{213}$H$_{323}$N$_{47}$O$_{65}$S$_2$ (M+4H$^+$) requires 1160.8.

Example 66: Compound 148

E-66

E-66 was prepared according to GP4 using 28.6 mg of resin (estimated loading 0.18 mmol/g) and I-61 to afford 2.4 mg of E-66 as a white solid. ESI-MS found 1059.8, C$_{191}$H$_{277}$N$_{47}$O$_{61}$S (M–4H)$^-$ requires 1059.3.

Example 67: Compound 152

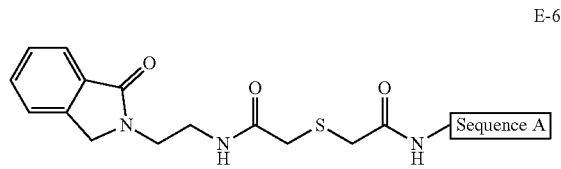

E-67 was prepared according to GP4 using 26.5 mg of resin (estimated loading 0.18 mmol/g) and I-62 to afford E-67 as a white solid. ESI-MS found 1068.0, $C_{196}H_{280}N_{46}O_{60}S$ (M–4H)⁻ requires 1067.5.

Example 68: Compound 109

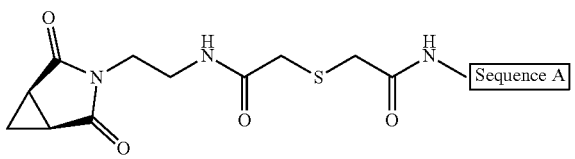

E-68 was prepared according to GP4 using 30.2 mg of resin (estimated loading 0.18 mmol/g) and I-64 to afford 4.6 mg of E-68 as a white solid. ESI-MS found 1064.0, $C_{193}H_{286}N_{46}O_{61}S$ (M+4H⁺) requires 1064.0.

Example 69: Compound 113

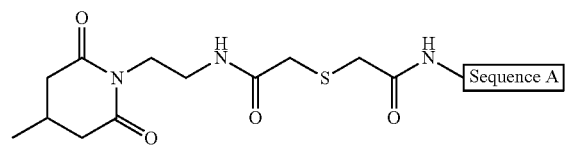

E-69 was prepared according to GP4 using 27.8 mg of resin (estimated loading 0.18 mmol/g) and I-66 to afford 2.9 mg of E-69 as a white solid. ESI-MS found 1067.9, $C_{194}H_{290}N_{46}O_{61}S$ (M+4H⁺) requires 1068.0.

Example 70: Compound 105

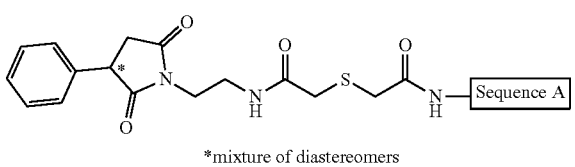 [SMILES: CNC(=O)CSCC(=O)NCCN1C(=O)CC(c2ccccc2)C1=O]

*mixture of diastereomers

Peptide E-70 was prepared from 35 mg of resin (approximate loading 0.18 mmol/g) using I-67 and GP4 to afford 2.4 mg of E-70 as a white solid. ESI-MS found 1080.0, $C_{198}H_{290}N_{46}O_{61}S$ (M+4H⁺) requires 1080.0.

Example 71: Compound 99

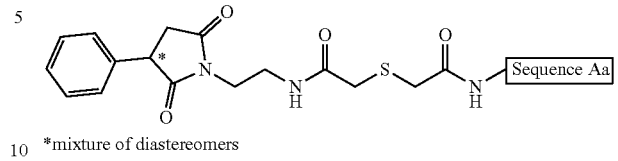

*mixture of diastereomers

Peptide E-71 was prepared from 35 mg of resin (approximate loading 0.125 mmol/g) using I-67 and GP4 to afford 1.5 mg of E-71 as a white solid. ESI-MS found 1171.9, $C_{219}H_{327}N_{47}O_{65}S$ (M+4H⁺) requires 1171.8.

Example 72: Compound 136

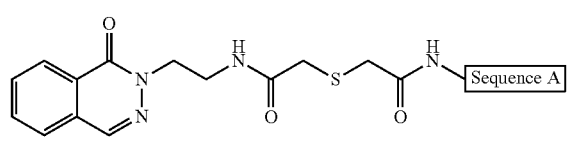

E-72 was prepared according to GP4 using 24.4 mg of resin (estimated loading 0.18 mmol/g) and I-68 to afford 2.5 mg of E-72 as a white solid. ESI-MS found 1071.3, $C_{196}H_{279}N_{47}O_{60}S$ (M–4H)⁻ requires 1070.8.

Example 73: Compound 17

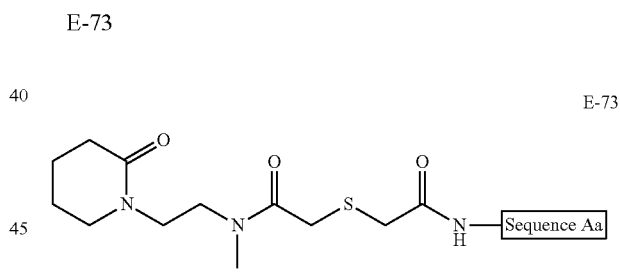

E-73 was prepared according to GP4 using 46.2 mg of resin (estimated loading 0.125 mmol/g) and I-69 to afford 6.6 mg of E-73 as a white solid. ESI-MS found 1156.8, $C_{215}H_{329}N_{47}O_{64}S$ (M+4H⁺) requires 1156.3.

Example 74: Compound 13

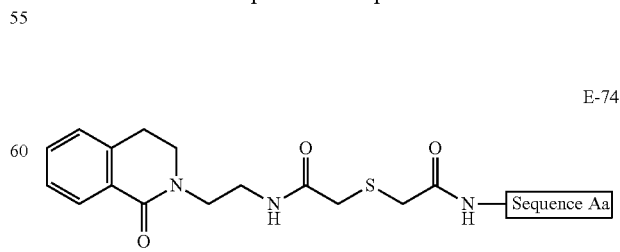

Peptide E-74 was prepared from 30 mg of resin (approximate loading 0.125 mmol/g) using I-70 and GP4 to afford 2.2 mg of E-74 as a white solid. ESI-MS found 1165.6, $C_{218}H_{327}N_{47}O_{64}S$ (M+4H$^+$) requires 1164.8.

Example 75: Compound 84

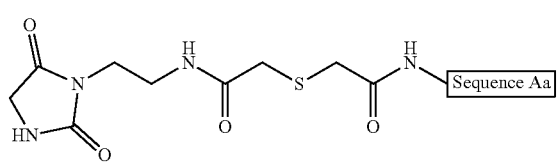

E-75 was prepared according to GP4 using 35.8 mg of resin (estimated loading 0.125 mmol/g) and I-71 to afford 3.2 mg of E-75 as a white solid. ESI-MS found 1153.5, $C_{212}H_{323}N_{48}O_{65}S$ (M+4H$^+$) requires 1153.1.

Example 76: Compound 87

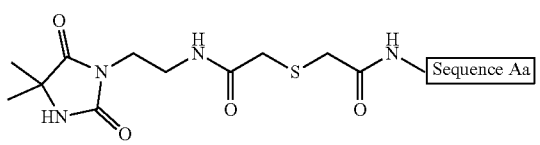

E-76 was prepared according to GP4 using 34.9 mg of resin (estimated loading 0.125 mmol/g) and I-72 to afford 3.5 mg of E-76 as a white solid. ESI-MS found 1160.5, $C_{214}H_{326}N_{48}O_{65}S$ (M+4H$^+$) requires 1160.1.

Example 77: Compound 90

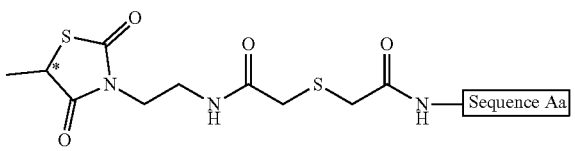

*mixture of diastereomers

Peptide E-77 was prepared from 37 mg of resin (approximate loading 0.125 mmol/g) using I-74 and GP1 to afford 3.1 mg of E-77 as a white solid. ESI-MS found 1161.4, $C_{213}H_{323}N_{47}O_{65}S_2$ (M+4H$^+$) requires 1160.8.

Example 78: Compound 94

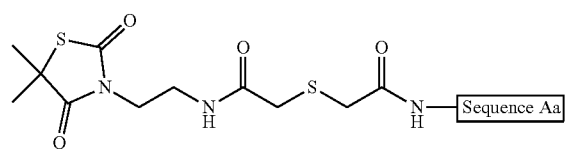

Peptide E-78 was prepared from 30 mg of resin (approximate loading 0.125 mmol/g) using I-76 and GP4 to afford 2.2 mg of E-78 as a white solid. ESI-MS found 1164.9, $C_{214}H_{325}N_{47}O_{65}S_2$ (M+4H$^+$) requires 1164.3.

Example 79: Compound 66

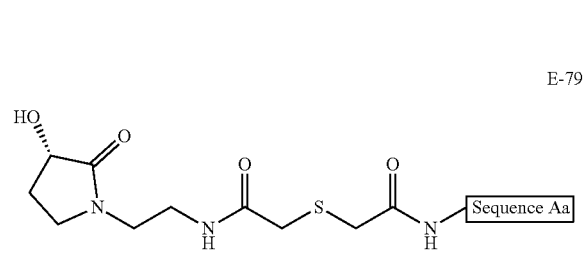 [SMILES: CNC(=O)CSCC(=O)NCCN1CC[C@H](O)C1=O]

E-79 was prepared according to GP4 using 38.4 mg of resin (estimated loading 0.125 mmol/g) and I-79 to afford 4.2 mg of E-79 as a white solid. ESI-MS found 1153.8, $C_{213}H_{325}N_{47}O_{65}S$ (M+4H$^+$) requires 1153.3.

Example 80: Compound 47

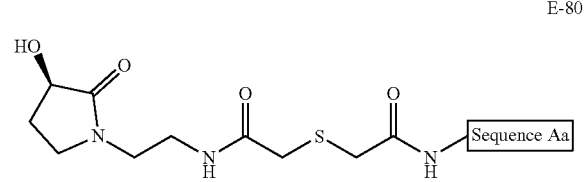 [SMILES: CNC(=O)CSCC(=O)NCCN1CC[C@@H](O)C1=O]

E-80 was prepared according to GP4 using 39.8 mg of resin (estimated loading 0.125 mmol/g) and I-80 to afford 2.5 mg of E-80 as a white solid. ESI-MS found 1153.8, $C_{213}H_{325}N_{47}O_{65}S$ (M+4H$^+$) requires 1153.3.

Example 81: Compound 88

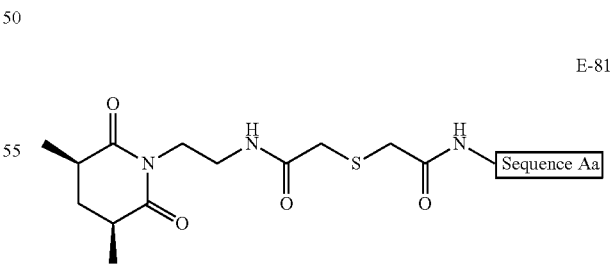

E-81 was prepared according to GP4 using 37.6 mg of resin (estimated loading 0.125 mmol/g) and I-82 to afford 2.1 mg of E-81 as a white solid. ESI-MS found 1163.8, $C_{216}H_{329}N_{47}O_{65}S$ (M+4H$^+$) requires 1163.3.

Example 82: Compound 35

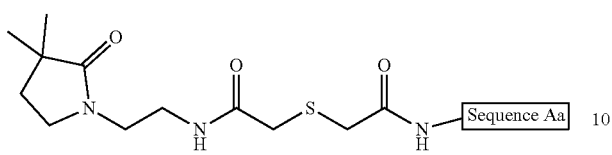

E-82 was prepared according to GP4 using 49.9 mg of resin (estimated loading 0.125 mmol/g) and I-85 to afford 6.5 mg of E-82 as a white solid. ESI-MS found 1156.9, $C_{215}H_{329}N_{47}O_{64}S$ (M+4H$^+$) requires 1156.3.

Example 83: Compound 41

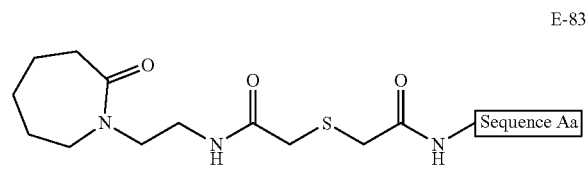 [SMILES: CNC(=O)CSCC(=O)NCCN1CCCCCC1=O]

E-83 was prepared according to GP4 using 50.8 mg of resin (estimated loading 0.125 mmol/g) and I-87 to afford 6.0 mg of E-83 as a white solid. ESI-MS found 1157.0, $C_{215}H_{329}N_{47}O_{64}S$ (M+4H$^+$) requires 1156.3.

Example 84: Compound 92

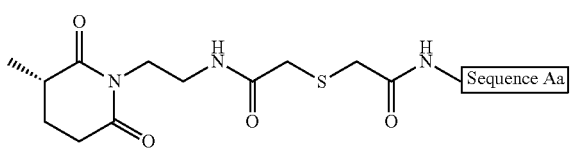

E-84 was prepared according to GP4 using 39.3 mg of resin (estimated loading 0.125 mmol/g) and I-89 to afford 2.9 mg of E-84 as a white solid. ESI-MS found 1160.4, $C_{215}H_{327}N_{47}O_{65}S$ (M+4H$^+$) requires 1159.8.

Example 85: Compound 85

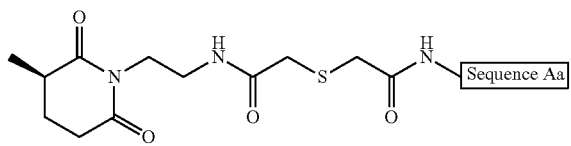

E-85 was prepared according to GP4 using 41.1 mg of resin (estimated loading 0.125 mmol/g) and I-90 to afford 3.7 mg of E-85 as a white solid. ESI-MS found 1160.4, $C_{215}H_{327}N_{47}O_{65}S$ (M+4H$^+$) requires 1159.8.

Example 86: Compound 97

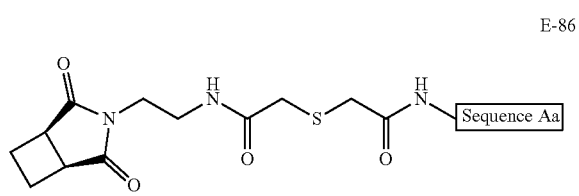 [SMILES: CNC(=O)CSCC(=O)NCCN1C(=O)[C@H]2CC[C@H]2C1=O]

E-86 was prepared according to GP4 using 30.9 mg of resin (estimated loading 0.125 mmol/g) and I-92 to afford 3.1 mg of E-86 as a white solid. ESI-MS found 1159.7, $C_{215}H_{325}N_{47}O_{65}S$ (M+4H$^+$) requires 1159.3.

Example 87: Compound 125

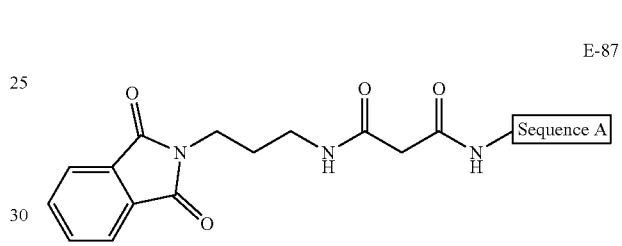

E-87 was prepared according to GP4 using 21.9 mg of resin (estimated loading 0.18 mmol/g) and I-94 to afford 2.2 mg of E-87 as a white solid. ESI-MS found 1063.5, $C_{196}H_{278}N_{46}O_{61}$ (M−4H)$^−$ requires 1063.0.

Example 88: Compound 128

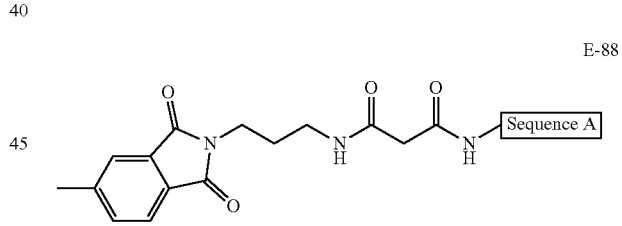

E-88 was prepared according to GP4 using 31 mg of resin (estimated loading 0.18 mmol/g) and I-96 to afford 3.4 mg of E-88 as a white solid. ESI-MS found 1067.0, $C_{197}H_{280}N_{46}O_{61}$ (M−4H)$^−$ requires 1066.5.

Example 89: Compound 126

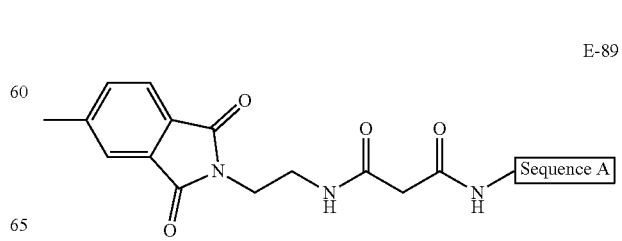

E-89 was prepared according to GP4 using 28.1 mg of resin (estimated loading 0.18 mmol/g) and I-98 to afford 2.5 mg of E-89 as a white solid. ESI-MS found 1063.5, $C_{196}H_{278}N_{46}O_{61}$ (M−4H)⁻ requires 1063.0.

Example 90: Compound 91

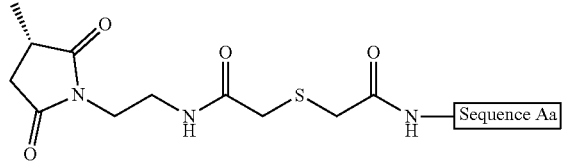

E-90

E-90 was prepared according to GP4 using 35.5 mg of resin (estimated loading 0.125 mmol/g) and I-101 to afford 4.8 mg of E-90 as a white solid. ESI-MS found 1156.8, $C_{214}H_{325}N_{47}O_{65}S$ (M+4H⁺) requires 1156.3.

Example 91: Compound 89

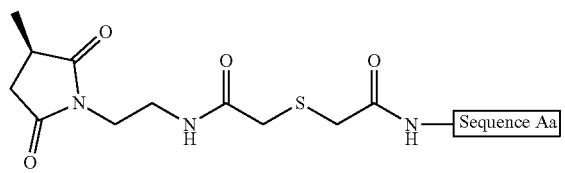

E-91

E-91 was prepared according to GP4 using 35.3 mg of resin (estimated loading 0.125 mmol/g) and I-100 to afford 3.2 mg of E-91 as a white solid. ESI-MS found 1156.8, $C_{214}H_{325}N_{47}O_{65}S$ (M+4H⁺) requires 1156.3.

Example 92: Compound 98

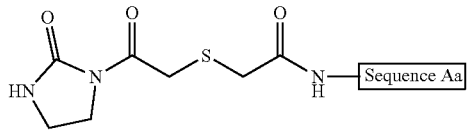

E-92

Peptide E-92 was prepared from 35 mg of resin (approximate loading 0.125 mmol/g) using I-104 and GP4 to afford 3.7 mg of E-92 as a white solid. ESI-MS found 1139.3, $C_{210}H_{319}N_{47}O_{64}S$ (M+4H⁺) requires 1138.8.

Example 93: Compound 103

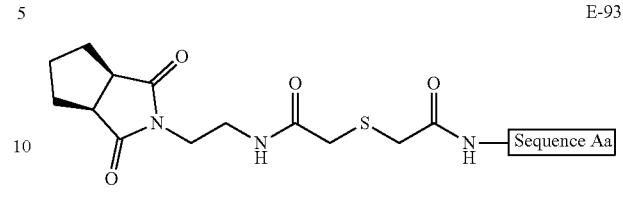

E-93

Peptide E-93 was prepared from 38 mg of resin (approximate loading 0.125 mmol/g) using I-106 and GP4 to afford 2.0 mg of E-93 as a white solid. ESI-MS found 1162.8, $C_{216}H_{327}N_{47}O_{65}S$ (M+4H⁺) requires 1162.8.

Example 94: Compound 106

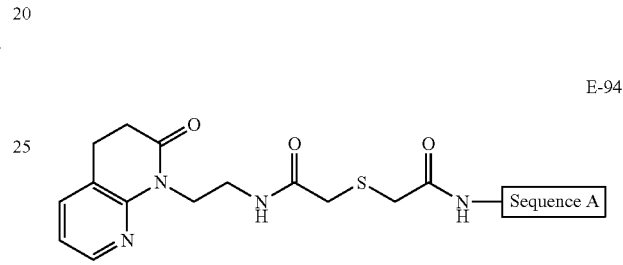

E-94

Peptide E-94 was prepared from 44 mg of resin (approximate loading 0.18 mmol/g) using I-109 and GP5 to afford 4.1 mg of E-94 as a white solid. ESI-MS found 1073.3, $C_{196}H_{289}N_{47}O_{60}S$ (M+4H⁺) requires 1073.2.

Example 95: Compound 107

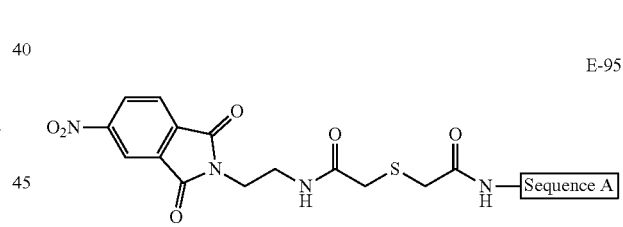

E-95

Peptide E-95 was prepared from 34 mg of resin (approximate loading 0.18 mmol/g) using I-111 and GP5 to afford 4.9 mg of E-95 as a white solid. ESI-MS found 1084.2, $C_{196}H_{285}N_{47}O_{63}S$ (M+4H⁺) requires 1084.2.

Example 96: Compound 108

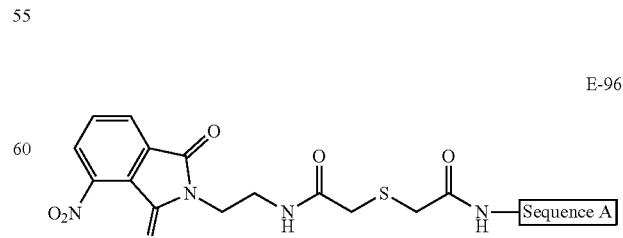

E-96

Peptide E-96 was prepared from 34 mg of resin (approximate loading 0.18 mmol/g) using I-113 and GP5 to afford

Example 97: Compound 86

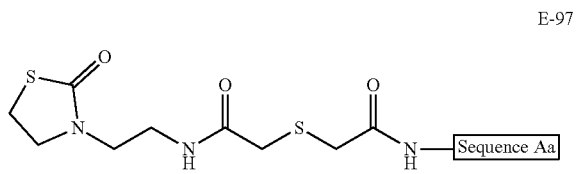 [SMILES: CNC(=O)CSCC(=O)NCCN1CCSC1=O]

E-97

Peptide E-97 was prepared from 35 mg of resin (approximate loading 0.125 mmol/g) using I-115 and GP4 to afford 2.5 mg of E-97 as a white solid. ESI-MS found 1154.4, $C_{212}H_{323}N_{47}O_{64}S_2$ (M+4H$^+$) requires 1153.8.

Example 98: Compound 146

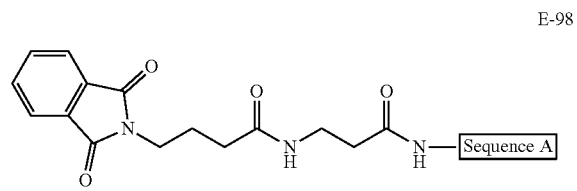 [SMILES: CNC(=O)CCNC(=O)CCCN1C(=O)c2ccccc2C1=O]

E-98

Peptide E-98 was prepared from 26 mg of resin (approximate loading 0.18 mmol/g) using I-118 and GP4 to afford E-98 as a white solid. ESI-MS found 1167.0, $C_{197}H_{282}N_{46}O_{59}S$ (M–4H)$^-$ requires 1167.0.

Example 99: Compound 115

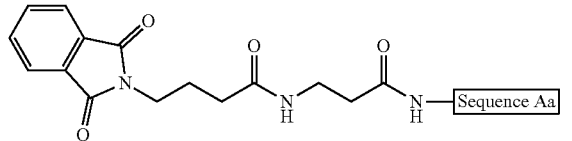

E-99

Peptide E-99 was prepared from 108 mg of resin (approximate loading 0.18 mmol/g) using I-118 and GP4 to afford 1.0 mg of E-99 as a white solid. ESI-MS found 1160.3, $C_{218}H_{325}N_{47}O_{65}$ (M+4H$^+$) requires 1160.3.

Example 100: Compound 154

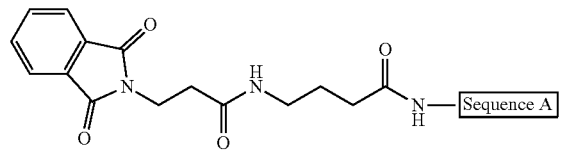

E-100

To 26 mg of resin (approximate loading 0.18 mmol/g, 4.68 μmol) in a 3 mL polypropylene tube with an end-cap was added 20% v/v piperidine/DMF (2 mL). The tube was capped, agitated at ambient temperature for 30 minutes, and then drained. The resin was washed with DMF (5×3 mL). A solution of carboxylic acid building block I-120 (8 mg, 5.6 equiv.) in DMF (2.8 mL) was added to the resin, followed by EDC (27.4 mg, 30.5 equiv.) and 1-hydroxybenzotriazole hydrate (34 mg, 43.1 equiv.). The reaction mixture was agitated at ambient temperature for 18 hours. The reaction mixture was drained; the resin was washed with DMF (5×3 mL), DCM (5×3 mL), and dried in vacuo for 30 minutes.

The resin was transferred to a 15 mL Falcon tube and 3 mL of cleavage reagent (95:2.5:2.5 v/v/v TFA/TIS/H$_2$O) was added. The reaction mixture was agitated at ambient temperature for 1 hour. The resin was filtered and washed with TFA (2×3 mL). The combined filtrate and washes were concentrated under reduced pressure to afford a residue, which was triturated with Et$_2$O (3 mL) to precipitate the peptide. The peptide was re-dissolved in glacial AcOH (2 mL) and purified by preparative HPLC (Phenomenex Jupiter 10 μM Proteo 90 Å LC column, 250×21.2 mm, with flow rate—15 mL/min, gradient of 0-100% acetonitrile in 25 mM aqueous ammonium acetate over 30 minutes) to afford E-100 as a white solid. ESI-MS found 1169.0, $C_{197}H_{288}N_{46}O_{61}$ (M+4H$^+$) requires 1168.5.

Example 101: Compound 156

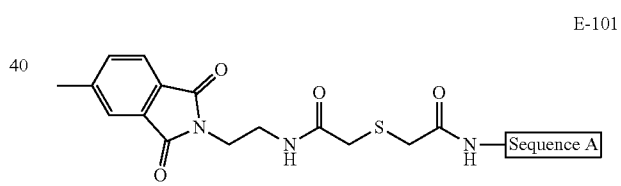

E-101

Peptide E-101 was prepared from 25 mg of resin (approximate loading 0.18 mmol/g) using I-122 and GP5 to afford E-101 as a white solid.

Example 102: Compound 157

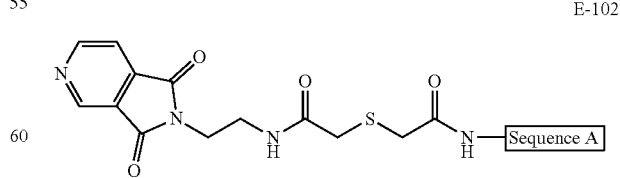

E-102

Peptide E-102 was prepared from 25 mg of resin (approximate loading 0.18 mmol/g) using I-124 and GP5 to afford E-102 as a white solid. ESI-MS found 1073.8, $C_{195}H_{285}N_{47}O_{61}S$ (M+4H$^+$) requires 1073.3.

Example 103: Compound 158

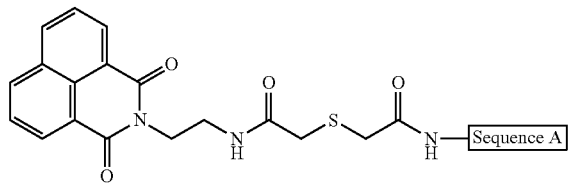

Peptide E-103 was prepared from 25 mg of resin (approximate loading 0.18 mmol/g) using I-126 and GP5 to afford E-103 as a white solid. ESI-MS found 1083.5, $C_{200}H_{280}N_{46}O_{61}S$ (M−4H)⁻ requires 1084.0.

Example 104: Compound 159

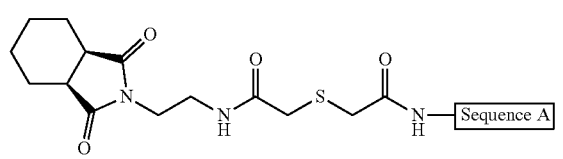

Peptide E-104 was prepared from 25 mg of resin (approximate loading 0.18 mmol/g) using I-129 and GP5 to afford E-104 as a white solid. ESI-MS found 1073.0, $C_{196}H_{284}N_{46}O_{61}S$ (M−4H)⁻ requires 1072.5.

Example 105: Compound 160

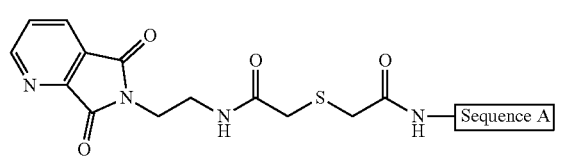

Peptide E-105 was prepared from 25 mg of resin (approximate loading 0.18 mmol/g) using I-131 and GP5 to afford E-105 as a white solid. ESI-MS found 1071.8, $C_{195}H_{277}N_{47}O_{61}S$ (M−4H)⁻ requires 1071.3.

Example 106: Compound 161

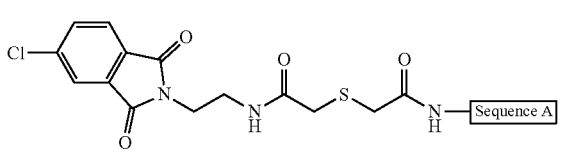

Peptide E-106 was prepared from 25 mg of resin (approximate loading 0.18 mmol/g) using I-133 and GP5 to afford E-106 as a white solid. ESI-MS found 1080.2, $C_{196}H_{277}N_{46}O_{61}SCl$ (M−4H)⁻ requires 1079.5.

Example 107: Compound 162

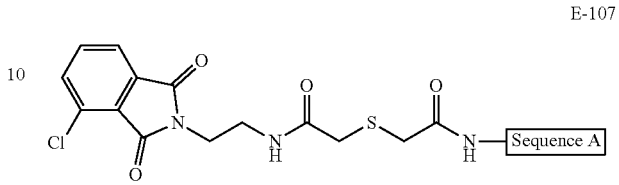

Peptide E-107 was prepared from 25 mg of resin (approximate loading 0.18 mmol/g) using I-135 and GP5 to afford E-107 as a white solid. ESI-MS found 1080.2, $C_{196}H_{277}N_{46}O_{61}SCl$ (M−4H)⁻ requires 1079.5.

Example 108: Compound 163

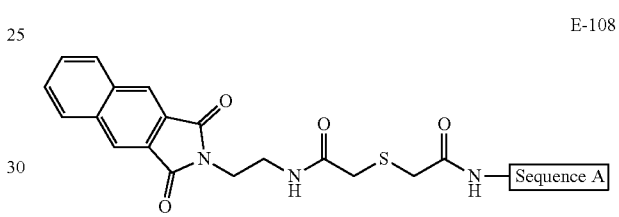

Peptide E-108 was prepared from 25 mg of resin (approximate loading 0.18 mmol/g) using I-137 and GP5 to afford E-108 as a white solid. ESI-MS found 1084.0, $C_{200}H_{280}N_{46}O_{61}S$ (M−4H)⁻ requires 1083.5.

Example 109: Compound 164

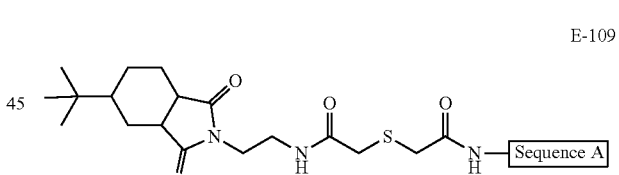

Peptide E-109 was prepared from 25 mg of resin (approximate loading 0.18 mmol/g) using I-139 and GP5 to afford E-109 as a white solid. ESI-MS found 1085.5, $C_{200}H_{290}N_{46}O_{61}S$ (M−4H)⁻ requires 1085.0.

Example 110: Compound 168

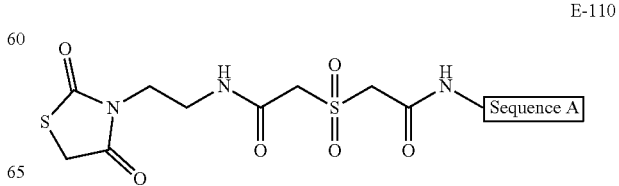

E-110 was prepared according to GP4 using 21.8 mg of resin (estimated loading 0.15 mmol/g) and I-141 to afford 2.0 mg of E-110 as a white solid. ESI-MS found 1072.0, $C_{191}H_{276}N_{46}O_{63}S_2$(M−4H)⁻ requires 1071.5.

Example 111: Compound 10

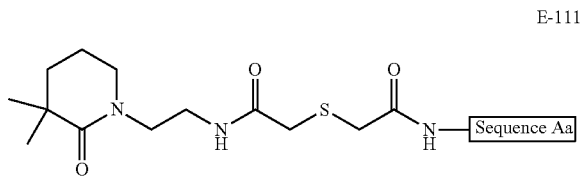

E-111

Peptide E-111 was prepared from 30 mg of resin (approximate loading 0.125 mmol/g) using I-145 and GP4 to afford 2.2 mg of E-111 as a white solid. ESI-MS found 1160.3, $C_{216}H_{331}N_{47}O_{64}S$ (M+4H⁺) requires 1159.8.

Example 112: Compound 16

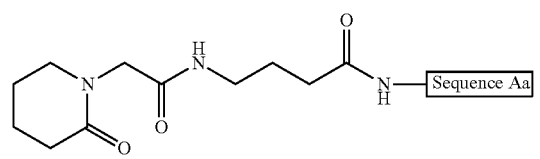

E-112

Peptide E-112 was prepared from 33 mg of resin (approximate loading 0.125 mmol/g) using I-146 and GP4 to afford 3.7 mg of E-112 as a white solid. ESI-MS found 1145.3, $C_{215}H_{329}N_{47}O_{64}$ (M+4H⁺) requires 1144.8.

Example 113: Compound 15

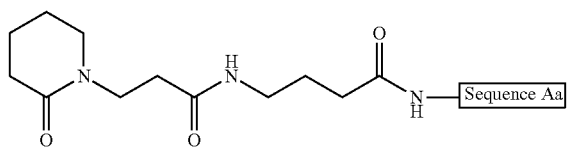

E-113

Peptide E-113 was prepared from 33 mg of resin (approximate loading 0.125 mmol/g) using I-147 and GP4 to afford 3.4 mg of E-113 as a white solid. ESI-MS found 1148.8, $C_{215}H_{329}N_{47}O_{64}$ (M+4H⁺) requires 1148.3.

Example 114: Compound 20

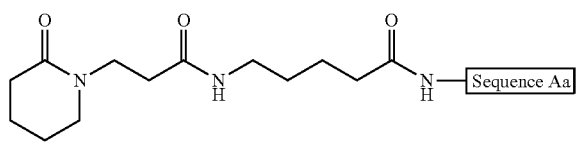

E-114

Peptide E-114 was prepared from 45 mg of resin (approximate loading 0.125 mmol/g) using I-148 and GP4 to afford 5.8 mg of E-114 as a white solid. ESI-MS found 1152.3, $C_{216}H_{331}N_{47}O_{64}$ (M+4H⁺) requires 1151.8.

Example 115: Compound 82

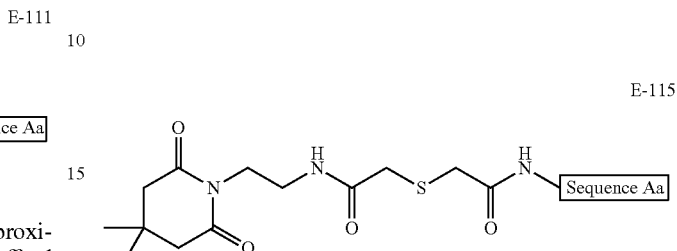

E-115

E-115 was prepared according to GP4 using 45.9 mg of resin (estimated loading 0.125 mmol/g) and I-150 to afford 6.0 mg of E-115 as a white solid. ESI-MS found 1163.9, $C_{216}H_{329}N_{47}O_{65}S$ (M+4H⁺) requires 1163.3.

Example 116: Compound 95

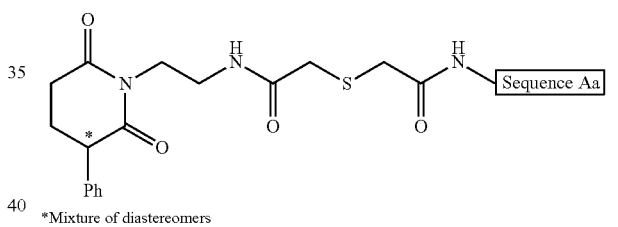

E-116

*Mixture of diastereomers

E-116 was prepared according to GP4 using 30.5 mg of resin (estimated loading 0.125 mmol/g) and I-152 to afford 2.4 mg of E-116 as a white solid. ESI-MS found 1175.9, $C_{220}H_{329}N_{47}O_{65}S$ (M+4H⁺) requires 1175.3.

Example 117: Compound 96

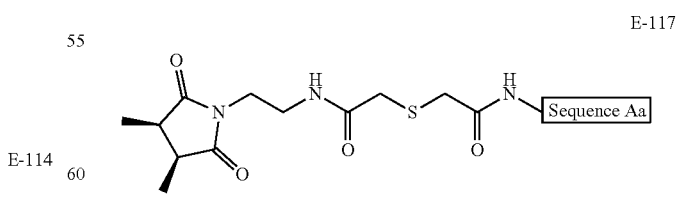

E-117

E-117 was prepared according to GP4 using 34.2 mg of resin (estimated loading 0.125 mmol/g) and I-155 to afford 2.1 mg of E-117 as a white solid. ESI-MS found 1160.3, $C_{215}H_{327}N_{47}O_{65}S$ (M+4H⁺) requires 1159.8.

Example 118: Compound 100

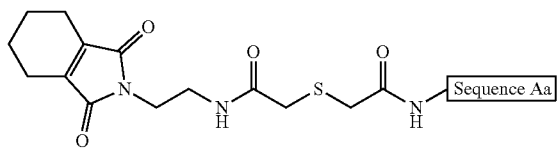

E-118 was prepared according to GP4 using 28 mg of resin (estimated loading 0.125 mmol/g) and I-157 to afford E-118 as a white solid. ESI-MS found 1166.4, $C_{217}H_{327}N_{47}O_{65}S$ (M+4H$^+$) requires 1165.8.

Example 119: Compound 101

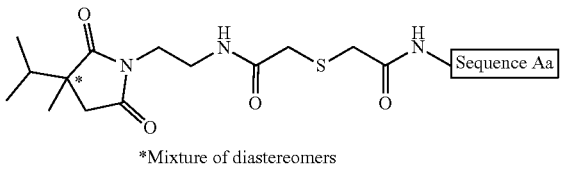

*Mixture of diastereomers

E-119 was prepared according to GP4 using 29.8 mg of resin (estimated loading 0.125 mmol/g) and I-159 to afford 3.6 mg of E-119 as a white solid. ESI-MS found 1167.1, $C_{217}H_{331}N_{47}O_{65}S$ (M+4H$^+$) requires 1166.8.

Example 120: Compound 102

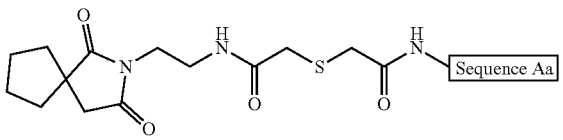

E-120 was prepared according to GP4 using 29.3 mg of resin (estimated loading 0.125 mmol/g) and I-161 to afford 4.4 mg of E-120 as a white solid. ESI-MS found 1166.8, $C_{217}H_{329}N_{47}O_{65}S$ (M+4H$^+$) requires 1166.3.

Example 121: Compound 104

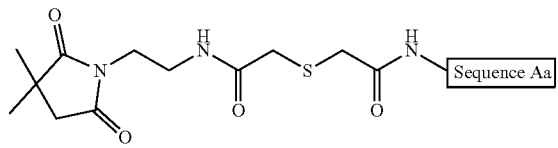

E-121 was prepared according to GP4 using 26.2 mg of resin (estimated loading 0.125 mmol/g) and I-163 to afford 3.2 mg of E-121 as a white solid. ESI-MS found 1160.3, $C_{215}H_{327}N_{47}O_{65}S$ (M+4H$^+$) requires 1159.8.

Example 122: Compound 110

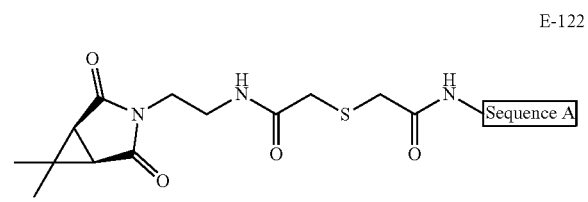

E-122 was prepared according to GP4 using 29.3 mg of resin (estimated loading 0.18 mmol/g) and I-165 to afford 0.6 mg of E-122 as a white solid. ESI-MS found 1070.9, $C_{195}H_{290}N_{46}O_{61}S$ (M+4H$^+$) requires 1071.0.

Example 123: Compound 111

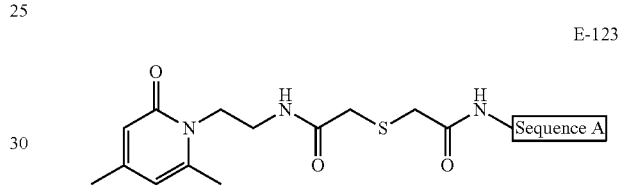

E-123 was prepared according to GP4 using 28.9 mg of resin (estimated loading 0.18 mmol/g) and I-167 to afford 4.1 mg of E-123 as a white solid. ESI-MS found 1067.1, $C_{195}H_{290}N_{46}O_{60}S$ (M+4H$^+$) requires 1067.0.

Example 124: Compound 26

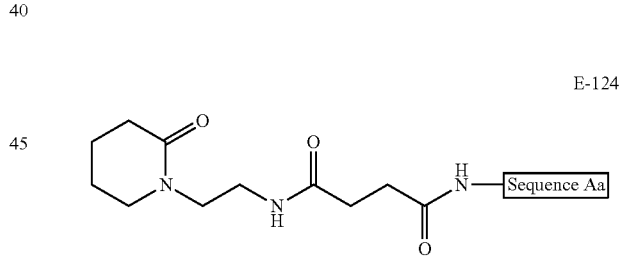

E-124 was prepared according to GP4 using 42.9 mg of resin (estimated loading 0.125 mmol/g) and I-168 to afford 18.6 mg of E-124 as a white solid. ESI-MS found 1145.4, $C_{214}H_{327}N_{47}O_{64}$ (M+4H$^+$) requires 1144.8.

Example 125: Compound 27

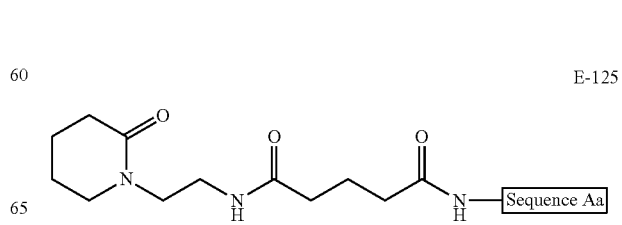

E-125 was prepared according to GP4 using 45.8 mg of resin (estimated loading 0.125 mmol/g) and I-169 to afford 5.4 mg of I-169 as a white solid. ESI-MS found 1148.9, $C_{215}H_{329}N_{47}O_{64}$ (M+4H$^+$) requires 1148.3.

Example 126: Compound 18

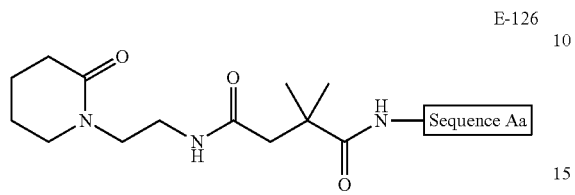

E-126 was prepared according to GP4 using 45.5 mg of resin (estimated loading 0.125 mmol/g) and I-170 to afford 4.7 mg of E-126 as a white solid. ESI-MS found 1152.3, $C_{216}H_{331}N_{47}O_{64}$ (M+4H$^+$) requires 1151.8.

Example 127: Compound 112

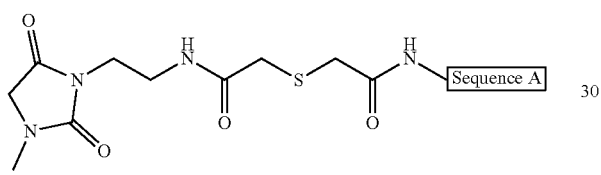

E-127 was prepared according to GP4 using 36.2 mg of resin (estimated loading 0.18 mmol/g) and I-172 to afford 2.1 mg of E-127 as a white solid. ESI-MS found 1064.8, $C_{192}H_{287}N_{47}O_{61}S$ (M+4H$^+$) requires 1064.8.

Example 128: Compound 9

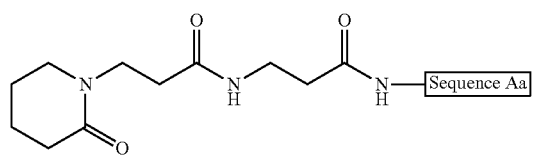

E-128 was prepared according to GP4 using 38.3 mg of resin (estimated loading 0.125 mmol/g) and I-174 to afford 3.1 mg of E-128 as a white solid. ESI-MS found 1145.4, $C_{214}H_{327}N_{47}O_{64}$ (M+4H$^+$) requires 1144.8.

Example 129: Compound 5

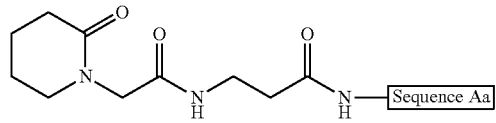

E-129 was prepared according to GP4 using 40.1 mg of resin (estimated loading 0.125 mmol/g) and I-176 to afford 5.2 mg of E-129 as a white solid. ESI-MS found 1141.8, $C_{213}H_{325}N_{47}O_{64}$ (M+4H$^+$) requires 1141.3.

Example 130: Compound 4

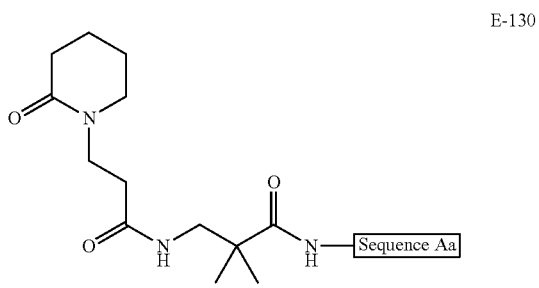 [SMILES: CNC(=O)C(C)(C)CNC(=O)CCN1CCCCC1=O]

E-130 was prepared according to GP4 using 40 mg of resin (estimated loading 0.125 mmol/g) and I-180 to afford 5.2 mg of E-130 as a white solid. ESI-MS found 1152.4, $C_{216}H_{331}N_{47}O_{64}$ (M+4H$^+$) requires 1151.8.

Example 131: Compound 3

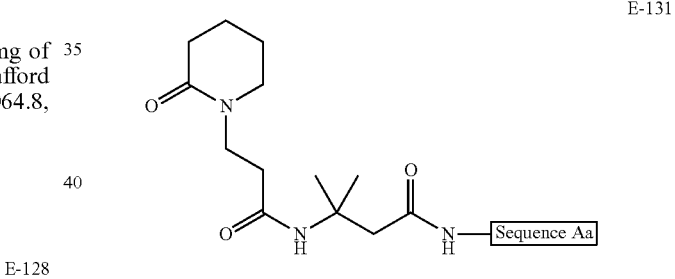

E-131 was prepared according to GP4 using 39.3 mg of resin (estimated loading 0.125 mmol/g) and I-183 to afford 3.0 mg of E-131 as a white solid. ESI-MS found 1152.3, $C_{216}H_{331}N_{47}O_{64}$ (M+4H$^+$) requires 1151.8.

Example 132: Compound 2

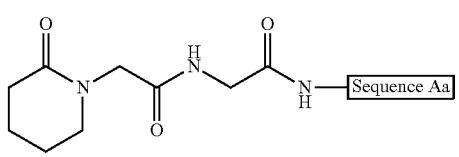

E-132 was prepared according to GP4 using 39.8 mg of resin (estimated loading 0.125 mmol/g) and I-184 to afford 5.7 mg of E-132 as a white solid. ESI-MS found 1138.3, $C_{212}H_{323}N_{47}O_{64}$ (M+4H$^+$) requires 1141.3.

Example 133: Compound 1

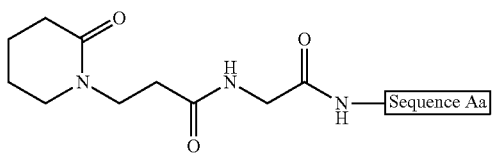
E-133

E-133 was prepared according to GP4 using 38.5 mg of resin (estimated loading 0.125 mmol/g) and I-185 to afford 4.3 mg of E-133 as a white solid. ESI-MS found 1141.8, $C_{213}H_{325}N_{47}O_{64}$ (M+4H$^+$) requires 1141.3.

Example 134: Compound 130

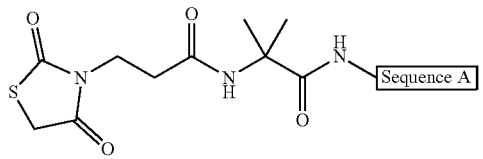
E-134

E-134 was prepared according to GP4 using 27 mg of resin (estimated loading 0.18 mmol/g) and I-187 to afford 1.6 mg of E-134 as a white solid. ESI-MS found 1059.5, $C_{192}H_{278}N_{46}O_{61}S$ (M–4H)$^-$ requires 1059.0.

Example 135: Compound 167

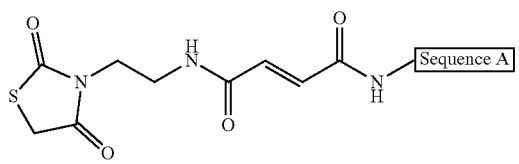
E-135

E-135 was prepared according to GP4 using 25.1 mg of resin (estimated loading 0.15 mmol/g) and I-188 to afford 3.7 mg of E-135 as a white solid. ESI-MS found 1055.5, $C_{191}H_{274}N_{46}O_{61}S$ (M–4H)$^-$ requires 1055.0.

Example 136: Compound 179

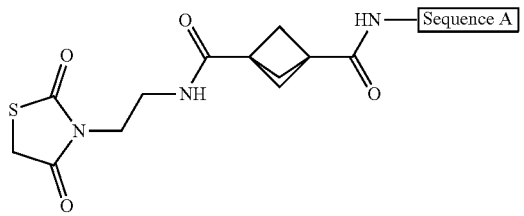
E-136

E-136 was prepared according to GP5 using 20.9 mg of resin (estimated loading 0.15 mmol/g) and I-191 to afford 1.6 mg of E-136 as a white solid. ESI-MS found 1065.5, $C_{194}H_{278}N_{46}O_{61}S$ (M–4H)$^-$ requires 1065.0.

Example 137: Compound 183

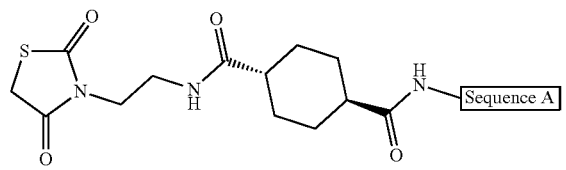
E-137

E-137 was prepared according to GP5 using 16.6 mg of resin (estimated loading 0.5 mmol/g) and I-194 to afford 1.3 mg of E-137 as a white solid. ESI-MS found 1069.5, $C_{195}H_{282}N_{46}O_{61}S$ (M–4H)$^-$ requires 1069.0.

Example 138: Compound 182

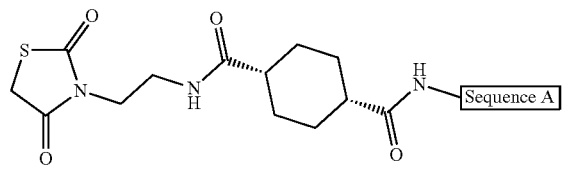
E-138

E-138 was prepared according to GP5 using 16.9 mg of resin (estimated loading 0.5 mmol/g) and I-197 to afford 1.0 mg of E-138 as a white solid. ESI-MS found 1069.5, $C_{195}H_{282}N_{46}O_{61}S$ (M–4H)$^-$ requires 1069.0.

Example 139: Compound 176

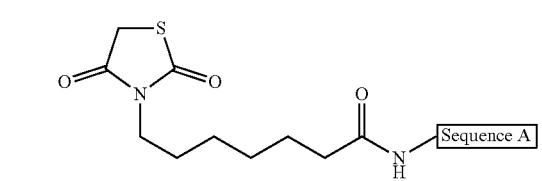
E-139

E-139 was prepared according to GP4 using 22.2 mg of resin (estimated loading 0.15 mmol/g) and I-200 to afford 0.9 mg of E-139 as a white solid. ESI-MS found 1052.3, $C_{192}H_{279}N_{45}O_{60}S$ (M–4H)$^-$ requires 1051.8.

Example 140: Compound 175

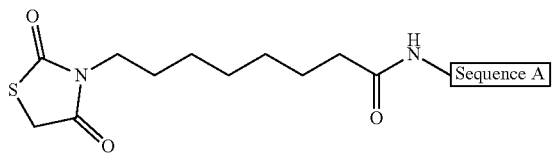

E-140 was prepared according to GP4 using 31 mg of resin (estimated loading 0.15 mmol/g) and I-202 to afford 2.7 mg of E-140 as a white solid. ESI-MS found 1055.8, $C_{193}H_{281}N_{45}O_{60}S$ (M−4H)⁻ requires 1055.3.

Example 141: Compound 174

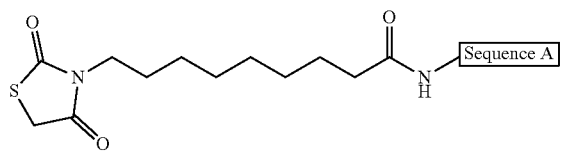

E-141 was prepared according to GP4 using 24.7 mg of resin (estimated loading 0.15 mmol/g) and I-204 to afford 1.6 mg of E-141 as a white solid. ESI-MS found 1059.3, $C_{194}H_{283}N_{45}O_{60}S$ (M−4H)⁻ requires 1058.8.

Example 142: Compound 166

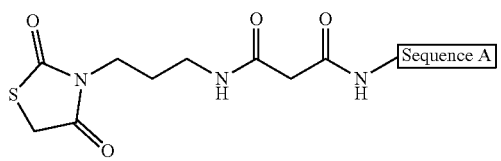

E-142 was prepared according to GP4 using 20.7 mg of resin (estimated loading 0.15 mmol/g) and I-209 to afford 2.4 mg of E-142 as a white solid. ESI-MS found 1056.0, $C_{191}H_{274}N_{46}O_{61}S$ (M−4H) requires 1055.5.

Example 143: Compound 165

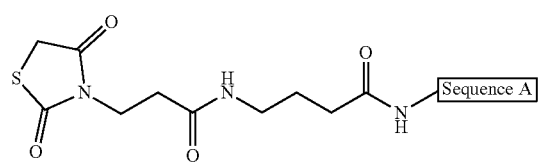

E-143 was prepared according to GP4 using 21 mg of resin (estimated loading 0.15 mmol/g) and I-213 to afford 2.1 mg of E-143 as a white solid. ESI-MS found 1059.5, $C_{192}H_{278}N_{46}O_{61}S$ (M−4H)⁻ requires 1059.0.

Example 144: Compound 51

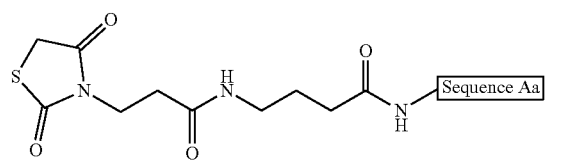

E-144 was prepared according to GP4 using 45.5 mg of resin (estimated loading 0.125 mmol/g) and I-213 to afford 4.8 mg of E-144 as a white solid. ESI-MS found 1153.1, $C_{213}H_{323}N_{47}O_{65}S$ (M+4H⁺) requires 1152.8.

Example 145: Compound 172

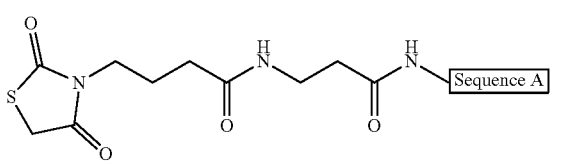

E-145 was prepared according to GP4 using 23 mg of resin (estimated loading 0.15 mmol/g) and I-217 to afford 3.0 mg of E-145 as a white solid. ESI-MS found 1059.5, $C_{192}H_{278}N_{46}O_{61}S$ (M−4H)⁻ requires 1059.0.

Example 146: Compound 171

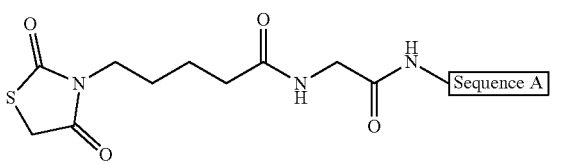

E-146 was prepared according to GP4 using 24.1 mg of resin (estimated loading 0.15 mmol/g) and I-221 to afford 2.5 mg of E-146 as a white solid. ESI-MS found 1059.5, $C_{192}H_{278}N_{46}O_{61}S$ (M−4H)⁻ requires 1059.0.

Example 147: Compound 48

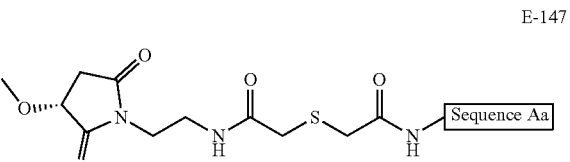

E-147 was prepared according to GP4 using 42.5 mg of resin (estimated loading 0.125 mmol/g) and I-225 to afford 1.7 mg of E-147 as a white solid. ESI-MS found 1160.8, $C_{214}H_{325}N_{47}O_{66}S$ (M+4H$^+$) requires 1160.3.

Example 148: Compound 49

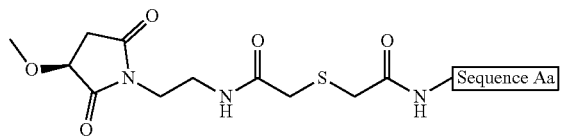

E-148

E-148 was prepared according to GP4 using 44.5 mg of resin (estimated loading 0.125 mmol/g) and I-229 to afford 2.8 mg of E-148 as a white solid. ESI-MS found 1160.7, $C_{214}H_{325}N_{47}O_{66}S$ (M+4H$^+$) requires 1160.3.

Example 149: Compound 28

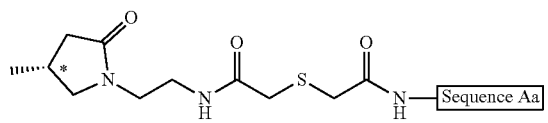

E-149

*Absolute configuration not known

E-149 was prepared according to GP4 using 38.9 mg of resin (estimated loading 0.125 mmol/g) and (R*)-I-234 to afford 5.7 mg of E-149 as a white solid. ESI-MS found 1153.3, $C_{214}H_{327}N_{47}O_{64}S$ (M+4H$^+$) requires 1152.8.

Example 150: Compound 64

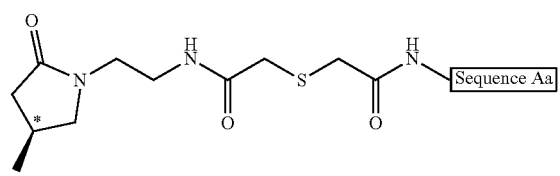

E-150

*Absolute configuration not known

E-150 was prepared according to GP4 using 39 mg of resin (estimated loading 0.125 mmol/g) and (S*)-I-234 to afford 4.2 mg of E-190 as a white solid. ESI-MS found 1153.3, $C_{214}H_{327}N_{47}O_{64}S$ (M+4H$^+$) requires 1152.8.

Example 151: Compound 55

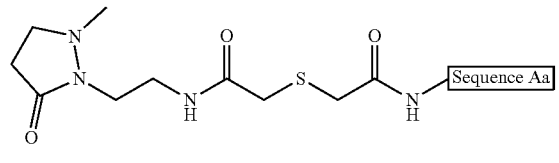

E-151

E-151 was prepared according to GP4 using 43.4 mg of resin (estimated loading 0.125 mmol/g) and I-240 to afford 6.0 mg of E-151 as a white solid. ESI-MS found 1153.6, $C_{213}H_{326}N_{48}O_{64}S$ (M+4H$^+$) requires 1153.1.

Example 152: Compound 58

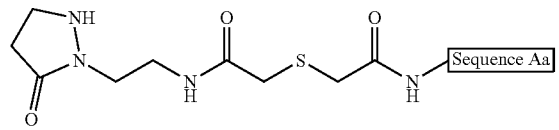

E-152

E-152 was prepared according to GP4 using 37.7 mg of resin (estimated loading 0.125 mmol/g) and I-243 to afford 1.8 mg of E-152 as a white solid. ESI-MS found 1150.0, $C_{212}H_{324}N_{48}O_{64}S$ (M+4H$^+$) requires 1149.6.

Example 153: Compound 65

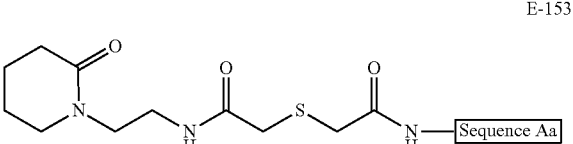

E-153

E-153 was prepared according to GP4 using 41 mg of resin (estimated loading 0.125 mmol/g) and I-248 to afford 4.1 mg of E-153 as a white solid. ESI-MS found 1153.3, $C_{214}H_{327}N_{47}O_{64}S$ (M+4H$^+$) requires 1152.8.

Example 154: Compound 57

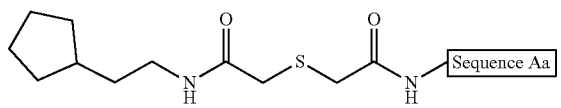

E-154

E-154 was prepared according to GP4 using 41.1 mg of resin (estimated loading 0.125 mmol/g) and I-249 to afford 6.5 mg of E-154 as a white solid. ESI-MS found 1146.1, $C_{214}H_{328}N_{46}O_{63}S$ (M+4H$^+$) requires 1145.6.

Example 155: Compound 54

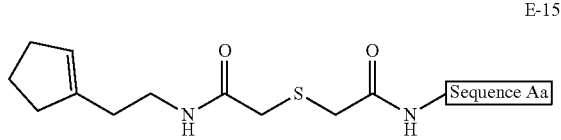

E-155 was prepared according to GP4 using 39.8 mg of resin (estimated loading 0.125 mmol/g) and I-250 to afford 4.7 mg of E-155 as a white solid. ESI-MS found 1145.6, $C_{214}H_{326}N_{46}O_{63}S$ (M+4H$^+$) requires 1145.

Example 156: Compound 50

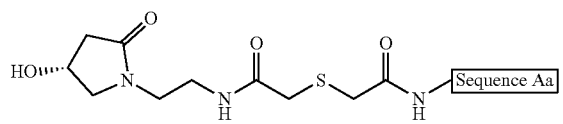

E-156 was prepared according to GP4 using 46.9 mg of resin (estimated loading 0.125 mmol/g) and I-257 to afford 2.7 mg of E-156 as a white solid. ESI-MS found 1153.8, $C_{213}H_{325}N_{47}O_{65}S$ (M+4H$^+$) requires 1153.3.

Example 157: Compound 45

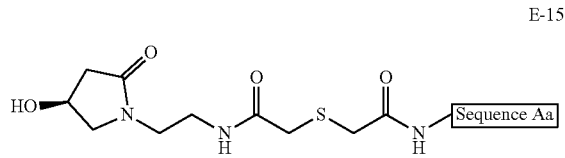

E-157 was prepared according to GP4 using 45.5 mg of resin (estimated loading 0.125 mmol/g) and I-264 to afford 7.0 mg of E-157 as a white solid. ESI-MS found 1153.7, $C_{213}H_{325}N_{47}O_{65}S$ (M+4H$^+$) requires 1153.3.

Example 158: Compound 43

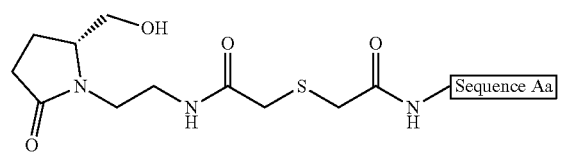

E-158 was prepared according to GP4 using 44.5 mg of resin (estimated loading 0.125 mmol/g) and I-271 to afford 2.7 mg of E-158 as a white solid. ESI-MS found 1157.2, $C_{214}H_{327}N_{47}O_{65}S$ (M+4H$^+$) requires 1156.8.

Example 159: Compound 44

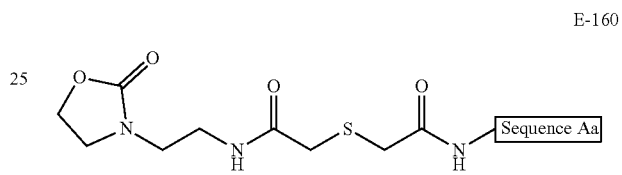

E-159 was prepared according to GP4 using 39.9 mg of resin (estimated loading 0.125 mmol/g) and I-278 to afford 2.6 mg of E-159 as a white solid. ESI-MS found 1157.3, $C_{214}H_{327}N_{47}O_{65}S$ (M+4H$^+$) requires 1156.8.

Example 160: Compound 39

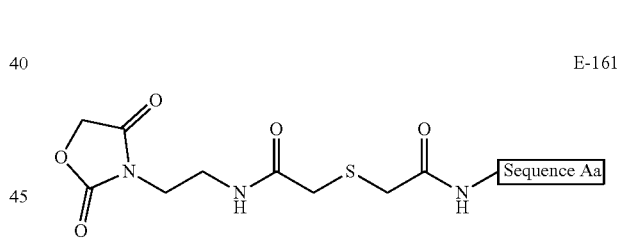

E-160 was prepared according to GP4 using 43.8 mg of resin (estimated loading 0.125 mmol/g) and I-279 to afford 5.5 mg of E-160 as a white solid. ESI-MS found 1150.3, $C_{212}H_{323}N_{47}O_{64}S$ (M+4H$^+$) requires 1149.8.

Example 161: Compound 59

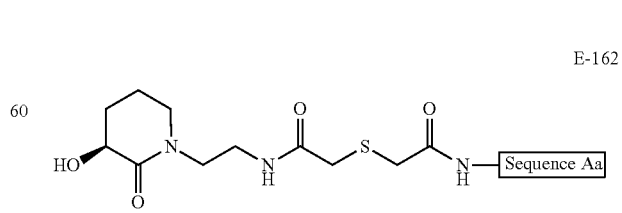

E-161 was prepared according to GP4 using 39.7 mg of resin (estimated loading 0.125 mmol/g) and I-282 to afford 4.8 mg of E-161 as a white solid. ESI-MS found 1153.9, $C_{212}H_{321}N_{47}O_{66}S$ (M+4H$^+$) requires 1153.3.

Example 162: Compound 21

E-162

E-162 was prepared according to GP4 using 40.4 mg of resin (estimated loading 0.125 mmol/g) and I-289 to afford 5.3 mg of E-162 as a white solid. ESI-MS found 1157.3, $C_{214}H_{327}N_{47}O_{65}S$ (M+4H$^+$) requires 1156.8.

Example 163: Compound 7

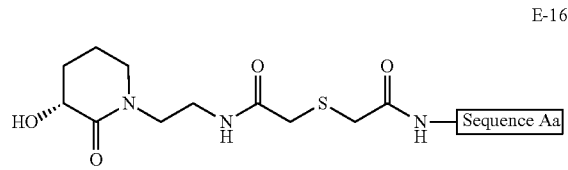

E-163 was prepared according to GP4 using 36.6 mg of resin (estimated loading 0.125 mmol/g) and I-296 to afford 2.9 mg of E-163 as a white solid. ESI-MS found 1157.4, $C_{214}H_{327}N_{47}O_{65}S$ (M+4H$^+$) requires 1156.8.

Example 164: Compound 34

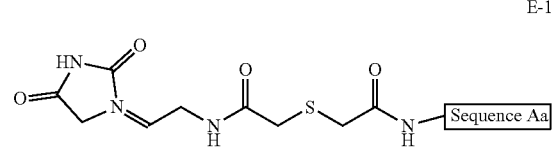

E-164 was prepared according to GP4 using 41.3 mg of resin (estimated loading 0.125 mmol/g) and I-301 to afford 2.0 mg of E-164 as a white solid. ESI-MS found 1153.7, $C_{212}H_{322}N_{48}O_{65}S$ (M+4H$^+$) requires 1153.1.

Example 165: Compound 46

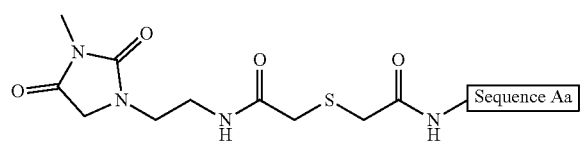

E-165 was prepared according to GP4 using 38.4 mg of resin (estimated loading 0.125 mmol/g) and I-307 to afford 5.3 mg of E-165 as a white solid. ESI-MS found 1157.1, $C_{213}H_{324}N_{48}O_{65}S$ (M+4H$^+$) requires 1156.6.

Example 166: Compound 25

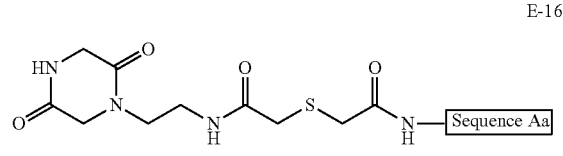

E-166 was prepared according to GP4 using 34.3 mg of resin (estimated loading 0.125 mmol/g) and I-311 to afford 3.3 mg of E-166 as a white solid. ESI-MS found 1157.1, $C_{213}H_{324}N_{48}O_{65}S$ (M+4H$^+$) requires 1156.6.

Example 167: Compound 12

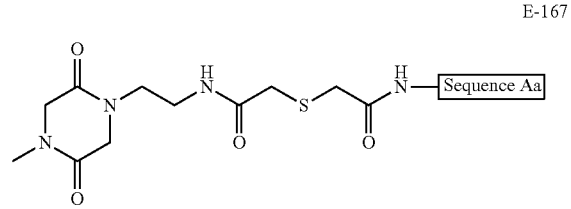

E-167 was prepared according to GP4 using 30 mg of resin (estimated loading 0.125 mmol/g) and I-320 to afford 4.0 mg of E-167 as a white solid. ESI-MS found 1160.6, $C_{214}H_{326}N_{48}O_{65}S$ (M+4H$^+$) requires 1160.1.

Example 168: Compound 33

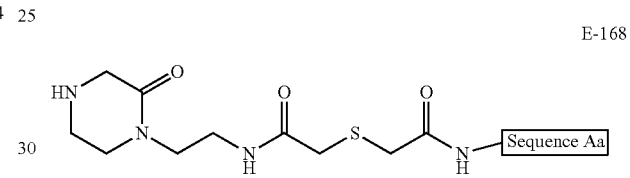

E-168 was prepared according to GP4 using 39.6 mg of resin (estimated loading 0.125 mmol/g) and I-325 to afford 4.9 mg of E-168 as a white solid. ESI-MS found 1153.7, $C_{213}H_{326}N_{48}O_{64}S$ (M+4H$^+$) requires 1153.1.

Example 169: Compound 24

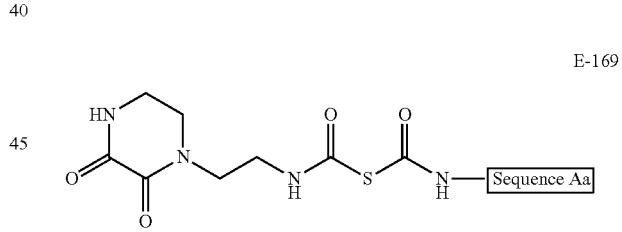

E-169 was prepared according to GP4 using 39.5 mg of resin (estimated loading 0.125 mmol/g) and I-328 to afford 5.8 mg of E-169 as a white solid. ESI-MS found 1157.1, $C_{213}H_{324}N_{48}O_{65}S$ (M+4H$^+$) requires 1156.6.

Example 170: Compound 30

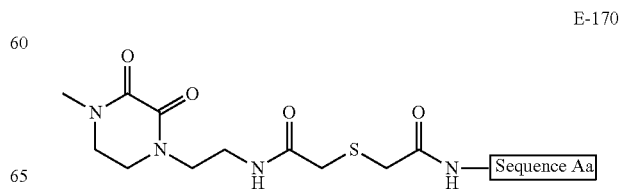

E-170 was prepared according to GP4 using 36.3 mg of resin (estimated loading 0.125 mmol/g) and I-332 to afford 4.4 mg of E-170 as a white solid. ESI-MS found 1160.7, $C_{214}H_{326}N_{48}O_{65}S$ (M+4H$^+$) requires 1160.1.

Example 171: Compound 38

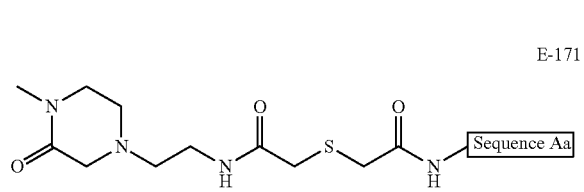

E-171 was prepared according to GP4 using 43.4 mg of resin (estimated loading 0.125 mmol/g) and I-335 to afford 4.3 mg of E-171 as a white solid. ESI-MS found 1157.2, $C_{214}H_{328}N_{48}O_{64}S$ (M+4H$^+$) requires 1156.6.

Example 172: Compound 37

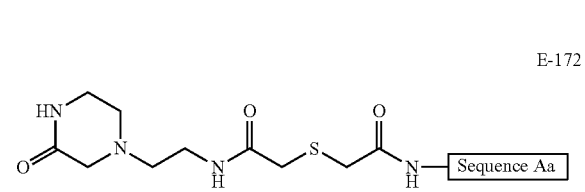 [SMILES: CNC(=O)CSCC(=O)NCCN1CCNC(=O)C1]

E-172 was prepared according to GP4 using 42.5 mg of resin (estimated loading 0.125 mmol/g) and I-338 to afford 4.5 mg of E-172 as a white solid. ESI-MS found 1153.5, $C_{213}H_{326}N_{48}O_{64}S$ (M+4H$^+$) requires 1153.1.

Example 173: Compound 32

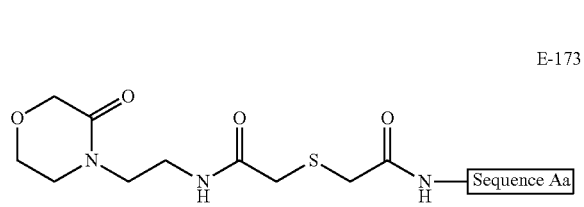 [SMILES: CNC(=O)CSCC(=O)NCCN1CCOCC1=O]

E-173 was prepared according to GP4 using 38.5 mg of resin (estimated loading 0.125 mmol/g) and I-343 to afford 4.5 mg of E-172 as a white solid. ESI-MS found 1153.9, $C_{213}H_{325}N_{47}O_{65}S$ (M+4H$^+$) requires 1153.3.

Example 174: Compound 36

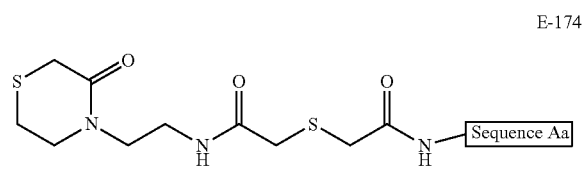 [SMILES: CNC(=O)CSCC(=O)NCCN1CCSCC1=O]

E-174 was prepared according to GP4 using 42.4 mg of resin (estimated loading 0.125 mmol/g) and I-348 to afford 4.5 mg of E-174 as a white solid. ESI-MS found 1157.9, $C_{213}H_{325}N_{47}O_{64}S_2$ (M+4H$^+$) requires 1157.3.

Example 175: Compound 29

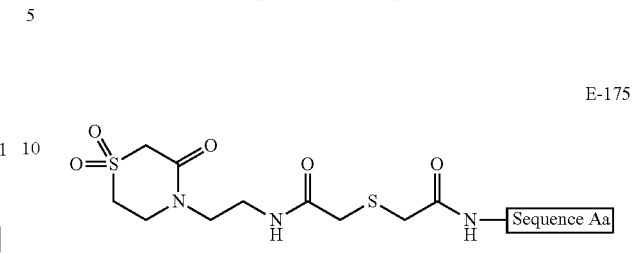

E-175 was prepared according to GP4 using 45 mg of resin (estimated loading 0.125 mmol/g) and I-351 to afford 6.5 mg of E-175 as a white solid. ESI-MS found 1165.8, $C_{213}H_{325}N_{47}O_{66}S2$ (M+4H$^+$) requires 1165.3.

Example 176: Compound 6

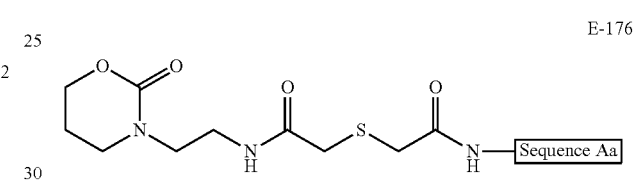

E-176 was prepared according to GP4 using 38.5 mg of resin (estimated loading 0.125 mmol/g) and I-356 to afford 5.1 mg of E-176 as a white solid. ESI-MS found 1153.9, $C_{213}H_{325}N_{47}O_{65}S$ (M+4H$^+$) requires 1153.3.

Example 177: Compound 23

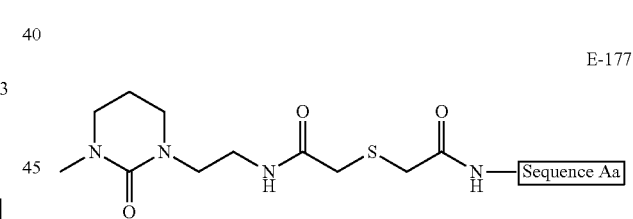

E-177 was prepared according to GP4 using 39 mg of resin (estimated loading 0.125 mmol/g) and I-363 to afford 5.2 mg of E-177 as a white solid. ESI-MS found 1157.2, $C_{214}H_{328}N_{48}O_{64}S$ (M+4H$^+$) requires 1156.6.

Example 178: Compound 31

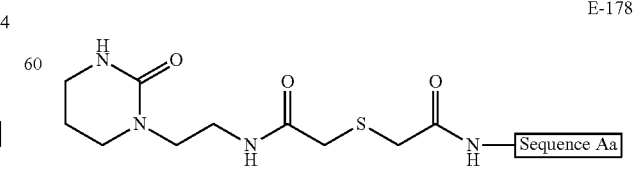

E-178 was prepared according to GP4 using 38.5 mg of resin (estimated loading 0.125 mmol/g) and I-366 to afford 4.8 mg of E-178 as a white solid. ESI-MS found 1153.7, $C_{213}H_{326}N_{48}O_{64}S$ (M+4H$^+$) requires 1153.1.

Example 179: Compound 11

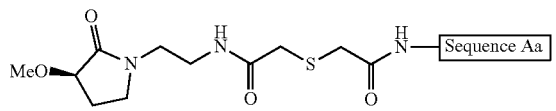

E-179

E-179 was prepared according to GP4 using 30 mg of resin (estimated loading 0.125 mmol/g) and I-373 to afford 4.1 mg of E-179 as a white solid. ESI-MS found 1157.3, $C_{214}H_{327}N_{47}O_{65}S$ (M+4H$^+$) requires 1156.8.

Example 180: Compound 14

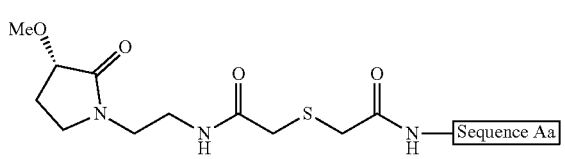

E-180

Peptide E-180 was prepared from 30 mg of resin (approximate loading 0.125 mmol/g) using I-380 and GP4 to afford 2.3 mg of E-180 as a white solid. ESI-MS found 1157.4, $C_{214}H_{327}N_{47}O_{65}S$ (M+4H$^+$) requires 1156.8.

Example 181: Compound 22

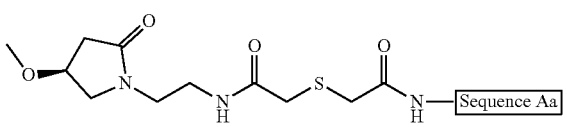

E-181

E-181 was prepared according to GP4 using 40.3 mg of resin (estimated loading 0.125 mmol/g) and I-386 to afford 5.5 mg of E-181 as a white solid. ESI-MS found 1157.3, $C_{214}H_{327}N_{47}O_{65}S$ (M+4H$^+$) requires 1156.8.

Example 182: Compound 8

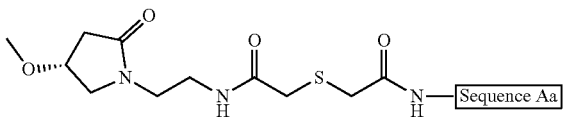

E-182

E-182 was prepared according to GP4 using 41 mg of resin (estimated loading 0.125 mmol/g) and I-392 to afford 5.1 mg of E-182 as a white solid. ESI-MS found 1157.3, $C_{214}H_{327}N_{47}O_{65}S$ (M+4H$^+$) requires 1156.8.

Example 183: Compound 62

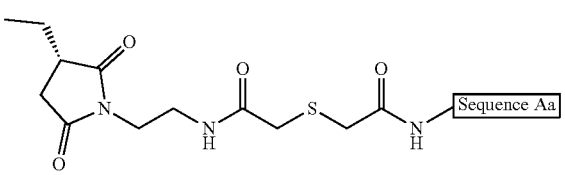

E-183

E-183 was prepared according to GP4 using 40.8 mg of resin (estimated loading 0.125 mmol/g) and (S*)-I-395 to afford 4.5 mg of E-183 as a white solid. ESI-MS found 1160.3, $C_{215}H_{327}N_{47}O_{65}S$ (M+4H$^+$) requires 1159.8.

Example 184: Compound 61

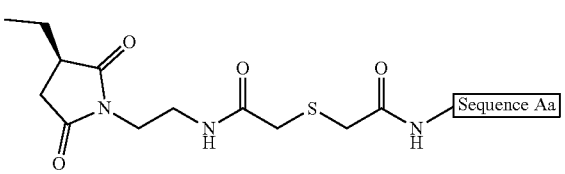

E-184

E-184 was prepared according to GP4 using 38 mg of resin (estimated loading 0.125 mmol/g) and (R*)-I-395 to afford 3.0 mg of E-184 as a white solid. ESI-MS found 1160.3, $C_{215}H_{327}N_{47}O_{65}S$ (M+4H$^+$) requires 1159.8.

Example 185: Compound 78

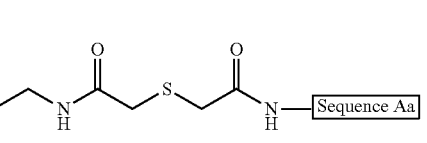

E-185

E-185 was prepared according to GP4 using 34 mg of resin (estimated loading 0.125 mmol/g) and I-398 to afford 2.5 mg of E-185 as a white solid. ESI-MS found 1157.2, $C_{213}H_{323}N_{47}O_{66}S$ (M+4H$^+$) requires 1156.8.

Example 186: Compound 79

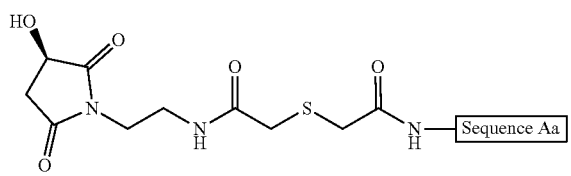

E-186 was prepared according to GP4 using 35.3 mg of resin (estimated loading 0.125 mmol/g) and I-399 to afford 1.3 mg of E-186 as a white solid. ESI-MS found 1157.3, $C_{213}H_{323}N_{47}O_{66}S$ (M+4H$^+$) requires 1156.8.

Example 187: Compound 63

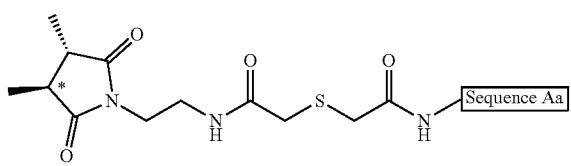

*Absolute configuration not known

E-187 was prepared according to GP4 using 39 mg of resin (estimated loading 0.125 mmol/g) and I-404 to afford 3.0 mg of E-187 as a white solid. ESI-MS found 1160.3, $C_{215}H_{327}N_{47}O_{65}S$ (M+4H$^+$) requires 1159.8.

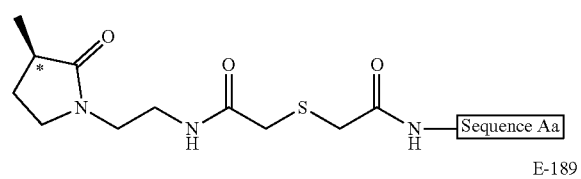

*Absolute configuration not determined

Example 188: Compound 69

E-188 was prepared according to GP4 using 45.9 mg of resin (estimated loading 0.125 mmol/g) and (R*)-I-409 to afford 4 mg of E-188 as a white solid. ESI-MS found 1153.3, $C_{214}H_{327}N_{47}O_{64}S$ (M+4H$^+$) requires 1152.8.

Example 189: Compound 68

E-189 was prepared according to GP4 using 43.8 mg of resin (estimated loading 0.125 mmol/g) and (S*)-I-409 to afford 4.3 mg of E-189 as a white solid. ESI-MS found 1153.3, $C_{214}H_{327}N_{47}O_{64}S$ (M+4H$^+$) requires 1152.8.

Example 190: Compound 77

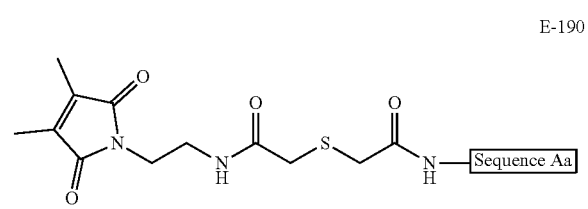

E-190 was prepared according to GP4 using 36.6 mg of resin (estimated loading 0.125 mmol/g) and I-412 to afford 0.5 mg of E-190 as a white solid. ESI-MS found 1159.7, $C_{215}H_{325}N_{47}O_{65}S$ (M+4H$^+$) requires 1159.3.

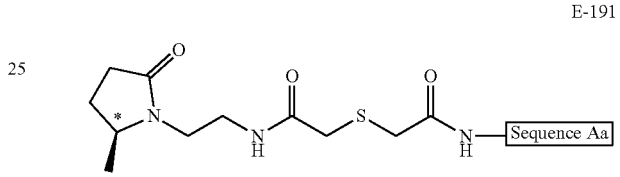

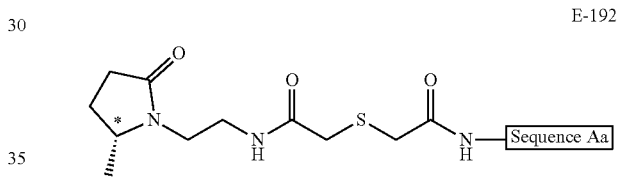

*Absolute configuration not determined

Example 191: Compound 75

E-191 was prepared according to GP4 using 30.2 mg of resin (estimated loading 0.125 mmol/g) and (S*)-I-413 to afford 2.9 mg of E-191 as a white solid. ESI-MS found 1153.4, $C_{214}H_{327}N_{47}O_{64}S$ (M+4H$^+$) requires 1152.8.

Example 192: Compound 74

E-192 was prepared according to GP4 using 31.1 mg of resin (estimated loading 0.125 mmol/g) and (R*)-I-413 to afford 3.3 mg of E-192 as a white solid. ESI-MS found 1153.4, $C_{214}H_{327}N_{47}O_{64}S$ (M+4H$^+$) requires 1152.8.

Example 193: Compound 67

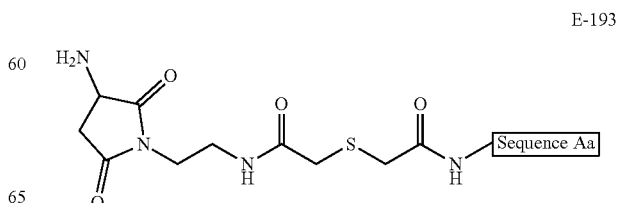

E-193 was prepared according to GP4 using 41.4 mg of resin (estimated loading 0.125 mmol/g) and I-417 to afford 4.1 mg of E-193 as a white solid. ESI-MS found 1157.1, $C_{213}H_{324}N_{48}O_{65}S$ (M+4H$^+$) requires 1156.6.

Example 194: Compound 42

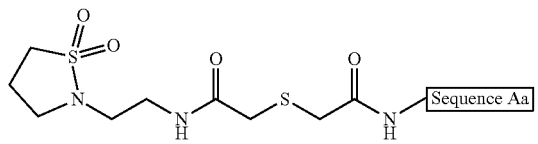

E-194

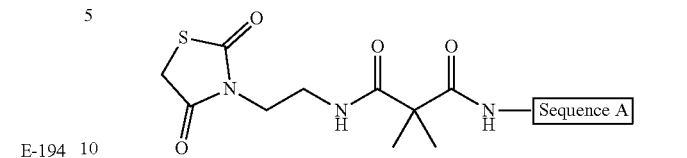

E-194 was prepared according to GP4 using 42.1 mg of resin (estimated loading 0.125 mmol/g) and I-421 to afford 5.4 mg of E-194 as a white solid. ESI-MS found 1158.8, $C_{212}H_{325}N_{47}O_{65}S_2$ (M+4H$^+$) requires 1158.3.

Example 195: Compound 40

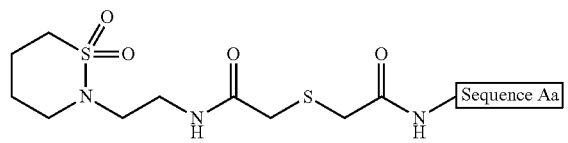

E-195

E-195 was prepared according to GP4 using 50.9 mg of resin (estimated loading 0.125 mmol/g) and I-425 to afford 5.8 mg of E-195 as a white solid. ESI-MS found 1162.3, $C_{213}H_{327}N_{47}O_{65}S_2$ (M+4H$^+$) requires 1161.8.

Example 196: Compound 153

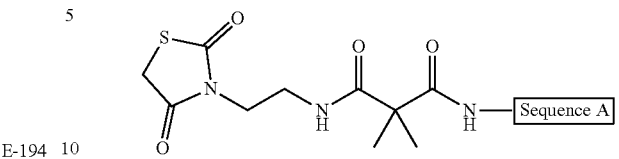

E-196

Peptide E-196 was prepared from 24.9 mg of resin (approximate loading 0.18 mmol/g) using I-426 and GP4 to afford 2.7 mg of E-196 as a white solid. ESI-MS found 1059.4989, $C_{192}H_{278}SN_{46}O_{61}$ (M−4H)$^−$ requires 1059.0.

C2. Synthesis of Additional Intermediates to Compounds Described in this Invention The synthesis of carboxylic acid I-430 is depicted in Scheme 138:

Scheme 138

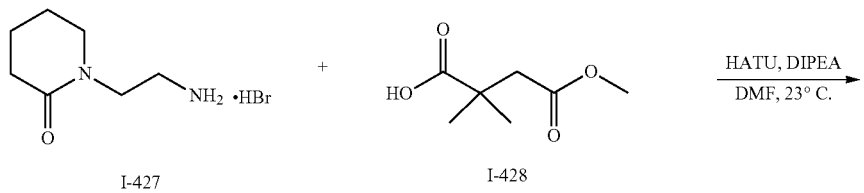

I-427     I-428

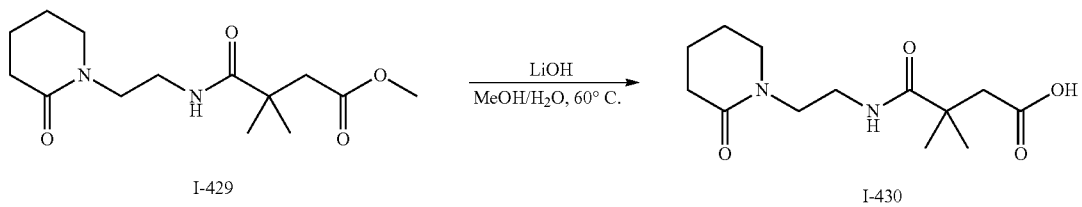

I-429     I-430

To a solution of amine salt I-427 (165.8 mg, 0.743 mmol), carboxylic acid I-428 (119 mg, 1.0 equiv.) and DIPEA (388 μL, 3.0 equiv.) in DMF (2 mL) at ambient temperature was added HATU (423.8 mg, 1.5 equiv.). The reaction mixture was maintained at ambient temperature for 23 hours and was then purified by preparative HPLC (Mobile Phase: MeCN/H$_2$O with 0.1% TFA) to afford ester I-429 as a colorless oil (180.7 mg, 86% yield).

To a solution of ester I-429 (90.3 mg, 0.318 mmol) in MeOH (3 mL) and H$_2$O (1 mL) was added lithium hydroxide (15.2 mg, 2.0 equiv.). The reaction mixture was heated to 60° C. for 23 hours, acidified with 6 N HCl to pH<2, and then purified by preparative HPLC (Mobile Phase: MeCN/H$_2$O with 0.1% TFA) to afford acid I-430 as a white solid (26.1 mg, 30% yield). ESI-MS found 271.3, $C_{13}H_{23}N_2O_4$ (M+4H)$^{4+}$ requires 271.3.

The syntheses of compounds I-439 & I-443 involved 8 steps as depicted in the following Scheme 139.

Scheme 139
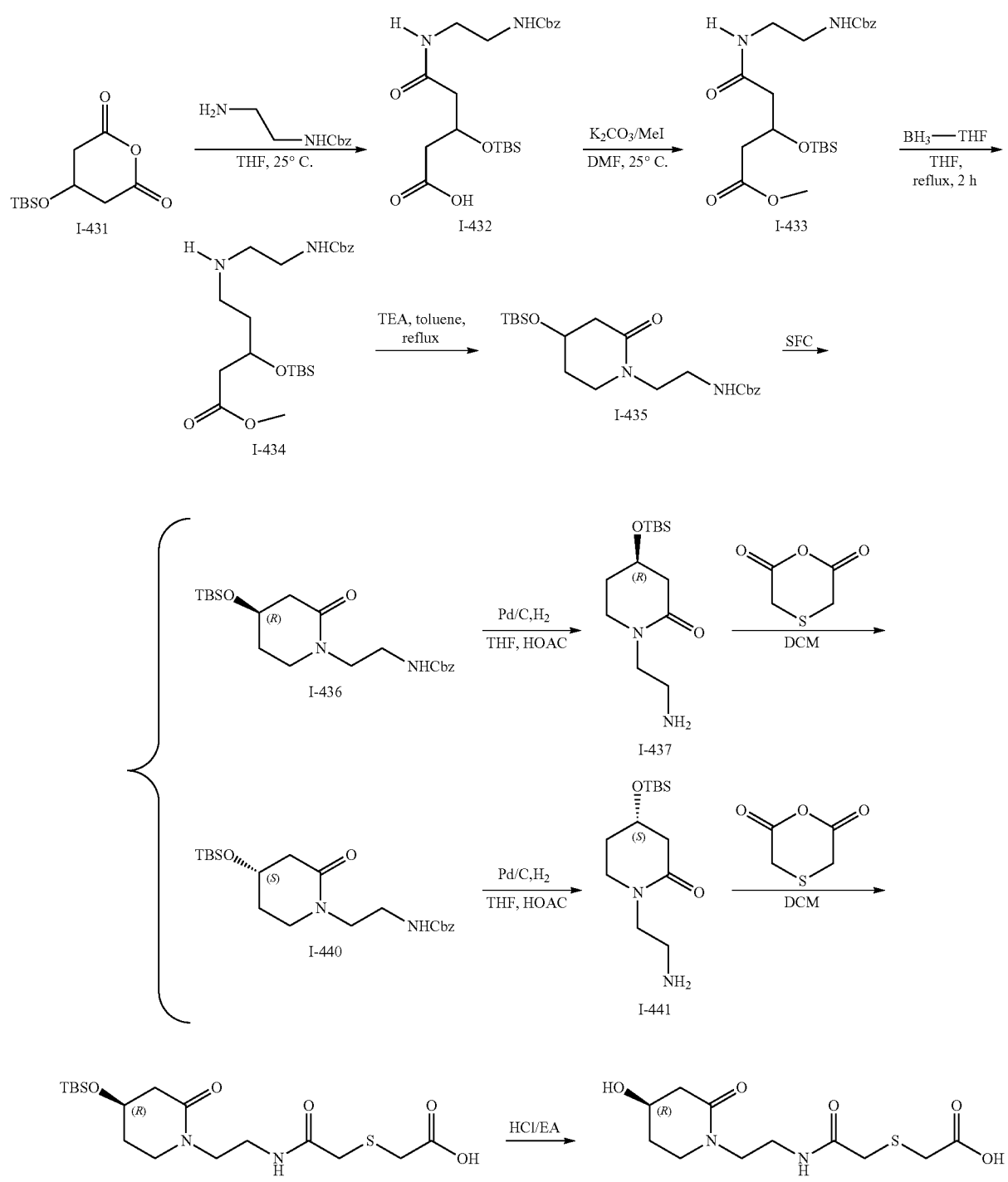
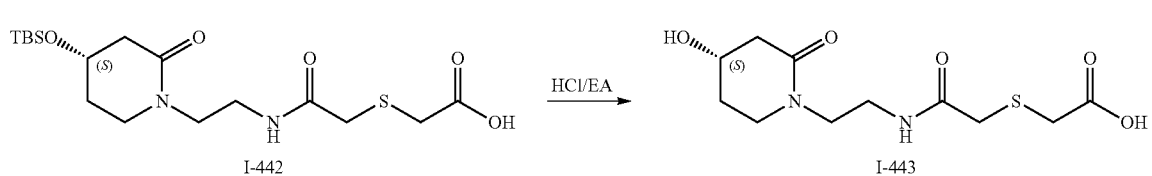

Step 1. 5-((2-(((benzyloxy)carbonyl)amino)ethyl)amino)-3-((tert-butyldimethylsilyl)oxy)-5-oxopentanoic acid (I-432)

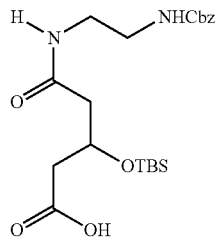 [SMILES: CC(C)(C)[Si](C)(C)OC(CC(=O)O)CC(=O)NCCNC(=O)OCc1ccccc1]

A solution of 4-((tert-butyldimethyl silyl)oxy)dihydro-2H-pyran-2,6(3H)-di one I-431 (cas: 91424-40-7, 5.0 g, 20.5 mmol), benzyl (2-aminoethyl)carbamate (cas: 72080-83-2, 3.97 g, 20.5 mmol) and TEA (6.2 g, 61.5 mmol) in anhydrous THF (150 mL) was stirred at 25° C. for 16 hours. The reaction mixture was concentrated to afford the crude 5-((2-(((benzyloxy)carbonyl) amino)ethyl)amino)-3-((tert-butyldimethylsilyl)oxy)-5-oxopentanoic acid I-432 (8.9 g), which was taken on to the next reaction without further purification. MS (ESI, positive ion) m/z: 439.2 (M+1).

Step 2. methyl 5-((2-(((benzyloxy)carbonyl)amino)ethyl)amino)-3-((tert-butyldimethylsilyl)oxy)-5-oxopentanoate (I-433)

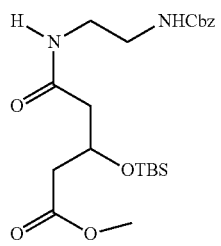 [SMILES: COC(=O)CC(CC(=O)NCCNC(=O)OCc1ccccc1)O[Si](C)(C)C(C)(C)C]

To a mixture of acid I-432 (5 g, 11.4 mmol) and K$_2$CO$_3$ (2.4 g, 17.1 mmol) in anhydrous DMF (30 mL) was added MeI (1.95 g, 13.7 mmol) at 25° C. under N$_2$. The reaction mixture was heated to 50° C. for 5 hours, then concentrated and dissolved in EtOAc (150 mL). The organic phase was washed with water (50 mL×3), dried and concentrated to afford the crude product, which was purified by silica gel chromatography (Petroleum ether:EtOAc=3:1 to 1:1) to provide a pale oil (4.5 g, 87% yield). MS (ESI, positive ion) m/z: 453.2 (M+1).

Step 3. methyl 5-((2-(((benzyloxy)carbonyl)amino)ethyl)amino)-3-((tert-butyldimethylsilyl)oxy) pentanoate (I-434)

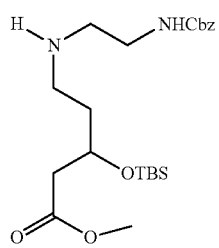 [SMILES: COC(=O)CC(CCNCCNC(=O)OCc1ccccc1)O[Si](C)(C)C(C)(C)C]

To a solution of ester I-433 (2 g, 4.4 mmol) in anhydrous THF (200 mL) was added BH$_3$-THF (1 M, 22 mL, 22 mmol) at 0° C. The reaction mixture was heated to 80° C. for 2 hours and cooled to 0° C., then quenched by adding 1 mL of concentrated HCl. The reaction mixture was concentrated and dissolved in EtOAc (150 mL). The organic phase was washed with water (50 mL×3), dried and concentrated to afford the crude amine I-434 (2.5 g), which was taken to the next reaction without further purification. MS (ESI, positive ion) m/z: 439.2 (M+1).

Step 4. Benzyl (2-(4-((tert-butyldimethylsilyl)oxy)-2-oxopiperidin-1-yl)ethyl)carbamate (I-435)

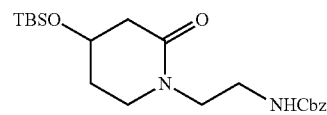 [SMILES: CC(C)(C)[Si](C)(C)OC1CCN(CCNC(=O)OCc2ccccc2)C(=O)C1]

A solution of amine I-434 (2.5 g, 5.7 mmol) and TEA (2.89 g, 28.5 mmol) in anhydrous toluene (150 ml) was heated to 50° C. for 16 hours. The reaction mixture was concentrated and purified by preparative HPLC (Mobile Phase: MeCN/H$_2$O with 0.1% TFA) to afford a brown oil (430 mg, 19% yield). MS (ESI, positive ion) m/z: 407.2 (M+1).

Step 5. Chiral SFC Separation

[5.0 cm I.D.×25 cm L CHIRALCEL OZ column at 35° C., flow rate 60 mL/min with Hexane/IPA=80/20 (V/V)] afforded enantiomers I-436 and I-440.

Step 6. (R or S)-1-(2-aminoethyl)-4-((tert-butyldimethylsilyl)oxy)piperidin-2-one (Peak 1) (I-437 or I-441)

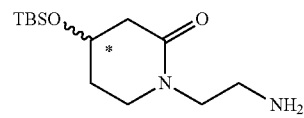

To a solution of benzyl (R or S)-(2-(4-((tert-butyldimethylsilyl)oxy)-2-oxopiperidin-1-yl)ethyl)carbamate I-436 (150 mg, 6.82 mmol) in THF (10 ml) was added Pd/C (170 mg) quickly under H$_2$. The reaction was then stirred at ambient temperature for 16 hours, when analysis by LC-MS indicated reaction completion. The reaction mixture was filtered, and the filtrate was concentrated under reduced pressure to afford crude amine I-437 (105 mg), which was taken to the next reaction without further purification. MS (ESI, positive ion) m/z: 273.2 (M+1).

Step 7. (R or S)-2-(2-(3-methoxy-2-oxopyrrolidin-1-yl)ethyl)isoindoline-1,3-dione (I-438 or I-442)

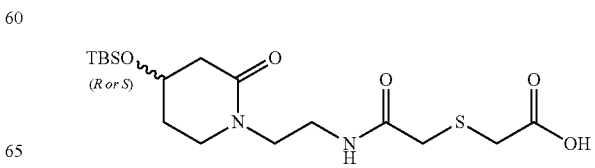

A solution of (R or S)-1-(2-hydroxyethyl)-3-methoxypyr-rolidin-2-one (I-437) (100 mg, 0.94 mmol) and thiodigly-colic anhydride (cas: 3261-87-8, 240 mg, 1.84 mmol) in anhydrous THF (5 mL) was stirred at 25° C. for 16 hours. The reaction mixture was concentrated to afford crude acid I-438 (340 mg), which was taken to the next reaction without further purification. MS (ESI, positive ion) m/z: 405.1 (M+1).

Step 8. (R or S)-2-((2-((2-(4-hydroxy-2-oxopiperi-din-1-yl)ethyl)amino)-2-oxoethyl)thio)acetic acid (I-439)

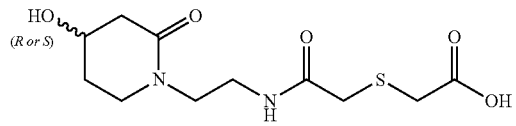 [SMILES: O=C(O)CSCC(=O)NCCN1CCC(O)CC1=O]

To a solution of crude acid I-438 (340 mg) in THF (10 mL) was added HCl/EtOAc (5 M, 2 mL) at 0° C. The reaction mixture was stirred for 12 hours at ambient temperature, then concentrated to afford a residue, which was purified by preparative HPLC (Mobile Phase: MeCN/H$_2$O with 0.1% TFA) to afford acid I-439 as a pale oil (22 mg, 9% yield). MS (ESI, positive ion) m/z: 291.2 (M+1). $^1$H NMR (400 MHz, D$_2$O) δ 4.05-4.03 (m, 1H), 3.44-3.24 (m, 6H), 3.22 (s, 2H), 3.17 (s, 2H), 2.55-2.50 (m, 1H), 2.20-2.15 (m, 1H), 1.91-1.87 (m, 1H), 1.73-1.68 (m, 1H).

A similar sequence of steps with carbamate I-441 afforded acid I-443 (40 mg, 16% yield) as a pale oil.

The syntheses of intermediates I-451 and I-454 involved 8 steps as depicted in the following Scheme 140.

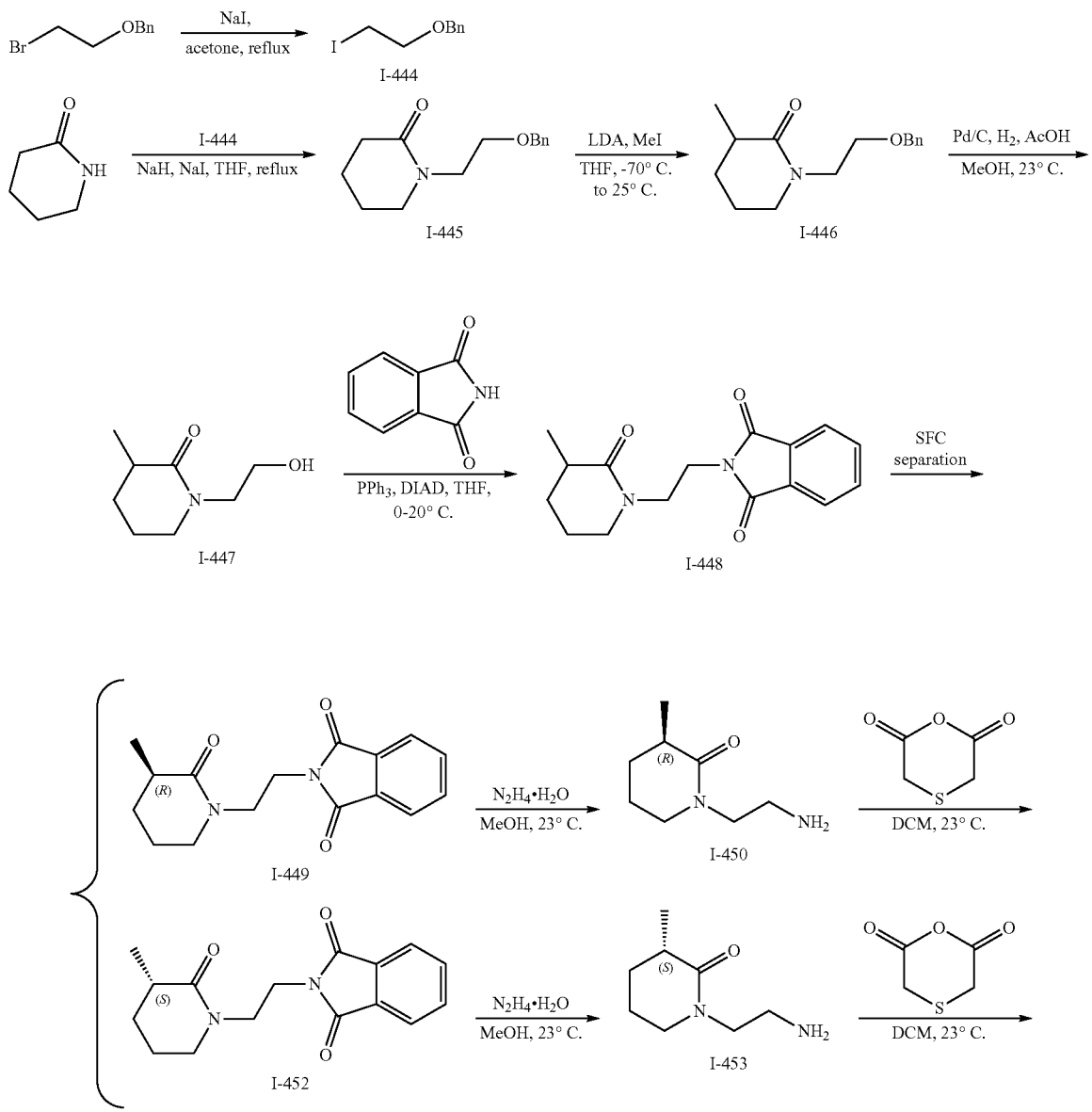

-continued

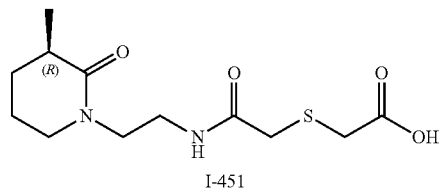
I-451

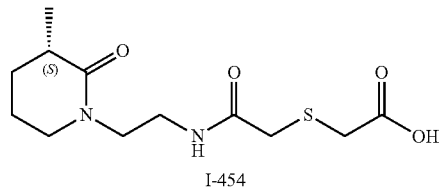
I-454

Step 1. ((2-iodoethoxy)methyl)benzene (I-444)

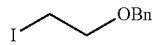

A mixture of ((2-bromoethoxy)methyl)benzene (cas: 1462-37-9, 10 g, 46.7 mmol) and sodium iodide (10.5 g, 1.5 equiv.) in acetone (250 mL) was heated to reflux for 16 hours. The reaction mixture was concentrated, and the residue was dissolved into EtOAc (200 mL) and diluted with water (100 mL). The organic layer was washed with brine (50 mL×3), dried over anhydrous Na$_2$SO$_4$ and concentrated to afford the crude product, which was purified by silica gel chromatography (Petroleum ether:EtOAc=20:1) to afford iodide I-444 as a brown liquid (7 g, yield: 60%).

Step 2. 1-(2-(benzyloxy)ethyl)piperidin-2-one (I-445)

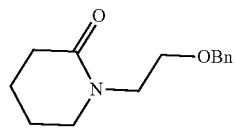 [SMILES: O=C1CCCCN1CCOCc1ccccc1]

A solution of 2-piperidone (cas: 675-20-7, 2 g, 20.2 mmol) in anhydrous THF (50 mL) was added NaH (60% in mineral oil, 1.2 g, 30.3 mmol) at 0°, then iodide I-444 (10.6 g, 40.4 mmol). The reaction mixture was heated at 80° C. for 16 hours, then quenched by adding 100 mL of saturated aqueous NH$_4$Cl at 0° C. The aqueous phase was extracted with EtOAc (50 mL×3). The organic extracts were combined, dried and concentrated afford the crude product, which was purified by silica gel chromatography (DCM:MeOH=20:1) to afford amide I-445 (1.2 g, yield: 25%) as a pale oil. MS (ESI, positive ion) m/z: 234.2 (M+1).

Step 3. 1-(2-(benzyloxy)ethyl)-3-methylpiperidin-2-one (I-446)

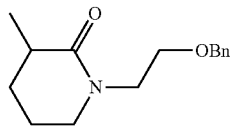 [SMILES: CC1CCCN(CCOCc2ccccc2)C1=O]

To a solution of amide I-445 (500 mg, 2.14 mmol) in anhydrous THF (20 mL) was added LDA (2 M, 1.6 mL, 3.2 mmol) at −78° C. under N$_2$. The reaction mixture was stirred for 30 minutes at the same temperature and MeI (914 mg, 6.44 mmol) was added. After 1 hour, LC-MS analysis indicated reaction completion. The reaction mixture was quenched with H$_2$O (20 mL) and extracted with EtOAc (20 mL×3). The combined organic extracts was concentrated to obtain crude product, which was purified by silica gel chromatography (DCM:MeOH=20:1) to provide lactam I-446 as a brown oil (380 mg, 72% yield). MS (ESI, positive ion) m/z: 248.2 (M+1).

Step 4. 1-(2-hydroxyethyl)-3-methylpiperidin-2-one (I-447)

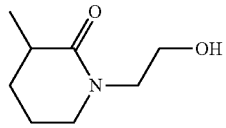

To a solution of lactam I-446 (5 g, 20.24 mmol) and acetic acid (0.5 mL) in MeOH (150 mL) was added 10% Pd(OH)$_2$ (300 mg) under H$_2$. The reaction mixture was heated to 50° C. under H$_2$ (3 atm) for 2 days. The reaction mixture was filtered, and the filtrate was concentrated to afford the crude product (3.2 g), which was taken to the next reaction without further purification. MS (ESI, positive ion) m/z: 158.2 (M+1).

Step 5. 2-(2-(3-methyl-2-oxopiperidin-1-yl)ethyl)isoindoline-1,3-dione (I-448)

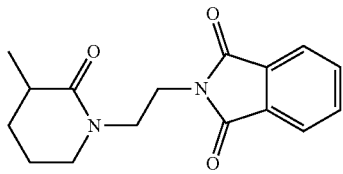 [SMILES: CC1CCCN(CCN2C(=O)c3ccccc3C2=O)C1=O]

A solution of lactam I-447 (200 mg, 1.27 mmol), phthalimide (374 mg, 2.54 mmol) and P(n-Bu)$_3$ (514 mg, 2.54 mmol) in anhydrous THF (10 mL) was stirred at 0° C. for 0.5 hours. Then DIAD (514 mg, 2.54 mmol) was added to the reaction dropwise and the reaction mixture was stirred for 18 hours at ambient temperature. The reaction mixture was concentrated to get crude product, which was purified by silica gel chromatography (Petroleum ether:EtOAc=1:1) to provide imide I-448 as a pale oil (180 mg, 49% yield). MS (ESI, positive ion) m/z: 287.2 (M+1).

Step 6

Phthalimide I-448 was subjected to chiral SFC to separate the racemate into its constituent enantiomers. Separation was accomplished using a Superchiral S-AD (Chiralway) column (2.1 cm I.D.×25 cm L, 5 μm at 35° C., flow rate 10 mL/min with Hexane/EtOH=55/45 (v/v), 30 mg injection) affording 137 mg of each enantiomer (I-449 and I-452) from 400 mg of racemate.

Step 7. (R or S)-2-(2-(3-methoxy-2-oxopyrrolidin-1-yl)ethyl)isoindoline-1,3-dione (I-450)

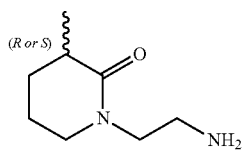

To a solution of I-449 (150 mg, 0.52 mmol) in MeOH (10 mL) was added Hydrazine hydrate (cas: 7803-57-8, 80%, 0.3 mL) at 0° C. The reaction mixture was stirred for 12 hours at ambient temperature, then filtered and the filtrate was concentrated. The residue afforded (210 mg) was used directly in the next step. MS (ESI, positive ion) m/z: 157.2 (M+1).

Step 8. (R or S)-2-((2-((2-(3-methyl-2-oxopiperidin-1-yl)ethyl)amino)-2-oxoethyl)thio)acetic acid (I-451)

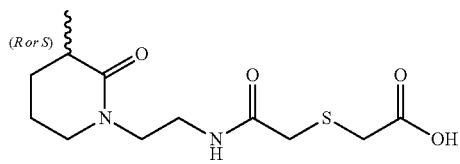 [SMILES: CC1CCCN(CCNC(=O)CSCC(=O)O)C1=O]

A solution of (R or S)-1-(2-aminoethyl)-3-methylpiperidin-2-one, I-450 (210 mg, 1.36 mmol) and thiodiglycolic anhydride (533 mg, 4.08 mmol) in 5 mL of DCM was stirred at 25° C. for 16 hours. The reaction mixture was concentrated to afford the crude product, which was purified by preparative HPLC (Mobile Phase: MeCN/H$_2$O (with 0.1% TFA)) to afford acid I-451 (40 mg, 11% yield) as a pale oil. MS (ESI, positive ion) m/z: 289.2 (M+1). $^1$H NMR (400 MHz, D$_2$O) δ 3.43-3.39 (m, 2H), 3.36-3.28 (m, 6H), 3.24 (s, 2H), 2.36-2.31 (m, 1H), 1.80-1.70 (m, 2H), 1.66-1.58 (m, 1H), 1.46-1.39 (m, 1H), 1.08-1.06 (d, 3H).

A similar sequence of steps from phthalimide I-452 afforded acid I-454 (43 mg, 12% yield) as a pale oil.

The synthesis of intermediate I-458 is depicted in Scheme 141:

Scheme 141

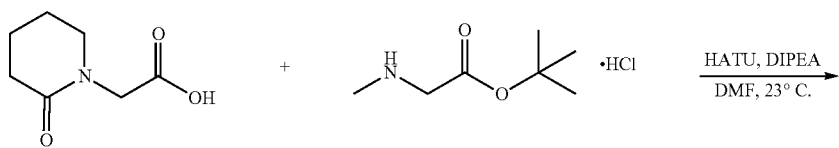

I-455    I-456

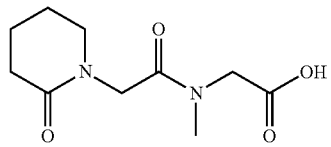

I-457

To a solution of amine salt I-456 (57.3 mg, 0.315 mmol), carboxylic acid I-455 (49.5 mg, 1.0 equiv.) and DIPEA (165 µL, 3.0 equiv.) in DMF (1 mL) at ambient temperature was added HATU (179.7 mg, 1.5 equiv.). The reaction mixture was maintained at ambient temperature for 2 hours and was then purified by preparative HPLC (Mobile Phase: MeCN/H$_2$O with 0.1% AcOH) to afford ester I-457 as a colorless oil (75.3 mg, 84% yield).

To ester I-457 (75.3 mg, 0.265 mmol) was added TFA (4 mL). The reaction mixture was maintained at ambient temperature for 4 hours, then concentrated. The residue afforded was purified by preparative HPLC (Mobile Phase: MeCN/H$_2$O with 0.1% TFA) to afford acid I-458 as a white solid (42.3 mg, 70% yield). ESI-MS found 227.1. $C_{10}H_{15}N_2O_4$ (M–H)$^-$ requires 227.1.

The synthesis of intermediate I-461 is depicted in Scheme 142:

Scheme 142

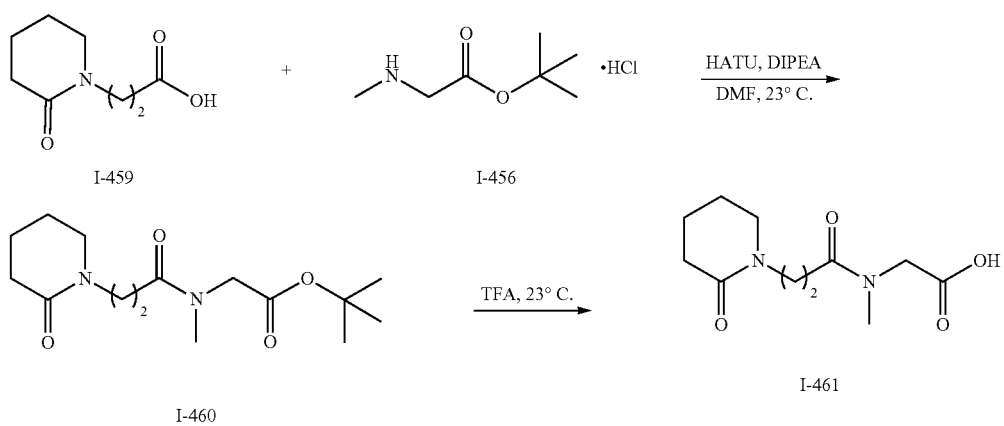

I-459

I-456

I-460

To a solution of amine salt I-456 (57.1 mg, 0.314 mmol), carboxylic acid I-455 (53.8 mg, 1.0 equiv.) and DIPEA (164 µL, 3.0 equiv.) in DMF (1 mL) at ambient temperature was added HATU (179.3 mg, 1.5 equiv.). The reaction mixture was maintained at ambient temperature for 3 hours and was then purified by preparative HPLC (Mobile Phase: MeCN/H$_2$O with 0.1% AcOH) to afford ester I-460 as a colorless oil (81.1 mg, 87% yield).

To ester I-460 (81.1 mg, 0.272 mmol) was added TFA (4 mL). The reaction mixture was maintained at ambient temperature for 4 hours, then concentrated. The residue afforded was purified by preparative HPLC (Mobile Phase: MeCN/H$_2$O with 0.1% TFA) to afford acid I-461 as a white solid (73.8 mg, quantitative yield). ESI-MS found 243.3. $C_{11}H_{19}N_2O_4$ (M+H)$^+$ requires 243.1.

The synthesis of intermediate I-464 is depicted in Scheme 143:

Scheme 143

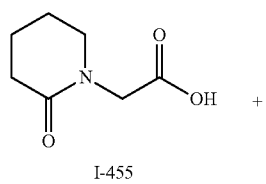

I-455

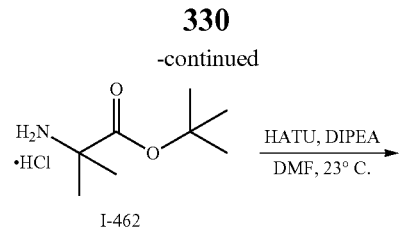

I-462

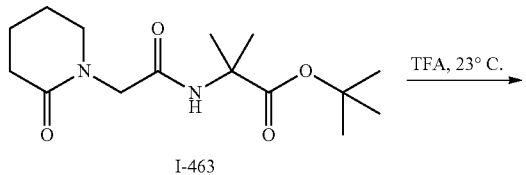

I-463

-continued

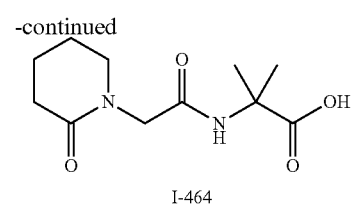

I-464

To a solution of amine salt I-462 (96.6 mg, 0.493 mmol), carboxylic acid I-455 (77.5 mg, 1.0 equiv.) and DIPEA (258 µL, 3.0 equiv.) in DMF (1 mL) at ambient temperature was added HATU (281.4 mg, 1.5 equiv.). The reaction mixture was maintained at ambient temperature for 16 hours and was then purified by preparative HPLC (Mobile Phase: MeCN/H$_2$O with 0.1% AcOH) to afford ester I-463 as a white solid (127.6 mg, 87% yield).

To ester I-463 (127.6 mg, 0.428 mmol) was added TFA (4 mL). The reaction mixture was maintained at ambient temperature for 4 hours, then concentrated. The residue afforded was purified by preparative HPLC (Mobile Phase: MeCN/H$_2$O with 0.1% TFA) to afford acid I-464 as a white solid (115.7 mg, quantitative yield). ESI-MS found 243.3. $C_{11}H_{19}N_2O_4$ (M+H)$^+$ requires 243.1.

The synthesis of intermediate I-466 is depicted in Scheme 144:

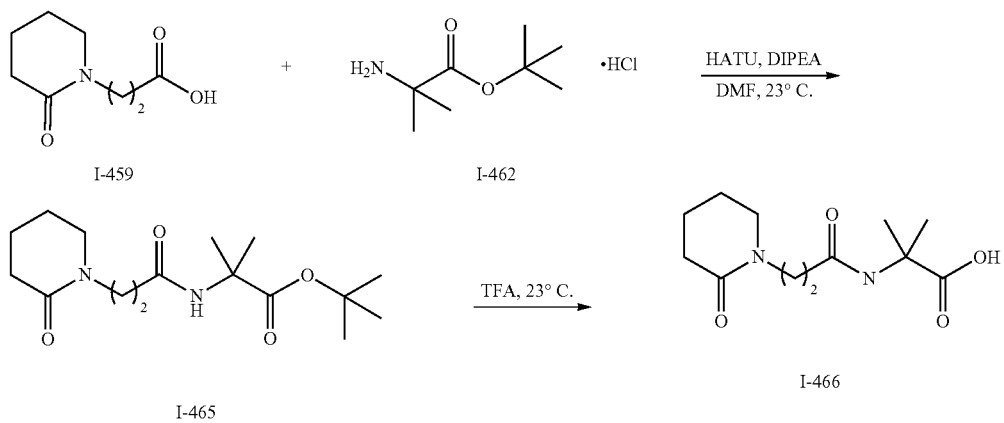

I-459

I-462

I-465

I-466

To a solution of amine salt I-462 (93.1 mg, 0.476 mmol), carboxylic acid I-459 (81.4 mg, 1.0 equiv.) and DIPEA (249 µL, 3.0 equiv.) in DMF (2 mL) at ambient temperature was added HATU (271.2 mg, 1.5 equiv.). The reaction mixture was maintained at ambient temperature for 3 hours and was then purified by preparative HPLC (Mobile Phase: MeCN/H$_2$O with 0.1% AcOH) to afford ester I-465 as a colorless oil (133 mg, 90% yield).

To ester I-465 (133 mg, 0.426 mmol) was added TFA (4 mL). The reaction mixture was maintained at ambient temperature for 4 hours, then concentrated. The residue afforded was purified by preparative HPLC (Mobile Phase: MeCN/H$_2$O with 0.1% TFA) to afford acid I-466 as a white solid (108.4 mg, >99% yield). ESI-MS found 257.3. $C_{12}H_{21}N_2O_4$ $(M+H)^+$ requires 257.1.

The synthesis of intermediate I-469 is depicted in Scheme 145:

To a solution of amine salt I-467 (80.1 mg, 0.441 mmol), carboxylic acid I-455 (69.3 mg, 1.0 equiv.) and DIPEA (231 µL, 3.0 equiv.) in DMF (2 mL) at ambient temperature was added HATU (251.6 mg, 1.5 equiv.). The reaction mixture was maintained at ambient temperature for 16 hours and was then purified by preparative HPLC (Mobile Phase: MeCN/H$_2$O with 0.1% AcOH) to afford ester I-468 as a colorless oil (112.4 mg, 90% yield).

To ester I-468 (112.4 mg, 0.395 mmol) was added TFA (4 mL). The reaction mixture was maintained at ambient temperature for 4 hours, then concentrated. The residue afforded was purified by preparative HPLC (Mobile Phase: MeCN/H$_2$O with 0.1% TFA) to afford acid I-469 as a white solid (79.1 mg, 88% yield). ESI-MS found 229.2. $C_{10}H_{17}N_2O_4$ $(M+H)^+$ requires 229.1.

The synthesis of intermediate I-471 is depicted in Scheme 146:

Scheme 145

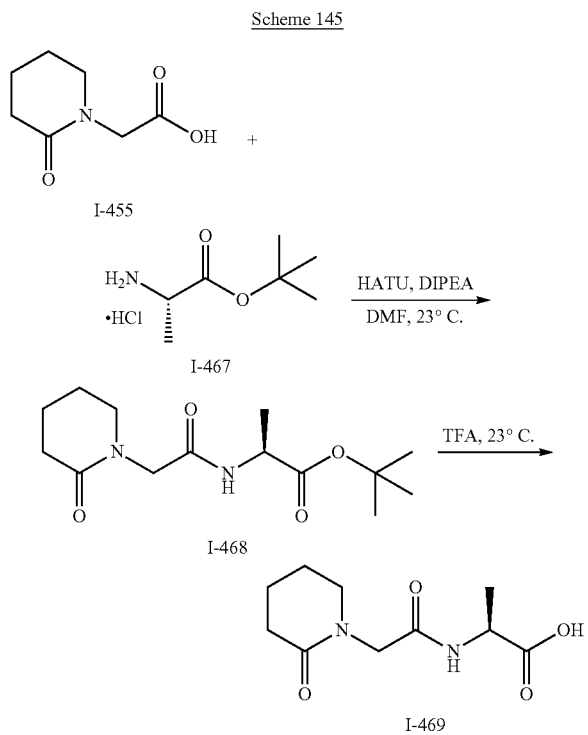

Scheme 146

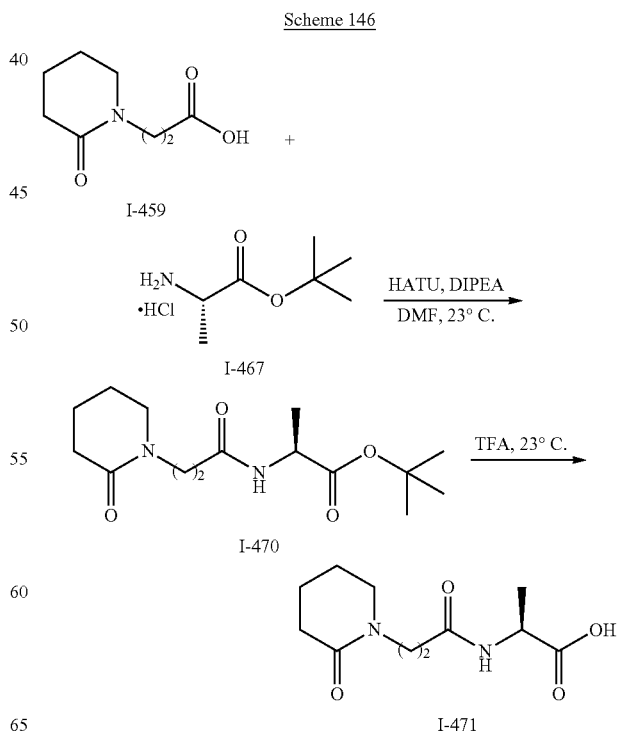

To a solution of amine salt I-467 (87.9 mg, 0.484 mmol), carboxylic acid I-459 (82.8 mg, 1.0 equiv.) and DIPEA (253 μL, 3.0 equiv.) in DMF (2 mL) at ambient temperature was added HATU (275.8 mg, 1.5 equiv.). The reaction mixture was maintained at ambient temperature for 16 hours and was then purified by preparative HPLC (Mobile Phase: MeCN/H₂O with 0.1% AcOH) to afford ester I-470 as a colorless oil (131.9 mg, 91% yield).

To ester I-470 (131.9 mg, 0.442 mmol) was added TFA (4 mL). The reaction mixture was maintained at ambient temperature for 4 hours, then concentrated. The residue afforded was purified by preparative HPLC (Mobile Phase: MeCN/H₂O with 0.1% TFA) to afford acid I-471 as a white solid (102.2 mg, 95% yield). ESI-MS found 243.3. $C_{11}H_{19}N_2O_4$ (M+H)⁺ requires 243.1.

The synthesis of intermediate I-474 is depicted in Scheme 147:

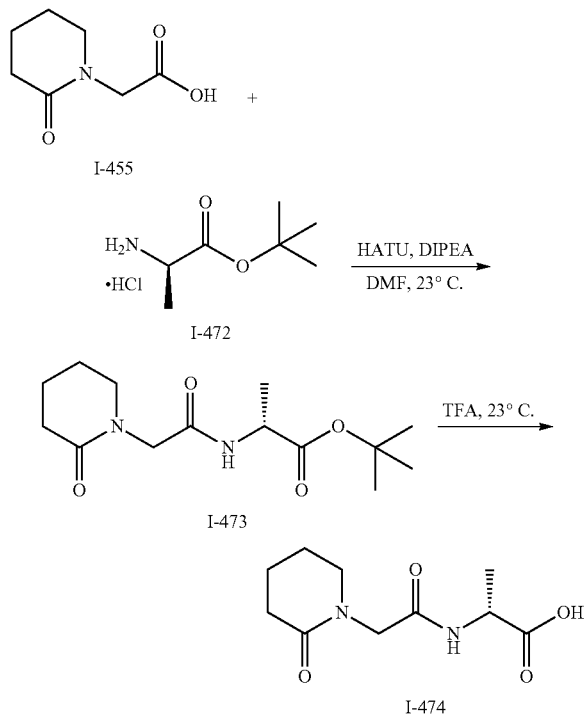

Scheme 147

To a solution of amine salt I-472 (79.1 mg, 0.436 mmol), carboxylic acid I-455 (68.4 mg, 1.0 equiv.) and DIPEA (228 μL, 3.0 equiv.) in DMF (2 mL) at ambient temperature was added HATU (248.4 mg, 1.5 equiv.). The reaction mixture was maintained at ambient temperature for 16 hours and was then purified by preparative HPLC (Mobile Phase: MeCN/H₂O with 0.1% AcOH) to afford ester I-473 as a colorless oil (105.9 mg, 86% yield).

To ester I-473 (105.9 mg, 0.372 mmol) was added TFA (4 mL). The reaction mixture was maintained at ambient temperature for 4 hours, then concentrated. The residue afforded was purified by preparative HPLC (Mobile Phase: MeCN/H₂O with 0.1% TFA) to afford acid I-474 as a white solid (100.5 mg, quantitative yield). ESI-MS found 229.2. $C_{10}H_{17}N_2O_4$ (M+H)⁺ requires 229.1.

The synthesis of intermediate I-476 is depicted in Scheme 148:

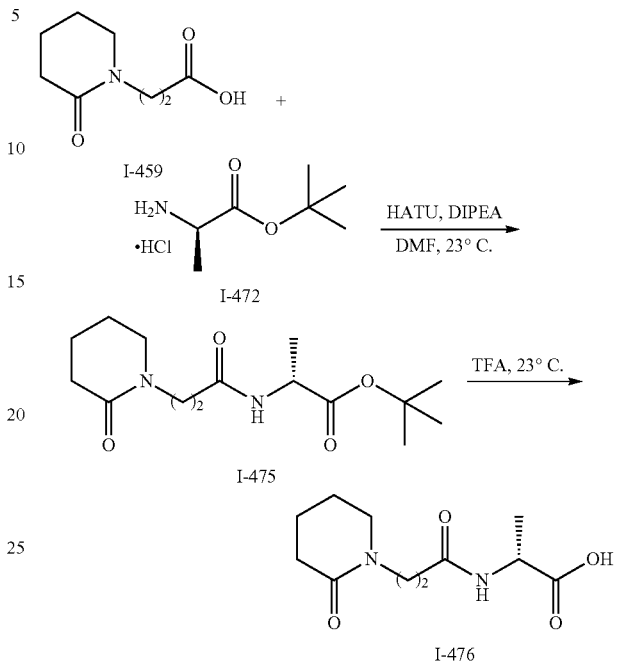

Scheme 148

To a solution of amine salt I-472 (74.4 mg, 0.41 mmol), carboxylic acid I-459 (70.1 mg, 1.0 equiv.) and DIPEA (214 μL, 3.0 equiv.) in DMF (2 mL) at ambient temperature was added HATU (233.6 mg, 1.5 equiv.). The reaction mixture was maintained at ambient temperature for 16 hours and was then purified by preparative HPLC (Mobile Phase: MeCN/H₂O with 0.1% AcOH) to afford ester I-475 as a colorless oil (104.3 mg, 85% yield).

To ester I-475 (104.3 mg, 0.35 mmol) was added TFA (4 mL). The reaction mixture was maintained at ambient temperature for 4 hours, then concentrated. The residue afforded was purified by preparative HPLC (Mobile Phase: MeCN/H₂O with 0.1% TFA) to afford acid I-476 as a white solid (96.6 mg, quantitative yield). ESI-MS found 243.2. $C_{11}H_{19}N_2O_4$ (M+H)⁺ requires 243.1.

The synthesis of intermediate I-478 is depicted in Scheme 149:

Scheme 149

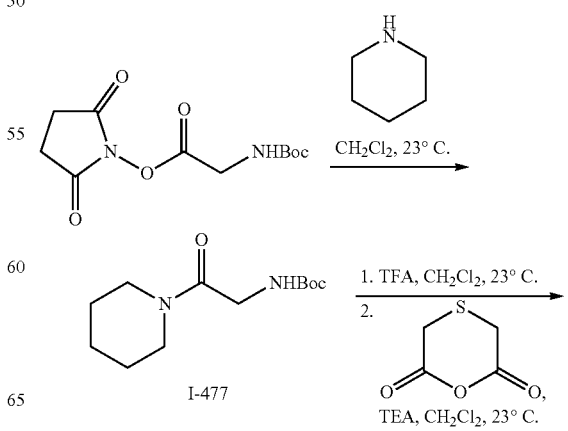

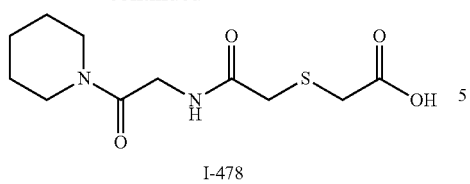

I-478

To a solution of 2,5-dioxopyrrolidin-1-yl (tert-butoxycarbonyl)glycinate (50 mg, 0.183 mmol) in 1 mL of anhydrous DCM was added piperidine (0.2 mL, 5 equiv.). The reaction mixture was stirred at room temperature for 18 hours, then diluted with 5 mL of DCM, washed with 1N HCl (5 mL), saturated aqueous NaHCO$_3$ (5 mL) and brine (5 mL). The organic extracts were dried (Na$_2$SO$_4$) and concentrated to afford a residue, which was purified by silica gel chromatography to afford the amide I-477 (35 mg, 81% yield).

Amide I-477 (35 mg, 0.15 mmol) was dissolved in 1:1 DCM/TFA (3 mL). After 1 hour at room temperature, the reaction mixture was concentrated and held under high vacuum for 1 hour. The resulting oil and thiodiglycolic anhydride (21.5 mg, 1.1 equiv.) were dissolved in DCM (3 mL), and TEA (65 µL, 2.5 equiv.) was added. After 25 minutes, the reaction mixture was concentrated and purified by preparative HPLC (H$_2$O/MeCN with 0.1% TFA) to afford 14.6 mg (5% yield) of acid I-478. ESI-MS found 275.1, C$_{11}$H$_{19}$N$_2$O$_4$S (MH$^+$) requires 275.1.

The synthesis of intermediate I-486 is depicted in Scheme 150:

Scheme 150

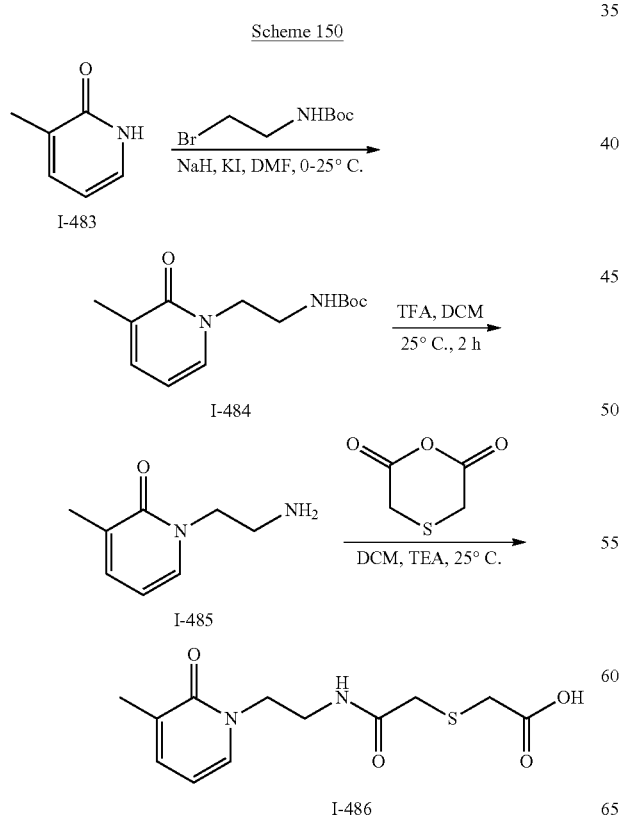

Step 1: Tert-butyl (2-(3-methyl-2-oxopyridin-1(2H)-yl)ethyl)carbamate (I-484)

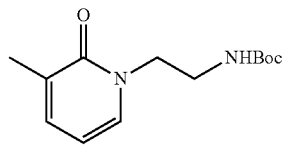 [SMILES: Cc1cccn(CCNC(=O)OC(C)(C)C)c1=O]

A solution of 3-methylpyridin-2(1H)-one, I-483 (cas: 1003-56-1, 3.0 g, 27.52 mmol, 1.0 equiv.), KI (0.913 g, 5.50 mmol, 0.2 equiv.), NaH (60%, 1.321 g, 33.02 mmol, 1.2 equiv.), in DMF (20 mL) was stirred under nitrogen at 0° C. for 1 hour. Then the reaction mixture was added to a solution of tert-butyl (2-bromoethyl)carbamate (cas: 39684-80-5, 9.205 g, 41.28 mmol, 1.5 equiv.) in DMF (20 mL) dropwise. The reaction mixture was stirred at 0° C. for other 1 hour and then 25° C. for another 48 hours. LCMS analysis showed ~50% conversion. Then H$_2$O (50 mL) was added and the mixture was extracted with EtOAc (100 mL×3). The organic phase was dried and purified by silica gel chromatography (20%-50% EtOAc with Petroleum ether) to afford the product tert-butyl (2-(3-methyl-2-oxopyridin-1(2H)-yl)ethyl)carbamate I-484 (1.2 g, 17% yield, 95% purity) as white solid, MS (ESI, positive ion) m/z: 253 (M+1) and byproduct: tert-butyl (2-((3-methylpyridin-2-yl)oxy)ethyl)carbamate (0.2 g, 3% yield, 95% purity), MS (ESI, positive ion) m/z: 253.1 (M+1).

Step 2: 1-(2-aminoethyl)-3-methylpyridin-2(1H)-one (I-485)

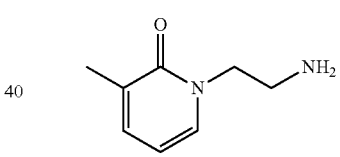

To the solution of tert-butyl (2-(3-methyl-2-oxopyridin-1(2H)-yl)ethyl)carbamate I-484 (1.2 g, 4.76 mmol, 1.0 equiv.) in DCM (20 mL) was added TFA (10 mL). The solution was stirred for 2 h at 25° C. After completion, the mixture was concentrated and the remained TFA was removed by centrifugation to give light yellow oil (0.7 g, TFA salt, 97% yield, 60% purity by LCMS). MS (ESI, positive ion) m/z: 153.1 (M+1).

Step 3: 2-((2-((2-(3-methyl-2-oxopyridin-1(2H)-yl)ethyl)amino)-2-oxoethyl)thio)acetic acid (I-486)

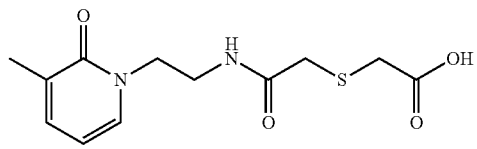 [SMILES: Cc1cccn(CCNC(=O)CSCC(=O)O)c1=O]

A solution of 1-(2-aminoethyl)-3-methylpyridin-2(1H)-one (0.7 g, 4.61 mmol, 1.0 equiv.), TEA (1.397 g, 13.83 mmol, 3.0 equiv.), thiodiglycolic anhydride (0.913 g, 6.92 mmol, 1.5 equiv.) in DCM (10 mL) was stirred for 36 hours at 25° C. After completion, the reaction mixture was concentrated. The residue was purified by Preparative HPLC (Mobile Phase: ACN-H₂O) to afford I-486 (119.7 mg, 9% yield, 99.2% purity) as a white solid. MS (ESI, positive ion) m/z: 285.1 (M+1). ¹H NMR (400 MHz, D₂O) δ 7.41-7.36 (m, 1H), 7.32 (dd, 1H), 6.31 (t, 1H), 4.07-4.01 (m, 2H), 3.54-3.48 (m, 2H), 3.17 (d, 4H), 1.99 (s, 3H).

The synthesis of intermediate I-490 is depicted in Scheme 151:

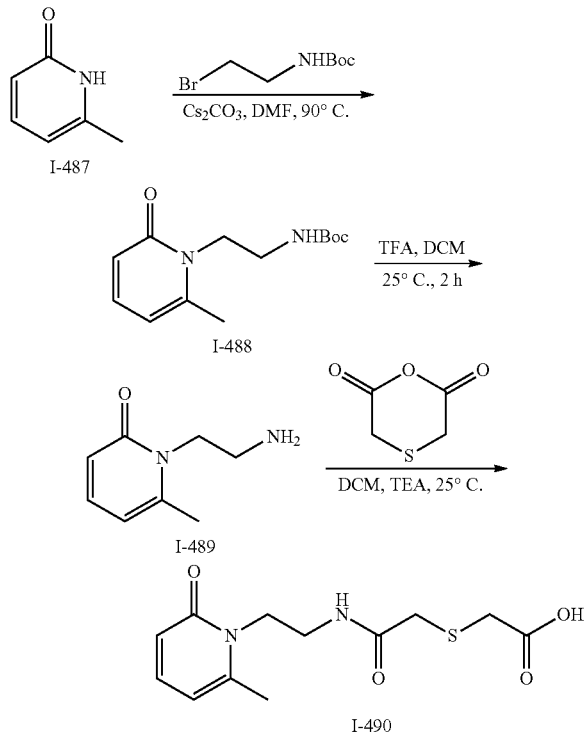

Step 1: tert-butyl (2-(6-methyl-2-oxopyridin-1(2H)-yl)ethyl)carbamate (I-488)

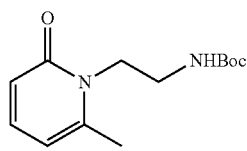 [SMILES: Cc1cccc(=O)n1CCNC(=O)OC(C)(C)C]

To a solution of 6-methylpyridin-2(1H)-one I-487 (cas: 3279-76-3, 5.0 g, 45.87 mmol, 1.0 equiv.), Cs₂CO₃ (29.91 g, 91.74 mmol, 2.0 equiv.) in anhydrous DMF (40 mL) was added tert-butyl (2-bromoethyl)carbamate (cas: 39684-80-5, 15.34 g, 68.81 mmol, 1.5 equiv.). The reaction mixture was stirred at 90° C. for 4 hours. After completion, the reaction mixture was purified by reversed flash column (Mobile Phase: MeCN-H₂O, Gradient: 20-30% H₂O) to afford tert-butyl (2-(6-methyl-2-oxopyridin-1(2H)-yl)ethyl)carbamate, I-488 (3.0 g, 26% yield, 95% purity) as a white solid, MS (ESI, positive ion) m/z: 253.1 (M+1) and byproduct: tert-butyl (2-((6-methylpyridin-2-yl)oxy)ethyl)carbamate (7.0 g, 61% yield, 95% purity) as a white solid, MS (ESI, positive ion) m/z: 253.1 (M+1).

Step 2: 1-(2-aminoethyl)-6-methylpyridin-2(1H)-one (I-489)

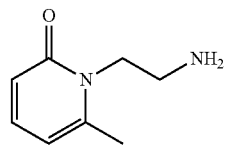

To a solution of tert-butyl (2-(6-methyl-2-oxopyridin-1(2H)-yl)ethyl)carbamate, I-488 (1.5 g, 5.95 mmol, 1.0 equiv.) in DCM (20 mL) was added TFA (10 mL). The reaction mixture was stirred for 2 hours at 25° C. After completion, the reaction mixture was concentrated and the remained TFA was removed by centrifugation to give amine I-489 as a light yellow oil (0.9 g, TFA salt, 101% yield, 90% purity). MS (ESI, positive ion) m/z: 153.1 (M+1).

Step 3: 2-((2-((2-(6-methyl-2-oxopyridin-1(2H)-yl)ethyl)amino)-2-oxoethyl)thio)acetic acid

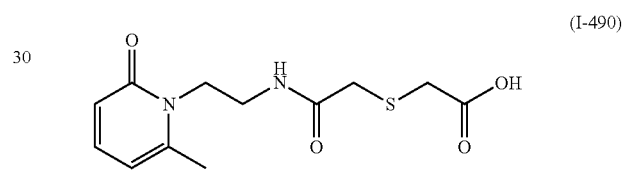

The solution of 1-(2-aminoethyl)-6-methylpyridin-2(1H)-one, I-489 (0.9 g, 5.92 mmol, 1.0 equiv.), TEA (1.79 g, 17.76 mmol, 3.0 equiv.), thiodiglycolic anhydride (1.172 g, 8.88 mmol, 1.5 equiv.) in DCM (10 mL) was stirred for 24 hours at 25° C. After completion, the reaction mixture was concentrated. The residue was purified by preparative HPLC (Mobile Phase: ACN-H₂O, Gradient: 5-10% MeCN) to afford carboxylic acid I-490 (119 mg, 7% yield, 99.6% purity) as a light yellow solid. MS (ESI, positive ion) m/z: 285.1 (M+1). ¹H NMR (400 MHz, D₂O) δ 7.39 (dd, 1H), 6.34 (dd, 2H), 4.13 (t, 2H), 3.50 (t, 2H), 3.20 (s, 2H), 3.17 (s, 2H), 2.35 (s, 3H).

The synthesis of carboxylic acid I-494 involved 3 steps as depicted in the following Scheme 152:

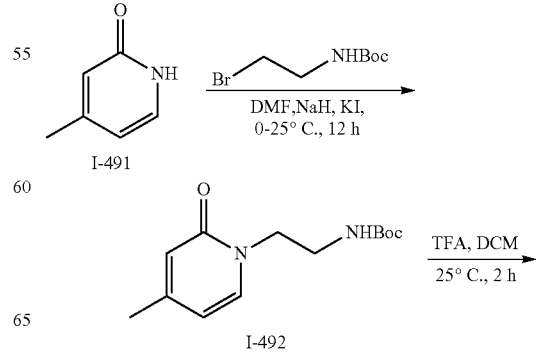

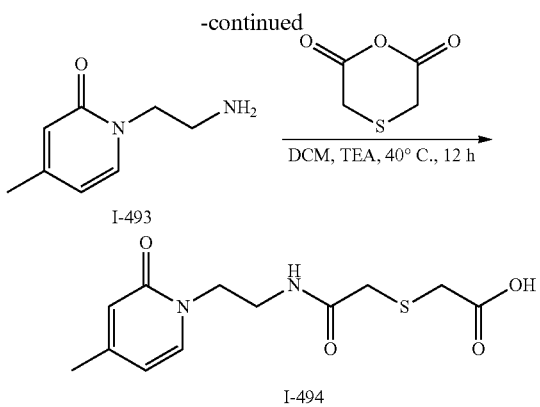

Step 1: Tert-butyl (2-(4-methyl-2-oxopyridin-1(2H)-yl)ethyl)carbamate (I-492)

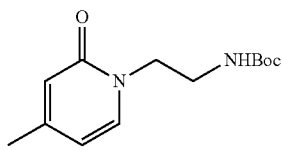 [SMILES: Cc1ccn(CCNC(=O)OC(C)(C)C)c(=O)c1]

A solution of 4-methylpyridin-2(1H)-one, I-491 (cas: 13466-41-6, 5.0 g, 45.87 mmol, 1.0 equiv.), KI (1.522 g, 9.17 mmol, 0.2 equiv.), NaH (60%, 2.20 g, 55.04 mmol, 1.2 equiv.) in DMF (20 ml) was stirred under nitrogen at 0° C. for 1 hour. Then the mixture was added to a solution of tert-butyl (2-bromoethyl)carbamate (cas: 39684-80-5, 15.34 g, 68.80 mmol, 1.5 equiv.) in DMF (30 mL) dropwise. The reaction mixture was stirred at 0° C. for 1 hour and then 25° C. for other 12 hours. LCMS showed ~50% conversion, at which point H₂O (50 mL) was added and the reaction mixture was extracted with EtOAc (100 mL×3). The organic phase was dried and purified by flash (20%-50% EtOAc with Petroleum ether) to afford tert-butyl (2-(4-methyl-2-oxopyridin-1(2H)-yl)ethyl)carbamate, I-492 (1.3 g, 11% yield, 95% purity) as a white solid, MS (ESI, positive ion) m/z: 253 (M+1) and by product: tert-butyl (2-((4-methylpyridin-2-yl)oxy)ethyl)carbamate (0.2 g, 2% yield, 95% purity), MS (ESI, positive ion) m/z: 253 (M+1).

Step 2: 1-(2-aminoethyl)-4-methylpyridin-2(1H)-one (I-493)

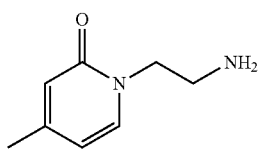

To a solution of tert-butyl (2-(4-methyl-2-oxopyridin-1(2H)-yl)ethyl)carbamate, I-492 (1.3 g, 5.16 mmol, 1.0 equiv.) in DCM (20 mL) was added TFA (10 ml). The solution was stirred for 2 hours at 25° C. After completion, the reaction mixture was concentrated and the remained TFA was removed by centrifugation to afford amine I-493 as a light yellow oil (0.8 g, TFA salt, 102% yield, 90% purity by LCMS). MS (ESI, positive ion) m/z: 153.1 (M+1).

Step 3: 2-((2-((2-(4-methyl-2-oxopyridin-1(2H)-yl)ethyl)amino)-2-oxoethyl)thio)acetic acid (I-494)

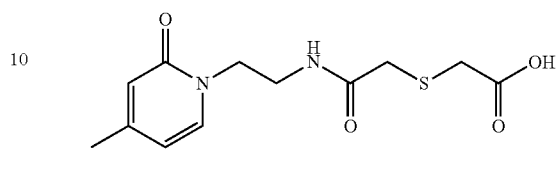

The solution of 1-(2-aminoethyl)-4-methylpyridin-2(1H)-one, I-493 (0.8 g, 5.26 mmol, 1.0 equiv.), TEA (1.593 g, 15.78 mmol, 3.0 equiv.), thiodiglycolic anhydride (1.041 g, 7.89 mmol, 1.5 equiv.) in DCM (10 mL) was stirred for 12 hours at 40° C. After completion, the reaction mixture was concentrated. The residue was purified by preparative HPLC (Mobile Phase: ACN-H₂O, Gradient: 5-10% MeCN) to afford I-494 (114.2 mg, 8% yield, 99.6% purity) as a white solid. MS (ESI, positive ion) m/z: 285.1 (M+1). ¹H NMR (400 MHz, D₂O) δ 7.36 (d, 1H), 6.36 (s, 1H), 6.31 (dd, 1H), 4.03-3.97 (m, 2H), 3.52-3.47 (m, 2H), 3.20 (s, 2H), 3.16 (s, 2H), 2.14 (s, 3H).

The synthesis of carboxylic acid I-498 involved 3 steps as depicted in the following Scheme 153.

Scheme 153

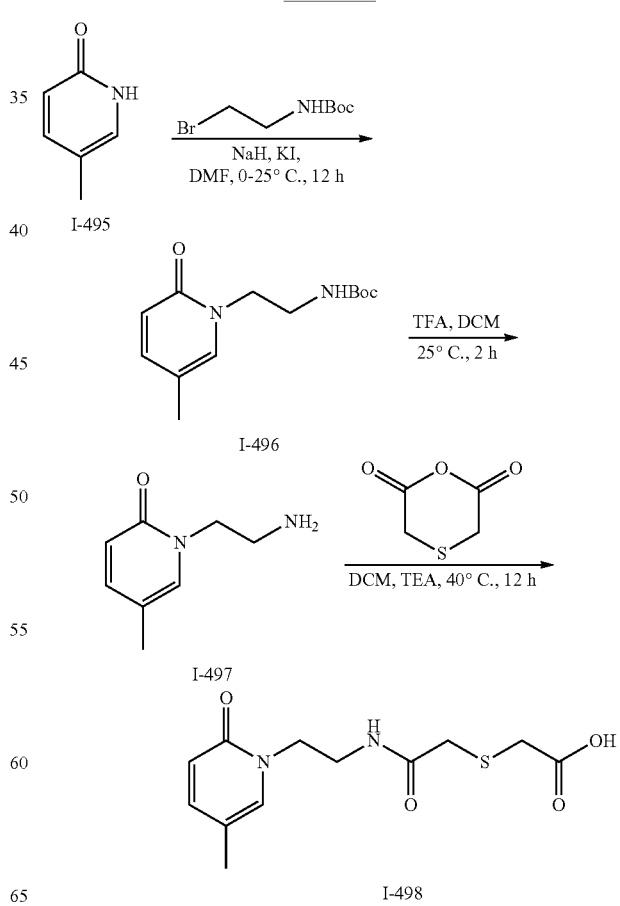

Step 1: Tert-butyl (2-(5-methyl-2-oxopyridin-1(2H)-yl)ethyl)carbamate (I-496)

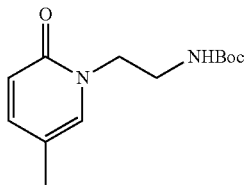 [SMILES: Cc1ccc(=O)n(CCNC(=O)OC(C)(C)C)c1]

A solution of 5-methylpyridin-2(1H)-one, I-495 (cas: 1003-68-5, 5.0 g, 45.87 mmol, 1.0 equiv.), KI (1.522 g, 9.17 mmol, 0.2 equiv.), and NaH (60%, 2.20 g, 55.04 mmol, 1.2 equiv.) in DMF (20 ml) was stirred under nitrogen at 0° C. for 1 hour. Then the reaction mixture was added to a solution of tert-butyl (2-bromoethyl)carbamate (cas: 39684-80-5, 15.34 g, 68.80 mmol, 1.5 equiv.) in DMF (30 mL) dropwise. The reaction mixture was stirred at 0° C. for 1 hour and then 25° C. for 12 hours. LCMS analysis showed ~50% conversion, at which point H₂O (50 mL) was added and the reaction mixture was extracted with EtOAc (100 mL×3). The organic phase was dried and purified by silica gel chromatography (20%-50% EtOAc with Petroleum ether) to give the product tert-butyl (2-(5-methyl-2-oxopyridin-1 (2H)-yl)ethyl)carbamate, I-496 (1.7 g, 15% yield, 95% purity) as a white solid, MS (ESI, positive ion) m/z: 253 (M+1) and byproduct: tert-butyl (2-((5-methylpyridin-2-yl)oxy)ethyl)carbamate (0.4 g, 3% yield, 95% purity), MS (ESI, positive ion) m/z: 253 (M+1).

Step 2: 1-(2-aminoethyl)-5-methylpyridin-2(1H)-one (I-497)

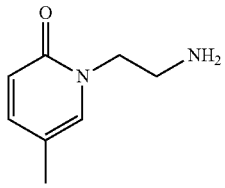

To a solution of tert-butyl (2-(4-methyl-2-oxopyridin-1 (2H)-yl)ethyl)carbamate, I-496 (1.7 g, 6.74 mmol, 1.0 equiv.) in DCM (20 mL) was added TFA (10 mL) and the reaction mixture was stirred for 2 hours at 25° C. After completion, the reaction mixture was concentrated and the remaining TFA was removed by centrifugation to give the amine I-497 as a light yellow oil (1.0 g, TFA salt, 103% yield, 90% purity by LCMS). MS (ESI, positive ion) m/z: 153.1 (M+1).

Step 3: 2-((2-((2-(5-methyl-2-oxopyridin-1(2H)-yl)ethyl)amino)-2-oxoethyl)thio)acetic acid (I-498)

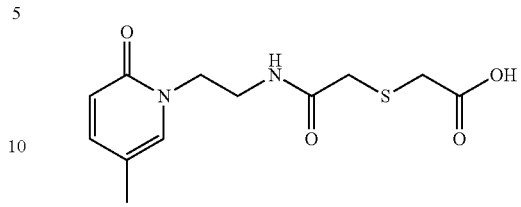

A solution of 1-(2-aminoethyl)-5-methylpyridin-2(1H)-one, I-497 (1.0 g, 6.58 mmol, 1.0 equiv.), TEA (1.994 g, 19.74 mmol, 3.0 equiv.), and thiodiglycolic anhydride (1.303 g, 9.87 mmol, 1.5 equiv.) was stirred in DCM (10 mL) for 12 hours at 40° C. After completion, the reaction mixture was concentrated. The residue was purified by preparative HPLC (Mobile Phase: ACN-H₂O, Gradient: 5-10% MeCN) to give I-498 (106 mg, 7% yield) as a white solid. MS (ESI, positive ion) m/z: 285.1 (M+1). ¹H NMR (400 MHz, D₂O) δ 7.44 (dd, 1H), 7.30 (s, 1H), 6.47 (d, 1H), 4.05-3.98 (m, 2H), 3.56-3.49 (m, 2H), 3.21 (s, 2H), 3.17 (s, 2H), 2.01 (s, 3H).

The synthesis of intermediate I-505 is depicted in Scheme 155:

Scheme 155

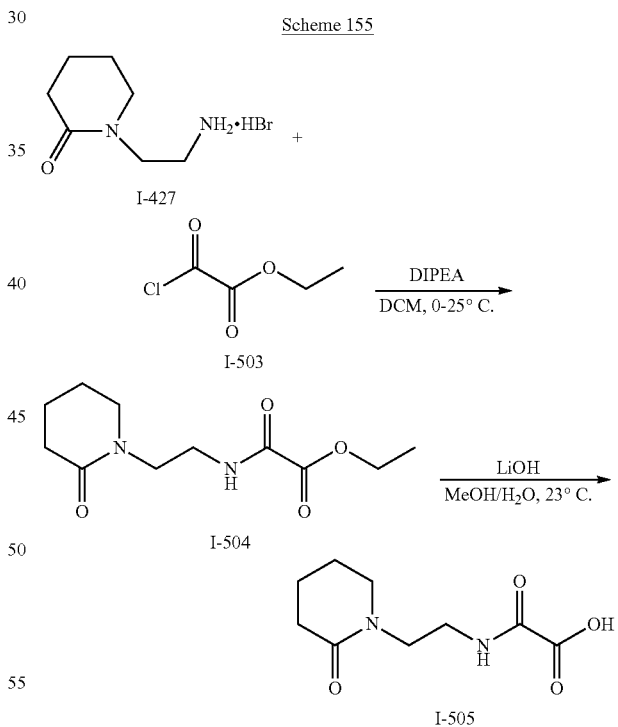

To a solution of amine hydrochloride I-427 (144 mg, 0.645 mmol) and DIPEA (225 µL, 2.0 equiv.) in DCM (5 mL) that had been cooled in an ice-water bath was added acid chloride I-503 (88.1 mg, 1.0 equiv.). The reaction mixture was gradually allowed to warm to ambient temperature and after 3 hours was concentrated to a residue that was purified by preparative HPLC (MeCN/H₂O with 0.1% TFA) to afford ester I-504 (163.8 mg, >99% yield) as a colorless oil.

To a solution of ester I-504 (78 mg, 0.322 mmol) in MeOH (3 mL) and H₂O (1 mL) was added lithium hydroxide (23.1 mg, 3.0 equiv.). The reaction mixture was stirred for 2 hours at ambient temperature at which point analysis by LC-MS indicated that the reaction was complete. The reaction mixture was concentrated and diluted with H₂O (1 mL), then acidified to pH ~1 with 2N HCl. The solution was subjected to purification by preparative HPLC (MeCN/H₂O with 0.1% TFA) to afford carboxylic acid I-505 (56.5 mg, 82% yield) as a white solid. ESI-MS found 215.3, $C_9H_{15}N_2O_4$ (MH⁺) requires 215.1.

The synthesis of intermediate I-507 is depicted in Scheme 156:

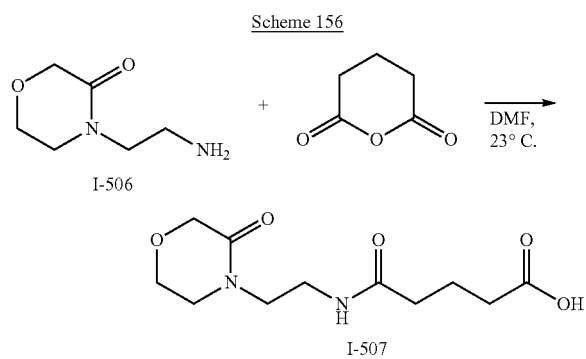

Amine I-506 (84.2 mg, 0.584 mmol) was treated with Glutaric anhydride (66.6 mg, 1.0 equiv.) in DMF (1.1 mL). After 1.5 hours the reaction mixture was subjected to purification by preparative HPLC (MeCN/H₂O with 0.1% TFA) to afford carboxylic acid I-507 (40 mg, 27% yield) as a colorless oil. ESI-MS found 259.2, $C_{11}H_{19}N_2O_5$ (MH⁺) requires 259.1.

The synthesis of intermediate I-508 is depicted in Scheme 157:

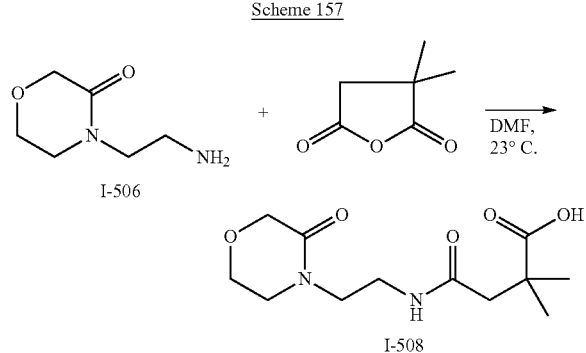

Amine I-506 (96 mg, 0.666 mmol) was treated with 2,2-dimethylsuccinic anhydride (96 mg, 1.1 equiv.) in DMF (1 mL). After 16 hours the reaction mixture was subjected to purification by preparative HPLC (MeCN/H₂O with 0.1% TFA) to afford carboxylic acid I-508 (24.8 mg, 14% yield) as a colorless oil.

The synthesis of intermediate I-510 is depicted in Scheme 158:

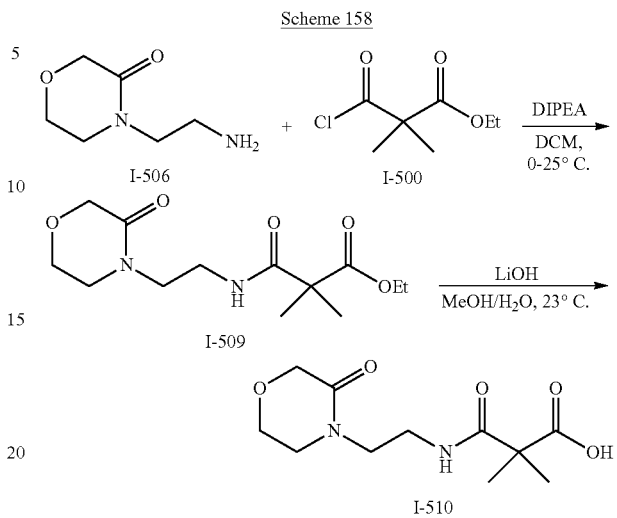

To a solution of amine I-506 (169.5 mg, 1.174 mmol) and DIPEA (614 µL, 3.0 equiv.) in DCM (5 mL) that had been cooled in an ice-water bath was added acid chloride I-500 (209.3 mg, 1.0 equiv.). The reaction mixture was allowed to warm to ambient temperature and after 1.5 hours was concentrated to a residue to afford crude ester I-509 as a colorless oil, which was redissolved in MeOH (3 mL). A solution of lithium hydroxide (84.4 mg mg, 3.0 equiv.) in H₂O (1 mL) was added. The reaction mixture was stirred for 17 hours at ambient temperature. The reaction mixture was concentrated and 1M NaHSO₄ and 6N HCl was added to afford a solution of pH ~ 1.5. Purification by preparative HPLC (MeCN/H₂O with 0.1% TFA) afforded carboxylic acid I-510 (125.3 mg, 41% yield) as a colorless oil. ESI-MS found 259.2, $C_{11}H_{19}N_2O_5$ (MH⁺) requires 259.1.

The synthesis of intermediate I-513 is depicted in Scheme 159:

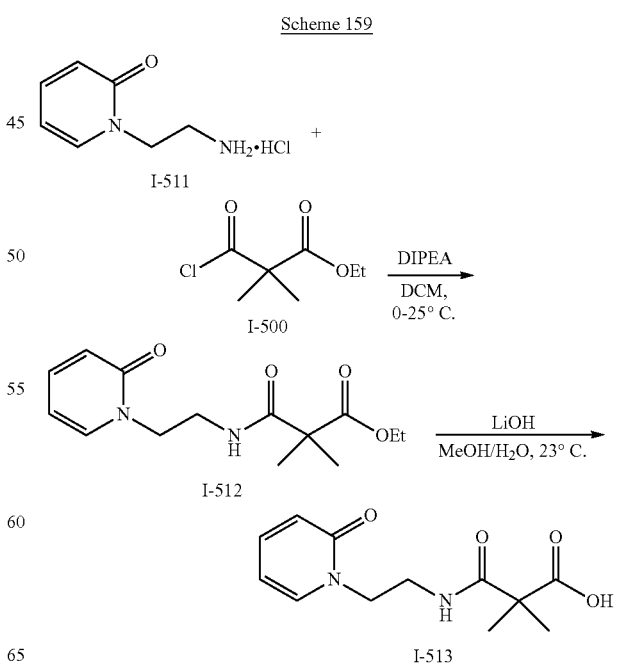

To a solution of amine dihydrochloride I-511 (138.5 mg, 0.656 mmol) and DIPEA (343 μL, 3.0 equiv.) in DCM (4 mL) that had been cooled in an ice-water bath was added acid chloride I-500 (117.2 mg, 1.0 equiv.). The reaction mixture was allowed to warm to ambient temperature and after 1.5 hours was deemed complete by LC-MS analysis. The reaction mixture was concentrated to a residue to afford crude ester I-512 as a colorless oil, which was redissolved in MeOH (2 mL). A solution of lithium hydroxide (47.2 mg mg, 3.0 equiv.) in $H_2O$ (1 mL) was added. The reaction mixture was stirred for 17 hours at ambient temperature. Additional LiOH (47.2 mg mg, 3.0 equiv.) in $H_2O$ (1 mL) was added and stirring was continued for 2 more hours. The reaction mixture was concentrated and 6N HCl was added to afford a solution of pH ~ 1.5. Purification by preparative HPLC (MeCN/$H_2O$ with 0.1% TFA) afforded carboxylic acid I-513 (136 mg, 82% yield). ESI-MS found 253.2, $C_{12}H_{17}N_2O_4$ (MH$^+$) requires 253.1.

The synthesis of intermediate I-516 is depicted in Scheme 160:

Scheme 160

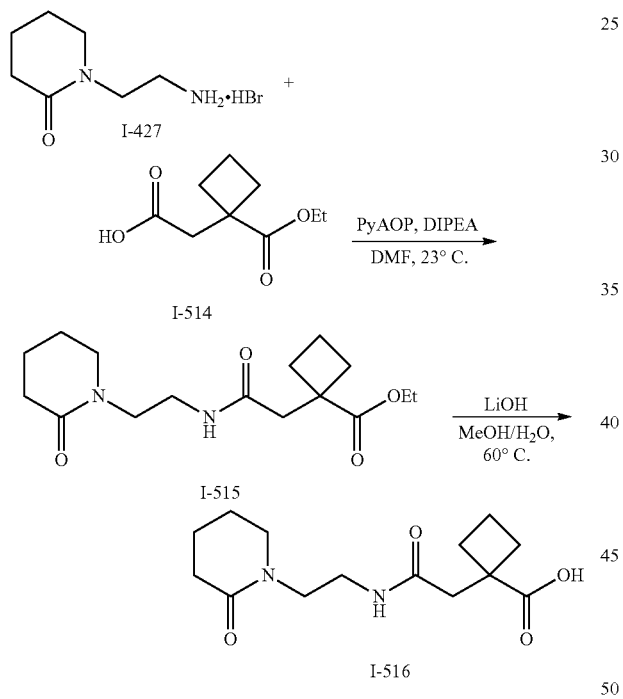

To a solution of amine salt I-427 (62.8 mg, 0.281 mmol), carboxylic acid I-514 (52.4 mg, 1.0 equiv.) and DIPEA (147 μL, 3.0 equiv.) in DMF (1 mL) at ambient temperature was added PyAOP (190.7 mg, 1.3 equiv.). The reaction mixture was maintained at ambient temperature for 17 hours and was then purified by preparative HPLC (Mobile Phase: MeCN/$H_2O$ with 0.1% TFA) to afford ester I-515 as a colorless oil (68.7 mg, 79% yield).

To a solution of ester I-515 (68.7 mg, 0.221 mmol) in MeOH (2 mL) and $H_2O$ (1 mL) was added lithium hydroxide (15.9 mg, 3.0 equiv.). The reaction mixture was stirred at ambient temperature for 3 hours, then acidified with 6 N HCl to pH<2, then purified by preparative HPLC (Mobile Phase: MeCN/$H_2O$ with 0.1% TFA) to afford acid I-516 as a white solid (33.9 mg, 54% yield). ESI-MS found 283.3, $C_{14}H_{23}N_2O_4$ (M+4H)$^{4+}$ requires 283.2.

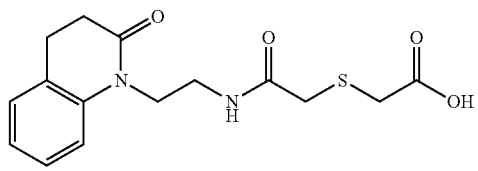

I-517

Prepared according to GP1. Yield: 32.5 mg (74%). ESI-MS found 323.1, $C_{15}H_{19}N_2O_4S$ (MH$^+$) requires 323.1.

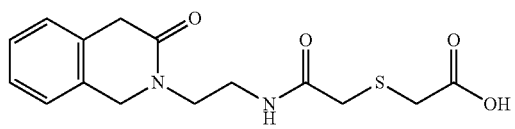

I-518

Prepared according to GP1. Yield: 18 mg (39%). ESI-MS found 323.3, $C_{15}H_{19}N_2O_4S$ (MH$^+$) requires 323.1.

Synthesis of Intermediate I-552

The synthesis of I-552 involved 5 steps as depicted in the following Scheme 161.

Scheme 161

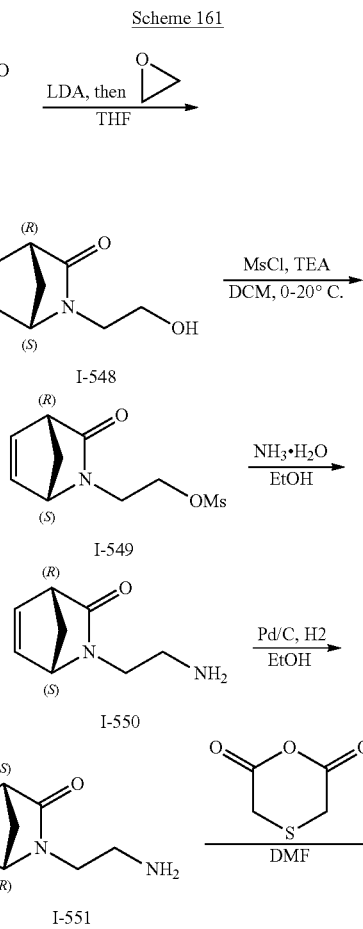

-continued

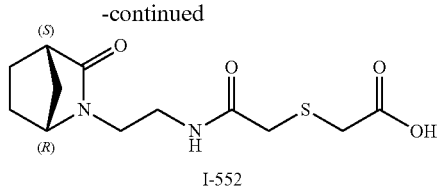

I-552

Summary

The chemical structure of the target compound was confirmed by ¹H NMR and LC-MS with the purity >90% (HPLC 214 & 254 nm).

Step 1: (1S,4R)-2-(2-hydroxyethyl)-2-azabicyclo[2.2.1]hept-5-en-3-one (I-548)

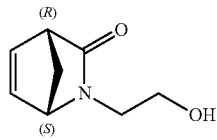

To a solution of (1S,4R)-2-azabicyclo[2.2.1]hept-5-en-3-one, I-547 (2.18 g, 20.0 mmol, CAS: 13031-83-8) in anhydrous THF (30 mL) was added LDA (10 mL, 2M in THF, 1.0 equiv.) at 0° C. The mixture was stirred at 0° C. for 0.5 hours and oxirane (20 mL, 20.0 equiv.) was added. The reaction mixture was allowed to warm to 20° C. and maintained at that temperature for another 16 hours. After the reaction was deemed complete, the pH of the reaction mixture was adjusted to 6 with 1N HCl. The reaction mixture was concentrated to a volume of approximately 5 mL and purified by reversed phase column chromatography ($C_{18}$ column, 20-35 μm, 100 Å, 80 g, 0.1% v/v Formic acid in MeCN/$H_2O$) to afford the alcohol I-548 (1.3 g, 43% yield). MS (ESI, pos. ion) m/z: 154.1, ($MH^+$).

Step 2: 2-((1S,4R)-3-oxo-2-azabicyclo[2.2.1]hept-5-en-2-yl)ethyl methanesulfonate (I-549)

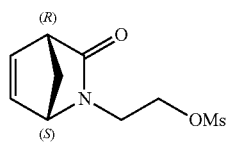

To a solution of methyl (1S,4R)-2-(2-hydroxyethyl)-2-azabicyclo[2.2.1]hept-5-en-3-one, I-548 (1.3 g, 8.50 mmol) and TEA (2.5 g, 3.0 equiv.) in anhydrous THF (20 mL) was added MsCl (1.46 g, 1.5 equiv.). The reaction mixture was stirred at 20° C. for 16 hours, then diluted with water (50 mL), and extracted with EtOAc (50 mL). The organic extract was dried over sodium sulfate, and concentrated to afford the crude mesylate I-549 as a yellow oil (1.8 g, 92% yield), which was used for the next step. MS (ESI, pos. ion) m/z: 232.0, ($MH^+$).

Step 3: (1S,4R)-2-(2-aminoethyl)-2-azabicyclo[2.2.1]hept-5-en-3-one (I-550)

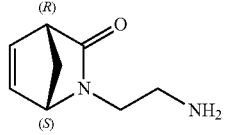

To a solution of crude 2-((1S,4R)-3-oxo-2-azabicyclo[2.2.1]hept-5-en-2-yl)ethyl methanesulfonate, I-549 (1.8 g, 7.79 mmol) in EtOH (20 mL) was added concentrated aqueous $NH_3$ (25-28% solution, 5 mL). The mixture was stirred at 100° C. for 0.5 hours. After completion, the reaction mixture was concentrated to ca. 5 mL and purified by reversed phase column chromatography (0.1% Formic acid in MeCN/$H_2O$) to afford the desired amine I-550 as a colorless syrup (550 mg, 47% yield). MS (ESI, pos. ion) m/z: 153.1, ($MH^+$).

Step 4: (1R,4S)-2-(2-aminoethyl)-2-azabicyclo[2.2.1]heptan-3-one (I-551)

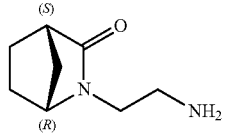

A slurry of (1S,4R)-2-(2-aminoethyl)-2-azabicyclo[2.2.1]hept-5-en-3-one, I-550 (200 mg, 1.32 mmol) and Pd/C (10%, 100 mg) in EtOH (6 mL) was stirred under $H_2$ (1 atm) at 20° C. for 16 hours. The reaction mixture was then filtered, and the filtrate was concentrated to afford the desired amine I-551 as a colorless syrup (200 mg, 98% yield). MS (ESI, pos. ion) m/z: 155.1, ($MH^+$).

Step 5: 2-((2-oxo-2-((2-((1R,4S)-3-oxo-2-azabicyclo[2.2.1]heptan-2-yl)ethyl)amino)ethyl)thio)acetic acid (I-552)

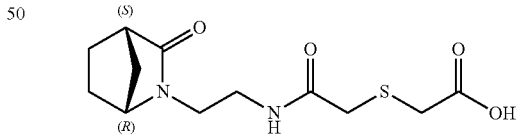

To a solution of (1R,4S)-2-(2-aminoethyl)-2-azabicyclo[2.2.1]heptan-3-one (200 mg, 1.30 mmol) in DMF (3 mL) was added thiodiglycolic anhydride (343 mg, 2.0 equiv.), and the reaction mixture was stirred at 40° C. for 16 hours, then purified by reversed phase column chromatography (0.1% Formic acid in MeCN/$H_2O$) to afford acid I-552 as a colorless syrup (160 mg, 42% yield). MS (ESI, pos. ion) m/z: 287.1, ($MH^+$). ¹H NMR (400 MHz, $D_2O$) δ 4.04 (s, 1H), 3.42-3.54 (m, 2H), 3.31-3.38 (m, 5H), 3.03-3.09 (m, 1H), 2.80-2.81 (m, 1H), 1.90-1.98 (m, 1H), 1.80-1.86 (m, 2H), 1.59-1.65 (m, 1H), 1.39-1.46 (m, 2H).

Synthesis of Intermediate I-557

The synthesis of intermediate I-557 involved 4 steps as described in the following Scheme 162.

Scheme 162

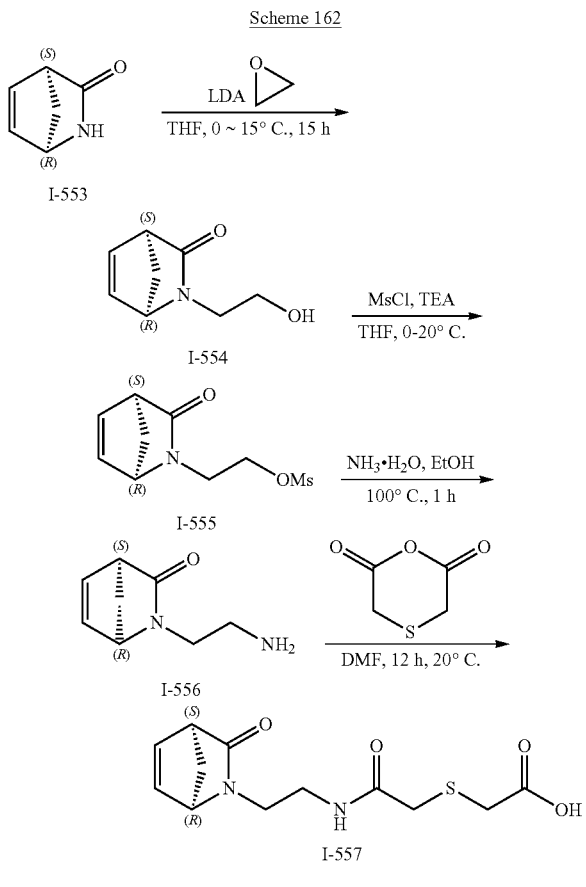

Summary

The chemical structure of the target compound was confirmed by $^1$H NMR and LC-MS with the purity >95% (HPLC 214 & 254 nm).

Step 1: (1R,4S)-2-(2-hydroxyethyl)-2-azabicyclo[2.2.1]hept-5-en-3-one (I-554)

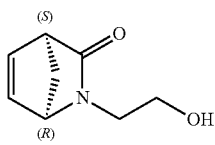

To a solution of (1R,4S)-2-azabicyclo[2.2.1]hept-5-en-3-one (3 g, CAS: 79200-56-9, 27.5 mmol) in THF (50 mL) was added LDA (2M in THF, 13.8 mL, 1.0 equiv.) at 25° C. The reaction mixture was stirred for 1 h at 25° C. and then oxirane (cas: 75-21-8, 20 mL, 17.6 g, 0.4 mol, 14.5 equiv.) was added. The reaction mixture was stirred at 25° C. for 48 hours. When the reaction was deemed complete by LC-MS analysis, the pH of the reaction mixture was adjusted to 6-7 with HCl (1M). The reaction mixture was concentrated to a residue, which was purified by reversed phase column chromatography (0.1% Formic acid in MeCN/H$_2$O) to afford (1R,4S)-2-(2-hydroxyethyl)-2-azabicyclo [2.2.1]hept-5-en-3-one, I-554 (2.8 g, 67% yield) as a yellow oil. MS (ESI, pos. ion) found m/z: 154.1 (MH$^+$).

Step 2: 2-((1R,4S)-3-oxo-2-azabicyclo[2.2.1]hept-5-en-2-yl)ethyl methanesulfonate (I-555)

To a solution of (1R,4S)-2-(2-hydroxyethyl)-2-azabicyclo [2.2.1]hept-5-en-3-one (2.8 g, 18.3 mmol) in THF (50 mL) was added TEA (5.5 g, 3.0 equiv.) and MsCl (2.08 g, 1.0 equiv.) at 25° C. The reaction mixture was stirred at 25° C. for 2 hours. When the reaction was deemed complete by LC-MS analysis, the reaction mixture diluted with water (50 mL), and extracted with EtOAc (50 mL). The organic extract was washed with water (2×40 mL), brine (2×30 mL) and dried over anhydrous Na$_2$SO$_4$, then concentrated to afford the crude mesylate I-555 (3.0 g, 71% yield) as a yellow solid, which was used for next step without further purification. MS (ESI, neg. ion) m/z: 232.0 (M+1).

Step 3: (1R,4S)-2-(2-aminoethyl)-2-azabicyclo[2.2.1]hept-5-en-3-one (I-556)

To a solution of crude mesylate I-555 (3.0 g, 12.9 mmol) in EtOH (20 mL) was added concentrated aqueous ammonia (25-28% solution, 5 mL), and the reaction mixture was stirred at 100° C. for 1 hour, then concentrated to ca. 5 mL and purified by reversed phase column chromatography (0.1% Formic acid in MeCN/H$_2$O) to afford the desired amine I-556 (1.8 g, 95% yield) as a colorless syrup. MS (ESI, pos. ion) m/z: 153.1, (MH$^+$).

Step 4: 2-((2-oxo-2-((2-(((1R,4S)-3-oxo-2-azabicyclo [2.2.1]hept-5-en-2-yl)ethyl)amino)ethyl) thio)acetic acid. (I-557)

To a solution of (1R,4S)-2-(2-aminoethyl)-2-azabicyclo [2.2.1]hept-5-en-3-one (1.4 g, 9.1 mmol) in DMF (3 mL)

was added thiodiglycolic anhydride (2.4 g, 2.0 equiv.), and the reaction mixture was stirred at 40° C. for 12 hours. The reaction mixture was purified by Preparatory HPLC (0.1% Formic acid in MeCN/H$_2$O) to afford carboxylic acid I-557 (33.1 mg, 1% yield) a white solid. MS (ESI, pos. ion) m/z: 285.1, (MH$^+$). $^1$H NMR (400 MHz, D$_2$O) δ6.18-6.24 (m, 1H), 6.01-6.05 (m, 1H), 5.59-5.61 (m, 0.5H), 5.25-5.27 (m, 0.5H), 4.17-4.24 (m, 0.5H), 3.89-3.95 (m, 0.5H), 3.56-3.82 (m, 4H), 3.37-3.54 (m, 4H), 2.44-2.61 (m, 2H).

Synthesis of Intermediate I-559

The synthesis of intermediate I-559 from previously described intermediate I-556 involved 2 steps as depicted in the following Scheme 163.

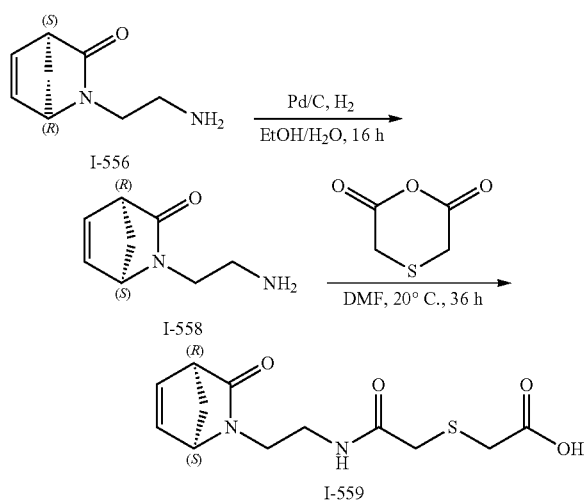

Summary

The chemical structure of the target compound was confirmed by $^1$H NMR and LC-MS with the purity >90% (HPLC 214 & 254 nm).

Step 1: (1S,4R)-2-(2-aminoethyl)-2-azabicyclo[2.2.1]heptan-3-one, I-588

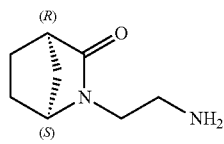

A solution of amine I-556 (1.0 g, 6.6 mmol) and 10% Pd/C (300 mg) in EtOH (10 mL) was stirred under H$_2$ (1 atm) at 20° C. for 16 hours. The reaction mixture was then filtered, and the filtrate was concentrated to afford the amine I-558 (1.0 g, 98% yield) as a colorless syrup. MS (ESI, pos. ion) m/z: 155.1 (M+1).

Step 2: 2-((2-oxo-2-((2-((1S,4R)-3-oxo-2-azabicyclo[2.2.1]heptan-2-yl)ethyl)amino)ethyl)thio)acetic acid (I-559)

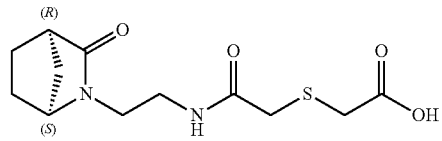

To a solution of amine I-558 (1.0 g, 6.6 mmol) in DMF (10 mL) was added thiodiglycolic anhydride (1.7 g, 2.0 equiv.). The reaction mixture was stirred at 40° C. for 36 hours, then purified directly by Preparative HPLC (0.1% TFA in MeCN/H$_2$O) to afford carboxylic acid I-559 (46.1 mg, 3% yield) as a colorless syrup. MS (ESI, pos. ion) m/z: 287.1, (MH$^+$). $^1$H NMR (400 MHz, D$_2$O) δ4.06 (s, 1H), 3.46-3.54 (m, 2H), 3.31-3.38 (m, 5H), 3.05-3.11 (m, 1H), 2.82 (s, 1H), 1.94-1.99 (m, 1H), 1.81-1.88 (m, 2H), 1.59-1.65 (m, 1H), 1.34-1.48 (m, 2H).

Synthesis of Intermediate I-571

The synthesis of I-571 involved 9 steps as described in the following Scheme 164.

Scheme 164

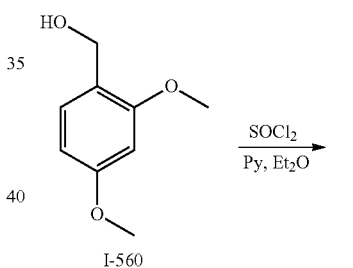

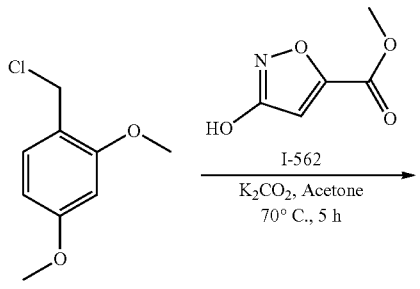

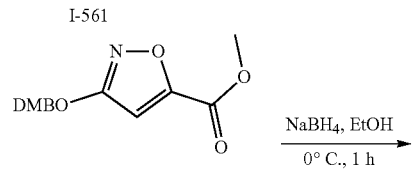

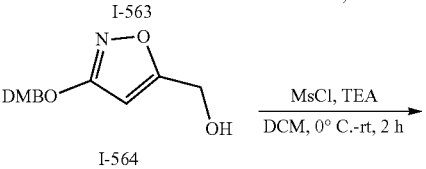

-continued

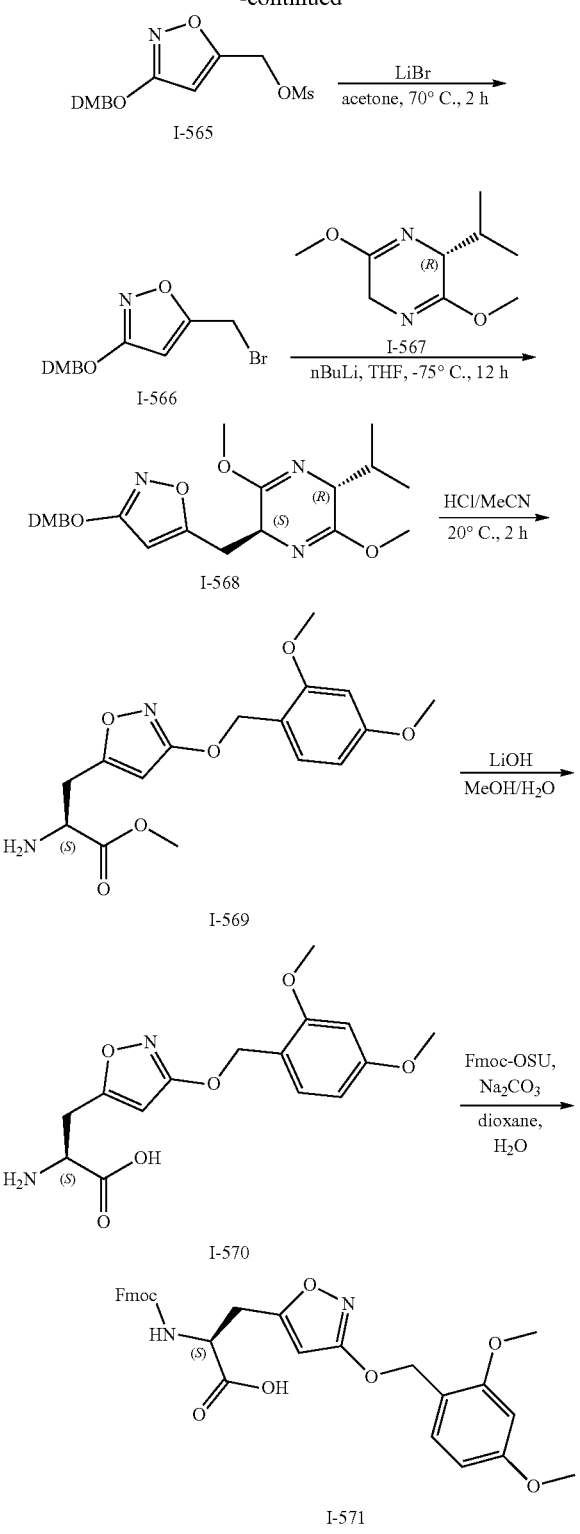

Summary

The chemical structure of the target compound was confirmed by ¹H NMR and LC-MS with the purity >95% (HPLC 214 & 254 nm).

Step 1: 1-(chloromethyl)-2,4-dimethoxybenzene. (I-561)

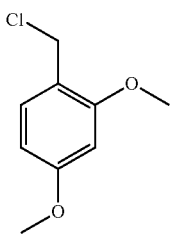

To a solution of (2,4-dimethoxyphenyl)methanol, I-560 (10 g, 59.5 mmol) in Et₂O (100 mL) was added pyridine (4.65 g, 1.0 equiv.), and SOCl₂ (7.02 g, 1.0 equiv.) at 0° C. The reaction mixture was stirred at 0° C. for 2 hours, then poured into ice water (120 mL) and the layers were separated. The aqueous layer was extracted with diethyl ether (2×60 mL) and the combined organic extracts were washed with ice water (60 mL) and a solution of 5:1 saturated aqueous sodium chloride:saturated aqueous sodium bicarbonate (2×60 mL), dried over anhydrous sodium sulfate, filtered, and concentrated to ~50 mL of solution. The crude solution was used directly in next step.

Step 2: Methyl 3-((3,4-dimethylbenzyl)oxy)isoxazole-5-carboxylate (I-563)

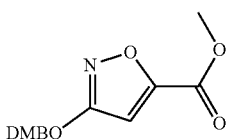

To a solution of 1-(chloromethyl)-2,4-dimethoxybenzene, I-561 (20 g, 107 mmol, 5.0 equiv.) in acetone (200 mL) was added methyl 3-hydroxyisoxazole-5-carboxylate, I-562 (3 g, 21.5 mmol) and K₂CO₃ (8.9 g, 3.0 equiv.). The reaction mixture was stirred at 70° C. for 19 hours. When the reaction was deemed complete by LC-MS analysis, the reaction mixture was concentrated under reduced pressure. The crude product was purified by column chromatography (silica gel, Petroleum/EtOAc=1:1) to afford methyl 3-((3,4-dimethylbenzyl)oxy)isoxazole-5-carboxylate, I-563 (2.0 g, 32% yield, as a yellow oil).

Step 3: (3-((3,4-dimethylbenzyl)oxy)isoxazol-5-yl)methanol. (I-564)

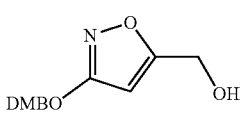

To a solution of methyl 3-[(3,4-dimethylphenyl)methoxy]-1,2-oxazole-5-carboxylate, I-563 (1.1 g, 4.2 mmol) in EtOH (10 mL) was added NaBH₄ (245 mg, 1.5 equiv.) at 0° C. The reaction mixture was allowed to warm to 25° C. and stirred for 2 hours. After completion, the reaction mixture was quenched with H₂O (5 mL), and extracted with DCM (20 mL). The organic extract was dried (Na₂SO₄), concentrated under reduced pressure and the residue obtained was purified by silica gel chromatography (Petroleum ether:EtOAc=1:1) to afford (3-((3,4-dimethylbenzyl)oxy)isoxazol-5-yl)methanol, I-564 (0.9 g, quantitative yield) as a yellow oil. MS (ESI, pos. ion) m/z: 288.1 (M+Na).

Step 4: (3-((3,4-dimethylbenzyl)oxy)isoxazol-5-yl)methyl methanesulfonate. (I-565)

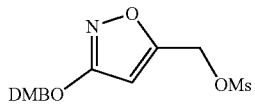

To a solution of {3-[(3,4-dimethylphenyl)methoxy]-1,2-oxazol-5-yl}methanol, I-564 (300 mg, 1.287 mmol) in DCM (5 mL) was added MsCl (440 mg, 3.0 equiv.) and TEA (258 mg, 2.0 equiv.) at 0° C. The reaction mixture was allowed to warm to 25° C. and stirred for 2 hours. After completion, the reaction mixture was quenched with H₂O (15 mL), and extracted with DCM (50 mL). The organic extract was dried (Na₂SO₄), concentrated under reduced pressure and the residue obtained was purified by silica gel chromatography (Petroleum ether:EtOAc=2:1) to afford (3-((3,4-dimethylbenzyl) oxy)isoxazol-5-yl)methyl methane sulfonate, I-565 (300 mg, 77% yield) as a yellow oil. MS (ESI, pos. ion) m/z: 366.0 (M+Na).

Step 5: 5-(bromomethyl)-3-((3,4-dimethylbenzyl)oxy)isoxazole. (I-566)

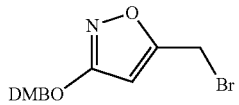

To a solution of {3-[(3,4-dimethylphenyl)methoxy]-1,2-oxazol-5-yl}methyl methane sulfonate, I-565 (2.9 g, 9.3 mmol) in acetone (50 mL) was added LiBr (2.4 g, 3.0 equiv.). The reaction mixture was stirred at 60° C. for 3 hours. When the reaction was deemed complete by LC-MS analysis, the reaction mixture was concentrated under reduced pressure to a residue, which was purified by silica gel column chromatography (DCM:MeOH=20:1) to afford 5-(bromomethyl)-3-((3,4-dimethylbenzyl)oxy)isoxazole, I-566 (2.5 g, 90% yield) as a yellow oil. MS (ESI, pos. ion) m/z: 350.0 (M+Na).

Step 6: 3-((3,4-dimethylbenzyl)oxy)-5-(((2S,5R)-5-isopropyl-3,6-dimethoxy-2,5-dihydropyrazin-2-yl)methyl)isoxazole. (I-568)

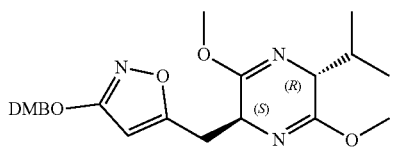

To a solution of (3R)-3-isopropyl-2,5-dimethoxy-3,6-dihydropyrazine, I-567 (46 mg, CAS: 109838-95-9, 0.25 mmol) in THF (5 mL) was added n-BuLi (2.5M in hexane, 0.1 ml, 1.0 equiv.) at −78° C. under N₂. After 30 minutes, 5-(bromomethyl)-3-[(3,4-dimethylphenyl)methoxy]-1,2-oxazole, I-566 (50 mg, 0.7 equiv.) was added. The flask was evacuated and purged again with nitrogen. The resulting mixture was slowly warmed to room temperature over 18 hours. When the reaction was deemed complete by LC-MS analysis, the reaction mixture was quenched with water (2 mL) and extracted with EtOAc (2×10 mL). The combined organic extracts were washed with brine, dried over Na₂SO₄, filtered and concentrated under reduced pressure. The residue was purified by silica gel chromatography (Petroleum:EtOAc=2:1) to afford 3-((3,4-dimethylbenzyl) oxy)-5-(((2S,5R)-5-isopropyl-3,6-dimethoxy-2,5-dihydropyrazin-2-yl)methyl)isoxazole, I-568 (20 mg, 30% yield) as a yellow oil. MS (ESI, pos. ion) m/z: 432.2 (MH⁺).

Step 7: Methyl (S)-2-amino-3-(3-((2,4-dimethoxybenzyl)oxy)isoxazol-5-yl)propanoate (I-569)

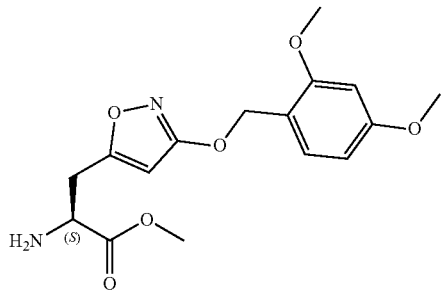

A mixture of (2S,5R)-2-({3-[(3,4-dimethylphenyl)methoxy]-1,2-oxazol-5-yl}methyl)-5-isopropyl-3,6-dimethoxy-2,5-dihydropyrazine, I-568 (30 mg, 0.05 mmol) in 1N HCl (1 mL) and MeCN (5 mL) was stirred under 30° C. for 3 hours. The solvent was then removed under reduced pressure to afford the crude methyl (S)-2-amino-3-(3-((2,4-dimethoxybenzyl)oxy) isoxazol-5-yl)propanoate, I-569 (20 mg, 86% yield) as a yellow oil, which was used in the next step without any purification. MS (ESI, pos. ion) m/z: 337.1 (MH⁺).

Step 8: (S)-2-amino-3-(3-((2,4-dimethoxybenzyl)oxy)isoxazol-5-yl)propanoic acid. (I-570)

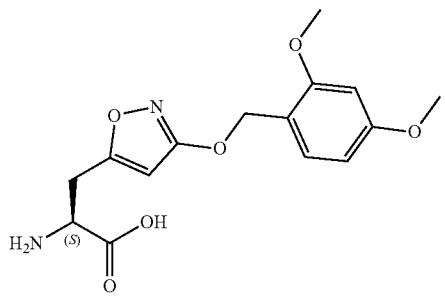

To a stirred solution of methyl (S)-2-amino-3-{3-[(2,4-dimethoxyphenyl)methoxy]-1,2-oxazol-5-yl}propanoate, I-569 (1.2 g, 3.57 mmol) in MeOH (20 mL) was added LiOH (246 mg, 3.0 equiv.) in H₂O (20 mL) at 0° C. The reaction mixture was allowed to warm to room temperature over 2 hours. The reaction mixture was then concentrated to a residue, which was purified by reverse phase HPLC (MeCN/H₂O with 0.5% formic acid) to afford (S)-2-amino-3-(3-((2,4-dimethoxybenzyl)oxy)isoxazol-5-yl)propanoic acid, I-570 (300 mg, 25% yield) as a yellow solid. MS (ESI, pos. ion) m/z: 323.1 (MH⁺).

Step 8: (S)-2-amino-3-(3-((2,4-dimethoxybenzyl)oxy)isoxazol-5-yl)propanoic acid (I-571)

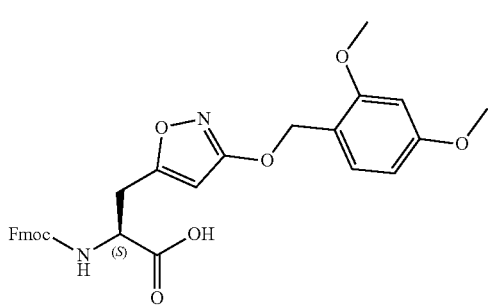

To a solution of (S)-2-amino-3-{3-[(2,4-dimethoxyphenyl)methoxy]-1,2-oxazol-5-yl}propanoic acid, I-570 (300 mg, 0.93 mmol) in dioxane (10 mL) and H₂O (10 mL) was added Fmoc-OSu (340 mg, 1.3 equiv.) and Na₂CO₃ (197 mg, 2.0 equiv.). The mixture was stirred for 2 hours at 20° C. When the reaction was deemed complete by LC-MS analysis, the pH of the reaction mixture was adjusted to 2 using 1N HCl. The reaction mixture was then extracted with DCM (30 mL), and the organic extract was dried (Na₂SO₄) and concentrated under reduced pressure. The residue obtained was purified by preparatory TLC (DCM:MeOH=10:1) to afford the desired carboxylic acid, I-571 (200 mg, 40% yield) as a white solid. MS (ESI, pos. ion) m/z: 545.2 (MH⁺).

¹H NMR (400 MHz, DMSO-d6) δ=7.89 (d, J=7.5, 2H), 7.65 (d, J=4.5, 2H), 7.41 (t, J=7.4, 2H), 7.37-7.23 (m, 2H), 6.97 (d, J=8.4, 1H), 6.53 (d, J=2.1, 1H), 6.41 (dd, J=8.3, 2.3, 1H), 5.56 (s, 1H), 4.76 (s, 2H), 4.21 (dd, J=15.1, 8.1, 3H), 3.86 (s, 1H), 3.74 (s, 3H), 3.69 (s, 3H), 2.96 (d, J=11.9, 1H), 2.84 (d, J=6.9, 1H).

D2. Additional Examples of Compounds Described in this Invention

Example 197: Compound 197

E-197

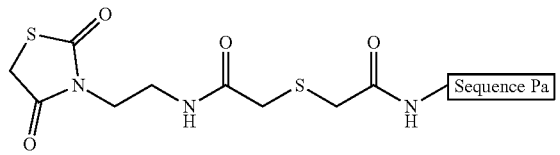

Peptide E-197 was prepared from 31.7 mg of the corresponding sequence immobilized on Rink amide resin (estimated loading 0.19 mmol/g) using I-34 and GP5 to afford 1.0 mg of E-197 as a white solid. ESI-MS found 1160.8, $C_{214}H_{327}S_2N_{47}O_{64}$ (M+4H)⁴⁺ requires 1160.8.

Example 198: Compound 198

E-198

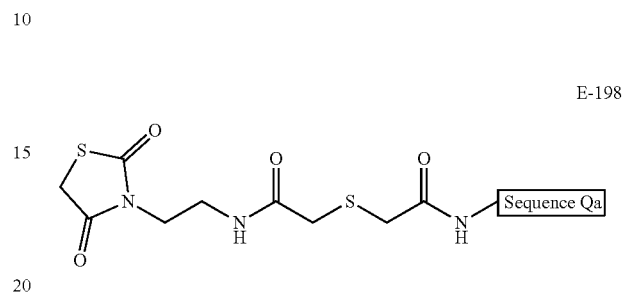

Peptide E-198 was prepared from 64.4 mg of the corresponding sequence immobilized on Rink amide resin (estimated loading 0.11 mmol/g) using I-9 and GP4 to afford 3.2 mg of E-198 as a white solid. ESI-MS found 1613.4, $C_{220}H_{335}S_2N_{52}O_{67}$ (M+3H)³⁺ requires 1613.8.

Example 199: Compound 199

E-199

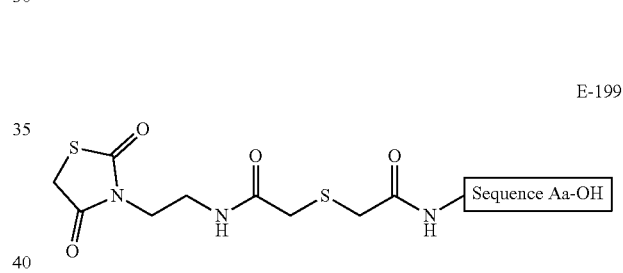

Peptide E-199 was prepared from 138.8 mg of the corresponding sequence immobilized on chlorotrityl resin (estimated loading 0.18 mmol/g) using I-9 and GP4 to afford 6.5 mg of E-199 as a white solid. ESI-MS found 1542.9, $C_{212}H_{319}S_2N_{46}O_{66}$ (M+3H)³⁺ requires 1543.1.

Example 200: Compound 200

E-200

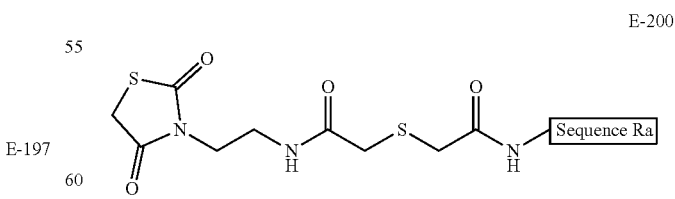

Peptide E-200 was prepared from 158 mg of the corresponding sequence immobilized on Rink amide resin (estimated loading 0.16 mmol/g) using I-9 and GP4 to afford 12 mg of E-200 as a white solid. ESI-MS found 1556.2, $C_{214}H_{325}S_2N_{48}O_{65}$ (M+3H)³⁺ requires 1557.1.

Example 201: Compound 201

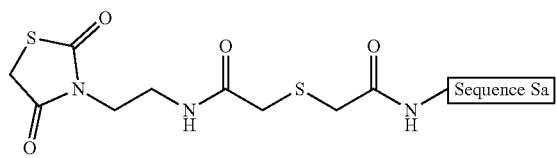
E-201

Peptide E-201 was prepared from 184 mg of the corresponding sequence immobilized on Rink amide resin (estimated loading 0.16 mmol/g) using I-9 and GP4 to afford 14 mg of E-201 as a white solid. ESI-MS found 1532.4, $C_{209}H_{323}S_2N_{48}O_{64}$ $(M+3H)^{3+}$ requires 1531.1.

Example 202: Compound 202

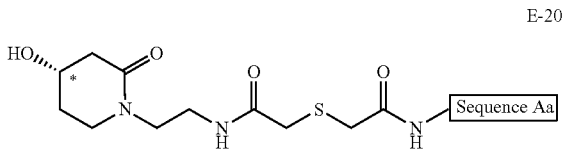
E-202

Peptide E-202 was prepared from 30 mg of resin R-1 (estimated loading 0.125 mmol/g) using I-443 (*absolute configuration arbitrarily assigned) and GP4 to afford 1.9 mg of E-202 as a white solid. ESI-MS found 1157.3, $C_{214}H_{327}SN_{47}O_{65}$ $(M+4H)^{4+}$ requires 1156.8.

Example 203: Compound 203

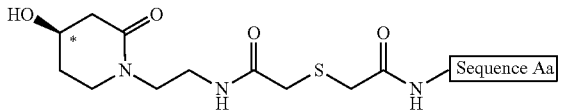
E-203

Peptide E-203 was prepared from 30 mg of resin R-1 (estimated loading 0.125 mmol/g) using I-439 (*absolute configuration arbitrarily assigned) and GP4 to afford 1.2 mg of E-203 as a white solid. ESI-MS found 1157.2, $C_{214}H_{327}SN_{47}O_{65}$ $(M+4H)^{4+}$ requires 1156.8.

Example 204: Compound 204

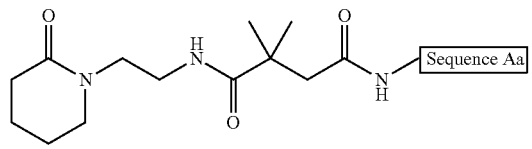
E-204

Peptide E-204 was prepared from 39.6 mg of resin R-1 (estimated loading 0.125 mmol/g) using I-430 and GP4 to afford 3.2 mg of E-204 as a white solid. ESI-MS found 1152.3, $C_{216}H_{331}N_{47}O_{64}$ $(M+4H)^{4+}$ requires 1151.8.

Example 205: Compound 208

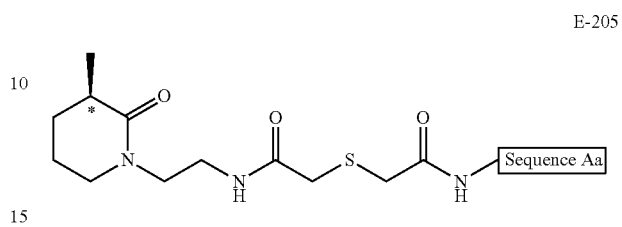
E-205

Peptide E-205 was prepared from 46.6 mg of resin R-1 (estimated loading 0.125 mmol/g) using I-451 and GP4 to afford 6.4 mg of E-205 as a white solid. ESI-MS found 1156.9, $C_{215}H_{329}SN_{47}O_{64}$ $(M+4H)^{4+}$ requires 1156.3.

Example 206: Compound 207

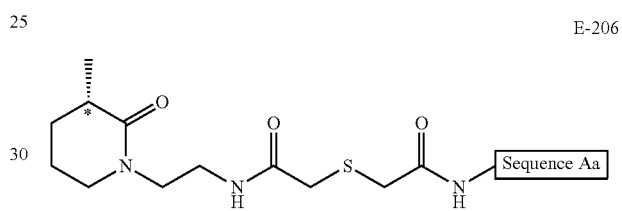
E-206

Peptide E-206 was prepared from 44.4 mg of resin R-1 (estimated loading 0.125 mmol/g) using I-454 and GP4 to afford 5.9 mg of E-206 as a white solid. ESI-MS found 1156.9, $C_{215}H_{329}SN_{47}O_{64}$ $(M+4H)^{4+}$ requires 1156.3.

Example 207: Compound 205

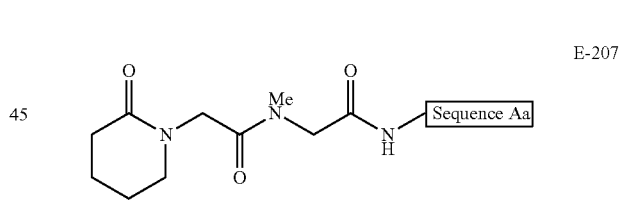
E-207

Peptide E-207 was prepared from 37 mg of resin R-1 (estimated loading 0.125 mmol/g) using I-458 and GP4 to afford 4.8 mg of E-207 as a white solid. ESI-MS found 1141.8, $C_{213}H_{325}N_{47}O_{64}$ $(M+4H)^{4+}$ requires 1141.3.

Example 208: Compound 206

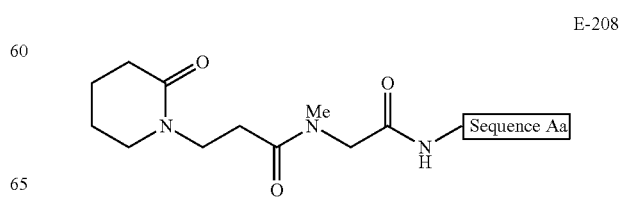
E-208

Peptide E-208 was prepared from 40.4 mg of resin R-1 (estimated loading 0.125 mmol/g) using I-461 and GP4 to afford 7 mg of E-208 as a white solid. ESI-MS found 1145.3, $C_{214}H_{327}N_{47}O_{64}$ $(M+4H)^{4+}$ requires 1144.8.

Example 209: Compound 209

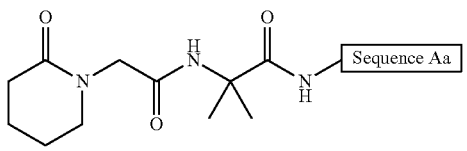

E-209

Peptide E-209 was prepared from 44.2 mg of resin R-1 (estimated loading 0.125 mmol/g) using I-464 and GP4 to afford 2.2 mg of E-209 as a white solid. ESI-MS found 1145.3, $C_{214}H_{327}N_{47}O_{64}$ $(M+4H)^{4+}$ requires 1144.8.

Example 210: Compound 210

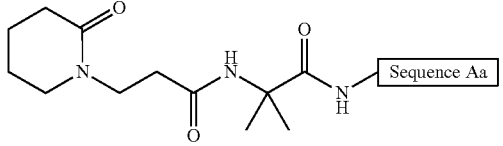

E-210

Peptide E-210 was prepared from 43.2 mg of resin R-1 (estimated loading 0.125 mmol/g) using I-466 and GP4 to afford 1.5 mg of E-210 as a white solid. ESI-MS found 1148.9, $C_{215}H_{329}N_{47}O_{64}$ $(M+4H)^{4+}$ requires 1148.3.

Example 211: Compound 211

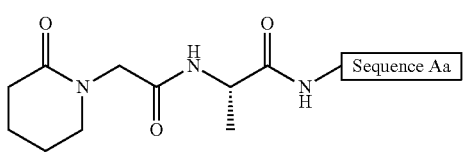

E-211

Peptide E-211 was prepared from 48.2 mg of resin R-1 (estimated loading 0.125 mmol/g) using I-469 and GP4 to afford 1.5 mg of E-211 as a white solid. ESI-MS found 1141.8, $C_{213}H_{325}N_{47}O_{64}$ $(M+4H)^{4+}$ requires 1141.3.

Example 212: Compound 212

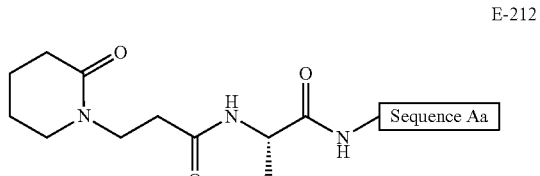

E-212

Peptide E-212 was prepared from 44.2 mg of resin R-1 (estimated loading 0.125 mmol/g) using I-471 and GP4 to afford 3.8 mg of E-212 as a white solid. ESI-MS found 1145.3, $C_{214}H_{327}N_{47}O_{64}$ $(M+4H)^{4+}$ requires 1144.8.

Example 213: Compound 213

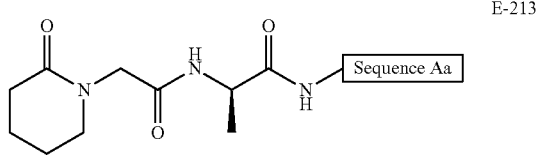 [SMILES: CNC(=O)[C@@H](C)NC(=O)CN1CCCCC1=O]

E-213

Peptide E-213 was prepared from 44.1 mg of resin R-1 (estimated loading 0.18 mmol/g) using I-474 and GP4 to afford 4.3 mg of E-213 as a white solid. ESI-MS found 1141.9, $C_{213}H_{325}N_{47}O_{64}$ $(M+4H)^{4+}$ requires 1141.3.

Example 214: Compound 214

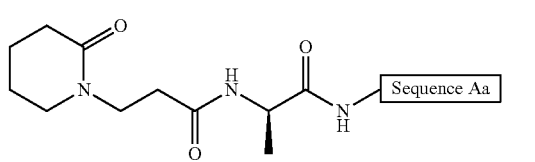

E-214

Peptide E-214 was prepared from 45.9 mg of resin R-1 (estimated loading 0.125 mmol/g) using I-476 and GP4 to afford 3.0 mg of E-214 as a white solid. ESI-MS found 1145.4, $C_{214}H_{327}N_{47}O_{64}$ $(M+4H)^{4+}$ requires 1144.8.

Example 215: Compound 217

The synthesis of example E-215 is depicted in Scheme 167:

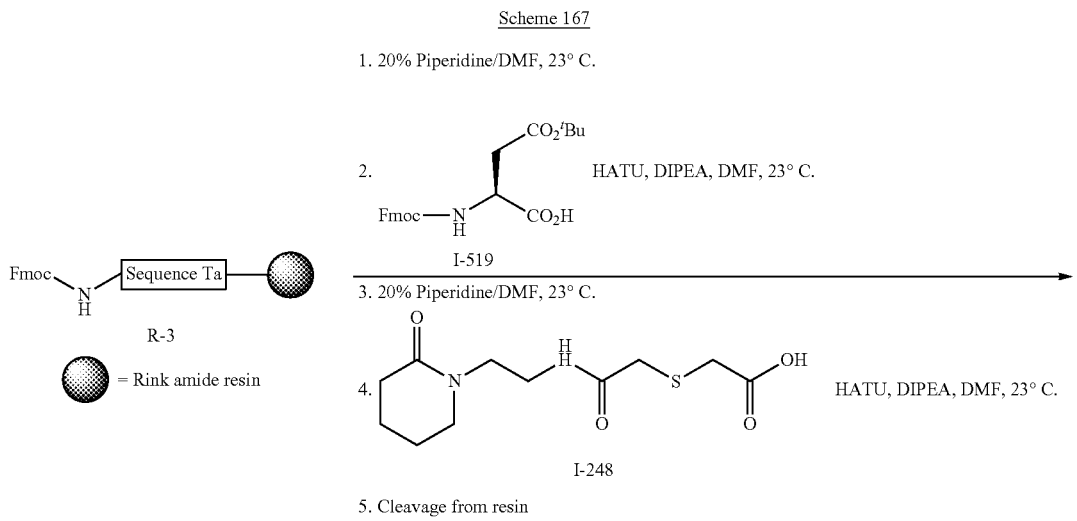

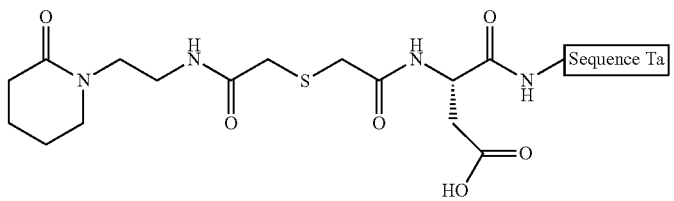

To Rink amide resin R-3 (0.17 mmol/g, 60 mg, 0.01 mmol) in a 3 mL polypropylene tube with an end-cap was added 20% v/v piperidine/DMF (2 mL). The tube was capped, agitated at ambient temperature for 20 minutes, and then drained. The resin was washed with DMF (5×3 mL). A solution of carboxylic acid I-519 (25.2 mg, 6.0 equiv.) in DMF (1.2 mL) was added, followed by DIPEA (27 μL, 15.0 equiv.) and HATU (34.9 mg, 9.0 equiv.). The reaction mixture was agitated at ambient temperature for 5 hours, then drained and the resin was washed with DMF (5×3 mL) and DCM (5×3 mL).

20% v/v piperidine/DMF (2 mL) was added to the resin. The tube was capped, agitated at ambient temperature for 20 minutes, and then drained. The resin was washed with DMF (5×3 mL). A solution of carboxylic acid I-248 (16.7 mg, 6.0 equiv.) in DMF (1.2 mL) was added, followed by DIPEA (27 μL, 15.0 equiv.) and HATU (34.9 mg, 9.0 equiv.). The reaction mixture was agitated at ambient temperature for 16 hours, then drained and the resin was washed with DMF (5×3 mL) and DCM (5×3 mL). The peptide was cleaved from the resin using 1 mL of cleavage reagent (88:2:5:5 v/v/v/v TFA/TIS/PhOH/H$_2$O) for 1 hour. The resin was filtered and washed with TFA (2×0.5 mL). The combined filtrate and washes were concentrated under reduced pressure to afford a residue, which was triturated with Et$_2$O (2 mL) to precipitate the peptide. The peptide was re-dissolved in glacial AcOH (1.2 mL) and purified by preparative HPLC (Phenomenex Jupiter 10 μM Proteo 90 Å LC column, 250×21.2 mm, with flow rate—15 mL/min, gradient of 0-100% acetonitrile in 25 mM aqueous ammonium acetate over 30 minutes) to afford 2.7 mg of E-215 as a white solid. ESI-MS found 1149.8, $C_{213}H_{325}SN_{47}O_{64}$ (M+4H)$^{4+}$ requires 1149.3.

Example 216: Compound 226

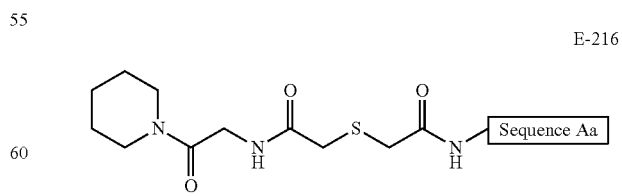

Peptide E-216 was prepared from 50 mg of resin R-1 (estimated loading 0.125 mmol/g) using I-478 and GP4 to afford 4.2 mg of E-216 as a white solid. ESI-MS found 1153.4, $C_{214}H_{327}SN_{47}O_{64}$ (M+4H)$^{4+}$ requires 1152.8.

Example 217: Compound 219

The synthesis of example E-217 is depicted in Scheme 168:

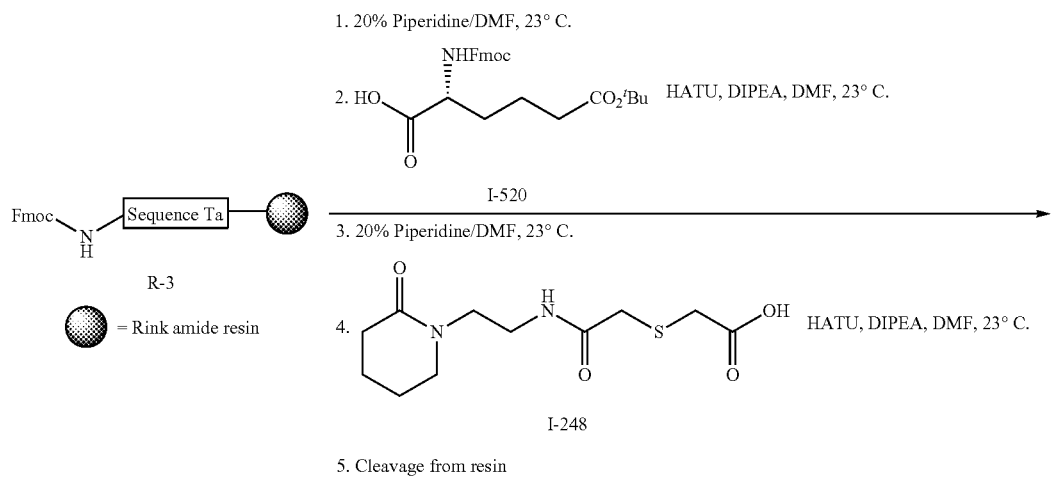

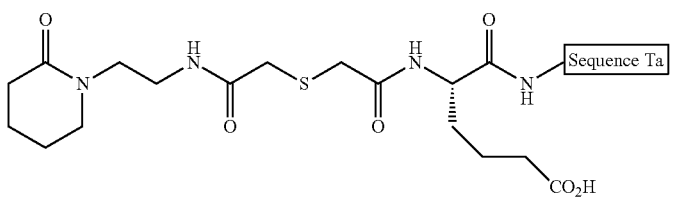

E-217

To Rink amide resin R-3 (0.17 mmol/g, 62.5 mg, 0.011 mmol) in a 3 mL polypropylene tube with an end-cap was added 20% v/v piperidine/DMF (2 mL). The tube was capped, agitated at ambient temperature for 20 minutes, and then drained. The resin was washed with DMF (5×3 mL). A solution of carboxylic acid I-520 (28 mg, 6.0 equiv.) in DMF (1.2 mL) was added, followed by DIPEA (28 µL, 15.0 equiv.) and HATU (36.3 mg, 9.0 equiv.). The reaction mixture was agitated at ambient temperature for 4 hours, then drained and the resin was washed with DMF (5×3 mL) and DCM (5×3 mL).

20% v/v piperidine/DMF (2 mL) was added to the resin. The tube was capped, agitated at ambient temperature for 20 minutes, and then drained. The resin was washed with DMF (5×3 mL). A solution of carboxylic acid I-248 (17.5 mg, 6.0 equiv.) in DMF (1.2 mL) was added, followed by DIPEA (28 µL, 15.0 equiv.) and HATU (36.3 mg, 9.0 equiv.). The reaction mixture was agitated at ambient temperature for 5 hours, then drained and the resin was washed with DMF (5×3 mL) and DCM (5×3 mL). The peptide was cleaved from the resin using 1 mL of cleavage reagent (88:2:5:5 v/v/v/v TFA/TIS/PhOH/H$_2$O) for 1 hour. The resin was filtered and washed with TFA (2×0.5 mL). The combined filtrate and washes were concentrated under reduced pressure to afford a residue, which was triturated with Et$_2$O (2 mL) to precipitate the peptide. The peptide was re-dissolved in glacial AcOH (1.2 mL) and purified by preparative HPLC (Phenomenex Jupiter 10 µM Proteo 90 Å LC column, 250×21.2 mm, with flow rate—15 mL/min, gradient of 0100% acetonitrile in 25 mM aqueous ammonium acetate over 30 minutes) to afford 2.5 mg of E-217 as a white solid. ESI-MS found 1156.8, $C_{215}H_{329}SN_{47}O_{64}$ $(M+4H)^{4+}$ requires 1156.3.

Example 218: Compound 223

The synthesis of example E-218 is depicted in Scheme 169:

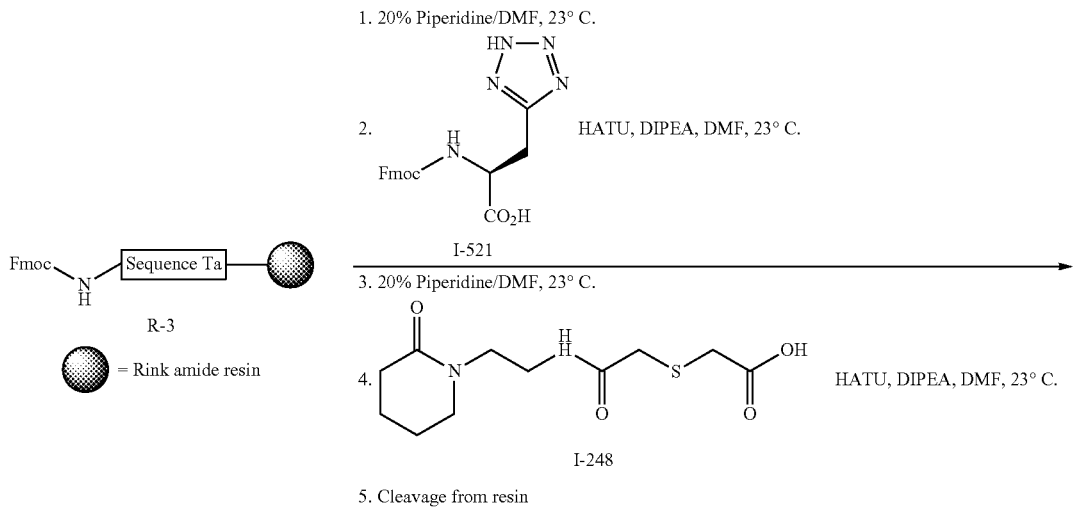

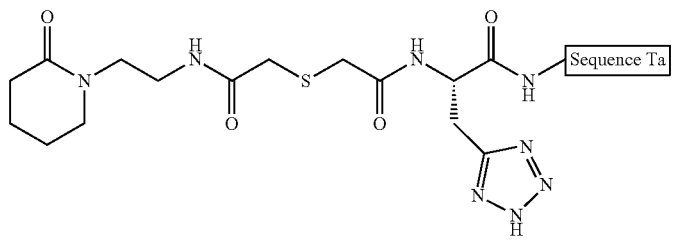

E-218

To Rink amide resin R-3 (0.17 mmol/g, 61.4 mg, 0.01 mmol) in a 3 mL polypropylene tube with an end-cap was added 20% v/v piperidine/DMF (2 mL). The tube was capped, agitated at ambient temperature for 20 minutes, and then drained. The resin was washed with DMF (5×3 mL). A solution of carboxylic acid I-521 (23.8 mg, 6.0 equiv.) in DMF (1.2 mL) was added, followed by DIPEA (27 µL, 15.0 equiv.) and HATU (35.6 mg, 9.0 equiv.). The reaction mixture was agitated at ambient temperature for 4 hours, then drained and the resin was washed with DMF (5×3 mL) and DCM (5×3 mL).

20% v/v piperidine/DMF (2 mL) was added to the resin. The tube was capped, agitated at ambient temperature for 20 minutes, and then drained. The resin was washed with DMF (5×3 mL). A solution of carboxylic acid I-248 (17.2 mg, 6.0 equiv.) in DMF (1.2 mL) was added, followed by DIPEA (27 µL, 15.0 equiv.) and HATU (35.6 mg, 9.0 equiv.). The reaction mixture was agitated at ambient temperature for 5 hours, then drained and the resin was washed with DMF (5×3 mL) and DCM (5×3 mL). The peptide was cleaved from the resin using 1 mL of cleavage reagent (88:2:5:5 v/v/v/v TFA/TIS/PhOH/H$_2$O) for 1 hour. The resin was filtered and washed with TFA (2×0.5 mL). The combined filtrate and washes were concentrated under reduced pressure to afford a residue, which was triturated with Et$_2$O (2 mL) to precipitate the peptide. The peptide was re-dissolved in glacial AcOH (1.2 mL) and purified by preparative HPLC (Phenomenex Jupiter 10 µM Proteo 90 Å LC column, 250×21.2 mm, with flow rate—15 mL/min, gradient of 0-100% acetonitrile in 25 mM aqueous ammonium acetate over 30 minutes) to afford 1.7 mg of E-218 as a white solid. ESI-MS found 1155.8, $C_{213}H_{325}SN_{51}O_{62}$ (M+4H)$^{4+}$ requires 1155.3.

Example 219: Compound 218

The synthesis of example E-219 is depicted in Scheme 170:

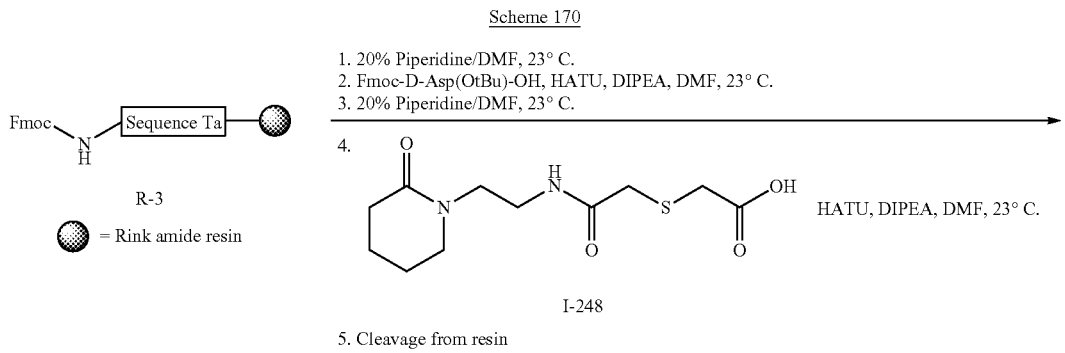

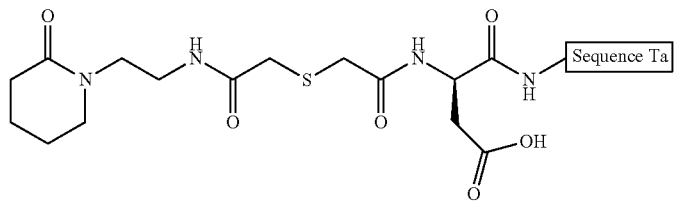

Fmoc cleavage from Rink amide resin R-3 (0.17 mmol/g, 66.7 mg, 0.011 mmol) was performed as described in example 218. A solution of Fmoc-D-Asp(O$^t$Bu)-OH (28 mg, 6.0 equiv.) in DMF (1.2 mL) was added, followed by DIPEA (30 μL, 15.0 equiv.) and HATU (38.8 mg, 9.0 equiv.). The reaction mixture was agitated at ambient temperature for 4 hours, then drained and the resin was washed with DMF (5×3 mL) and DCM (5×3 mL). After further Fmoc cleavage, A solution of carboxylic acid I-248 (18.7 mg, 6.0 equiv.) in DMF (1.2 mL) was added, followed by DIPEA (28 μL, 15.0 equiv.) and HATU (38.8 mg, 9.0 equiv.). The reaction mixture was agitated at ambient temperature for 5 hours, then drained and the resin was washed with DMF (5×3 mL) and DCM (5×3 mL). The peptide was cleaved from the resin and purified as described in example 218 to afford 4.3 mg of E-219 as a white solid. ESI-MS found 1149.8, $C_{213}H_{325}SN_{47}O_{64}$ (M+4H)$^{4+}$ requires 1149.3.

Example 220: Compound 221

The synthesis of example E-220 is depicted in Scheme 171:

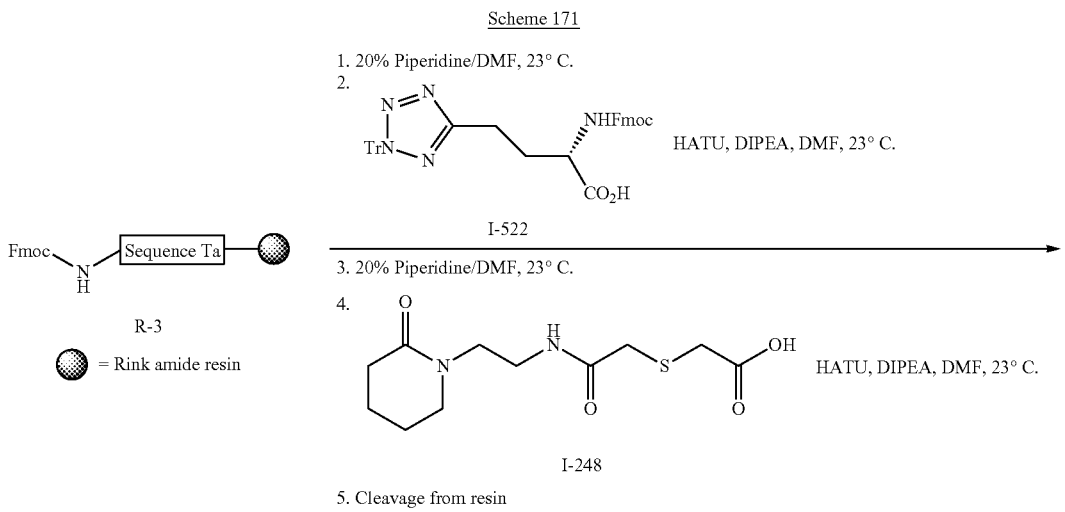

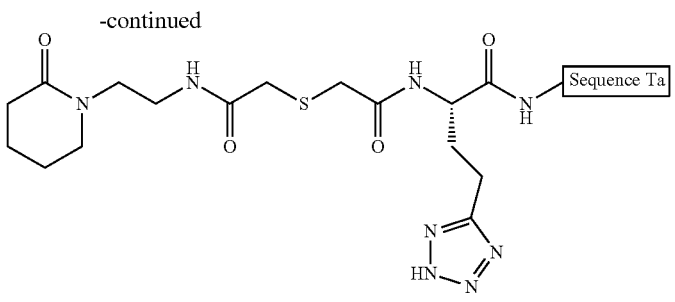

E-220

Fmoc cleavage from Rink amide resin R-3 (0.17 mmol/g, 65.5 mg, 0.011 mmol) was performed as described in example 218. A solution of carboxylic acid I-522 (42.5 mg, 6.0 equiv.) in DMF (1.2 mL) was added, followed by DIPEA (29 μL, 15.0 equiv.) and HATU (38 mg, 9.0 equiv.). The reaction mixture was agitated at ambient temperature for 4 hours, then drained and the resin was washed with DMF (5×3 mL) and DCM (5×3 mL). After further Fmoc cleavage, a solution of carboxylic acid I-248 (18.3 mg, 6.0 equiv.) in DMF (1.2 mL) was added, followed by DIPEA (29 μL, 15.0 equiv.) and HATU (38 mg, 9.0 equiv.). The reaction mixture was agitated at ambient temperature for 5 hours, then drained and the resin was washed with DMF (5×3 mL) and DCM (5×3 mL). The peptide was cleaved from the resin and purified as described in example 218 to afford 2.0 mg of E-220 as a white solid. ESI-MS found 1159.3, $C_{214}H_{327}SN_{51}O_{62}$ $(M+4H)^{4+}$ requires 1158.8.

Example 221: Compound 222

The synthesis of example E-221 is depicted in Scheme 172:

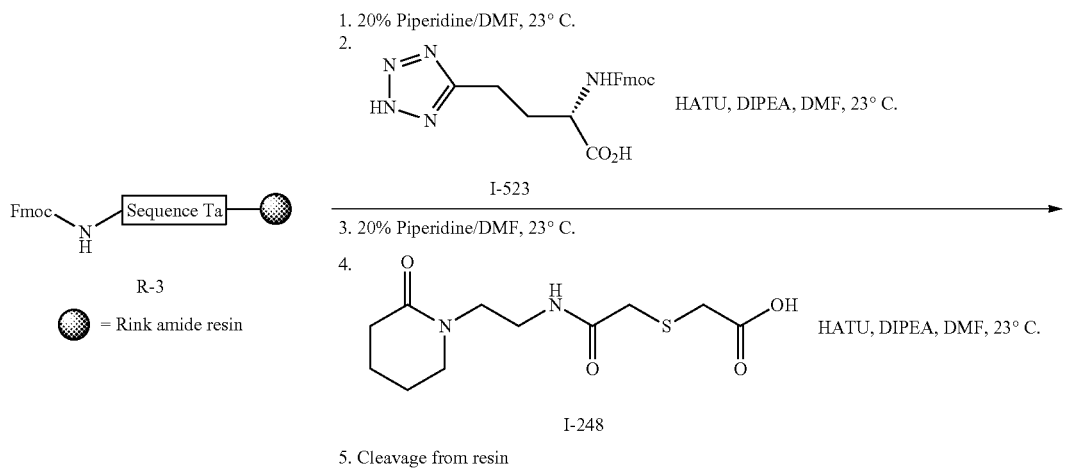

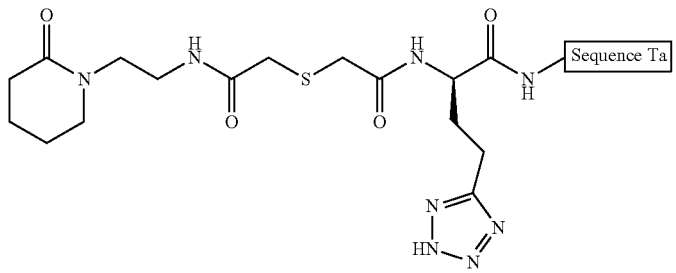

E-221

Fmoc cleavage from Rink amide resin R-3 (0.17 mmol/g, 64.8 mg, 0.011 mmol) was performed as described in example 218. A solution of carboxylic acid I-523 (26 mg, 6.0 equiv.) in DMF (1.2 mL) was added, followed by DIPEA (29 µL, 15.0 equiv.) and HATU (37.6 mg, 9.0 equiv.). The reaction mixture was agitated at ambient temperature for 4 hours, then drained and the resin was washed with DMF (5×3 mL) and DCM (5×3 mL). After further Fmoc cleavage, a solution of carboxylic acid I-248 (18.1 mg, 6.0 equiv.) in DMF (1.2 mL) was added, followed by DIPEA (29 µL, 15.0 equiv.) and HATU (37.6 mg, 9.0 equiv.). The reaction mixture was agitated at ambient temperature for 5 hours, then drained and the resin was washed with DMF (5×3 mL) and DCM (5×3 mL). The peptide was cleaved from the resin and purified as described in example 218 to afford 1.4 mg of E-221 as a white solid. ESI-MS found 1159.4, $C_{214}H_{327}SN_{51}O_{62}$ (M+4H)$^{4+}$ requires 1158.8.

Example 222: Compound 224

The synthesis of example E-222 is depicted in Scheme 173:

Fmoc cleavage from Rink amide resin R-3 (0.17 mmol/g, 62.8 mg, 0.011 mmol) was performed as described in example 218. A solution of carboxylic acid I-524 (24.3 mg, 6.0 equiv.) in DMF (1.2 mL) was added, followed by DIPEA (29 µL, 15.0 equiv.) and HATU (36.6 mg, 9.0 equiv.). The reaction mixture was agitated at ambient temperature for 4 hours, then drained and the resin was washed with DMF (5×3 mL) and DCM (5×3 mL). After further Fmoc cleavage, a solution of carboxylic acid I-248 (17.6 mg, 6.0 equiv.) in DMF (1.2 mL) was added, followed by DIPEA (29 µL, 15.0 equiv.) and HATU (36.6 mg, 9.0 equiv.). The reaction mixture was agitated at ambient temperature for 5 hours, then drained and the resin was washed with DMF (5×3 mL) and DCM (5×3 mL). The peptide was cleaved from the resin and purified as described in example 218 to afford 2.5 mg of E-222 as a white solid. ESI-MS found 1155.9, $C_{213}H_{325}SN_{51}O_{62}$ (M+4H)$^{4+}$ requires 1155.3.

Example 228: Compound 232

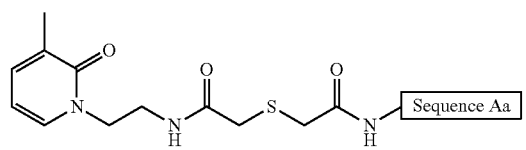

E-228

Scheme 173

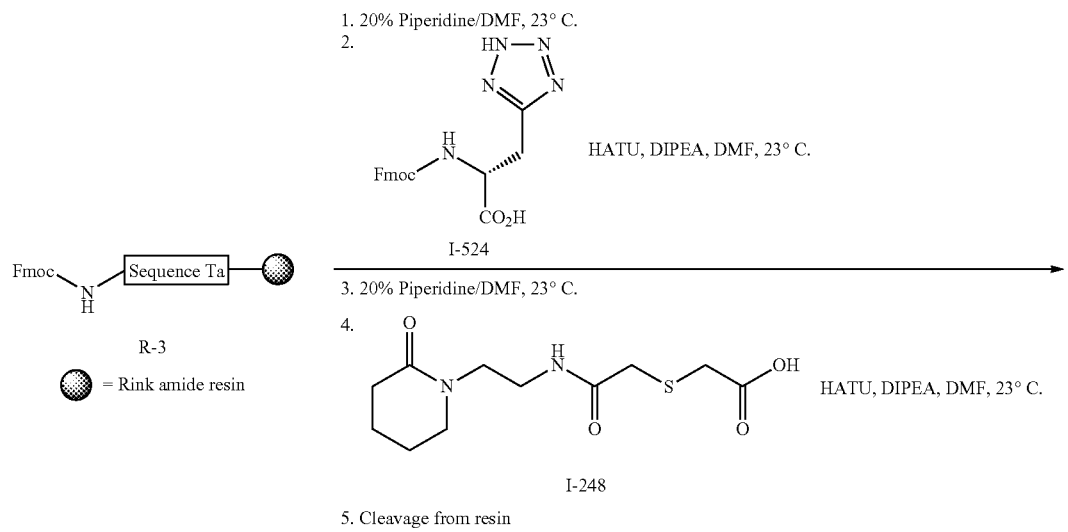

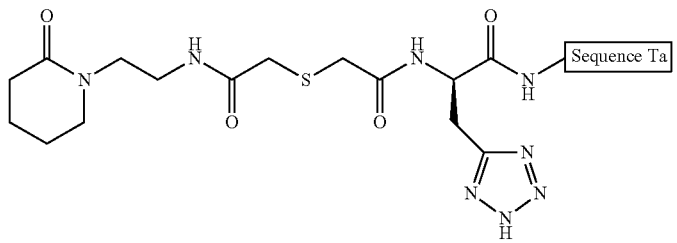

E-222

Peptide E-228 was prepared from 44.5 mg of resin R-1 (estimated loading 0.125 mmol/g) using I-486 and GP4 to afford 4.8 mg of E-228 as a white solid. ESI-MS found 1155.8, $C_{215}H_{325}SN_{47}O_{64}$ (M+4H)$^{4+}$ requires 1155.3.

Example 229: Compound 233

The synthesis of example E-229 is depicted in Scheme 179:

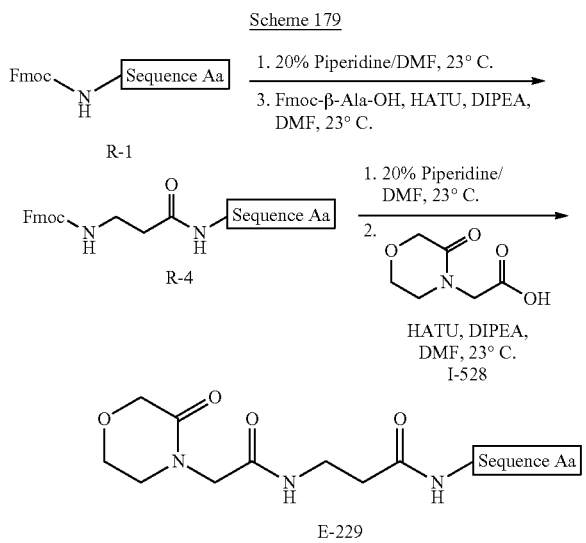

Fmoc cleavage from Rink amide resin R-1 (estimated loading 0.125 mmol/g, 121.6 mg, 0.015 mmol) was performed as described in example 218. A solution of Fmoc-β-Ala-OH (28.4 mg, 6.0 equiv.) in DMF (3 mL) was added, followed by DIPEA (40 μL, 15.0 equiv.) and HATU (52 mg, 9.0 equiv.). The reaction mixture was agitated at ambient temperature for 2 hours, then drained and the resin was washed with DMF (5×3 mL) and DCM (5×3 mL) and dried in vacuo to afford resin R-4.

Resin R-4 (49.3 mg, estimated loading 0.125 mmol/g, 6.2 μmol) was subjected to Fmoc cleavage as described above, and a solution of carboxylic acid I-528 (6 mg, 6.0 equiv.) in DMF (1.2 mL) was added, followed by DIPEA (16 μL, 15.0 equiv.) and HATU (21 mg, 9.0 equiv.). The reaction mixture was agitated at ambient temperature for 16 hours, then drained and the resin was washed with DMF (5×3 mL) and DCM (5×3 mL) and dried in vacuo. The peptide was cleaved from the resin and purified as described in example 218 to afford 5.6 mg of Peptide E-229 as a white solid. ESI-MS found 1142.3, $C_{212}H_{323}N_{47}O_{65}$ (M+4H)$^{4+}$ requires 1141.8.

Example 230: Compound 234

The synthesis of example E-230 is depicted in Scheme 180:

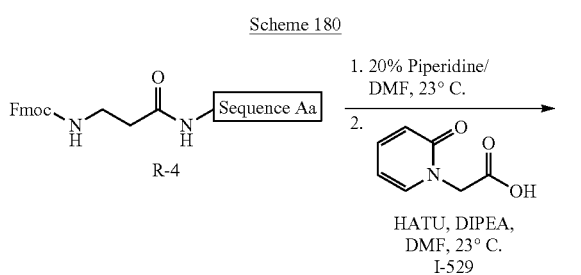

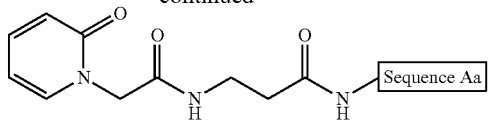

Resin R-4 (52.2 mg, estimated loading 0.125 mmol/g, 6.5 μmol) was subjected to Fmoc cleavage as described in example 218, and a solution of carboxylic acid I-529 (6 mg, 6.0 equiv.) in DMF (1.2 mL) was added, followed by DIPEA (17 μL, 15.0 equiv.) and HATU (22 mg, 9.0 equiv.). The reaction mixture was agitated at ambient temperature for 16 hours, then drained and the resin was washed with DMF (5×3 mL) and DCM (5×3 mL) and dried in vacuo. The peptide was cleaved from the resin and purified as described in example 218 to afford 4.3 mg of E-230 as a white solid. ESI-MS found 1140.8, $C_{213}H_{321}N_{47}O_{64}$ (M+4H)$^{4+}$ requires 1140.3.

Example 234: Compound 238

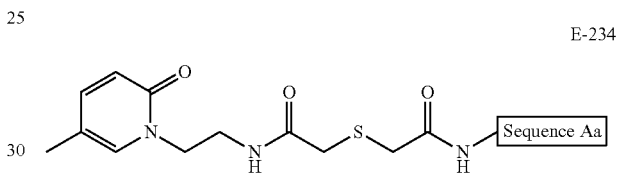

Peptide E-234 was prepared from 46.2 mg of resin R-1 (estimated loading 0.125 mmol/g) using I-498 and GP4 to afford 6.1 mg of E-234 as a white solid. ESI-MS found 1155.8, $C_{215}H_{325}SN_{47}O_{64}$ (M+4H)$^{4+}$ requires 1155.3.

Example 235: Compound 239

The synthesis of example E-235 is depicted in Scheme 184:

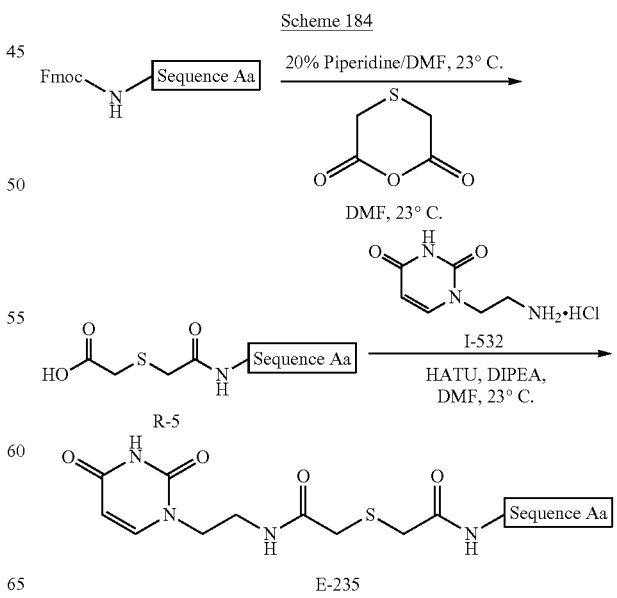

Fmoc deprotection of resin R-1 (111.9 mg, estimated loading 0.125 mmol/g, 0.014 mmol) was carried out as described in example 218, then a solution of thiodiglycolic anhydride (14.8 mg, 8.0 equiv.) in DMF (1.2 mL) was added and the reaction mixture was agitated for 6 hours at ambient temperature. The solution was drained and the resin was washed with DMF (5×) and DCM (5×) and dried in vacuo to afford resin R-5.

To resin R-5 (40.5 mg, estimated loading 0.125 mmol/g, 5.1 µmol) was added a solution of amine hydrochloride I-532 (7.8 mg, 8.0 equiv.) and DIPEA (18 µL, 20.0 equiv.) in DMF (1.2 mL), followed by HATU (15.4 mg, 8.0 equiv.). The reaction mixture was agitated at ambient temperature for 5 hours, then the solution was drained and the resin was washed with DMF (5×) and DCM (5×) and dried in vacuo. The peptide was cleaved from resin and purified as described in example 218 to afford 1.7 mg of peptide E-235 as a white solid. ESI-MS found 1156.0, $C_{213}H_{322}SN_{48}O_{65}$ $(M+4H)^{4+}$ requires 1156.1.

Example 236: Compound 240

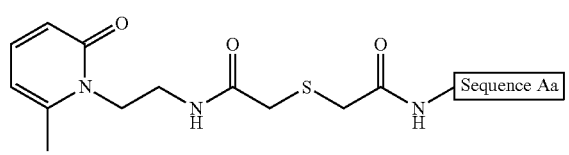

Peptide E-236 was prepared from 42.2 mg of resin R-1 (estimated loading 0.125 mmol/g) using I-490 and GP4 to afford 2.7 mg of E-236 as a white solid. ESI-MS found 1155.3, $C_{215}H_{325}SN_{47}O_{64}$ $(M+4H)^{4+}$ requires 1155.3.

Example 237: Compound 241

The synthesis of example E-237 is depicted in Scheme 185:

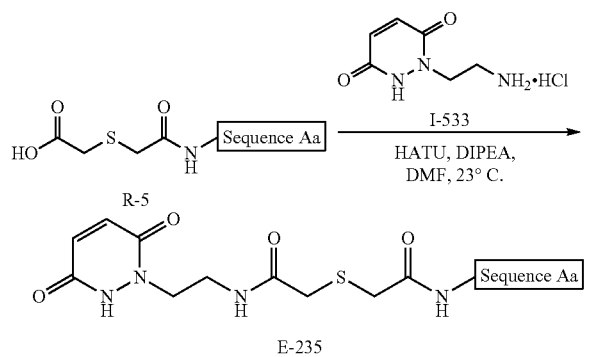

To resin R-5 (41.3 mg, estimated loading 0.125 mmol/g, 5.2 µmol) was added a solution of amine hydrochloride I-533 (7.9 mg, 8.0 equiv.) and DIPEA (18 µL, 20.0 equiv.) in DMF (1.2 mL), followed by HATU (15.7 mg, 8.0 equiv.). The reaction mixture was agitated at ambient temperature for 3.5 hours, then the solution was drained and the resin was washed with DMF (5×) and DCM (5×) and dried in vacuo.

The peptide was cleaved from resin and purified as described in example 218 to afford 2.3 mg of peptide E-237 as a white solid. ESI-MS found 1156.0, $C_{213}H_{322}SN_{48}O_{65}$ $(M+4H)^{4+}$ requires 1156.1.

Example 239: Compound 215

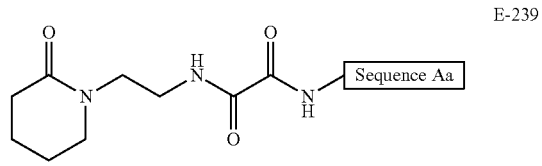 [SMILES: CNC(=O)C(=O)NCCN1CCCCC1=O]

Peptide E-239 was prepared from 49.5 mg of resin (estimated loading 0.125 mmol/g) using I-505 and GP4 to afford 5.3 mg of E-239 as a white solid. ESI-MS found 1137.7, $C_{212}H_{323}N_{47}O_{64}$ $(M+4H)^{4+}$ requires 1137.8.

Example 240: Compound 243

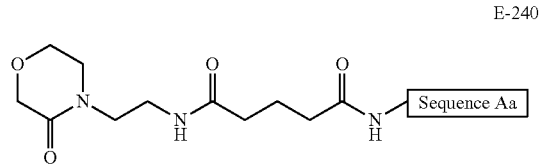 [SMILES: CNC(=O)CCCC(=O)NCCN1CCOCC1=O]

Peptide E-240 was prepared from 47.1 mg of resin (estimated loading 0.125 mmol/g) using I-507 and GP4 to afford 5.0 mg of E-240 as a white solid. ESI-MS found 1148.7, $C_{214}H_{327}N_{47}O_{65}$ $(M+4H)^{4+}$ requires 1148.8.

Example 241: Compound 244

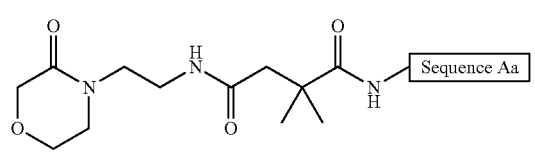

Peptide E-241 was prepared from 53.3 mg of resin (estimated loading 0.125 mmol/g) using I-508 and GP4 to afford 3.7 mg of E-241 as a white solid. ESI-MS found 1152.3, $C_{215}H_{329}N_{47}O_{65}$ $(M+4H)^{4+}$ requires 1152.3.

Example 244: Compound 247

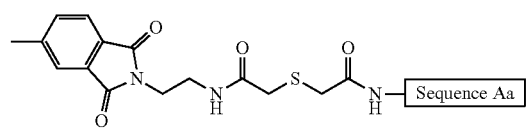

Peptide E-244 was prepared from 47.8 mg of resin (estimated loading 0.125 mmol/g) using I-122 and GP5 to afford 7.0 mg of E-244 as a white solid. ESI-MS found 1168.2, $C_{218}H_{325}SN_{47}O_{65}$ $(M+4H)^{4+}$ requires 1168.3

Example 245: Compound 248

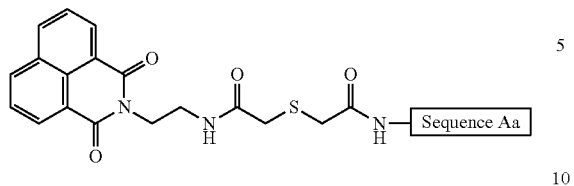

E-245

Peptide E-245 was prepared from 44.3 mg of resin (estimated loading 0.125 mmol/g) using I-126 and GP5 to afford 3.3 mg of E-245 as a white solid. ESI-MS found 1177.3, $C_{221}H_{325}SN_{47}O_{65}$ $(M+4H)^{4+}$ requires 1177.3.

Example 246: Compound 249

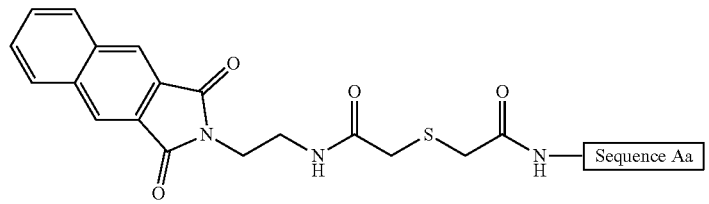

E-246

Peptide E-246 was prepared from 21.2 mg of resin (estimated loading 0.125 mmol/g) using I-137 and GP5 to afford 1.5 mg of E-246 as a white solid. ESI-MS found 1177.3, $C_{221}H_{325}SN_{47}O_{65}$ $(M+4H)^{4+}$ requires 1177.3.

Example 251: Compound 220

The synthesis of example E-251 is depicted in Scheme 190:

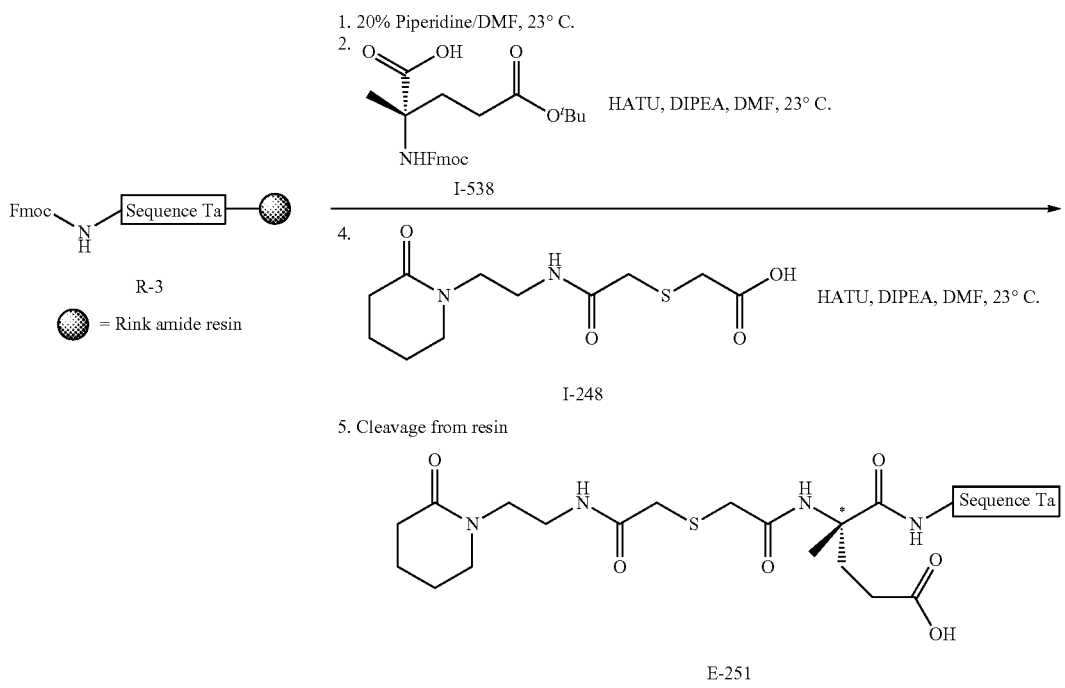

381

Fmoc cleavage from Rink amide resin R-3 (0.18 mmol/g, 51.5 mg, 0.009 mmol) was performed as described in example 218. A solution of carboxylic acid I-538 (24.4 mg, 6.0 equiv., *absolute configuration not established) in 20% Collidine/DMF (1.5 mL) was added, followed by HATU (19.4 mg, 5.5 equiv.). The reaction mixture was agitated at ambient temperature for 16 hours, then drained and the resin was washed with DMF (5×3 mL) and DCM (5×3 mL). After further Fmoc cleavage, a solution of carboxylic acid I-248 (15.3 mg, 6.0 equiv.) in 20% Collidine/DMF (1.5 mL) was added, followed by HATU (19.4 mg, 5.5 equiv.). The reaction mixture was agitated at ambient temperature for 16 hours, then drained and the resin was washed with DMF (5×3 mL) and DCM (5×3 mL). The peptide was cleaved from the resin and purified as described in example 218 to afford 3.6 mg of E-251 as a white solid. ESI-MS found 1156.8, $C_{215}H_{329}SN_{47}O_{64}$ (M+4H)$^{4+}$ requires 1156.3.

Example 252: Compound 254

The synthesis of example E-252 is depicted in Scheme 191:

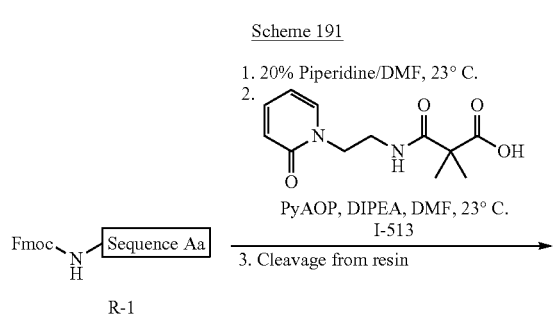
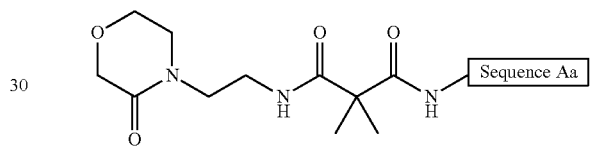

382

-continued

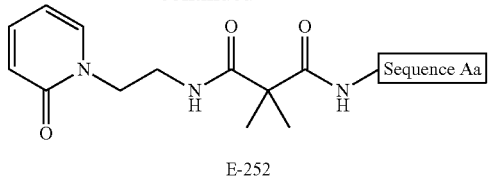

E-252

Fmoc cleavage from resin R-1 (estimated loading 0.125 mmol/g, 42 mg, 5.3 µmol) was performed as described in example 218. A solution of carboxylic acid I-513 (8 mg, 6.0 equiv.) in DMF (1.3 mL) was then added to the resin, followed by DIPEA (14 µL, 15.0 equiv.) and PyAOP (19.2 mg, 7.0 equiv.). The reaction mixture was agitated at ambient temperature for 20 hours and then the resin was drained and washed with DMF (5×), DCM (5×) and dried in vacuo. Cleavage of the peptide from resin and purification was performed as described for example 218 to afford 4.0 mg of E-252 as a white solid. ESI-MS found 1147.8, $C_{215}H_{325}N_{47}O_{64}$ (M+4H)$^{4+}$ requires 1147.3.

Example 255: Compound 257

E-255

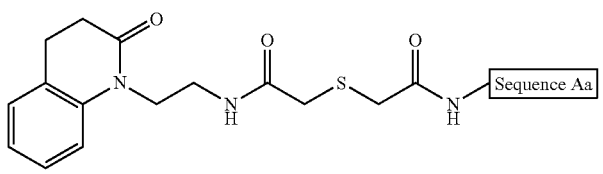

Peptide E-255 was prepared from 49.7 mg of resin (estimated loading 0.125 mmol/g) using I-510 as described for example 252 (coupling time: 5 hours) to afford 5.7 mg of E-255 as a white solid. ESI-MS found 1149.4, $C_{214}H_{327}N_{47}O_{65}$ (M+4H)$^{4+}$ requires 1148.8.

Example 258: Compound 260

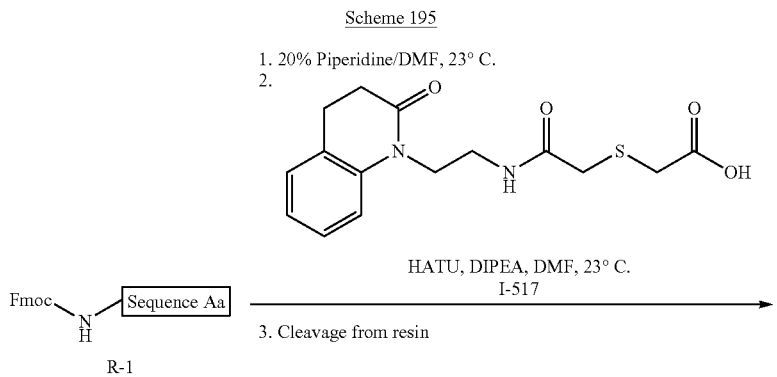

Fmoc cleavage from resin R-1 (estimated loading 0.125 mmol/g, 46.2 mg, 5.8 µmol) was performed as described in example 218. A solution of carboxylic acid I-517 (11.2 mg, 6.0 equiv.) in DMF (1.3 mL) was then added to the resin, followed by DIPEA (15 µL, 15.0 equiv.) and HATU (12.1 mg, 5.5 equiv.). The reaction mixture was agitated at ambient temperature for 2 hours and then the resin was drained and washed with DMF (5×), DCM (5×) and dried in vacuo. Cleavage of the peptide from resin and purification was performed as described for example 218 to afford 3.9 mg of E-258 as a white solid. ESI-MS found 1165.4, $C_{218}H_{327}SN_{47}O_{64}$ $(M+4H)^{4+}$ requires 1164.8.

Example 262: Compound 264

Scheme 199

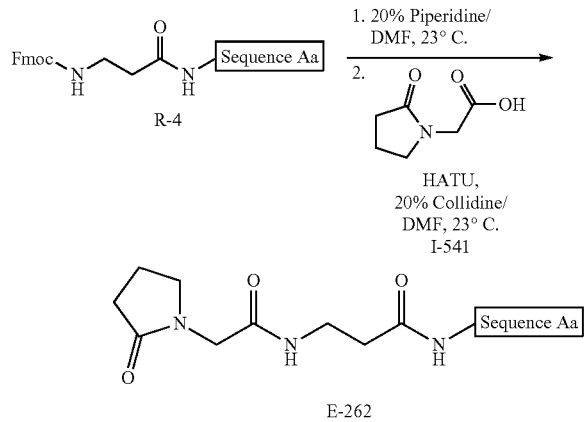

Resin R-4 (39.3 mg, estimated loading 0.125 mmol/g, 4.9 µmol) was subjected to Fmoc cleavage as described in example 218, and a solution of carboxylic acid I-541 (4.2 mg, 6.0 equiv.) in 20% Collidine/DMF (1.3 mL) was added, followed by HATU (10.3 mg, 5.5 equiv.). The reaction mixture was agitated at ambient temperature for 5 hours, then drained and the resin was washed with DMF (5×3 mL) and DCM (5×3 mL) and dried in vacuo. The peptide was cleaved from the resin and purified as described in example 218 to afford 6.5 mg of E-262 as a white solid. ESI-MS found 1138.4, $C_{212}H_{323}N_{47}O_{64}$ $(M+4H)^{4+}$ requires 1137.8.

Example 263: Compound 265

Scheme 200

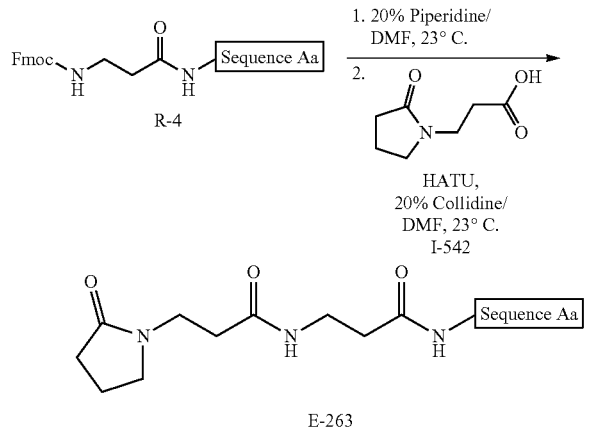

Resin R-4 (40.7 mg, estimated loading 0.125 mmol/g, 5.1 µmol) was subjected to Fmoc cleavage as described in example 218, and a solution of carboxylic acid I-542 (9.2 mg, 11.5 equiv.) in 20% Collidine/DMF (1.3 mL) was added, followed by HATU (10.3 mg, 5.5 equiv.). The reaction mixture was agitated at ambient temperature for 19 hours, then drained and the resin was washed with DMF (5×3 mL) and DCM (5×3 mL) and dried in vacuo. The peptide was cleaved from the resin and purified as described in example 218 to afford 5.0 mg of E-263 as a white solid. ESI-MS found 1141.8, $C_{213}H_{325}N_{47}O_{64}$ $(M+4H)^{4+}$ requires 1141.3.

Example 264: Compound 266

Scheme 201

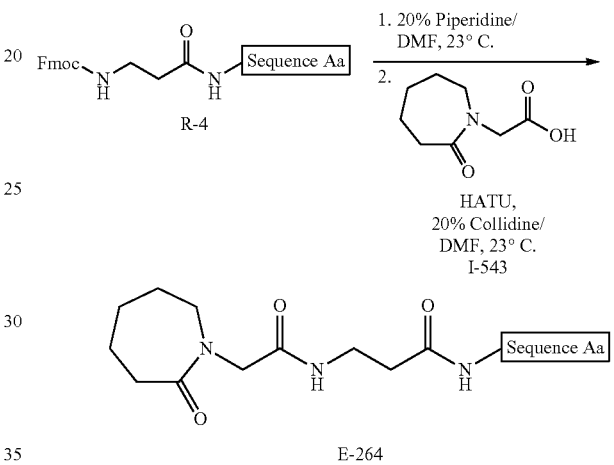

Resin R-4 (43 mg, estimated loading 0.125 mmol/g, 5.4 µmol) was subjected to Fmoc cleavage as described in example 218, and a solution of carboxylic acid I-543 (8.2 mg, 8.9 equiv.) in 20% Collidine/DMF (1.3 mL) was added, followed by HATU (11.2 mg, 5.5 equiv.). The reaction mixture was agitated at ambient temperature for 19 hours, then drained and the resin was washed with DMF (5×3 mL) and DCM (5×3 mL) and dried in vacuo. The peptide was cleaved from the resin and purified as described in example 218 to afford 4.3 mg of E-264 as a white solid. ESI-MS found 1145.3, $C_{214}H_{327}N_{47}O_{64}$ $(M+4H)^{4+}$ requires 1144.8.

Example 265: Compound 267

Scheme 202

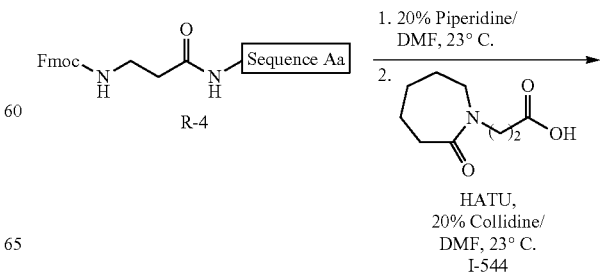

-continued

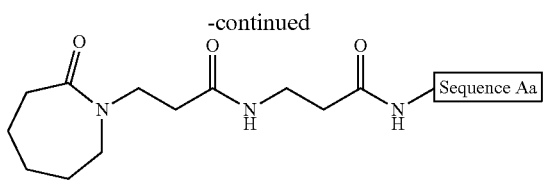

E-265

Resin R-4 (36.6 mg, estimated loading 0.125 mmol/g, 4.6 µmol) was subjected to Fmoc cleavage as described in example 218, and a solution of carboxylic acid I-544 (7.3 mg, 8.6 equiv.) in 20% Collidine/DMF (1.3 mL) was added, followed by HATU (9.6 mg, 5.5 equiv.). The reaction mixture was agitated at ambient temperature for 19 hours, then drained and the resin was washed with DMF (5×3 mL) and DCM (5×3 mL) and dried in vacuo. The peptide was cleaved from the resin and purified as described in example 218 to afford 4.4 mg of E-265 as a white solid. ESI-MS found 1148.9, $C_{215}H_{329}N_{47}O_{64}$ (M+4H)$^{4+}$ requires 1148.3.

Example 268: Compound 270

E-268

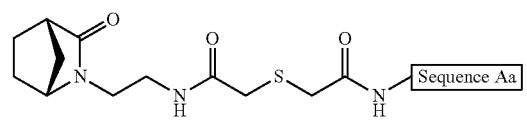

Peptide E-268 was prepared from 55.1 mg of resin R-1 (estimated loading 0.125 mmol/g) using I-518 as described in example 252 to afford 5.7 mg of E-268 as a white solid. ESI-MS found 1165.4, $C_{218}H_{327}SN_{47}O_{64}$ (M+4H)$^{4+}$ requires 1164.8.

Example 283: Compound 225

E-283

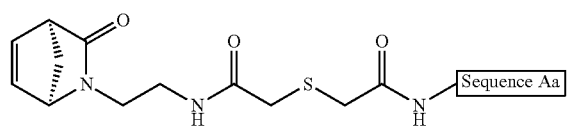

Peptide E-283 was prepared from 102 mg of the corresponding sequence immobilized on Rink amide resin (estimated loading 0.19 mmol/g) using I-248 and GP4 to afford 6.6 mg of E-283 as a white solid. ESI-MS found 1156.8, $C_{215}H_{329}SN_{47}O_{64}$ (M+4H)$^{4+}$ requires 1156.3.

Example 284: Compound 285

E-284

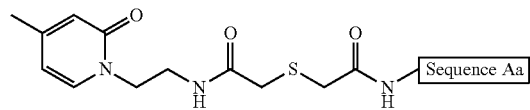

Peptide E-284 was prepared from 50.2 mg of resin R-1 (estimated loading 0.125 mmol/g) using I-494 and GP4 to afford 5.1 mg of E-284 as a white solid. ESI-MS found 1155.8, $C_{215}H_{325}SN_{47}O_{64}$ (M+4H)$^{4+}$ requires 1155.3.

Example 288: Compound 289

E-288

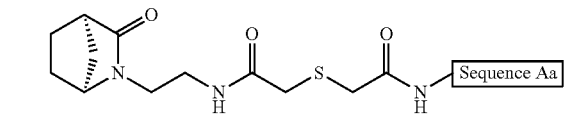

Peptide E-288 was prepared from 72.4 mg of resin R-1 (estimated loading 0.125 mmol/g) using I-552 as described in example 254 to afford 7.5 mg of E-288 as a white solid. ESI-MS found 1156.4, $C_{215}H_{327}N_{47}O_{64}S$ (M+4H)$^{4+}$ requires 1155.8.

Example 289: Compound 290

E-289

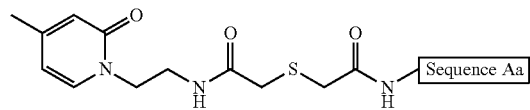

Peptide E-289 was prepared from 65.4 mg of resin R-1 (estimated loading 0.125 mmol/g) using I-557 as described in example 254 to afford 9.3 mg of E-289 as a white solid. ESI-MS found 1155.8, $C_{215}H_{325}N_{47}O_{64}S$ (M+4H)$^{4+}$ requires 1155.3.

Example 290: Compound 291

E-290

Peptide E-290 was prepared from 70.7 mg of resin R-1 (estimated loading 0.125 mmol/g) using I-559 as described in example 254 to afford 4.8 mg of E-290 as a white solid. ESI-MS found 1156.4, $C_{215}H_{327}N_{47}O_{64}S$ (M+4H)$^{4+}$ requires 1155.8.

Example 291: Compound 292

The synthesis of example E-291 is depicted in Scheme 208:

Scheme 208

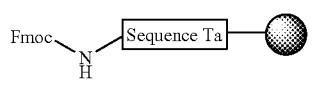

R-3

● = Rink amide resin 1. 20% Piperidine/DMF, 23° C.

2. 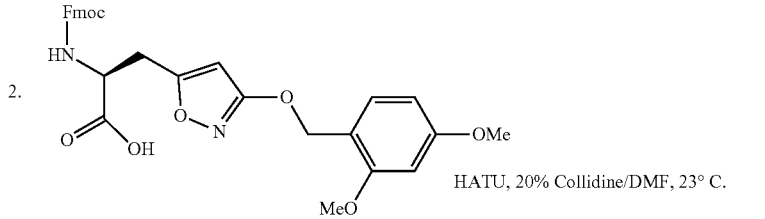
HATU, 20% Collidine/DMF, 23° C.

I-571

3. 20% Piperidine/DMF, 23° C.

4. 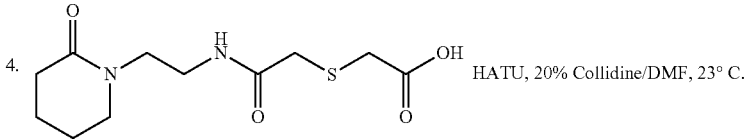
HATU, 20% Collidine/DMF, 23° C.

I-248

5. Cleavage from resin

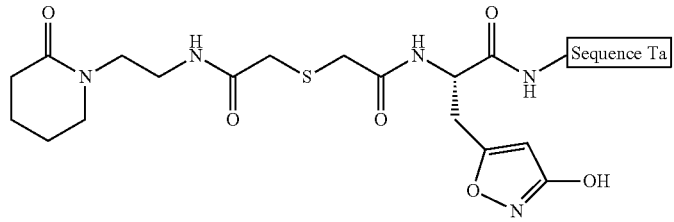

E-291

Fmoc cleavage from Rink amide resin R-3 (0.19 mmol/g, 79.1 mg, 0.015 mmol) was performed as described in example 218. A solution of carboxylic acid I-571 (49 mg, 6.0 equiv.) in 20% Collidine/DMF (1.5 mL) was added, followed by HATU (31.4 mg, 5.5 equiv.). The reaction mixture was agitated at ambient temperature for 14.5 hours, then drained and the resin was washed with DMF (5×3 mL) and DCM (5×3 mL). After further Fmoc cleavage, a solution of carboxylic acid I-248 (24.7 mg, 6.0 equiv.) in 20% Collidine/DMF (1.5 mL) was added, followed by HATU (31.4 mg, 5.5 equiv.). The reaction mixture was agitated at ambient temperature for 6.5 hours, then drained and the resin was washed with DMF (5×3 mL) and DCM (5×3 mL). The peptide was cleaved from the resin and purified as described in example 218 to afford 5.3 mg of E-291 as a white solid. ESI-MS found 1159.4, $C_{215}H_{326}SN_{48}O_{64}$ $(M+4H)^{4+}$ requires 1159.1.

E. BIOLOGICAL ASSAYS a) HitHunter cAMP Assay

Suspension cells were harvested and resuspended in 1×HBSS (+10 mM IEPES, 625 μM IBMX, 0.2% BSA) according to the following procedure: 5 uL of 2× cell suspension+1× antibody were added to each well, where the optimal cell density was 10,000 cells per well in a low volume 384-well plate. Agonist serial dilutions in a separate 384 well dilution plate in a 22-point series of 2× dilutions of agonist in DMSO were performed as follows. 80 μL of the highest concentration of Agonist/DMSO was added to well No. 1. 40 μL was removed from well No. 1 and added it to well No. 2, followed by gentle mixing. 40 μL was removed from well No. 2 and added it to well No. 3, followed by gentle mixing. This process was repeated until well No. 22. Additional serial dilutions for additional agonists were set up in a similar manner. 50 nL of each 2× agonist serial dilution was added in duplicate to the designated agonist rows of the assay plate using the Labcyte ECHO. Assay plate was incubated for 30 minutes at room temperature. Following agonist incubation, 5 μL of cAMP Antibody Reagent was added to all wells. A stock of cAMP Working Detection Solution in a separate 15 ml polypropylene tube was prepared by mixing 19 parts of cAMP Lysis Buffer, 5 parts of Substrate Reagent 1, 1 part Substrate Reagent 2, and 25 parts of cAMP Solution D. 5 μL of cAMP Working Detection Solution was added to all wells of the assay plate [Note: Do not pipette up and down in the vial to mix or vortex plates]. Plates were spun down briefly. Assay plate was incubated for 1 hour at room temperature in the dark for the immunocompetition reaction to occur. 5 μL of cAMP Solution A was added to all wells of the assay plate [Note: Do not pipette up and down in the vial to mix or vortex plates]. Plates were spun down briefly. Assay plate was incubated O/N at room temperature in the dark. Samples were read on Tecan i-control plate reader using luminescence mode with 300 ms integration time. Data analysis was performed using GraphPad Prism. Results of the HitHunter cAMP assay are presented in Table 3 and Table 3A.

Note:

In table 3 "+++++" denotes $EC_{50}<0.1$ nM; "++++" denotes $0.1$ nM$\leq EC_{50}<1$ nM; "+++" denotes $1$ nM$\leq EC_{50}<10$ nM; "++" denotes $10$ nM$\leq EC_{50}<100$ nM; "+" denotes $100$ nM$\leq EC_{50}\leq 1000$ nM; and "−" denotes $EC_{50}>1000$ nM.

In table 3A, for GLP-1R data: "+++++" denotes $EC_{50}<0.1$ nM; "++++" denotes $0.1$ nM$\leq EC_{50}<1$ nM; "+++" denotes $1$ nM$\leq EC_{50}<10$ nM; "++" denotes $10$ nM$\leq EC_{50}<100$ nM; "+" denotes $100$ nM$\leq EC_{50}<1000$ nM; and "−" denotes $EC_{50}>1000$ nM.

In table 3A, for GIP-R data: "+++++" denotes $EC_{50}<0.1$ nM; "++++" denotes $0.1$ nM$\leq EC_{50}<1$ nM; "+++" denotes $1$ nM$\leq EC_{50}<10$ nM; "++" denotes $10$ nM$\leq EC_{50}<100$ nM or Emax<300; "+" denotes $100$ nM$\leq EC_{50}\leq 1000$ nM or Emax<20; and "−" denotes $EC_{50}>1000$ nM or Emax<10%.

TABLE 3

| Compound # | $EC_{50}(E_{max})$ GLP-1R/nM | $EC_{50}(E_{max})$ GIP-R/nM |
|---|---|---|
| 1 | ++++ (97) | +++ (23) |
| 2 | +++++ (99) | +++ (46) |
| 3 | ++++ (96) | — |
| 4 | +++++ (100) | +++ (23) |
| 5 | +++++ (95) | +++ (74) |
| 6 | ++++ (95) | +++ (75) |
| 7 | +++++ (94) | +++ (29) |
| 8 | +++++ (90) | +++ (57) |
| 9 | +++++ (100) | +++ (48) |
| 10 | ++++ (95) | +++ (32) |
| 11 | ++++ (96) | +++ (39) |
| 12 | +++ (91) | ++++ (85) |
| 13 | +++ (69) | +++ (25) |
| 14 | ++++ (81) | ++ (<10) |
| 15 | ++++ (93) | +++ (20) |
| 16 | +++++ (97) | +++ (22) |
| 17 | ++++ (92) | +++ (55) |
| 18 | +++++ (101) | ++++ (80) |
| 19 | +++++ (93) | ++++ (50) |
| 20 | ++++ (91) | +++ (22) |
| 21 | +++++ (95) | +++ (20) |
| 22 | ++++ (90) | ++++ (46) |
| 23 | +++ (83) | +++ (37) |
| 24 | ++++ (92) | +++ (15) |
| 25 | +++ (86) | +++ (43) |
| 26 | ++++ (95) | +++ (64) |
| 27 | ++++ (95) | +++ (45) |
| 28 | ++++ (101) | +++ (57) |
| 29 | +++ (98) | +++ (11) |
| 30 | ++++ (97) | +++ (59) |
| 31 | +++ (102) | ++ (37) |
| 32 | +++++ (103) | +++ (65) |
| 33 | ++++ (100) | ++ (43) |
| 34 | ++++ (107) | +++ (20-38) |
| 35 | ++++ (110) | +++ (20-37) |
| 36 | +++++/++++ (108) | ++++/+++ (51-75) |
| 37 | +++++/++++ (110) | +++ (10-21) |
| 38 | ++++ (97-104) | +++ (18-43) |
| 39 | +++++/++++ (102-104) | ++++/+++ (40-60) |
| 40 | ++++ (101-105) | +++ (14-34) |
| 41 | ++++ (100-104) | +++ (75) |
| 42 | +++++/++++ (102-109) | ++++/+++ (28-46) |
| 43 | ++++ (93-97) | +++ (60-73) |
| 44 | ++++ (97-99) | +++ (54-67) |
| 45 | ++++ (100) | +++ (42) |
| 46 | +++ (100) | +++ (46) |
| 47 | +++++ (100) | +++ (24) |
| 48 | ++++ (104) | ++++ (65) |
| 49 | ++++ (101) | ++++ (48) |
| 50 | ++++ (103) | +++ (26) |
| 51 | ++++ (98) | +++ (65) |
| 52 | +++++ (101) | +++ (56-61) |

TABLE 3-continued

| Compound # | $EC_{50}(E_{max})$ GLP-1R/nM | $EC_{50}(E_{max})$ GIP-R/nM |
|---|---|---|
| 53 | +++ (99) | +++ (62) |
| 54 | +++++ (107) | (6 at 1 µM) |
| 55 | ++++ (104) | +++ (47) |
| 56 | ++++ (110) | +++ (60) |
| 57 | ++++ (109) | (7 at 1 µM) |
| 58 | ++++ (108) | +++ (26) |
| 59 | +++++ (108) | +++ (31) |
| 60 | ++++ (98) | +++ (37) |
| 61 | +++ (96) | +++ (56) |
| 62 | +++ (101) | +++ (48) |
| 63 | +++ (91) | +++ (24) |
| 64 | +++++ (97) | +++ (35) |
| 65 | ++++ (96) | +++ (42) |
| 66 | +++++ (113) | +++ (11) |
| 67 | ++++ (100) | +++ (65) |
| 68 | ++++ (109) | ++++ (87) |
| 69 | ++++ (104) | +++ (75) |
| 70 | ++++ (102) | +++ (86) |
| 71 | ++++/+++ (102) | +++ (77-87) |
| 72 | ++++ (105) | ++++ (87) |
| 73 | ++++ (93) | ++ (78) |
| 74 | ++++ (92) | +++ (47) |
| 75 | ++++ (99) | +++ (39) |
| 76 | +++ (95) | ++++ (89) |
| 77 | ++++ (90) | ++++ (82) |
| 78 | ++++ (94) | +++ (58) |
| 79 | ++++ (102) | ++++ (77) |
| 80 | ++++ (92) | +++ (73) |
| 81 | ++++ (96) | ++++ (89) |
| 82 | +++ (95) | +++ (82) |
| 83 | ++++ (106) | +++ (73) |
| 84 | ++++ (107) | +++ (53) |
| 85 | +++ (103) | ++++ (83) |
| 86 | ++++ (110) | +++ (61) |
| 87 | +++ (89) | +++ (62) |
| 88 | +++ (108) | +++ (102) |
| 89 | +++ (108) | ++++ (81) |
| 90 | +++ (108) | +++ (74) |
| 91 | +++ (98) | +++ (85) |
| 92 | +++ (94-104) | ++++ (85-88) |
| 93 | ++++ (99) | +++ (73) |
| 94 | +++ (89) | +++ (46) |
| 95 | ++ (84) | +++ (20) |
| 96 | +++ (94) | ++++ (90) |
| 97 | +++ (99) | ++++ (93) |
| 98 | ++++ (96) | — (<5 at 1 µM) |
| 99 | +++ (102) | — (11 at 1 µM) |
| 100 | ++ (95) | +++ (100) |
| 101 | ++ (92) | — |
| 102 | +++ (104) | ++ (34) |
| 103 | +++ (95) | +++ (68) |
| 104 | +++ (104-106) | +++ (43-47) |
| 105 | ++ (90) | ++ (<10 at 1 µM) |
| 106 | ++ (95) | ++ (37) |
| 107 | ++ (57) | ++++ (124) |
| 108 | — (18 at 1 µM) | ++ (69) |
| 109 | +++ (101) | ++ (36) |
| 110 | ++ (88) | ++ (33) |
| 111 | ++ (94) | ++ (12 at 1 µM) |
| 112 | ++ (94) | ++ (26 at 1 µM) |
| 113 | ++ (89) | ++ (52) |
| 114 | ++++/+++ (94-103) | +++ (42-63) |
| 115 | +++ (91) | +++ (67) |
| 116 | +++++ (98) | ++ (50) |
| 117 | +++ (92) | ++ (70) |
| 118 | +++++ (95) | +++ (35) |
| 119 | +++++ (97) | ++ (41) |
| 120 | +++ (91) | — (6 at 1 µM) |
| 121 | ++++ (90) | ++ (27) |
| 122 | +++ (91) | — (<1 at 1 µM) |
| 123 | +++ (104) | ++++ (111) |
| 124 | ++ (73) | — (10 at 1 µM) |
| 125 | ++ (94-100) | +++ (54-60) |
| 126 | ++ (84) | ++ (42-51) |
| 127 | +++ (95-107) | +++ (98-102) |
| 128 | +++ (99) | +++/++ (68) |
| 129 | +++/++ (91-95) | ++++/+++ (102-109) |

TABLE 3-continued

| Compound # | EC$_{50}$(E$_{max}$) GLP-1R/nM | EC$_{50}$(E$_{max}$) GIP-R/nM |
|---|---|---|
| 130 | ++++ (114) | +++ (64) |
| 131 | +++ (95) | — (3.2) |
| 132 | +++++ (103-114) | +++ (61-64) |
| 133 | +++ (98) | ++++ (104) |
| 134 | +++++ (103-108) | ++ (30) |
| 135 | +++++/++++ (106-111) | ++ (15-22) |
| 136 | ++ (91-94) | +++++ (105) |
| 137 | +++ (103) | ++ (8) |
| 138 | +++ (87) | +++ (81) |
| 139 | ++++ (102) | +++ (79) |
| 140 | +++++ (107) | +++ (63) |
| 141 | +++ (98-100) | ++ (46-50) |
| 142 | +++++ (101-105) | ++ (14.2-17) |
| 143 | ++++ (99-108) | +++ (99-107) |
| 144 | +++ (93-119) | +++++ (127-140) |
| 145 | +++ (100-104) | +++++/++++ (125) |
| 146 | +++ (86-92) | +++ (83-97) |
| 147 | +++ (87-97) | +++++ (114-128) |
| 148 | ++++ (99) | +++ (64-67) |
| 149 | +++ (86-92) | +++++ (113) |
| 150 | +++ (95-113) | +++++/++++ (118-130) |
| 151 | +++ (103-107) | ++++ (117-119) |
| 152 | ++ (85) | +++ (103) |
| 153 | +++++ (107) | ++ (75-85) |
| 154 | +++ (80) | +++ (78) |
| 155 | ++++ (102) | +++ (80) |
| 156 | +++ (95-100) | +++++ (116-118) |
| 157 | +++/++ (93-95) | ++++/+++ (103-105) |
| 158 | ++ (31-38) | ++++ (104-107) |
| 159 | ++ (87-91) | +++ (89-92) |
| 160 | +++ (85-95) | ++++ (109-113) |
| 161 | ++ (89-101) | +++/++ (58-107) |
| 162 | ++ (42-46) | ++++/+++ (103-107) |
| 163 | ++ (73) | +++++ (106) |
| 164 | ++ (68) | ++ (99-105) |
| 165 | ++++ (101-106) | +++ (91-98) |
| 166 | +++++ (109) | +++/++ (77-84) |
| 167 | ++++/+++ (94-99) | — (<1 at 1 µM) |
| 168 | +++ (92) | — (6-14 at 1 µM) |
| 169 | +++ (96) | — (6-8 at 1 µM) |
| 170 | +++ (99) | — (5-8 at 1 µM) |
| 171 | +++ (93-98) | — (6.5 at 1 µM) |
| 172 | +++ (98-101) | ++ (63-71) |
| 173 | +++ (90-105) | ++++ (92-111) |
| 174 | ++/+ (17-73) | + (30-66) |
| 175 | ++ (87-94) | ++ (38) |
| 176 | ++ (92) | — (1.8 at 1 µM) |
| 177 | +++ (96) | — (9 at 1 µM) |
| 178 | +++ (97) | + (38) |
| 179 | ++++ (103) | — (2 at 1 µM) |
| 180 | ++ (94) | ++ (84) |
| 181 | ++ (103) | +++ (102) |
| 182 | ++++ (96) | + (12 at 1 µM) |
| 183 | ++ (95) | — (1.4 at 1 µM) |
| 184 | +++ (99) | ++ (43) |
| 185 | ++++ (97) | — (8.6 at 1 µM) |
| 186 | +++ (94) | — (4 at 1 µM) |
| 187 | ++ (89) | ++ (58) |
| 188 | ++ (101) | +++ (107) |
| 189 | +++ (94) | — (4.5 at 1 µM) |
| 190 | +++ (97-119) | ++++/+++ (88-119) |
| 191 | +++ (97) | ++ (68) |
| 192 | ++++ (111) | ++ (63) |
| 193 | +++ (117) | ++ (44) |
| 194 | +++ (98) | — (12 at 1 µM) |
| 195 | ++++/+++ (93-113) | ++++/+++ (46-87) |
| 196 | ++++/+++ (93-104) | +++/++ (41-86) |

TABLE 3A

| Compound # | EC$_{50}$(E$_{max}$) GLP-1R/nM | EC$_{50}$(E$_{max}$) GIP-R/nM | Compound # | EC$_{50}$(E$_{max}$) GLP-1R/nM | EC$_{50}$(E$_{max}$) GIP-R/nM |
|---|---|---|---|---|---|
| 1 | ++++ (97) | ++ (23) | 99 | +++ (102) | — |
| 2 | +++++ (99) | +++ (46) | 100 | ++ (95) | +++ (100) |
| 3 | ++++ (96) | — | 101 | ++ (92) | — |
| 4 | +++++ (100) | ++ (23) | 102 | +++ (104) | ++ (34) |
| 5 | +++++ (95) | +++ (74) | 103 | ++ (95) | +++ (68) |
| 6 | ++++ (95) | +++ (75) | 104 | +++ (104-106) | +++ (43-47) |
| 7 | +++++ (94) | ++ (29) | 105 | ++ (90) | — |
| 8 | +++++ (90) | +++ (57) | 106 | ++ (95) | ++ (37) |
| 9 | +++++ (100) | +++ (48) | 107 | ++ (57) | ++++ (124) |
| 10 | ++++ (95) | +++ (32) | 108 | — (18 at 1 µM) | ++ (69) |
| 11 | ++++ (96) | +++ (39) | 109 | +++ (101) | ++ (36) |
| 12 | +++ (91) | ++++ (85) | 110 | ++ (88) | ++ (33) |
| 13 | +++ (69) | ++ (25) | 111 | ++ (94) | + (12 at 1 µM) |
| 14 | ++++ (81) | — | 112 | ++ (94) | ++ (26 at 1 µM) |
| 15 | ++++ (93) | ++ (20) | 113 | ++ (89) | ++ (52) |
| 16 | +++++ (97) | ++ (22) | 114 | ++++/+++ (94-103) | +++ (42-63) |
| 17 | ++++ (92) | +++ (55) | 115 | +++ (91) | +++ (67) |
| 18 | +++++ (101) | ++++ (80) | 116 | +++++ (98) | ++ (50) |
| 19 | +++++ (93) | ++++ (50) | 117 | +++ (92) | ++ (70) |
| 20 | ++++ (91) | ++ (22) | 118 | +++++ (95) | +++ (35) |
| 21 | +++++ (95) | ++ (20) | 119 | +++++ (97) | ++ (41) |
| 22 | ++++ (90) | ++++ (46) | 120 | +++ (91) | — |
| 23 | +++ (83) | +++ (37) | 121 | ++++ (90) | ++ (27) |
| 24 | ++++ (92) | + (15) | 122 | +++ (91) | — |
| 25 | +++ (86) | +++ (43) | 123 | +++ (104) | ++++ (111) |
| 26 | ++++ (95) | +++ (64) | 124 | ++ (73) | — |
| 27 | ++++ (95) | +++ (45) | 125 | ++ (94-100) | +++ (54-60) |
| 28 | ++++ (101) | +++ (57) | 126 | ++ (84) | ++ (42-51) |
| 29 | +++ (98) | + (11) | 127 | +++ (95-107) | +++ (98-102) |
| 30 | ++++ (97) | +++ (59) | 128 | +++ (99) | +++/++ (68) |
| 31 | +++ (102) | ++ (37) | 129 | +++/++ (91-95) | ++++/+++ (102-109) |
| 32 | +++++ (103) | +++ (65) | 130 | ++++ (114) | +++ (64) |
| 33 | ++++ (100) | ++ (43) | 131 | +++ (95) | — |
| 34 | ++++ (107) | ++/+++ (20-38) | 132 | +++++ (103-114) | +++ (61-64) |
| 35 | ++++ (110) | ++/+++ (20-37) | 133 | +++ (98) | ++++ (104) |

TABLE 3A-continued

| Compound # | EC$_{50}$(E$_{max}$) GLP-1R/nM | EC$_{50}$(E$_{max}$) GIP-R/nM | Compound # | EC$_{50}$(E$_{max}$) GLP-1R/nM | EC$_{50}$(E$_{max}$) GIP-R/nM |
|---|---|---|---|---|---|
| 36 | +++++/++++ (108) | ++++/+++ (51-75) | 134 | +++++ (103-108) | ++ (30) |
| 37 | +++++/++++ (110) | +/++ (10-21) | 135 | +++++/++++ (106-111) | +/++ (15-22) |
| 38 | ++++ (97-104) | +/+++ (18-43) | 136 | ++ (91-94) | ++++ (105) |
| 39 | +++++/++++ (102-104) | ++++/+++ (40-60) | 137 | +++ (103) | — |
| 40 | ++++ (101-105) | +/+++ (14-34) | 138 | +++ (87) | +++ (81) |
| 41 | ++++ (100-104) | +++ (75) | 139 | ++++ (102) | +++ (79) |
| 42 | +++++/++++ (102-109) | ++++/++ (28-46) | 140 | +++++ (107) | +++ (63) |
| 43 | ++++ (93-97) | +++ (60-73) | 141 | +++ (98-100) | ++ (46-50) |
| 44 | ++++ (97-99) | +++ (54-67) | 142 | +++++ (101-105) | + (14.2-17) |
| 45 | ++++ (100) | +++ (42) | 143 | ++++ (99-108) | +++ (99-107) |
| 46 | +++ (100) | +++ (46) | 144 | +++ (93-119) | +++++ (127-140) |
| 47 | +++++ (100) | ++ (24) | 145 | +++ (100-104) | +++++/++++ (125) |
| 48 | ++++ (104) | ++++ (65) | 146 | +++ (86-92) | +++ (83-97) |
| 49 | ++++ (101) | ++++ (48) | 147 | +++ (87-97) | +++++ (114-128) |
| 50 | ++++ (103) | ++ (26) | 148 | ++++ (99) | +++ (64-67) |
| 51 | ++++ (98) | +++ (65) | 149 | +++ (86-92) | +++++ (113) |
| 52 | +++++ (101) | +++ (56-61) | 150 | +++ (95-113) | +++++/++++ (118-130) |
| 53 | +++ (99) | +++ (62) | 151 | +++ (103-107) | ++++ (117-119) |
| 54 | +++++ (107) | — | 152 | ++ (85) | +++ (103) |
| 55 | ++++ (104) | +++ (47) | 153 | +++++ (107) | ++ (75-85) |
| 56 | ++++ (110) | +++ (60) | 154 | +++ (80) | +++ (78) |
| 57 | ++++ (109) | — | 155 | ++++ (102) | +++ (80) |
| 58 | ++++ (108) | ++ (26) | 156 | +++ (95-100) | +++++ (116-118) |
| 59 | +++++ (108) | +++ (31) | 157 | +++++ (93-95) | ++++/+++ (103-105) |
| 60 | ++++ (98) | +++ (37) | 158 | ++ (31-38) | ++++ (104-107) |
| 61 | +++ (96) | +++ (56) | 159 | ++ (87-91) | +++ (89-92) |
| 62 | +++ (101) | +++ (48) | 160 | +++ (85-95) | ++++ (109-113) |
| 63 | +++ (91) | ++ (24) | 161 | ++ (89-101) | +++/++ (58-107) |
| 64 | +++++ (97) | +++ (35) | 162 | ++ (42-46) | ++++/+++ (103-107) |
| 65 | ++++ (96) | +++ (42) | 163 | ++ (73) | +++++ (106) |
| 66 | +++++ (113) | + (11) | 164 | ++ (68) | ++ (99-105) |
| 67 | ++++ (100) | +++ (65) | 165 | ++++ (101-106) | +++ (91-98) |
| 68 | ++++ (109) | ++++ (87) | 166 | +++++ (109) | +++++ (77-84) |
| 69 | ++++ (104) | +++ (75) | 167 | ++++/+++ (94-99) | — |
| 70 | ++++ (102) | +++ (86) | 168 | +++ (92) | — |
| 71 | ++++/+++ (102) | +++ (77-87) | 169 | +++ (96) | — |
| 72 | ++++ (105) | ++++ (87) | 170 | +++ (99) | — |
| 73 | ++++ (93) | ++ (78) | 171 | +++ (93-98) | — |
| 74 | ++++ (92) | +++ (47) | 172 | +++ (98-101) | ++ (63-71) |
| 75 | ++++ (99) | +++ (39) | 173 | +++ (90-105) | ++++ (92-111) |
| 76 | +++ (95) | ++++ (89) | 174 | ++/+ (17-73) | + (30-66) |
| 77 | ++++ (90) | ++++ (82) | 175 | ++ (87-94) | ++ (38) |
| 78 | ++++ (94) | +++ (58) | 176 | ++ (92) | — |
| 79 | ++++ (102) | ++++ (77) | 177 | +++ (96) | — |
| 80 | ++++ (92) | +++ (73) | 178 | +++ (97) | + (38) |
| 81 | +++++ (96) | ++++ (89) | 179 | ++++ (103) | — |
| 82 | +++ (95) | +++ (82) | 180 | ++ (94) | ++ (84) |
| 83 | ++++ (106) | +++ (73) | 181 | ++ (103) | +++ (102) |
| 84 | ++++ (107) | +++ (53) | 182 | ++++ (96) | + (12 at 1 µM) |
| 85 | +++ (103) | ++++ (83) | 183 | ++ (95) | — |
| 86 | ++++ (110) | +++ (61) | 184 | +++ (99) | ++ (43) |
| 87 | +++ (89) | +++ (62) | 185 | ++++ (97) | — |
| 88 | +++ (108) | +++ (102) | 186 | +++ (94) | — |
| 89 | +++ (108) | ++++ (81) | 187 | ++ (89) | ++ (58) |
| 90 | +++ (108) | +++ (74) | 188 | ++ (101) | +++ (107) |
| 91 | +++ (98) | +++ (85) | 189 | +++ (94) | — |
| 92 | +++ (94-104) | ++++ (85-88) | 190 | +++ (97-119) | ++++/+++ (88-119) |
| 93 | ++++ (99) | +++ (73) | 191 | +++ (97) | ++ (68) |
| 94 | +++ (89) | +++ (46) | 192 | ++++ (111) | ++ (63) |
| 95 | ++ (84) | ++ (20) | 193 | +++ (117) | ++ (44) |
| 96 | +++ (94) | ++++ (90) | 194 | +++ (98) | — |
| 97 | +++ (99) | ++++ (93) | 195 | ++++/+++ (93-113) | ++++/+++ (46-87) |
| 98 | ++++ (96) | — | 196 | ++++/+++ (93-104) | +++/++ (41-86) |
| 197 | +++ (95) | + (20) | 247 | ++++ (102) | +++++ (110) |
| 198 | ++ (95) | ++ (81) | 248 | ++ (80) | +++ (105) |
| 199 | ++++ (92) | +++ (78) | 249 | ++ (101) | +++ (105) |
| 200 | ++ (89) | + (66) | 220 | +++ | — |
| 201 | +++ (99) | +++ (105) | 254 | +++++ | +++ (80) |
| 202 | +++++ | ++++ (67) | 257 | +++++ | ++ (40) |
| 203 | ++++ | +++ (44) | 260 | +++ | + |
| 204 | +++++ | ++ (98) | 264 | +++++ (100) | +++ (90) |
| 208 | +++++ | +++ (59) | 265 | +++++ (100) | ++++ (80) |
| 207 | ++++ | +++ (68) | 266 | +++++ (100) | +++ (70) |
| 205 | +++++ | +++ (61) | 267 | +++++ (100) | +++ (40) |
| 206 | +++++ | + (18) | 270 | +++ (90) | +++ (90) |
| 209 | +++++ (94) | ++ (27) | 225 | ++++ | +++ (70-80) |
| 210 | +++++ (90) | ++ (40) | 285 | +++++ (99) | ++++ (97) |

TABLE 3A-continued

| Compound # | EC$_{50}$(E$_{max}$) GLP-1R/nM | EC$_{50}$(E$_{max}$) GIP-R/nM | Compound # | EC$_{50}$(E$_{max}$) GLP-1R/nM | EC$_{50}$(E$_{max}$) GIP-R/nM |
|---|---|---|---|---|---|
| 211 | +++++ (91) | ++++ (50) | 291 | ++++ (100) | +++ (60) |
| 212 | +++++ (90) | +++ (50) | 289 | +++++ (100) | ++ (20) |
| 213 | +++++ (90) | ++++ (59) | 290 | +++++ (100) | ++ (10) |
| 214 | +++++ (95) | +++ (45) | 292 | +++ (90) | ++ (50) |
| 217 | +++++ (97) | +++ (58) | | | |
| 226 | +++ (89) | + (17) | | | |
| 219 | ++ (89) | +++ (75) | | | |
| 223 | +++++ (101) | ++++ (91) | | | |
| 218 | ++++ (96) | +/++ (19-23) | | | |
| 221 | +++ (95) | +++ (68) | | | |
| 222 | +++ (99) | >1 mM | | | |
| 224 | ++++ (98) | ++ (76) | | | |
| 232 | ++++ (95) | +++ (78) | | | |
| 233 | +++++ (96) | +++ (77) | | | |
| 234 | ++++ (97) | +++ (76) | | | |
| 238 | ++++ (95) | +++ (82) | | | |
| 239 | ++++ (100) | ++ (46) | | | |
| 240 | ++++ (97) | +++ (60) | | | |
| 241 | +++ (100) | ++ (46) | | | |
| 215 | +++ (103) | — | | | |
| 243 | +++++ (103) | ++ (20) | | | |
| 244 | +++++ (100) | +++ (50) | | | | b) Glucose Tolerance Test (GTT)

Materials:

Freestyle Lite glucometer and strips; compounds to be tested; sterilized glucose solution 200 mg/ml.

Procedure:

Compounds were diluted in PBS from the 1 mM DMSO stocks right before injection. Body weight and baseline blood glucose level for each mouse were measured. Tails were snipped using sterile scissors; blood from tails was used to measure glucose. For 0.25 h GTT, mice were fasted for 5-6 h and injected with compound subcutaneously 15 mins before glucose injection. For 4 h GTT, mice were fasted O/N for 16 h and injected with compound subcutaneously 4 h before glucose injection. For 16 h GTT, mice were injected with compound subcutaneously 16 h before glucose injection; food was removed at the same time. For 24 h GTT, mice were injected with compound subcutaneously 24 h before glucose injection; food was removed 5-6 h before glucose injection. 20% glucose in water was prepared; the solution was sterilized by 0.2 μm-filtration. An intraperitoneal injection of glucose (2 g/kg) was given to the mouse. Continued to take blood samples from the tail. Blood glucose was measured at 10, 20, 30, 40, 60, 90, and 120 minutes after glucose injection. Between each of these time points, the mouse was returned to its cage and monitored (at least 6 replicate mice were used for each time-point). The average glucose measurements were plotted as a function of time and the area under the curve (AUC) was determined. AUC results of the GTT test are presented in Table 4, below.

TABLE 4

| | 24 h Glucose Tolerance Test (GTT) | |
|---|---|---|
| Compound # | Dose range (nmol/kg) | AUC score |
| 1 | 2-5 | 3 |
| 2 | 2-5 | 2 |
| 5 | 2-5 | 2 |
| 16 | 2-5 | 2 |
| 18 | 2-5 | 2 |
| 32 | 2-5 | 2 |
| 41 | 2-5 | 4 |
| 59 | 2-5 | 3 |
| 64 | 2-5 | 3 |
| 65 | 2-5 | 2 |
| 66 | 2-5 | 2 |
| 68 | 2-5 | 2 |
| 69 | 2-5 | 2 |
| 77 | 5.1-15 | 2 |
| 79 | 5.1-15 | 2 |
| 81 | 2-5 | 3 |
| 83 | 2-5 | 2 |
| 91 | 2-5 | 3 |
| 96 | 5.1-15 | 4 |
| 98 | 5.1-15 | 2 |
| 114 | 2-5 | 3 |
| 195 | 2-5 | 2 |
| 233 | 2-5 | 2 |
| 234 | 2-5 | 3 |
| 264 | 2-5 | 3 |
| 266 | 2-5 | 2 |
| Liraglutide | 50 | 4 |
| Liraglutide | 200 | 2 |
| Semaglutide | 2.5 | 3 |

Note:
AUC score is based on percent compared to vehicle which is set to 100%; AUC score 1 = 0-25%, AUC score 2 = 26-50%, AUC score 3 = 51-75%, AUC score 4 = 76-100%.

c) PathHunter β-Arrestin Assay 5,000 cells were seeded in appropriate cell culture media per well in a low volume 384-well tissue culture plate. The assay plate was incubated with cells overnight at 37° C. and 5% CO2. The media was removed, and 5 uL of appropriate cell culture media containing 0.2% BSA was added. Agonist serial dilutions in a separate 384 well dilution plate in a 22-point series of 2× dilutions of agonist in DMSO were performed as follows. 80 μL of the highest concentration of Agonist/DMSO was added to well No. 1. 40 μL was removed from well No. 1, and added to well No. 2, followed by gentle mixing. 40 μL was removed from well No. 2 and added to well No. 3, followed by gentle mixing. This process was repeated until well No. 22. Additional serial dilutions for additional agonists were set up in a similar manner. 100 nL of each 2× agonist serial dilution was added in duplicate to the designated agonist rows of the assay plate using the Labcyte ECHO. Assay plate was incubated for 90 minutes at 37° C. and 5% $CO_2$. A stock of Working Detection Solution in a separate 15 ml polypropylene tube was prepared by mixing 19 parts of Cell Assay Buffer, 5 parts of Substrate Reagent 1, 1 part Substrate Reagent 2. Following agonist incubation, 3 μL of Working Detection Solution was added to all wells of the assay plate [Note: Do not pipette up and down in the vial to mix or vortex plates]. Plates were spun down briefly. Assay plate was incubated for 3 hour at room temperature in the dark for the immunocompetition reaction to occur. Samples were read on Tecan i-control plate reader using luminescence mode with 100 ms integration time. Data analysis was performed using GraphPad Prism. $EC_{50}$ values were only assigned to compounds with an Emax greater than 1000 of positive controls (GLP-1 and liraglutide were used as positive controls for this assay). The results of the PathHunter β-arrestin assay was summarized in Table 5, below.

TABLE 5

β-arrestin activity

| Compound # | $EC_{50}$ | Compound # | $EC_{50}$ |
|---|---|---|---|
| 1 | >1 μM | 114 | >1 μM |
| 2 | >1 μM | 116 | >1 μM |
| 3 | >1 μM | 118 | >1 μM |
| 4 | 0.01-1 μM | 119 | <0.01 μM |
| 5 | 0.01-1 μM | 121 | >1 μM |
| 6 | >1 μM | 123 | >1 μM |
| 7 | >1 μM | 128 | >1 μM |
| 8 | >1 μM | 129 | >1 μM |
| 9 | >1 μM | 130 | >1 μM |
| 10 | >1 μM | 132 | 0.01-1 μM |
| 11 | >1 μM | 133 | >1 μM |
| 12 | >1 μM | 134 | 0.01-1 μM |
| 13 | >1 μM | 135 | >1 μM |
| 14 | >1 μM | 136 | >1 μM |
| 15 | >1 μM | 137 | >1 μM |
| 16 | <0.01 μM | 138 | >1 μM |
| 17 | >1 μM | 139 | >1 μM |
| 18 | <0.01 μM | 140 | >1 μM |
| 19 | <0.01 μM | 141 | >1 μM |
| 20 | >1 μM | 142 | 0.01-1 μM |
| 21 | >1 μM | 143 | >1 μM |
| 22 | >1 μM | 144 | >1 μM |
| 23 | >1 μM | 145 | >1 μM |
| 24 | >1 μM | 146 | >1 μM |
| 25 | >1 μM | 147 | >1 μM |
| 26 | >1 μM | 148 | >1 μM |
| 27 | >1 μM | 149 | >1 μM |
| 28 | >1 μM | 150 | >1 μM |
| 29 | >1 μM | 151 | >1 μM |
| 30 | >1 μM | 152 | >1 μM |
| 31 | >1 μM | 153 | 0.01-1 μM |
| 32 | >1 μM | 154 | >1 μM |
| 33 | >1 μM | 155 | >1 μM |
| 34 | >1 μM | 156 | >1 μM |
| 35 | >1 μM | 157 | >1 μM |
| 36 | >1 μM | 158 | >1 μM |
| 37 | >1 μM | 159 | >1 μM |
| 38 | >1 μM | 160 | >1 μM |
| 39 | >1 μM | 161 | >1 μM |
| 40 | >1 μM | 162 | >1 μM |
| 41 | >1 μM | 163 | >1 μM |
| 42 | >1 μM | 164 | >1 μM |
| 43 | >1 μM | 165 | >1 μM |
| 44 | >1 μM | 166 | >1 μM |
| 60 | >1 μM | 167 | >1 μM |
| 64 | >1 μM | 170 | >1 μM |
| 65 | >1 μM | 171 | >1 μM |
| 66 | >1 μM | 172 | >1 μM |

TABLE 5-continued

β-arrestin activity

| Compound # | $EC_{50}$ | Compound # | $EC_{50}$ |
|---|---|---|---|
| 68 | >1 μM | 173 | >1 μM |
| 69 | >1 μM | 176 | >1 μM |
| 71 | >1 μM | 177 | >1 μM |
| 72 | >1 μM | 178 | >1 μM |
| 73 | >1 μM | 179 | 0.01-1 μM |
| 74 | >1 μM | 180 | >1 μM |
| 75 | >1 μM | 181 | >1 μM |
| 77 | >1 μM | 182 | >1 μM |
| 79 | >1 μM | 183 | >1 μM |
| 81 | >1 μM | 184 | >1 μM |
| 83 | >1 μM | 185 | >1 μM |
| 85 | >1 μM | 186 | >1 μM |
| 86 | >1 μM | 187 | >1 μM |
| 91 | >1 μM | 188 | >1 μM |
| 92 | >1 μM | 189 | >1 μM |
| 93 | >1 μM | 190 | >1 μM |
| 94 | >1 μM | 191 | >1 μM |
| 96 | >1 μM | 192 | >1 μM |
| 97 | >1 μM | 193 | >1 μM |
| 98 | >1 μM | 194 | >1 μM |
| 104 | >1 μM | 195 | >1 μM |
| 111 | >1 μM | 196 | >1 μM |
| GLP-1 | <0.01 μM | liraglutide | 0.01-1 μM |
| 202 | >1 μM | 234 | >1 μM |
| 203 | >1 μM | 238 | >1 μM |
| 204 | 0.02-1 μM | 239 | >1 μM |
| 208 | >1 μM | 240 | >1 μM |
| 207 | >1 μM | 241 | >1 μM |
| 205 | >1 μM | 243 | >1 μM |
| 206 | >1 μM | 244 | 0.01-1 μM |
| 209 | 0.01-1 μM | 264 | <0.01 μM |
| 210 | 0.01-1 μM | 265 | <0.01 μM |
| 211 | 0.01-1 μM | 266 | <0.01 μM |
| 212 | 0.01-1 μM | 225 | >1 μM |
| 213 | 0.01-1 μM | 285 | >1 μM |
| 214 | 0.01-1 μM | | |
| 217 | >1 μM | | |
| 226 | >1 μM | | |
| 223 | 0.01-1 μM | | |
| 218 | >1 μM | | |
| 232 | >1 μM | | |
| 233 | 0.01-1 μM | | | d) Conditioned Taste Aversion (CTA) in Mice

One week before start of experiment (Day −7), animals were transferred to single house double grommet cages. A 50 ml water bottle was placed, and consistently replaced when refilled in the same grommet to habituate the animal to a "water" side. After 7 days of baseline water consumption, animals began the taste preference procedure. On Day 1, the animals were weighed and deprived of water at 6 pm. On acquisition day (Day 2), mice had access to a single bottle containing 0.15% saccharin solution, on the opposite side to the "water" habituated side and allowed to consume for 3 h, from 6 pm until 9 pm. The saccharine bottles were then removed and weighed to record the 3 h consumption. The mice were assigned to form balanced groups based on saccharine consumption and animals that did not consume saccharine were removed from the study. After the groups were formed, the animals were either injected subcutaneously with test drug, vehicle (solvent) or positive aversive drug (200 nmol/kg liraglutide) based on weight from Day 1 and returned to cages with weighed water bottles. On Day 3, the water was removed and weighed at 6 pm. On Day 4, both saccharine and water bottles were weighed and returned simultaneously to respective grommet at 6 pm. On Day 5, the bottles were removed at 6 pm and weighed. Saccharine consumption was measured as a percent of the total amount of fluid consumed. The reduction of saccharin consumption during the retrieval was used as a measure of CTA strength. Liraglutide and semaglutide were used as positive controls. The results are summarized in Table 6.

TABLE 6

Conditioned taste aversion (CTA)

| Compound # | Dose (nmol/kg) | CTA score |
|---|---|---|
| 2 | 30 | 2 |
| 5 | 30 | 1 |
| 16 | 30 | 1 |
| 32 | 30 | 2 |
| 65 | 30 | 3 |
| 66 | 50 | 2 |
| 68 | 30 | 3 |
| 69 | 30 | 3/4 |
| 83 | 30 | 2 |
| 91 | 30 | 4 |
| 96 | 30 | 4 |
| 98 | 30 | 4 |
| 114 | 50 | 2 |
| 195 | 30 | 3 |
| 202 | 30 | 4 |

TABLE 6-continued

Conditioned taste aversion (CTA)

| Compound # | Dose (nmol/kg) | CTA score |
|---|---|---|
| 233 | 30 | 1 |
| 234 | 30 | 1 |
| 264 | 30 | 1 |
| 266 | 30 | 1 |
| Liraglutide | 50 | 2 |
| Liraglutide | 200 | 1 |
| Semaglutide | 10 | 2 |
| Semaglutide | 20 | 1 |

Note: Saccharine preference score is compared to vehicle (preferred saccharine solution) which is set to 100%; Score 1=0-25%, Score 2=26-50%, Score 3=51-75%, Score 4=76-100%.

A number of embodiments of the invention have been described. Nevertheless, it will be understood that various modifications may be made without departing from the spirit and scope of the invention. Accordingly, other embodiments are within the scope of the following claims.

What is claimed is:

1. A compound having formula (IAA), or a pharmaceutically acceptable salt thereof:

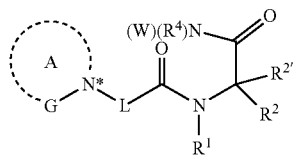

(IAA)

wherein:

ring A is:

(i) a saturated or unsaturated monocyclic ring that includes from 3-8 ring atoms (inclusive of G and the nitrogen atom labelled N*); or (ii) a saturated or unsaturated bicyclic or tricyclic ring that includes from 6-14 ring atoms (inclusive of G and the nitrogen atom labelled N*), wherein:

G is C(O), S(O), or $SO_2$; and the dotted, circular line connecting G and N* is a divalent group that includes from 1-6 ring atoms; wherein:

(a) from 0-2 of the divalent group's ring atoms are ring heteroatoms, which are each independently selected from the group consisting of N, N($R^a$), O, S, and $SO_2$; and (b) from 1-6 of the divalent group's ring atoms are ring carbon atoms, which are each independently selected from the group consisting of C, CH, $CH_2$, $CR^b$, $C(R^b)_2$, and $CHR^b$;

wherein:

(1) when ring A is a monocyclic ring, then each of the divalent group's 1-6 ring carbon atoms is independently selected from the group consisting of CH, CH$_2$, CR$^b$, C(R$^b$)$_2$, and CHR$^b$; and
(2) when ring A is a bicyclic or tricyclic ring, then (A) or (B) applies:
(A) two or three adjacent ring carbon atoms of the divalent group are each independently selected from the group consisting of C, CH, CH$_2$, CR$^b$, C(R$^b$)$_2$, and CHR$^b$ and are fused to a second ring that is selected from the group consisting of:
  (a) C$_{6-10}$ aryl optionally substituted with from 1-5 independently selected R$^c$;
  (b) heteroaryl including from 5-10 ring atoms, wherein from 1-4 ring atoms are each independently selected from the group consisting of N, N(R$^a$), O, and S, wherein the heteroaryl is optionally substituted with from 1-3 independently selected R$^c$;
  (c) C$_{3-10}$ cycloalkyl optionally substituted with from 1-4 independently selected R$^d$;
  (d) heterocyclyl including from 3-10 ring atoms, wherein from 1-3 ring atoms are each independently selected from the group consisting of N(R$^a$), O, and S, wherein the heterocyclyl is optionally substituted with from 1-4 independently selected R$^d$; or
(B) one of the divalent group's ring carbon atoms is C and is spiro-fused to a second ring that is selected from the group consisting of:
  (a) C$_{3-10}$ cycloalkyl optionally substituted with from 1-4 independently selected R$^d$;
  (b) heterocyclyl including from 3-10 ring atoms, wherein from 1-3 ring atoms are each independently selected from the group consisting of N(R$^a$), O, and S, wherein the heterocyclyl is optionally substituted with from 1-4 independently selected R$^d$;
L is:
(i) —(CH$_2$)$_m$—X$^1$—(CH$_2$)$_n$—X$^2$—(CH$_2$)$_p$— (formula VIII), wherein m is from 1-6; n is from 0-2; and p is from 0-8;
(ii) —C(O)—(CH$_2$)$_n$—X$^3$—(CH$_2$)$_p$— (formula IX), wherein n is from 0-2; and p is from 0-8;
(iii) —(CH$_2$)$_q$—, wherein q is from 1-10;
(iv) —C(O)—; or
(v) —(CH$_2$)$_m$—X$^1$—(CH$_2$)$_p$— (formula VIII), wherein m is from 1-6; and p is from 0-8;
X$^1$ is: —C(O)—; —N(R')C(O)—; —C(O)N(R')—; or —N(R')C(O)NR'—; wherein each occurrence of R' is independently selected from the group consisting of: H and C$_{1-4}$ alkyl;
X$^2$ is:
(i) —O—;
(ii) —S—;
(iii) —S(O)$_t$—, wherein t is 1 or 2;
(iv) —C(Q$^1$)(Q$^2$)-, wherein each of Q$^1$ and Q$^2$ is independently selected from the group consisting of H and C$_{1-4}$ alkyl; or Q$^1$ and Q$^2$, together with the carbon atom to which each is attached forms C$_{3-10}$ cycloalkyl that is optionally substituted with from 1-4 independently selected R$^d$ and optionally fused to phenyl;
(v) C$_{6-10}$ arylene optionally substituted with from 1-5 independently selected R$^c$;
(vi) heteroarylene including from 5-10 ring atoms, wherein from 1-4 ring atoms are each independently selected from the group consisting of N, N(R$^a$), O, and S; and which is optionally substituted with from 1-5 independently selected R$^c$;
(vii) C$_{3-10}$ cycloalkylene optionally substituted with from 1-4 independently selected R$^d$;
(viii) heterocycloalkylene including from 3-10 ring atoms, wherein from 1-3 ring atoms are each independently selected from the group consisting of N(R$^a$), O, and S; and which is optionally substituted with from 1-5 independently selected R$^d$;
(ix) C$_2$-C$_4$ alkenylene optionally substituted with from 1-2 R$^e$; or
(x) C$_2$-C$_4$ alkynylene optionally substituted with from 1-2 R$^e$;
X$^3$ is: —O—; —S—; or —S(O)$_t$—, wherein t is 1 or 2;
each of R$^1$, R$^2$, and R$^4$ is independently selected from the group consisting of H and unsubstituted C$_{1-3}$ alkyl;
R$^{2'}$ is as defined according to (AA) or (BB) below:
(AA)
R$^{2'}$ is wherein:
R$^3$ is —C(O)OH, —C(O)OR$^{31}$, —CH(C(O)OH)$_2$ or a carboxylic acid isostere;
a is 0-5;
a' is 0 or 1; and
each of R$^{3a}$ and R$^{3b}$ is independently H or C$_{1-3}$ alkyl;
(BB)
R$^{2'}$ and R$^4$ taken together with the atoms connecting them form a ring including from 5-8 ring atoms, wherein from 3-7 are ring carbon atoms each substituted with from 1-2 substituents independently selected from H, halo, hydroxy, oxo, and C$_{1-3}$ alkyl; and from 0-1 is a heteroatom (in addition to the N attached to R$^1$) selected from O, —NH, —N(C$_{1-3}$ alkyl), and S;
R$^{31}$ is:
(i) C$_{1-6}$ alkyl optionally substituted with from 1-2 independently selected R$^e$;
(ii) —(C$_{0-3}$ alkylene)-C$_{3-10}$ cycloalkyl, wherein the cycloalkyl is optionally substituted with from 1-4 independently selected R$^d$;
(iii) —(C$_{0-3}$ alkylene)-heterocyclyl including from 3-10 ring atoms, wherein from 1-3 ring atoms are each independently selected from the group consisting of N(R$^a$), O, and S, wherein the heterocyclyl is optionally substituted with from 1-4 independently selected R$^d$;
(iv) —(C$_{0-3}$ alkylene)-C$_{6-10}$ aryl, wherein the aryl is optionally substituted with from 1-5 independently selected R$^c$; or
(v) —(C$_{0-3}$ alkylene)-heteroaryl including from 5-10 ring atoms, wherein from 1-4 ring atoms are each independently selected from the group consisting of N, N(R$^a$), O, and S, wherein the heteroaryl is optionally substituted with from 1-3 independently selected R$^c$;
each occurrence of R$^a$ is independently selected from the group consisting of: H; C$_{1-4}$ alkyl; C$_{3-6}$ cycloalkyl; —C(=O)(C$_{1-6}$ alkyl); —C(=O)O(C$_{1-6}$ alkyl); and —S(O)$_{1-2}$(C$_{1-6}$ alkyl);
each occurrence of R$^b$ is independently selected from the group consisting of: R$^{31}$; C$_{1-4}$ haloalkyl; —OH; oxo; —F; —N(R$^a$)(R''); C$_{1-4}$ alkoxy; C$_{1-4}$ haloalkoxy; —C(=O)(C$_{1-4}$ alkyl); —C(=O)O(C$_{1-6}$ alkyl); —C(=O)OH, —C(=O)N(R''')(R''''), —S(O)$_{1-2}$(C$_{1-6}$ alkyl); and cyano;

each occurrence of $R^c$ is independently selected from the group consisting of: $C_{1-6}$ alkyl optionally substituted with from 1-2 independently selected $R^e$; $C_{3-6}$ cycloalkyl; $C_{1-4}$ haloalkyl; —OH; -halo; —$NO_2$; $N_3$; —N($R^a$)(R"); $C_{1-4}$ alkoxy; $C_{1-4}$ thioalkoxy; $C_{1-4}$ haloalkoxy; —OC(=O)($C_{1-6}$ alkyl); —C(=O)($C_{1-6}$ alkyl); —C(=O)O($C_{1-6}$ alkyl); —C(=O)OH, —C(=O)N(R''')(R''''), —S(O)$_{1-2}$($C_{1-6}$ alkyl); and cyano;

each occurrence of $R^d$ is independently selected from the group consisting of: $C_{1-6}$ alkyl optionally substituted with from 1-2 independently selected $R^e$; $C_{1-4}$ haloalkyl; —OH; —F; Cl; —N($R^a$)(R"); oxo; $C_{1-4}$ alkoxy; $C_{1-4}$ haloalkoxy; —OC(=O)($C_{1-6}$ alkyl); —C(=O)($C_{1-6}$ alkyl); —C(=O)O($C_{1-6}$ alkyl); —C(=O)OH, —C(=O)N(R''')(R''''), —S(O)$_{1-2}$($C_{1-6}$ alkyl); and cyano;

each occurrence of $R^e$ is independently selected from the group consisting of: —OH; —N(R')(R"); $C_{1-4}$ alkoxy; $C_{1-4}$ haloalkoxy; —OC(=O)($C_{1-6}$ alkyl); —C(=O)O($C_{1-6}$ alkyl); —C(=O)OH, —C(=O)N(R''')(R''''), —S(O)$_{1-2}$($C_{1-6}$ alkyl); and cyano;

each occurrence of R", R''', and R'''' is independently selected from the group consisting of: H and $C_{1-6}$ alkyl; and —N($R^4$)W is a peptide having formula (XIV):
GTF(Xaa4)SD(Xaa7)S(Xaa9)(Xaa10)(Xaa11)(Xaa12)(Xaa13)QA(Xaa16)(Xaa17)(Xaa18)F-(Xaa20)(Xaa21)WL(Xaa24)(Xaa25)GGPSSGAPPPS-$R^5$ (SEQ ID NO: 2);

wherein:

Xaa4 is T or I;

Xaa7 is Y, V, or L;

Xaa9 is I or S;

Xaa10 is Y, Q, or A;

Xaa11 is L, M, or L*;

Xaa12 is D or E;

Xaa13 is K, G, or E;

Xaa16 is A or V;

Xaa17 is (Aib) or K;

Xaa18 is E or L;

Xaa20 is V or I;

Xaa21 is N, A, or E;

Xaa24 is L or V; and

Xaa25 is A or K;

wherein $R^5$ is a C-terminal amino acid, amino acid ester, or amino acid amide that is optionally substituted with from 1-2 modifying groups.

2. The compound of claim 1, wherein the compound has formula (IA), or a pharmaceutically acceptable salt thereof:

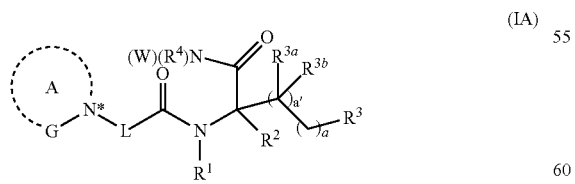

(IA)

wherein:

ring A is:

(i) a saturated or unsaturated monocyclic ring that includes from 3-8 ring atoms (inclusive of G and the nitrogen atom labelled N*); or (ii) a saturated or unsaturated bicyclic or tricyclic ring that includes from 6-14 ring atoms (inclusive of G and the nitrogen atom labelled N*), wherein:

G is C(O), S(O), or $SO_2$; and the dotted, circular line connecting G and N* is a divalent group that includes from 1-6 ring atoms; wherein:

(a) from 0-2 of the divalent group's ring atoms are ring heteroatoms, which are each independently selected from the group consisting of N, N($R^a$), O, S, and $SO_2$; and (b) from 1-6 of the divalent group's ring atoms are ring carbon atoms, which are each independently selected from the group consisting of C, CH, $CH_2$, $CR^b$, $C(R^b)_2$, and $CHR^b$;

wherein:

(1) when ring A is a monocyclic ring, then each of the divalent group's 1-6 ring carbon atoms is independently selected from the group consisting of CH, $CH_2$, $CR^b$, $C(R^b)_2$, and $CHR^b$; and (2) when ring A is a bicyclic or tricyclic ring, then (A) or (B) applies:

(A) two or three adjacent ring carbon atoms of the divalent group are each independently selected from the group consisting of C, CH, and, $CR^b$ and are fused to a second ring that is selected from the group consisting of:

(a) $C_{6-10}$ aryl optionally substituted with from 1-5 independently selected $R^c$;

(b) heteroaryl including from 5-10 ring atoms, wherein from 1-4 ring atoms are each independently selected from the group consisting of N, N($R^a$), O, and S, wherein the heteroaryl is optionally substituted with from 1-3 independently selected $R^c$;

(c) $C_{3-10}$ cycloalkyl optionally substituted with from 1-4 independently selected $R^d$;

(d) heterocyclyl including from 3-10 ring atoms, wherein from 1-3 ring atoms are each independently selected from the group consisting of N($R^a$), O, and S, wherein the heterocyclyl is optionally substituted with from 1-4 independently selected $R^d$; or (B) one of the divalent group's ring carbon atoms is C and is spiro-fused to a second ring that is selected from the group consisting of:

(a) $C_{3-10}$ cycloalkyl optionally substituted with from 1-4 independently selected $R^d$;

(b) heterocyclyl including from 3-10 ring atoms, wherein from 1-3 ring atoms are each independently selected from the group consisting of N($R^a$), O, and S, wherein the heterocyclyl is optionally substituted with from 1-4 independently selected $R^d$;

L is:

(i) —$(CH_2)_m$—$X^1$—$(CH_2)_n$—$X^2$—$(CH_2)_p$— (formula VIII), wherein m is from 1-6; n is from 0-2; and p is from 0-8;

(ii) —C(O)—$(CH_2)_n$—$X^3$—$(CH_2)_p$— (formula IX), wherein n is from 0-2; and p is from 0-8;

(iii) —$(CH_2)_q$—, wherein q is from 1-10;

(iv) —C(O)—; or (v) —$(CH_2)_m$—$X^1$—$(CH_2)_p$— (formula VIII), wherein m is from 1-6; and p is from 0-8;

$X^1$ is —C(O)—; —N(R')C(O)—; —C(O)N(R')—; or —N(R')C(O)NR')—; wherein each occurrence of R' is independently selected from the group consisting of: H and $C_{1-4}$ alkyl;

X² is:
(i) —O—;
(ii) —S—;
(iii) —S(O)$_t$—, wherein t is 1 or 2;
(iv) —C(Q¹)(Q²)-, wherein each of Q¹ and Q² is independently selected from the group consisting of H and $C_{1-4}$ alkyl; or Q¹ and Q², together with the carbon atom to which each is attached forms $C_{3-10}$ cycloalkyl that is optionally substituted with from 1-4 independently selected R$^d$ and optionally fused to phenyl;
(v) $C_{6-10}$ arylene optionally substituted with from 1-5 independently selected R$^c$;
(vi) heteroarylene including from 5-10 ring atoms, wherein from 1-4 ring atoms are each independently selected from the group consisting of N, N(R$^a$), O, and S; and which is optionally substituted with from 1-5 independently selected R$^c$;
(vii) $C_{3-10}$ cycloalkylene optionally substituted with from 1-4 independently selected R$^d$;
(viii) heterocycloalkylene including from 3-10 ring atoms, wherein from 1-3 ring atoms are each independently selected from the group consisting of N(R$^a$), O, and S; and which is optionally substituted with from 1-5 independently selected R$^d$;
(ix) $C_2$-$C_4$ alkenylene optionally substituted with from 1-2 R$^e$; or
(x) $C_2$-$C_4$ alkynylene optionally substituted with from 1-2 R$^e$;
X³ is: —O—; —S—; or —S(O)$_t$—, wherein t is 1 or 2;
each of R¹, R², and R⁴ is independently selected from the group consisting of H and unsubstituted $C_{1-3}$ alkyl;
R³ is —C(O)OH, —C(O)OR³¹, —CH(C(O)OH)₂ or a carboxylic acid isostere
a is 0-5;
a' is 0 or 1;
each of R$^{3a}$ and R$^{3b}$ is independently H or $C_{1-3}$ alkyl;
R³¹ is:
(i) $C_{1-6}$ alkyl optionally substituted with from 1-2 independently selected R$^e$;
(ii) —($C_{0-3}$ alkylene)-$C_{3-10}$ cycloalkyl, wherein the cycloalkyl is optionally substituted with from 1-4 independently selected R$^d$;
(iii) —($C_{0-3}$ alkylene)-heterocyclyl including from 3-10 ring atoms, wherein from 1-3 ring atoms are each independently selected from the group consisting of N(R$^a$), O, and S, wherein the heterocyclyl is optionally substituted with from 1-4 independently selected R$^d$;
(iv) —($C_{0-3}$ alkylene)-$C_{6-10}$ aryl, wherein the aryl is optionally substituted with from 1-5 independently selected R$^c$; or
(v) —($C_{0-3}$ alkylene)-heteroaryl including from 5-10 ring atoms, wherein from 1-4 ring atoms are each independently selected from the group consisting of N, N(R$^a$), O, and S, wherein the heteroaryl is optionally substituted with from 1-3 independently selected R$^c$;
each occurrence of R$^a$ is independently selected from the group consisting of: H; $C_{1-4}$ alkyl; $C_{3-6}$ cycloalkyl; —C(=O)($C_{1-6}$ alkyl); —C(=O)O($C_{1-6}$ alkyl); and —S(O)$_{12}$($C_{1-6}$ alkyl);
each occurrence of R$^b$ is independently selected from the group consisting of: R³¹; $C_{1-4}$ haloalkyl; —OH; oxo; —F; —N(R$^a$)(R''); $C_{1-4}$ alkoxy; $C_{1-4}$ haloalkoxy; —C(=O)($C_{1-4}$ alkyl); —C(=O)O($C_{1-6}$ alkyl); —C(=O)OH, —C(=O)N(R''')(R''''), —S(O)$_{1-2}$($C_{1-6}$ alkyl); and cyano;
each occurrence of R$^c$ is independently selected from the group consisting of: $C_{1-6}$ alkyl optionally substituted with from 1-2 independently selected R$^e$; $C_{3-6}$ cycloalkyl; $C_{1-4}$ haloalkyl; —OH; -halo; —NO₂; N₃; —N(R$^a$)(R''); $C_{1-4}$ alkoxy; $C_{1-4}$ thioalkoxy; $C_{1-4}$ haloalkoxy; —OC(=O)($C_{1-6}$ alkyl); —C(=O)($C_{1-6}$ alkyl); —C(=O)O($C_{1-6}$ alkyl); —C(=O)OH, —C(=O)N(R''')(R''''), —S(O)$_{1-2}$($C_{1-6}$ alkyl); and cyano;
each occurrence of R$^d$ is independently selected from the group consisting of: $C_{1-6}$ alkyl optionally substituted with from 1-2 independently selected R$^e$; $C_{1-4}$ haloalkyl; —OH; —F; Cl; —N(R$^a$)(R''); oxo; $C_{1-4}$ alkoxy; $C_{1-4}$ haloalkoxy; —OC(=O)($C_{1-6}$ alkyl); —C(=O)($C_{1-6}$ alkyl); —C(=O)O($C_{1-6}$ alkyl); —C(=O)OH, —C(=O)N(R''')(R''''), —S(O)$_{1-2}$($C_{1-6}$ alkyl); and cyano;
each occurrence of R$^e$ is independently selected from the group consisting of: —OH; —N(R$^a$)(R''); $C_{1-4}$ alkoxy; $C_{1-4}$ haloalkoxy; —OC(=O)($C_{1-6}$ alkyl); —C(=O)O($C_{1-6}$ alkyl); —C(=O)OH, —C(=O)N(R''')(R''''), —S(O)$_{1-2}$($C_{1-6}$ alkyl); and cyano;
each occurrence of R'', R''', and R'''' is independently selected from the group consisting of: H and $C_{1-6}$ alkyl; and
—N(R⁴)W is a peptide having formula (XIV):
GTF(Xaa4)SD(Xaa7)S(Xaa9)(Xaa10)(Xaa11)(Xaa12)(Xaa13)QA(Xaa16)(Xaa17)(Xaa18)F-(Xaa20)(Xaa21)WL(Xaa24)(Xaa25)GGPSSGAPPPS-R⁵ (SEQ ID NO: 2);
wherein:
Xaa4 is T or I;
Xaa7 is Y, V, or L;
Xaa9 is I or S;
Xaa10 is Y, Q, or A;
Xaa11 is L, M, or L*;
Xaa12 is D or E;
Xaa13 is K, G, or E;
Xaa16 is A or V;
Xaa17 is (Aib) or K;
Xaa18 is E or L;
Xaa20 is V or I;
Xaa21 is N, A, or E;
Xaa24 is L or V; and
Xaa25 is A or K;
wherein R⁵ is a C-terminal amino acid, amino acid ester, or amino acid amide that is optionally substituted with from 1-2 modifying groups.

3. The compound of claim 1, wherein the compound has formula (I) or a pharmaceutically acceptable salt thereof:

wherein:
ring A is:
(i) a saturated or unsaturated monocyclic ring that includes from 3-8 ring atoms (inclusive of G and the nitrogen atom labelled N*); or
(ii) a saturated or unsaturated bicyclic or tricyclic ring that includes from 6-14 ring atoms (inclusive of G and the nitrogen atom labelled N*), wherein:
G is C(O), S(O), or SO₂; and
the dotted, circular line connecting G and N* is a divalent group that includes from 1-6 ring atoms; wherein:

(a) from 0-2 of the divalent group's ring atoms are ring heteroatoms, which are each independently selected from the group consisting of N, N(R$^a$), O, S, and SO$_2$; and (b) from 1-6 of the divalent group's ring atoms are ring carbon atoms, which are each independently selected from the group consisting of C, CH, CH$_2$, CR$^b$, C(R$^b$)$_2$, and CHR$^b$;

wherein:

(1) when ring A is a monocyclic ring, then each of the divalent group's 1-6 ring carbon atoms is independently selected from the group consisting of CH, CH$_2$, CR$^b$, C(R$^b$)$_2$, and CHR$^b$; and (2) when ring A is a bicyclic or tricyclic ring, then (A) or (B) applies:

(A) two or three adjacent ring carbon atoms of the divalent group are each independently selected from the group consisting of C, CH, and, CR$^b$ and are fused to a second ring that is selected from the group consisting of:

(a) C$_{6-10}$ aryl optionally substituted with from 1-5 independently selected R$^c$;

(b) heteroaryl including from 5-10 ring atoms, wherein from 1-4 ring atoms are each independently selected from the group consisting of N, N(R$^a$), O, and S, wherein the heteroaryl is optionally substituted with from 1-3 independently selected R$^c$;

(c) C$_{3-10}$ cycloalkyl optionally substituted with from 1-4 independently selected R$^d$;

(d) heterocyclyl including from 3-10 ring atoms, wherein from 1-3 ring atoms are each independently selected from the group consisting of N(R$^a$), O, and S, wherein the heterocyclyl is optionally substituted with from 1-4 independently selected R$^d$; or (B) one of the divalent group's ring carbon atoms is C and is spiro-fused to a second ring that is selected from the group consisting of:

(a) C$_{3-10}$ cycloalkyl optionally substituted with from 1-4 independently selected R$^d$;

(b) heterocyclyl including from 3-10 ring atoms, wherein from 1-3 ring atoms are each independently selected from the group consisting of N(R$^a$), O, and S, wherein the heterocyclyl is optionally substituted with from 1-4 independently selected R$^d$;

L is:

(i) —(CH$_2$)$_m$—X$^1$—(CH$_2$)$_n$—X$^2$—(CH$_2$)$_p$— (formula VIII), wherein m is from 1-6; n is from 0-2; and p is from 0-8;

(ii) —C(O)—(CH$_2$)$_n$—X$^3$—(CH$_2$)$_p$— (formula IX), wherein n is from 0-2; and p is from 0-8;

(iii) —(CH$_2$)$_q$—, wherein q is from 1-10;

(iv) —C(O)—; or (v) —(CH$_2$)$_m$—X$^1$—(CH$_2$)$_p$— (formula VIII), wherein m is from 1-6; and p is from 0-8;

X$^1$ is —C(O)—; —N(R')C(O)—; —C(O)N(R')—; or —N(R')C(O)NR')—; wherein each occurrence of R' is independently selected from the group consisting of: H and C$_{1-4}$ alkyl;

X$^2$ is:

(i) —O—;

(ii) —S—;

(iii) —S(O)$_t$—, wherein t is 1 or 2;

(iv) —C(Q$^1$)(Q$^2$)-, wherein each of Q$^1$ and Q$^2$ is independently selected from the group consisting of H and C$_{1-4}$ alkyl; or Q$^1$ and Q$^2$, together with the carbon atom to which each is attached forms C$_{3-10}$ cycloalkyl that is optionally substituted with from 1-4 independently selected R$^d$ and optionally fused to phenyl;

(v) C$_{6-10}$ arylene optionally substituted with from 1-5 independently selected R$^c$;

(vi) heteroarylene including from 5-10 ring atoms, wherein from 1-4 ring atoms are each independently selected from the group consisting of N, N(R$^a$), O, and S; and which is optionally substituted with from 1-5 independently selected R$^c$;

(vii) C$_{3-10}$ cycloalkylene optionally substituted with from 1-4 independently selected R$^d$;

(viii) heterocycloalkylene including from 3-10 ring atoms, wherein from 1-3 ring atoms are each independently selected from the group consisting of N(R$^a$), O, and S; and which is optionally substituted with from 1-5 independently selected R$^d$;

(ix) C$_2$-C$_4$ alkenylene optionally substituted with from 1-2 R$^e$; or (x) C$_2$-C$_4$ alkynylene optionally substituted with from 1-2 R$^e$;

X$^3$ is: —O—; —S—; or —S(O)$_t$—, wherein t is 1 or 2;

each of R$^1$, R$^2$, and R$^4$ is independently selected from the group consisting of H and unsubstituted C$_{1-3}$ alkyl;

R$^3$ is —C(O)OH, —C(O)OR$^{31}$, or a carboxylic acid isostere; wherein R$^{31}$ is:

(i) C$_{1-6}$ alkyl optionally substituted with from 1-2 independently selected R$^e$;

(ii) —(C$_{0-3}$ alkylene)-C$_{3-10}$ cycloalkyl, wherein the cycloalkyl is optionally substituted with from 1-4 independently selected R$^d$;

(iii) —(C$_{0-3}$ alkylene)-heterocyclyl including from 3-10 ring atoms, wherein from 1-3 ring atoms are each independently selected from the group consisting of N(R$^a$), O, and S, wherein the heterocyclyl is optionally substituted with from 1-4 independently selected R$^d$;

(iv) —(C$_{0-3}$ alkylene)-C$_{6-10}$ aryl, wherein the aryl is optionally substituted with from 1-5 independently selected R$^c$; or (v) —(C$_{0-3}$ alkylene)-heteroaryl including from 5-10 ring atoms, wherein from 1-4 ring atoms are each independently selected from the group consisting of N, N(R$^a$), O, and S, wherein the heteroaryl is optionally substituted with from 1-3 independently selected R$^c$;

a is 0-5;

each occurrence of R$^a$ is independently selected from the group consisting of: H; C$_{1-4}$ alkyl; C$_{3-6}$ cycloalkyl; —C(=O)(C$_{1-6}$ alkyl); —C(=O)O(C$_{1-6}$ alkyl); and —S(O)$_{1-2}$(C$_{1-6}$ alkyl);

each occurrence of R$^b$ is independently selected from the group consisting of: R$^{31}$; C$_{1-4}$ haloalkyl; —OH; oxo; —F; —N(R$^a$)(R''); C$_{1-4}$ alkoxy; C$_{1-4}$ haloalkoxy; —C(=O)(C$_{1-4}$ alkyl); —C(=O)O(C$_{1-6}$ alkyl); —C(=O)OH, —C(=O)N(R''')(R''''), —S(O)$_{1-2}$(C$_{1-6}$ alkyl); and cyano;

each occurrence of R$^c$ is independently selected from the group consisting of: C$_{1-6}$ alkyl optionally substituted with from 1-2 independently selected R$^e$; C$_{3-6}$ cycloalkyl; C$_{1-4}$ haloalkyl; —OH; -halo; —NO$_2$; N$_3$; —N(R$^a$)(R''); C$_{1-4}$ alkoxy; C$_{1-4}$ thioalkoxy; C$_{1-4}$ haloalkoxy; —OC(=O)(C$_{1-6}$ alkyl); —C(=O)(C$_{1-6}$ alkyl); —C(=O)O(C$_{1-6}$ alkyl); —C(=O)OH, —C(=O)N(R''')(R''''), —S(O)$_{1-2}$(C$_{1-6}$ alkyl); and cyano;

each occurrence of R$^d$ is independently selected from the group consisting of: C$_{1-6}$ alkyl optionally substituted with from 1-2 independently selected R$^e$; C$_{1-4}$ haloalkyl; —OH; —F; Cl; —N(R$^a$)(R''); oxo; C$_{1-4}$ alkoxy; C$_{1-4}$ haloalkoxy; —OC(=O)(C$_{1-6}$ alkyl); —C(=O)

(C$_{1-6}$ alkyl); —C(=O)O(C$_{1-6}$ alkyl); —C(=O)OH, —C(=O)N(R''')(R''''), —S(O)$_{1-2}$(C$_{1-6}$ alkyl); and cyano;

each occurrence of R$^e$ is independently selected from the group consisting of: —OH; —N(R')(R''); C$_{1-4}$ alkoxy; C$_{1-4}$ haloalkoxy; —OC(=O)(C$_{1-6}$ alkyl); —C(=O)O (C$_{1-6}$ alkyl); —C(=O)OH, —C(=O)N(R''')(R''''), —S(O)$_{1-2}$(C$_{1-6}$ alkyl); and cyano;

each occurrence of R'', R''', and R'''' is independently selected from the group consisting of: H and C$_{1-6}$ alkyl; and —N(R$^4$)W is a peptide having the formula (XIV):
GTF(Xaa4)SD(Xaa7)S(Xaa9)(Xaa10)(Xaa11)(Xaa12)(Xaa13)QA(Xaa16)(Xaa17)(Xaa18)F-(Xaa20)(Xaa21)WL(Xaa24)(Xaa25)GGPSSGAPPPS-R$^5$ (SEQ ID NO: 2);

wherein:
Xaa4 is T or I;
Xaa7 is Y, V, or L;
Xaa9 is I or S;
Xaa10 is Y, Q, or A;
Xaa11 is L, M, or L*;
Xaa12 is D or E;
Xaa13 is K, G, or E;
Xaa16 is A or V;
Xaa17 is (Aib) or K;
Xaa18 is E or L;
Xaa20 is V or I;
Xaa21 is N, A, or E;
Xaa24 is L or V; and
Xaa25 is A or K;
wherein R$^5$ is a C-terminal amino acid, amino acid ester, or amino acid amide that is optionally substituted with from 1-2 modifying groups.

4. The compound of claim 1, wherein the compound has formula (IIA):

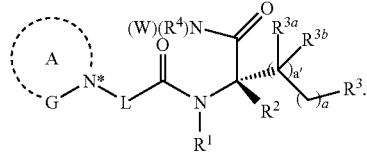

(IIA)

5. The compound of claim 1, wherein G is C(O).
6. The compound of claim 1, wherein G is S(O) or SO$_2$.
7. The compound of claim 1, wherein ring A is a saturated or unsaturated monocyclic ring that includes from 3-8 ring atoms.
8. The compound of claim 1, wherein ring A is a saturated monocyclic ring that includes from 3-8 ring atoms.
9. The compound of claim 1, wherein ring A has the following formula (III):

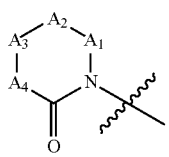

III wherein:
A$_1$ is a bond, A$^{1A}$-A$^{1B}$, C(O), CH$_2$, CHR$^b$, or C(R$^b$)$_2$;
each of A$^{1A}$ and A$^{1B}$ is independently C(O), CH$_2$, CHR$^b$, or C(R$^b$)$_2$;
A$_2$ is C(O), CH$_2$, CHR$^b$, or C(R$^b$)$_2$;
A$_3$ is C(O), CH$_2$, CHR$^b$, or C(R$^b$)$_2$; O; S; SO$_2$; or N(R$^a$);
A$_4$ is C(O), CH$_2$, CHR$^b$, or C(R$^b$)$_2$; O; S; or N(R$^a$);
provided that A$_3$ and A$_4$ cannot both be O; S; or N(R$^a$);
or a combination thereof.

10. The compound of claim 9, wherein A$_1$ is a C(O), CH$_2$, CHR$^b$, or C(R$^b$)$_2$, and ring A is a 6-membered ring.

11. The compound of claim 9, wherein A$_1$ is a bond, and ring A has the following formula:

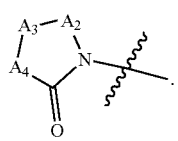

(III-A)

12. The compound of claim 1, wherein ring A is an unsaturated monocyclic ring that includes from 3-8 ring atoms.

13. The compound of claim 12, wherein ring A has formula (IV):

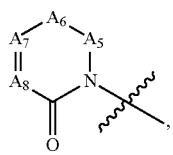

(IV)

wherein:
each of A$_6$, and A$_7$ is independently selected from CH and CR$^b$; and
each of A$_5$ and A$_8$ is independently N, CH, or CR$^b$.

14. The compound of claim 1, wherein ring A is a saturated or unsaturated bicyclic or tricyclic ring that includes from 6-14 ring atoms.

15. The compound of claim 1, wherein ring A is a saturated bicyclic or tricyclic ring that includes from 8-10 ring atoms.

16. The compound of claim 1, wherein L has formula (VIII): —(CH$_2$)$_m$—X$^1$—(CH$_2$)$_n$—X$^2$—(CH$_2$)$_p$—.

17. The compound of claim 16, wherein:
m is from 2-6;
n+p≥2; and
X$^2$ is: —O—; —S—; —S(O)$_t$—, or CH$_2$.

18. The compound of claim 16, wherein:
m is 1;
n+p≤2; and
X$^2$ is: —O—; —S—; —S(O)$_t$—, or C(Q$^1$)(Q$^2$).

19. The compound of claim 16, wherein L has formula (IX): —C(O)—(CH$_2$)$_n$—X$^3$—(CH$_2$)$_p$—.

20. The compound of claim 1, wherein R$^5$ is a C-terminal amino acid amide that is optionally substituted with from 1-2 modifying groups.

21. The compound of claim 1, wherein $R^5$ has formula (XI):

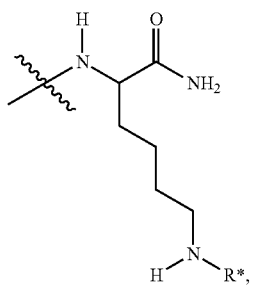

(XI)

wherein R* is H or a modifying group.

22. The compound of claim 1, wherein $R^5$ is a a C-terminal amino acid that is optionally substituted with from 1-2 modifying groups.

23. The compound of claim 1, wherein $R^5$ has formula (XI-OH):

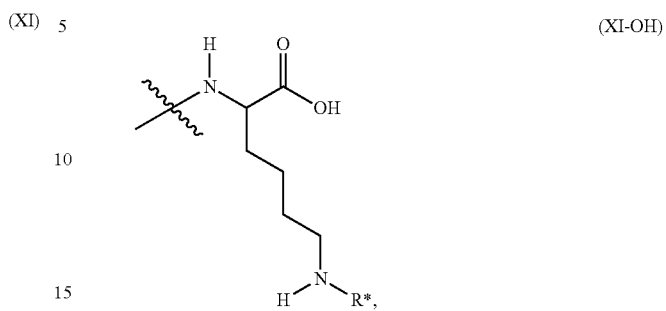

(XI-OH)

wherein R* is H or a modifying group.

24. The compound of claim 1, wherein the compound is selected from the group consisting of 455
Compound 70
456
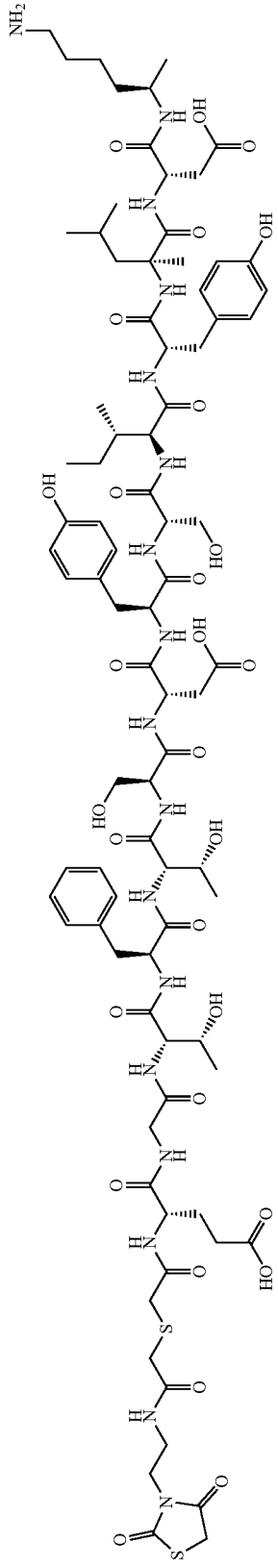
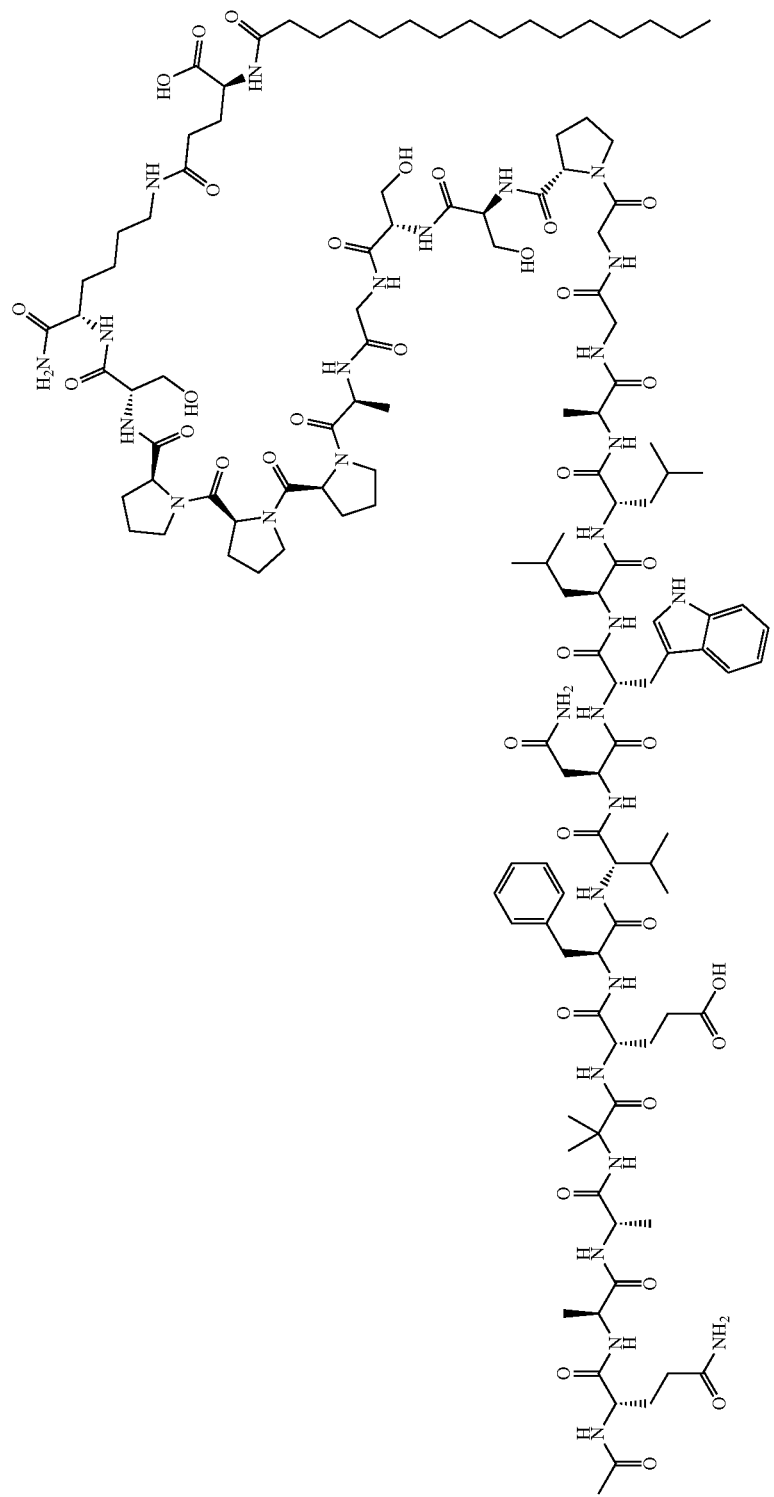

457
Compound 71
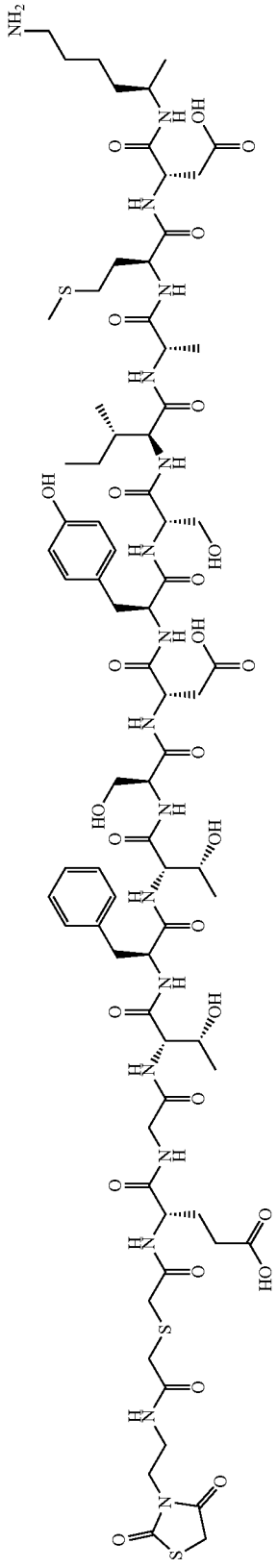
-continued
458
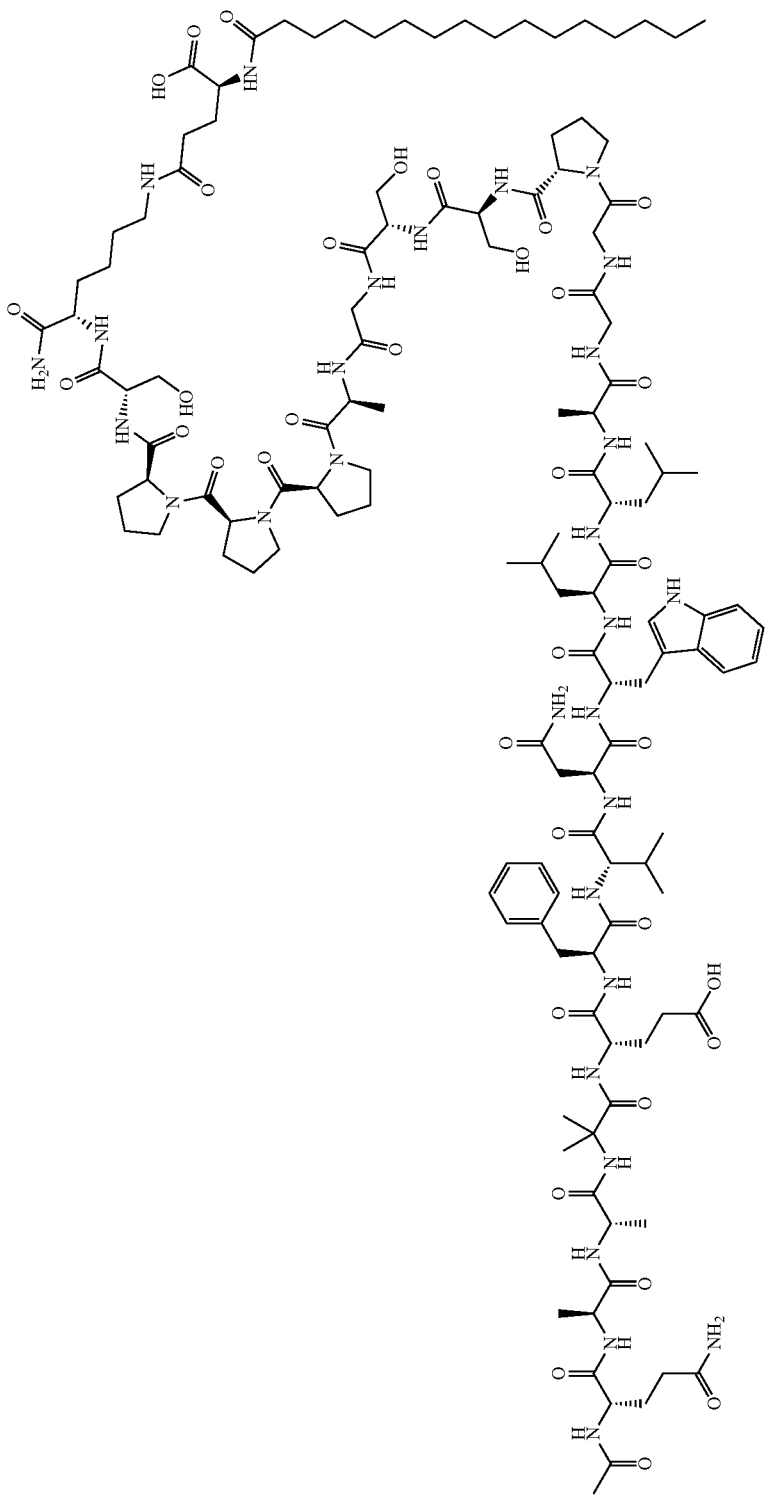

459
Compound 72
-continued
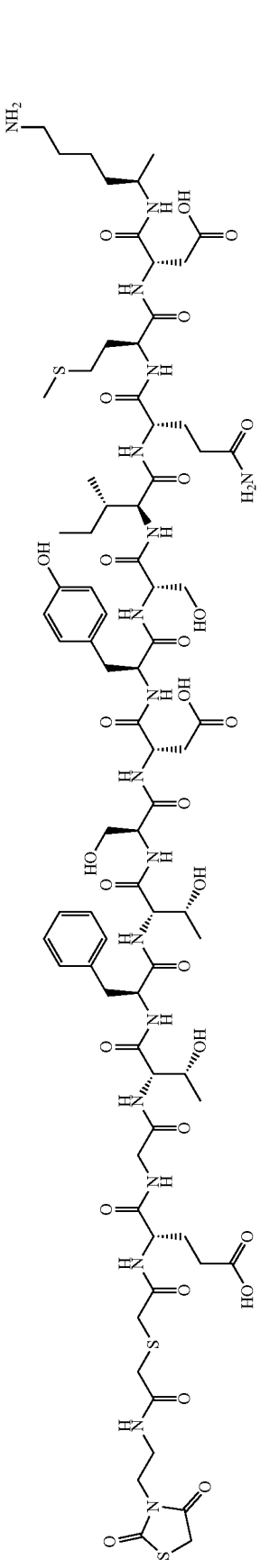
460
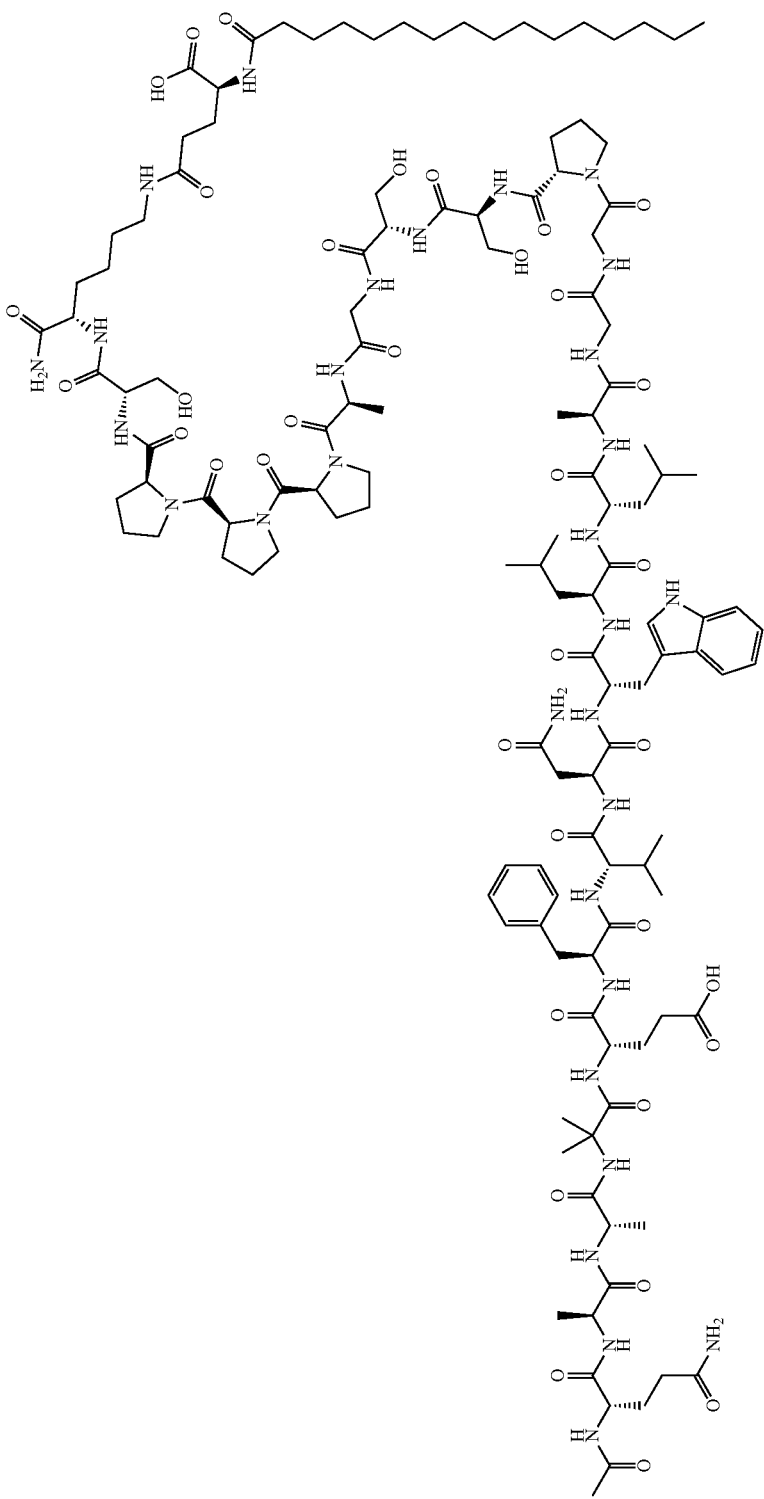

-continued
Compound 106
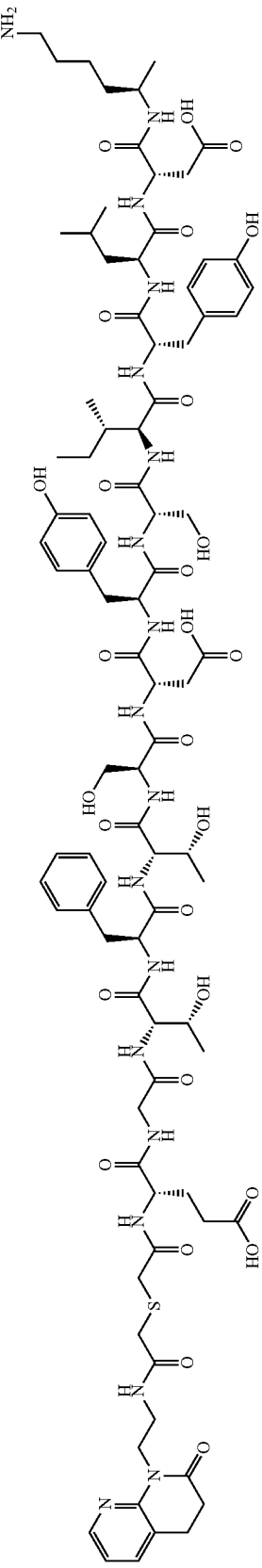
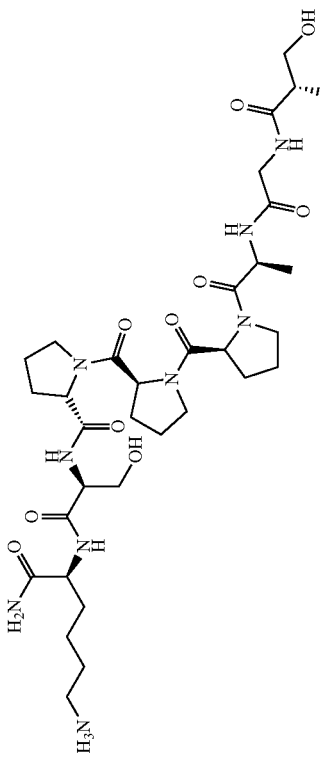
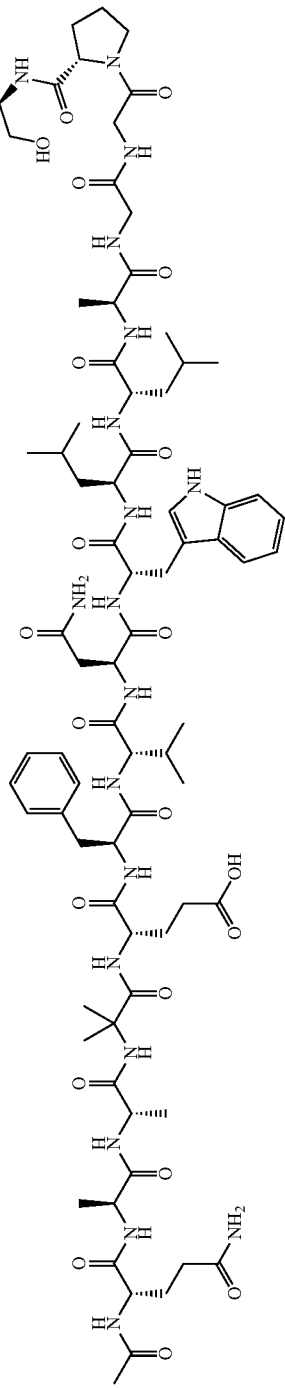

463
464
Compound 107
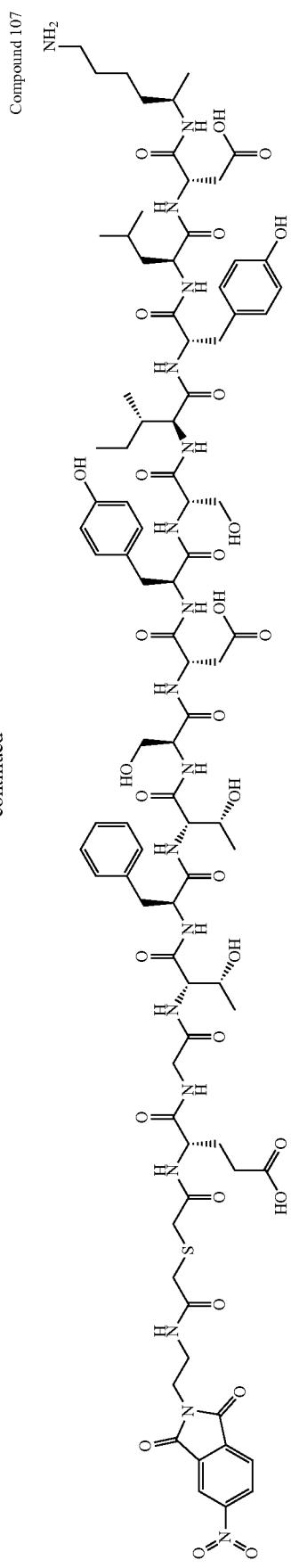
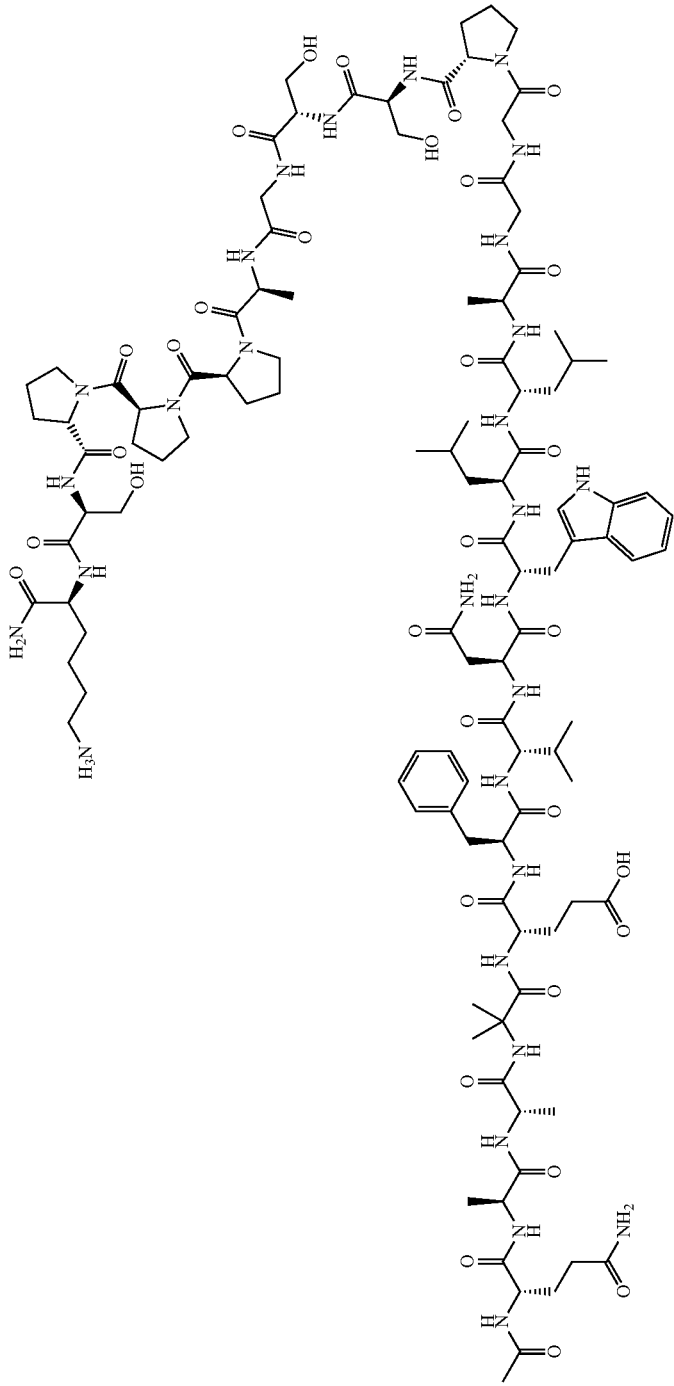

Compound 108
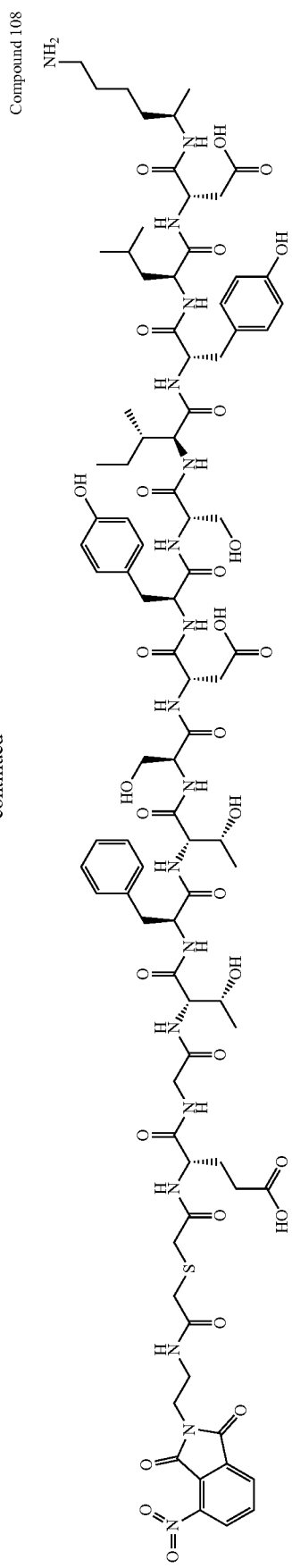
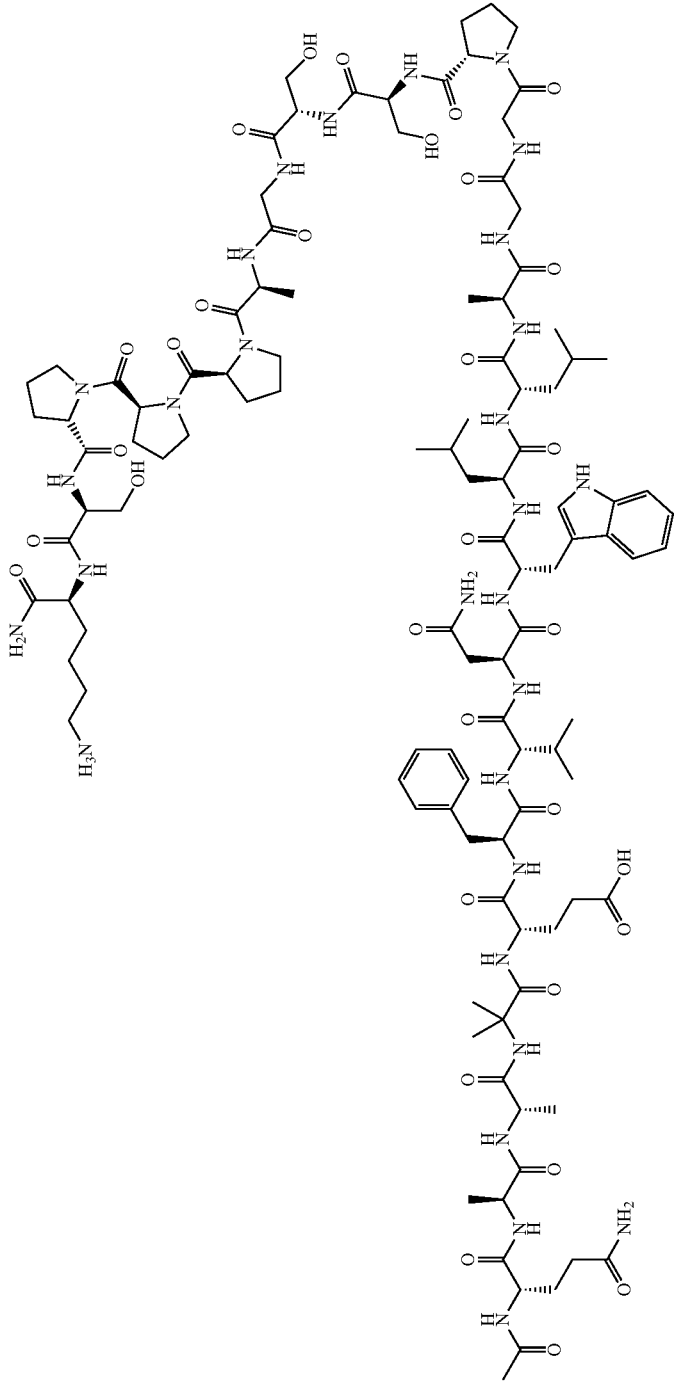

-continued
Compound 109
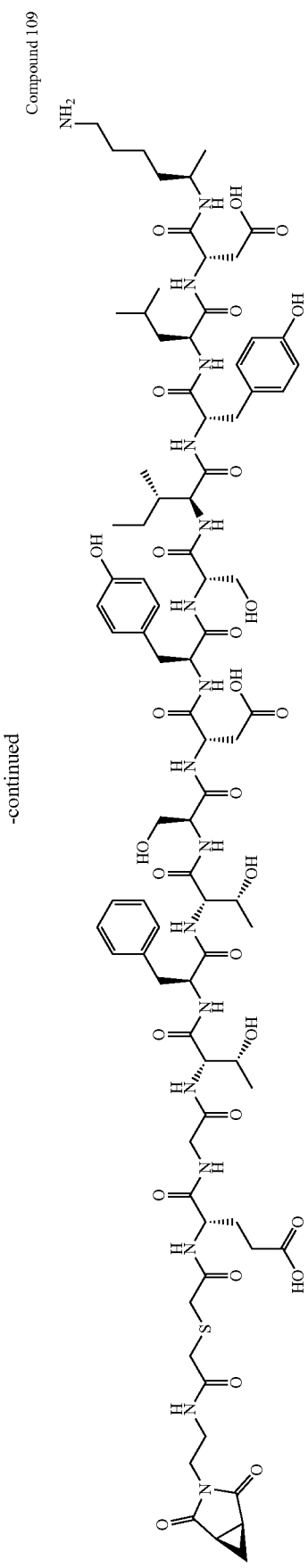
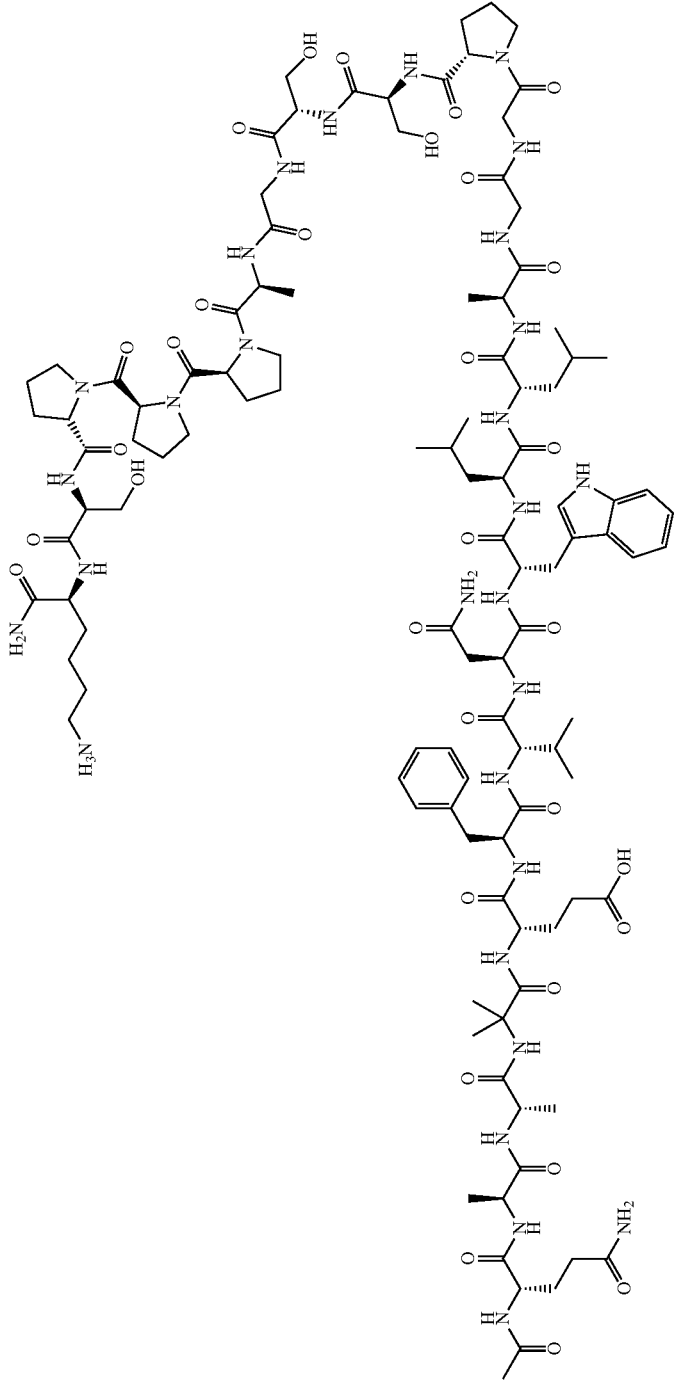

Compound 109
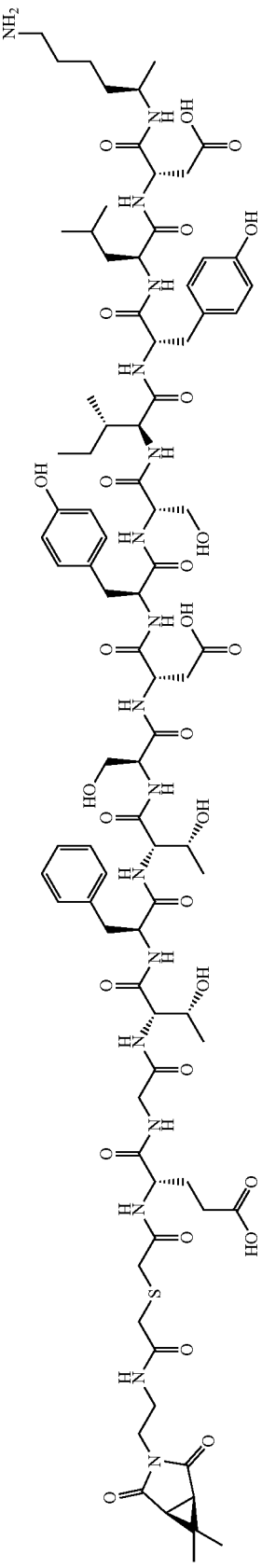
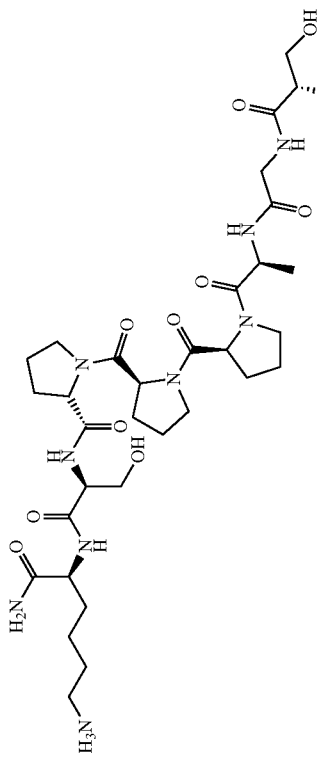
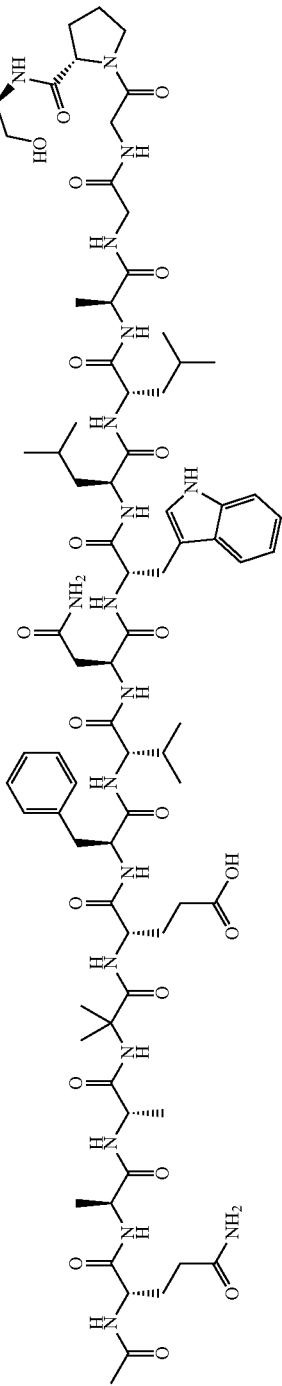

471
Compound 111
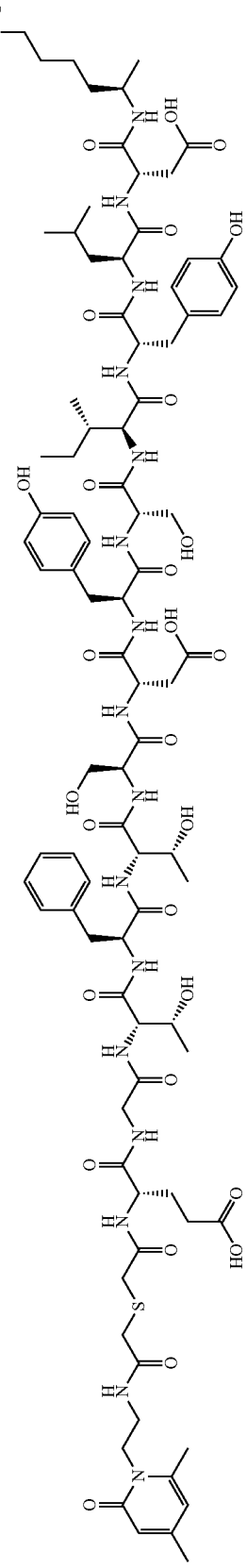
-continued
472
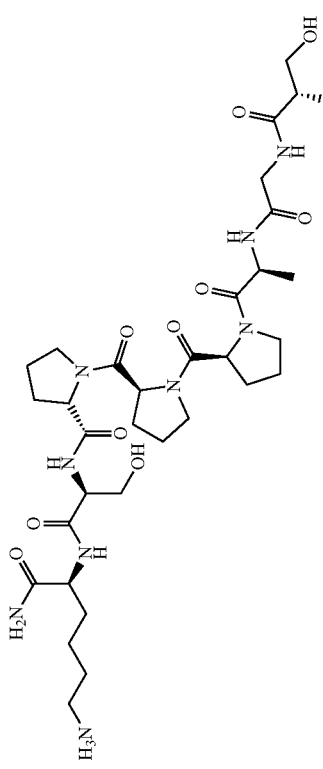
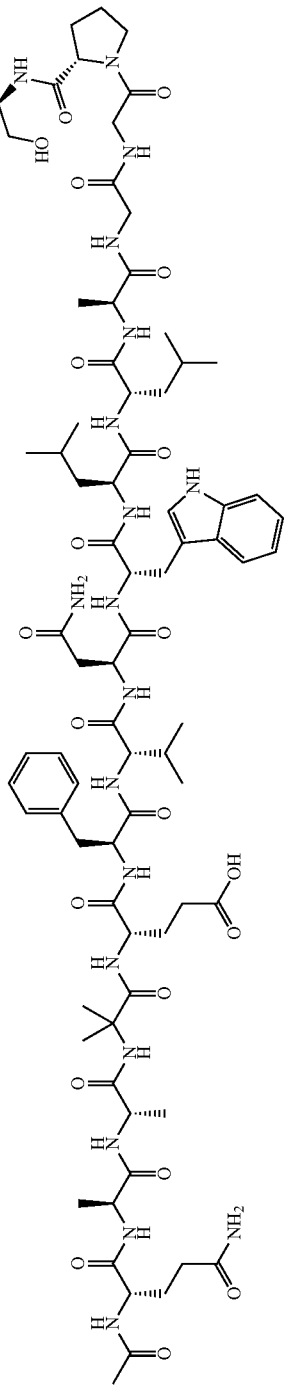

Compound 112
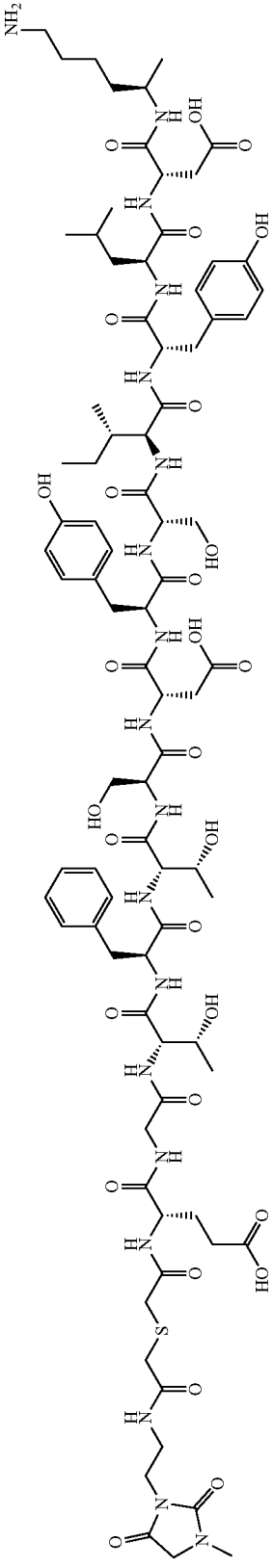
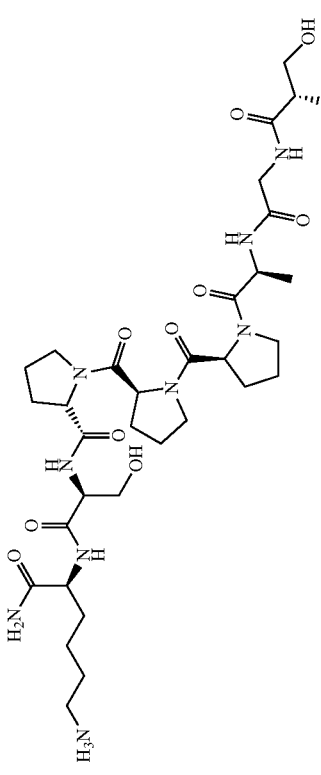
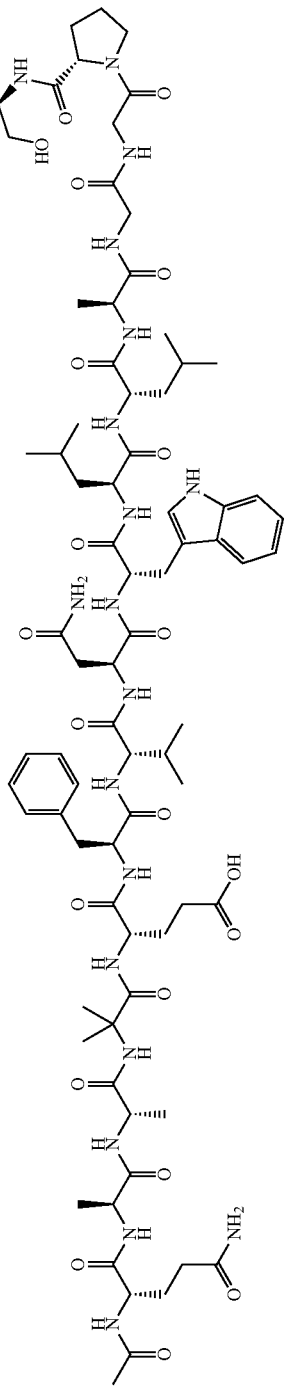

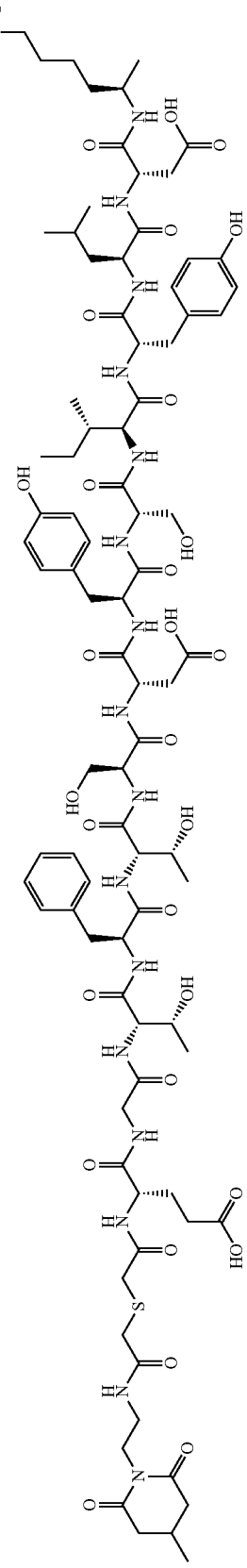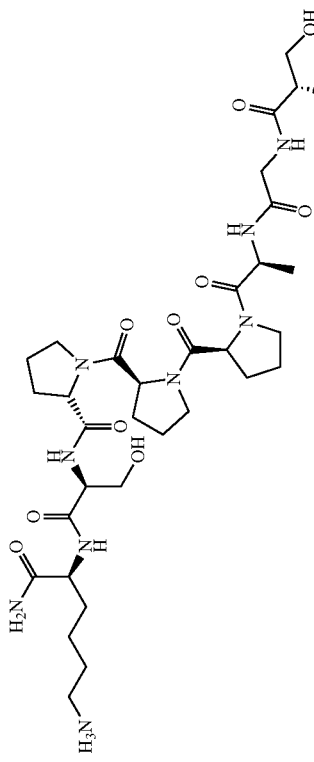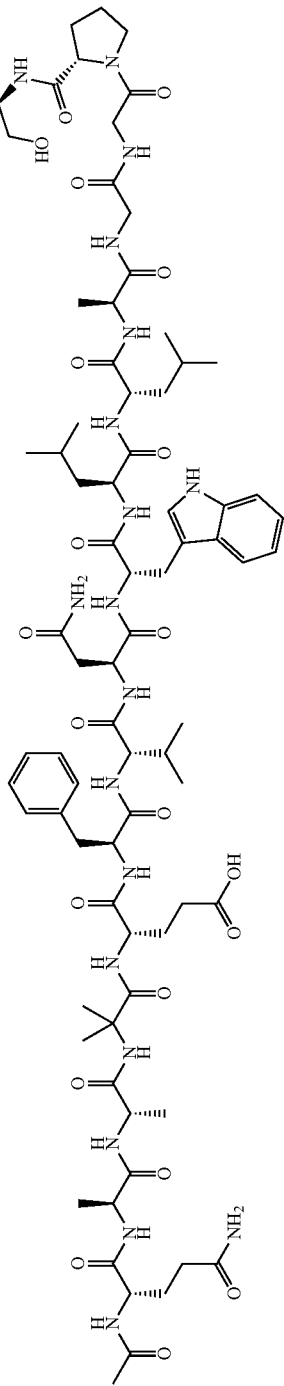

Compound 114
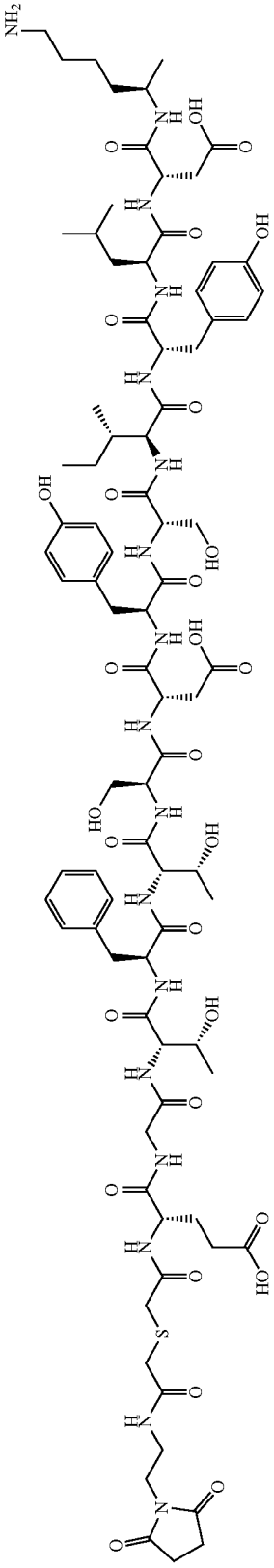
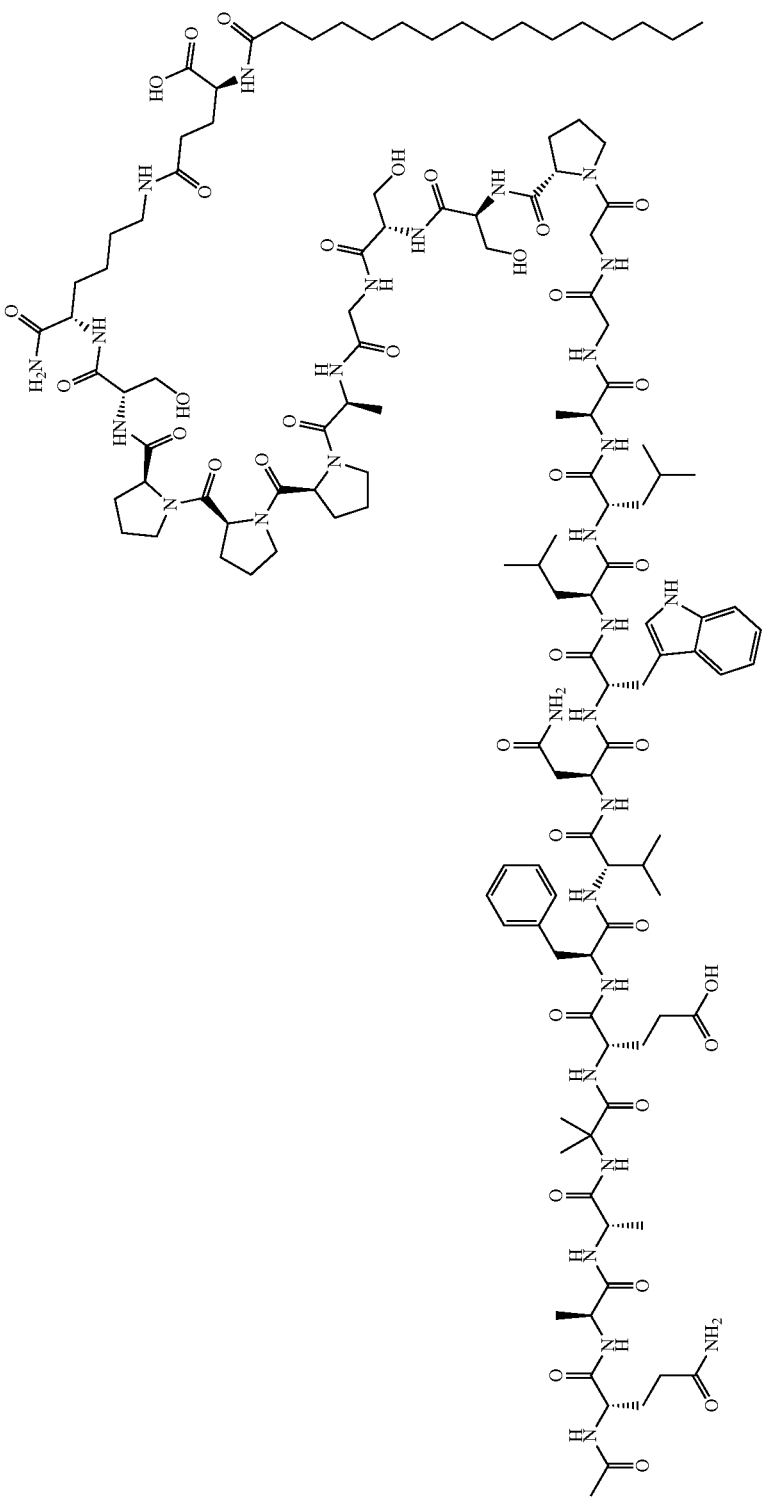

479
480
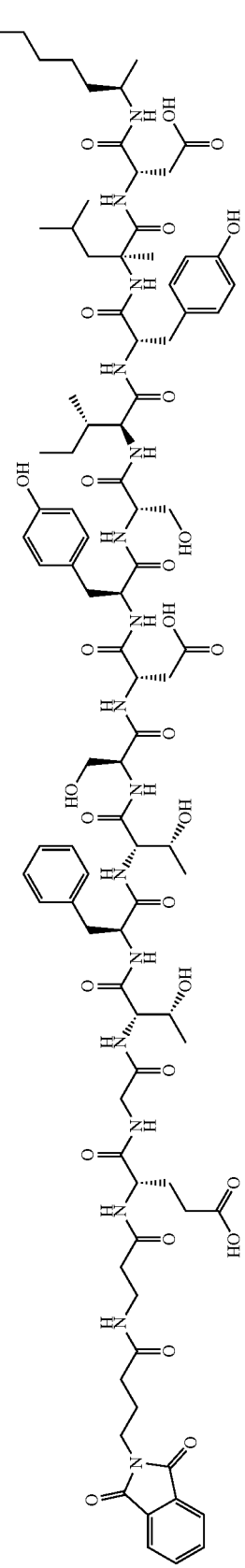
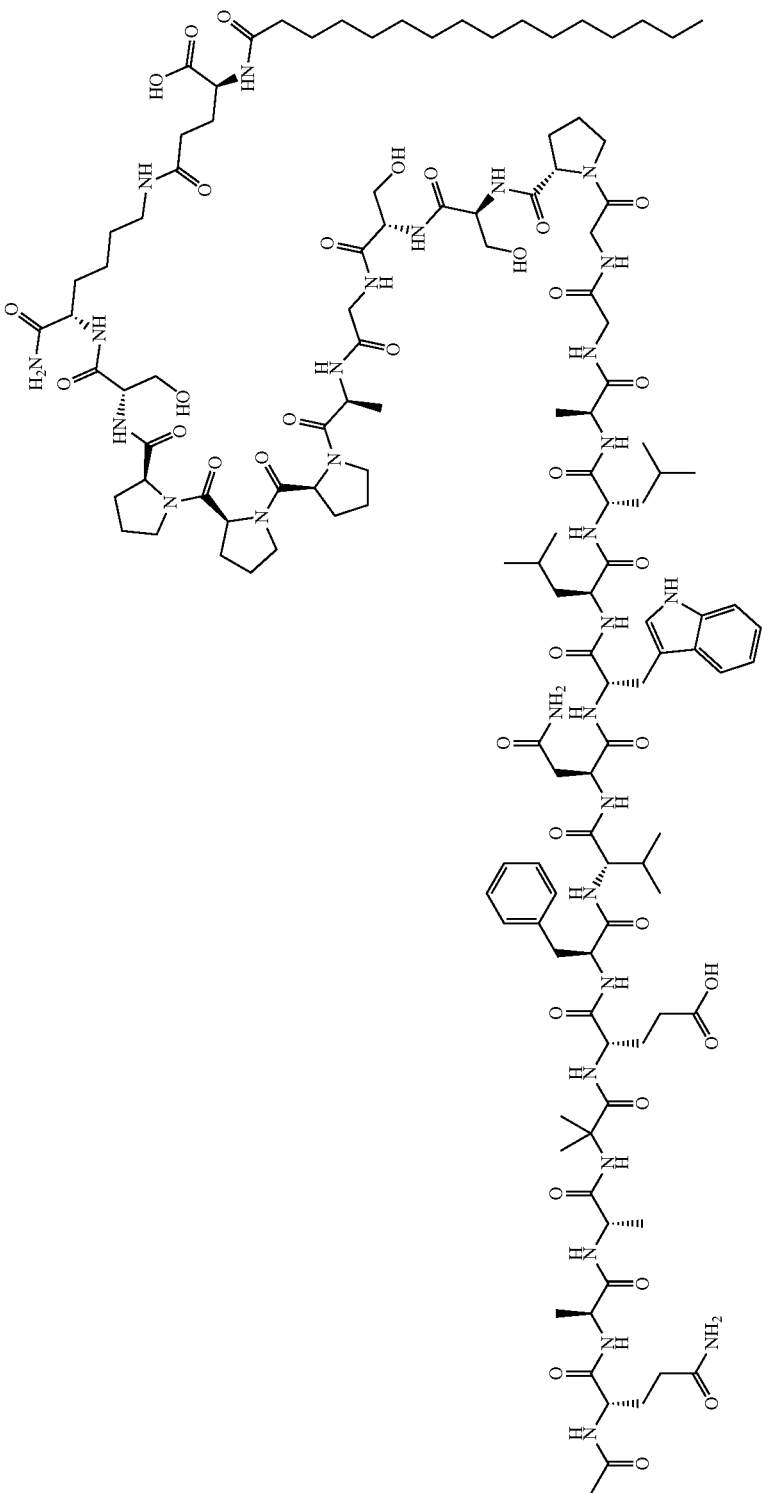
Compound 115
-continued

Compound 116
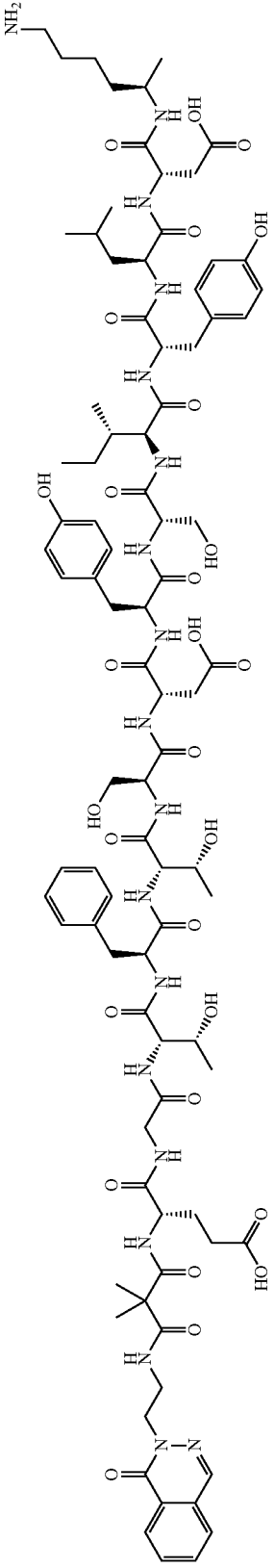
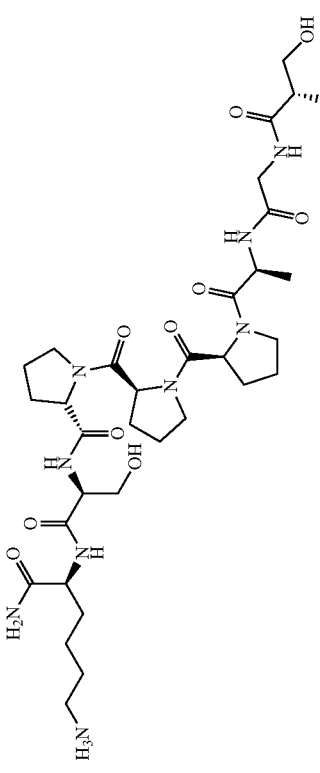
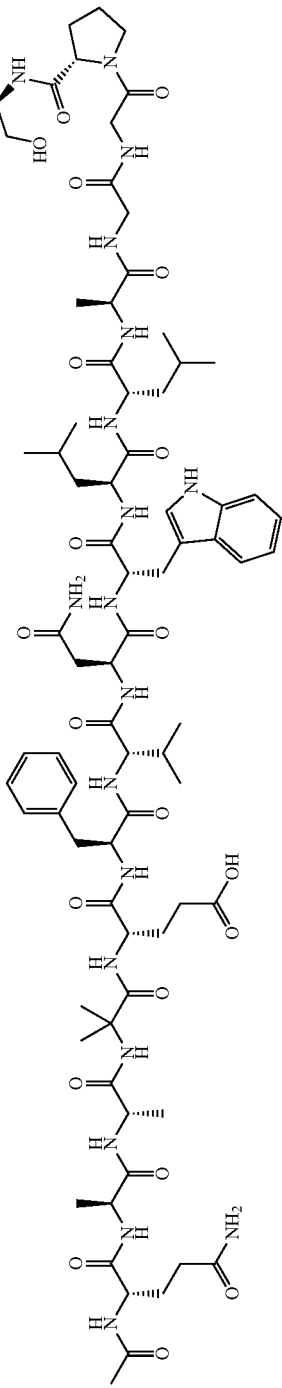

483
484
Compound 117
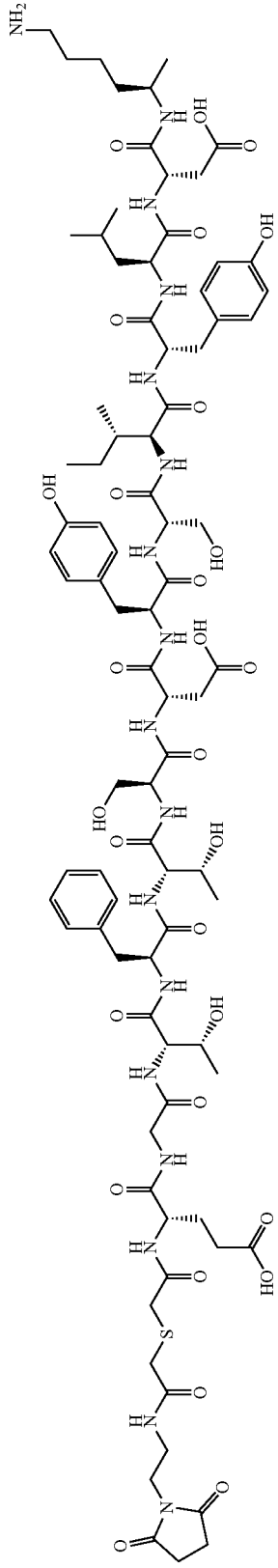
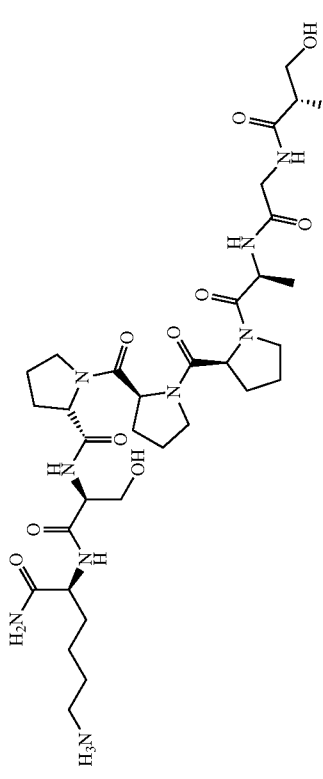
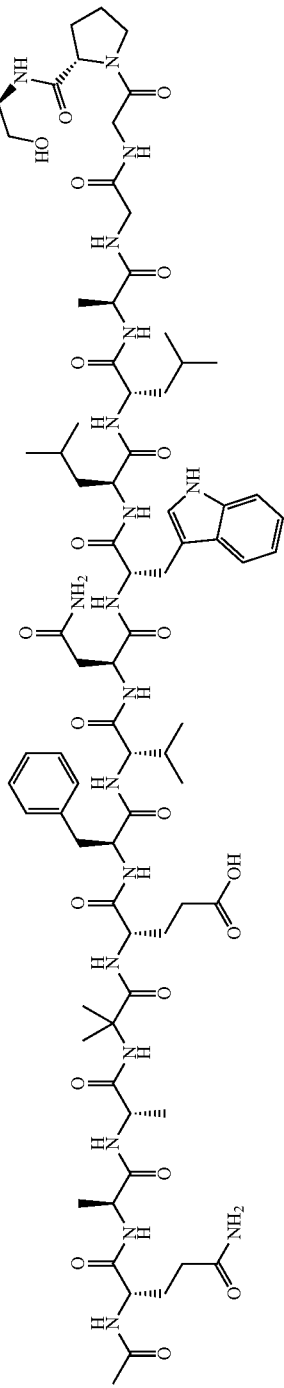

485 486
Compound 118
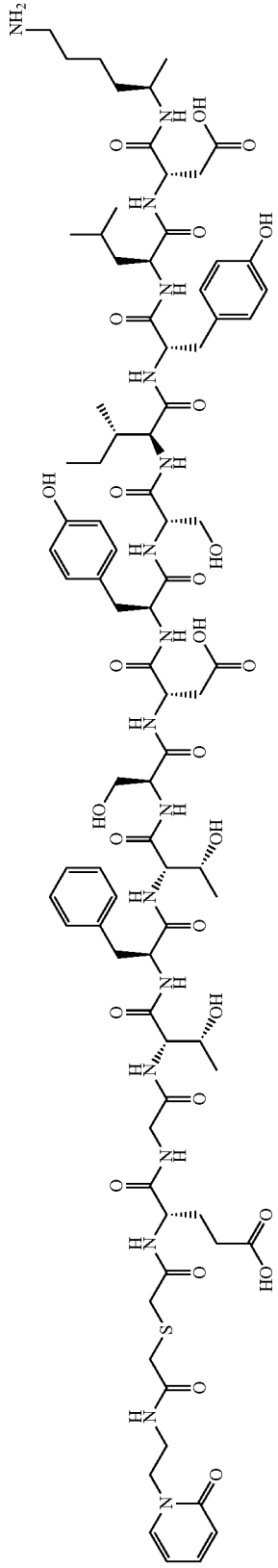
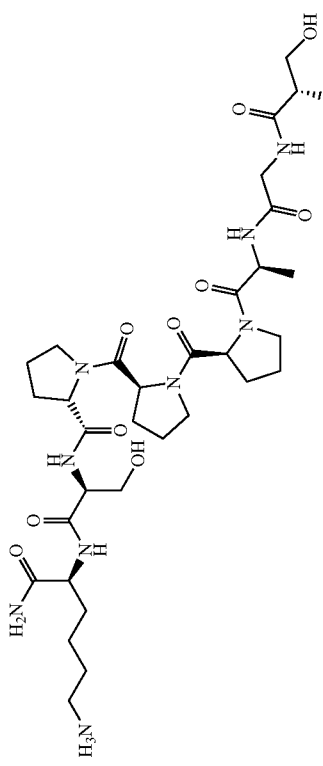
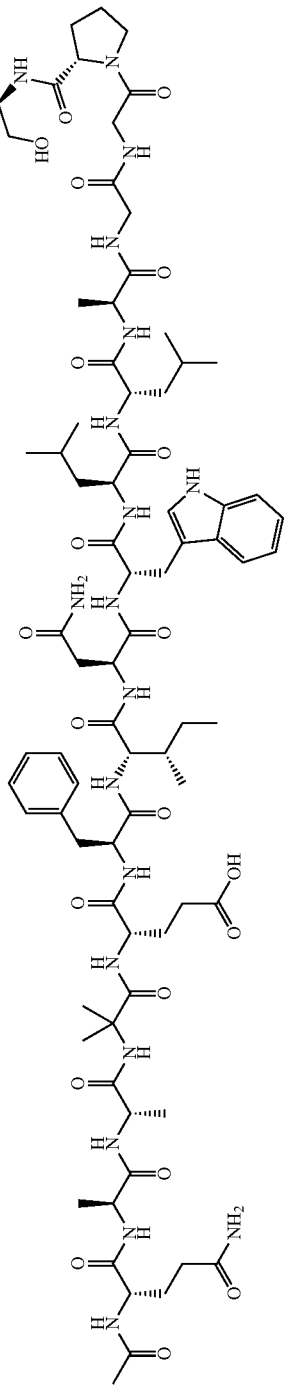

Compound 119 -continued
487
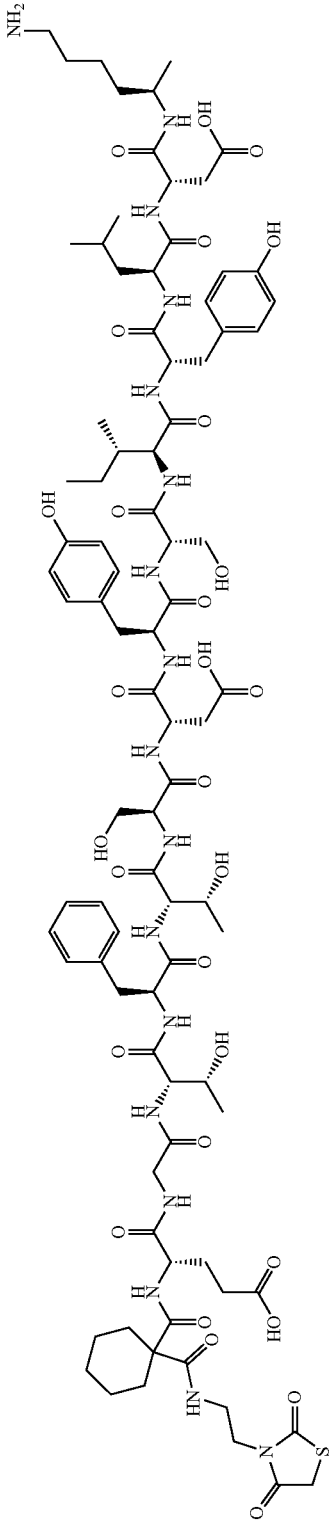
488
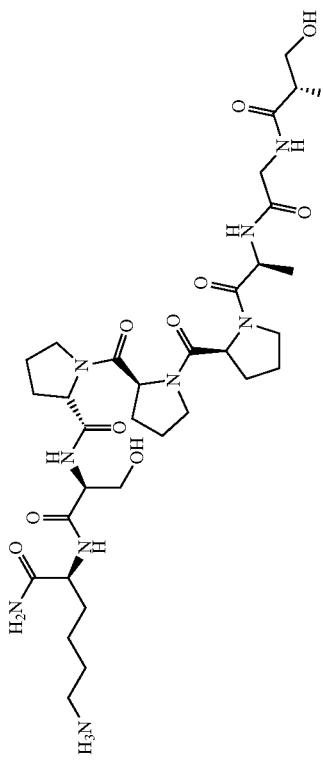
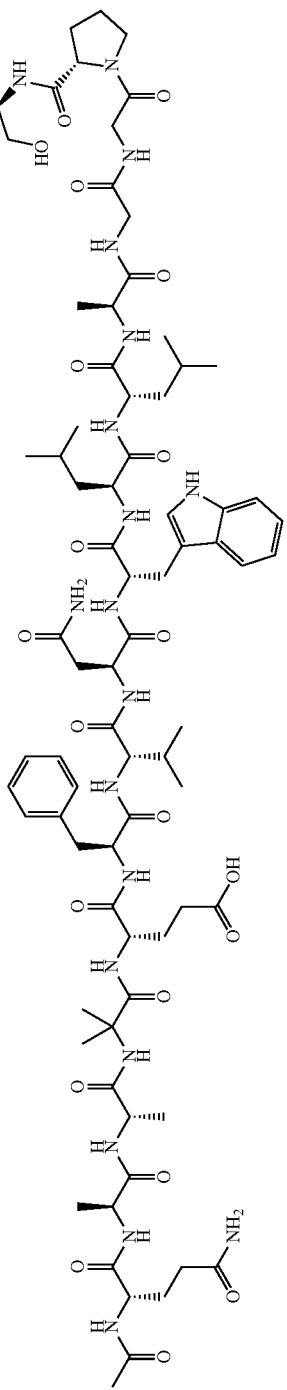

489
Compound 120
490
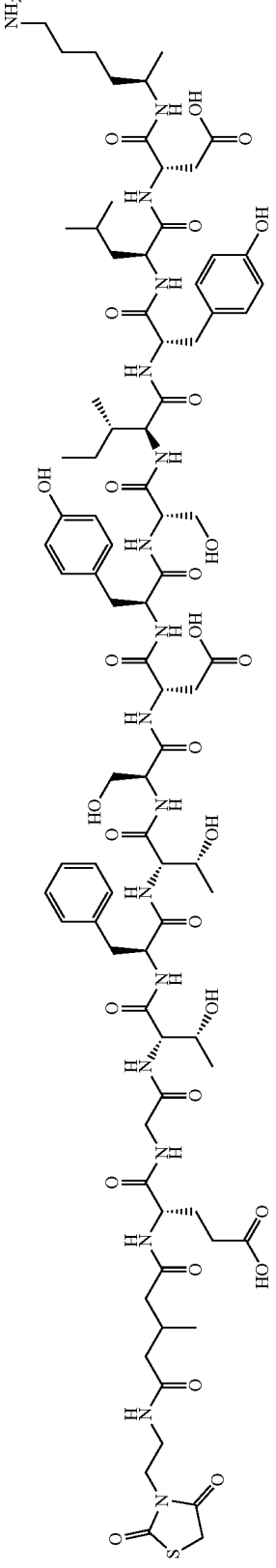
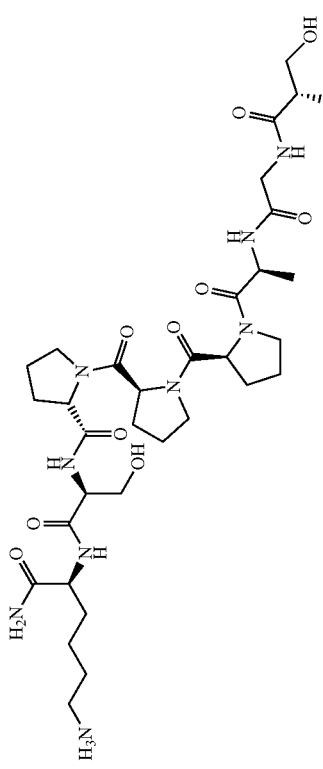
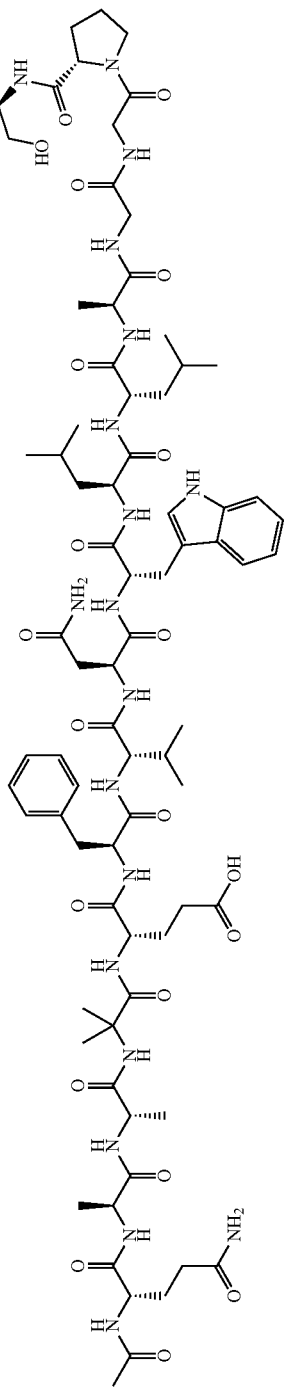

Compound 121
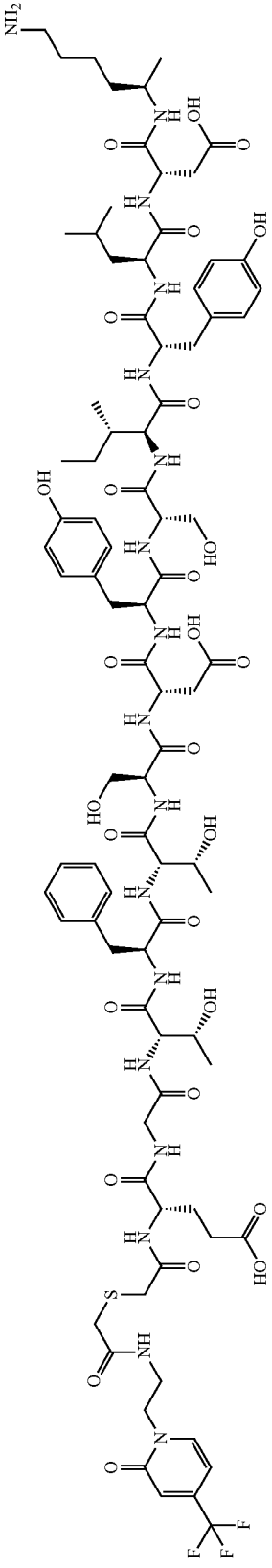
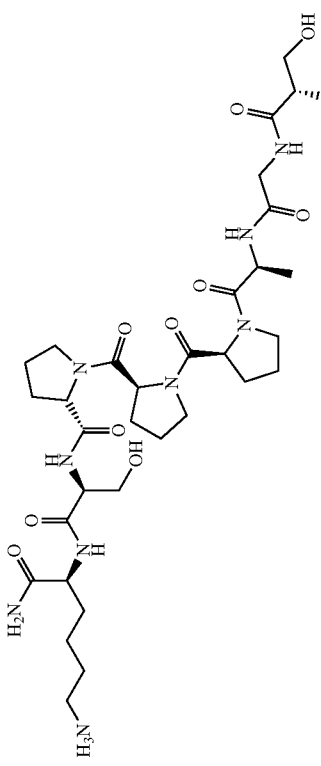
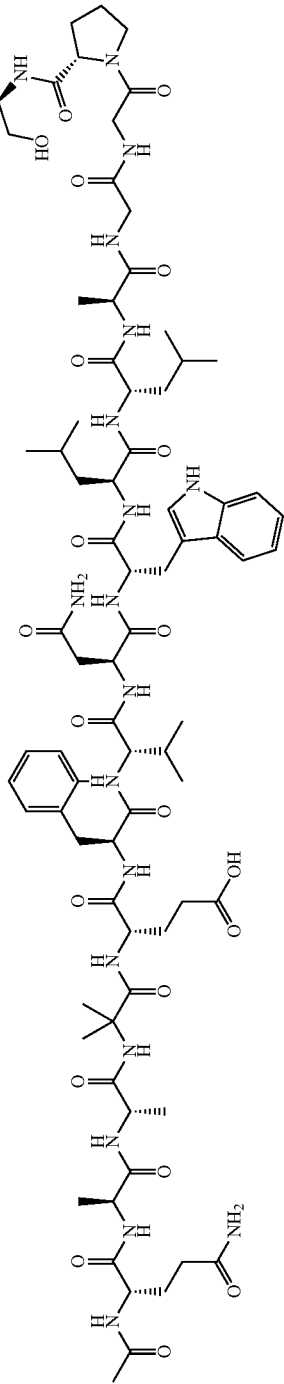

Compound 122
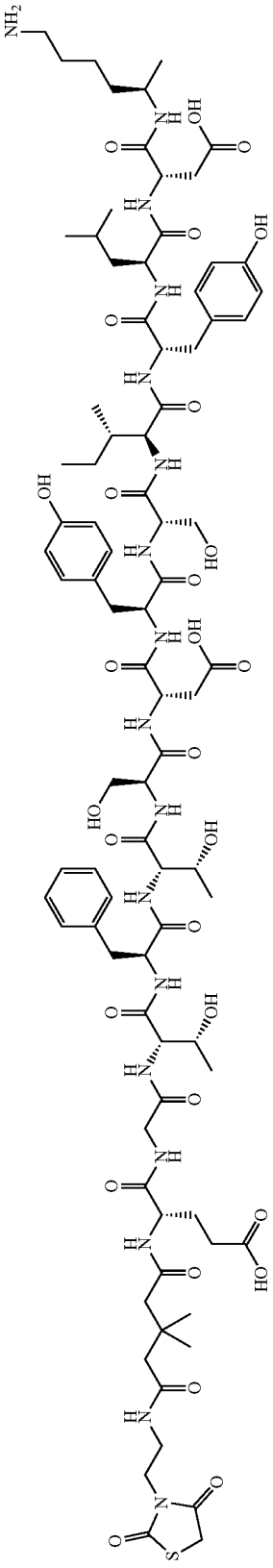
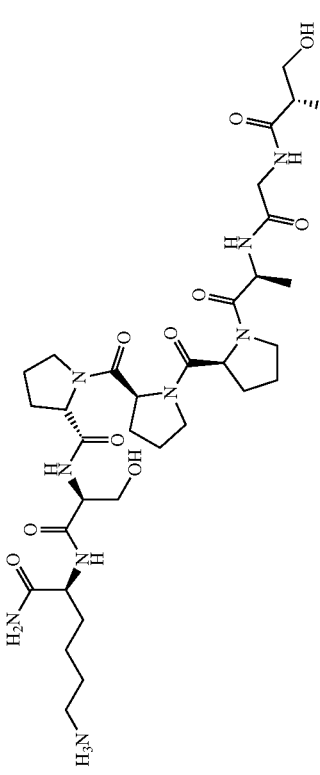
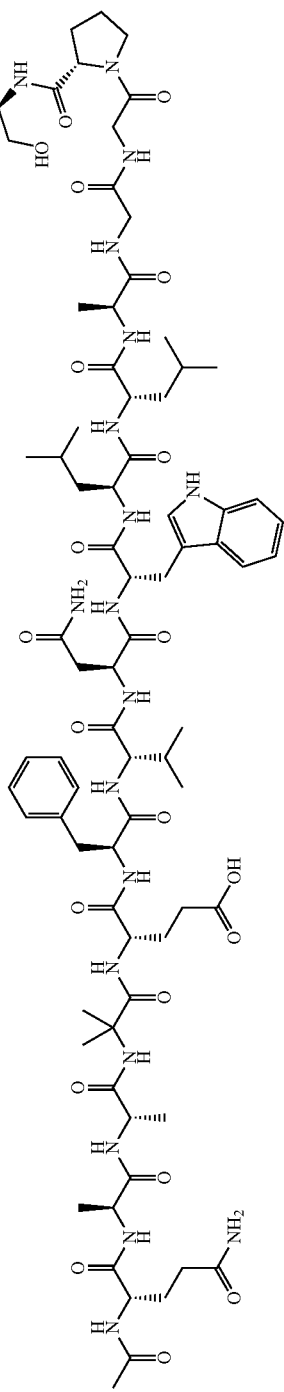

495
Compound 123
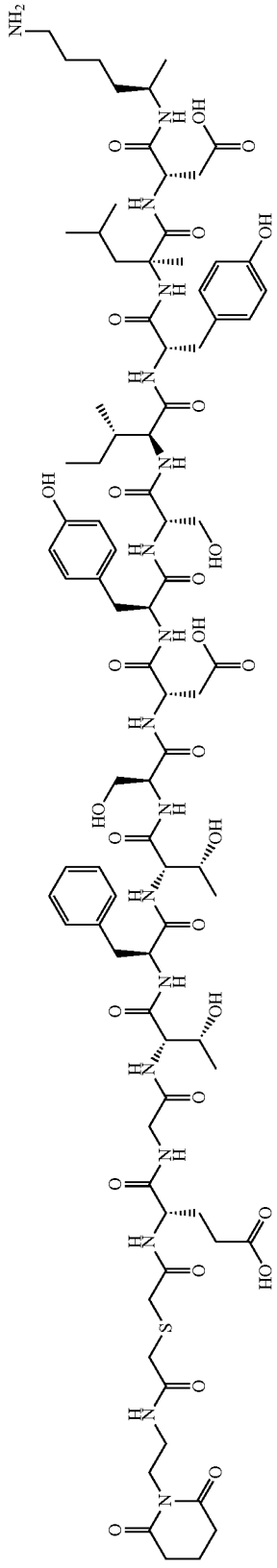
496
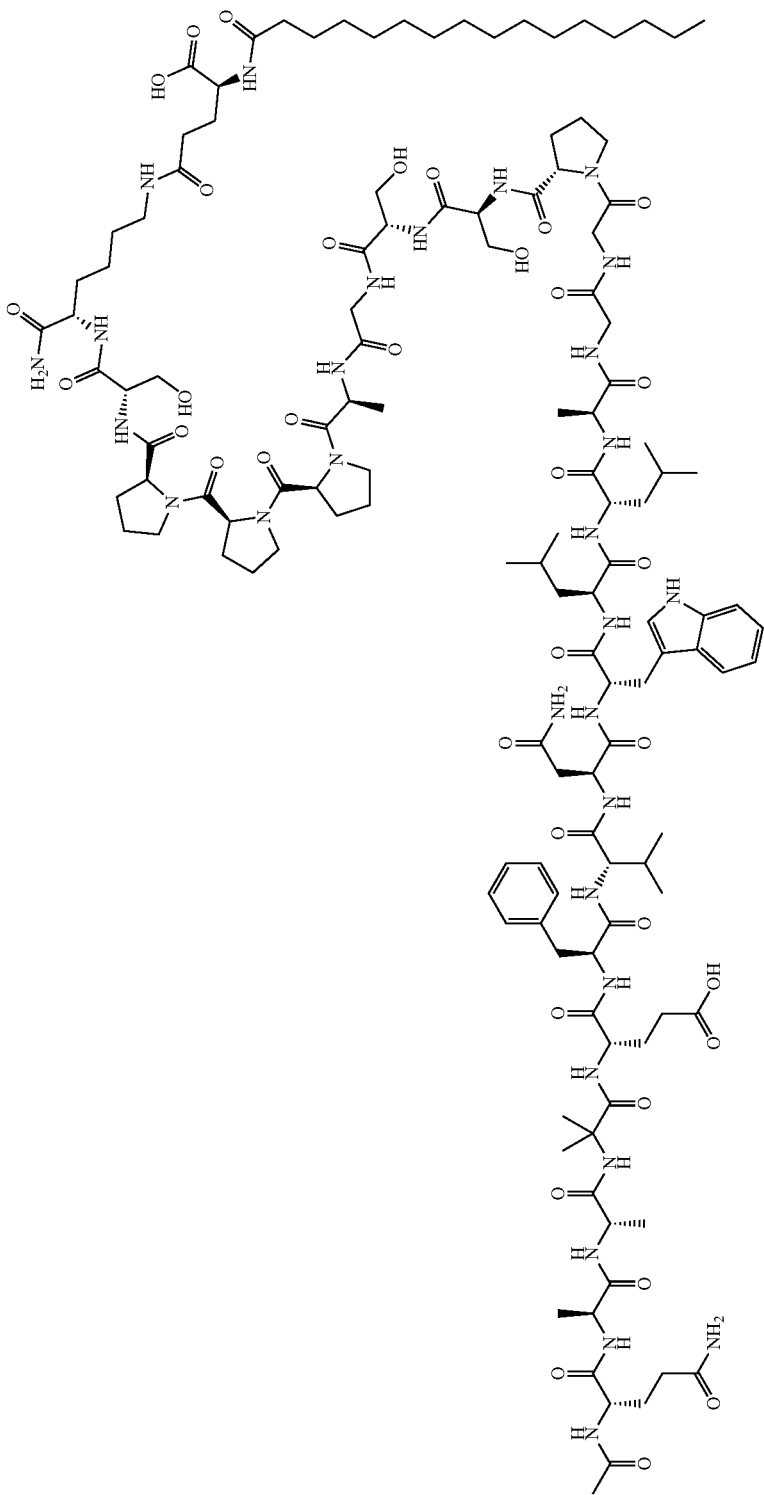

Compound 124
497
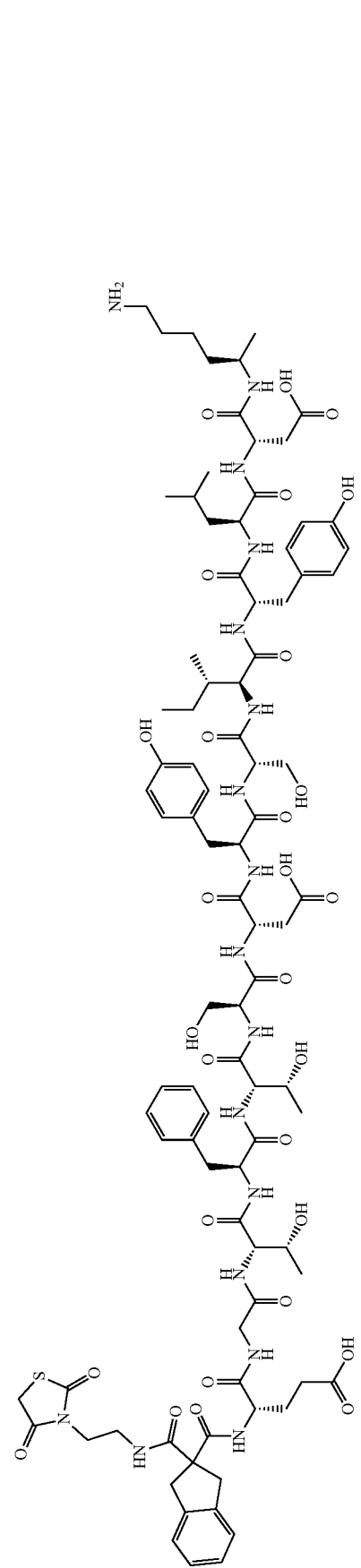
498
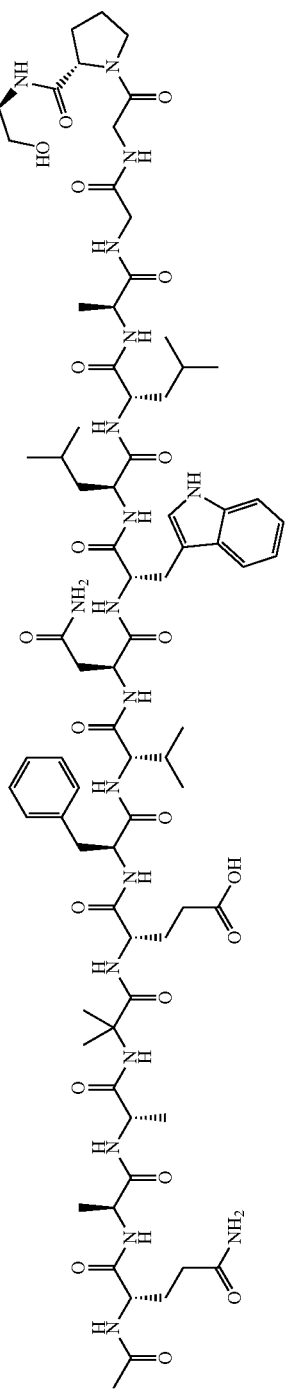

Compound 125
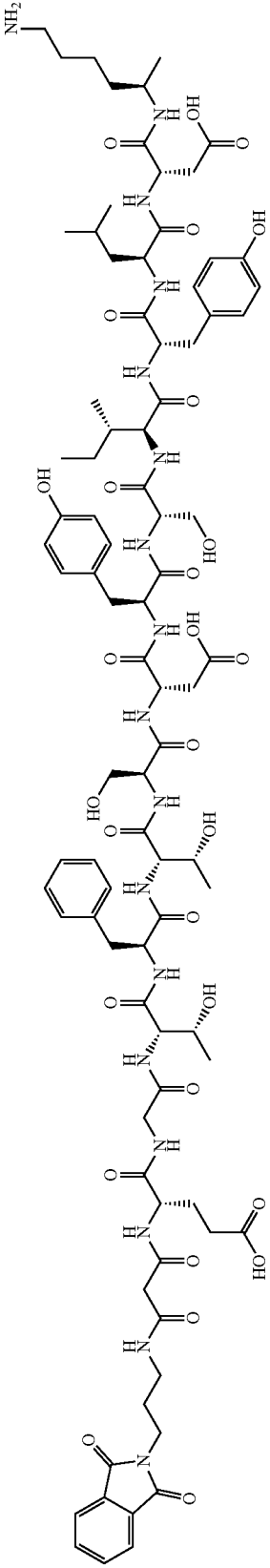
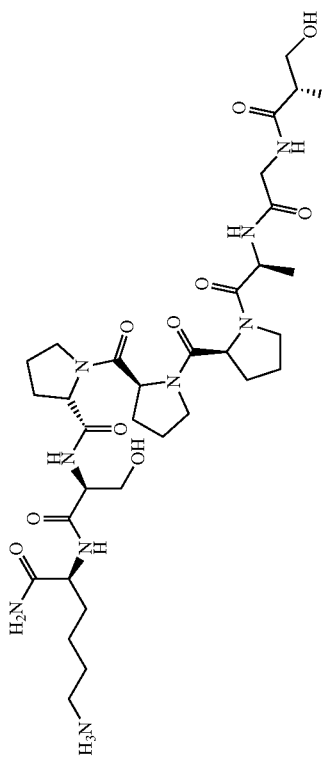
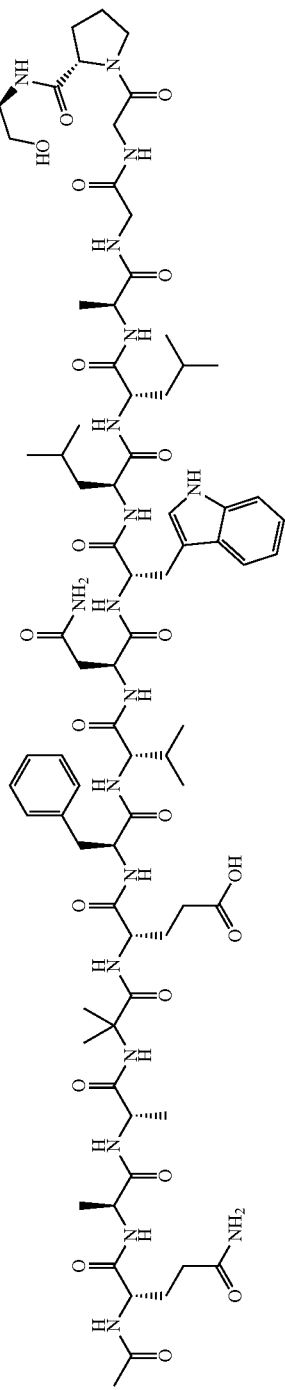

-continued
Compound 127
501
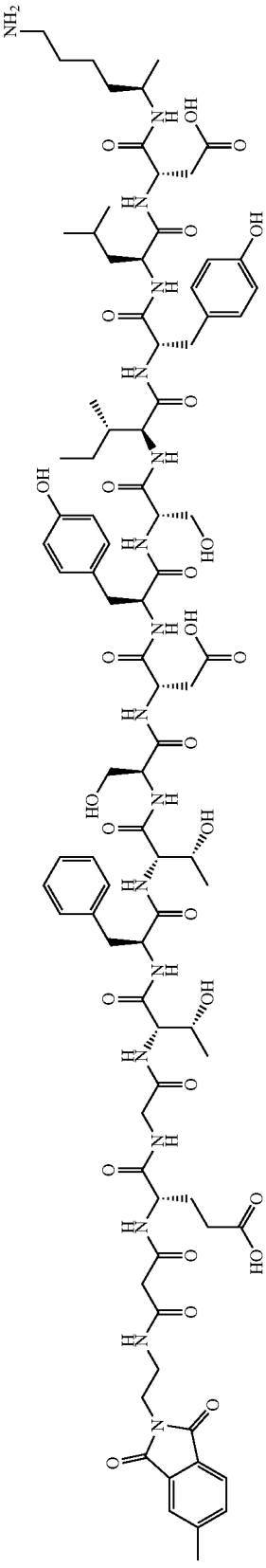
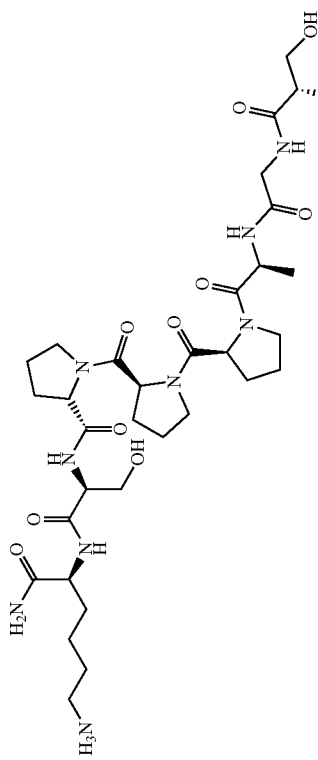
502
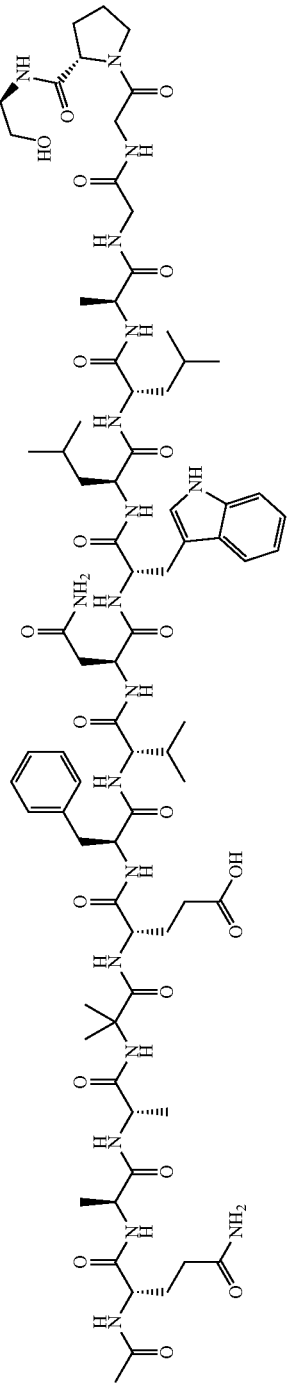

-continued
Compound 127
503
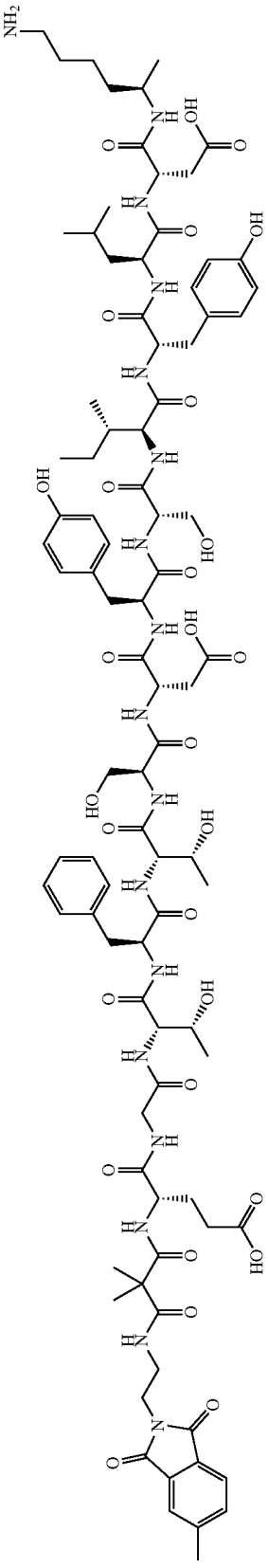
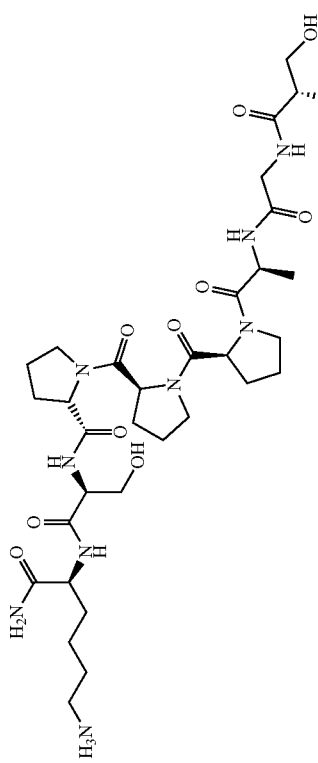
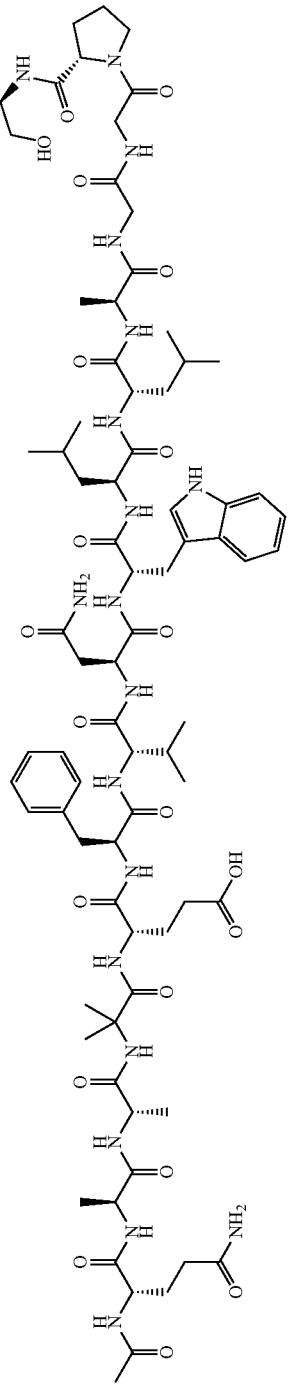
504

505 506
Compound 128
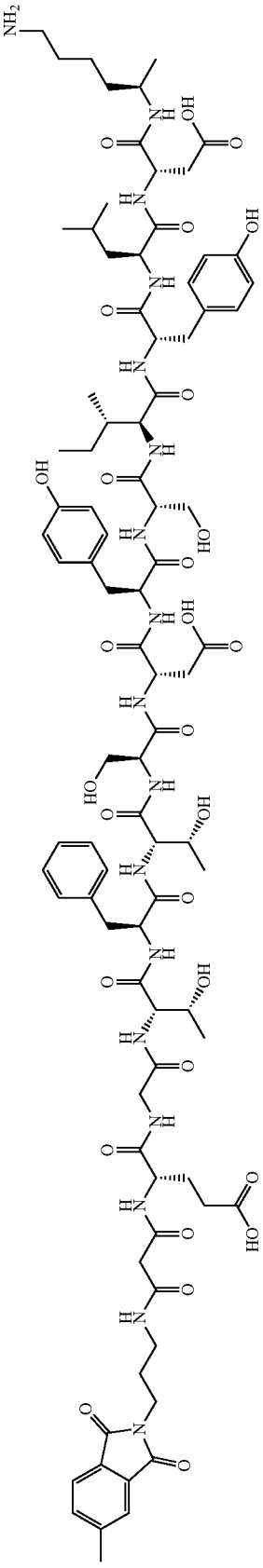
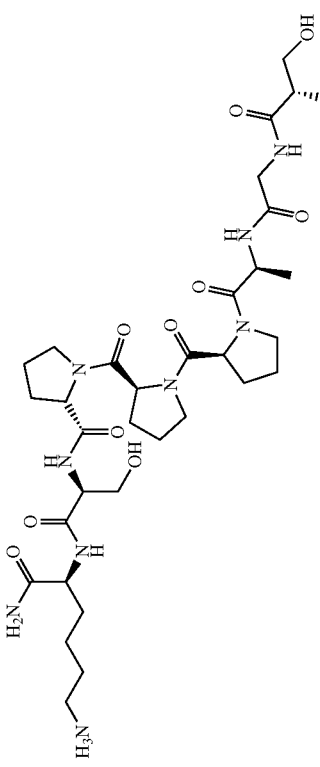
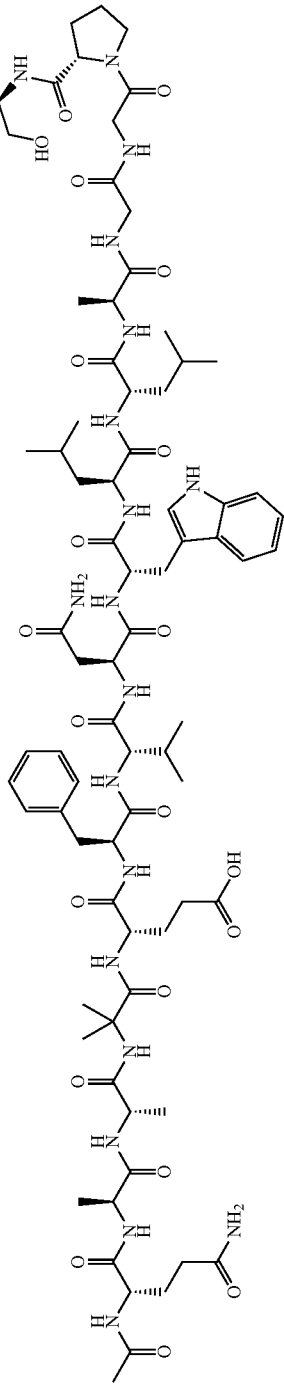

-continued
Compound 129
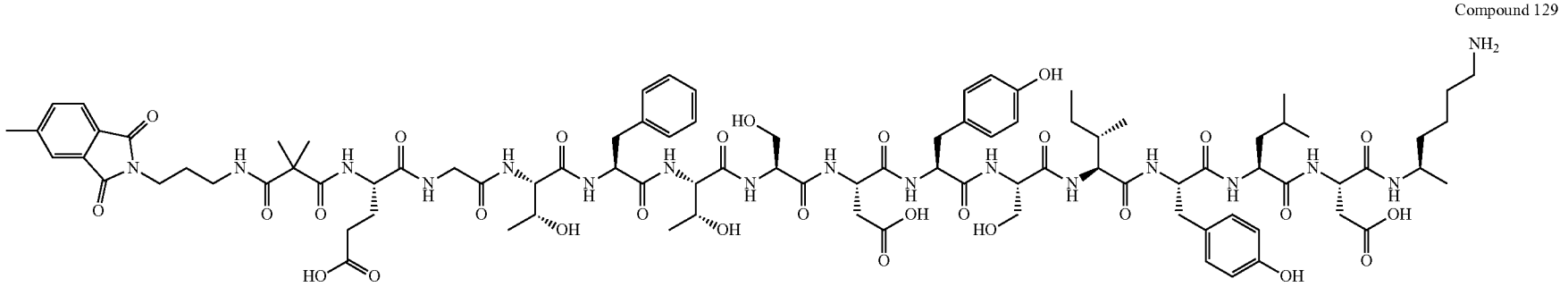
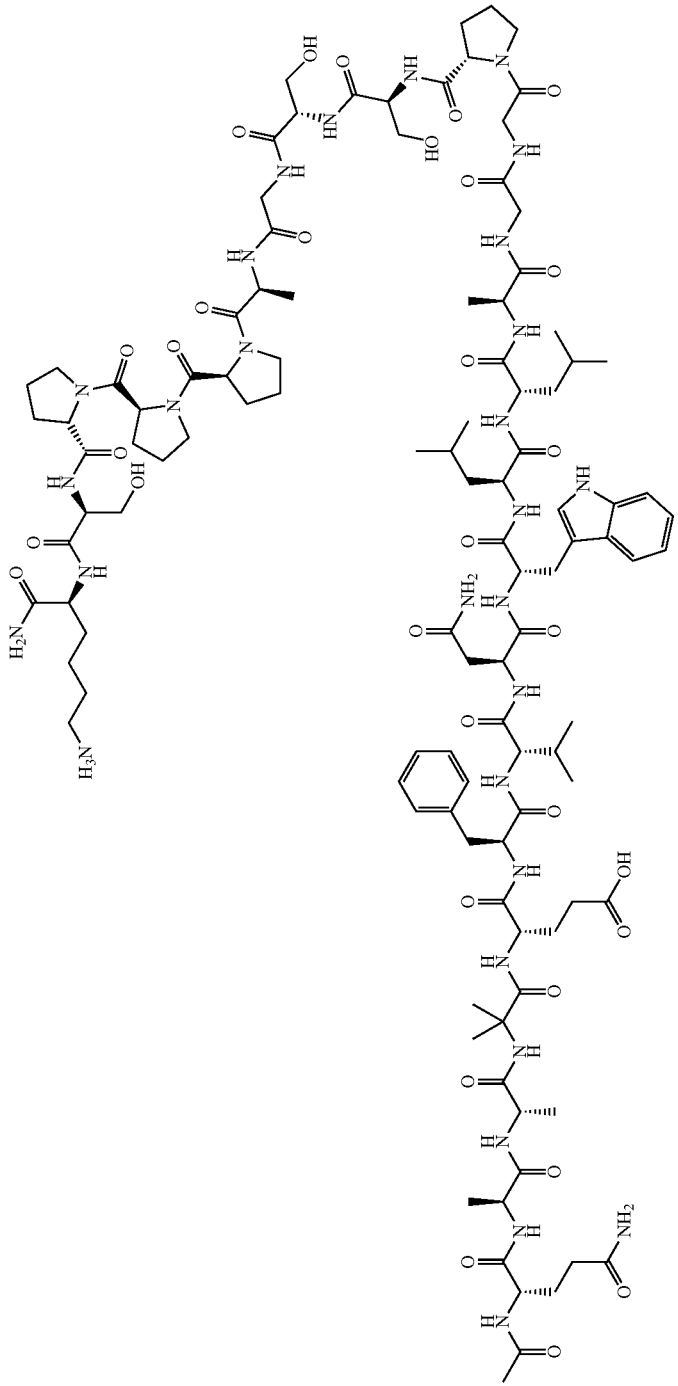

Compound 130
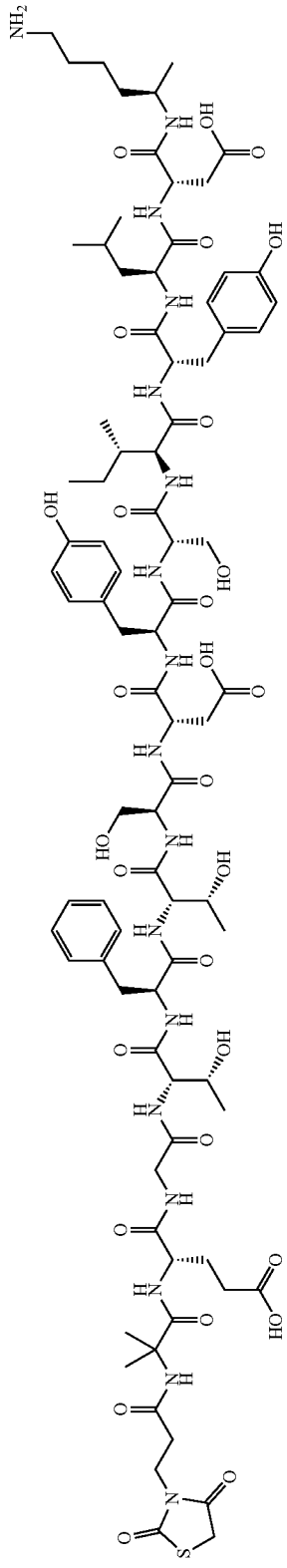
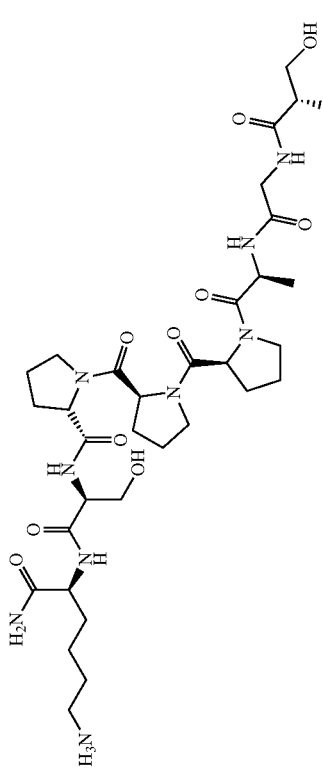
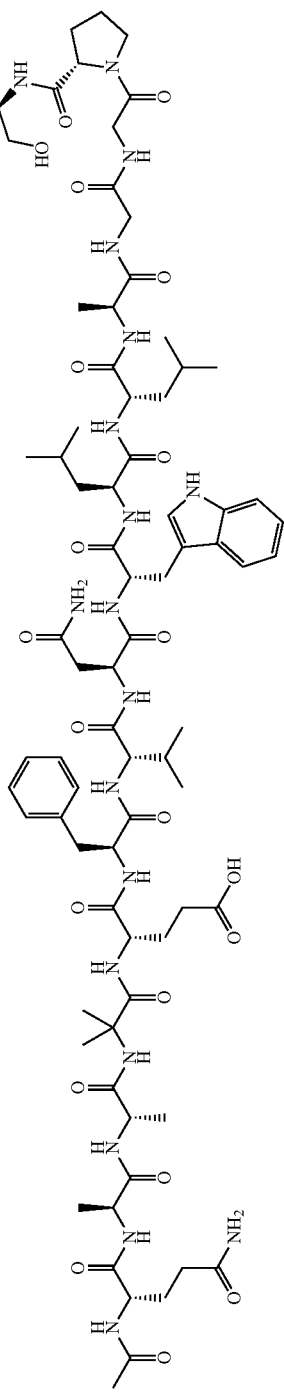

Compound 131
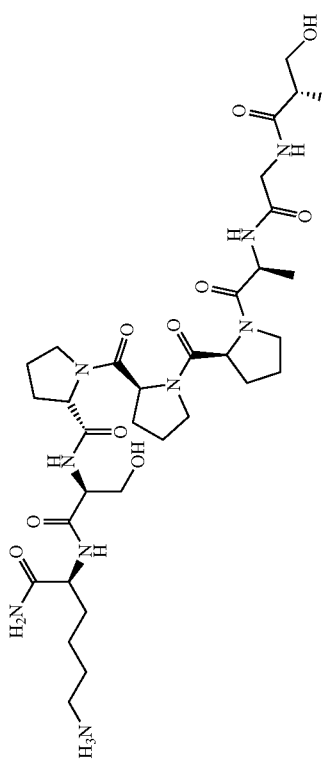
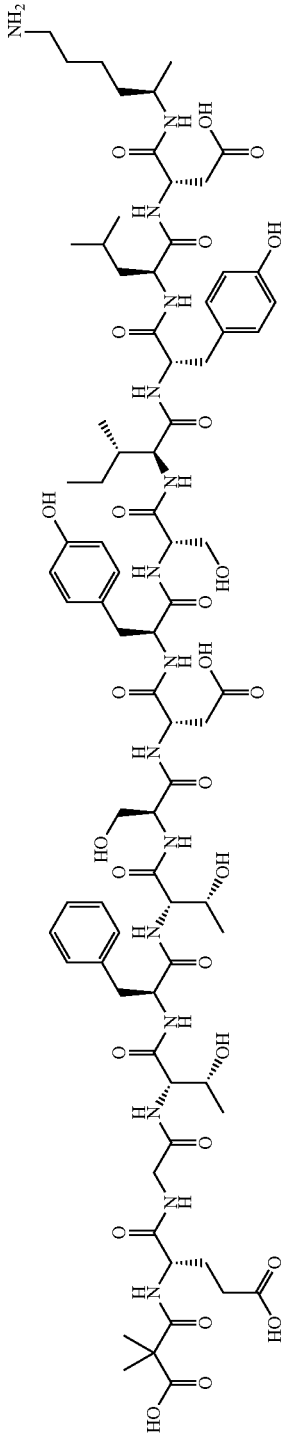
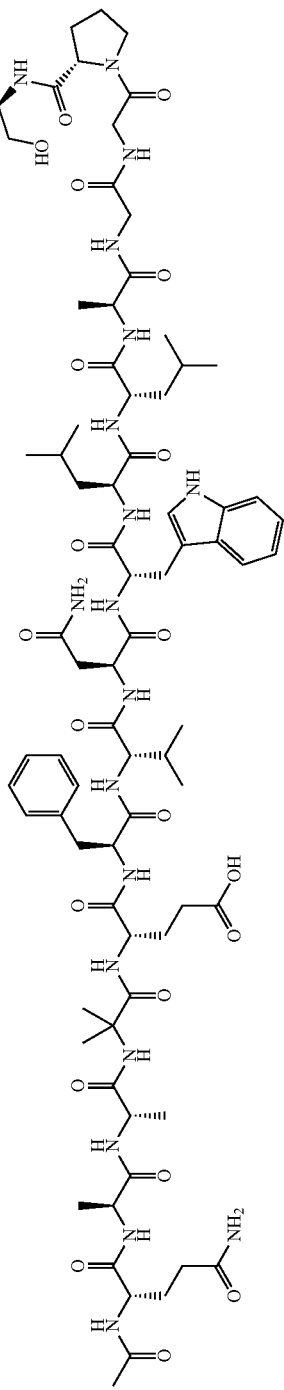

Compound 132
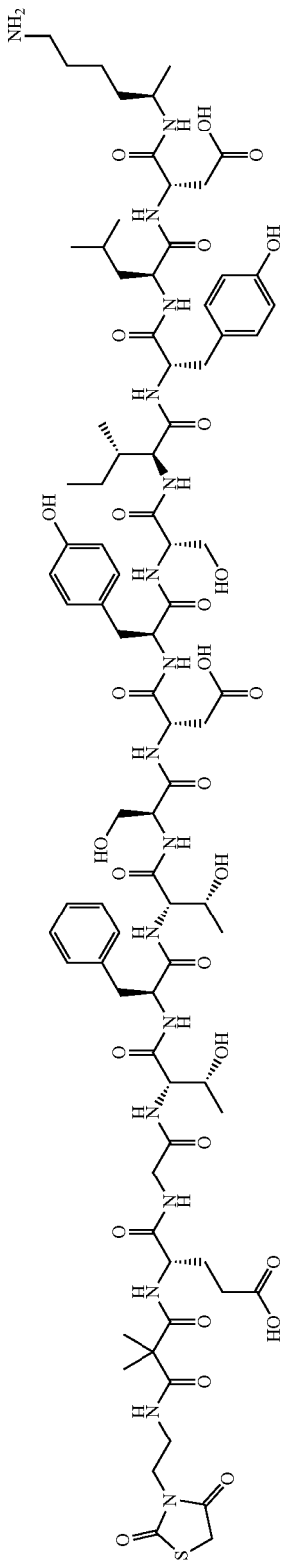
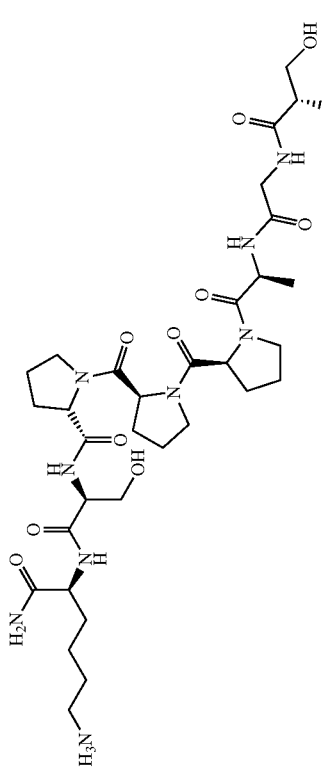
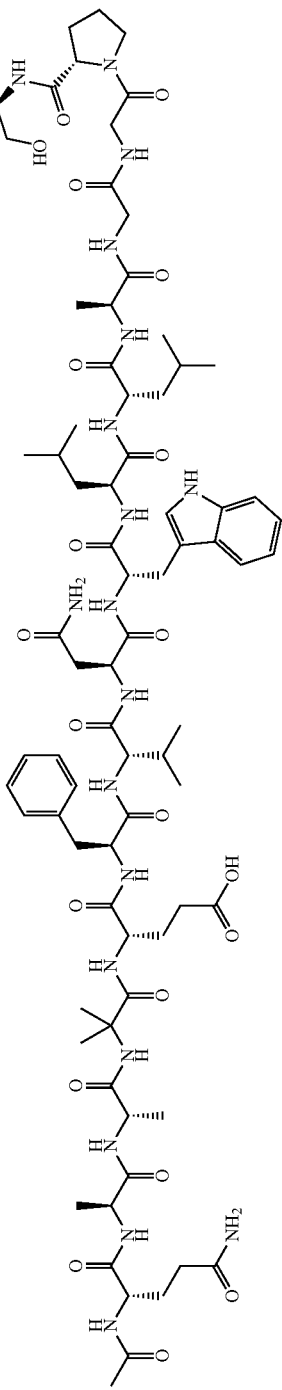

Compound 133
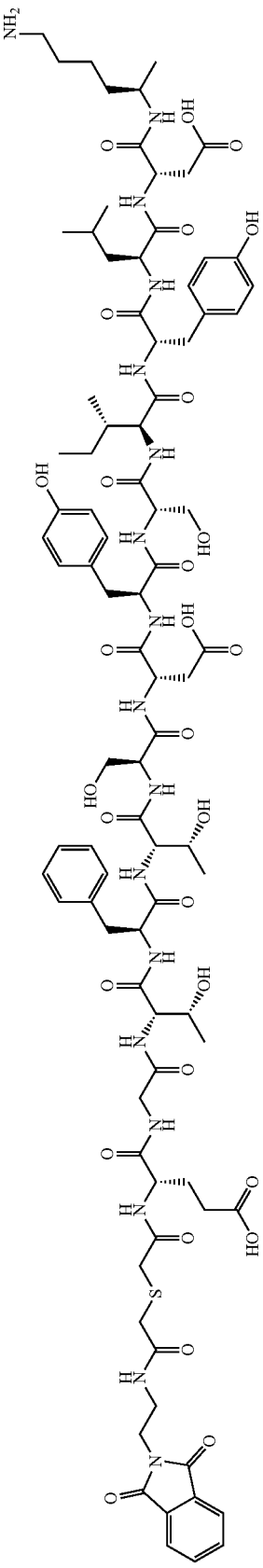
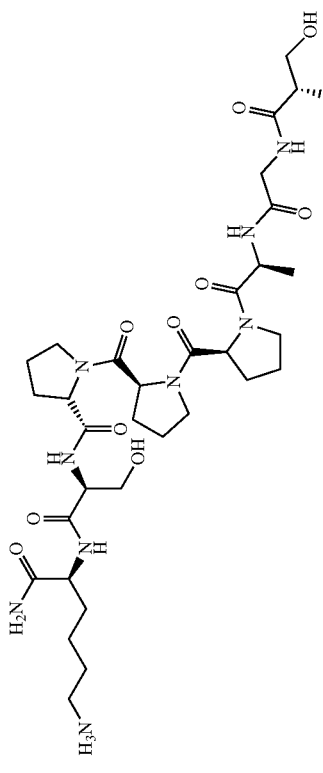
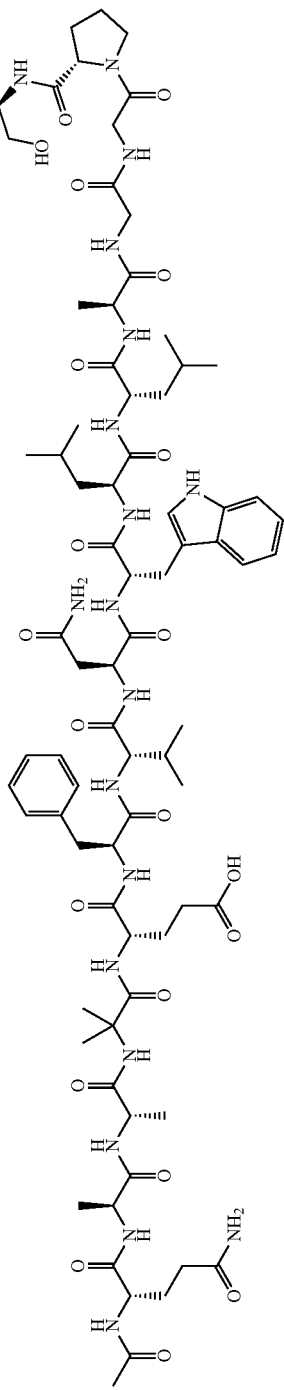

517 518
Compound 134
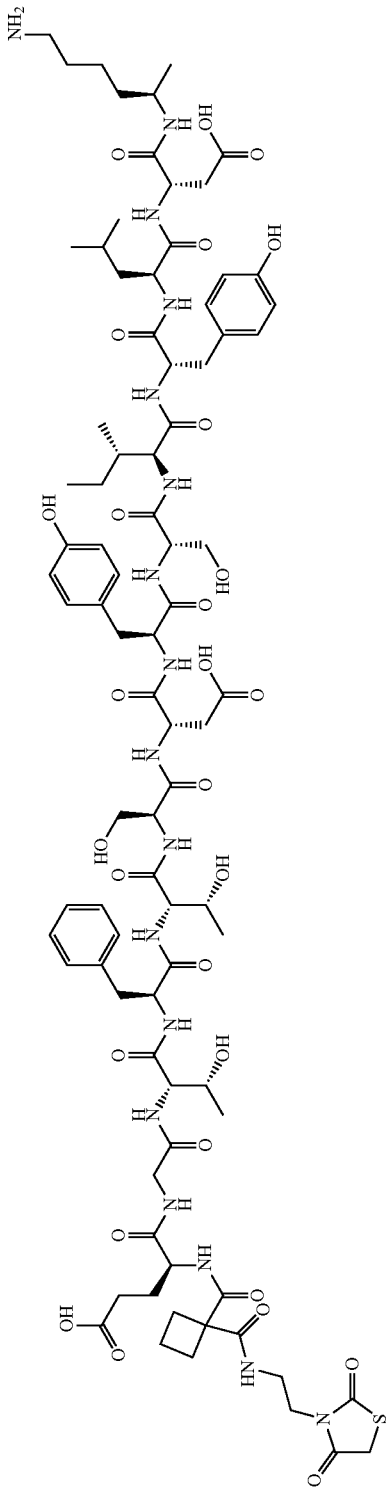
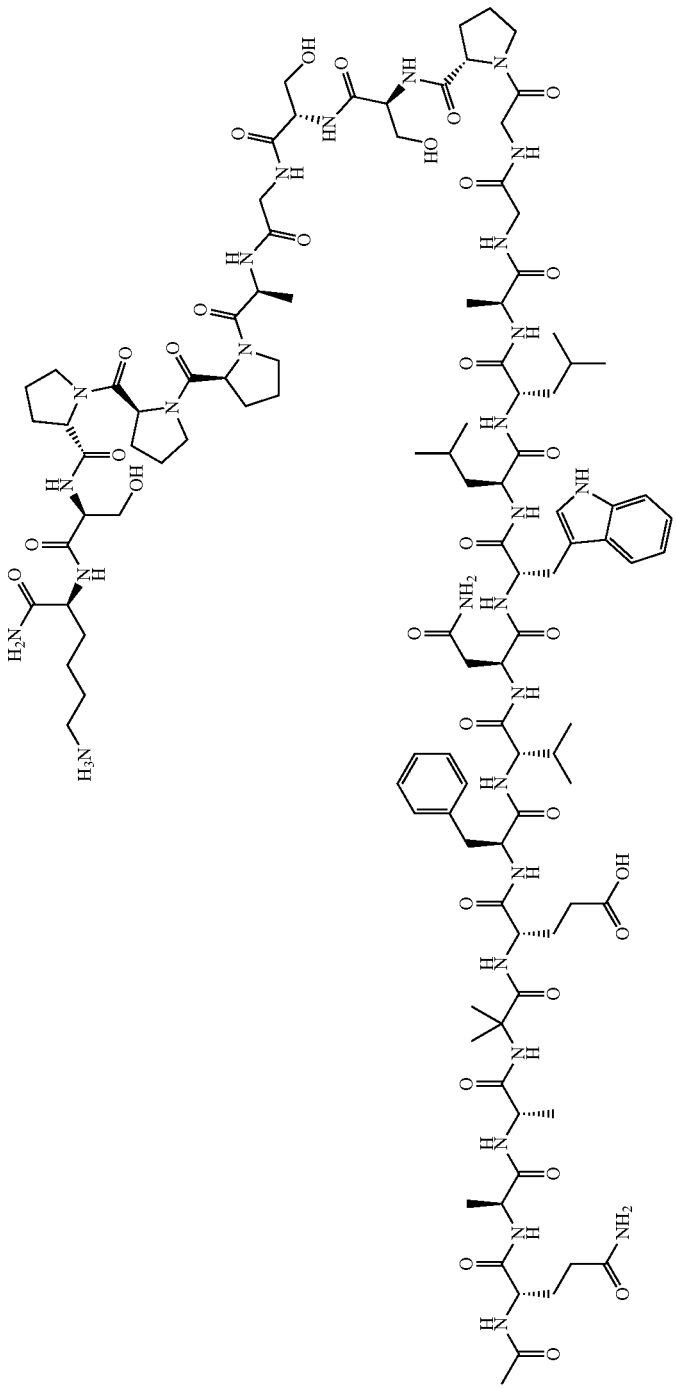

Compound 135
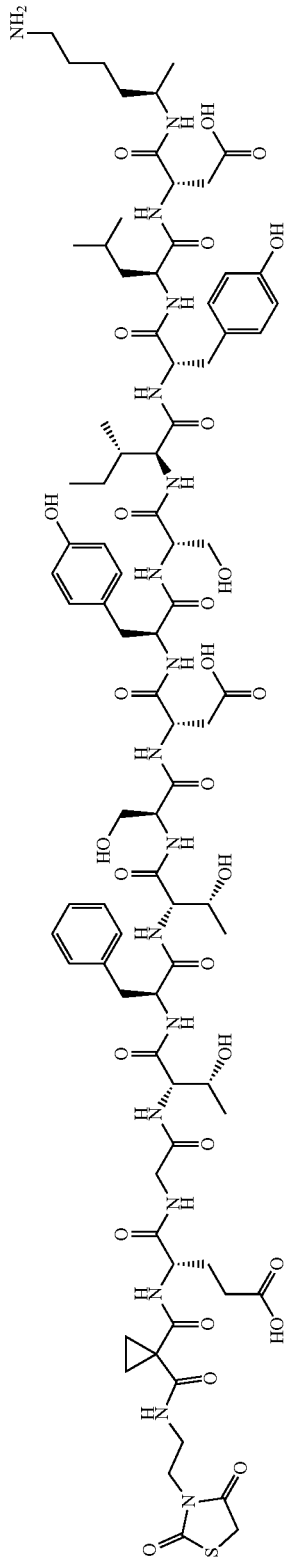
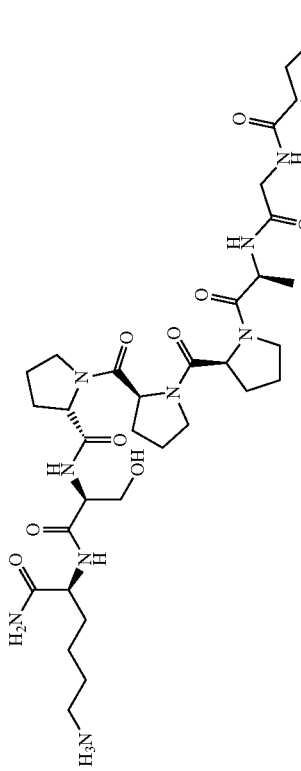
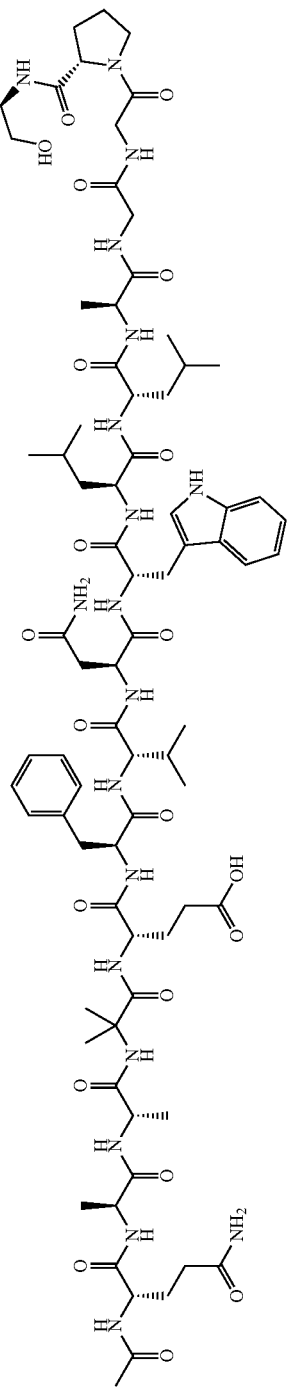

521
Compound 136
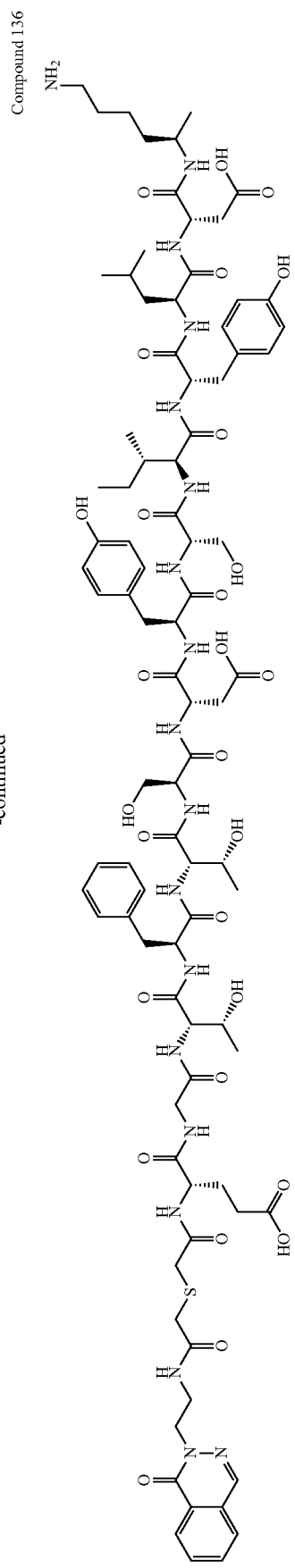
522
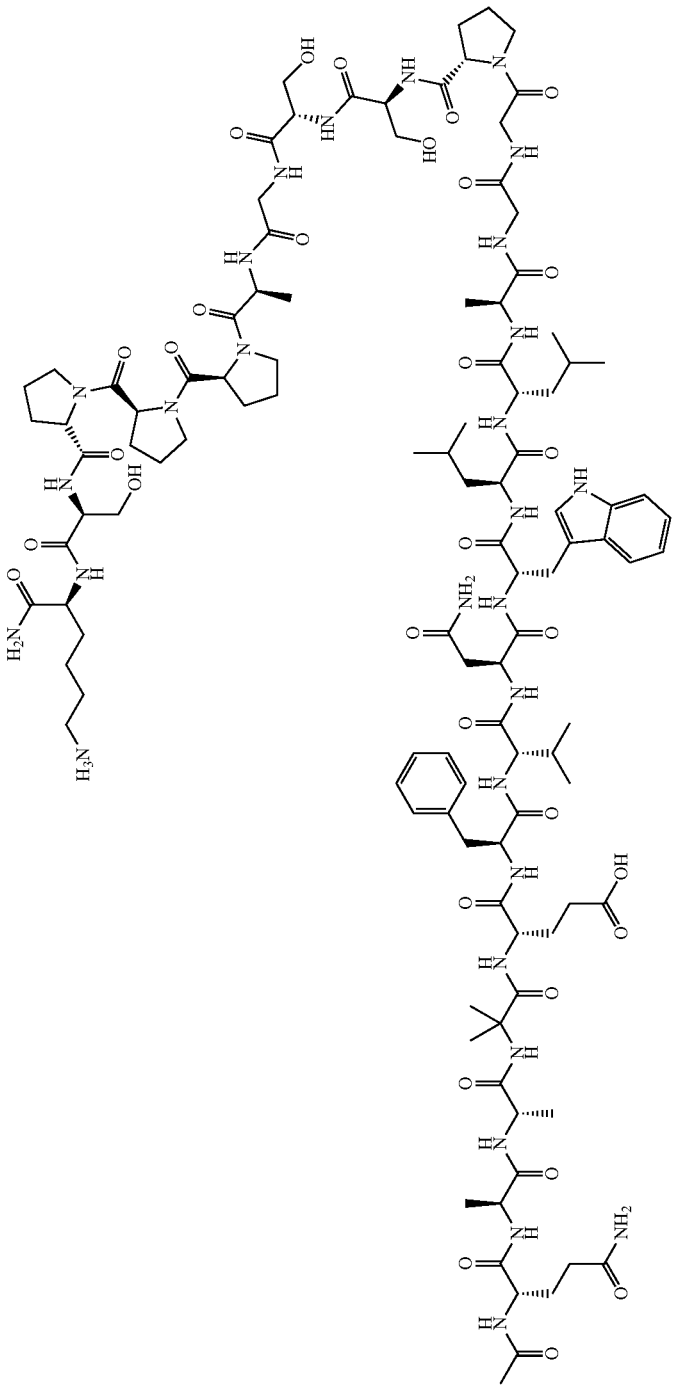

Compound 137
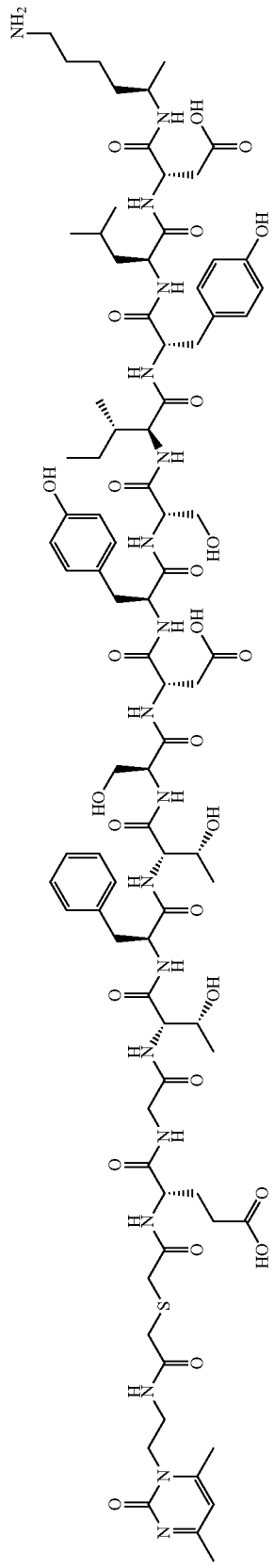
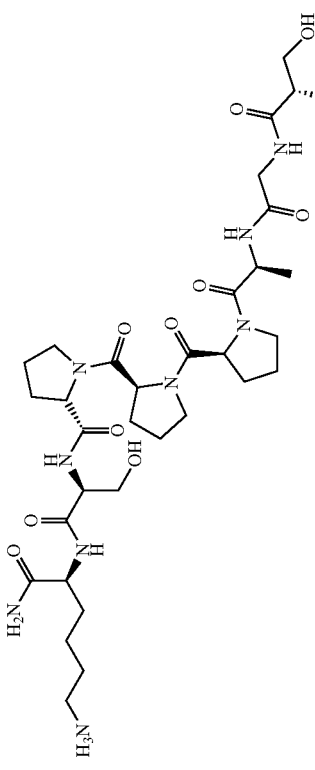
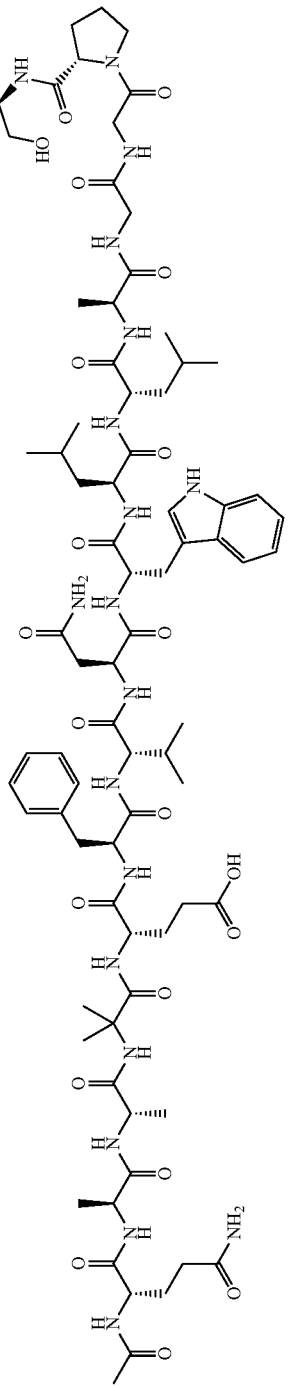

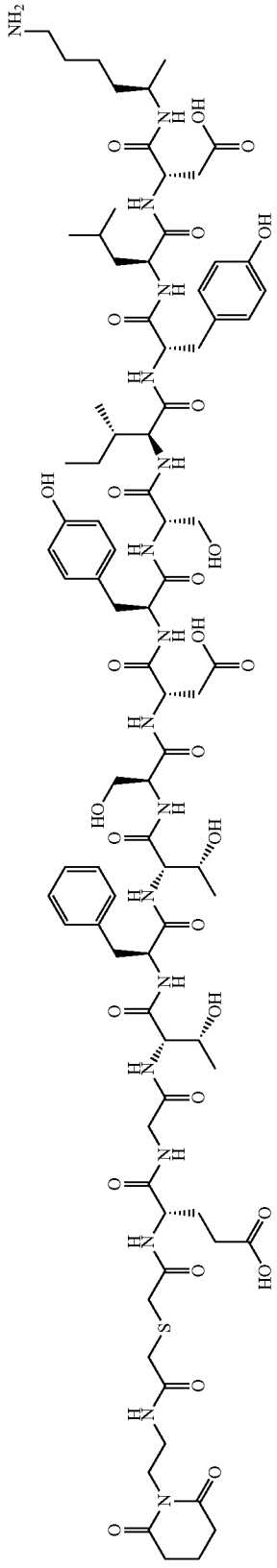
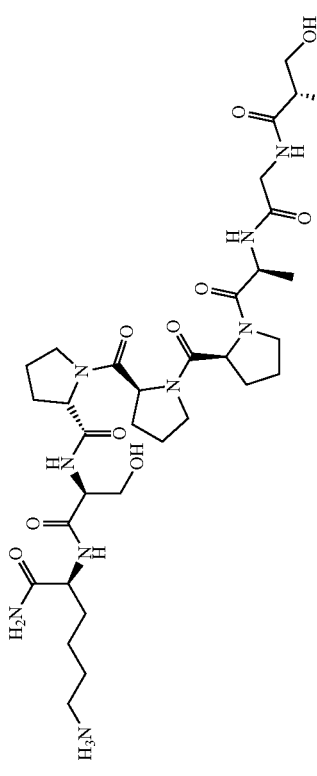
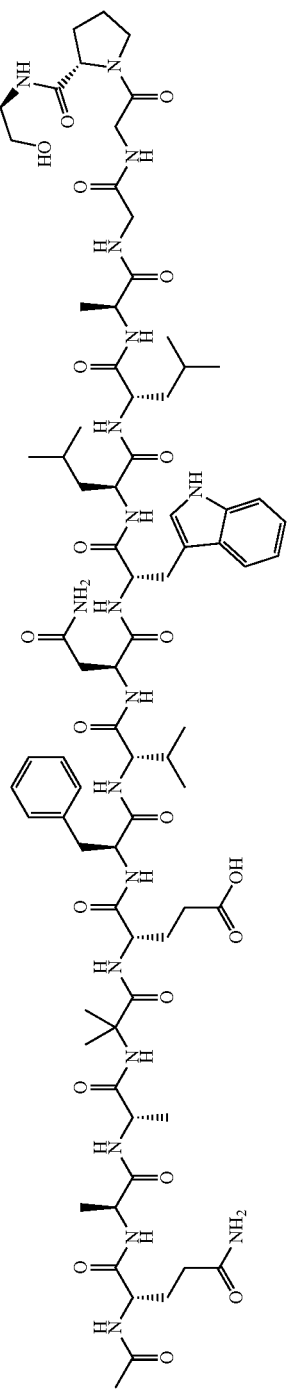

Compound 139
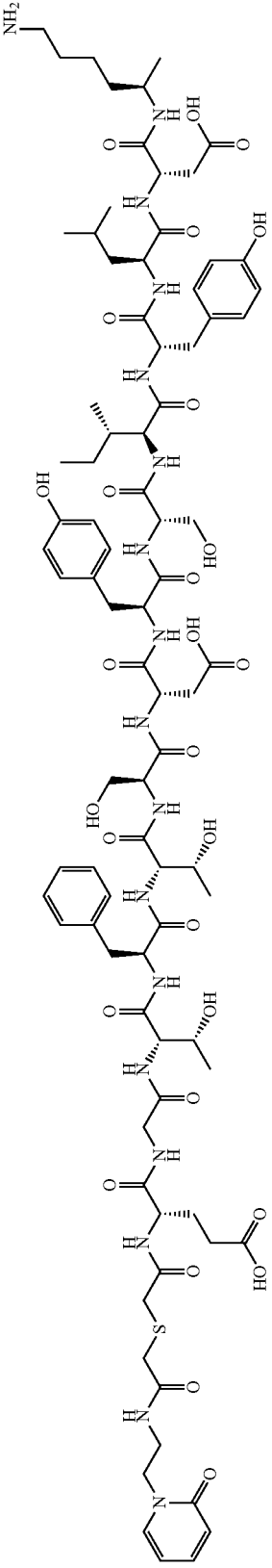
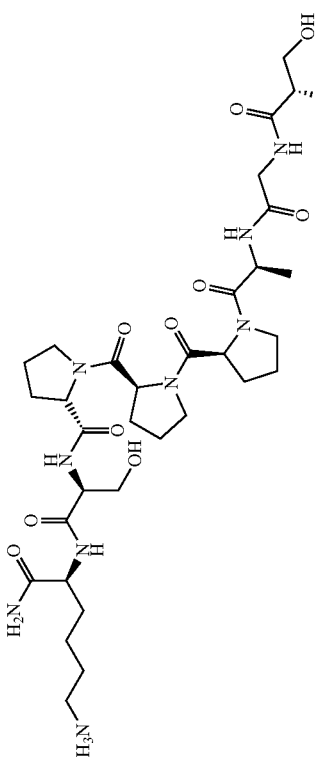
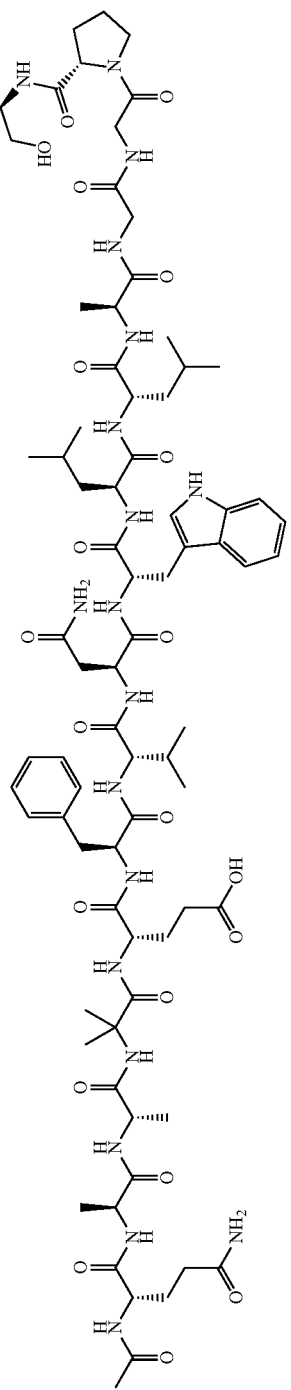

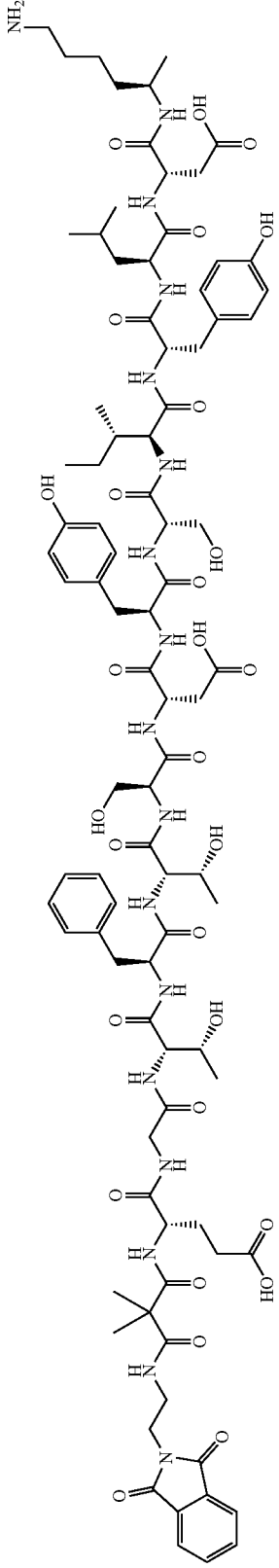
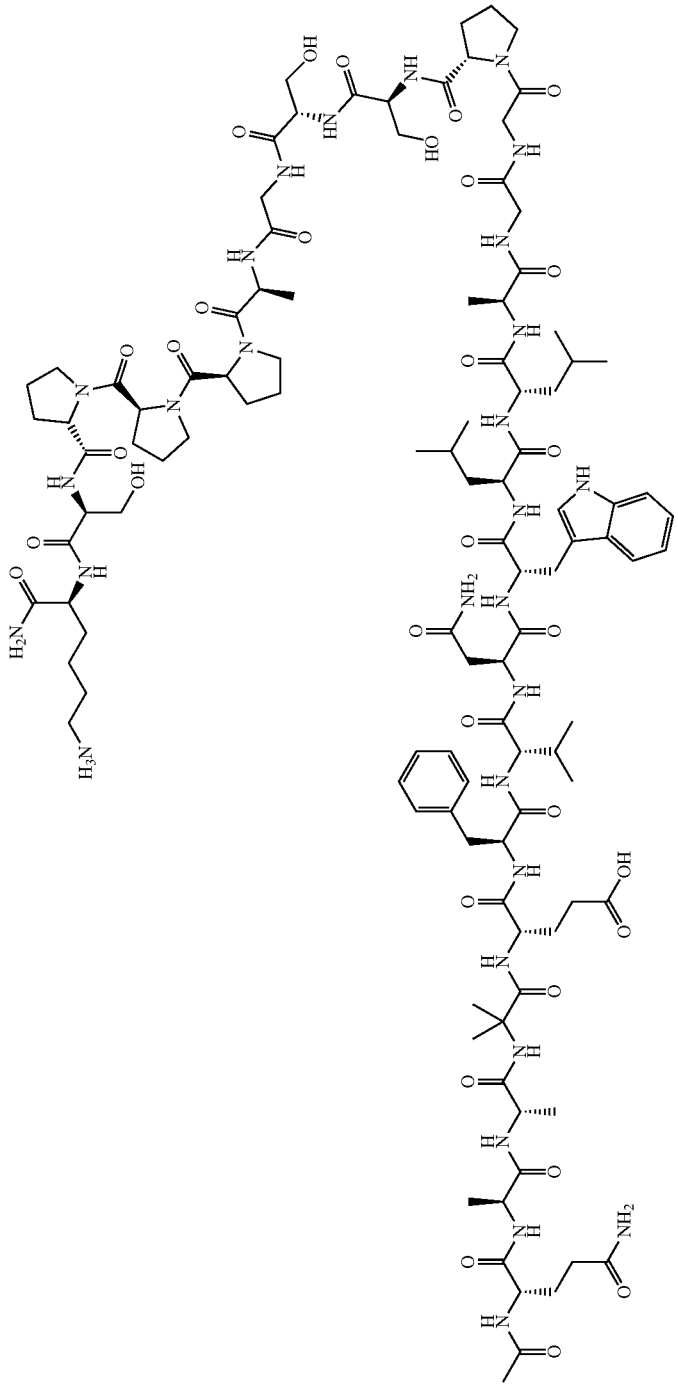
Compound 140

Compound 141
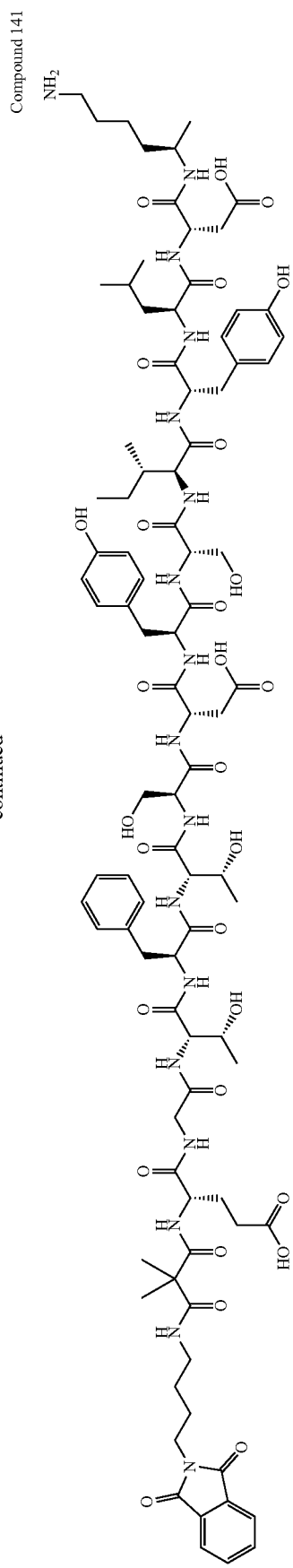
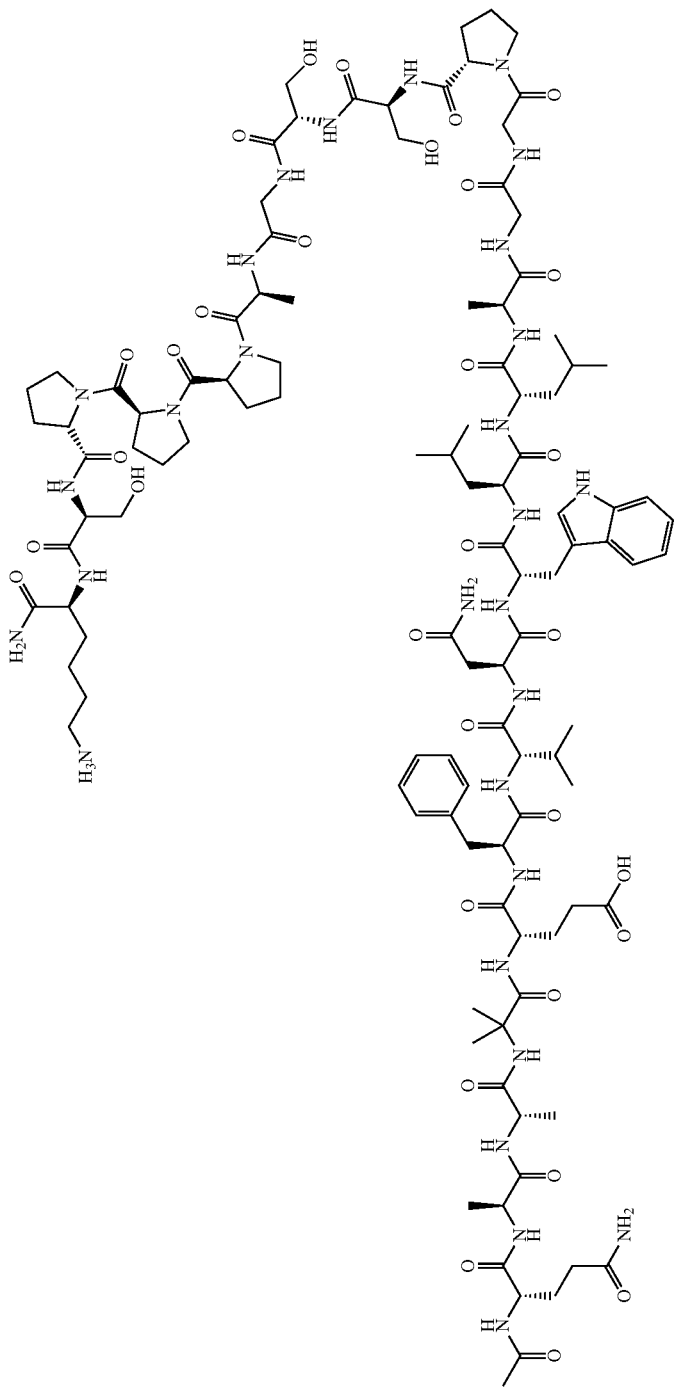

Compound 142
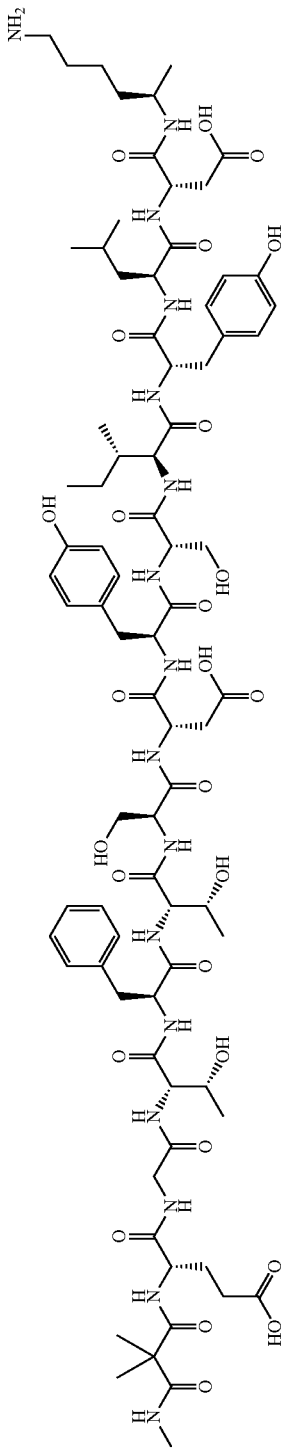
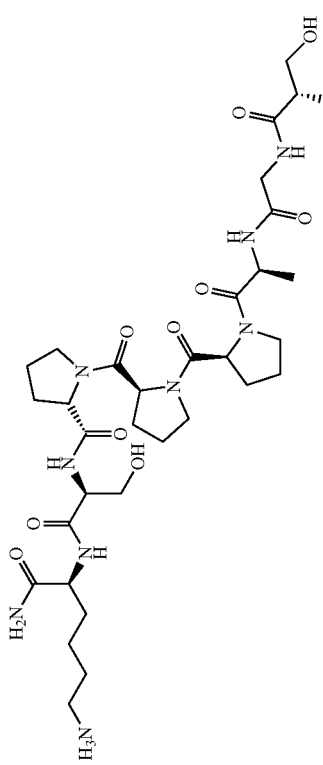
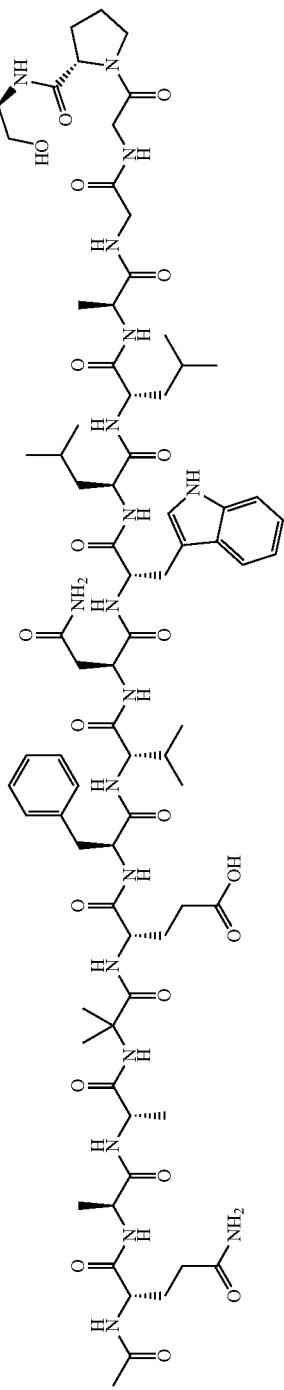

Compound 143
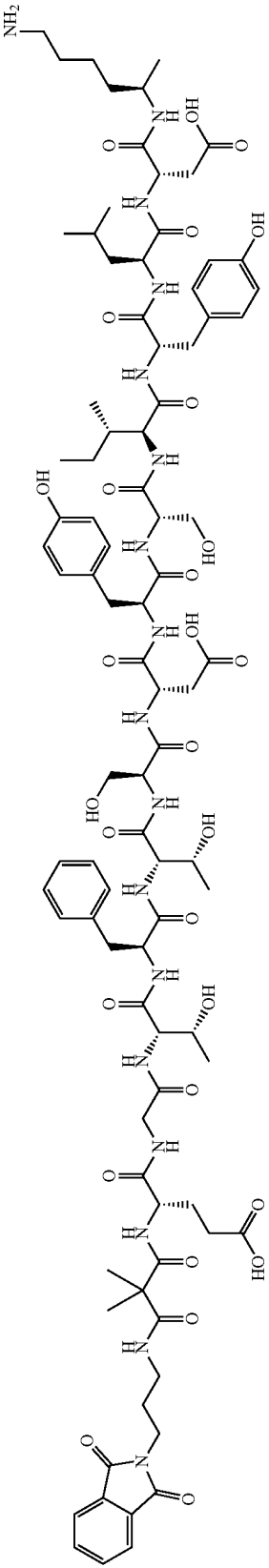
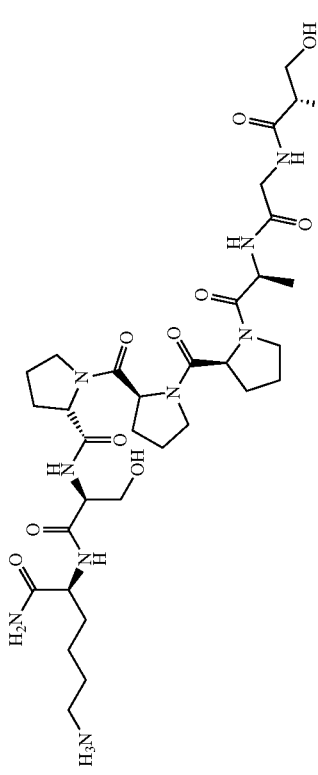
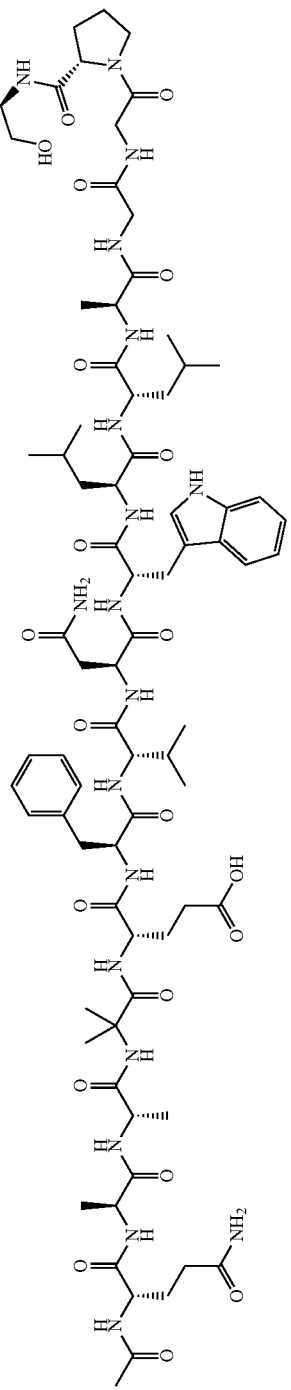

Compound 144
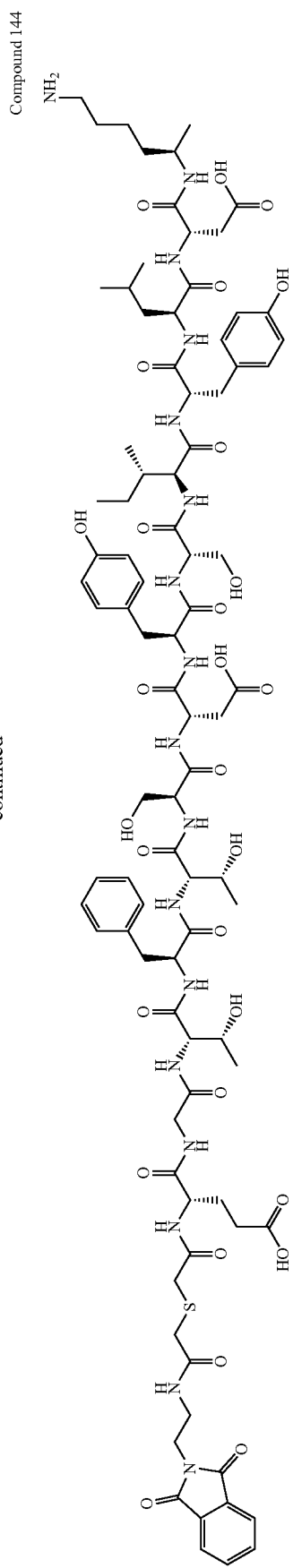
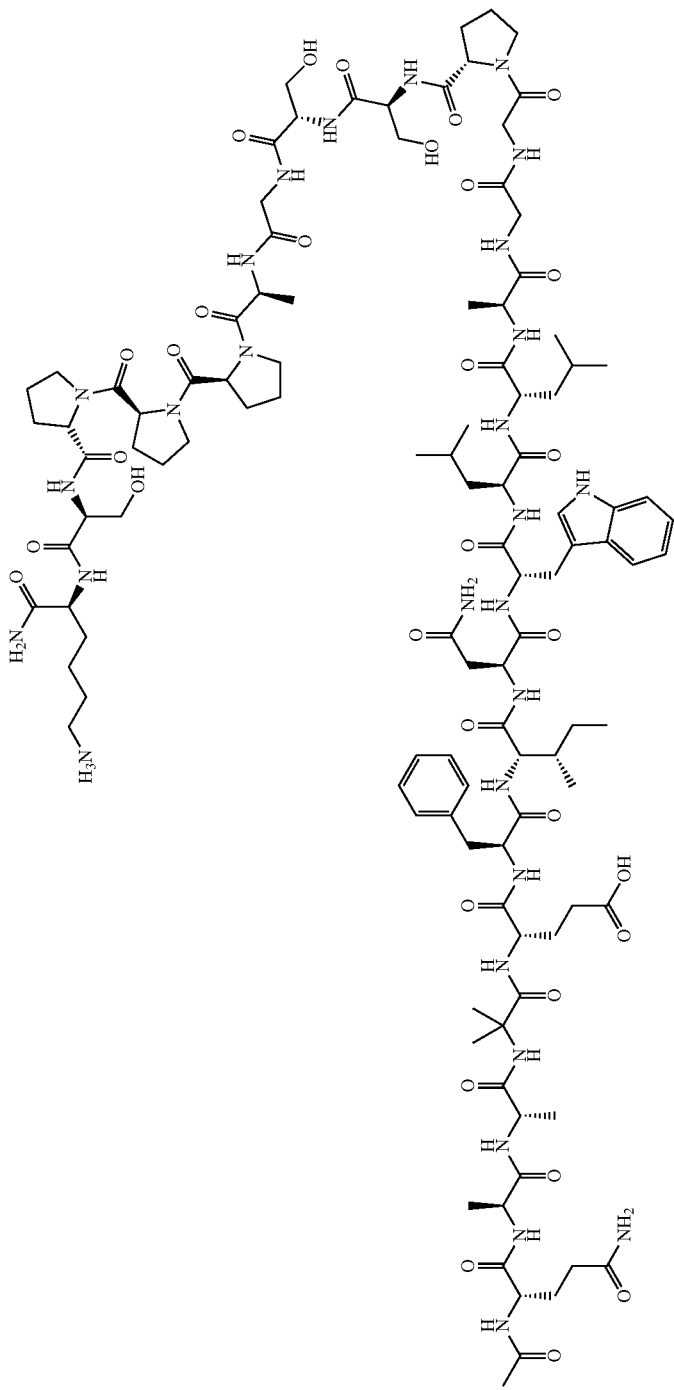

Compound 145
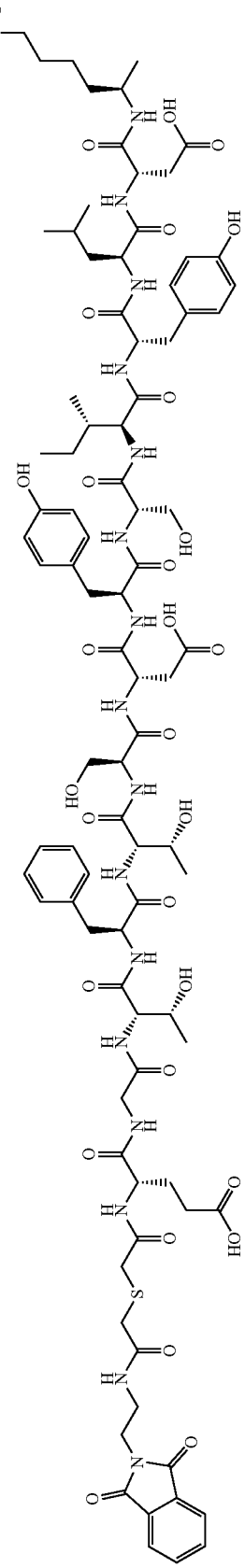
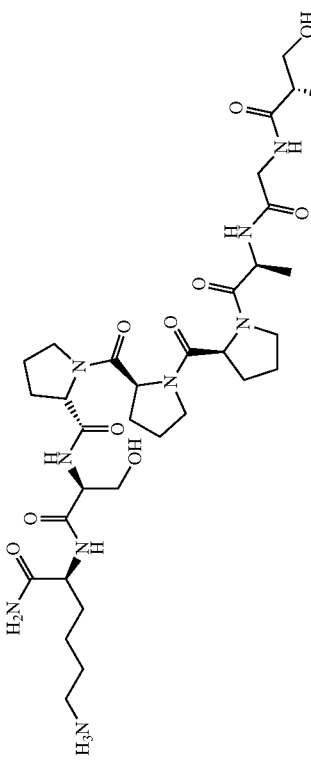
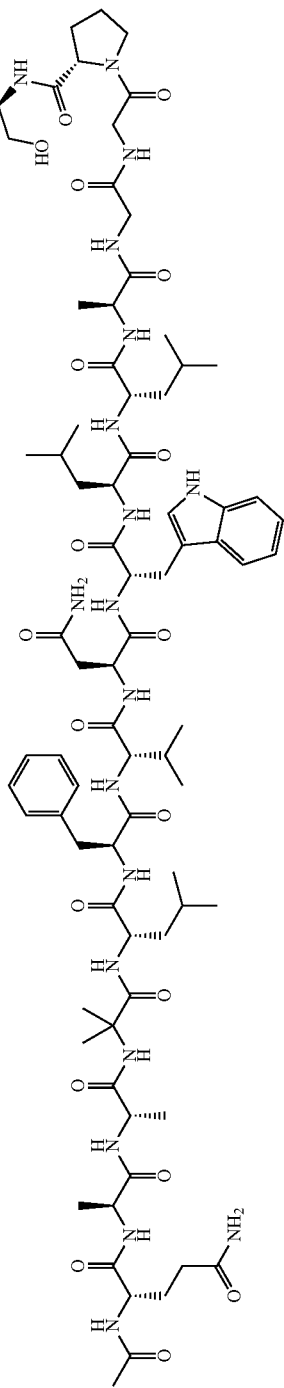

541   542
-continued
Compound 146
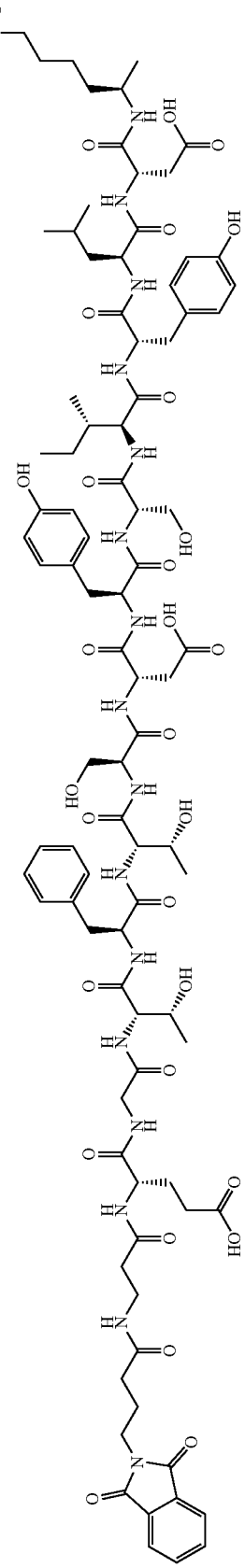
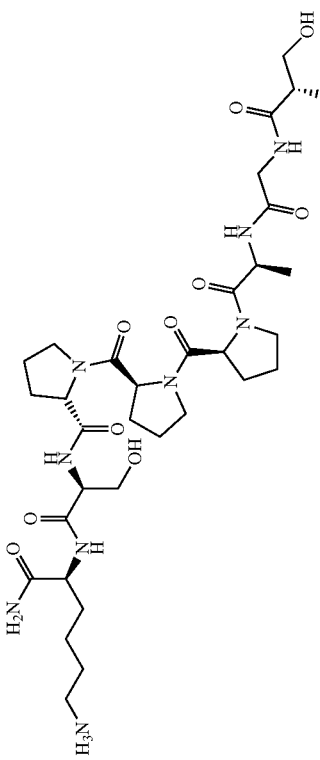
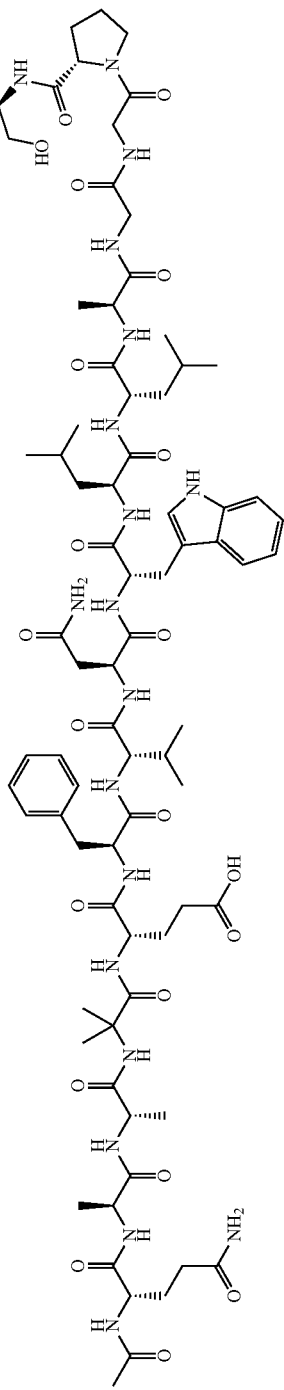

543 544
Compound 147
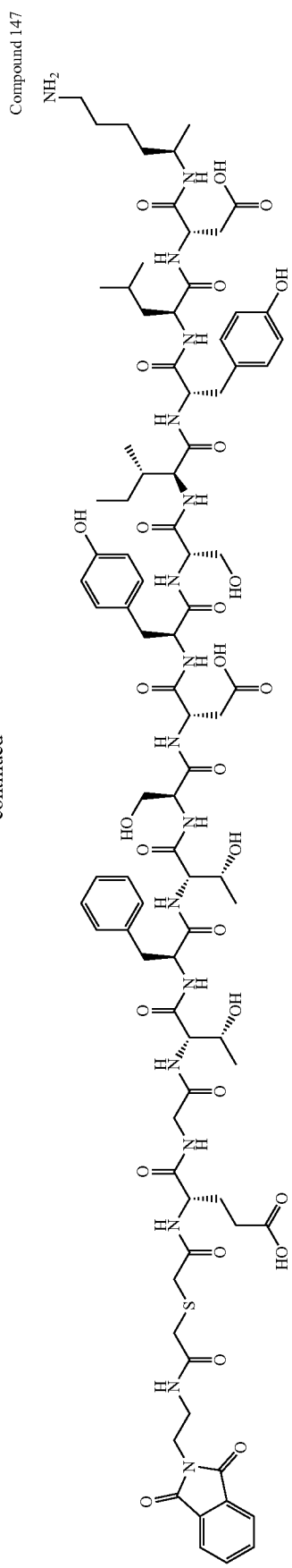
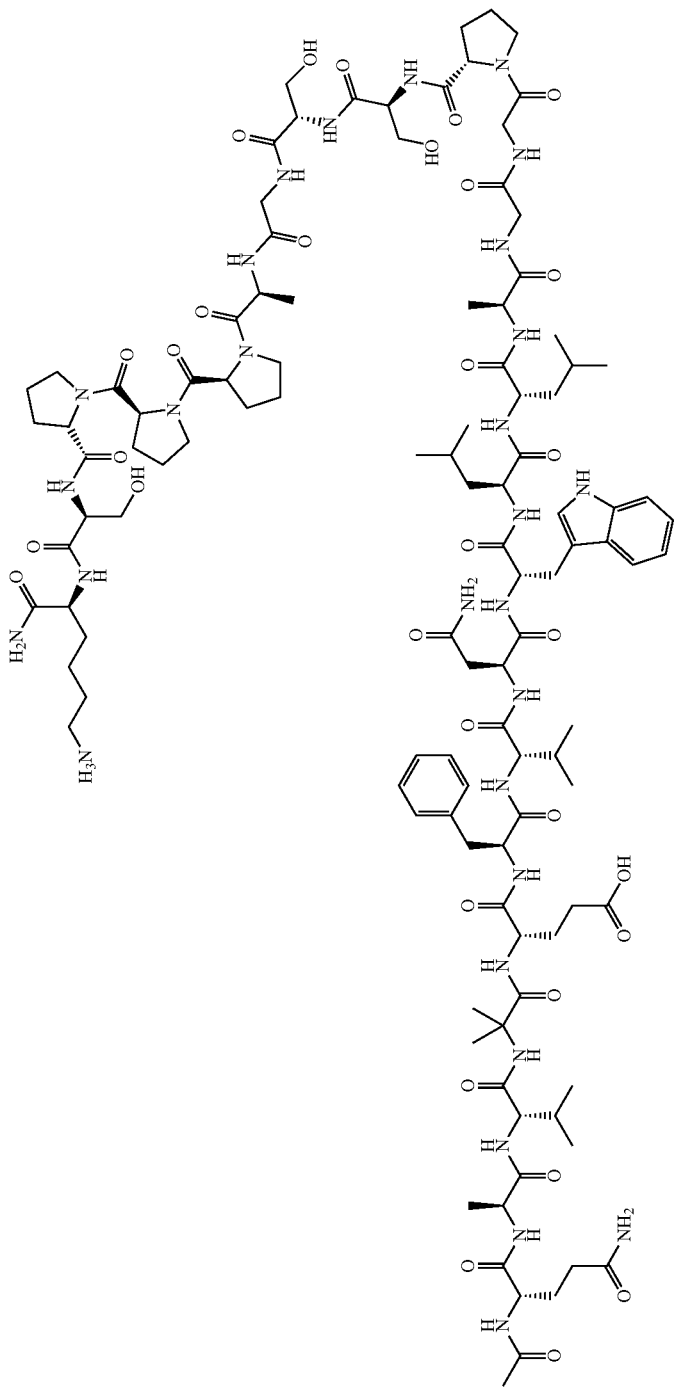

Compound 1
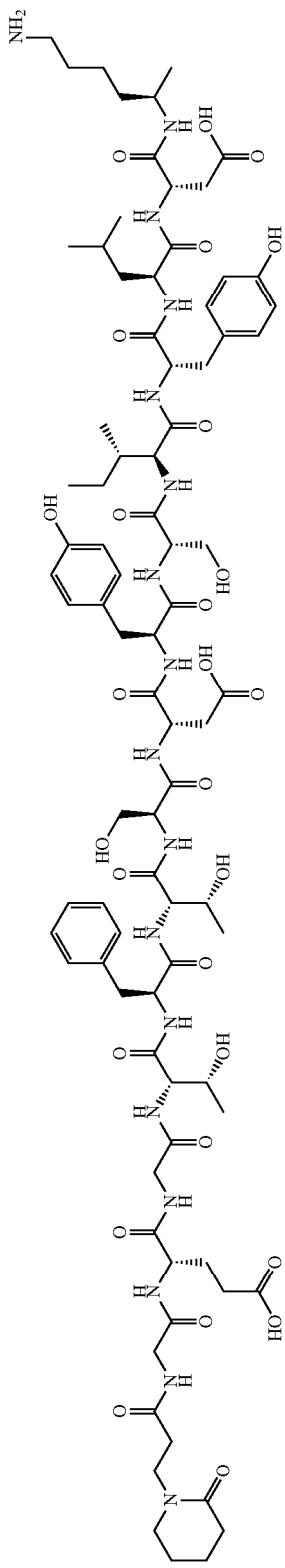
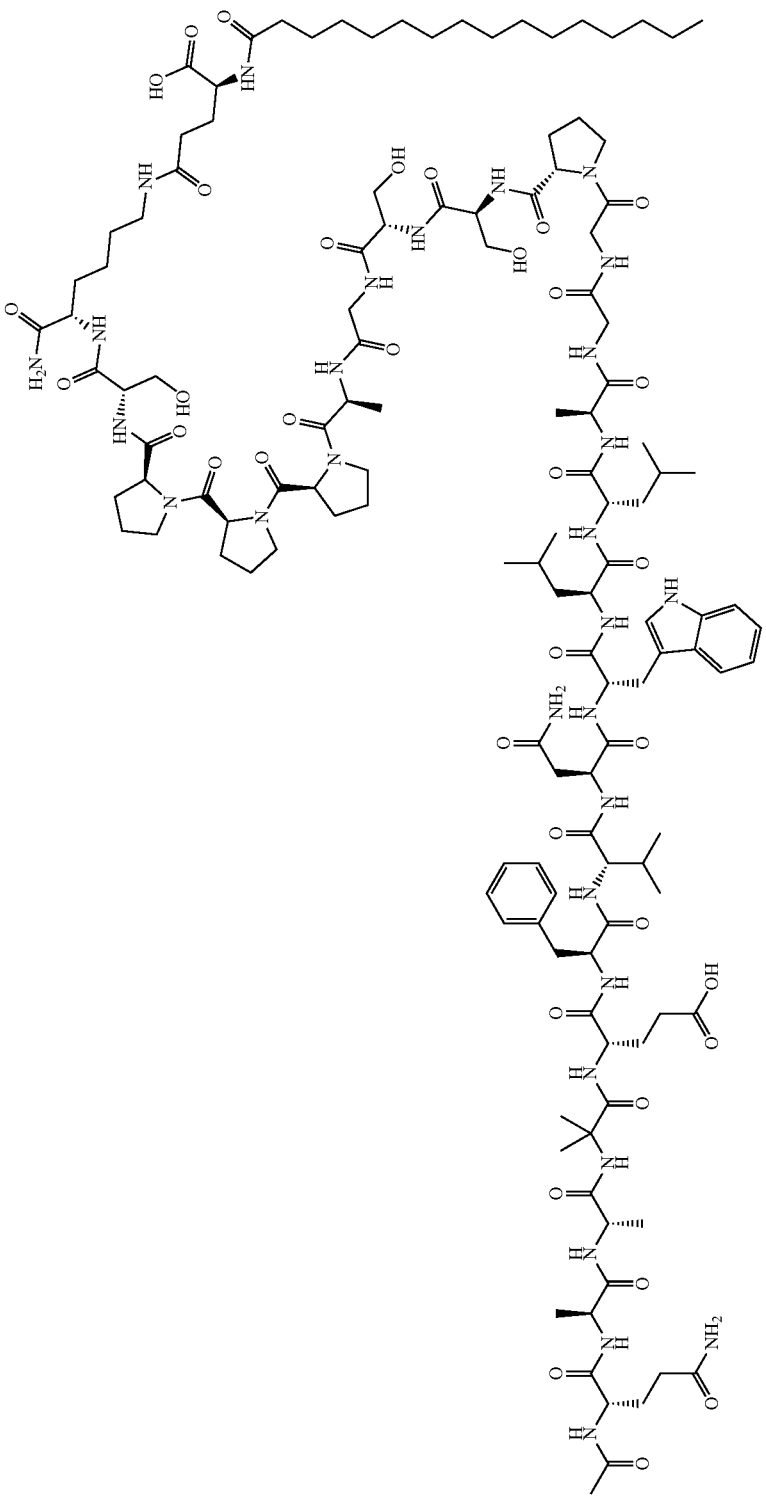

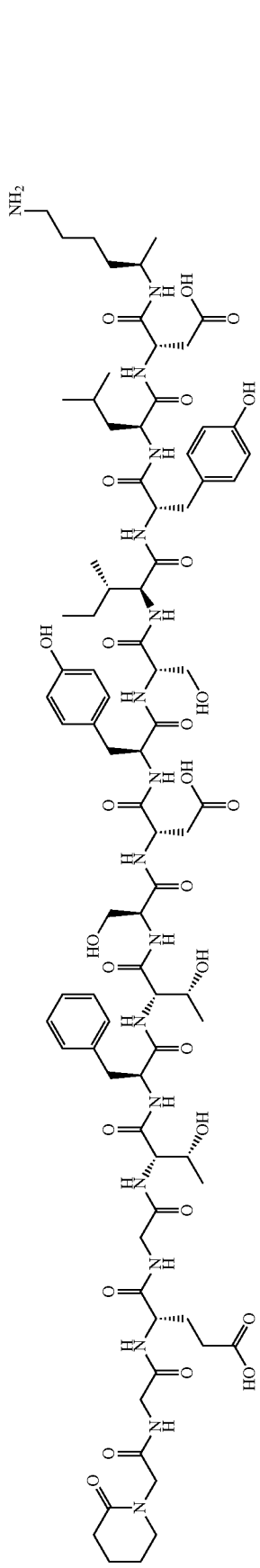
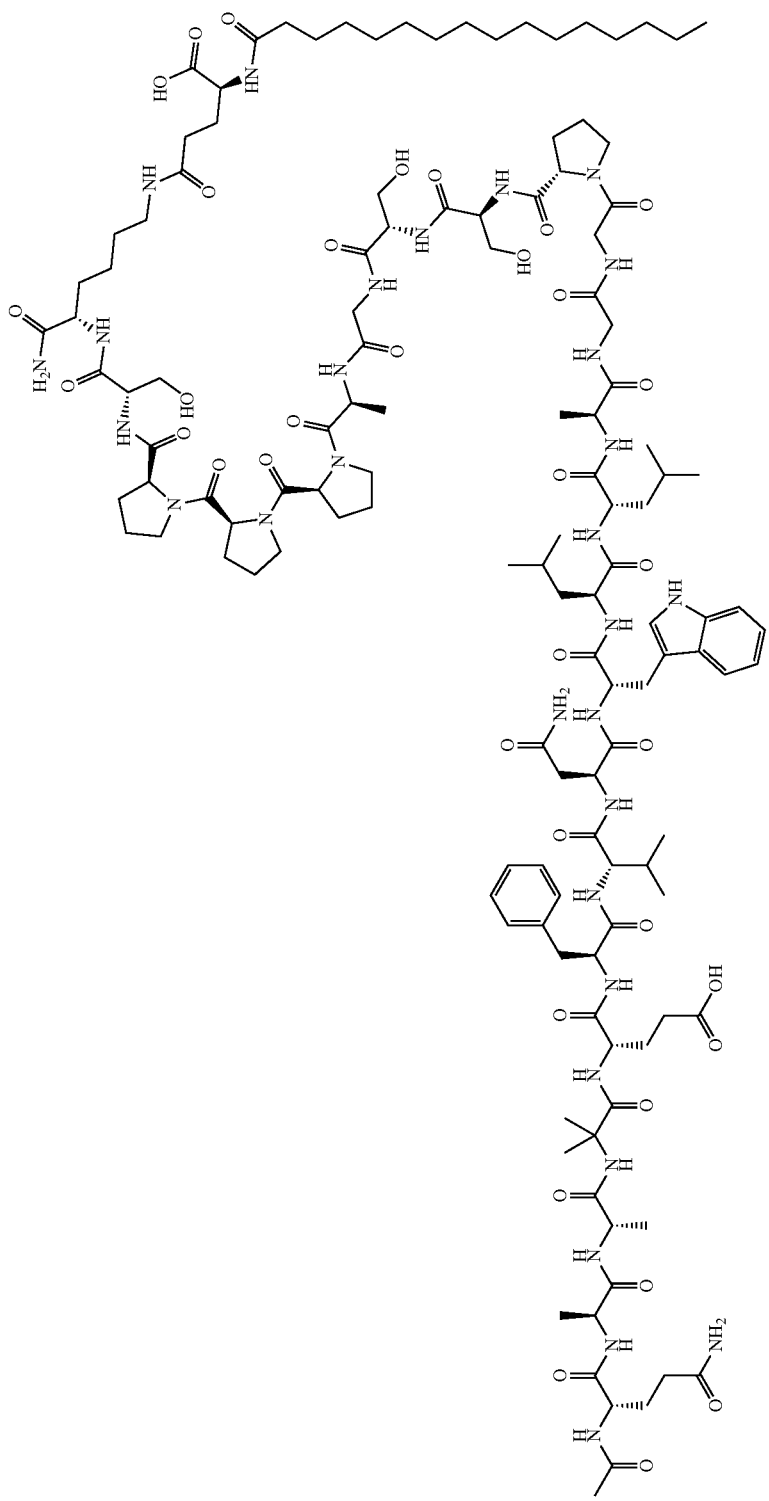

Compound 3
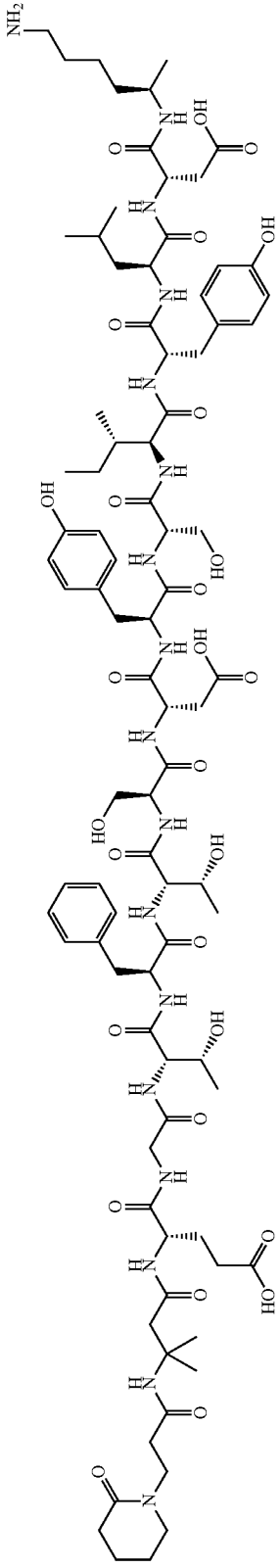
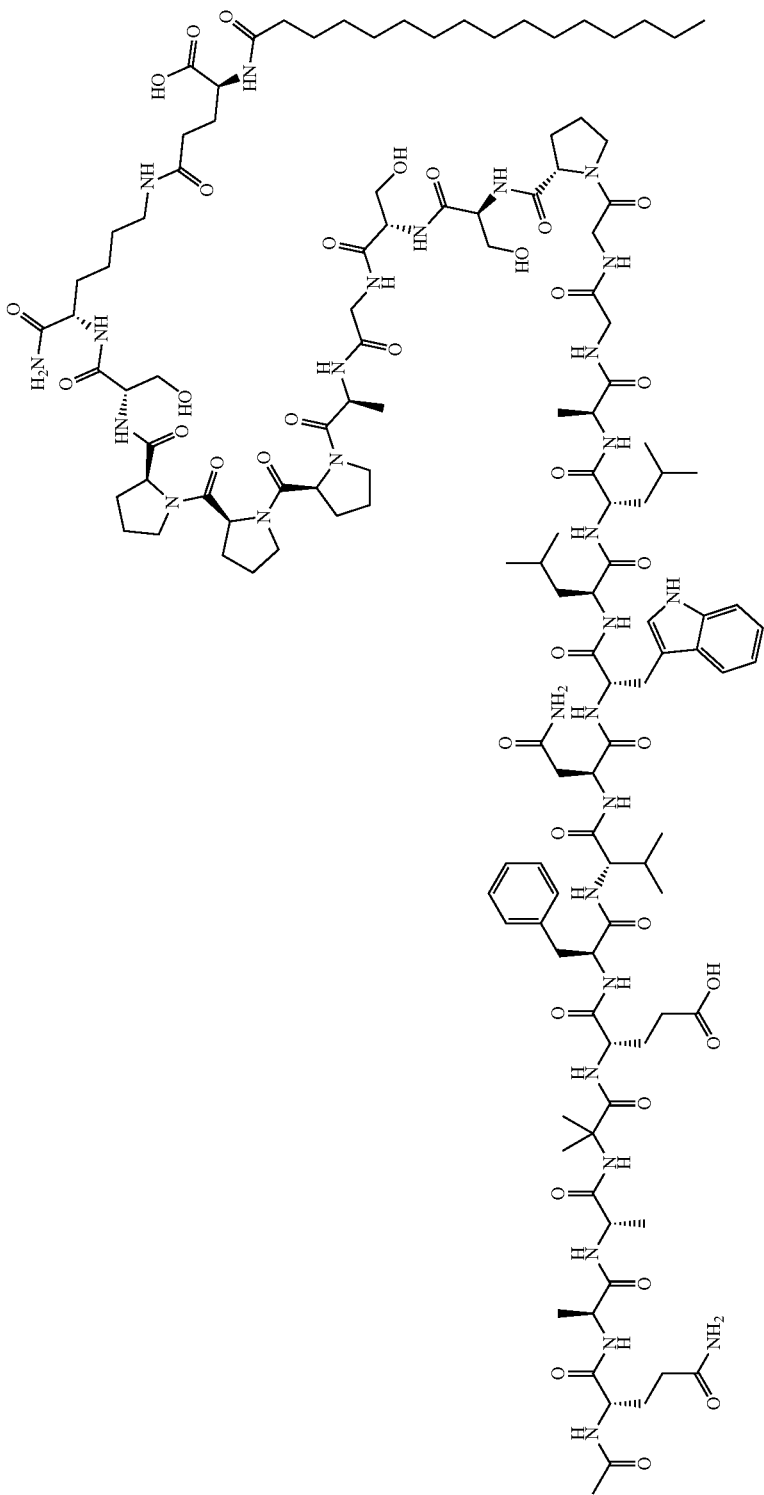

551
552
Compound 4
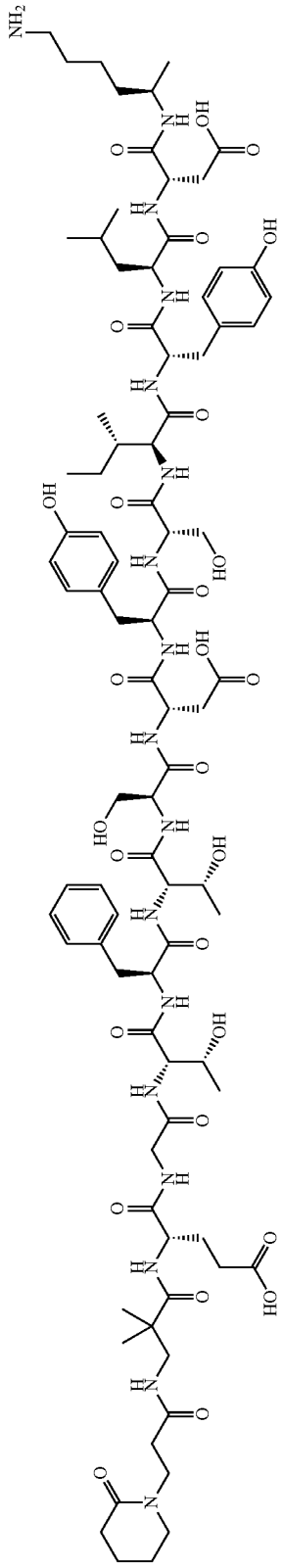
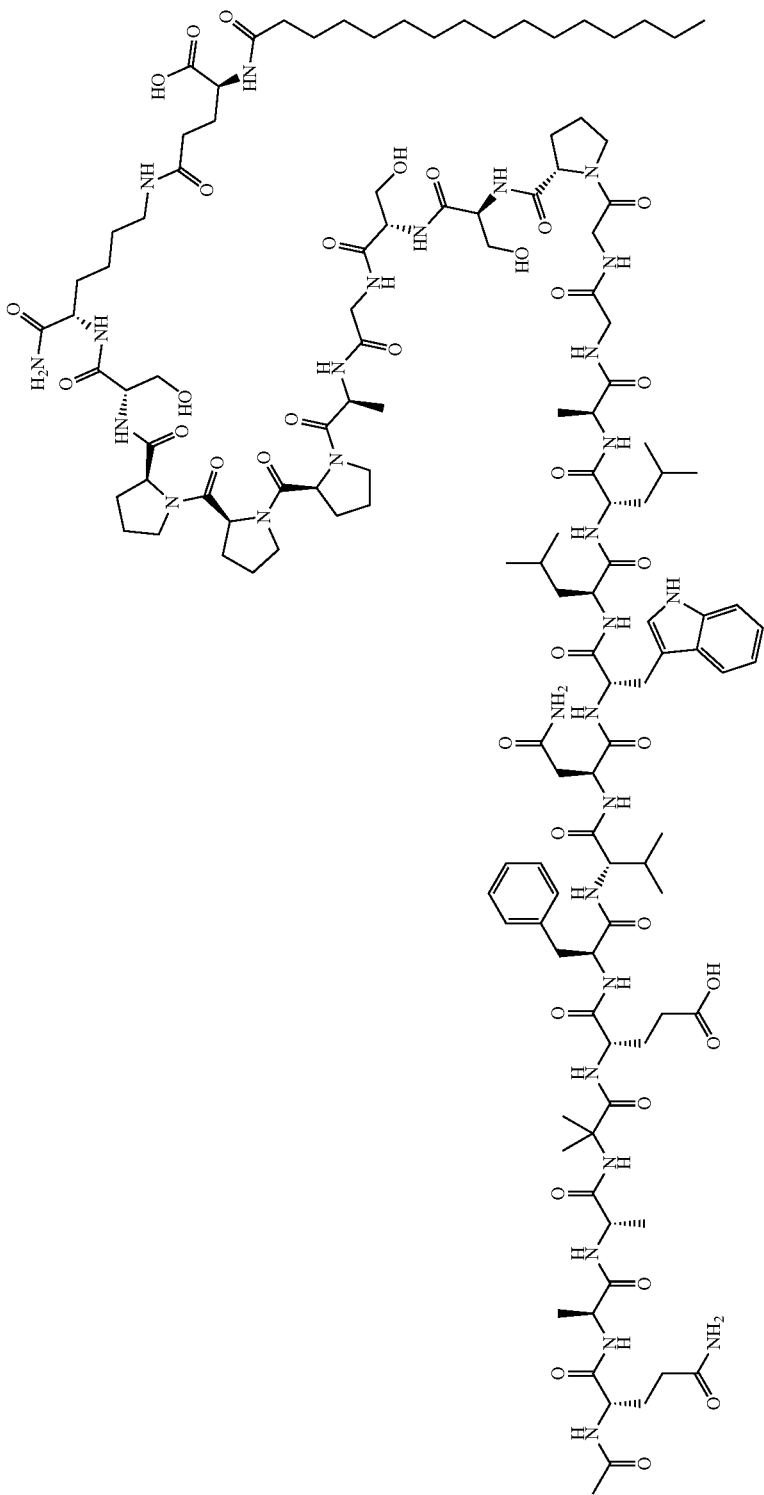

553 554
Compound 5
-continued
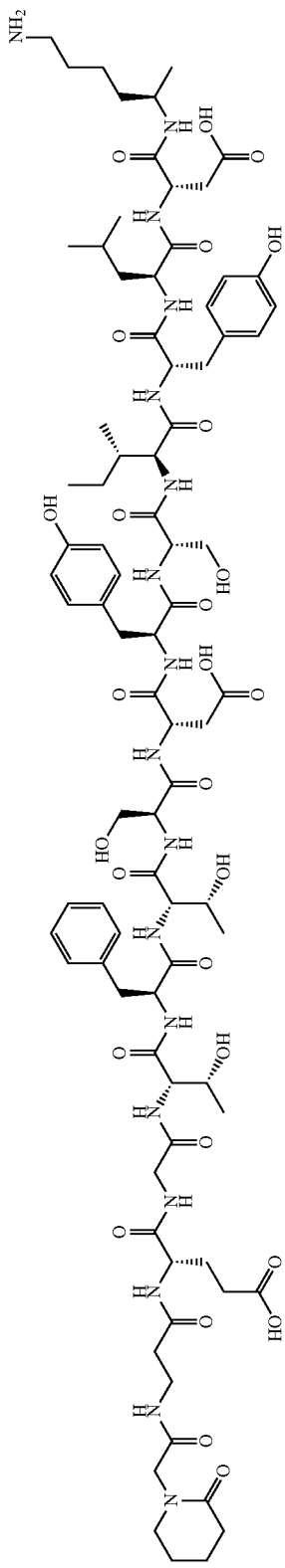
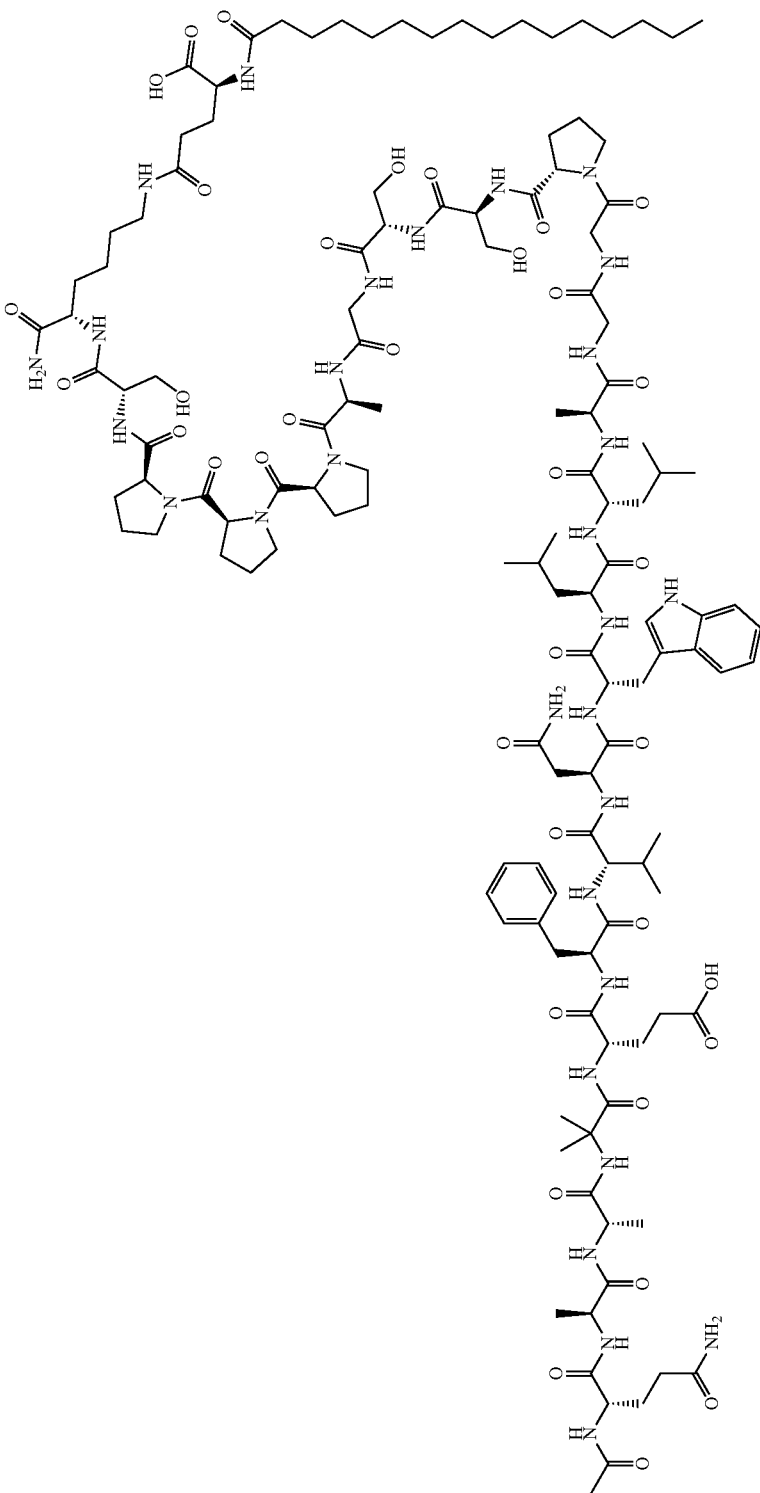

555
Compound 6
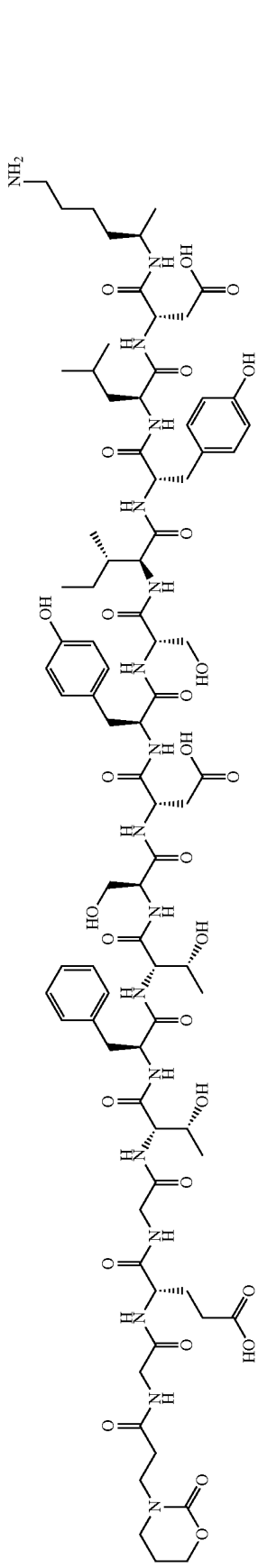
556
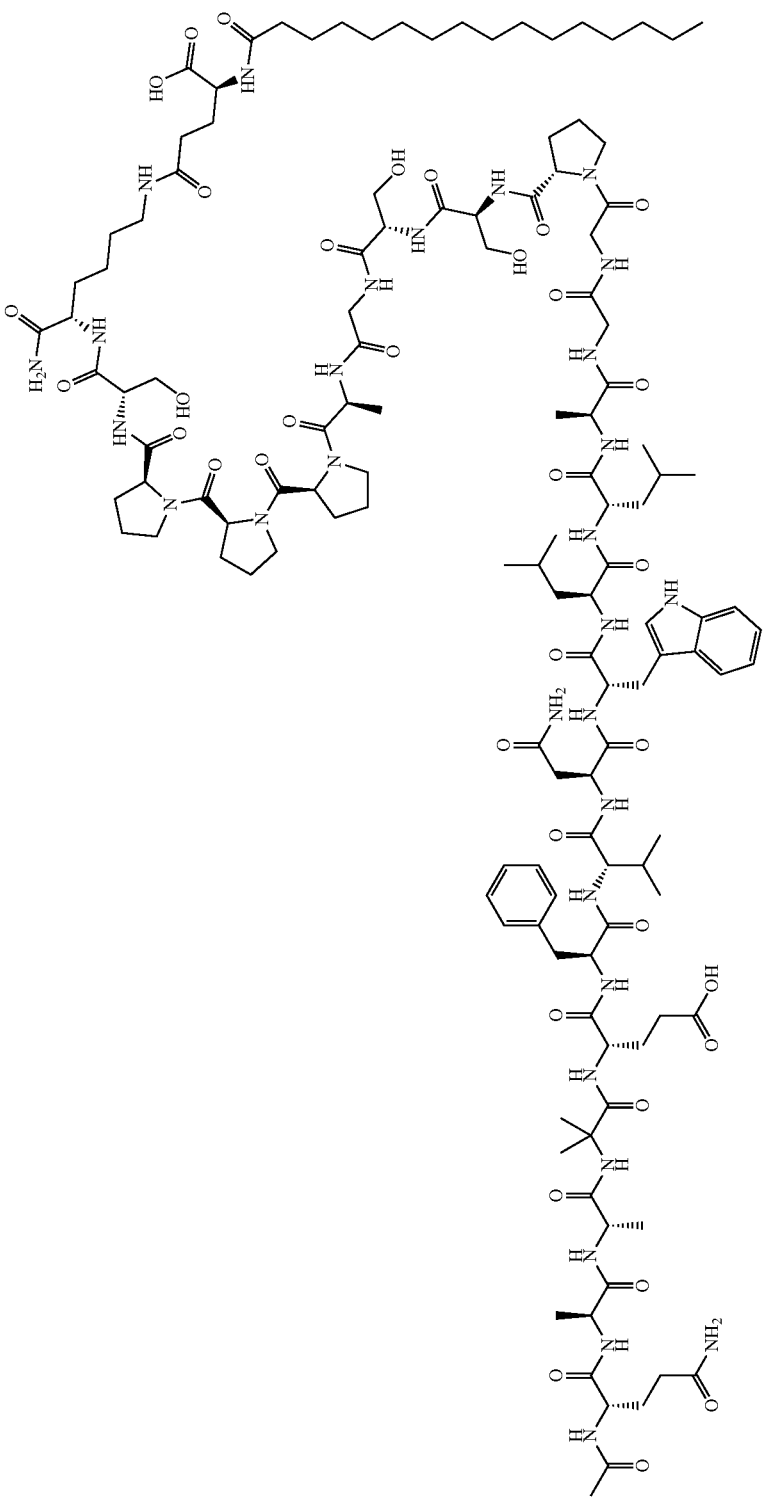

557
Compound 7
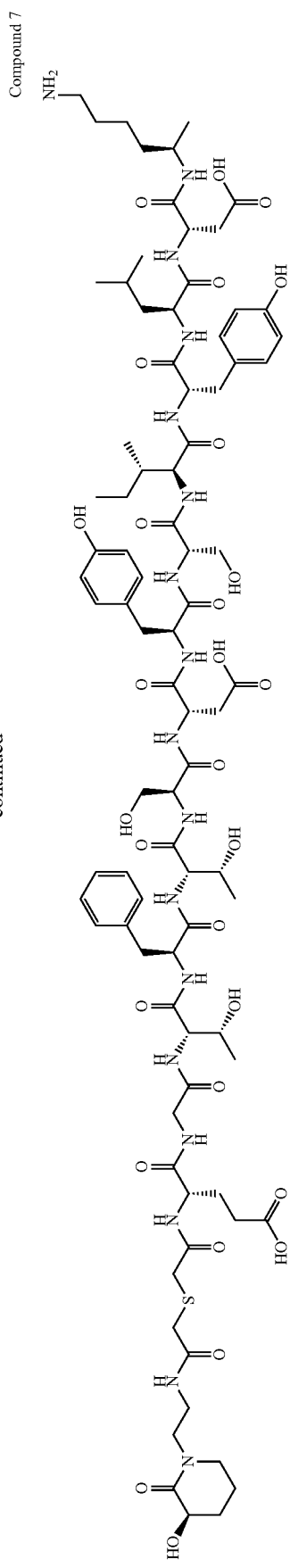
-continued
558
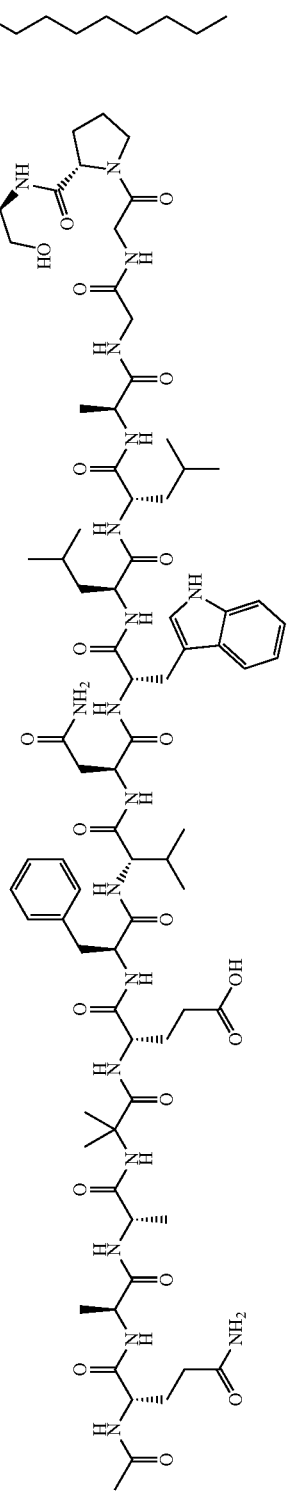

559
Compound 8
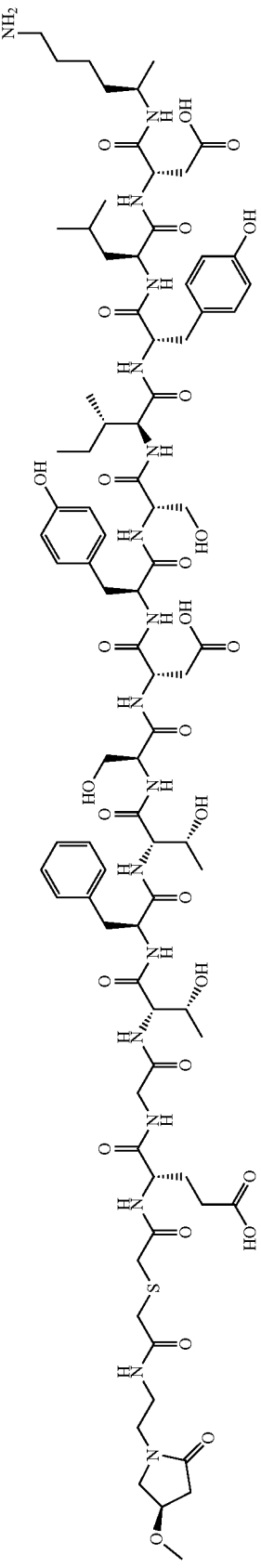
-continued
560
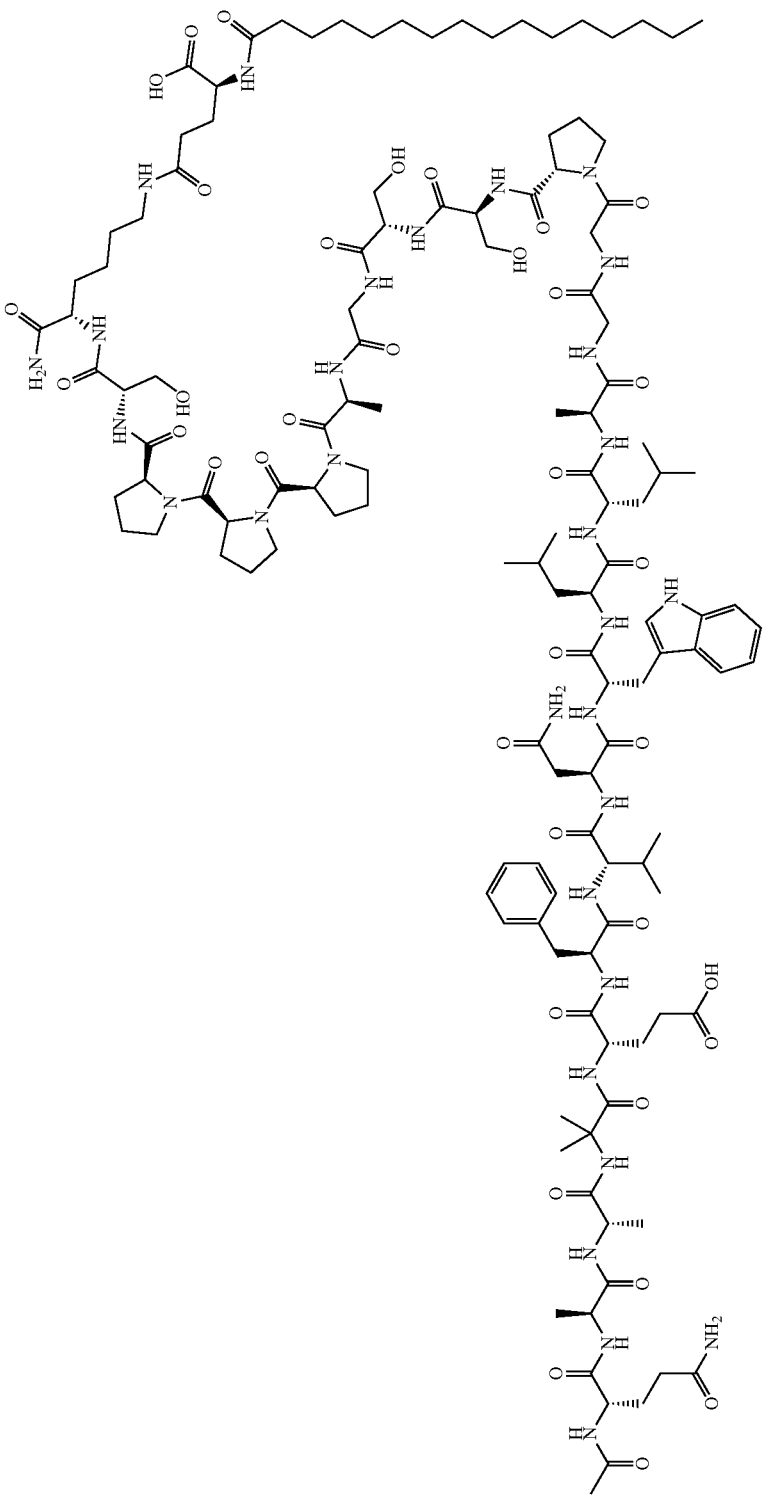

Compound 9
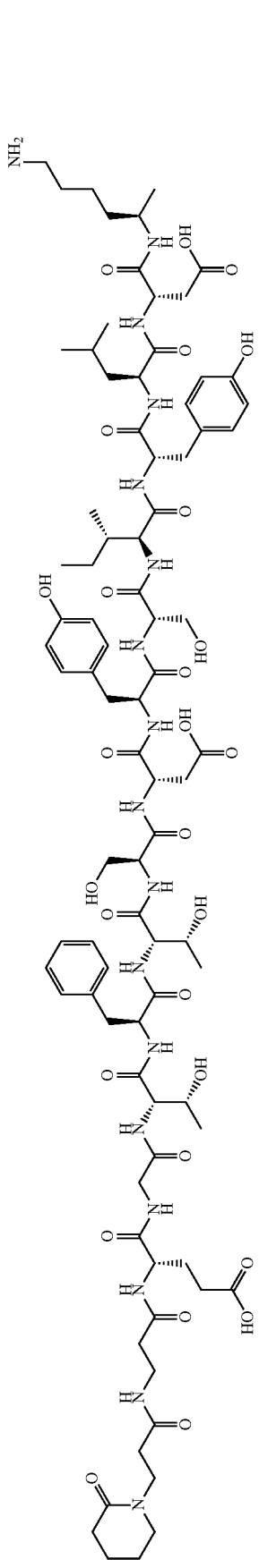
561
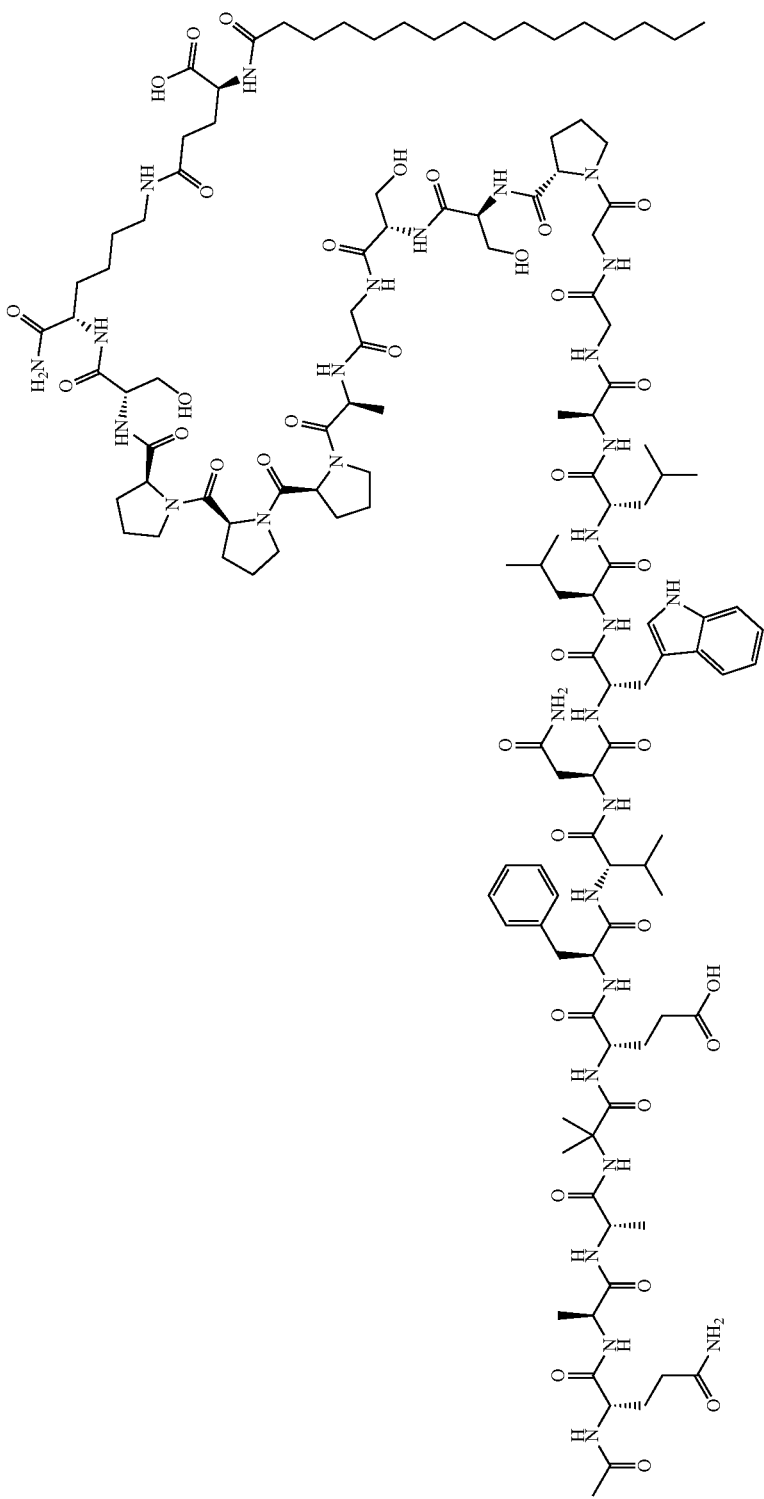
562

563
Compound 10
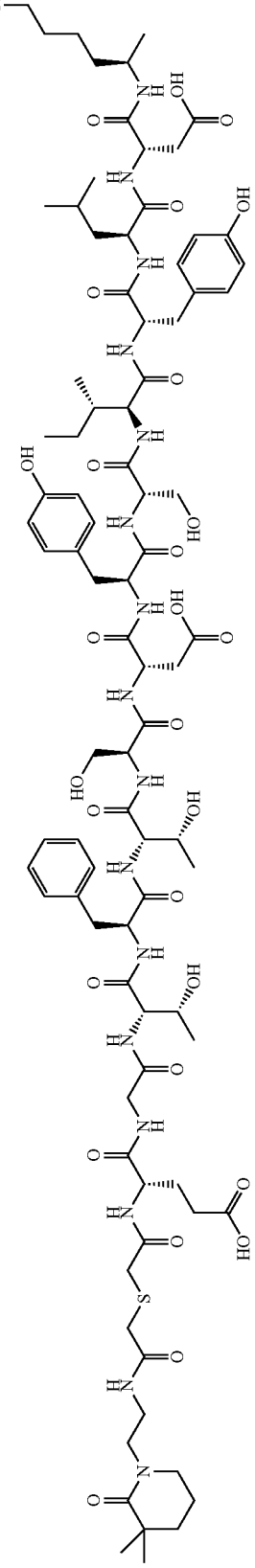
-continued
564
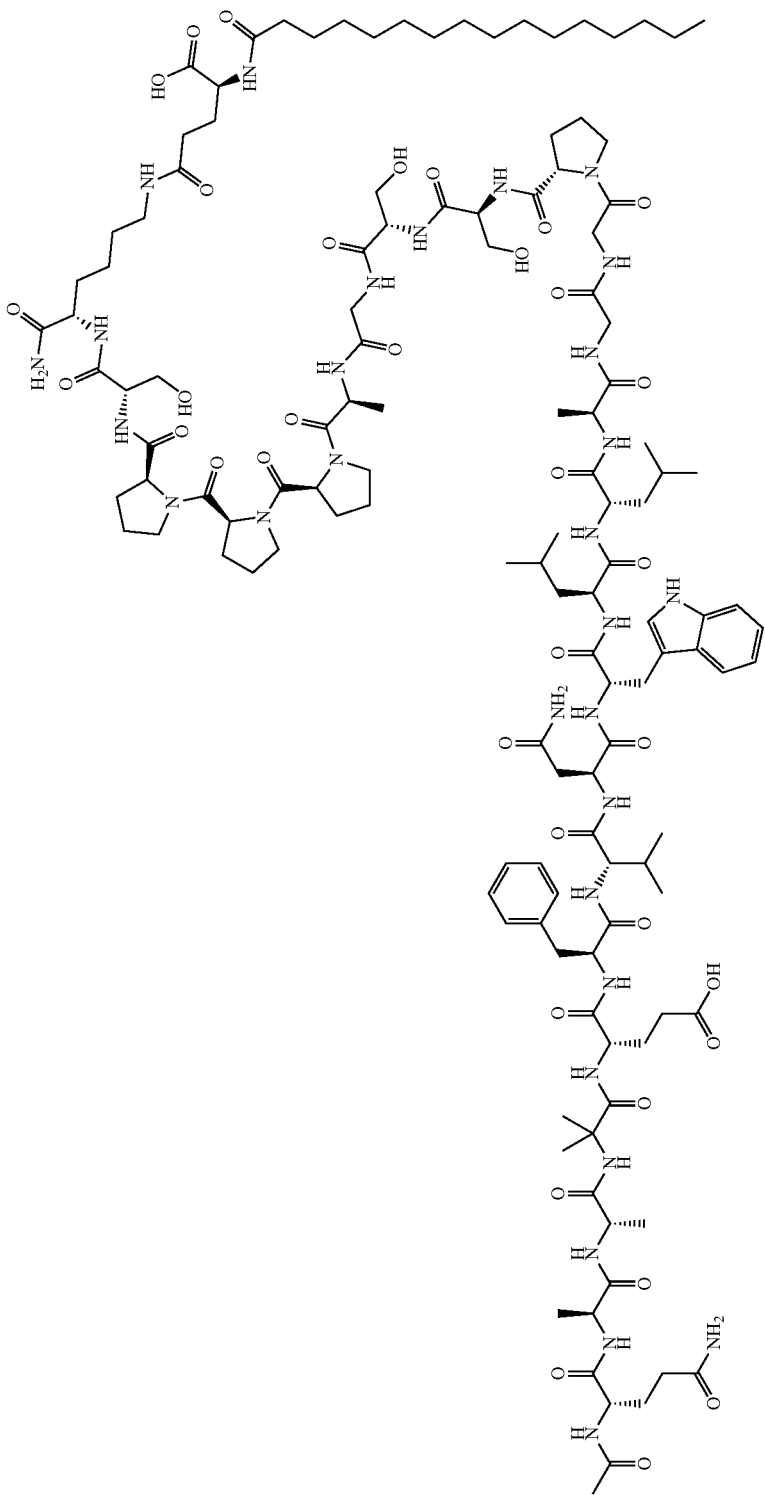

565
Compound 11
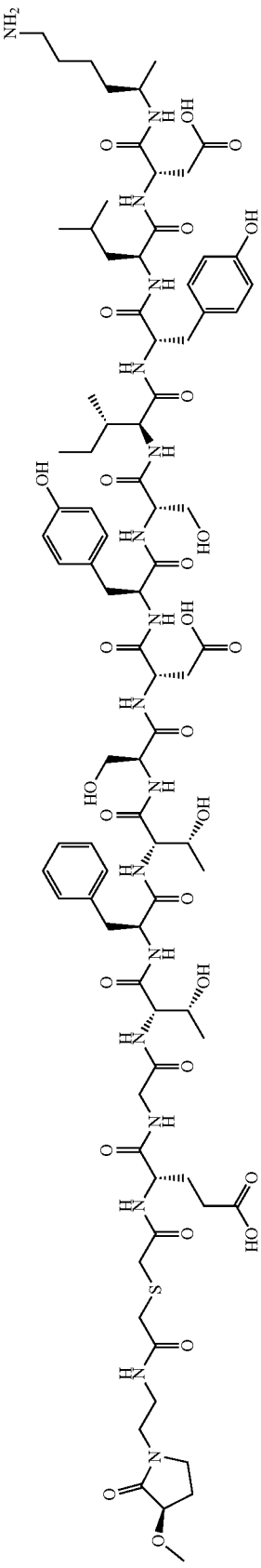
566
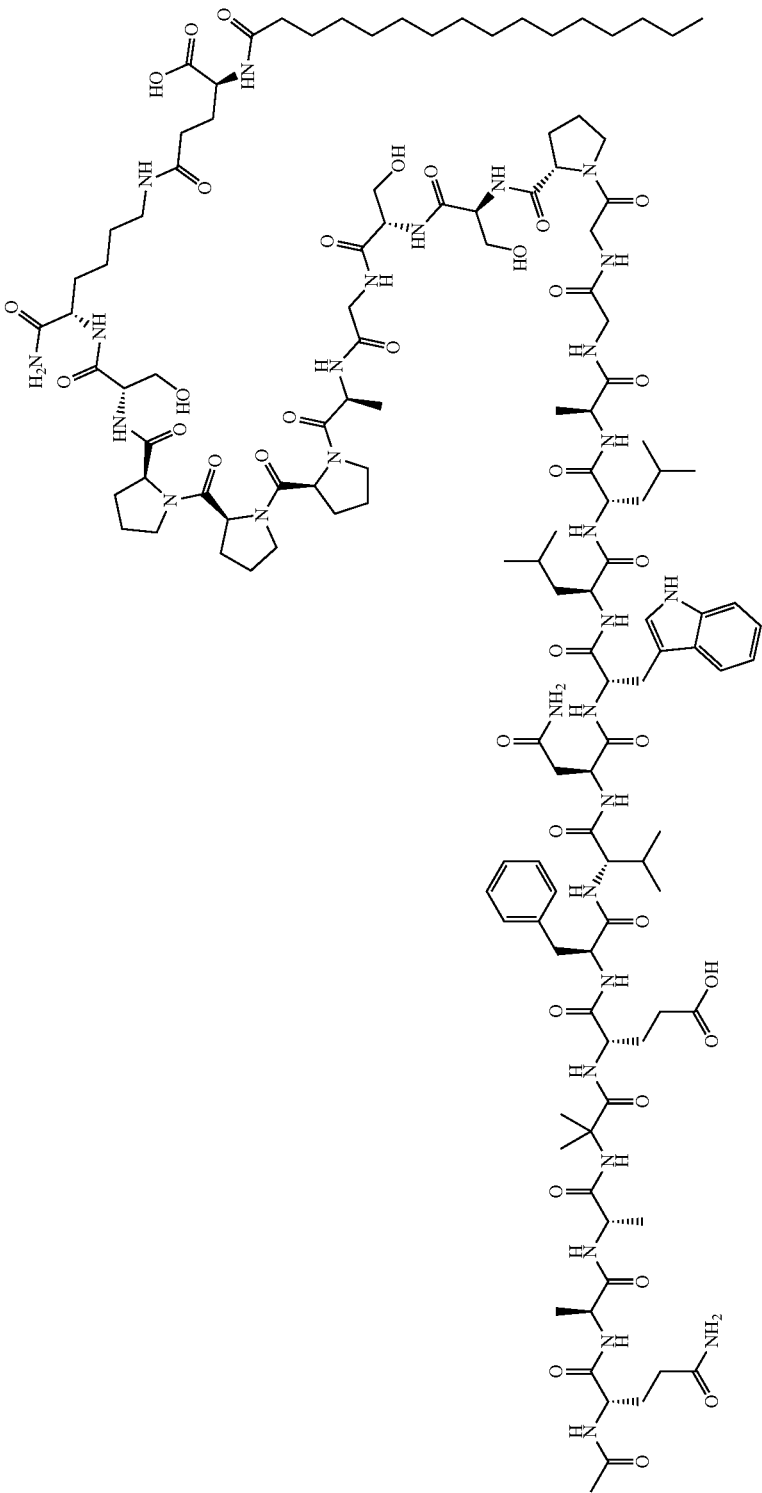

Compound 12
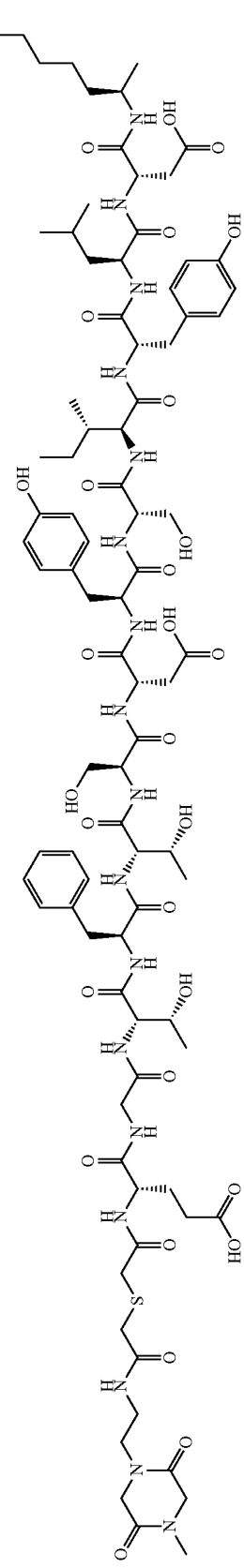
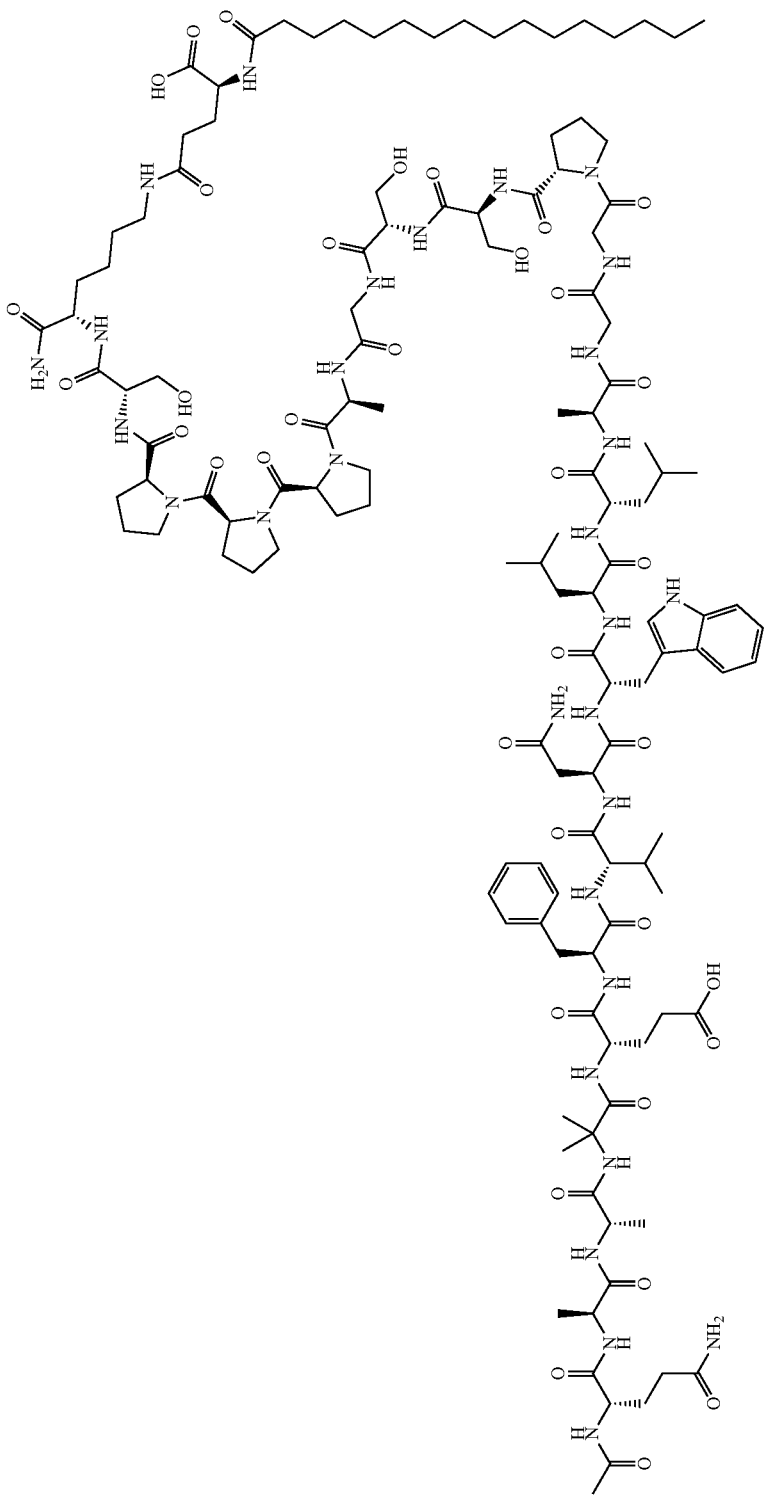

Compound 13
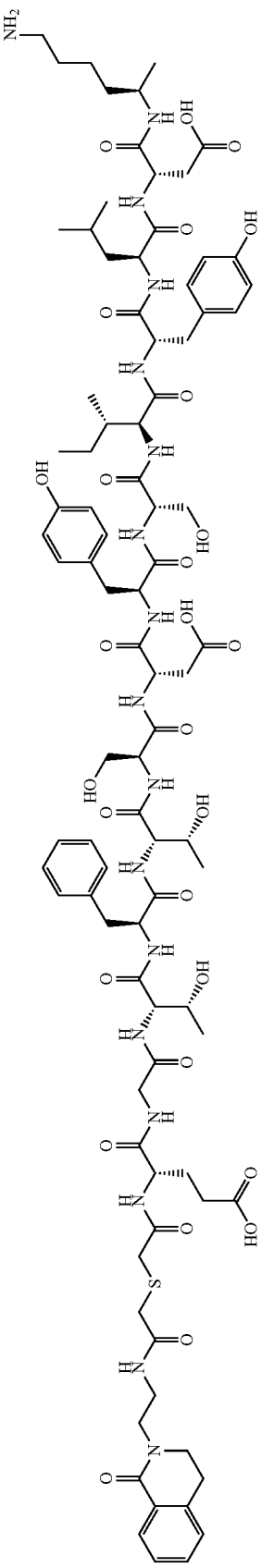
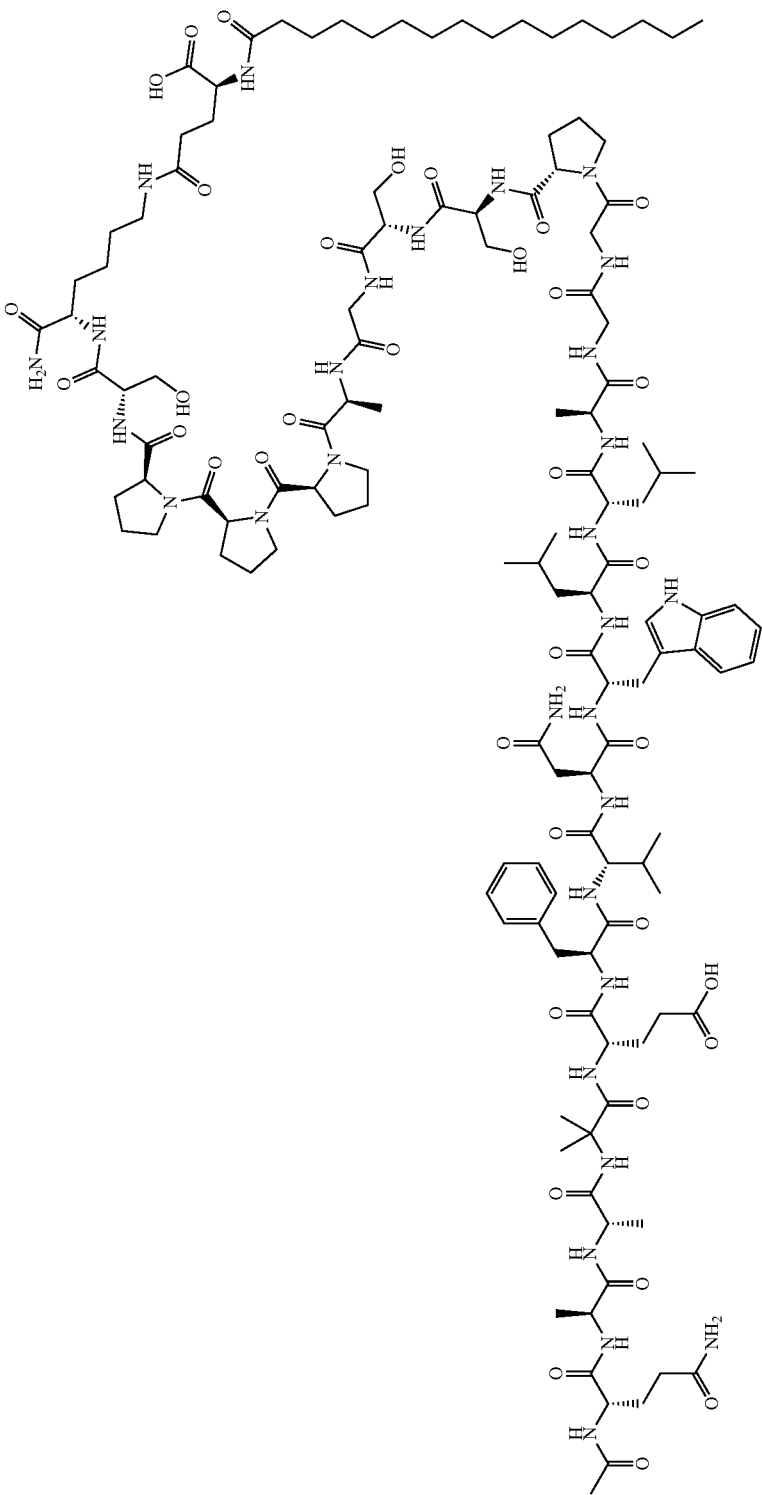

571
572
Compound 14
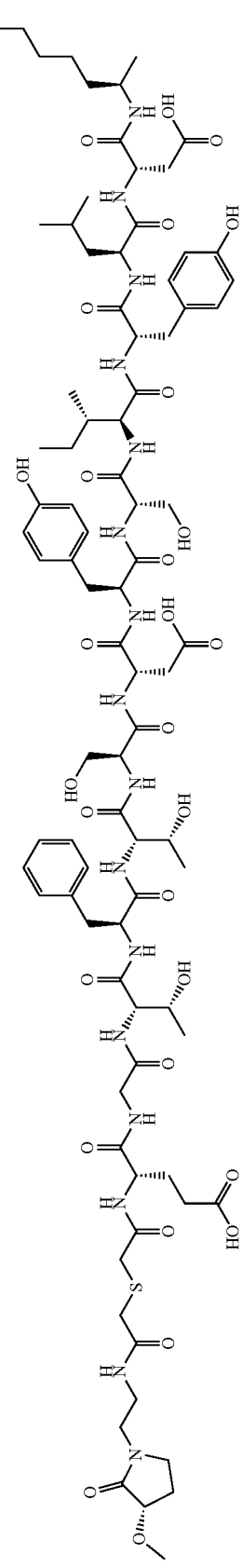
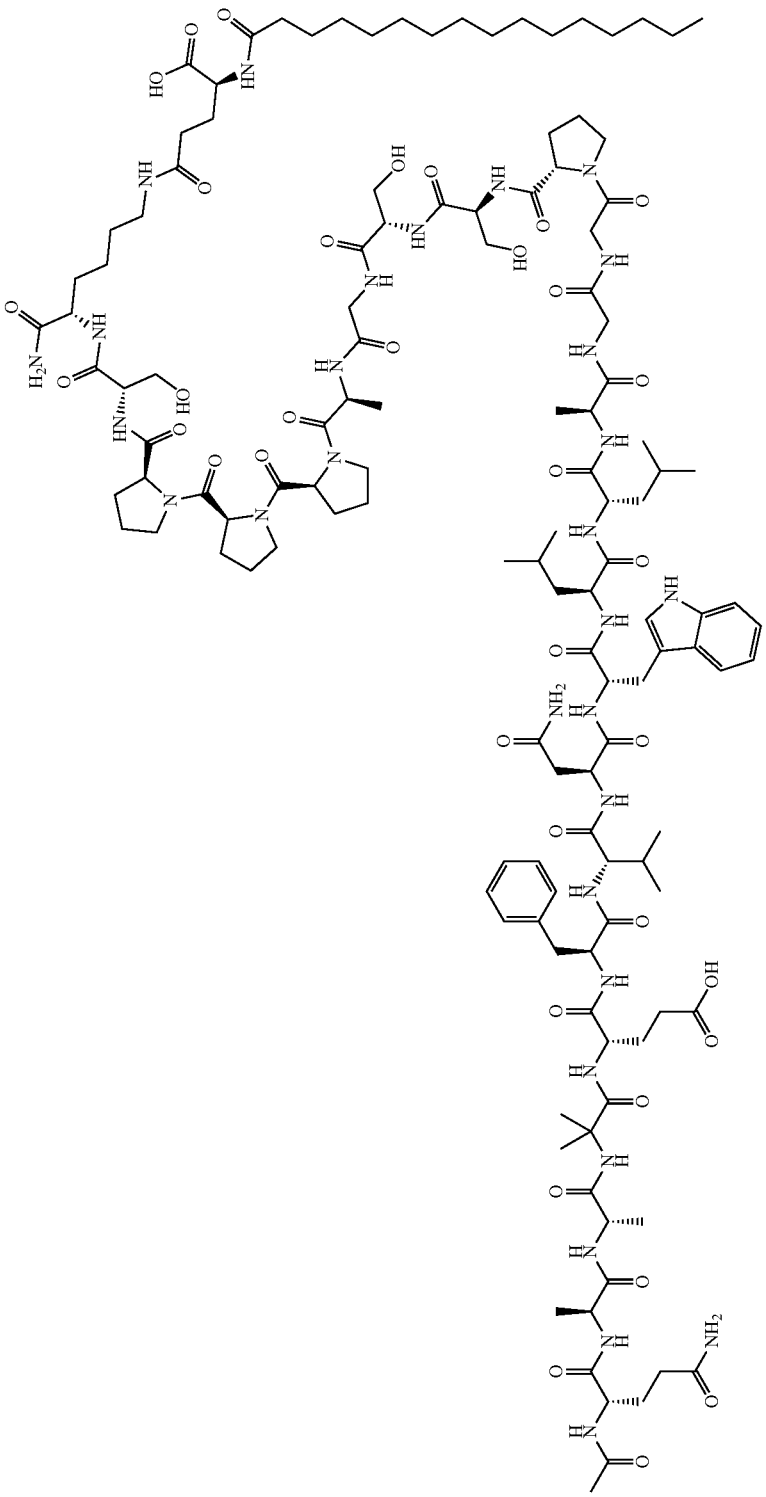
-continued

Compound 15
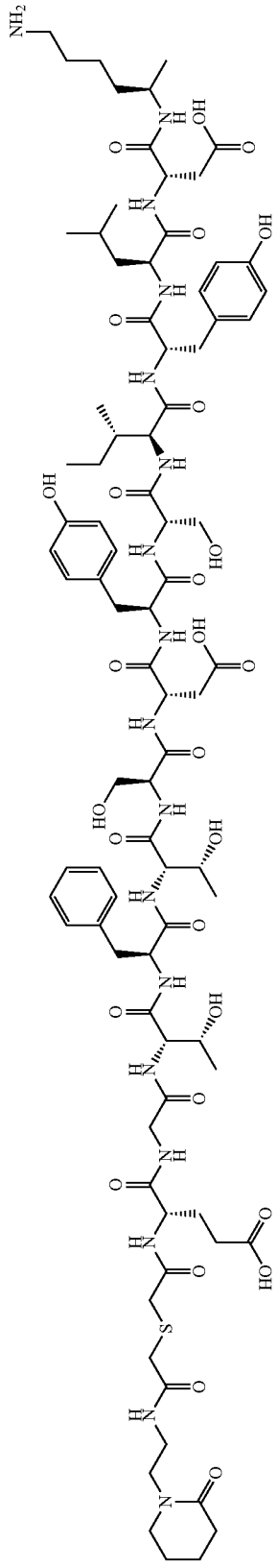
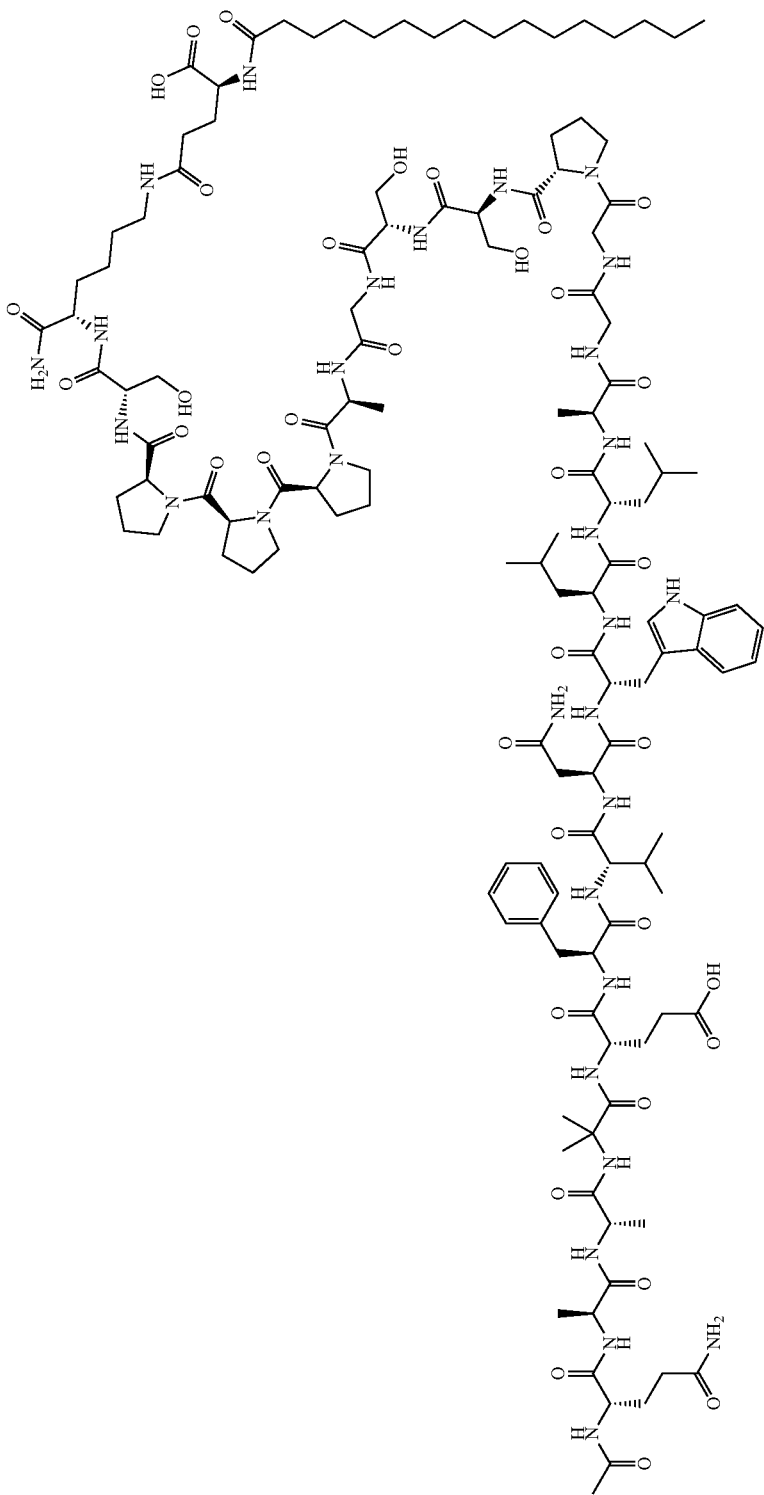

Compound 16
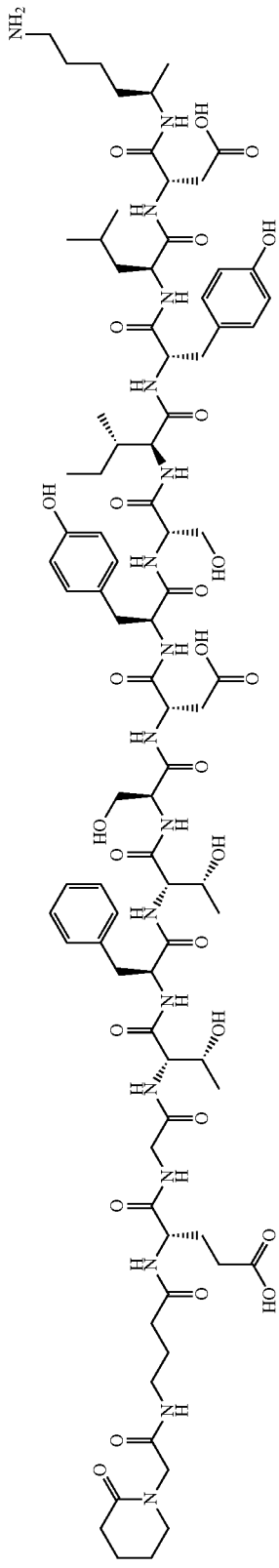
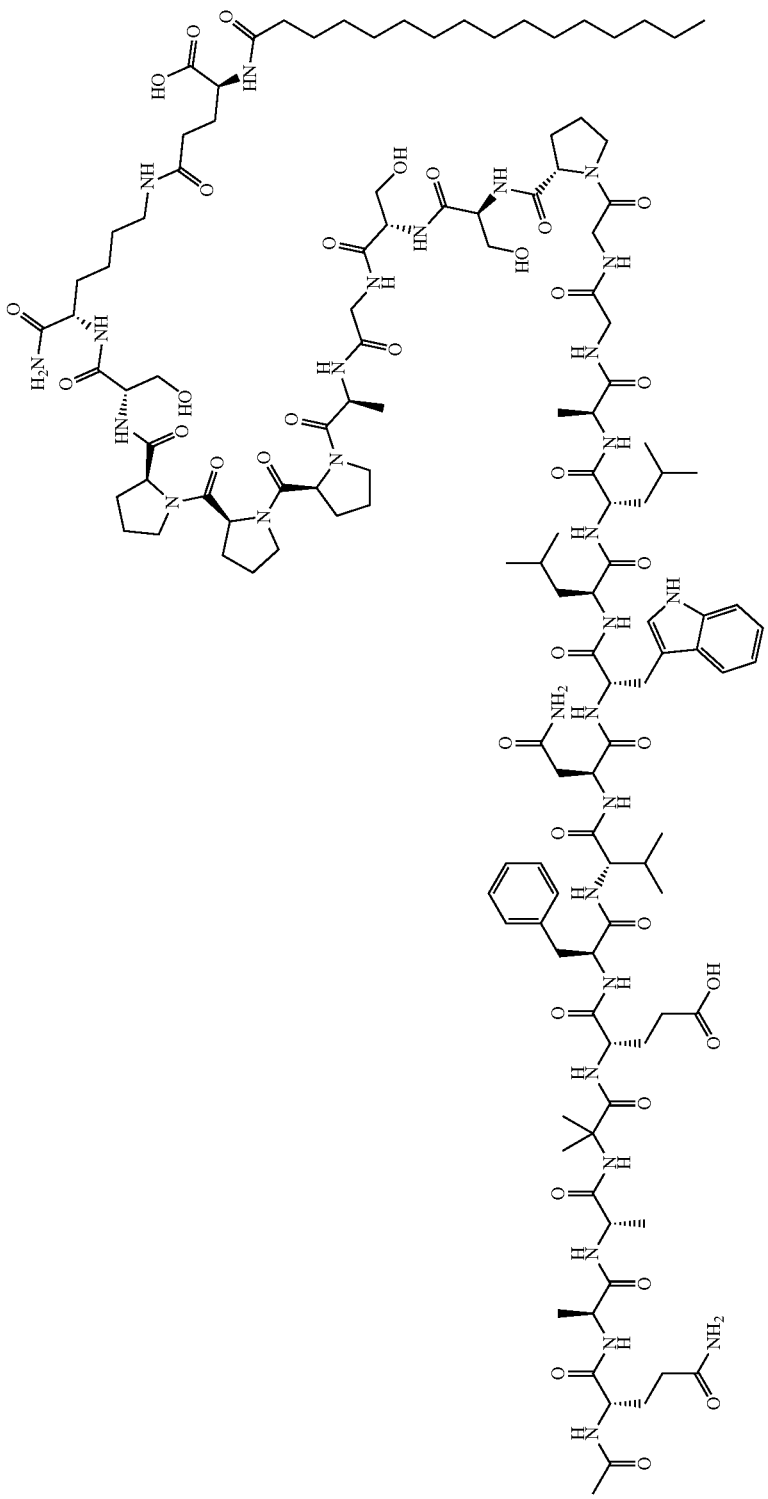

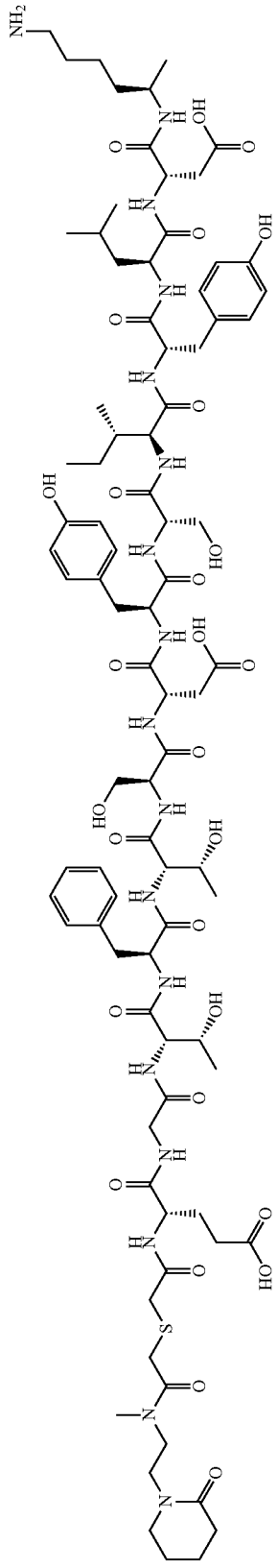
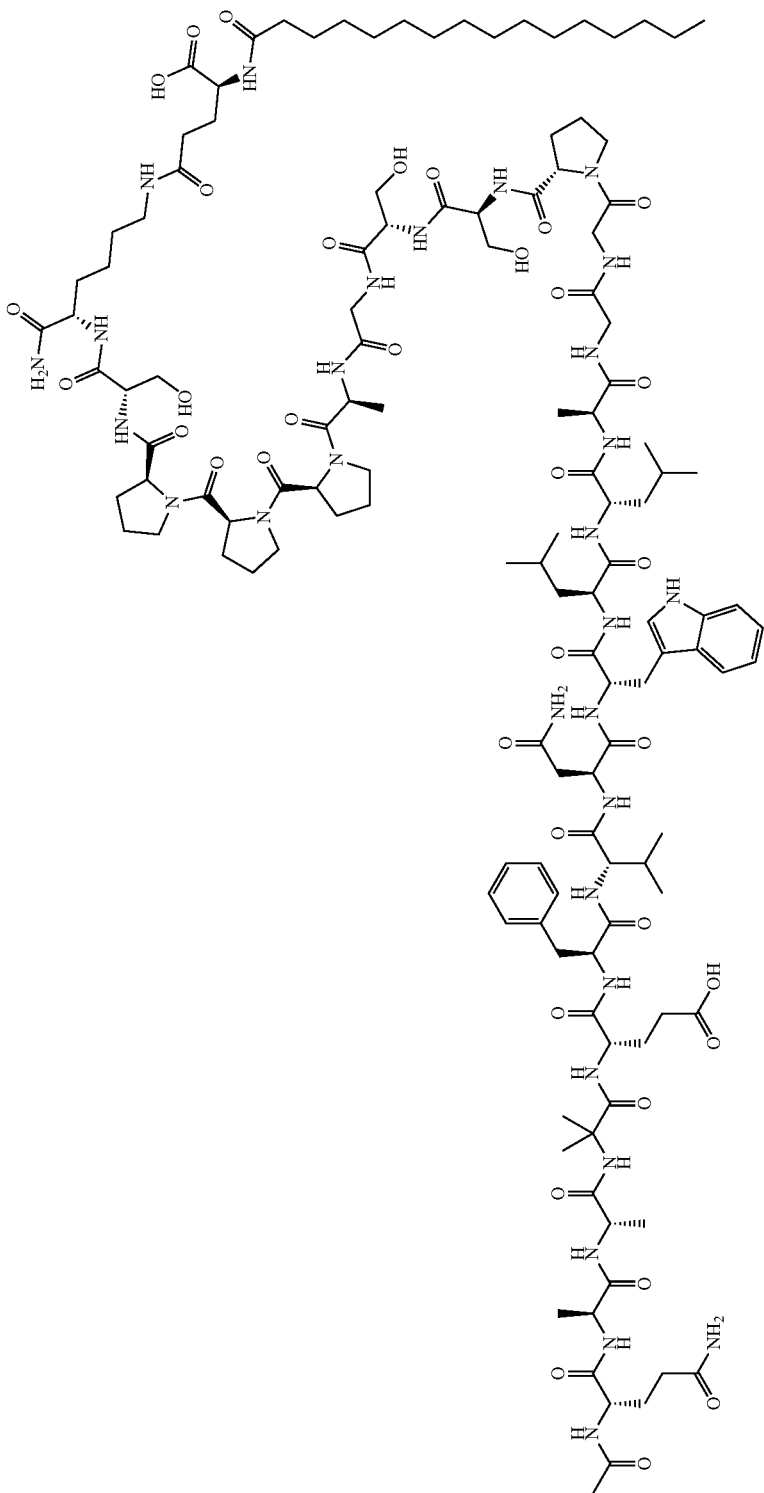
Compound 17

Compound 18
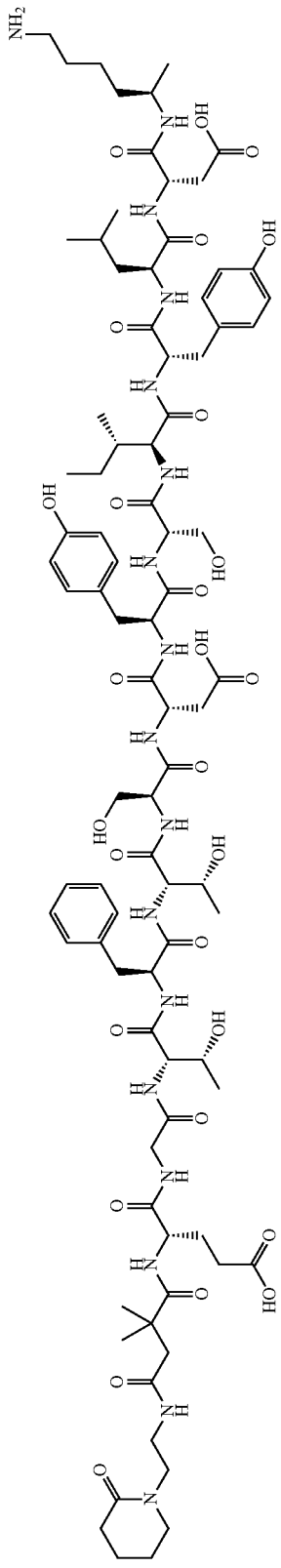
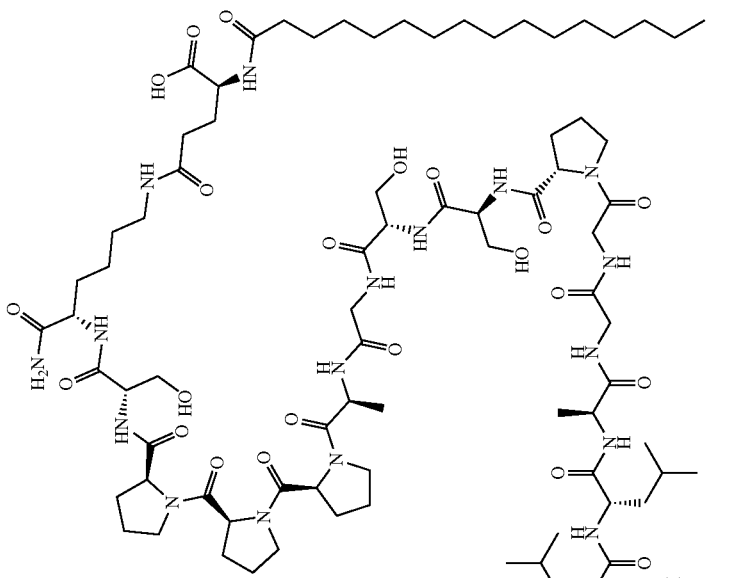
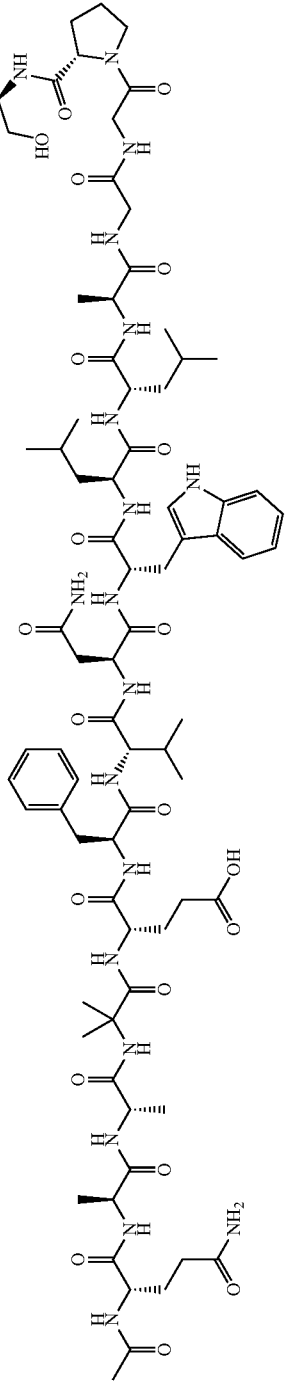

Compound 19
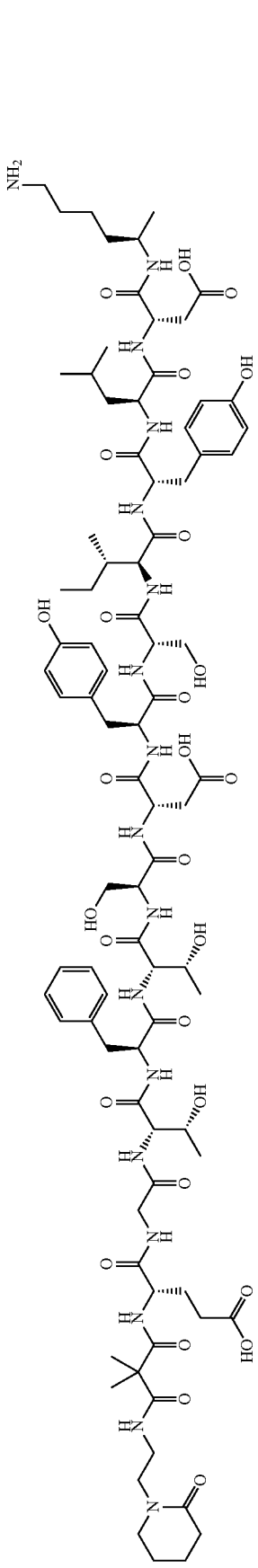
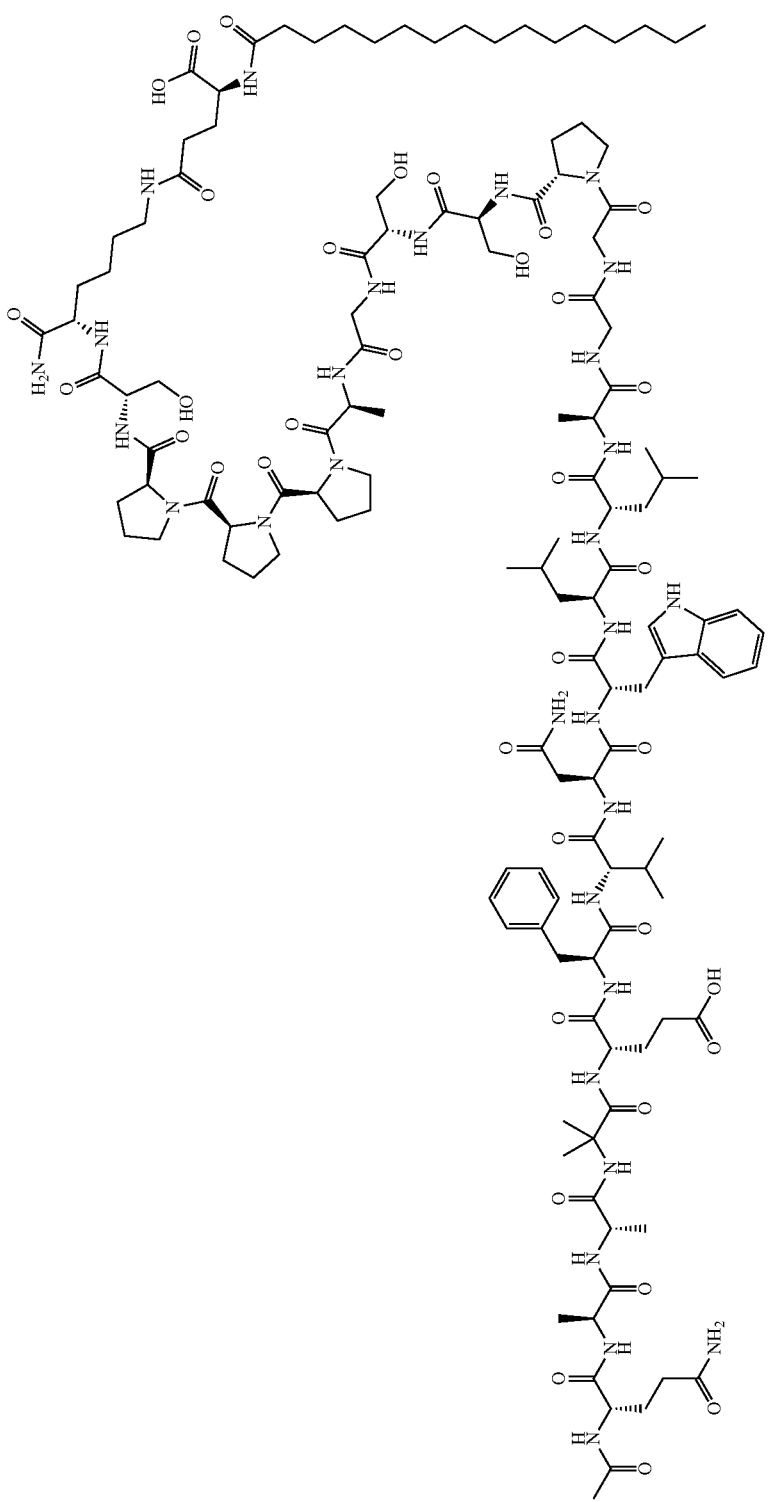

583
584
Compound 20
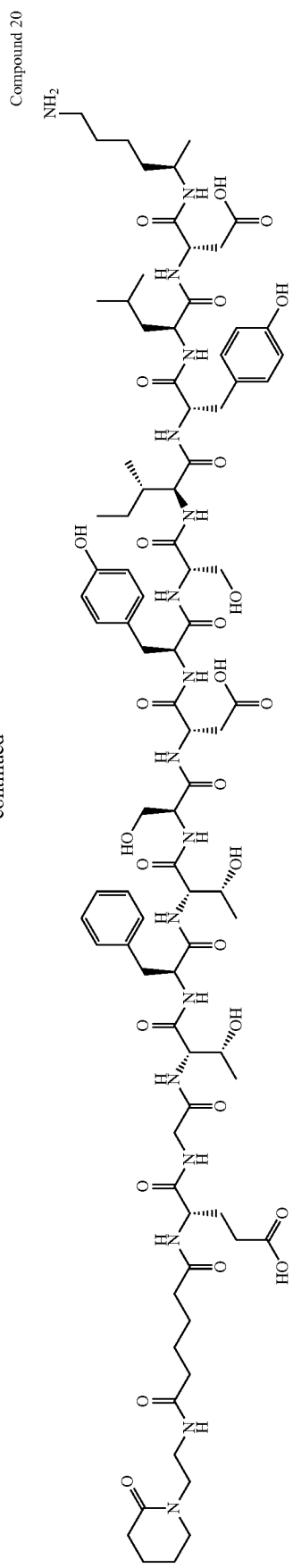
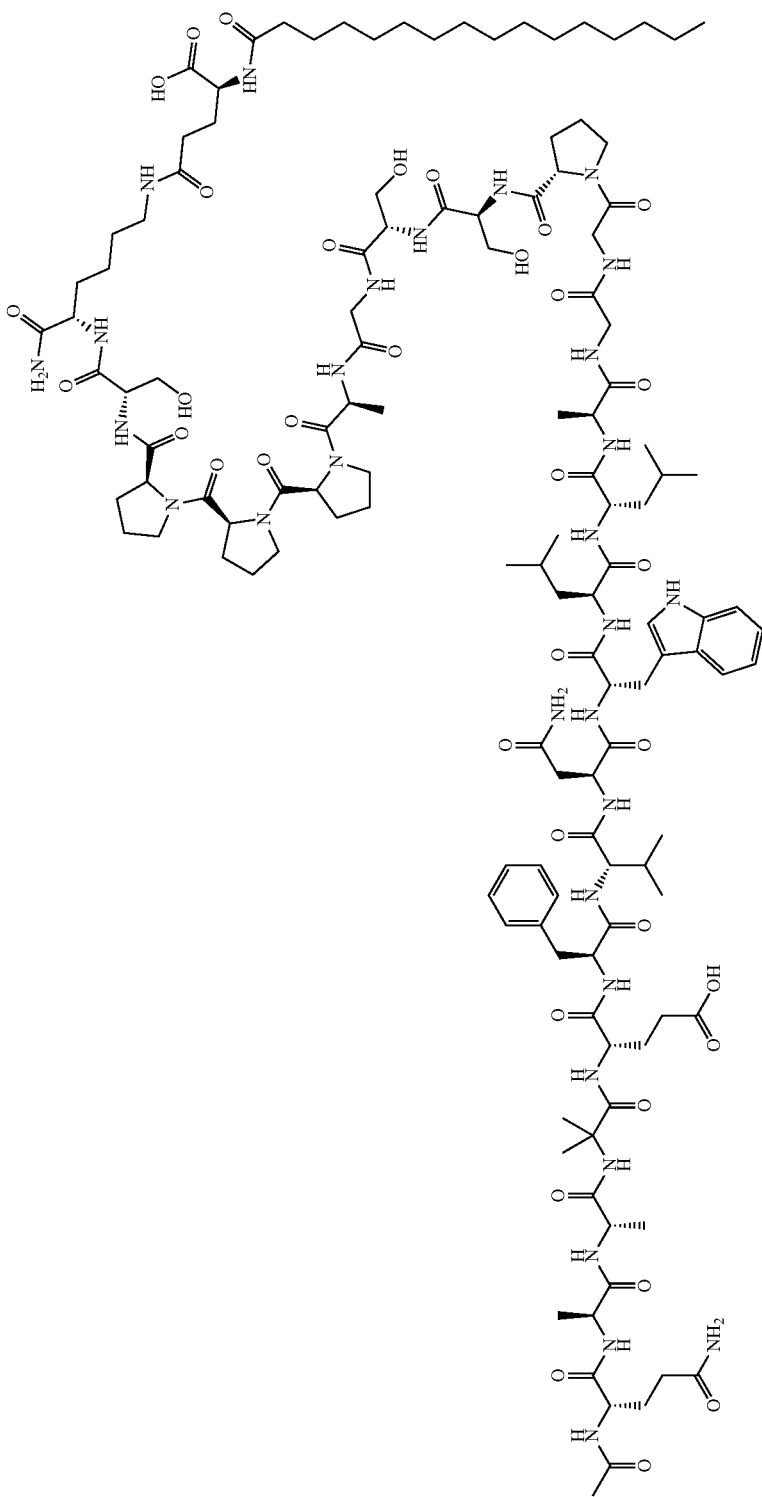

585
Compound 21
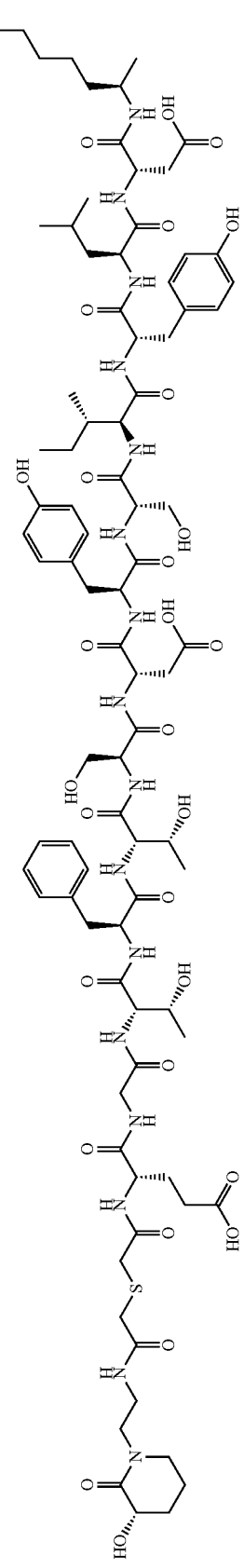
586
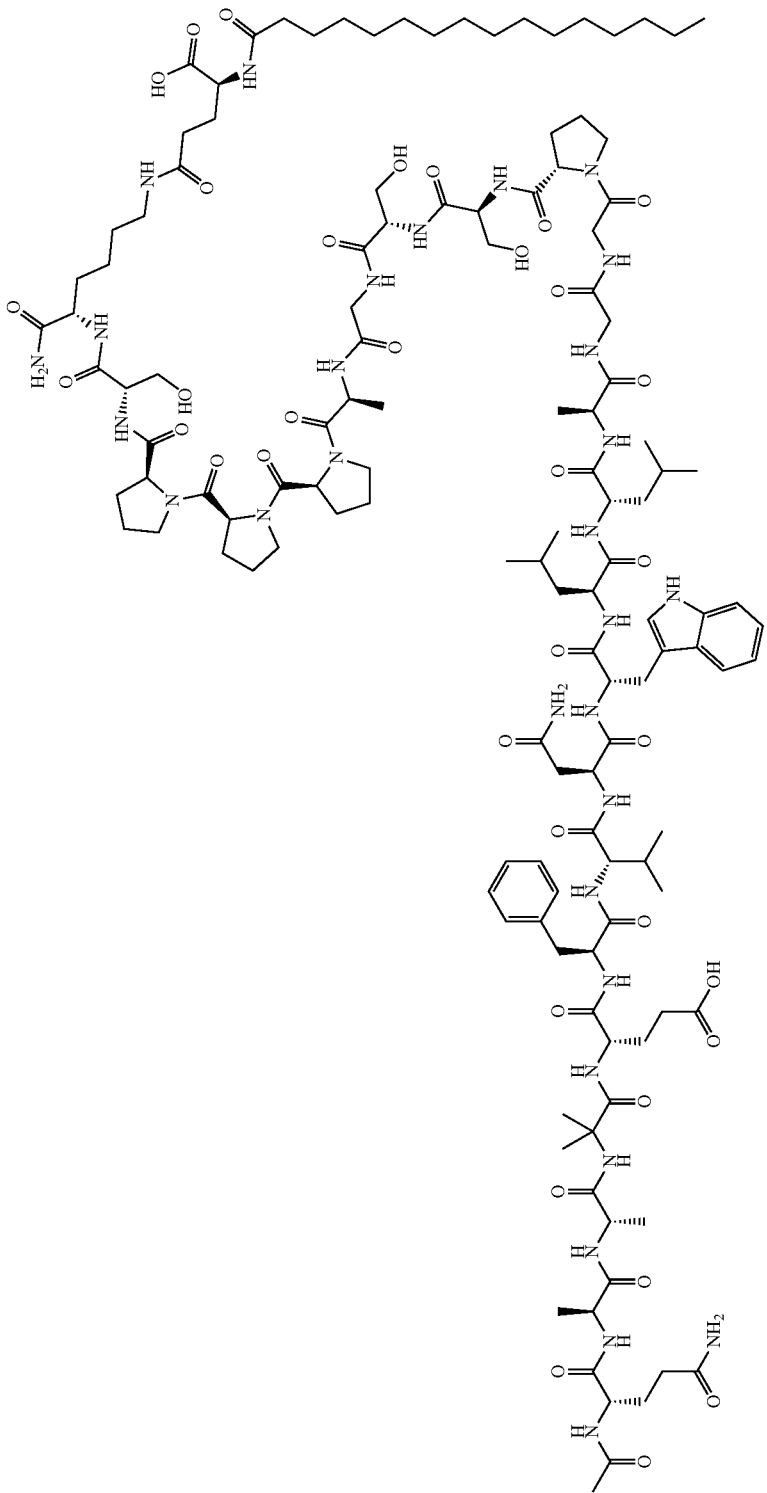

587
Compound 22
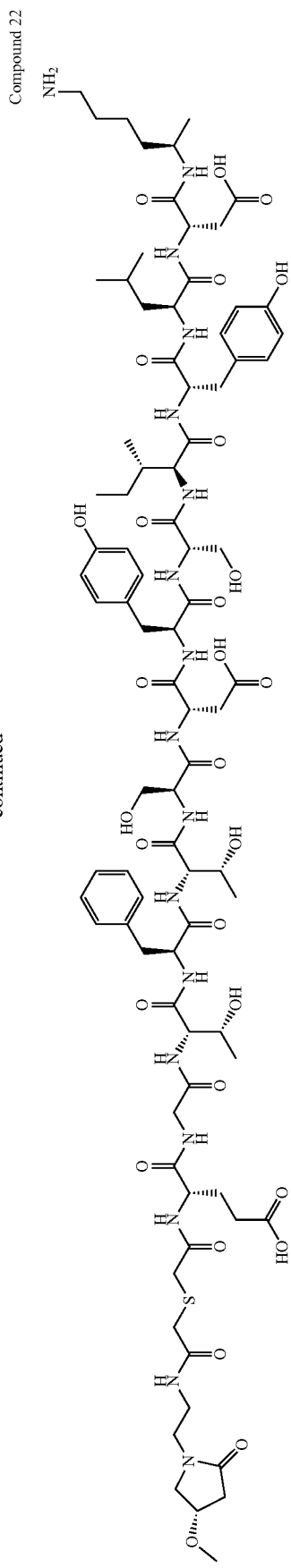
-continued
588
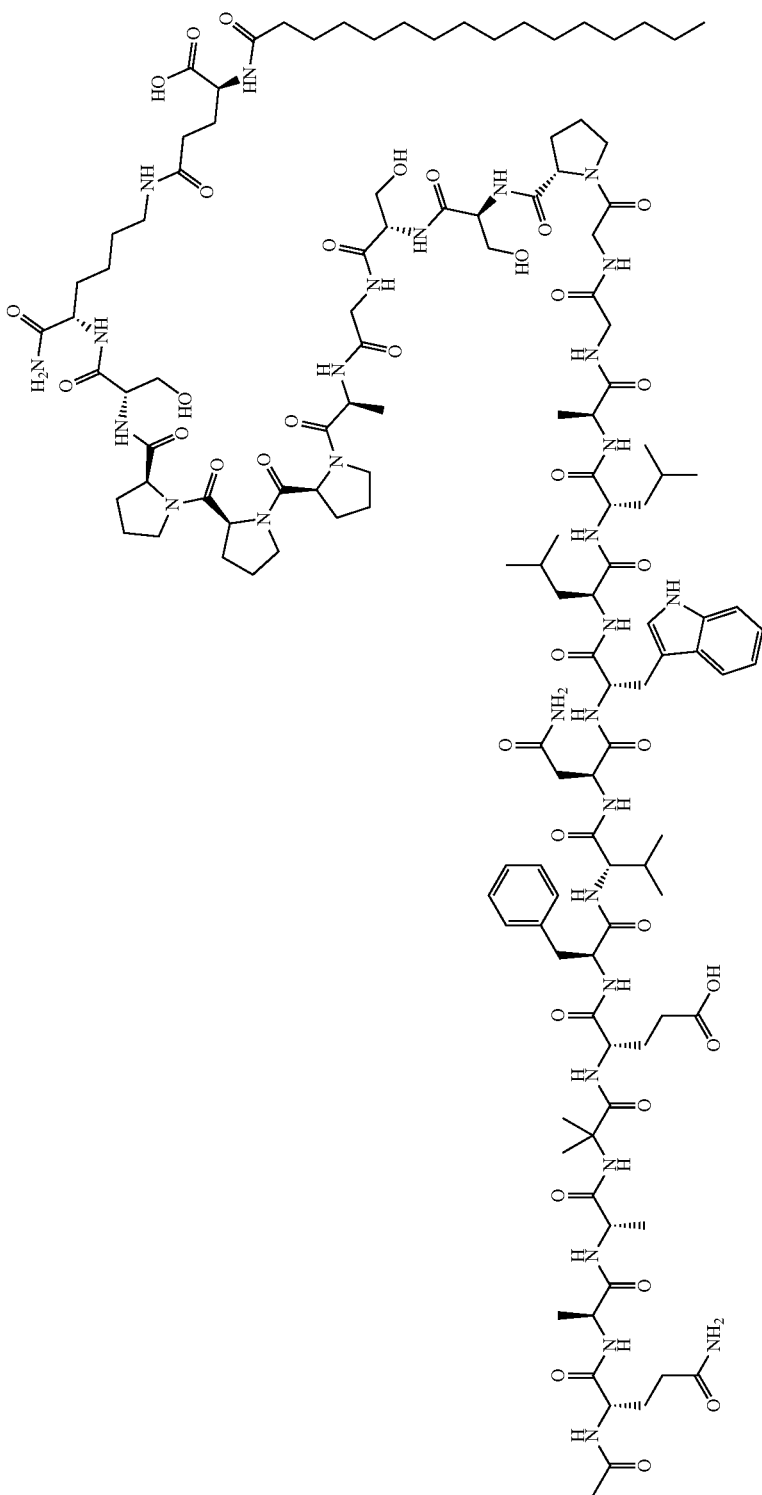

Compound 23
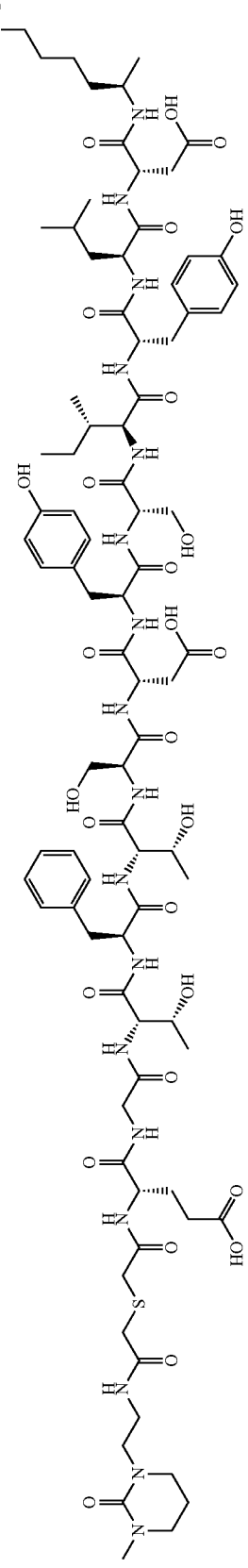
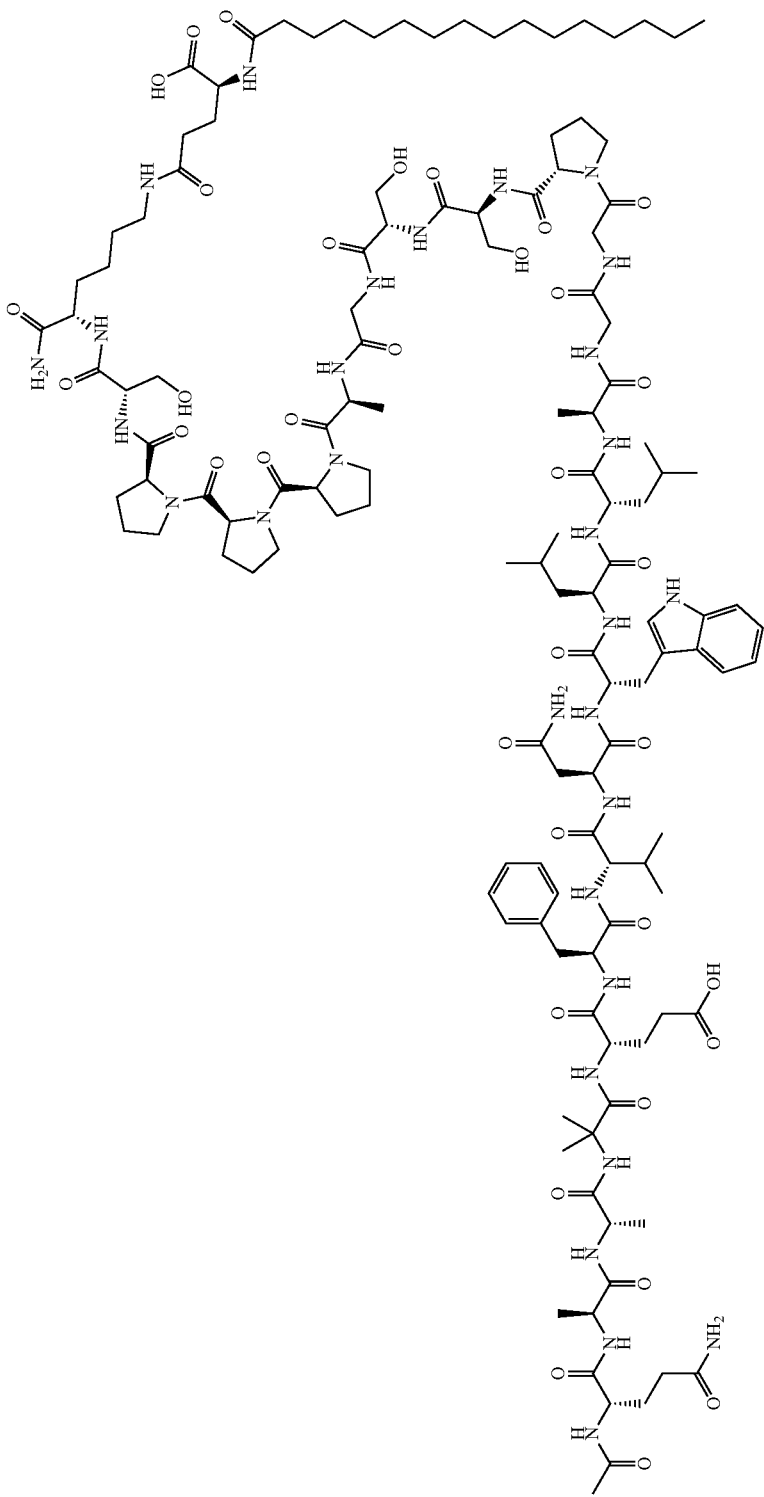

591
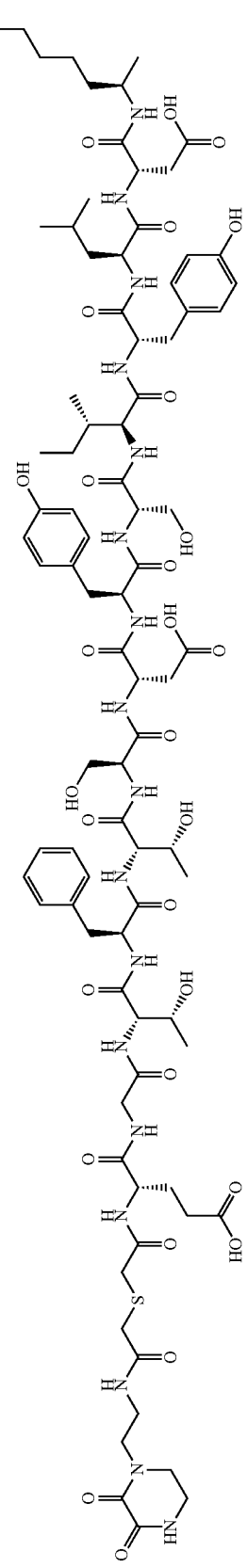
Compound 24
592
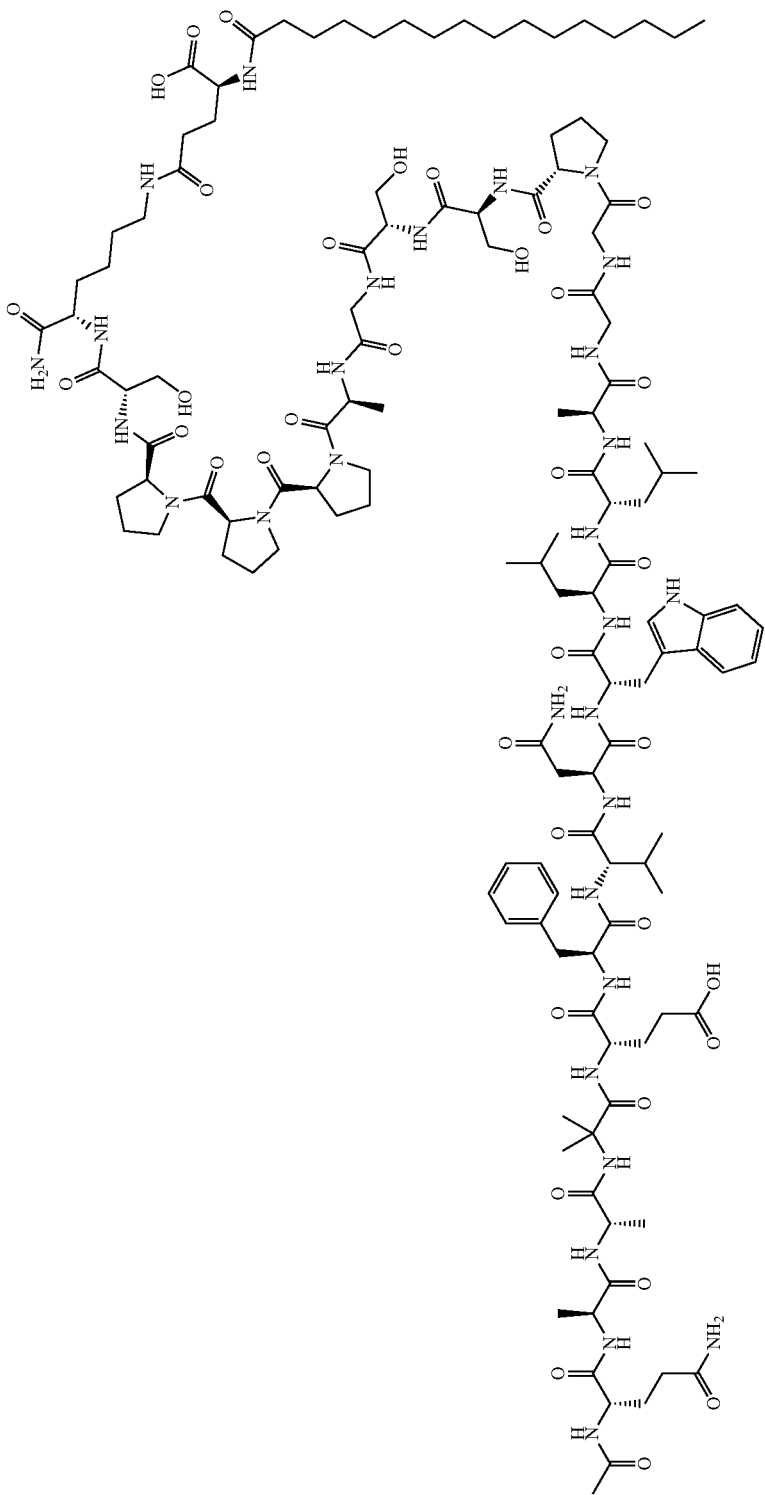

593 594
Compound 25
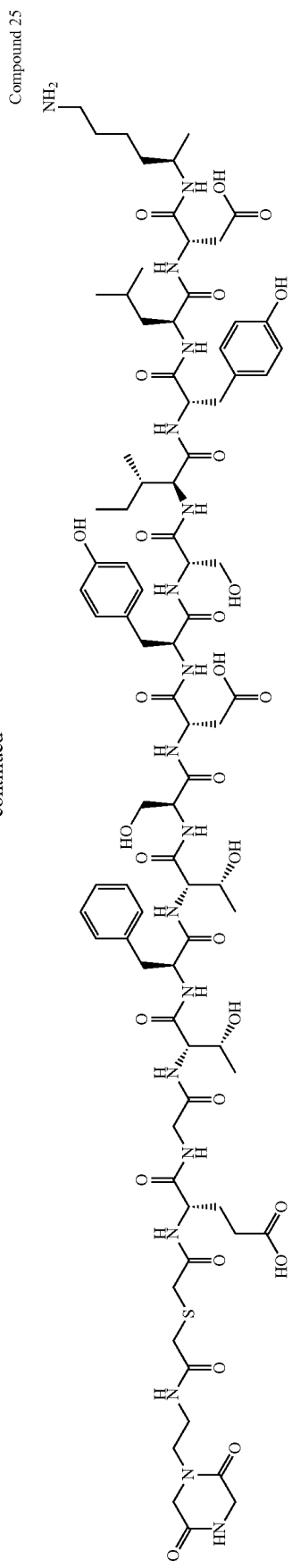
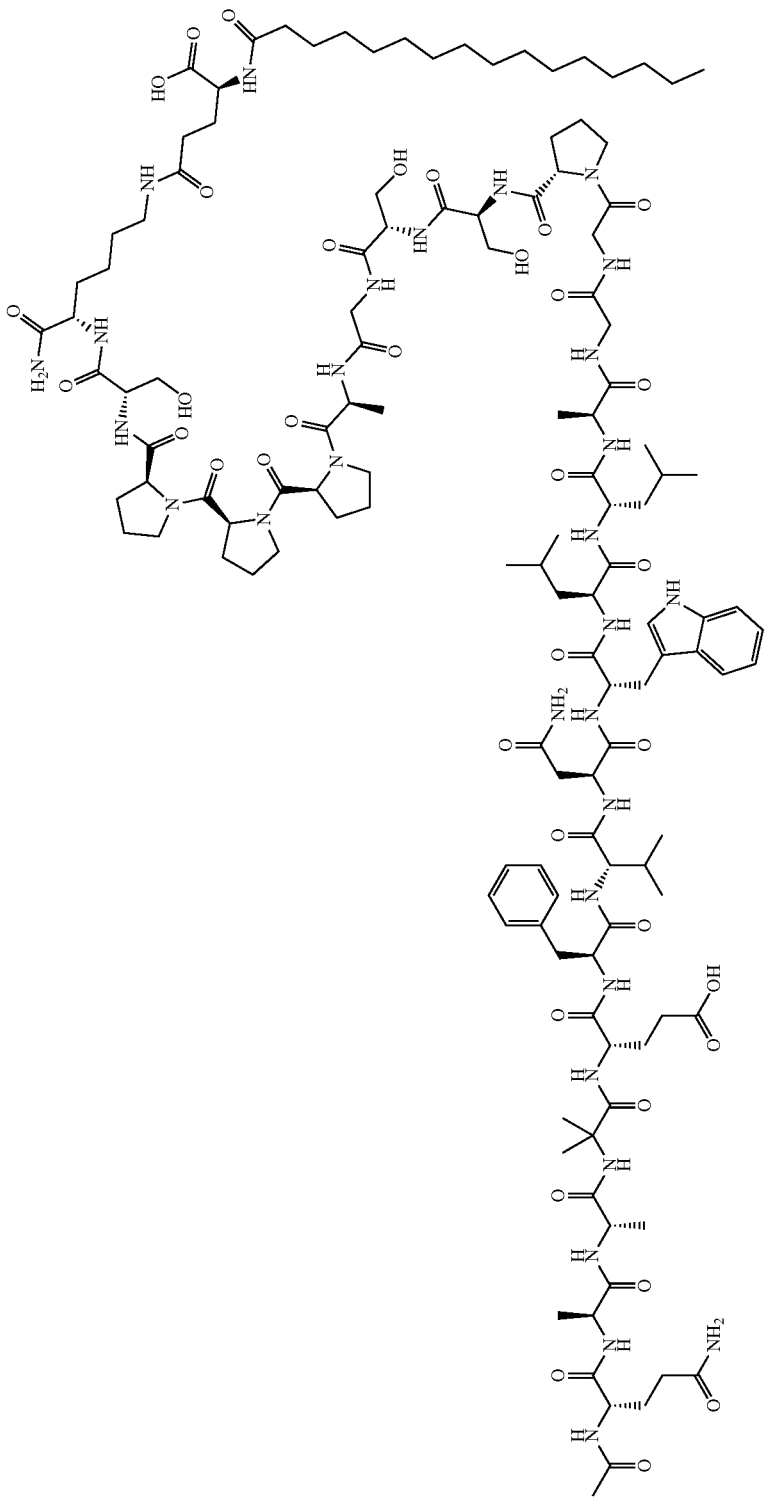
-continued 595    596
Compound 26
-continued
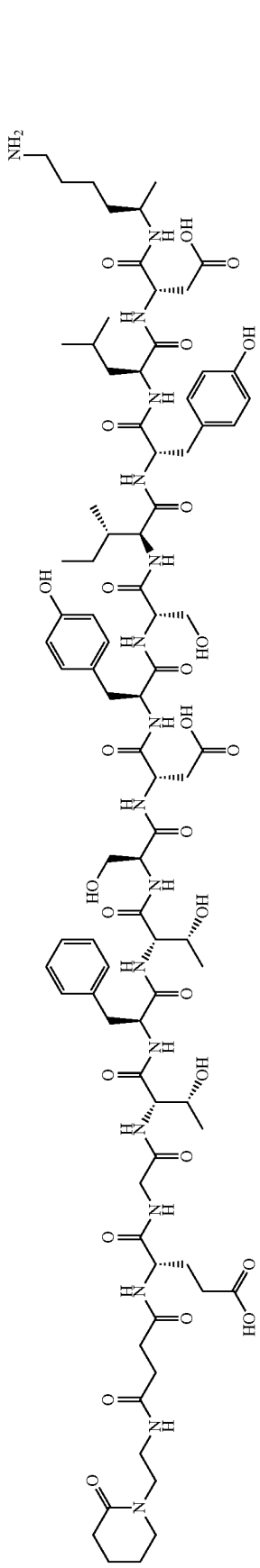
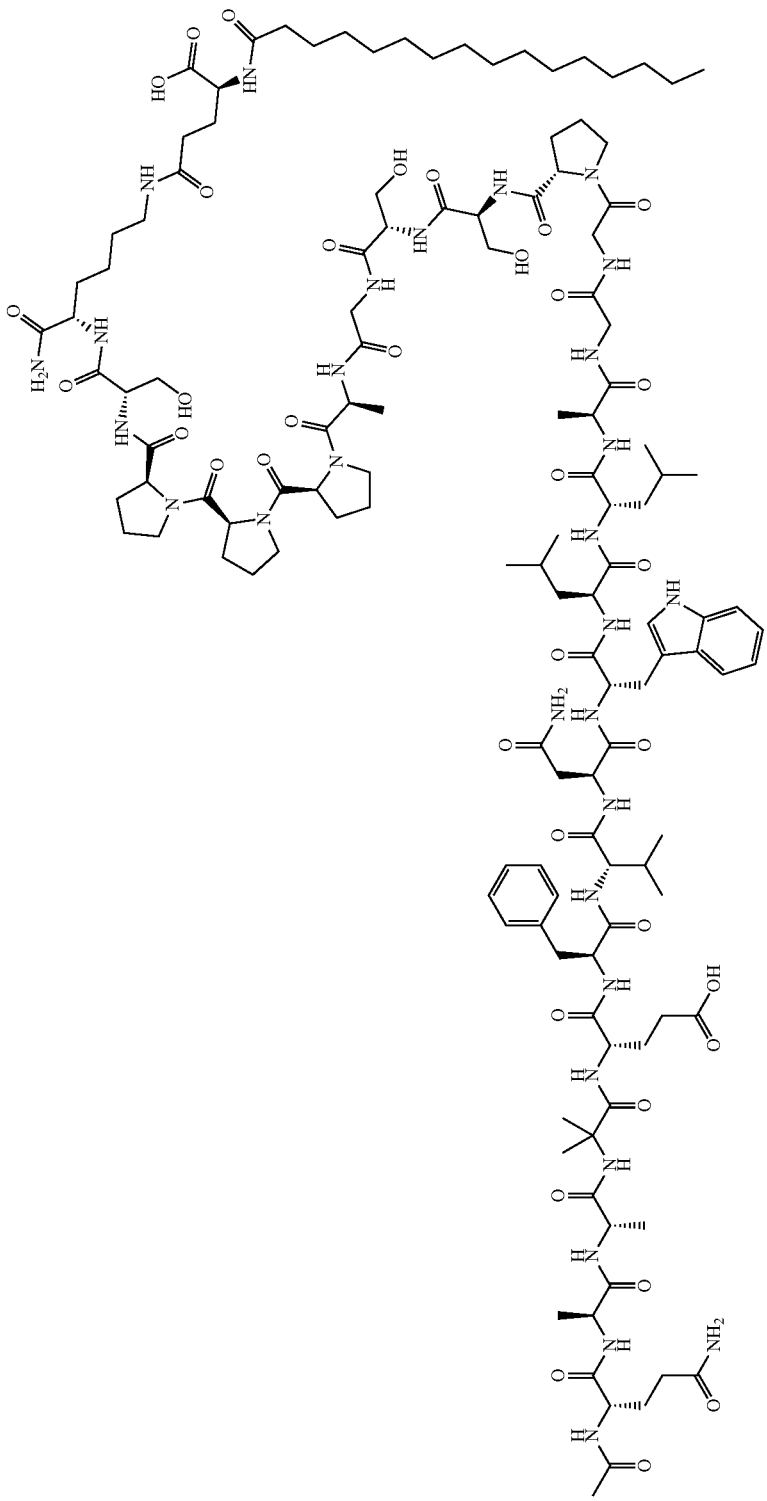

Compound 27 -continued
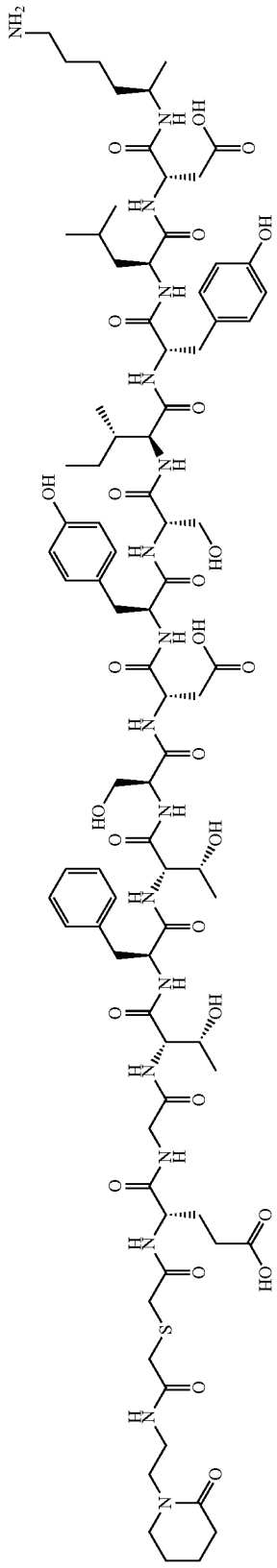
597
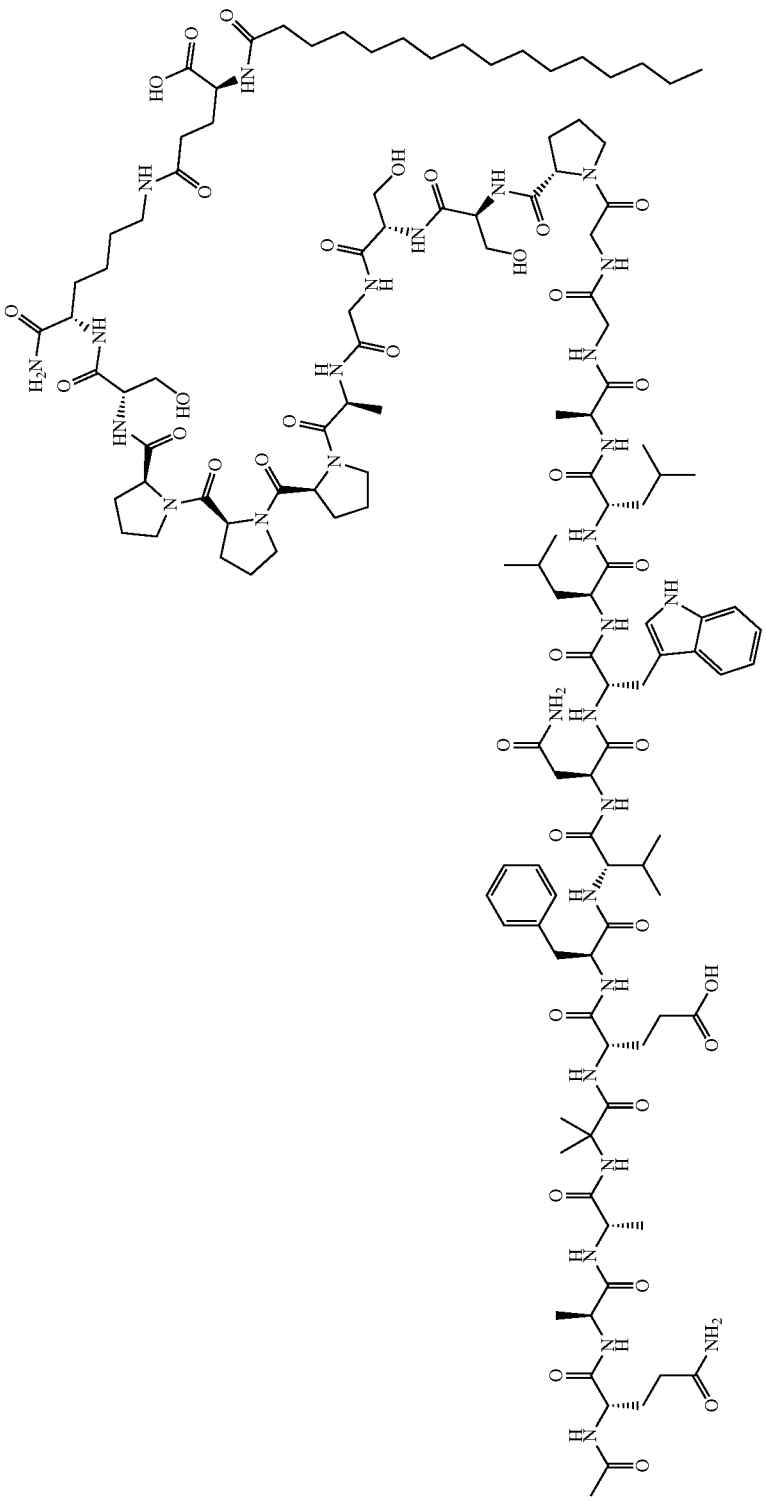
598

599
Compound 28
600
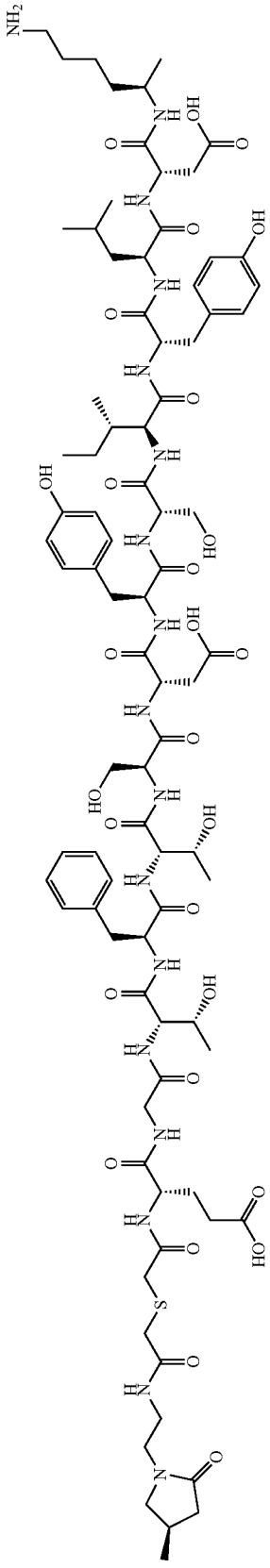
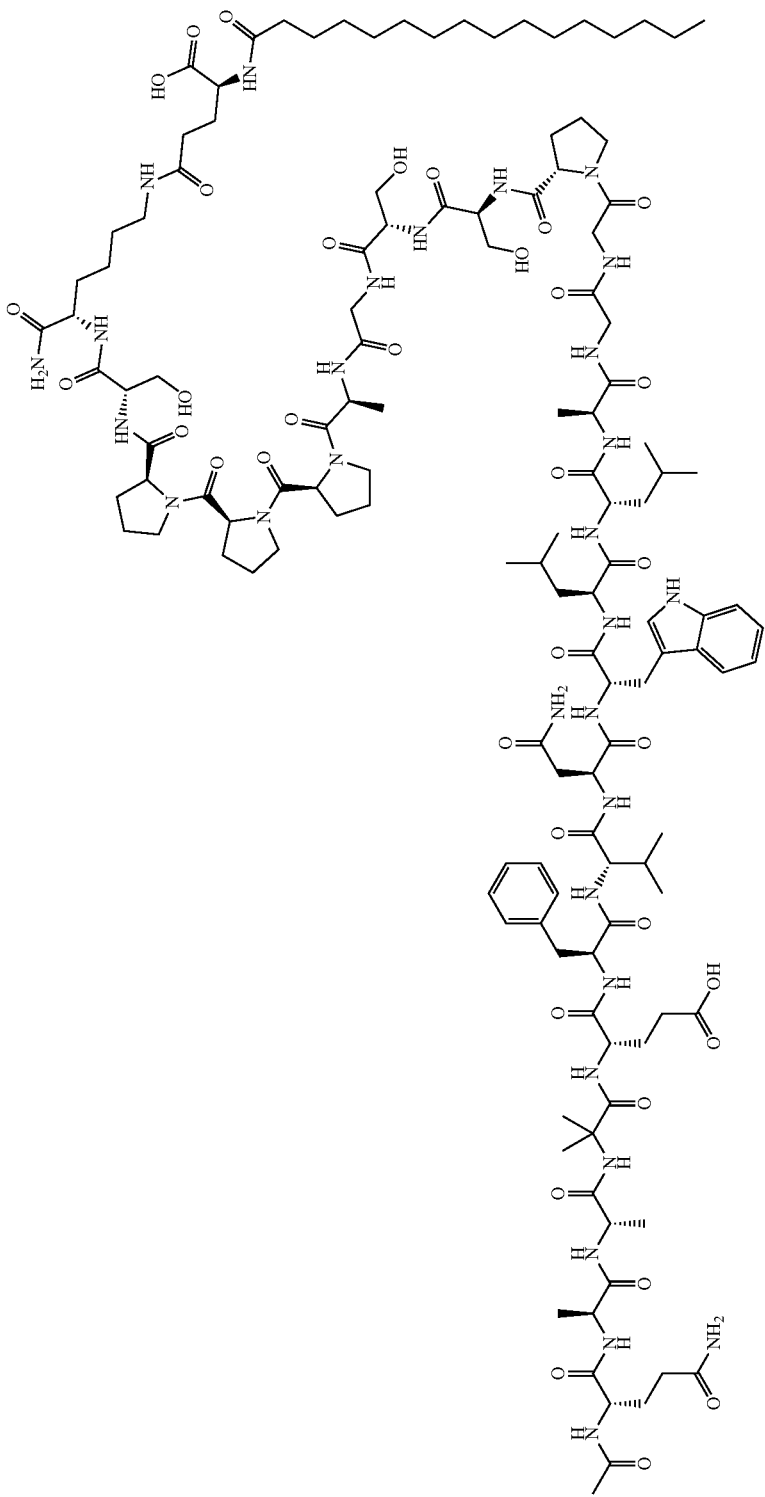

601
Compound 29
602
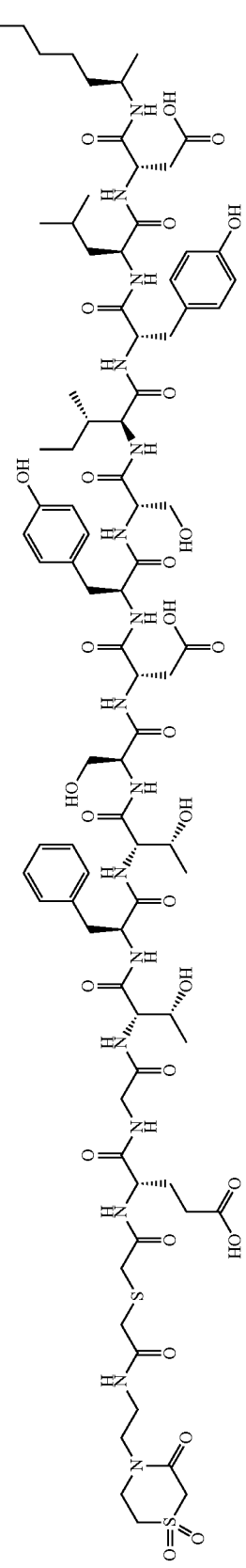
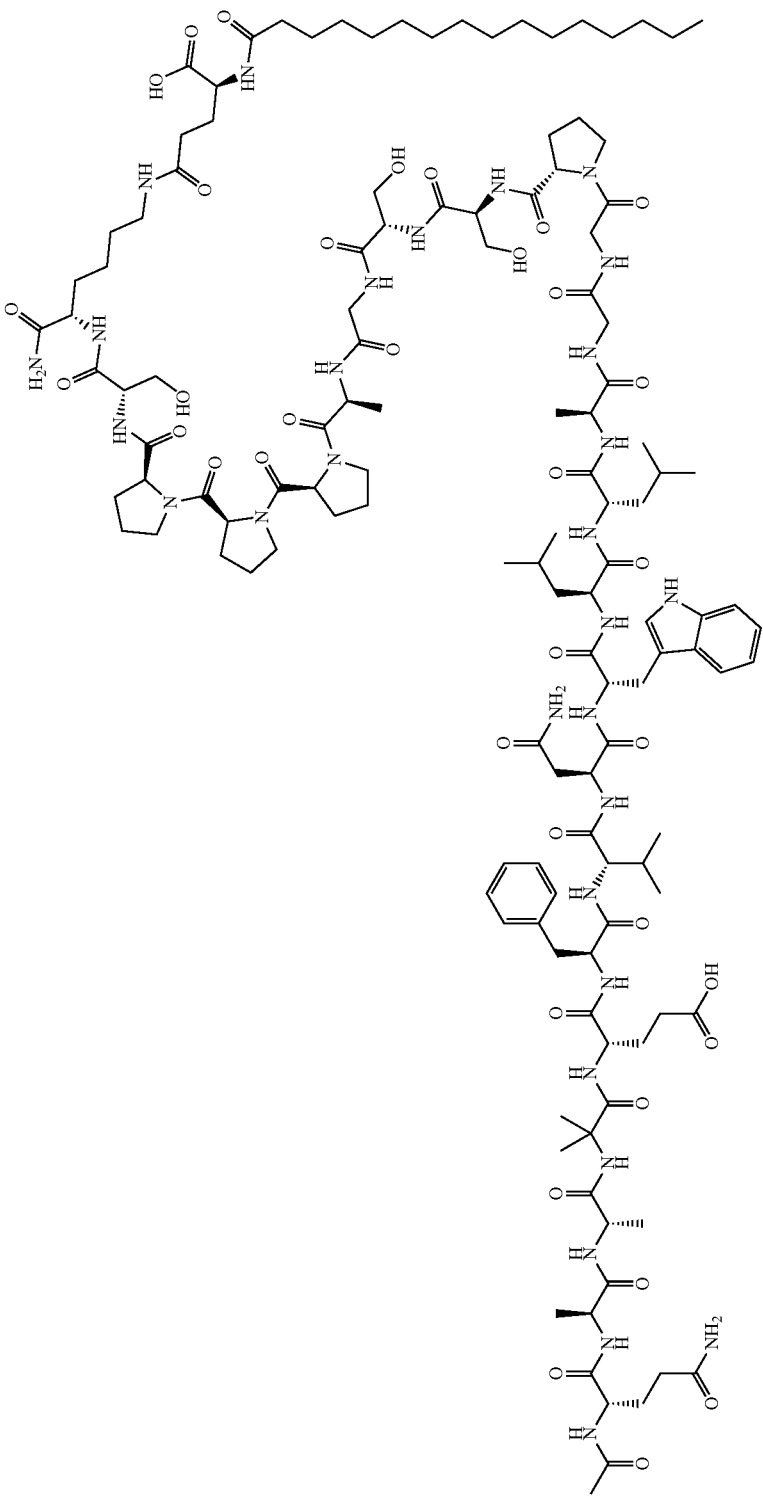

603
Compound 30
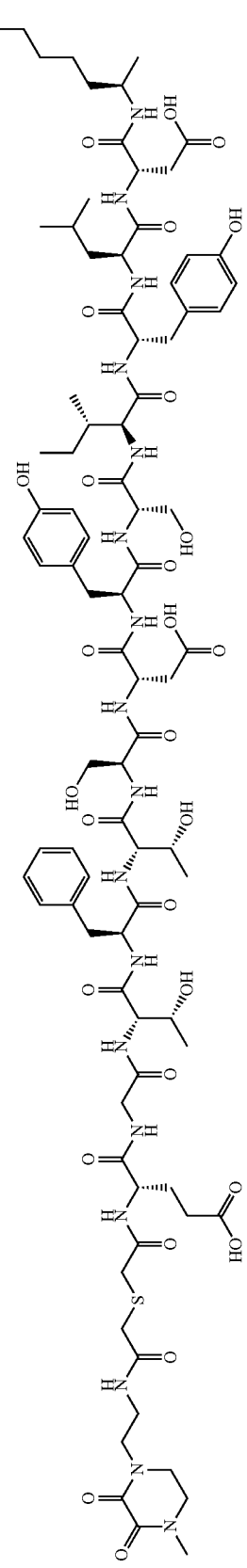
-continued
604
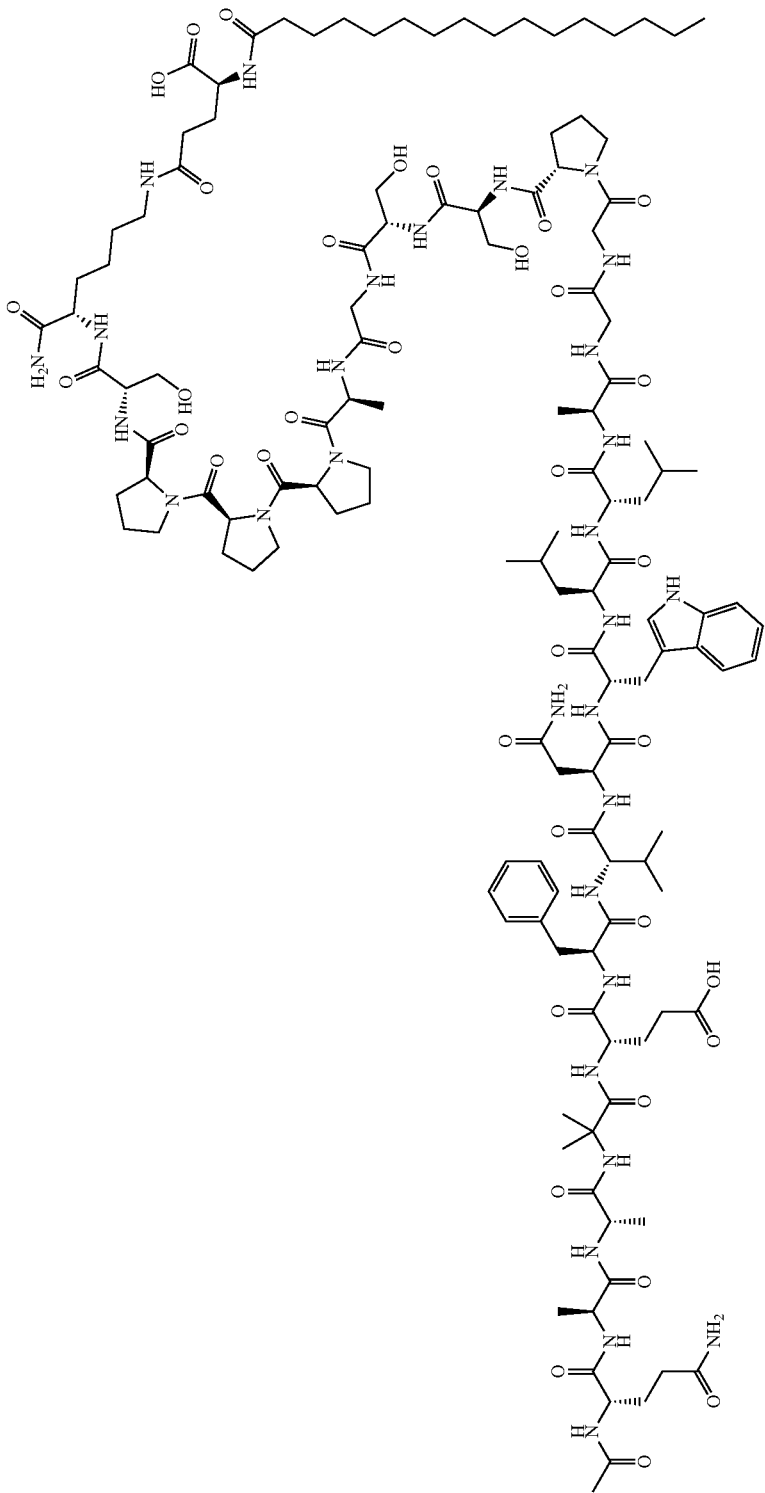

605
606
Compound 31
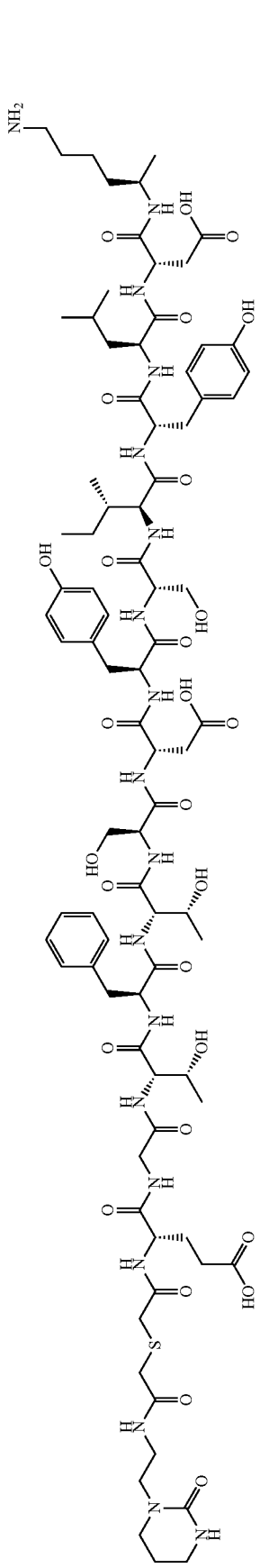
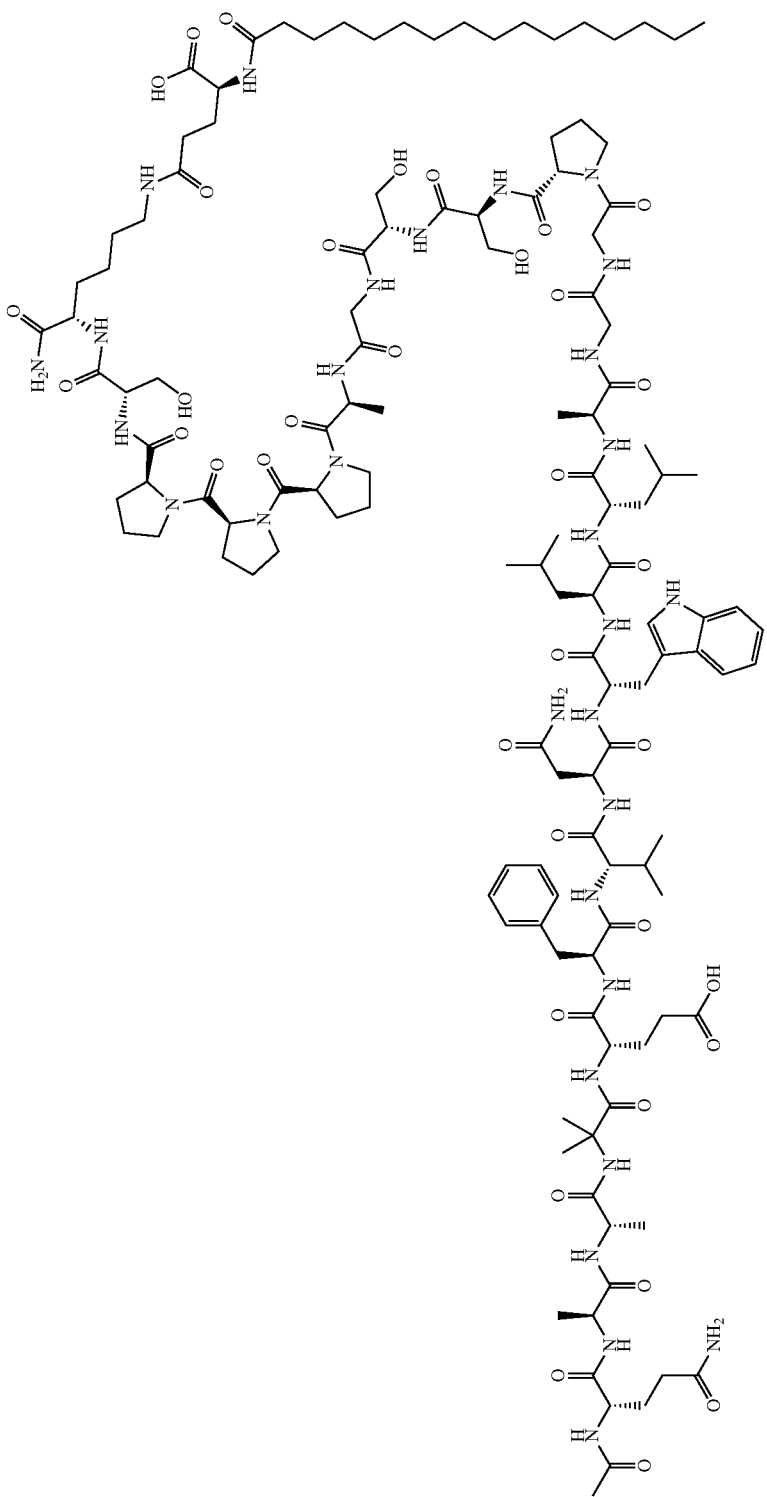
-continued

Compound 32
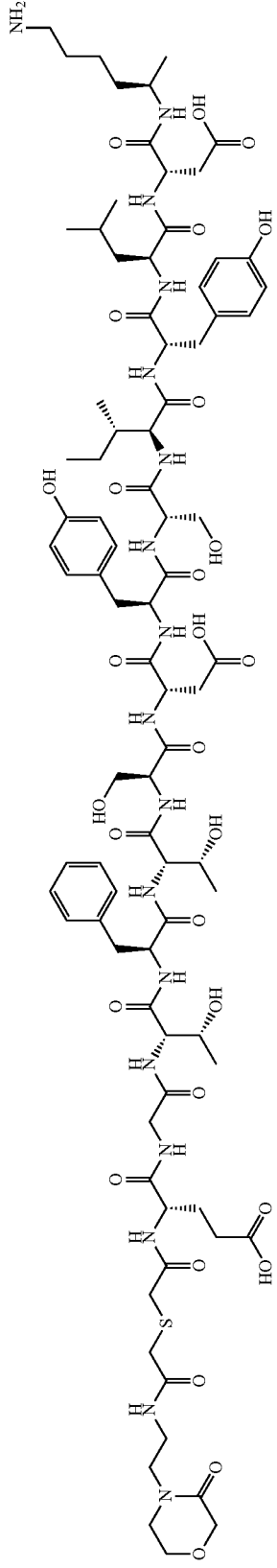
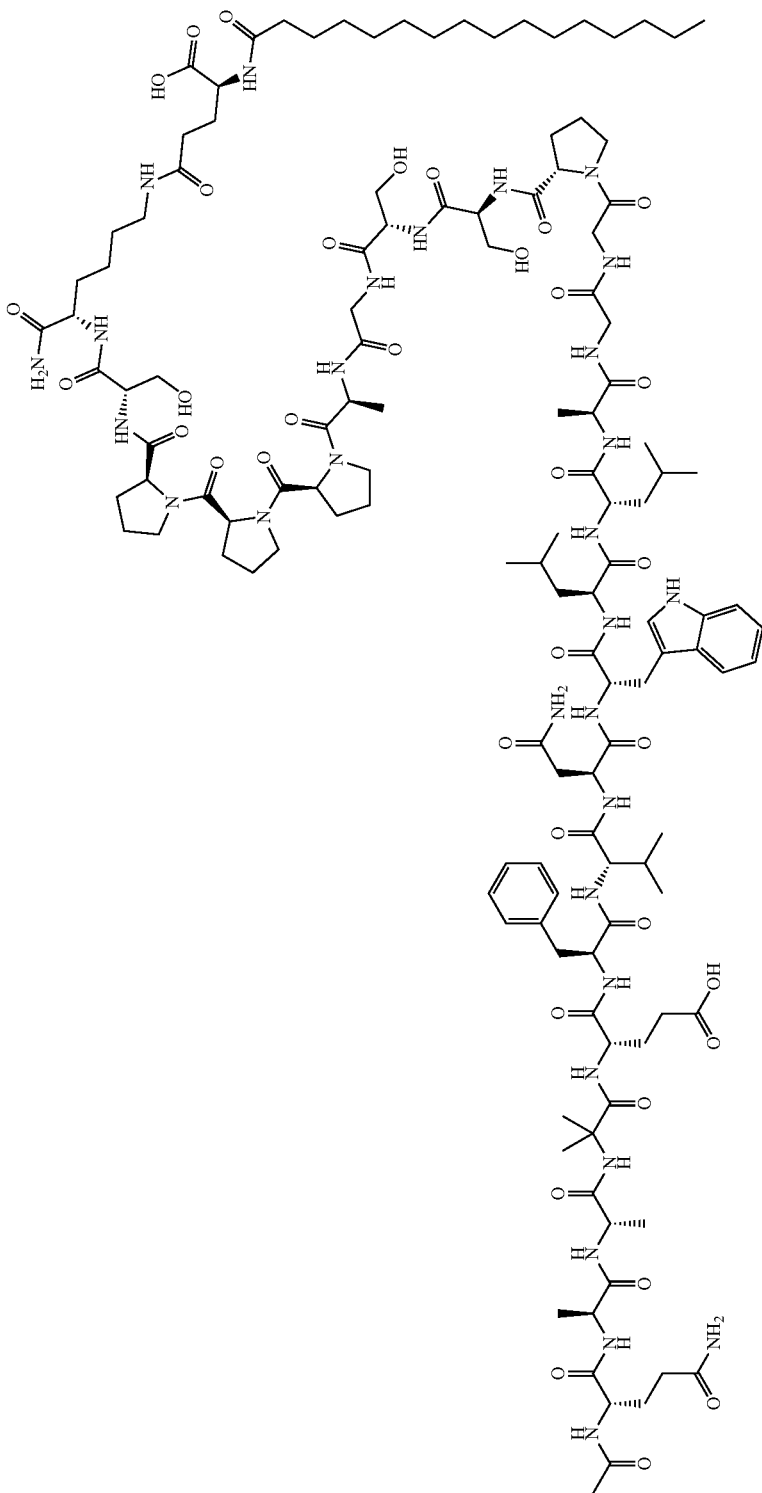

Compound 33
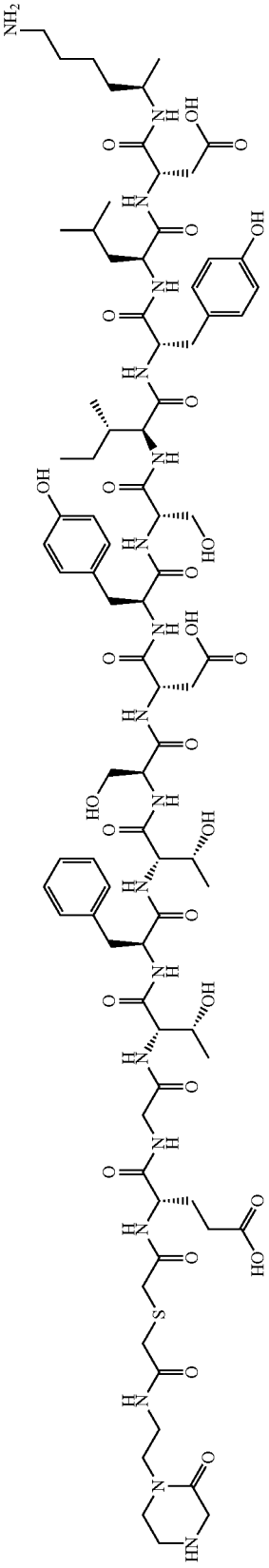
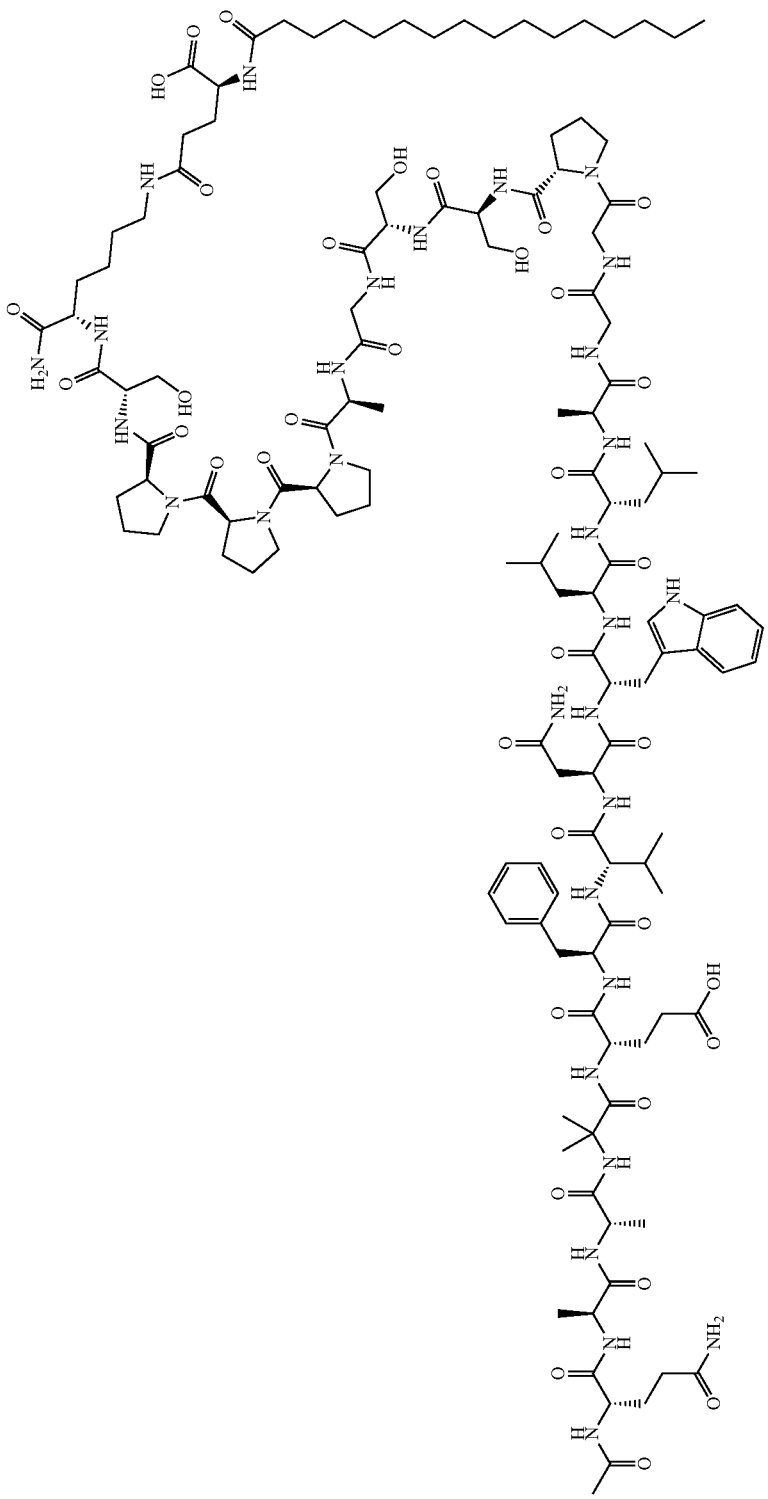

611
Compound 34
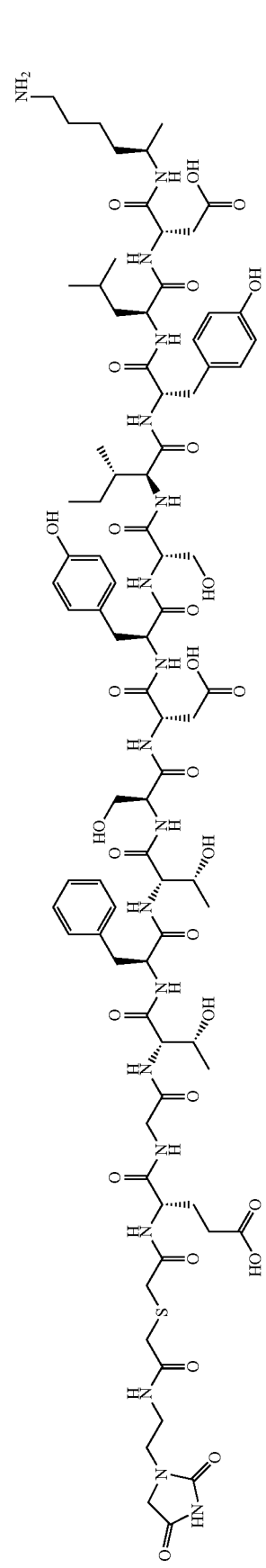
612
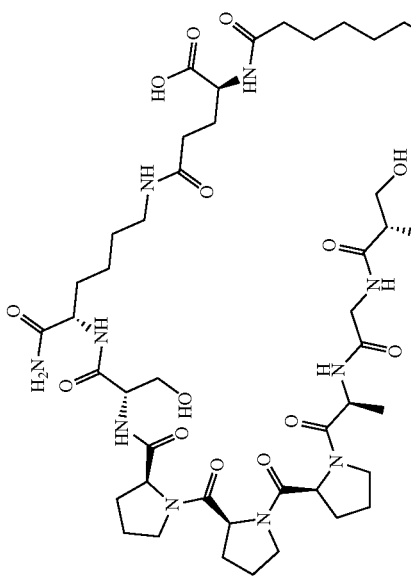
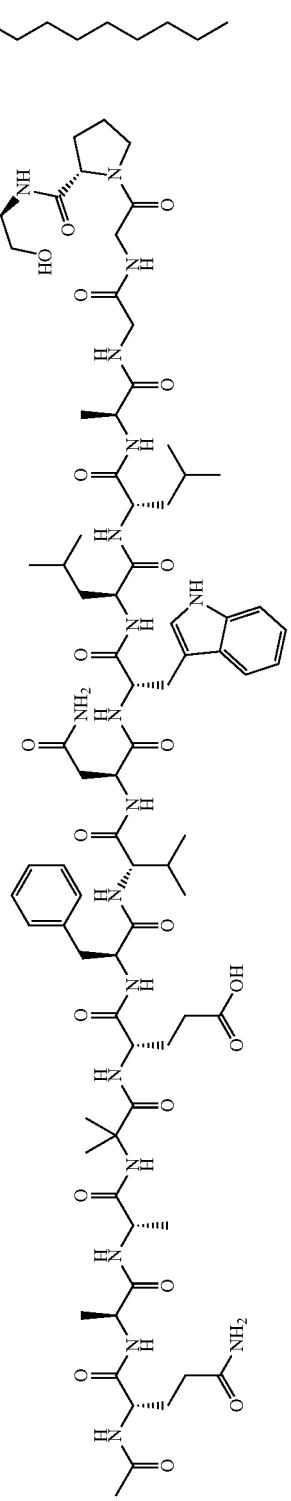

613
614
Compound 35
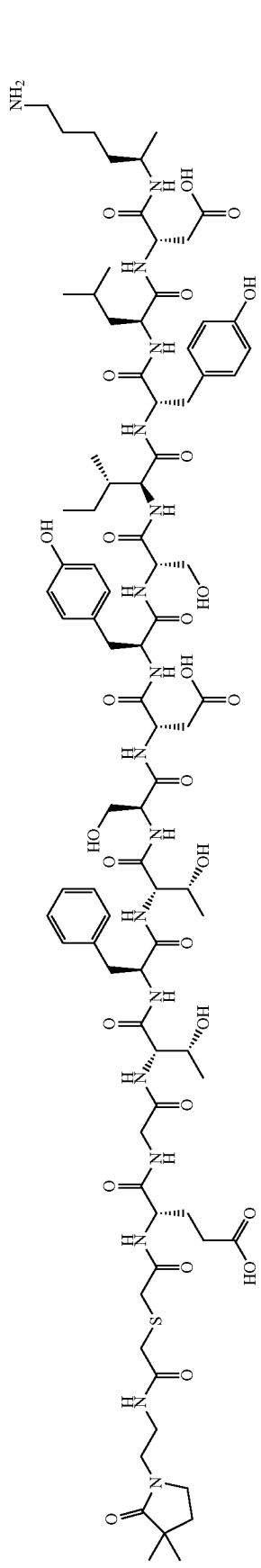
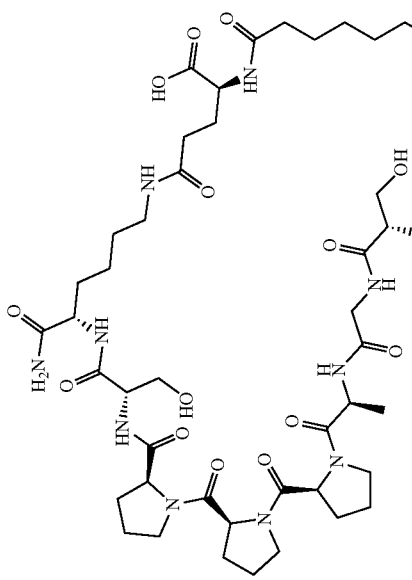
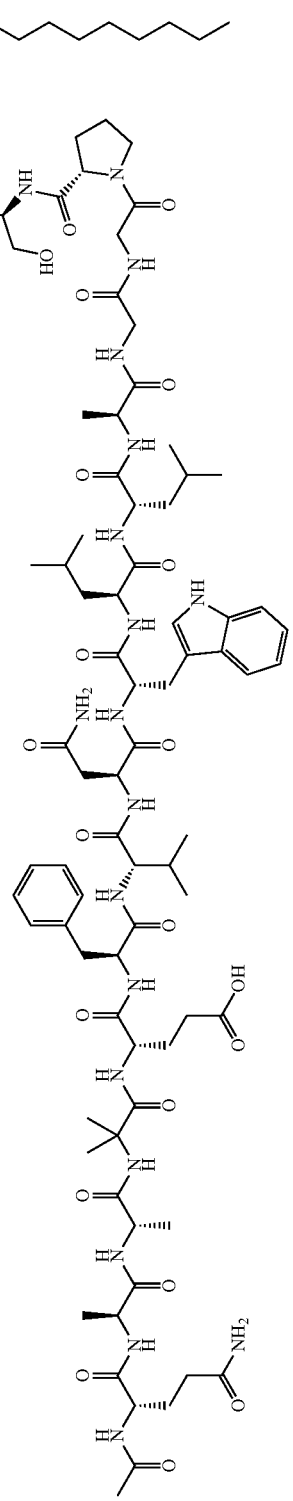

615
Compound 36
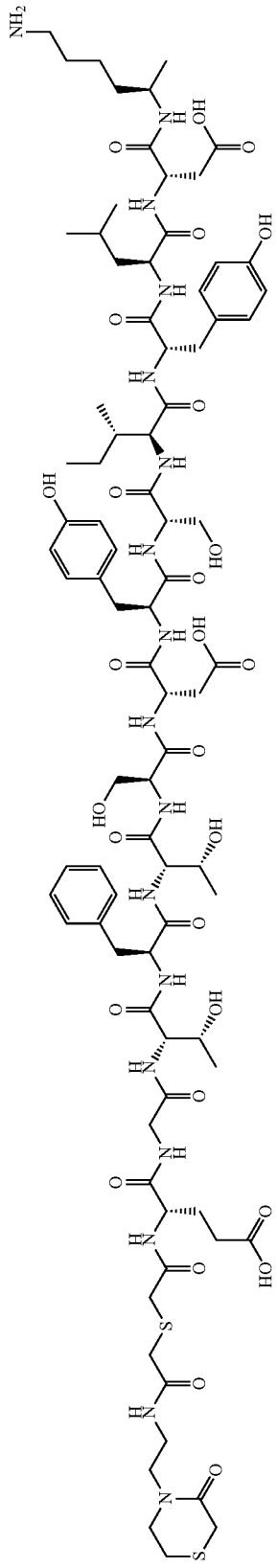
616
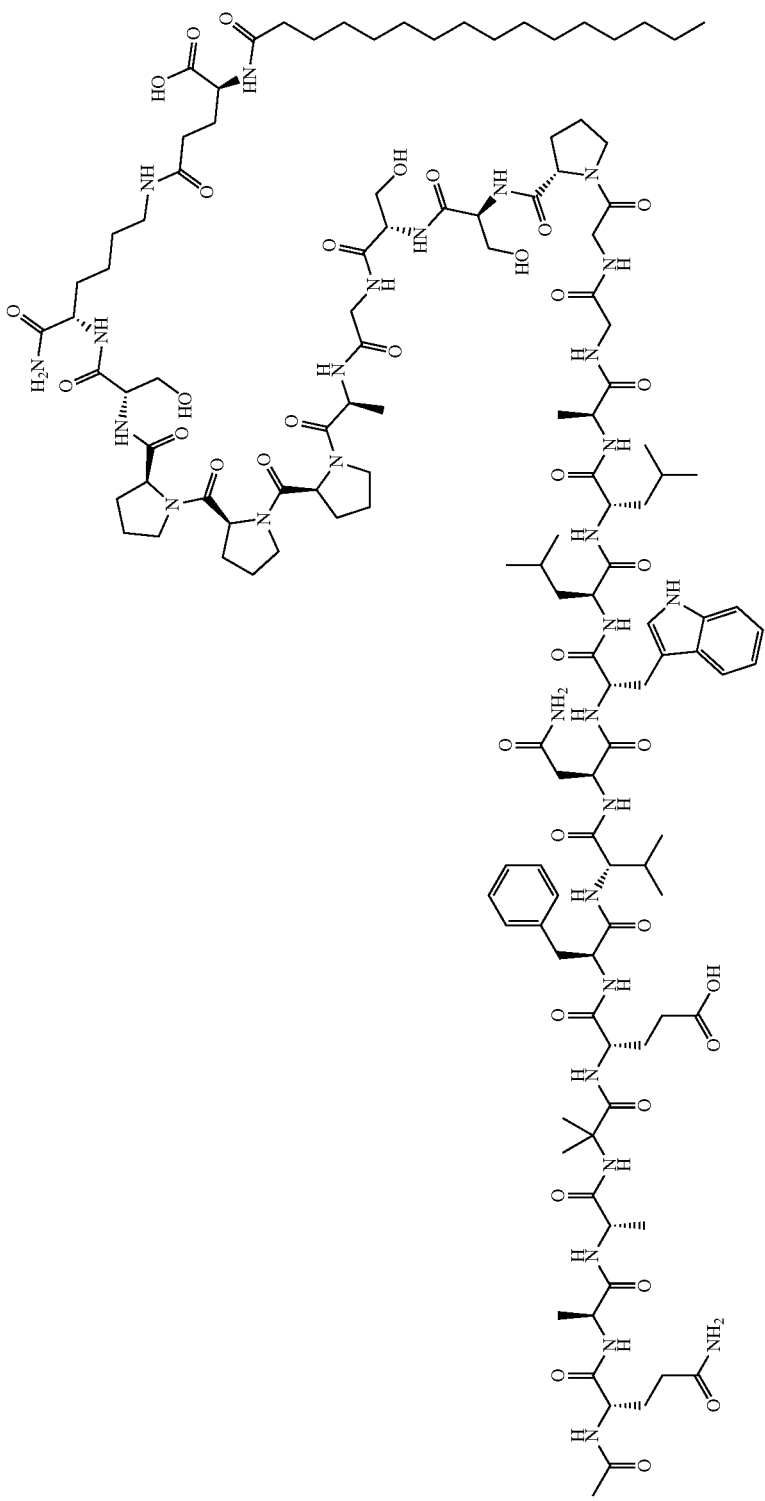

Compound 37
617
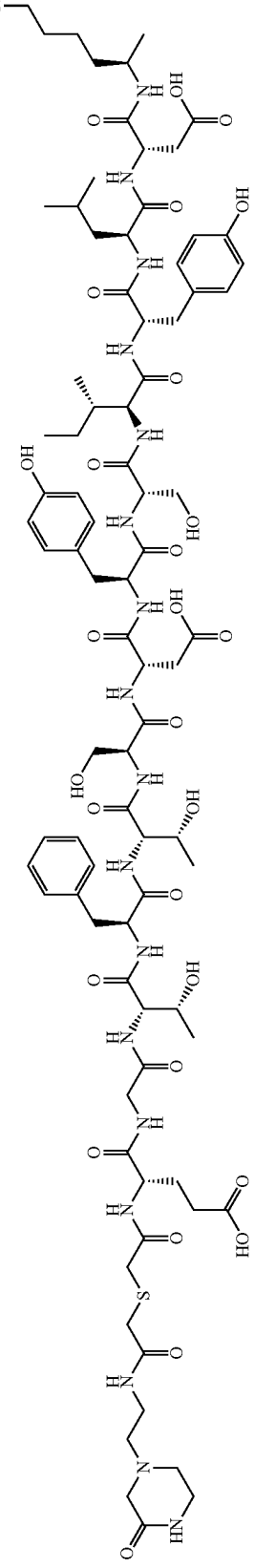
618
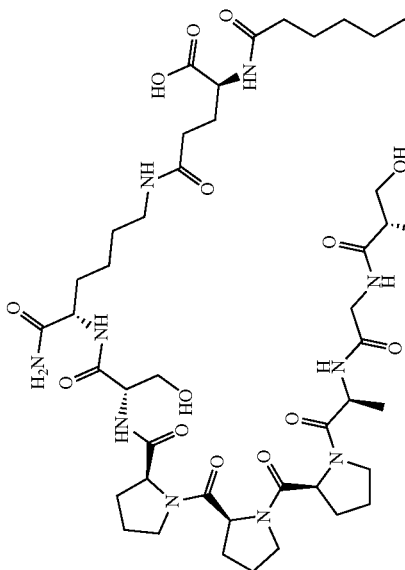
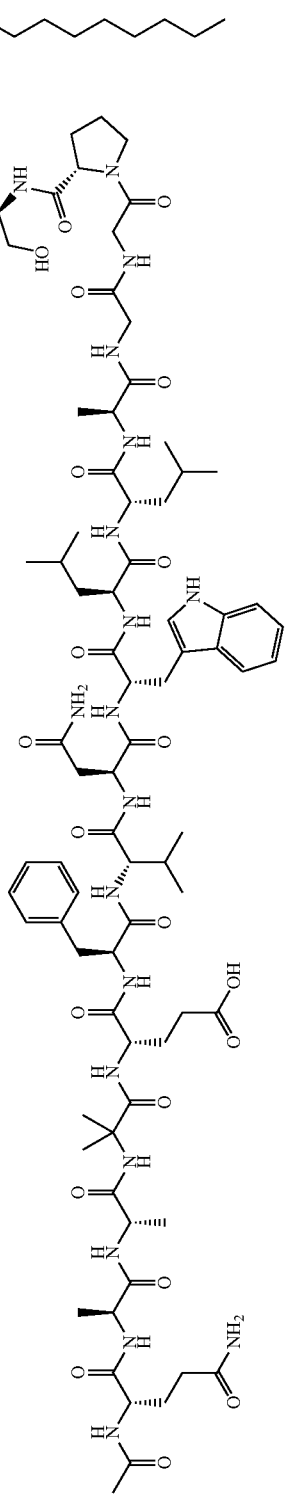

619
Compound 38
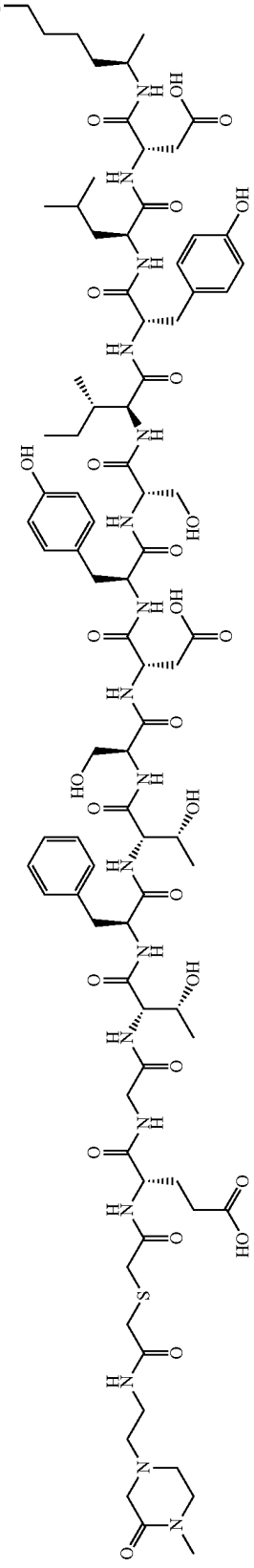
620
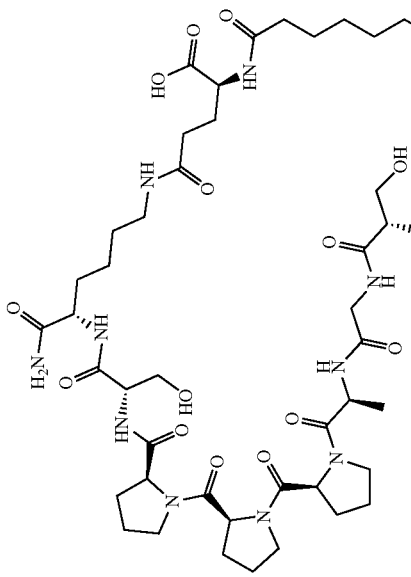
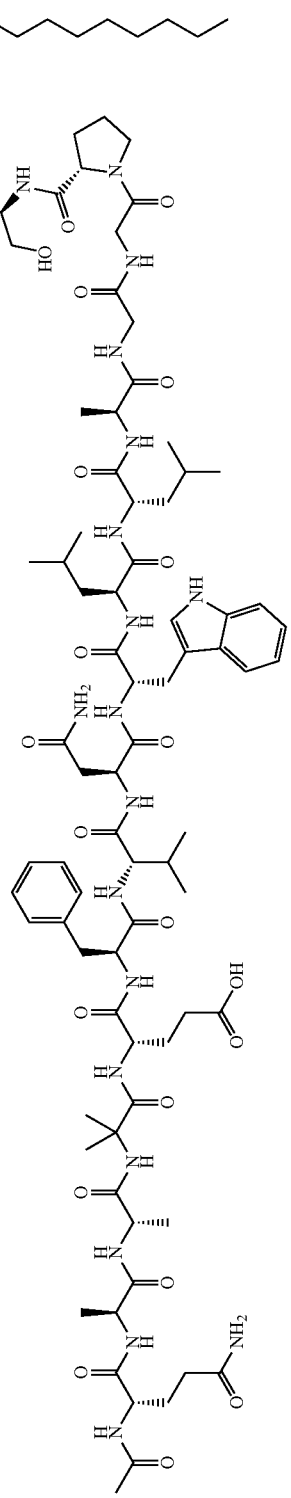

621
Compound 39
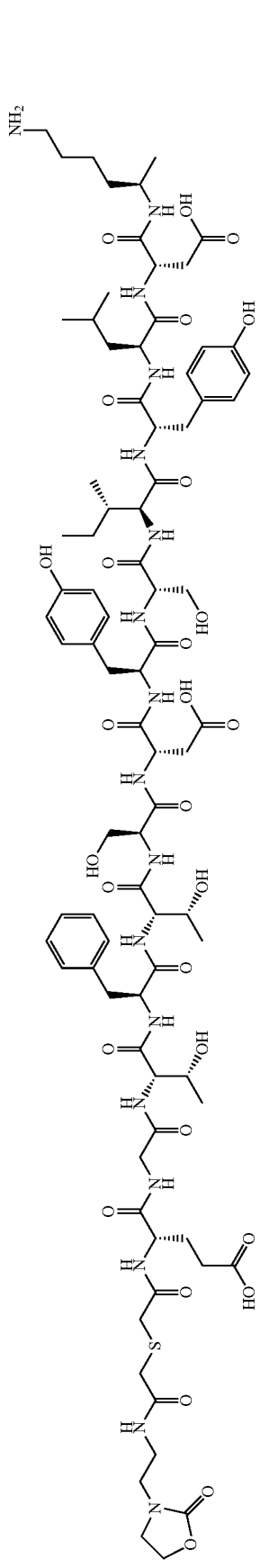
622
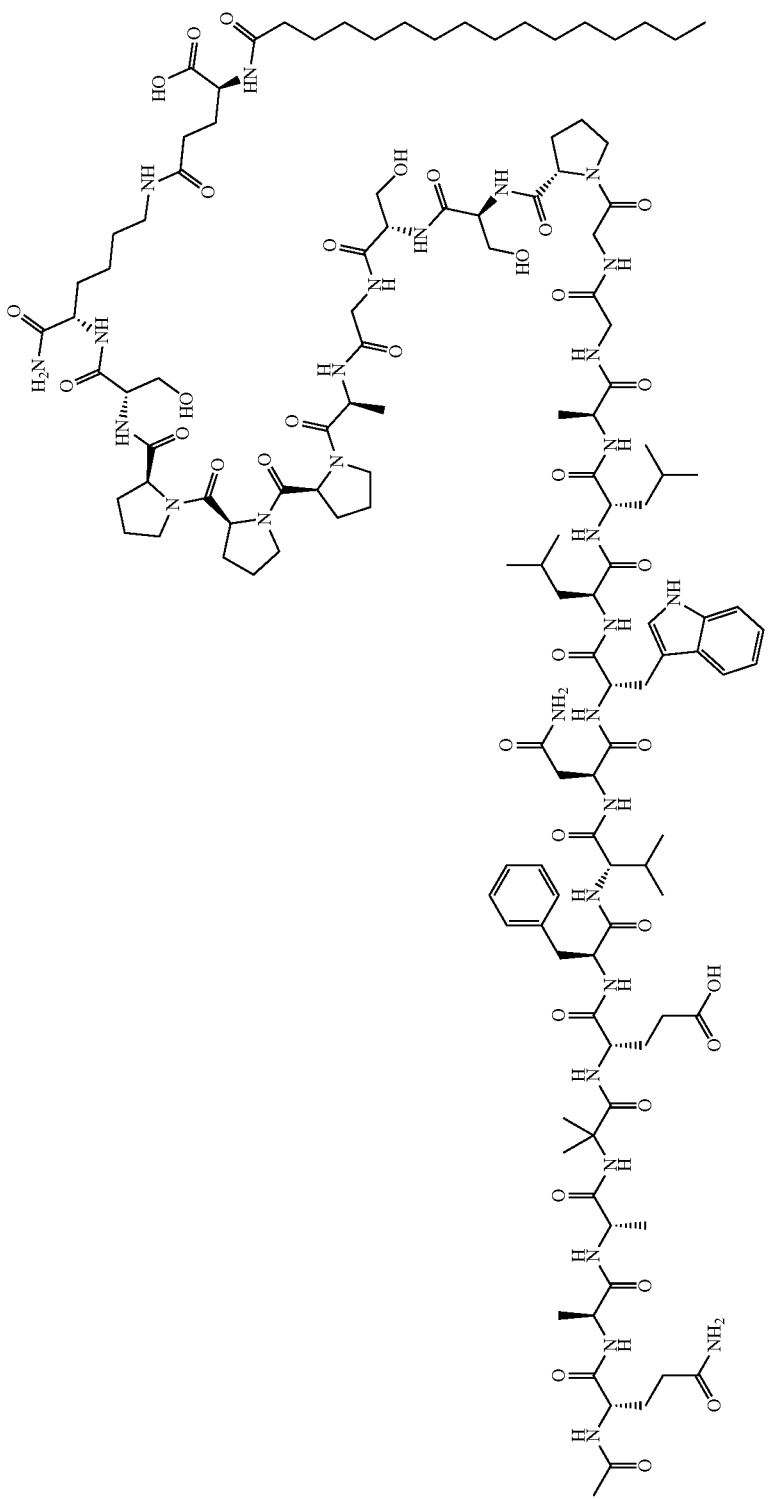

623
624
Compound 40
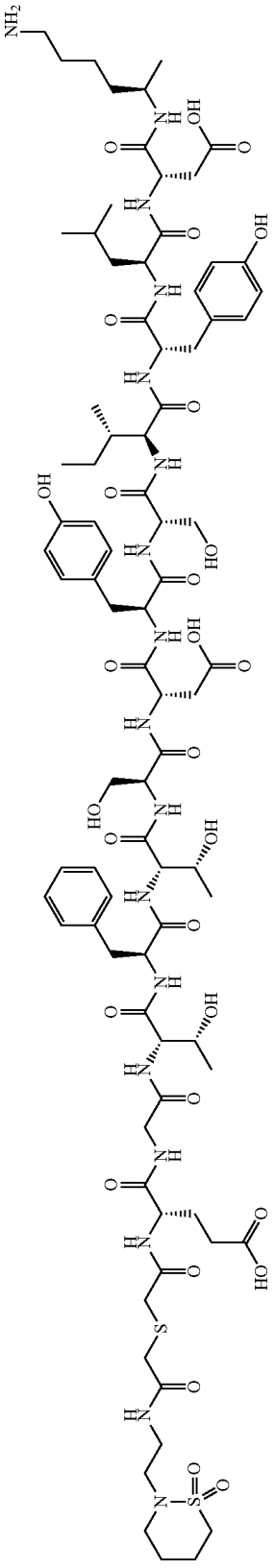
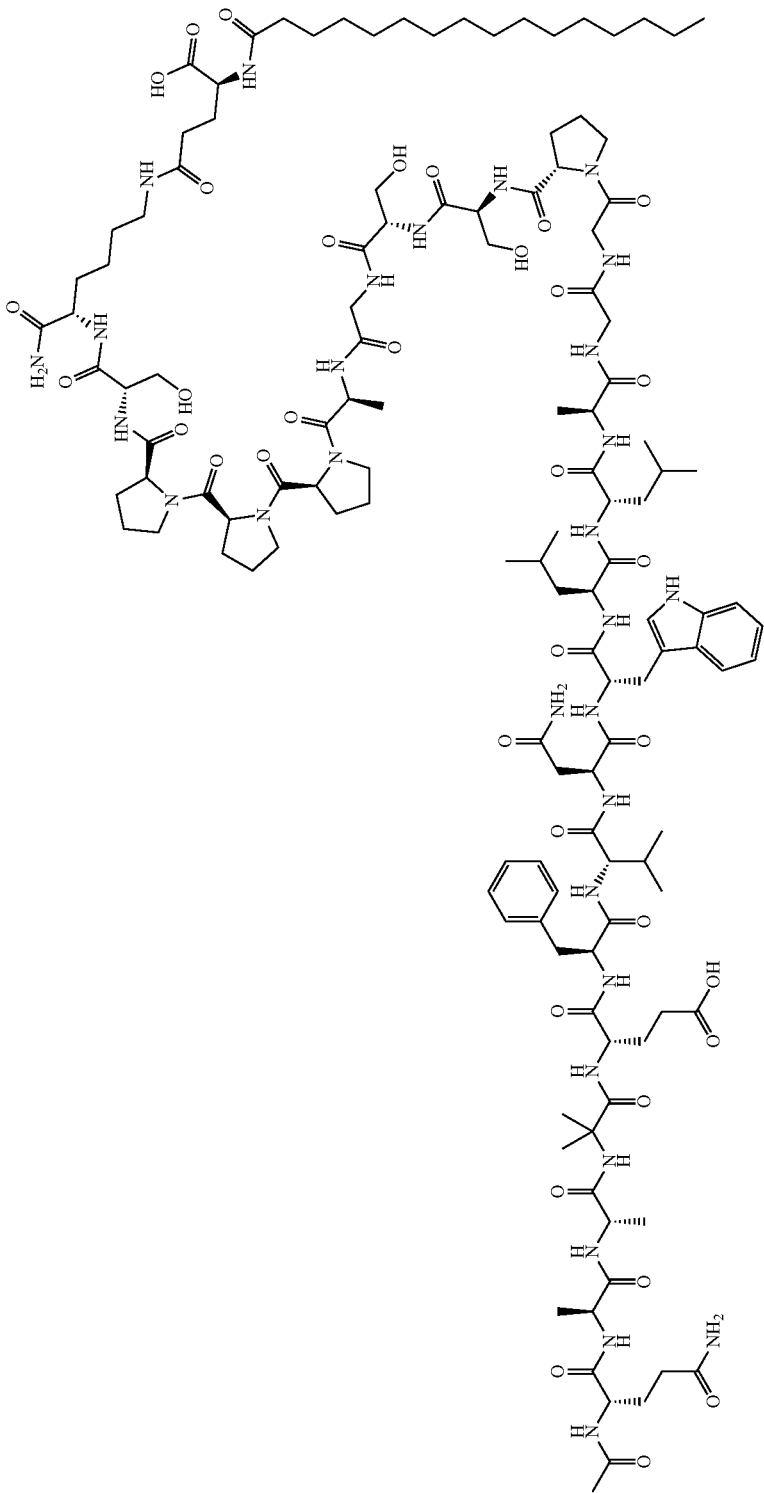

-continued
Compound 41
625
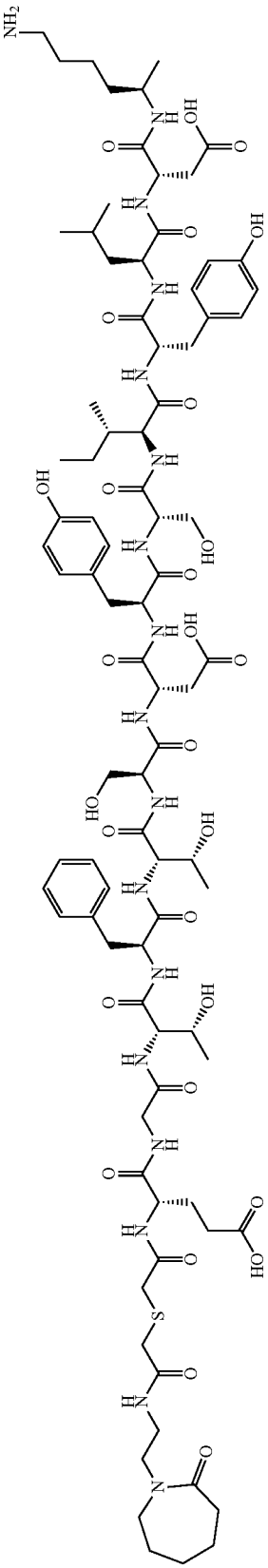
626
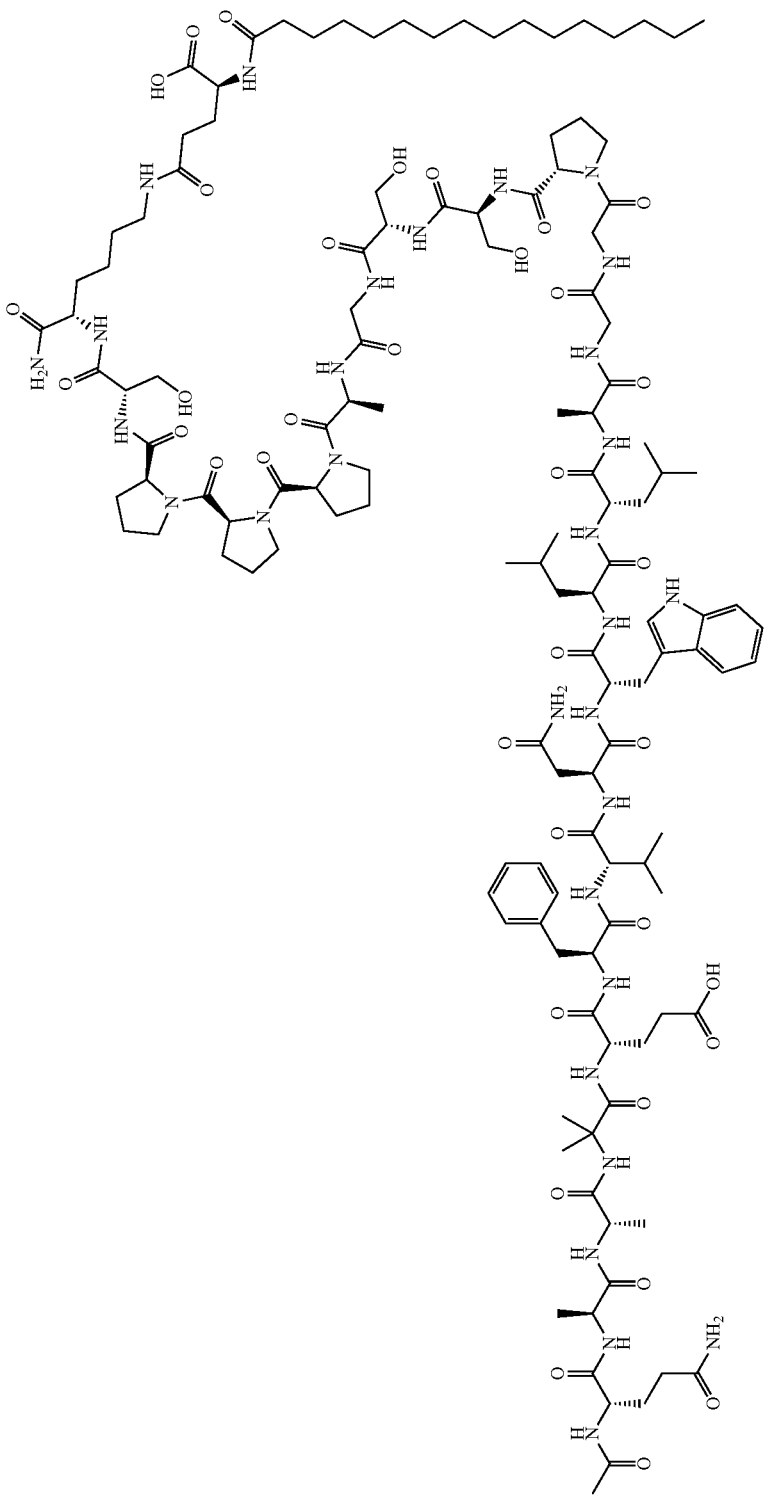

627 628
Compound 42
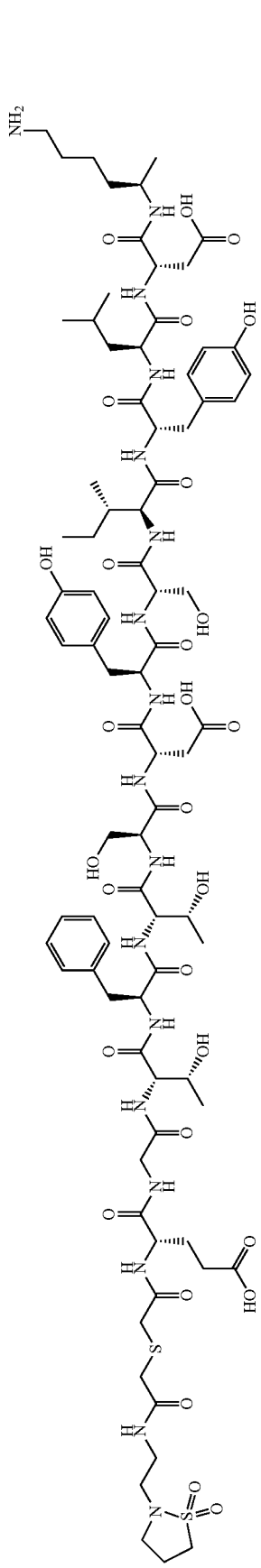
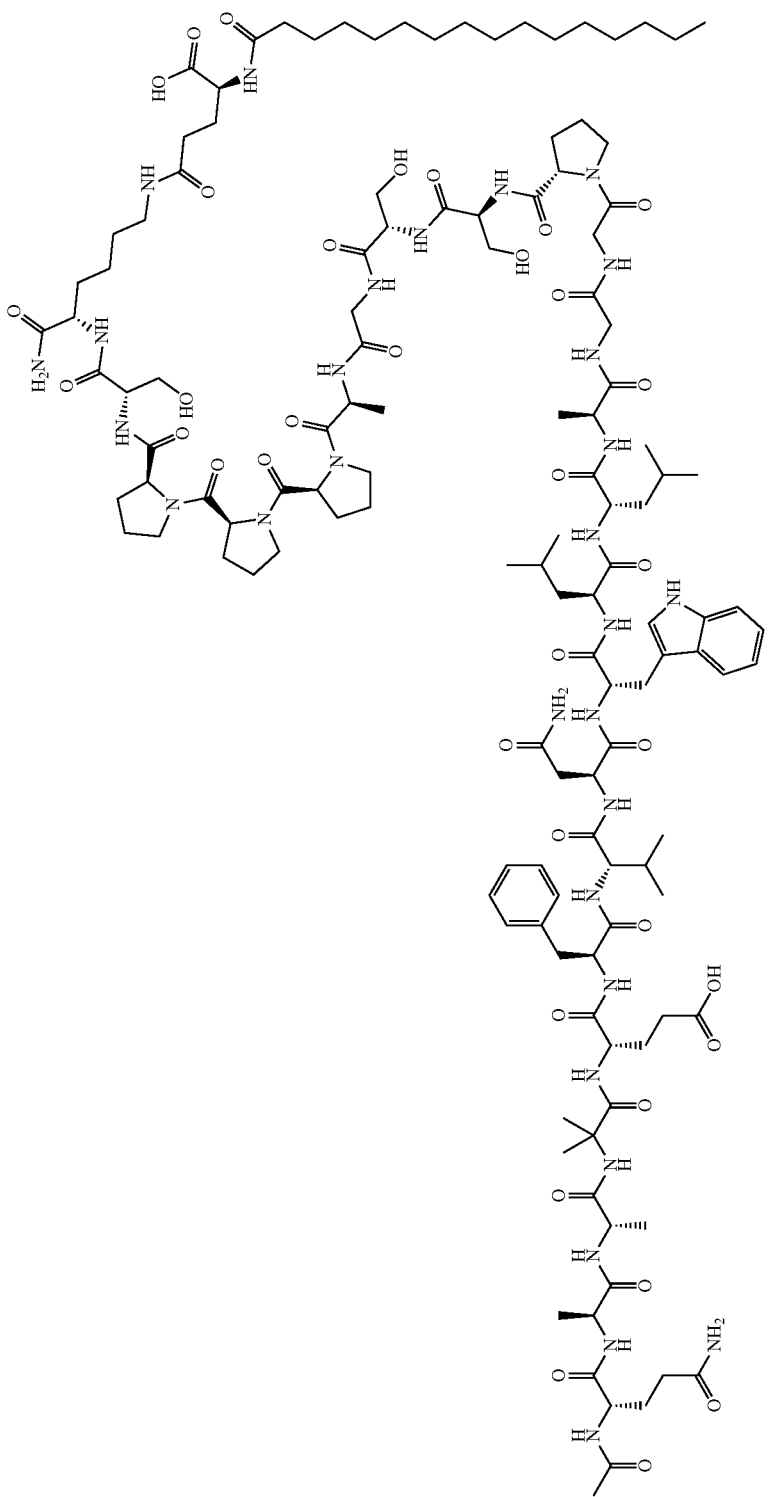

629
Compound 43
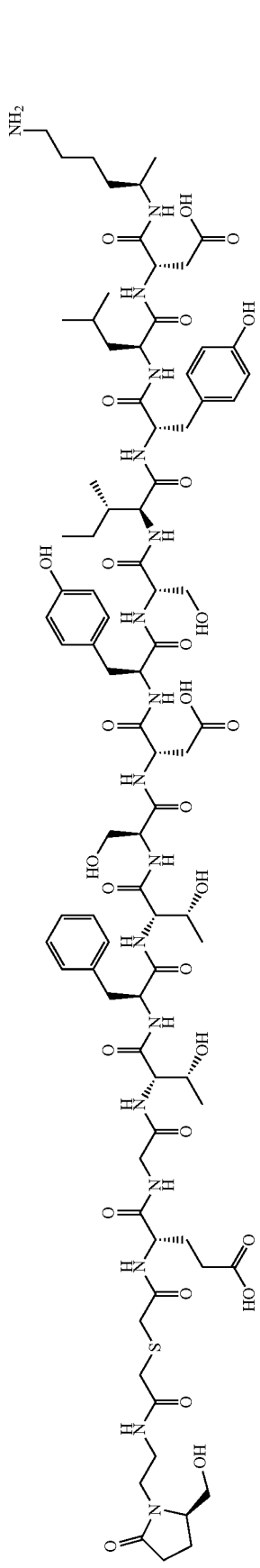
630
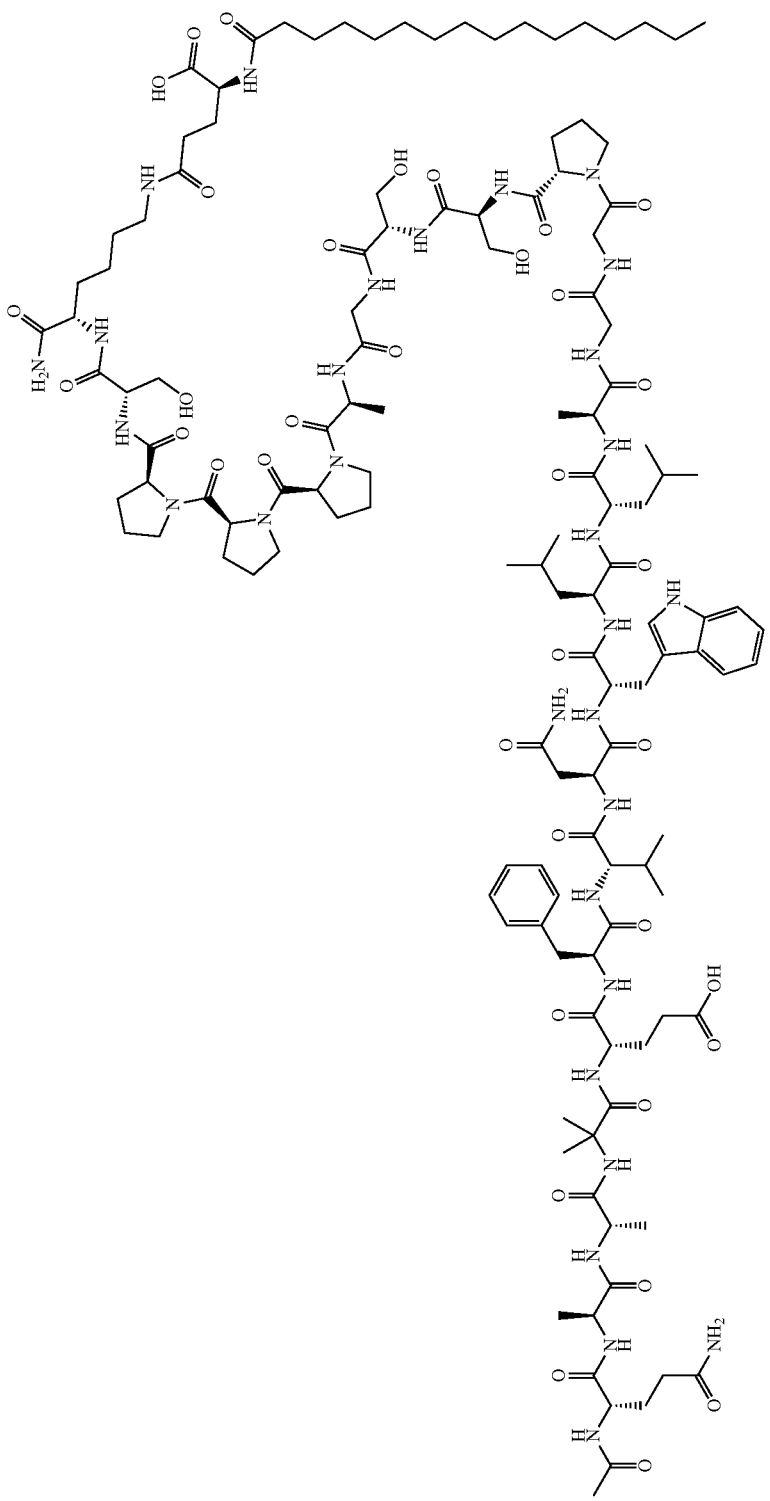

631
Compound 44
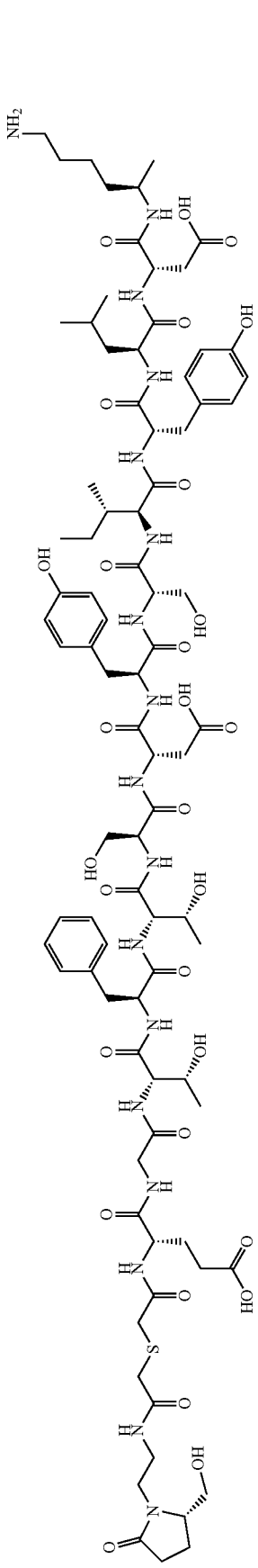
632
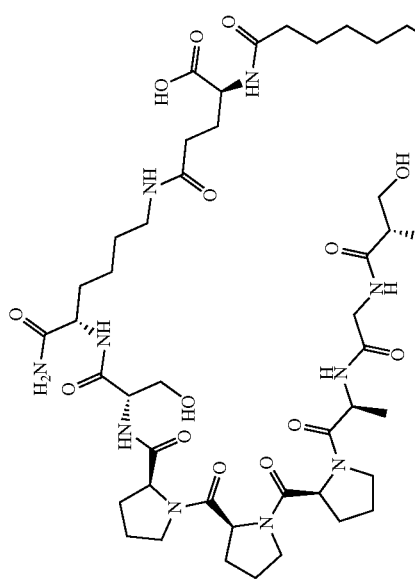
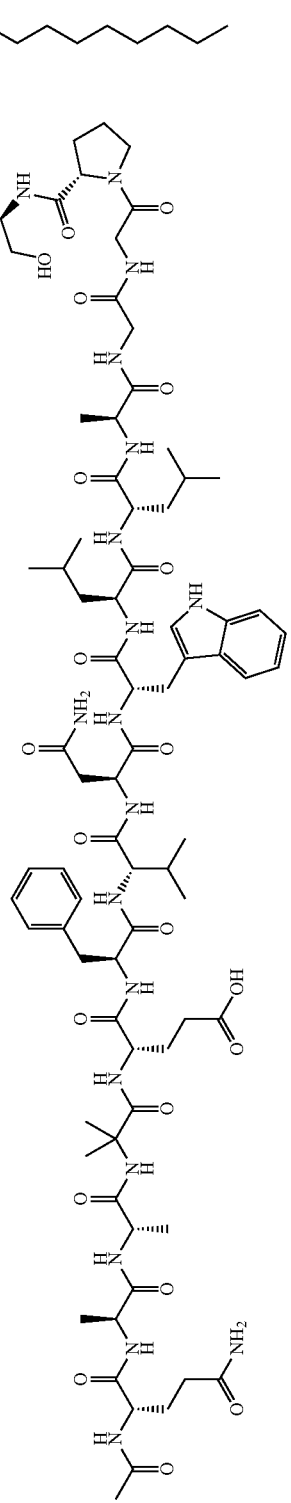

633
634
Compound 45
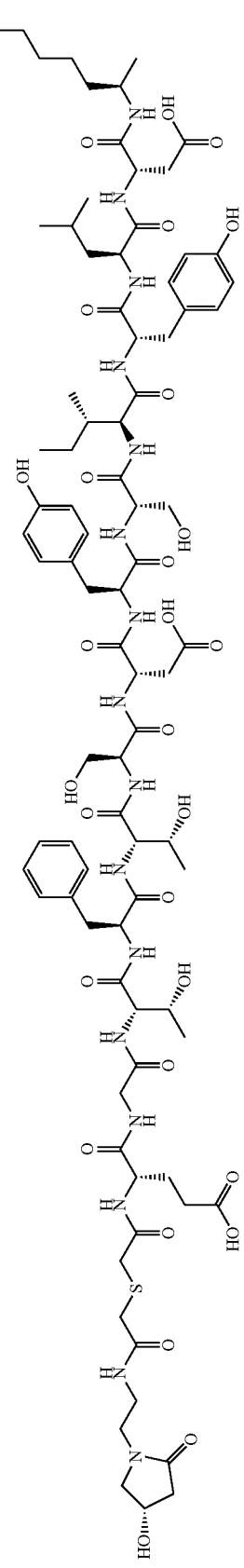
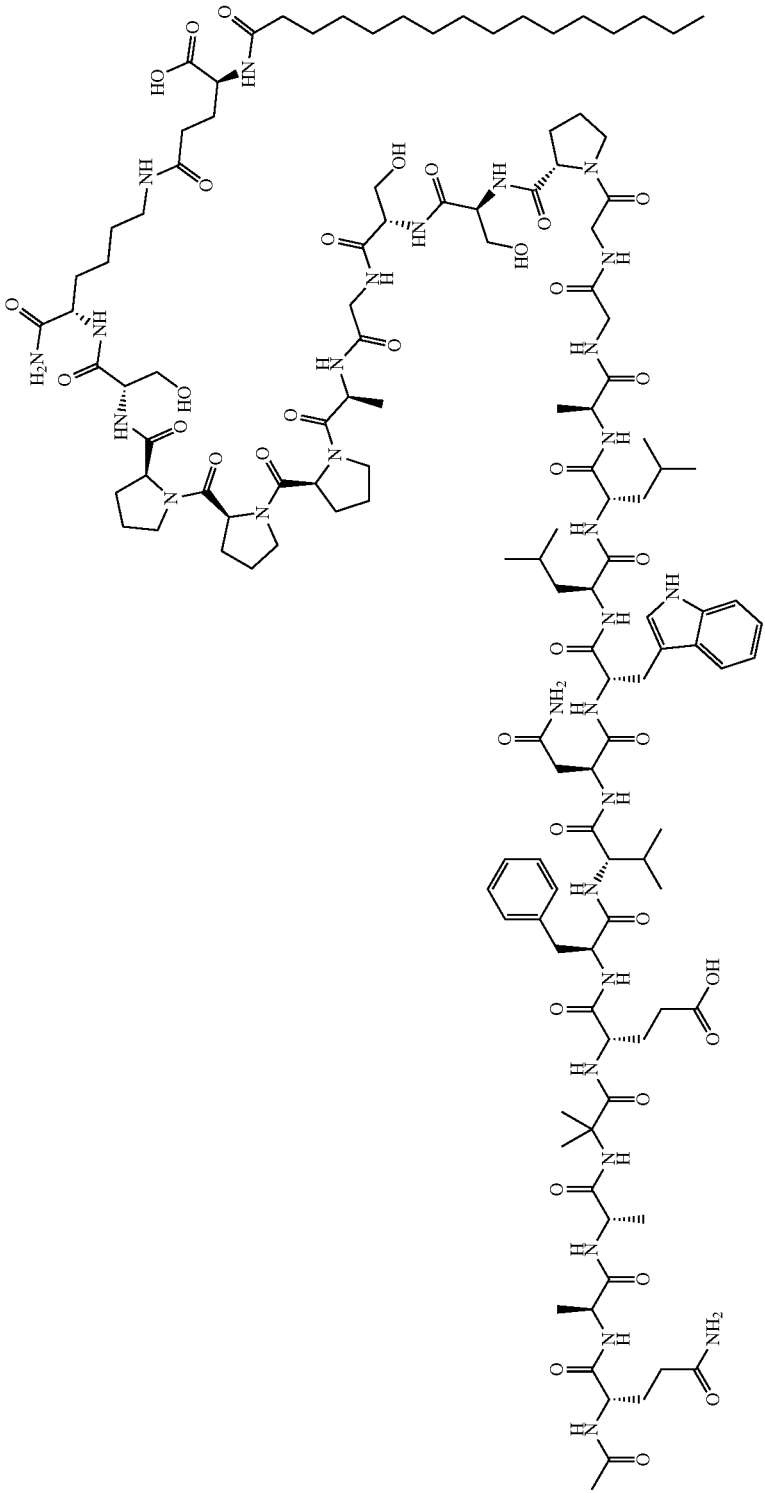

635 636
Compound 46
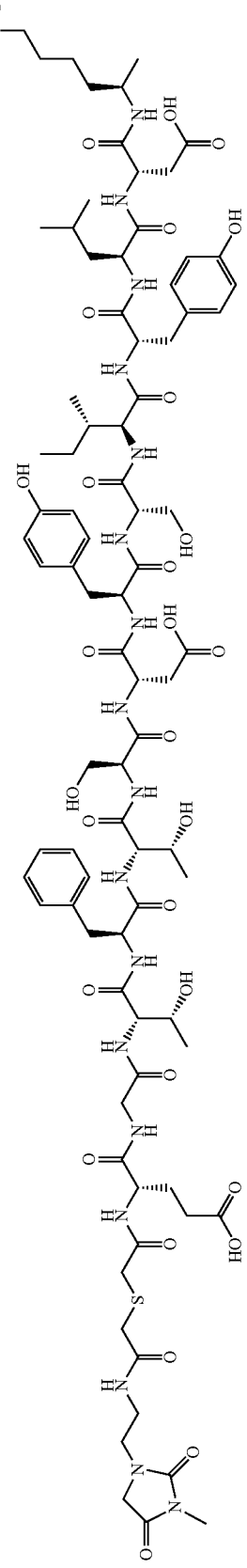
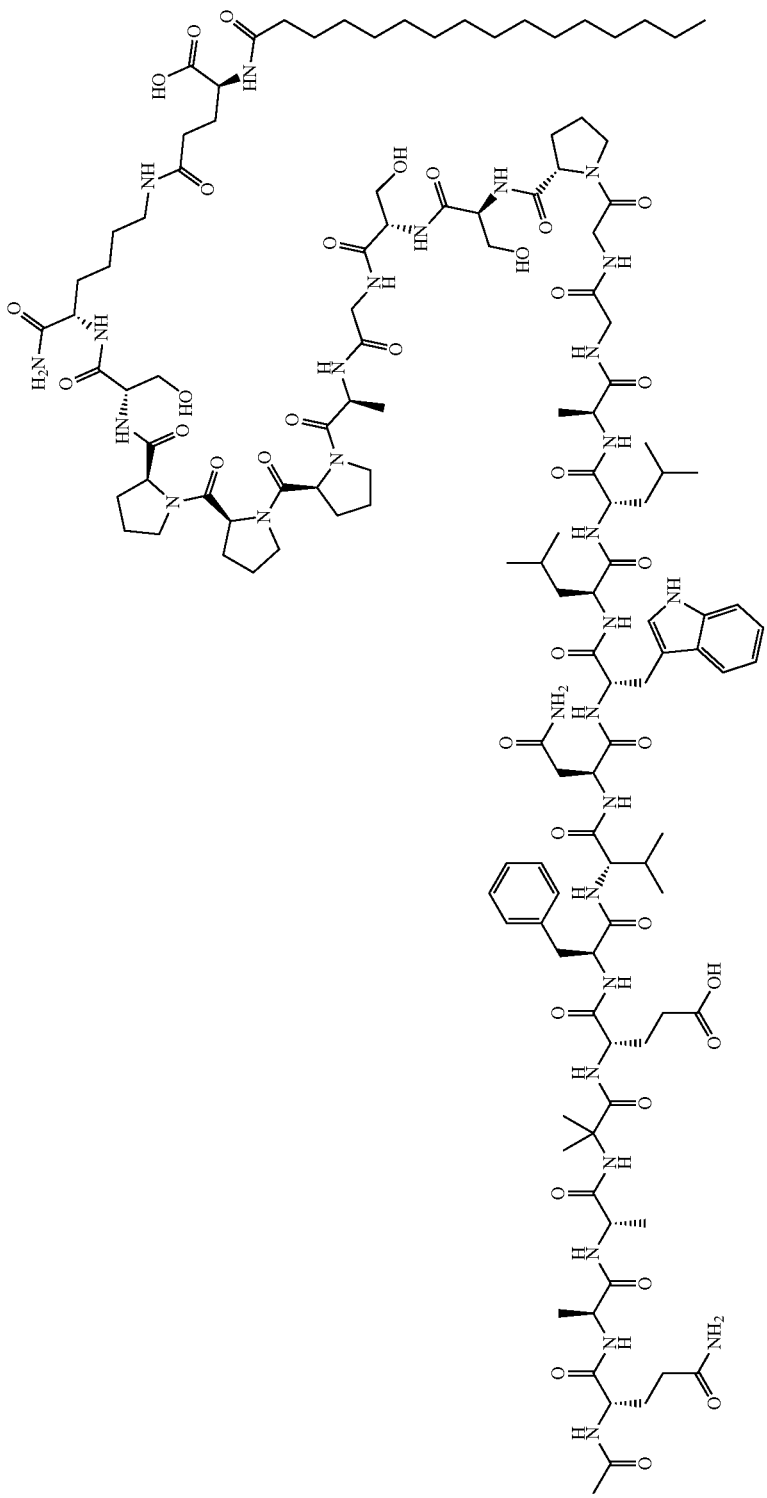

637 638
Compound 47
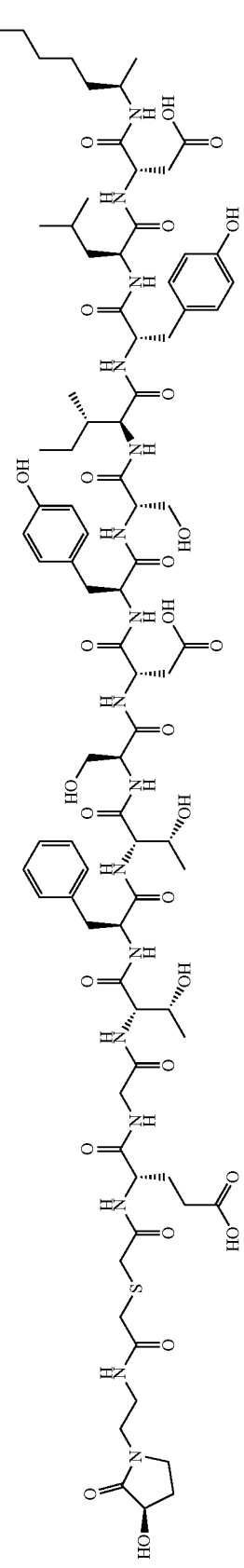
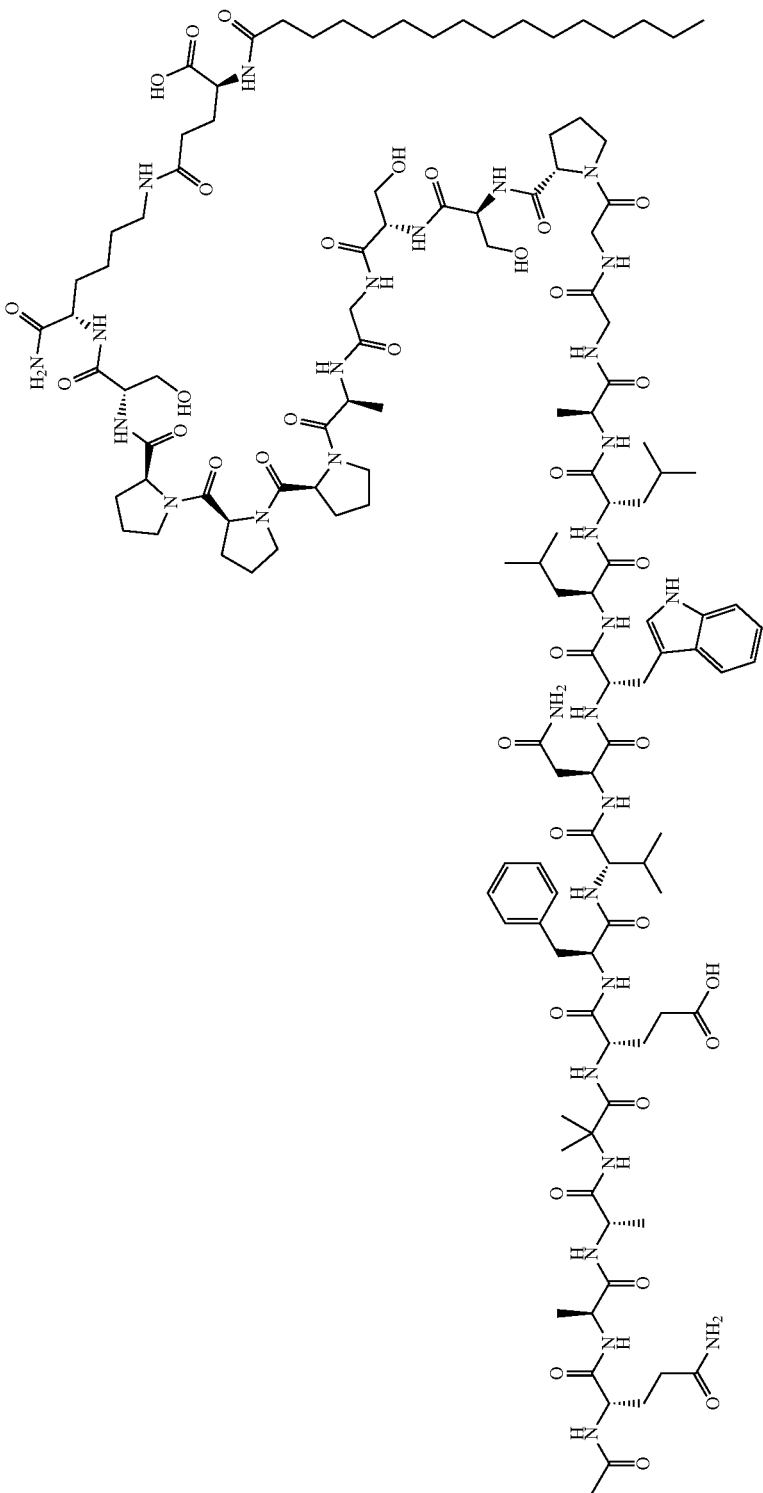

639 640
Compound 48
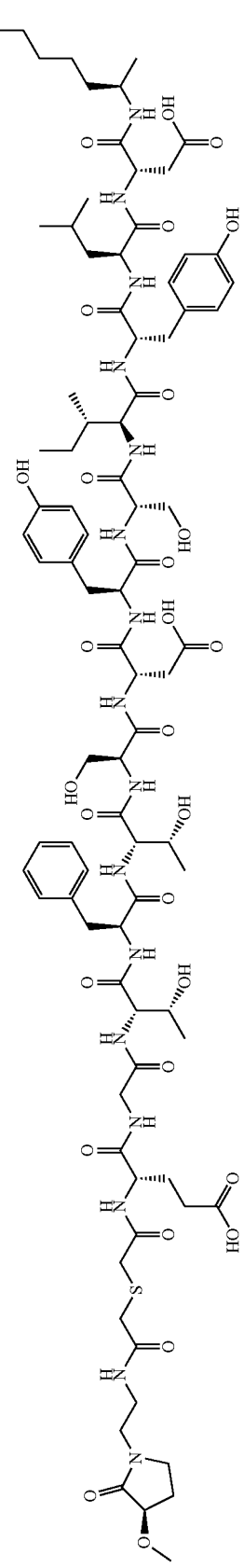
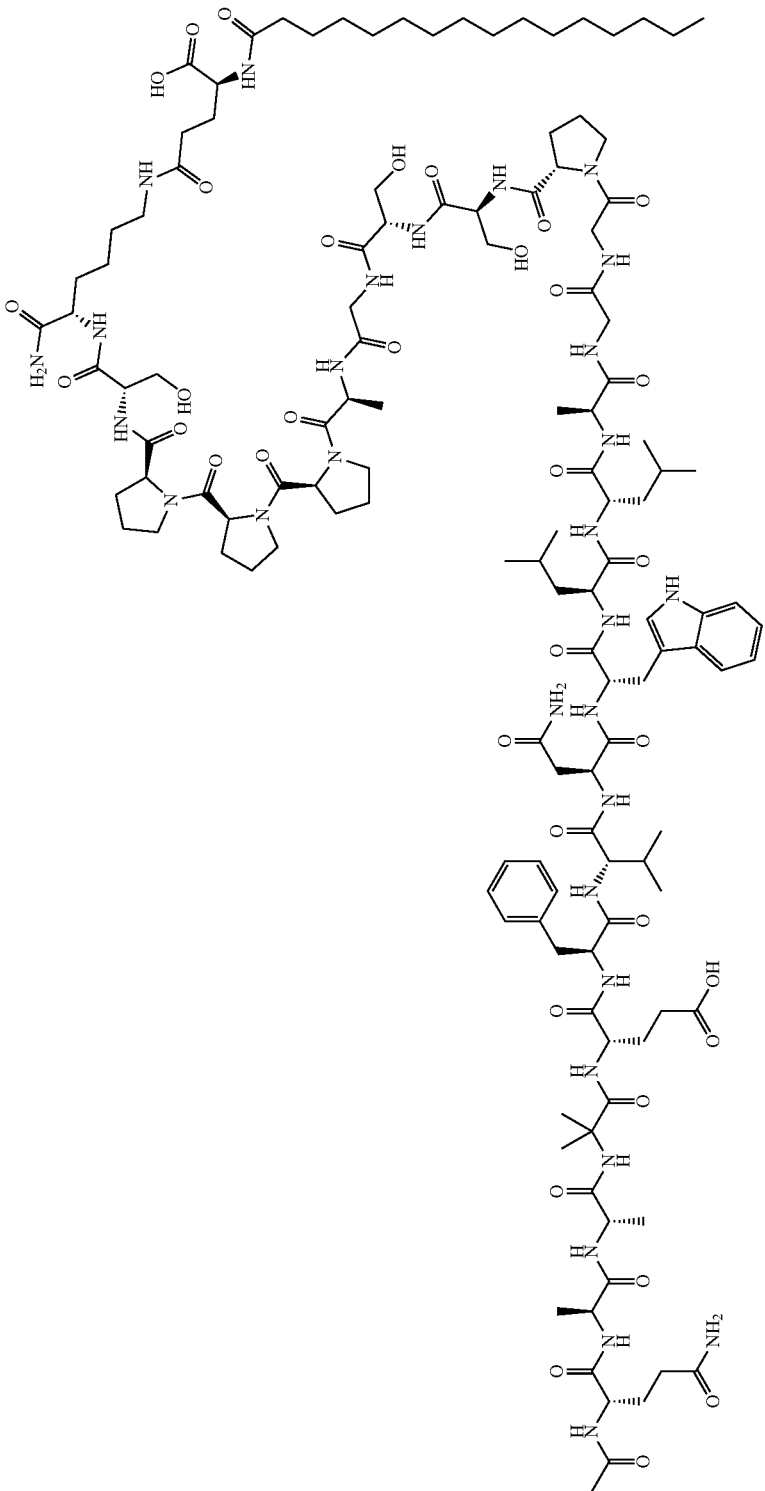

641
642
Compound 49
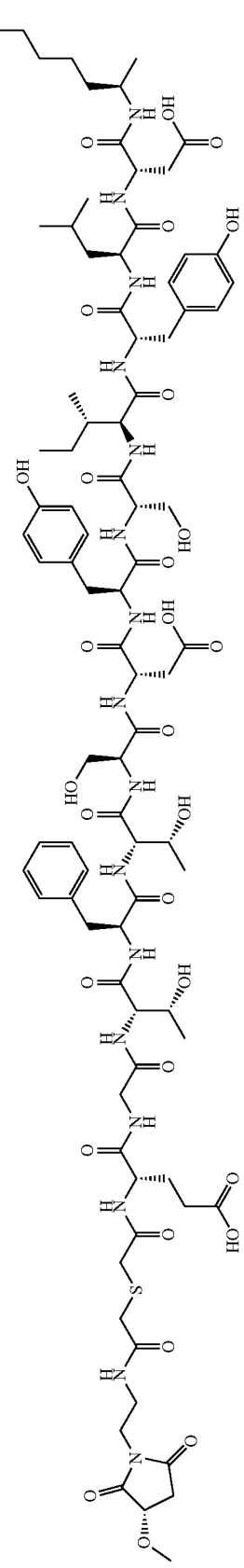
-continued
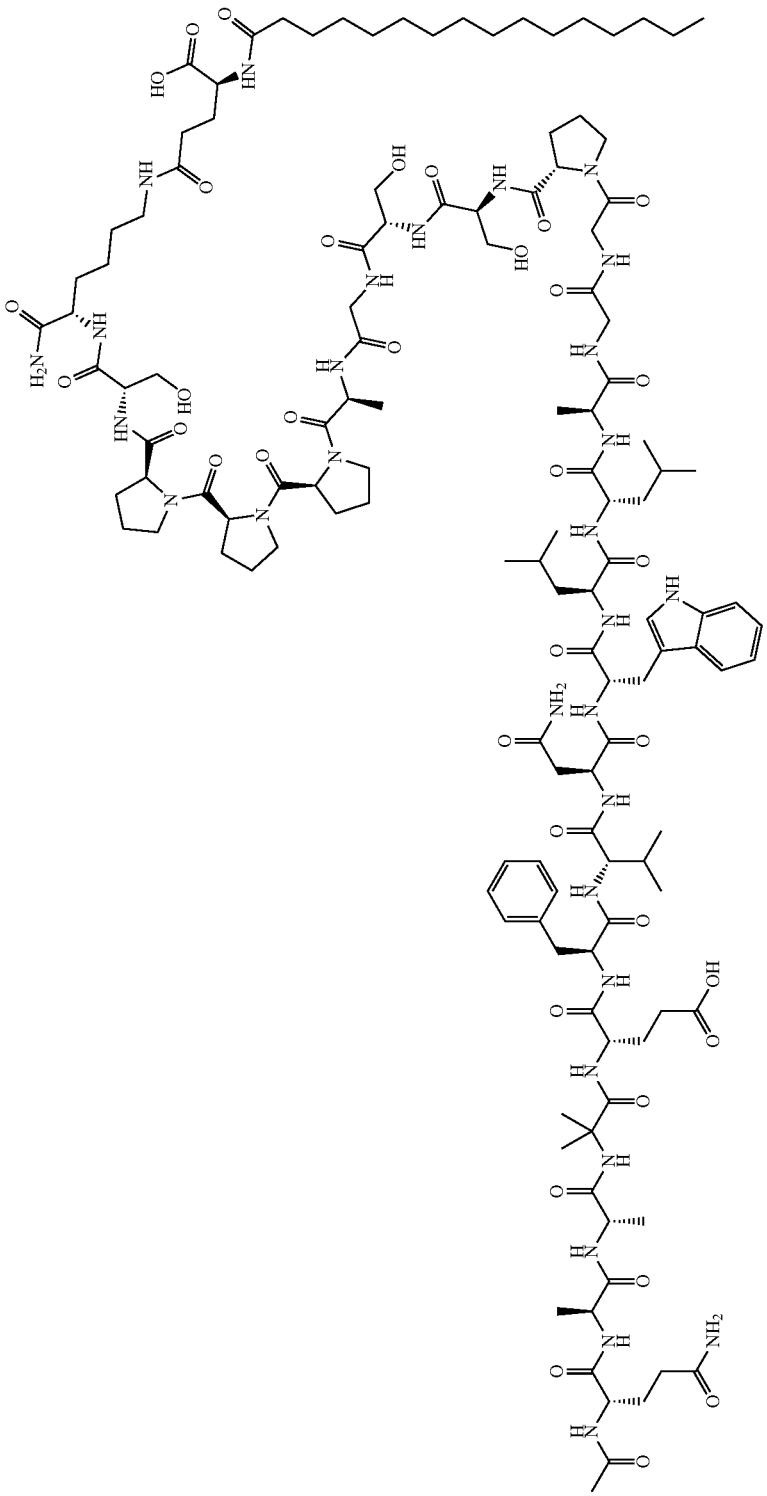

643
644
Compound 50
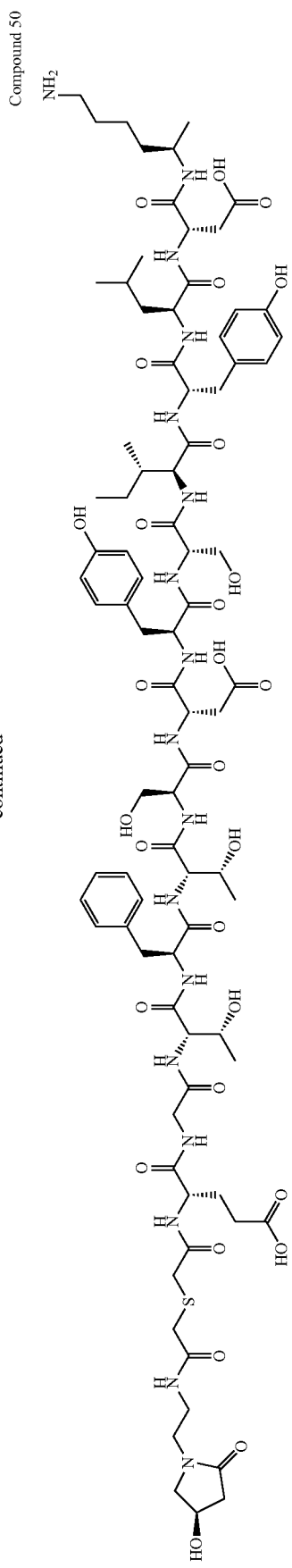
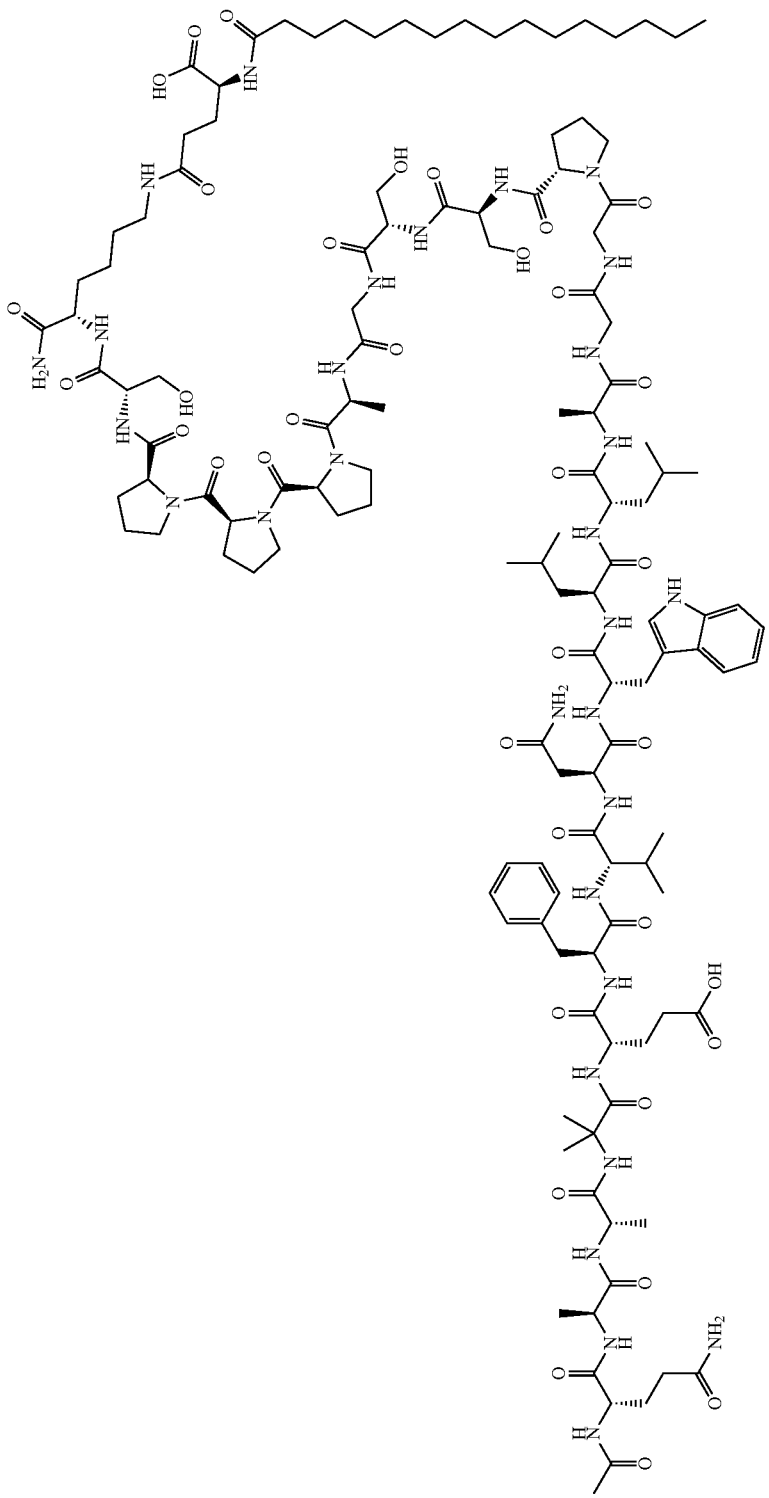

645
646
Compound 51
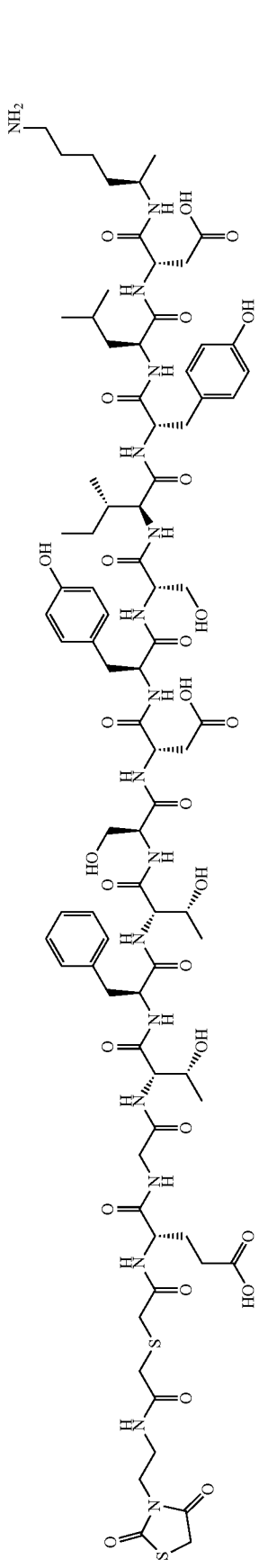
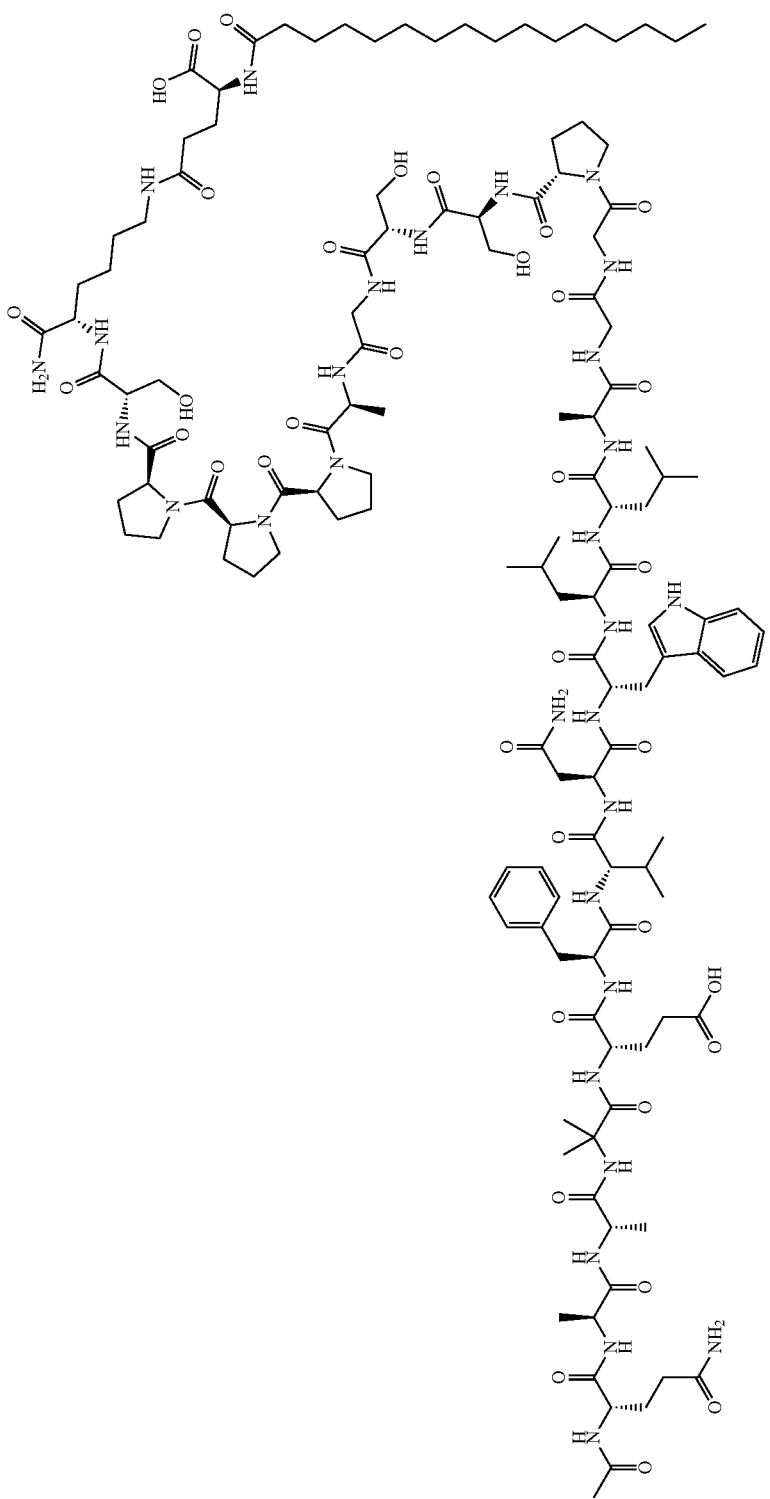

Compound 52
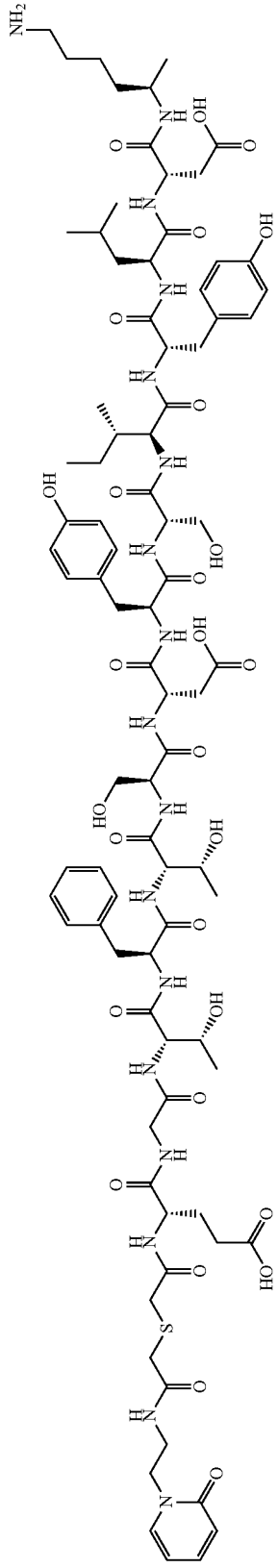
647
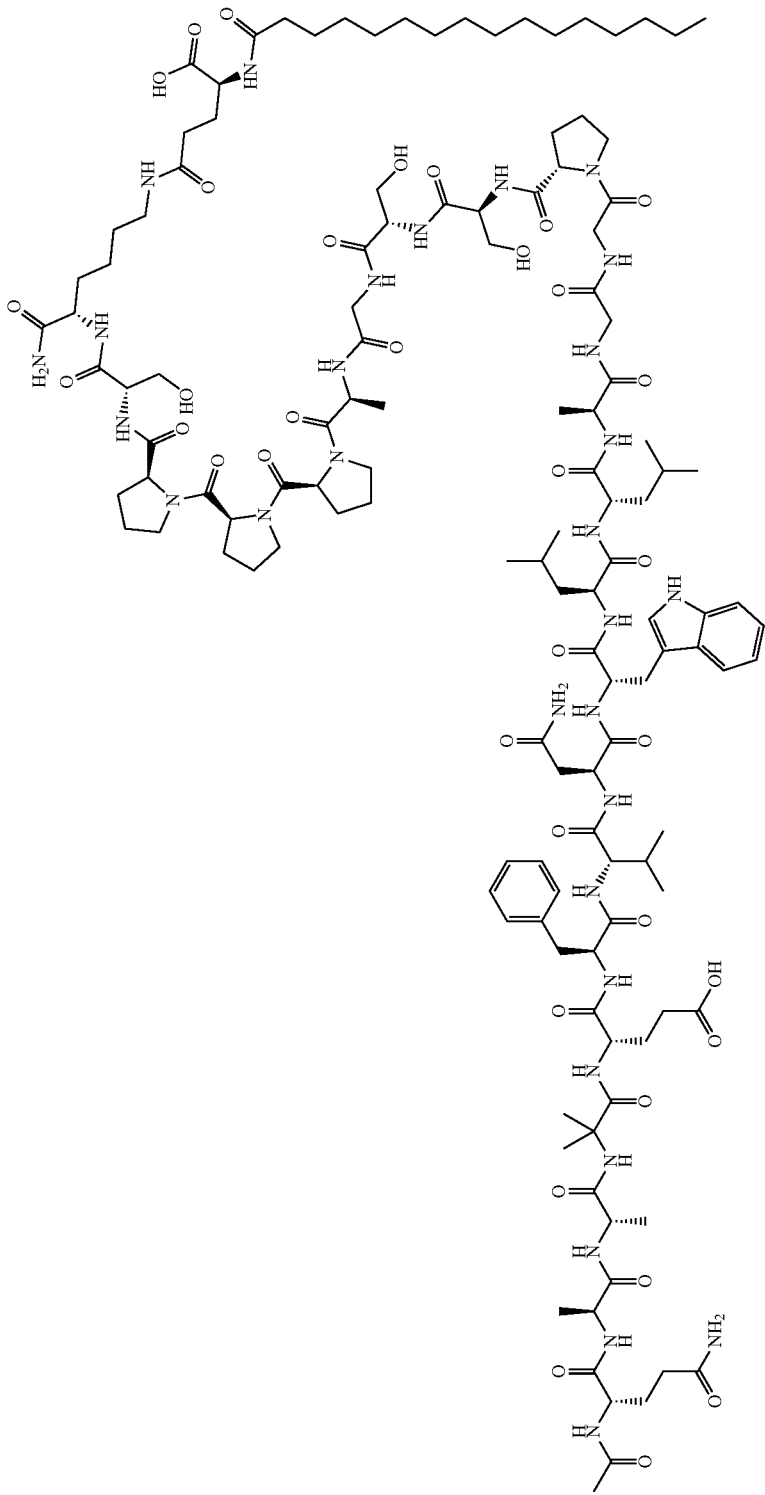
648

Compound 53
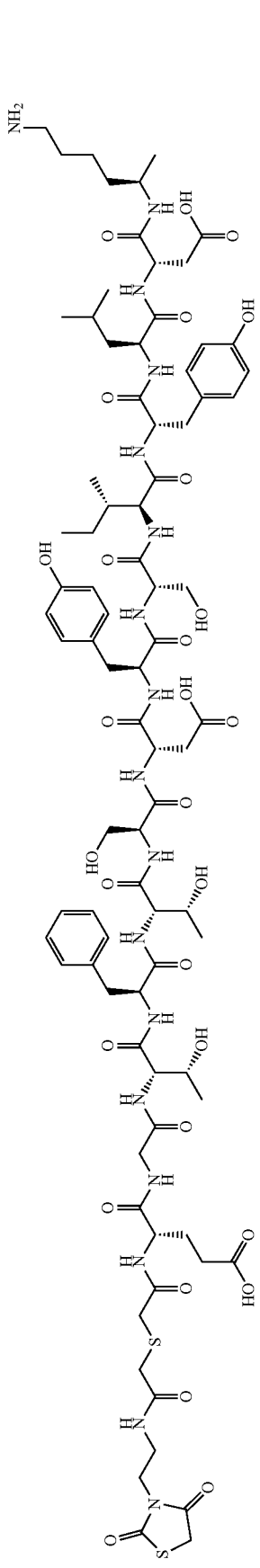
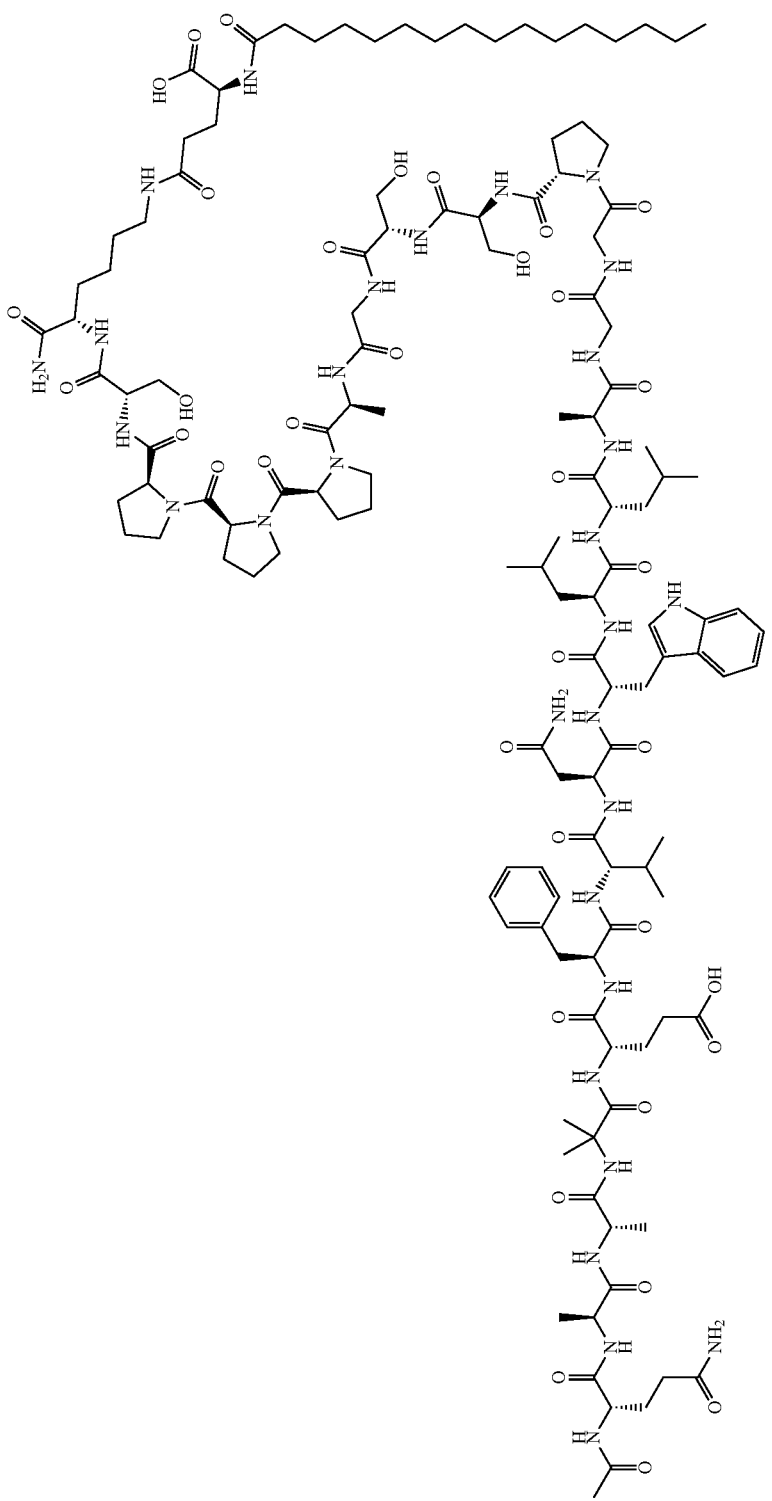

651 652
Compound 54
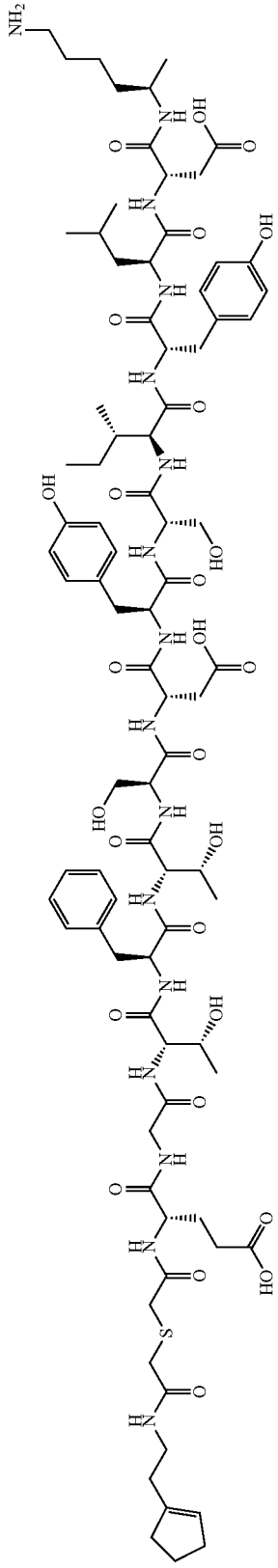
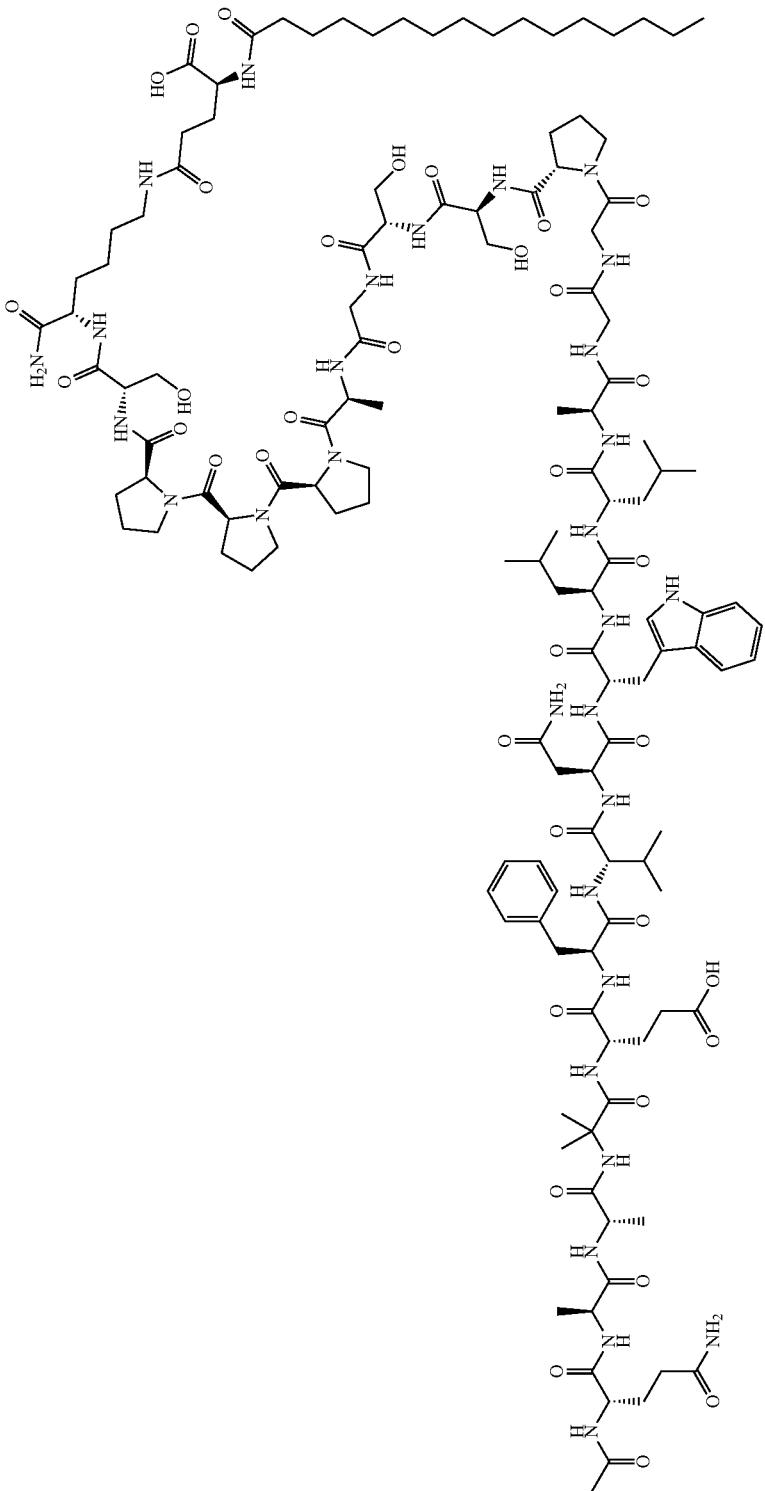

653 654
Compound 55
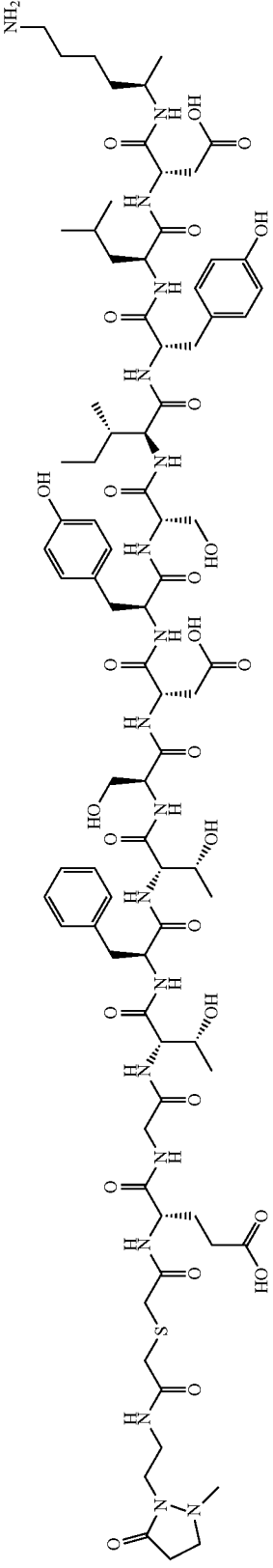
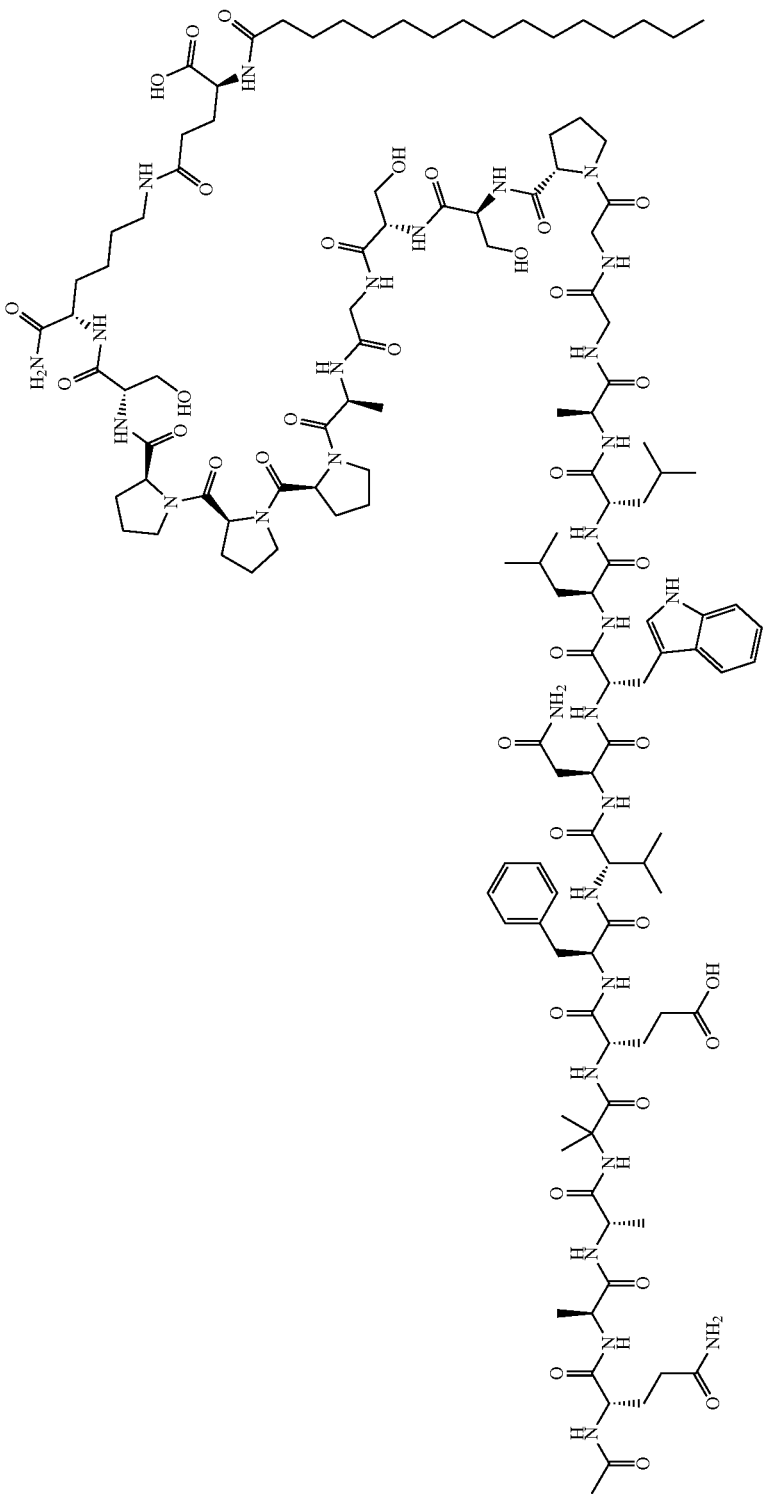

655
656
Compound 56
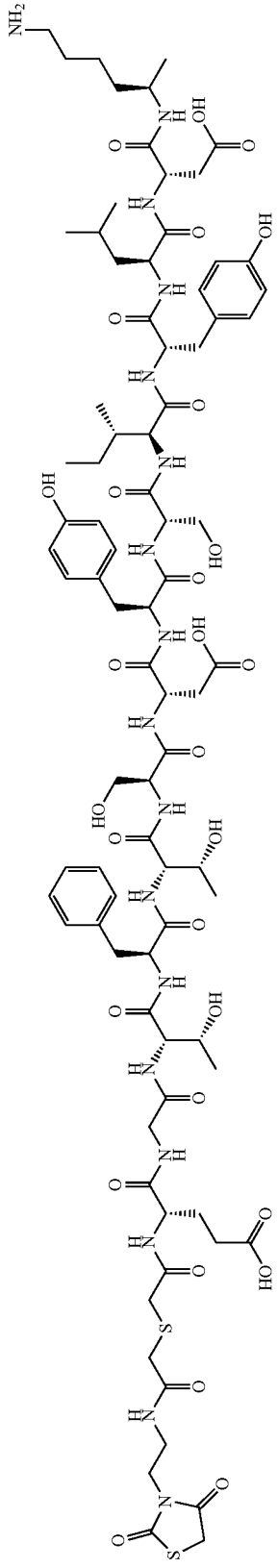
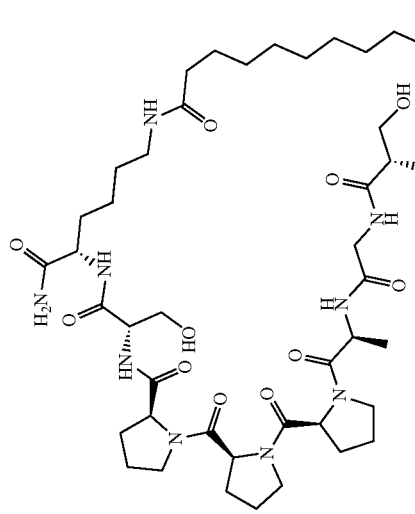
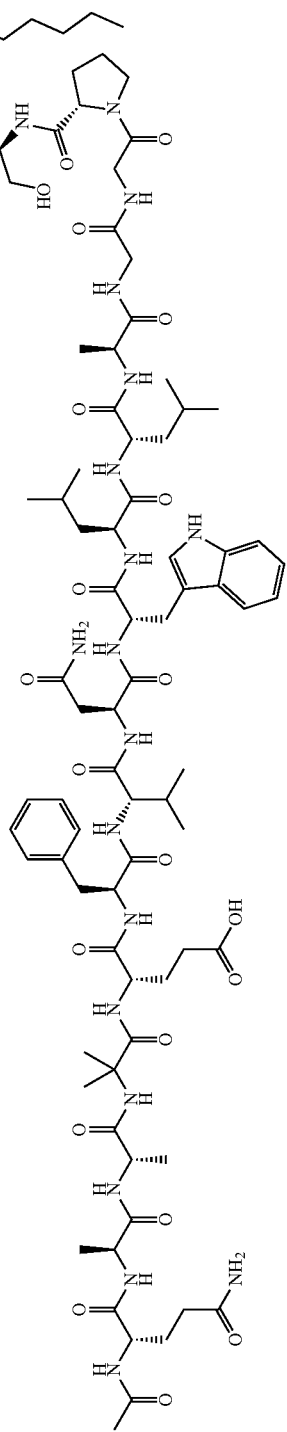

657
Compound 57
658
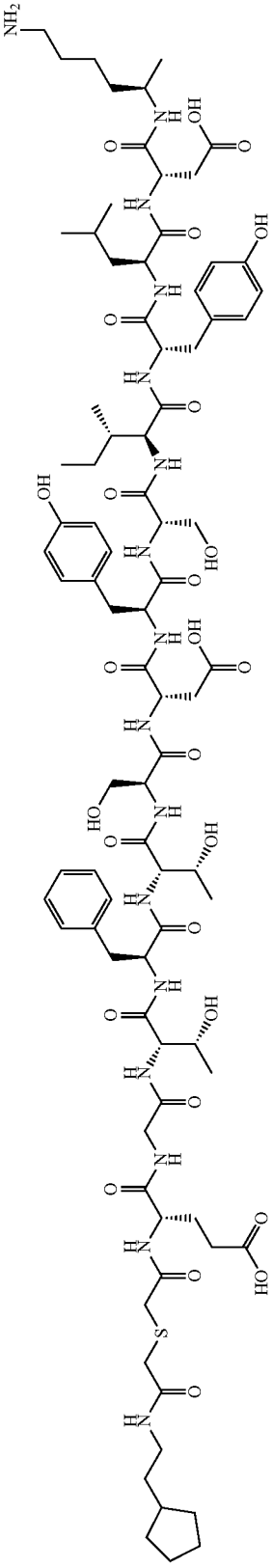
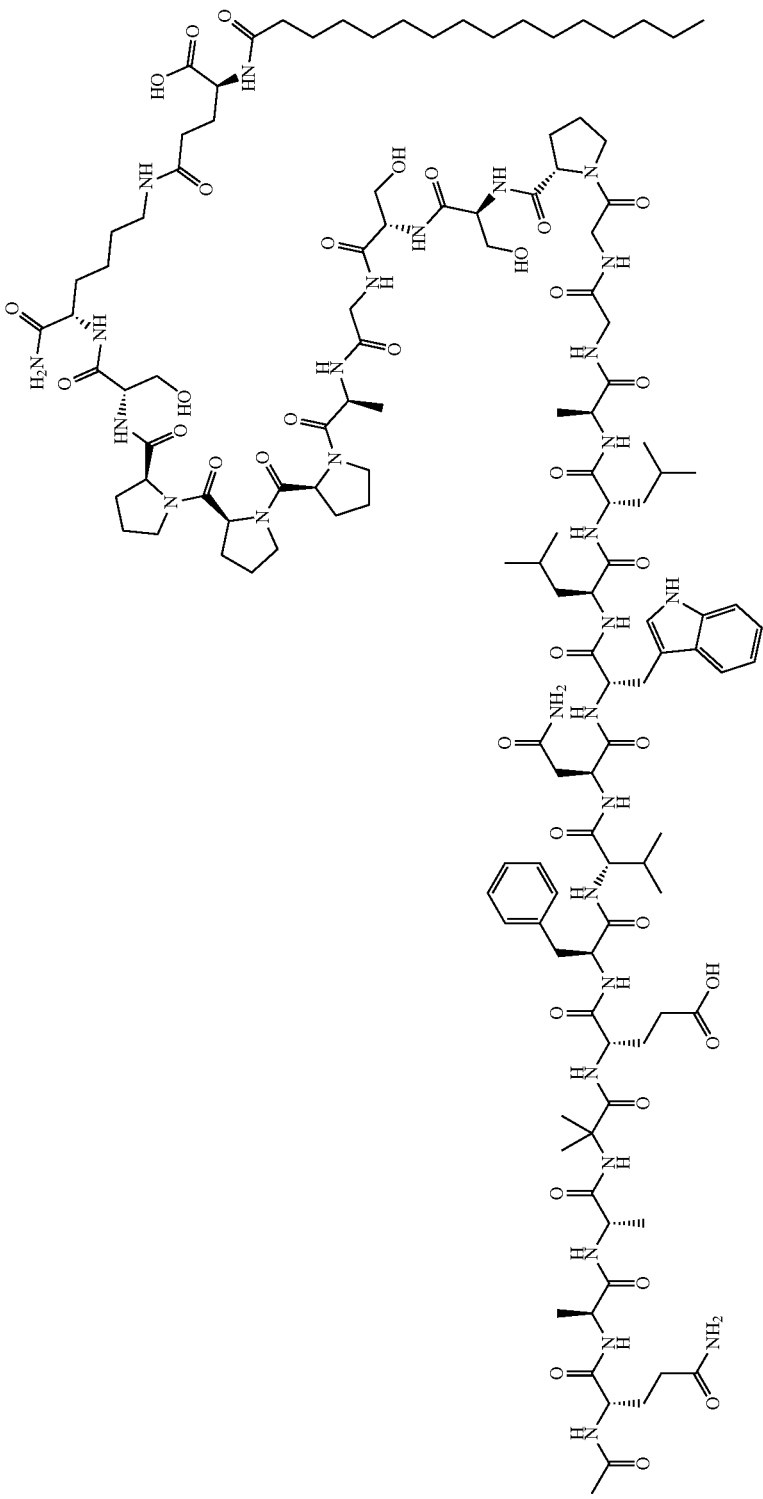

659
Compound 58
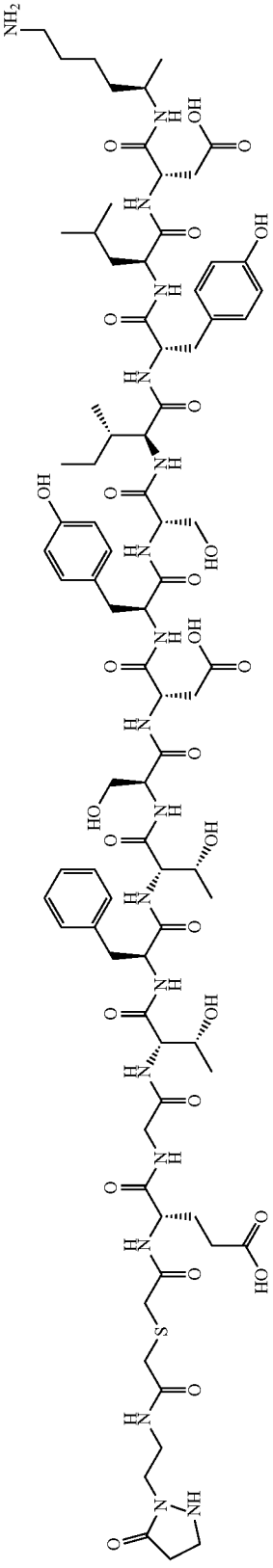
-continued
660
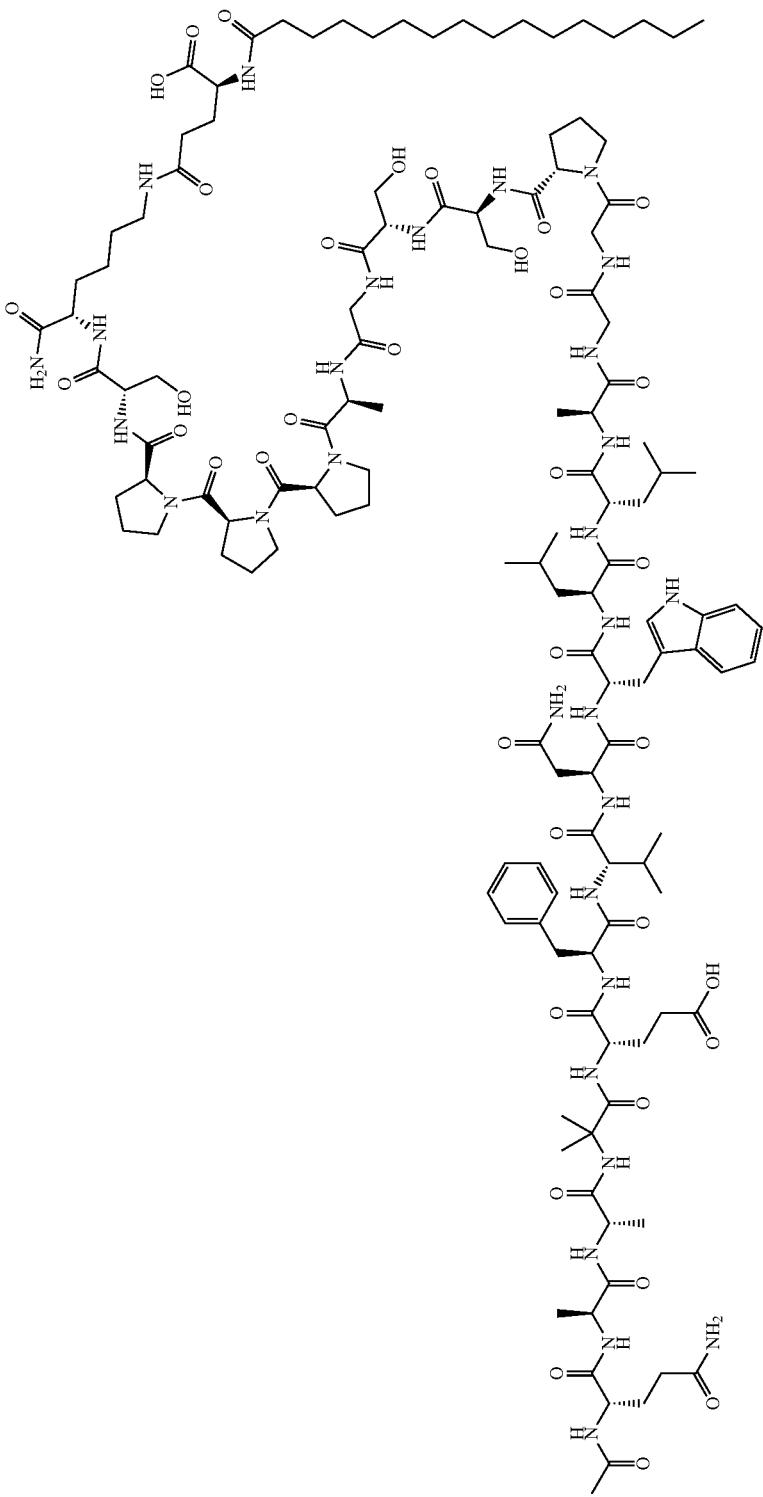

661
662
Compound 59
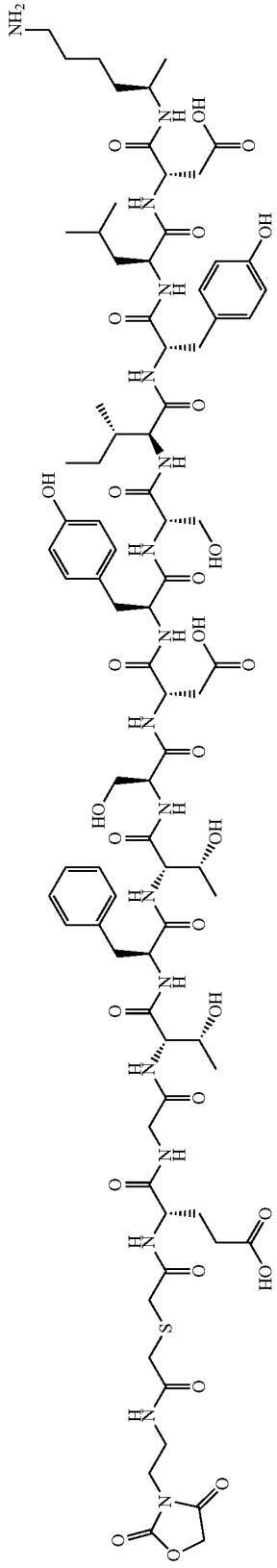
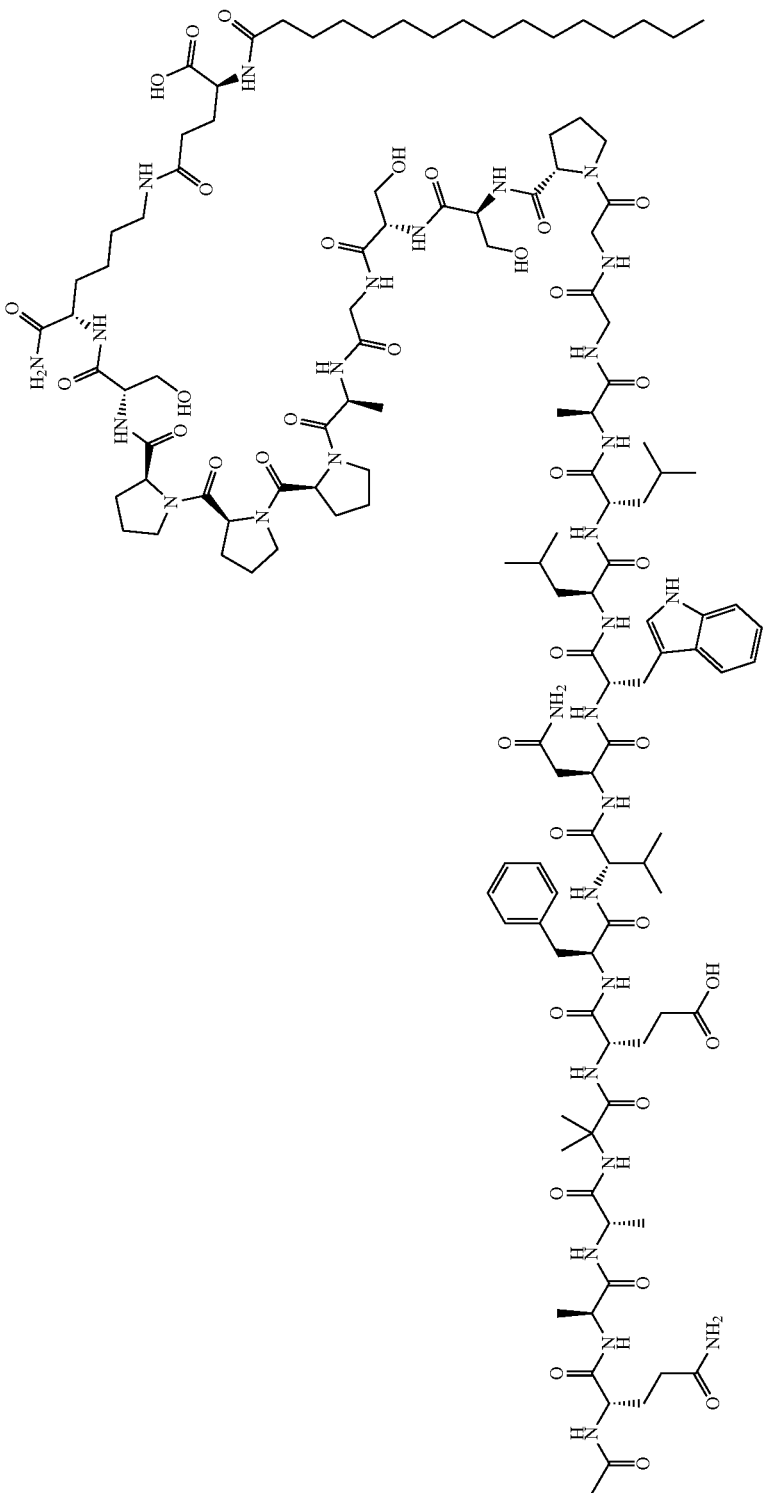

663                                            664
Compound 60
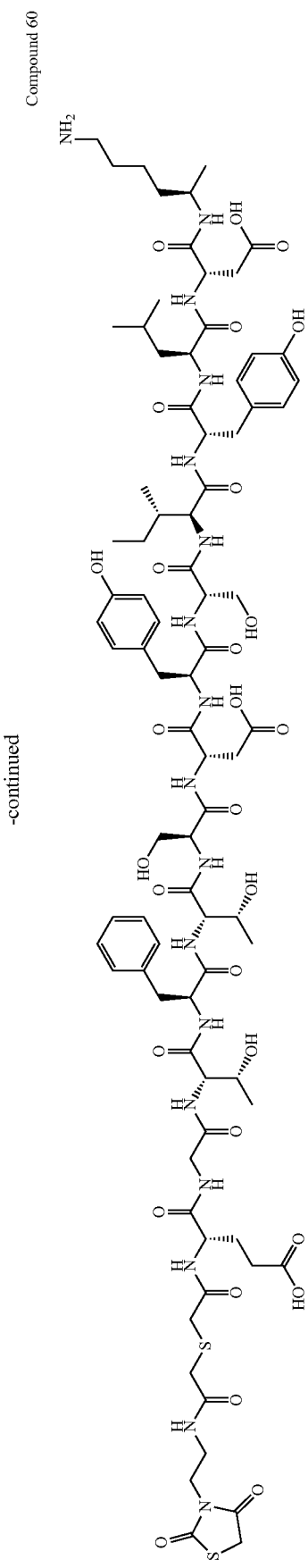
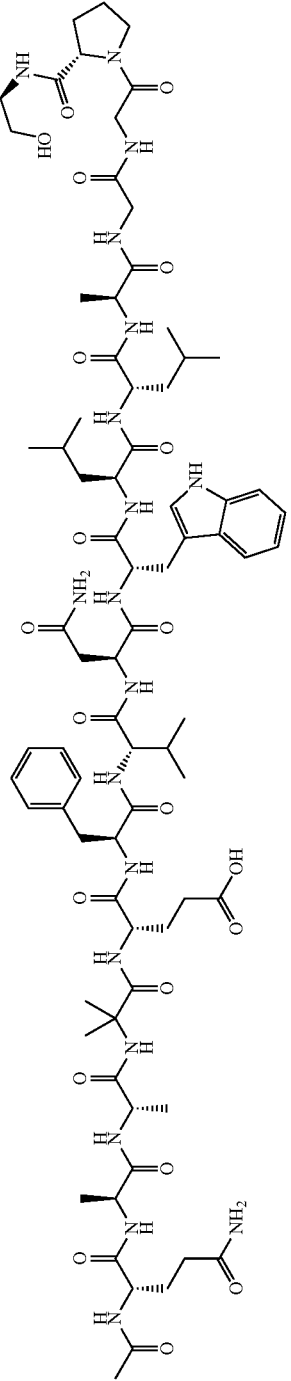

665 666
Compound 61
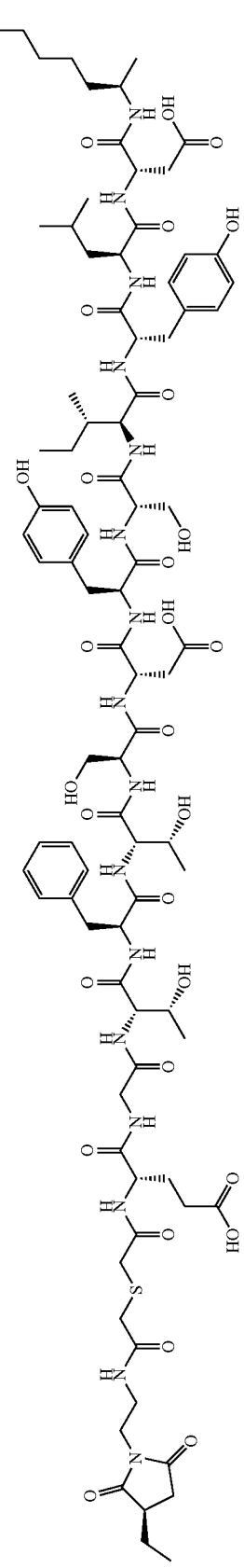
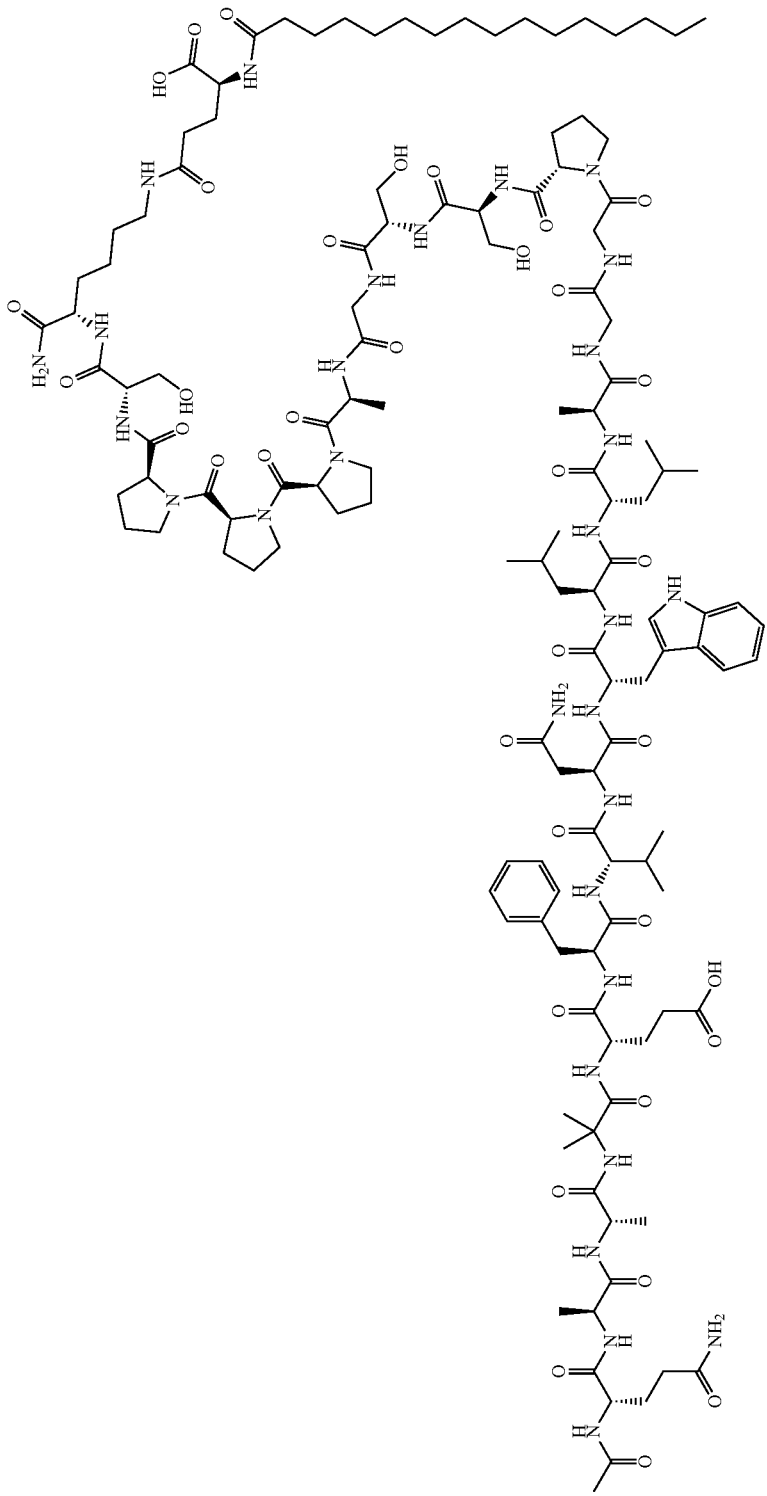

667 668
Compound 62
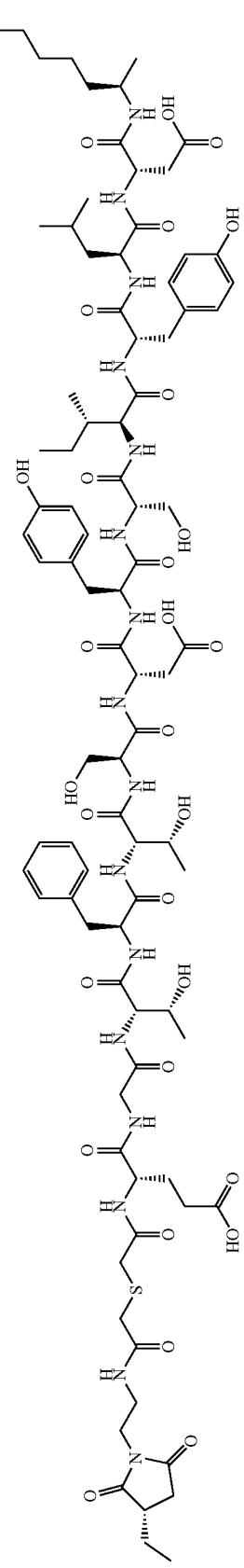
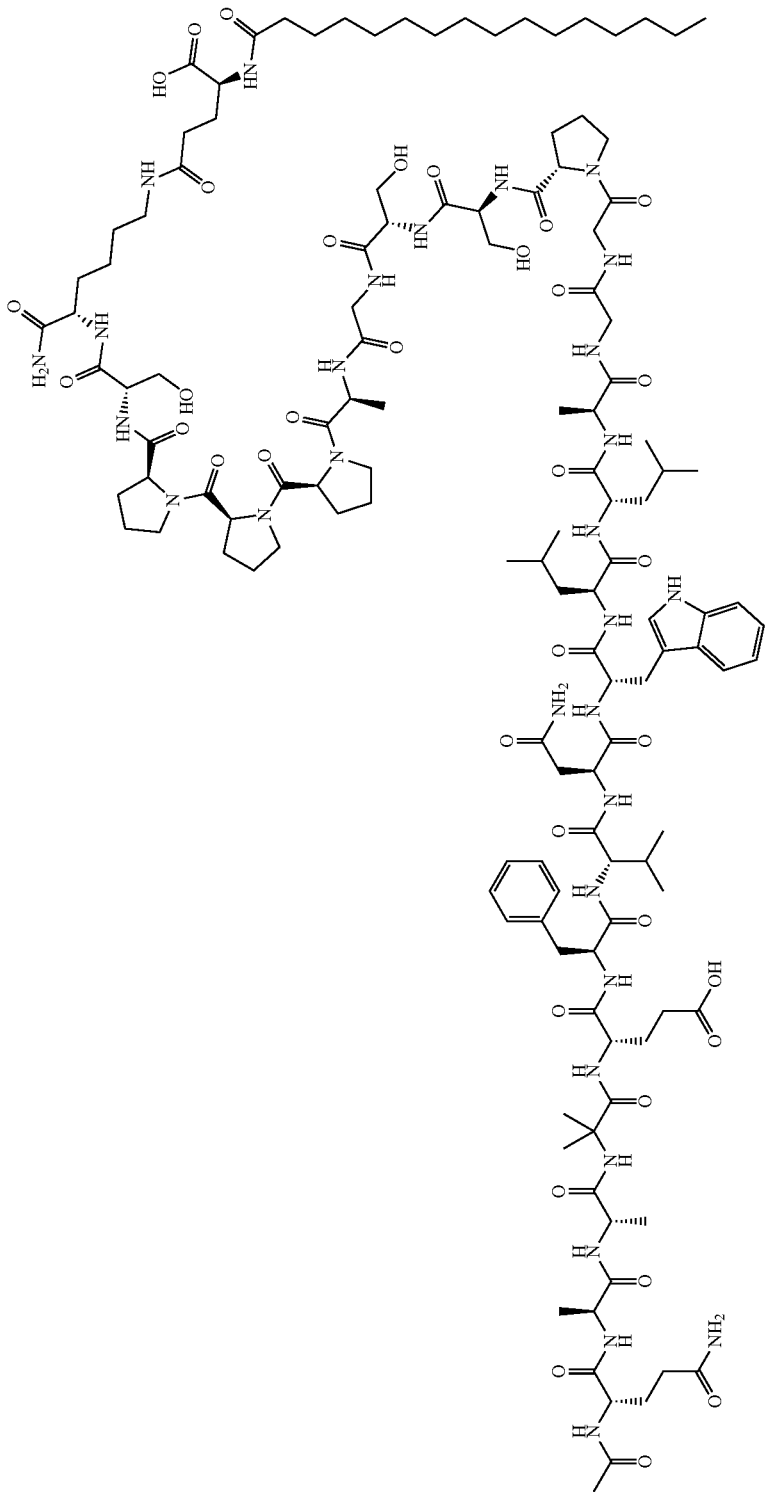

Compound 63
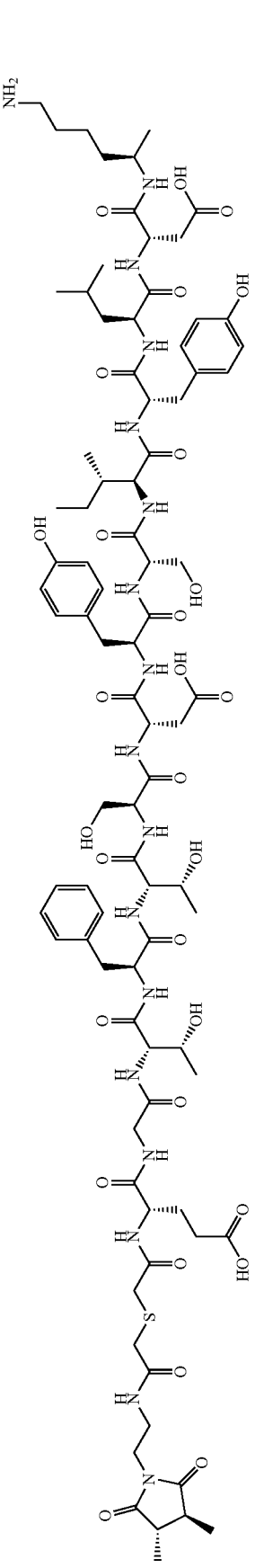
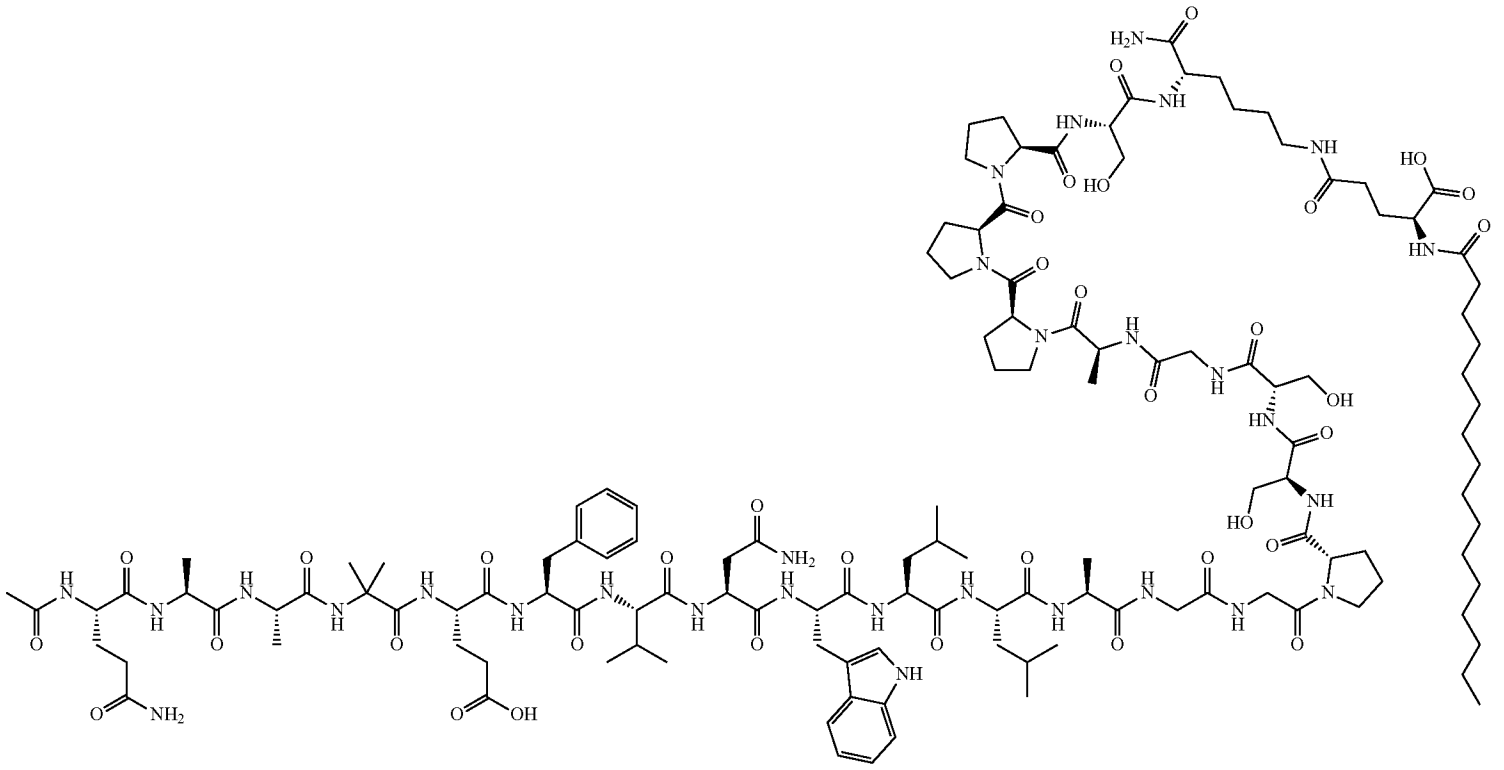 [SMILES: CCCCCCCCCCCCCCCC(=O)N[C@@H](CCC(=O)NCCCC[C@H](NC(=O)[C@H](CO)NC(=O)[C@@H]1CCCN1C(=O)[C@@H]1CCCN1C(=O)[C@@H]1CCCN1C(=O)[C@H](C)NC(=O)CNC(=O)[C@H](CO)NC(=O)[C@H](CO)NC(=O)[C@@H]1CCCN1C(=O)CNC(=O)CNC(=O)[C@H](C)NC(=O)[C@H](CC(C)C)NC(=O)[C@H](CC(C)C)NC(=O)[C@H](Cc1c[nH]c2ccccc12)NC(=O)[C@H](CC(N)=O)NC(=O)[C@@H](NC(=O)[C@H](Cc1ccccc1)NC(=O)[C@H](CCC(=O)O)NC(=O)C(C)(C)NC(=O)[C@H](C)NC(=O)[C@H](C)NC(=O)[C@H](CCC(N)=O)NC(C)=O)C(C)C)C(N)=O)C(=O)O]

Compound 64
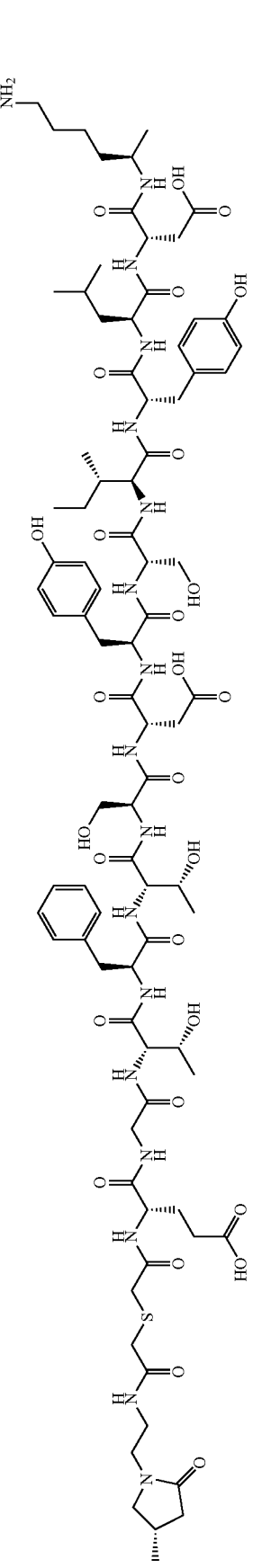
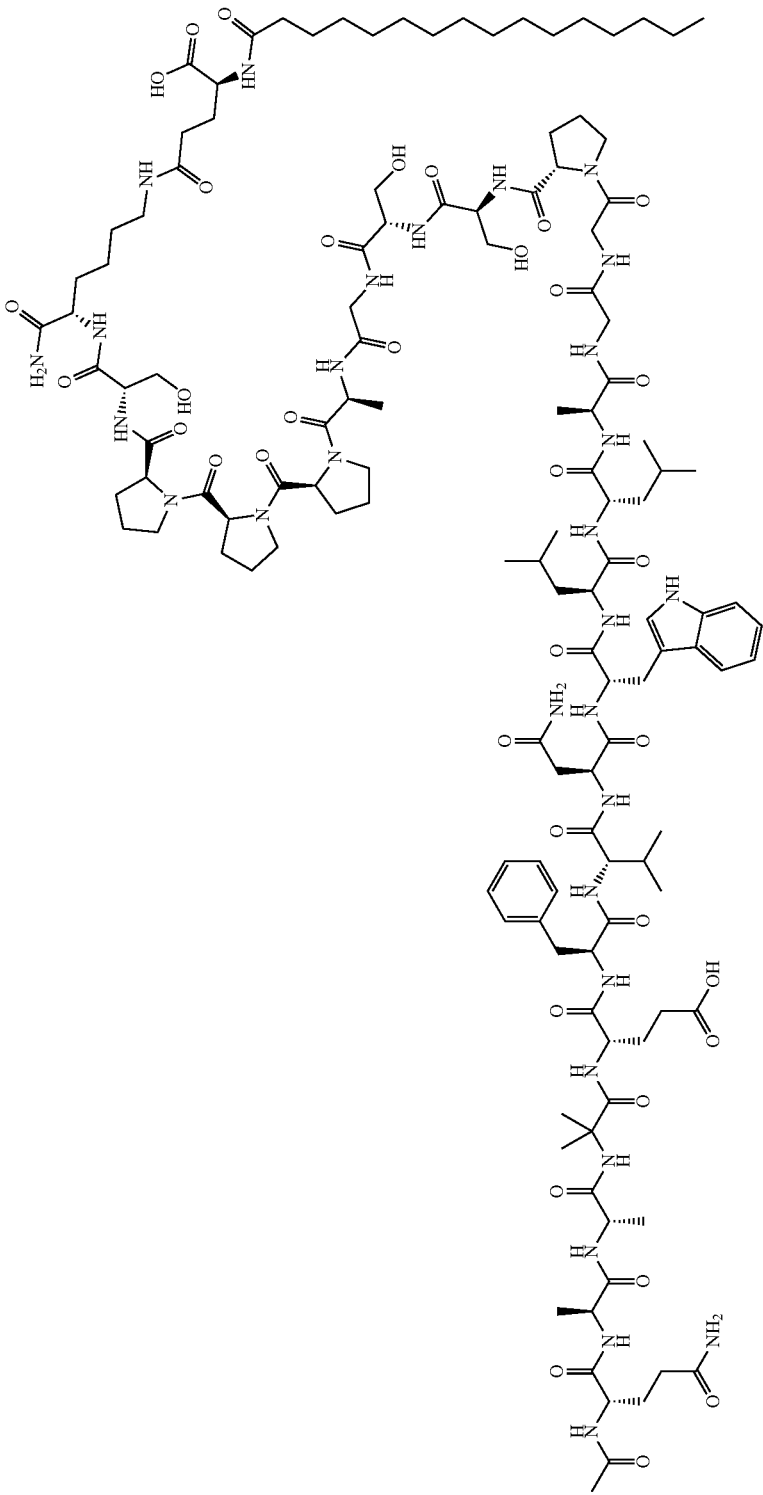

673
Compound 65
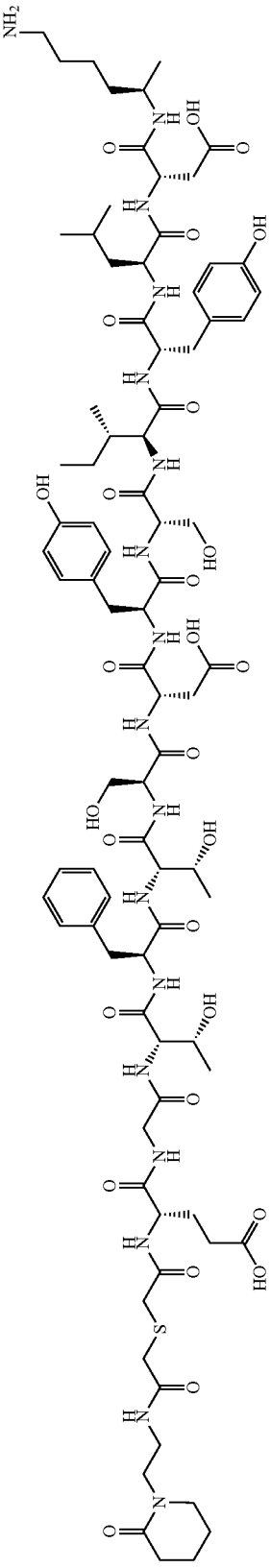
-continued
674
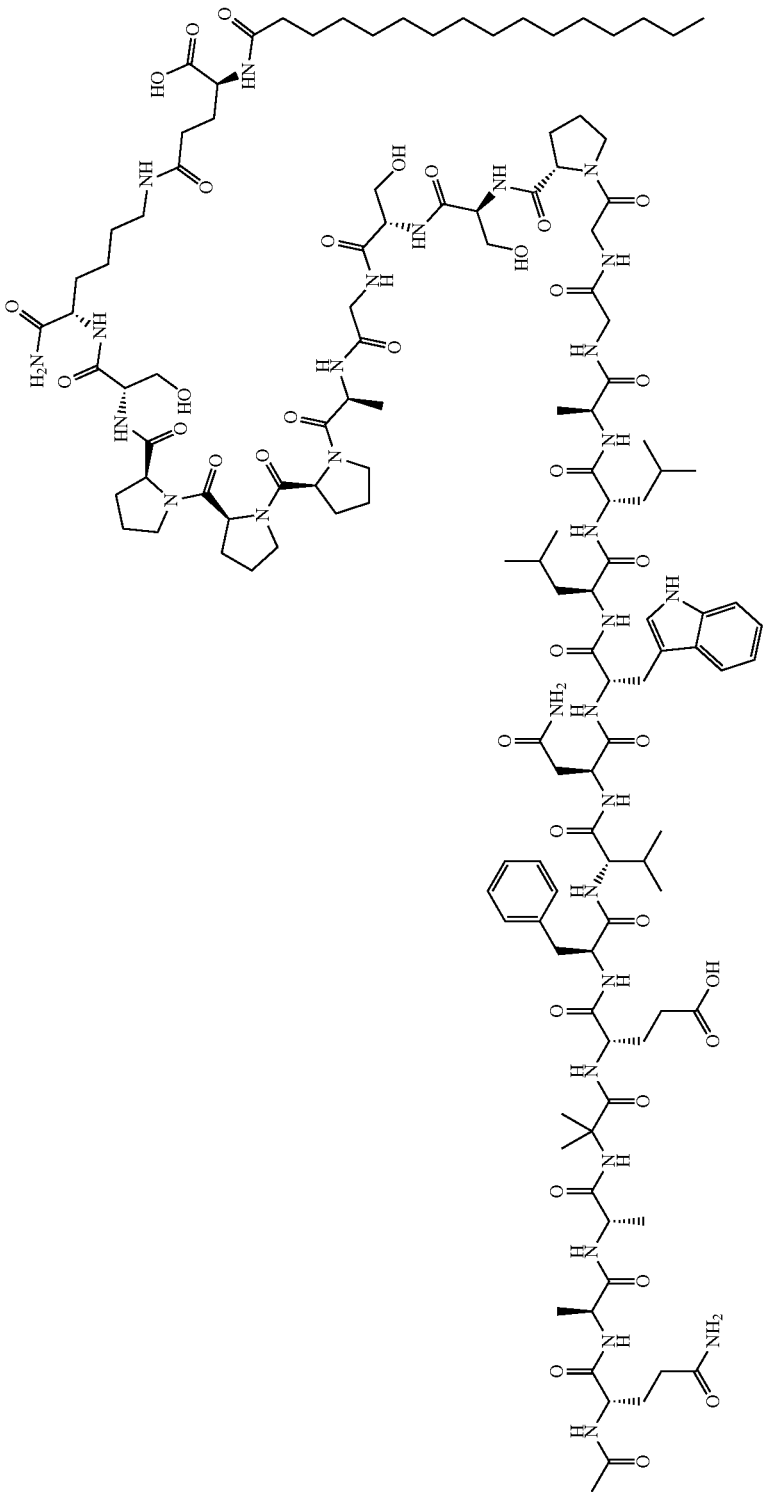

Compound 66
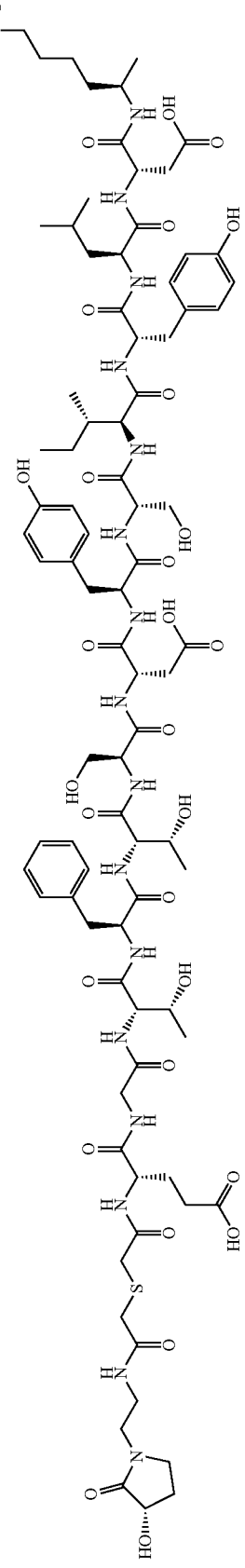
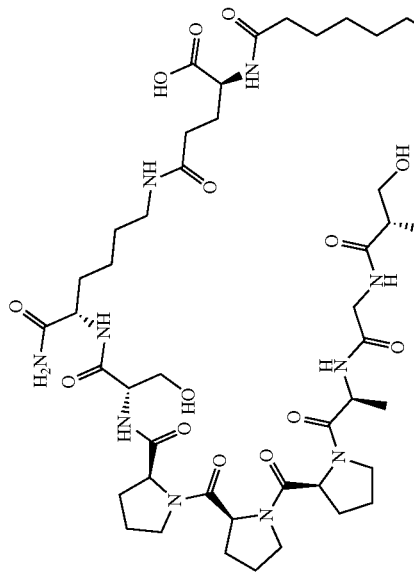
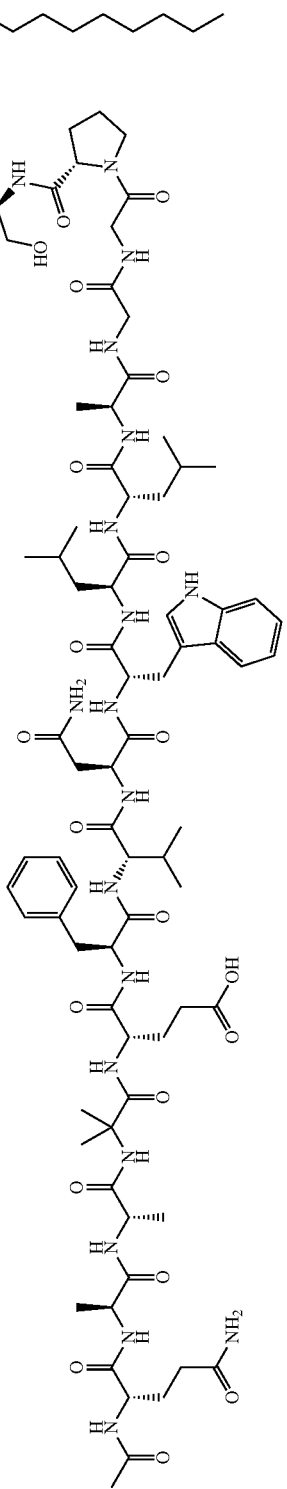

677 678
Compound 67
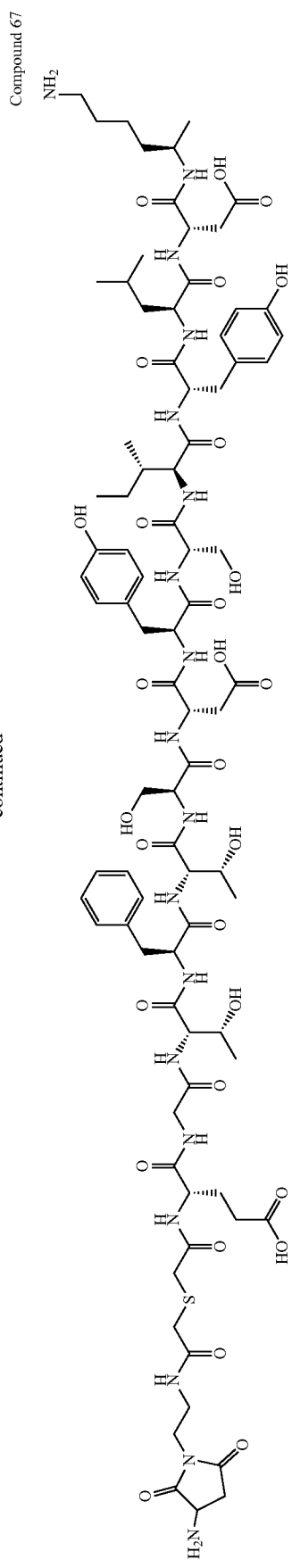
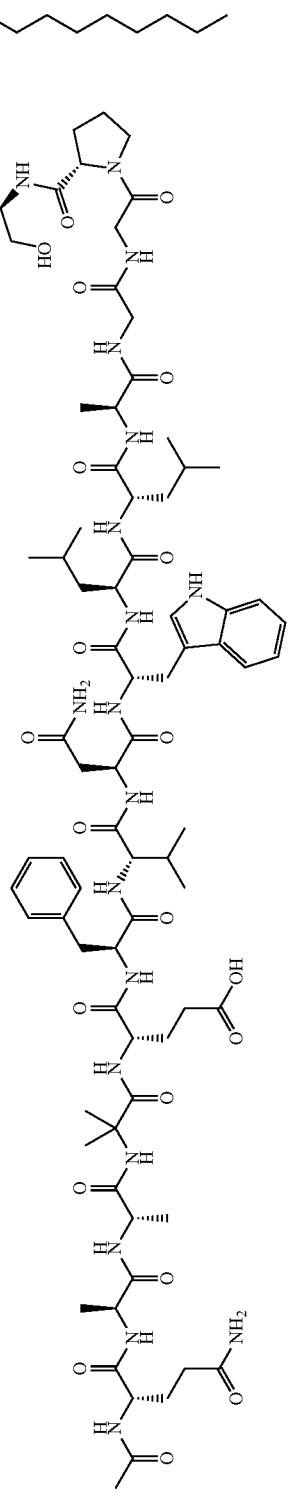

Compound 68
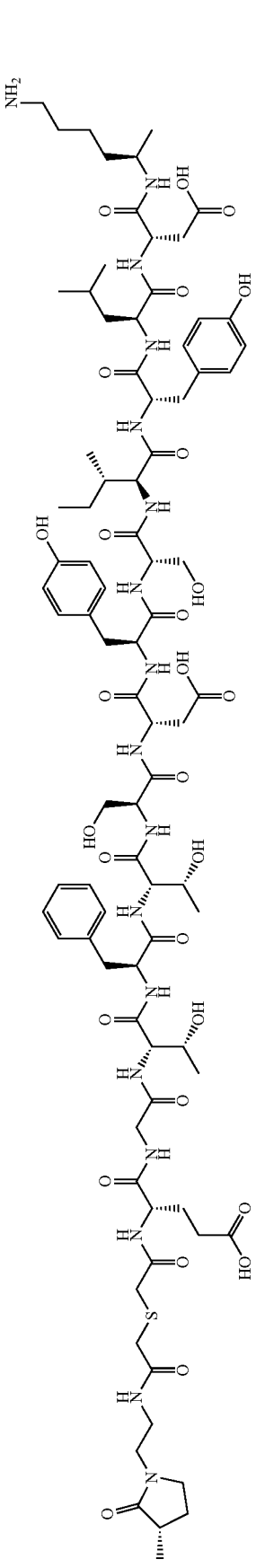
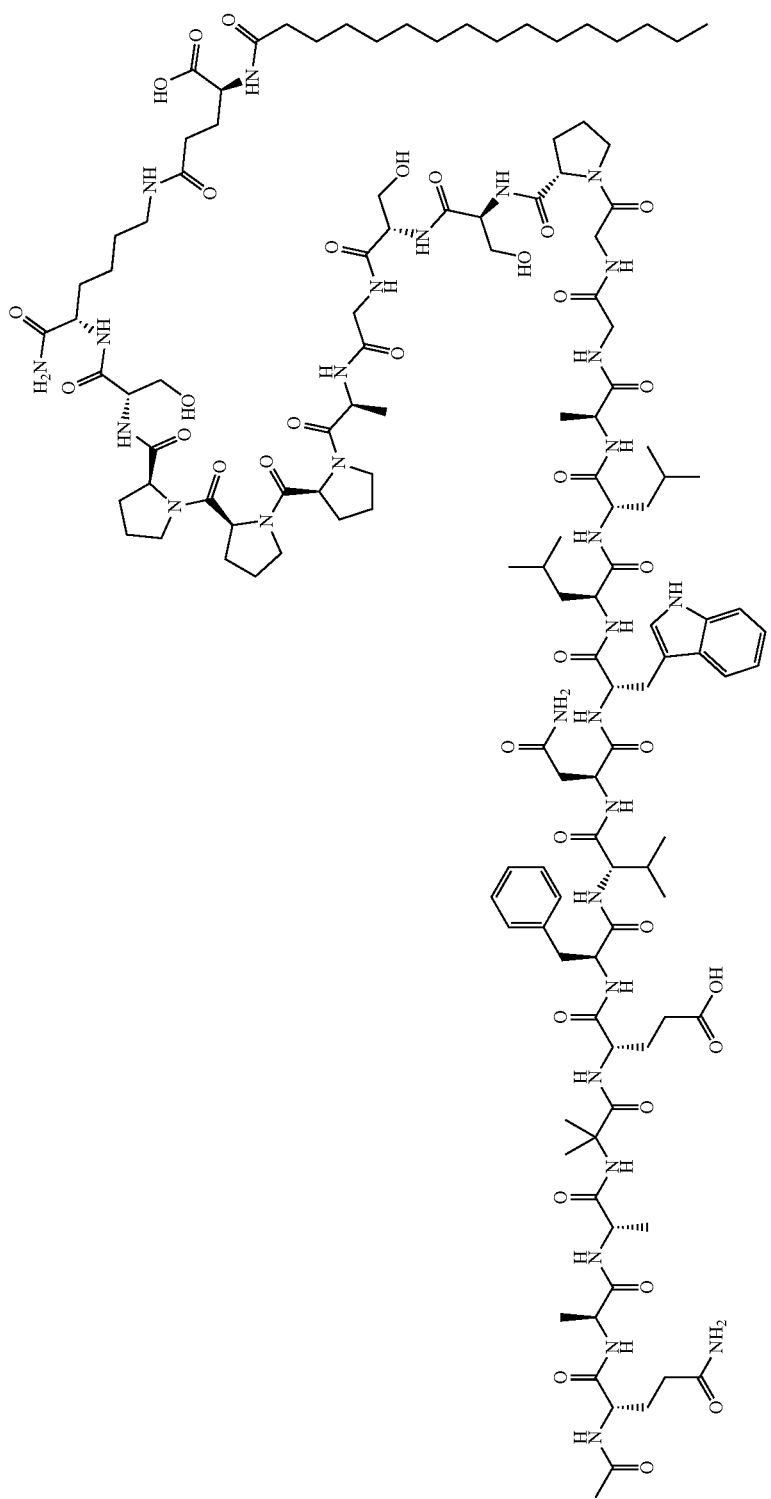

681
Compound 69
682
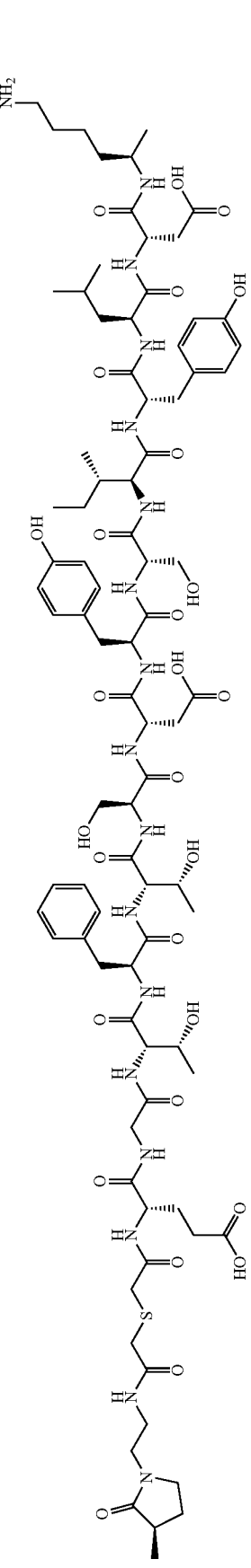
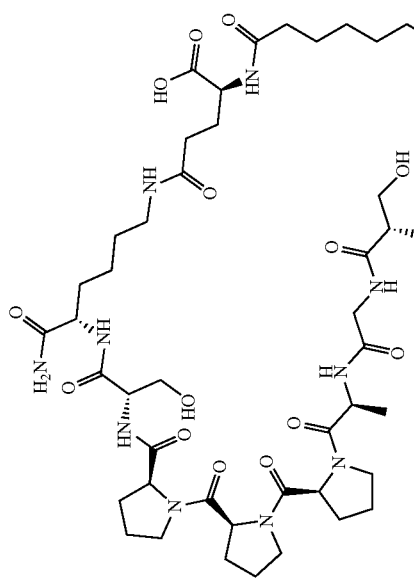
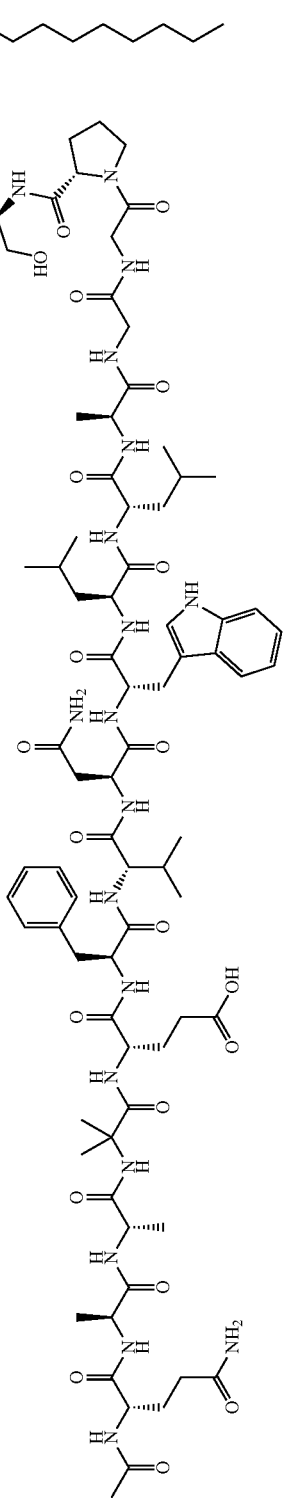

683
Compound 73
684
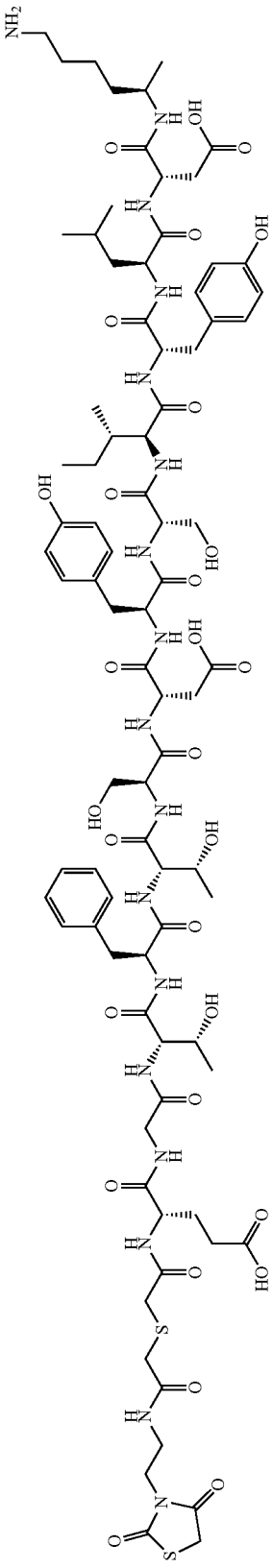
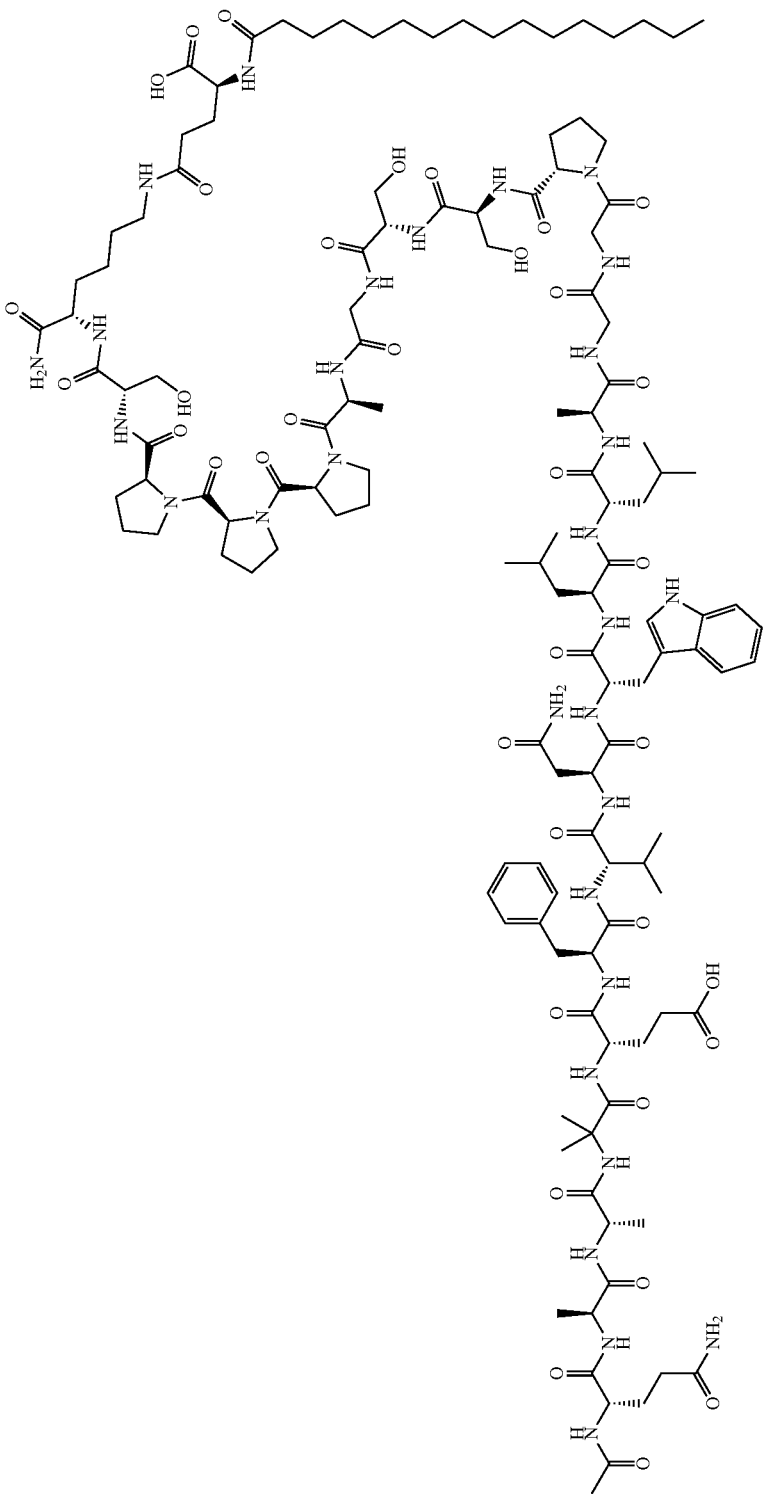

685                               686
Compound 74
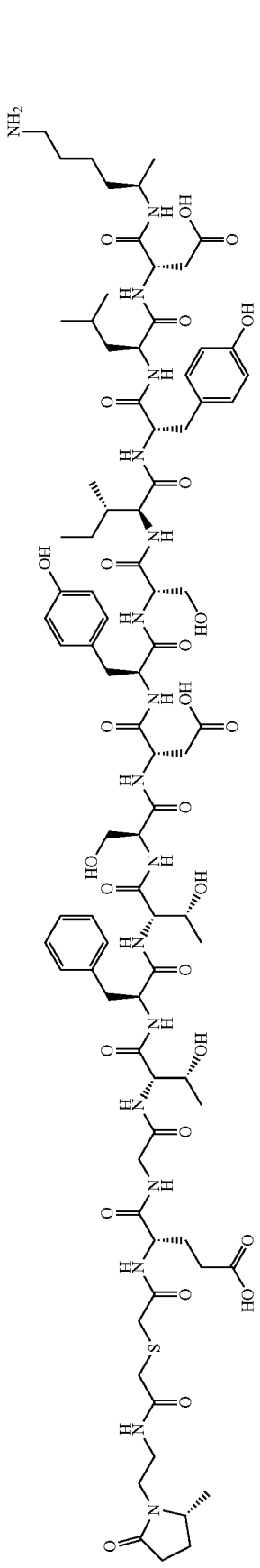
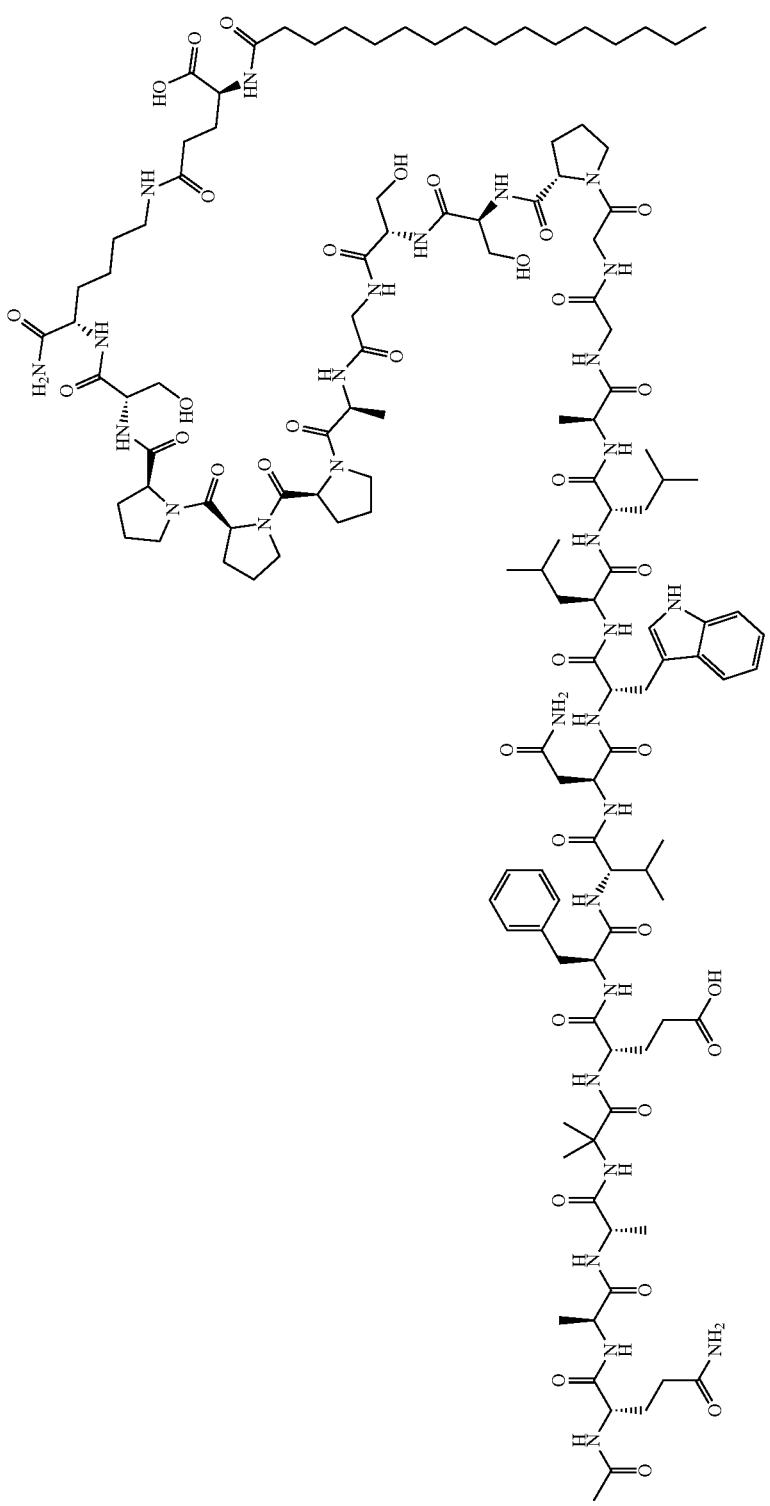

687 688
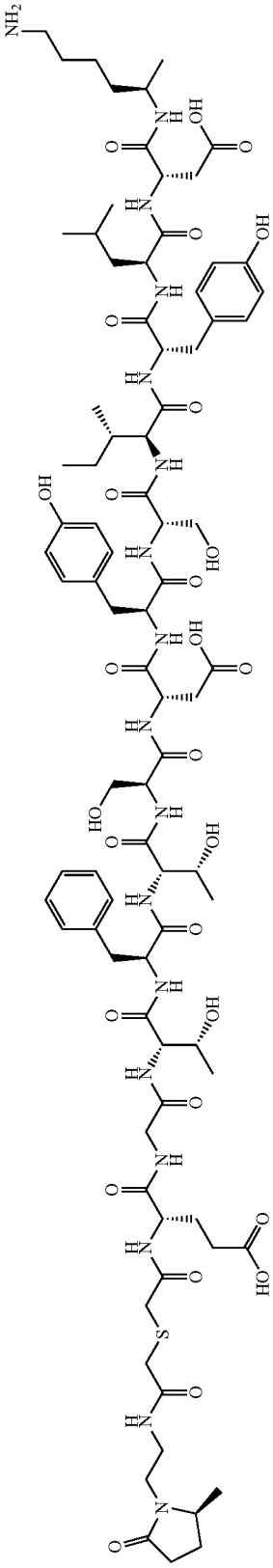
Compound 75
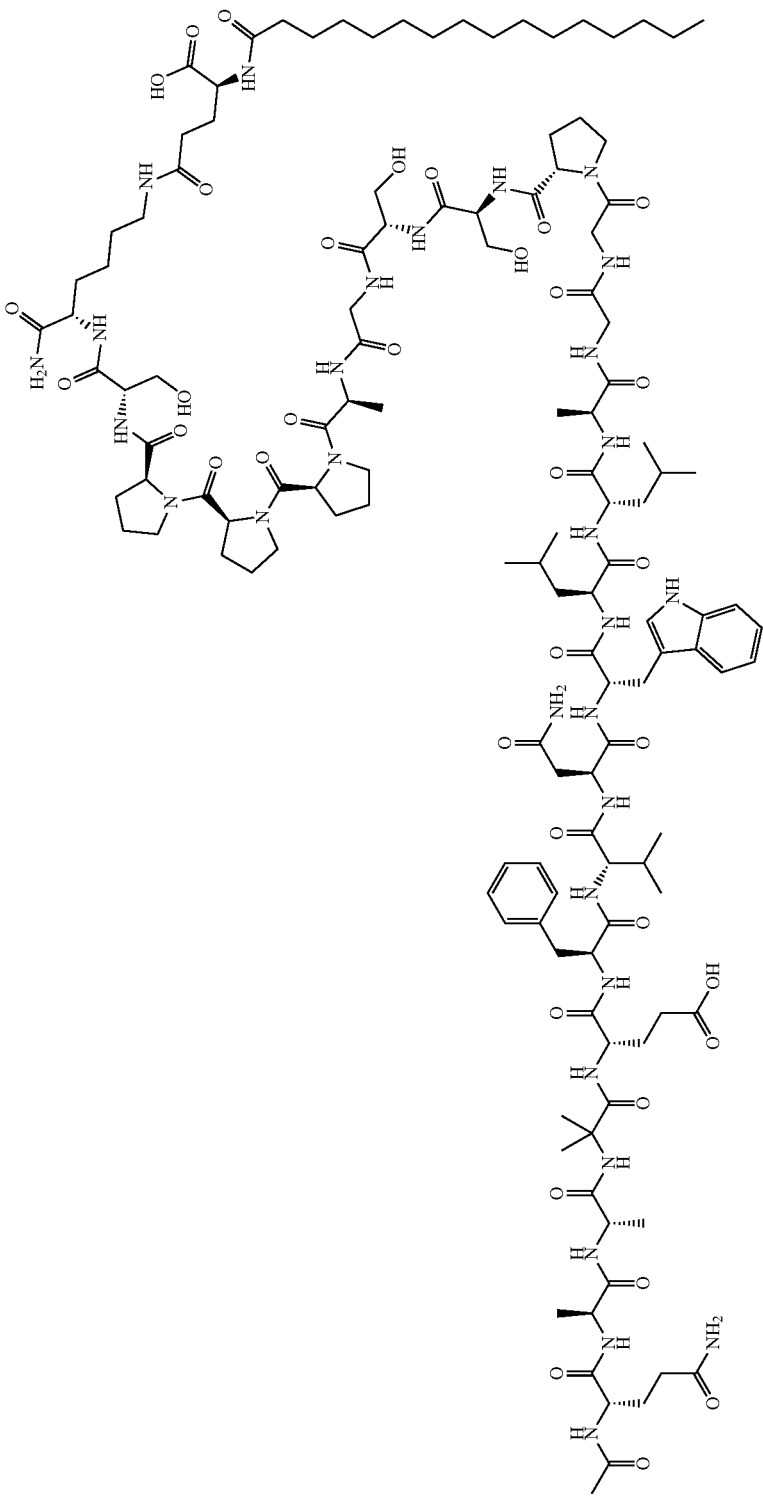

689
690
Compound 78
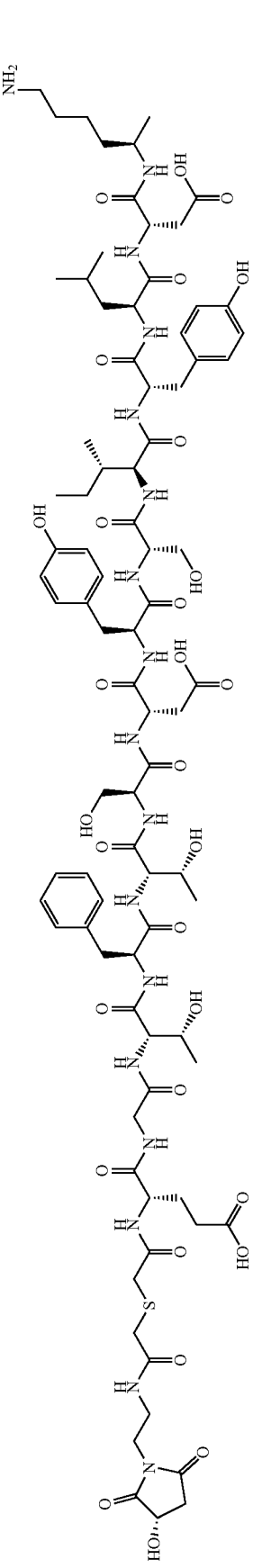
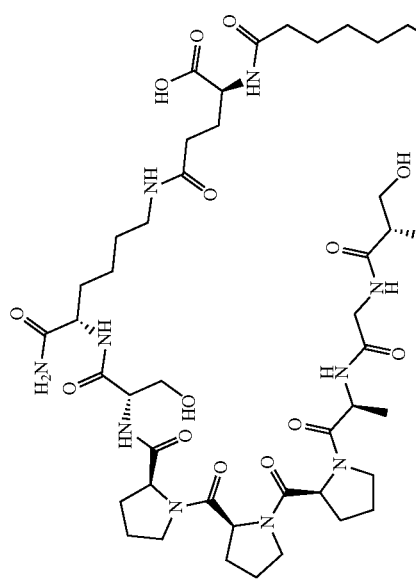
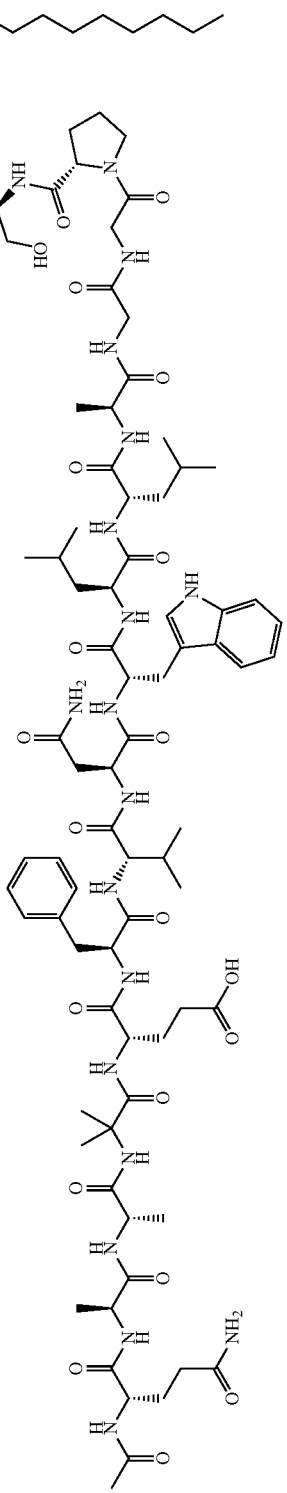

691
692
Compound 79
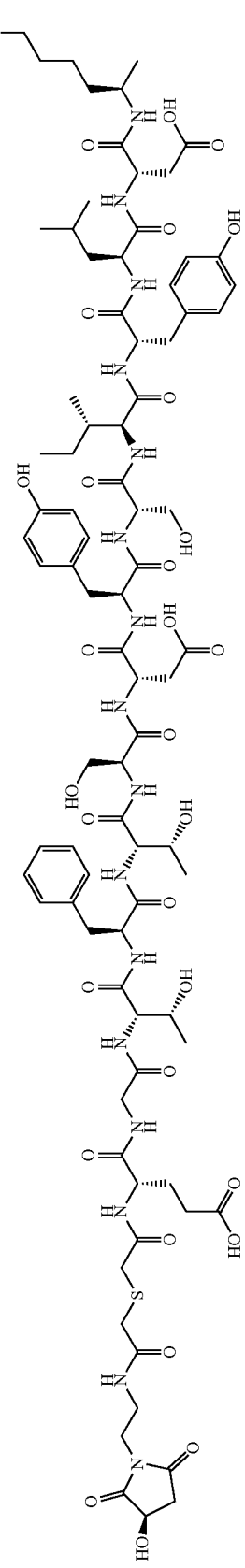
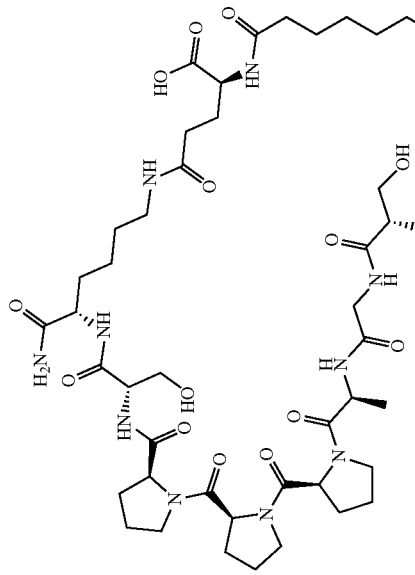
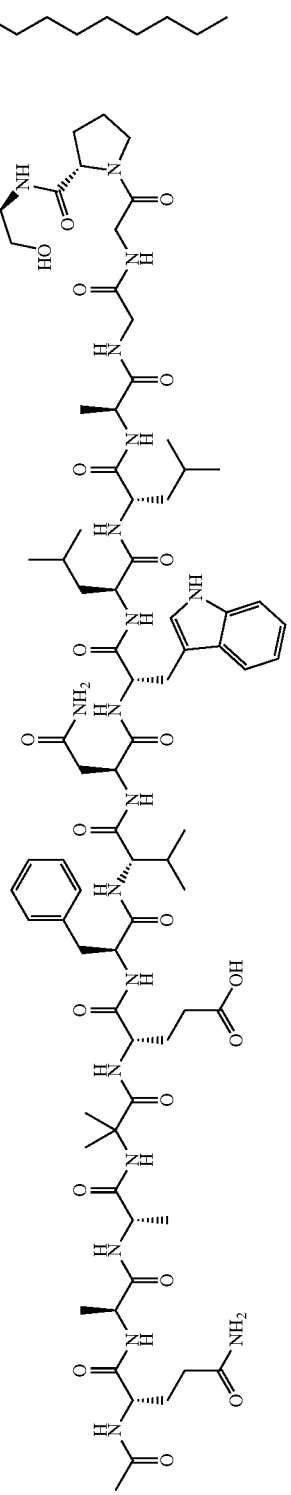

Compound 80
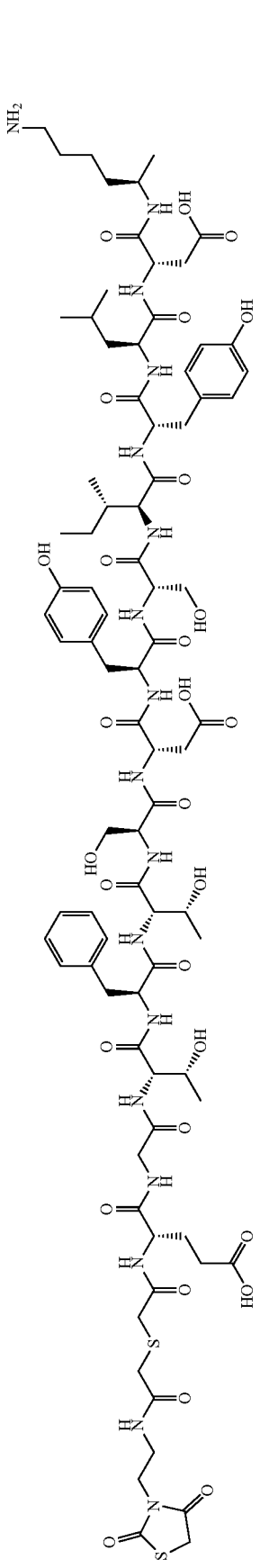
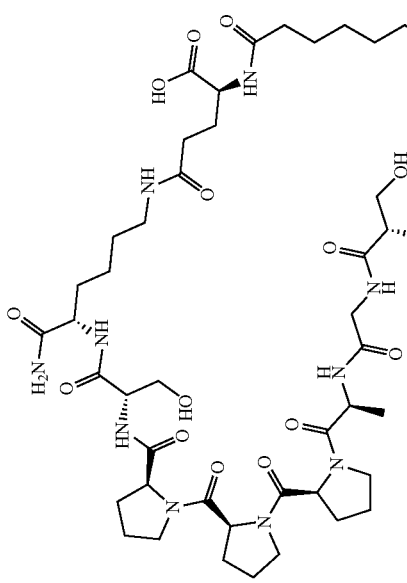
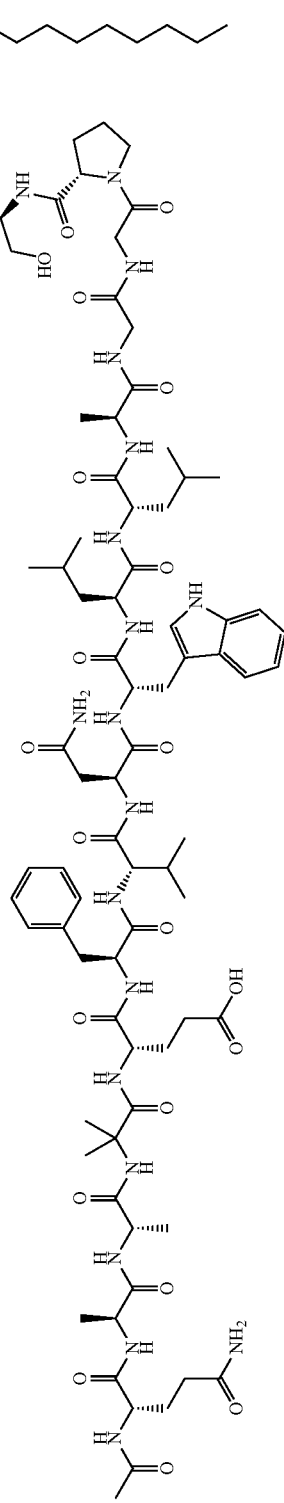
693
694

Compound 81
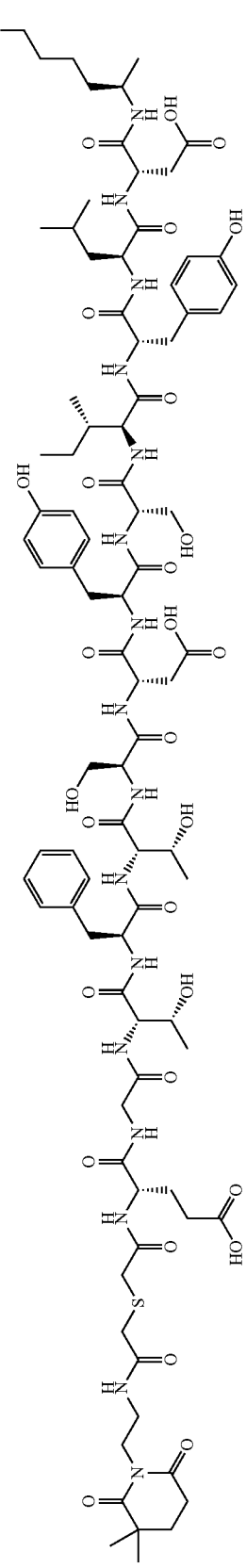
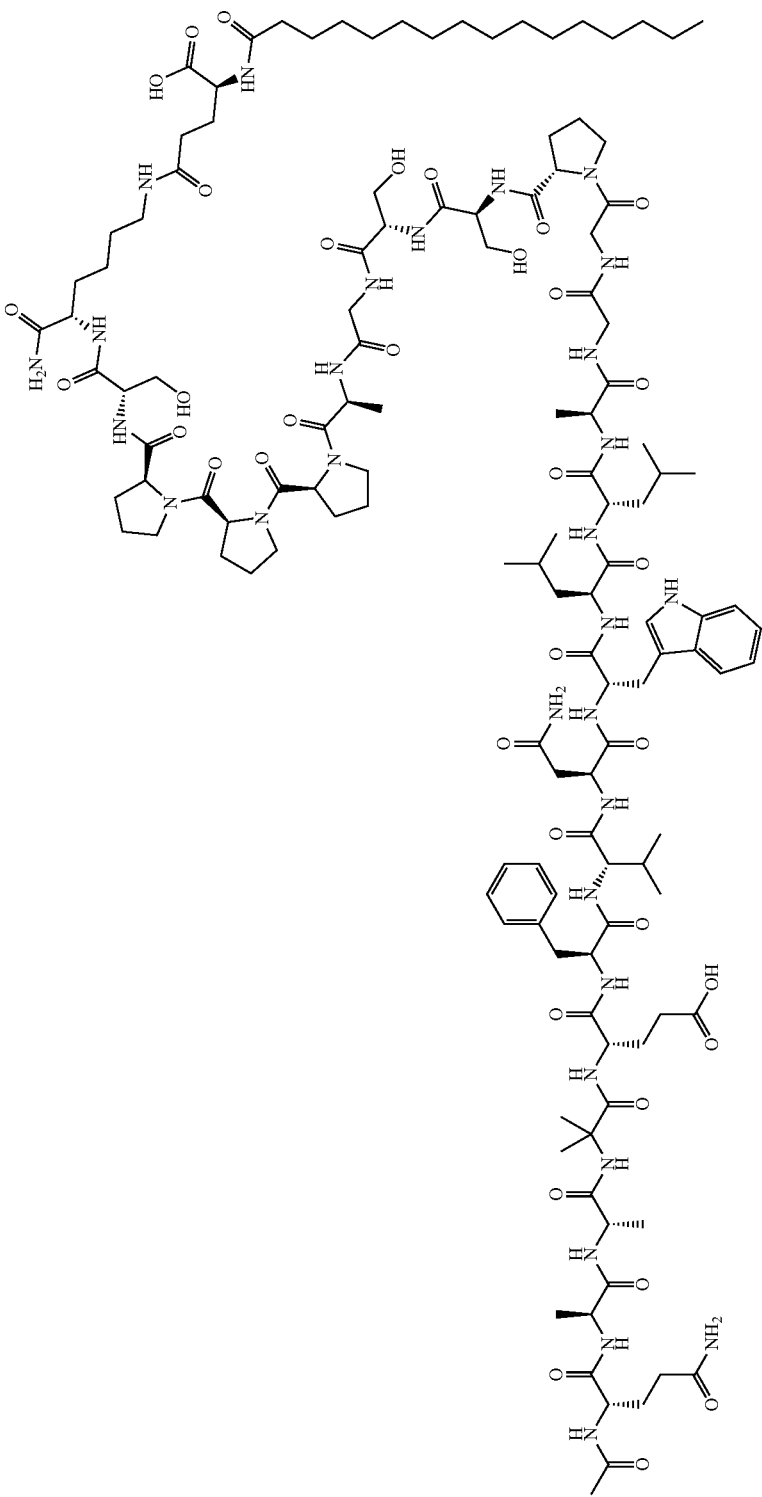

Compound 82
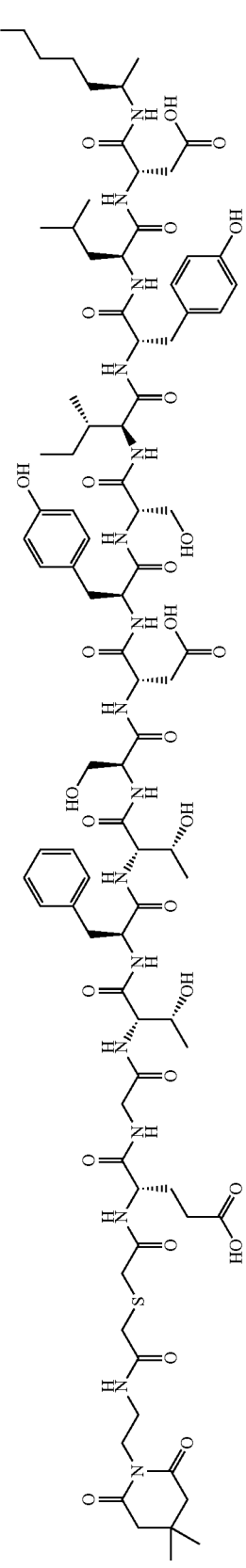
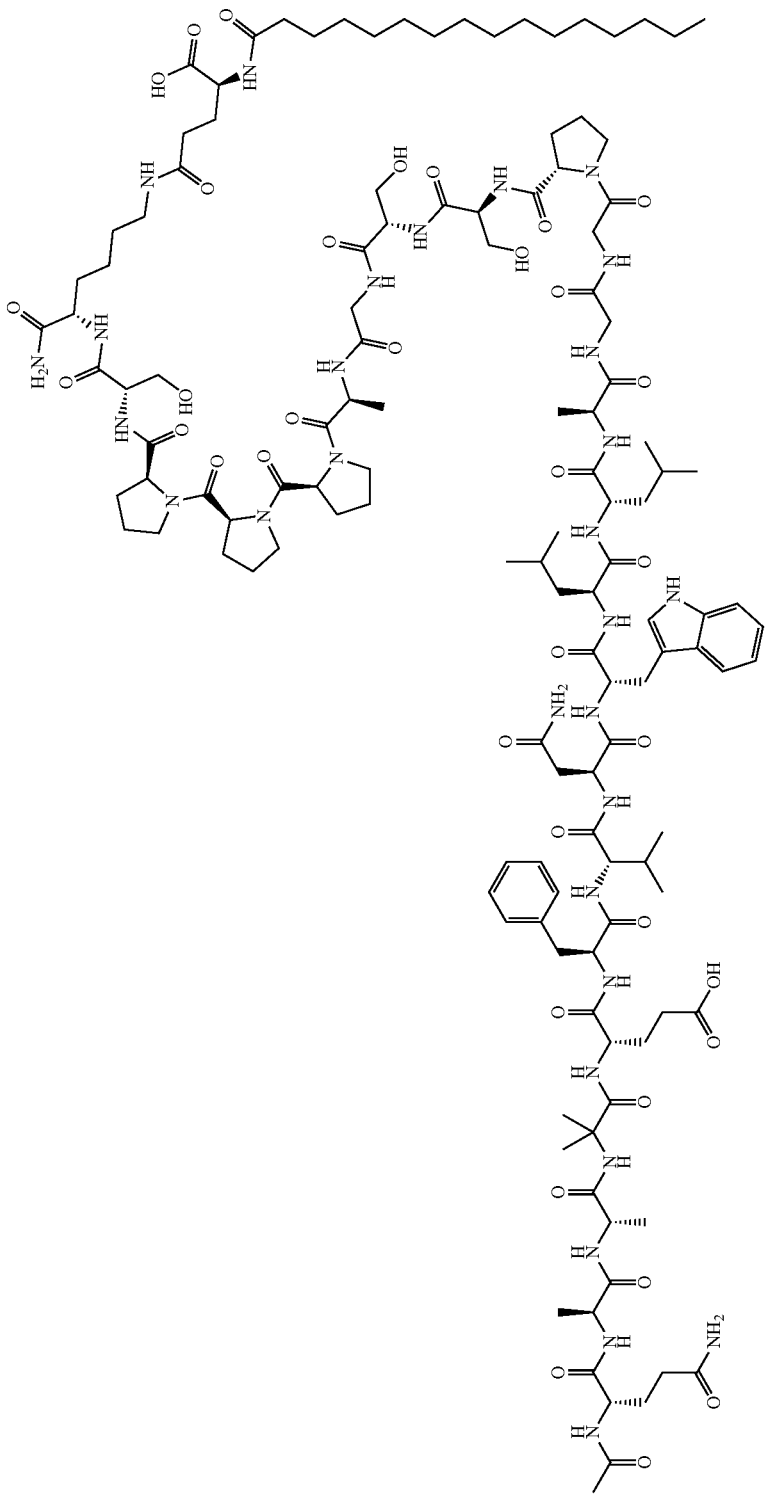

Compound 83
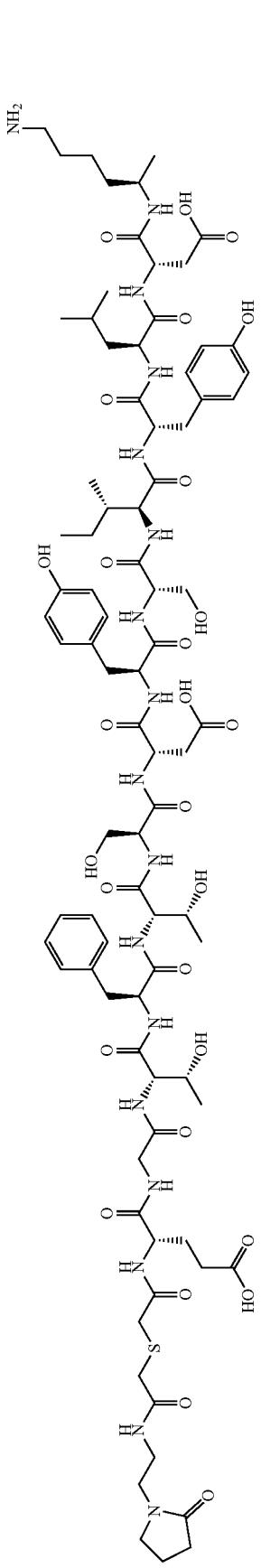
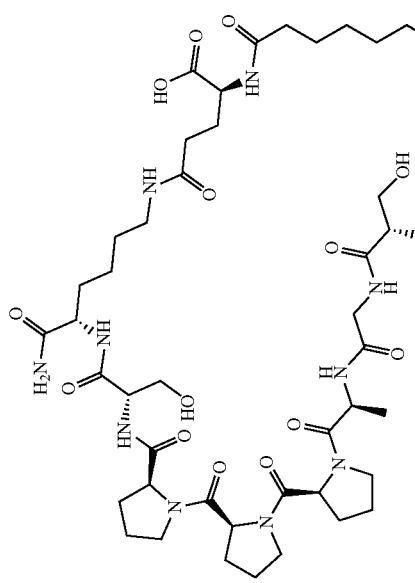
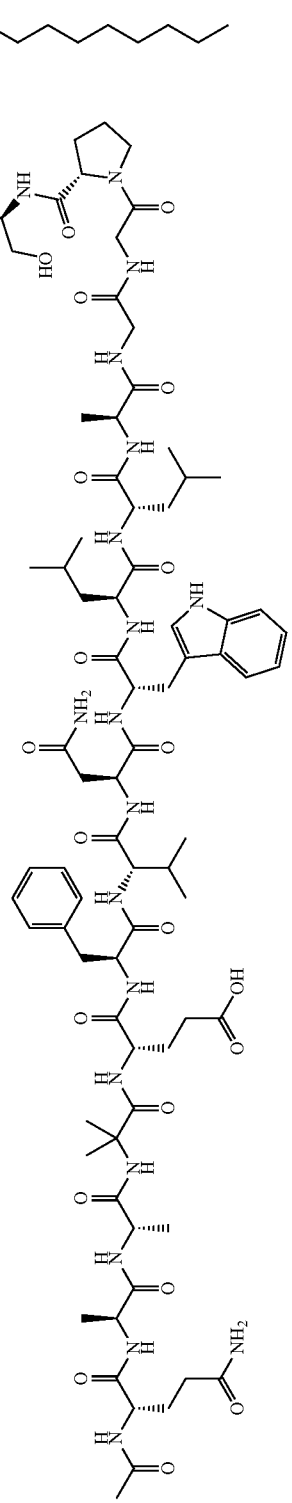

Compound 84
701
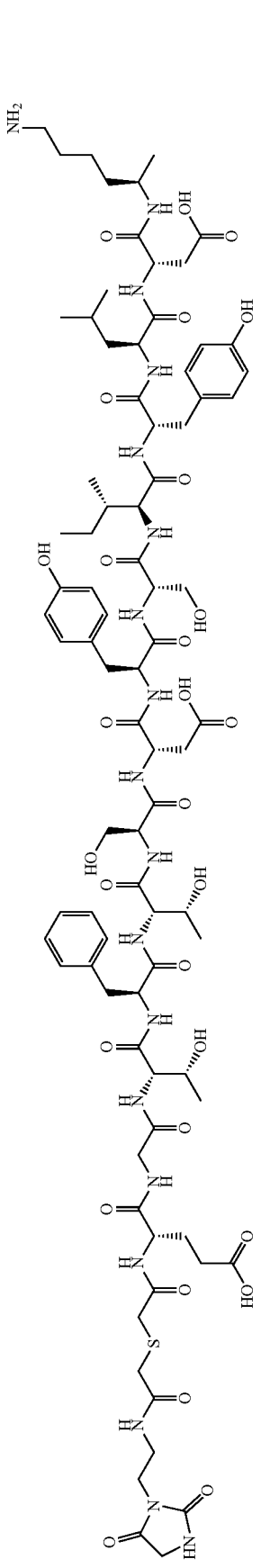
702
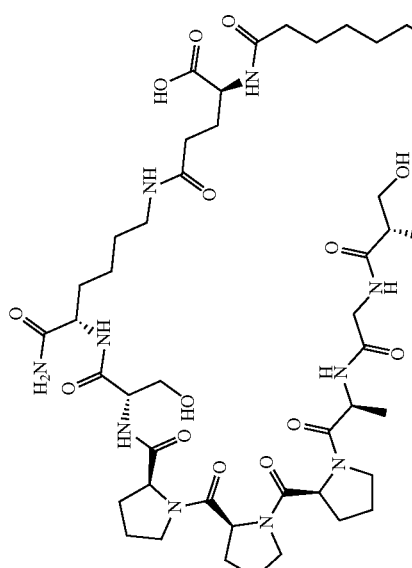
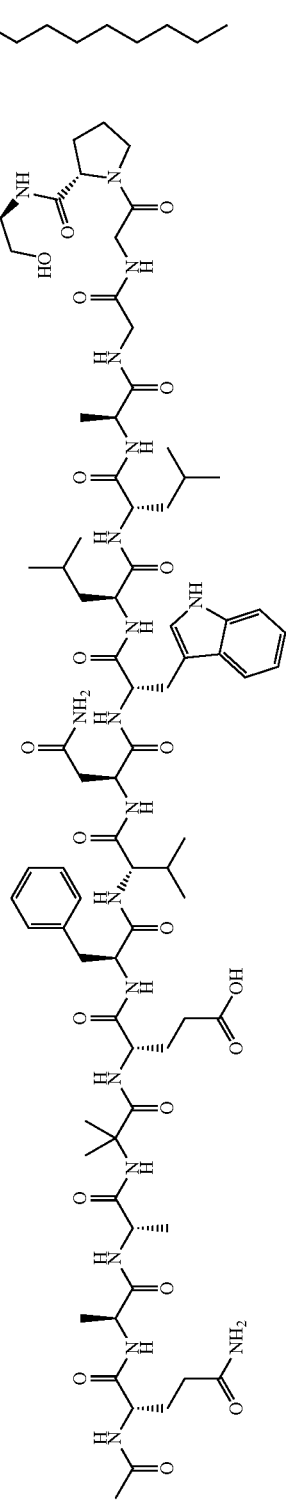

703
Compound 85
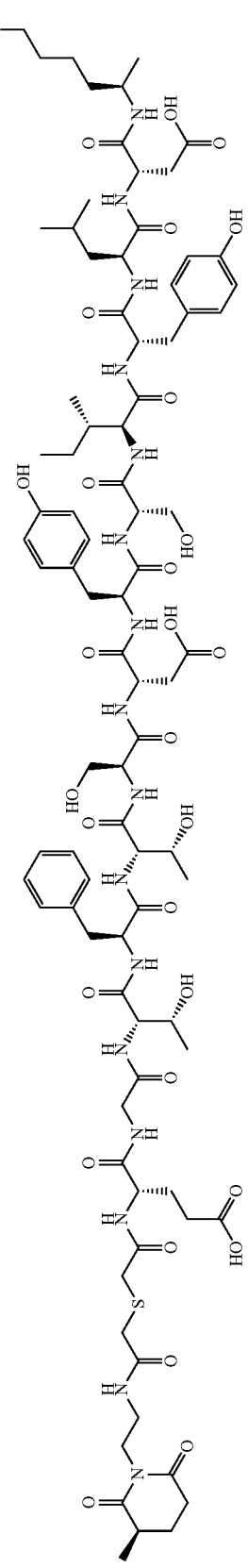
-continued
704
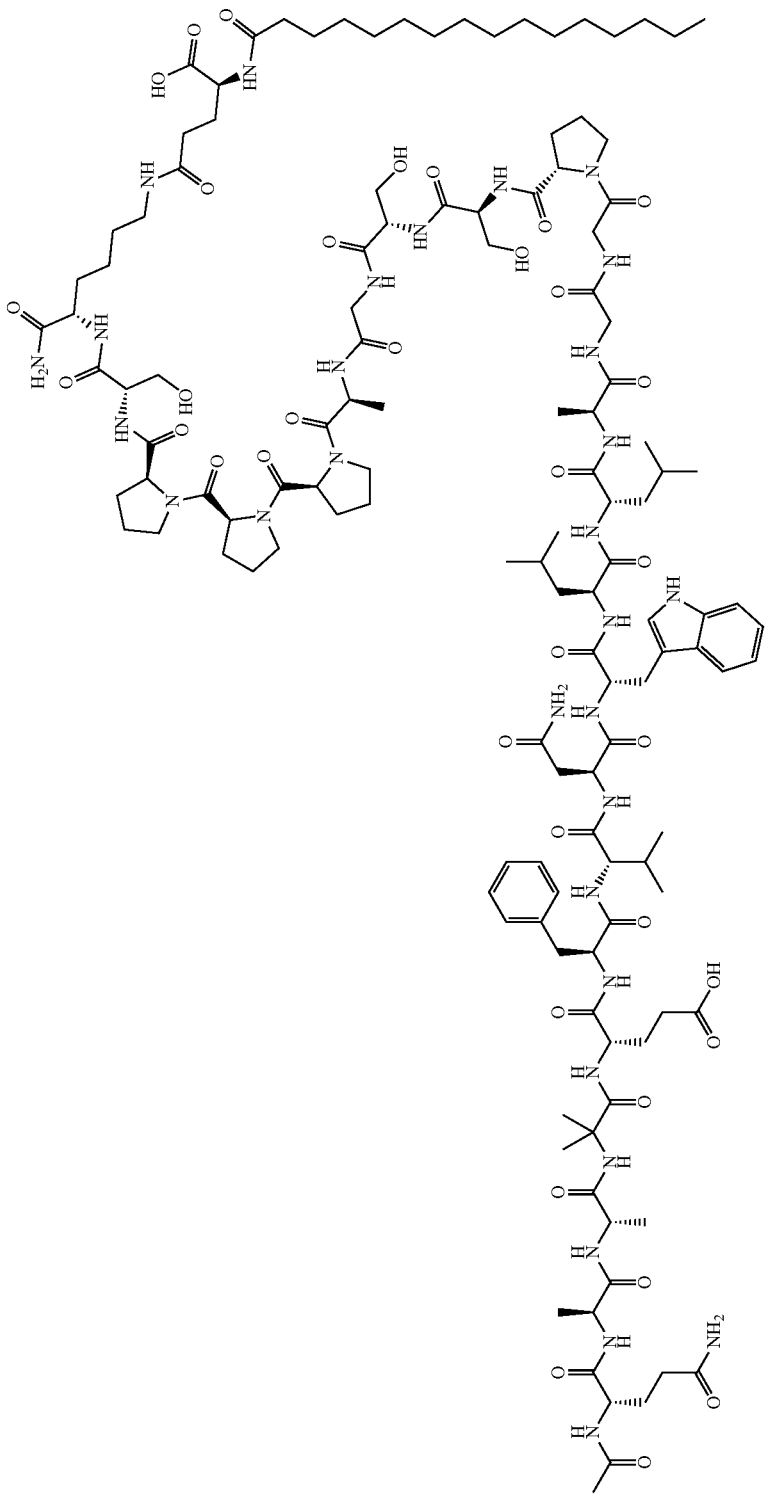

705
Compound 86
706
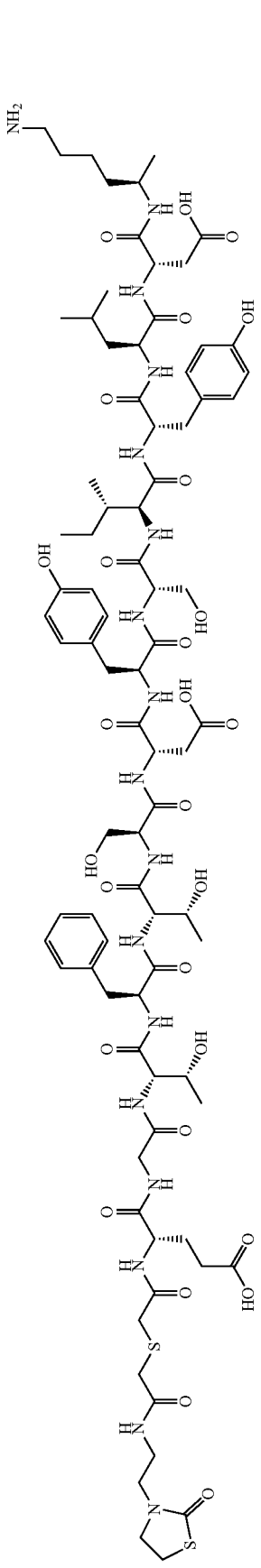
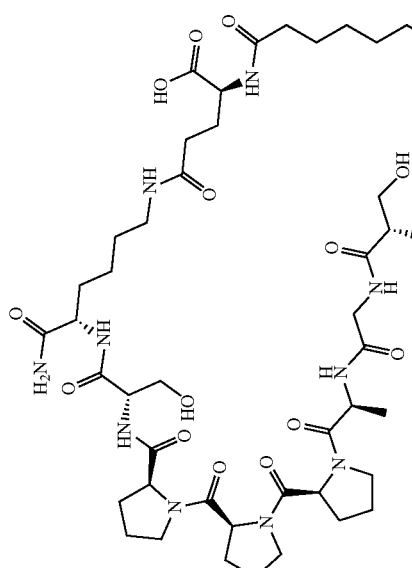
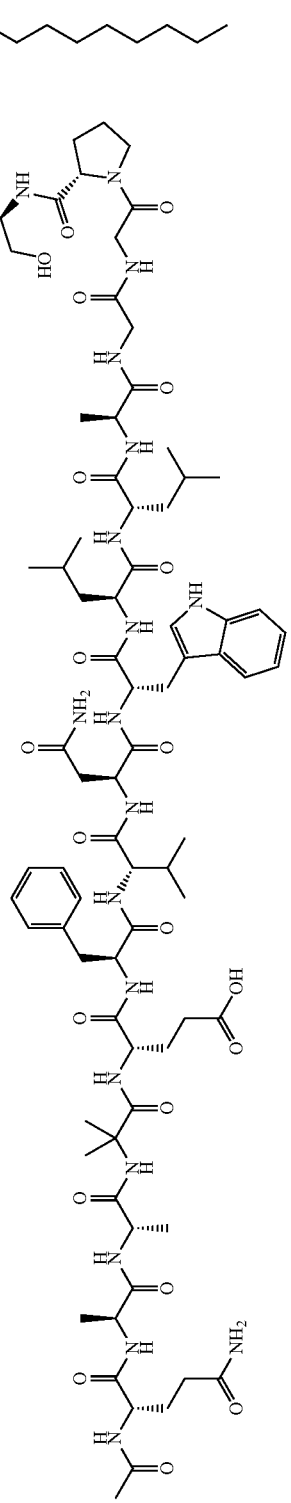

707
Compound 87
708
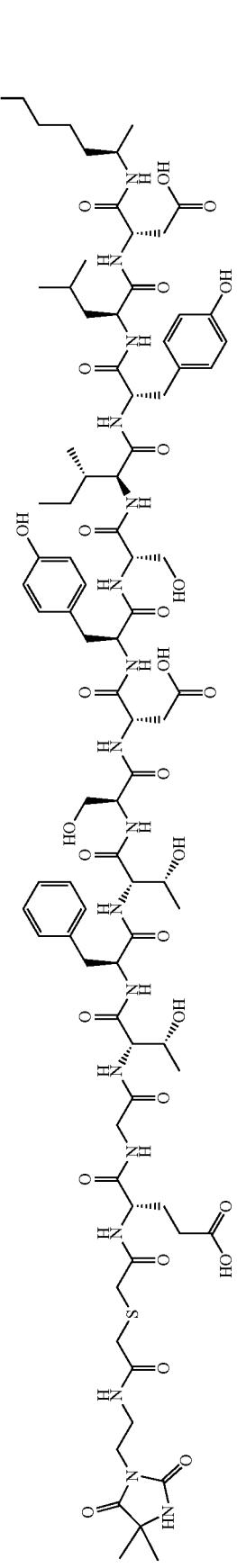
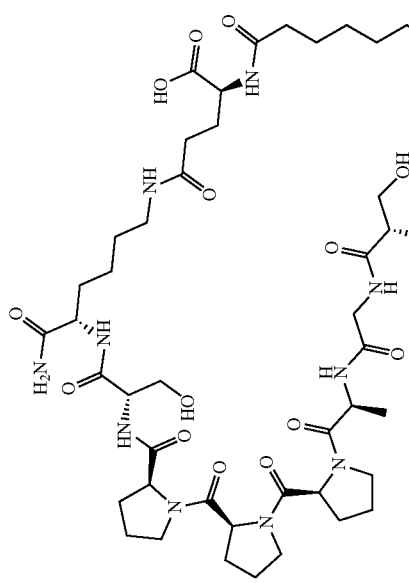
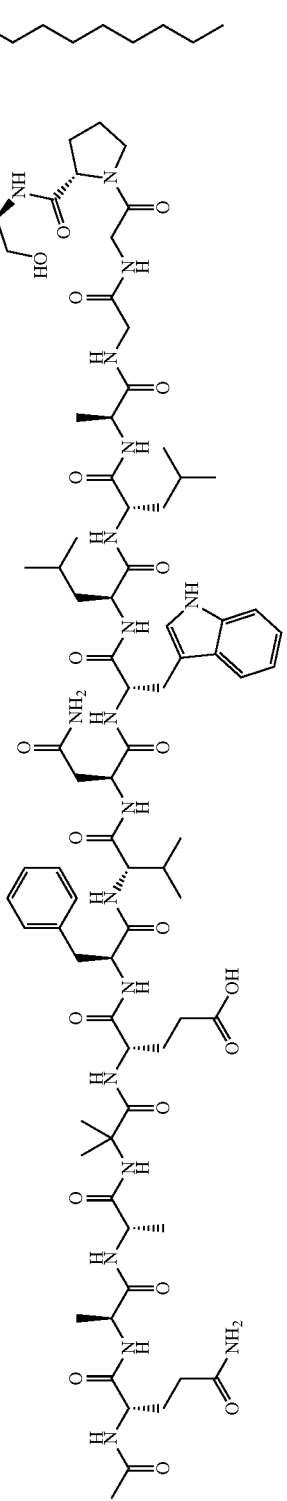
-continued 709
710
Compound 88
-continued
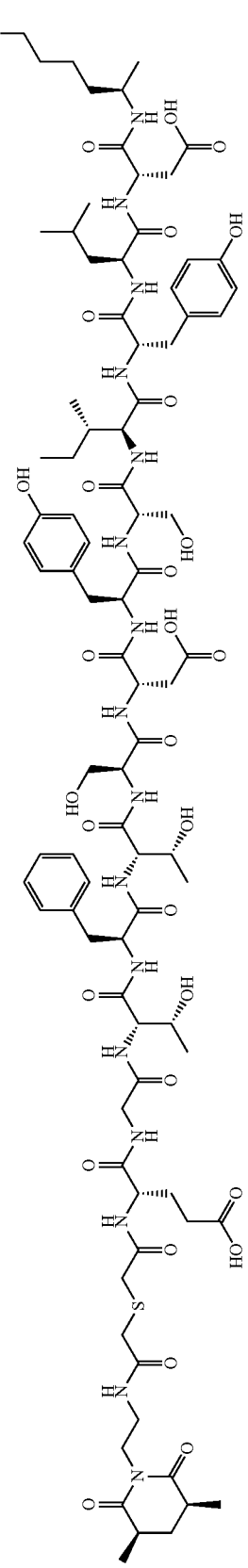
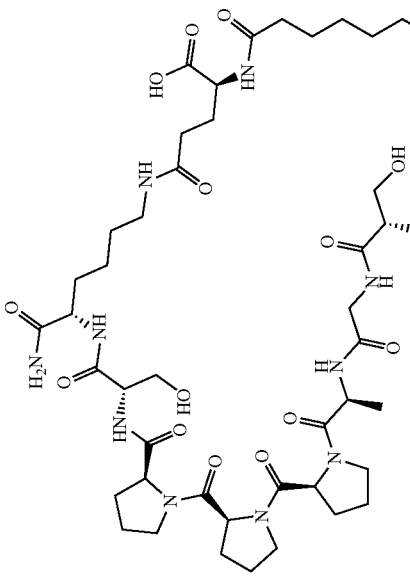
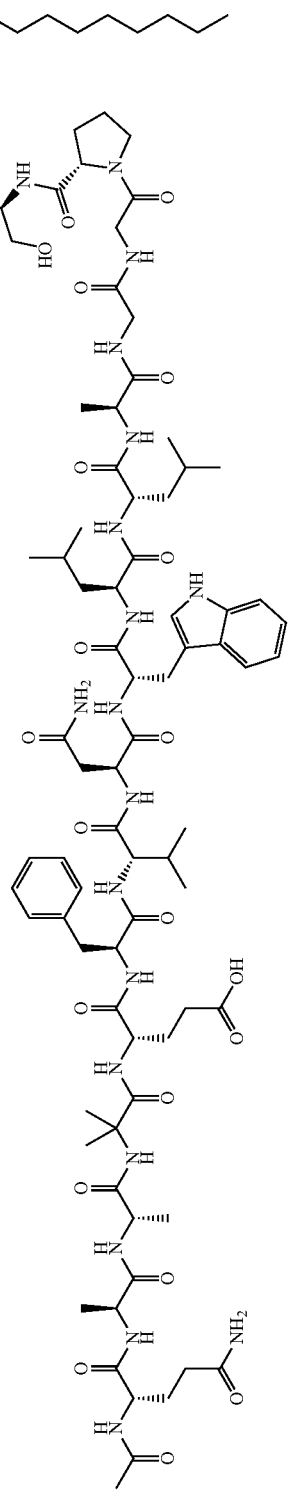

711 712
Compound 89
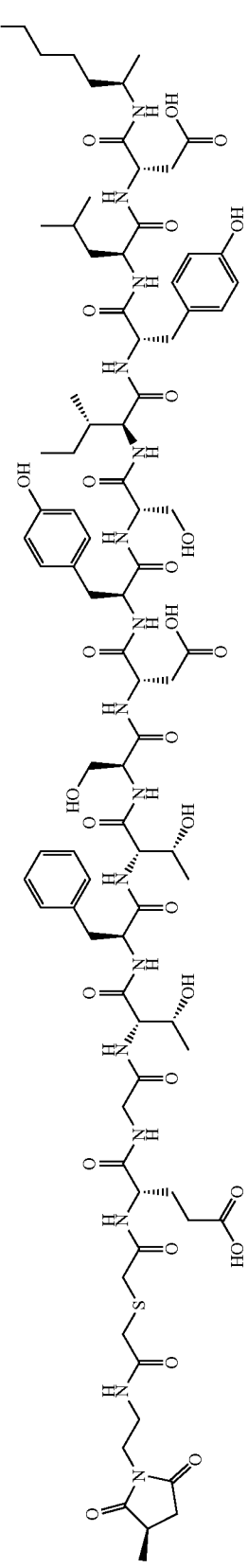
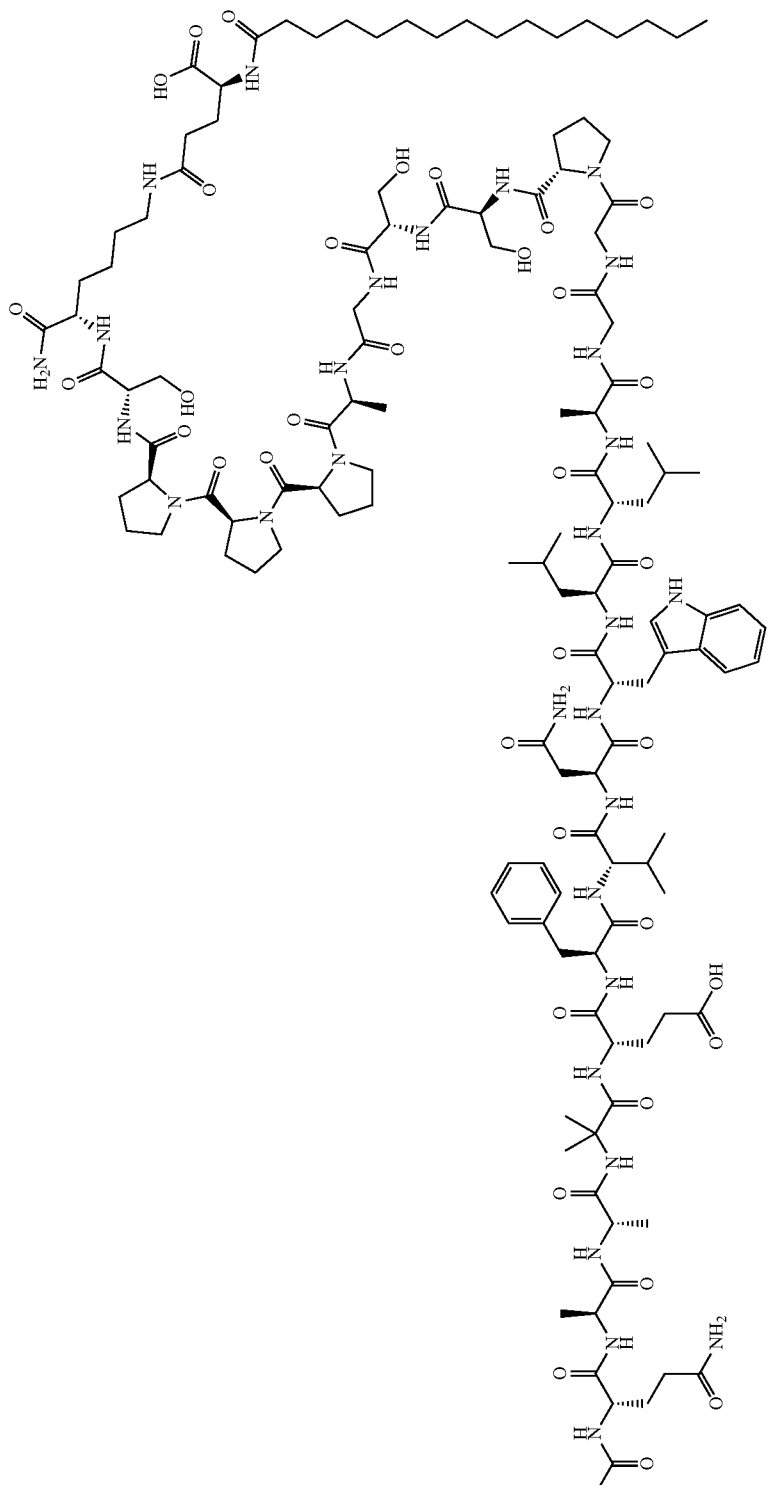

713
Compound 90
714
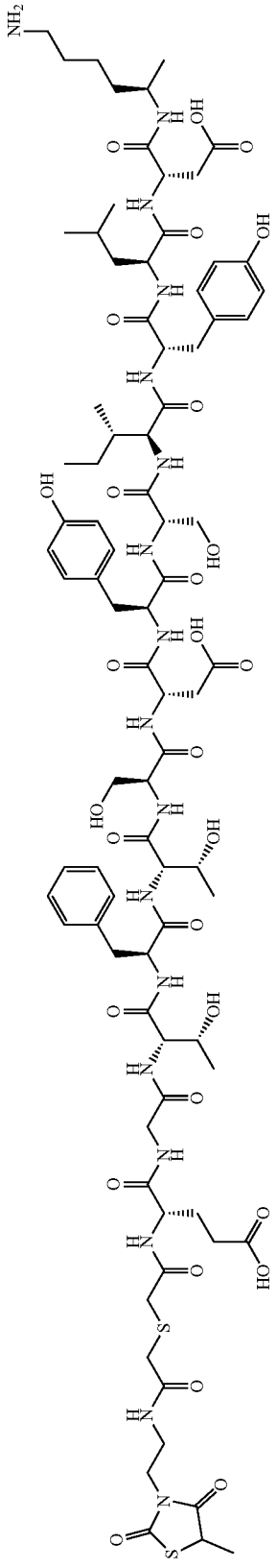
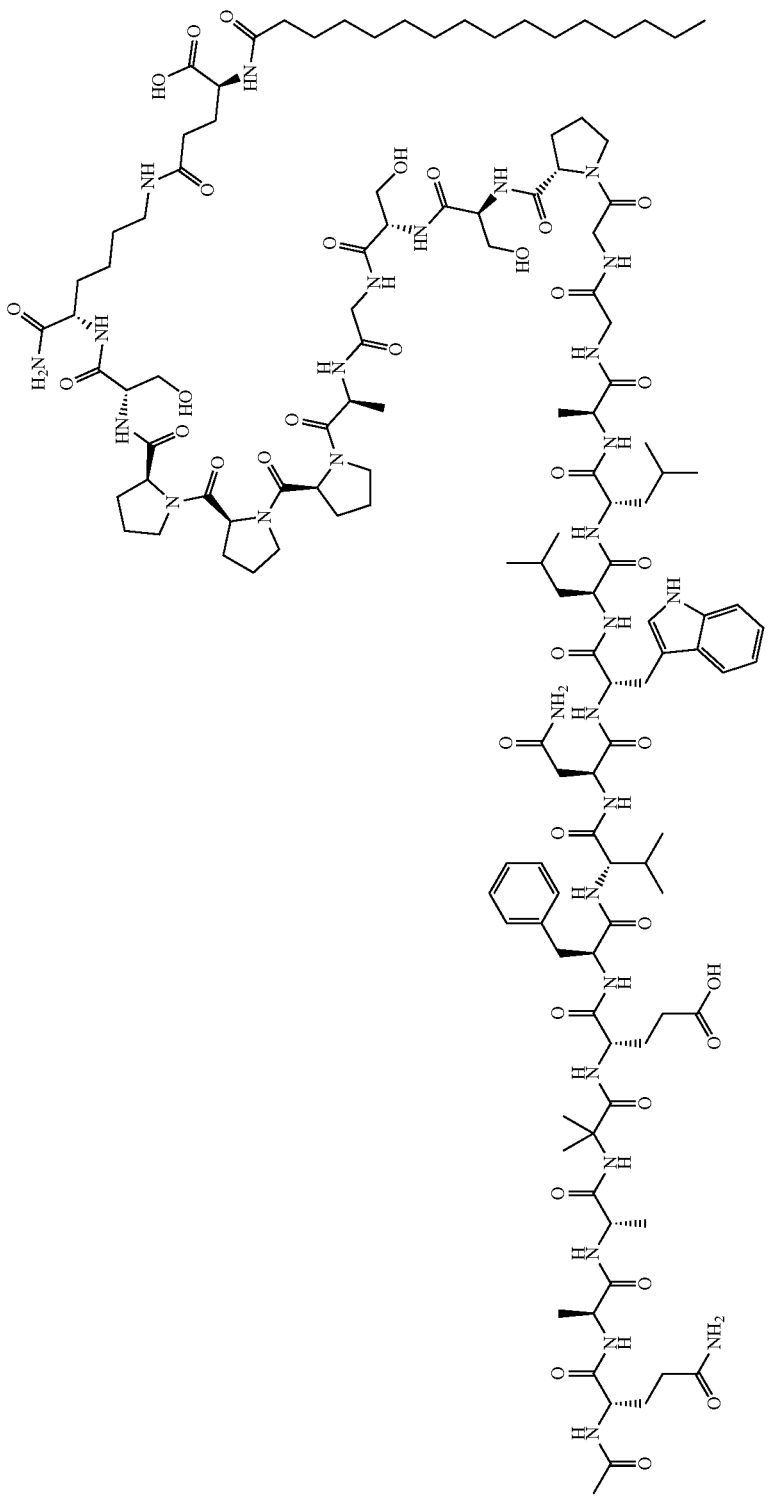

715                                716
Compound 91
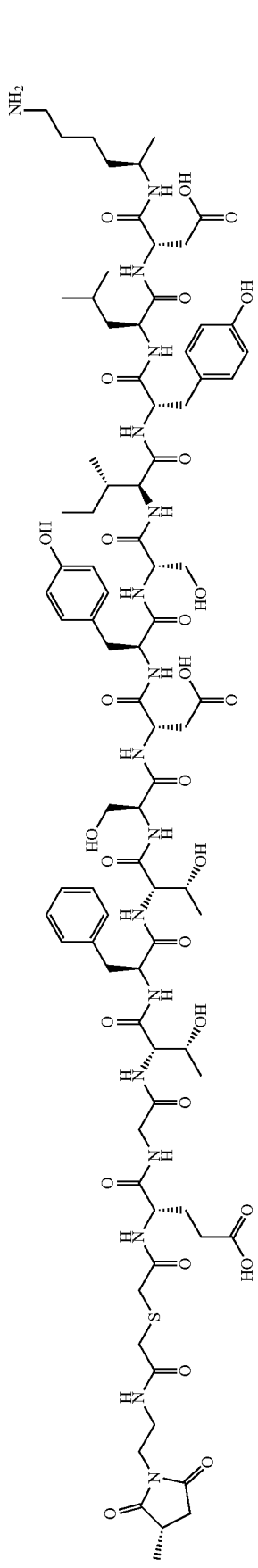
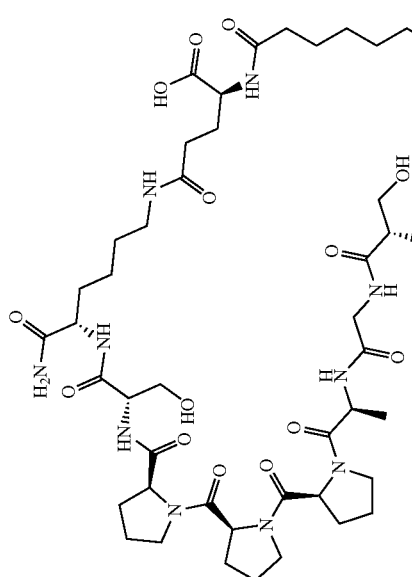
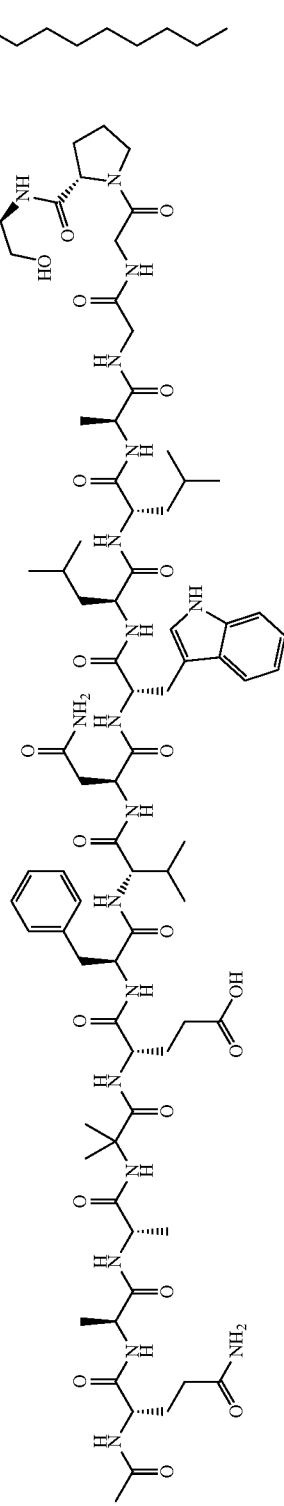

717
Compound 92
718
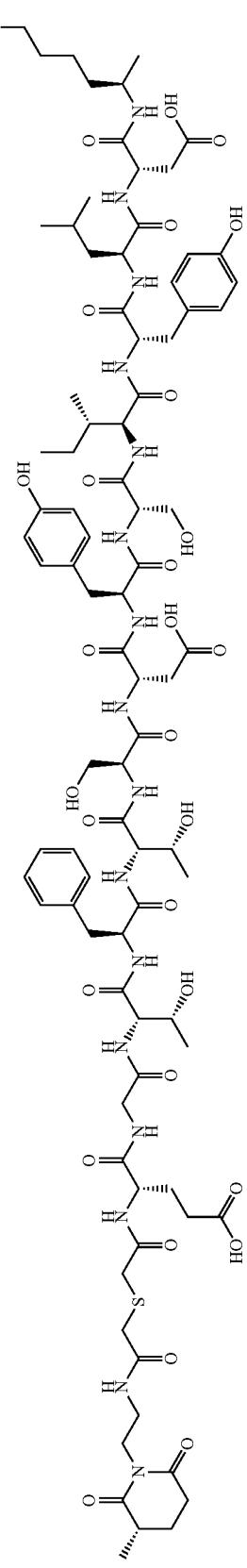
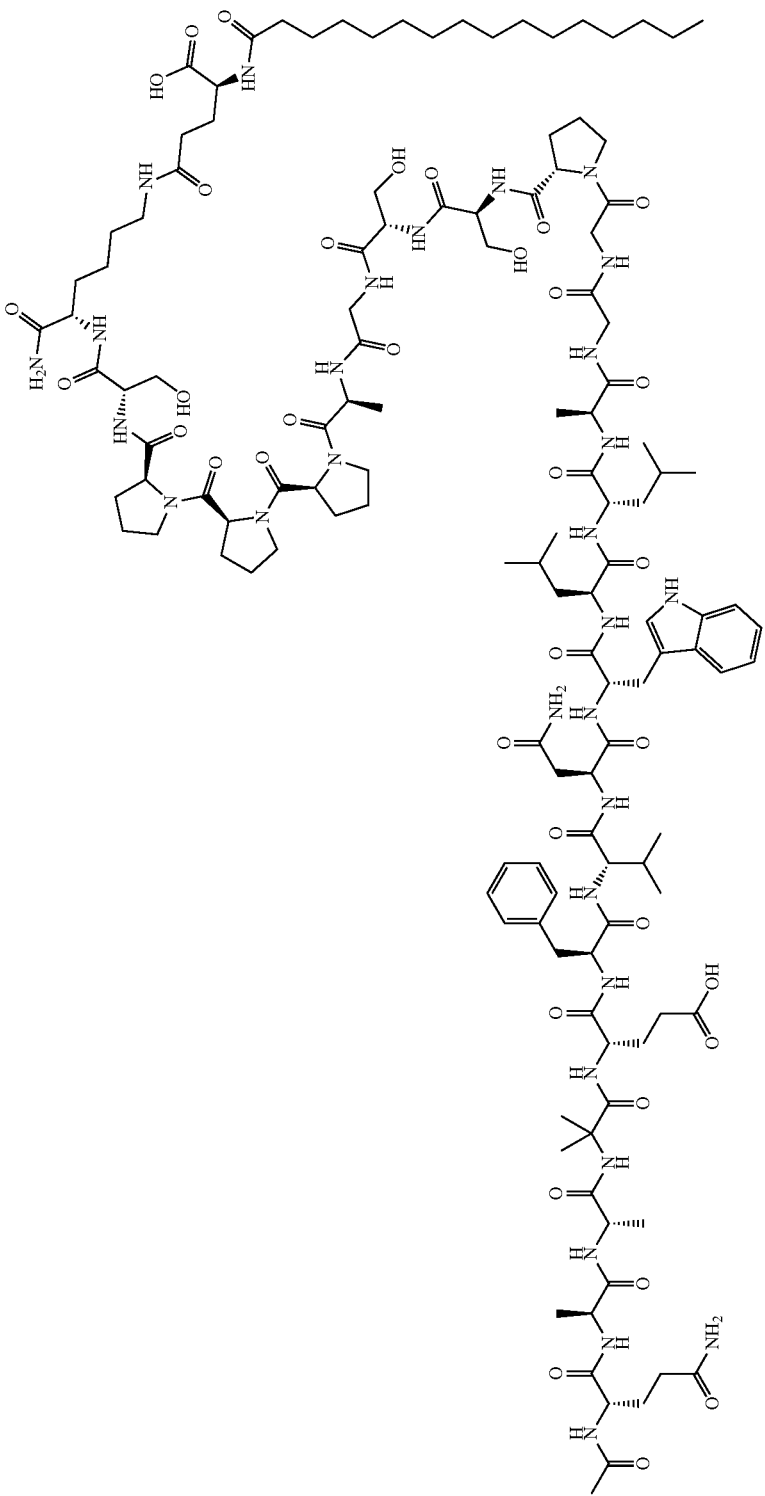

719
720
Compound 93
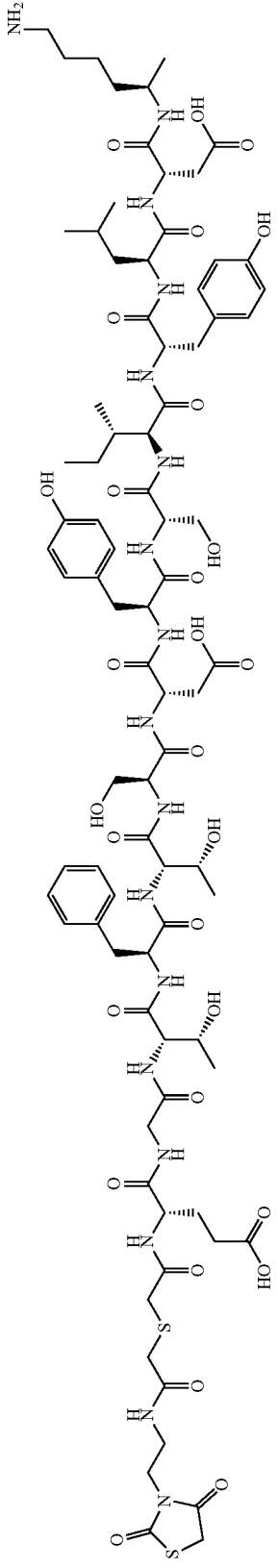
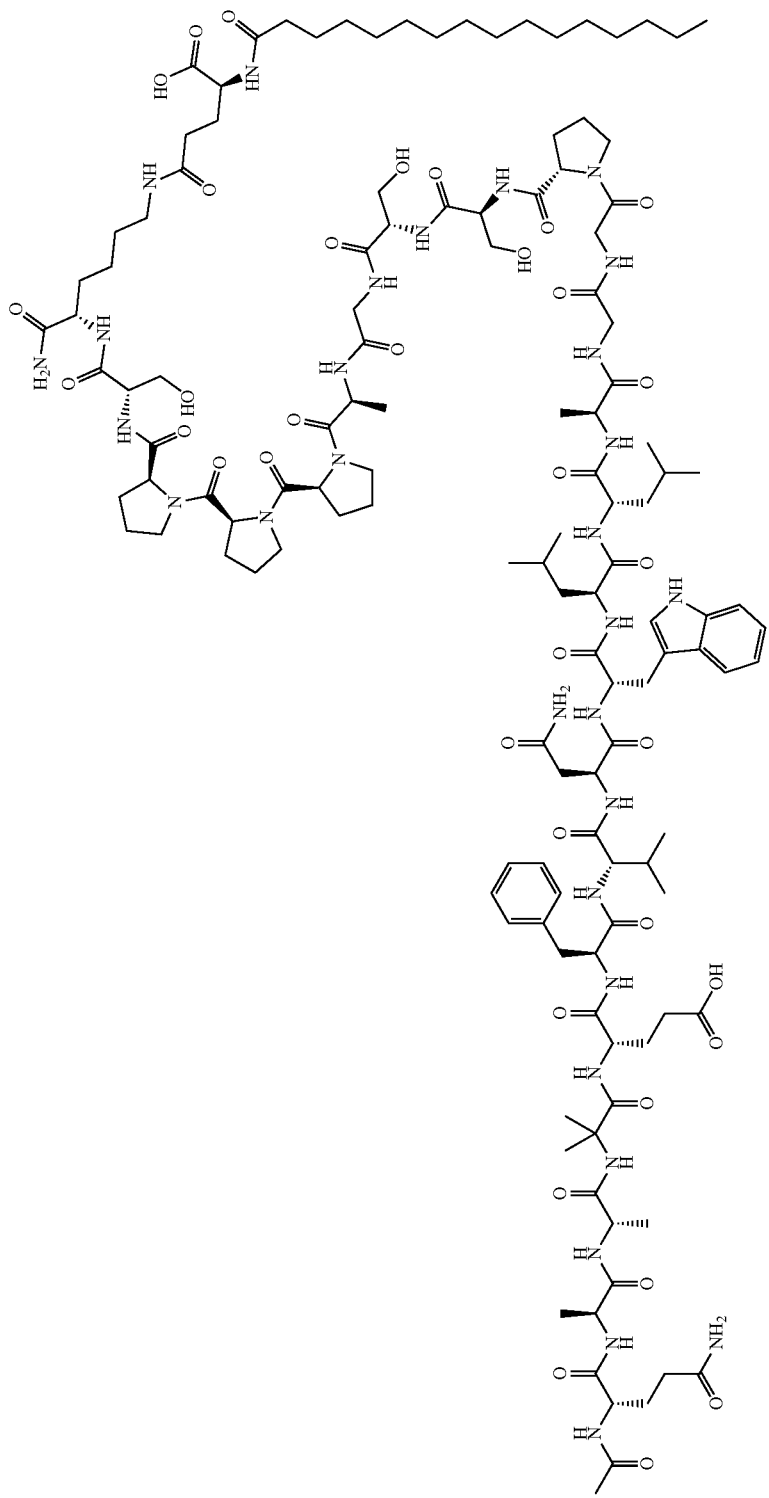

721
722
Compound 94
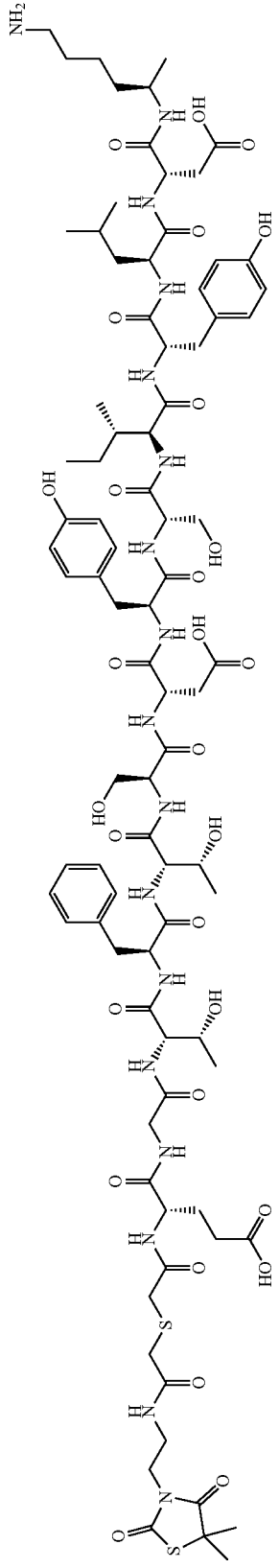
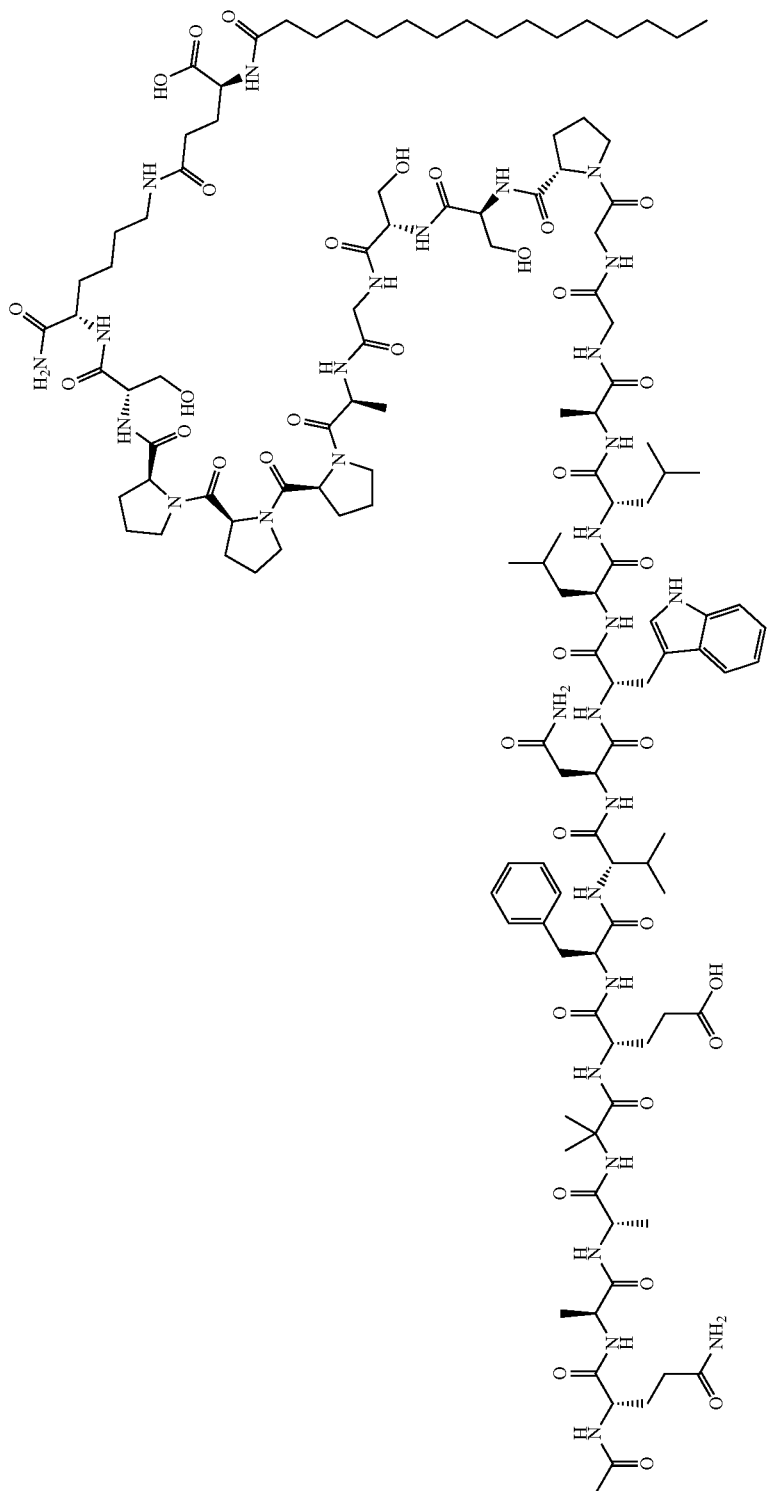

723                    724
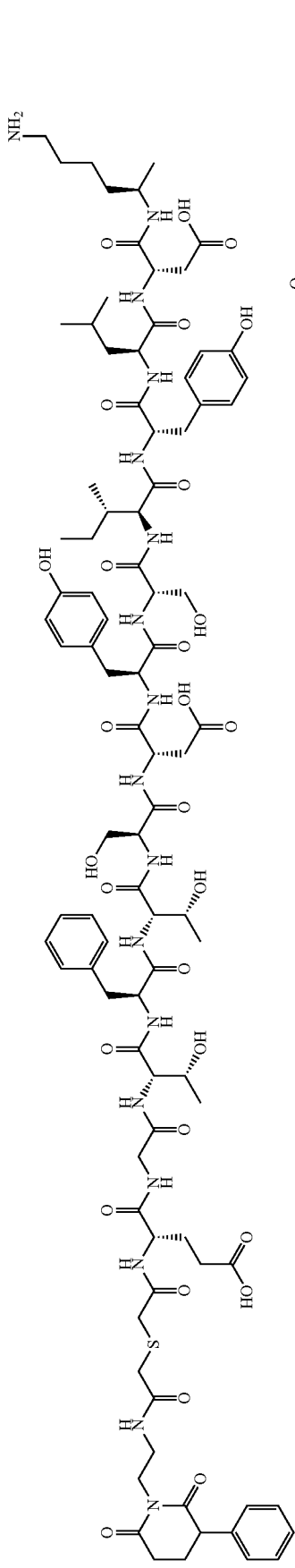
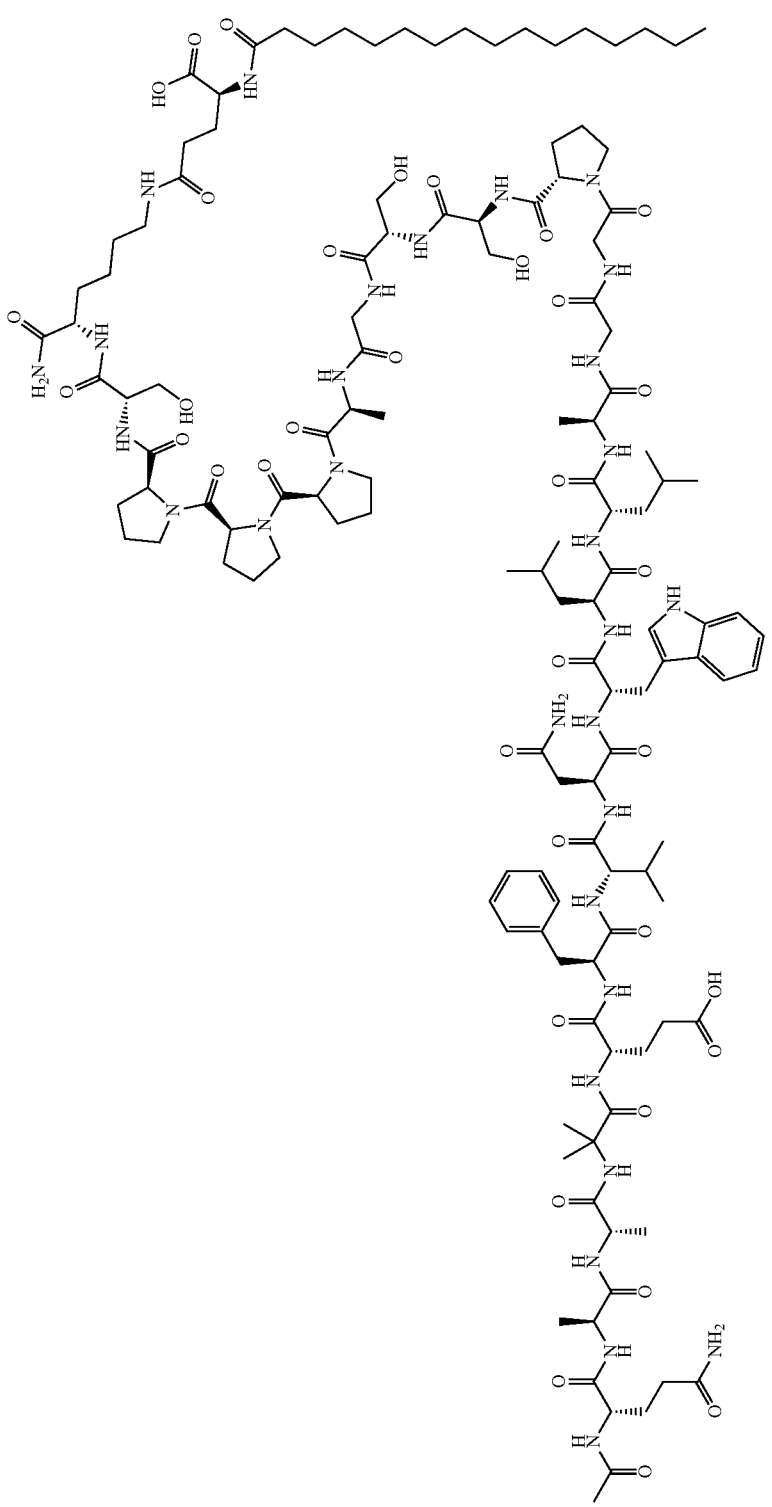
Compound 95
-continued 725
Compound 96
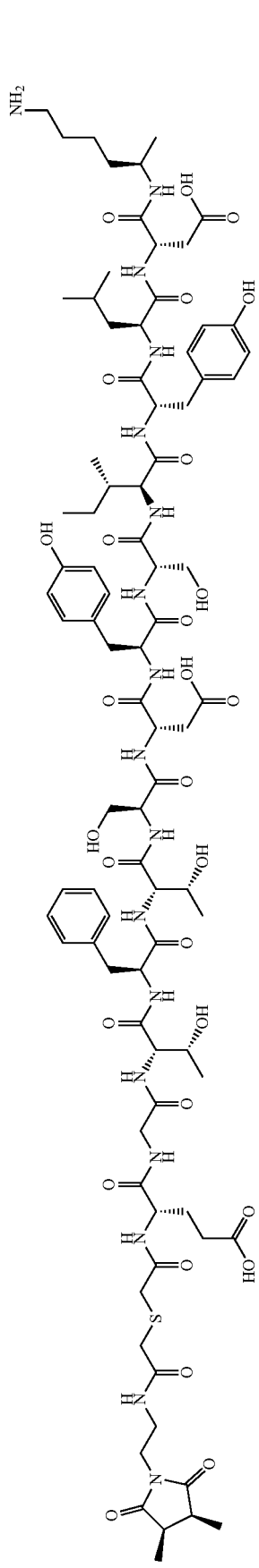
-continued
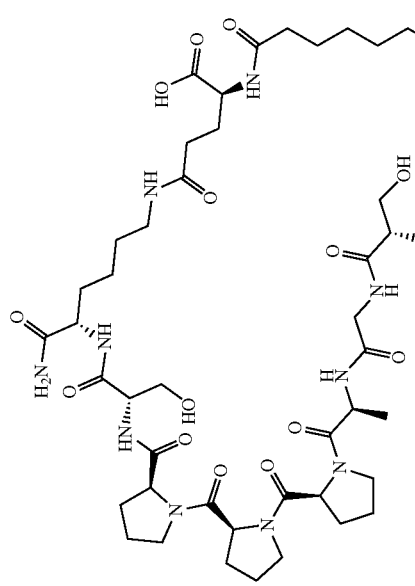
726
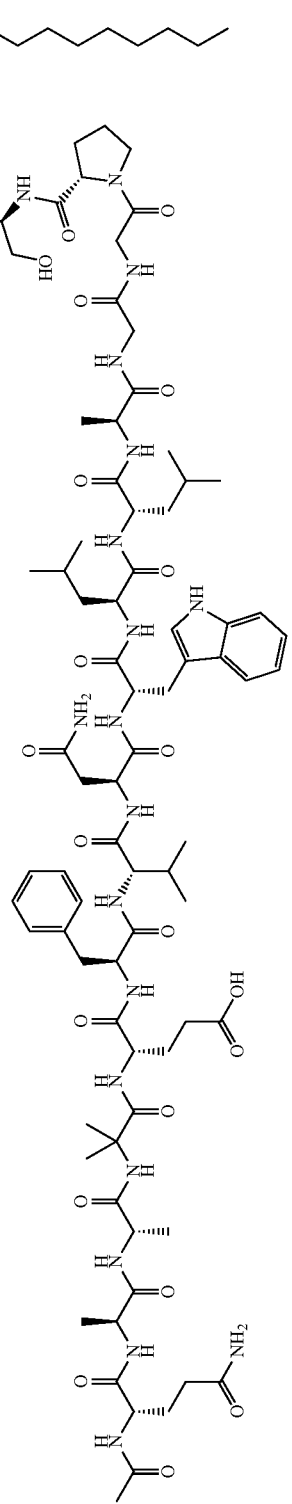

727 728
Compound 97
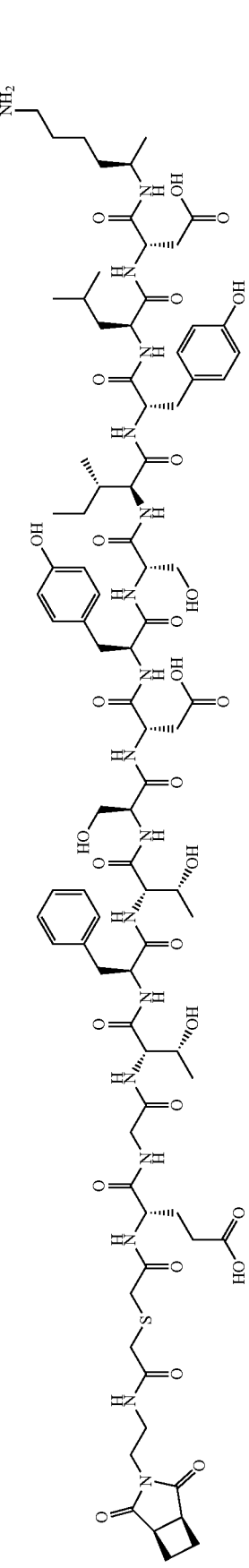
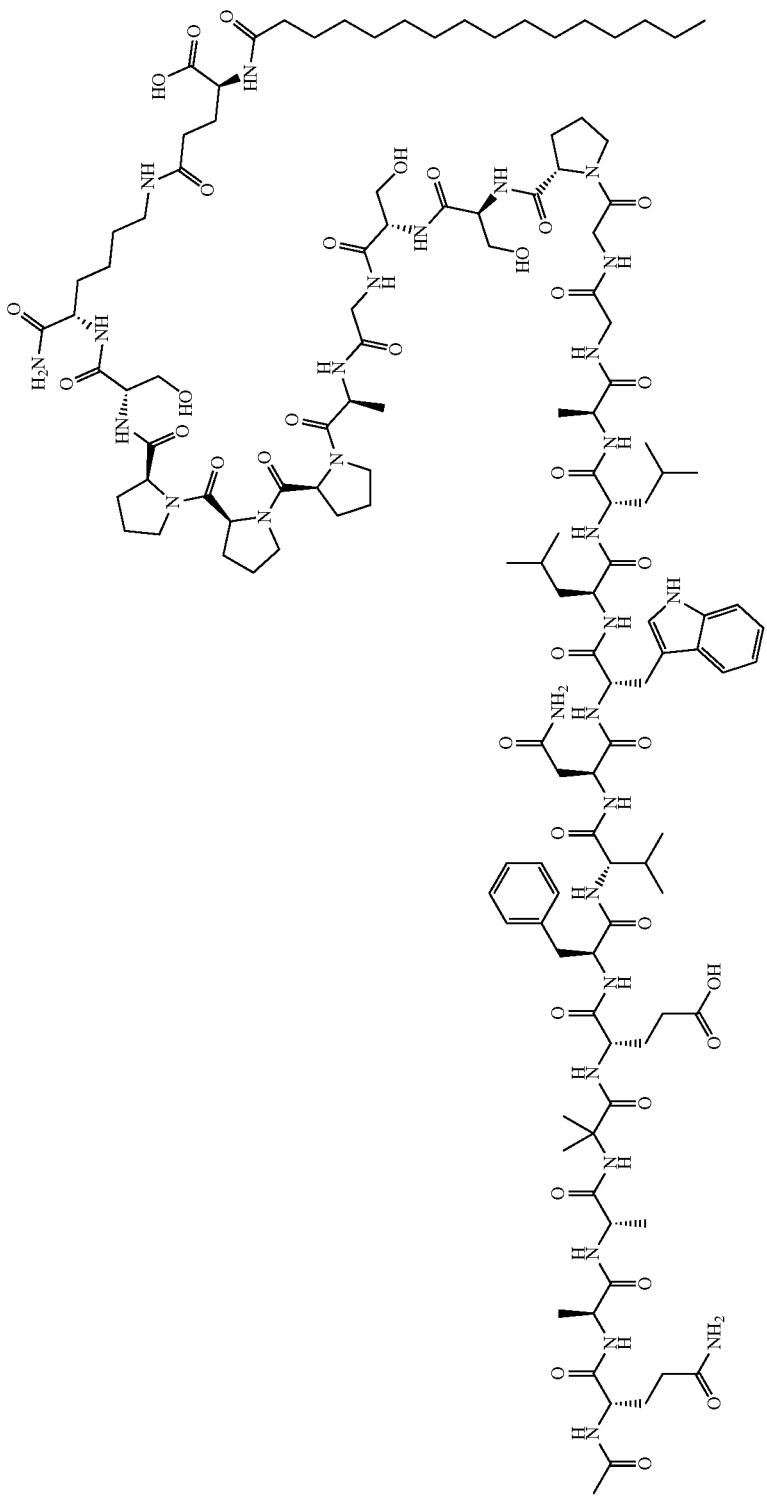

Compound 98
729
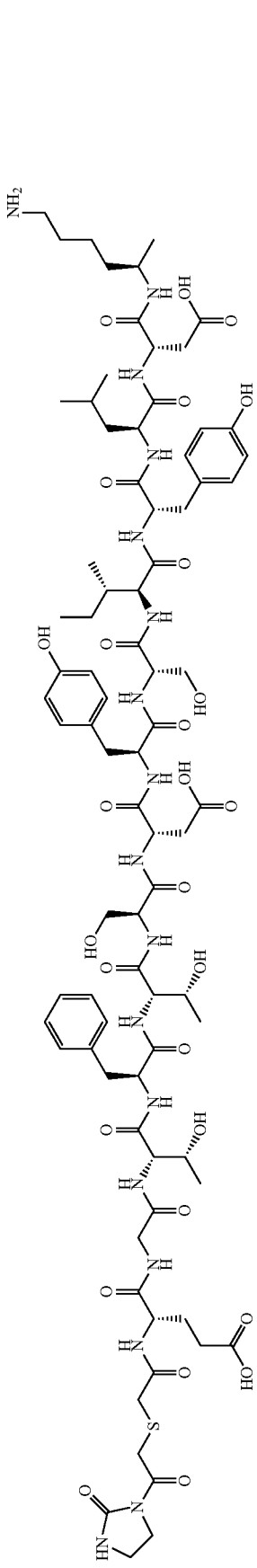
730
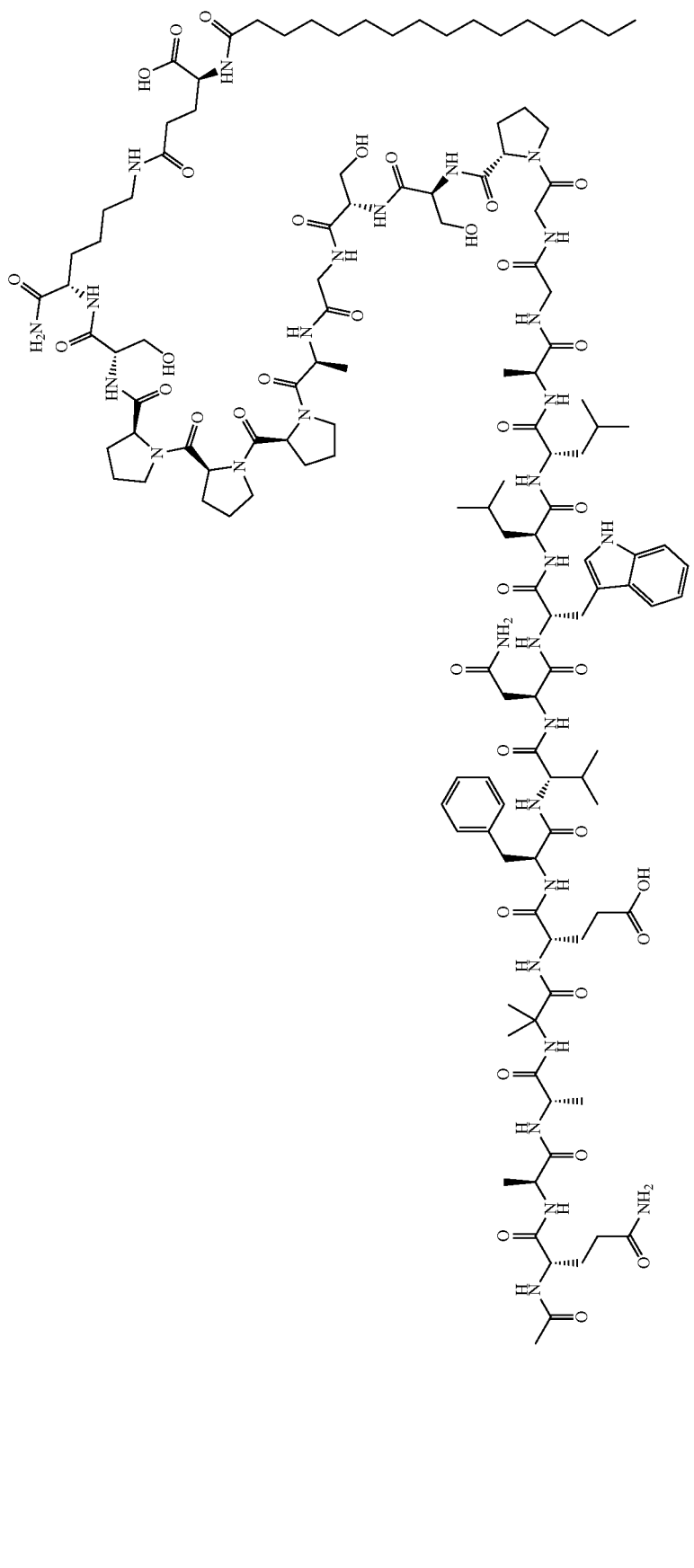

731
732
Compound 99
-continued
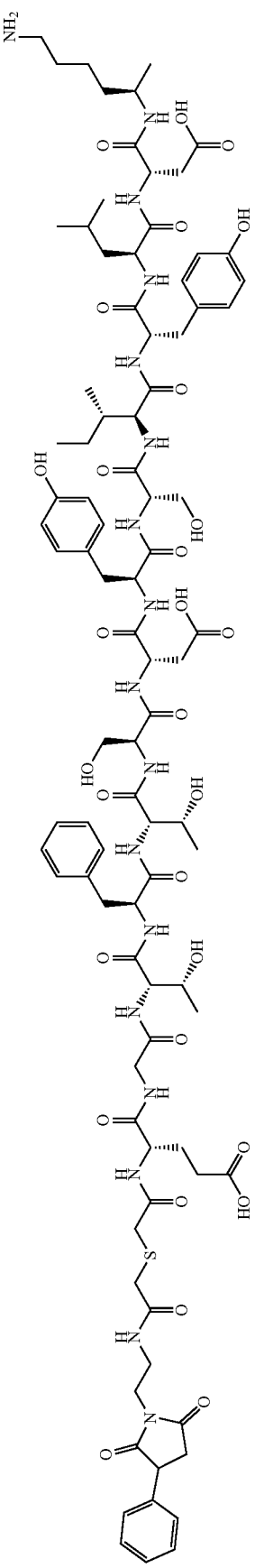
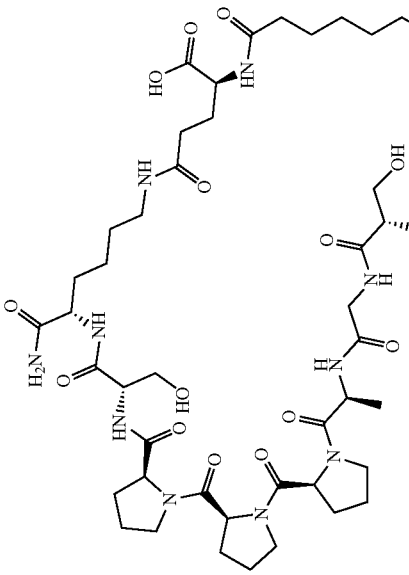
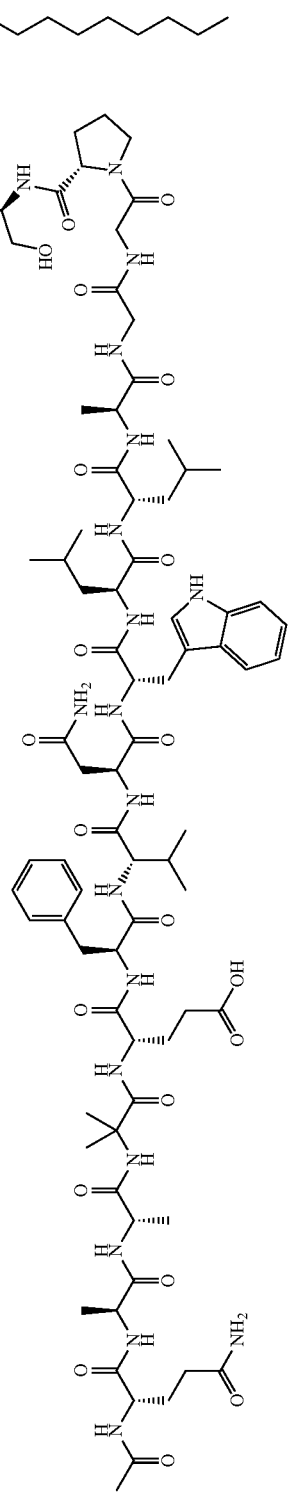

Compound 100
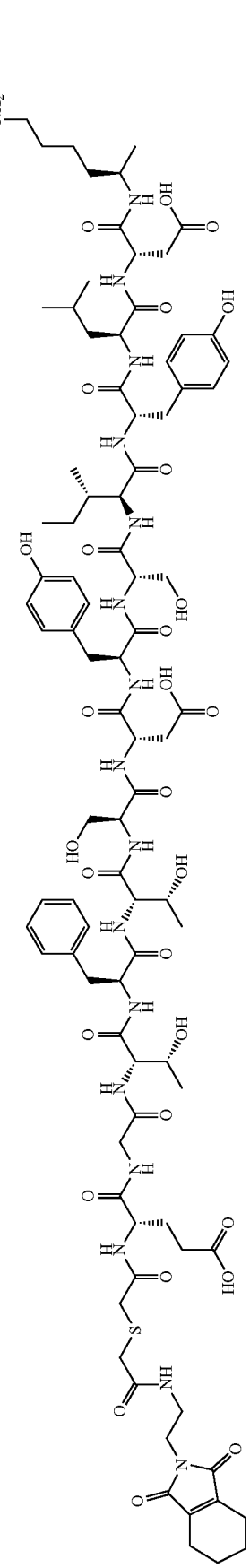
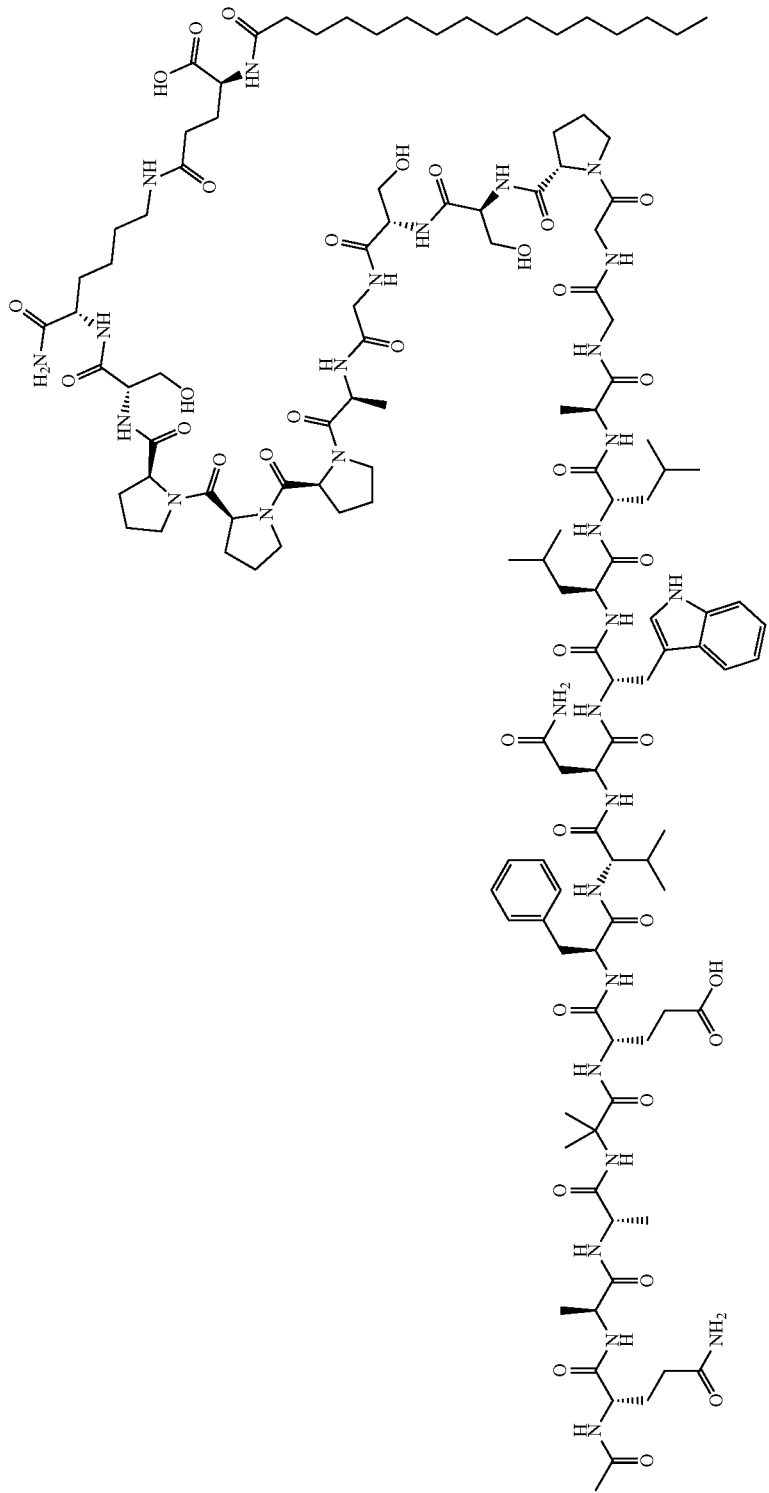

735
Compound 101
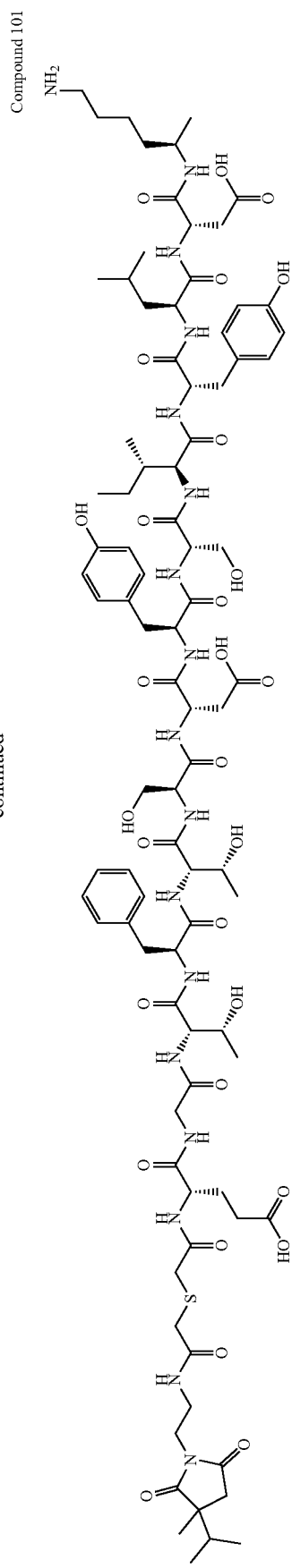
-continued
736
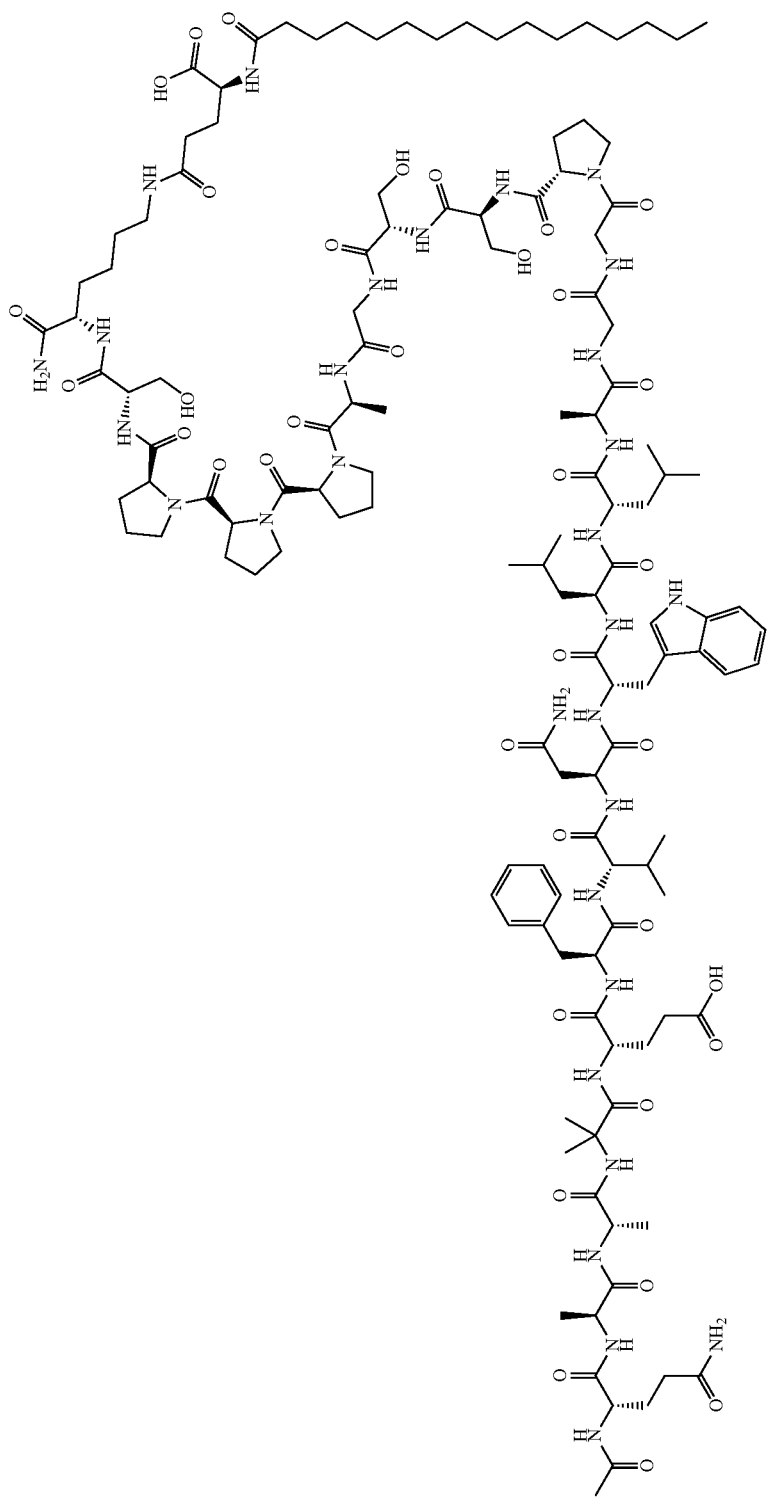

737
738
Compound 102
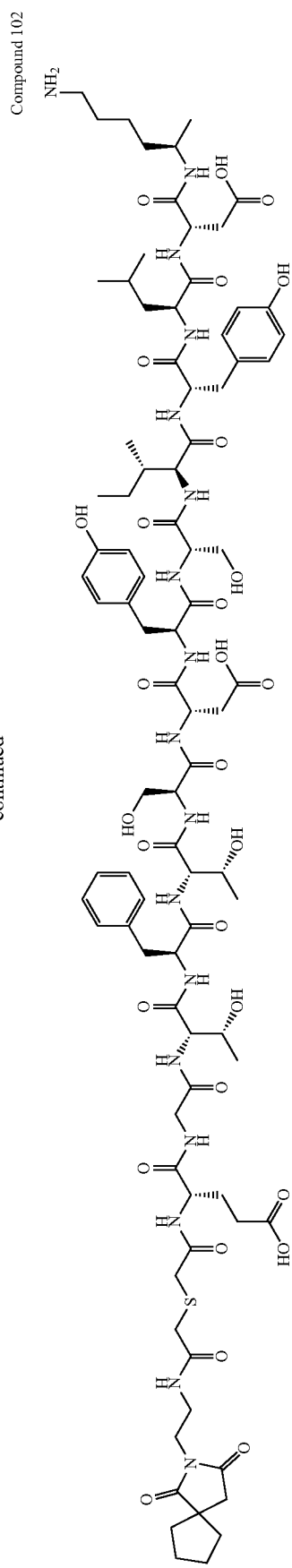
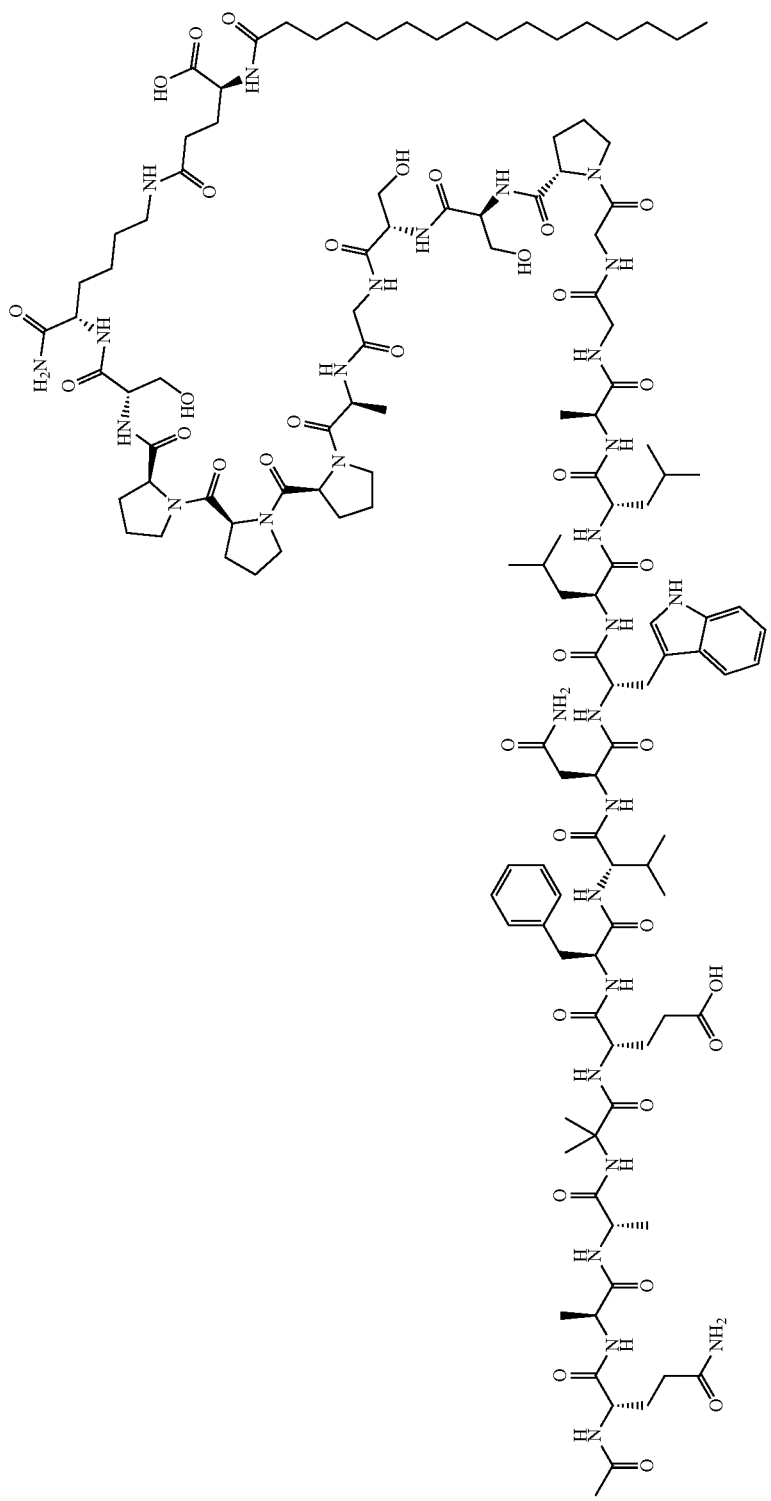
-continued

Compound 103
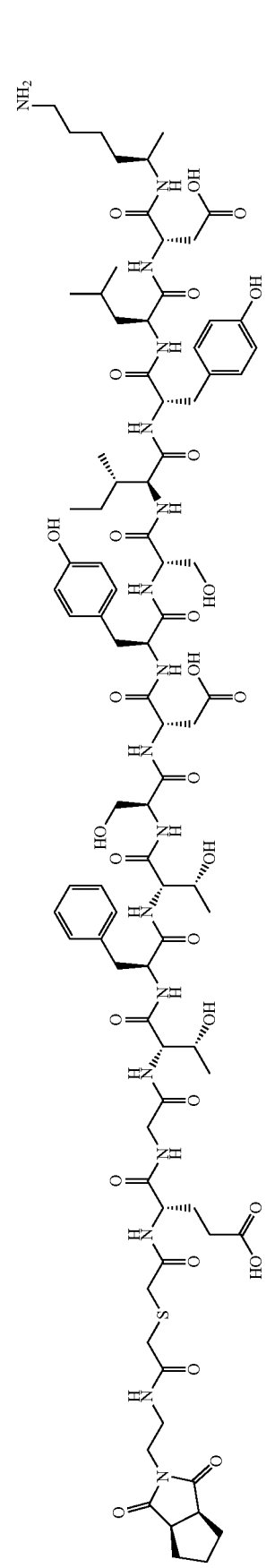
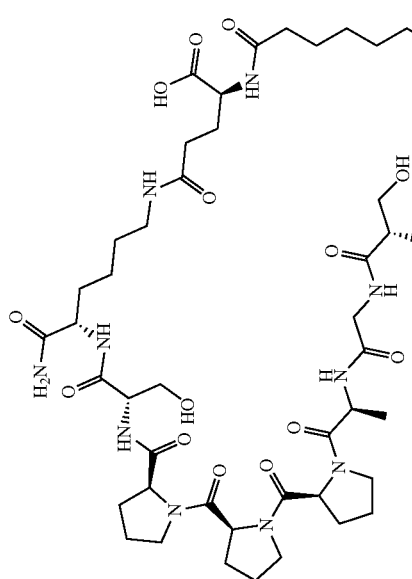
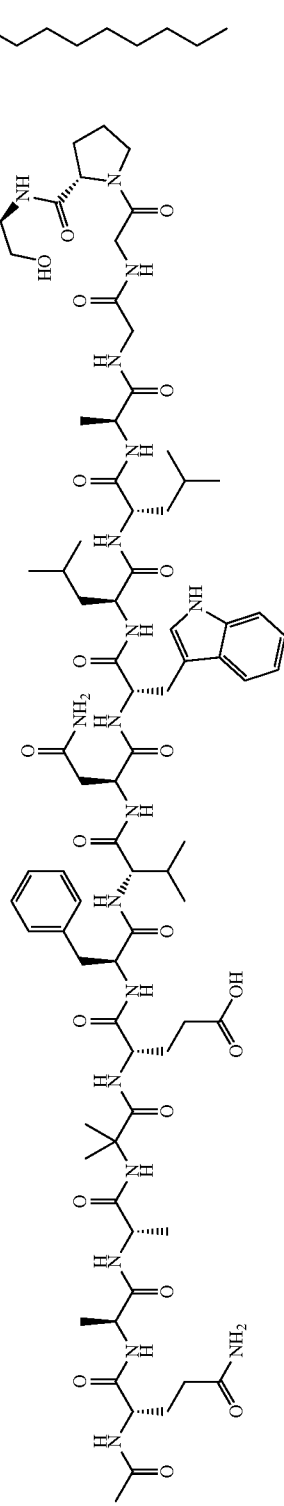

Compound 104
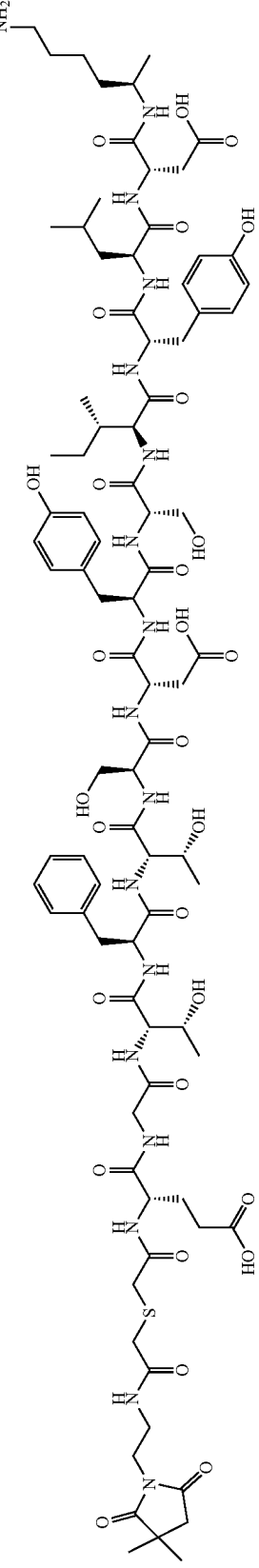
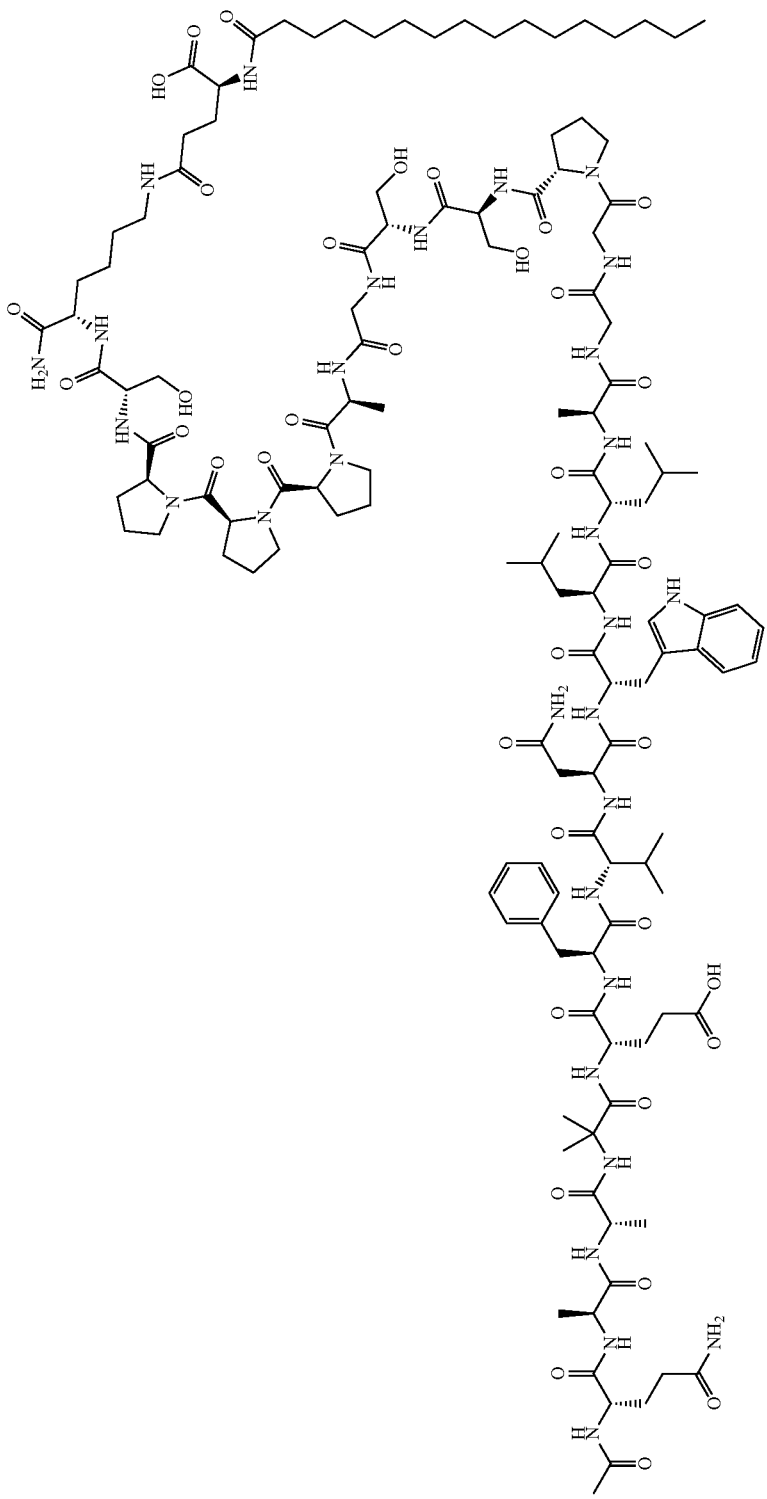

743
Compound 105
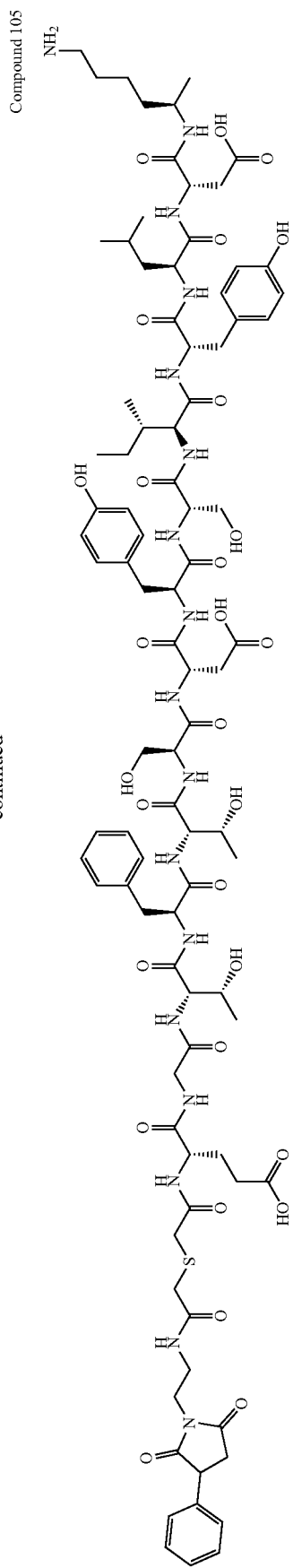
744
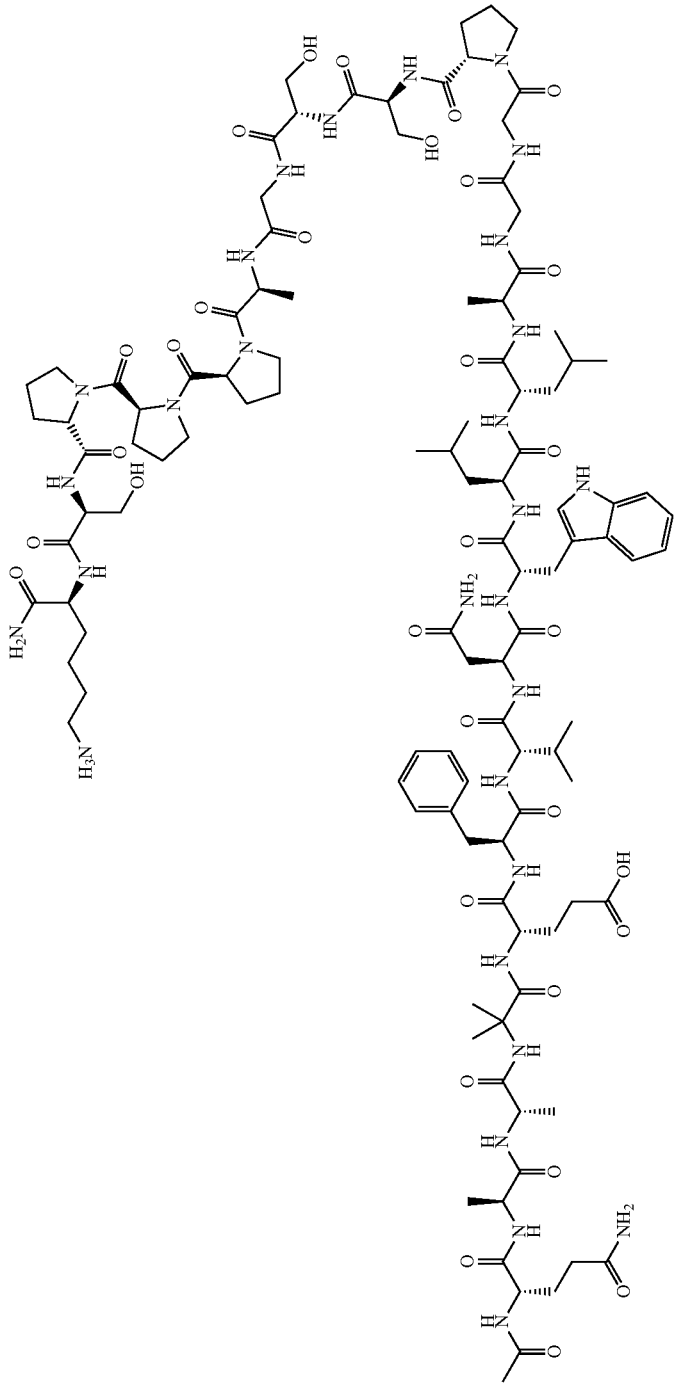

745
Compound 202
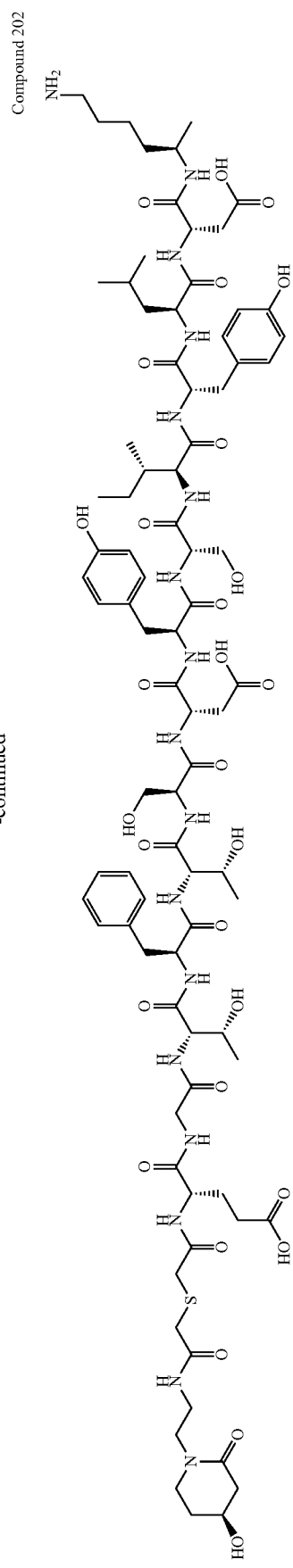
746
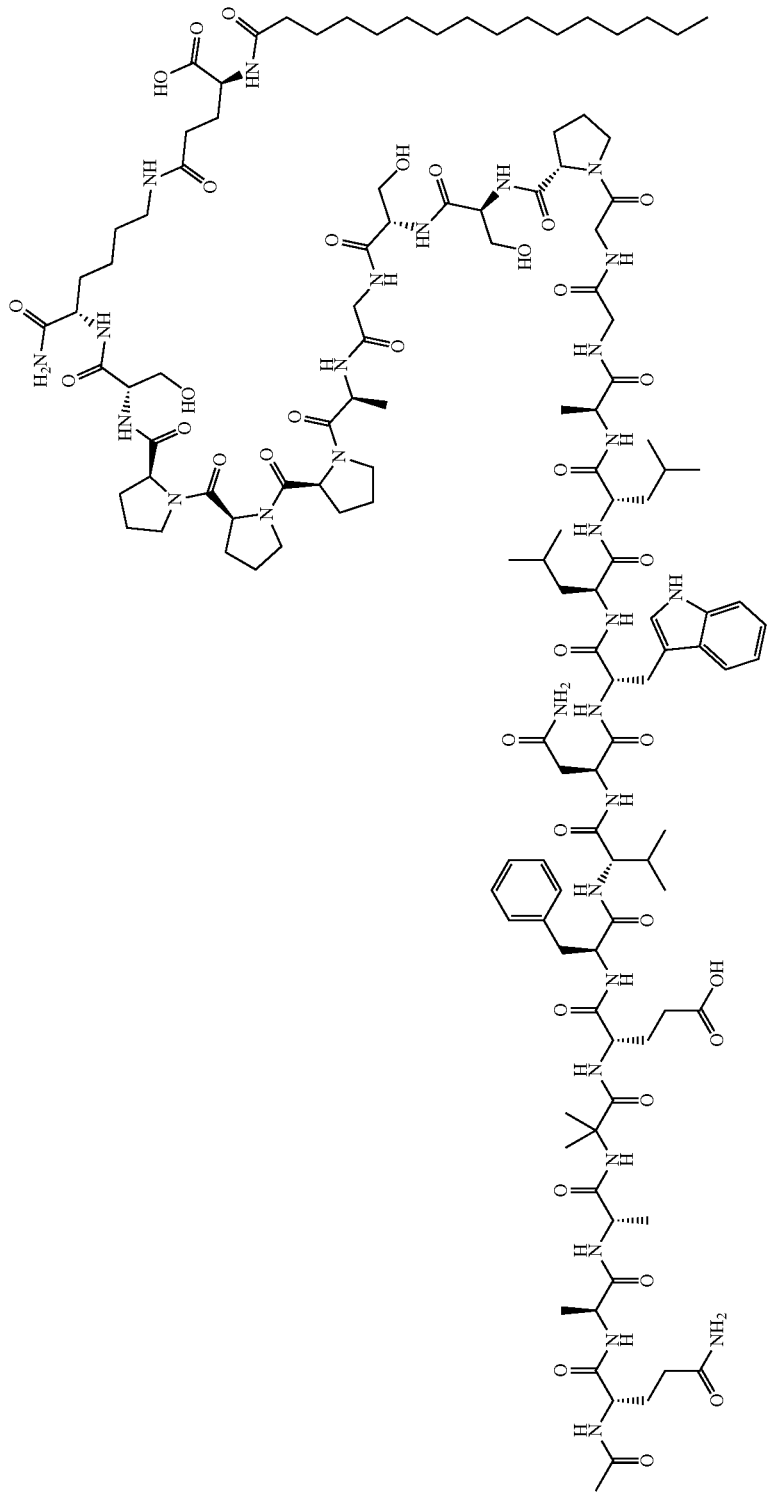

747
Compound 203
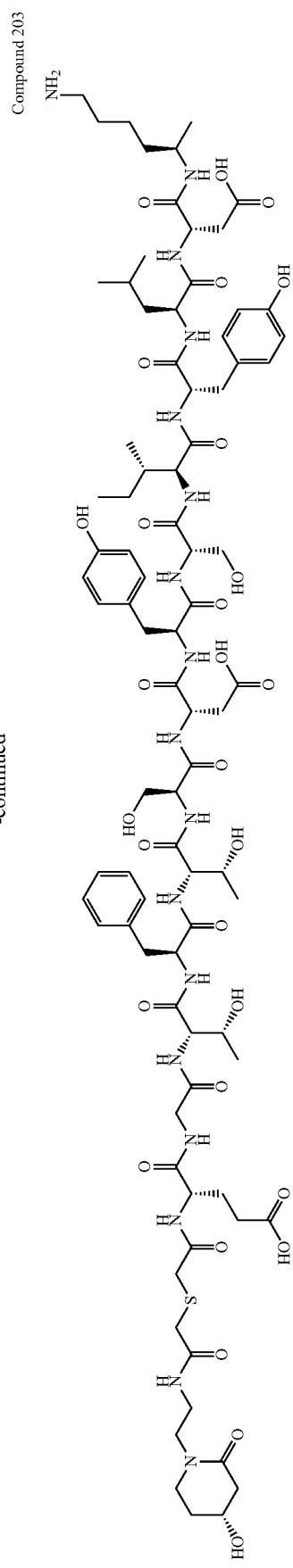
-continued
748
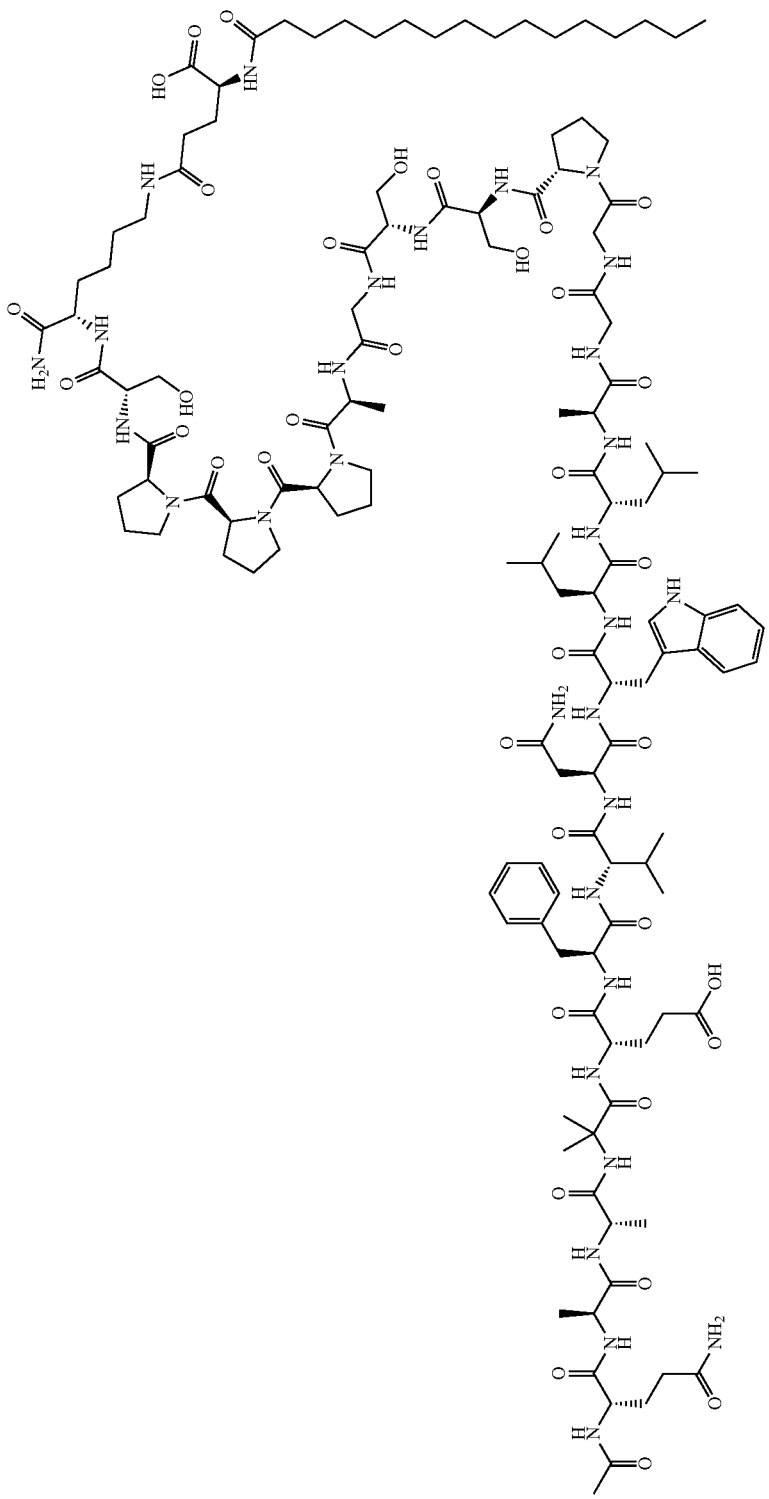

749 750
Compound 204
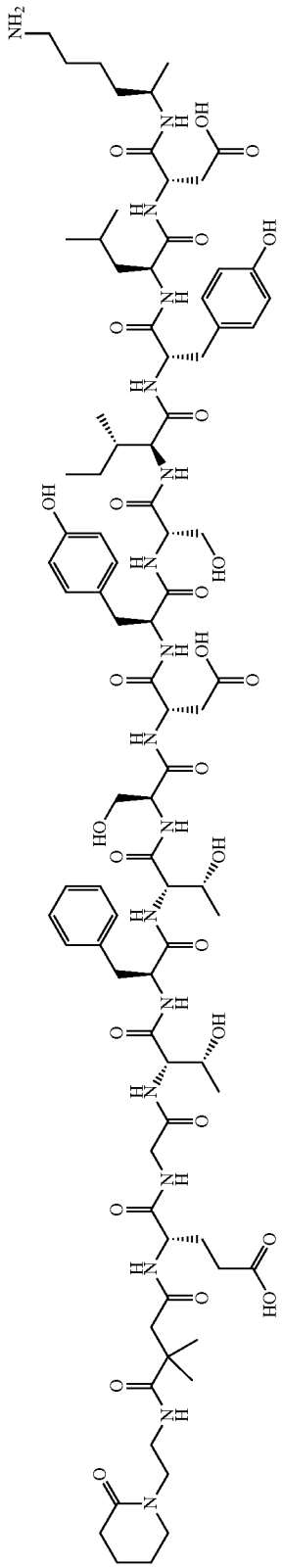
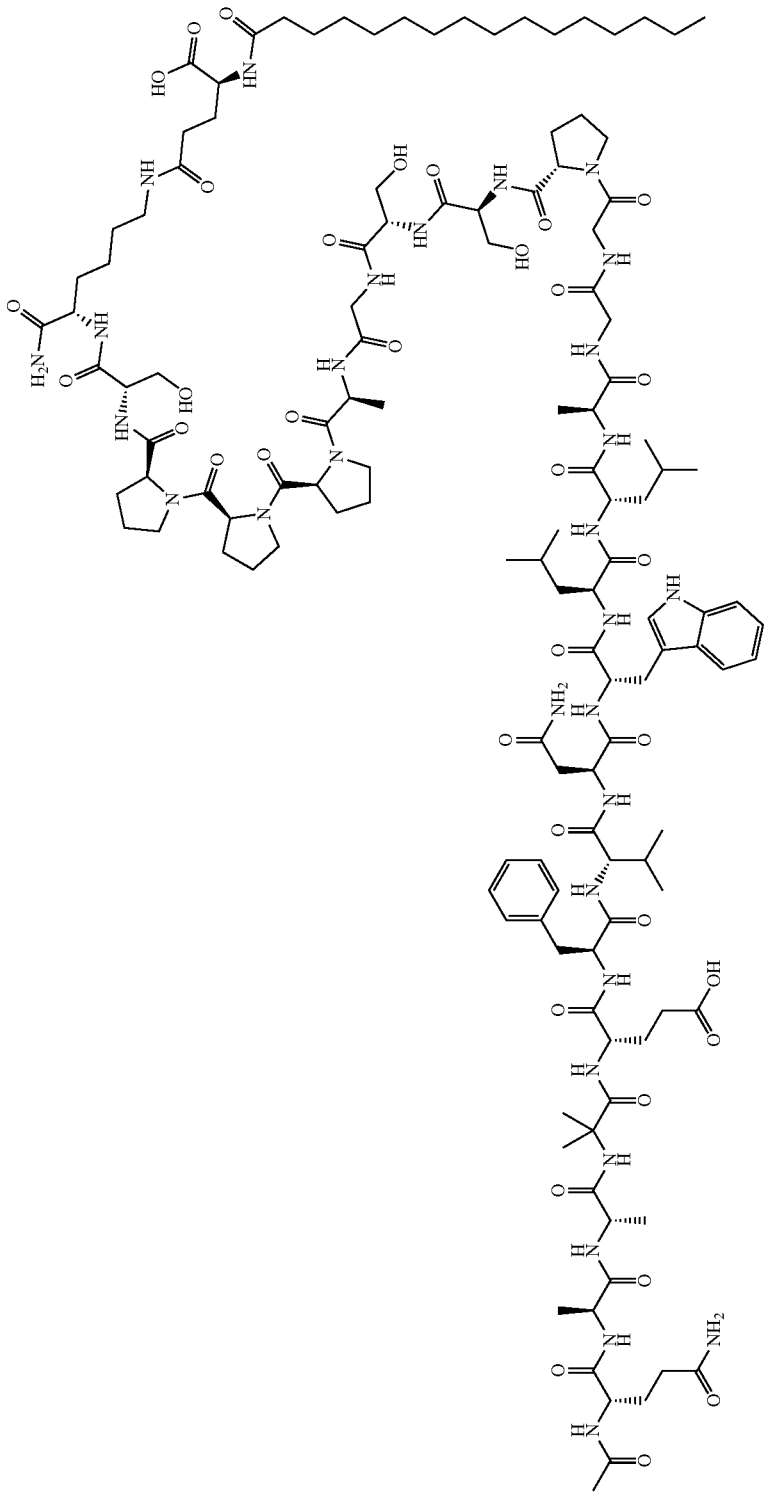

Compound 205 -continued
751
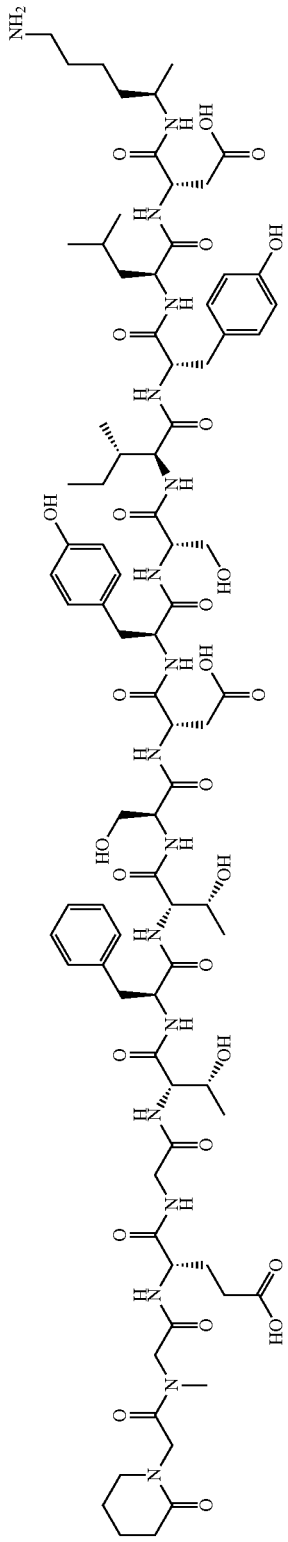
752
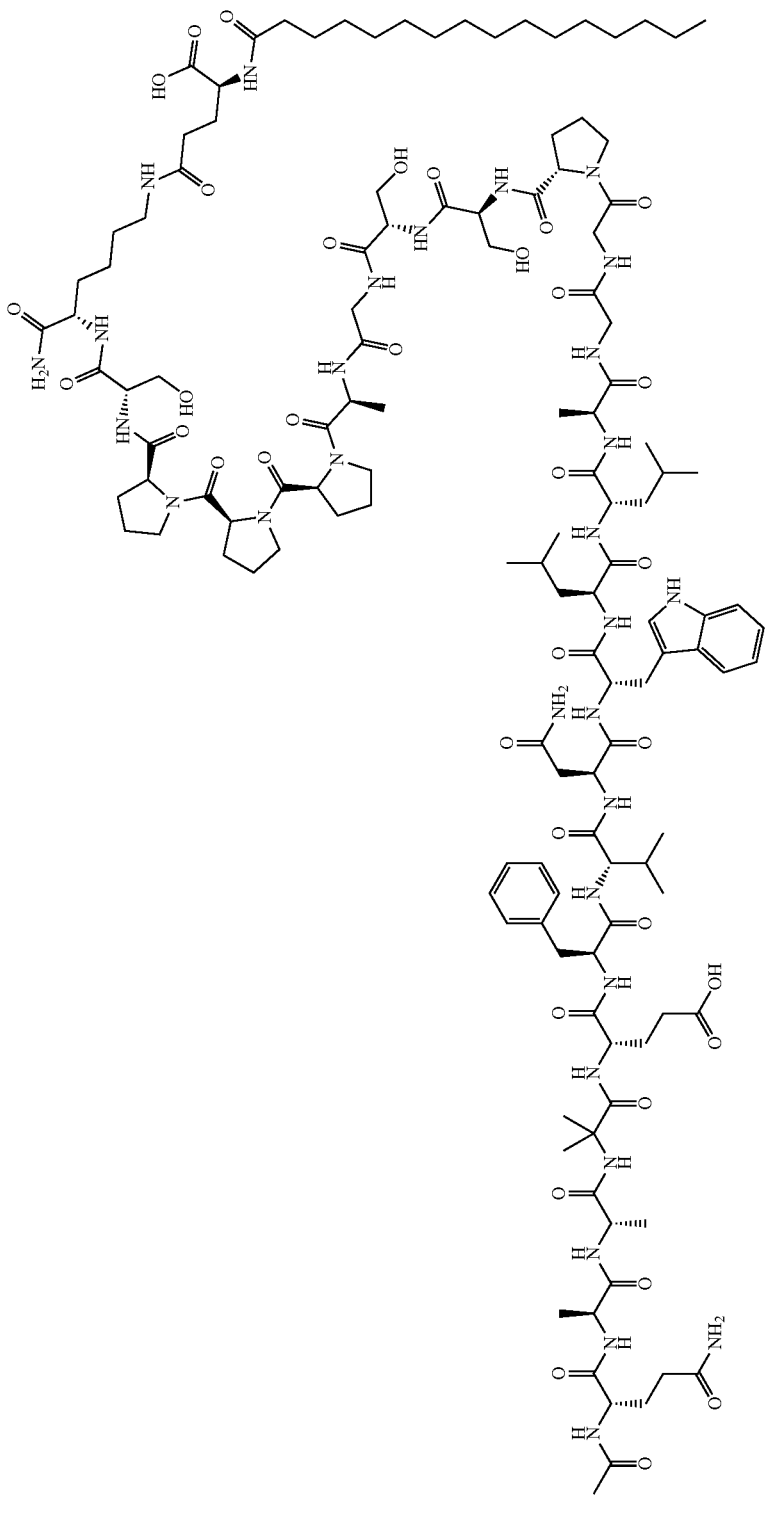

753 754
Compound 206
-continued
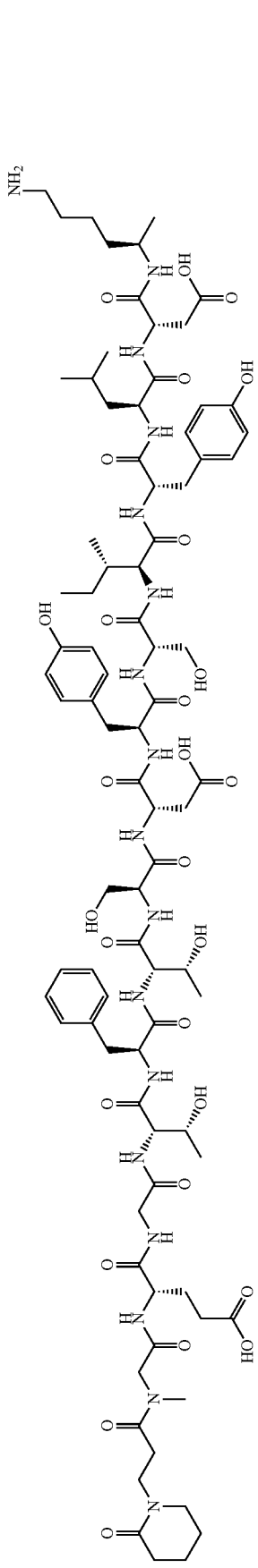
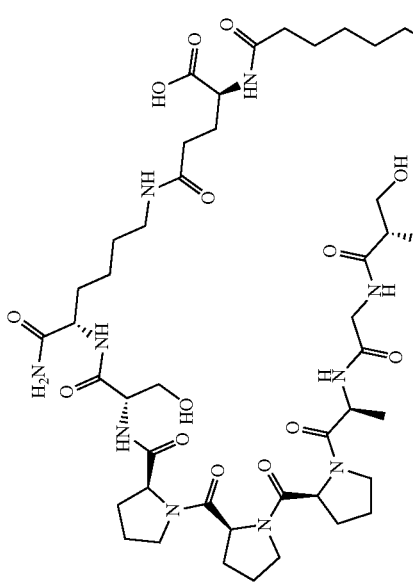
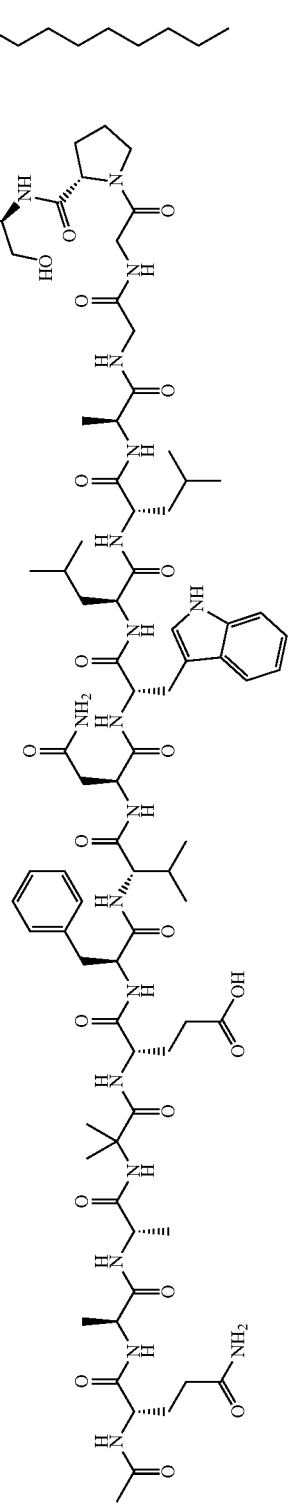

Compound 207
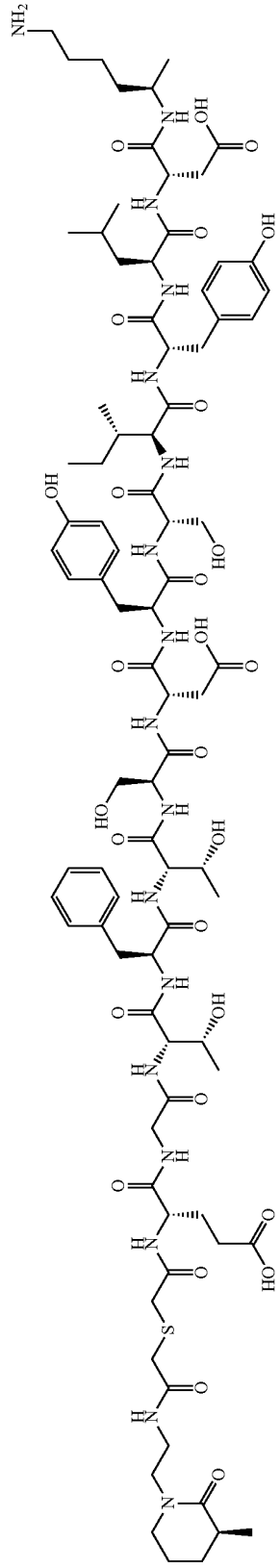
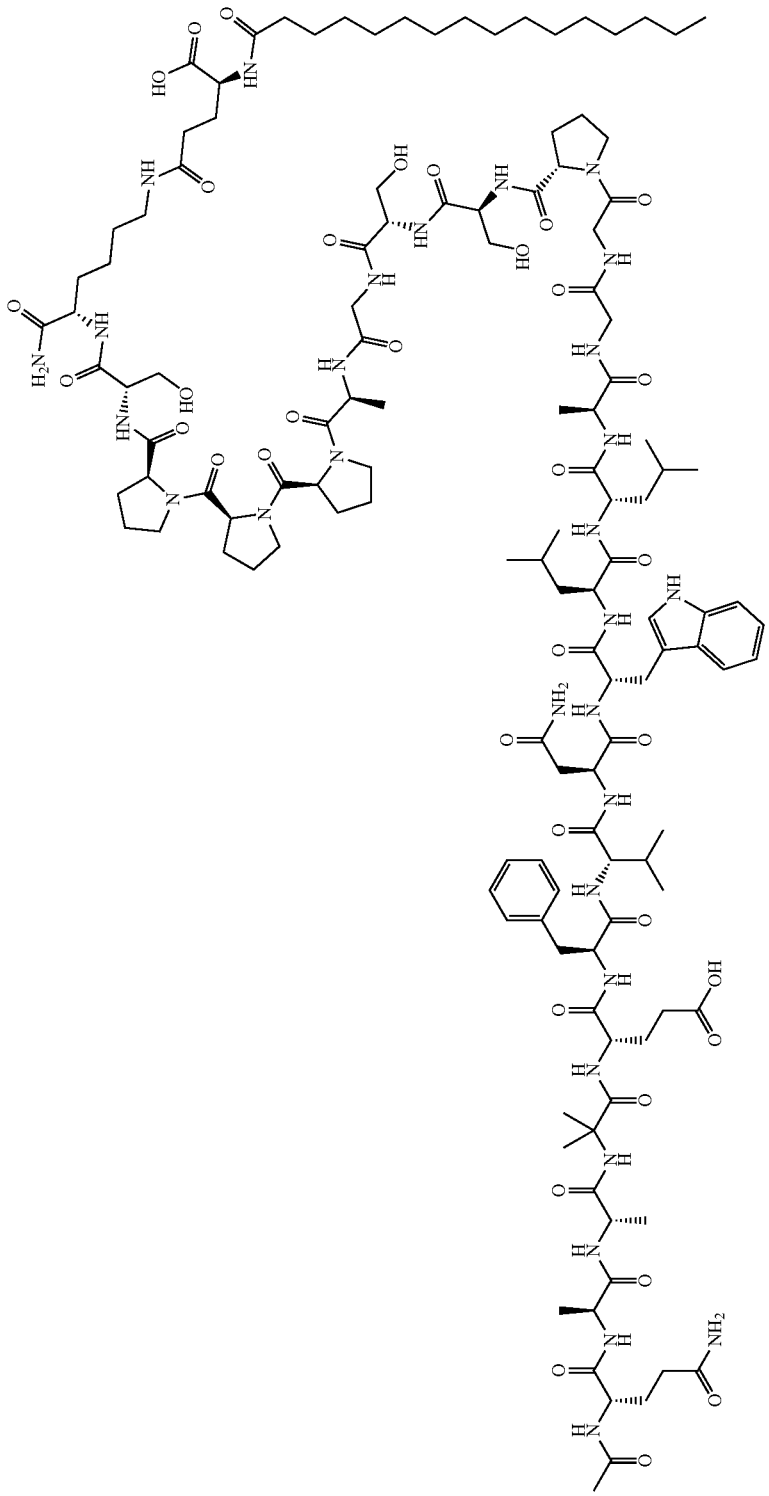

Compound 208
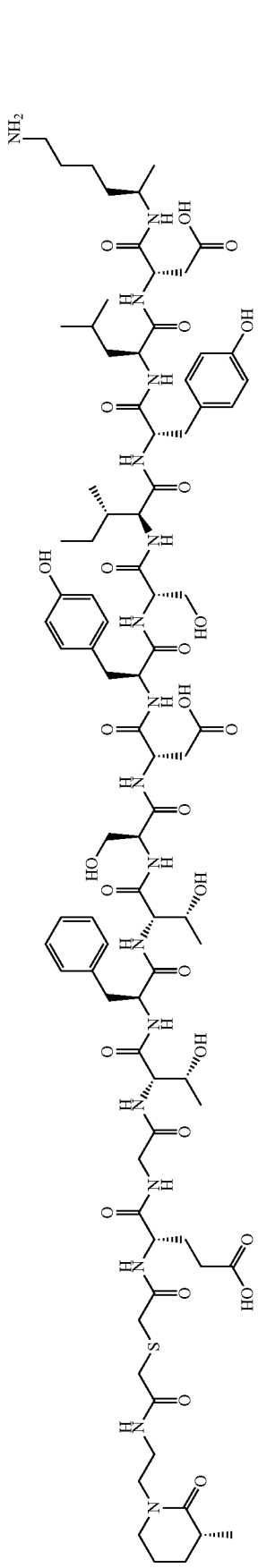
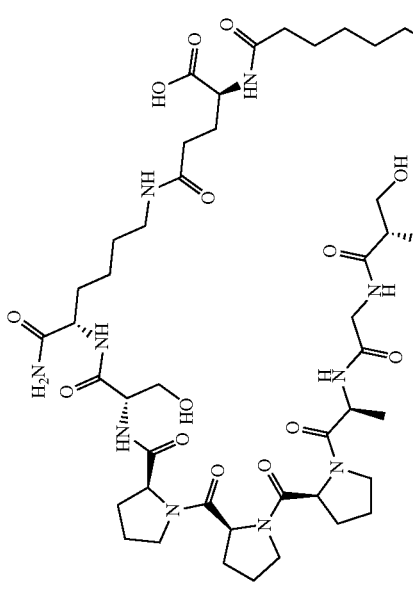
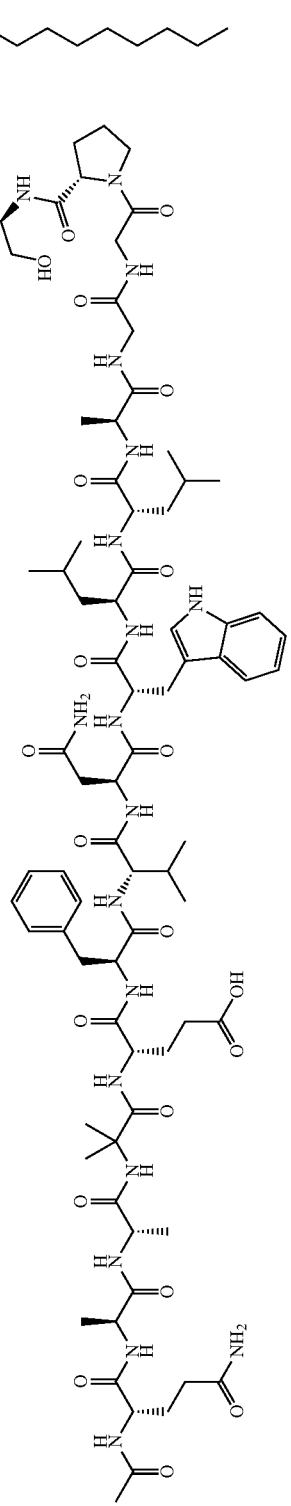

Compound 209
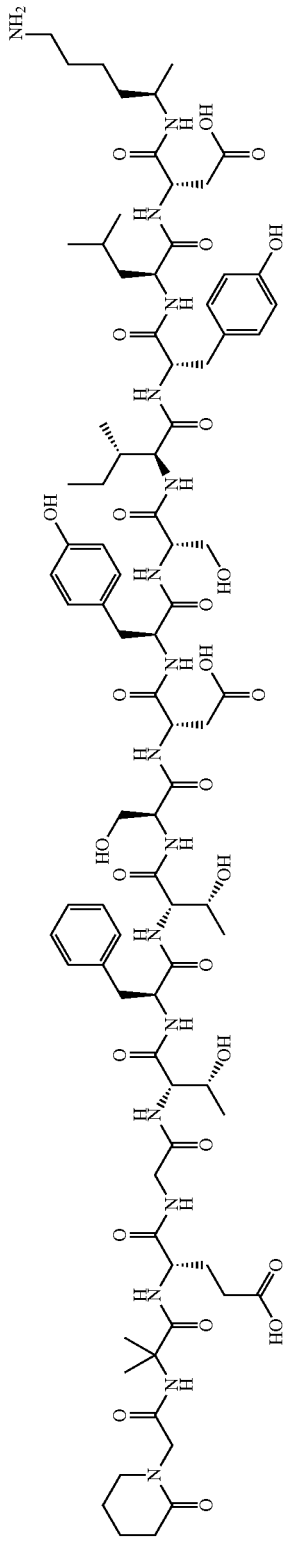
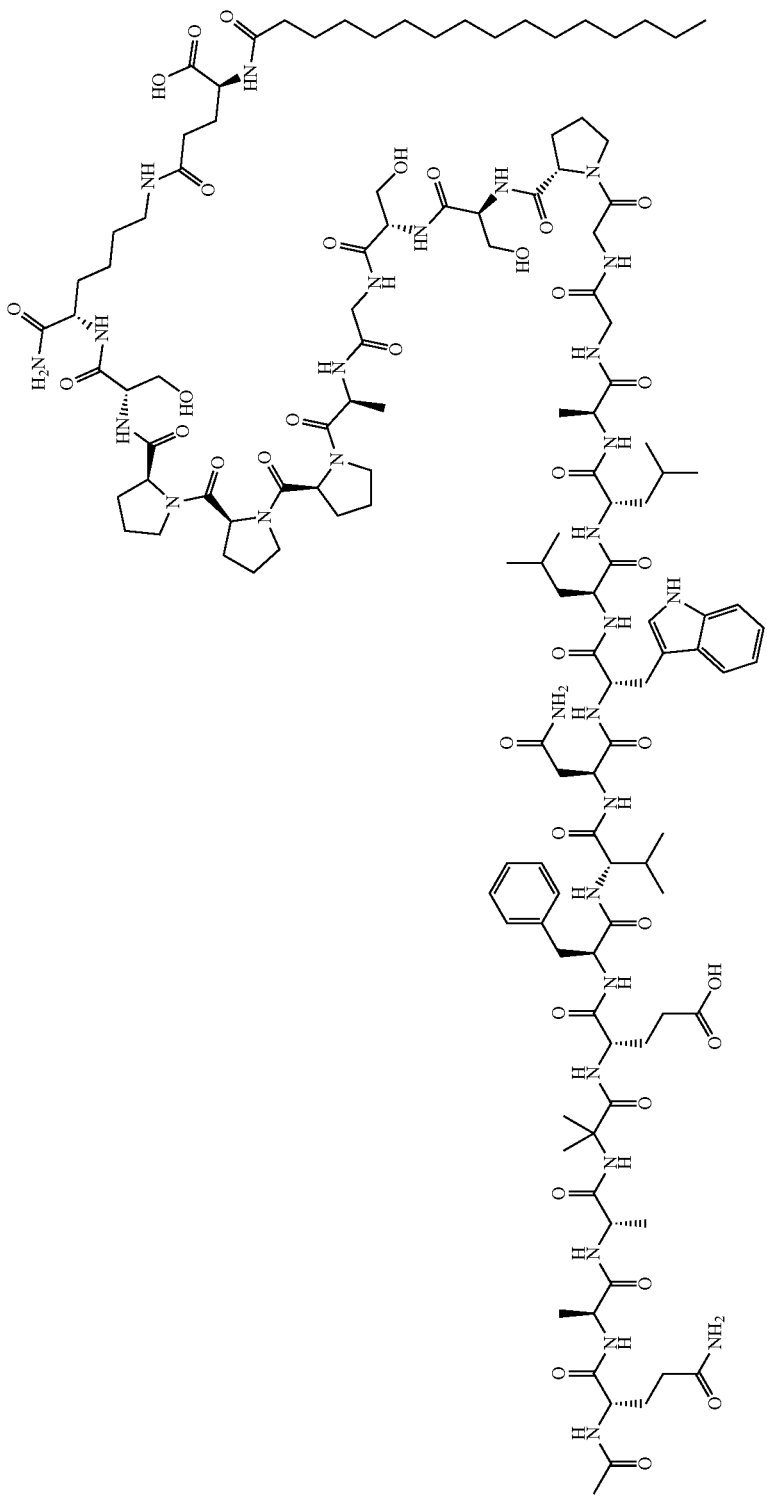

Compound 210
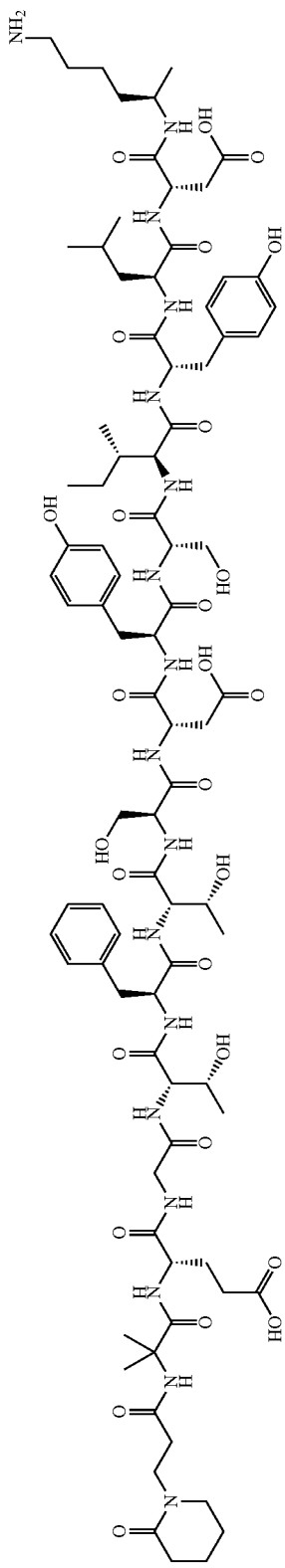
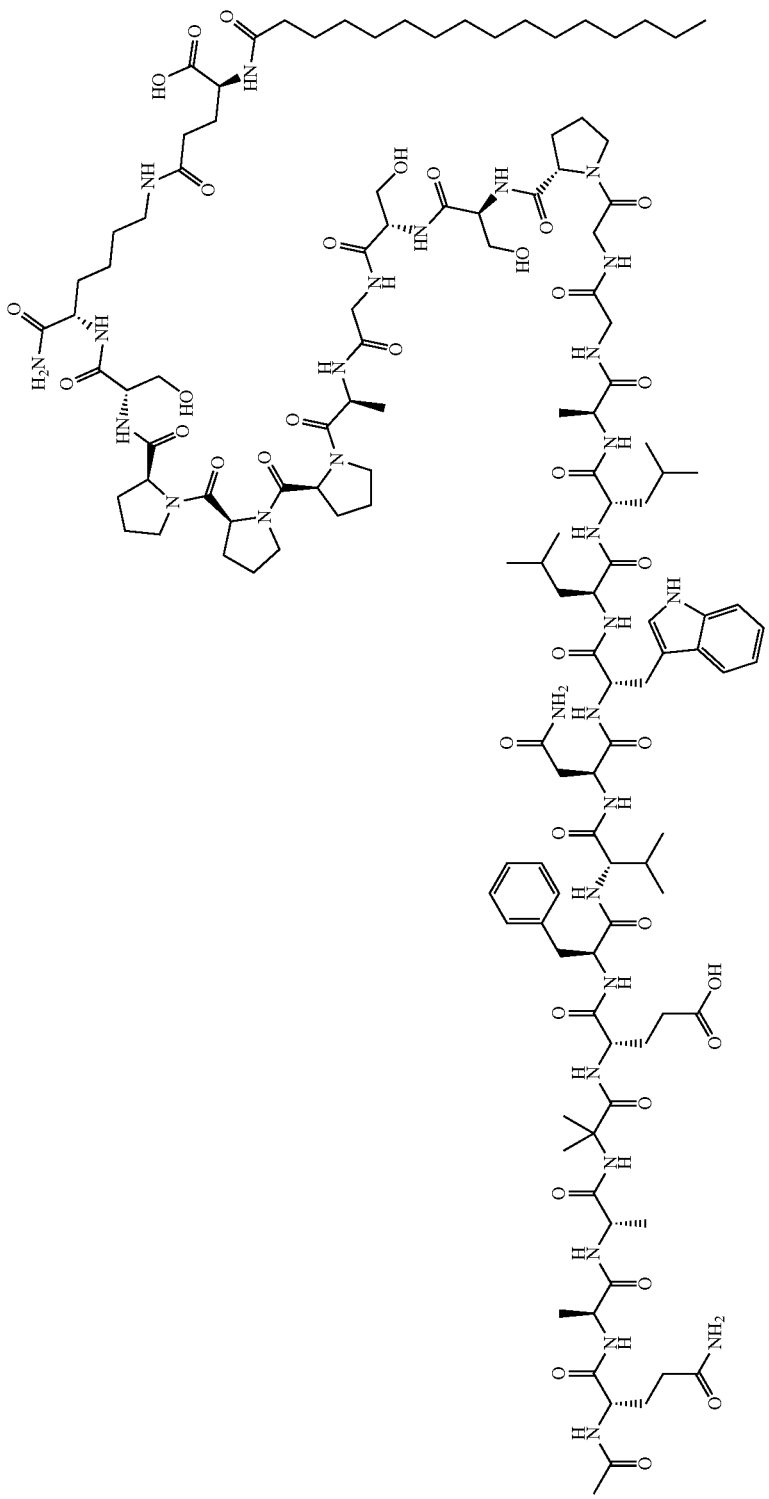

763 764
Compound 211
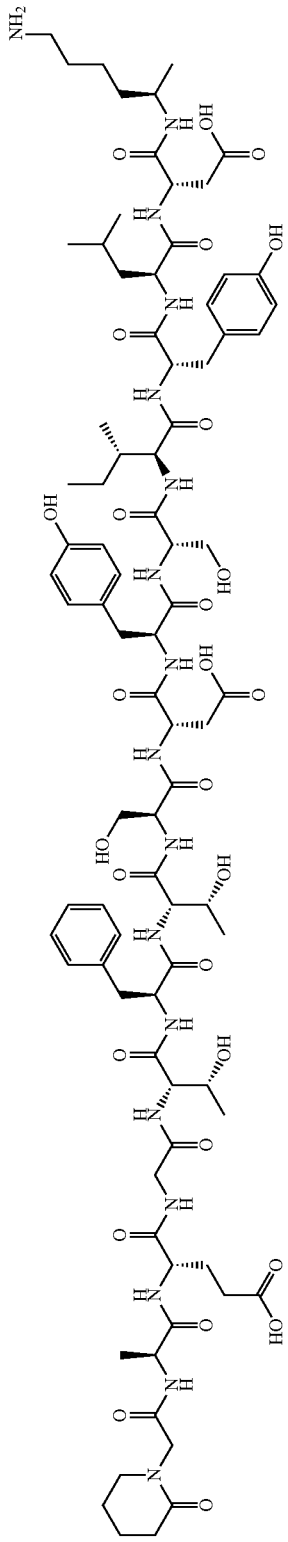
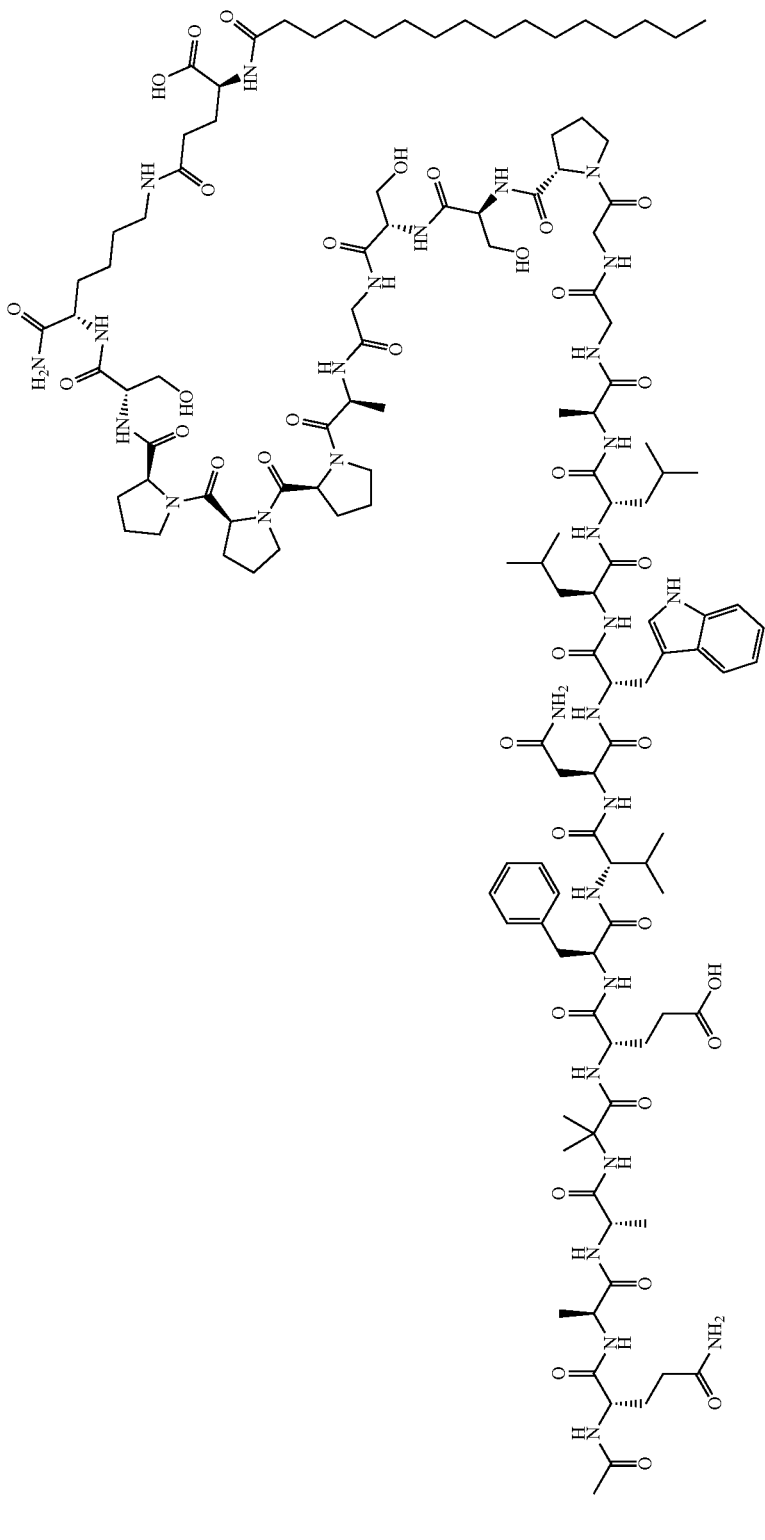

Compound 212
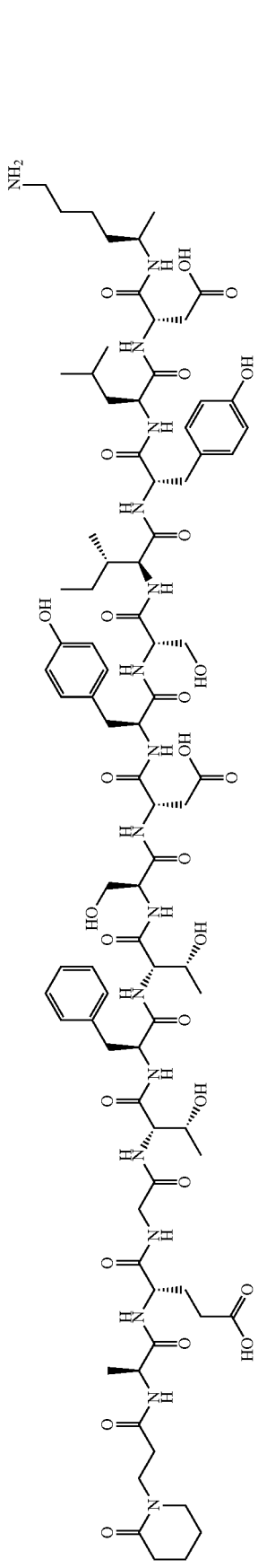
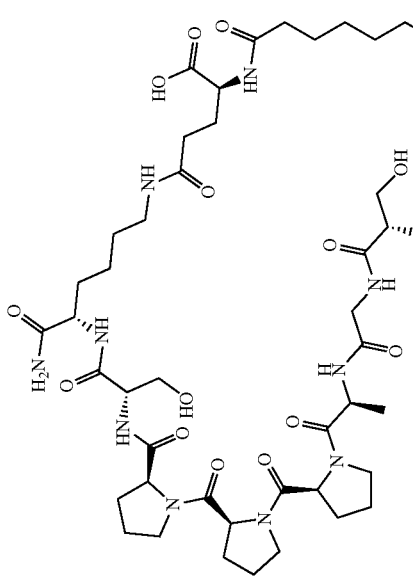
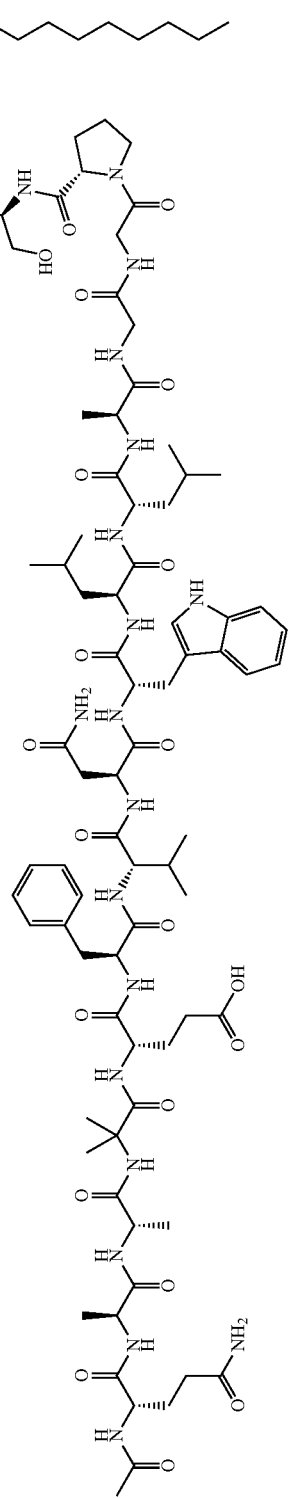

Compound 213
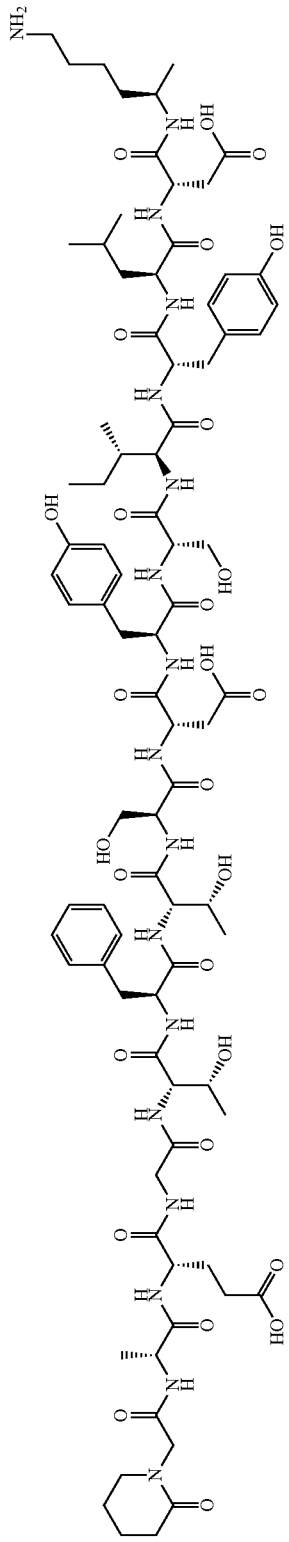
767
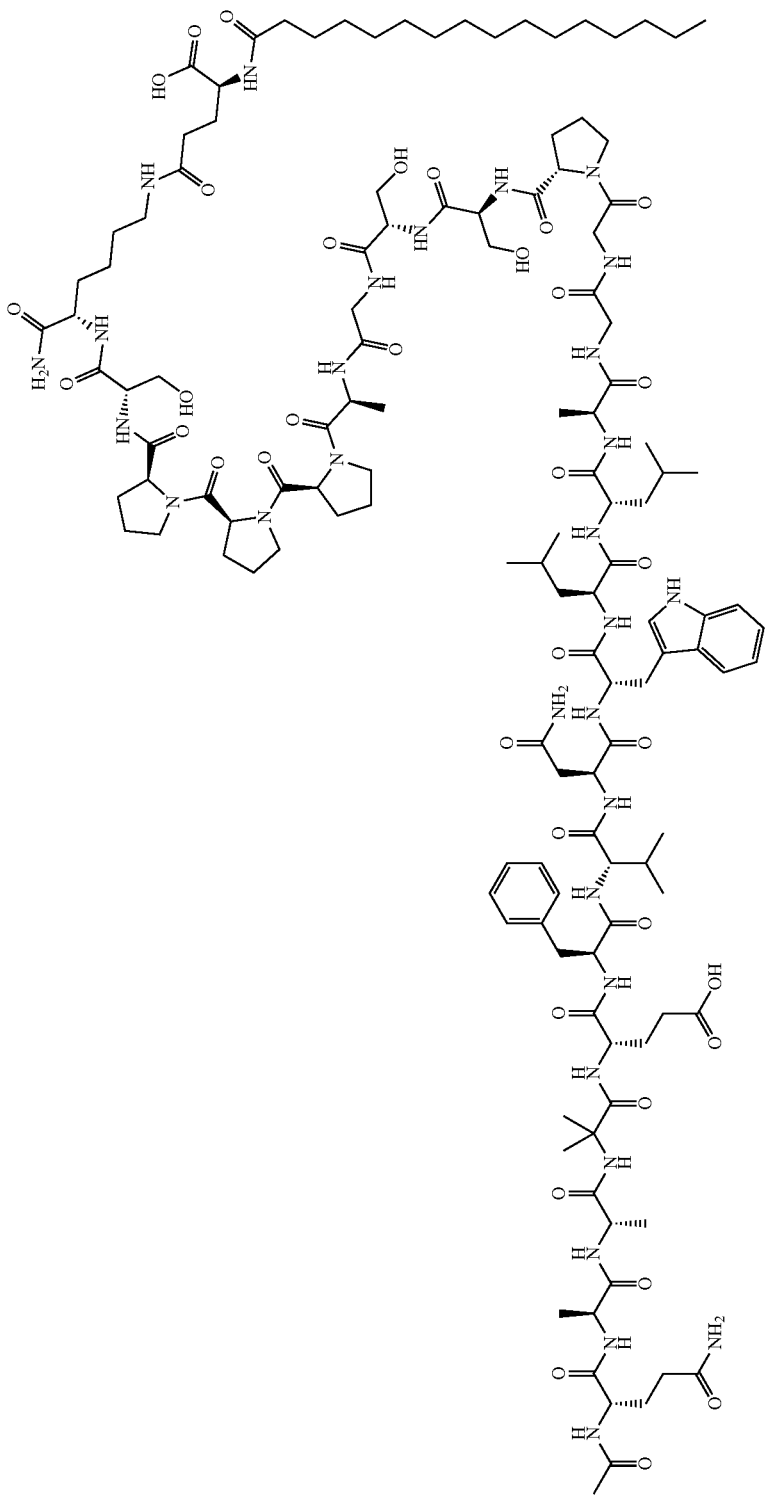
768

Compound 214
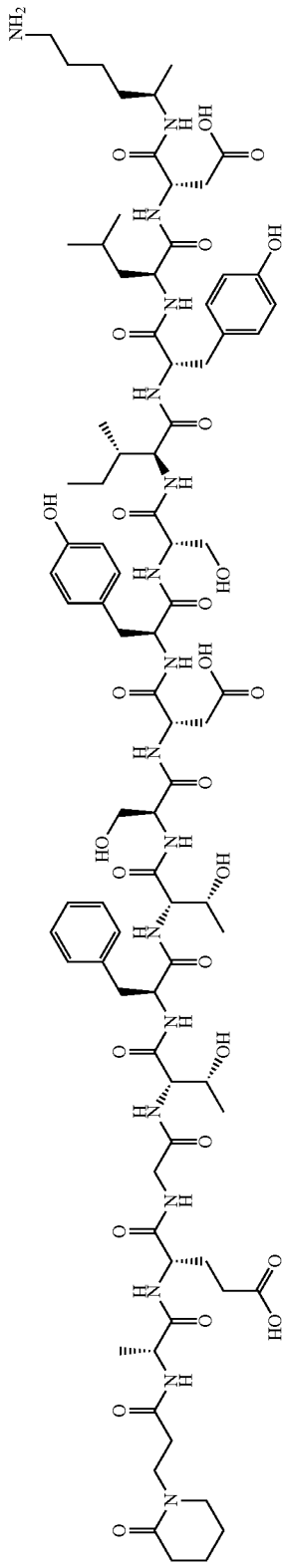
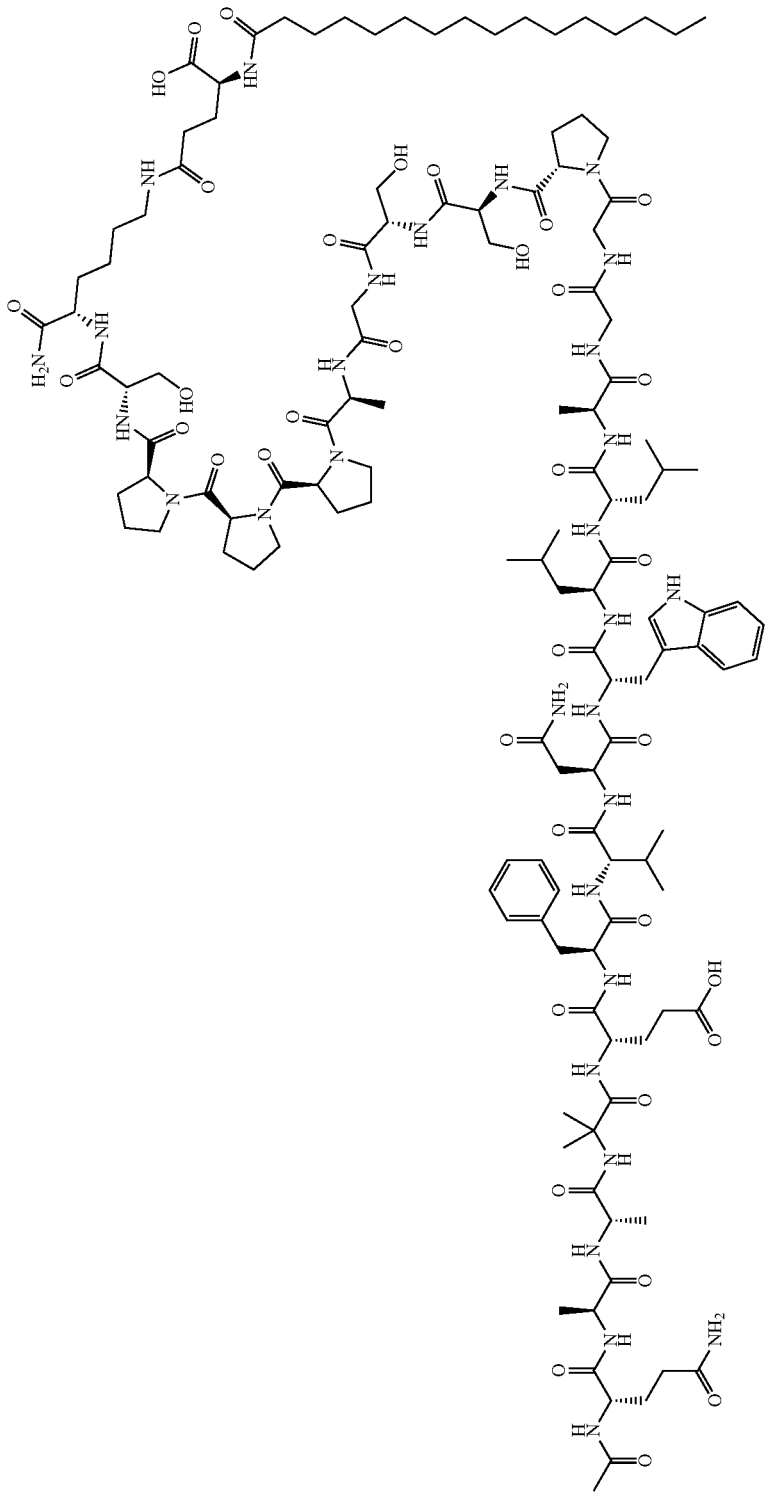

Compound 215
771 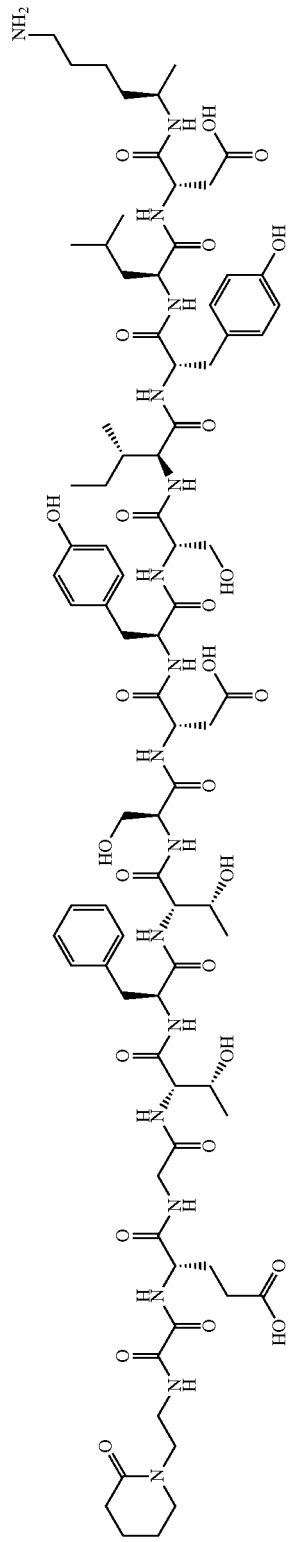
772 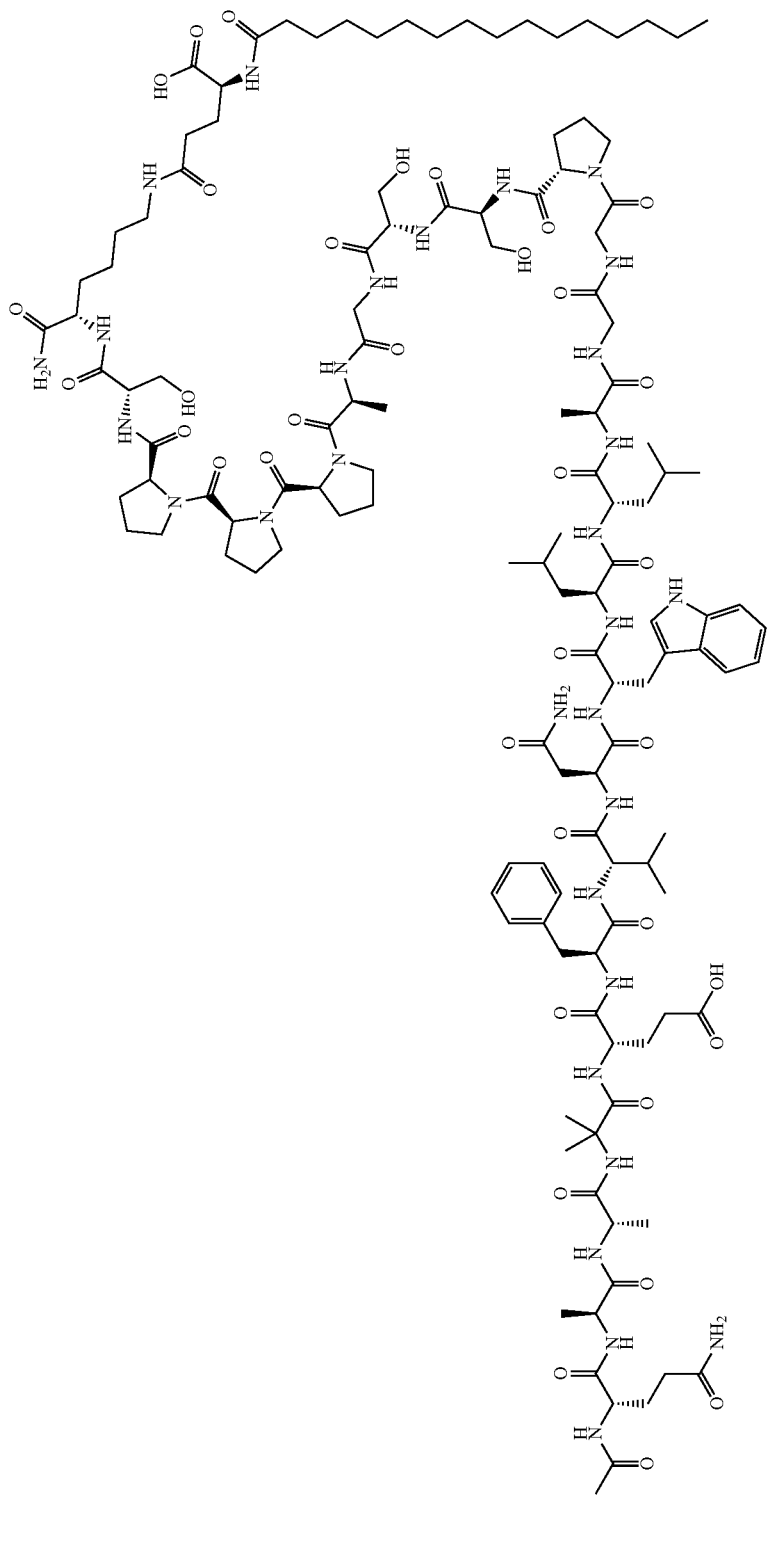

773
Compound 226
774
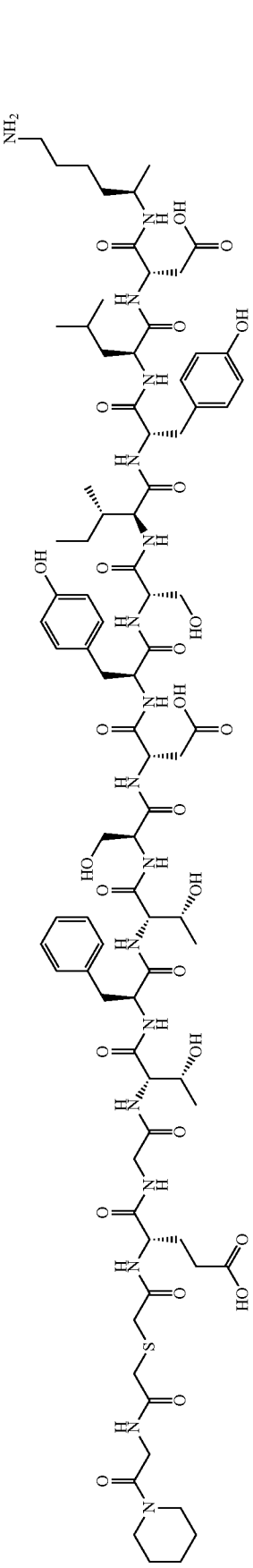
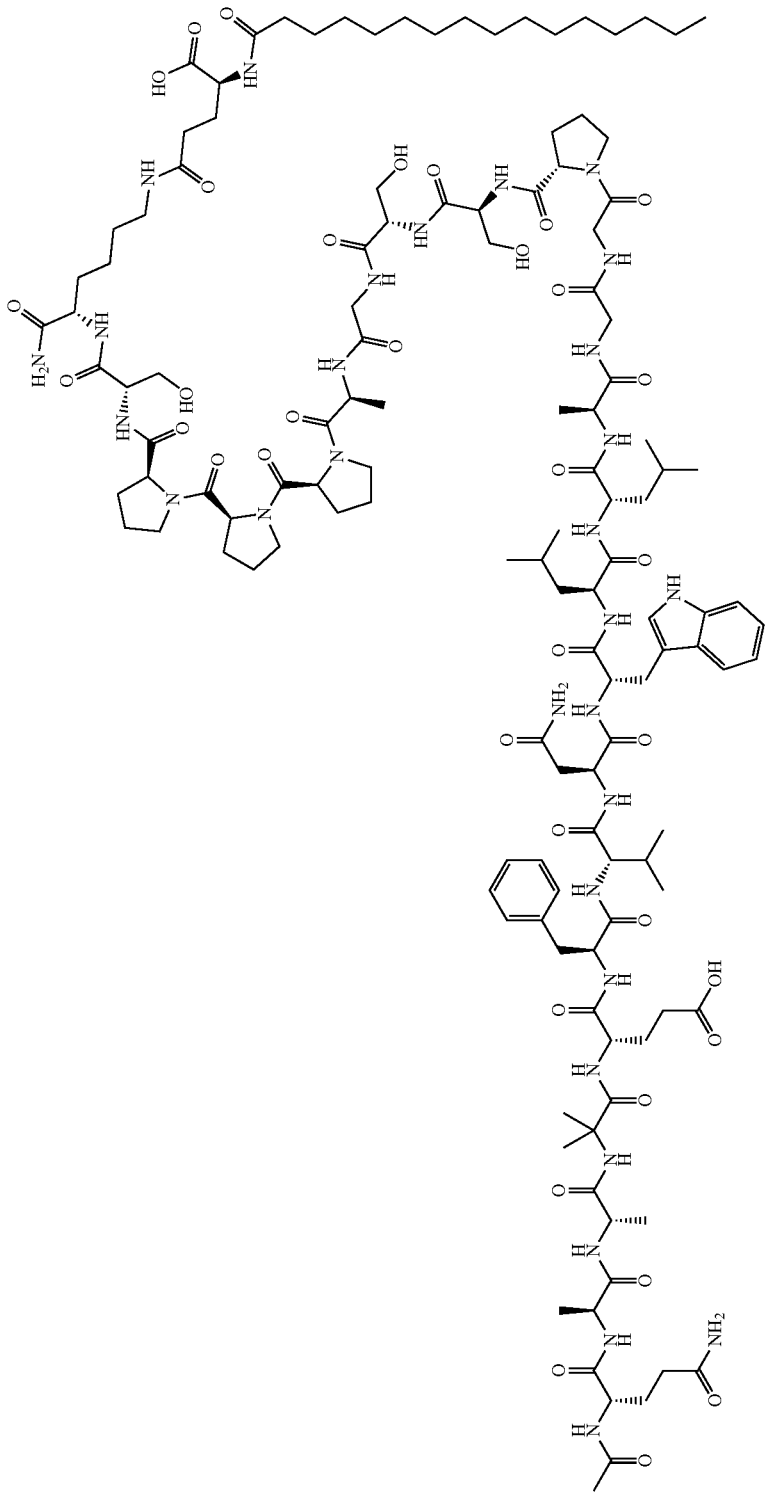

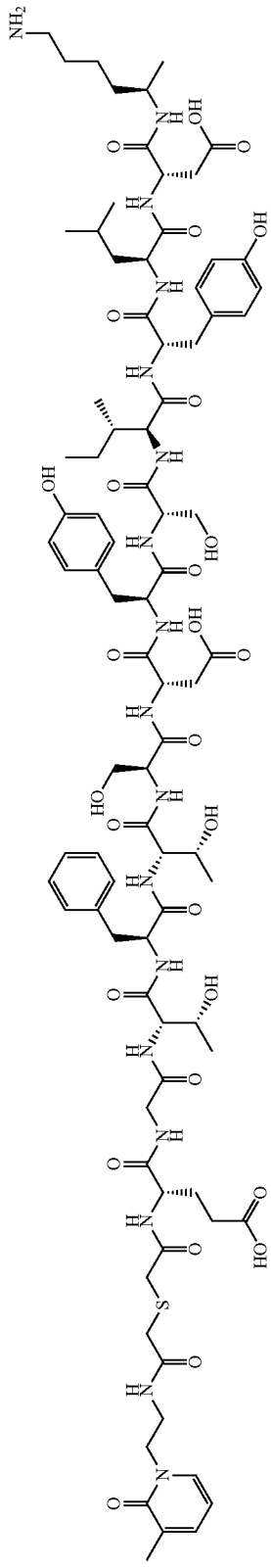
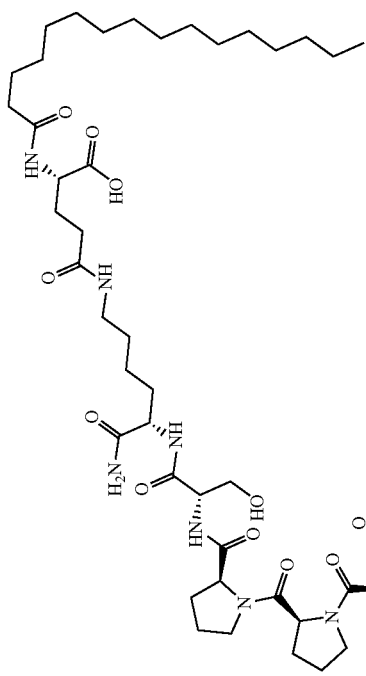
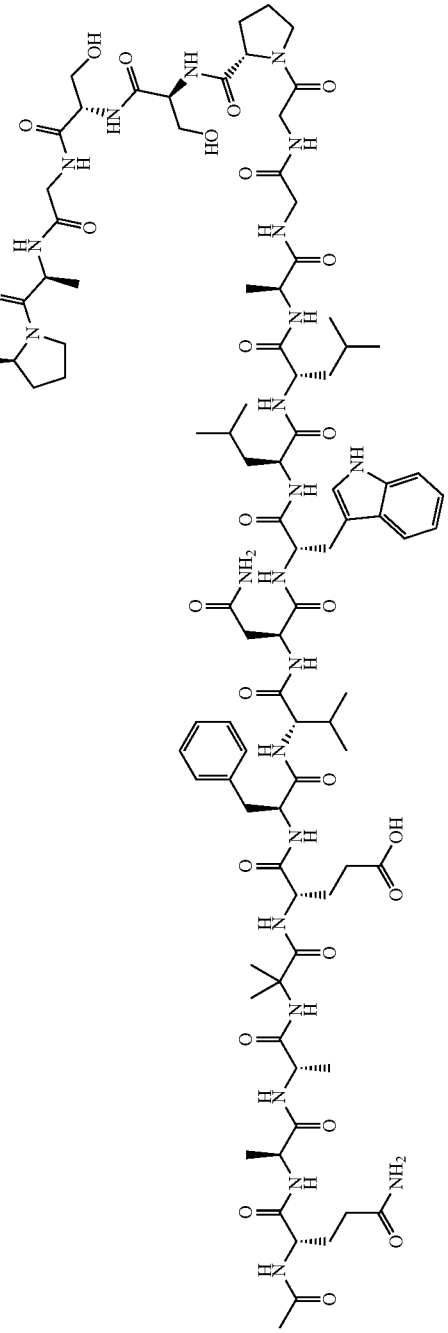
Compound 232

-continued
Compound 233
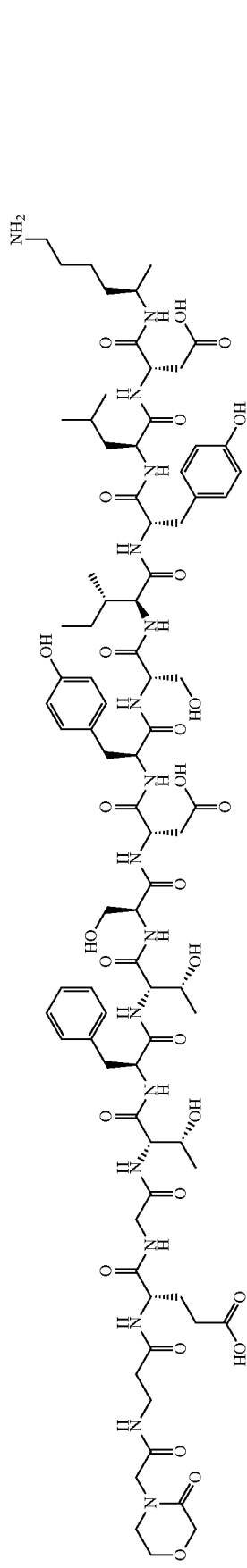
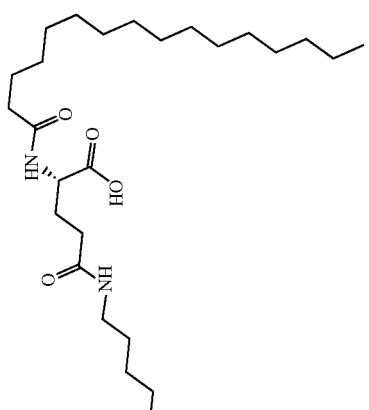
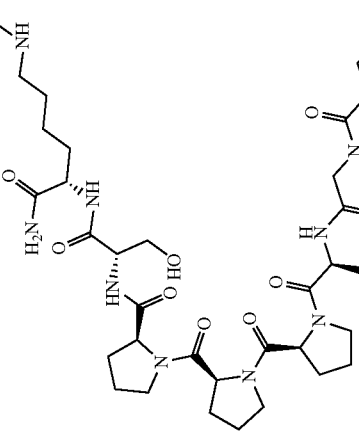
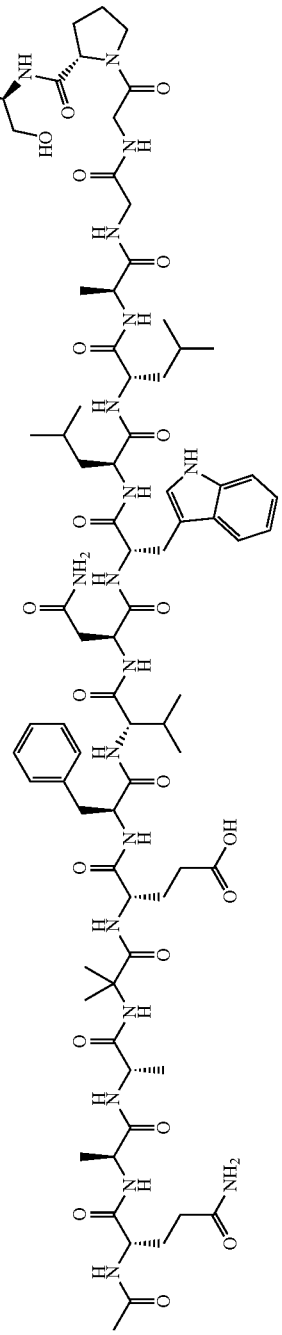

Compound 234
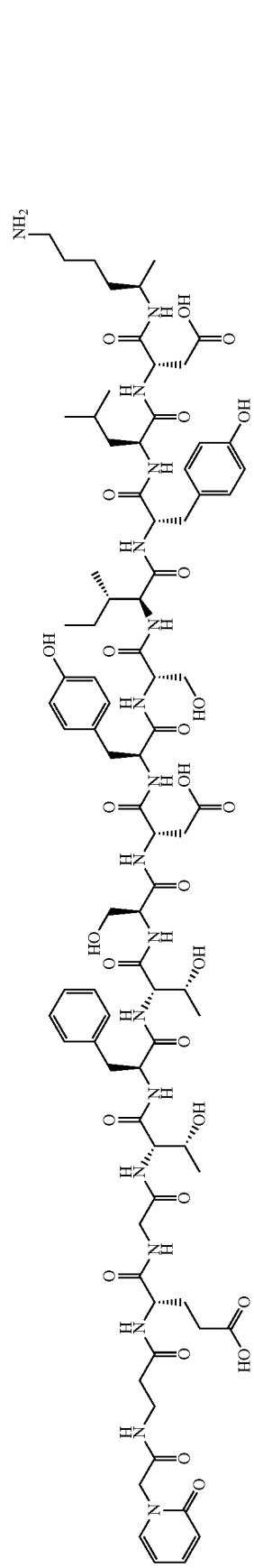
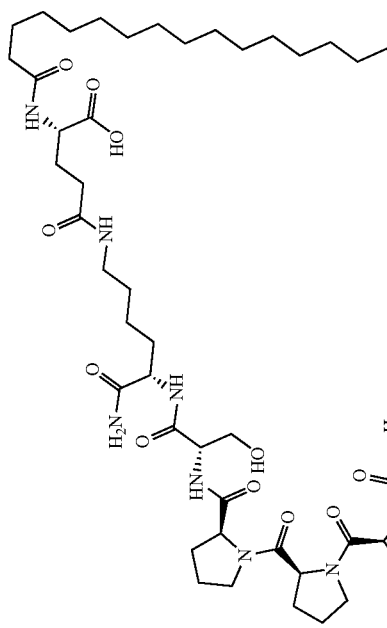
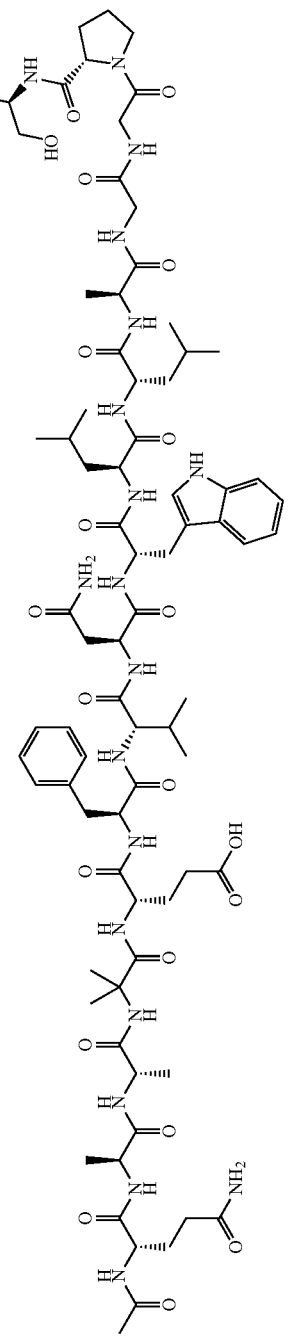

781
782
Compound 238
-continued
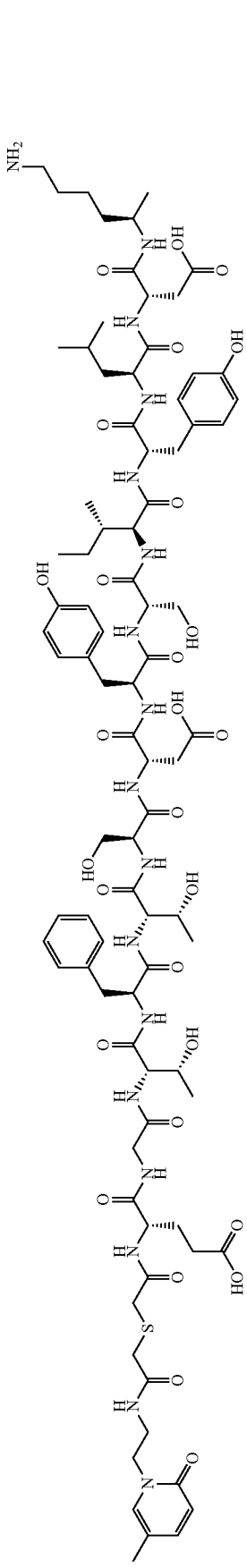
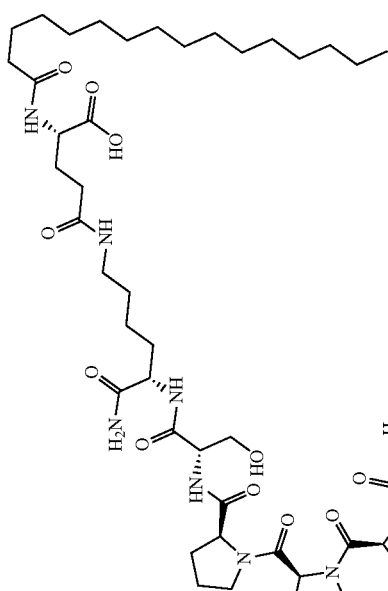
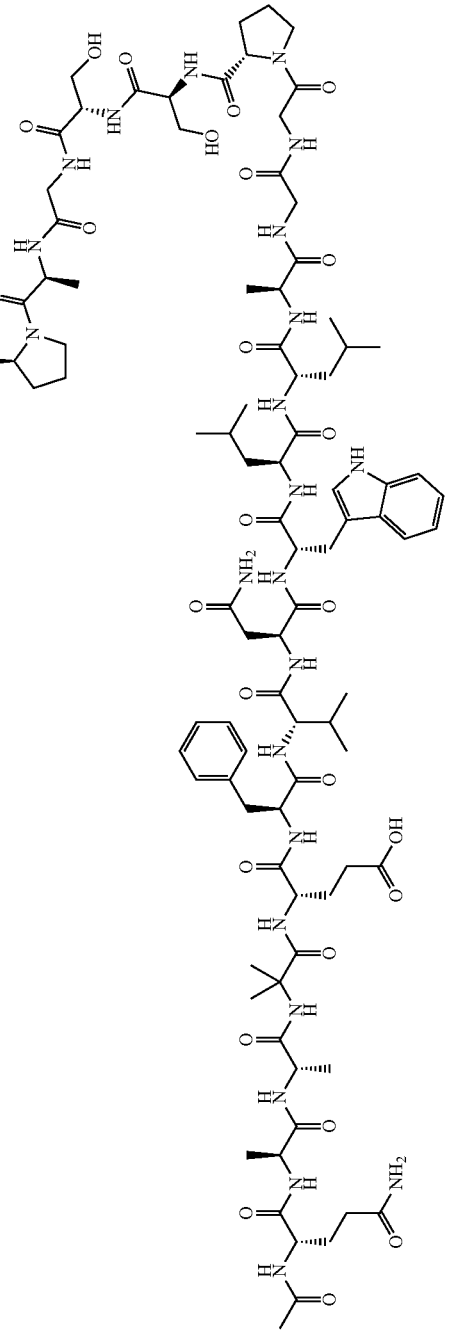

783 784
Compound 239
-continued
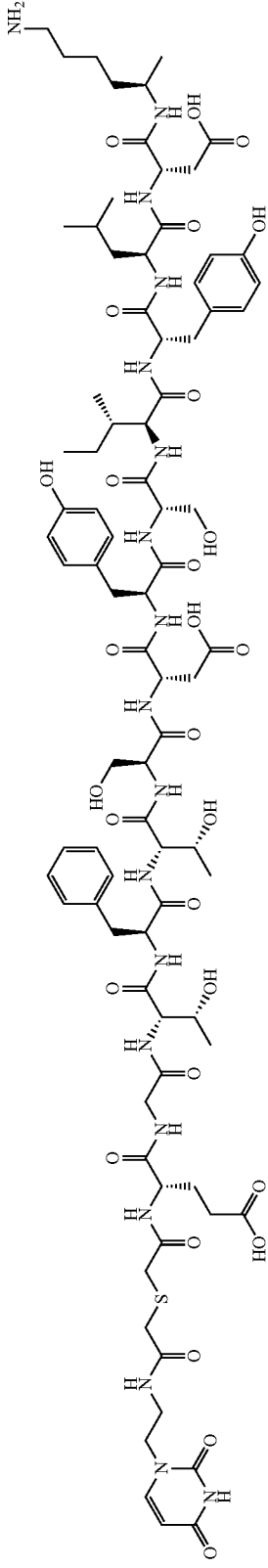
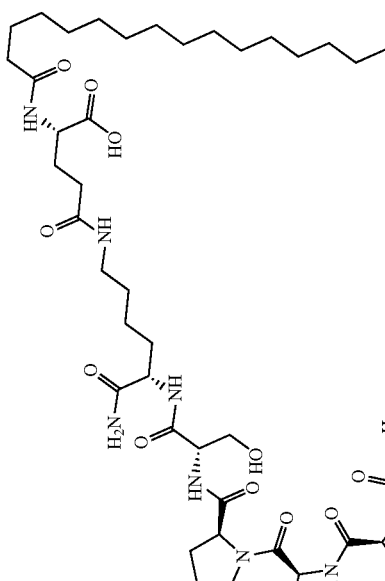
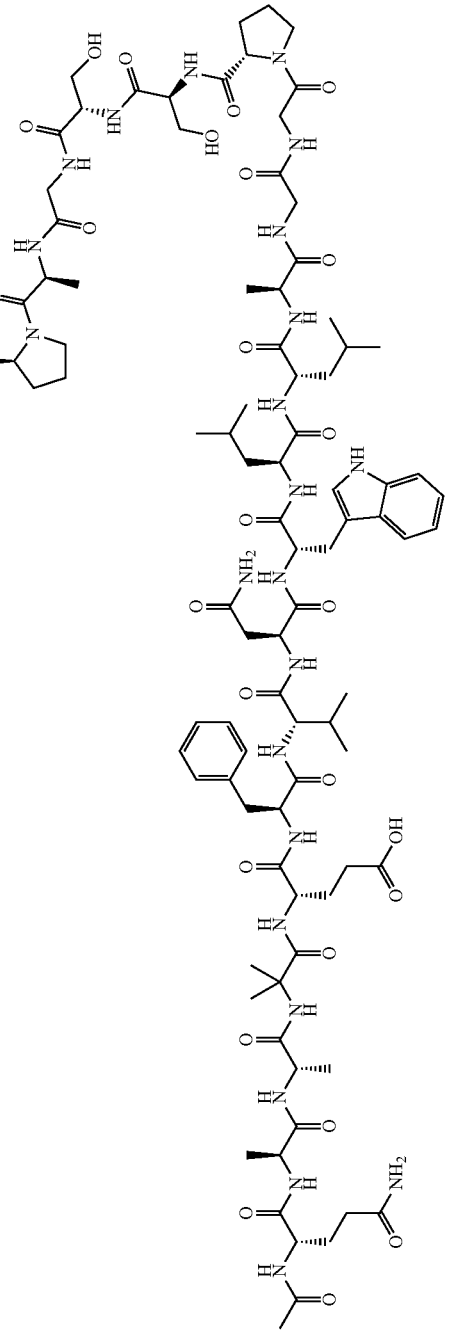

Compound 240
-continued
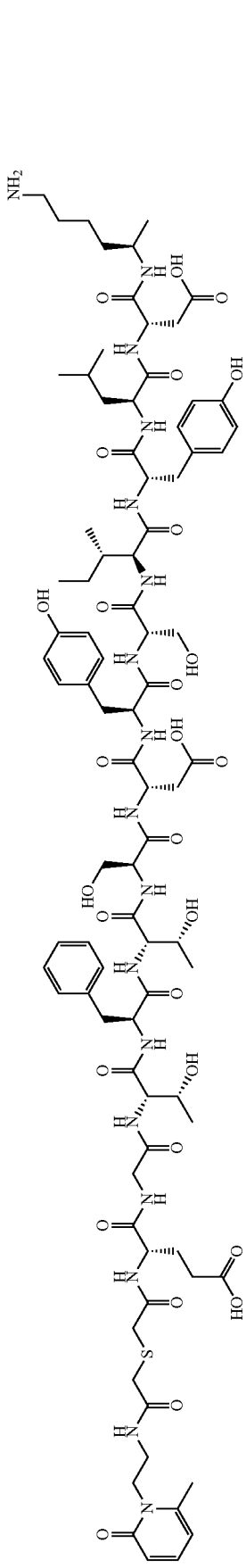
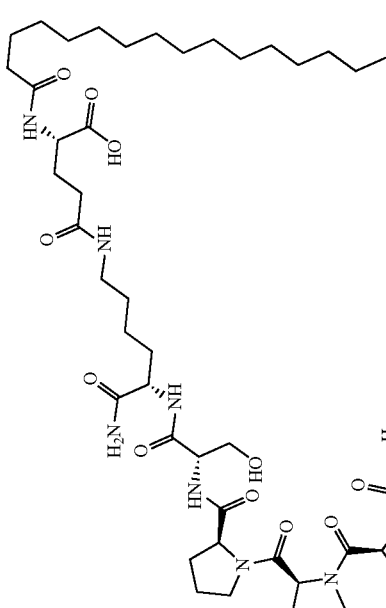
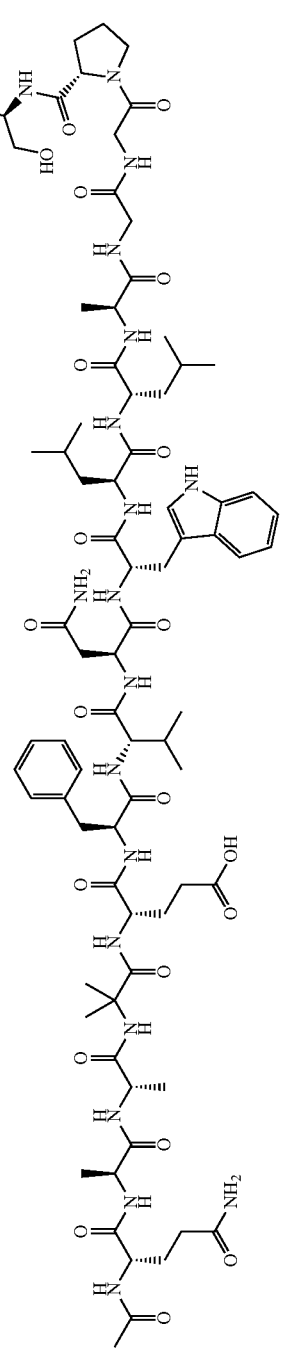

787 788
Compound 241
-continued
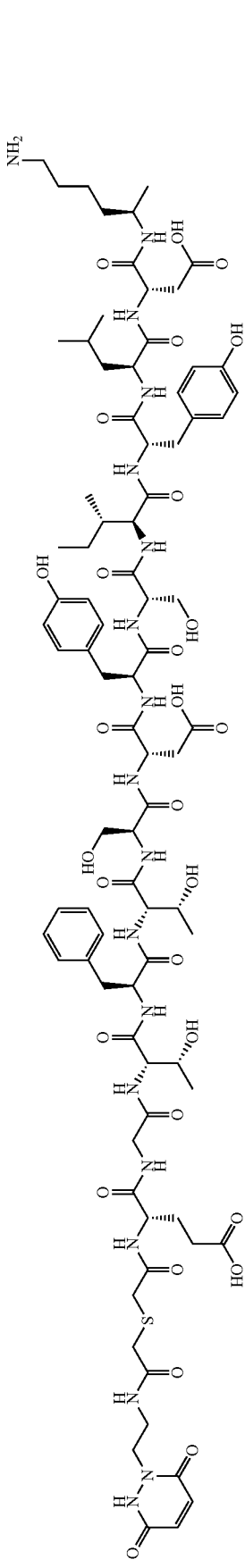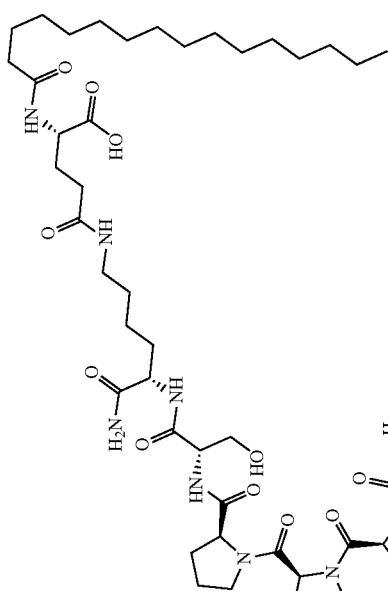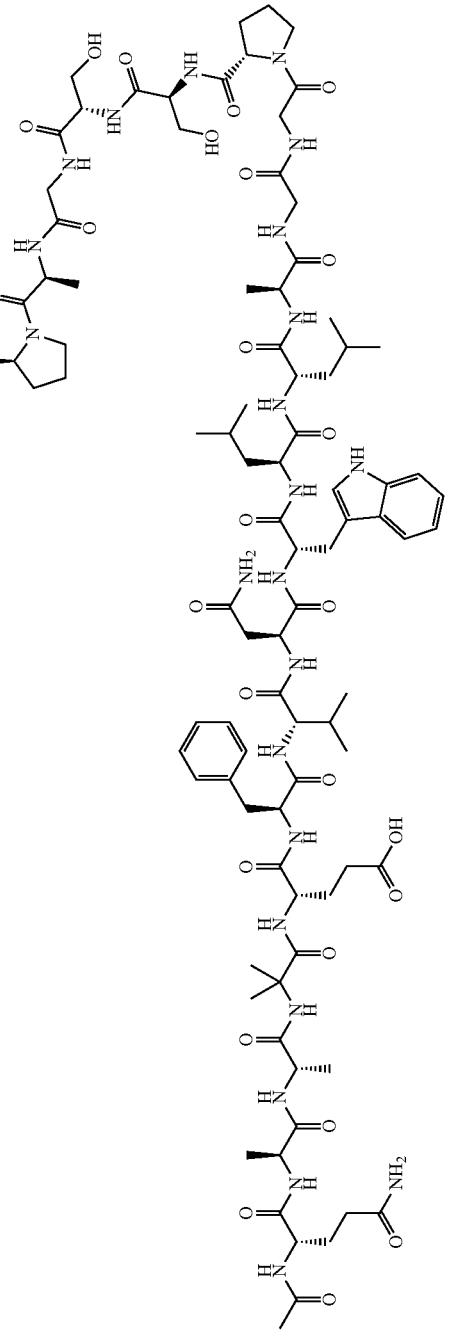

789 790
Compound 243
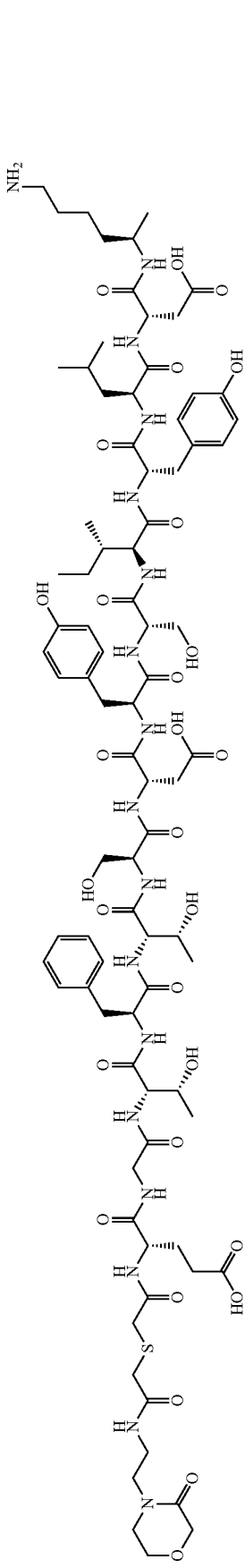
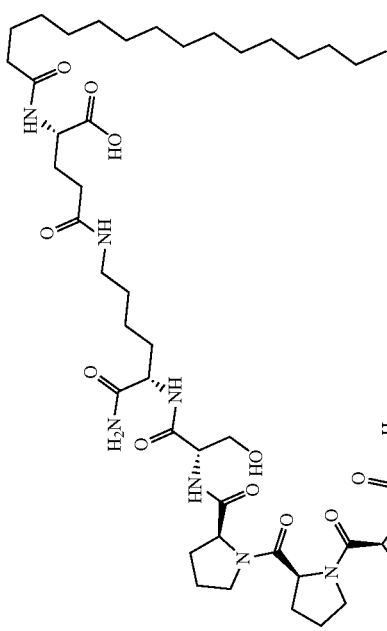
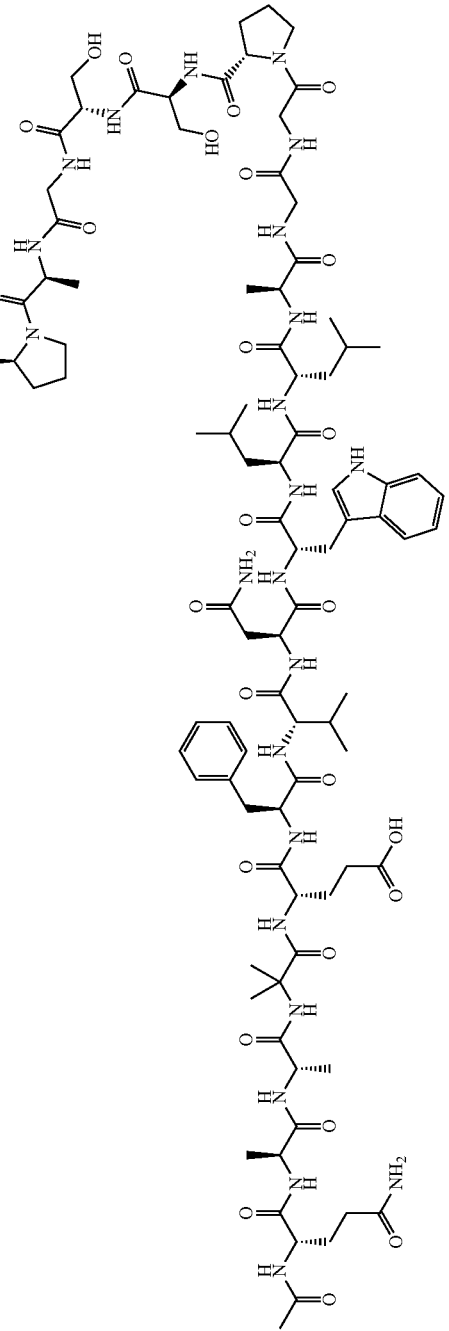

Compound 244
-continued
791
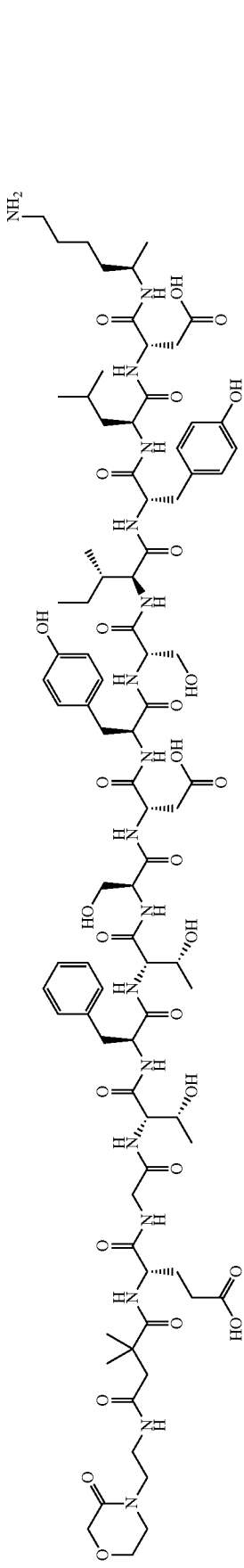
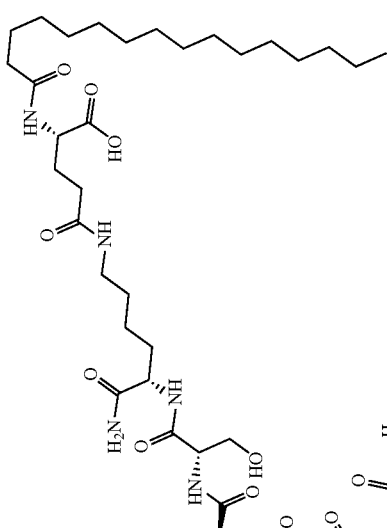
792
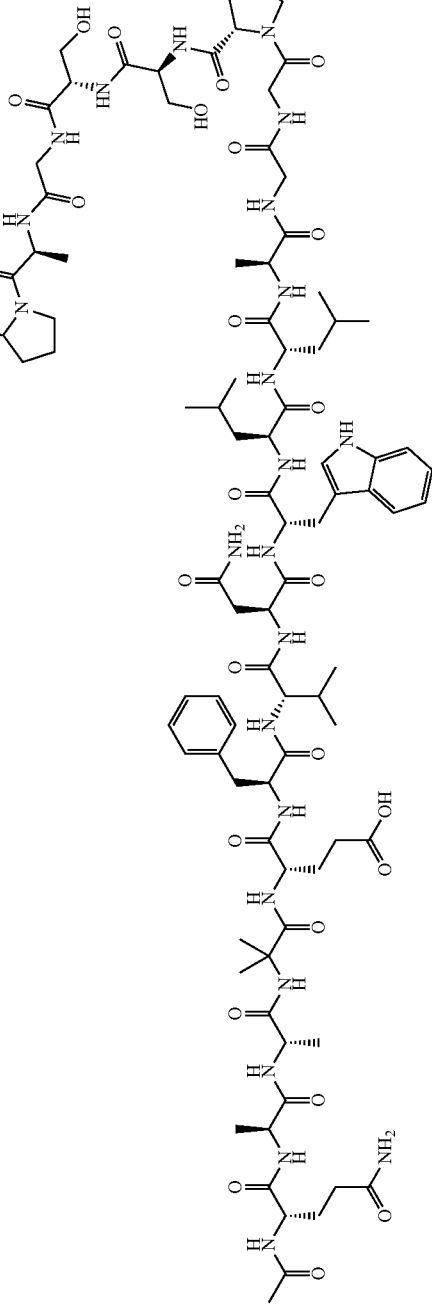

793
794
Compound 247
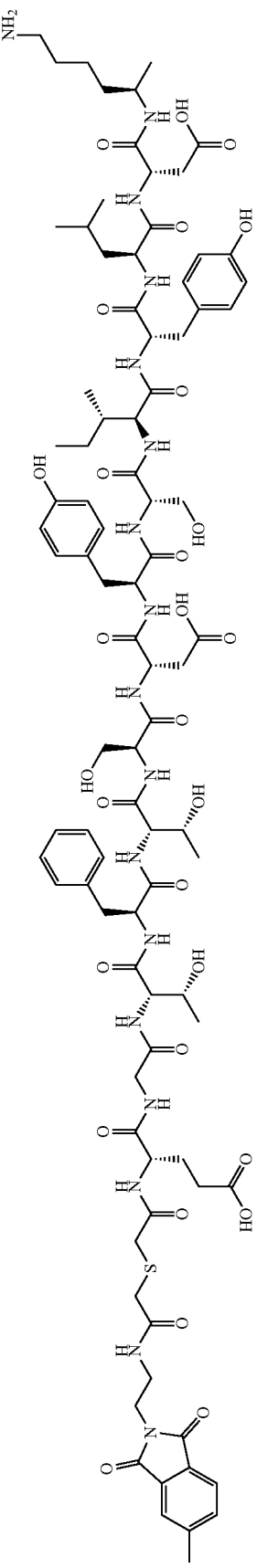
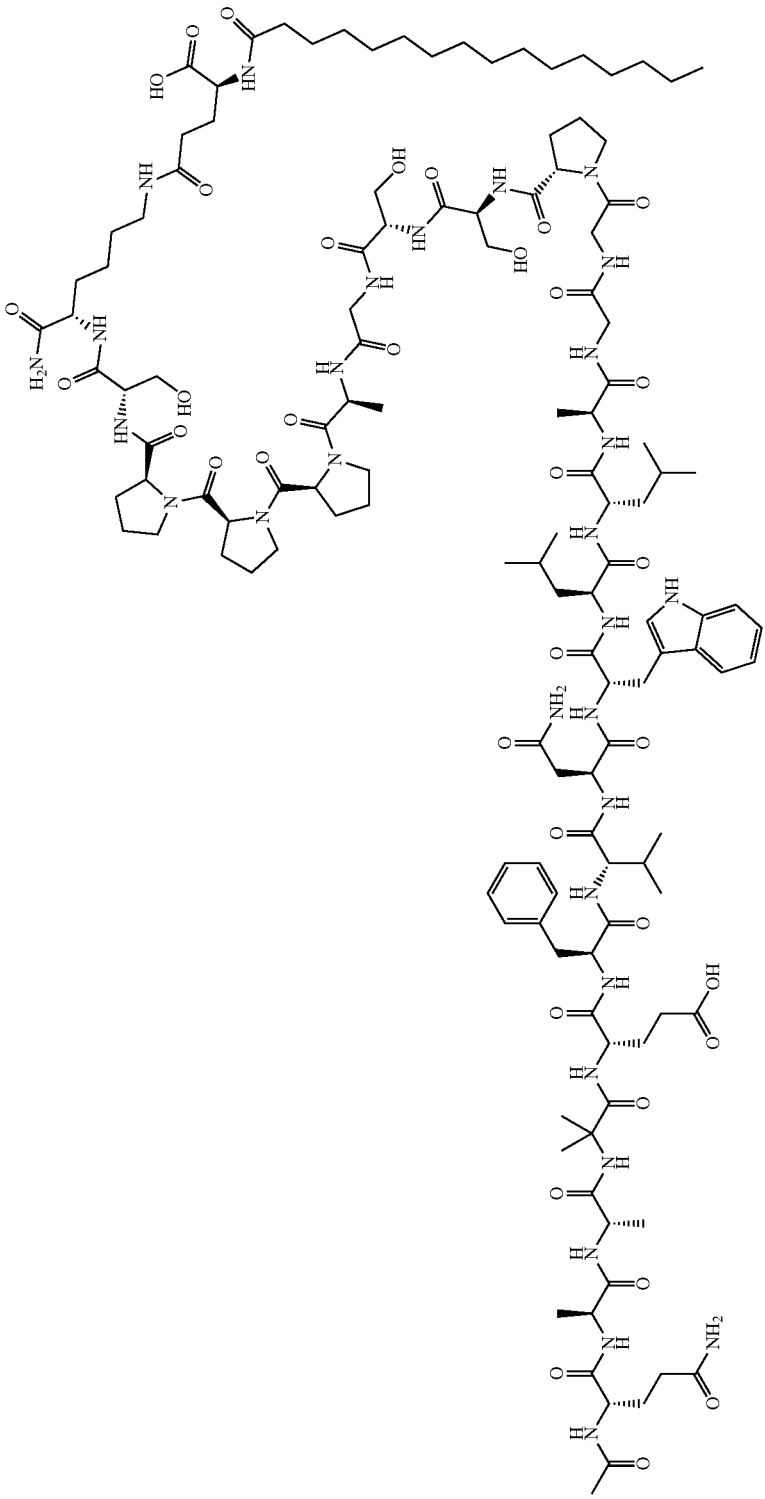

Compound 248
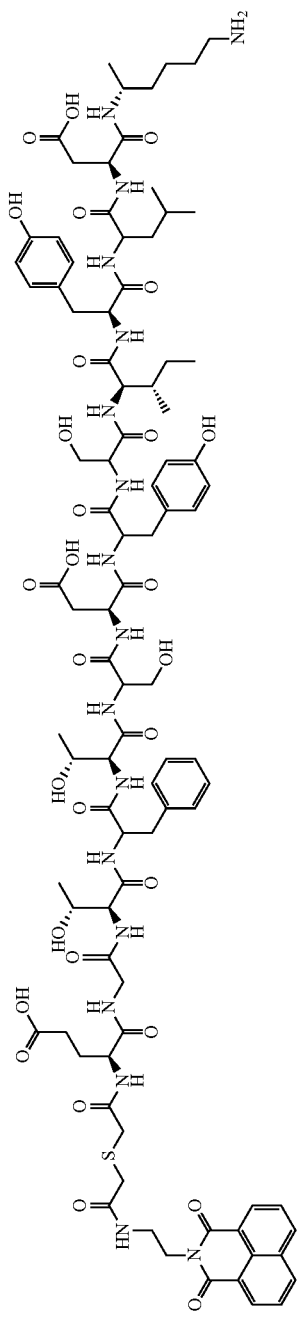

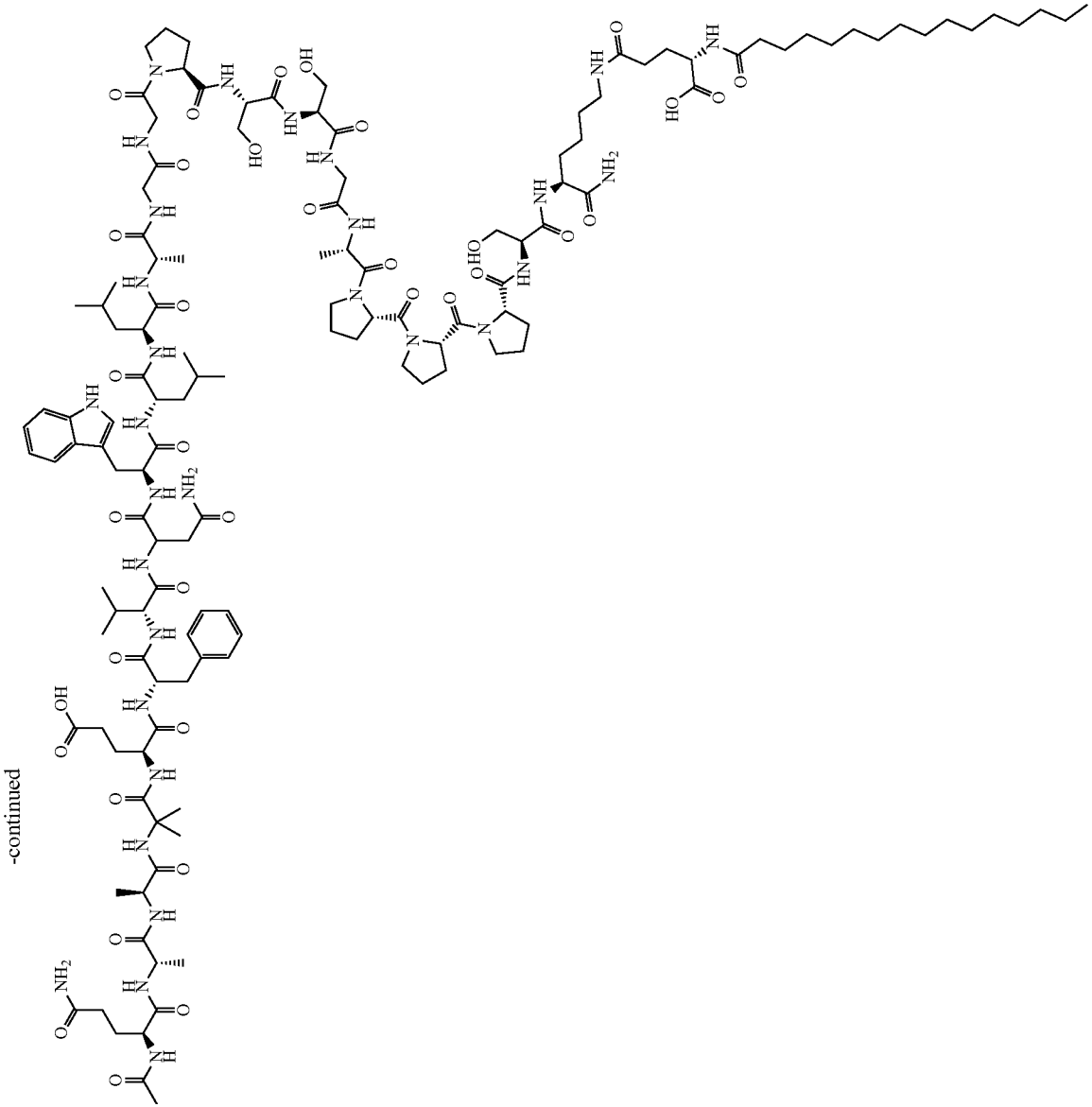

Compound 249
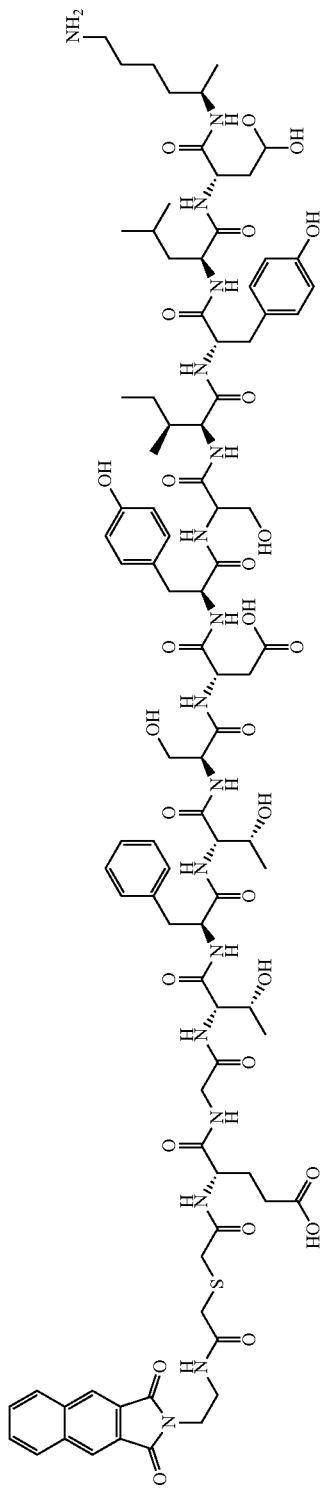
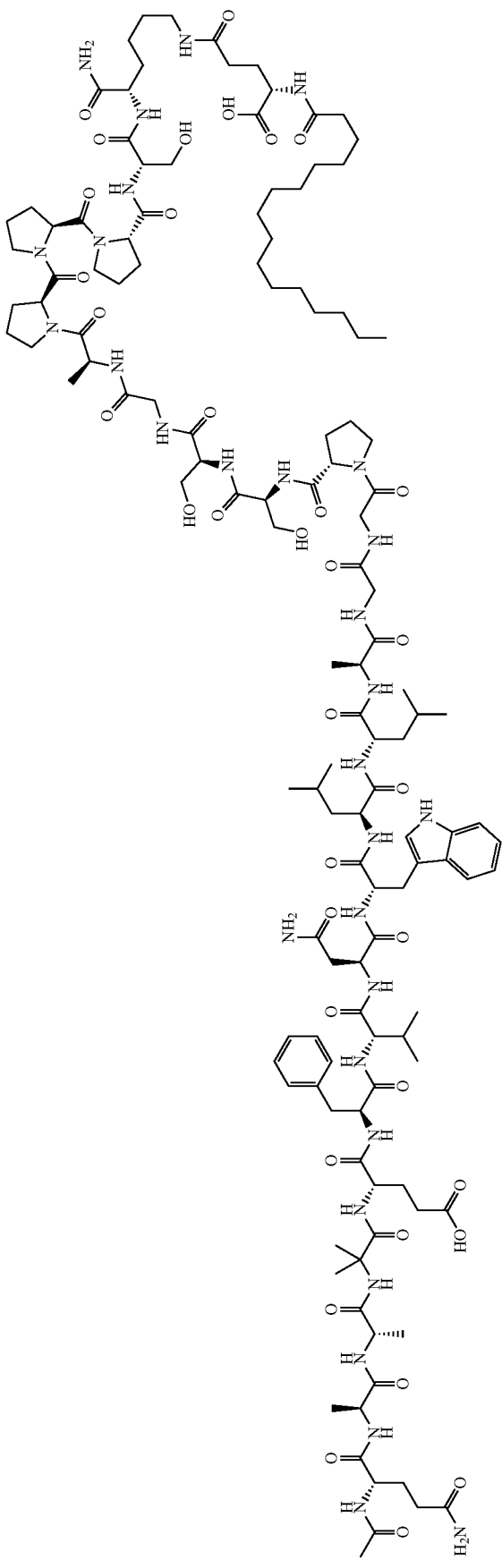

801
Compound 254
-continued
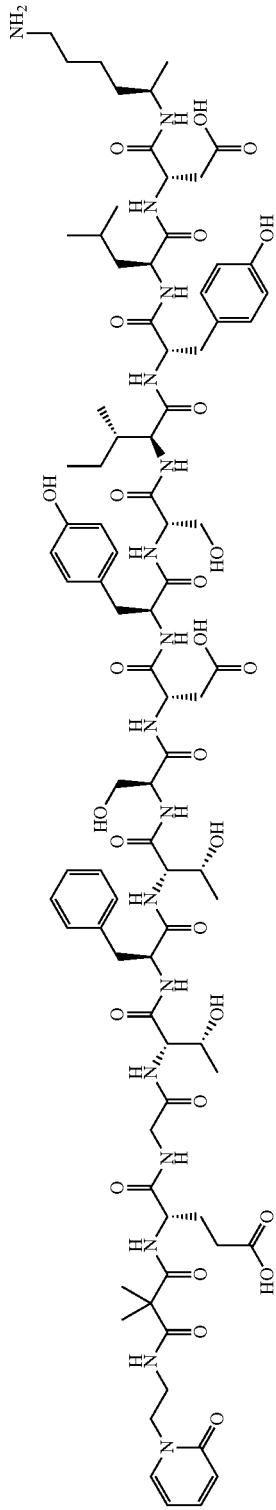
802
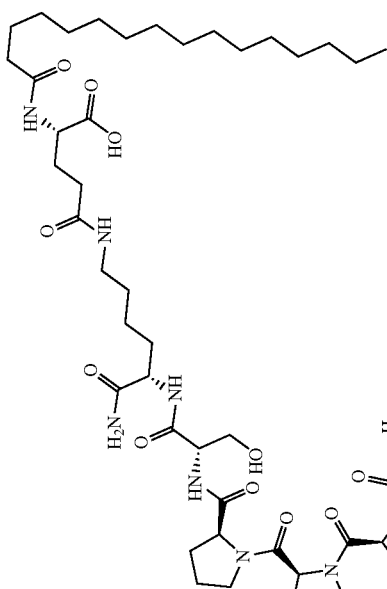
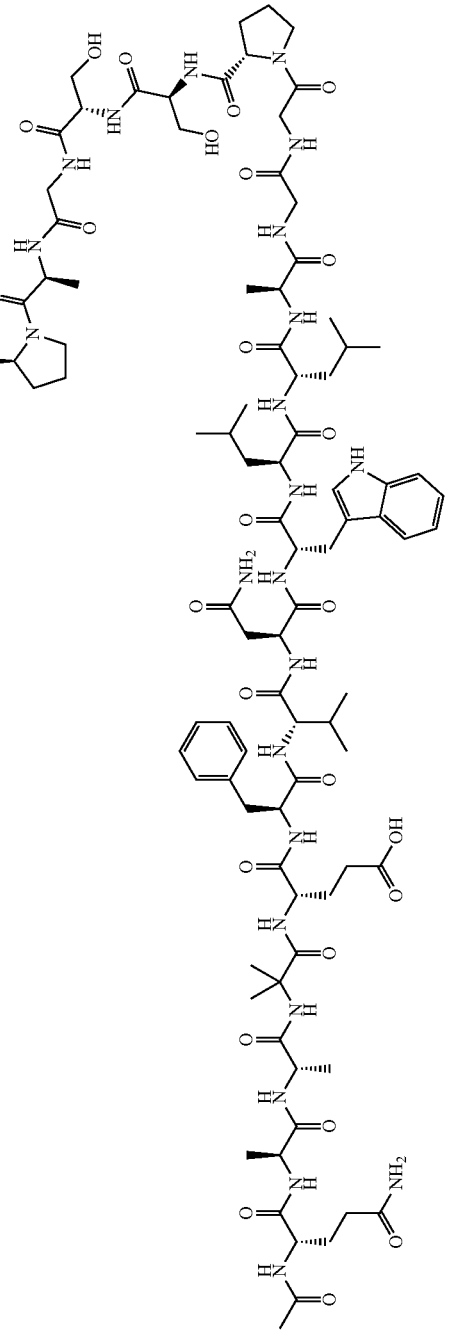

803 804
Compound 257
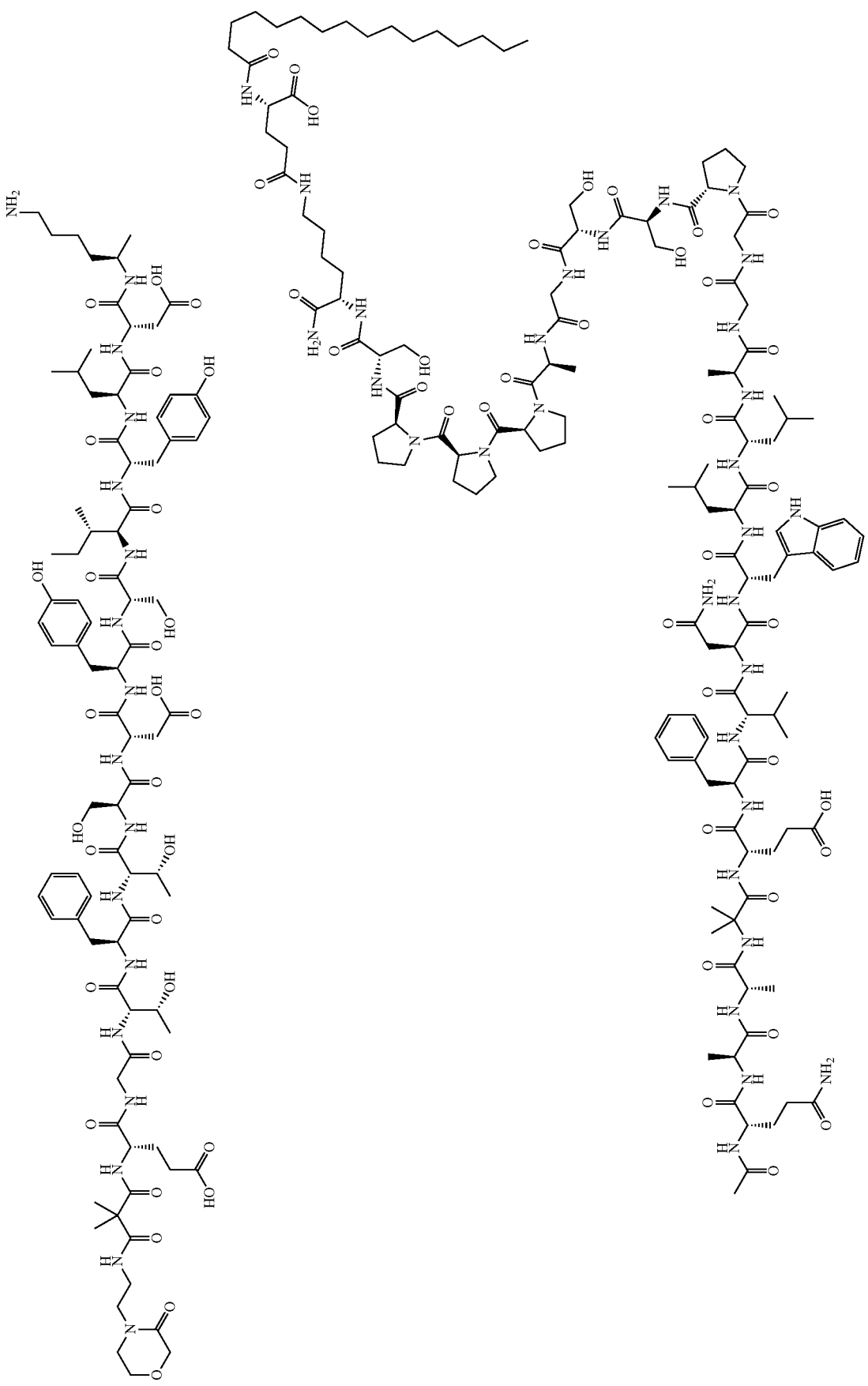

-continued
Compound 260
805
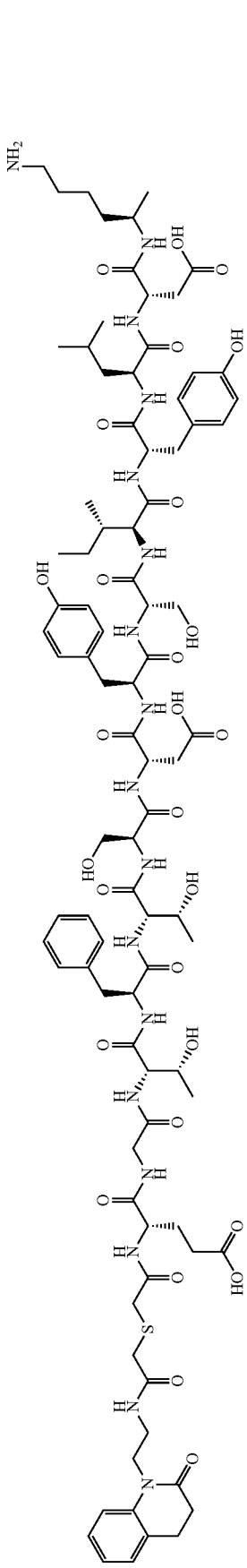
806
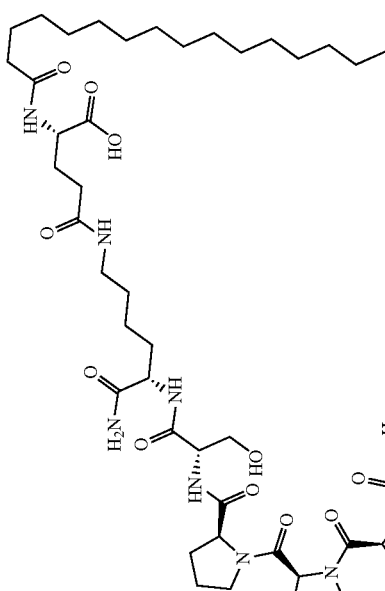
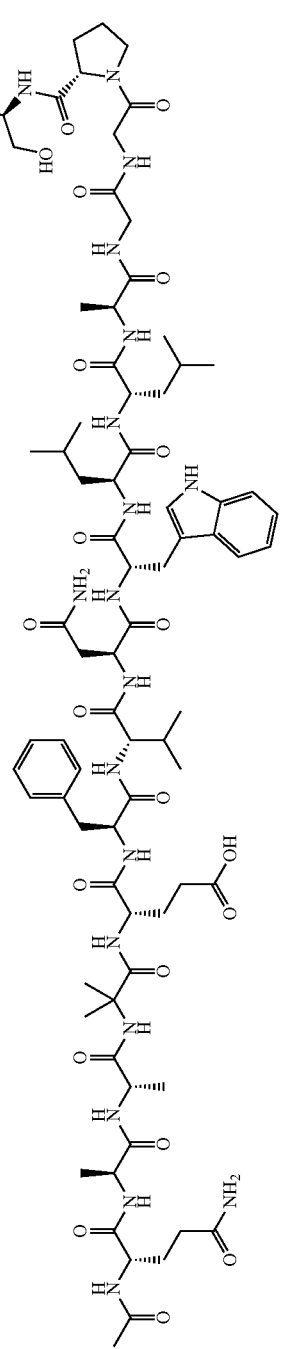

Compound 264
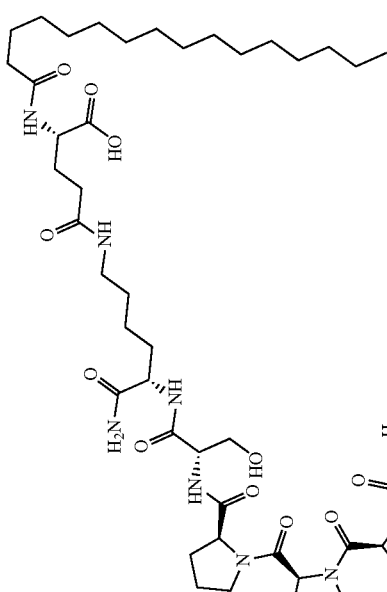
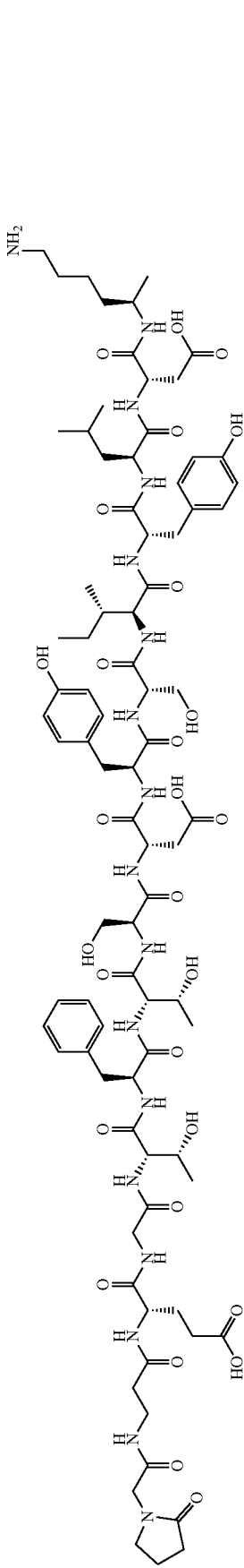
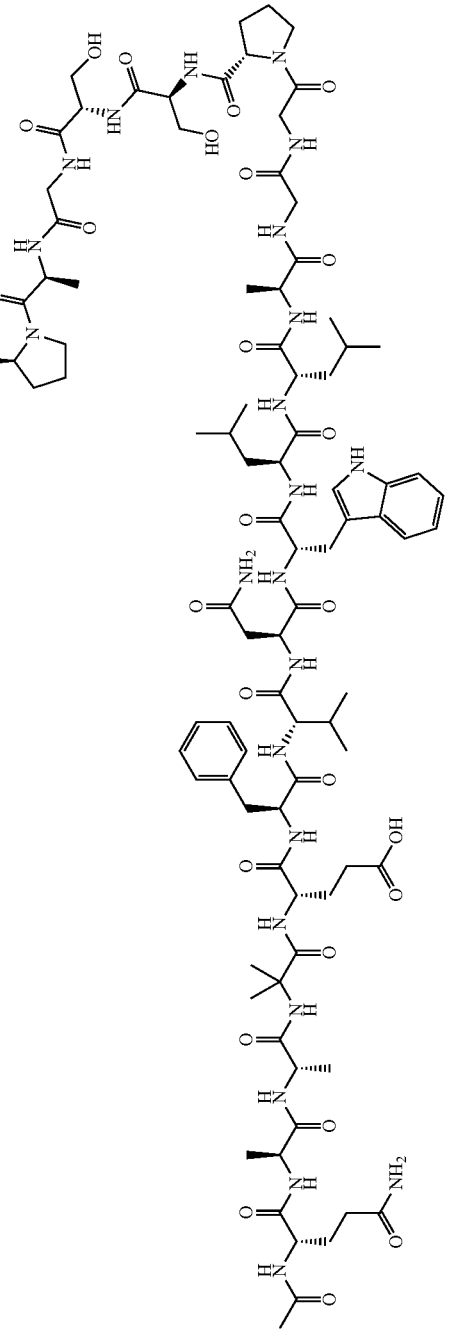
807 808

Compound 265
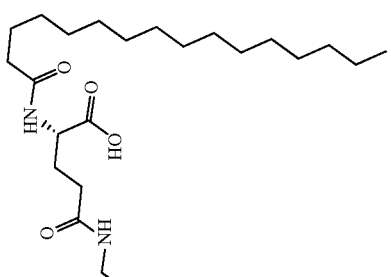
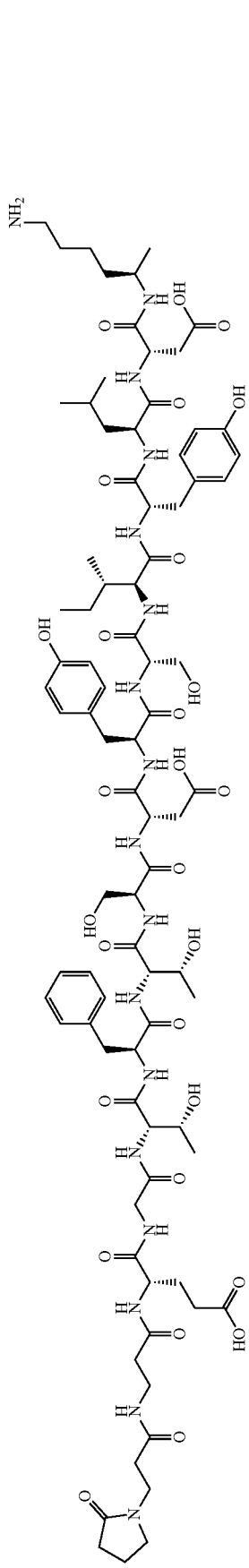
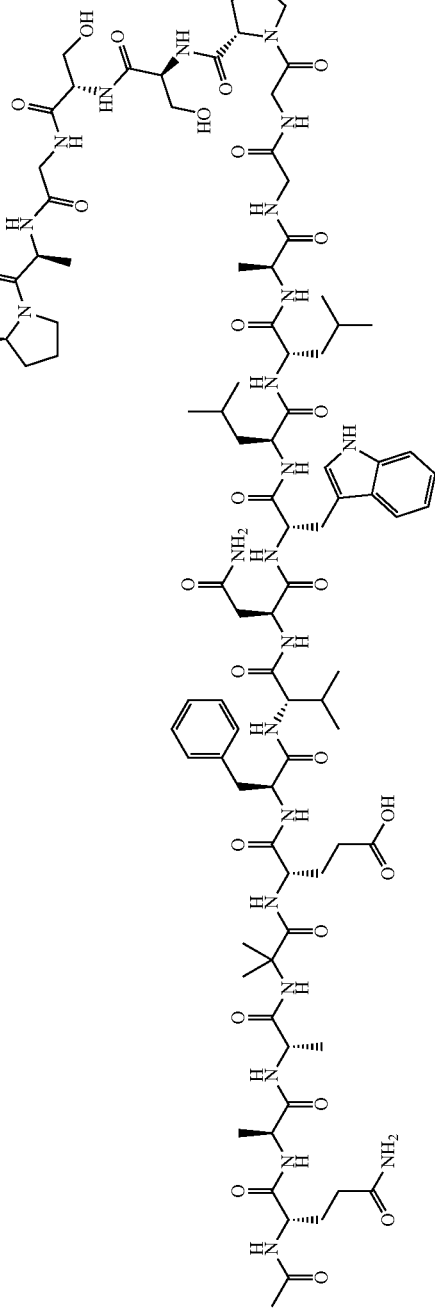

Compound 266
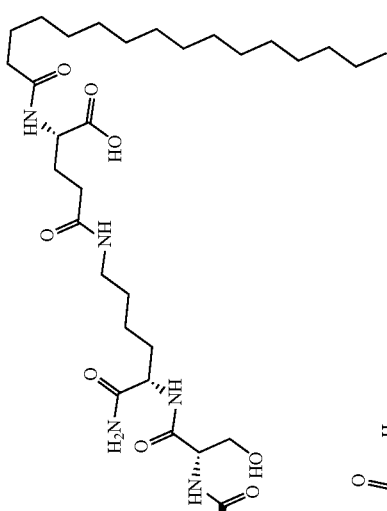
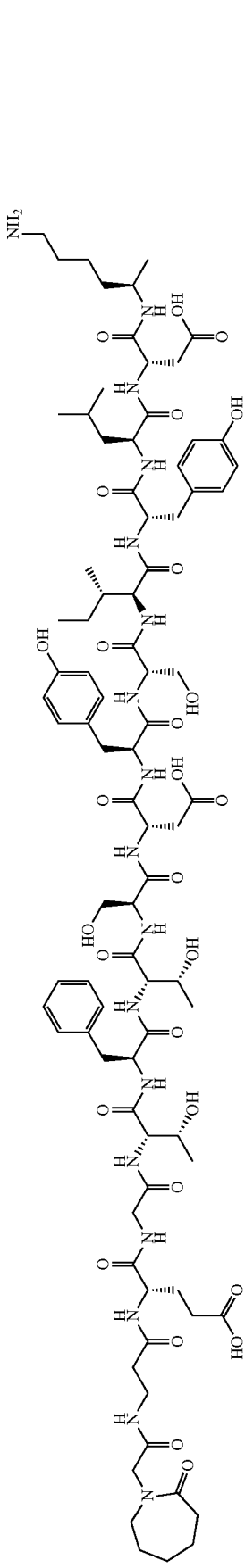
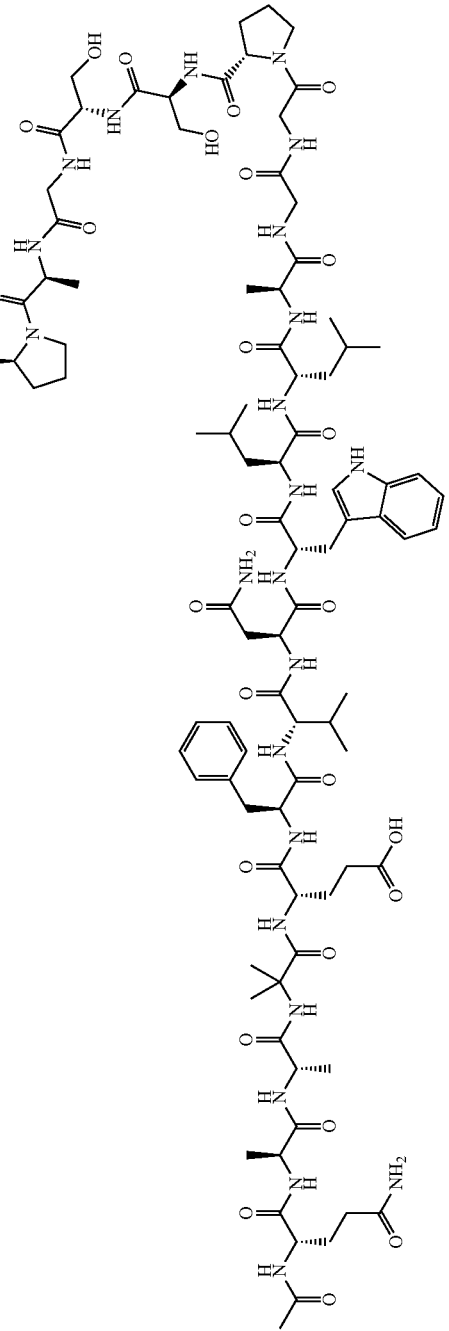

813 814
Compound 267
-continued
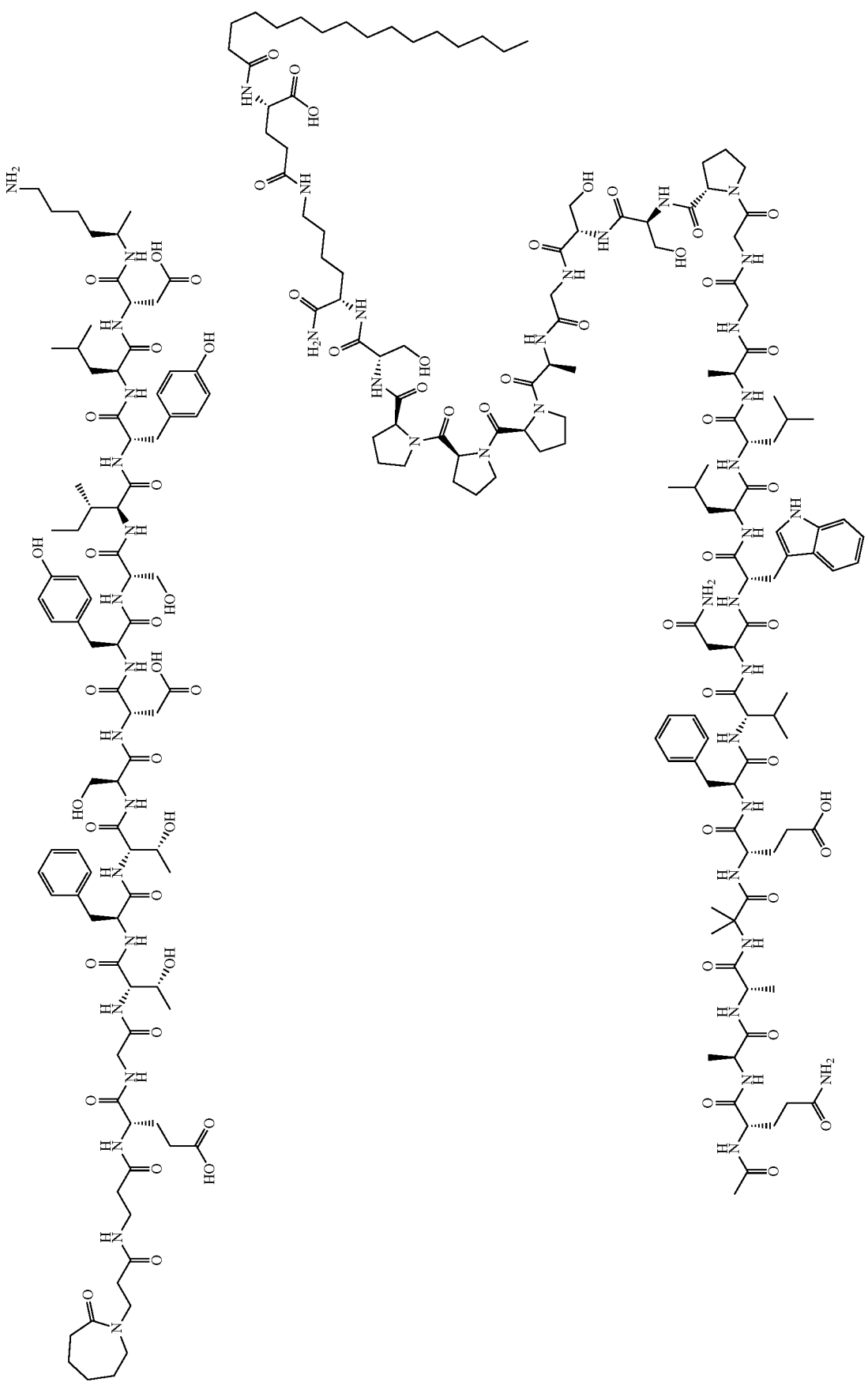

815
Compound 270
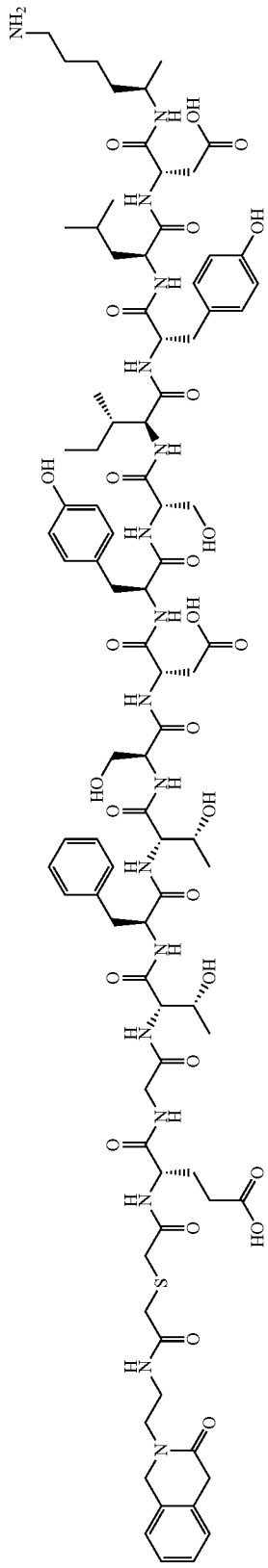
816
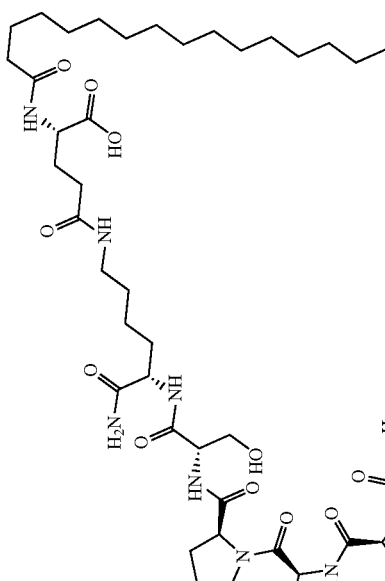
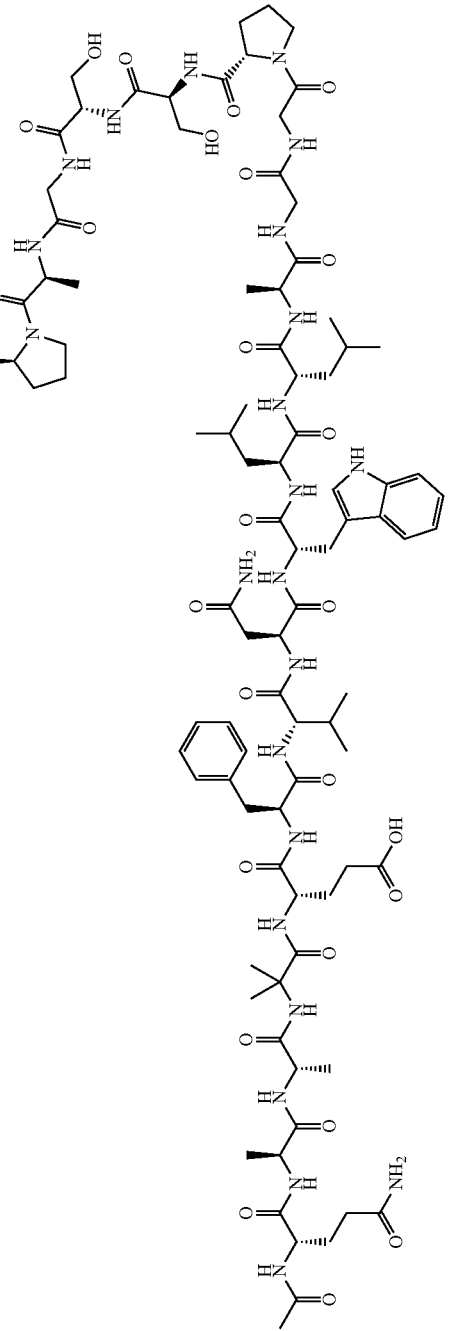

-continued
Compound 285
817
818
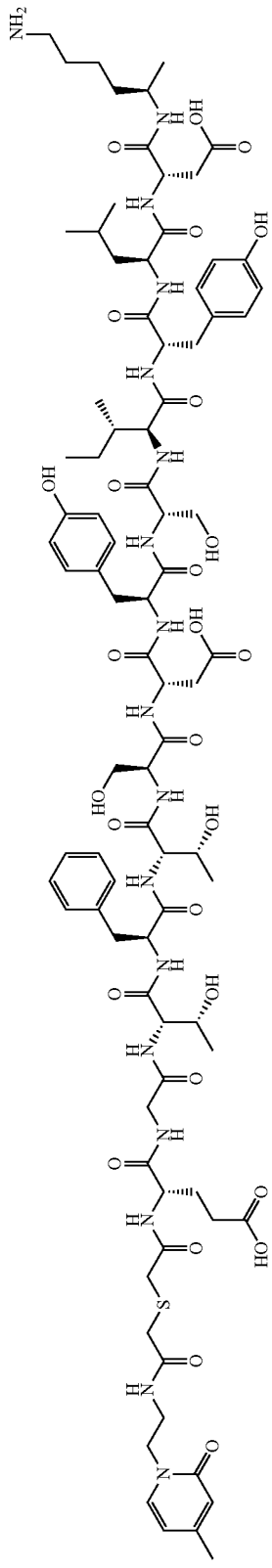
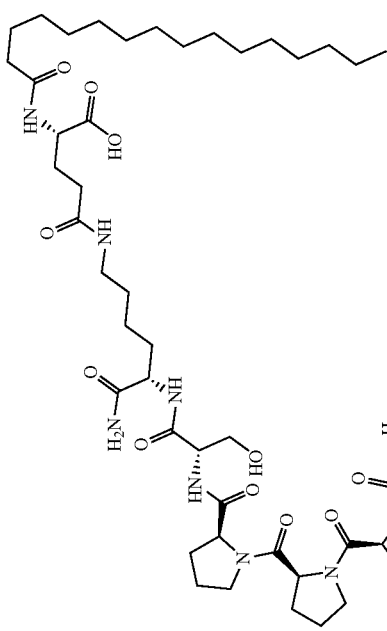
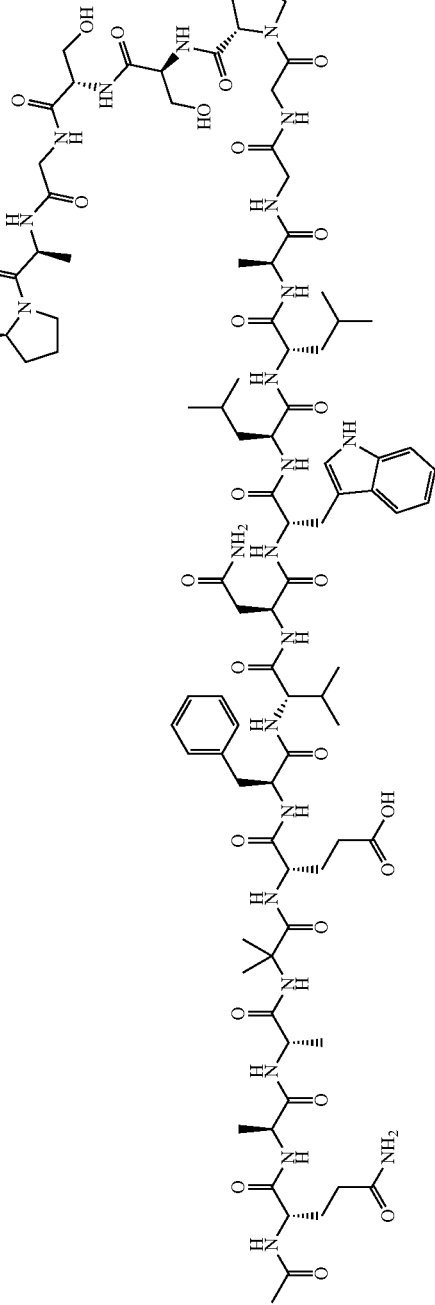

Compound 289
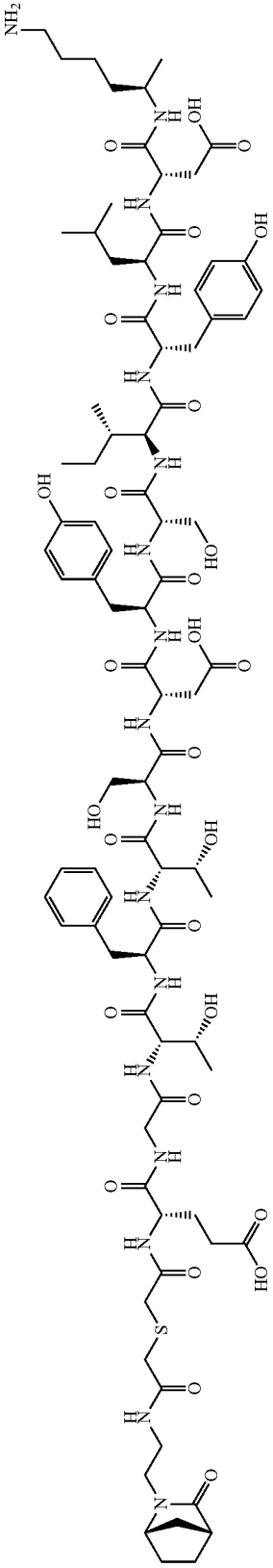
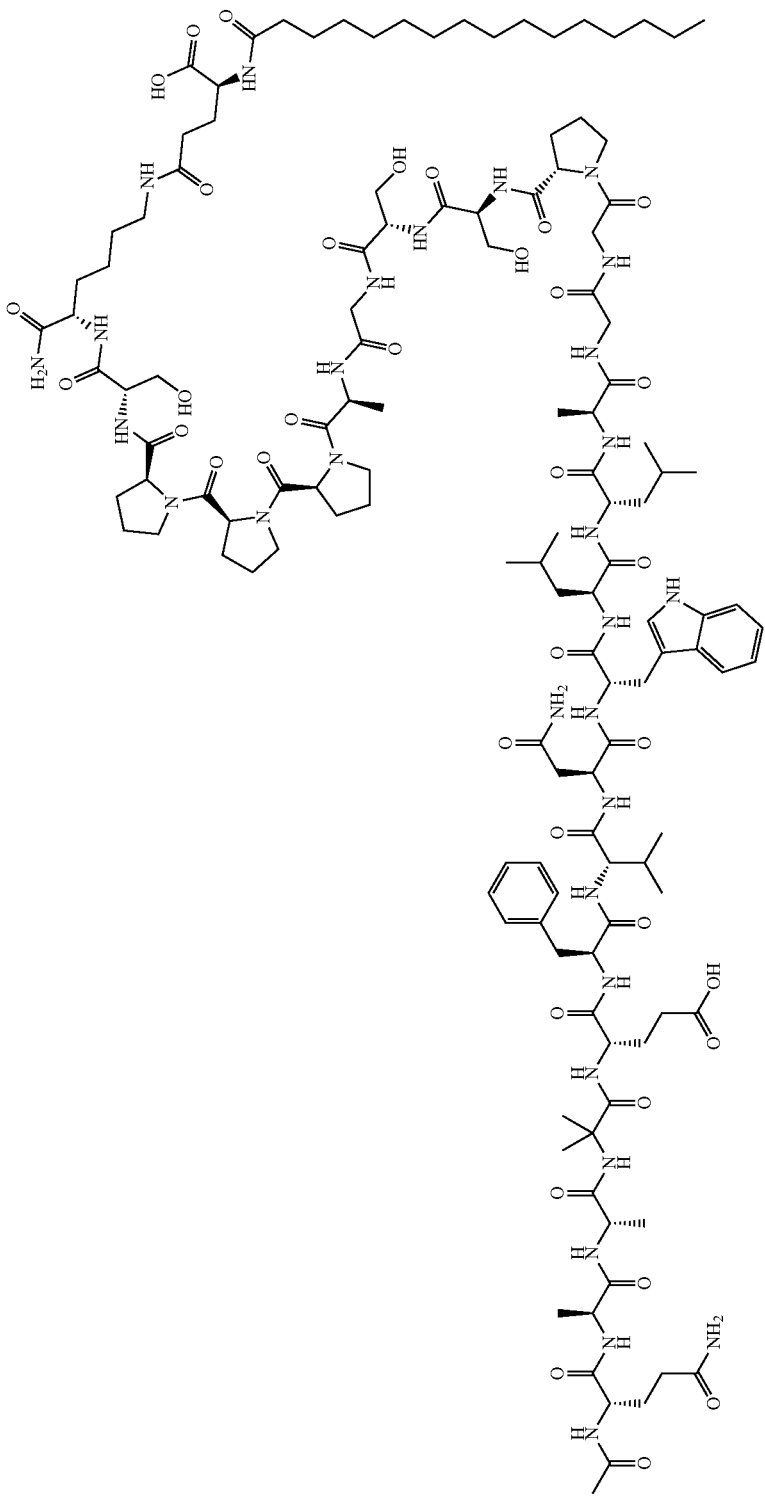

821    822
Compound 290
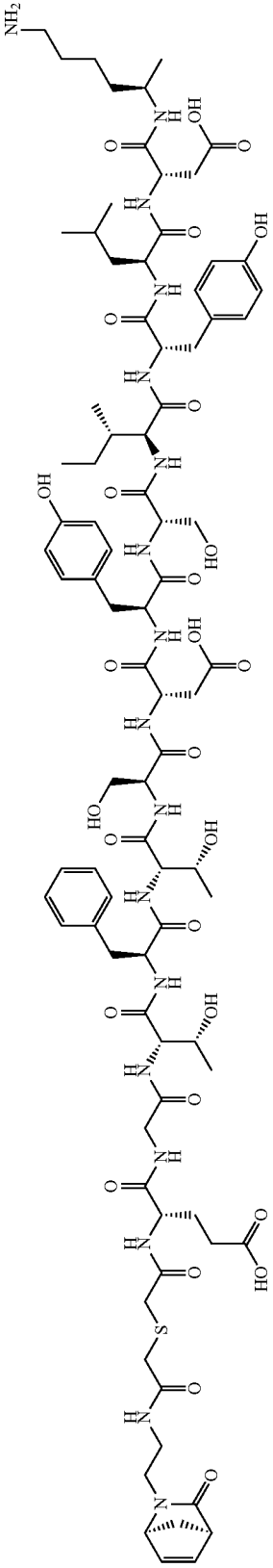
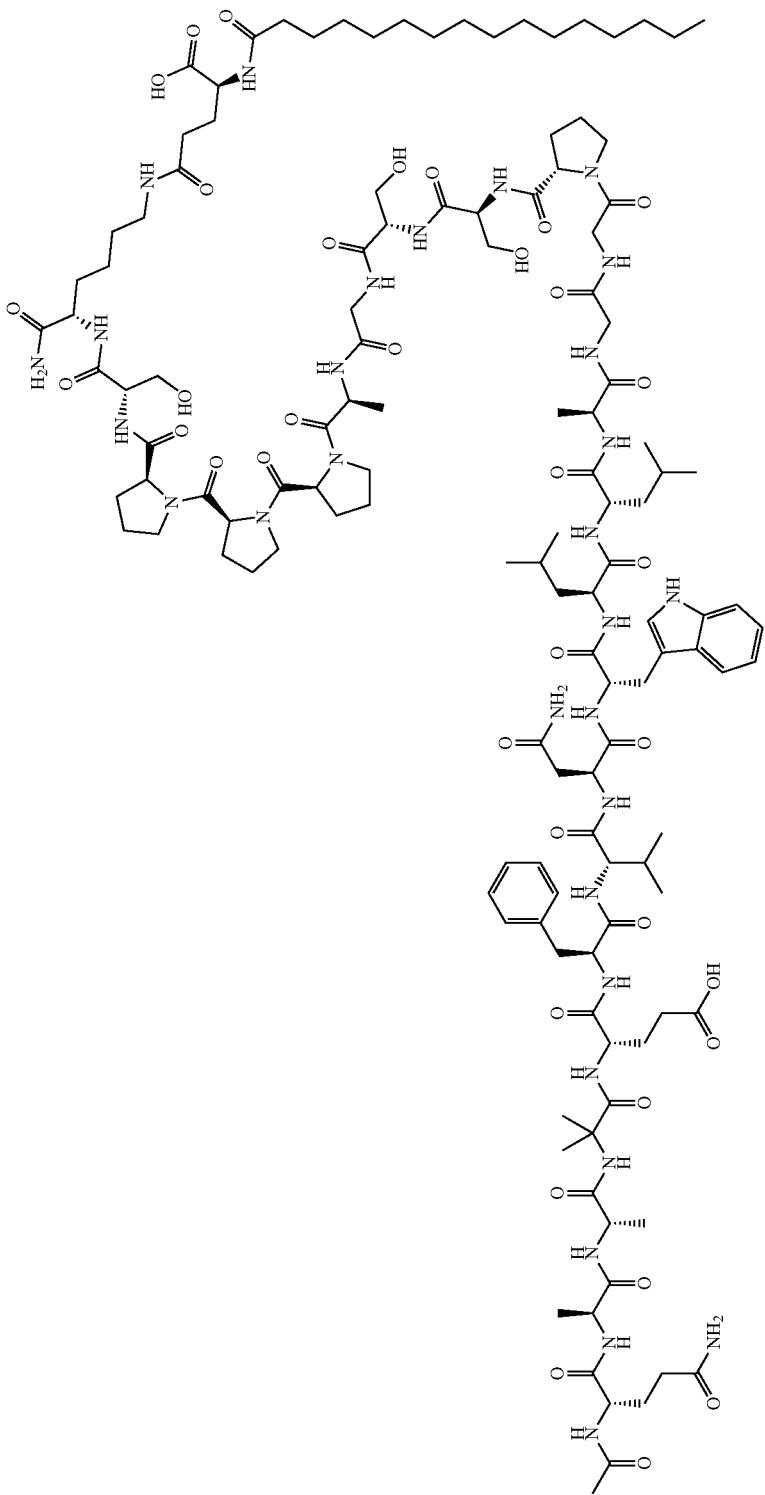
-continued

823
Compound 291
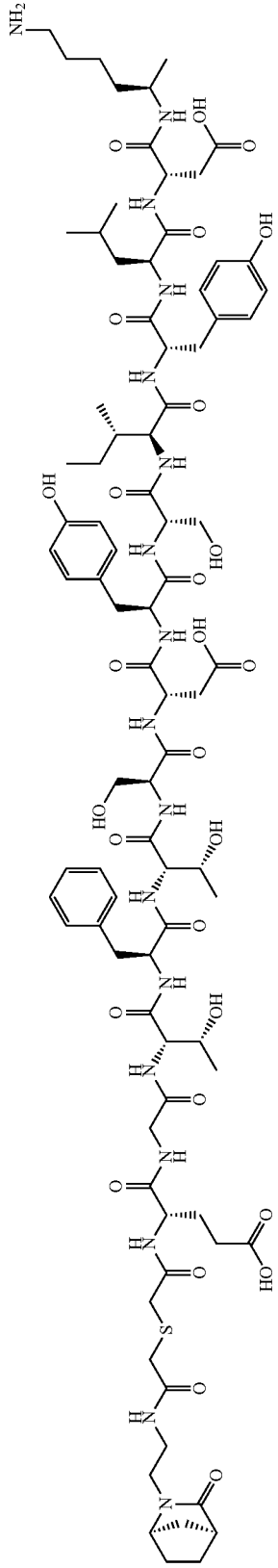
824
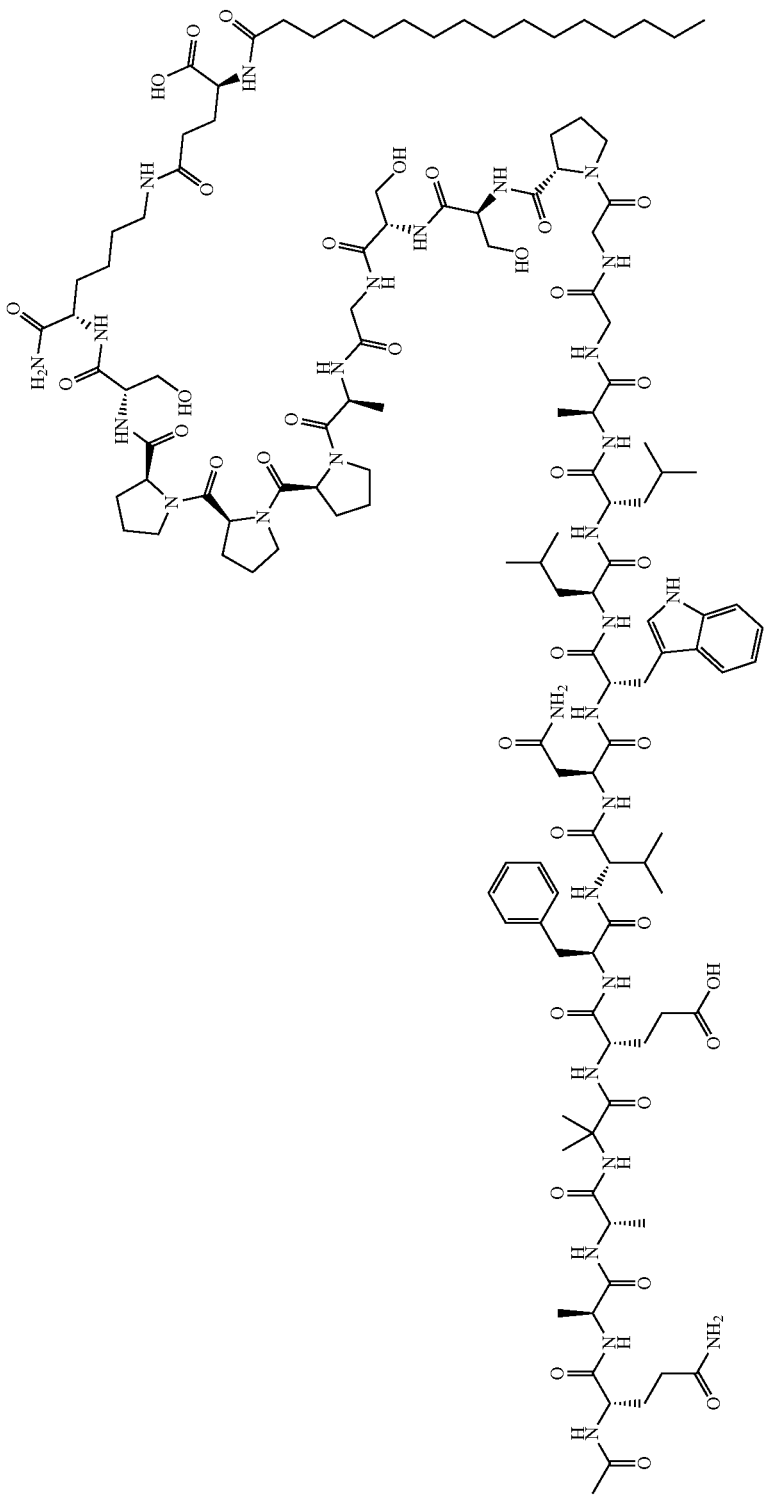

Compound 148
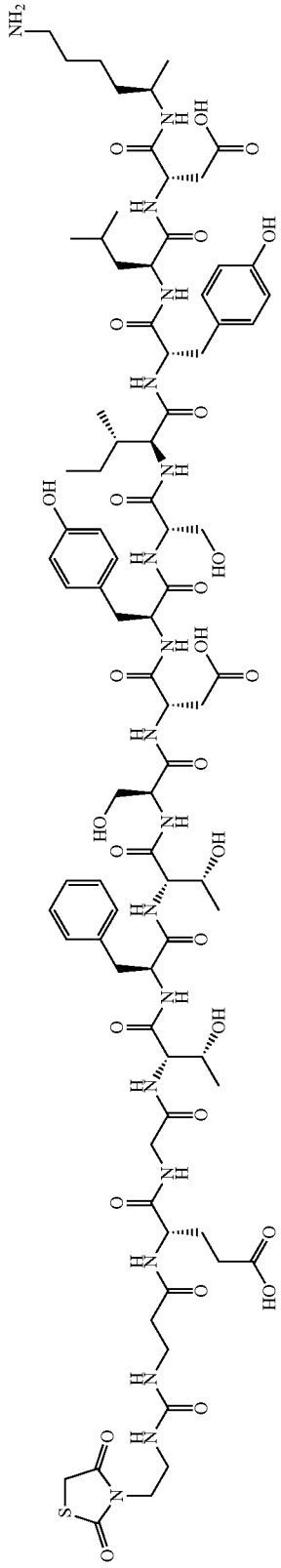
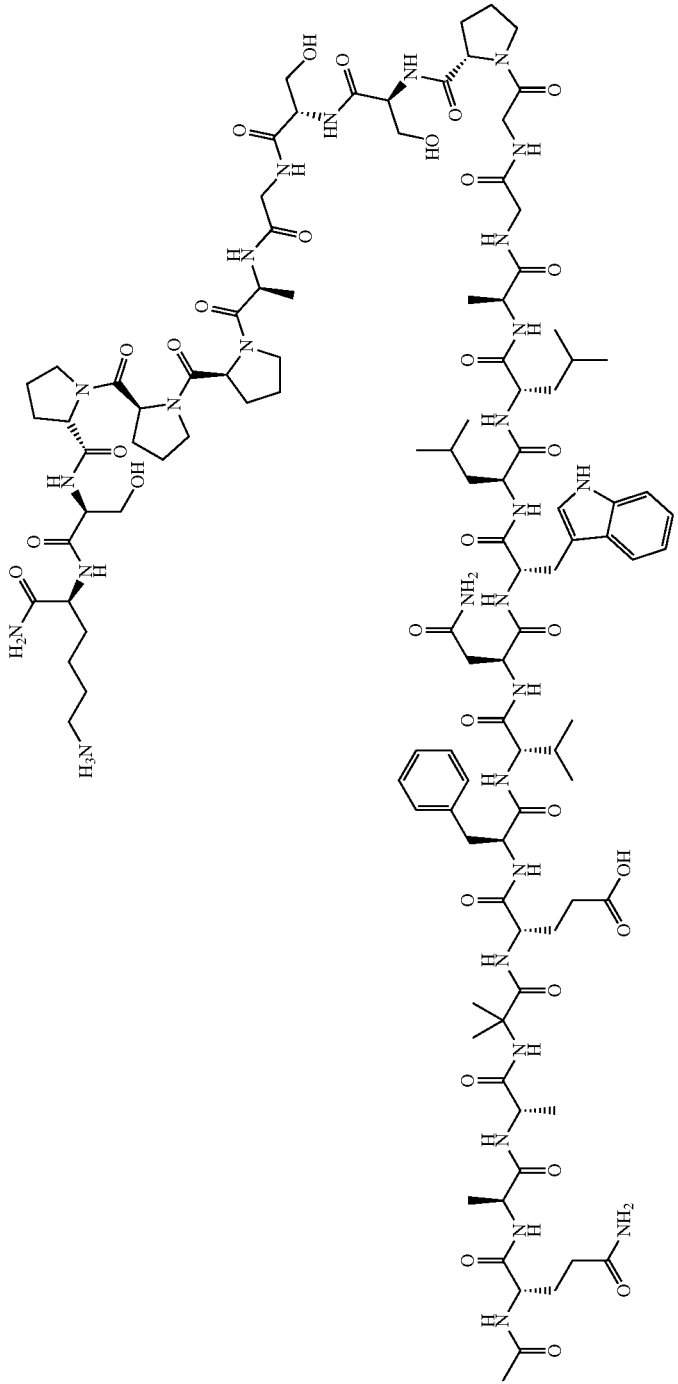

Compound 149
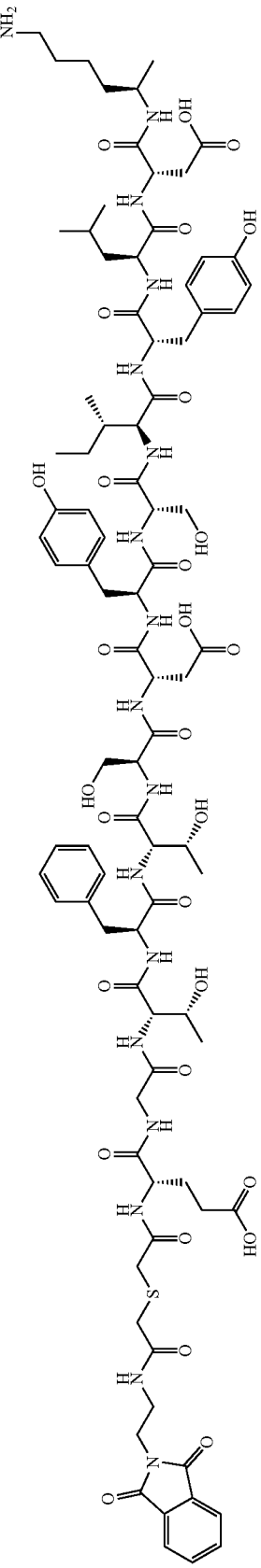
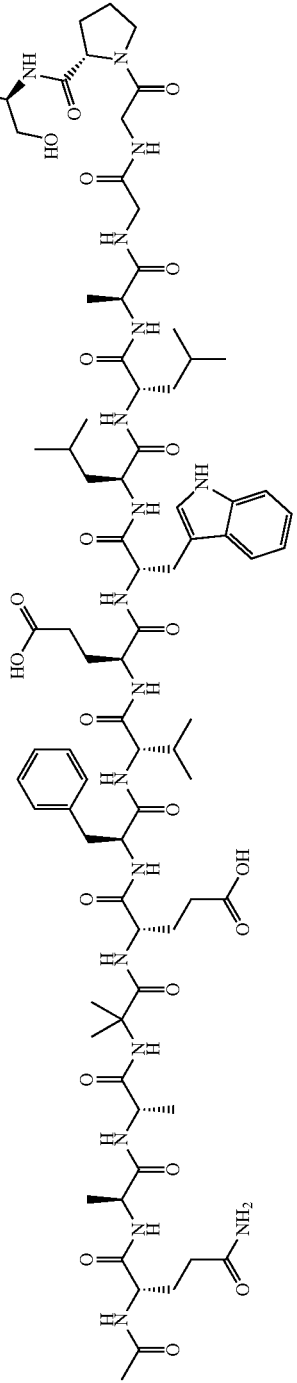

829 830
Compound 150
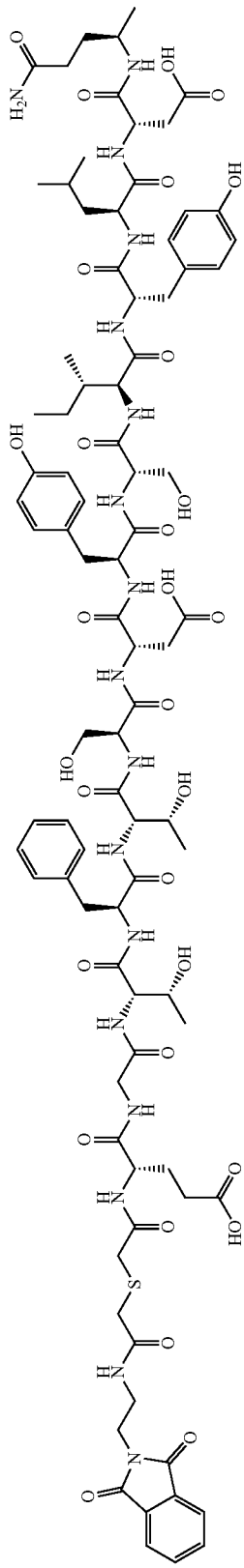
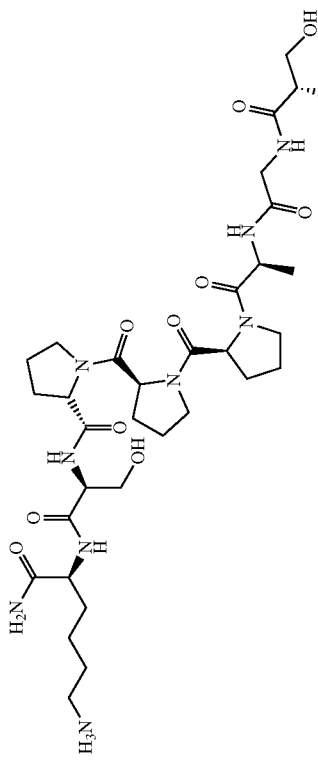
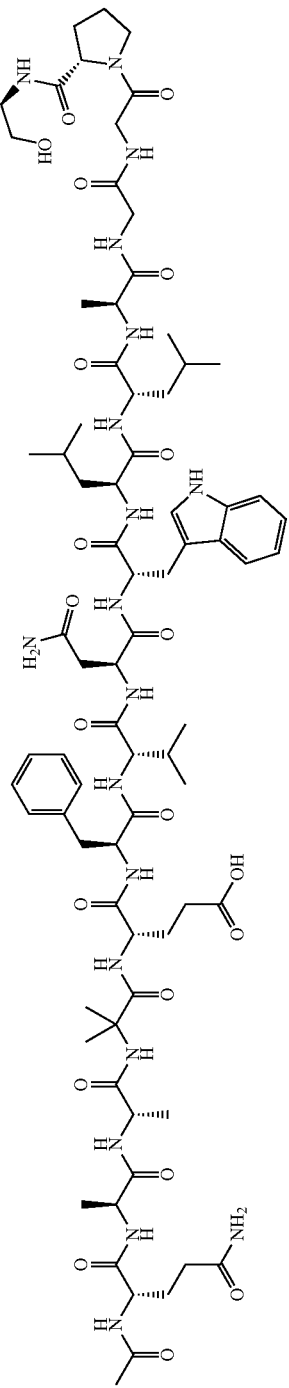

831 832
Compound 151
-continued
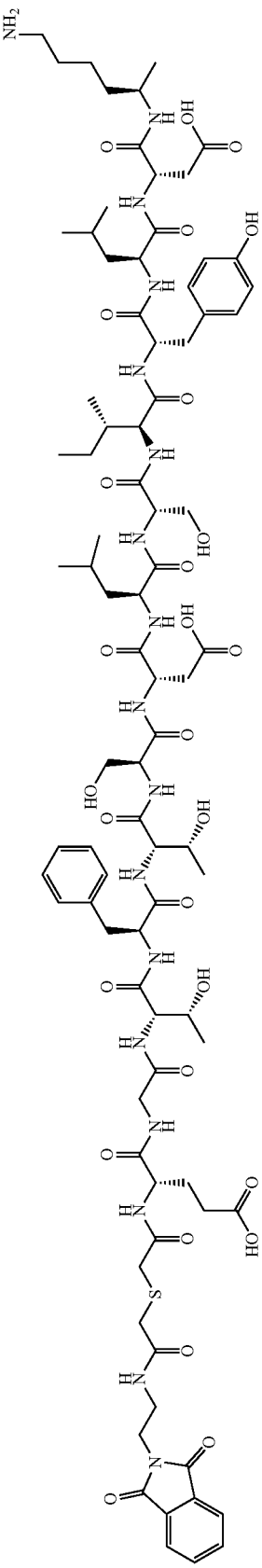
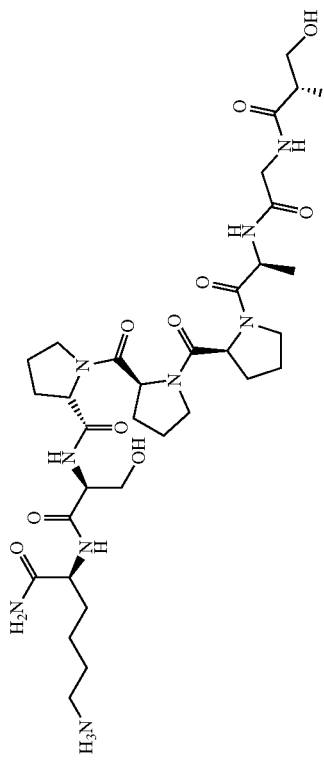
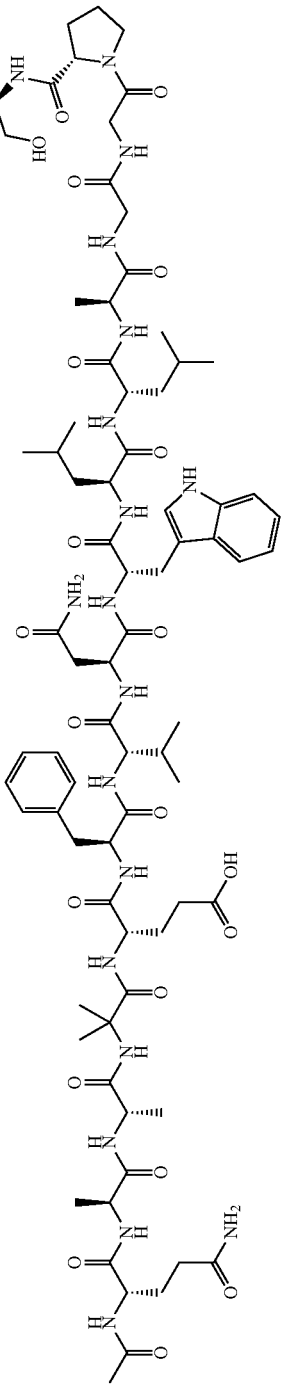

833 834
Compound 152
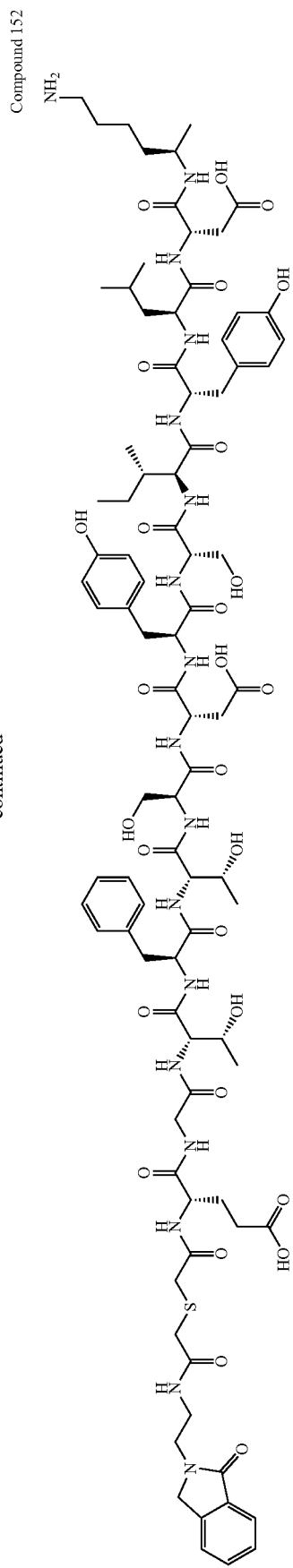
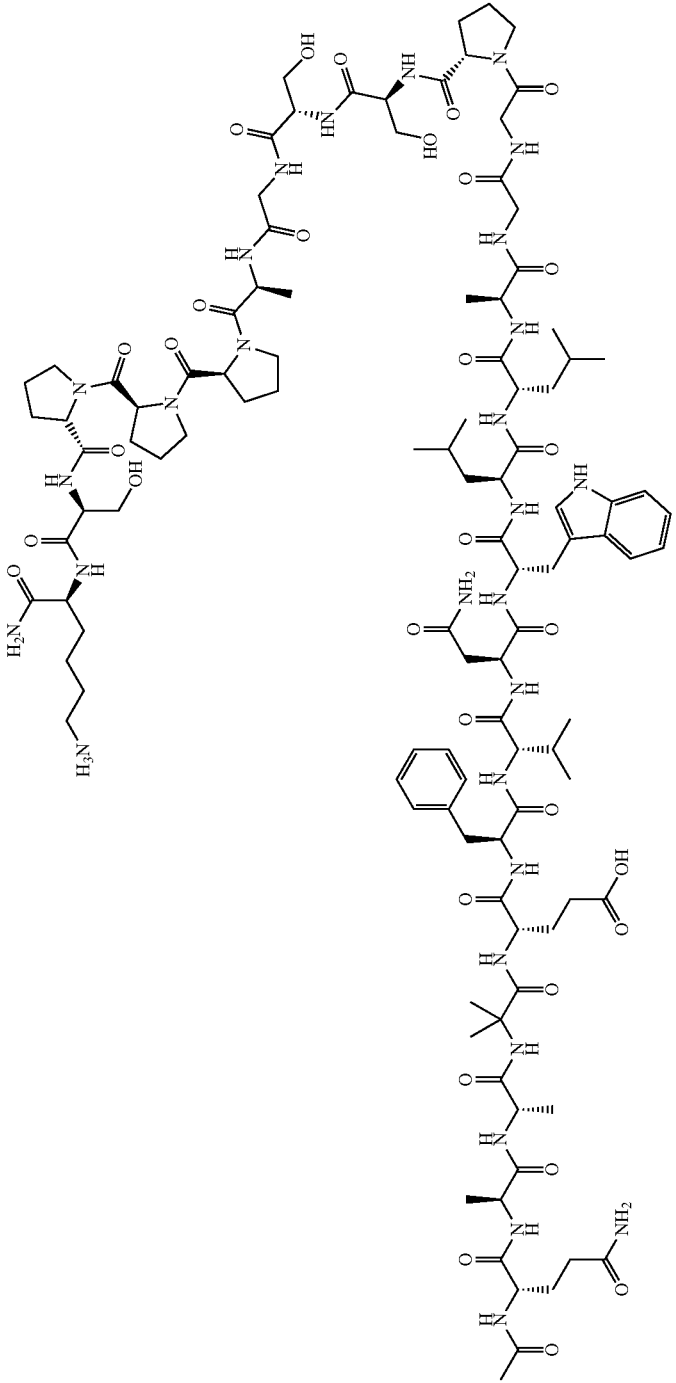

Compound 153
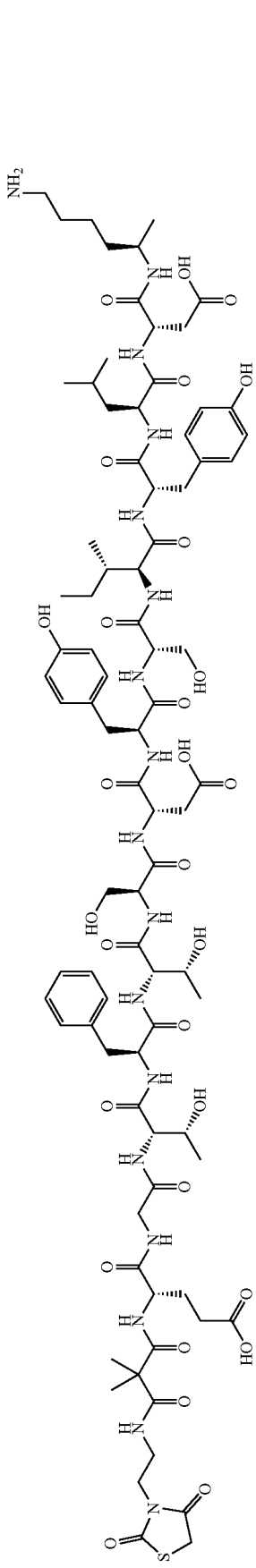
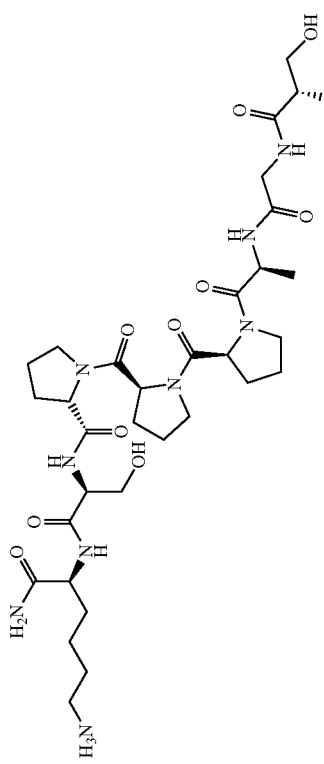
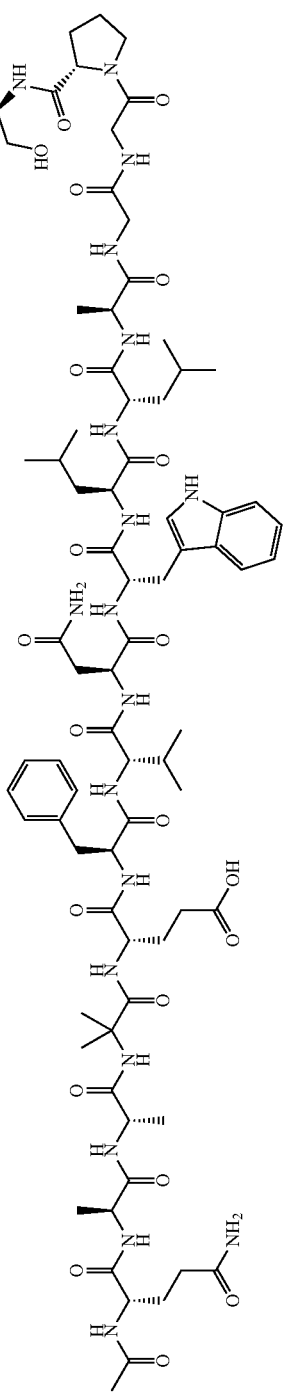

837 838
Compound 154
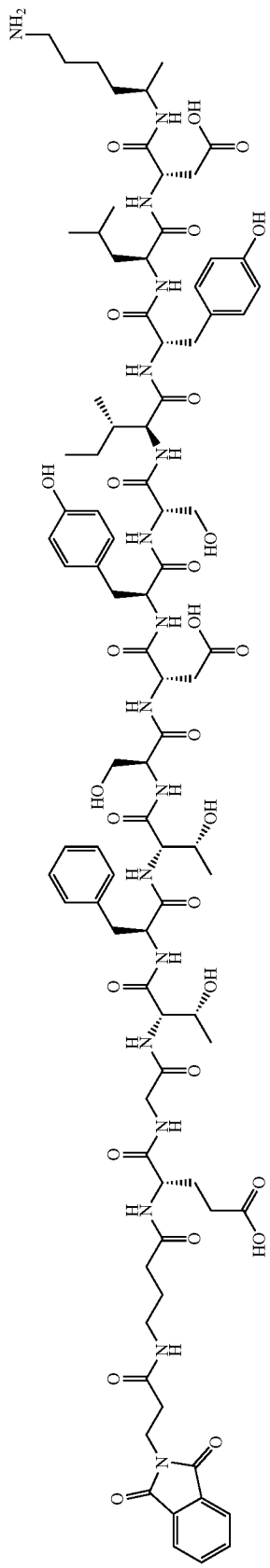
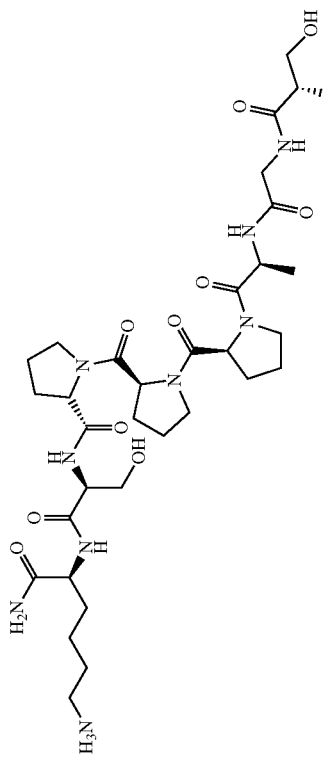
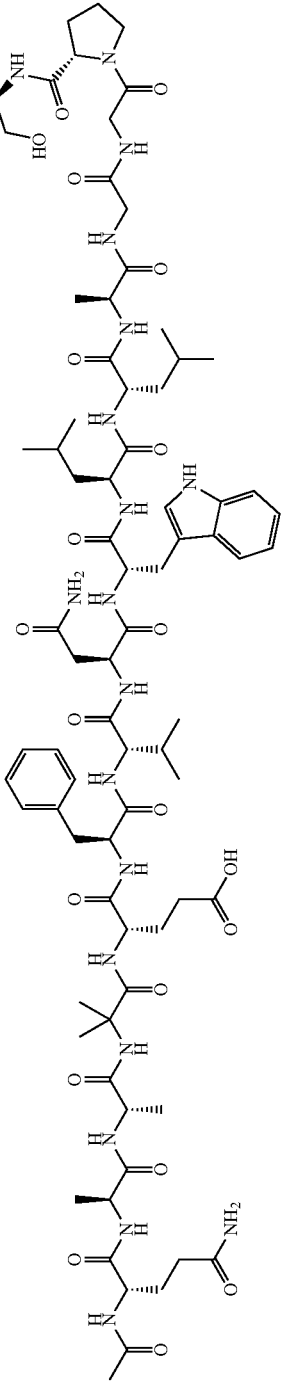

Compound 155
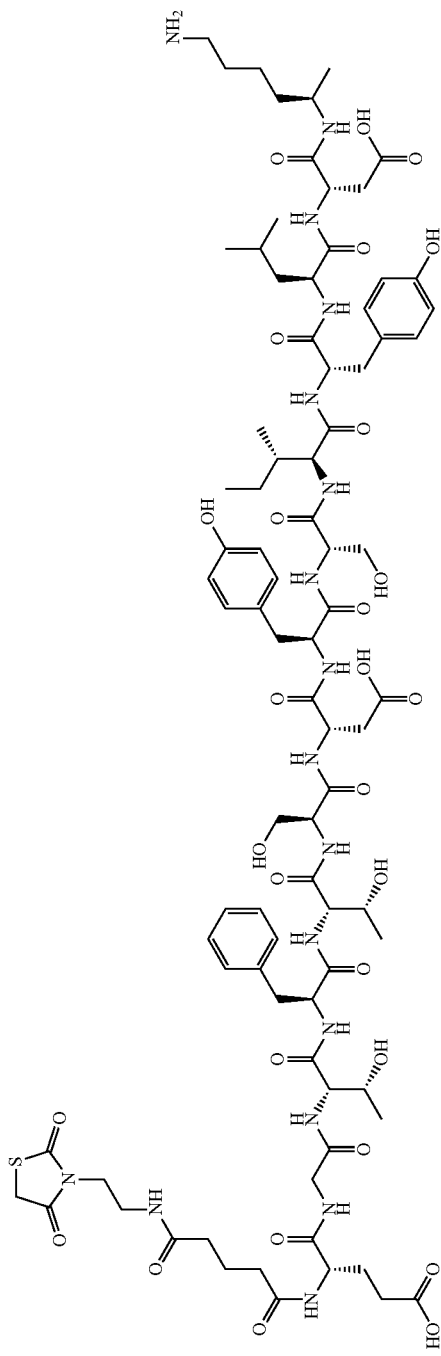

841 842
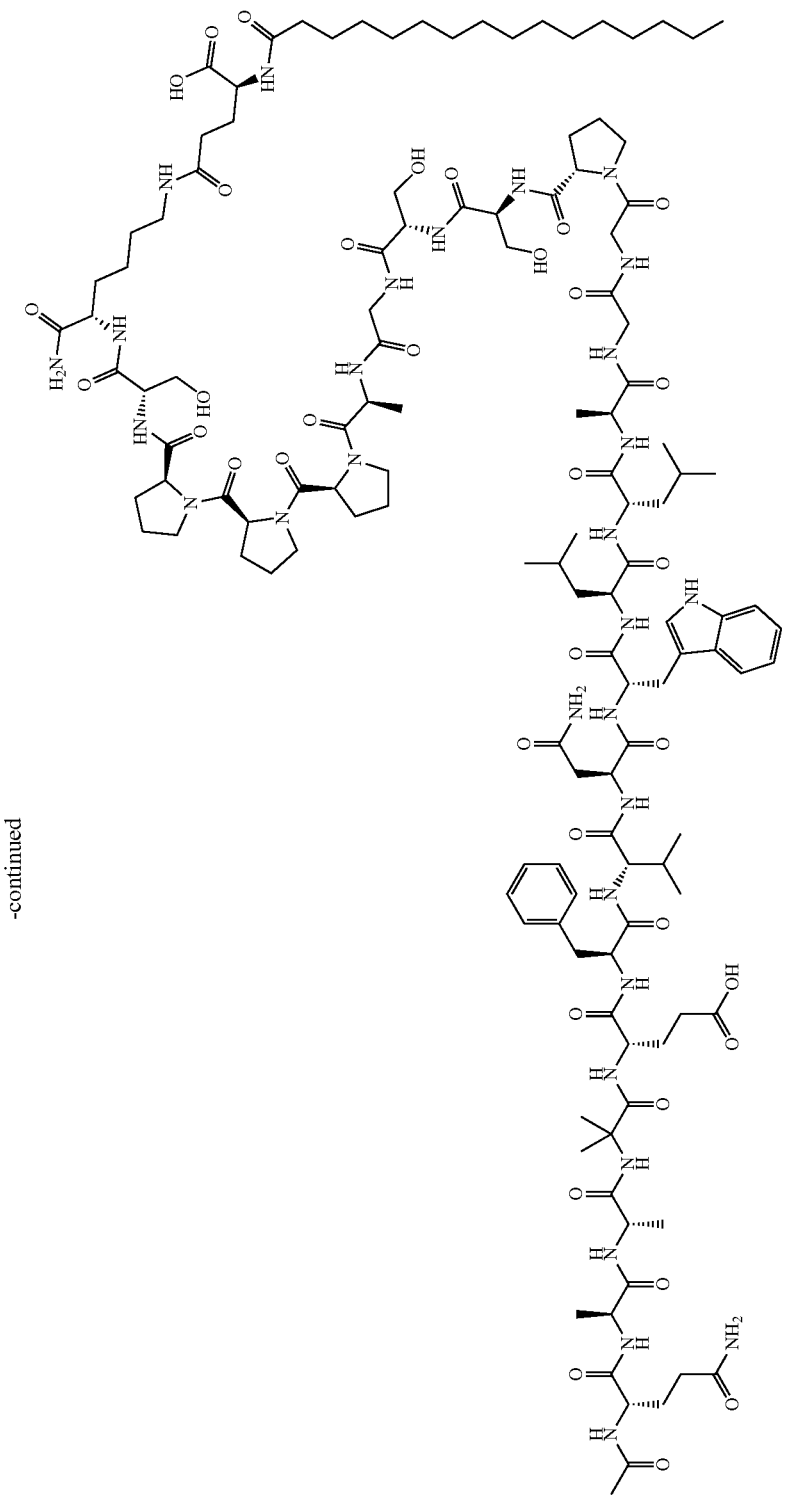
-continued

Compound 156
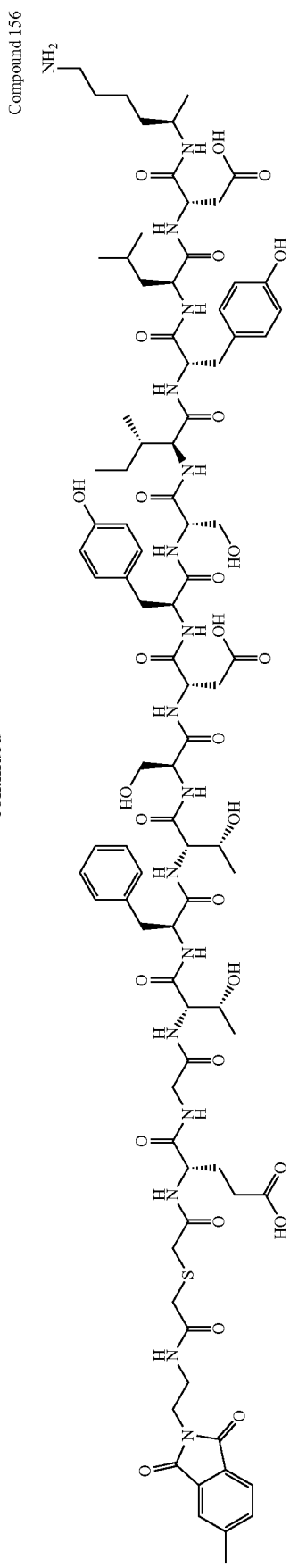
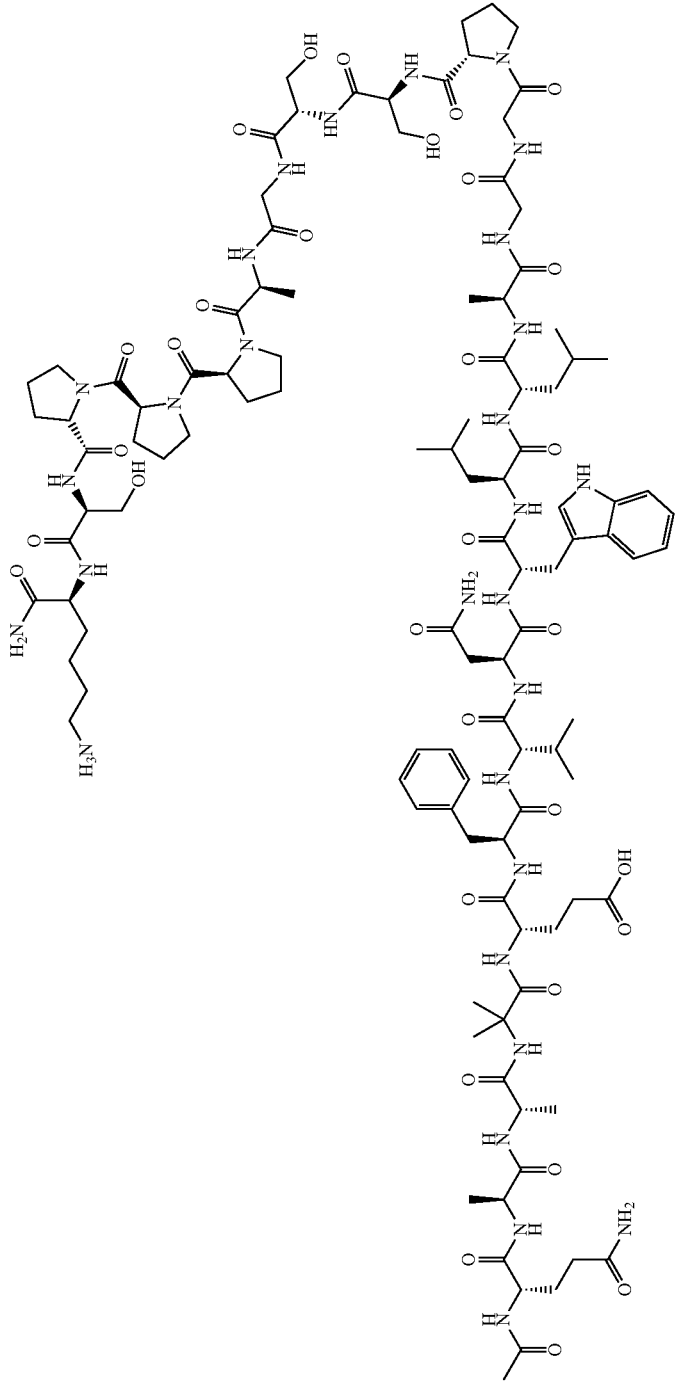

845
846
Compound 157
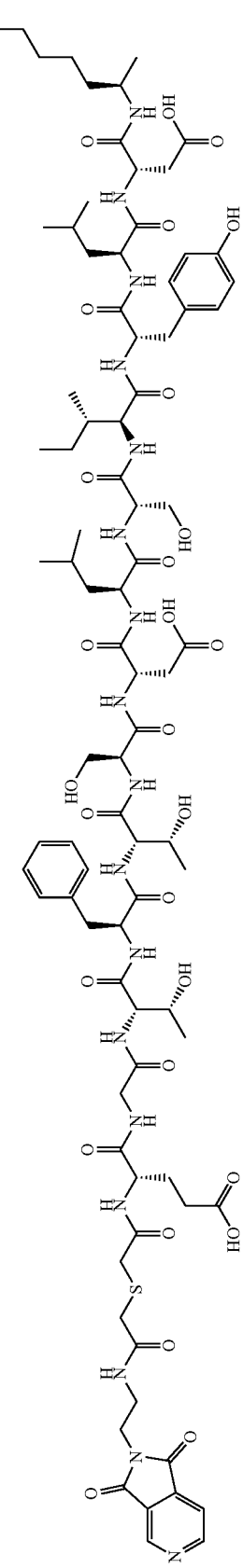
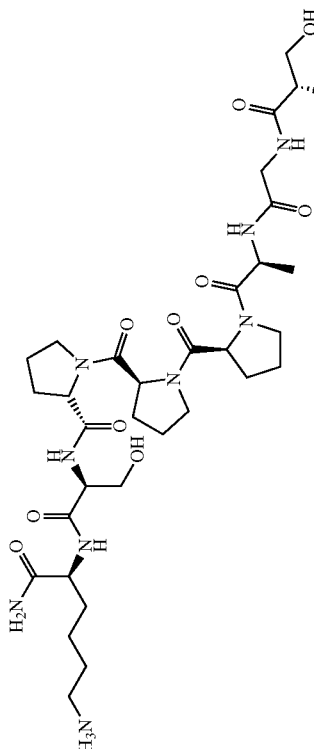
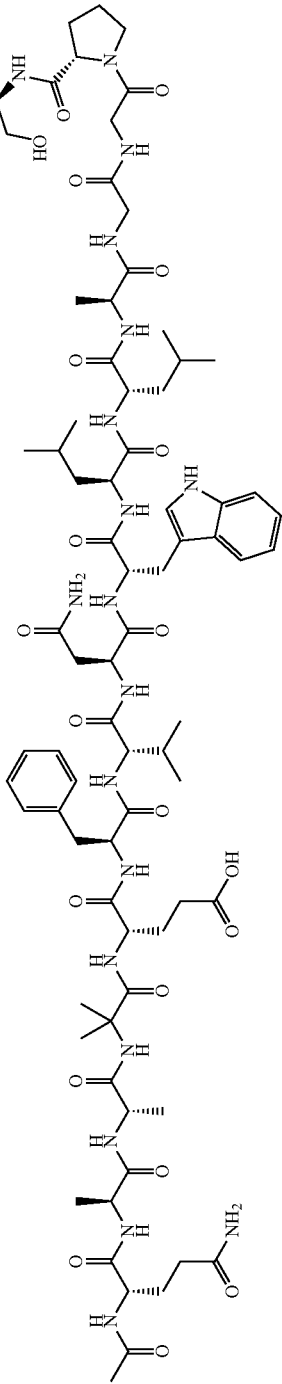

847 848
Compound 158
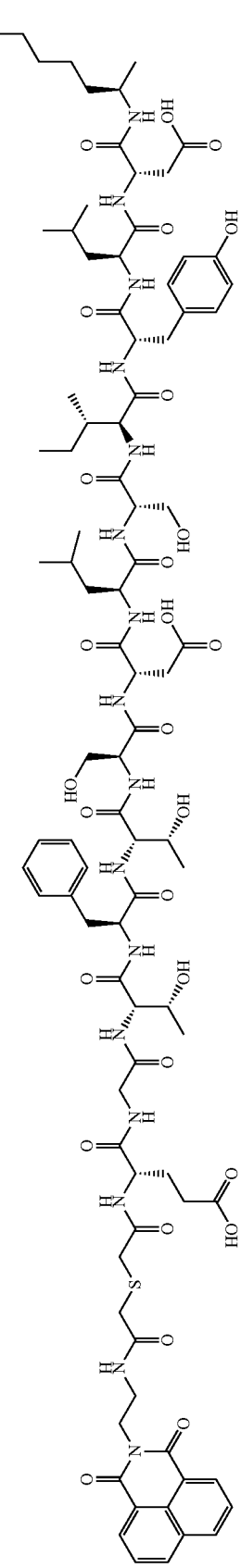
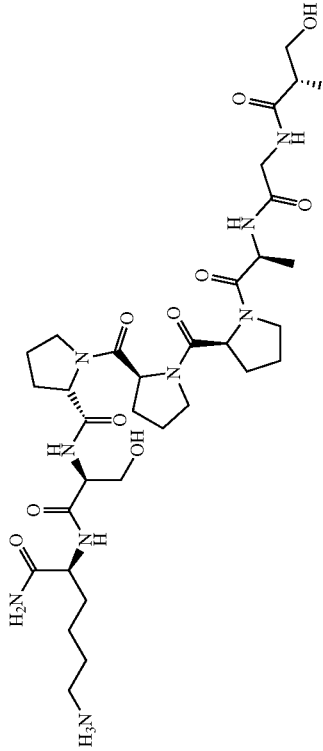
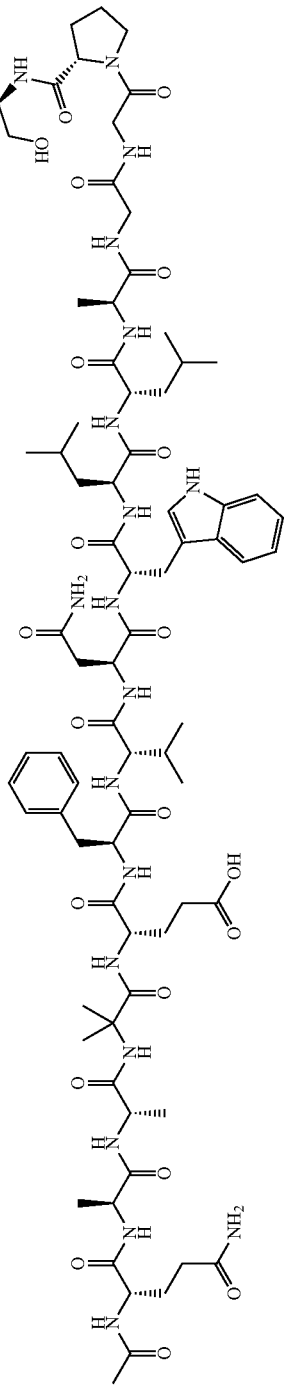

849 850
Compound 159
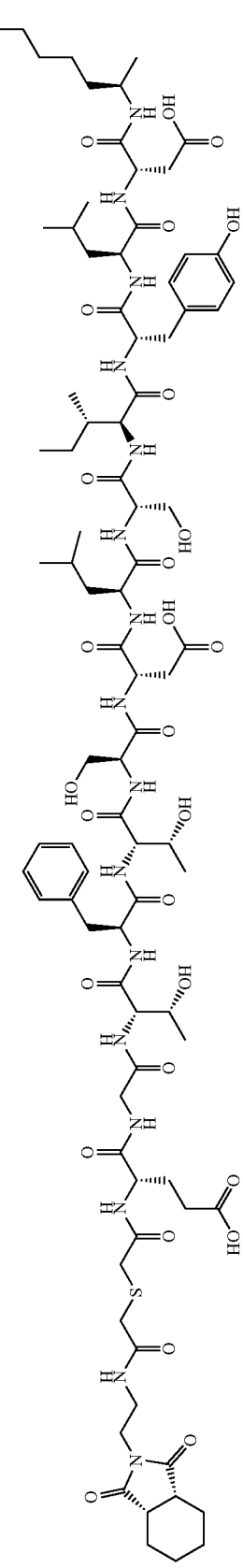
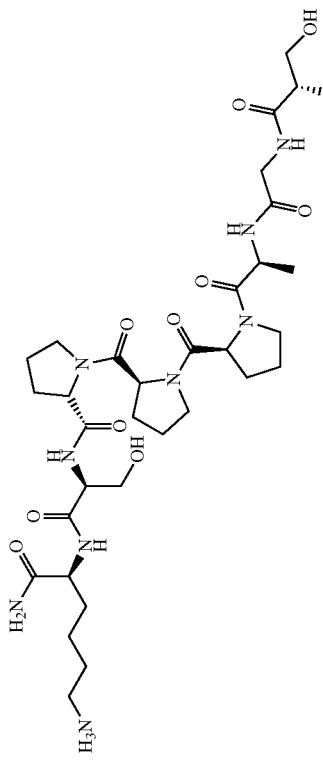
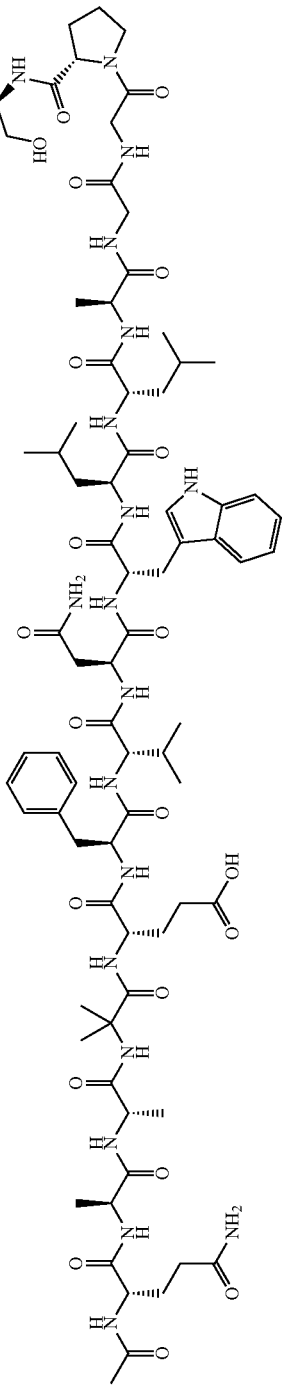

Compound 160
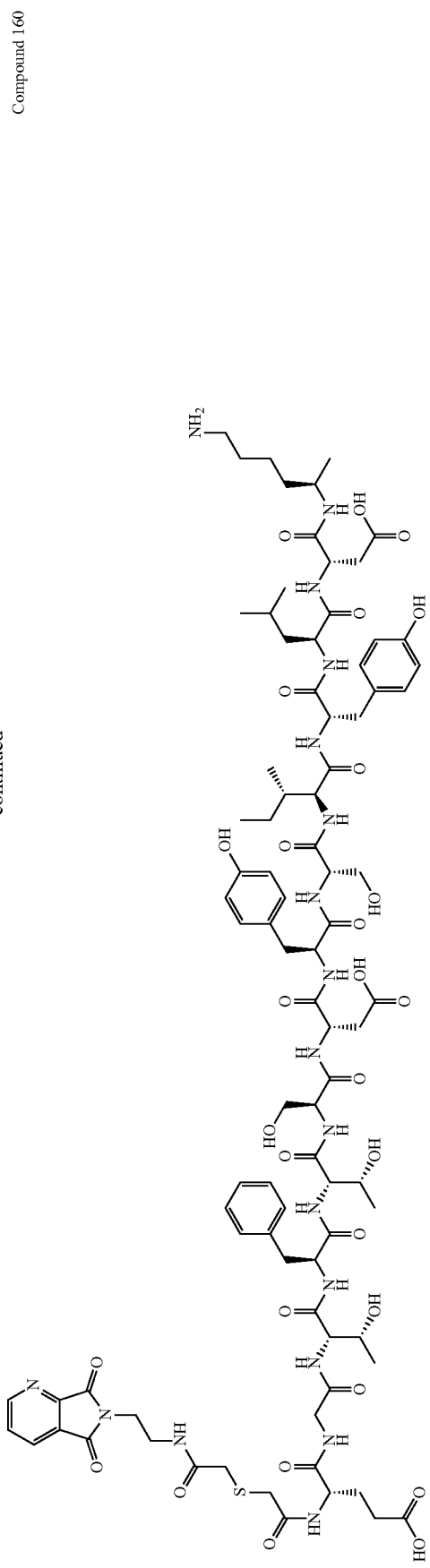
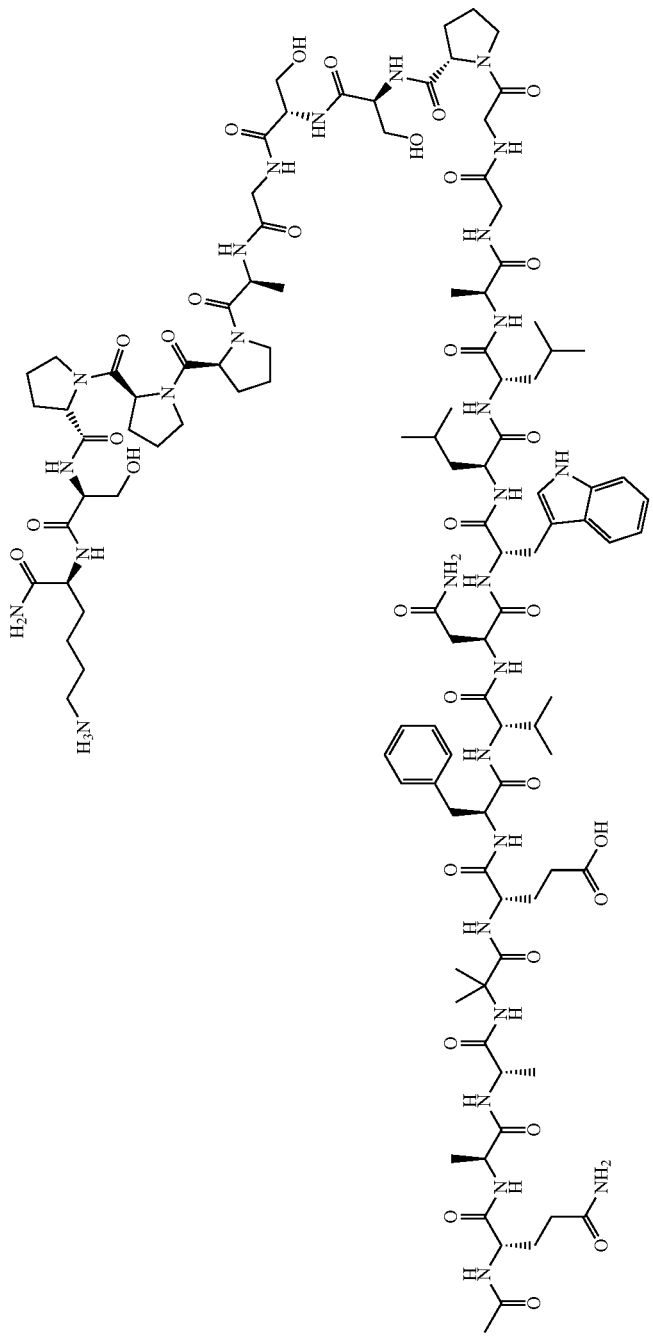

853 854
Compound 161
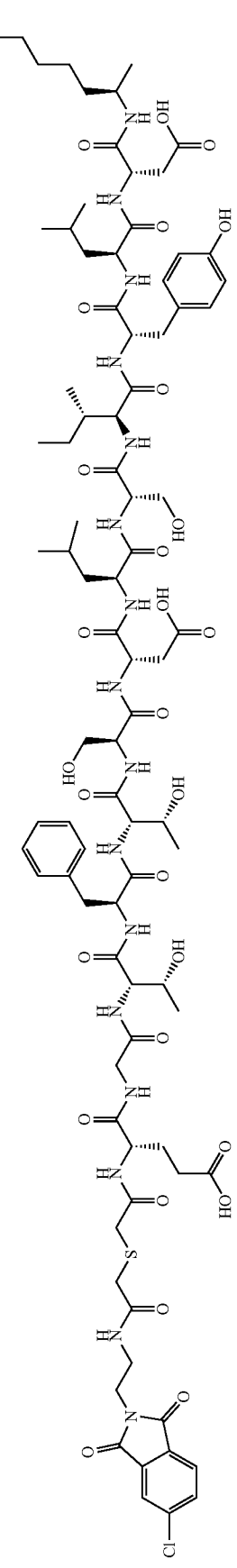
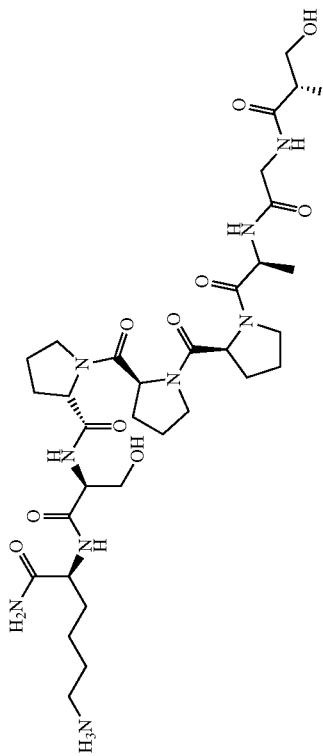
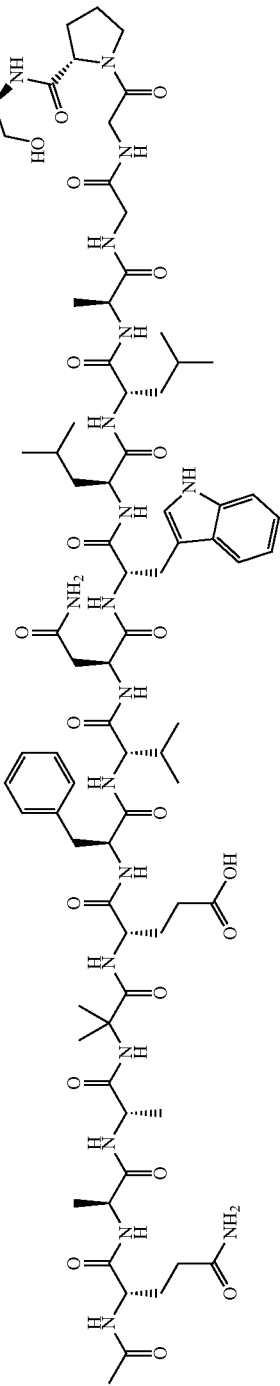

855   856
Compound 162
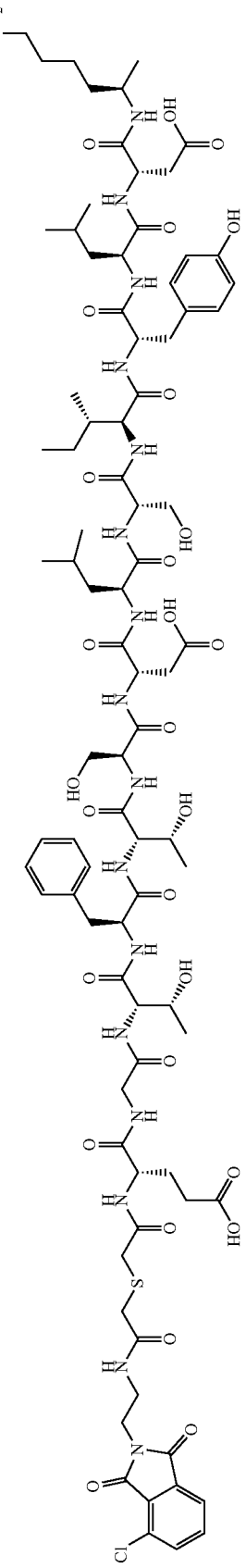
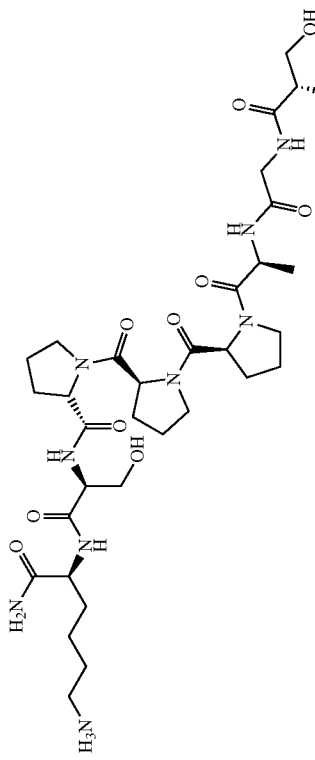
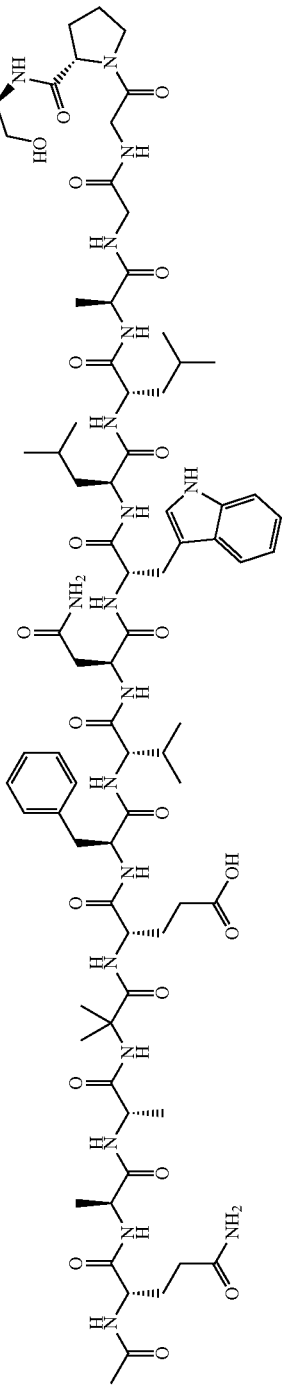

857 858
Compound 163
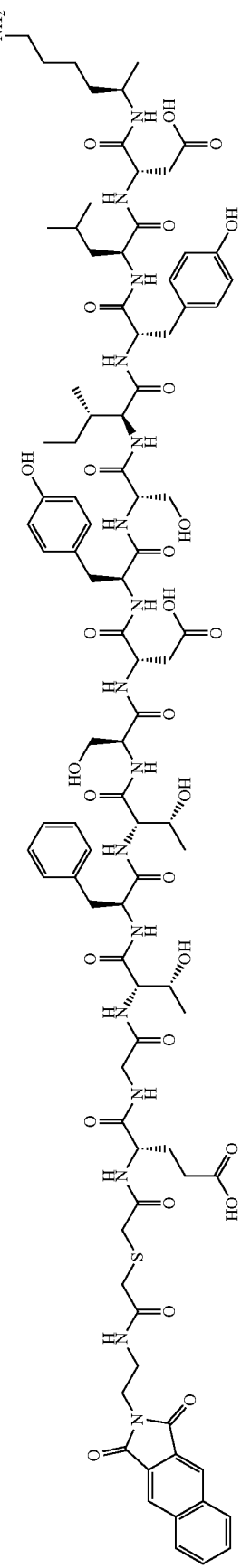
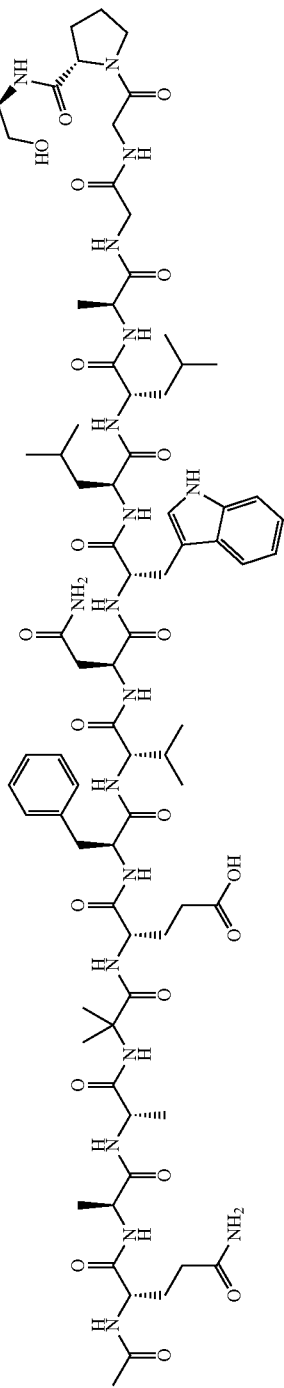

859
860
Compound 164
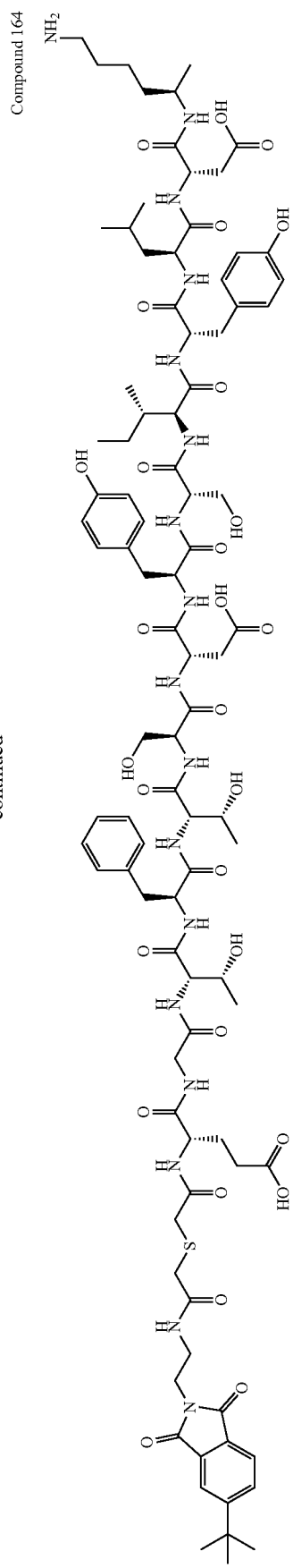
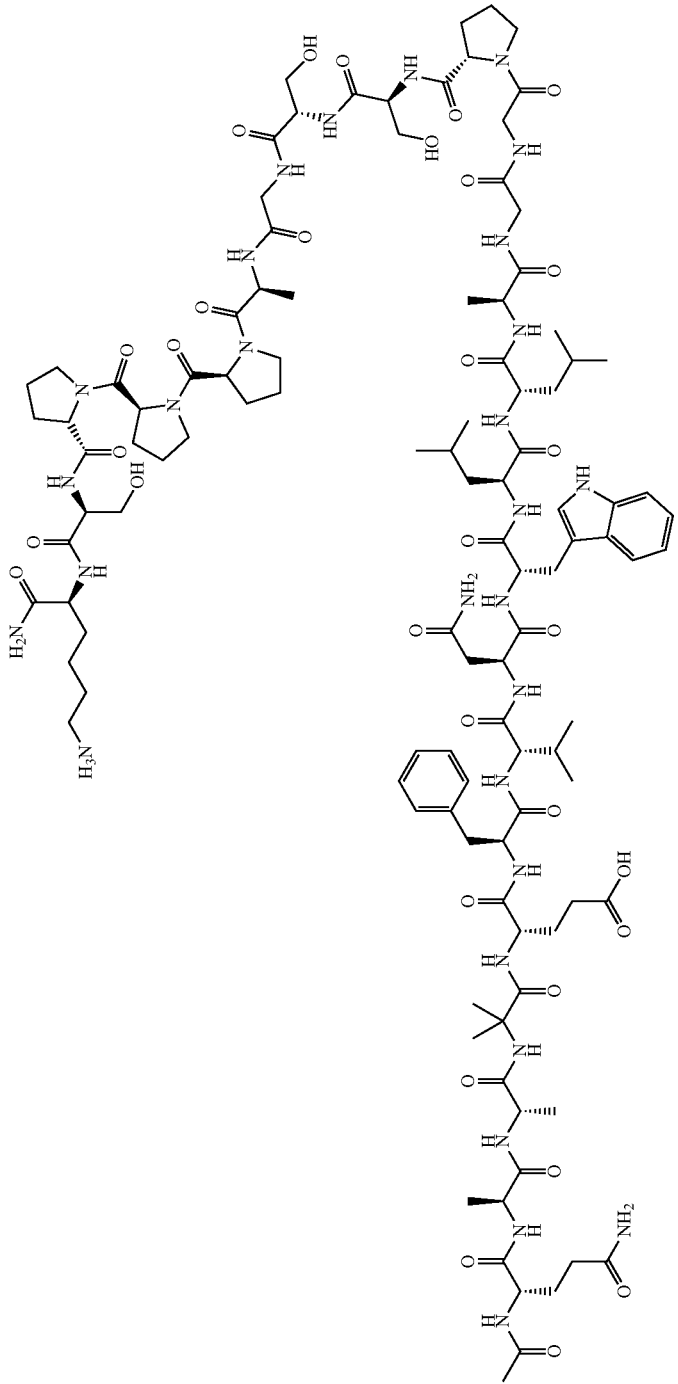
-continued

Compound 165
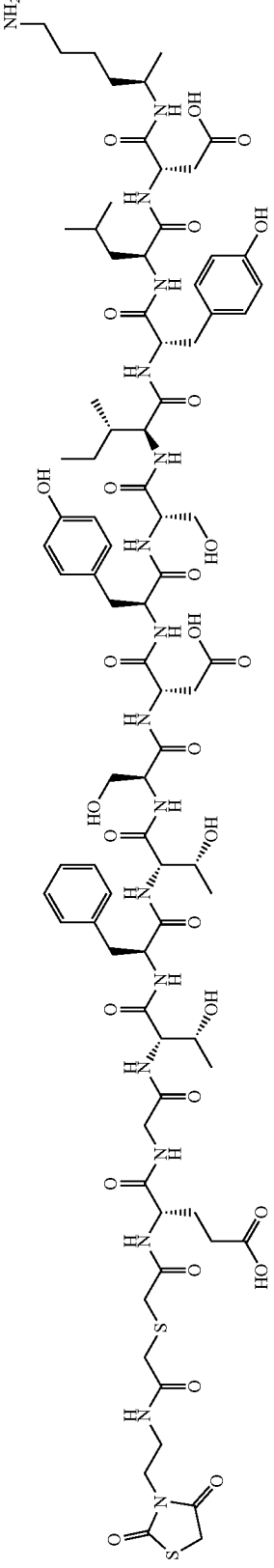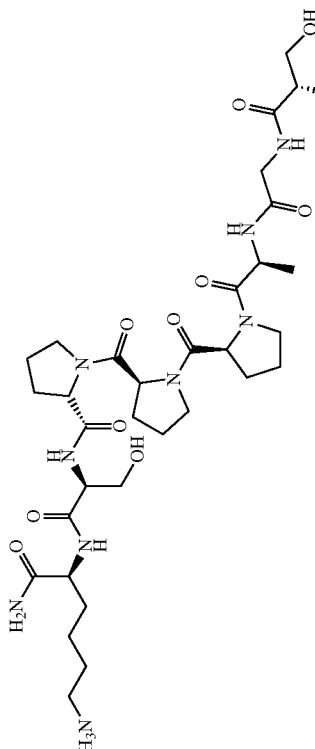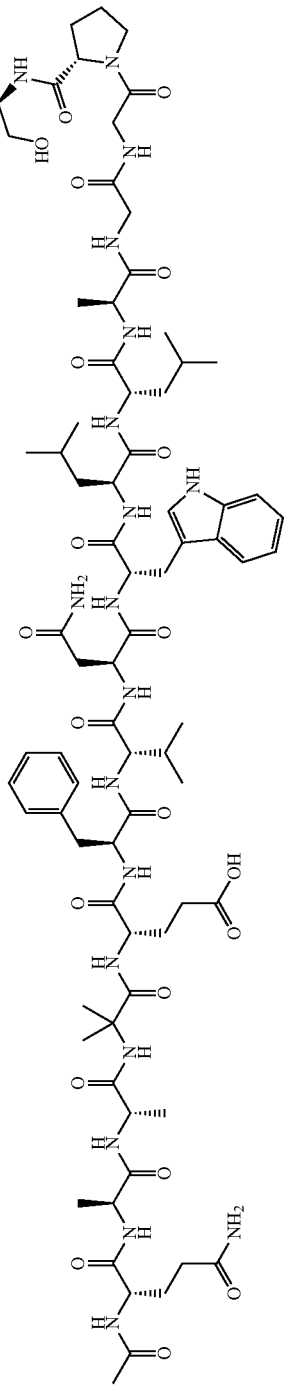

Compound 166
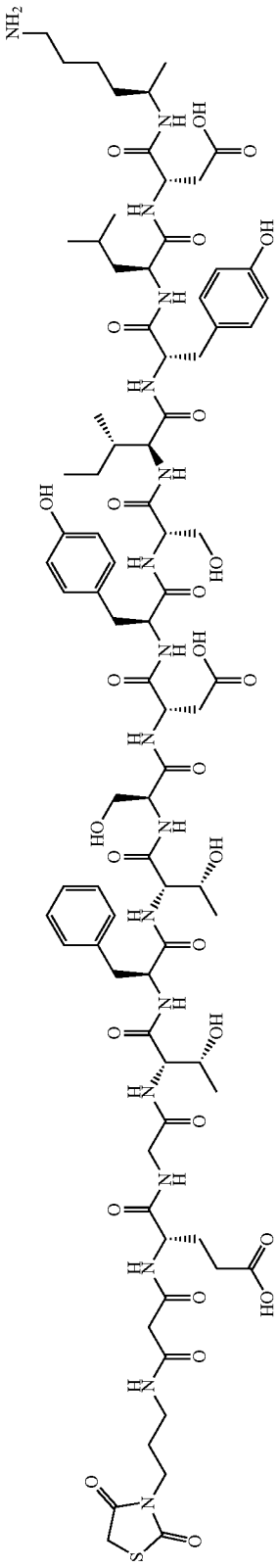
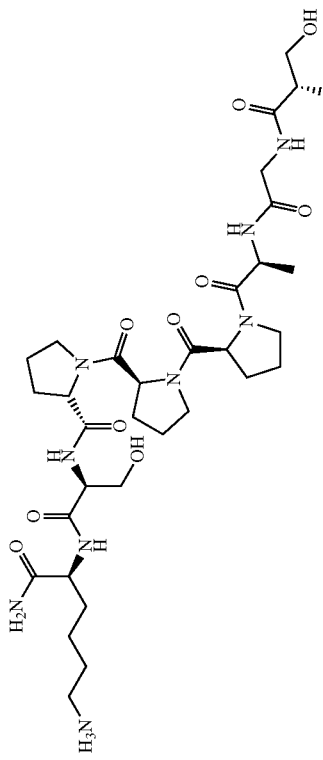
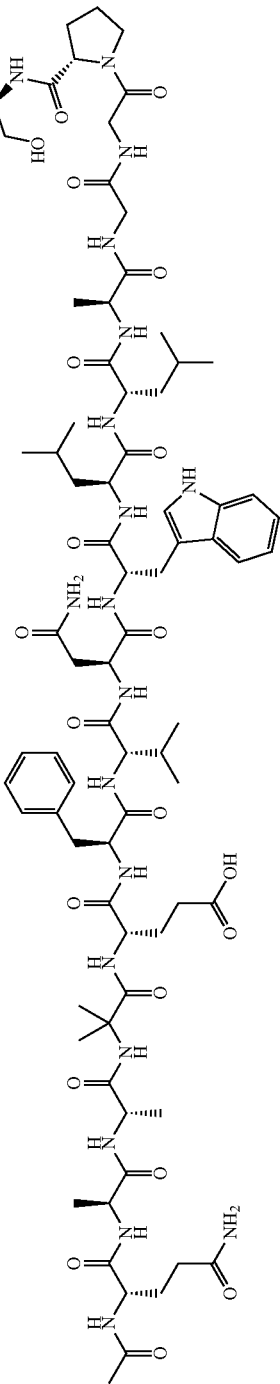

Compound 167
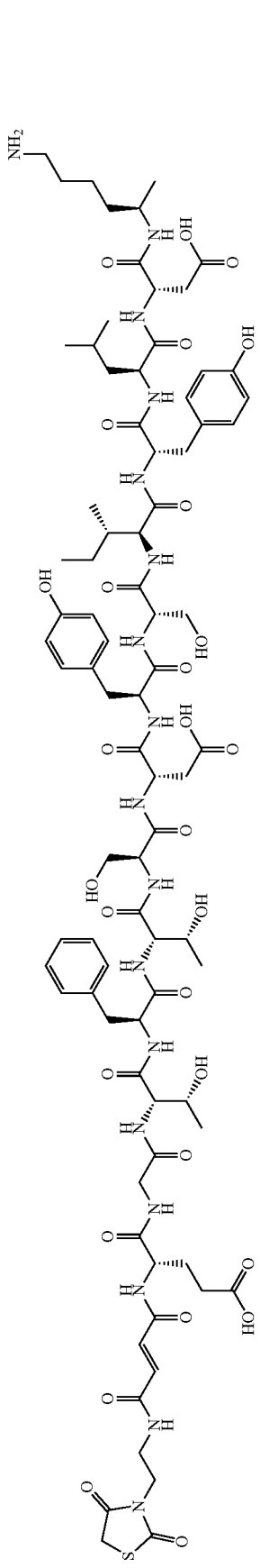
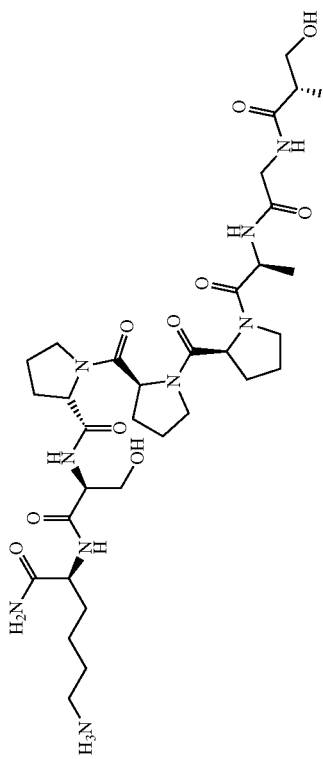
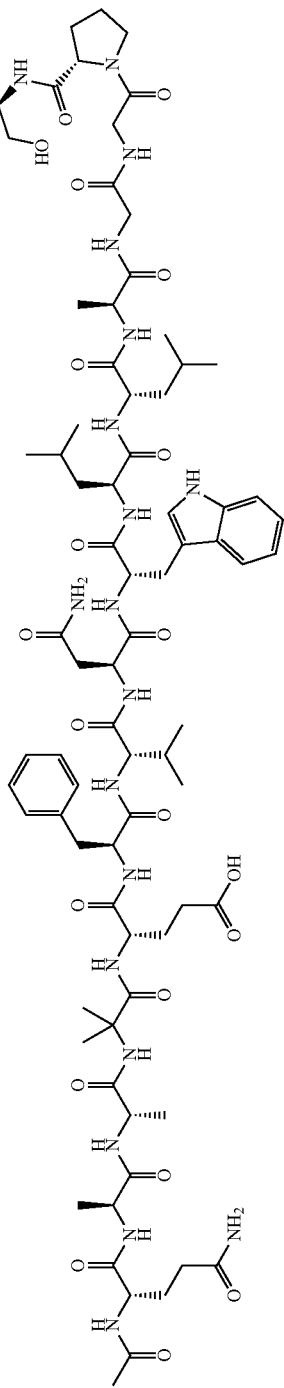

867
Compound 168
-continued
868
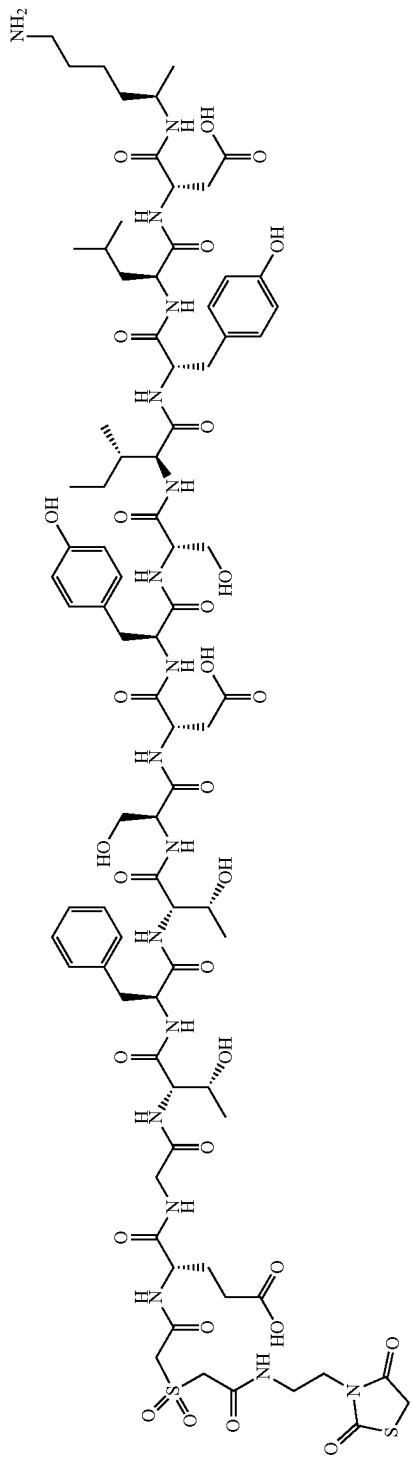
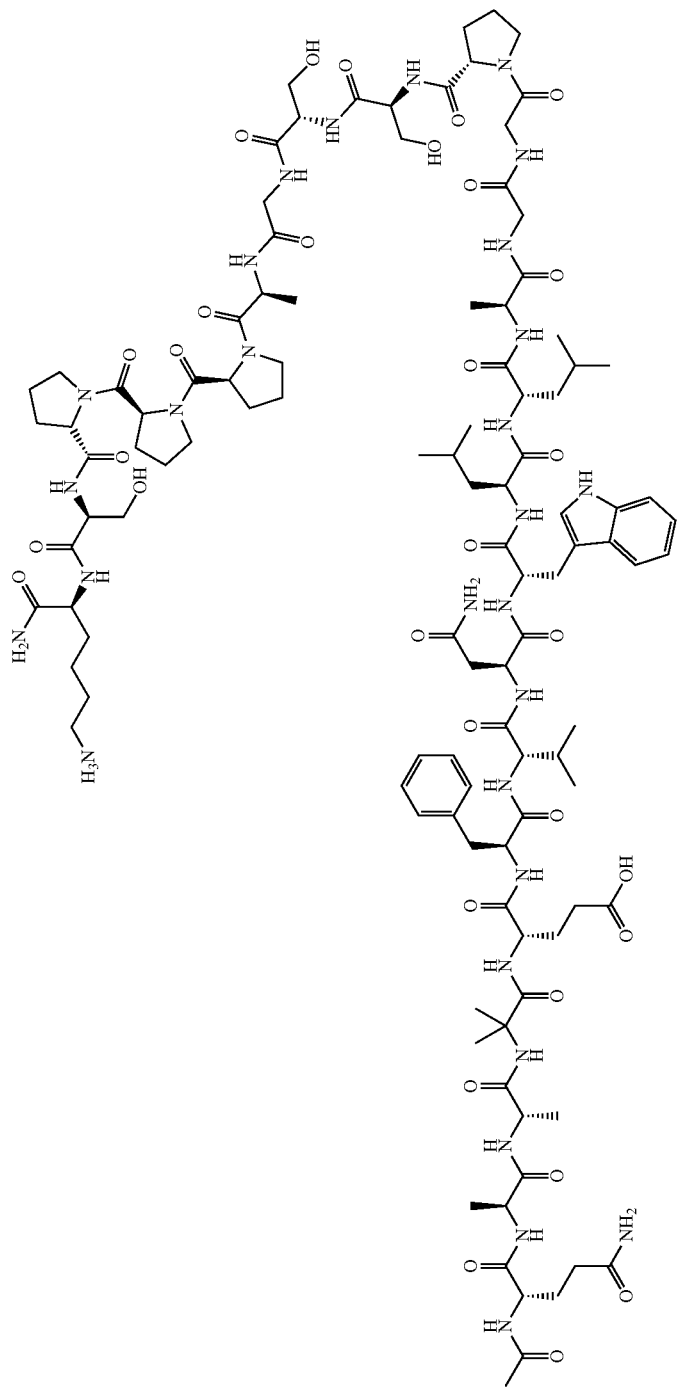

Compound 169
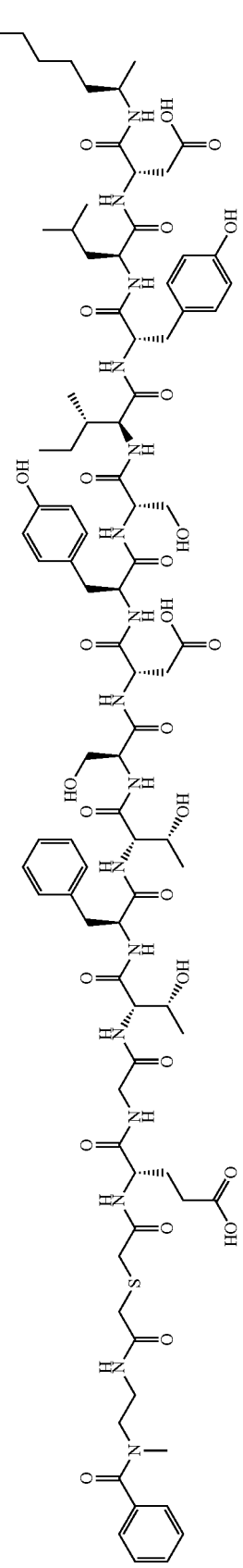
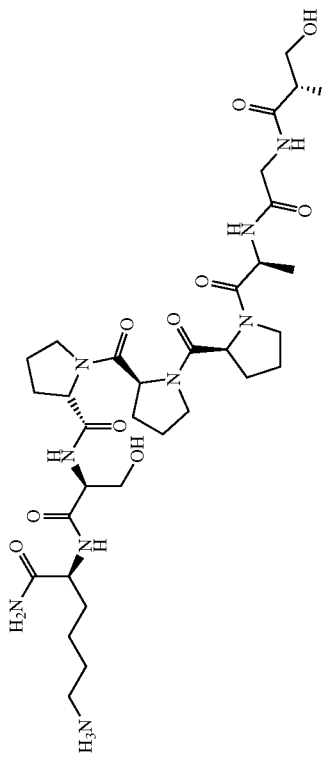
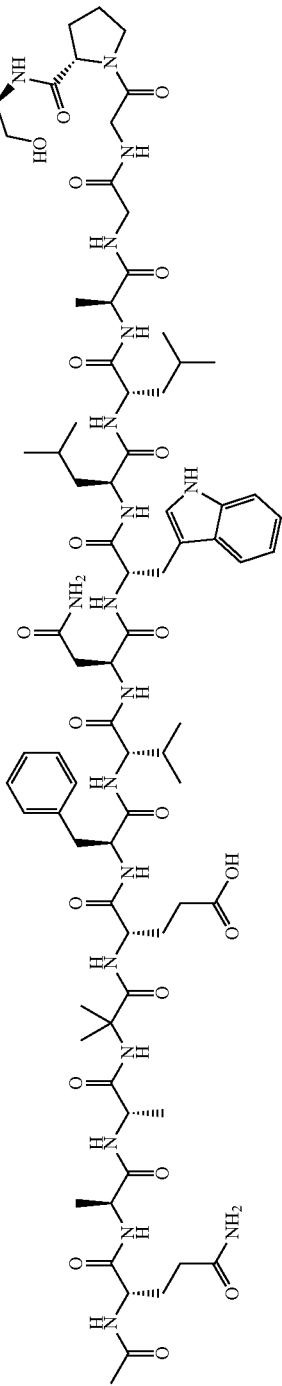

871 872
Compound 170
-continued
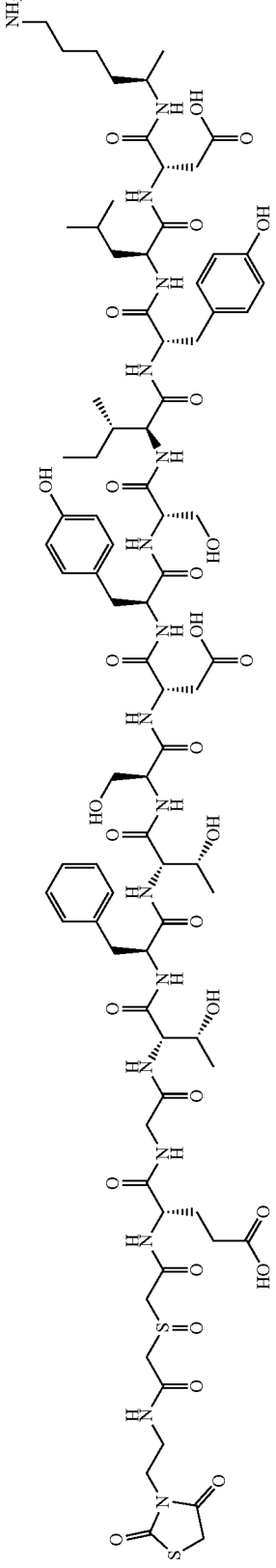 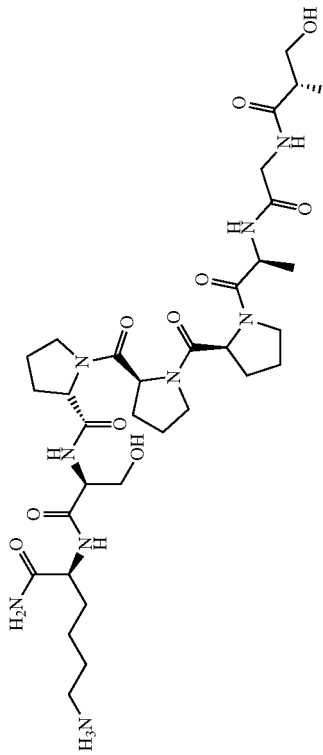 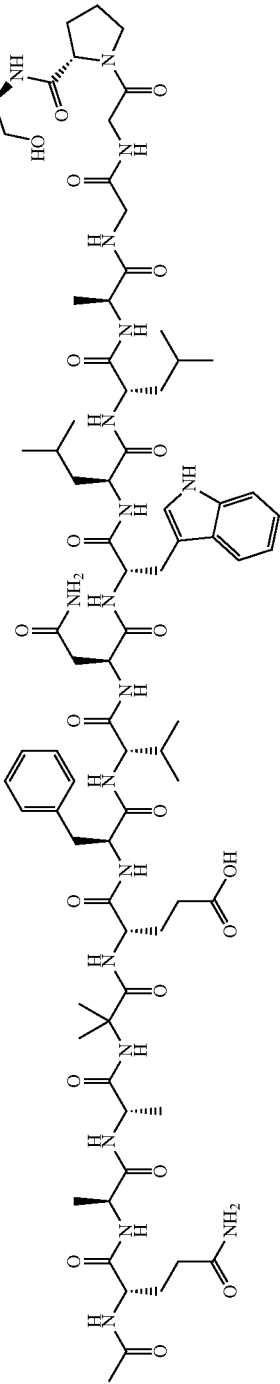

Compound 171
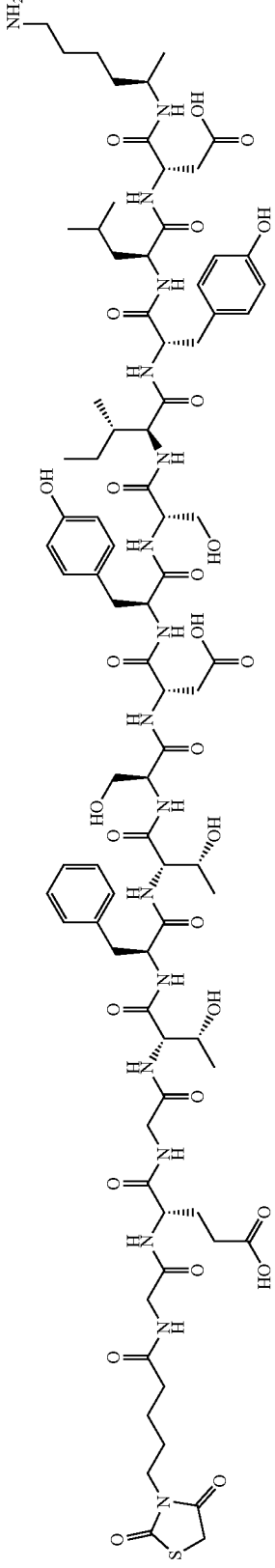
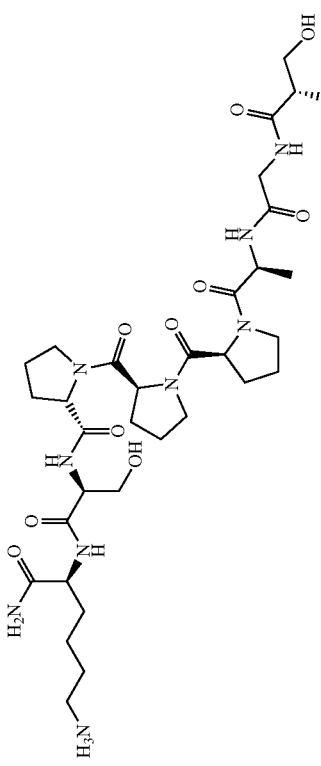
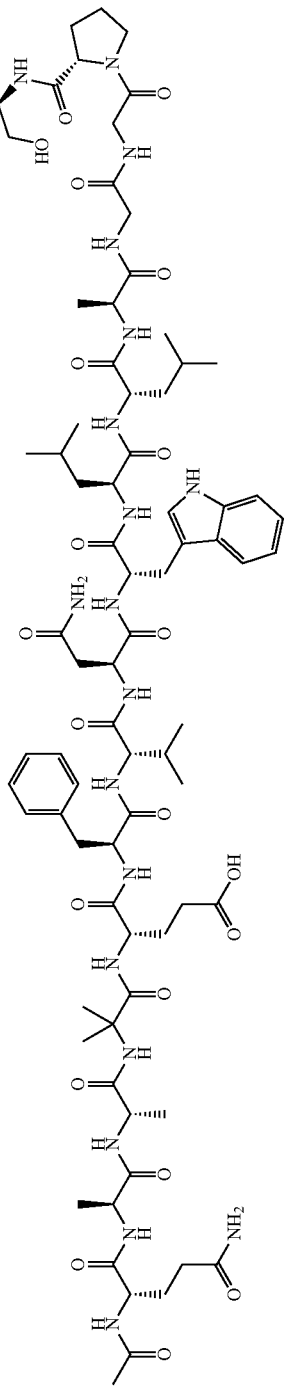

Compound 172
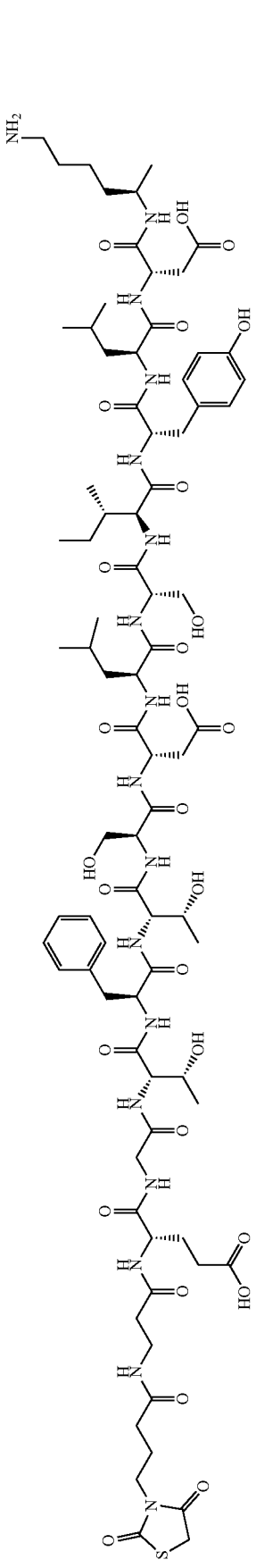
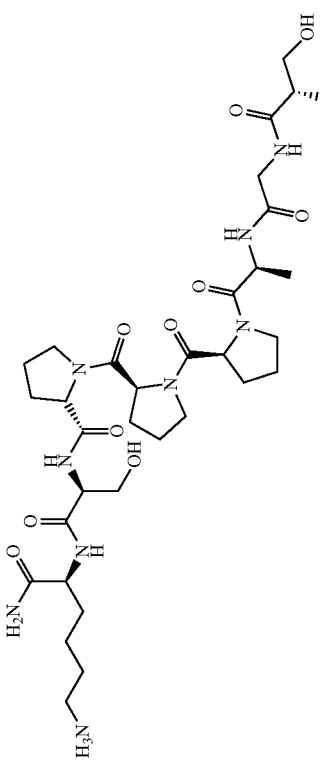
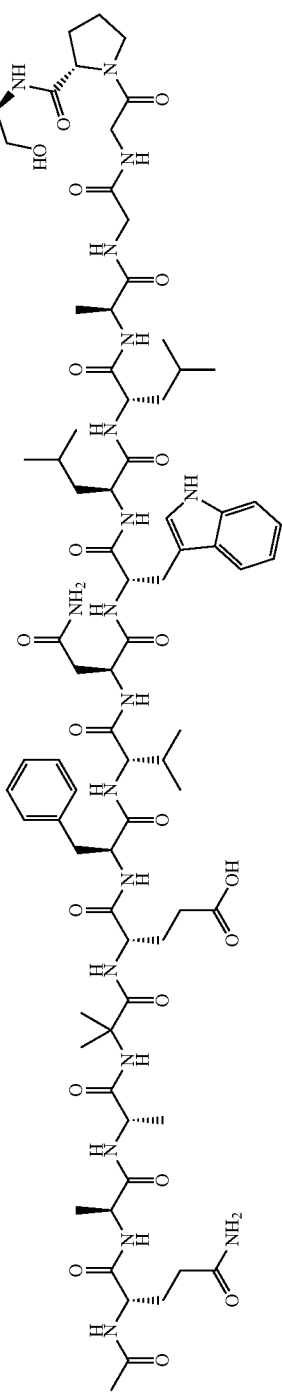

877 878
Compound 173
-continued
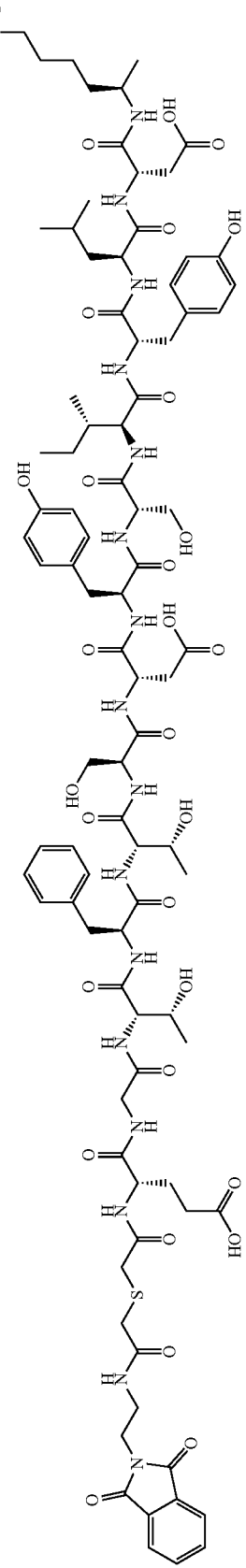
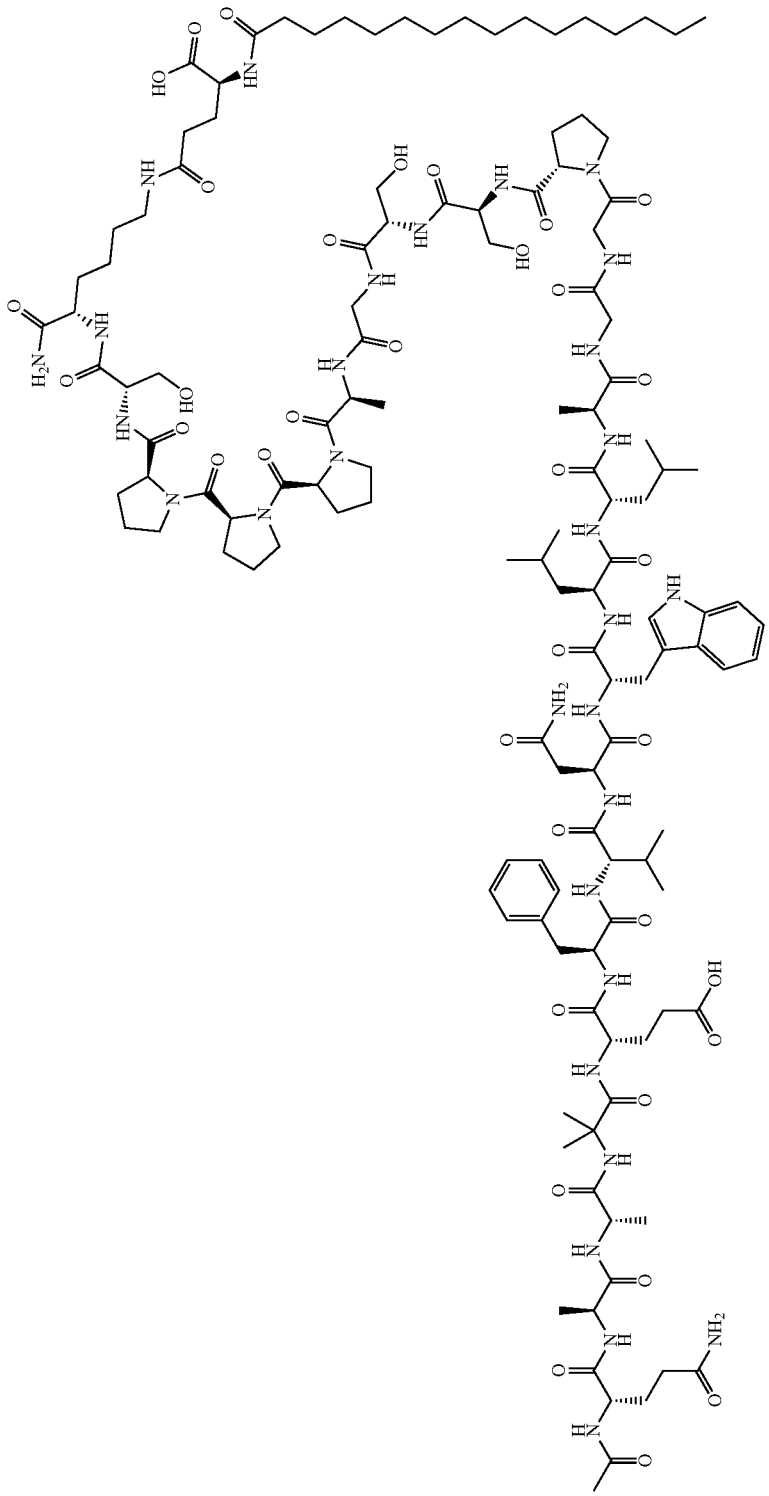

Compound 174
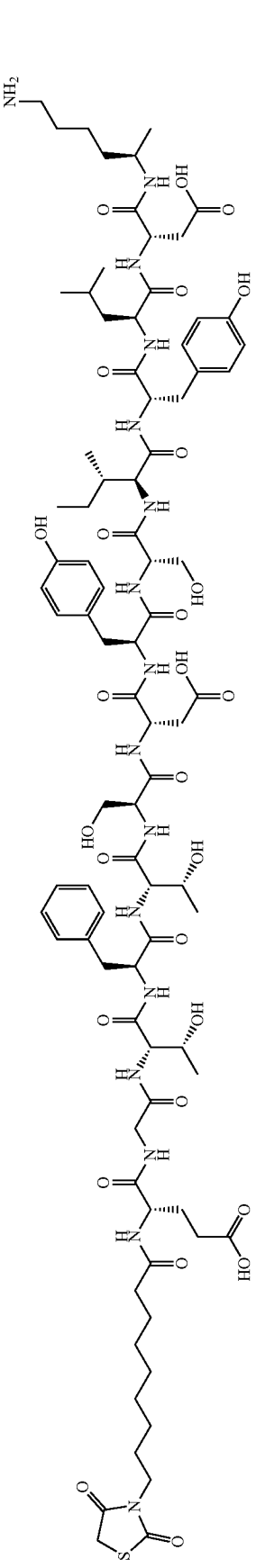
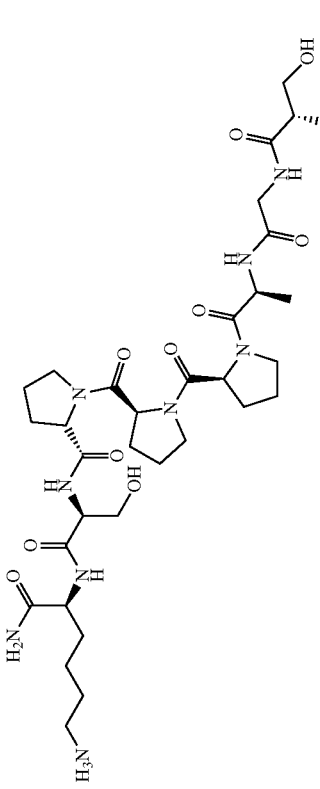
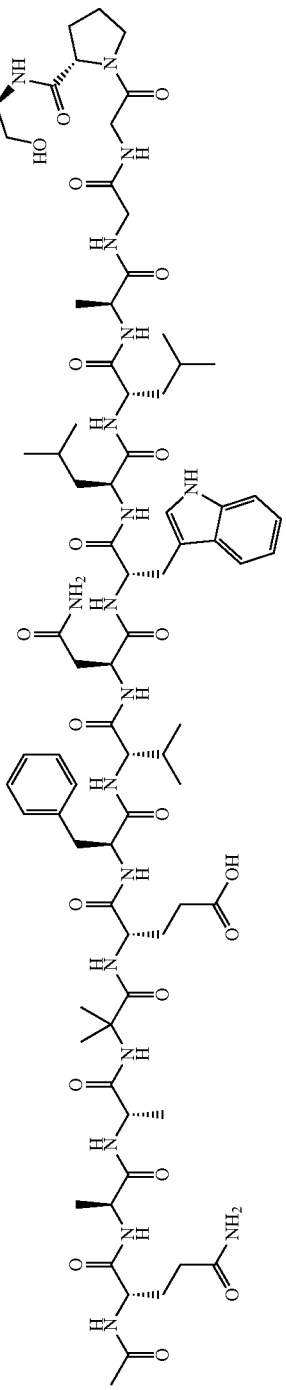

881 882
Compound 175
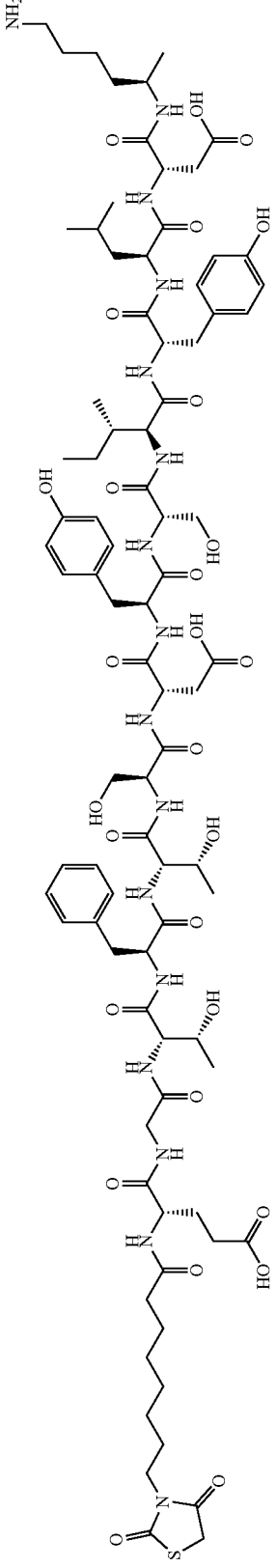
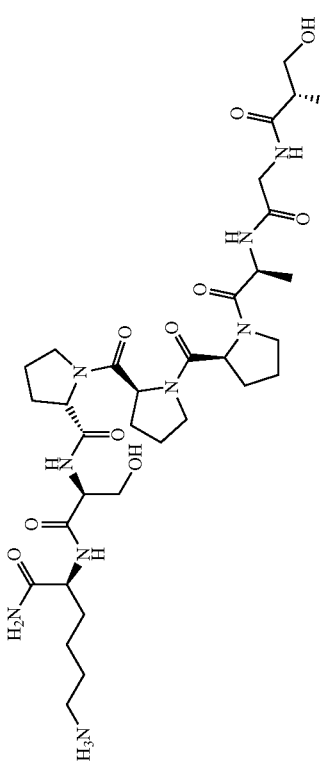
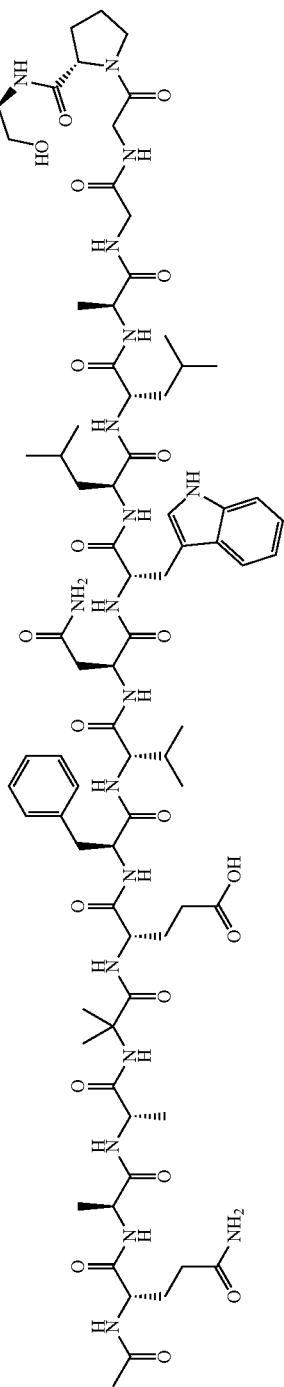

Compound 176
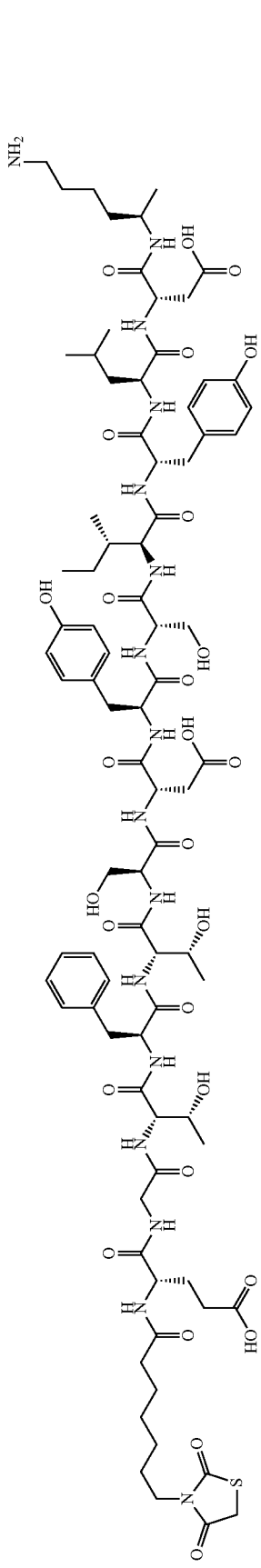
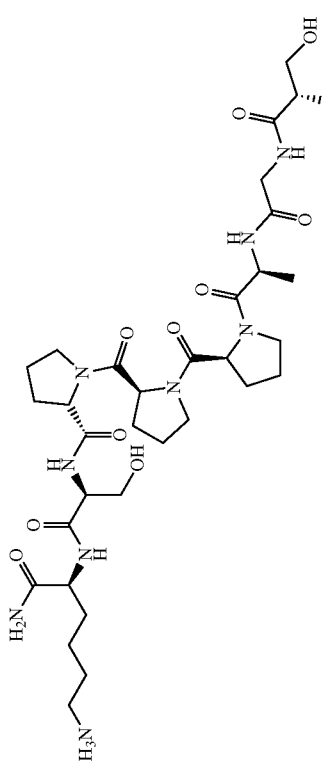
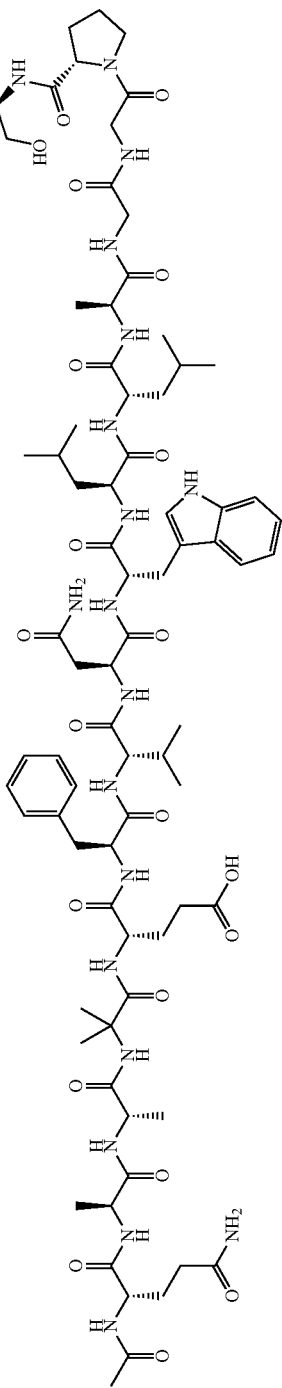

Compound 175
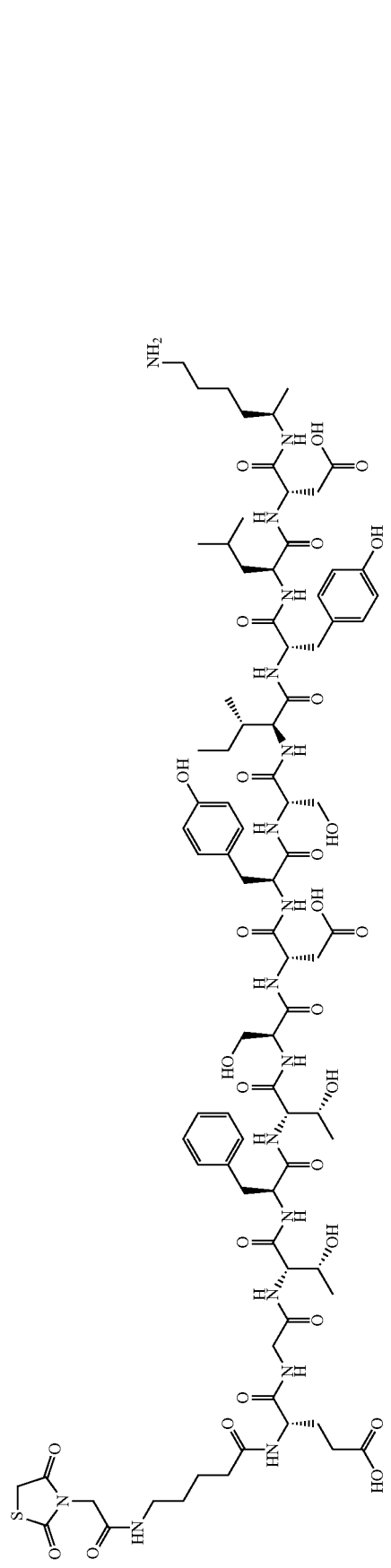
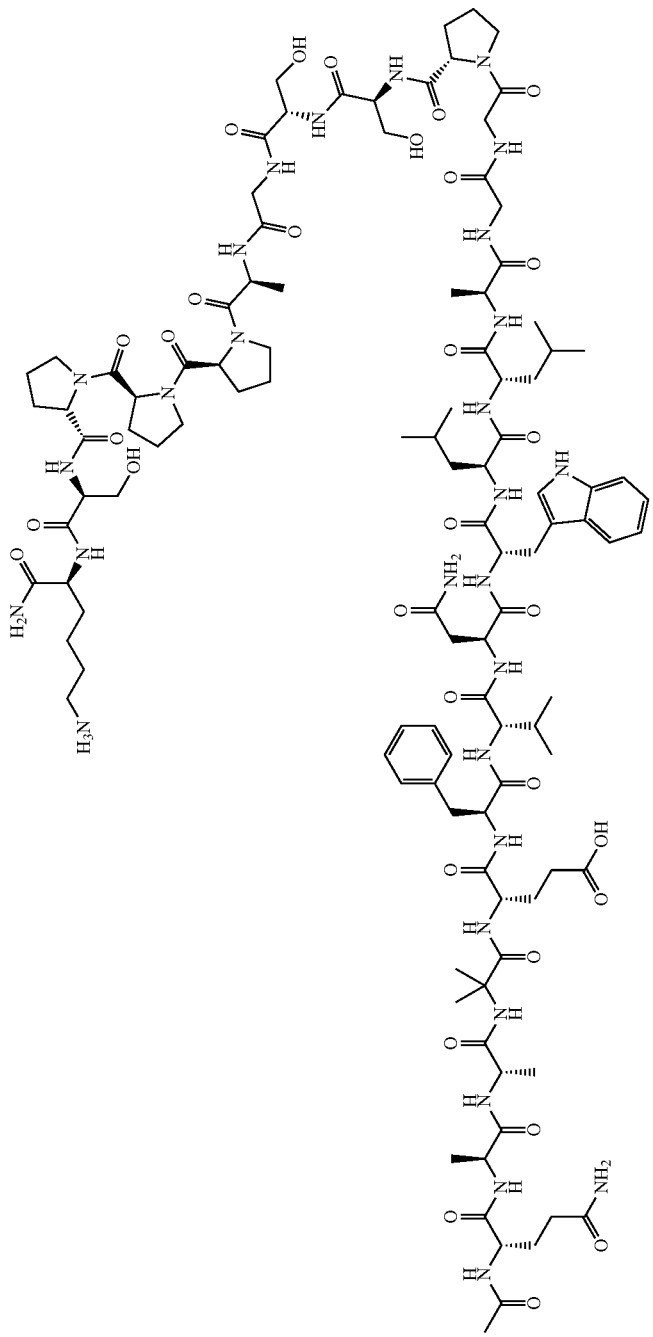

887
Compound 178
-continued
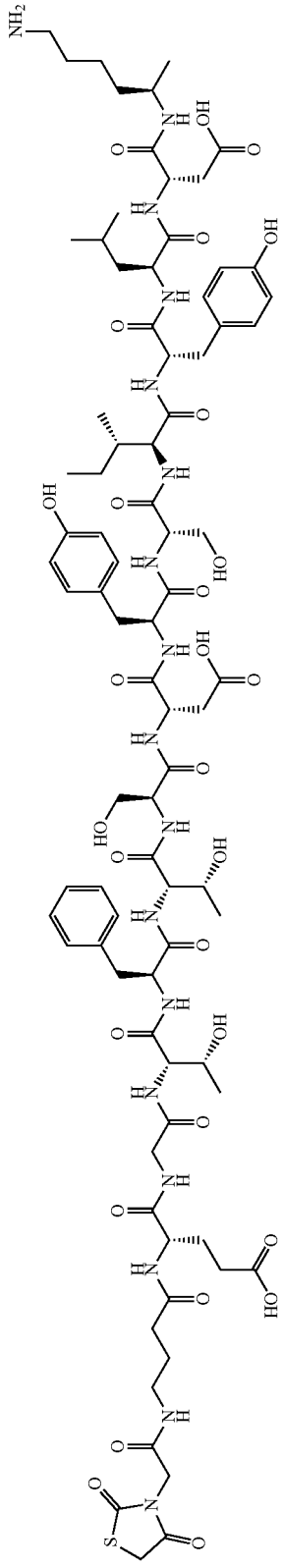
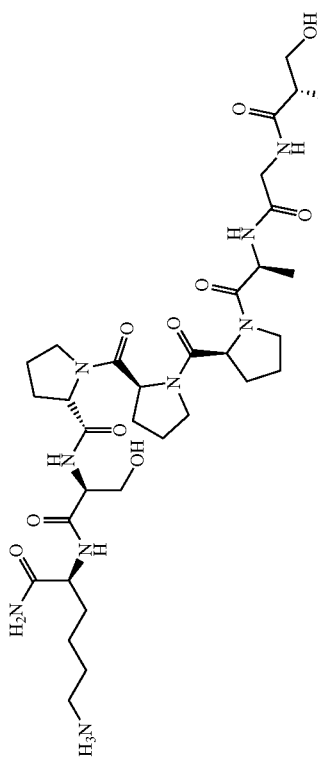
888
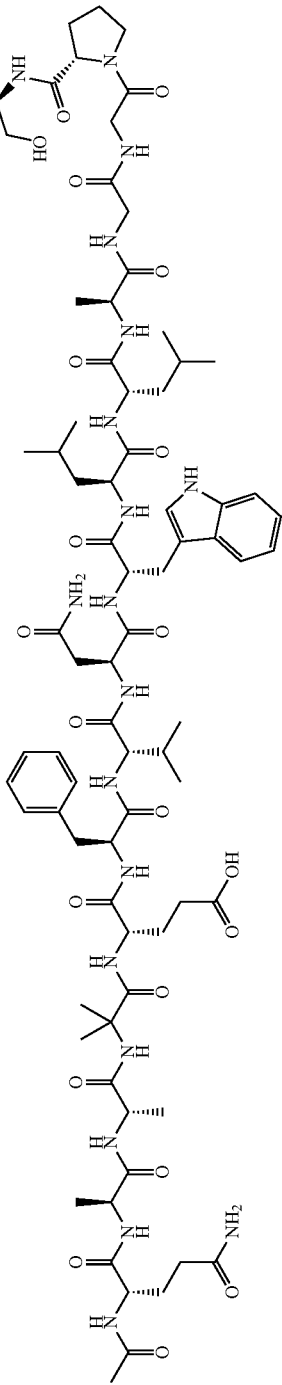

Compound 179
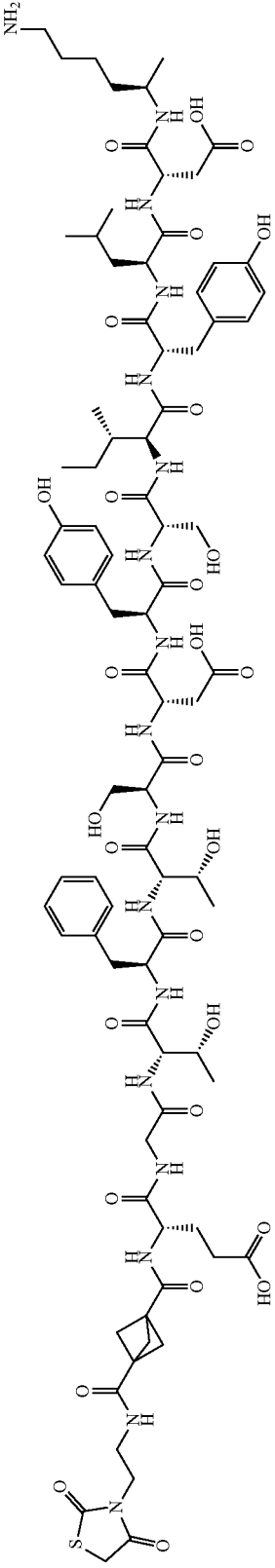
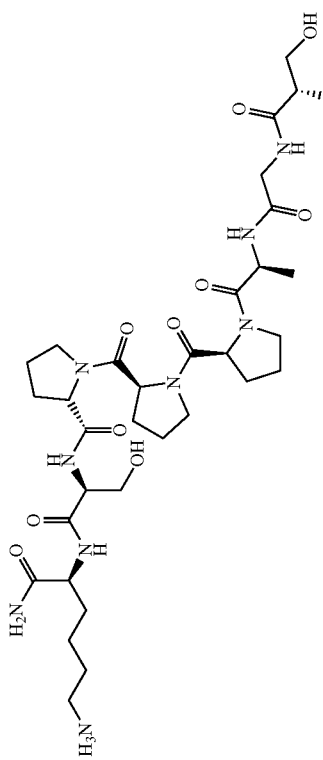
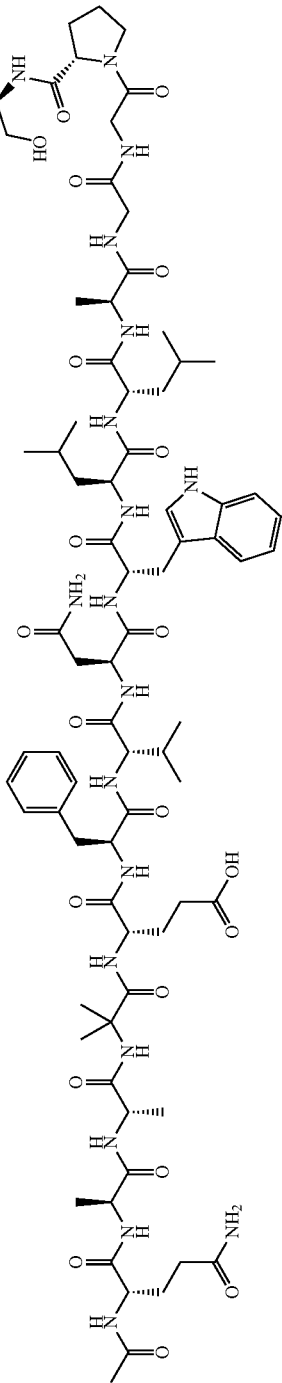

891    892
Compound 180
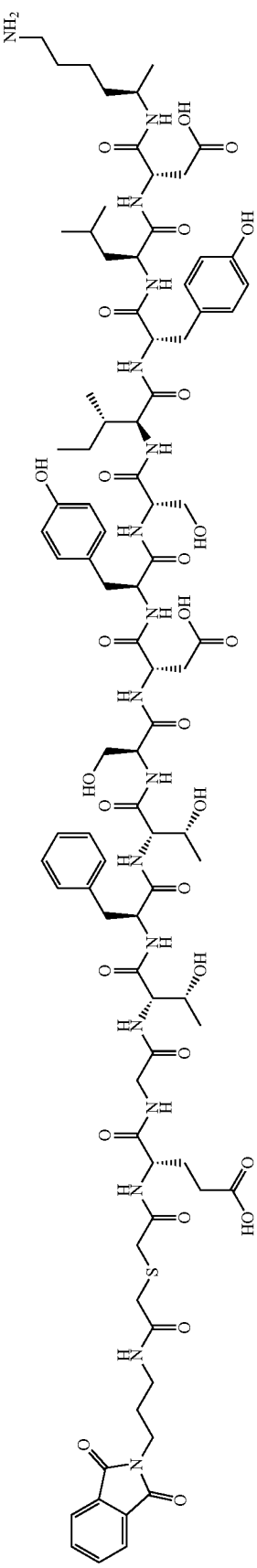
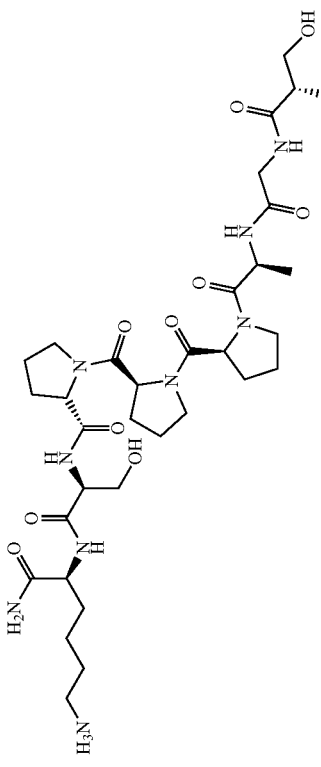
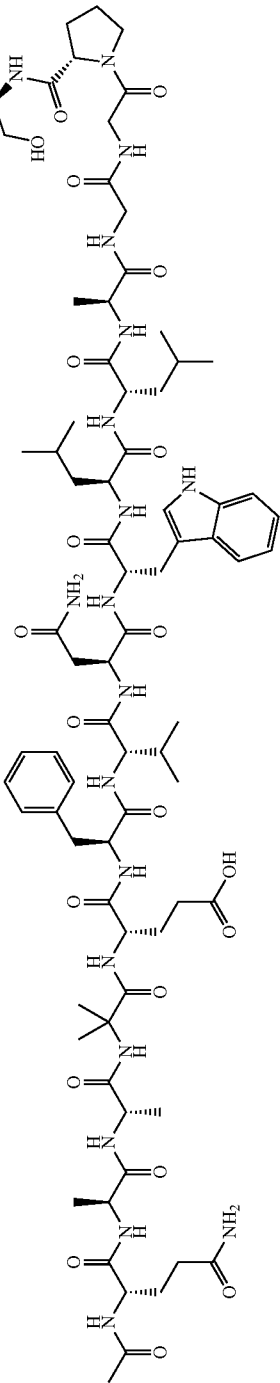

893
894
Compound 181
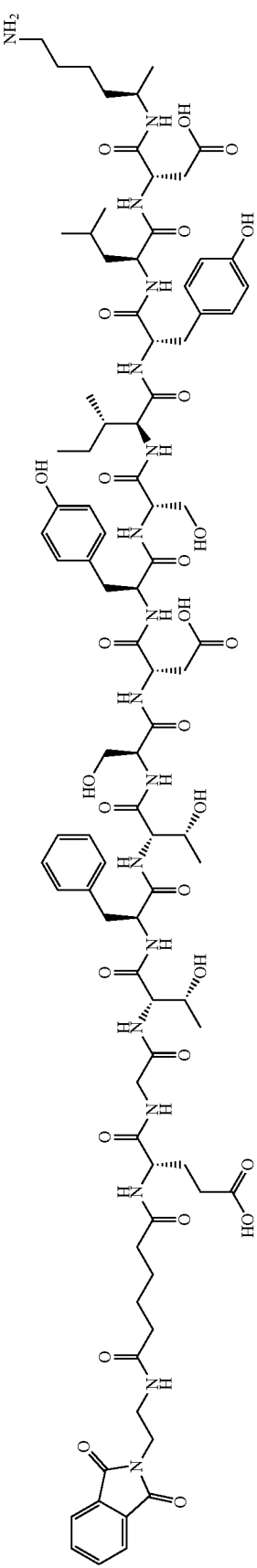
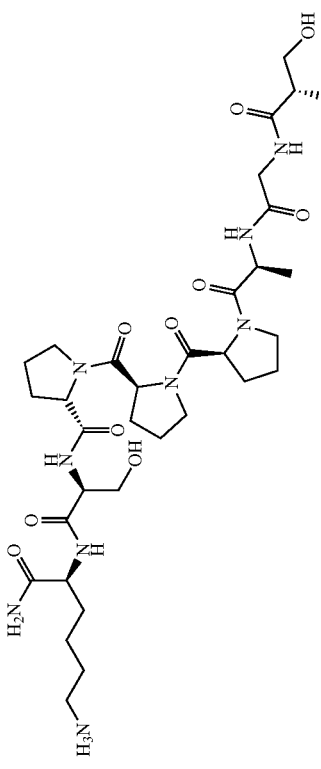
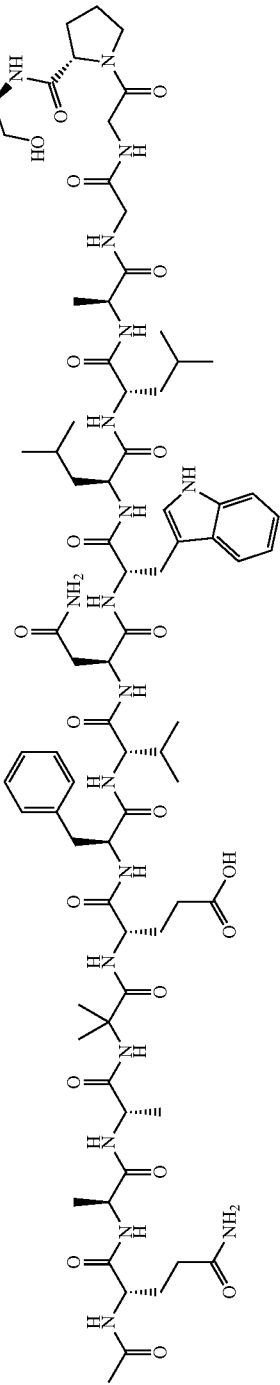

895
Compound 182
896
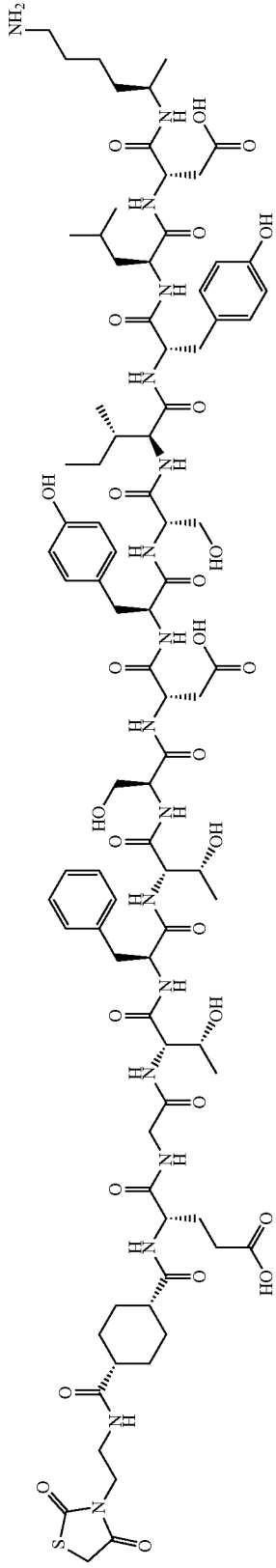
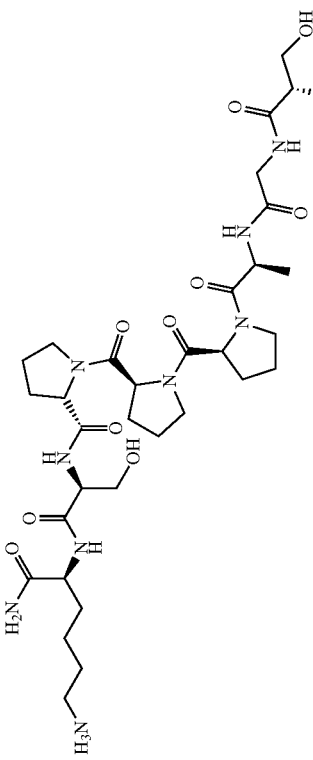
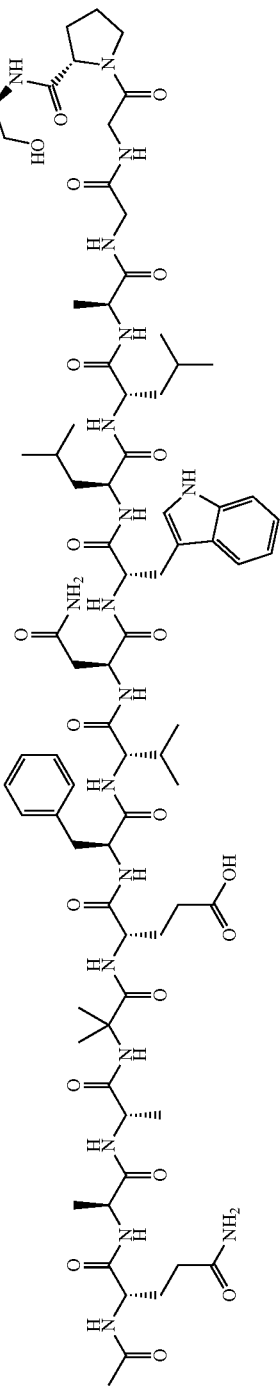

897
Compound 183
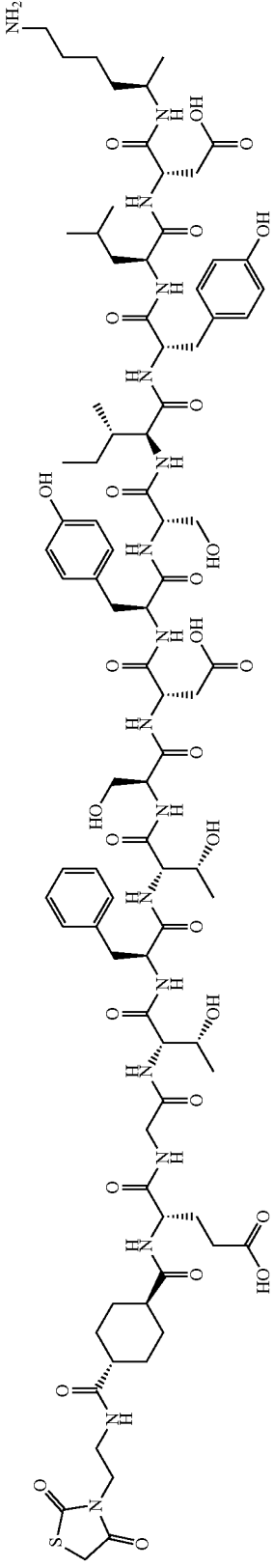
898
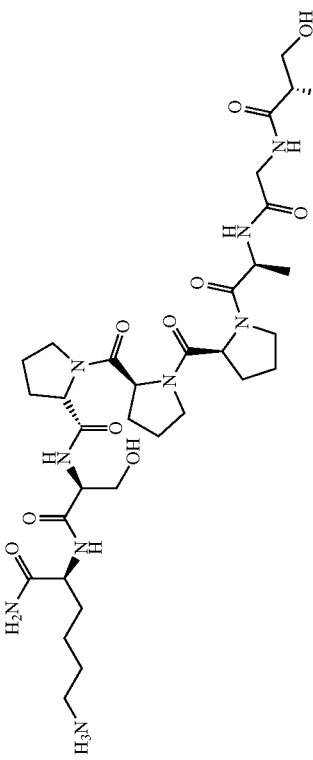
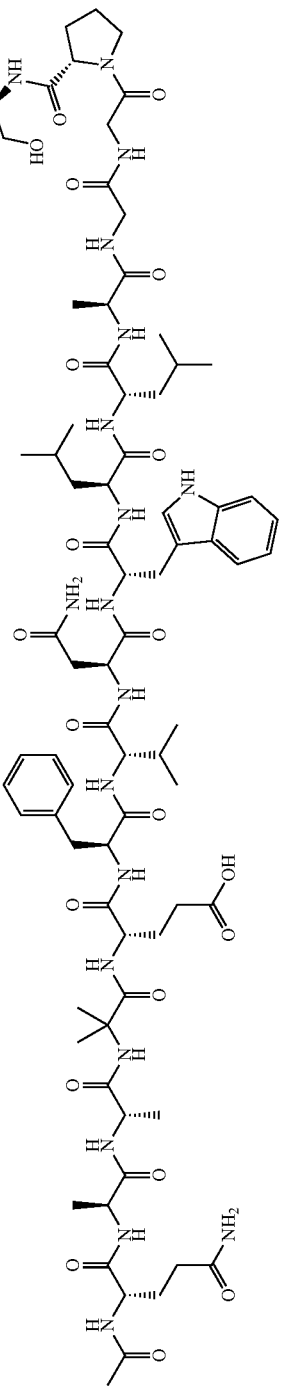

899 900
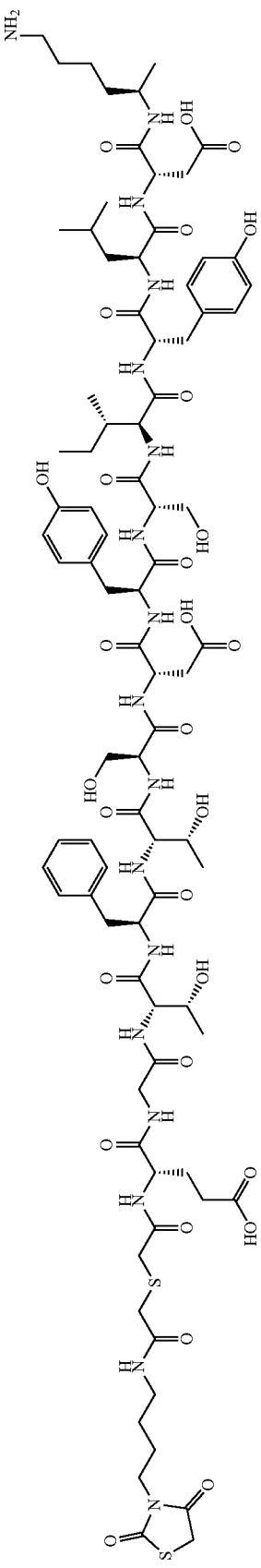
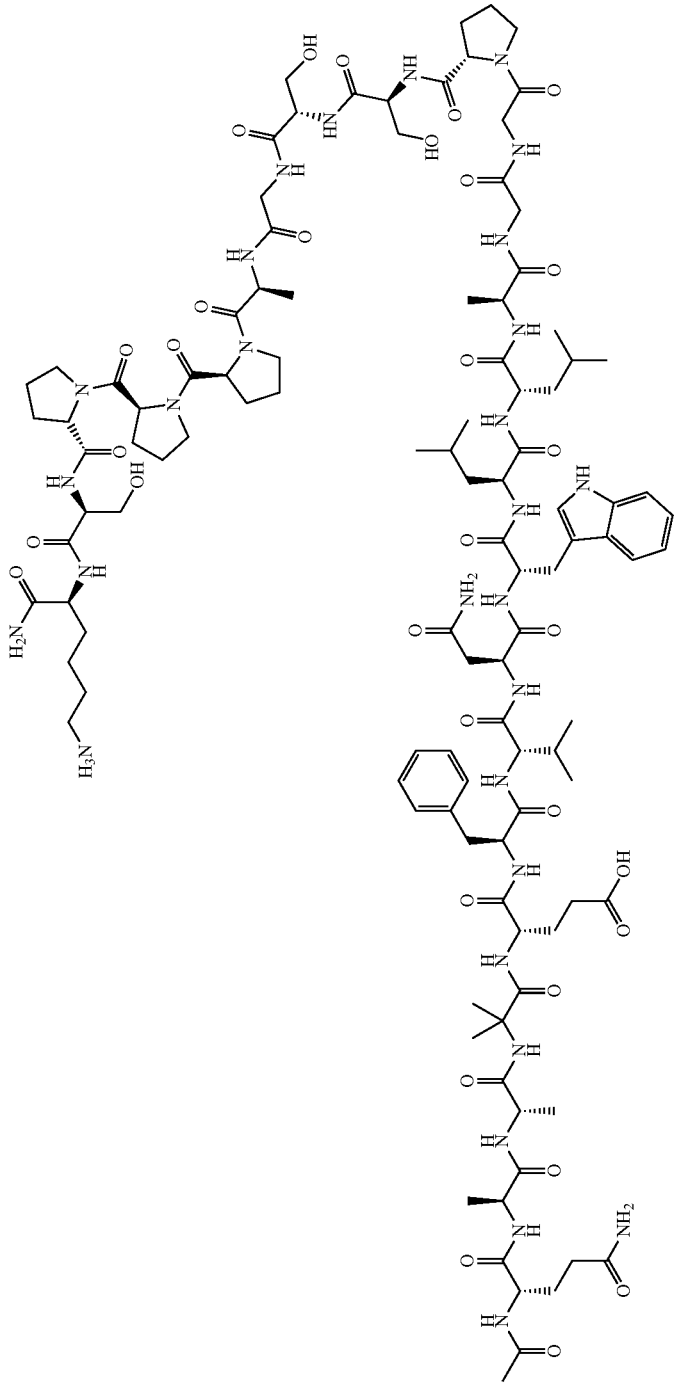
Compound 184
-continued

Compound 185
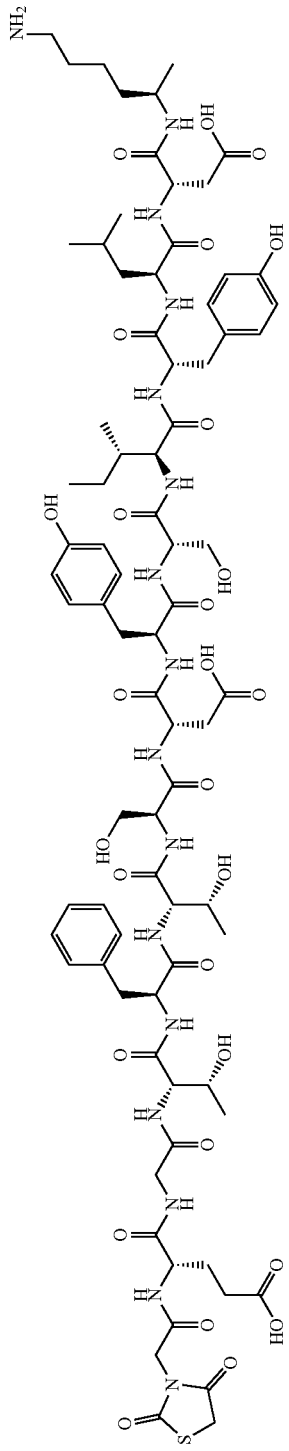
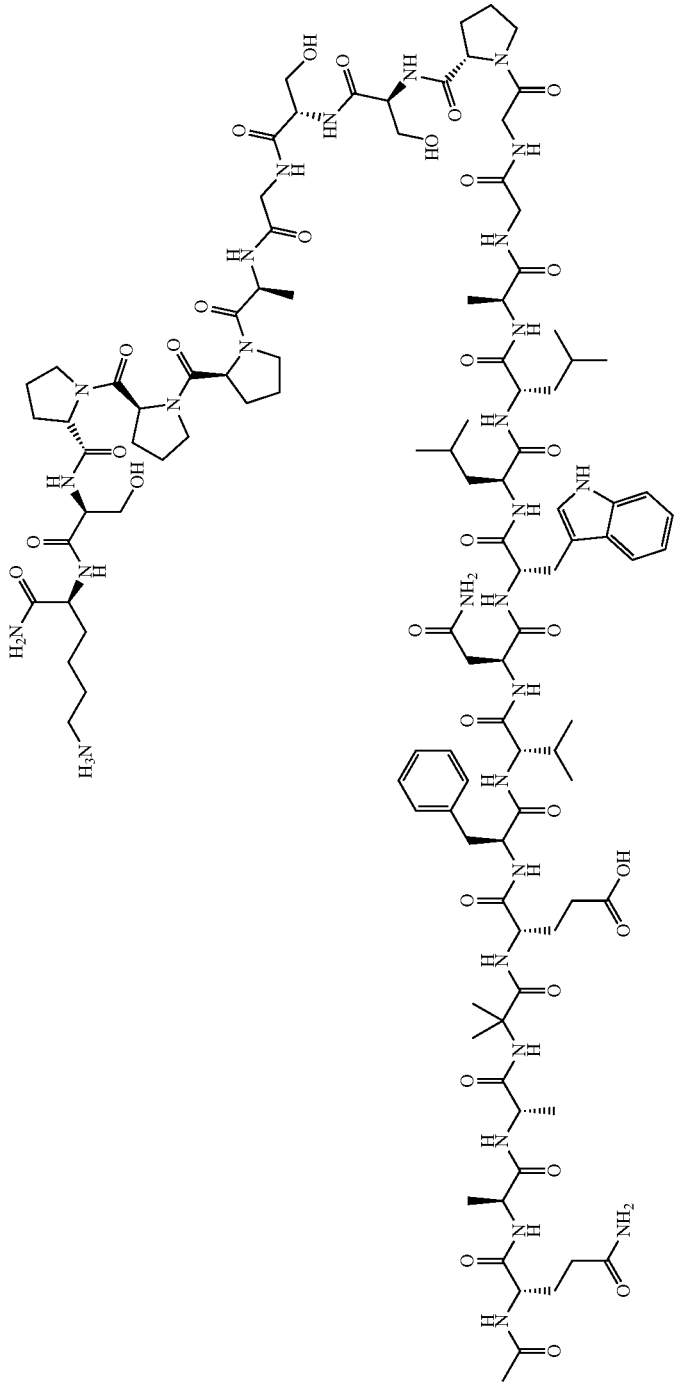
901
902

903
Compound 186
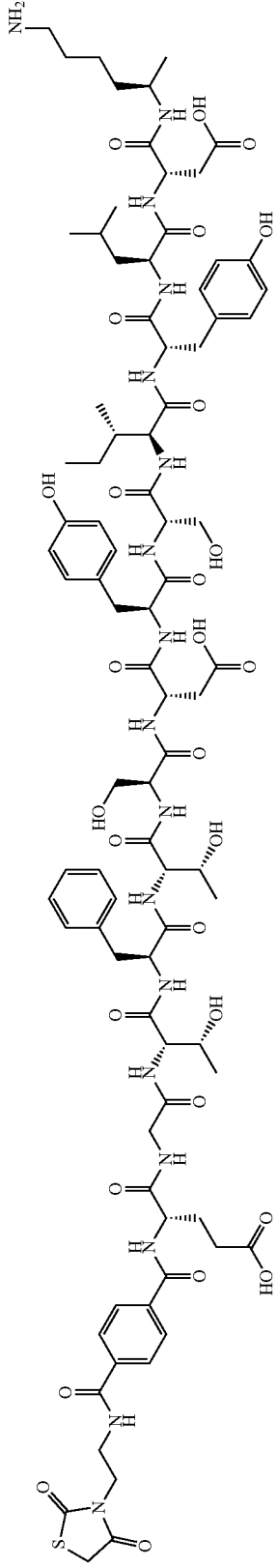
904
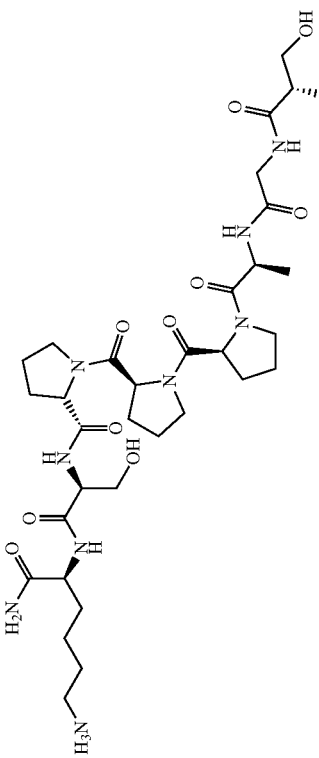
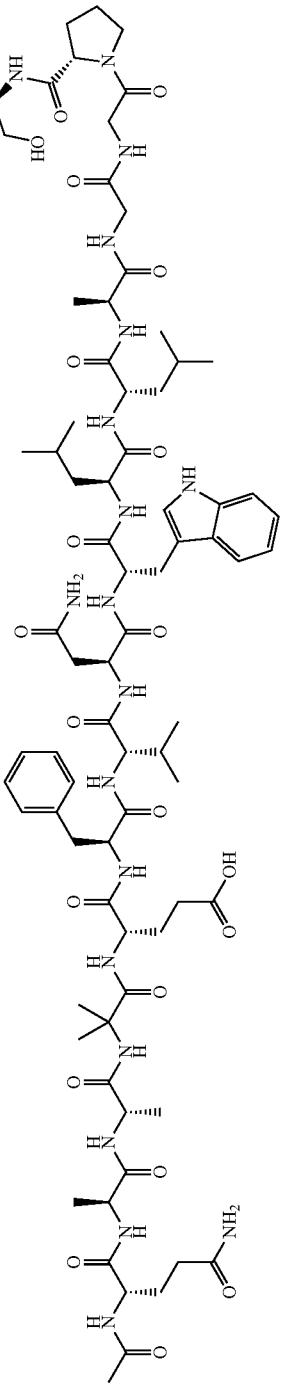

905
Compound 187
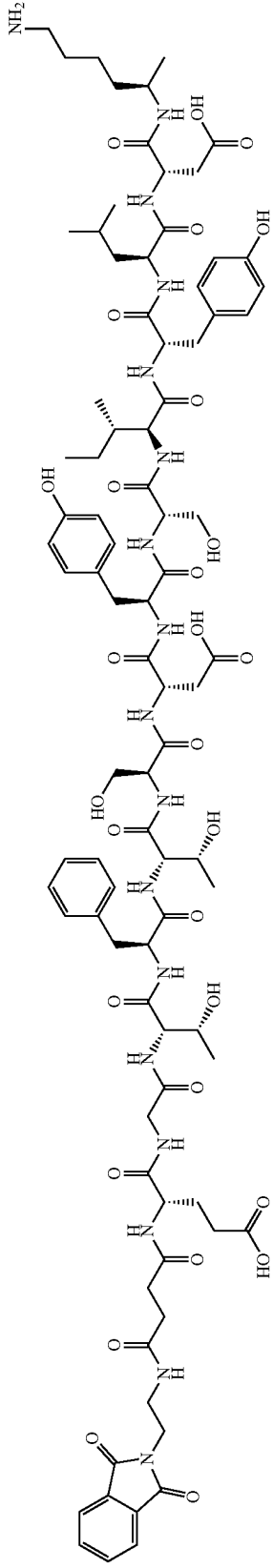
906
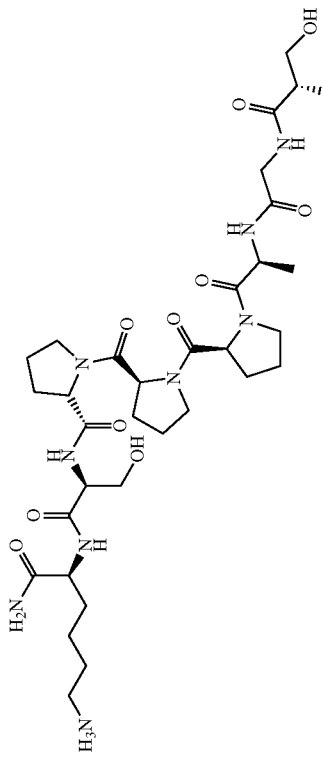
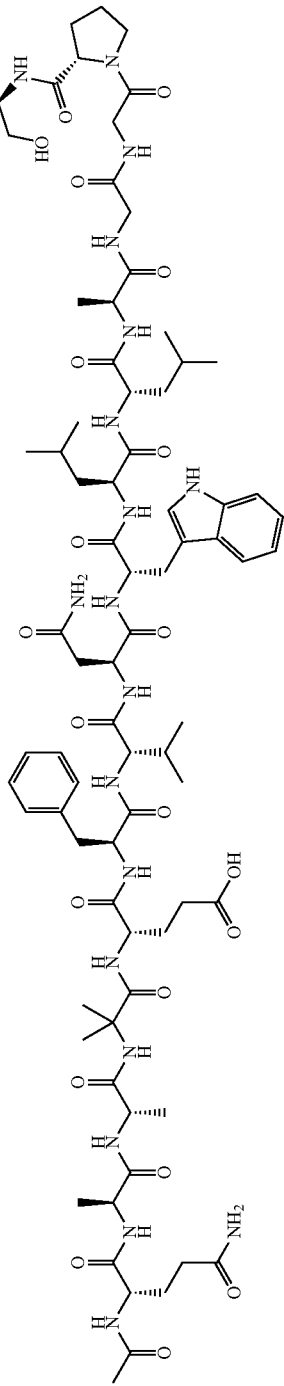

907
Compound 188
908
-continued
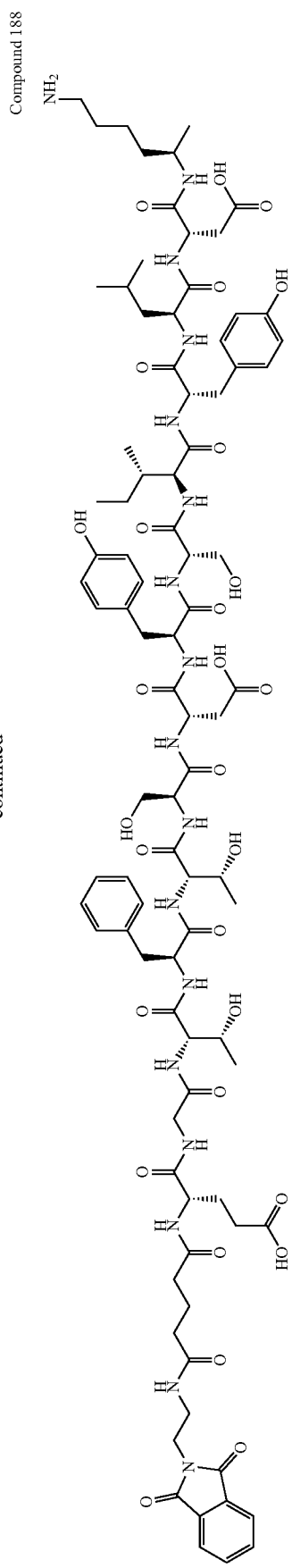
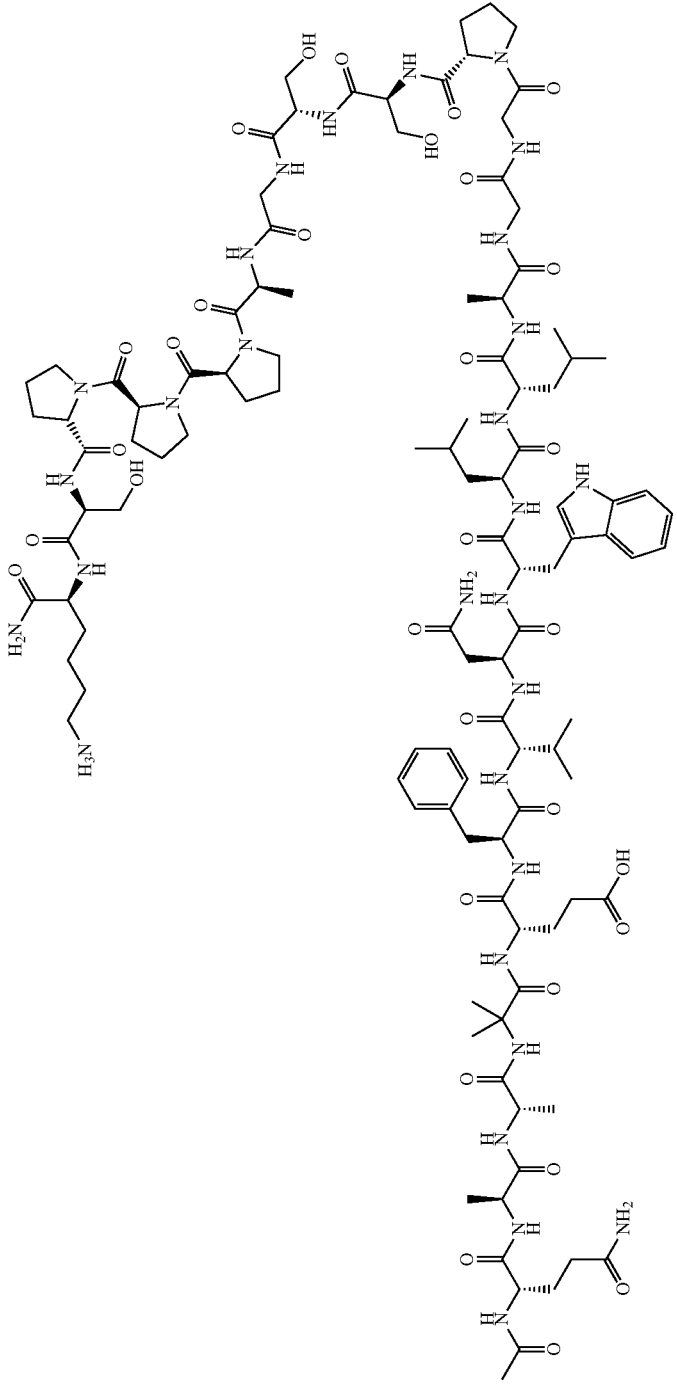

909                                                                 910
-continued
Compound 189
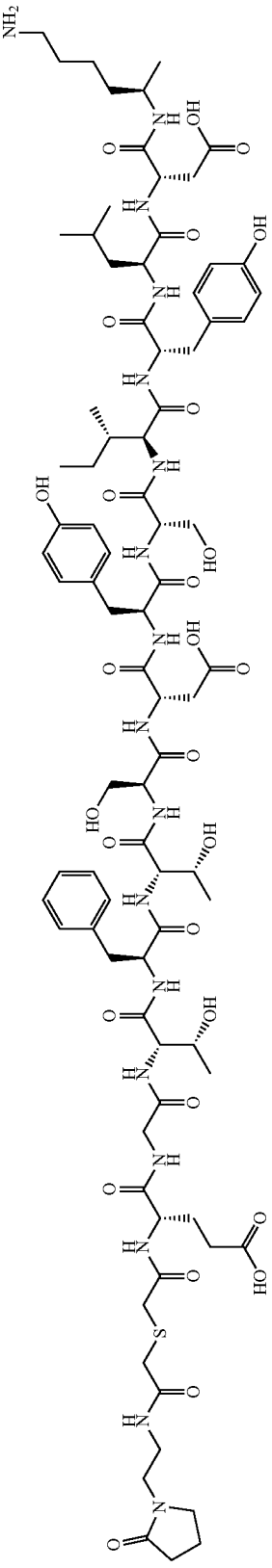
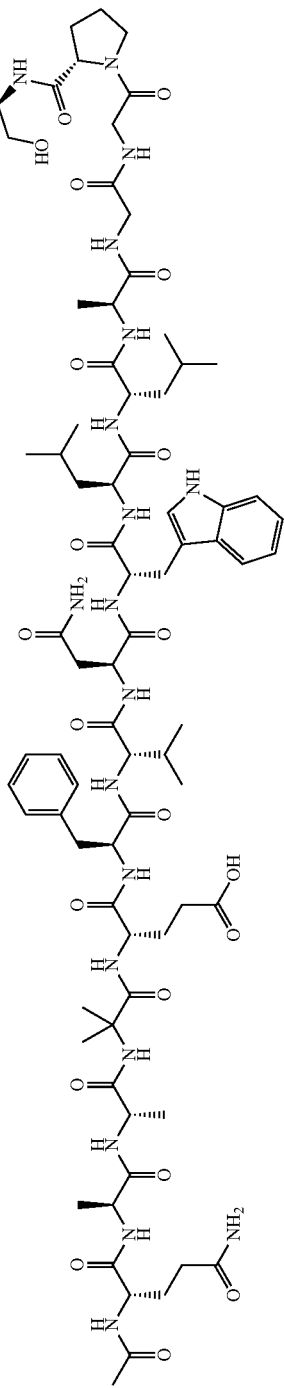

911
Compound 190
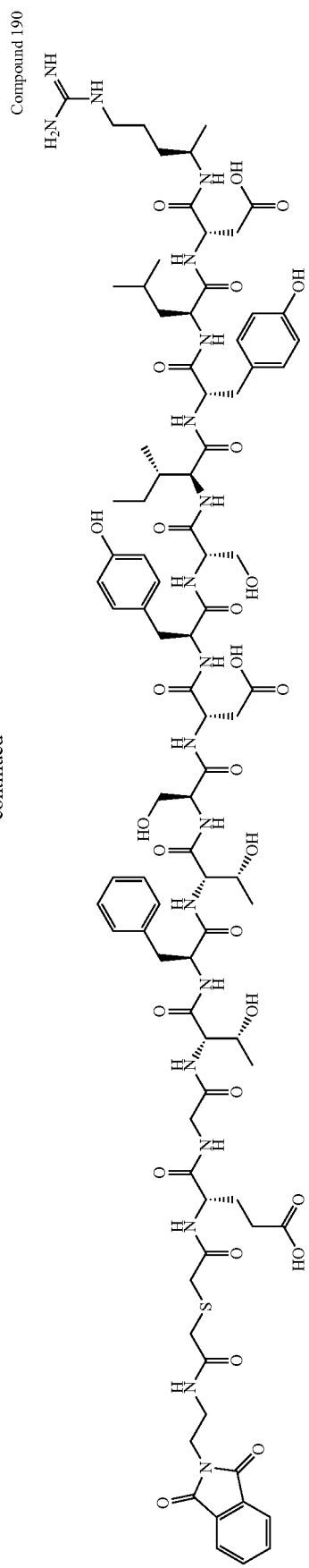
912
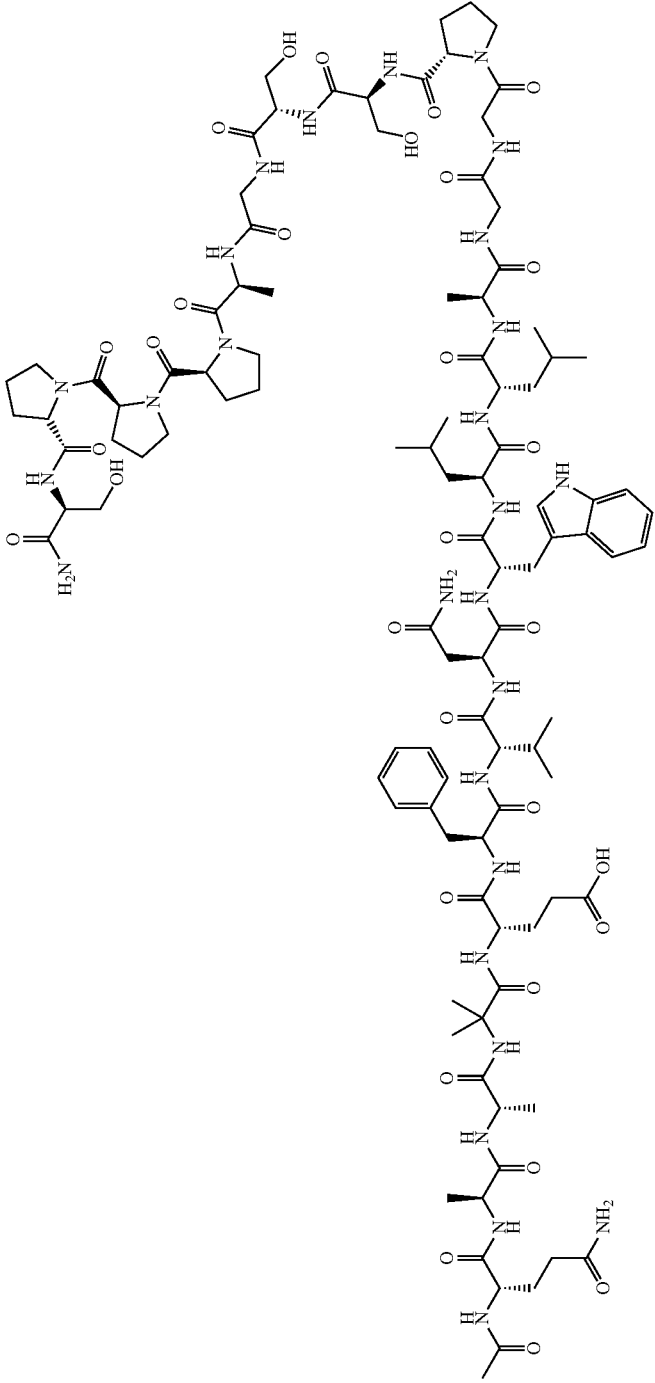

913
914
Compound 191
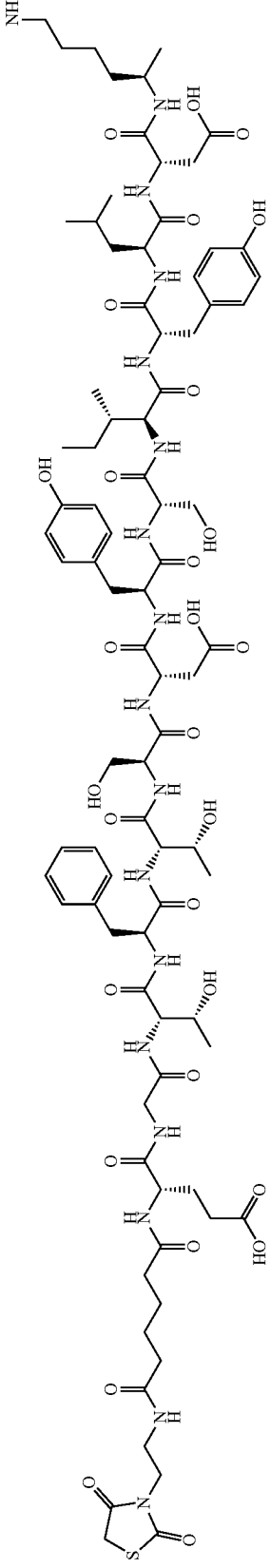
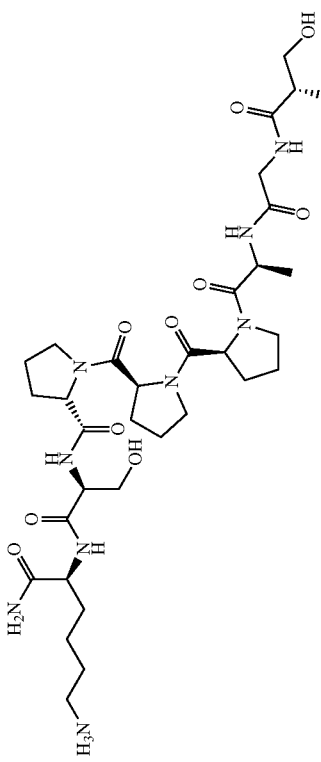
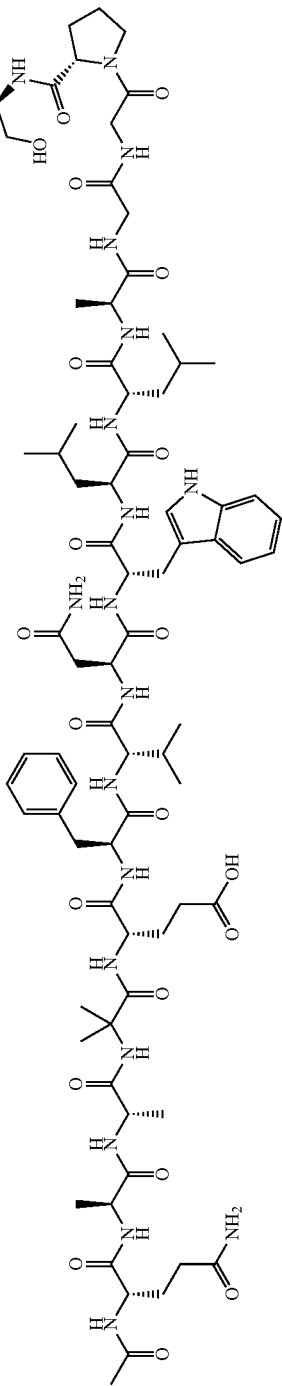

915
Compound 192
916
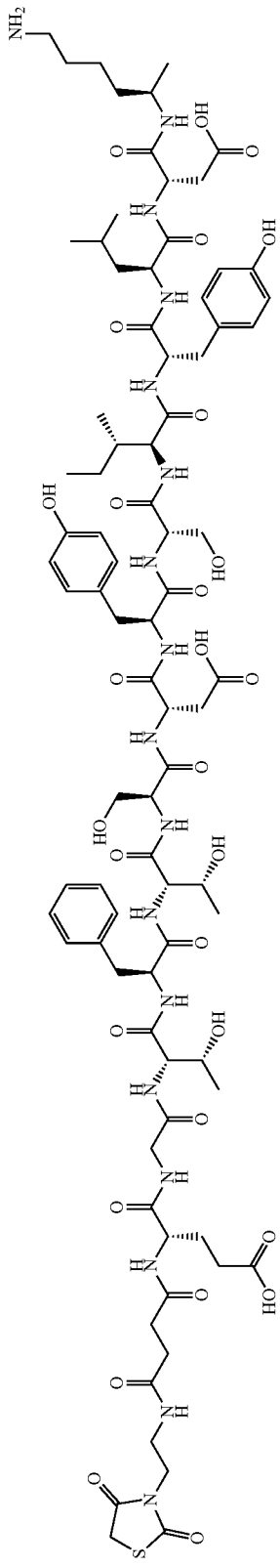
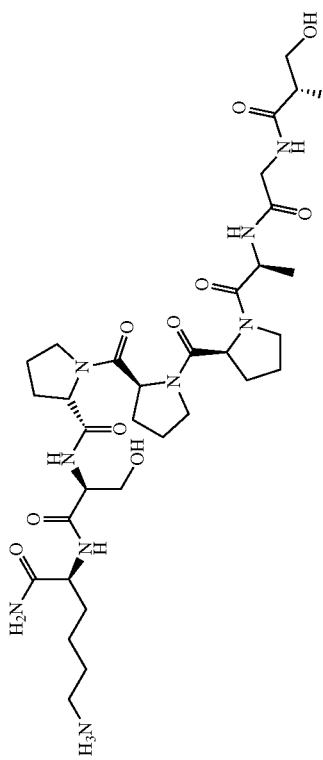
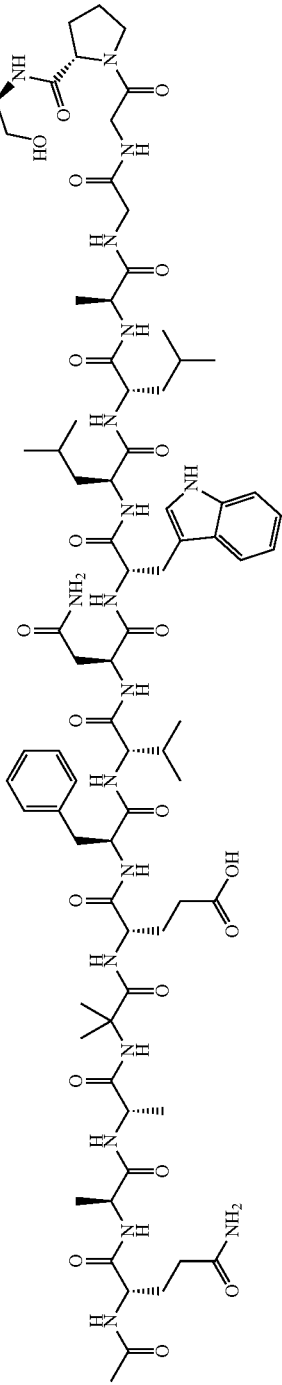

917 918
Compound 193
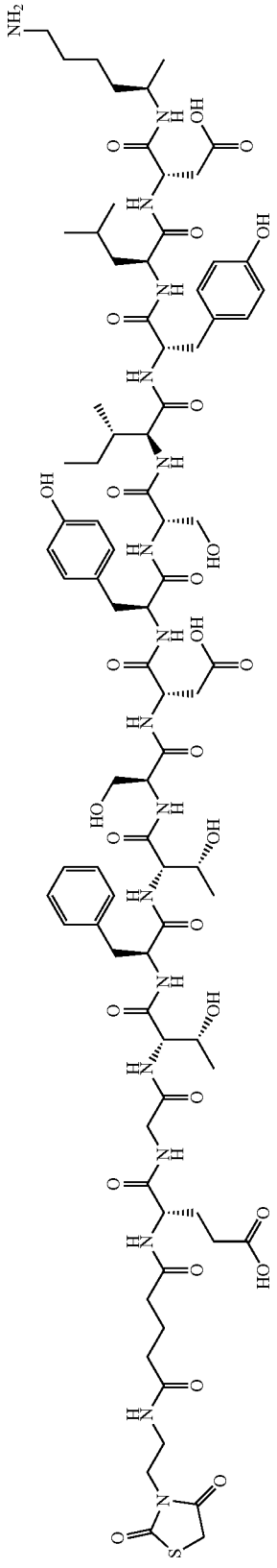
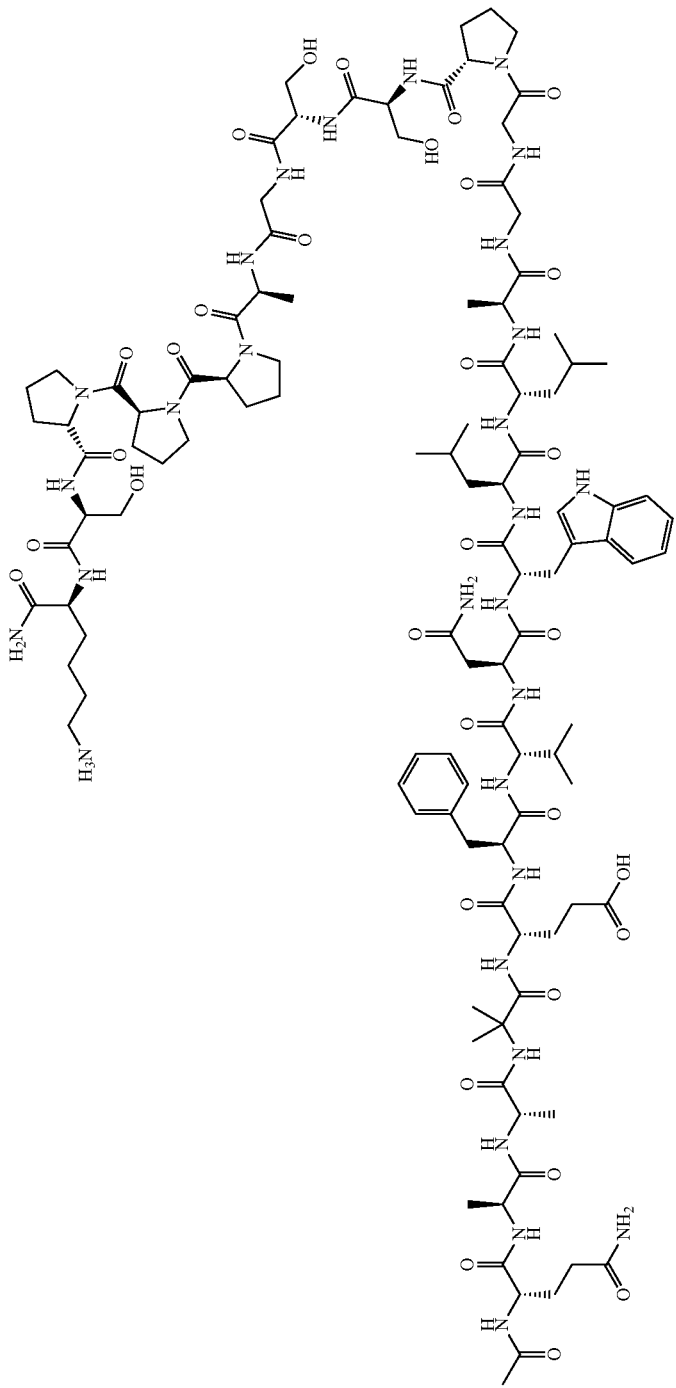

Compound 194
919
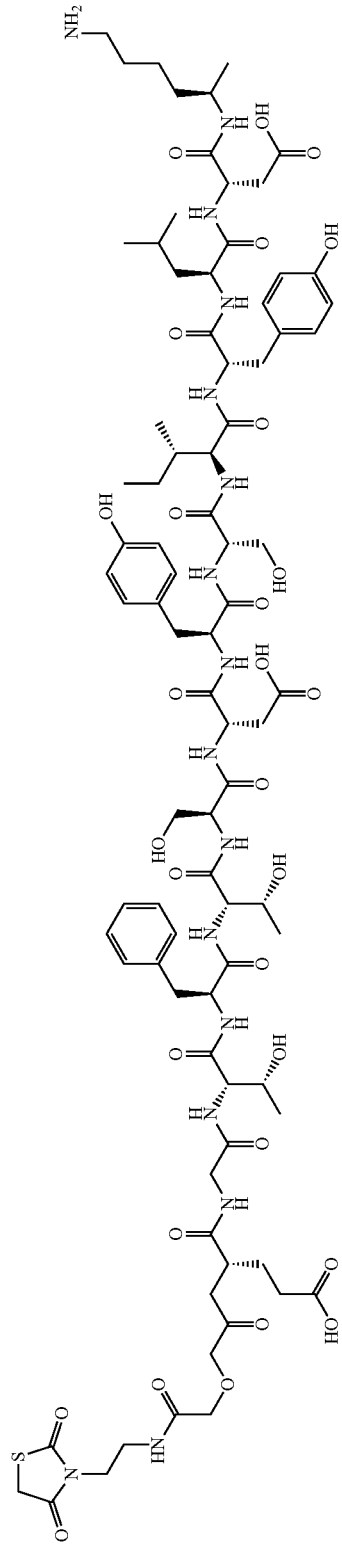
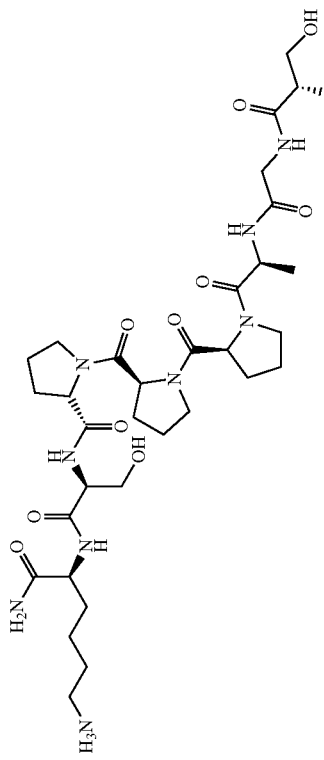
920
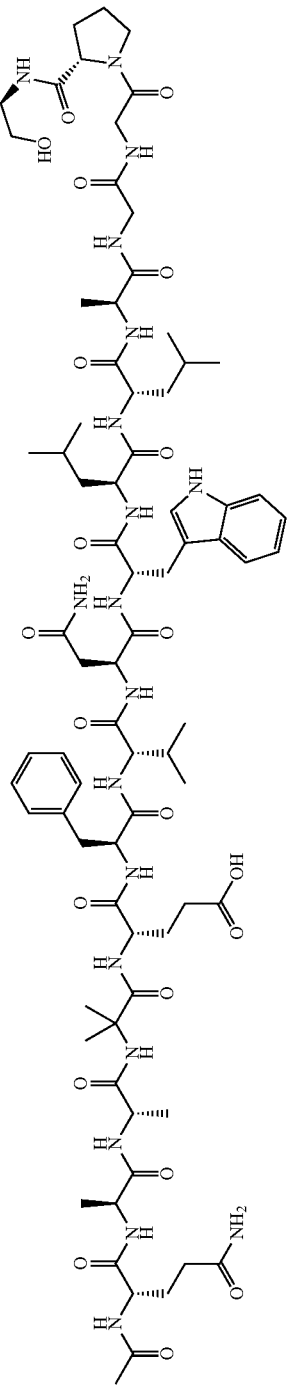

921
922
Compound 195 -continued
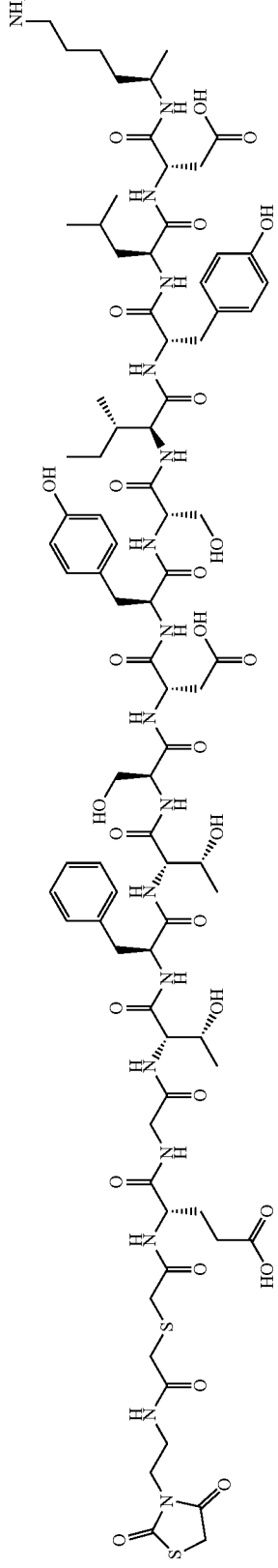
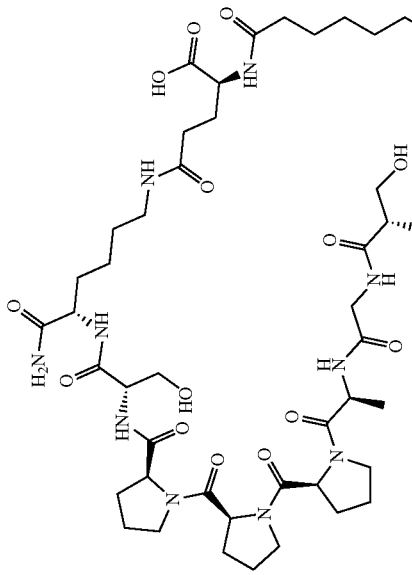
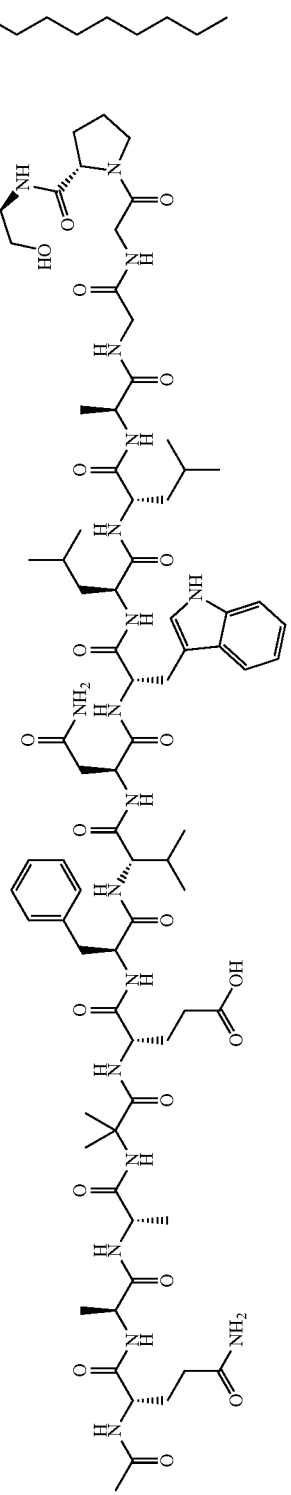

923
Compound 196
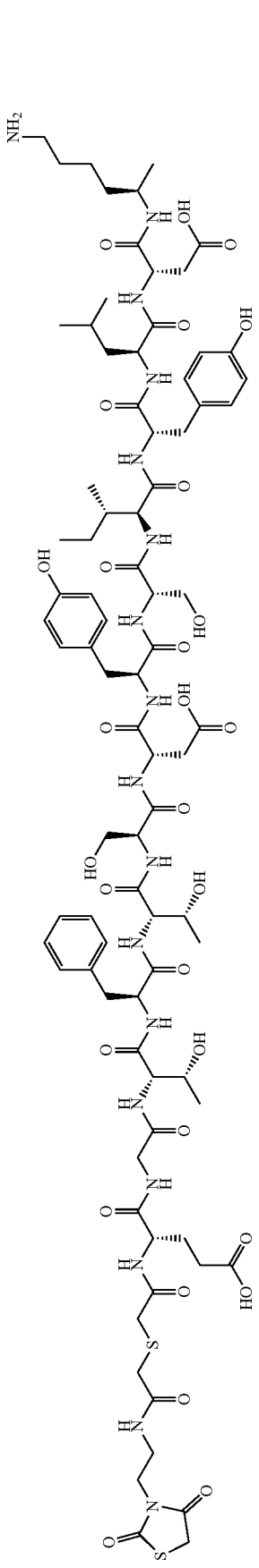
924
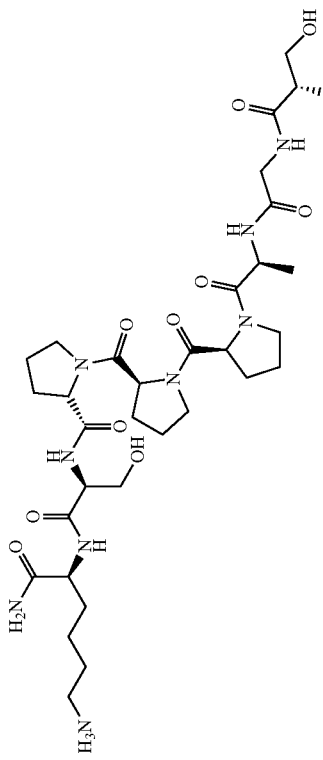
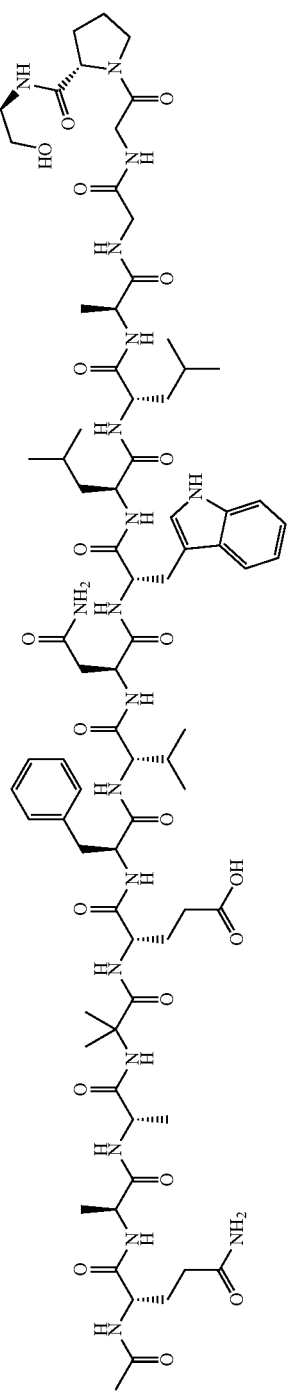

925
926
Compound 197
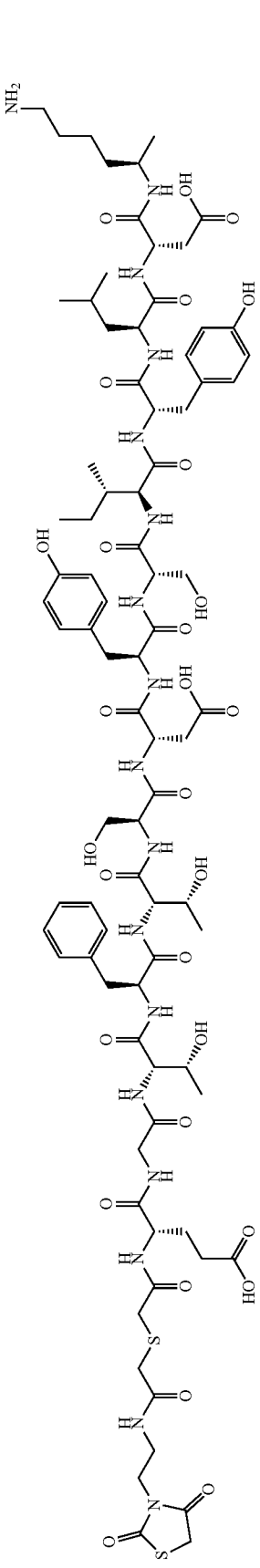
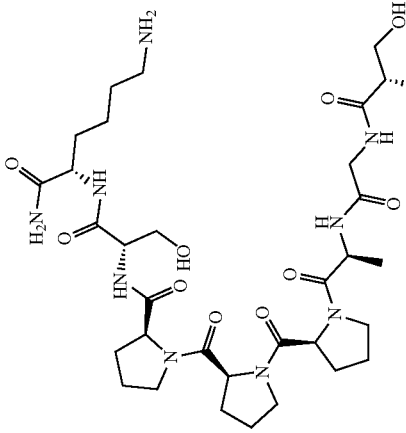
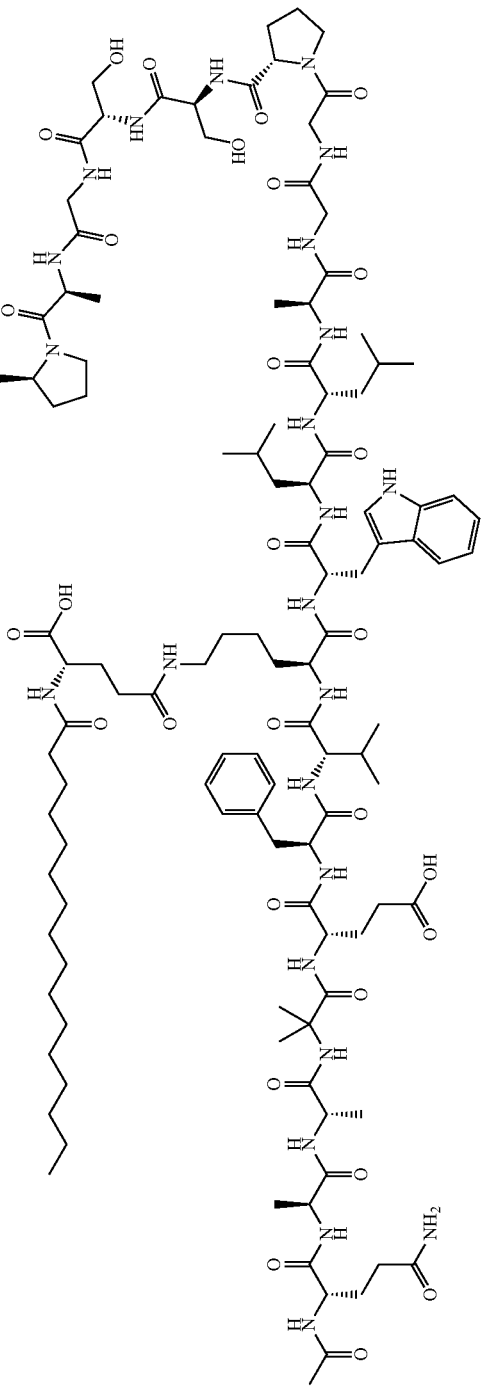

927
928
Compound 198
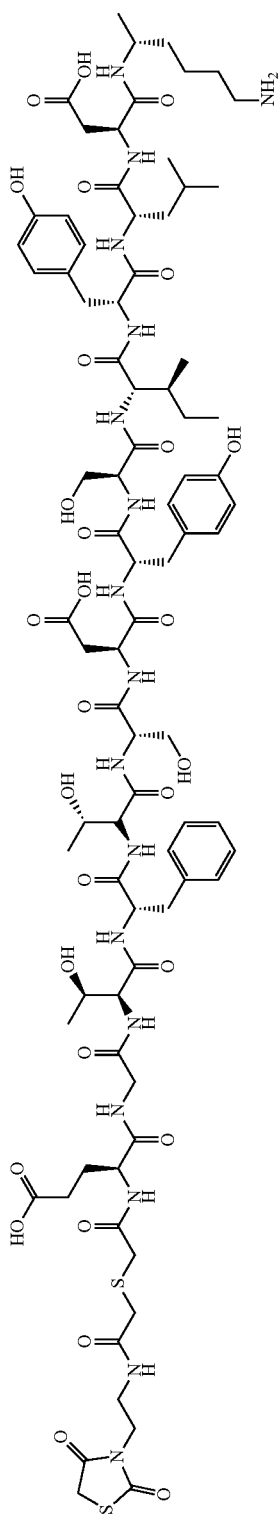
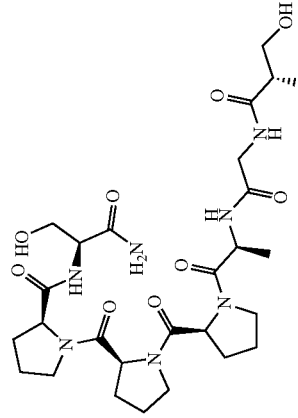
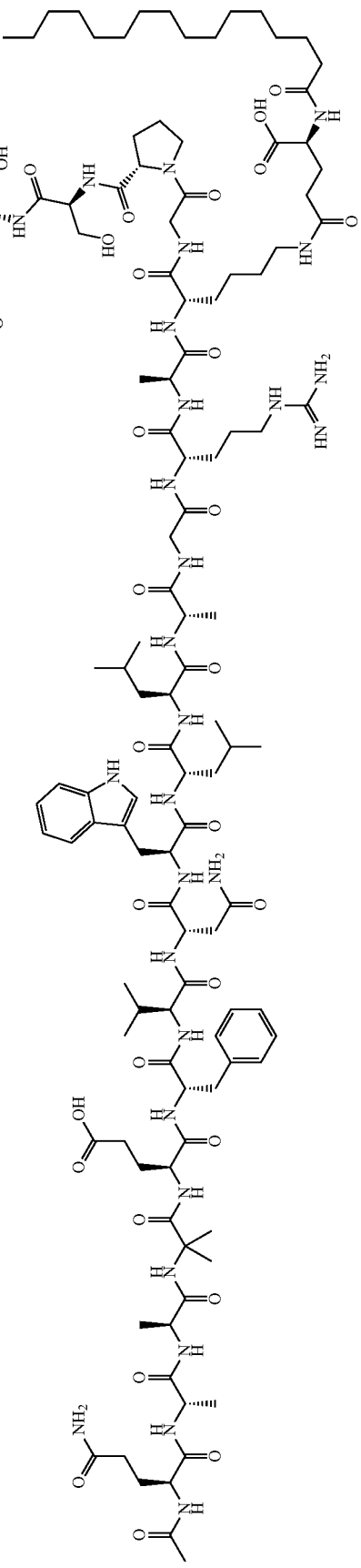

Compound 199
929
930
-continued
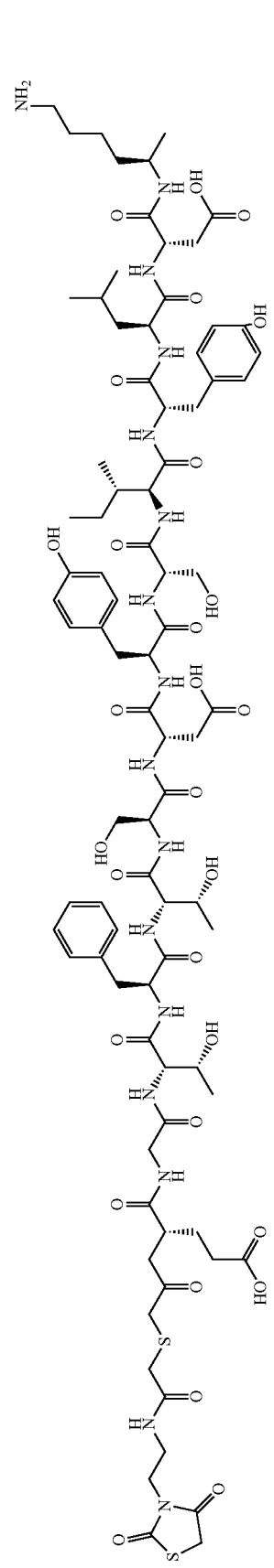
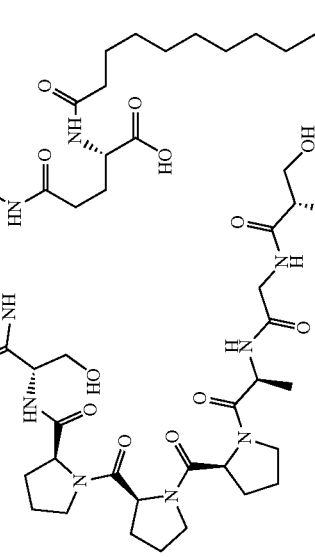
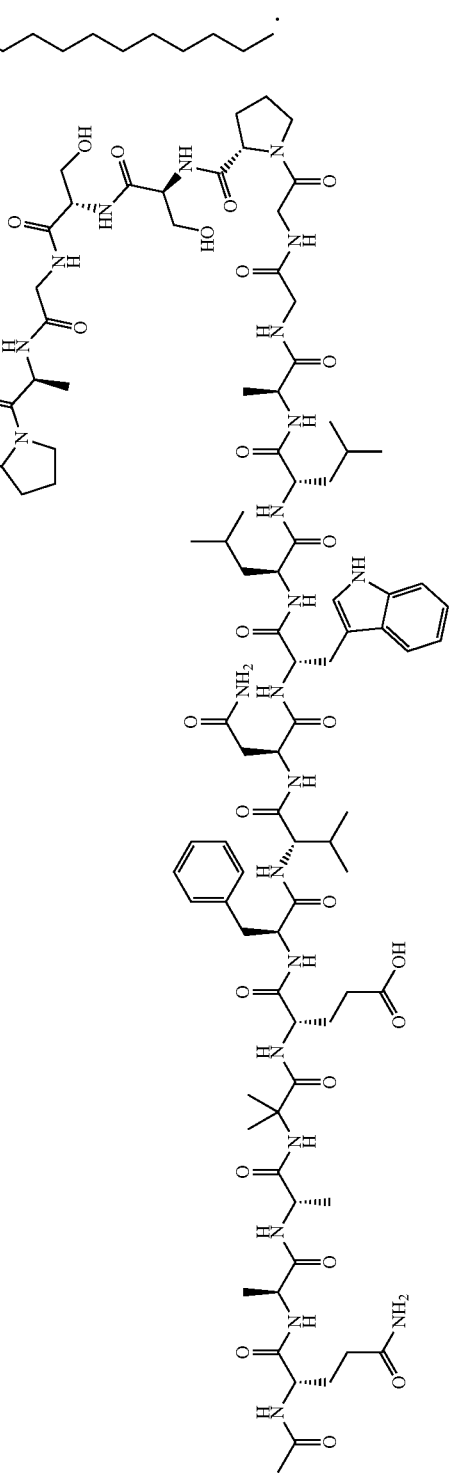

25. A pharmaceutical composition comprising a compound or salt as claimed in claim 1 and one or more pharmaceutically acceptable excipients.

26. A method for modulating GLP-1R and/or GIPR activity, the method comprising contacting GLP-1R and/or GIPR with a compound as claimed in claim 1.

27. A method for treating GLP-1R and/or GIPR induced aversion, nausea and/or vomiting in a subject, the method comprising administering to the subject an effective amount of a compound as claimed in claim 1.

28. A method for increasing insulin levels in a subject in need of such increasing, the method comprising administering to the subject an effective amount of a compound as claimed in claim 1.

29. A method for decreasing glucose levels in a subject in need of such decreasing, the method comprising administering to the subject an effective amount of a compound as claimed in claim 1.

30. A method for treating a disease, disorder, or condition selected from the group consisting of diabetes, NASH, obesity, fatty liver disease, and steatohepatitis in a subject in need thereof, the method comprising administering to the subject in need thereof an effective amount of a compound as claimed in claim 1.

31. The method of claim 30, wherein the subject in need thereof is a human.

32. The compound of claim 1, wherein —N(R$^4$)W has formula (XIV-A):

GTF(Xaa4)SD(Xaa7)S(Xaa9)(Xaa10)(Xaa11)(Xaa12)(Xaa13)QA(Xaa16)(Aib)-(Xaa18)F(Xaa20)(Xaa21)WL(Xaa24)(Xaa25)GGPSSGAPPPS-R$^5$ (SEQ ID NO: 3), wherein Xaa4 is T or I;
Xaa7 is Y, V, or L;
Xaa9 is I or S;
Xaa10 is Y, Q, or A;
Xaa11 is L, M, or L*;
Xaa12 is D or E;
Xaa13 is K, G, or E;
Xaa16 is A or V;
Xaa18 is E or L;
Xaa20 is V or I;
Xaa21 is N, A, or E;
Xaa24 is L or V; and
Xaa25 is A or K.

33. The compound of claim 1, wherein —N(R$^4$)W has formula (XIV-B):

GTFTSDYSIYLDKQAA(Aib)EFVNWL-LAGGPSSGAPPPS-R$^5$ (SEQ ID NO: 4).

34. The compound of claim 1, wherein —N(R$^4$)W is selected from the group consisting of:

| SEQ ID NO: | Sequence |
|---|---|
| 5 | GTFTSDYSIYLDKQAA(Aib)EFVNWLLAGGPSSGAPPPSK—NH$_2$ |
| 6 | GTFTSDYSIYLDKQAA(Aib)EFVNWLLAGGPSSGAPPPSK* |

K* =

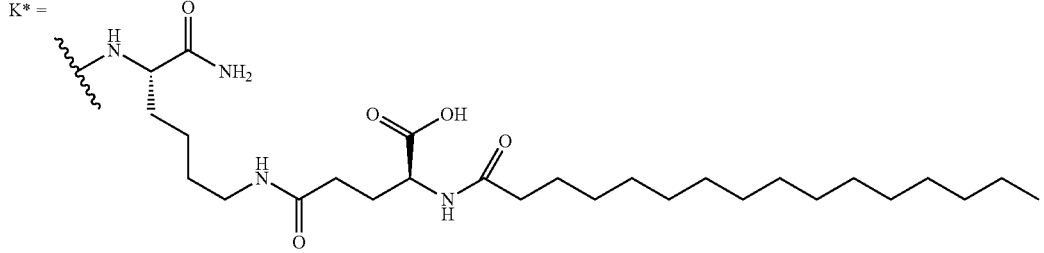 [SMILES: *N[C@@H](CCCCNC(=O)CC[C@H](NC(=O)CCCCCCCCCCCCCCC)C(=O)O)C(N)=O]

| 7 | GTFTSDYSIYLDKQAA(Aib)EFVNWLLAGGPSSGAPPPSK* |

K* =

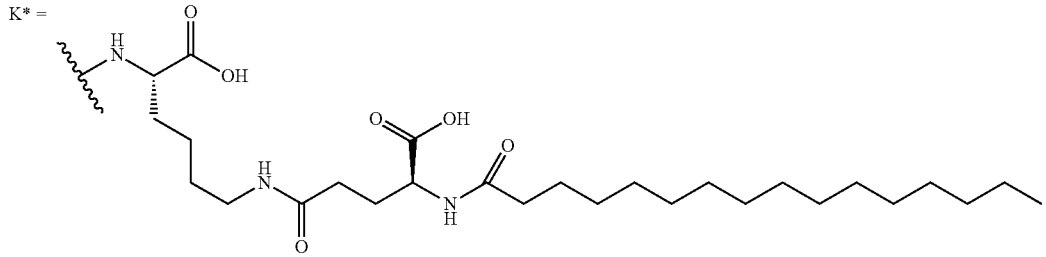 [SMILES: *N[C@@H](CCCCNC(=O)CC[C@H](NC(=O)CCCCCCCCCCCCCCC)C(=O)O)C(=O)O]

| 8 | GTFTSDYSIYLDKQAA(Aib)EFVNWLLAGGPSSGAPPPSK* |

K* =

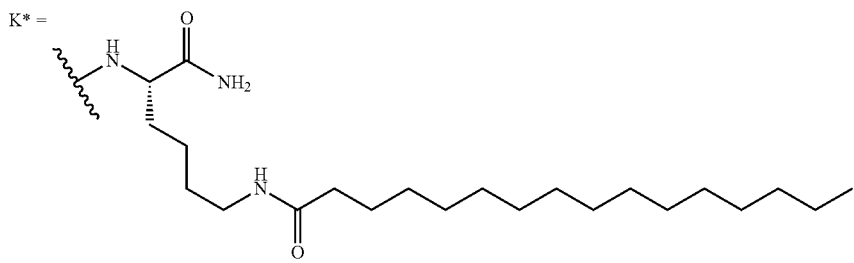 [SMILES: *N[C@@H](CCCCNC(=O)CCCCCCCCCCCCCCC)C(N)=O]

| SEQ ID NO: | Sequence |
|---|---|
| 9 | GTFTSDYSIYLDKQAA(Aib)EFVNWLLAGGPSSGAPPPSK\*, |

K* = 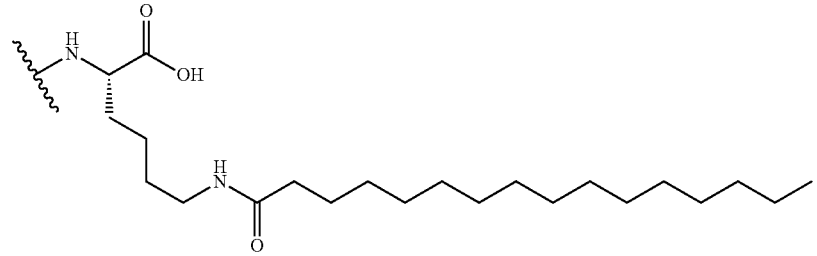

| 10 | **GTFTSDVSSYLEGQAAKEFIAWLVKGGPSSGAPPPSK\*—NH$_2$**, |

K* = 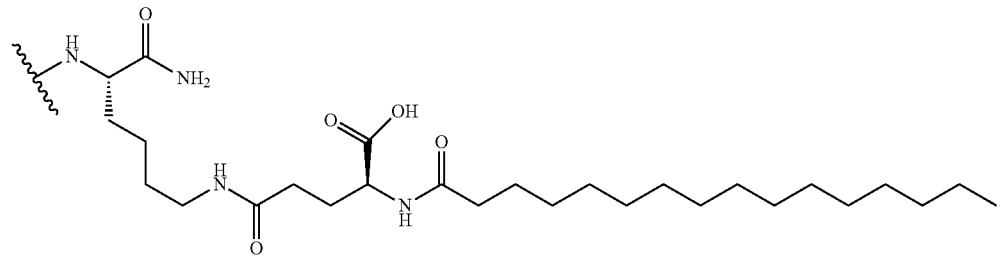

| 12 | GTFTSDLSIYLDKQAA(Aib)EFVNWLLAGGPSSGAPPPSK—NH$_2$ |
| 13 | GTFTSDYSIYLDEQAA(Aib)EFVNWLLAGGPSSGAPPPSK—NH$_2$ |
| 14 | GTFTSDYSIYLDKQAV(Aib)EFVNWLLAGGPSSGAPPPSK—NH$_2$ |
| 15 | GTFTSDYSIYLDKQAA(Aib)LFVNWLLAGGPSSGAPPPSK—NH$_2$ |
| 16 | GTFTSDYSIYLDKQAA(Aib)EFINWLLAGGPSSGAPPPSK—NH$_2$ |
| 17 | GTFTSDYSIYLDKQAA(Aib)EFVEWLLAGGPSSGAPPPSK—NH$_2$ |
| 18 | GTFTSDYSIYLDKQAV(Aib)EFINWLLAGGPSSGAPPPSK—NH$_2$ |
| 19 | **GTFTSDYSIQMDKQAA(Aib)EFVNWLLAGGPSSGAPPPSK\*—NH$_2$** |

K* = 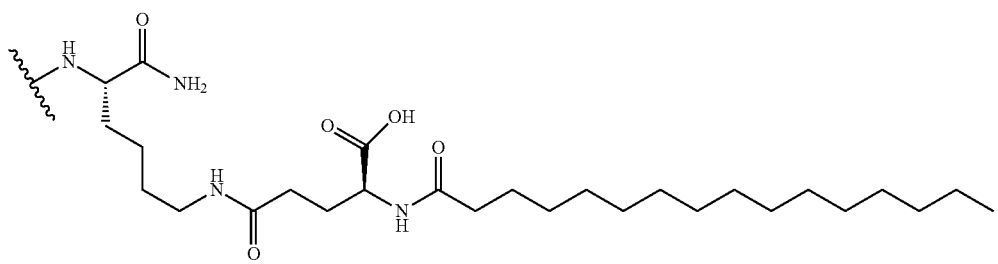

| 20 | **GTFTSDYSIAMDKQAA(Aib)EFVNWLLAGGPSSGAPPPSK\*—NH$_2$** |

K* = 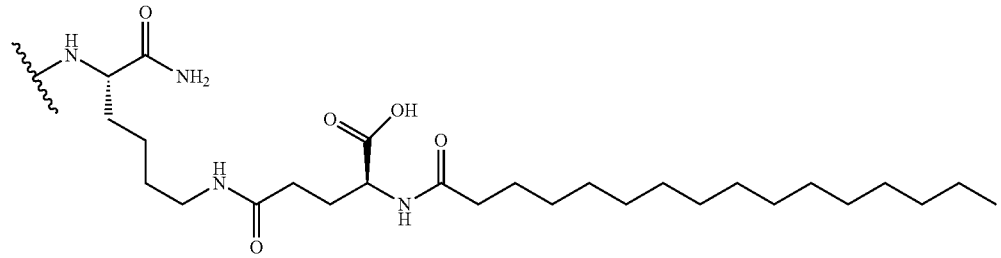

-continued
| SEQ ID NO: | Sequence |
|---|---|
| 21 | **GTFTSDYSIYL\*DKQAA(Aib)EFVNWLLAGGPSSGAPPPSK\*—NH$_2$** |
K* = 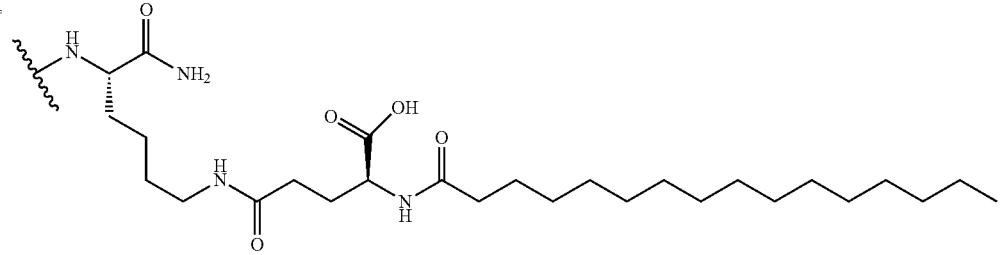
L* = 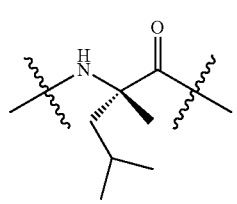
| 22 | GTFTSDYSIYLDRQAA(Aib)EFVNWLLAGGPSSGAPPPS—NH$_2$ |
| 28 | **GTFTSDYSIYLDKQAA(Aib)EFVNWLLAGGPSSGAPPPSK\*—NH$_2$** |
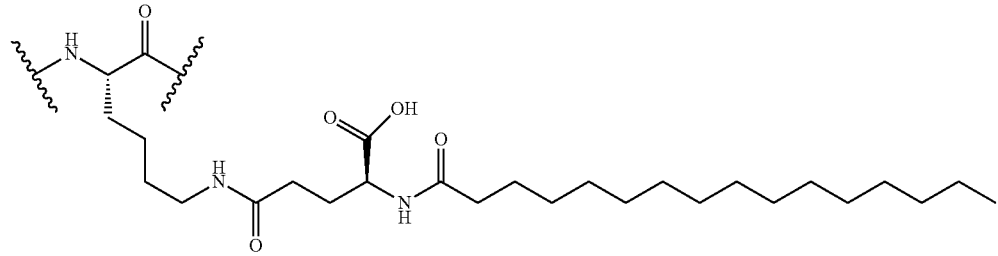 = K*
| 30 | **GTFTSDYSIYLDKQAV(Aib)EFVNWLLAGGPSSGAPPPSK\*—NH$_2$** |
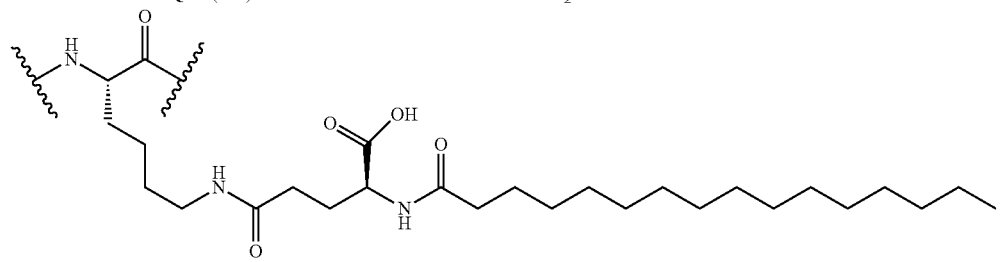 = K*.
\* \* \* \* \*

UNITED STATES PATENT AND TRADEMARK OFFICE
CERTIFICATE OF CORRECTION

PATENT NO. : 11,535,660 B1
APPLICATION NO. : 17/040653
DATED : December 27, 2022
INVENTOR(S) : Johan Enquist et al.

It is certified that error appears in the above-identified patent and that said Letters Patent is hereby corrected as shown below:

On the Title Page

Under Item (73), please correct the Assignee name from "Cannot Therapeutics, Inc." to --Carmot Therapeutics, Inc.--

Signed and Sealed this
Third Day of October, 2023

Katherine Kelly Vidal
*Director of the United States Patent and Trademark Office*

SEQUENCE LISTING

```
<160> NUMBER OF SEQ ID NOS: 58

<210> SEQ ID NO 1
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(33)
<223> OTHER INFORMATION: Any amino acid
<220> FEATURE:
<221> NAME/KEY: MISC_FEATURE
<222> LOCATION: (4)..(33)
<223> OTHER INFORMATION: This region may encompass 20-30 residues
<220> FEATURE:
<223> OTHER INFORMATION: See specification as filed for detailed
      description of substitutions and preferred embodiments

<400> SEQUENCE: 1

Gly Thr Phe Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Gly Pro Ser Ser Gly Ala Pro Pro Pro Ser
        35                  40

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Thr or Ile
<220> FEATURE:
<221> NAME/KEY: MOD_RES
<222> LOCATION: (7)..(7)
<223> OTHER INFORMATION: Tyr, Val or Leu
<220> FEATURE:
<221> NAME/KEY: MOD_RES
```

```
<222> LOCATION: (9)..(9)
<223> OTHER INFORMATION: Ile or Ser
<220> FEATURE:
<221> NAME/KEY: MOD_RES
<222> LOCATION: (10)..(10)
<223> OTHER INFORMATION: Tyr, Gln or Ala
<220> FEATURE:
<221> NAME/KEY: MOD_RES
<222> LOCATION: (11)..(11)
<223> OTHER INFORMATION: Leu, Met or 2-amino-2-methylpentanoic acid
<220> FEATURE:
<221> NAME/KEY: MOD_RES
<222> LOCATION: (12)..(12)
<223> OTHER INFORMATION: Asp or Glu
<220> FEATURE:
<221> NAME/KEY: MOD_RES
<222> LOCATION: (13)..(13)
<223> OTHER INFORMATION: Lys, Gly or Glu
<220> FEATURE:
<221> NAME/KEY: MOD_RES
<222> LOCATION: (16)..(16)
<223> OTHER INFORMATION: Ala or Val
<220> FEATURE:
<221> NAME/KEY: MOD_RES
<222> LOCATION: (17)..(17)
<223> OTHER INFORMATION: 2-aminoisobutyric acid or Lys
<220> FEATURE:
<221> NAME/KEY: MOD_RES
<222> LOCATION: (18)..(18)
<223> OTHER INFORMATION: Glu or Leu
<220> FEATURE:
<221> NAME/KEY: MOD_RES
<222> LOCATION: (20)..(20)
<223> OTHER INFORMATION: Val or Ile
<220> FEATURE:
<221> NAME/KEY: MOD_RES
<222> LOCATION: (21)..(21)
<223> OTHER INFORMATION: Asn, Ala or Glu
<220> FEATURE:
<221> NAME/KEY: MOD_RES
<222> LOCATION: (24)..(24)
<223> OTHER INFORMATION: Leu or Val
<220> FEATURE:
<221> NAME/KEY: MOD_RES
<222> LOCATION: (25)..(25)
<223> OTHER INFORMATION: Ala or Lys
<220> FEATURE:
<223> OTHER INFORMATION: See specification as filed for detailed
      description of substitutions and preferred embodiments

<400> SEQUENCE: 2

Gly Thr Phe Xaa Ser Asp Xaa Ser Xaa Xaa Xaa Xaa Xaa Gln Ala Xaa
1               5                   10                  15

Xaa Xaa Phe Xaa Xaa Trp Leu Xaa Xaa Gly Gly Pro Ser Ser Gly Ala
            20                  25                  30

Pro Pro Pro Ser
        35

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Thr or Ile
<220> FEATURE:
<221> NAME/KEY: MOD_RES
<222> LOCATION: (7)..(7)
<223> OTHER INFORMATION: Tyr, Val or Leu
<220> FEATURE:
<221> NAME/KEY: MOD_RES
```

```
<222> LOCATION: (9)..(9)
<223> OTHER INFORMATION: Ile or Ser
<220> FEATURE:
<221> NAME/KEY: MOD_RES
<222> LOCATION: (10)..(10)
<223> OTHER INFORMATION: Tyr, Gln or Ala
<220> FEATURE:
<221> NAME/KEY: MOD_RES
<222> LOCATION: (11)..(11)
<223> OTHER INFORMATION: Leu, Met or 2-amino-2-methylpentanoic acid
<220> FEATURE:
<221> NAME/KEY: MOD_RES
<222> LOCATION: (12)..(12)
<223> OTHER INFORMATION: Asp or Glu
<220> FEATURE:
<221> NAME/KEY: MOD_RES
<222> LOCATION: (13)..(13)
<223> OTHER INFORMATION: Lys, Gly or Glu
<220> FEATURE:
<221> NAME/KEY: MOD_RES
<222> LOCATION: (16)..(16)
<223> OTHER INFORMATION: Ala or Val
<220> FEATURE:
<221> NAME/KEY: MOD_RES
<222> LOCATION: (17)..(17)
<223> OTHER INFORMATION: 2-aminoisobutyric acid
<220> FEATURE:
<221> NAME/KEY: MOD_RES
<222> LOCATION: (18)..(18)
<223> OTHER INFORMATION: Glu or Leu
<220> FEATURE:
<221> NAME/KEY: MOD_RES
<222> LOCATION: (20)..(20)
<223> OTHER INFORMATION: Val or Ile
<220> FEATURE:
<221> NAME/KEY: MOD_RES
<222> LOCATION: (21)..(21)
<223> OTHER INFORMATION: Asn, Ala or Glu
<220> FEATURE:
<221> NAME/KEY: MOD_RES
<222> LOCATION: (24)..(24)
<223> OTHER INFORMATION: Leu or Val
<220> FEATURE:
<221> NAME/KEY: MOD_RES
<222> LOCATION: (25)..(25)
<223> OTHER INFORMATION: Ala or Lys
<220> FEATURE:
<223> OTHER INFORMATION: See specification as filed for detailed
      description of substitutions and preferred embodiments

<400> SEQUENCE: 3

Gly Thr Phe Xaa Ser Asp Xaa Ser Xaa Xaa Xaa Xaa Gln Ala Xaa
1               5                  10                  15

Xaa Xaa Phe Xaa Xaa Trp Leu Xaa Xaa Gly Gly Pro Ser Ser Gly Ala
            20                  25                  30

Pro Pro Pro Ser
        35

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid

<400> SEQUENCE: 4

Gly Thr Phe Thr Ser Asp Tyr Ser Ile Tyr Leu Asp Lys Gln Ala Ala
1               5                  10                  15
```

-continued

Xaa Glu Phe Val Asn Trp Leu Leu Ala Gly Gly Pro Ser Ser Gly Ala
            20                  25                  30

Pro Pro Pro Ser
        35

<210> SEQ ID NO 5
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid

<400> SEQUENCE: 5

Gly Thr Phe Thr Ser Asp Tyr Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
        35

<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 6

Gly Thr Phe Thr Ser Asp Tyr Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
        35

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 7

Gly Thr Phe Thr Ser Asp Tyr Ser Ile Tyr Leu Asp Lys Gln Ala Ala
1               5                   10                  15

Xaa Glu Phe Val Asn Trp Leu Leu Ala Gly Gly Pro Ser Ser Gly Ala

-continued

```
                    20                  25                  30

Pro Pro Pro Ser Lys
            35

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 8

Gly Thr Phe Thr Ser Asp Tyr Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
            35

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 9

Gly Thr Phe Thr Ser Asp Tyr Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
            35

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 10

Gly Thr Phe Thr Ser Asp Val Ser Ser Tyr Leu Glu Gly Gln Ala Ala
1               5                   10                  15

Lys Glu Phe Ile Ala Trp Leu Val Lys Gly Gly Pro Ser Ser Gly Ala
            20                  25                  30
```

Pro Pro Pro Ser Lys
        35

<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 11

Gly Thr Phe Ile Ser Asp Tyr Ser Ile Ala Met Asp Lys Ile Arg Gln
1               5                   10                  15

Gln Asp Phe Val Asn Trp Leu Leu Ala Gln Arg Gly Pro Ser Ser Gly
            20                  25                  30

Ala Pro Pro Pro Ser Lys
        35

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid

<400> SEQUENCE: 12

Gly Thr Phe Thr Ser Asp Leu Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
        35

<210> SEQ ID NO 13
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid

<400> SEQUENCE: 13

Gly Thr Phe Thr Ser Asp Tyr Ser Ile Tyr Leu Asp Glu Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
        35

<210> SEQ ID NO 14
<211> LENGTH: 37
<212> TYPE: PRT
<213> ORGANISM: Artificial Sequence -continued
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid

<400> SEQUENCE: 14

Gly Thr Phe Thr Ser Asp Tyr Ser Ile Tyr Leu Asp Lys Gln Ala Val
1               5                   10                  15

Xaa Glu Phe Val Asn Trp Leu Leu Ala Gly Gly Pro Ser Ser Gly Ala
            20                  25                  30

Pro Pro Pro Ser Lys
            35

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid

<400> SEQUENCE: 15

Gly Thr Phe Thr Ser Asp Tyr Ser Ile Tyr Leu Asp Lys Gln Ala Ala
1               5                   10                  15

Xaa Leu Phe Val Asn Trp Leu Leu Ala Gly Gly Pro Ser Ser Gly Ala
            20                  25                  30

Pro Pro Pro Ser Lys
            35

<210> SEQ ID NO 16
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid

<400> SEQUENCE: 16

Gly Thr Phe Thr Ser Asp Tyr Ser Ile Tyr Leu Asp Lys Gln Ala Ala
1               5                   10                  15

Xaa Glu Phe Ile Asn Trp Leu Leu Ala Gly Gly Pro Ser Ser Gly Ala
            20                  25                  30

Pro Pro Pro Ser Lys
            35

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid

<400> SEQUENCE: 17

Gly Thr Phe Thr Ser Asp Tyr Ser Ile Tyr Leu Asp Lys Gln Ala Ala
1               5                   10                  15

Xaa Glu Phe Val Glu Trp Leu Leu Ala Gly Gly Pro Ser Ser Gly Ala
            20                  25                  30

Pro Pro Pro Ser Lys
        35

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid

<400> SEQUENCE: 18

Gly Thr Phe Thr Ser Asp Tyr Ser Ile Tyr Leu Asp Lys Gln Ala Val
1               5                   10                  15

Xaa Glu Phe Ile Asn Trp Leu Leu Ala Gly Gly Pro Ser Ser Gly Ala
            20                  25                  30

Pro Pro Pro Ser Lys
        35

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 19

Gly Thr Phe Thr Ser Asp Tyr Ser Ile Gln Met Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
        35

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

```
<400> SEQUENCE: 20

Gly Thr Phe Thr Ser Asp Tyr Ser Ile Ala Met Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
            35

<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: 2-amino-2-methylpentanoic acid
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 21

Gly Thr Phe Thr Ser Asp Tyr Ser Ile Tyr Xaa Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
            35

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid

<400> SEQUENCE: 22

Gly Thr Phe Thr Ser Asp Tyr Ser Ile Tyr Leu Asp Arg Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser
            35

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid
<220> FEATURE:
```

```
<223> OTHER INFORMATION: See specification as filed for detailed
      description of substitutions and preferred embodiments

<400> SEQUENCE: 23

Glu Gly Thr Phe Thr Ser Asp Tyr Ser Ile Tyr Leu Asp Lys Gln Ala
1               5                   10                  15

Val Xaa Glu Phe Val Asn Trp Leu Leu Ala Gly Gly Pro Ser Ser Gly
            20                  25                  30

Ala Pro Pro Pro Ser Lys
            35

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 24

Glu Gly Thr Phe Thr Ser Asp Tyr Ser Ile Tyr Leu Asp Lys Gln Ala
1               5                   10                  15

Ala Xaa Glu Phe Val Lys Trp Leu Leu Ala Gly Gly Pro Ser Ser Gly
            20                  25                  30

Ala Pro Pro Pro Ser Lys
            35

<210> SEQ ID NO 25
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 25

Glu Gly Thr Phe Thr Ser Asp Tyr Ser Ile Tyr Leu Asp Lys Gln Ala
1               5                   10                  15

Ala Xaa Glu Phe Val Asn Trp Leu Leu Ala Gly Arg Gly Lys Gly Pro
            20                  25                  30

Ser Ser Gly Ala Pro Pro Pro Ser
            35                  40

<210> SEQ ID NO 26
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments
```

<400> SEQUENCE: 26

Glu Gly Thr Phe Thr Ser Asp Tyr Ser Ile Tyr Leu Asp Lys Gln Ala
1               5                   10                  15

Ala Lys Glu Phe Val Asn Trp Leu Leu Ala Gly Gly Pro Ser Ser Gly
            20                  25                  30

Ala Pro Pro Pro Ser Lys
        35

<210> SEQ ID NO 27
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 27

Glu Gly Thr Phe Thr Ser Asp Lys Ser Ile Tyr Leu Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser Lys
        35

<210> SEQ ID NO 28
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 28

Gly Thr Phe Thr Ser Asp Tyr Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
        35

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: 2-amino-3-(4-hydroxyphenyl)-2-methylpropanoic
      acid

```
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 29

Gly Thr Phe Thr Ser Asp Tyr Ser Ile Xaa Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
        35

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 30

Gly Thr Phe Thr Ser Asp Tyr Ser Ile Tyr Leu Asp Lys Gln Ala Val
1               5                   10                  15

Xaa Glu Phe Val Asn Trp Leu Leu Ala Gly Gly Pro Ser Ser Gly Ala
            20                  25                  30

Pro Pro Pro Ser Lys
        35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 31

Gly Thr Phe Thr Ser Asp Tyr Ser Ile Tyr Leu Asp Lys Gln Ala Ala
1               5                   10                  15

Xaa Glu Phe Val Lys Trp Leu Leu Ala Gly Gly Pro Ser Ser Gly Ala
            20                  25                  30

Pro Pro Pro Ser Lys
        35

<210> SEQ ID NO 32
<211> LENGTH: 39
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 32

Gly Thr Phe Thr Ser Asp Tyr Ser Ile Tyr Leu Asp Lys Gln Ala Ala
1               5                   10                  15

Xaa Glu Phe Val Asn Trp Leu Leu Ala Gly Arg Gly Lys Gly Pro Ser
            20                  25                  30

Ser Gly Ala Pro Pro Ser
        35

<210> SEQ ID NO 33
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 33

Gly Thr Phe Thr Ser Asp Tyr Ser Ile Tyr Leu Asp Lys Gln Ala Ala
1               5                   10                  15

Lys Glu Phe Val Asn Trp Leu Leu Ala Gly Gly Pro Ser Ser Gly Ala
            20                  25                  30

Pro Pro Pro Ser Lys
        35

<210> SEQ ID NO 34
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 34

Gly Thr Phe Thr Ser Asp Lys Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Lys
        35

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<220> FEATURE:
<221> NAME/KEY: MOD_RES
<222> LOCATION: (4)..(4)
<223> OTHER INFORMATION: Thr or Ile
<220> FEATURE:
<221> NAME/KEY: MOD_RES
<222> LOCATION: (7)..(7)
<223> OTHER INFORMATION: Tyr, Val, Leu or Lys
<220> FEATURE:
<221> NAME/KEY: MOD_RES
<222> LOCATION: (9)..(9)
<223> OTHER INFORMATION: Ile or Ser
<220> FEATURE:
<221> NAME/KEY: MOD_RES
<222> LOCATION: (10)..(10)
<223> OTHER INFORMATION: Tyr, 2-amino-3-(4-hydroxyphenyl)-2-
     methylpropanoic acid, Gln, Ala or 2-aminoisobutyric acid
<220> FEATURE:
<221> NAME/KEY: MOD_RES
<222> LOCATION: (11)..(11)
<223> OTHER INFORMATION: Leu, Met or 2-amino-2-methylpentanoic acid
<220> FEATURE:
<221> NAME/KEY: MOD_RES
<222> LOCATION: (12)..(12)
<223> OTHER INFORMATION: Asp or Glu
<220> FEATURE:
<221> NAME/KEY: MOD_RES
<222> LOCATION: (13)..(13)
<223> OTHER INFORMATION: Lys, Gly, Arg or Glu
<220> FEATURE:
<221> NAME/KEY: MOD_RES
<222> LOCATION: (14)..(14)
<223> OTHER INFORMATION: Gln or Ile
<220> FEATURE:
<221> NAME/KEY: MOD_RES
<222> LOCATION: (15)..(15)
<223> OTHER INFORMATION: Ala, His or Arg
<220> FEATURE:
<221> NAME/KEY: MOD_RES
<222> LOCATION: (16)..(16)
<223> OTHER INFORMATION: Ala, Gln or Val
<220> FEATURE:
<221> NAME/KEY: MOD_RES
<222> LOCATION: (17)..(17)
<223> OTHER INFORMATION: Ala, 2-aminoisobutyric acid, Lys or Gln
<220> FEATURE:
<221> NAME/KEY: MOD_RES
<222> LOCATION: (18)..(18)
<223> OTHER INFORMATION: Ala, Asp, Glu, 2-aminoisobutyric acid or Leu
<220> FEATURE:
<221> NAME/KEY: MOD_RES
<222> LOCATION: (19)..(19)
<223> OTHER INFORMATION: Phe or Ala
<220> FEATURE:
<221> NAME/KEY: MOD_RES
<222> LOCATION: (20)..(20)
<223> OTHER INFORMATION: Val or Ile
<220> FEATURE:
<221> NAME/KEY: MOD_RES
<222> LOCATION: (21)..(21)
<223> OTHER INFORMATION: Asn, Ala, Gln, Lys or Glu
<220> FEATURE:
<221> NAME/KEY: MOD_RES
<222> LOCATION: (24)..(24)
<223> OTHER INFORMATION: Ile, Leu or Val
<220> FEATURE:
<221> NAME/KEY: MOD_RES
<222> LOCATION: (25)..(25)
<223> OTHER INFORMATION: Ala, Lys or Ile
<220> FEATURE:
<221> NAME/KEY: MOD_RES
<222> LOCATION: (26)..(29)
<223> OTHER INFORMATION: This region may encompass 'Gly-Arg-Gly-Lys' or
     'Gln-Arg' or 'Gln' or 'Gly'
<220> FEATURE:
<221> NAME/KEY: MOD_RES
<222> LOCATION: (39)..(39)
<223> OTHER INFORMATION: Ser or absent
<220> FEATURE:
```

<223> OTHER INFORMATION: See specification as filed for detailed
      description of substitutions and preferred embodiments

<400> SEQUENCE: 35

Gly Thr Phe Xaa Ser Asp Xaa Ser Xaa Xaa Xaa Xaa Xaa Xaa Xaa
1               5                   10                  15

Xaa Xaa Xaa Xaa Xaa Trp Leu Xaa Xaa Xaa Xaa Xaa Xaa Gly Pro Ser
                20                  25                  30

Ser Gly Ala Pro Pro Pro Xaa
            35

<210> SEQ ID NO 36
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid

<400> SEQUENCE: 36

Glu Gly Thr Phe Thr Ser Asp Tyr Ser Ile Tyr Leu Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser Lys
            35

<210> SEQ ID NO 37
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 37

Glu Gly Thr Phe Thr Ser Asp Tyr Ser Ile Tyr Leu Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser Lys
            35

<210> SEQ ID NO 38
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: D-Glu
<220> FEATURE:
<221> NAME/KEY: MOD_RES -continued

```
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 38

Glu Gly Thr Phe Thr Ser Asp Tyr Ser Ile Tyr Leu Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser Lys
        35

<210> SEQ ID NO 39
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 39

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Gly Pro Ser Ser Gly
            20                  25                  30

Ala Pro Pro Pro Ser Lys
        35

<210> SEQ ID NO 40
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 40

Glu Gly Thr Phe Ile Ser Asp Tyr Ser Ile Ala Met Asp Lys Ile Arg
1               5                   10                  15

Gln Gln Asp Phe Val Asn Trp Leu Leu Ala Gln Arg Gly Pro Ser Ser
            20                  25                  30

Gly Ala Pro Pro Pro Ser Lys
        35

<210> SEQ ID NO 41
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid

<400> SEQUENCE: 41

Glu Gly Thr Phe Thr Ser Asp Leu Ser Ile Tyr Leu Asp Lys Gln Ala
```

```
                1               5                  10                  15
Ala Xaa Glu Phe Val Asn Trp Leu Leu Ala Gly Gly Pro Ser Ser Gly
                               20                  25                  30

Ala Pro Pro Pro Ser Lys
                35

<210> SEQ ID NO 42
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid

<400> SEQUENCE: 42

Glu Gly Thr Phe Thr Ser Asp Tyr Ser Ile Tyr Leu Asp Glu Gln Ala
1               5                   10                  15

Ala Xaa Glu Phe Val Asn Trp Leu Leu Ala Gly Gly Pro Ser Ser Gly
                20                  25                  30

Ala Pro Pro Pro Ser Lys
                35

<210> SEQ ID NO 43
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid

<400> SEQUENCE: 43

Glu Gly Thr Phe Thr Ser Asp Tyr Ser Ile Tyr Leu Asp Lys Gln Ala
1               5                   10                  15

Val Xaa Glu Phe Val Asn Trp Leu Leu Ala Gly Gly Pro Ser Ser Gly
                20                  25                  30

Ala Pro Pro Pro Ser Lys
                35

<210> SEQ ID NO 44
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid

<400> SEQUENCE: 44

Glu Gly Thr Phe Thr Ser Asp Tyr Ser Ile Tyr Leu Asp Lys Gln Ala
1               5                   10                  15

Ala Xaa Leu Phe Val Asn Trp Leu Leu Ala Gly Gly Pro Ser Ser Gly
                20                  25                  30

Ala Pro Pro Pro Ser Lys
                35
```

<210> SEQ ID NO 45
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid

<400> SEQUENCE: 45

Glu Gly Thr Phe Thr Ser Asp Tyr Ser Ile Tyr Leu Asp Lys Gln Ala
1               5                   10                  15

Ala Xaa Glu Phe Ile Asn Trp Leu Leu Ala Gly Gly Pro Ser Ser Gly
            20                  25                  30

Ala Pro Pro Pro Ser Lys
        35

<210> SEQ ID NO 46
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid

<400> SEQUENCE: 46

Glu Gly Thr Phe Thr Ser Asp Tyr Ser Ile Tyr Leu Asp Lys Gln Ala
1               5                   10                  15

Ala Xaa Glu Phe Val Glu Trp Leu Leu Ala Gly Gly Pro Ser Ser Gly
            20                  25                  30

Ala Pro Pro Pro Ser Lys
        35

<210> SEQ ID NO 47
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid

<400> SEQUENCE: 47

Glu Gly Thr Phe Thr Ser Asp Tyr Ser Ile Tyr Leu Asp Lys Gln Ala
1               5                   10                  15

Val Xaa Glu Phe Ile Asn Trp Leu Leu Ala Gly Gly Pro Ser Ser Gly
            20                  25                  30

Ala Pro Pro Pro Ser Lys
        35

<210> SEQ ID NO 48
<211> LENGTH: 38
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 48

Glu Gly Thr Phe Thr Ser Asp Tyr Ser Ile Gln Met Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser Lys
                35

<210> SEQ ID NO 49
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 49

Glu Gly Thr Phe Thr Ser Asp Tyr Ser Ile Ala Met Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser Lys
                35

<210> SEQ ID NO 50
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: 2-amino-2-methylpentanoic acid
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 50

Glu Gly Thr Phe Thr Ser Asp Tyr Ser Ile Tyr Xaa Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser Lys
                35

<210> SEQ ID NO 51
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid

<400> SEQUENCE: 51

Glu Gly Thr Phe Thr Ser Asp Tyr Ser Ile Tyr Leu Asp Arg Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser
        35

<210> SEQ ID NO 52
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 52

Glu Gly Thr Phe Thr Ser Asp Tyr Ser Ile Tyr Leu Asp Lys Gln Ala
1               5                   10                  15

Val Xaa Glu Phe Val Asn Trp Leu Leu Ala Gly Gly Pro Ser Ser Gly
            20                  25                  30

Ala Pro Pro Pro Ser Lys
        35

<210> SEQ ID NO 53
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 53

Glu Gly Thr Phe Thr Ser Asp Tyr Ser Ile Tyr Leu Asp Lys Gln Ala
1               5                   10                  15

Ala Xaa Glu Phe Val Lys Trp Leu Leu Ala Gly Gly Pro Ser Ser Gly
            20                  25                  30

Ala Pro Pro Ser Lys
        35

```
<210> SEQ ID NO 54
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 54

Glu Gly Thr Phe Thr Ser Asp Tyr Ser Ile Tyr Leu Asp Lys Gln Ala
1               5                   10                  15

Ala Xaa Glu Phe Val Asn Trp Leu Leu Ala Gly Arg Gly Lys Gly Pro
            20                  25                  30

Ser Ser Gly Ala Pro Pro Pro Ser
        35                  40

<210> SEQ ID NO 55
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 55

Glu Gly Thr Phe Thr Ser Asp Tyr Ser Ile Tyr Leu Asp Lys Gln Ala
1               5                   10                  15

Ala Lys Glu Phe Val Asn Trp Leu Leu Ala Gly Gly Pro Ser Ser Gly
            20                  25                  30

Ala Pro Pro Pro Ser Lys
        35

<210> SEQ ID NO 56
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 56

Glu Gly Thr Phe Thr Ser Asp Lys Ser Ile Tyr Leu Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser Lys
        35

<210> SEQ ID NO 57
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 57

Gly Thr Phe Thr Ser Asp Tyr Ser Ile Tyr Leu Asp Lys Gln Ala Ala
1               5                   10                  15

Xaa Glu Phe Val Asn Trp Leu Leu Ala Gly Gly Pro Ser Ser Gly Ala
                20                  25                  30

Pro Pro Pro Ser Lys
            35

<210> SEQ ID NO 58
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: 2-amino-3-(4-hydroxyphenyl)-2-methylpropanoic
      acid
<220> FEATURE:
<221> NAME/KEY: MOD_RES
<222> LOCATION: (18)..(18)
<223> OTHER INFORMATION: 2-aminoisobutyric acid
<220> FEATURE:
<223> OTHER INFORMATION: See specification as filed for detailed
      description of substitutions and preferred embodiments

<400> SEQUENCE: 58

Glu Gly Thr Phe Thr Ser Asp Tyr Ser Ile Xaa Leu Asp Lys Gln Ala
1               5                   10                  15

Ala Xaa Glu Phe Val Asn Trp Leu Leu Ala Gly Gly Pro Ser Ser Gly
                20                  25                  30

Ala Pro Pro Pro Ser Lys
            35
```